US012435354B2

(12) United States Patent
Binkowski et al.

(10) Patent No.: US 12,435,354 B2
(45) **Date of Patent: *Oct. 7, 2025**

(54) ***OPLOPHORUS*-DERIVED LUCIFERASES, NOVEL COELENTERAZINE SUBSTRATES, AND METHODS OF USE**

(71) Applicant: Promega Corporation, Madison, WI (US)

(72) Inventors: Brock Binkowski, Sauk City, WI (US); Lance P. Encell, Fitchburg, WI (US); Mary Hall, Waunakee, WI (US); Matthew B. Robers, Madison, WI (US); Michael R. Slater, Madison, WI (US); Keith V. Wood, Mount Horeb, WI (US); Monika G. Wood, Mount Horeb, WI (US)

(73) Assignee: Promega Corporation, Madison, WI (US)

( * ) Notice: Subject to any disclaimer, the term of this patent is extended or adjusted under 35 U.S.C. 154(b) by 81 days.

This patent is subject to a terminal disclaimer.

(21) Appl. No.: 18/471,901

(22) Filed: Sep. 21, 2023

(65) Prior Publication Data

US 2024/0158831 A1 May 16, 2024

Related U.S. Application Data

(60) Continuation of application No. 17/332,459, filed on May 27, 2021, now Pat. No. 12,215,375, which is a continuation of application No. 17/011,597, filed on Sep. 3, 2020, now Pat. No. 11,661,623, which is a continuation of application No. 15/948,070, filed on Apr. 9, 2018, now Pat. No. 10,774,364, which is a continuation of application No. 14/160,282, filed on Jan. 21, 2014, now Pat. No. 9,951,373, which is a division of application No. 13/287,986, filed on Nov. 2, 2011, now Pat. No. 8,669,103.

(60) Provisional application No. 61/409,422, filed on Nov. 2, 2010.

(51) Int. Cl.

| | |
|---|---|
| ***C12N 9/02*** | (2006.01) |
| ***C07D 487/04*** | (2006.01) |
| ***C12N 15/52*** | (2006.01) |
| ***C12Q 1/66*** | (2006.01) |

(52) U.S. Cl.

CPC ............ *C12Q 1/66* (2013.01); *C07D 487/04* (2013.01); *C12N 9/0004* (2013.01); *C12N 9/0069* (2013.01); *C12N 15/52* (2013.01); *C12Y 113/12005* (2013.01); *C12Y 113/12007* (2013.01); *A01K 2217/072* (2013.01)

(58) Field of Classification Search

None

See application file for complete search history.

(56) References Cited

U.S. PATENT DOCUMENTS

| | | | |
|---|---|---|---|
| 5,670,356 | A | 9/1997 | Sherf et al. |
| 5,837,465 | A | 11/1998 | Squirrel |
| 5,998,204 | A | 12/1999 | Tsien et al. |
| 6,132,983 | A | 10/2000 | Lowe |
| 6,171,808 | B1 | 1/2001 | Squirrell |
| 6,265,177 | B1 | 7/2001 | Squirrell |
| 6,387,675 | B1 | 5/2002 | Wood et al. |
| 6,544,754 | B2 | 4/2003 | Inoye |
| 6,552,179 | B1 | 4/2003 | Wood et al. |
| 6,602,677 | B1 | 8/2003 | Wood et al. |
| 7,078,181 | B2 | 7/2006 | Hawkins et al. |
| 7,108,996 | B2 | 9/2006 | Hawkins et al. |
| 7,118,878 | B1 | 10/2006 | Hawkins |
| 7,125,697 | B2 | 10/2006 | Inoye |
| 7,238,842 | B2 | 7/2007 | Wood et al. |
| 7,241,584 | B2 | 7/2007 | Wood et al. |
| 7,268,229 | B2 | 9/2007 | Wood et al. |
| 7,416,854 | B2 | 8/2008 | Riss et al. |
| 7,425,436 | B2 | 9/2008 | Darzins et al. |
| 7,429,472 | B2 | 9/2008 | Darzins et al. |
| 7,537,912 | B2 | 5/2009 | Wood et al. |
| 7,553,632 | B2 | 6/2009 | Niles et al. |
| 7,692,002 | B2 | 4/2010 | Alberto |
| 7,692,022 | B2 | 4/2010 | Cali et al. |
| 7,728,118 | B2 | 6/2010 | Wood et al. |

(Continued)

FOREIGN PATENT DOCUMENTS

| | | |
|---|---|---|
| EP | 1281762 | 2/2003 |
| EP | 1479763 | 11/2004 |

(Continued)

OTHER PUBLICATIONS

Angelucci, F. et al., Schistosoma mansoni fatty acid binding protein: specificity and functional control as revealed by crystallographic structure, Biochem. (2004) 43:13000-13011.

(Continued)

*Primary Examiner* — David Steadman

(74) *Attorney, Agent, or Firm* — David W. Staple; Casimir Jones, S.C.

(57) ABSTRACT

An isolated polynucleotide encoding a modified luciferase polypeptide and substrates. The OgLuc variant polypeptide has at least 60% amino acid sequence identity to SEQ ID NO: 1 and at least one amino acid substitution at a position corresponding to an amino acid in SEQ ID NO: 1. The OgLuc variant polypeptide has at least one of enhanced luminescence, enhanced signal stability, and enhanced protein stability relative to the corresponding polypeptide of the wild-type *Oplophorus* luciferase.

5 Claims, 118 Drawing Sheets

Specification includes a Sequence Listing.

(56) References Cited

U.S. PATENT DOCUMENTS

| | | | | |
|---|---|---|---|---|
| 7,741,067 | B2 | 6/2010 | Hawkins et al. | |
| 7,867,726 | B2 | 1/2011 | Wood et al. | |
| 7,879,540 | B1 | 2/2011 | Wood et al. | |
| 7,888,086 | B2 | 2/2011 | Darzins et al. | |
| 7,906,282 | B2 | 3/2011 | Wood | |
| 7,906,298 | B1 | 3/2011 | Squirrell et al. | |
| 7,935,803 | B2 | 5/2011 | Darzins et al. | |
| 7,951,550 | B2 | 5/2011 | Cali | |
| 8,008,006 | B2 | 8/2011 | Wood et al. | |
| 8,030,017 | B2 | 10/2011 | Wood et al. | |
| 8,106,052 | B2 | 1/2012 | Wood et al. | |
| 8,168,405 | B2 | 5/2012 | Darzins et al. | |
| 8,183,007 | B2 | 5/2012 | Zegzouti | |
| 8,183,036 | B2 | 5/2012 | Fan | |
| 8,202,700 | B2 | 6/2012 | Darzins et al. | |
| 8,557,970 | B2 * | 10/2013 | Encell | C12Q 1/66 435/189 |
| 8,669,103 | B2 | 3/2014 | Binkowski et al. | |
| 8,809,529 | B2 * | 8/2014 | Klaubert | C12Y 113/12005 548/335.1 |
| 9,139,836 | B2 * | 9/2015 | Klaubert | C12Q 1/66 |
| 9,777,311 | B2 * | 10/2017 | Encell | C12Y 113/12007 |
| 9,840,730 | B2 | 12/2017 | Binkowski et al. | |
| 9,938,564 | B2 * | 4/2018 | Klaubert | C12N 15/52 |
| 9,951,373 | B2 | 4/2018 | Binkowski et al. | |
| 10,233,485 | B2 * | 3/2019 | Encell | C12N 15/52 |
| 10,633,690 | B2 * | 4/2020 | Encell | C12N 15/52 |
| 10,774,364 | B2 | 9/2020 | Binkowski et al. | |
| 10,844,422 | B2 * | 11/2020 | Encell | C12Q 1/66 |
| 11,365,436 | B2 * | 6/2022 | Encell | C12Y 113/12007 |
| 11,661,623 | B2 * | 5/2023 | Binkowski | C12Y 113/12005 435/325 |
| 11,667,950 | B2 * | 6/2023 | Encell | C12N 9/0004 435/69.1 |
| 12,215,375 | B2 * | 2/2025 | Binkowski | C12N 15/52 |
| 2003/0068801 | A1 | 4/2003 | Wood et al. | |
| 2003/0153090 | A1 | 8/2003 | Wood et al. | |
| 2003/0166905 | A1 | 9/2003 | Wood et al. | |
| 2003/0232404 | A1 | 12/2003 | Wood et al. | |
| 2004/0002127 | A1 | 1/2004 | Inoue et al. | |
| 2004/0096924 | A1 | 5/2004 | Hawkins et al. | |
| 2004/0171099 | A1 | 9/2004 | Cali et al. | |
| 2004/0178545 | A1 | 9/2004 | Cates et al. | |
| 2004/0214258 | A1 | 10/2004 | Wood et al. | |
| 2004/0224377 | A1 | 11/2004 | Hawkins et al. | |
| 2005/0026171 | A1 | 2/2005 | Hawkins et al. | |
| 2005/0153310 | A1 | 7/2005 | Fan et al. | |
| 2005/0164321 | A1 | 7/2005 | Riss et al. | |
| 2005/0272114 | A1 | 12/2005 | Darzins et al. | |
| 2006/0024808 | A1 | 2/2006 | Darzins et al. | |
| 2006/0051827 | A1 | 3/2006 | Hawkins et al. | |
| 2006/0068395 | A1 | 3/2006 | Wood et al. | |
| 2006/0127988 | A1 | 6/2006 | Wood | |
| 2006/0183212 | A1 | 8/2006 | Wood et al. | |
| 2007/0015790 | A1 | 1/2007 | Cali | |
| 2007/0087400 | A1 | 4/2007 | Darzins et al. | |
| 2008/0026407 | A1 | 1/2008 | Wood et al. | |
| 2008/0050760 | A1 | 2/2008 | Wood et al. | |
| 2008/0070299 | A1 | 3/2008 | Wood et al. | |
| 2008/0090291 | A1 | 4/2008 | Wood et al. | |
| 2008/0145882 | A1 | 6/2008 | Darzins et al. | |
| 2008/0248511 | A1 | 10/2008 | Daily | |
| 2008/0268482 | A1 | 10/2008 | Riss et al. | |
| 2008/0274488 | A1 | 11/2008 | Darzins et al. | |
| 2008/0299593 | A1 | 12/2008 | Cali | |
| 2009/0017482 | A1 | 1/2009 | Riss et al. | |
| 2009/0023173 | A1 | 1/2009 | Cali et al. | |
| 2009/0098627 | A1 | 4/2009 | Darzins et al. | |
| 2009/0137019 | A1 | 5/2009 | Wood et al. | |
| 2009/0253131 | A1 | 10/2009 | Wigdal et al. | |
| 2009/0275051 | A1 | 11/2009 | Niles et al. | |
| 2009/0305280 | A1 | 12/2009 | Binkowski et al. | |
| 2009/0311769 | A1 | 12/2009 | Wood et al. | |
| 2010/0075350 | A1 | 3/2010 | Zegzouti et al. | |
| 2010/0273186 | A1 | 10/2010 | Wood et al. | |
| 2010/0281552 | A1 | 11/2010 | Encell | |
| 2011/0003316 | A1 | 1/2011 | Cali et al. | |
| 2011/0039257 | A1 | 2/2011 | Binkowski et al. | |
| 2011/0081670 | A1 | 4/2011 | Hawkins et al. | |
| 2011/0171673 | A1 | 7/2011 | Darzins et al. | |
| 2011/0177540 | A1 | 7/2011 | Squirrell | |
| 2011/0201024 | A1 | 8/2011 | Wood et al. | |
| 2011/0207195 | A1 | 8/2011 | Darzins et al. | |
| 2011/0283373 | A1 | 11/2011 | Binkowski et al. | |
| 2012/0009647 | A1 | 1/2012 | Wood et al. | |
| 2012/0058505 | A1 | 3/2012 | Helms et al. | |
| 2020/0399676 | A1 | 12/2020 | Binkowski et al. | |

FOREIGN PATENT DOCUMENTS

| | | |
|---|---|---|
| EP | 1630231 | 3/2006 |
| EP | 1894933 | 3/2008 |
| EP | 1935980 | 6/2008 |
| EP | 1935986 | 6/2008 |
| EP | 1978091 | 10/2008 |
| EP | 1978092 | 10/2008 |
| EP | 2071023 | 6/2009 |
| EP | 2272972 | 1/2011 |
| EP | 2272973 | 1/2011 |
| EP | 2277872 | 1/2011 |
| EP | 2284271 | 2/2011 |
| EP | 2298902 | 3/2011 |
| EP | 2308978 | 4/2011 |
| EP | 2325328 | 5/2011 |
| EP | 2325329 | 5/2011 |
| EP | 2327768 | 6/2011 |
| EP | 2341134 | 7/2011 |
| EP | 2366777 | 9/2011 |
| EP | 2366778 | 9/2011 |
| EP | 2366779 | 9/2011 |
| EP | 2366780 | 9/2011 |
| EP | 2368976 | 9/2011 |
| EP | 2368977 | 9/2011 |
| EP | 2369006 | 9/2011 |
| EP | 2374875 | 10/2011 |
| EP | 2395078 | 12/2011 |
| EP | 2395358 | 12/2011 |
| EP | 2420573 | 2/2012 |
| WO | WO 1995/018853 | 7/1995 |
| WO | WO 1995/025798 | 9/1995 |
| WO | WO 1996/007100 | 3/1996 |
| WO | WO 1996/022376 | 7/1996 |
| WO | WO 1998/046729 | 10/1998 |
| WO | WO 1998/046739 | 10/1998 |
| WO | WO 1999/014336 | 3/1999 |
| WO | WO 2000/024878 | 5/2000 |
| WO | WO 2001/020002 | 3/2001 |
| WO | WO 2001/031028 | 5/2001 |
| WO | WO 2001/096862 | 12/2001 |
| WO | WO 2002/016944 | 2/2002 |
| WO | WO 2003/040100 | 5/2003 |
| WO | WO 2004/027378 | 4/2004 |
| WO | WO 2004/059294 | 7/2004 |
| WO | WO 2004/072232 | 8/2004 |
| WO | WO 2004/072299 | 8/2004 |
| WO | WO 2005/038029 | 4/2005 |
| WO | WO 2005/073722 | 8/2005 |
| WO | WO 2006/034061 | 3/2006 |
| WO | WO 2006/093529 | 9/2006 |
| WO | WO 2006/130551 | 12/2006 |
| WO | WO 2007/120522 | 10/2007 |
| WO | WO 2008/054821 | 5/2008 |
| WO | WO 2008/086035 | 7/2008 |
| WO | WO 2008/118445 | 10/2008 |
| WO | WO 2009/061413 | 5/2009 |
| WO | WO 2009/142735 | 11/2009 |
| WO | WO 2010/011607 | 1/2010 |
| WO | WO 2010/127368 | 11/2010 |
| WO | WO 2011/038219 | 3/2011 |

(56) References Cited

FOREIGN PATENT DOCUMENTS

| | | |
|---|---|---|
| WO | WO 2011/143339 | 11/2011 |
| WO | WO 2012/030960 | 3/2012 |

OTHER PUBLICATIONS

Arnold, K. et al., The SWISS-MODEL workspace: a web-based environment for protein structure homology modelling, Bioinformatics (2006) 22(2):195-201.
Becker, M.M. et al., Gene cloning, overproduction and purification of a functionally active cytoplasmic fatty acid-binding protein (Sj-FABPc) from the human blood fluke Schistosoma japonicum, Gene (1994) 148:321-325.
Chakravarty et al., Accuracy of structure-derived properties in simple comparative models of protein structures. Nucleic Acids Research 2009, 33(1): 244-259.
Cowan, S.W. et al., Crystallographic studies on a family of cellular lipophilic transport proteins, J. Mol. Biol. (1993) 230;1225-1246.
Daughtery, P.S. et al., Quantitative analysis of the effect of the mutation frequency on the affinity maturation of single chain Fv antibodies, Proc. Natl. Acad. Sci. USA (2000) 97(5):2029-2034.
Dennell, R. et al., Observations on the luminescence of bathypelagic crustacea decapoda of the Bermuda area, J. linnean. Soc. London (1955) XLII:393-406.
Flower, D.R. et al., A structural signature characteristic of the calycin protein superfamily, Protein Pept. Lett. (1995) 2(2):341-350.
Flower, D.R. et al., Structure and sequence relationships in the lipocalins and related proteins, Protein Sci. (1993) 2:753-761.
Flower, D.R. et al., The lipocalin protein family—structure and function, Biochem. J. (1996) 318:1-14.
Flower, D.R. et al., The lipocalin protein family-structural and sequence overview, Biochimica et Biophysica Acta (2000) 1482:9-24.
Fujii et al. Increase in Bioluminescence intensity of firefly luciferase using genetic modification. Analy. Biochem. Jun. 2007, 366 (2):131-136.
Genbank Accession No. BAB13776, Sep. 2000.
Head, J.F. et al., The crystal structure of the photoprotein aequorin at 2.3A resolution, Nature (2000) 405:372-376.
Herring, P.J. et al., Bioluminescence in crustacea, J. Crust. Biol. (1985) 5(4):557-573.
Herring, P.J. et al., The spectral characteristics of luminous marine organisms, Proc. Royal Society London Series B. Biological Sciences (1983) 220(1219):183-217.
Herring, P.J., Bioluminescence in decapod crustacea, J. Mar. Biol. Assoc. UK (1976) 156:1029-1047.
Inouye, S. et al., Complete structure of renilla luciferin and luciferyl sulfate, Tetra. Lett (1977) 31:2685-2688.
Inouye et al., Secretional luciferase of the luminous shrimp Oplophorus gracilirostris: cDNA cloning of a novel imidazopyazinon luciferase. FEBS Letters Sep. 2000, 481(1):19-25.
Inouye, S. et al., Overexpression, purification and characterization of the catalytic component of oplophorus luciferase in the deep sea shrimp, Protein Exp. Purification (2007) 56(2):261-268.
Inouye et al., Expression, purification and luminescence properties of coelenterazine-utilizing luciferases from Renilla, Oplophorus and Gaussia: comparison of substrate specificity for C2-modified coelenterazines. Protein Expr Purif. Mar. 2013;88(1):150-6.
Johnson, F.H. et al., Introduction to the cypridina system, Meth. Enzym. (1978) 57:331-364.
Kabsch, W. et al., Dictionary of protein secondary structure: pattern recognition of hydrogen-bonded and geometrical features, Biopolymers (1983) 22:2577-2637.
Karplus, K. et al., Hidden Markov models for detecting remote protein homologies, Bioinformatics (1998) 14(10):846-856.
King, R.D. et al., Identification and application of the concepts important for accurate and reliable protein secondary structure prediction, Protein Sci. (1996) 5:2298-2310.
Kunkel, T.A., Rapid and efficient site-specific mutagenesis without phenotypic selection, Proc. Natl. Acad. Sci. USA (1985) 82(2):488-492.
Kurowski, M.A. et al., GeneSilico protein structure prediction meta-server, Nucl. Acids. Res. (2003) 31(13):3305-3307.
Loening et al., Concensus guided mutagenesis of Renilla Luciferase yields enhanced stability and light output. Protein Engineering, Des and Sel. Sep. 2006, 391-400.
Lorenz, W.W. et al., Isolation and expression of a cDNA encoding renilla reinformis luciferase, Proc. Natl. Acad. Sci. USA (1991) 88:4438-4442.
Mcguffin, L.J. et al., The PSIPRED protein structure prediction server, Bioinformatics (2000) 16(4):404-405.
Murray, E.E. et al., Codon usage in plant genes, Nucl. Acids. Res. (1989) 17(2):477-498.
Nakamura, H. et al., Efficient bioluminescence of bisdeoxycoelenterazine with the luciferase of a deep-sea shrimp oplophorus, Tetra. Lett. (1997) 38(36):6405-6406.
Needleman, S.B. et al., A general method applicable to the search for similarities in the amino acid sequence of two proteins, J. Mol. Biol. (1970) 48:443-453.
Nowel, M.S. et al., Cuticular photophores of two decapod crustaceans, oplophorus spinosus and systellaspis debilis, Biol. Bull. (1998) 195:290-307.
Parsons, M.R. et al., Crystal structure of a quinoenzyme: copper amine oxidase of *Escherichia coli* at 2 A resolution, Structure (1995) 3:1171-1184.
Pearson, W.R. et al., Improved tools for biological sequence comparison, Proc. Natl. Acad. Sci. USA (1988) 85:2444-2448.
Pichler et al., Imaging reversal of multidrug resistance in living mice with bioluminescence: MDR1 P-glycoprotein transports coelenterazine. Proc. Natl. Acaa. Sci. USA 2004, 101(6): 1702-1707.
Pollastri, G. et al., Porter: a new, accurate server for protein secondary structure prediction, Bioinformatics (2005) 21(8):1719-1720.
Poupin, J., Plancton marin bioluminescent, Rapport Scientifique du Leon (Sep. 1999) 1-83.
"Renilla Luciferase Assay System", Technical Manual , Promega, 2011.
Schagat, T. et al., KRX autoinduction protocol: a convenient method for protein expression, Promega Notes (2008) 98:16-18.
Schultz, L.W. et al., Crystal structure of a pH-regulated luciferase catalyzing the bioluminescent oxidation of an open tetrapyrrole, Proc. Natl. Acad. Sci. USA (2005) 102(5):1378-1383.
Shimomura et al., Sem-synthetic aequorins with improved sensitivity to CA2+ ions. Biochem. J. 1989, 261:913-920.
Shimomura, O. et al., Properties and reaction mechanism of the bioluminescence system of the deep-sea shrimp oplophorus gracilorostris, Biochem. (1978) 17:994-998.
Skerra, A., Lipocalins as a scaffold, Biochem et Biophys. Acta (2000) 1482:337-350.
Skolnick & Fetrow, From genes to protein structure and function: novel applications of computational approaches in the genomic era. Tibtech Jan. 2000, 18:34-39.
Smith, T.F. et al., Identification of common molecular subsequences, J. Mol. Biol. (1981) 147:195-197.
Thompson, E.M et al., Cloning and expression of cDNA for the luciferase from the marine ostracod Vargula hilgendorfii, Proc. Natl. Acad. Sci. USA (1989) 86:6567-6571.
Todd et al., Evolution of Function in Protein Superfamilies, from a Structural Perspective. J. Mol. Biol 2001, 307:1113-1143.
Tomabechi et al., Crystal structure of nanoKAZ: The mutated 19 kDa component of Oplophorus luciferase catalyzing the bioluminescent reaction with coelenterazine. Biochem Biophys Res Commun. Jan. 29, 2016;470(1):88-93.
Topell et al. Circularly permuted variants of the green fluorescent protein, FEBS Lett, 1999:457:283-289.
Verhoef et al. Multiplex detection of protein-protein interactions using a next generation luciferase reporter, Biochim. Biophys. Acta, 2016:1863:284-292.
Wada, K. et al., Codon usage tabulated from the GenBank genetic sequence data, Nucl. Acids Res. (1990) 18(Supp): 2367-2411.

(56) References Cited

OTHER PUBLICATIONS

Wells, J.A. Additivity of Mutational Effects in Proteins. Perspectives in Biotechnology, American Chemical Society Sep. 18, 1990, 29(37): 5809-5817.
International Search Report and Written Opinion for Application No. PCT/US2010/033449 dated Aug. 18, 2010 (12 pages).
International Search Report and Written Opinion for Application No. PCT/US2011/058924 dated Jan. 24, 2012 (8 pages).
International Search Report and Written Opinion for Application No. PCT/US2011/059017 dated Jan. 18, 2012 (8 pages).
Extended European Search Report for EP19150069.3, mailed Mar. 14, 2019, 14 pages.

* cited by examiner

Native Coelenterazine (Coel)

Coelenterazine-hh (Coel hh)

Coelenterazine-h (Coel h)

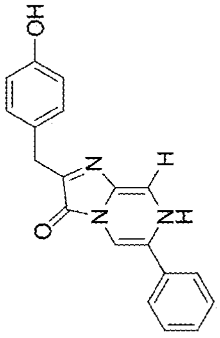
3894
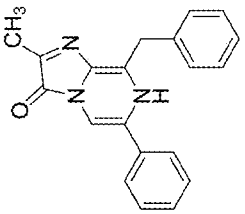
3932
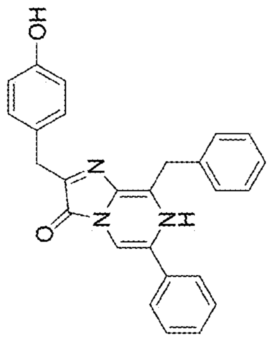
3840
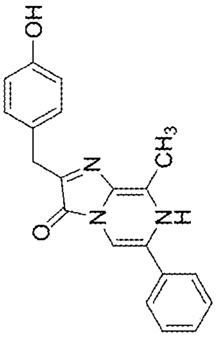
3896
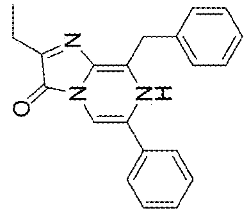
3925
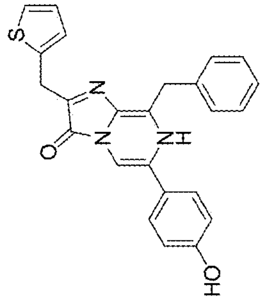
4002
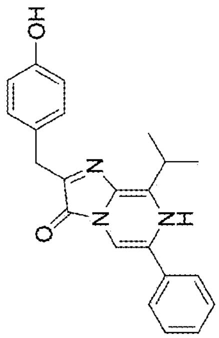
3841
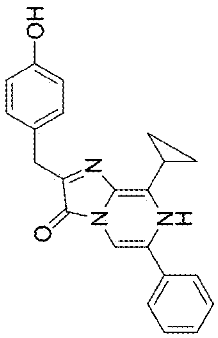
3897
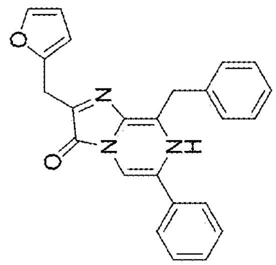
3939
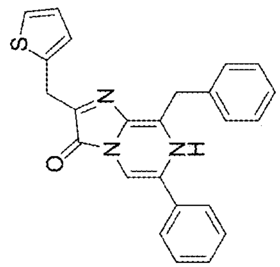
3889
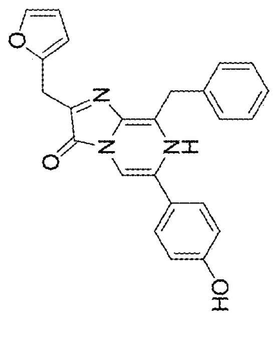
3945
FIG. 2

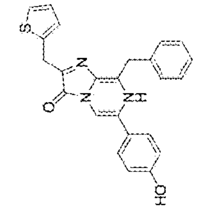
4002
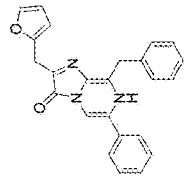
3939
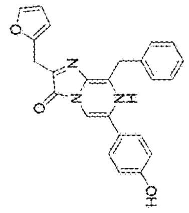
3945
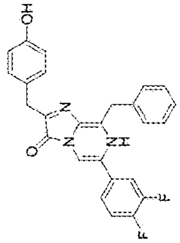
3913
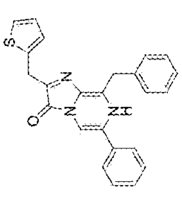
3889
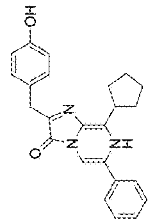
3842
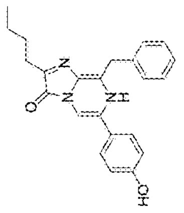
3900
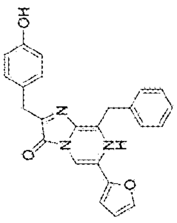
3887
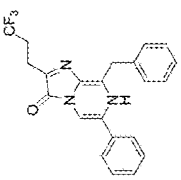
3946
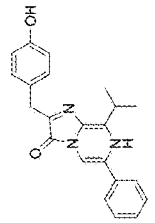
3841
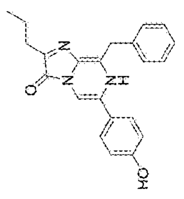
3899
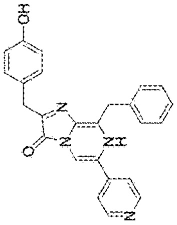
3857
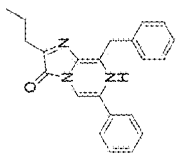
3933
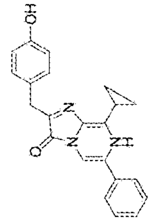
3897
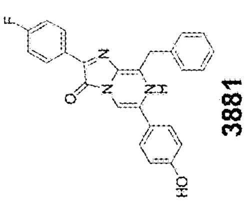
3881
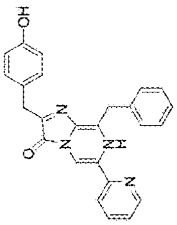
3886
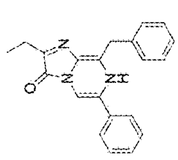
3925
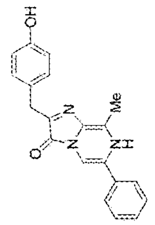
3896
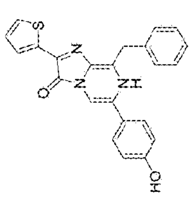
3882
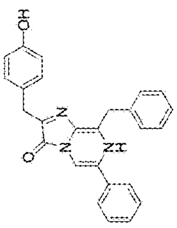
3840
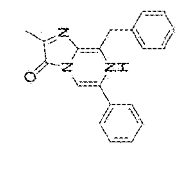
3932
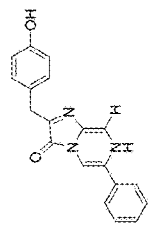
3894
FIG. 4

| POSITION | Clone(AA sequence) | Colenteh | h | h,h | 2-me | PBI-3840 | PBI-3897 | PBI-3889 | PBI-3899 | PBI-3900 |
|---|---|---|---|---|---|---|---|---|---|---|
| 15 | 03F2 (G15R) | 0.004 | 0.059 | 0.024 | 0.004 | 0.008 | 0.003 | 0.031 | 0.003 | 0.011 |
| 18 | 40H11 (Q18L) | 0.38 | 0.26 | 0.51 | 0.20 | 0.28 | **4.46** | 0.53 | 0.17 | 0.43 |
| 20 | 16C5 (Q20R) | **5.66** | **1.96** | **1.88** | **9.02** | **4.72** | **6.50** | **1.61** | **4.92** | **2.41** |
| 22 | 14C1 (L22I) | 0.17 | 0.63 | 0.47 | 0.41 | 0.14 | 0.08 | 0.43 | 0.49 | 0.66 |
| 27 | 11E 8 (L27V) | 0.34 | **1.74** | **1.88** | 0.55 | 0.35 | 0.03 | **2.03** | 0.88 | **2.22** |
| 54 | 18F8 (F54S) | 0.21 | 0.40 | **1.78** | 0.13 | 0.53 | 0.55 | **1.62** | 0.18 | 0.69 |
| 54 | 29H7 (F54I) | **11.30** | **1.71** | **1.48** | **24.59** | **18.11** | **18.09** | **2.32** | **10.57** | **2.99** |
| 58 | 30E 4 (V58I) | 0.27 | 0.89 | 1.00 | 0.96 | 0.43 | 0.21 | 1.15 | 0.65 | 1.02 |
| 72 | 04G7 (L72Q) | **4.46** | 1.25 | 1.15 | **9.36** | **5.65** | **8.84** | 1.13 | **4.04** | **1.53** |
| 75 | 28B2 (M75K) | **4.16** | **1.57** | **2.30** | **5.43** | **4.92** | **5.67** | **2.38** | **4.03** | **2.11** |
| 77 | 18C4 (F77T) | **1.62** | 0.55 | 1.22 | **7.82** | **2.06** | **2.28** | **1.33** | **2.67** | 0.86 |
| 77 | 42E 4 (F77C) | 0.13 | 0.46 | 0.99 | **3.43** | 0.20 | 0.02 | 1.27 | 0.56 | 0.58 |
| 77 | 50D12 (F77T) | **1.48** | 0.52 | 1.15 | **7.75** | **1.87** | **2.20** | 1.24 | **2.46** | 0.78 |
| 89 | 35D11 (K89E) | **3.02** | 0.59 | 1.26 | **5.27** | **3.39** | **5.19** | **1.41** | **2.32** | 0.95 |
| 90 | 10F2 (I90T) | **2.20** | 0.48 | 0.66 | 0.00 | **3.90** | **5.41** | 0.84 | **1.36** | 0.55 |
| 92 | 04A12 (L92H) | 0.89 | 0.39 | 0.61 | **7.31** | **3.72** | **14.25** | 0.53 | 0.89 | 0.45 |
| 109 | 43F9 (Y109F) | 0.48 | 0.33 | 0.97 | 0.36 | **1.49** | **24.83** | 0.94 | 0.43 | 0.56 |
| 127 | 30D6 (V127A) | 0.23 | 0.50 | 0.54 | 0.26 | 0.81 | 1.00 | 0.57 | 0.26 | 0.42 |
| 139 | 27B8 (D139G) | 0.01 | 0.03 | 0.14 | 0.00 | 0.03 | 0.00 | 0.16 | 0.00 | 0.02 |
| 164 | 25A1 (C164S) | **2.47** | **1.79** | **1.53** | **2.74** | **3.37** | **5.10** | **1.63** | **2.87** | **2.05** |
| 14-89 | 25F2 (A14V,K89E) | **3.05** | 0.81 | 1.22 | **5.43** | **3.82** | **6.21** | **1.58** | **2.32** | 0.91 |
| 27-33 | 47D8(**L27M,K33N**) | 0.59 | **1.71** | **2.05** | 0.85 | 0.95 | 0.27 | **2.12** | 1.23 | **1.85** |
| 49-72 | 26F1 (E49K,**L72Q**) | **6.19** | **1.48** | **1.35** | **10.72** | **6.90** | **9.99** | **1.32** | **4.76** | **1.70** |
| 54-66 | 48G3 (**F54I**, S66T) | **7.33** | 1.06 | 0.91 | **16.39** | **11.27** | **8.28** | **1.42** | **6.63** | **1.85** |
| 54-67 | 35B8 (**F54S**,G67S) | 0.33 | 0.75 | **2.49** | 0.19 | 0.78 | 0.87 | **2.25** | 0.27 | 1.05 |
| 55-117 | 05H8 (D55G,I117F) | 0.24 | 0.53 | 0.62 | 0.00 | 0.25 | 0.22 | 0.65 | 0.21 | 0.45 |
| 56-93 | 46A11(I56V,H93R) | 0.35 | 0.61 | **1.53** | 0.22 | 0.42 | 0.18 | **1.50** | 0.36 | 0.88 |
| 68-75 | 04E 2 (**F68S,M75K**) | **3.43** | 1.20 | **1.53** | **4.37** | **3.91** | **4.12** | **1.62** | **3.24** | **1.57** |
| 77-126 | 27B9 (**F77T**,T126R) | 0.87 | 0.15 | 0.69 | **4.87** | 0.80 | 1.00 | 0.79 | 1.14 | 0.32 |
| 77-39 | 33E 2 (**F77T**,T39I) | 0.95 | 0.34 | 0.69 | **6.30** | **1.32** | **1.64** | 0.74 | **1.47** | 0.47 |
| 89-148 | 50 E7 (**K89E**, S148T) | **1.81** | 0.48 | 0.85 | **3.74** | **2.23** | **3.20** | 0.94 | **1.59** | 0.65 |
| 90-77 | 02D10 (**I90V,F77T**) | **2.05** | 0.70 | 1.17 | **17.39** | **6.32** | **10.88** | 1.05 | **2.37** | 0.73 |
| 106-164 | 17E 6 (M106K,**C164S**) | **4.14** | **2.46** | **2.52** | **3.77** | **5.06** | **7.72** | **2.71** | **3.80** | **2.82** |
| 23-58-169 | 47G12 (E23K,V58L,A169V) | 0.06 | 0.44 | 0.49 | **1.49** | 0.10 | 0.01 | 0.68 | 0.58 | 0.92 |
| 33-76-89 | 17C5 (**K33N**,I76N,**K89E**) | 1.27 | 0.68 | **2.02** | **1.33** | **2.22** | 1.12 | **2.24** | 1.07 | 0.79 |
| 68-90-145 | 04D10 (**F68S,I90V**,P145L) | **4.17** | **1.40** | **1.65** | 0.00 | **6.09** | **5.96** | **1.72** | **3.82** | **1.49** |
| 59-109-113-136 | 41H10 (I59T, **Y109F**, P113T, L136M) | 0.06 | 0.06 | 0.26 | 0.04 | 0.46 | **8.09** | 0.25 | 0.06 | 0.10 |

FIG. 6A

| POSITION | Clone(AA sequence) | Colenterazine | H | h,h | v | PBI-3912 | PBI-3913 | PBI-3925 | PBI-3897 | PBI-3899 |
|---|---|---|---|---|---|---|---|---|---|---|
| 15 | 03F2 (G15R) | 0.003 | 0.040 | 0.018 | 0.022 | 0.005 | 0.019 | 0.005 | 0.002 | 0.003 |
| 18 | 40H11 (Q18L) | 0.20 | 0.18 | 0.30 | 0.11 | 0.13 | 0.14 | 0.06 | **3.24** | 0.09 |
| 20 | 16C5 (Q20R) | **4.08** | 1.30 | 1.14 | **5.25** | **5.27** | **5.34** | **4.83** | **3.33** | **3.32** |
| 22 | 14C1 (L22I) | 0.13 | 0.56 | 0.40 | 0.13 | 0.10 | 0.11 | 0.21 | 0.06 | 0.39 |
| 27 | 11E 8 (L27V) | 0.16 | 1.01 | 0.95 | 0.22 | 0.07 | 0.08 | 0.26 | 0.02 | 0.45 |
| 54 | 18F8 (F54S) | 0.16 | 0.37 | **1.44** | 0.55 | 0.17 | 0.22 | 0.26 | 0.38 | 0.14 |
| 54 | 29H7 (F54I) | **10.34** | **1.45** | 1.06 | **8.28** | **18.52** | **15.79** | **18.92** | **11.15** | **9.62** |
| 58 | 30E 4 (V58I) | 0.17 | 0.63 | 0.69 | 0.20 | 0.19 | 0.21 | 0.83 | 0.13 | 0.43 |
| 72 | 04G7 (L72Q) | **2.96** | 1.02 | 0.69 | 1.03 | **5.81** | **5.81** | **5.65** | **7.42** | **3.09** |
| 75 | 28B2 (M75K) | **2.93** | **1.35** | **1.53** | 1.06 | **3.98** | **3.89** | **3.86** | **4.73** | **2.93** |
| 77 | 18C4 (F77T) | 1.01 | 0.53 | 0.85 | **1.31** | 0.78 | 0.74 | **7.08** | **1.69** | **2.30** |
| 77 | 42E 4 (F77C) | 0.10 | 0.34 | 0.70 | 0.61 | 0.03 | 0.04 | 0.88 | 0.01 | 0.41 |
| 77 | 50D12 (F77T) | 0.88 | 0.46 | 0.72 | 1.21 | 0.62 | 0.60 | **5.94** | **1.41** | **1.92** |
| 89 | 35D11 (K89E) | **2.17** | 0.53 | 0.89 | 0.76 | **3.64** | **3.98** | **3.51** | **3.89** | **1.77** |
| 90 | 10F2 (I90T) | **1.86** | 0.39 | 0.49 | **1.71** | **10.44** | **11.10** | **3.76** | **3.61** | 1.20 |
| 92 | 04A12 (L92H) | 0.65 | 0.08 | 0.27 | **27.76** | **4.48** | **2.79** | **5.01** | **6.72** | 0.60 |
| 109 | 43F9 (Y109F) | 0.36 | 0.20 | 0.76 | 0.84 | 0.73 | 0.60 | 1.04 | **18.04** | 0.31 |
| 127 | 30D6 (V127A) | 0.16 | 0.31 | 0.30 | 0.16 | 0.32 | 0.45 | 0.50 | 0.43 | 0.15 |
| 139 | 27B8 (D139G) | 0.00 | 0.02 | 0.08 | 0.10 | 0.02 | 0.04 | 0.01 | 0.00 | 0.00 |
| 164 | 25A1 (C164S) | **3.10** | **1.71** | **1.47** | **3.91** | **3.04** | **3.29** | **3.43** | **4.33** | **3.14** |
| 14-89 | 25F2 (A14V,K89E) | **3.31** | 0.75 | 1.16 | **1.34** | **5.26** | **5.90** | **5.28** | **4.68** | **2.46** |
| 27-33 | 47D8(**L27M**,**K33N**) | 0.52 | **1.41** | **1.46** | **1.55** | 0.41 | 0.41 | 1.21 | 0.17 | 1.05 |
| 49-72 | 26F1 (E49K,**L72Q**) | **3.61** | 1.09 | 0.76 | **2.24** | **6.83** | **6.59** | **6.42** | **6.33** | **3.40** |
| 54-66 | 48G3 (**F54I**, S66T) | **10.15** | **1.40** | 1.01 | **7.67** | **17.73** | **14.90** | **18.29** | **10.14** | **9.44** |
| 54-67 | 35B8 (**F54S**,G67S) | 0.23 | 0.46 | **1.73** | 1.28 | 0.23 | 0.29 | 0.32 | 0.42 | 0.18 |
| 55-117 | 05H8 (D55G,I117F) | 0.18 | 0.38 | 0.46 | 0.44 | 0.12 | 0.14 | 0.10 | 0.14 | 0.16 |
| 56-93 | 46A11(I56V,H93R) | 0.24 | 0.39 | 0.96 | 0.88 | 0.10 | 0.11 | 0.21 | 0.11 | 0.24 |
| 68-75 | 04E 2 (**F68S**,**M75K**) | **2.39** | 1.01 | 1.04 | 0.74 | **3.01** | **3.04** | **3.61** | **3.58** | **2.47** |
| 77-126 | 27B9 (**F77T**,T126R) | 0.34 | 0.15 | 0.37 | 0.51 | 0.28 | 0.24 | **2.16** | 0.58 | 0.74 |
| 77-39 | 33E 2 (**F77T**,T39I) | 0.50 | 0.24 | 0.35 | 0.67 | 0.42 | 0.38 | **3.27** | 0.96 | 0.96 |
| 89-148 | 50 E7 (**K89E**, S148T) | **2.97** | 0.66 | 1.15 | **1.50** | **4.57** | **5.01** | **4.36** | **3.91** | **2.28** |
| 90-77 | 02D10 (**I90V**,**F77T**) | **1.44** | 0.63 | 0.80 | **3.79** | **2.80** | **2.47** | **24.43** | **7.82** | **2.14** |
| 106-164 | 17E 6 (M106K,**C164S**) | **2.71** | **1.50** | **1.52** | **4.80** | **2.79** | **2.92** | **2.93** | **3.47** | **2.48** |
| 23-58-169 | 47G12 (E23K,V58L,A169V) | 0.05 | 0.41 | 0.39 | 0.31 | 0.03 | 0.03 | 1.24 | 0.01 | 0.48 |
| 33-76-89 | 17C5 (**K33N**,I76N,**K89E**) | **1.53** | 0.63 | **1.74** | **2.16** | 0.86 | 0.94 | **1.38** | 0.91 | 1.03 |
| 68-90-145 | 04D10 (**F68S**,**I90V**,P145L) | **2.63** | 0.88 | 0.95 | **2.74** | **4.40** | **4.42** | **5.96** | **4.82** | **2.48** |
| 59-109-113-136 | 41H10 (I59T, **Y109F**, P113T, L136M) | 0.08 | 0.07 | 0.29 | 0.20 | 0.23 | 0.22 | 0.41 | **7.52** | 0.07 |

FIG. 6B

| POSITION | Clone(AA sequence) | coel | h | h,h | 2-me | PBI-3889 | PBI-3939 | PBI-3933 | PBI-3932 | PBI-3946 | PBI-3897 | PBI-3841 | PB-3896 | PBI-3925 |
|---|---|---|---|---|---|---|---|---|---|---|---|---|---|---|
| 15 | 03F2 (G15R) | 0.003 | 0.041 | 0.021 | 0.005 | 0.025 | 0.019 | 0.003 | 0.009 | 0.003 | 0.002 | 0.003 | 0.013 | 0.004 |
| 18 | 40H11 (Q18L) | 0.31 | 0.34 | 0.48 | 0.19 | 0.43 | 0.39 | 0.09 | 0.08 | 0.09 | 3.86 | 4.08 | 61.25 | 0.09 |
| 20 | 16C5 (Q20R) | 2.84 | 1.04 | 0.92 | 3.91 | 0.86 | 1.15 | 2.79 | 4.70 | 2.18 | 2.70 | 3.59 | 3.78 | 3.81 |
| 22 | 14C1 (L22I) | 0.12 | 0.52 | 0.39 | 0.30 | 0.33 | 0.29 | 0.20 | 0.15 | 0.20 | 0.06 | 0.09 | 0.12 | 0.20 |
| 27 | 11E 8 (L27V) | 0.25 | 1.64 | 1.48 | 0.40 | 1.53 | 1.44 | 0.47 | 0.52 | 0.61 | 0.03 | 0.04 | 0.09 | 0.40 |
| 54 | 18F8 (F54S) | 0.2 | 0.6 | 1.6 | 0.1 | 1.4 | 1.3 | 0.4 | 0.3 | 0.5 | 0.4 | 0.4 | 0.5 | 0.3 |
| 54 | 29H7 (F54I) | 6.77 | 1.18 | 0.78 | out of range | 1.57 | 0.50 | 5.38 | 17.81 | 3.69 | 8.04 | 6.14 | 9.69 | 12.97 |
| 58 | 30E 4 (V58I) | 0.17 | 0.66 | 0.72 | 0.62 | 0.80 | 0.91 | 0.63 | 0.90 | 0.48 | 0.12 | 0.14 | 0.27 | 0.83 |
| 72 | 04G7 (L72Q) | 4.07 | 1.27 | 0.93 | 7.23 | 1.08 | 1.27 | 5.03 | 7.66 | 3.14 | 6.40 | 7.30 | 6.20 | 6.85 |
| 75 | 28B2 (M75K) | 3.25 | 1.44 | 1.68 | 3.97 | 1.86 | 2.01 | 3.77 | 4.33 | 3.33 | 3.89 | 3.85 | 3.41 | 4.15 |
| 77 | 18C4 (F77T) | 0.86 | 0.48 | 0.74 | 4.98 | 0.96 | 0.81 | 3.37 | 4.84 | 1.81 | 1.32 | 0.56 | 0.91 | 5.04 |
| 77 | 42E 4 (F77C) | 0.07 | 0.30 | 0.65 | 1.89 | 0.77 | 0.46 | 0.50 | 2.18 | 0.34 | 0.02 | 0.02 | 0.08 | 0.63 |
| 77 | 50D12 (F77T) | 0.87 | 0.50 | 0.76 | 4.89 | 0.99 | 0.85 | 3.45 | 4.92 | 1.86 | 1.30 | 0.55 | 0.88 | 5.14 |
| 89 | 35D11 (K89E) | 2.17 | 0.60 | 0.88 | 3.39 | 0.97 | 1.02 | 2.28 | 3.65 | 2.09 | 3.17 | 2.95 | 2.56 | 3.01 |
| 90 | 10F2 (I90T) | 1.68 | 0.37 | 0.51 | 2.60 | 0.72 | 0.62 | 2.08 | 4.64 | 1.35 | 2.99 | 1.93 | 4.51 | 3.57 |
| 92 | 04A12 (L92H) | 0.59 | 0.03 | 0.24 | 5.44 | 0.23 | 0.11 | 1.86 | 3.25 | 0.88 | 8.81 | 23.30 | 22.13 | 3.53 |
| 109 | 43F9 (Y109F) | 0.25 | 0.20 | 0.65 | 0.11 | 0.73 | 0.64 | 0.64 | 0.71 | 0.44 | 13.07 | 4.80 | 1.20 | 0.85 |
| 127 | 30D6 (V127A) | 0.22 | 0.40 | 0.46 | 0.15 | 0.48 | 0.52 | 0.65 | 0.75 | 0.62 | 0.50 | 0.55 | 0.53 | 0.66 |
| 139 | 27B8 (D139G) | 0.00 | 0.02 | 0.11 | 0.01 | 0.10 | 0.09 | 0.02 | 0.01 | 0.02 | 0.01 | 0.01 | 0.04 | 0.01 |
| 164 | 25A1 (C164S) | 2.10 | 1.30 | 1.12 | 1.71 | 1.28 | 1.30 | 2.30 | 2.26 | 2.11 | 3.14 | 5.76 | 1.96 | 2.66 |
| 14-89 | 25F2 (A14V,K89E) | 1.93 | 0.53 | 0.73 | 2.80 | 0.98 | 1.00 | 2.15 | 3.78 | 1.88 | 3.07 | 2.32 | 2.94 | 3.01 |
| 27-33 | 47D8(**L27M,K33N**) | 0.38 | 1.26 | 1.37 | 0.46 | 1.73 | 1.79 | 1.27 | 0.92 | 1.46 | 0.16 | 0.21 | 0.25 | 1.02 |
| 49-72 | 26F1 (E49K,**L72Q**) | 4.26 | 1.22 | 0.91 | 7.26 | 1.10 | 1.26 | 5.21 | 7.70 | 3.23 | 6.66 | 7.28 | 6.41 | 6.91 |
| 54-66 | 48G3 (**F54I**, S66T) | 10.93 | 1.88 | 1.21 | out of range | 2.46 | 0.76 | 8.62 | 28.26 | 5.88 | 9.90 | 7.53 | 11.93 | 20.94 |
| 54-67 | 35B8 (**F54S**,G67S) | 0.19 | 0.59 | 1.64 | 0.10 | 1.44 | 1.30 | 0.47 | 0.30 | 0.58 | 0.43 | 0.51 | 0.47 | 0.32 |
| 55-117 | 05H8 (D55G,I117F) | 0.17 | 0.37 | 0.49 | 0.08 | 0.51 | 0.54 | 0.15 | 0.09 | 0.19 | 0.12 | 0.10 | 0.13 | 0.10 |
| 56-93 | 46A11(I56V,H93R) | 0.21 | 0.45 | 0.99 | 0.12 | 0.97 | 0.80 | 0.26 | 0.13 | 0.14 | 0.09 | 0.06 | 0.15 | 0.18 |
| 68-75 | 04E 2 (**F68S,M75K**) | 2.80 | 1.14 | 1.27 | 4.47 | 1.50 | 1.62 | 3.71 | 4.35 | 3.04 | 3.91 | 3.46 | 2.89 | 4.20 |
| 77-126 | 27B9 (**F77T**,T126R) | 0.55 | 0.26 | 0.54 | 3.68 | 0.67 | 0.59 | 1.91 | 2.34 | 1.06 | 0.67 | 0.32 | 0.49 | 2.58 |
| 77-39 | 33E 2 (**F77T**,T39I) | 0.70 | 0.35 | 0.51 | 4.35 | 0.67 | 0.53 | 2.39 | 4.01 | 1.20 | 1.12 | 0.50 | 0.67 | 3.74 |
| 89-148 | 50 E7 (**K89E**, S148T) | 2.62 | 0.76 | 1.04 | 3.34 | 1.21 | 1.24 | 2.76 | 4.62 | 2.49 | 2.89 | 2.61 | 2.58 | 3.71 |
| 90-77 | 02D10 (**I90V,F77T**) | 1.55 | 0.60 | 0.82 | 13.12 | 1.08 | 0.84 | 6.71 | 30.62 | 1.77 | 8.13 | 4.09 | 12.85 | 20.94 |
| 106-164 | 17E 6 (M106K,**C164S**) | 1.65 | 1.06 | 1.11 | 1.32 | 1.27 | 1.29 | 1.98 | 1.77 | 1.82 | 2.58 | 4.79 | 1.60 | 2.16 |
| 23-58-169 | 47G12 (E23K,V58L,A169V) | 0.05 | 0.42 | 0.46 | 1.16 | 0.62 | 0.79 | 0.84 | 1.54 | 0.30 | 0.02 | 0.03 | 0.12 | 1.32 |
| 33-76-89 | 17C5 (**K33N**,I76N,**K89E**) | 1.11 | 0.59 | 1.48 | 0.93 | 1.89 | 1.79 | 1.30 | 1.13 | 1.56 | 0.74 | 0.32 | 0.65 | 0.99 |
| 68-90-145 | 04D10 (**F68S,I90V**,P145L) | 3.91 | 1.33 | 1.45 | 5.59 | 1.74 | 1.99 | 6.12 | 8.68 | 4.09 | 3.86 | 3.64 | 6.08 | 8.66 |
| 59-109-113-136 | 41H10 (I59T, **Y109F**, P113T, L136M) | 0.06 | 0.07 | 0.24 | 0.03 | 0.26 | 0.20 | 0.25 | 0.30 | 0.16 | 5.44 | 2.21 | 0.43 | 0.36 |

FIG. 6C

| POSITION | Clone(AA sequence) | coel. | h,h | PBI-3945 |
|---|---|---|---|---|
| 15 | 03F2 (G15R) | 0.002 | 0.010 | 0.024 |
| 18 | 40H11 (Q18L) | 0.38 | 0.53 | 0.39 |
| 20 | 16C5 (Q20R) | **2.58** | 0.82 | 0.80 |
| 22 | 14C1 (L22I) | 0.12 | 0.33 | 0.44 |
| 27 | 11E 8 (L27V) | 0.21 | 1.20 | **1.30** |
| 54 | 18F8 (F54S) | 0.59 | 0.25 | 0.03 |
| 54 | 29H7 (F54I) | **6.20** | 0.65 | 1.29 |
| 58 | 30E 4 (V58I) | 0.18 | 0.69 | 0.77 |
| 72 | 04G7 (L72Q) | **4.19** | 1.01 | **1.49** |
| 75 | 28B2 (M 75K) | **4.11** | **2.21** | **2.06** |
| 77 | 18C4 (F77T) | 0.93 | 0.74 | 0.33 |
| 77 | 42E 4 (F77C) | 0.08 | 0.75 | 0.28 |
| 77 | 50D12 (F77T) | 0.81 | 0.64 | 0.29 |
| 89 | 35D11 (K89E) | **2.18** | 0.88 | 0.61 |
| 90 | 10F2 (I90T) | **1.45** | 0.38 | 0.32 |
| 92 | 04A12 (L92H) | 0.62 | 0.27 | 0.03 |
| 109 | 43F9 (Y109F) | 0.22 | 0.54 | 0.07 |
| 127 | 30D6 (V127A) | 0.11 | 0.22 | 0.19 |
| 139 | 27B8 (D139G) | 0.00 | 0.08 | 0.01 |
| 164 | 25A1 (C164S) | 0.56 | 0.61 | 0.63 |
| 14-89 | 25F2 (A14V,K89E) | **1.91** | 0.66 | 0.49 |
| 27-33 | 47D8(L27M ,K33N ) | 0.40 | 1.24 | 1.12 |
| 49-72 | 26F1 (E49K,L72Q) | 1.17 | 1.08 | 1.14 |
| 54-66 | 48G3 (F54I, S66T) | **6.17** | 0.66 | **1.31** |
| 54-67 | 35B8 (F54S,G67S) | 0.13 | 0.99 | 0.24 |
| 55-117 | 05H8 (D55G,I117F) | 0.11 | 0.30 | 0.30 |
| 56-93 | 46A11(I56V,H93R) | 0.15 | 0.64 | 0.26 |
| 68-75 | 04E 2 (F68S,M 75K) | **4.11** | **1.78** | **1.94** |
| 77-126 | 27B9 (F77T,T126R) | 0.49 | 0.47 | 0.13 |
| 77-39 | 33E 2 (F77T,T39I) | 0.58 | 0.44 | 0.20 |
| 89-148 | 50 E7 (K89E, S148T) | **2.06** | 0.85 | 0.59 |
| 90-77 | 02D10 (I90V,F77T) | **1.85** | 1.01 | 0.56 |
| 106-164 | 17E 6 (M 106K,C164S) | **2.16** | **1.30** | **1.35** |
| 23-58-169 | 47G12 (E23K,V58L,A169V) | 0.04 | 0.37 | 0.47 |
| 33-76-89 | 17C5 (K33N ,I76N ,K89E) | **1.31** | **1.75** | 0.60 |
| 68-90-145 | 04D10 (F68S,I90V,P145L) | **3.01** | 1.11 | 1.07 |
| 59-109-113-136 | 41H10 (I59T, Y109F, P113T, L136M ) | 0.05 | 0.20 | 0.02 |

FIG. 6D

| Clone | 18 | 20 | 54 | 59 | 72 | 77 | 89 | 92 | 109 | 113 | 127 | 136 | 164 |
|---|---|---|---|---|---|---|---|---|---|---|---|---|---|
| QC#1 (Q20R, L92H, F77C) | | X | | | | X | | X | | | | | |
| QC#3 (F77C) | | | | | | X | | | | | | | |
| QC#5 (L92H) | | | | | | | | X | | | | | |
| QC#6 (F54I, F77C) | | | X | | | X | | | | | | | |
| QC#7 (Q20R, F54I, F77C) | | X | X | | | X | | | | | | | |
| QC#8 (Q20R, F54I) | | X | X | | | | | | | | | | |
| QC#9 (F54I, F77C, L92H) | | | X | | | X | | X | | | | | |
| QC#10 (Q20R, F54I, F77C, L92H) | | X | X | | | X | | X | | | | | |
| QC#13 (Q20R, Y109F) | | X | | | | | | | X | | | | |
| QC#14 (L92H, Y109F) | | | | | | | | X | X | | | | |
| QC#15 (Y109F) | | | | | | | | | X | | | | |
| QC#16 (F54I, L92H, Y109F) | | | X | | | | | X | X | | | | |
| QC#20 (F54I, Y109F) | | | X | | | | | | X | | | | |
| QC#22 (Q18L, L92H, Y109F) | X | | | | | | | X | X | | | | |
| QC#27 (Q18L, F54I, L92H, Y109F) | X | | X | | | | | X | X | | | | |
| QC#32 (Q18L, I59T, L92H, Y109F, P113T, V127A, K136M) | X | | | X | | | | X | X | X | X | X | |
| QC#36 (Q20R,F54I, L72Q, K89E, C164S) | | X | X | | X | | X | | | | | | X |
| QC#37 (F54I, L72Q, K89E, C164S) | | | X | | X | | X | | | | | | X |
| QC#38 (F54I, C164S) | | | X | | | | | | | | | | X |
| QC #1 C2 (Q18L, Y109F) | X | | | | | | | | X | | | | |
| QC #1 B4 (Q18L, F54I) | X | | X | | | | | | | | | | |
| QC #1 C3 (Q18L, F54I, Y109F) | X | | X | | | | | | X | | | | |
| QC#1 A7 (F54I, K89E, C164S) | | | X | | | | X | | | | | | X |
| QC#1 A11 (Q20R, F54I, L72Q, K89E) | | X | X | | X | | X | | | | | | |
| QC#1 B9 Q20R,F54I, L72Q, C164S) | | X | X | | X | | | | | | | | X |
| QC#1 D11 (F54I, L72Q,K89E,C164S) | | | X | | X | | X | | | | | | X |

FIG. 7

| Sample | coelenterazine | h | h,h | PBI-3840 | PBI-3925 | PBI-3912 |
|---|---|---|---|---|---|---|
| QC#1 (Q20R, L92H, F77C) | 0.17 | 0.03 | 0.19 | 0.74 | 1.03 | 0.56 |
| QC#3 (F77C) | 0.09 | 0.36 | 0.89 | 0.16 | 1.06 | 0.04 |
| QC#5 (L92H) | 0.73 | 0.04 | 0.38 | **4.49** | **6.92** | **5.64** |
| QC#6 (F54I, F77C) | 0.85 | 0.59 | 0.91 | **1.89** | **3.80** | 0.41 |
| QC#7 (Q20R, F54I, F77C) | 0.72 | 0.22 | 0.20 | **1.85** | **2.83** | **1.50** |
| QC#8 (Q20R, F54I) | **6.48** | 0.89 | 0.34 | **11.73** | **21.51** | **35.04** |
| QC#9 (F54I, F77C, L92H) | 0.39 | 0.07 | 0.16 | 0.81 | **1.58** | 0.64 |
| QC#10 (Q20R, F54I, F77C, L92H) | 0.27 | 0.05 | 0.07 | 0.75 | **2.24** | **1.53** |
| QC#13 (Q20R, Y109F) | 0.21 | 0.07 | 0.25 | 1.08 | **1.74** | **4.18** |
| QC#14 (L92H, Y109F) | 0.06 | 0.00 | 0.08 | 0.78 | **1.84** | **2.63** |
| QC#15 (Y109F) | 0.21 | 0.15 | 0.54 | 0.95 | 0.68 | 0.46 |
| QC#16 (F54I, L92H, Y109F) | 0.35 | 0.02 | 0.05 | 1.01 | **3.73** | **8.75** |
| QC#20 (F54I, Y109F) | **4.49** | 0.82 | 0.51 | **9.41** | **12.43** | **10.39** |
| QC#22 (Q18L, L92H, Y109F) | 0.05 | 0.01 | 0.05 | 0.15 | 0.06 | 0.14 |
| QC#27 (Q18L, F54I, L92H, Y109F) | 0.08 | 0.01 | 0.10 | 0.68 | 0.59 | 1.06 |
| QC#32 (Q18L, I59T, L92H, Y109F, P113T, V127A, K136M) | 0.003 | 0.001 | 0.007 | 0.022 | 0.015 | 0.020 |
| QC#36 (Q20R,F54I, L72Q, K89E, C164S) | 0.99 | 0.14 | 0.06 | **1.34** | **1.86** | **16.93** |
| QC#37 (F54I, L72Q, K89E, C164S) | **2.01** | 0.30 | 0.14 | **3.16** | **4.63** | **23.45** |
| QC#38 (F54I, C164S) | **3.39** | 0.65 | 0.48 | **5.25** | **4.56** | **9.48** |
| C1A4E | 1.00 | 1.00 | 1.00 | 1.00 | 1.00 | 1.00 |

FIG. 8A

| Sample | Coel. | h | h,h | 2-me | PBI-3889 | PBI-3939 | PBI-3933 | PBI-3932 | PBI-3946 | PBI-3841 | PBI-3896 | PBI-3925 |
|---|---|---|---|---|---|---|---|---|---|---|---|---|
| **QC#1 (Q20R, L92H, F77C)** | 0.13 | 0.02 | 0.11 | **1.62** | 0.15 | 0.12 | 0.45 | **3.87** | 0.18 | 0.25 | 0.17 | 0.58 |
| **QC#3 (F77C)** | 0.07 | 0.25 | 0.55 | 1.14 | 0.63 | 0.38 | 0.41 | **1.79** | 0.28 | 0.04 | 0.04 | 0.55 |
| **QC#5 (L92H)** | 0.51 | 0.03 | 0.24 | **4.99** | 0.23 | 0.10 | **1.68** | **2.88** | 0.80 | **25.89** | **23.26** | **3.28** |
| **QC#6 (F54I, F77C)** | 0.69 | 0.48 | 0.67 | **22.92** | 0.31 | 0.07 | 0.51 | **35.10** | 0.44 | 0.08 | 0.15 | **2.55** |
| **QC#7 (Q20R, F54I, F77C)** | 0.54 | 0.18 | 0.15 | **22.57** | 0.09 | 0.03 | 0.39 | **32.08** | 0.21 | 0.39 | 0.41 | **2.24** |
| **QC#8 (Q20R, F54I)** | **5.32** | 0.79 | 0.28 | **28.12** | 0.49 | 0.11 | **2.80** | **40.88** | **1.43** | **26.40** | **43.55** | **17.18** |
| **QC#9 (F54I, F77C, L92H)** | 0.26 | 0.05 | 0.10 | **3.69** | 0.13 | 0.09 | 0.55 | **5.63** | 0.22 | 0.21 | 0.23 | 1.03 |
| **QC#10 (Q20R, F54I, F77C, L92H)** | 0.20 | 0.03 | 0.05 | **5.91** | 0.07 | 0.05 | 0.45 | **11.18** | 0.19 | 0.54 | 0.45 | **1.58** |
| **QC#13 (Q20R, Y109F)** | 0.26 | 0.10 | 0.31 | 1.05 | 0.37 | 0.29 | 0.66 | **3.37** | 0.25 | **19.06** | **74.46** | **1.82** |
| **QC#14 (L92H, Y109F)** | 0.10 | 0.003 | 0.11 | 1.18 | 0.11 | 0.06 | 0.52 | **2.24** | 0.07 | **13.47** | **65.50** | **1.64** |
| **QC#15 (Y109F)** | 0.29 | 0.22 | 0.74 | 0.38 | 0.83 | 0.69 | 0.68 | 0.74 | 0.47 | **6.43** | **1.61** | 0.89 |
| **QC#16 (F54I, L92H, Y109F)** | 0.44 | 0.02 | 0.06 | **6.00** | 0.11 | 0.06 | 0.46 | **9.48** | 0.03 | **5.53** | **269.14** | **3.50** |
| **QC#20 (F54I, Y109F)** | **4.22** | 0.90 | 0.50 | **5.86** | 1.19 | 0.61 | **3.68** | **14.10** | **1.82** | **44.89** | **15.18** | **12.45** |
| **QC#22 (Q18L, L92H, Y109F)** | 0.06 | 0.01 | 0.06 | 0.06 | 0.06 | 0.05 | 0.05 | 0.03 | 0.01 | **14.10** | **242.95** | 0.04 |
| **QC#27 (Q18L, F54I, L92H, Y109F)** | 0.13 | 0.02 | 0.12 | 0.33 | 0.15 | 0.12 | 0.30 | 0.24 | 0.10 | 0.60 | **561.32** | 0.40 |
| **QC#32 (Q18L, I59T, L92H, Y109F, P113T, V127A, K136M)** | 0.004 | 0.001 | 0.011 | 0.01 | 0.01 | 0.01 | 0.01 | 0.01 | 0.00 | **16.29** | **51.72** | 0.02 |
| **QC#36 (Q20R,F54I, L72Q, K89E, C164S)** | 0.78 | 0.14 | 0.07 | **23.49** | 0.02 | 0.002 | 0.09 | **28.30** | 0.06 | **64.90** | **49.30** | **2.04** |
| **QC#37 (F54I, L72Q, K89E, C164S)** | **1.87** | 0.32 | 0.17 | **26.86** | 0.08 | 0.01 | 0.32 | **33.42** | 0.22 | **71.56** | **37.60** | **5.30** |
| **QC#38 (F54I, C164S)** | **4.51** | 0.92 | 0.67 | **11.22** | 0.49 | 0.06 | 1.15 | **12.46** | 1.13 | **22.07** | **11.03** | **6.46** |
| **C1A4E** | 1.00 | 1.00 | 1.00 | 1.00 | 1.00 | 1.00 | 1.00 | 1.00 | 1.00 | 1.00 | 1.00 | 1.00 |

FIG. 8B

| Sample | Coel | h,h | PBI-3939 | PBI-3945 | PBI-3840 | PBI-3932 | PBI-3925 | PBI-9894 | PBI-3896 |
|---|---|---|---|---|---|---|---|---|---|
| QC C2 (Q18L, Y109F) | 0.01 | 0.06 | 0.04 | 0.04 | 0.03 | 0.01 | 0.01 | 19.87 | 24.80 |
| QC B4 (Q18L, F54I) | 5.71 | 1.84 | 1.23 | 1.19 | 6.04 | 8.23 | 7.02 | 67.35 | 719.58 |
| QC C3 (Q18L, F54I, Y109F) | 0.18 | 0.52 | 0.65 | 0.22 | 0.49 | 0.13 | 0.46 | 407.08 | 454.48 |
| QC E6 (Q18L, I59T, Y109F, P113T, V127A, K136M) | 0.0004 | 0.01 | 0.01 | 0.002 | 0.01 | 0.01 | 0.00 | 3.88 | 9.03 |
| QC A7 (F54I, K89E, C164S) | 2.63 | 0.21 | 0.01 | 0.28 | 4.05 | 17.21 | 4.86 | 11.82 | 23.95 |
| QC A11 (Q20R, F54I, L72Q, K89E) | 3.76 | 0.13 | 0.02 | 0.31 | 3.21 | 94.34 | 15.76 | 46.29 | 127.88 |
| QC B9 Q20R, F54I, L72Q, C164S) | 1.67 | 0.10 | 0.005 | 0.10 | 1.89 | 25.28 | 3.37 | 13.58 | 42.27 |
| QC D11 (F54I, L72Q, K89E, C164S | 1.95 | 0.13 | 0.01 | 0.16 | 2.45 | 27.69 | 4.84 | 13.38 | 33.69 |
| QC#6 (F54I, F77C) | 0.67 | 0.76 | 0.06 | 0.36 | 1.24 | 39.37 | 3.14 | 0.52 | 1.32 |
| QC# 7 (Q20R, F54I, F77C0 | 0.51 | 0.15 | 0.03 | 0.07 | 1.01 | 32.09 | 2.26 | 1.67 | 1.30 |
| QC#9 (F54I, F77C, L92H) | 0.22 | 0.10 | 0.09 | 0.06 | 0.33 | 4.97 | 1.01 | 0.26 | 0.32 |
| QC #8 (Q20R, F54I) | 6.37 | 0.35 | 0.14 | 0.93 | 8.42 | 46.87 | 21.22 | 13.40 | 33.57 |
| QC# 13 (Q20R, Y109F) | 0.18 | 0.26 | 0.25 | 0.02 | 0.79 | 2.54 | 1.58 | 6.85 | 49.23 |
| QC#14 (L92H, Y109F) | 0.04 | 0.07 | 0.04 | 0.001 | 0.29 | 1.35 | 1.43 | 4.53 | 37.03 |
| QC#16 (F54I, L92H, Y109F) | 0.30 | 0.05 | 0.05 | 0.01 | 0.46 | 7.07 | 3.42 | 19.64 | 157.70 |
| QC# 20 (F54I, Y109F) | 4.25 | 0.56 | 0.62 | 1.04 | 6.93 | 13.08 | 11.84 | 8.73 | 10.47 |
| QC#22 (Q18L, L92H, Y109F) | 0.04 | 0.05 | 0.04 | 0.01 | 0.09 | 0.03 | 0.05 | 38.41 | 138.45 |
| QC#27 (Q18L, F54I, L92H, Y109F) | 0.07 | 0.08 | 0.10 | 0.01 | 0.28 | 0.17 | 0.42 | 392.98 | 283.85 |
| QC#32 (Q18L, I59T, L92H, Y109F, P113T, V127A, K136M) | 0.003 | 0.01 | 0.01 | 0.0002 | 0.02 | 0.01 | 0.02 | 11.79 | 33.46 |
| QC#36 (Q20R, F54I, L72Q, K89E, C164S) | 0.92 | 0.06 | 0.002 | 0.05 | 1.07 | 24.56 | 2.12 | 10.40 | 35.04 |

FIG. 9

| Clone | 18 | 20 | 54 | 71 | 77 | 90 | 92 | 109 | 127 |
|---|---|---|---|---|---|---|---|---|---|
| QC#2 1 (Q20R,F77C,I90V,L92H,V127A) | | x | | | x | x | x | | x |
| QC#2 2 (Q20R,G71D,F77C,I90V,L92H,V127A) | | x | | x | x | x | x | | x |
| QC#2 3 (Q20R,G71D,F77C,L92H,V127A) | | x | | x | x | | x | | x |
| QC#2 6 (F54I,G71D,F77C,L92H,V127A) | | | x | x | x | | x | | x |
| QC#2 7 (F54I,G71D,F77C,I90V,L92H) | | | x | x | x | x | x | | |
| QC#2 8 (F54I,G71D,F77C,I90V,L92H,V127A) | | | x | x | x | x | x | | x |
| QC#2 11 (Q20R,F54I,G71D,F77C,I90V,L92H,V127A) | | x | x | x | x | x | x | | x |
| QC#2 16 (G71D,I90V,L92H,Y109F,L127A) | | | | x | | x | x | x | x |
| QC#2 18 (G71D,L92H,Y109F,L127A) | | | | x | | | x | x | x |
| QC#2 21(Q20R,F54I,G71D,F77C,I90V,L92H,V127A) | | x | x | x | x | x | x | | x |
| QC#2 26 (Q18L,G71D,F77Y,I90V,L92H,Y109F,V127A) | x | | | x | x | x | x | x | x |
| QC#2 31 (Q18L,F54I,G71D,F77Y,I90V,L92H,Y109F,V127A) | x | | x | x | x | x | x | x | x |
| QC#2 41 (G71D,F77C,I90V,L92H,V127A) | | | | x | x | x | x | | x |
| QC#2 44 (G71D,F77C,I90V,V127A) | | | | x | x | x | | | x |
| QC#2 A3 (Q20R,G71D,F77C,L92H) | | x | | x | x | | x | | |
| QC#2 C6 (F54I,G71D,F77C,L92H) | | | x | x | x | | x | | |
| QC#2 A7 (Q20R,F54I,G71D,F77C,L92H,V127A) | | x | x | x | x | | x | | x |
| QC#2 C10 (I90V,L92H,Y109F,V127A) | | | | | | x | x | x | x |
| QC#2 E1 (F54I,I90V,L92H,Y109F,V127A) | | | x | | | x | x | x | x |
| QC#2 E2 (F54I,G71D,I90V,L92H,Y109F) | | | x | x | | x | x | x | |
| QC#2 E4 (Q18L,G71D,F77Y,L92H,Y109F,V127A) | x | | | x | x | | x | x | x |
| QC#2 F4(Q18L,F77Y,I90V,L92H,Y109F,V127A) | x | | | | x | x | x | x | x |
| QC#2 E7 (Q18L,F54I,F77Y,I90V,L92H,Y109F,V127A) | x | | x | | x | x | x | x | x |
| QC#2 E8 (Q18L,F54I,I90V,L92H,Y109F,V127A) | x | | x | | | x | x | x | x |
| QC#2 F7 (Q18L,F54I,G71D,F77Y,L92H,Y109F,V127A) | x | | x | x | x | | x | x | x |
| QC#2 H11 (G71D,F77C) | | | | x | x | | | | |
| LE1 (I90V/L92H) | | | | | | x | x | | |
| LE2 (I90V,Y109F) | | | | | | x | | x | |
| LE3 (I90V/L92H/Y109F) | | | | | | x | x | x | |

FIG. 10

| Sample | Coel | h,h | PBI-3939 | PBI-3945 | PBI-3840 | PBI-3932 | PBI-3925 | PBI-3894 | PBI-3896 |
|---|---|---|---|---|---|---|---|---|---|
| QC#2 1 (Q20R,F77C,I90V,L92H,V127A) | 0.04 | 0.04 | 0.05 | 0.004 | 0.17 | ***4.04*** | 0.62 | 0.19 | 0.13 |
| QC#2 2 (Q20R,G71D,F77C,I90V,L92H,V127A) | 0.07 | 0.05 | 0.07 | 0.01 | 0.24 | ***6.19*** | 0.98 | 0.26 | 0.20 |
| QC#2 3 (Q20R,G71D,F77C,L92H,V127A) | 0.09 | 0.07 | 0.09 | 0.01 | 0.30 | ***5.02*** | 0.88 | 0.34 | 0.21 |
| QC#2 6 (F54I,G71D,F77C,L92H,V127A | 0.11 | 0.07 | 0.08 | 0.03 | 0.19 | ***2.43*** | 0.51 | 0.15 | 0.11 |
| QC#2 7 (F54I,G71D,F77C,I90V,L92H) | 0.40 | 0.11 | 0.12 | 0.09 | 0.39 | ***13.65*** | ***2.15*** | 0.38 | 0.41 |
| QC#2 8 (F54I,G71D,F77C,I90V,L92H,V127A) | 0.11 | 0.06 | 0.08 | 0.03 | 0.16 | ***4.12*** | 0.68 | 0.15 | 0.18 |
| QC#2 11 (Q20R,F54I,G71D,F77C,I90V,L92H,V127A) | 0.10 | 0.03 | 0.05 | 0.02 | 0.17 | ***6.66*** | 1.11 | 0.40 | 0.24 |
| QC#2 16 (G71D,I90V,L92H,Y109F,L127A,) | 0.11 | 0.06 | 0.04 | 0.001 | 0.29 | ***1.49*** | ***1.51*** | ***7.72*** | ***55.11*** |
| QC#2 18 (G71D,L92H,Y109F,L127A) | 0.08 | 0.04 | 0.03 | 0.0005 | 0.28 | ***1.33*** | 1.29 | ***7.30*** | ***48.97*** |
| QC#2 21(Q20R,F54I,G71D,F77C,I90V,L92H,V127A) | 0.27 | 0.02 | 0.02 | 0.004 | 0.31 | ***7.57*** | ***2.49*** | ***30.02*** | ***160.54*** |
| QC#2 26 (Q18L,G71D,F77Y,I90V,L92H,Y109F,V127A) | 0.00 | 0.01 | 0.01 | 0.001 | 0.00 | 0.01 | 0.02 | ***1.38*** | ***7.86*** |
| QC#2 31 (Q18L,F54I,G71D,F77Y,I90V,L92H,Y109F,V127A) | 0.01 | 0.03 | 0.03 | 0.004 | 0.01 | 0.05 | 0.06 | ***8.04*** | ***77.32*** |
| QC#2 41 (G71D,F77C,I90V,L92H,V127A) | 0.05 | 0.07 | 0.08 | 0.01 | 0.12 | ***2.50*** | 0.37 | 0.10 | 0.07 |
| QC#2 44 (G71D,F77C,I90V,V127A) | 0.17 | 0.15 | 0.15 | 0.03 | 0.15 | ***2.92*** | 0.41 | 0.18 | 0.10 |
| QC#2 A3 (Q20R,G71D,F77C,L92H) | 0.23 | 0.20 | 0.22 | 0.03 | 0.52 | ***6.75*** | 1.11 | 0.39 | 0.24 |
| QC#2 C6 (F54I,G71D,F77C,L92H) | 0.44 | 0.18 | 0.18 | 0.13 | 0.60 | ***12.27*** | ***2.43*** | 0.50 | 0.30 |
| QC#2 A7 (Q20R,F54I,G71D,F77C,L92H,V127A) | 0.13 | 0.05 | 0.06 | 0.02 | 0.28 | ***6.93*** | 1.25 | 0.32 | 0.22 |
| QC#2 C10 (I90V,L92H,Y109F,V127A) | 0.06 | 0.04 | 0.02 | 0.0004 | 0.22 | 1.08 | 1.05 | ***4.33*** | ***34.52*** |
| QC#2 E1 (F54I,I90V,L92H,Y109F,V127A) | 0.18 | 0.04 | 0.03 | 0.004 | 0.25 | ***2.74*** | ***1.66*** | ***6.96*** | ***49.09*** |
| QC#1 E2 (F54I,G71D,I90V,L92H,Y109F) | 0.39 | 0.06 | 0.04 | 0.01 | 0.24 | ***9.71*** | ***3.63*** | ***25.77*** | ***185.63*** |
| QC#2 E4 (Q18L,G71D,F77Y,L92H,Y109F,V127A) | 0.0005 | 0.009 | 0.008 | 0.0005 | 0.001 | 0.009 | 0.004 | 0.58 | ***3.48*** |
| QC#2 F4(Q18L,F77Y,I90V,L92H,Y109F,V127A) | 0.0002 | 0.0057 | 0.0062 | 0.0003 | 0.0013 | 0.0069 | 0.0048 | 0.56 | ***4.18*** |
| QC#2 E7 (Q18L,F54I,F77Y,I90V,L92H,Y109F,V127A) | 0.003 | 0.013 | 0.015 | 0.002 | 0.006 | 0.020 | 0.024 | ***3.17*** | ***36.43*** |
| QC#2 E8 (Q18L,F54I,I90V,L92H,Y109F,V127A) | 0.06 | 0.04 | 0.05 | 0.002 | 0.13 | 0.05 | 0.11 | ***145.44*** | ***331.26*** |
| QC#2 F7 (Q18L,F54I,G71D,F77Y,L92H,Y109F,V127A | 0.01 | 0.03 | 0.03 | 0.004 | 0.01 | 0.03 | 0.04 | ***3.22*** | ***30.50*** |
| QC#2 H11 (G71D,F77C) | 0.07 | 0.69 | 0.61 | 0.24 | 0.13 | ***3.46*** | 1.02 | 0.16 | 0.10 |
| C1A4E | 1.00 | 1.00 | 1.00 | 1.00 | 1.00 | 1.00 | 1.00 | 1.00 | 1.00 |

FIG. 11

| Sample | Coel. | hh | PBI-3939 | PBI-3945 | PBI-3889 | PBI-3840 | PBI-3932 | PBI-3925 | PBI-3894 | PBI-3896 | PBI-3897 |
|---|---|---|---|---|---|---|---|---|---|---|---|
| C1A4E | 1 | 1 | 1 | 1 | 1 | 1 | 1 | 1 | 1 | 1 | 1 |
| I90V | **1.49** | 0.77 | 1.21 | 0.51 | 1.12 | **2.86** | **22.13** | **14.69** | **8.48** | **2.30** | **6.43** |
| Y109F | 0.13 | 0.42 | 0.35 | 0.15 | 0.42 | 0.58 | 0.37 | 0.41 | 1.05 | 0.35 | **12.70** |
| LE2 (I90V,Y109F) | 0.31 | 0.29 | 0.26 | 0.06 | 0.33 | **1.80** | **10.20** | **6.09** | **5.15** | **3.04** | **60.24** |
| QC #27(Q18L/L92H/Y109F/F54I) | 0.15 | 0.06 | 0.08 | 0.01 | 0.06 | 0.23 | 0.12 | 0.20 | **196.86** | **140.68** | **13.83** |
| QC#2 E7 (Q18L,F54I,F77Y,I90V,L92H,Y109F,V127A) | 0.002 | 0.02 | 0.02 | 0.0022 | 0.0076 | 0.0054 | 0.02 | 0.02 | **1.83** | **6.57** | **31.17** |
| QC#2 F4(Q18L,F77Y,I90V,L92H,Y109F,V127A) | 0.0008 | 0.005 | 0.0046 | 0.0004 | 0.0021 | 0.0021 | 0.01 | 0.05 | 0.24 | 0.80 | **7.04** |
| QC#1 A11 (Q20R, F54I, L72Q, K89E) | **3.50** | 0.12 | 0.02 | 0.16 | 0.08 | **3.51** | **82.84** | **11.19** | **59.12** | **24.00** | **42.51** |

FIG. 12

| Sample | POSITION | Sequence | COELENTERAZINE | H,H | PBI-3897 | PBI-3896 | PBI-3894 |
|---|---|---|---|---|---|---|---|
| 29H3 | 18 | L18I | 1.17 | 0.32 | 0.94 | **2.37** | **3.25** |
| 25A11 | 21 | V21L | 0.06 | 0.11 | 0.53 | 0.55 | 0.19 |
| 4F3 | 67 | G67S | **1.75** | 0.63 | **1.37** | 1.24 | 1.06 |
| 24B12 | 68 | F68Y | **1.88** | 0.88 | **1.52** | **1.62** | **1.44** |
| 29C4 | 72 | L72Q | **1.69** | 0.77 | **1.37** | **2.33** | **2.38** |
| 3H11 | 75 | M75K | **2.33** | 1.09 | **1.90** | **2.19** | **1.90** |
| 3F10 | 76 | I76F | 0.50 | 0.81 | 1.27 | 0.17 | 0.08 |
| 27E 4 | 90 | I90T | 0.24 | 0.17 | 0.76 | 0.10 | 0.04 |
| 1B6 | 92 | H92R | 0.10 | 0.46 | 0.98 | 0.06 | 0.02 |
| 47H12 | 22-74 | L22F-E74K | 0.03 | 0.12 | 0.29 | 0.02 | 0.03 |
| 11F10 | 158-1 | F1I,V158I | **2.49** | **2.53** | **2.37** | **1.67** | **1.40** |
| 48D5 | 11-109 | R11Q,F109Y | **6.24** | **2.74** | 0.39 | 1.04 | 0.17 |
| 18A8 | 18-98 | **L18I,** V98F | 0.64 | 0.19 | 0.54 | 1.25 | **1.56** |
| 43G9 | 21-106 | **V21M,M106I** | 0.02 | 0.04 | 0.05 | 0.23 | 0.49 |
| 33A5 | 31-102 | F31I,**V102M** | 0.73 | 0.68 | 0.67 | 1.06 | 1.16 |
| 11G9 | 32-92 | Q32H,**H92R** | 0.10 | 0.47 | 1.02 | 0.06 | 0.01 |
| 9D7 | 45-76 | V45E,**I76V** | **1.66** | 0.71 | **1.33** | **1.72** | **1.80** |
| 33H2 | 92-159 | **H92R,**T159S | 0.05 | 0.37 | 0.58 | 0.04 | 0.01 |
| 1G5 | 92-170 | **H92R**,G170R | 0.58 | **N/A** | **1.50** | 0.16 | 0.31 |
| 19C10 | 18-49-86 | **L18Q**,E49D,H86R | **3.29** | 0.15 | 0.52 | 0.05 | 0.05 |
| 44H1 | 21-47-51 | **V21M,** S47P, G51E | 0.01 | 0.02 | 0.02 | 0.10 | 0.22 |
| 14C2 | 46-106-168 | L46Q, **M106I**, L168F | **1.77** | 0.97 | **1.52** | **1.51** | **1.33** |
| 24D7 | 48-99-76 | G48R,**I99V,I76F** | 0.38 | 0.63 | 1.04 | 0.10 | 0.05 |
| 18E 8 | 55-92-96 | D55E,**H92Q**,T96A | **1.40** | **3.78** | **2.41** | 0.39 | 0.36 |
| 7D9 | 74-92-99 | E74I,**H92R,I99T** | 0.14 | 0.36 | 0.77 | 0.04 | 0.01 |
| 8C2 | 21-68-69-142 | **V21M,F68L**,Q69H,L142V | 0.01 | 0.02 | 0.02 | 0.11 | 0.22 |
| QC #27 HT7 | | | 1.00 | 1.00 | 1.00 | 1.00 | 1.00 |

| Positions in common with C1A4E library |
|---|
| 18 |
| 22 |
| 68 |
| 72 |
| 75 |
| 90 |
| 92 |
| 106 |
| 109 |

FIG. 13

| Sequence | Clone | 21 | 68 | 72 | 75 | 76 | 90 | 92 | 158 |
|---|---|---|---|---|---|---|---|---|---|
| F68Y, L72Q, M75K, V158I | QC27 #1 | | X | X | X | | | | X |
| I90T, H92R | QC27 #2 | | | | | | X | X | |
| F68Y, L72Q, M75K, I90T, H92R, V158I | QC27 #3 | | X | X | X | | X | X | X |
| V21L, I76F, I90T, H92R | QC27 #4 | X | | | | X | X | X | |
| V21L,I76F | QC27 #6A | X | | | | X | | | |
| V21L,F68Y,L72Q,M75K,I90T | QC27 #7A | X | X | X | X | | X | | |
| V21L,I76F,H92R | QC27 #8 | X | | | | X | | X | |
| V21L,F68Y,L72Q,M75K,H92R,V158I | QC27 #9A | X | X | X | X | | | X | X |
| V21L,F68Y,L72Q,M75K,I76F,I90T,H92R,V158I | QC27 #10 | X | X | X | X | X | X | X | X |
| F68Y,L72Q,M75K,H92R | QC27 #12A | | X | X | X | | | X | |
| V21L,H92R | QC27 #13 | X | | | | | | X | |
| F68Y,L72Q,M75K,H92R,V158I | QC27 #14A | | X | X | X | | | X | X |
| V21L, F68Y, L72Q, M75K, I90T, H92R, V158I | QC27 #5 | X | X | X | X | | X | X | X |
| V21L, I90T, I76F | QC27 #6 | X | | | | X | X | | |
| V21L,F68Y,L72Q,M75K, I76F,V158I | QC27 #9B | X | X | X | X | X | | | X |

FIG. 14

| Sample | AA change | Coelenterazine | h,h | PBI-3897 | PBI-3841 | PBI-3896 | PBI-3894 |
|---|---|---|---|---|---|---|---|
| QC27 #1 | F68Y, L72Q, M75K, V158I | **2.59** | **3.95** | **2.90** | **2.90** | **5.19** | **6.72** |
| QC27 #2 | I90T, H92R | 0.0189 | 0.17 | 0.19 | 0.19 | 0.02 | 0.00 |
| QC27 #3 | F68Y, L72Q, M75K, V158I, I90T, H92R | 0.1212 | 0.77 | 0.88 | 0.92 | 0.10 | 0.02 |
| QC27 #4 | V21L, I76F, I90T, H92R | 0.0006 | 0.00 | 0.06 | 0.08 | 0.04 | 0.00 |
| QC27 #6A | V21L,I76F | 0.0060 | 0.07 | 0.26 | 0.20 | 0.12 | 0.03 |
| QC27 #7A | V21L,F68Y,L72Q,M75K,I90T | 0.0370 | 0.40 | **1.76** | **1.54** | 1.09 | 0.16 |
| QC27 #8 | V21L,I76F,H92R | 0.0730 | 0.21 | 0.50 | 0.59 | 0.28 | 0.11 |
| QC27 #9A | V21L,F68Y,L72Q,M75K,H92R,V158I | 0.0041 | 0.08 | 0.81 | **1.35** | 0.32 | 0.03 |
| QC27 #10 | V21L,F68Y,L72Q,M75K,I76F,I90T,H92R,V158I | 0.0049 | 0.01 | 0.33 | 0.48 | 0.20 | 0.02 |
| QC27 #12A | F68Y,L72Q,M75K,H92R | 0.2767 | **2.64** | **2.82** | **3.17** | 0.31 | 0.09 |
| QC27 #13 | V21L,H92R | 0.0007 | 0.01 | 0.12 | 0.20 | 0.05 | 0.00 |
| QC27 #14A | F68Y,L72Q,M75K,H92R,V158I | 0.2283 | **2.38** | **2.51** | **2.71** | 0.26 | 0.07 |
| QC27 #5 | V21L, F68Y, L72Q, M75K, I90T, H92R, V158I | 0.0013 | 0.02 | 0.15 | 0.25 | 0.07 | 0.01 |
| QC27 #6 | V21L, I90T, I76F | 0.0014 | 0.00 | 0.09 | 0.05 | 0.03 | 0.00 |
| QC27 #9B | V21L,F68Y,L72Q,M75K, I76F,V158I | 0.0530 | 0.43 | 1.14 | 1.19 | 0.93 | 0.32 |
| QC27 ctrl. | | 1 | 1 | 1 | 1 | 1 | 1 |

FIG. 15

| Sample | Position | AA change | Coelenterazine | H | HH | PBI-3841 | PBI-3897 |
|---|---|---|---|---|---|---|---|
| 30D12 | 22 | L22F | 0.08 | 0.01 | 0.08 | 0.28 | 0.26 |
| 26D4 | 36 | V36M | **1.70** | **1.40** | **2.19** | 1.21 | 1.08 |
| 40B10 | 76 | I76F | **3.66** | 0.54 | 0.57 | **1.65** | **1.97** |
| 5C3 | 128 | T128A | 0.19 | 0.26 | 0.45 | 0.43 | 0.47 |
| 22C2 | 128-154 | T128S,T154S | 0.24 | 0.33 | 0.52 | 0.43 | 0.46 |
| 22G9 | 135-152 | N135Y,R152H | 0.09 | 0.13 | 0.16 | 0.20 | 0.24 |
| 39H11 | 18-145 | L18I,P145Q | **42.10** | **3.20** | **18.30** | **2.51** | **2.37** |
| 36C11 | 18-99 | L18V,I99T | **125.68** | **2.64** | **24.99** | **2.15** | **2.17** |
| 3E 2 | 67-159 | G67D,T159I | 0.39 | 0.51 | 0.63 | 0.77 | 0.80 |
| 48C5 | 46-51-138 | L46Q,G51R,I138S | 0.43 | 0.49 | 0.96 | 0.87 | 0.95 |
| 3C10 | 51-112-113 | G51V,R112C,P113H | 0.24 | 0.31 | 0.72 | 0.93 | 0.67 |
| QC279a HT | | | 1 | 1 | 1 | 1 | 1 |

FIG. 16

| Sample | Position | AA change | Coelenterazine | h,h | PBI-3939 | PBI-3945 | PBI-3889 | PBI-4002 |
|---|---|---|---|---|---|---|---|---|
| IVY 29H12 | 19 | D19N | 0.002 | 0.03 | 0.04 | 0.15 | 0.03 | 0.11 |
| IVY 47E11 | 20 | Q20P | 0.054 | 1.05 | **1.36** | 1.22 | 1.22 | 1.12 |
| IVY 36E11 | 38 | V38I | 0.169 | 0.96 | 1.26 | 1.18 | 1.23 | 1.09 |
| IVY 21D1 | 44 | I44F | 0.128 | 0.67 | 0.65 | 0.39 | 0.73 | 0.38 |
| IVY 5B8 | 76 | I76N | 0.208 | 0.32 | 0.39 | 0.50 | 0.36 | 0.44 |
| IVY 50G8 | 77 | Y77N | 0.141 | 0.86 | 0.23 | 0.61 | 0.62 | 0.85 |
| IVY 27E6 | 95 | G95S | 0.106 | 0.73 | 0.70 | 0.61 | 0.78 | 0.62 |
| IVY 2G6 | 95 | G95D | 0.004 | 0.07 | 0.07 | 0.33 | 0.06 | 0.30 |
| IVY 27B7 | 110 | F110I | 0.022 | 0.13 | 0.18 | 0.44 | 0.17 | 0.37 |
| IVY 26H7 | 149 | L149I | 0.266 | 0.94 | 0.82 | 0.90 | 0.89 | 0.94 |
| IVY 21A4 | 152 | R152S | 0.242 | 0.78 | 0.83 | 0.63 | 0.99 | 0.60 |
| IVY 5C2 | 38-43 | V38F,K43N | 0.008 | 0.45 | 0.51 | 0.56 | 0.46 | 0.51 |
| IVY 43D3 | 49-32 | E49G,Q32P | 0.170 | 0.93 | 1.23 | 1.15 | 1.20 | 1.07 |
| IVY 20E12 | 60-119 | I60V,V119M | 0.289 | 0.38 | 0.44 | 0.62 | 0.43 | 0.57 |
| IVY 26B6 | 18-69-124 | Q18H,Q69H,K124M | 0.006 | 0.29 | 0.39 | 0.29 | 0.40 | 0.26 |
| IVY 23F3 | 33-43-94 | K33N,K43N,Y94F | 0.004 | 0.24 | 0.25 | 0.34 | 0.21 | 0.34 |
| IVY+HT7 | | | 1.00 | 1.00 | 1.00 | 1.00 | 1.00 | 1.00 |

FIG. 18

| Sample | position | AA | Coel. | H | H,H | PBI-3939 | PBI-3945 | PBI-3889 | PBI-4002 |
|---|---|---|---|---|---|---|---|---|---|
| 34B9 | 18 | Q18L | 0.22 | 0.52 | 0.74 | 0.92 | 0.38 | 1.12 | 0.48 |
| 8E 3 | 27 | L27V | 0.19 | 1.06 | 1.12 | **1.35** | 1.17 | **1.33** | 1.11 |
| 33C4 | 28 | S28Y | 0.07 | 0.83 | 0.80 | 0.78 | 0.88 | 0.83 | 0.80 |
| 21C5 | 33 | K33N | 0.96 | **1.41** | **1.68** | **1.68** | **1.36** | **1.74** | **1.34** |
| 25F10 | 36 | V36E | 0.14 | 0.39 | 0.46 | 0.40 | 0.36 | 0.60 | 0.41 |
| 25H7 | 40 | P40T | 0.003 | 0.13 | 0.27 | 0.47 | 0.28 | 0.46 | 0.23 |
| 28A8 | 135 | N135D | 0.04 | 0.50 | 0.69 | 0.73 | 0.51 | 0.86 | 0.47 |
| 44G12 | 155 | I155T | 0.08 | 0.51 | 0.85 | 0.63 | 0.48 | 0.87 | 0.48 |
| 46A6 | 32-6 | F6Y,Q32L | 0.12 | 0.61 | 0.76 | 0.75 | 0.57 | 0.80 | 0.56 |
| 26D5 | 18-51-86 | Q18L,G51R,H86L | 0.47 | 0.95 | **1.39** | **1.58** | 0.62 | **1.95** | 0.83 |
| 3E 12 | 6-42-50 | F6Y,Q42H,N50K | 0.12 | 0.60 | 0.84 | 1.03 | 0.61 | 1.04 | 0.61 |

FIG. 19

| Sequence | Sample | 19 | 20 | 27 | 32 | 38 | 43 | 49 | 58 | 77 | 95 | 110 | 149 |
|---|---|---|---|---|---|---|---|---|---|---|---|---|---|
| Q20P,Q32P,E49G,L149I | C1.1 | | X | | X | | | X | | | | | X |
| Q20P,Q32P,E49G,F77Y,G95D,F110I,L149I | C4.13 | | X | | X | | | X | | X | X | X | X |
| Q20P,L27V,V38I,L149I | C5.16 | | X | X | | X | | | | | | | X |
| L27V,V38I,L149I | C5.19 | | | X | | X | | | | | | | X |
| D19N,Q20P,V38I,L149I | C7.26 | X | X | | | X | | | | | | | X |
| V38I,G95D,F110I,L149I | C8.28 | | | | | X | | | | | X | X | X |
| D19N,Q20P,V38I,G95D,F110I,L149I | C8.29 | X | X | | | X | | | | | X | X | X |
| L27V,V38F,K43N,L149I | C11.40 | | | X | | X | X | | | | | | X |
| L27V,V38F,K43N,V58I,L149I | C11.42 | | | X | | X | X | | X | | | | X |
| L27V,V38F,K43N,V58I,F110I,L149I | C12.46 | | | X | | X | X | | X | | | X | X |
| Q20P,L27V,L149I | C13.50 | | X | X | | | | | | | | | X |
| Q20P,L27V,V38I,F110I | C14.51 | | X | X | | X | | | | | | X | |
| L27V,V38I,F110I,L149I | C14.52 | | | X | | X | | | | | | X | X |

FIG. 20

| Sample | Sequence | Coelenterazine | H | H,H | PBI-3939 | PBI-3945 | PBI-4002 | PBI-3932 | PBI-3840 |
|---|---|---|---|---|---|---|---|---|---|
| C1.1 | Q20P,Q32P,E49G,L149I | 0.00006 | 0.00026 | 0.00033 | 0.00069 | 0.00050 | 0.00051 | 0.00014 | 0.00008 |
| C4.13 | Q20P,Q32P,E49G,F77Y,G95D,F110I,L149I | 0.00006 | 0.00008 | 0.00009 | 0.00008 | 0.00005 | 0.00006 | 0.00013 | 0.00010 |
| C5.16 | Q20P,L27V,V38I,L149I | 0.0002 | 0.0013 | 0.0003 | 0.0011 | 0.0034 | 0.0036 | 0.0001 | 0.0001 |
| C5.19 | L27V,V38I,L149I | 0.0010 | 0.2747 | 0.0663 | 0.1595 | 0.5082 | 0.5129 | 0.0015 | 0.0003 |
| C7.26 | D19N,Q20P,V38I,L149I | 0.0001 | 0.0017 | 0.0011 | 0.0020 | 0.0032 | 0.0037 | 0.0001 | 0.0000 |
| C8.29 | D19N,Q20P,V38I,G95D,F110I,L149I | 0.000016 | 0.000025 | 0.000036 | 0.000016 | 0.000014 | 0.000031 | 0.000040 | 0.000025 |
| C11.40 | L27V,V38F,K43N,L149I | 0.00010 | 0.01172 | 0.00714 | 0.01853 | 0.04124 | 0.02485 | 0.00036 | 0.00006 |
| C11.42 | L27V,V38F,K43N,V58I,L149I | 0.0001 | 0.0016 | 0.0011 | 0.0044 | 0.0093 | 0.0040 | 0.0001 | 0.0001 |
| C12.46 | L27V,V38F,K43N,V58I,F110I,L149I | 0.00002 | 0.00004 | 0.00005 | 0.00001 | 0.00008 | 0.00006 | 0.00006 | 0.00004 |
| C13.50 | Q20P,L27V,L149I | 0.0001 | 0.0124 | 0.0036 | 0.0027 | 0.0109 | 0.0100 | 0.0001 | 0.0000 |
| C14.51 | Q20P,L27V,V38I,F110I | 0.00003 | 0.00010 | 0.00004 | 0.00001 | 0.00008 | 0.00011 | 0.00003 | 0.00004 |
| C14.52 | L27V,V38I,F110I,L149I | 0.00007 | 0.00041 | 0.00008 | 0.00006 | 0.00034 | 0.00046 | 0.00012 | 0.00008 |
| IVY-HT7 | | 1 | 1 | 1 | 1 | 1 | 1 | 1 | 1 |

FIG. 21

| Sequence | clone | 6 | 18 | 27 | 28 | 33 | 34 | 36 | 40 | 50 | 51 | 135 | 155 |
|---|---|---|---|---|---|---|---|---|---|---|---|---|---|
| F6Y,Q18L,K33N,N135D | C1.1 | X | X | | | X | | | | | | X | |
| F6Y,Q18L,K33N,N135D,I155T | C1.2 | X | X | | | X | | | | | | X | X |
| F6Y,K33N,N135D,I155T | C1.3 | X | | | | X | | | | | | X | X |
| K33N,P40T,N135D,I155T | C2.6 | | | | | X | | | X | | | X | X |
| F6Y,Q18L,K33N,P40T,N135D,I155T | C2.7 | X | X | | | X | | | X | | | X | X |
| F6Y,K33N,P40T,N135D,I155T | C2.8 | X | | | | X | | | X | | | X | X |
| F6Y,Q18L,K33N,V36E,P40T,N50S,G51RN135D,I155T | C3.13 | X | X | | | X | | X | X | X | X | X | X |
| F6Y,Q18L,N135D,I155T | C4.16 | X | X | | | | | | | | | X | X |
| Q18L,N135D,I155T | C4.17 | | X | | | | | | | | | X | X |
| F6Y,Q18L,L27V,S28Y,N135D,I155T | C4.18 | X | X | X | X | | | | | | | X | X |
| F6Y,Q18L,L27V,S28Y,P40T | C5.23 | X | X | X | X | | | | X | | | | |
| Q18L,L27V,S28Y,K33N,V36E,N135D,I155T | C6.26 | | X | X | X | X | | X | | | | X | X |
| F6Y,Q18L,L27V,S28Y,K33N,V36E,N135D,I155T | C6.28 | X | X | X | X | X | | X | | | | X | X |
| F6Y,Q18L,P40T,N135D,I155T | C7.31 | X | X | | | | | | X | | | X | X |
| F6Y,Q18L,L27V,S28Y,K33N,P40T,N135D,I155T | C7.33 | X | X | X | X | X | | | X | | | X | X |
| Q18L,P40T,N135D,I155T | C7.34 | | X | | | | | | X | | | X | X |
| F6Y,Q18L,K33M,L34M,N135D,I155T | C8.36 | X | X | | | X | X | | | | | X | X |
| Q18L,K33M,L34M,N135D,I155T | C8.38 | | X | | | X | X | | | | | X | X |
| F6Y,Q18L,K33M,L34M,I55T | C8.40 | X | X | | | X | X | | | | | | X |
| F6Y,Q18L,K33M,L34M,P40T,N135D | C9.44 | X | X | | | X | X | | X | | | X | |
| F6Y,Q18L,L27V,S28Y,N50S,G51R,N135D | C10.46 | X | X | X | X | | | | | X | X | X | |
| F6Y,Q18L,N50S,G51R,N135D,I155T | C10.48 | X | X | | | | | | | X | X | X | X |
| Q18L,N50S,G51R,N135D,I155T | C10.49 | | X | | | | | | | X | X | X | X |
| Q18L,L27V,S28Y,N50S,G51R,N135D,I155T | C10.50 | | X | X | X | | | | | X | X | X | X |
| F6Y,Q18L,L27V,S28Y,N50S,G51R,N135D,I155T | C11.54 | X | X | X | X | | | | | X | X | X | X |

FIG. 22

| Sample | Sequence | Coelenterazine | H | HH | PBI-3939 | PBI-3945 | PBI-3889 | PBI-4002 | PBI-3932 | PBI-3840 |
|---|---|---|---|---|---|---|---|---|---|---|
| C1.1 | F6Y,Q18L,K33N,N135D | 0.0055128 | 0.130 | 0.463 | 0.444 | 0.127 | 0.290 | 0.159 | 0.0083435 | 0.017 |
| C1.2 | F6Y,Q18L,K33N,N135D,I155T | 0.0000068 | 0.0015688 | 0.0043713 | 0.0066058 | 0.0013479 | 0.0027420 | 0.0009303 | 0.0000844 | 0.0000782 |
| C1.3 | F6Y,K33N,N135D,I155T | 0.0000257 | 0.0088297 | 0.036 | 0.048 | 0.0083438 | 0.023 | 0.0057396 | 0.0002600 | 0.0004430 |
| C2.6 | K33N,P40T,N135D,I155T | 0.0000009 | 0.0000288 | 0.0001711 | 0.0017877 | 0.0001365 | 0.0002859 | 0.0000858 | 0.0000035 | 0.0000025 |
| C2.7 | F6Y,Q18L,K33N,P40T,N135D,I155T | 0.0000008 | 0.0000091 | 0.0000318 | 0.0000611 | 0.0002445 | 0.0003744 | 0.0002560 | 0.0000013 | 0.0000020 |
| C2.8 | F6Y,K33N,P40T,N135D,I155T | 0.0000004 | 0.0000107 | 0.0000641 | 0.0007157 | 0.0000848 | 0.0001958 | 0.0000447 | 0.0000019 | 0.0000011 |
| C3.13 | F6Y,Q18L,K33N,V36E,P40T,N50S,G51R,N135D,I155T | 0.0000003 | 0.0000006 | 0.0000015 | 0.0000037 | 0.0000010 | 0.0000031 | 0.0000018 | 0.0000064 | 0.0000017 |
| C4.16 | F6Y,Q18L,N135D,I155T | 0.0000299 | 0.0046508 | 0.012 | 0.017 | 0.0052284 | 0.010 | 0.0037895 | 0.0000946 | 0.0002504 |
| C4.17 | Q18L,N135D,I155T | 0.0000222 | 0.0032164 | 0.0081703 | 0.011 | 0.0034948 | 0.0066376 | 0.0026060 | 0.0000717 | 0.0001691 |
| C4.18 | F6Y,Q18L,L27V,S28Y,N135D,I155T | 0.0000008 | 0.0000325 | 0.0001094 | 0.0003355 | 0.0001157 | 0.0001447 | 0.0000548 | 0.0000060 | 0.0000025 |
| C5.23 | F6Y,Q18L,L27V,S28Y,P40T | 0.0000579 | 0.0002759 | 0.0000464 | 0.0004978 | 0.0017611 | 0.0002812 | 0.0013044 | 0.0000144 | 0.0000132 |
| C6.26 | Q18L,L27V,S28Y,K33N,V36E,N135D,I155T | 0.0000055 | 0.0000276 | 0.0001950 | 0.0004882 | 0.0000838 | 0.0003453 | 0.0000663 | 0.0003772 | 0.0000586 |
| C6.28 | F6Y,Q18L,L27V,S28Y,K33N,V36E,N135D,I155T | 0.0000016 | 0.0000067 | 0.0000451 | 0.0001166 | 0.0000200 | 0.0000805 | 0.0000158 | 0.0000852 | 0.0000157 |
| C7.31 | F6Y,Q18L,P40T,N135D,I155T | 0.0000003 | 0.0000017 | 0.0000024 | 0.0000174 | 0.0000084 | 0.0000113 | 0.0000067 | 0.0000018 | 0.0000005 |
| C7.33 | F6Y,Q18L,L27V,S28Y,K33N,P40T,N135D,I155T | 0.0000004 | 0.0000007 | 0.0000013 | 0.0000017 | 0.0000008 | 0.0000011 | 0.0000006 | 0.0000016 | 0.0000009 |
| C7.34 | Q18L,P40T,N135D,I155T | 0.0000007 | 0.0000021 | 0.0000024 | 0.0000253 | 0.0000131 | 0.0000159 | 0.0000101 | 0.0000048 | 0.0000009 |
| C8.36 | F6Y,Q18L,K33M,L34M,N135D,I155T | 0.0000024 | 0.0000249 | 0.0000898 | 0.0001137 | 0.0000298 | 0.0000823 | 0.0000269 | 0.0000163 | 0.0000195 |
| C8.38 | Q18L,K33M,L34M,N135D,I155T | 0.0000047 | 0.0000956 | 0.0003420 | 0.0004501 | 0.0001128 | 0.0003207 | 0.0001027 | 0.0000476 | 0.0000710 |
| C8.40 | F6Y,Q18L,K33M,L34M,I55T | 0.0002632 | 0.010 | 0.015 | 0.018 | 0.011 | 0.015 | 0.0097703 | 0.0008447 | 0.0018540 |
| C9.44 | F6Y,Q18L,K33M,L34M,P40T,N135D | 0.0000041 | 0.0000139 | 0.0000153 | 0.0000379 | 0.0000423 | 0.0000474 | 0.0000534 | 0.0000284 | 0.0000486 |
| C10.46 | F6Y,Q18L,L27V,S28Y,N50S,G51R,N135D | 0.0002613 | 0.016 | 0.015 | 0.030 | 0.026 | 0.014 | 0.014 | 0.0004421 | 0.0002678 |
| C10.48 | F6Y,Q18L,N50S,G51R,N135D,I155T | 0.0000064 | 0.0005384 | 0.0011439 | 0.0016621 | 0.0006785 | 0.0010704 | 0.0004835 | 0.0000176 | 0.0000290 |
| C10.49 | Q18L,N50S,G51R,N135D,I155T | 0.0000184 | 0.0023853 | 0.0052253 | 0.0072753 | 0.0028335 | 0.0045995 | 0.0021987 | 0.0000853 | 0.0001334 |
| C10.50 | Q18L,L27V,S28Y,N50S,G51R,N135D,I155T | 0.0000095 | 0.0000547 | 0.0001427 | 0.0004411 | 0.0002044 | 0.0001929 | 0.0000965 | 0.0000697 | 0.0000099 |
| C11.54 | F6Y,Q18L,L27V,S28Y,N50S,G51R,N135D,I155T | 0.0000009 | 0.0000157 | 0.0000467 | 0.0001215 | 0.0000541 | 0.0000547 | 0.0000266 | 0.0000065 | 0.0000023 |

FIG. 23

| Sequence | clone | 1 | 4 | 18 | 27 | 33 | 38 | 68 | 70 | 72 | 75 | 102 |
|---|---|---|---|---|---|---|---|---|---|---|---|---|
| Q18L | 1D6 | | | X | | | | | | | | |
| F1I,L27V,V38I | 8A3 | X | | | X | | X | | | | | |
| F1I,L27V | 8A7 | X | | | X | | | | | | | |
| F1I,V38I | 8E2 | X | | | | | X | | | | | |
| L27V | 8F2 | | | | X | | | | | | | |
| M75K,L72Q,F68Y,Q18L | 9B8 | | | X | | | | X | | X | X | |
| M75K,L72Q,F68Y,L27V,Q18L,V38I | 9F6 | | | X | X | | X | X | | X | X | |
| F1I,M75K,L72Q,F68Y,L27V,V38I | 10A7 | X | | | X | | X | X | | X | X | |
| F1I,M75K,L72Q,M70V,Q18L | 10G10 | X | | X | | | | | X | X | X | |
| K33N | 14A2 | | | | | X | | | | | | |
| F1I,M75K,L72Q,F68Y,K33N,V102E | 14C4 | X | | | | X | | X | | X | X | X |
| E4K,M75K,L72Q,F68Y,K33N | 15C1 | | X | | | X | | X | | X | X | |

FIG. 26

| Sample | Sequence | Coel. | H | HH | PBI-3939 | PBI-3945 | PBI-3889 | PBI-4002 |
|---|---|---|---|---|---|---|---|---|
| IV | | 1 | 1 | 1 | 1 | 1 | 1 | 1 |
| 1D6 | Q18L | 0.77 | 0.92 | **2.16** | **4.08** | 1.04 | **2.27** | **1.32** |
| 8A3 | F1I,L27V,V38I | 0.01 | 0.81 | 0.87 | 0.43 | 0.90 | 0.48 | 0.77 |
| 8A7 | F1I,L27V | 0.43 | **1.55** | **1.95** | 1.26 | **1.50** | **1.50** | **1.50** |
| 8E 2 | F1I,V38I | 0.13 | 0.53 | 0.61 | 0.75 | 0.60 | 0.64 | 0.51 |
| 8F2 | L27V | 0.40 | **1.54** | **1.87** | 1.06 | **1.53** | **1.37** | **1.49** |
| 9B8 | M75K,L72Q,F68Y,Q18L | **1.40** | **1.69** | **2.52** | **4.37** | **1.44** | **2.35** | **1.72** |
| 9F6 | M75K,L72Q,F68Y,L27V,Q18L,V38I | 0.09 | **2.05** | **1.67** | 1.11 | **1.98** | 1.04 | **1.62** |
| 10A7 | F1I,M75K,L72Q,F68Y,L27V,V38I | 0.08 | **1.40** | 1.17 | 0.82 | **1.74** | 0.89 | 1.23 |
| 10G10 | F1I,M75K,L72Q,M70V,Q18L | 1.03 | **1.51** | **2.30** | **4.25** | **1.35** | **2.33** | **1.60** |
| 14A2 | K33N | 1.12 | **1.62** | **1.93** | **1.80** | **1.80** | **2.23** | **1.66** |
| 14C4 | F1I,M75K,L72Q,F68Y,K33N,V102E | 1.27 | **1.33** | 1.08 | **1.36** | **1.53** | 0.84 | 1.11 |
| 15C1 | E4K,M75K,L72Q,F68Y,K33N | **2.63** | **2.61** | **2.10** | **2.60** | **2.94** | **1.67** | **2.20** |

FIG. 27

FIG. 30A

Native coelenterazine

| Amino acid | Relative activity |
|---|---|
| Ala | 1.0 |
| Phe | 3.2 |
| Lys | 19.2 |
| Arg | 26.8 |

FIG. 30B

Coelenterazine-h

| Amino acid | Relative activity |
|---|---|
| Ser | 1.1 |
| Ile | 1.4 |
| Lys | 11.6 |
| Arg | 15.9 |
| Phe | 55.9 |

FIG. 30C

PBI-3939

| Amino acid | Relative activity |
|---|---|
| Ser | 1.8 |
| Glu | 4.6 |
| Ile | 10.0 |
| Lys | 17.5 |
| Arg | 26.4 |
| Phe | 444.4 |

FIG. 30D

| Amino acid substitution | Relative activity (in context of wt OgLuc) | Relative activity (in context of N166R) |
|---|---|---|
| L27V | 62.2 | 45.4 |
| A33N | 0.6 | 1.3 |
| K43R | 1.1 | 17.1 |
| M75K | 65.7 | 467.7 |
| T39T | 118.6 | 1.5 |
| L72Q | 2.0 | 5.0 |
| F68D | 3.0 | 5.4 |

| Sample | 1/2 life (hours) 60C |
|---|---|
| 9B8 opt | 5.7 |
| 9B8 opt +K33N | 6.8 |

L27V=hatched,
Luc2=black

1. L27V 50ng
2. Luc2 50ng
3. L27V 5 ng
4. Luc2 5 ng
5. L27V 0.5ng
6. Luc2 0.5ng

| Threshold | Hit rate (%) |
|---|---|
| 10—30% | 1.2 |
| >30% | 0 |

FIG. 52A
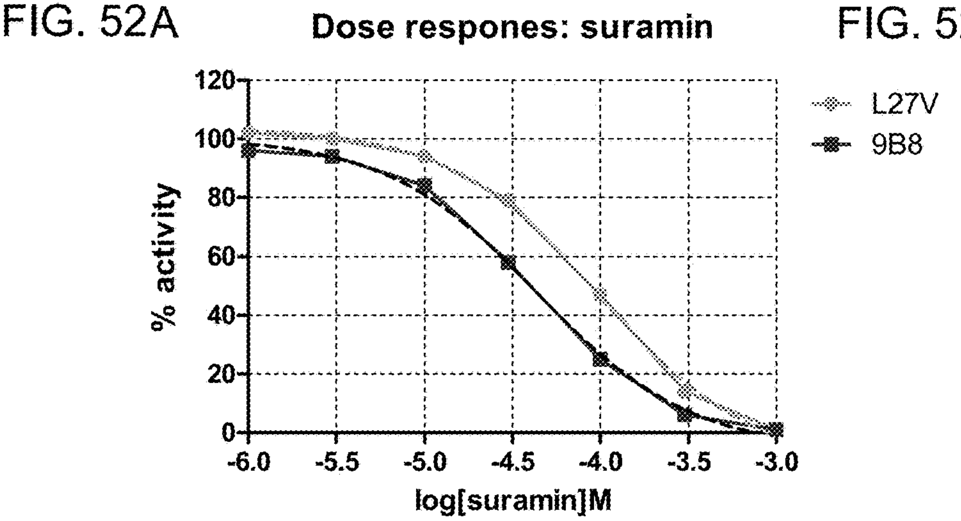
FIG. 52B
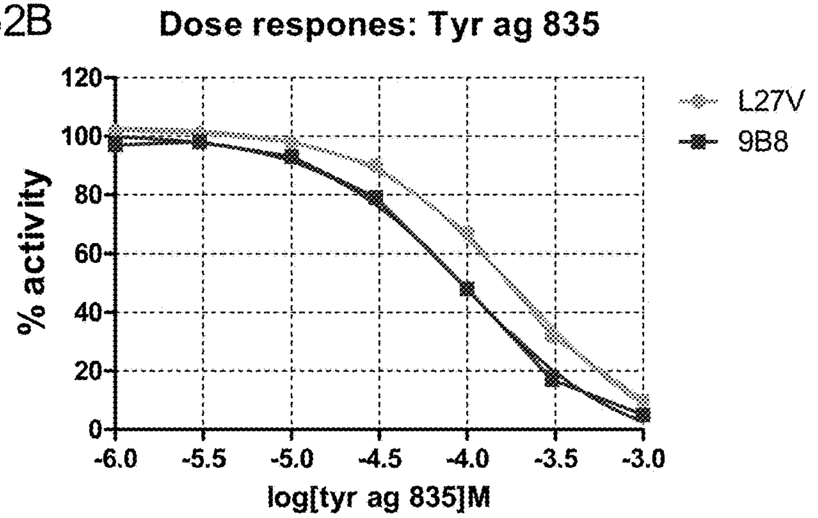
FIG. 52C
| Sample | 9B8 IC50 (uM) | L27V IC50(uM) |
|---|---|---|
| Suramin | 44.4 | 100.4 |
| Tyr ag 835 | 105 | 198 |
FIG. 52D
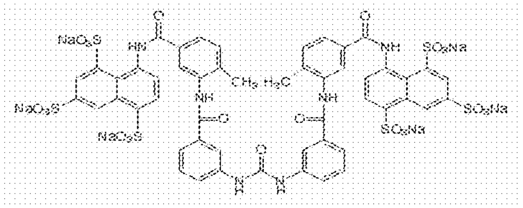
Suramin
FIG. 52E
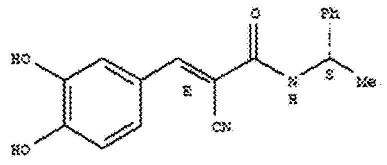
Tvr ag 835

| | FLucP | FLuc | L27V02P | L27V02 |
|---|---|---|---|---|
| Avg. RLU / luc2P | 1.00 | 7.5 | 21.6 | 168.5 |
| S/B | 781 | 268 | 1768 | 224 |
| EC50 (μM) | 6.3 | 5.9 | 10.3 | 5.9 |

FIG. 59C

| Exp. system | RLUs Oluc/FLuc | RLUs OLucP/FLucP | S/B, Oluc | S/B, OLucP | S/B, FLuc | S/B, FLucP |
|---|---|---|---|---|---|---|
| 293/CRE | 22 | 22 | 224 | 1768 | 268 | 781 |
| 293/NFkB | 75 | 8 | 22 | 514 | 233 | 347 |
| Hela/NFkB | 14 | 2 | 40 | 47 | 54 | 44 |
| HepG2/NFkB | 267 | 5 | 7 | 11 | 11 | 19 |
| Jurkat/NFkB | 16 | 6 | 18 | 15 | 6 | 11 |
| Jurkat/CRE | 19 | 4 | 14 | 123 | 28 | 40 |
| ME180/CRE | 56 | 12 | 2 | 6 | 4 | 5 |
| ME180/NFkB | 149 | 21 | 7 | 19 | 7 | 25 |
| HCT116/NFkB | 22 | 16 | 10 | 605 | 4 | 47 |
| U2OS/NFkB | 114 | 16 | 15 | 18 | 11 | 20 |

HEK-293

*IL-6 signal sequence

| sample | 9B8 | V2 | L27V | 9B8 (Sec.) | V2 (sec) | L27V (sec) |
|---|---|---|---|---|---|---|
| Media | 21,284,716 | 23,787,770 | 18,299,776 | 417,440,788 | 625,387,280 | 578,186,357 |
| Lysate | 1,478,846,480 | 1,468,338,592 | 1,474,480,208 | 177,409,200 | 299,355,128 | 243,323,506 |

| sample | 9B8 | V2 | L27V | 9B8 (Sec.) | V2 (sec) | L27V (sec) |
|---|---|---|---|---|---|---|
| Media | 14,206,429 | 27,753,862 | 28,932,890 | 447,675,259 | 660,425,952 | 377,700,912 |
| Lysate | 984,347,600 | 1,876,585,440 | 1,319,113,560 | 343,880,163 | 643,107,747 | 369,662,727 |

| DNA | Met-luc (Ready-To Glow ™) | 9B8-3939 | V2-3939 |
|---|---|---|---|
| 100ng | 2,502,116 | 3,307,464,875 | 3,992,245,760 |
| 10ng | 297,024 | 33,947,989 | 51,683,999 |

IL6 signal

IL6 signal

Native Oluc signal

| CP site ("CP#") | SEQ ID NOs: | response to TEV | CP site ("CP#") | SEQ ID NOs: | response to TEV | CP site ("CP#") | SEQ ID NOs: | response to TEV | CP site ("CP#") | SEQ ID NOs: | response to TEV |
|---|---|---|---|---|---|---|---|---|---|---|---|
| 5 | 114 and 115 | 1.3 | 53 | 160 and 161 | 2100 | 95 | 204 and 205 | 512.9 | 136 | 246 and 247 | / |
| 6 | 116 and 117 | 7.0 | 54 | 162 and 163 | 12.3 | 97 | 206 and 207 | 9.1 | 139 | 248 and 249 | 1.9 |
| 7 | 118 and 119 | / | 55 | 164 and 165 | 7744.3 | 98 | 447 and 448 | 5.4 | 140 | 250 and 251 | / |
| 9 | 120 and 121 | 2.2 | 56 | 166 and 167 | / | 100 | 208 and 209 | 7515.2 | 141 | 252 and 253 | / |
| 11 | 122 and 123 | / | 57 | 445 and 446 | 17.6 | 101 | 210 and 211 | 6329.9 | 142 | 254 and 255 | 5.3 |
| 12 | 124 and 125 | 1.6 | 58 | 168 and 169 | 116.7 | 102 | 212 and 213 | 3205.1 | 143 | 256 and 257 | 871.4 |
| 15 | 126 and 127 | / | 64 | 170 and 171 | 1.4 | 103 | 214 and 215 | 3456.8 | 144 | 258 and 259 | 1.6 |
| 18 | 128 and 129 | 2.1 | 67 | 172 and 173 | / | 104 | 216 and 217 | 3036.9 | 145 | 260 and 261 | 3.7 |
| 21 | 130 and 131 | / | 70 | 174 and 175 | / | 105 | 218 and 219 | 4931.6 | 146 | 262 and 263 | 6.6 |
| 24 | 132 and 133 | 3.8 | 73 | 176 and 177 | / | 106 | 220 and 221 | 5.3 | 147 | 264 and 265 | 2.0 |
| 27 | 134 and 135 | 3.1 | 76 | 178 and 179 | / | 109 | 222 and 223 | 12.3 | 148 | 266 and 267 | 3.8 |
| 34 | 136 and 137 | 9.3 | 79 | 180 and 181 | / | 112 | 224 and 225 | 82.7 | 149 | 268 and 269 | 4.4 |
| 40 | 138 and 139 | 1.8 | 80 | 182 and 183 | 1.3 | 13 | 443 and 444 | 160.8 | 150 | 270 and 271 | 867.4 |
| 43 | 140 and 141 | / | 81 | 184 and 185 | 1.3 | 115 | 226 and 227 | / | 151 | 272 and 273 | 6.3 |
| 44 | 142 and 143 | 12.9 | 82 | 186 and 187 | 1.5 | 120 | 228 and 229 | 1661 | 154 | 274 and 275 | / |
| 45 | 144 and 145 | 1057.7 | 83 | 188 and 189 | 1.5 | 121 | 230 and 231 | 1.5 | 156 | 276 and 277 | 942.1 |
| 46 | 146 and 147 | 1277.9 | 84 | 190 and 191 | 1.2 | 123 | 232 and 233 | 323.6 | 157 | 278 and 279 | 1467.9 |
| 47 | 148 and 149 | 1.5 | 85 | 192 and 193 | 1.4 | 124 | 234 and 235 | 1548.2 | 158 | 280 and 281 | 1526.5 |
| 48 | 150 and 151 | 6.7 | 86 | 194 and 195 | 1.2 | 125 | 236 and 237 | 1141.8 | 160 | 282 and 283 | 12.4 |
| 49 | 152 and 153 | 12.5 | 87 | 196 and 197 | 1.5 | 129 | 238 and 239 | 40.2 | 163 | 284 and 285 | / |
| 50 | 154 and 155 | 2.2 | 88 | 198 and 199 | 1.8 | 130 | 240 and 241 | 2,043.0 | 166 | 286 and 287 | / |
| 51 | 156 and 157 | 2.8 | 91 | 200 and 201 | 324.2 | 131 | 242 and 243 | 612.5 | | | |
| 52 | 158 and 159 | 15.9 | 94 | 202 and 203 | 5.5 | 133 | 244 and 245 | 1.5 | | | |

FIG. 73E

| CP# | Response |
|---|---|
| 12 | 36.8 |
| 24 | 1.4 |
| 27 | 1.6 |
| 49 | 5.4 |
| 52 | 5.2 |
| 84 | 1.2 |
| 86 | 1.2 |
| 103 | 7.4 |
| 124 | 4.0 |
| 130 | 3.4 |
| 145 | 1.3 |
| 148 | 1.3 |
| 157 | 9.4 |

FK506

Rapamycin

L27V
(1:10 DNA)

pGEM3ZF

Unfused

Transcription factor (Nrf2)

GPCR

4377

+ Dexamethasone, 13 min

+ Dexamethasone, 0 min

+ 100 nM PMA, 0 min

+ 100 nM PMA, 20 min

+ 50 μM Chloroquine, 16 h untreated

SEQUENCE LISTING

```
Sequence total quantity: 593
SEQ ID NO: 1            moltype = AA  length = 169
FEATURE                 Location/Qualifiers
source                  1..169
                        mol_type = protein
                        organism = Oplophorus gracilirostris
SEQUENCE: 1
FTLADFVGDW QQTAGYNQDQ VLEQGGLSSL FQALGVSVTP IQKVVLSGEN GLKADIHVII  60
PYEGLSGFQM GLIEMIFKVV YPVDDHHFKI ILHYGTLVID GVTPNMIDYF GRPYPGIAVF  120
DGKQITVTGT LWNGNKIYDE RLINPDGSLL FRVTINGVTG WRLCENILA              169

SEQ ID NO: 2            moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 2
atggtgttta cattggagga tttcgttgga gactggcggc agacagctgg atacaaccaa  60
gatcaagtgt tagaacaagg aggattgtct agtctgttcc aaaagctggg agtgtcagtc  120
accccaatcc agaaaattgt gctgtctggg gagaatgggt taaaatttga tattcatgtc  180
```

-continued

```
atcatccctt acgagggact cagtggtttt caaatgggtc tgattgaaat gatcttcaaa  240
gttgtttacc cagtggatga tcatcatttc aagattattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                               513

SEQ ID NO: 3            moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 3
MVFTLEDFVG DWRQTAGYNQ DQVLEQGGLS SLFQKLGVSV TPIQKIVLSG ENGLKFDIHV  60
IIPYEGLSGF QMGLIEMIFK VVYPVDDHHF KIILHYGTLV IDGVTPNMID YFGRPYEGIA  120
VFDGKKITVT GTLWNGNKII DERLINPDGS LLFRVTINGV TGWRLCERIL A           171

SEQ ID NO: 4            moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 4
atggtgttta cattggagga tttcgttgga gactggcggc agacagctgg atacaaccta  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aagattattc accattatgg tacactcgtt  300
attgacggtg tgacaccaaa catgattgac ttctttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                               513

SEQ ID NO: 5            moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 5
MVFTLEDFVG DWRQTAGYNL DQVLEQGGLS SLFQKLGVSV TPIQKIVLSG ENGLKIDIHV  60
IIPYEGLSGF QMGLIEMIFK VVYPVDDHHF KIIHHYGTLV IDGVTPNMID FFGRPYEGIA  120
VFDGKKITVT GTLWNGNKII DERLINPDGS LLFRVTINGV TGWRLCERIL A           171

SEQ ID NO: 6            moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 6
atggtgttta cattggagga tttcgttgga gactggcggc agacagctgg atacaaccta  60
gatcaactgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aagattattc gccattatgg tacactcgtt  300
attgacggtg tgacaccaaa catgattgac ttctttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggaatc  480
accggatggc gcctttgcga gcgtattctt gcc                               513

SEQ ID NO: 7            moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
```

```
SEQUENCE: 7
MVFTLEDFVG DWRQTAGYNL DQLLEQGGLS SLFQKLGVSV TPIQKIVLSG ENGLKIDIHV  60
IIPYEGLSGY QMGQIEKIFK VVYPVDDHHF KIIRHYGTLV IDGVTPNMID FFGRPYEGIA  120
VFDGKKITVT GTLWNGNKII DERLINPDGS LLFRVTINGI TGWRLCERIL A           171

SEQ ID NO: 8           moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 8
atggtgttta cattggagga tttcgttgga gactggcggc agacagctgg atacaaccaa  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatctacaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                                513

SEQ ID NO: 9           moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 9
MVFTLEDFVG DWRQTAGYNQ DQVLEQGGLS SLFQKLGVSV TPIQKIVLSG ENGLKIDIHV  60
IIPYEGLSGF QMGLIEMIYK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 10          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 10
atggtgttta cattggagga ttacgttgga gactggcggc agacagctgg atacaaccaa  60
gatcaagtgt tagaacaagg aggattgtct agtctgttcc aaaatctggg agtgtctgtc  120
accccaatcc agaaaattgt gctgtctggg gagaatgggt taaaaattga tattcatgtc  180
atcatccctt acgagggact cagtggtttt caaatgggtc tgattgaaat gatctacaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcga caagatcatt  420
gatgagcgcc tgatcaaccc agatggttca ctcctcttcc gcgttactac caatggagtc  480
accggatggc gcctttgcga gcgtattctt gcc                                513

SEQ ID NO: 11          moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 11
MVFTLEDYVG DWRQTAGYNQ DQVLEQGGLS SLFQNLGVSV TPIQKIVLSG ENGLKIDIHV  60
IIPYEGLSGF QMGLIEMIYK VVYPVDDHHF KVILHYGTLV IDGVTPNMID YFGRPYEGIA  120
VFDGKKITVT GTLWNGDKII DERLINPDGS LLFRVTTNGV TGWRLCERIL A           171

SEQ ID NO: 12          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 12
atggtgttta cattggagga tttcgttgga gactggcggc agacagctgg atacaaccaa  60
```

-continued

```
gatcaagtgt tagaacaagg aggagtgtct agtctgttcc aaaagctggg agtgtcaatc  120
accccaatcc agaaaattgt gctgtctggg gagaatgggt taaaaattga tattcatgtc  180
atcatccctt acgagggact cagtggtttt caaatgggtc tgattgaaat gatctacaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca atcctcttcc gcgttactat caatggagtc  480
accggatggc gcctttgcga gcgtattctt gcc                               513

SEQ ID NO: 13          moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 13
MVFTLEDFVG DWRQTAGYNQ DQVLEQGGVS SLFQKLGVSI TPIQKIVLSG ENGLKIDIHV  60
IIPYEGLSGF QMGLIEMIYK VVYPVDDHHF KVILHYGTLV IDGVTPNMID YFGRPYEGIA  120
VFDGKKITVT GTLWNGNKII DERLINPDGS ILFRVTINGV TGWRLCERIL A           171

SEQ ID NO: 14          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 14
atggtgttta cattggagga tttcgttgga gactggcggc agacagctgg atacaaccaa  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                               513

SEQ ID NO: 15          moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 15
MVFTLEDFVG DWRQTAGYNQ DQVLEQGGLS SLFQKLGVSV TPIQKIVLSG ENGLKIDIHV  60
IIPYEGLSGF QMGLIEMIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 16          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 16
atggtgttta cattgaagga tttcgttgga gactggcggc agacagctgg atacaaccaa  60
gatcaagtgt tagaacaagg aggattgtct agtctgttcc aaaatctggg agtgtcagtc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                               513

SEQ ID NO: 17          moltype = AA  length = 171
FEATURE                Location/Qualifiers
REGION                 1..171
                       note = Description of Artificial Sequence: Synthetic
                        polypeptide
source                 1..171
```

```
                        mol_type = protein
                        organism = synthetic construct
SEQUENCE: 17
MVFTLKDFVG DWRQTAGYNQ DQVLEQGGLS SLFQNLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 18           moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 18
atggtgttta cattggagga tttcgttgga gactggcggc agacagctgg atacaaccta  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                              513

SEQ ID NO: 19           moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 19
MVFTLEDFVG DWRQTAGYNL DQVLEQGGLS SLFQKLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 20           moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 20
atggtgttta cattggagga tttcgttgga gactggcggc agacagctgg atacaaccta  60
gatcaagtgt tagaacaagg aggagtgtct agtctgttcc aaaagctggg agtgtcaatc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                              513

SEQ ID NO: 21           moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 21
MVFTLEDFVG DWRQTAGYNL DQVLEQGGVS SLFQKLGVSI TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 22           moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
```

```
SEQUENCE: 22
atggtgttta cactcgaaga tttcgtaggg gactggcggc agacagccgg ctacaaccaa  60
gaccaagtcc ttgagcaggg cggtctgtcc agtttgtttc agaaactcgg ggtgtccgta  120
acaccgatcc aaaagattgt cctgagcggt gaaaacggcc tgaagatcga catccatgtc  180
atcatcccgt atgaaggtct gagcggcttc cagatgggcc tcattgagat gatctttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                              513

SEQ ID NO: 23          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 23
atggtattca cactggagga ttttgtcggt gattggcggc aaaccgctgg gtacaaccag  60
gaccaggttc tcgaacaagg gggcctcagc tccctgtttc aaaaactggg tgttagcgtt  120
acacctattc aaaaaatcgt gctctccggg gaaaacgggc tcaaaatcga tattcatgtg  180
attatccctt acgaagggct ctccgggttt cagatggggc tgatcgaaat gatctttaag  240
gtcgtctatc ccgtagatga tcaccacttc aaggtgatcc tccactacgg gaccctcgta  300
attgatggcg tgacccccaa catgatcgac tattttgggc gcccttacga ggggattgct  360
gtcttcgatg gcaaaaaaat tacagtgaca ggcacactct ggaacgggaa taagatcatt  420
gatgagcgcc tgattaatcc cgatgggagc ctgctctttc gggtgacaat taacggcgta  480
acaggctggc gcctctgtga acggattctg gcg                              513

SEQ ID NO: 24          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 24
atggtgttta cactcgaaga tttcgtaggg gactggcggc agacagccgg ctacaacctg  60
gaccaagtcc ttgagcaggg cggtctgtcc agtttgtttc agaaactcgg ggtgtccgta  120
acaccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                              513

SEQ ID NO: 25          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 25
atggtattca cactggagga ttttgtcggt gattggcggc aaaccgctgg gtacaacctc  60
gaccaggttc tcgaacaagg gggcctcagc tccctgtttc aaaaactggg tgttagcgtt  120
acacctattc aaaaaatcgt gctctccggg gaaaacgggc tcaaaatcga tattcatgtg  180
attatccctt acgaagggct ctccgggtat cagatggggc agatcgaaaa aatctttaag  240
gtcgtctatc ccgtagatga tcaccacttc aaggtgatcc tccactacgg gaccctcgta  300
attgatggcg tgacccccaa catgatcgac tattttgggc gcccttacga ggggattgct  360
gtcttcgatg gcaaaaaaat tacagtgaca ggcacactct ggaacgggaa taagatcatt  420
gatgagcgcc tgattaatcc cgatgggagc ctgctctttc gggtgacaat taacggcgta  480
acaggctggc gcctctgtga acggattctg gcg                              513

SEQ ID NO: 26          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 26
atggtgatta cattggagga tttcgttgga gactggcggc agacagctgg atacaaccaa  60
gatcaagtgt tagaacaagg aggagtgtct agtctgttcc aaaagctggg agtgtcaatc  120
```

```
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                               513

SEQ ID NO: 27          moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 27
MVITLEDFVG DWRQTAGYNQ DQVLEQGGVS SLFQKLGVSI TPIQKIVLSG ENGLKIDIHV  60
IIPYEGLSGF QMGLIEMIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 28          moltype = DNA  length = 1650
FEATURE                Location/Qualifiers
source                 1..1650
                       mol_type = genomic DNA
                       organism = Photinus pyralis
SEQUENCE: 28
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg ccagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagagc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtt                                   1650

SEQ ID NO: 29          moltype = AA  length = 550
FEATURE                Location/Qualifiers
source                 1..550
                       mol_type = protein
                       organism = Photinus pyralis
SEQUENCE: 29
MEDAKNIKKG PAPFYPLEDG TAGEQLHKAM KRYALVPGTI AFTDAHIEVD ITYAEYFEMS  60
VRLAEAMKRY GLNTNHRIVV CSENSLQFFM PVLGALFIGV AVAPANDIYN ERELLNSMGI  120
SQPTVVFVSK KGLQKILNVQ KKLPIIQKII IMDSKTDYQG FQSMYTFVTS HLPPGFNEYD  180
FVPESFDRDK TIALIMNSSG STGLPKGVAL PHRTACVRFS HARDPIFGNQ IIPDTAILSV  240
VPFHHGFGMF TTLGYLICGF RVVLMYRFEE ELFLRSLQDY KIQSALLVPT LFSFFAKSTL  300
IDKYDLSNLH EIASGGAPLS KEVGEAVAKR FHLPGIRQGY GLTETTSAIL ITPEGDDKPG  360
AVGKVVPFFE AKVVDLDTGK TLGVNQRGEL CVRGPMIMSG YVNNPEATNA LIDKDGWLHS  420
GDIAYWDEDE HFFIVDRLKS LIKYKGYQVA PAELESILLQ HPNIFDAGVA GLPDDDAGEL  480
PAAVVVLEHG KTMTEKEIVD YVASQVTTAK KLRGGVVFVD EVPKGLTGKL DARKIREILI  540
KAKKGGKIAV                                                         550

SEQ ID NO: 30          moltype = DNA  length = 933
FEATURE                Location/Qualifiers
misc_feature           1..933
                       note = Description of Artificial Sequence: Synthetic
                        polynucleotide
source                 1..933
```

```
                         mol_type = other DNA
                         organism = synthetic construct
SEQUENCE: 30
atggcttcca aggtgtacga ccccgagcaa cgcaaacgca tgatcactgg gcctcagtgg  60
tgggctcgct gcaagcaaat gaacgtgctg gactccttca tcaactacta tgattccgag  120
aagcacgccg agaacgccgt gatttttctg catggtaacg ctgcctccag ctacctgtgg  180
aggcacgtcg tgcctcacat cgagcccgtg gctagatgca tcatccctga tctgatcgga  240
atgggtaagt ccggcaagag cgggaatggc tcatatcgcc tcctggatca ctacaagtac  300
ctcaccgctt ggttcgagct gctgaacctt ccaaagaaaa tcatctttgt gggccacgac  360
tgggggggctt gtctggcctt tcactactcc tacgagcacc aagacaagat caaggccatc  420
gtccatgctg agagtgtcgt ggacgtgatc gagtcctggg acgagtggcc tgacatcgag  480
gaggatatcg ccctgatcaa gagcgaagag ggcgagaaaa tggtgcttga gaataacttc  540
ttcgtcgaga ccatgctccc aagcaagatc atgcggaaac tggagcctga ggagttcgct  600
gcctacctgg agccattcaa ggagaagggc gaggttagac ggcctaccct ctcctggcct  660
cgcgagatcc ctctcgttaa gggaggcaag cccgacgtcg tccagattgt ccgcaactac  720
aacgcctacc ttcgggccag cgacgatctg cctaagatgt tcatcgagtc cgaccctggg  780
ttcttttcca acgctattgt cgagggagct aagaagttcc ctaacaccga gttcgtgaag  840
gtgaagggcc tccacttcag ccaggaggac gctccagatg aaatgggtaa gtacatcaag  900
agcttcgtgg agcgcgtgct gaagaacgag cag                               933

SEQ ID NO: 31            moltype = AA  length = 311
FEATURE                  Location/Qualifiers
REGION                   1..311
                         note = Description of Artificial Sequence: Synthetic
                          polypeptide
source                   1..311
                         mol_type = protein
                         organism = synthetic construct
SEQUENCE: 31
MASKVYDPEQ RKRMITGPQW WARCKQMNVL DSFINYYDSE KHAENAVIFL HGNAASSYLW  60
RHVVPHIEPV ARCIIPDLIG MGKSGKSGNG SYRLLDHYKY LTAWFELLNL PKKIIFVGHD  120
WGACLAFHYS YEHQDKIKAI VHAESVVDVI ESWDEWPDIE EDIALIKSEE GEKMVLENNF  180
FVETMLPSKI MRKLEPEEFA AYLEPFKEKG EVRRPTLSWP REIPLVKGGK PDVVQIVRNY  240
NAYLRASDDL PKMFIESDPG FFSNAIVEGA KKFPNTEFVK VKGLHFSQED APDEMGKYIK  300
SFVERVLKNE Q                                                       311

SEQ ID NO: 32            moltype = DNA  length = 2295
FEATURE                  Location/Qualifiers
misc_feature             1..2295
                         note = Description of Artificial Sequence: Synthetic
                          polynucleotide
source                   1..2295
                         mol_type = other DNA
                         organism = synthetic construct
SEQUENCE: 32
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggcttcca aggtgtacga ccccgagcaa cgcaaacgca tgatcactgg gcctcagtgg  480
tgggctcgct gcaagcaaat gaacgtgctg gactccttca tcaactacta tgattccgag  540
aagcacgccg agaacgccgt gatttttctg catggtaacg ctgcctccag ctacctgtgg  600
aggcacgtcg tgcctcacat cgagcccgtg gctagatgca tcatccctga tctgatcgga  660
atgggtaagt ccggcaagag cgggaatggc tcatatcgcc tcctggatca ctacaagtac  720
ctcaccgctt ggttcgagct gctgaacctt ccaaagaaaa tcatctttgt gggccacgac  780
tgggggggctt gtctggcctt tcactactcc tacgagcacc aagacaagat caaggccatc  840
gtccatgctg agagtgtcgt ggacgtgatc gagtcctggg acgagtggcc tgacatcgag  900
gaggatatcg ccctgatcaa gagcgaagag ggcgagaaaa tggtgcttga gaataacttc  960
ttcgtcgaga ccatgctccc aagcaagatc atgcggaaac tggagcctga ggagttcgct  1020
gcctacctgg agccattcaa ggagaagggc gaggttagac ggcctaccct ctcctggcct  1080
cgcgagatcc ctctcgttaa gggaggcaag cccgacgtcg tccagattgt ccgcaactac  1140
aacgcctacc ttcgggccag cgacgatctg cctaagatgt tcatcgagtc cgaccctggg  1200
ttcttttcca acgctattgt cgagggagct aagaagttcc ctaacaccga gttcgtgaag  1260
gtgaagggcc tccacttcag ccaggaggac gctccagatg aaatgggtaa gtacatcaag  1320
agcttcgtgg agcgcgtgct gaagaacgag caggtttctc tcgagccaac cactgaggat  1380
ctgtactttc agagcgataa cgatggatcc gaaatcggta ctggctttcc attcgacccc  1440
cattatgtgg aagtcctggg cgagcgcatg cactacgtcg atgttggtcc gcgcgatggc  1500
acccctgtgc tgttcctgca cggtaacccg acctcctcct acgtgtggcg caacatcatc  1560
ccgcatgttg caccgaccca tcgctgcatt gctccagacc tgatcggtat gggcaaatcc  1620
gacaaaccag acctgggtta tttcttcgac gaccacgtcc gcttcatgga tgccttcatc  1680
gaagccctgg gtctggaaga ggtcgtcctg gtcattcacg actggggctc cgctctgggt  1740
ttccactggg ccaagcgcaa tccagagcgc gtcaaaggta ttgcatttat ggagttcatc  1800
cgccctatcc cgacctggga cgaatggcca gaatttgccc gcgagacctt ccaggccttc  1860
cgcaccaccg acgtcggccg caagctgatc atcgatcaga acgtttttat cgagggtacg  1920
ctgccgatgg gtgtcgtccg cccgctgact gaagtcgaga tggaccatta ccgcgagccg  1980
ttcctgaatc ctgttgaccg cgagccactg tggcgcttcc caaacgagct gccaatcgcc  2040
```

```
ggtgagccag cgaacatcgt cgcgctggtc gaagaataca tggactggct gcaccagtcc  2100
cctgtcccga agctgctgtt ctggggcacc ccaggcgttc tgatcccacc ggccgaagcc  2160
gctcgcctgg ccaaaagcct gcctaactgc aaggctgtgg acatcggccc gggtctgaat  2220
ctgctgcaag aagacaaccc ggacctgatc ggcagcgaga tcgcgcgctg gctgtctact  2280
ctggagattt ccggt                                                   2295

SEQ ID NO: 33           moltype = AA  length = 765
FEATURE                 Location/Qualifiers
REGION                  1..765
                        note = Description of Artificial Sequence: Synthetic
                         polypeptide
source                  1..765
                        mol_type = protein
                        organism = synthetic construct
SEQUENCE: 33
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MASKVYDPEQ RKRMITGPQW WARCKQMNVL DSFINYYDSE  180
KHAENAVIFL HGNAASSYLW RHVVPHIEPV ARCIIPDLIG MGKSGKSGNG SYRLLDHYKY  240
LTAWFELLNL PKKIIFVGHD WGACLAFHYS YEHQDKIKAI VHAESVVDVI ESWDEWPDIE  300
EDIALIKSEE GEKMVLENNF FVETMLPSKI MRKLEPEEFA AYLEPFKEKG EVRRPTLSWP  360
REIPLVKGGK PDVVQIVRNY NAYLRASDDL PKMFIESDPG FFSNAIVEGA KKFPNTEFVK  420
VKGLHFSQED APDEMGKYIK SFVERVLKNE QVSLEPTTED LYFQSDNDGS EIGTGFPFDP  480
HYVEVLGERM HYVDVGPRDG TPVLFLHGNP TSSYVWRNII PHVAPTHRCI APDLIGMGKS  540
DKPDLGYFFD DHVRFMDAFI EALGLEEVVL VIHDWGSALG FHWAKRNPER VKGIAFMEFI  600
RPIPTWDEWP EFARETFQAF RTTDVGRKLI IDQNVFIEGT LPMGVVRPLT EVEMDHYREP  660
FLNPVDREPL WRFPNELPIA GEPANIVALV EEYMDWLHQS PVPKLLFWGT PGVLIPPAEA  720
ARLAKSLPNC KAVDIGPGLN LLQEDNPDLI GSEIARWLST LEISG                  765

SEQ ID NO: 34           moltype = DNA  length = 1455
FEATURE                 Location/Qualifiers
misc_feature            1..1455
                        note = Description of Artificial Sequence: Synthetic
                         polynucleotide
source                  1..1455
                        mol_type = other DNA
                        organism = synthetic construct
SEQUENCE: 34
atggtgatta cattggagga tttcgttgga gactggcggc agacagctgg atacaaccaa  60
gatcaagtgt tagaacaagg aggagtgtct agtctgttcc aaaagctggg agtgtcaatc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                   1455

SEQ ID NO: 35           moltype = AA  length = 485
FEATURE                 Location/Qualifiers
REGION                  1..485
                        note = Description of Artificial Sequence: Synthetic
                         polypeptide
source                  1..485
                        mol_type = protein
                        organism = synthetic construct
SEQUENCE: 35
MVITLEDFVG DWRQTAGYNQ DQVLEQGGVS SLFQKLGVSI TPIQKIVLSG ENGLKIDIHV  60
IIPYEGLSGF QMGLIEMIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
```

```
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                              485

SEQ ID NO: 36          moltype = DNA  length = 1455
FEATURE                Location/Qualifiers
misc_feature           1..1455
                       note = Description of Artificial Sequence: Synthetic
                        polynucleotide
source                 1..1455
                       mol_type = other DNA
                       organism = synthetic construct
SEQUENCE: 36
atggtgttta cattggagga tttcgttgga gactggcggc agacagctgg atacaaccta  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                   1455

SEQ ID NO: 37          moltype = AA  length = 485
FEATURE                Location/Qualifiers
REGION                 1..485
                       note = Description of Artificial Sequence: Synthetic
                        polypeptide
source                 1..485
                       mol_type = protein
                       organism = synthetic construct
SEQUENCE: 37
MVFTLEDFVG DWRQTAGYNL DQVLEQGGLS SLFQKLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                              485

SEQ ID NO: 38          moltype = DNA  length = 1455
FEATURE                Location/Qualifiers
misc_feature           1..1455
                       note = Description of Artificial Sequence: Synthetic
                        polynucleotide
source                 1..1455
                       mol_type = other DNA
                       organism = synthetic construct
SEQUENCE: 38
atggtgttta cattggagga tttcgttgga gactggcggc agacagctgg atacaaccta  60
gatcaagtgt tagaacaagg aggagtgtct agtctgttcc aaaagctggg agtgtcaatc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
```

-continued

```
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                   1455
```

```
SEQ ID NO: 39          moltype = AA  length = 485
FEATURE                Location/Qualifiers
REGION                 1..485
                       note = Description of Artificial Sequence: Synthetic
                        polypeptide
source                 1..485
                       mol_type = protein
                       organism = synthetic construct
SEQUENCE: 39
MVFTLEDFVG DWRQTAGYNL DQVLEQGGVS SLFQKLGVSI TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                              485
```

```
SEQ ID NO: 40          moltype = DNA  length = 1876
FEATURE                Location/Qualifiers
misc_feature           1..1876
                       note = Description of Artificial Sequence: Synthetic
                        polynucleotide
source                 1..1876
                       mol_type = other DNA
                       organism = synthetic construct
SEQUENCE: 40
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gaccaagtcc ttgagcaggg cggtctgtcc agtttgtttc agaaactcgg ggtgtccgta  540
acaccgatcc aaaagattgt cctgagcggt gaaaacggcc tgaagatcga catccatgtc  600
atcatcccgt atgaaggtct gagcggctat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgtattctt gccggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
accccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggtt                                                  1876
```

```
SEQ ID NO: 41          moltype = AA  length = 625
FEATURE                Location/Qualifiers
REGION                 1..625
                       note = Description of Artificial Sequence: Synthetic
```

```
                         polypeptide
source                  1..625
                        mol_type = protein
                        organism = synthetic construct
SEQUENCE: 41
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQKLGVSV  180
TPIQKIVLSG ENGLKIDIHV IIPYEGLSGY QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                     625

SEQ ID NO: 42           moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 42
atggtgttta cactcgaaga tttcgtaggg gactggcggc agacagccgg ctacaacctg  60
gaccaagtcc ttgagcaggg cggtctgtcc agtttgtttc agaatctcgg ggtgtccgta  120
acaccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                            513

SEQ ID NO: 43           moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 43
MVFTLEDFVG DWRQTAGYNL DQVLEQGGLS SLFQNLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A        171

SEQ ID NO: 44           moltype = DNA  length = 1455
FEATURE                 Location/Qualifiers
misc_feature            1..1455
                        note = Description of Artificial Sequence: Synthetic
                         polynucleotide
source                  1..1455
                        mol_type = other DNA
                        organism = synthetic construct
SEQUENCE: 44
atggtgttta cattggagga tttcgttgga gactggcggc agacagctgg atacaaccta  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aagattattc accattatgg tacactcgtt  300
attgacggtg tgacaccaaa catgattgac ttctttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
```

```
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                    1455

SEQ ID NO: 45          moltype = AA  length = 485
FEATURE                Location/Qualifiers
REGION                 1..485
                       note = Description of Artificial Sequence: Synthetic
                        polypeptide
source                 1..485
                       mol_type = protein
                       organism = synthetic construct
SEQUENCE: 45
MVFTLEDFVG DWRQTAGYNL DQVLEQGGLS SLFQKLGVSV TPIQKIVLSG ENGLKIDIHV  60
IIPYEGLSGF QMGLIEMIFK VVYPVDDHHF KIIHHYGTLV IDGVTPNMID FFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                              485

SEQ ID NO: 46          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 46
atggtgttta cattggagga tttcgttgga gactggcggc agacagctgg atacaaccaa  60
gatcaagtgt tagaacaagg aggagtgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gcc                                513

SEQ ID NO: 47          moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 47
MVFTLEDFVG DWRQTAGYNQ DQVLEQGGVS SLFQKLGVSV TPIQKIVLSG ENGLKIDIHV  60
IIPYEGLSGF QMGLIEMIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 48          moltype = DNA  length = 1455
FEATURE                Location/Qualifiers
misc_feature           1..1455
                       note = Description of Artificial Sequence: Synthetic
                        polynucleotide
source                 1..1455
                       mol_type = other DNA
                       organism = synthetic construct
SEQUENCE: 48
atggtgttta cattggagga tttcgttgga gactggcggc agacagctgg atacaaccaa  60
gatcaagtgt tagaacaagg aggattgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
```

-continued

```
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                  1455

SEQ ID NO: 49          moltype = AA  length = 485
FEATURE                Location/Qualifiers
REGION                 1..485
                       note = Description of Artificial Sequence: Synthetic
                        polypeptide
source                 1..485
                       mol_type = protein
                       organism = synthetic construct
SEQUENCE: 49
MVFTLEDFVG DWRQTAGYNQ DQVLEQGGLS SLFQKLGVSV TPIQKIVLSG ENGLKIDIHV  60
IIPYEGLSGF QMGLIEMIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                             485

SEQ ID NO: 50          moltype = DNA  length = 1455
FEATURE                Location/Qualifiers
misc_feature           1..1455
                       note = Description of Artificial Sequence: Synthetic
                        polynucleotide
source                 1..1455
                       mol_type = other DNA
                       organism = synthetic construct
SEQUENCE: 50
atggtgttta cattggagga tttcgttgga gactggcggc agacagctgg atacaaccaa  60
gatcaagtgt tagaacaagg aggagtgtct agtctgttcc aaaagctggg agtgtcagtc  120
accccaatcc agaaaattgt gctgtctggg gagaatgggt taaaaattga tattcatgtc  180
atcatccctt acgagggact cagtggtttt caaatgggtc tgattgaaat gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                  1455

SEQ ID NO: 51          moltype = AA  length = 485
FEATURE                Location/Qualifiers
REGION                 1..485
                       note = Description of Artificial Sequence: Synthetic
                        polypeptide
source                 1..485
                       mol_type = protein
                       organism = synthetic construct
SEQUENCE: 51
MVFTLEDFVG DWRQTAGYNQ DQVLEQGGVS SLFQKLGVSV TPIQKIVLSG ENGLKIDIHV  60
IIPYEGLSGF QMGLIEMIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
```

```
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                             485

SEQ ID NO: 52           moltype = DNA  length = 1455
FEATURE                 Location/Qualifiers
misc_feature            1..1455
                        note = Description of Artificial Sequence: Synthetic
                         polynucleotide
source                  1..1455
                        mol_type = other DNA
                        organism = synthetic construct
SEQUENCE: 52
atggtgttta cattgaagga tttcgttgga gactggcggc agacagctgg atacaaccaa  60
gatcaagtgt tagaacaagg aggattgtct agtctgttcc aaaatctggg agtgtcagtc  120
accccaatcc agaaaattgt gctgtctggg gagaatgggt taaaaattga tattcatgtc  180
atcatccctt acgagggact cagtggttat caaatgggtc agattgaaaa gatcttcaaa  240
gttgtttacc cagtggatga tcatcatttc aaggttattc tccattatgg tacactcgtt  300
attgacggtg tgacaccaaa catgattgac tactttggac gcccttacga gggaattgct  360
gtgtttgacg gcaagaagat cacagttact ggaactctgt ggaacggcaa caagatcatt  420
gatgagcgcc tgatcaaccc agatggttca ctcctcttcc gcgttactat caatggagtc  480
accggatggc gcctttgcga gcgtattctt gccggatatc tcgagccaac cactgaggat  540
ctgtactttc agagcgataa cgatggatcc gaaatcggta ctggctttcc attcgacccc  600
cattatgtgg aagtcctggg cgagcgcatg cactacgtcg atgttggtcc gcgcgatggc  660
acccctgtgc tgttcctgca cggtaacccg acctcctcct acgtgtggcg caacatcatc  720
ccgcatgttg caccgaccca tcgctgcatt gctccagacc tgatcggtat gggcaaatcc  780
gacaaaccag acctgggtta tttcttcgac gaccacgtcc gcttcatgga tgccttcatc  840
gaagccctgg gtctggaaga ggtcgtcctg gtcattcacg actggggctc cgctctgggt  900
ttccactggg ccaagcgcaa tccagagcgc gtcaaaggta ttgcatttat ggagttcatc  960
cgccctatcc cgacctggga cgaatggcca gaatttgccc gcgagacctt ccaggccttc  1020
cgcaccaccg acgtcggccg caagctgatc atcgatcaga acgtttttat cgagggtacg  1080
ctgccgatgg gtgtcgtccg cccgctgact gaagtcgaga tggaccatta ccgcgagccg  1140
ttcctgaatc ctgttgaccg cgagccactg tggcgcttcc caaacgagct gccaatcgcc  1200
ggtgagccag cgaacatcgt cgcgctggtc gaagaataca tggactggct gcaccagtcc  1260
cctgtcccga agctgctgtt ctggggcacc ccaggcgttc tgatcccacc ggccgaagcc  1320
gctcgcctgg ccaaaagcct gcctaactgc aaggctgtgg acatcggccc gggtctgaat  1380
ctgctgcaag aagacaaccc ggacctgatc ggcagcgaga tcgcgcgctg gctgtctact  1440
ctggagattt ccggt                                                  1455

SEQ ID NO: 53           moltype = AA  length = 485
FEATURE                 Location/Qualifiers
REGION                  1..485
                        note = Description of Artificial Sequence: Synthetic
                         polypeptide
source                  1..485
                        mol_type = protein
                        organism = synthetic construct
SEQUENCE: 53
MVFTLKDFVG DWRQTAGYNQ DQVLEQGGLS SLFQNLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGYLEPTTED  180
LYFQSDNDGS EIGTGFPFDP HYVEVLGERM HYVDVGPRDG TPVLFLHGNP TSSYVWRNII  240
PHVAPTHRCI APDLIGMGKS DKPDLGYFFD DHVRFMDAFI EALGLEEVVL VIHDWGSALG  300
FHWAKRNPER VKGIAFMEFI RPIPTWDEWP EFARETFQAF RTTDVGRKLI IDQNVFIEGT  360
LPMGVVRPLT EVEMDHYREP FLNPVDREPL WRFPNELPIA GEPANIVALV EEYMDWLHQS  420
PVPKLLFWGT PGVLIPPAEA ARLAKSLPNC KAVDIGPGLN LLQEDNPDLI GSEIARWLST  480
LEISG                                                             485

SEQ ID NO: 54           moltype = DNA  length = 81
FEATURE                 Location/Qualifiers
source                  1..81
                        mol_type = genomic DNA
                        organism = Oplophorus gracilirostris
SEQUENCE: 54
atggcttact ccacactgtt catcattgct ctcacagccg tcgtaacaca agcctcctcc  60
acacagaaaa gcaacctgac a                                           81

SEQ ID NO: 55           moltype = DNA  length = 1875
FEATURE                 Location/Qualifiers
misc_feature            1..1875
                        note = Description of Artificial Sequence: Synthetic
                         polynucleotide
source                  1..1875
                        mol_type = other DNA
                        organism = synthetic construct
SEQUENCE: 55
atgcttggtc tgtcggagca aagcgtgtcc atctcgcgct gcgctgggac gcgcctgccc  60
```

```
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cattggagga tttcgttgga gactggcggc agacagctgg atacaaccaa  480
gatcaagtgt tagaacaagg aggattgtct agtctgttcc aaaagctggg agtgtcagtc  540
accccaatcc agaaaattgt gctgtctggg gagaatgggt taaaatttga tattcatgtc  600
atcatccctt acgagggact cagtggtttt caaatgggtc tgattgaaat gatcttcaaa  660
gttgtttacc cagtggatga tcatcatttc aagattattc tccattatgg tacactcgtt  720
attgacggtg tgacaccaaa catgattgac tactttggac gcccttacga gggaattgct  780
gtgtttgacg gcaagaagat cacagttact ggaactctgt ggaacggcaa caagatcatt  840
gatgagcgcc tgatcaaccc agatggttca ctcctcttcc gcgttactat caatggagtc  900
accggatggc gcctttgcga gcgtattctt gccggatctc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                  1875
```

```
SEQ ID NO: 56          moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 56
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNQ DQVLEQGGLS SLFQKLGVSV  180
TPIQKIVLSG ENGLKFDIHV IIPYEGLSGF QMGLIEMIFK VVYPVDDHHF KIILHYGTLV  240
IDGVTPNMID YFGRPYEGIA VFDGKKITVT GTLWNGNKII DERLINPDGS LLFRVTINGV  300
TGWRLCERIL AGSLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                     625
```

```
SEQ ID NO: 57          moltype = DNA  length = 1875
FEATURE                Location/Qualifiers
misc_feature           1..1875
                       note = Description of Artificial Sequence: Synthetic
                        polynucleotide
source                 1..1875
                       mol_type = other DNA
                       organism = synthetic construct
SEQUENCE: 57
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cattggagga tttcgttgga gactggcggc agacagctgg atacaaccaa  480
gatcaagtgt tagaacaagg aggattgtct agtctgttcc aaaagctggg agtgtcagtc  540
accccaatcc agaaaattgt gctgtctggg gagaatgggt taaaaattga tattcatgtc  600
atcatccctt acgagggact cagtggtttt caaatgggtc tgattgaaat gatcttcaaa  660
gttgtttacc cagtggatga tcatcatttc aaggttattc tccattatgg tacactcgtt  720
attgacggtg tgacaccaaa catgattgac tactttggac gcccttacga gggaattgct  780
gtgtttgacg gcaagaagat cacagttact ggaactctgt ggaacggcaa caagatcatt  840
gatgagcgcc tgatcaaccc agatggttca ctcctcttcc gcgttactat caatggagtc  900
accggatggc gcctttgcga gcgtattctt gccgtttctc tcgagccaac cactgaggat  960
ctgtactttc agagcgataa cgatggatcc gaaatcggta ctggctttcc attcgacccc  1020
```

```
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                    1875

SEQ ID NO: 58          moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 58
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNQ DQVLEQGGLS SLFQKLGVSV  180
TPIQKIVLSG ENGLKIDIHV IIPYEGLSGF QMGLIEMIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AVSLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                         625

SEQ ID NO: 59          moltype = DNA  length = 1875
FEATURE                Location/Qualifiers
misc_feature           1..1875
                       note = Description of Artificial Sequence: Synthetic
                        polynucleotide
source                 1..1875
                       mol_type = other DNA
                       organism = synthetic construct
SEQUENCE: 59
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gaccaagtcc ttgagcaggg cggtctgtcc agtttgtttc agaatctcgg ggtgtccgta  540
acaccgatcc aaaagattgt cctgagcggt gaaaacggcc tgaagatcga catccatgtc  600
atcatcccgt atgaaggtct gagcggctat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                    1875
```

```
SEQ ID NO: 60          moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 60
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQNLGVSV  180
TPIQKIVLSG ENGLKIDIHV IIPYEGLSGY QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                      625

SEQ ID NO: 61          moltype = DNA  length = 1875
FEATURE                Location/Qualifiers
misc_feature           1..1875
                       note = Description of Artificial Sequence: Synthetic
                        polynucleotide
source                 1..1875
                       mol_type = other DNA
                       organism = synthetic construct
SEQUENCE: 61
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cattggagga tttcgttgga gactggcggc agacagctgg atacaaccta  480
gatcaagtgt tagaacaagg aggattgtct agtctgttcc aaaagctggg agtgtcagtc  540
accccaatcc agaaaattgt gctgtctggg gagaatgggt taaaaattga tattcatgtc  600
atcatccctt acgagggact cagtggttat caaatgggtc agattgaaaa gatcttcaaa  660
gttgtttacc cagtggatga tcatcatttc aaggttattc tccattatgg tacactcgtt  720
attgacggtg tgacaccaaa catgattgac tactttggac gcccttacga gggaattgct  780
gtgtttgacg gcaagaagat cacagttact ggaactctgt ggaacggcaa caagatcatt  840
gatgagcgcc tgatcaaccc agatggttca ctcctcttcc gcgttactat caatggagtc  900
accggatggc gcctttgcga gcgtattctt gccgtttctc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                 1875

SEQ ID NO: 62          moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 62
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQKLGVSV  180
TPIQKIVLSG ENGLKIDIHV IIPYEGLSGY QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AVSLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
```

```
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                        625

SEQ ID NO: 63           moltype = DNA  length = 1875
FEATURE                 Location/Qualifiers
misc_feature            1..1875
                        note = Description of Artificial Sequence: Synthetic
                         polynucleotide
source                  1..1875
                        mol_type = other DNA
                        organism = synthetic construct
SEQUENCE: 63
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cattggagga tttcgttgga gactggcggc agacagctgg atacaaccta  480
gatcaagtgt tagaacaagg aggagtgtct agtctgttcc aaaagctggg agtgtcaatc  540
accccaatcc agaaaattgt gctgtctggg gagaatgggt taaaaattga tattcatgtc  600
atcatccctt acgagggact cagtggttat caaatgggtc agattgaaaa gatcttcaaa  660
gttgtttacc cagtggatga tcatcatttc aaggttattc tccattatgg tacactcgtt  720
attgacggtg tgacaccaaa catgattgac tactttggac gcccttacga gggaattgct  780
gtgtttgacg gcaagaagat cacagttact ggaactctgt ggaacggcaa caagatcatt  840
gatgagcgcc tgatcaaccc agatggttca ctcctcttcc gcgttactat caatggagtc  900
accggatggc gcctttgcga gcgtattctt gccgtttctc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                   1875

SEQ ID NO: 64           moltype = AA  length = 625
FEATURE                 Location/Qualifiers
REGION                  1..625
                        note = Description of Artificial Sequence: Synthetic
                         polypeptide
source                  1..625
                        mol_type = protein
                        organism = synthetic construct
SEQUENCE: 64
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGAIA MVFTLEDFVG DWRQTAGYNL DQVLEQGGVS SLFQKLGVSI  180
TPIQKIVLSG ENGLKIDIHV IIPYEGLSGY QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AVSLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                        625

SEQ ID NO: 65           moltype = DNA  length = 636
FEATURE                 Location/Qualifiers
misc_feature            1..636
                        note = Description of Artificial Sequence: Synthetic
                         polynucleotide
source                  1..636
                        mol_type = other DNA
                        organism = synthetic construct
SEQUENCE: 65
atggtgttta cactcgaaga tttcgtaggg gactggcggc agacagccgg ctacaacctg  60
gaccaagtcc ttgagcaggg cggtctgtcc agtttgtttc agaaactcgg ggtgtccgta  120
```

```
acaccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcgaattctc acggcttccc tcccgaggtg  540
gaggagcagg ccgccggcac cctgcccatg agctgcgccc aggagagcgg catggataga  600
caccctgctg cttgcgccag cgccaggatc aacgtc                            636

SEQ ID NO: 66          moltype = DNA  length = 82
FEATURE                Location/Qualifiers
misc_feature           1..82
                       note = Description of Unknown: antioxidant response element
                        (2X ARE) oligonucleotide
source                 1..82
                       mol_type = other DNA
                       organism = unidentified
SEQUENCE: 66
tagcttggaa atgacattgc taatggtgac aaagcaactt ttagcttgga aatgacattg  60
ctaatggtga caaagcaact tt                                          82

SEQ ID NO: 67          moltype = DNA  length = 45
FEATURE                Location/Qualifiers
misc_feature           1..45
                       note = Description of Unknown: heat shock response element
                        (HRE) oligonucleotide
source                 1..45
                       mol_type = other DNA
                       organism = unidentified
SEQUENCE: 67
ctggaatttt ctagactgga attttctaga ctggaatttt ctaga                 45

SEQ ID NO: 68          moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 68
atggtgttta cactcgaaga tttcgtaggg gactggcggc agacagccgg ctacaacctg  60
gaccaagtcc ttgagcaggg cggtctgtcc agtttgtttc agaatctcgg ggtgtccgta  120
acaccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcggga                            516

SEQ ID NO: 69          moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 69
MVFTLEDFVG DWRQTAGYNL DQVLEQGGLS SLFQNLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AG          172

SEQ ID NO: 70          moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 70
atggtgttta cactcgaaga tttcgtaggg gactggcggc agacagccgg ctacaacctg  60
gaccaagtcc ttgagcaggg cggtctgtcc agtttgtttc agaatctcgg ggtgtccgta  120
actccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
```

```
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcggga                            516

SEQ ID NO: 71          moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 71
MVFTLEDFVG DWRQTAGYNL DQVLEQGGLS SLFQNLGVSV TPIQKIVLSG ENGLKIDIHV  60
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AG          172

SEQ ID NO: 72          moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 72
atggtgttta cactcgaaga tttcgtaggg gactggcggc agacagccgg ctacaacctg  60
gaccaagtcc ttgagcaggg cggcctgtcc agtttgtttc agaatctcgg ggtgtccgta  120
acaccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
atcgacgggg ttacgccgaa cttgatcgac tatttcggac gtccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcggga                            516

SEQ ID NO: 73          moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 73
MVFTLEDFVG DWRQTAGYNL DQVLEQGGLS SLFQNLGVSV TPIQKIVLSG ENGLKIDIHV  60
IIPYEGLSGY QMGQIEKIFK VVYPVDDHHF KVILHYGTLV IDGVTPNLID YFGRPYEGIA  120
VFDGKKITVT GTLWNGNKII DERLINPDGS LLFRVTINGV TGWRLCERIL AG          172

SEQ ID NO: 74          moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 74
atggtgttta cactcgaaga tttcgtaggg gactggcagc agacagccgg ctacaacctg  60
gaccaagtcc ttgagcaggg cggtctgtcc agtttgtttc agaatctcgg ggtgtccgta  120
actccgatcc aaaagattgt cctgagcggt gaaaacggcc tgaagatcga catccatgtc  180
atcatcccgt atgaaggtct gagcggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcggga                            516

SEQ ID NO: 75          moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 75
MVFTLEDFVG DWQQTAGYNL DQVLEQGGLS SLFQNLGVSV TPIQKIVLSG ENGLKIDIHV  60
```

-continued

```
IIPYEGLSGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AG          172

SEQ ID NO: 76           moltype = DNA  length = 1797
FEATURE                 Location/Qualifiers
misc_feature            1..1797
                        note = Description of Artificial Sequence: Synthetic
                         polynucleotide
source                  1..1797
                        mol_type = other DNA
                        organism = synthetic construct
SEQUENCE: 76
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gaccaagtcc ttgagcaggg cggcctgtcc agtttgtttc agaatctcgg ggtgtccgta  540
acaccgatcc aaaagattgt cctgagcggt gaaaacggcc tgaagatcga catccatgtc  600
atcatcccgt atgaaggtct gagcggctat cagatgggcc agatcgaaaa aatttttaag  660
gtggtgtacc ctgtggatga tcatcacttt aaggtgattc tgcactatgg cacactggta  720
atcgacgggg ttacgccgaa cttgatcgac tatttcggac gtccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctg     1797

SEQ ID NO: 77           moltype = AA  length = 599
FEATURE                 Location/Qualifiers
REGION                  1..599
                        note = Description of Artificial Sequence: Synthetic
                         polypeptide
source                  1..599
                        mol_type = protein
                        organism = synthetic construct
SEQUENCE: 77
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQNLGVSV  180
TPIQKIVLSG ENGLKIDIHV IIPYEGLSGY QMGQIEKIFK VVYPVDDHHF KVILHYGTLV  240
IDGVTPNLID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGL   599

SEQ ID NO: 78           moltype = DNA  length = 1875
FEATURE                 Location/Qualifiers
misc_feature            1..1875
                        note = Description of Artificial Sequence: Synthetic
                         polynucleotide
source                  1..1875
                        mol_type = other DNA
                        organism = synthetic construct
SEQUENCE: 78
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
```

-continued

```
atggtgttta cactcgaaga tttcgtaggg gactggcagc agacagccgg ctacaacctg  480
gaccaagtcc ttgagcaggg cggtctgtcc agtttgtttc agaatctcgg ggtgtccgta  540
actccgatcc aaaagattgt cctgagcggt gaaaacggcc tgaagatcga catccatgtc  600
atcatcccgt atgaaggtct gagcggctat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
accoctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                   1875
```

```
SEQ ID NO: 79          moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 79
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWQQTAGYNL DQVLEQGGLS SLFQNLGVSV  180
TPIQKIVLSG ENGLKIDIHV IIPYEGLSGY QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                        625
```

```
SEQ ID NO: 80          moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 80
atggtgttta cactcgaaga tttcgtaggg gactggcggc agacagccgg ctacaacctg  60
gaccaagtcc ttgagcaggg cggtctgtcc agtttgtttc agaatctcgg ggtgtccgta  120
acaccgatcc aaaggattgt cctgagcggt gaaaacggcc tgaagatcga catccatgtc  180
atcatcccgt atgaaggtct gagcggcgat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcggga                            516
```

```
SEQ ID NO: 81          moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 81
MVFTLEDFVG DWRQTAGYNL DQVLEQGGLS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AG          172
```

```
SEQ ID NO: 82           moltype = DNA  length = 516
FEATURE                 Location/Qualifiers
misc_feature            1..516
                        note = Description of Artificial Sequence: Synthetic
                         polynucleotide
source                  1..516
                        mol_type = other DNA
                        organism = synthetic construct
SEQUENCE: 82
atggtgttta cactcgaaga tttcgtaggg gactggcggc agacagccgg ctacaacctg  60
gatcaagtcc ttgagcaggg cggtctgtcc agtttgtttc agaatctcgg ggtgtccgta  120
acaccgatcc aaaagattgt cctgagcggt gaaaacggcc tgaagatcga catccatgtc  180
atcatcccgt atgaaggtct gaacggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcggga                            516

SEQ ID NO: 83           moltype = AA  length = 172
FEATURE                 Location/Qualifiers
REGION                  1..172
                        note = Description of Artificial Sequence: Synthetic
                         polypeptide
source                  1..172
                        mol_type = protein
                        organism = synthetic construct
SEQUENCE: 83
MVFTLEDFVG DWRQTAGYNL DQVLEQGGLS SLFQNLGVSV TPIQKIVLSG ENGLKIDIHV  60
IIPYEGLNGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AG          172

SEQ ID NO: 84           moltype = DNA  length = 1866
FEATURE                 Location/Qualifiers
misc_feature            1..1866
                        note = Description of Artificial Sequence: Synthetic
                         polynucleotide
source                  1..1866
                        mol_type = other DNA
                        organism = synthetic construct
SEQUENCE: 84
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gaccaagtcc ttgagcaggg cggtctgtcc agtttgtttc agaatctcgg ggtgtccgta  540
acaccgatcc aaaggattgt cctgagcggt gaaaacggcc tgaagatcga catccatgtc  600
atcatcccgt atgaaggtct gagcggcgat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggag                                                             1866

SEQ ID NO: 85           moltype = AA  length = 625
FEATURE                 Location/Qualifiers
REGION                  1..625
                        note = Description of Artificial Sequence: Synthetic
                         polypeptide
```

```
source                  1..625
                        mol_type = protein
                        organism = synthetic construct
SEQUENCE: 85
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQNLGVSV  180
TPIQRIVLSG ENGLKIDIHV IIPYEGLSGD QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                      625

SEQ ID NO: 86           moltype = DNA  length = 1875
FEATURE                 Location/Qualifiers
misc_feature            1..1875
                        note = Description of Artificial Sequence: Synthetic
                         polynucleotide
source                  1..1875
                        mol_type = other DNA
                        organism = synthetic construct
SEQUENCE: 86
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gatcaagtcc ttgagcaggg cggtctgtcc agtttgtttc agaatctcgg ggtgtccgta  540
acaccgatcc aaaagattgt cctgagcggt gaaaacggcc tgaagatcga catccatgtc  600
atcatcccgt atgaaggtct gaacggctat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                 1875

SEQ ID NO: 87           moltype = AA  length = 625
FEATURE                 Location/Qualifiers
REGION                  1..625
                        note = Description of Artificial Sequence: Synthetic
                         polypeptide
source                  1..625
                        mol_type = protein
                        organism = synthetic construct
SEQUENCE: 87
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQNLGVSV  180
TPIQKIVLSG ENGLKIDIHV IIPYEGLNGY QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                      625
```

```
SEQ ID NO: 88          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 88
atggtgttta cactcgaaga tttcgtaggg gactggcggc agacagccgg ctacaacctg  60
gaccaagtcc ttgagcaggg cggtgtgtcc agtttgtttc agaatctcgg ggtgtccgta  120
actccgatcc aaaggattgt cctgagcggt gaaaacggcc tgaagatcga catccatgtc  180
atcatcccgt atgaaggtct gagcggcgat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                              513

SEQ ID NO: 89          moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 89
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 90          moltype = DNA  length = 1875
FEATURE                Location/Qualifiers
misc_feature           1..1875
                       note = Description of Artificial Sequence: Synthetic
                        polynucleotide
source                 1..1875
                       mol_type = other DNA
                       organism = synthetic construct
SEQUENCE: 90
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg gggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gaccaagtcc ttgagcaggg cggtgtgtcc agtttgtttc agaatctcgg ggtgtccgta  540
actccgatcc aaaggattgt cctgagcggt gaaaacggcc tgaagatcga catccatgtc  600
atcatcccgt atgaaggtct gagcggcgat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                  1875

SEQ ID NO: 91          moltype = AA  length = 625
FEATURE                Location/Qualifiers
REGION                 1..625
                       note = Description of Artificial Sequence: Synthetic
                        polypeptide
```

```
source                  1..625
                        mol_type = protein
                        organism = synthetic construct
SEQUENCE: 91
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGVS SLFQNLGVSV  180
TPIQRIVLSG ENGLKIDIHV IIPYEGLSGD QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                      625

SEQ ID NO: 92           moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 92
atggtgttta cactcgaaga tttcgtaggg gactggcggc agacagccgg ctacaacctg  60
gaccaagtcc ttgagcaggg cggtctgtcc agtttgtttc agaatctcgg ggtgtccgta  120
actccgatcc aaaggattgt cctgagcggt gaaaacggcc tgaagatcga catccatgtc  180
atcatcccgt atgaaggtct gagcggcgat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                             513

SEQ ID NO: 93           moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 93
MVFTLEDFVG DWRQTAGYNL DQVLEQGGLS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 94           moltype = DNA  length = 1875
FEATURE                 Location/Qualifiers
misc_feature            1..1875
                        note = Description of Artificial Sequence: Synthetic
                         polynucleotide
source                  1..1875
                        mol_type = other DNA
                        organism = synthetic construct
SEQUENCE: 94
atgcttggtc tgtcggagca aagcgtgtcc atctcgcgct gcgctgggac gcgcctgccc  60
gccttgctgg acgagcagca ggtgaacgtc ctgctctacg acatgaacgg ctgctactca  120
cgcctcaagg agctggtgcc caccctgccc cagaaccgca aagtgagcaa ggtggagatc  180
ctgcagcatg taatcgacta catcagggac ctgcagctgg agctgaactc ggagtctgaa  240
gtcgggacca ccggaggccg ggactgcct gtccgcgccc cgctcagcac cctgaacggc  300
gagatcagtg ccttggcggc cgaggcggca tgtgttccag ccgacgatcg catcttgtgt  360
cgcgtttctc ttgagaatct ttattttcag gcgtctggag gtggtggcgg agcgatcgcc  420
atggtgttta cactcgaaga tttcgtaggg gactggcggc agacagccgg ctacaacctg  480
gaccaagtcc ttgagcaggg cggtctgtcc agtttgtttc agaatctcgg ggtgtccgta  540
actccgatcc aaaggattgt cctgagcggt gaaaacggcc tgaagatcga catccatgtc  600
atcatcccgt atgaaggtct gagcggcgat cagatgggcc agatcgaaaa aatttttaag  660
gtggtgtacc ctgtggatga tcatcacttt aaggtgattc tgcactatgg cacactggta  720
atcgacgggg ttacgccgaa catgatcgac tatttcggac ggccgtatga aggcatcgcc  780
gtgttcgacg gcaaaaagat cactgtaacc gggaccctgt ggaacggcaa caaaattatc  840
gacgagcgcc tgatcaaccc cgacggctcc ctgctgttcc gcgtaaccat caacggagtg  900
accggctggc ggctgtgcga gcgcattttg gcgggatatc tcgagccaac cactgaggat  960
ctgtactttc agagcgataa cgatggatcc gaaatcggta ctggctttcc attcgacccc  1020
cattatgtgg aagtcctggg cgagcgcatg cactacgtcg atgttggtcc gcgcgatggc  1080
acccctgtgc tgttcctgca cggtaacccg acctcctcct acgtgtggcg caacatcatc  1140
ccgcatgttg caccgaccca tcgctgcatt gctccagacc tgatcggtat gggcaaatcc  1200
gacaaaccag acctgggtta tttcttcgac gaccacgtcc gcttcatgga tgccttcatc  1260
gaagccctgg gtctggaaga ggtcgtcctg gtcattcacg actggggctc cgctctgggt  1320
```

-continued

```
ttccactggg ccaagcgcaa tccagagcgc gtcaaaggta ttgcatttat ggagttcatc  1380
cgccctatcc cgacctggga cgaatggcca gaatttgccc gcgagacctt ccaggccttc  1440
cgcaccaccg acgtcggccg caagctgatc atcgatcaga acgtttttat cgagggtacg  1500
ctgccgatgg gtgtcgtccg cccgctgact gaagtcgaga tggaccatta ccgcgagccg  1560
ttcctgaatc ctgttgaccg cgagccactg tggcgcttcc caaacgagct gccaatcgcc  1620
ggtgagccag cgaacatcgt cgcgctggtc gaagaataca tggactggct gcaccagtcc  1680
cctgtcccga agctgctgtt ctggggcacc ccaggcgttc tgatcccacc ggccgaagcc  1740
gctcgcctgg ccaaaagcct gcctaactgc aaggctgtgg acatcggccc gggtctgaat  1800
ctgctgcaag aagacaaccc ggacctgatc ggcagcgaga tcgcgcgctg gctgtctact  1860
ctggagattt ccggt                                                    1875

SEQ ID NO: 95          moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 95
MLGLSEQSVS ISRCAGTRLP ALLDEQQVNV LLYDMNGCYS RLKELVPTLP QNRKVSKVEI  60
LQHVIDYIRD LQLELNSESE VGTTGGRGLP VRAPLSTLNG EISALAAEAA CVPADDRILC  120
RVSLENLYFQ ASGGGGGAIA MVFTLEDFVG DWRQTAGYNL DQVLEQGGLS SLFQNLGVSV  180
TPIQRIVLSG ENGLKIDIHV IIPYEGLSGD QMGQIEKIFK VVYPVDDHHF KVILHYGTLV  240
IDGVTPNMID YFGRPYEGIA VFDGKKITVT GTLWNGNKII DERLINPDGS LLFRVTINGV  300
TGWRLCERIL AGYLEPTTED LYFQSDNDGS EIGTGFPFDP HYVEVLGERM HYVDVGPRDG  360
TPVLFLHGNP TSSYVWRNII PHVAPTHRCI APDLIGMGKS DKPDLGYFFD DHVRFMDAFI  420
EALGLEEVVL VIHDWGSALG FHWAKRNPER VKGIAFMEFI RPIPTWDEWP EFARETFQAF  480
RTTDVGRKLI IDQNVFIEGT LPMGVVRPLT EVEMDHYREP FLNPVDREPL WRFPNELPIA  540
GEPANIVALV EEYMDWLHQS PVPKLLFWGT PGVLIPPAEA ARLAKSLPNC KAVDIGPGLN  600
LLQEDNPDLI GSEIARWLST LEISG                                         625

SEQ ID NO: 96          moltype = DNA  length = 87
FEATURE                Location/Qualifiers
misc_feature           1..87
                       note = Description of Unknown: cAMP-response element (CRE)
                        oligonucleotide
source                 1..87
                       mol_type = other DNA
                       organism = unidentified
SEQUENCE: 96
gcaccagaca gtgacgtcag ctgccagatc ccatggccgt catactgtga cgtctttcag  60
acacccccttg acgtcaatgg gagaaca                                      87

SEQ ID NO: 97          moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 97
atggatgatc atcactttaa ggtgattctg cactatggca cactggtaat cgacggggtt  60
acgccgaaca tgatcgacta tttcggacgg ccgtatgaag gcatcgccgt gttcgacggc  120
aaaaagatca ctgtaaccgg gaccctgtgg aacggcaaca aaattatcga cgagcgcctg  180
atcaaccccg acggctccct gctgttccgc gtaaccatca acggagtgac cggctggcgg  240
ctgtgcgagc gcattttggc gatggtgttt acactcgaag atttcgtagg ggactggcgg  300
cagacagccg gctacaacct ggaccaagtc cttgagcagg gcggtgtgtc cagtttgttt  360
cagaatctcg ggtgtccgt aactccgatc caaaggattg tcctgagcgg tgaaaacggc  420
ctgaagatcg acatccatgt catcatcccg tatgaaggtc tgagcggcga tcagatgggc  480
cagatcgaaa aaatttttaa ggtggtgtac cctgtg                             516

SEQ ID NO: 98          moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 98
MDDHHFKVIL HYGTLVIDGV TPNMIDYFGR PYEGIAVFDG KKITVTGTLW NGNKIIDERL  60
INPDGSLLFR VTINGVTGWR LCERILAMVF TLEDFVGDWR QTAGYNLDQV LEQGGVSSLF  120
QNLGVSVTPI QRIVLSGENG LKIDIHVIIP YEGLSGDQMG QIEKIFKVVY PV           172

SEQ ID NO: 99          moltype = DNA  length = 531
FEATURE                Location/Qualifiers
misc_feature           1..531
```

```
                        note = Description of Artificial Sequence: Synthetic
                         polynucleotide
source                  1..531
                        mol_type = other DNA
                        organism = synthetic construct
SEQUENCE: 99
atggatgatc atcactttaa ggtgattctg cactatggca cactggtaat cgacggggtt  60
acgccgaaca tgatcgacta tttcggacgg ccgtatgaag gcatcgccgt gttcgacggc  120
aaaaagatca ctgtaaccgg gaccctgtgg aacggcaaca aaattatcga cgagcgcctg  180
atcaaccccg acggctccct gctgttccgc gtaaccatca acggagtgac cggctggcgg  240
ctgtgcgagc gcattttggc ggggagctcc ggtggaatgg tgtttacact cgaagatttc  300
gtaggggact ggcggcagac agccggctac aacctggacc aagtccttga gcagggcggt  360
gtgtccagtt tgtttcagaa tctcggggtg tccgtaactc cgatccaaag gattgtcctg  420
agcggtgaaa acggcctgaa gatcgacatc catgtcatca tcccgtatga aggtctgagc  480
ggcgatcaga tgggccagat cgaaaaaatt tttaaggtgg tgtaccctgt g           531

SEQ ID NO: 100          moltype = AA  length = 177
FEATURE                 Location/Qualifiers
REGION                  1..177
                        note = Description of Artificial Sequence: Synthetic
                         polypeptide
source                  1..177
                        mol_type = protein
                        organism = synthetic construct
SEQUENCE: 100
MDDHHFKVIL HYGTLVIDGV TPNMIDYFGR PYEGIAVFDG KKITVTGTLW NGNKIIDERL  60
INPDGSLLFR VTINGVTGWR LCERILAGSS GGMVFTLEDF VGDWRQTAGY NLDQVLEQGG  120
VSSLFQNLGV SVTPIQRIVL SGENGLKIDI HVIIPYEGLS GDQMGQIEKI FKVVYPV     177

SEQ ID NO: 101          moltype = DNA  length = 546
FEATURE                 Location/Qualifiers
misc_feature            1..546
                        note = Description of Artificial Sequence: Synthetic
                         polynucleotide
source                  1..546
                        mol_type = other DNA
                        organism = synthetic construct
SEQUENCE: 101
atggatgatc atcactttaa ggtgattctg cactatggca cactggtaat cgacggggtt  60
acgccgaaca tgatcgacta tttcggacgg ccgtatgaag gcatcgccgt gttcgacggc  120
aaaaagatca ctgtaaccgg gaccctgtgg aacggcaaca aaattatcga cgagcgcctg  180
atcaaccccg acggctccct gctgttccgc gtaaccatca acggagtgac cggctggcgg  240
ctgtgcgagc gcattttggc gggaagttct ggtggaggga gctccggtgg aatggtgttt  300
acactcgaag atttcgtagg ggactggcgg cagacagccg gctacaacct ggaccaagtc  360
cttgagcagg gcggtgtgtc cagtttgttt cagaatctcg gggtgtccgt aactccgatc  420
caaaggattg tcctgagcgg tgaaaacggc ctgaagatcg acatccatgt catcatcccg  480
tatgaaggtc tgagcggcga tcagatgggc cagatcgaaa aaatttttaa ggtggtgtac  540
cctgtg                                                             546

SEQ ID NO: 102          moltype = AA  length = 182
FEATURE                 Location/Qualifiers
REGION                  1..182
                        note = Description of Artificial Sequence: Synthetic
                         polypeptide
source                  1..182
                        mol_type = protein
                        organism = synthetic construct
SEQUENCE: 102
MDDHHFKVIL HYGTLVIDGV TPNMIDYFGR PYEGIAVFDG KKITVTGTLW NGNKIIDERL  60
INPDGSLLFR VTINGVTGWR LCERILAGSS GGGSSGGMVF TLEDFVGDWR QTAGYNLDQV  120
LEQGGVSSLF QNLGVSVTPI QRIVLSGENG LKIDIHVIIP YEGLSGDQMG QIEKIFKVVY  180
PV                                                                 182

SEQ ID NO: 103          moltype = DNA  length = 576
FEATURE                 Location/Qualifiers
misc_feature            1..576
                        note = Description of Artificial Sequence: Synthetic
                         polynucleotide
source                  1..576
                        mol_type = other DNA
                        organism = synthetic construct
SEQUENCE: 103
atggatgatc atcactttaa ggtgattctg cactatggca cactggtaat cgacggggtt  60
acgccgaaca tgatcgacta tttcggacgg ccgtatgaag gcatcgccgt gttcgacggc  120
aaaaagatca ctgtaaccgg gaccctgtgg aacggcaaca aaattatcga cgagcgcctg  180
atcaaccccg acggctccct gctgttccgc gtaaccatca acggagtgac cggctggcgg  240
ctgtgcgagc gcattttggc gggaagttct ggtggaggga gctccggtgg aggaagttct  300
ggtggaggga gctccggtgg aatggtgttt acactcgaag atttcgtagg ggactggcgg  360
cagacagccg gctacaacct ggaccaagtc cttgagcagg gcggtgtgtc cagtttgttt  420
```

```
cagaatctcg gggtgtccgt aactccgatc caaaggattg tcctgagcgg tgaaaacggc  480
ctgaagatcg acatccatgt catcatcccg tatgaaggtc tgagcggcga tcagatgggc  540
cagatcgaaa aaatttttaa ggtggtgtac cctgtg                            576

SEQ ID NO: 104         moltype = AA  length = 192
FEATURE                Location/Qualifiers
REGION                 1..192
                       note = Description of Artificial Sequence: Synthetic
                        polypeptide
source                 1..192
                       mol_type = protein
                       organism = synthetic construct
SEQUENCE: 104
MDDHHFKVIL HYGTLVIDGV TPNMIDYFGR PYEGIAVFDG KKITVTGTLW NGNKIIDERL  60
INPDGSLLFR VTINGVTGWR LCERILAGSS GGGSSGGGSS GGGSSGGMVF TLEDFVGDWR  120
QTAGYNLDQV LEQGGVSSLF QNLGVSVTPI QRIVLSGENG LKIDIHVIIP YEGLSGDQMG  180
QIEKIFKVVY PV                                                      192

SEQ ID NO: 105         moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 105
atgggcacac tggtaatcga cggggttacg ccgaacatga tcgactattt cggacggccg  60
tatgaaggca tcgccgtgtt cgacggcaaa aagatcactg taaccgggac cctgtggaac  120
ggcaacaaaa ttatcgacga gcgcctgatc aaccccgacg gctccctgct gttccgcgta  180
accatcaacg gagtgaccgg ctggcggctg tgcgagcgca ttttggcgat ggtgtttaca  240
ctcgaagatt tcgtagggga ctggcggcag acagccggct acaacctgga ccaagtcctt  300
gagcagggcg gtgtgtccag tttgtttcag aatctcgggg tgtccgtaac tccgatccaa  360
aggattgtcc tgagcggtga aaacggcctg aagatcgaca tccatgtcat catcccgtat  420
gaaggtctga gcggcgatca gatgggccag atcgaaaaaa tttttaaggt ggtgtaccct  480
gtggatgatc atcactttaa ggtgattctg cactat                            516

SEQ ID NO: 106         moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 106
MGTLVIDGVT PNMIDYFGRP YEGIAVFDGK KITVTGTLWN GNKIIDERLI NPDGSLLFRV  60
TINGVTGWRL CERILAMVFT LEDFVGDWRQ TAGYNLDQVL EQGGVSSLFQ NLGVSVTPIQ  120
RIVLSGENGL KIDIHVIIPY EGLSGDQMGQ IEKIFKVVYP VDDHHFKVIL HY          172

SEQ ID NO: 107         moltype = DNA  length = 531
FEATURE                Location/Qualifiers
misc_feature           1..531
                       note = Description of Artificial Sequence: Synthetic
                        polynucleotide
source                 1..531
                       mol_type = other DNA
                       organism = synthetic construct
SEQUENCE: 107
atgggcacac tggtaatcga cggggttacg ccgaacatga tcgactattt cggacggccg  60
tatgaaggca tcgccgtgtt cgacggcaaa aagatcactg taaccgggac cctgtggaac  120
ggcaacaaaa ttatcgacga gcgcctgatc aaccccgacg gctccctgct gttccgcgta  180
accatcaacg gagtgaccgg ctggcggctg tgcgagcgca ttttggcggg gagctccggt  240
ggaatggtgt ttacactcga agatttcgta ggggactggc ggcagacagc cggctacaac  300
ctggaccaag tccttgagca gggcggtgtg tccagtttgt ttcagaatct cggggtgtcc  360
gtaactccga tccaaaggat tgtcctgagc ggtgaaaacg gcctgaagat cgacatccat  420
gtcatcatcc cgtatgaagg tctgagcggc gatcagatgg gccagatcga aaaaattttt  480
aaggtggtgt accctgtgga tgatcatcac tttaaggtga ttctgcacta t           531

SEQ ID NO: 108         moltype = AA  length = 177
FEATURE                Location/Qualifiers
REGION                 1..177
                       note = Description of Artificial Sequence: Synthetic
                        polypeptide
source                 1..177
                       mol_type = protein
                       organism = synthetic construct
SEQUENCE: 108
MGTLVIDGVT PNMIDYFGRP YEGIAVFDGK KITVTGTLWN GNKIIDERLI NPDGSLLFRV  60
```

```
TINGVTGWRL CERILAGSSG GMVFTLEDFV GDWRQTAGYN LDQVLEQGGV SSLFQNLGVS  120
VTPIQRIVLS GENGLKIDIH VIIPYEGLSG DQMGQIEKIF KVVYPVDDHH FKVILHY     177

SEQ ID NO: 109         moltype = DNA  length = 546
FEATURE                Location/Qualifiers
misc_feature           1..546
                       note = Description of Artificial Sequence: Synthetic
                        polynucleotide
source                 1..546
                       mol_type = other DNA
                       organism = synthetic construct
SEQUENCE: 109
atgggcacac tggtaatcga cggggttacg ccgaacatga tcgactattt cggacggccg  60
tatgaaggca tcgccgtgtt cgacggcaaa aagatcactg taaccgggac cctgtggaac  120
ggcaacaaaa ttatcgacga gcgcctgatc aaccccgacg gctccctgct gttccgcgta  180
accatcaacg gagtgaccgg ctggcggctg tgcgagcgca ttttggcggg aagttctggt  240
ggagggagct ccggtggaat ggtgtttaca ctcgaagatt tcgtagggga ctggcggcag  300
acagccggct acaacctgga ccaagtcctt gagcagggcg gtgtgtccag tttgtttcag  360
aatctcgggg tgtccgtaac tccgatccaa aggattgtcc tgagcggtga aaacggcctg  420
aagatcgaca tccatgtcat catcccgtat gaaggtctga gcggcgatca gatgggccag  480
atcgaaaaaa tttttaaggt ggtgtaccct gtggatgatc atcactttaa ggtgattctg  540
cactat                                                             546

SEQ ID NO: 110         moltype = AA  length = 182
FEATURE                Location/Qualifiers
REGION                 1..182
                       note = Description of Artificial Sequence: Synthetic
                        polypeptide
source                 1..182
                       mol_type = protein
                       organism = synthetic construct
SEQUENCE: 110
MGTLVIDGVT PNMIDYFGRP YEGIAVFDGK KITVTGTLWN GNKIIDERLI NPDGSLLFRV  60
TINGVTGWRL CERILAGSSG GGSSGGMVFT LEDFVGDWRQ TAGYNLDQVL EQGGVSSLFQ  120
NLGVSVTPIQ RIVLSGENGL KIDIHVIIPY EGLSGDQMGQ IEKIFKVVYP VDDHHFKVIL  180
HY                                                                 182

SEQ ID NO: 111         moltype = DNA  length = 576
FEATURE                Location/Qualifiers
misc_feature           1..576
                       note = Description of Artificial Sequence: Synthetic
                        polynucleotide
source                 1..576
                       mol_type = other DNA
                       organism = synthetic construct
SEQUENCE: 111
atgggcacac tggtaatcga cggggttacg ccgaacatga tcgactattt cggacggccg  60
tatgaaggca tcgccgtgtt cgacggcaaa aagatcactg taaccgggac cctgtggaac  120
ggcaacaaaa ttatcgacga gcgcctgatc aaccccgacg gctccctgct gttccgcgta  180
accatcaacg gagtgaccgg ctggcggctg tgcgagcgca ttttggcggg aagttctggt  240
ggagggagct ccggtggagg aagttctggt ggagggagct ccggtggaat ggtgtttaca  300
ctcgaagatt tcgtagggga ctggcggcag acagccggct acaacctgga ccaagtcctt  360
gagcagggcg gtgtgtccag tttgtttcag aatctcgggg tgtccgtaac tccgatccaa  420
aggattgtcc tgagcggtga aaacggcctg aagatcgaca tccatgtcat catcccgtat  480
gaaggtctga gcggcgatca gatgggccag atcgaaaaaa tttttaaggt ggtgtaccct  540
gtggatgatc atcactttaa ggtgattctg cactat                            576

SEQ ID NO: 112         moltype = AA  length = 192
FEATURE                Location/Qualifiers
REGION                 1..192
                       note = Description of Artificial Sequence: Synthetic
                        polypeptide
source                 1..192
                       mol_type = protein
                       organism = synthetic construct
SEQUENCE: 112
MGTLVIDGVT PNMIDYFGRP YEGIAVFDGK KITVTGTLWN GNKIIDERLI NPDGSLLFRV  60
TINGVTGWRL CERILAGSSG GGSSGGGSSG GGSSGGMVFT LEDFVGDWRQ TAGYNLDQVL  120
EQGGVSSLFQ NLGVSVTPIQ RIVLSGENGL KIDIHVIIPY EGLSGDQMGQ IEKIFKVVYP  180
VDDHHFKVIL HY                                                      192

SEQ ID NO: 113         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 113
```

```
GSSGG                                                             5

SEQ ID NO: 114          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 114
atggatttcg taggggactg gcggcagaca gccggctaca acctggacca agtccttgag  60
cagggcggtg tgtccagttt gtttcagaat ctcggggtgt ccgtaactcc gatccaaagg  120
attgtcctga gcggtgaaaa cggcctgaag atcgacatcc atgtcatcat cccgtatgaa  180
ggtctgagcg gcgatcagat gggccagatc gaaaaaattt ttaaggtggt gtaccctgtg  240
gatgatcatc actttaaggt gattctgcac tatggcacac tggtaatcga cggggttacg  300
ccgaacatga tcgactattt cggacggccg tatgaaggca tcgccgtgtt cgacggcaaa  360
aagatcactg taaccgggac cctgtggaac ggcaacaaaa ttatcgacga gcgcctgatc  420
aaccccgacg gctccctgct gttccgcgta accatcaacg gagtgaccgg ctggcggctg  480
tgcgagcgca ttttggcggg aagttctggt ggaggaagtt ctggtggaga gcctactact  540
gagaacttgt acttccagag cgataacgga agttctggtg gaggaagttc tggtggaatg  600
gtgtttacac tcgaa                                                  615

SEQ ID NO: 115          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 115
MDFVGDWRQT AGYNLDQVLE QGGVSSLFQN LGVSVTPIQR IVLSGENGLK IDIHVIIPYE  60
GLSGDQMGQI EKIFKVVYPV DDHHFKVILH YGTLVIDGVT PNMIDYFGRP YEGIAVFDGK  120
KITVTGTLWN GNKIIDERLI NPDGSLLFRV TINGVTGWRL CERILAGSSG GGSSGGEPTT  180
ENLYFQSDNG SSGGGSSGGM VFTLE                                       205

SEQ ID NO: 116          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 116
atgttcgtag gggactggcg gcagacagcc ggctacaacc tggaccaagt ccttgagcag  60
ggcggtgtgt ccagtttgtt tcagaatctc ggggtgtccg taactccgat ccaaaggatt  120
gtcctgagcg gtgaaaacgg cctgaagatc gacatccatg tcatcatccc gtatgaaggt  180
ctgagcggcg atcagatggg ccagatcgaa aaaattttta aggtggtgta ccctgtggat  240
gatcatcact ttaaggtgat tctgcactat ggcacactgg taatcgacgg ggttacgccg  300
aacatgatcg actatttcgg acggccgtat gaaggcatcg ccgtgttcga cggcaaaaag  360
atcactgtaa ccgggaccct gtggaacggc aacaaaatta tcgacgagcg cctgatcaac  420
cccgacggct ccctgctgtt ccgcgtaacc atcaacggag tgaccggctg gcggctgtgc  480
gagcgcattt tggcgggaag ttctggtgga ggaagttctg gtggagagcc tactactgag  540
aacttgtact tccagagcga taacggaagt tctggtggag gaagttctgg tggaatggtg  600
tttacactcg aagat                                                  615

SEQ ID NO: 117          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 117
MFVGDWRQTA GYNLDQVLEQ GGVSSLFQNL GVSVTPIQRI VLSGENGLKI DIHVIIPYEG  60
LSGDQMGQIE KIFKVVYPVD DHHFKVILHY GTLVIDGVTP NMIDYFGRPY EGIAVFDGKK  120
ITVTGTLWNG NKIIDERLIN PDGSLLFRVT INGVTGWRLC ERILAGSSGG GSSGGEPTTE  180
NLYFQSDNGS SGGGSSGGMV FTLED                                       205

SEQ ID NO: 118          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
```

```
                        organism = synthetic construct
SEQUENCE: 118
atggtagggg actggcggca gacagccggc tacaacctgg accaagtcct tgagcagggc  60
ggtgtgtcca gtttgtttca gaatctcggg gtgtccgtaa ctccgatcca aaggattgtc  120
ctgagcggtg aaaacggcct gaagatcgac atccatgtca tcatcccgta tgaaggtctg  180
agcggcgatc agatgggcca gatcgaaaaa atttttaagg tggtgtaccc tgtggatgat  240
catcacttta aggtgattct gcactatggc acactggtaa tcgacggggt tacgccgaac  300
atgatcgact atttcggacg gccgtatgaa ggcatcgccg tgttcgacgg caaaaagatc  360
actgtaaccg ggaccctgtg gaacggcaac aaaattatcg acgagcgcct gatcaacccc  420
gacggctccc tgctgttccg cgtaaccatc aacggagtga ccggctggcg gctgtgcgag  480
cgcattttgg cgggaagttc tggtggagga agttctggtg gagagcctac tactgagaac  540
ttgtacttcc agagcgataa cggaagttct ggtggaggaa gttctggtgg aatggtgttt  600
acactcgaag atttc                                                   615

SEQ ID NO: 119          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 119
MVGDWRQTAG YNLDQVLEQG GVSSLFQNLG VSVTPIQRIV LSGENGLKID IHVIIPYEGL  60
SGDQMGQIEK IFKVVYPVDD HHFKVILHYG TLVIDGVTPN MIDYFGRPYE GIAVFDGKKI  120
TVTGTLWNGN KIIDERLINP DGSLLFRVTI NGVTGWRLCE RILAGSSGGG SSGGEPTTEN  180
LYFQSDNGSS GGGSSGGMVF TLEDF                                        205

SEQ ID NO: 120          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 120
atggactggc ggcagacagc cggctacaac ctggaccaag tccttgagca gggcggtgtg  60
tccagtttgt ttcagaatct cggggtgtcc gtaactccga tccaaaggat tgtcctgagc  120
ggtgaaaacg gcctgaagat cgacatccat gtcatcatcc cgtatgaagg tctgagcggc  180
gatcagatgg gccagatcga aaaaattttt aaggtggtgt accctgtgga tgatcatcac  240
tttaaggtga ttctgcacta tggcacactg gtaatcgacg gggttacgcc gaacatgatc  300
gactatttcg gacggccgta tgaaggcatc gccgtgttcg acggcaaaaa gatcactgta  360
accgggaccc tgtggaacgg caacaaaatt atcgacgagc gcctgatcaa ccccgacggc  420
tccctgctgt tccgcgtaac catcaacgga gtgaccggct ggcggctgtg cgagcgcatt  480
ttggcgggaa gttctggtgg aggaagttct ggtggagagc ctactactga gaacttgtac  540
ttccagagcg ataacggaag ttctggtgga ggaagttctg gtggaatggt gtttacactc  600
gaagatttcg taggg                                                   615

SEQ ID NO: 121          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 121
MDWRQTAGYN LDQVLEQGGV SSLFQNLGVS VTPIQRIVLS GENGLKIDIH VIIPYEGLSG  60
DQMGQIEKIF KVVYPVDDHH FKVILHYGTL VIDGVTPNMI DYFGRPYEGI AVFDGKKITV  120
TGTLWNGNKI IDERLINPDG SLLFRVTING VTGWRLCERI LAGSSGGGSS GGEPTTENLY  180
FQSDNGSSGG GSSGGMVFTL EDFVG                                        205

SEQ ID NO: 122          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 122
atgcggcaga cagccggcta caacctggac caagtccttg agcagggcgg tgtgtccagt  60
ttgtttcaga atctcggggt gtccgtaact ccgatccaaa ggattgtcct gagcggtgaa  120
aacggcctga agatcgacat ccatgtcatc atcccgtatg aaggtctgag cggcgatcag  180
atgggccaga tcgaaaaaat ttttaaggtg gtgtaccctg tggatgatca tcactttaag  240
gtgattctgc actatggcac actggtaatc gacggggtta cgccgaacat gatcgactat  300
ttcggacggc cgtatgaagg catcgccgtg ttcgacggca aaaagatcac tgtaaccggg  360
accctgtgga acggcaacaa aattatcgac gagcgcctga tcaaccccga cggctccctg  420
```

```
ctgttccgcg taaccatcaa cggagtgacc ggctggcggc tgtgcgagcg cattttggcg  480
ggaagttctg gtggaggaag ttctggtgga gagcctacta ctgagaactt gtacttccag  540
agcgataacg gaagttctgg tggaggaagt tctggtggaa tggtgtttac actcgaagat  600
ttcgtagggg actgg                                                   615

SEQ ID NO: 123         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 123
MRQTAGYNLD QVLEQGGVSS LFQNLGVSVT PIQRIVLSGE NGLKIDIHVI IPYEGLSGDQ  60
MGQIEKIFKV VYPVDDHHFK VILHYGTLVI DGVTPNMIDY FGRPYEGIAV FDGKKITVTG  120
TLWNGNKIID ERLINPDGSL LFRVTINGVT GWRLCERILA GSSGGGSSGG EPTTENLYFQ  180
SDNGSSGGGS SGGMVFTLED FVGDW                                        205

SEQ ID NO: 124         moltype = DNA  length = 603
FEATURE                Location/Qualifiers
misc_feature           1..603
                       note = Description of Artificial Sequence: Synthetic
                        polynucleotide
source                 1..603
                       mol_type = other DNA
                       organism = synthetic construct
SEQUENCE: 124
cagacagccg gctacaacct ggaccaagtc cttgagcagg gcggtgtgtc cagtttgttt  60
cagaatctcg gggtgtccgt aactccgatc caaaggattg tcctgagcgg tgaaaacggc  120
ctgaagatcg acatccatgt catcatcccg tatgaaggtc tgagcggcga tcagatgggc  180
cagatcgaaa aaatttttaa ggtggtgtac cctgtggatg atcatcactt taaggtgatt  240
ctgcactatg gcacactggt aatcgacggg gttacgccga acatgatcga ctatttcgga  300
cggccgtatg aaggcatcgc cgtgttcgac ggcaaaaaga tcactgtaac cgggaccctg  360
tggaacggca acaaaattat cgacgagcgc ctgatcaacc ccgacggctc cctgctgttc  420
cgcgtaacca tcaacggagt gaccggctgg cggctgtgcg agcgcatttt ggcgggaagt  480
tctggtggag gaagttctgg tggagagcct actactgaga acttgtactt ccagagcgat  540
aacggaagtt ctggtggagg aagttctggt ggaatggtgt ttacactcga agatttcgta  600
ggg                                                                603

SEQ ID NO: 125         moltype = AA  length = 201
FEATURE                Location/Qualifiers
REGION                 1..201
                       note = Description of Artificial Sequence: Synthetic
                        polypeptide
source                 1..201
                       mol_type = protein
                       organism = synthetic construct
SEQUENCE: 125
QTAGYNLDQV LEQGGVSSLF QNLGVSVTPI QRIVLSGENG LKIDIHVIIP YEGLSGDQMG  60
QIEKIFKVVY PVDDHHFKVI LHYGTLVIDG VTPNMIDYFG RPYEGIAVFD GKKITVTGTL  120
WNGNKIIDER LINPDGSLLF RVTINGVTGW RLCERILAGS SGGGSSGGEP TTENLYFQSD  180
NGSSGGGSSG GMVFTLEDFV G                                            201

SEQ ID NO: 126         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 126
atgggctaca acctggacca agtccttgag cagggcggtg tgtccagttt gtttcagaat  60
ctcggggtgt ccgtaactcc gatccaaagg attgtcctga gcggtgaaaa cggcctgaag  120
atcgacatcc atgtcatcat cccgtatgaa ggtctgagcg gcgatcagat gggccagatc  180
gaaaaaattt ttaaggtggt gtaccctgtg gatgatcatc actttaaggt gattctgcac  240
tatggcacac tggtaatcga cggggttacg ccgaacatga tcgactattt cggacggccg  300
tatgaaggca tcgccgtgtt cgacggcaaa aagatcactg taaccgggac cctgtggaac  360
ggcaacaaaa ttatcgacga gcgcctgatc aaccccgacg gctccctgct gttccgcgta  420
accatcaacg gagtgaccgg ctggcggctg tgcgagcgca ttttggcggg aagttctggt  480
ggaggaagtt ctggtggaga gcctactact gagaacttgt acttccagag cgataacgga  540
agttctggtg gaggaagttc tggtggaatg gtgtttacac tcgaagattt cgtaggggac  600
tggcggcaga cagcc                                                   615

SEQ ID NO: 127         moltype = AA  length = 205
FEATURE                Location/Qualifiers
REGION                 1..205
                       note = Description of Artificial Sequence: Synthetic
```

```
                         polypeptide
source                  1..205
                        mol_type = protein
                        organism = synthetic construct
SEQUENCE: 127
MGYNLDQVLE QGGVSSLFQN LGVSVTPIQR IVLSGENGLK IDIHVIIPYE GLSGDQMGQI  60
EKIFKVVYPV DDHHFKVILH YGTLVIDGVT PNMIDYFGRP YEGIAVFDGK KITVTGTLWN  120
GNKIIDERLI NPDGSLLFRV TINGVTGWRL CERILAGSSG GGSSGGEPTT ENLYFQSDNG  180
SSGGGSSGGM VFTLEDFVGD WRQTA                                        205

SEQ ID NO: 128          moltype = DNA  length = 612
FEATURE                 Location/Qualifiers
misc_feature            1..612
                        note = Description of Artificial Sequence: Synthetic
                         polynucleotide
source                  1..612
                        mol_type = other DNA
                        organism = synthetic construct
SEQUENCE: 128
ctggaccaag tccttgagca gggcggtgtg tccagtttgt ttcagaatct cggggtgtcc  60
gtaactccga tccaaaggat tgtcctgagc ggtgaaaacg gcctgaagat cgacatccat  120
gtcatcatcc cgtatgaagg tctgagcggc gatcagatgg gccagatcga aaaaattttt  180
aaggtggtgt accctgtgga tgatcatcac tttaaggtga ttctgcacta tggcacactg  240
gtaatcgacg gggttacgcc gaacatgatc gactatttcg gacggccgta tgaaggcatc  300
gccgtgttcg acggcaaaaa gatcactgta accgggaccc tgtggaacgg caacaaaatt  360
atcgacgagc gcctgatcaa ccccgacggc tccctgctgt tccgcgtaac catcaacgga  420
gtgaccggct ggcggctgtg cgagcgcatt ttggcgggaa gttctggtgg aggaagttct  480
ggtggagagc ctactactga gaacttgtac ttccagagcg ataacggaag ttctggtgga  540
ggaagttctg gtggaatggt gtttacactc gaagatttcg taggggactg gcggcagaca  600
gccggctaca ac                                                      612

SEQ ID NO: 129          moltype = AA  length = 204
FEATURE                 Location/Qualifiers
REGION                  1..204
                        note = Description of Artificial Sequence: Synthetic
                         polypeptide
source                  1..204
                        mol_type = protein
                        organism = synthetic construct
SEQUENCE: 129
LDQVLEQGGV SSLFQNLGVS VTPIQRIVLS GENGLKIDIH VIIPYEGLSG DQMGQIEKIF  60
KVVYPVDDHH FKVILHYGTL VIDGVTPNMI DYFGRPYEGI AVFDGKKITV TGTLWNGNKI  120
IDERLINPDG SLLFRVTING VTGWRLCERI LAGSSGGGSS GGEPTTENLY FQSDNGSSGG  180
GSSGGMVFTL EDFVGDWRQT AGYN                                         204

SEQ ID NO: 130          moltype = DNA  length = 612
FEATURE                 Location/Qualifiers
misc_feature            1..612
                        note = Description of Artificial Sequence: Synthetic
                         polynucleotide
source                  1..612
                        mol_type = other DNA
                        organism = synthetic construct
SEQUENCE: 130
gtccttgagc agggcggtgt gtccagtttg tttcagaatc tcggggtgtc cgtaactccg  60
atccaaagga ttgtcctgag cggtgaaaac ggcctgaaga tcgacatcca tgtcatcatc  120
ccgtatgaag gtctgagcgg cgatcagatg ggccagatcg aaaaaatttt taaggtggtg  180
taccctgtgg atgatcatca ctttaaggtg attctgcact atggcacact ggtaatcgac  240
ggggttacgc cgaacatgat cgactatttc ggacggccgt atgaaggcat cgccgtgttc  300
gacggcaaaa agatcactgt aaccgggacc ctgtggaacg gcaacaaaat tatcgacgag  360
cgcctgatca accccgacgg ctccctgctg ttccgcgtaa ccatcaacgg agtgaccggc  420
tggcggctgt gcgagcgcat tttggcggga agttctggtg gaggaagttc tggtggagag  480
cctactactg agaacttgta cttccagagc gataacggaa gttctggtgg aggaagttct  540
ggtggaatgg tgtttacact cgaagatttc gtaggggact ggcggcagac agccggctac  600
aacctggacc aa                                                      612

SEQ ID NO: 131          moltype = AA  length = 204
FEATURE                 Location/Qualifiers
REGION                  1..204
                        note = Description of Artificial Sequence: Synthetic
                         polypeptide
source                  1..204
                        mol_type = protein
                        organism = synthetic construct
SEQUENCE: 131
VLEQGGVSSL FQNLGVSVTP IQRIVLSGEN GLKIDIHVII PYEGLSGDQM GQIEKIFKVV  60
YPVDDHHFKV ILHYGTLVID GVTPNMIDYF GRPYEGIAVF DGKKITVTGT LWNGNKIIDE  120
RLINPDGSLL FRVTINGVTG WRLCERILAG SSGGGSSGGE PTTENLYFQS DNGSSGGGSS  180
GGMVFTLEDF VGDWRQTAGY NLDQ                                         204
```

```
SEQ ID NO: 132          moltype = DNA  length = 612
FEATURE                 Location/Qualifiers
misc_feature            1..612
                        note = Description of Artificial Sequence: Synthetic
                         polynucleotide
source                  1..612
                        mol_type = other DNA
                        organism = synthetic construct
SEQUENCE: 132
cagggcggtg tgtccagttt gtttcagaat ctcggggtgt ccgtaactcc gatccaaagg  60
attgtcctga gcggtgaaaa cggcctgaag atcgacatcc atgtcatcat cccgtatgaa  120
ggtctgagcg gcgatcagat gggccagatc gaaaaaattt ttaaggtggt gtaccctgtg  180
gatgatcatc actttaaggt gattctgcac tatggcacac tggtaatcga cggggttacg  240
ccgaacatga tcgactattt cggacggccg tatgaaggca tcgccgtgtt cgacggcaaa  300
aagatcactg taaccgggac cctgtggaac ggcaacaaaa ttatcgacga gcgcctgatc  360
aaccccgacg gctccctgct gttccgcgta accatcaacg gagtgaccgg ctggcggctg  420
tgcgagcgca ttttggcggg aagttctggt ggaggaagtt ctggtggaga gcctactact  480
gagaacttgt acttccagag cgataacgga agttctggtg gaggaagttc tggtggaatg  540
gtgtttacac tcgaagattt cgtaggggac tggcggcaga cagccggcta caacctggac  600
caagtccttg ag                                                      612

SEQ ID NO: 133          moltype = AA  length = 204
FEATURE                 Location/Qualifiers
REGION                  1..204
                        note = Description of Artificial Sequence: Synthetic
                         polypeptide
source                  1..204
                        mol_type = protein
                        organism = synthetic construct
SEQUENCE: 133
QGGVSSLFQN LGVSVTPIQR IVLSGENGLK IDIHVIIPYE GLSGDQMGQI EKIFKVVYPV  60
DDHHFKVILH YGTLVIDGVT PNMIDYFGRP YEGIAVFDGK KITVTGTLWN GNKIIDERLI  120
NPDGSLLFRV TINGVTGWRL CERILAGSSG GGSSGGEPTT ENLYFQSDNG SSGGGSSGGM  180
VFTLEDFVGD WRQTAGYNLD QVLE                                         204

SEQ ID NO: 134          moltype = DNA  length = 612
FEATURE                 Location/Qualifiers
misc_feature            1..612
                        note = Description of Artificial Sequence: Synthetic
                         polynucleotide
source                  1..612
                        mol_type = other DNA
                        organism = synthetic construct
SEQUENCE: 134
gtgtccagtt tgtttcagaa tctcggggtg tccgtaactc cgatccaaag gattgtcctg  60
agcggtgaaa acggcctgaa gatcgacatc catgtcatca tcccgtatga aggtctgagc  120
ggcgatcaga tgggccagat cgaaaaaatt tttaaggtgg tgtaccctgt ggatgatcat  180
cactttaagg tgattctgca ctatggcaca ctggtaatcg acggggttac gccgaacatg  240
atcgactatt tcggacggcc gtatgaaggc atcgccgtgt tcgacggcaa aaagatcact  300
gtaaccggga ccctgtggaa cggcaacaaa attatcgacg agcgcctgat caaccccgac  360
ggctccctgc tgttccgcgt aaccatcaac ggagtgaccg gctggcggct gtgcgagcgc  420
attttggcgg gaagttctgg tggaggaagt tctggtggag agcctactac tgagaacttg  480
tacttccaga gcgataacgg aagttctggt ggaggaagtt ctggtggaat ggtgtttaca  540
ctcgaagatt tcgtagggga ctggcggcag acagccggct acaacctgga ccaagtcctt  600
gagcagggcg gt                                                      612

SEQ ID NO: 135          moltype = AA  length = 204
FEATURE                 Location/Qualifiers
REGION                  1..204
                        note = Description of Artificial Sequence: Synthetic
                         polypeptide
source                  1..204
                        mol_type = protein
                        organism = synthetic construct
SEQUENCE: 135
VSSLFQNLGV SVTPIQRIVL SGENGLKIDI HVIIPYEGLS GDQMGQIEKI FKVVYPVDDH  60
HFKVILHYGT LVIDGVTPNM IDYFGRPYEG IAVFDGKKIT VTGTLWNGNK IIDERLINPD  120
GSLLFRVTIN GVTGWRLCER ILAGSSGGGS SGGEPTTENL YFQSDNGSSG GGSSGGMVFT  180
LEDFVGDWRQ TAGYNLDQVL EQGG                                         204

SEQ ID NO: 136          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
```

SEQUENCE: 136
atgctcgggg tgtccgtaac tccgatccaa aggattgtcc tgagcggtga aaacggcctg 60
aagatcgaca tccatgtcat catcccgtat gaaggtctga gcggcgatca gatgggccag 120
atcgaaaaaa tttttaaggt ggtgtaccct gtggatgatc atcactttaa ggtgattctg 180
cactatggca cactggtaat cgacggggtt acgccgaaca tgatcgacta tttcggacgg 240
ccgtatgaag gcatcgccgt gttcgacggc aaaaagatca ctgtaaccgg gaccctgtgg 300
aacggcaaca aaattatcga cgagcgcctg atcaaccccg acggctccct gctgttccgc 360
gtaaccatca acggagtgac cggctggcgg ctgtgcgagc gcattttggc gggaagttct 420
ggtggaggaa gttctggtgg agagcctact actgagaact tgtacttcca gagcgataac 480
ggaagttctg gtggaggaag ttctggtgga atggtgttta cactcgaaga tttcgtaggg 540
gactggcggc agacagccgg ctacaacctg gaccaagtcc ttgagcaggg cggtgtgtcc 600
agtttgtttc agaat 615

SEQ ID NO: 137 moltype = AA length = 205
FEATURE Location/Qualifiers
REGION 1..205
note = Description of Artificial Sequence: Synthetic
polypeptide
source 1..205
mol_type = protein
organism = synthetic construct
SEQUENCE: 137
MLGVSVTPIQ RIVLSGENGL KIDIHVIIPY EGLSGDQMGQ IEKIFKVVYP VDDHHFKVIL 60
HYGTLVIDGV TPNMIDYFGR PYEGIAVFDG KKITVTGTLW NGNKIIDERL INPDGSLLFR 120
VTINGVTGWR LCERILAGSS GGGSSGGEPT TENLYFQSDN GSSGGGSSGG MVFTLEDFVG 180
DWRQTAGYNL DQVLEQGGVS SLFQN 205

SEQ ID NO: 138 moltype = DNA length = 615
FEATURE Location/Qualifiers
misc_feature 1..615
note = Description of Artificial Sequence: Synthetic
polynucleotide
source 1..615
mol_type = other DNA
organism = synthetic construct
SEQUENCE: 138
atgccgatcc aaaggattgt cctgagcggt gaaaacggcc tgaagatcga catccatgtc 60
atcatcccgt atgaaggtct gagcggcgat cagatgggcc agatcgaaaa aatttttaag 120
gtggtgtacc ctgtggatga tcatcacttt aaggtgattc tgcactatgg cacactggta 180
atcgacgggg ttacgccgaa catgatcgac tatttcggac ggccgtatga aggcatcgcc 240
gtgttcgacg gcaaaaagat cactgtaacc gggaccctgt ggaacggcaa caaaattatc 300
gacgagcgcc tgatcaaccc cgacggctcc ctgctgttcc gcgtaaccat caacggagtg 360
accggctggc ggctgtgcga gcgcattttg gcgggaagtt ctggtggagg aagttctggt 420
ggagagccta ctactgagaa cttgtacttc cagagcgata acggaagttc tggtggagga 480
agttctggtg gaatggtgtt tacactcgaa gatttcgtag gggactggcg gcagacagcc 540
ggctacaacc tggaccaagt ccttgagcag ggcggtgtgt ccagtttgtt tcagaatctc 600
ggggtgtccg taact 615

SEQ ID NO: 139 moltype = AA length = 205
FEATURE Location/Qualifiers
REGION 1..205
note = Description of Artificial Sequence: Synthetic
polypeptide
source 1..205
mol_type = protein
organism = synthetic construct
SEQUENCE: 139
MPIQRIVLSG ENGLKIDIHV IIPYEGLSGD QMGQIEKIFK VVYPVDDHHF KVILHYGTLV 60
IDGVTPNMID YFGRPYEGIA VFDGKKITVT GTLWNGNKII DERLINPDGS LLFRVTINGV 120
TGWRLCERIL AGSSGGGSSG GEPTTENLYF QSDNGSSGGG SSGGMVFTLE DFVGDWRQTA 180
GYNLDQVLEQ GGVSSLFQNL GVSVT 205

SEQ ID NO: 140 moltype = DNA length = 615
FEATURE Location/Qualifiers
misc_feature 1..615
note = Description of Artificial Sequence: Synthetic
polynucleotide
source 1..615
mol_type = other DNA
organism = synthetic construct
SEQUENCE: 140
atgaggattg tcctgagcgg tgaaaacggc ctgaagatcg acatccatgt catcatcccg 60
tatgaaggtc tgagcggcga tcagatgggc cagatcgaaa aatttttaa ggtggtgtac 120
cctgtggatg atcatcactt taaggtgatt ctgcactatg gcacactggt aatcgacggg 180
gttacgccga acatgatcga ctatttcgga cggccgtatg aaggcatcgc cgtgttcgac 240
ggcaaaaaga tcactgtaac cgggaccctg tggaacggca acaaaattat cgacgagcgc 300
ctgatcaacc ccgacggctc cctgctgttc cgcgtaacca tcaacggagt gaccggctgg 360
cggctgtgcg agcgcatttt ggcgggaagt tctggtggag gaagttctgg tggagagcct 420
actactgaga acttgtactt ccagagcgat aacggaagtt ctggtggagg aagttctggt 480

```
ggaatggtgt ttacactcga agatttcgta ggggactggc ggcagacagc cggctacaac  540
ctggaccaag tccttgagca gggcggtgtg tccagtttgt ttcagaatct cggggtgtcc  600
gtaactccga tccaa                                                   615

SEQ ID NO: 141         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 141
MRIVLSGENG LKIDIHVIIP YEGLSGDQMG QIEKIFKVVY PVDDHHFKVI LHYGTLVIDG  60
VTPNMIDYFG RPYEGIAVFD GKKITVTGTL WNGNKIIDER LINPDGSLLF RVTINGVTGW  120
RLCERILAGS SGGGSSGGEP TTENLYFQSD NGSSGGGSSG GMVFTLEDFV GDWRQTAGYN  180
LDQVLEQGGV SSLFQNLGVS VTPIQ                                        205

SEQ ID NO: 142         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 142
atgattgtcc tgagcggtga aaacggcctg aagatcgaca tccatgtcat catcccgtat  60
gaaggtctga gcggcgatca gatgggccag atcgaaaaaa tttttaaggt ggtgtaccct  120
gtggatgatc atcactttaa ggtgattctg cactatggca cactggtaat cgacggggtt  180
acgccgaaca tgatcgacta tttcggacgg ccgtatgaag gcatcgccgt gttcgacggc  240
aaaaagatca ctgtaaccgg gaccctgtgg aacggcaaca aaattatcga cgagcgcctg  300
atcaaccccg acggctccct gctgttccgc gtaaccatca acggagtgac cggctggcgg  360
ctgtgcgagc gcattttggc gggaagttct ggtggaggaa gttctggtgg agagcctact  420
actgagaact tgtacttcca gagcgataac ggaagttctg gtggaggaag ttctggtgga  480
atggtgttta cactcgaaga tttcgtaggg gactggcggc agacagccgg ctacaacctg  540
gaccaagtcc ttgagcaggg cggtgtgtcc agtttgtttc agaatctcgg ggtgtccgta  600
actccgatcc aaagg                                                   615

SEQ ID NO: 143         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 143
MIVLSGENGL KIDIHVIIPY EGLSGDQMGQ IEKIFKVVYP VDDHHFKVIL HYGTLVIDGV  60
TPNMIDYFGR PYEGIAVFDG KKITVTGTLW NGNKIIDERL INPDGSLLFR VTINGVTGWR  120
LCERILAGSS GGGSSGGEPT TENLYFQSDN GSSGGGSSGG MVFTLEDFVG DWRQTAGYNL  180
DQVLEQGGVS SLFQNLGVSV TPIQR                                        205

SEQ ID NO: 144         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 144
atggtcctga gcggtgaaaa cggcctgaag atcgacatcc atgtcatcat cccgtatgaa  60
ggtctgagcg gcgatcagat gggccagatc gaaaaaattt ttaaggtggt gtaccctgtg  120
gatgatcatc actttaaggt gattctgcac tatggcacac tggtaatcga cggggttacg  180
ccgaacatga tcgactattt cggacggccg tatgaaggca tcgccgtgtt cgacggcaaa  240
aagatcactg taaccgggac cctgtggaac ggcaacaaaa ttatcgacga gcgcctgatc  300
aaccccgacg gctccctgct gttccgcgta accatcaacg gagtgaccgg ctggcggctg  360
tgcgagcgca ttttggcggg aagttctggt ggaggaagtt ctggtggaga gcctactact  420
gagaacttgt acttccagag cgataacgga agttctggtg gaggaagttc tggtggaatg  480
gtgtttacac tcgaagattt cgtaggggac tggcggcaga cagccggcta caacctggac  540
caagtccttg agcagggcgg tgtgtccagt ttgtttcaga atctcggggt gtccgtaact  600
ccgatccaaa ggatt                                                   615

SEQ ID NO: 145         moltype = AA  length = 205
FEATURE                Location/Qualifiers
REGION                 1..205
                       note = Description of Artificial Sequence: Synthetic
                        polypeptide
```

```
source                  1..205
                        mol_type = protein
                        organism = synthetic construct
SEQUENCE: 145
MVLSGENGLK IDIHVIIPYE GLSGDQMGQI EKIFKVVYPV DDHHFKVILH YGTLVIDGVT  60
PNMIDYFGRP YEGIAVFDGK KITVTGTLWN GNKIIDERLI NPDGSLLFRV TINGVTGWRL  120
CERILAGSSG GGSSGGEPTT ENLYFQSDNG SSGGGSSGGM VFTLEDFVGD WRQTAGYNLD  180
QVLEQGGVSS LFQNLGVSVT PIQRI                                       205

SEQ ID NO: 146          moltype = DNA  length = 612
FEATURE                 Location/Qualifiers
misc_feature            1..612
                        note = Description of Artificial Sequence: Synthetic
                         polynucleotide
source                  1..612
                        mol_type = other DNA
                        organism = synthetic construct
SEQUENCE: 146
atgctgagcg gtgaaaacgg cctgaagatc gacatccatg tcatcatccc gtatgaaggt  60
ctgagcggcg atcagatggg ccagatcgaa aaaattttta aggtggtgta ccctgtggat  120
gatcatcact ttaaggtgat tctgcactat ggcacactgg taatcgacgg ggttacgccg  180
aacatgatcg actatttcgg acggccgtat gaaggcatcg ccgtgttcga cggcaaaaag  240
atcactgtaa ccgggaccct gtggaacggc aacaaaatta tcgacgagcg cctgatcaac  300
cccgacggct ccctgctgtt ccgcgtaacc atcaacggag tgaccggctg gcggctgtgc  360
gagcgcattt tggcgggaag ttctggtgga ggaagttctg gtggagagcc tactactgag  420
aacttgtact tccagagcga taacggaagt tctggtggag gaagttctgg tggaatggtg  480
tttacactcg aagatttcgt aggggactgg cggcagacag ccggctacaa cctggaccaa  540
gtccttgagc agggcggtgt gtccagtttg tttcagaatc tcggggtgtc cgtaactccg  600
atccaaagga tt                                                     612

SEQ ID NO: 147          moltype = AA  length = 204
FEATURE                 Location/Qualifiers
REGION                  1..204
                        note = Description of Artificial Sequence: Synthetic
                         polypeptide
source                  1..204
                        mol_type = protein
                        organism = synthetic construct
SEQUENCE: 147
MLSGENGLKI DIHVIIPYEG LSGDQMGQIE KIFKVVYPVD DHHFKVILHY GTLVIDGVTP  60
NMIDYFGRPY EGIAVFDGKK ITVTGTLWNG NKIIDERLIN PDGSLLFRVT INGVTGWRLC  120
ERILAGSSGG GSSGGEPTTE NLYFQSDNGS SGGGSSGGMV FTLEDFVGDW RQTAGYNLDQ  180
VLEQGGVSSL FQNLGVSVTP IQRI                                        204

SEQ ID NO: 148          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 148
atgagcggtg aaaacggcct gaagatcgac atccatgtca tcatcccgta tgaaggtctg  60
agcggcgatc agatgggcca gatcgaaaaa atttttaagg tggtgtaccc tgtggatgat  120
catcacttta aggtgattct gcactatggc acactggtaa tcgacggggt tacgccgaac  180
atgatcgact atttcggacg gccgtatgaa ggcatcgccg tgttcgacgg caaaaagatc  240
actgtaaccg ggaccctgtg gaacggcaac aaaattatcg acgagcgcct gatcaacccc  300
gacggctccc tgctgttccg cgtaaccatc aacggagtga ccggctggcg gctgtgcgag  360
cgcattttgg cgggaagttc tggtggagga agttctggtg gagagcctac tactgagaac  420
ttgtacttcc agagcgataa cggaagttct ggtggaggaa gttctggtgg aatggtgttt  480
acactcgaag atttcgtagg ggactggcgg cagacagccg gctacaacct ggaccaagtc  540
cttgagcagg gcggtgtgtc cagtttgttt cagaatctcg gggtgtccgt aactccgatc  600
caaaggattg tcctg                                                  615

SEQ ID NO: 149          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 149
MSGENGLKID IHVIIPYEGL SGDQMGQIEK IFKVVYPVDD HHFKVILHYG TLVIDGVTPN  60
MIDYFGRPYE GIAVFDGKKI TVTGTLWNGN KIIDERLINP DGSLLFRVTI NGVTGWRLCE  120
RILAGSSGGG SSGGEPTTEN LYFQSDNGSS GGGSSGGMVF TLEDFVGDWR QTAGYNLDQV  180
LEQGGVSSLF QNLGVSVTPI QRIVL                                       205
```

```
SEQ ID NO: 150          moltype = DNA  length = 616
FEATURE                 Location/Qualifiers
misc_feature            1..616
                        note = Description of Artificial Sequence: Synthetic
                         polynucleotide
source                  1..616
                        mol_type = other DNA
                        organism = synthetic construct
SEQUENCE: 150
atgggtgaaa acggcctgaa gatcgacatc catgtcatca tcccgtatga aggtctgagc  60
ggcgatcaga tgggccagat cgaaaaaatt tttaaggtgg tgtaccctgt ggatgatcat  120
cactttaagg tgattctgca ctatggcaca ctggtaatcg acggggttac gccgaacatg  180
atcgactatt tcggacggcc gtatgaaggc atcgccgtgt tcgacggcaa aaagatcact  240
gtaaccggga ccctgtggaa cggcaacaaa attatcgacg agcgcctgat caaccccgac  300
ggctccctgc tgttccgcgt aaccatcaac ggagtgaccg gctggcggct gtgcgagcgc  360
attttggcgg gaagttctgg tggaggaagt tctggtggag agcctactac tgagaacttg  420
tacttccaga gcgataacgg aagttctggt ggaggaagtt ctggtggaat ggtgtttaca  480
ctcgaagatt tcgtagggga ctggcggcag acagccggct acaacctgga ccaagtcctt  540
gagcagggcg gtgtgtccag tttgtttcag aatctcgggg tgtccgtaac tccgatccaa  600
aggattgtcc tgagcg                                                  616

SEQ ID NO: 151          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 151
MGENGLKIDI HVIIPYEGLS GDQMGQIEKI FKVVYPVDDH HFKVILHYGT LVIDGVTPNM  60
IDYFGRPYEG IAVFDGKKIT VTGTLWNGNK IIDERLINPD GSLLFRVTIN GVTGWRLCER  120
ILAGSSGGGS SGGEPTTENL YFQSDNGSSG GGSSGGMVFT LEDFVGDWRQ TAGYNLDQVL  180
EQGGVSSLFQ NLGVSVTPIQ RIVLS                                        205

SEQ ID NO: 152          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 152
atggaaaacg gcctgaagat cgacatccat gtcatcatcc cgtatgaagg tctgagcggc  60
gatcagatgg gccagatcga aaaaattttt aaggtggtgt accctgtgga tgatcatcac  120
tttaaggtga ttctgcacta tggcacactg gtaatcgacg gggttacgcc gaacatgatc  180
gactatttcg gacggccgta tgaaggcatc gccgtgttcg acggcaaaaa gatcactgta  240
accgggaccc tgtggaacgg caacaaaatt atcgacgagc gcctgatcaa ccccgacggc  300
tccctgctgt tccgcgtaac catcaacgga gtgaccggct ggcggctgtg cgagcgcatt  360
ttggcgggaa gttctggtgg aggaagttct ggtggagagc ctactactga gaacttgtac  420
ttccagagcg ataacggaag ttctggtgga ggaagttctg gtggaatggt gtttacactc  480
gaagatttcg taggggactg gcggcagaca gccggctaca acctggacca agtccttgag  540
cagggcggtg tgtccagttt gtttcagaat ctcggggtgt ccgtaactcc gatccaaagg  600
attgtcctga gcggt                                                   615

SEQ ID NO: 153          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 153
MENGLKIDIH VIIPYEGLSG DQMGQIEKIF KVVYPVDDHH FKVILHYGTL VIDGVTPNMI  60
DYFGRPYEGI AVFDGKKITV TGTLWNGNKI IDERLINPDG SLLFRVTING VTGWRLCERI  120
LAGSSGGGSS GGEPTTENLY FQSDNGSSGG GSSGGMVFTL EDFVGDWRQT AGYNLDQVLE  180
QGGVSSLFQN LGVSVTPIQR IVLSG                                        205

SEQ ID NO: 154          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 154
```

```
atgaacggcc tgaagatcga catccatgtc atcatcccgt atgaaggtct gagcggcgat  60
cagatgggcc agatcgaaaa aatttttaag gtggtgtacc ctgtggatga tcatcacttt  120
aaggtgattc tgcactatgg cacactggta atcgacgggg ttacgccgaa catgatcgac  180
tatttcggac ggccgtatga aggcatcgcc gtgttcgacg gcaaaaagat cactgtaacc  240
gggaccctgt ggaacggcaa caaaattatc gacgagcgcc tgatcaaccc cgacggctcc  300
ctgctgttcc gcgtaaccat caacggagtg accggctggc ggctgtgcga gcgcattttg  360
gcgggaagtt ctggtggagg aagttctggt ggagagccta ctactgagaa cttgtacttc  420
cagagcgata acggaagttc tggtggagga agttctggtg gaatggtgtt tacactcgaa  480
gatttcgtag ggactggcg gcagacagcc ggctacaacc tggaccaagt ccttgagcag  540
ggcggtgtgt ccagtttgtt tcagaatctc ggggtgtccg taactccgat ccaaaggatt  600
gtcctgagcg gtgaa                                                  615

SEQ ID NO: 155         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 155
MNGLKIDIHV IIPYEGLSGD QMGQIEKIFK VVYPVDDHHF KVILHYGTLV IDGVTPNMID  60
YFGRPYEGIA VFDGKKITVT GTLWNGNKII DERLINPDGS LLFRVTINGV TGWRLCERIL  120
AGSSGGGSSG GEPTTENLYF QSDNGSSGGG SSGGMVFTLE DFVGDWRQTA GYNLDQVLEQ  180
GGVSSLFQNL GVSVTPIQRI VLSGE                                       205

SEQ ID NO: 156         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 156
atgggcctga agatcgacat ccatgtcatc atcccgtatg aaggtctgag cggcgatcag  60
atgggccaga tcgaaaaaat ttttaaggtg gtgtaccctg tggatgatca tcactttaag  120
gtgattctgc actatggcac actggtaatc gacggggtta cgccgaacat gatcgactat  180
ttcggacggc cgtatgaagg catcgccgtg ttcgacggca aaaagatcac tgtaaccggg  240
accctgtgga acggcaacaa aattatcgac gagcgcctga tcaaccccga cggctccctg  300
ctgttccgcg taaccatcaa cggagtgacc ggctggcggc tgtgcgagcg cattttggcg  360
ggaagttctg gtggaggaag ttctggtgga gagcctacta ctgagaactt gtacttccag  420
agcgataacg gaagttctgg tggaggaagt tctggtggaa tggtgtttac actcgaagat  480
ttcgtagggg actggcggca gacagccggc tacaacctgg accaagtcct tgagcagggc  540
ggtgtgtcca gtttgtttca gaatctcggg gtgtccgtaa ctccgatcca aaggattgtc  600
ctgagcggtg aaaac                                                  615

SEQ ID NO: 157         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 157
MGLKIDIHVI IPYEGLSGDQ MGQIEKIFKV VYPVDDHHFK VILHYGTLVI DGVTPNMIDY  60
FGRPYEGIAV FDGKKITVTG TLWNGNKIID ERLINPDGSL LFRVTINGVT GWRLCERILA  120
GSSGGGSSGG EPTTENLYFQ SDNGSSGGGS SGGMVFTLED FVGDWRQTAG YNLDQVLEQG  180
GVSSLFQNLG VSVTPIQRIV LSGEN                                       205

SEQ ID NO: 158         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 158
atgctgaaga tcgacatcca tgtcatcatc ccgtatgaag gtctgagcgg cgatcagatg  60
ggccagatcg aaaaaatttt taaggtggtg taccctgtgg atgatcatca ctttaaggtg  120
attctgcact atggcacact ggtaatcgac ggggttacgc cgaacatgat cgactatttc  180
ggacggccgt atgaaggcat cgccgtgttc gacggcaaaa agatcactgt aaccgggacc  240
ctgtggaacg gcaacaaaat tatcgacgag cgcctgatca accccgacgg ctccctgctg  300
ttccgcgtaa ccatcaacgg agtgaccggc tggcggctgt gcgagcgcat tttggcggga  360
agttctggtg gaggaagttc tggtggagag cctactactg agaacttgta cttccagagc  420
gataacggaa gttctggtgg aggaagttct ggtggaatgg tgtttacact cgaagatttc  480
gtaggggact ggcggcagac agccggctac aacctggacc aagtccttga gcagggcggt  540
```

```
gtgtccagtt tgtttcagaa tctcggggtg tccgtaactc cgatccaaag gattgtcctg  600
agcggtgaaa acggc                                                   615

SEQ ID NO: 159         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 159
MLKIDIHVII PYEGLSGDQM GQIEKIFKVV YPVDDHHFKV ILHYGTLVID GVTPNMIDYF  60
GRPYEGIAVF DGKKITVTGT LWNGNKIIDE RLINPDGSLL FRVTINGVTG WRLCERILAG  120
SSGGGSSGGE PTTENLYFQS DNGSSGGGSS GGMVFTLEDF VGDWRQTAGY NLDQVLEQGG  180
VSSLFQNLGV SVTPIQRIVL SGENG                                        205

SEQ ID NO: 160         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 160
atgaagatcg acatccatgt catcatcccg tatgaaggtc tgagcggcga tcagatgggc  60
cagatcgaaa aaatttttaa ggtggtgtac cctgtggatg atcatcactt taaggtgatt  120
ctgcactatg gcacactggt aatcgacggg gttacgccga acatgatcga ctatttcgga  180
cggccgtatg aaggcatcgc cgtgttcgac ggcaaaaaga tcactgtaac cgggaccctg  240
tggaacggca acaaaattat cgacgagcgc ctgatcaacc ccgacggctc cctgctgttc  300
cgcgtaacca tcaacggagt gaccggctgg cggctgtgcg agcgcatttt ggcgggaagt  360
tctggtggag gaagttctgg tggagagcct actactgaga acttgtactt ccagagcgat  420
aacggaagtt ctggtggagg aagttctggt ggaatggtgt ttacactcga agatttcgta  480
ggggactggc ggcagacagc cggctacaac ctggaccaag tccttgagca gggcggtgtg  540
tccagtttgt ttcagaatct cggggtgtcc gtaactccga tccaaaggat tgtcctgagc  600
ggtgaaaacg gcctg                                                   615

SEQ ID NO: 161         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 161
MKIDIHVIIP YEGLSGDQMG QIEKIFKVVY PVDDHHFKVI LHYGTLVIDG VTPNMIDYFG  60
RPYEGIAVFD GKKITVTGTL WNGNKIIDER LINPDGSLLF RVTINGVTGW RLCERILAGS  120
SGGGSSGGEP TTENLYFQSD NGSSGGGSSG GMVFTLEDFV GDWRQTAGYN LDQVLEQGGV  180
SSLFQNLGVS VTPIQRIVLS GENGL                                        205

SEQ ID NO: 162         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 162
atgatcgaca tccatgtcat catcccgtat gaaggtctga gcggcgatca gatgggccag  60
atcgaaaaaa tttttaaggt ggtgtaccct gtggatgatc atcactttaa ggtgattctg  120
cactatggca cactggtaat cgacggggtt acgccgaaca tgatcgacta tttcggacgg  180
ccgtatgaag gcatcgccgt gttcgacggc aaaaagatca ctgtaaccgg gaccctgtgg  240
aacggcaaca aaattatcga cgagcgcctg atcaaccccg acggctccct gctgttccgc  300
gtaaccatca acggagtgac cggctggcgg ctgtgcgagc gcattttggc gggaagttct  360
ggtggaggaa gttctggtgg agagcctact actgagaact tgtacttcca gagcgataac  420
ggaagttctg gtggaggaag ttctggtgga atggtgttta cactcgaaga tttcgtaggg  480
gactggcggc agacagccgg ctacaacctg gaccaagtcc ttgagcaggg cggtgtgtcc  540
agtttgtttc agaatctcgg ggtgtccgta actccgatcc aaaggattgt cctgagcggt  600
gaaaacggcc tgaag                                                   615

SEQ ID NO: 163         moltype = AA  length = 205
FEATURE                Location/Qualifiers
REGION                 1..205
                       note = Description of Artificial Sequence: Synthetic
                        polypeptide
source                 1..205
```

```
                        mol_type = protein
                        organism = synthetic construct
SEQUENCE: 163
MIDIHVIIPY EGLSGDQMGQ IEKIFKVVYP VDDHHFKVIL HYGTLVIDGV TPNMIDYFGR  60
PYEGIAVFDG KKITVTGTLW NGNKIIDERL INPDGSLLFR VTINGVTGWR LCERILAGSS  120
GGGSSGGEPT TENLYFQSDN GSSGGGSSGG MVFTLEDFVG DWRQTAGYNL DQVLEQGGVS  180
SLFQNLGVSV TPIQRIVLSG ENGLK                                       205

SEQ ID NO: 164          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 164
atggacatcc atgtcatcat cccgtatgaa ggtctgagcg gcgatcagat gggccagatc  60
gaaaaaattt ttaaggtggt gtaccctgtg gatgatcatc actttaaggt gattctgcac  120
tatggcacac tggtaatcga cggggttacg ccgaacatga tcgactattt cggacggccg  180
tatgaaggca tcgccgtgtt cgacggcaaa aagatcactg taaccgggac cctgtggaac  240
ggcaacaaaa ttatcgacga gcgcctgatc aaccccgacg gctccctgct gttccgcgta  300
accatcaacg gagtgaccgg ctggcggctg tgcgagcgca ttttggcggg aagttctggt  360
ggaggaagtt ctggtggaga gcctactact gagaacttgt acttccagag cgataacgga  420
agttctggtg gaggaagttc tggtggaatg gtgtttacac tcgaagattt cgtaggggac  480
tggcggcaga cagccggcta caacctggac caagtccttg agcagggcgg tgtgtccagt  540
ttgtttcaga atctcggggt gtccgtaact ccgatccaaa ggattgtcct gagcggtgaa  600
aacggcctga agatc                                                  615

SEQ ID NO: 165          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 165
MDIHVIIPYE GLSGDQMGQI EKIFKVVYPV DDHHFKVILH YGTLVIDGVT PNMIDYFGRP  60
YEGIAVFDGK KITVTGTLWN GNKIIDERLI NPDGSLLFRV TINGVTGWRL CERILAGSSG  120
GGSSGGEPTT ENLYFQSDNG SSGGGSSGGM VFTLEDFVGD WRQTAGYNLD QVLEQGGVSS  180
LFQNLGVSVT PIQRIVLSGE NGLKI                                       205

SEQ ID NO: 166          moltype = DNA  length = 614
FEATURE                 Location/Qualifiers
misc_feature            1..614
                        note = Description of Artificial Sequence: Synthetic
                         polynucleotide
source                  1..614
                        mol_type = other DNA
                        organism = synthetic construct
SEQUENCE: 166
atgatccatg tcatcatccc gtatgaaggt ctgagcggcg atcagatggg ccagatcgaa  60
aaaattttta aggtggtgta ccctgtggat gatcatcact ttaaggtgat tctgcactat  120
ggcacactgg taatcgacgg ggttacgccg aacatgatcg actatttcgg acggccgtat  180
gaaggcatcg ccgtgttcga cggcaaaaag atcactgtaa ccgggaccct gtggaacggc  240
aacaaaatta tcgacgagcg cctgatcaac cccgacggct ccctgctgtt ccgcgtaacc  300
atcaacggag tgaccggctg gcggctgtgc gagcgcattt tggcgggaag ttctggtgga  360
ggaagttctg gtggagagcc tactactgag aacttgtact tccagagcga taacggaagt  420
tctggtggag gaagttctgg tggaatggtg tttacactcg aagatttcgt aggggactgg  480
cggcagacag ccggctacaa cctggaccaa gtccttgagc agggcggtgt gtccagtttg  540
tttcagaatc tcggggtgtc cgtaactccg atccaaagga ttgtcctgag cggtgaaaac  600
ggcctgaaga tcga                                                   614

SEQ ID NO: 167          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 167
MIHVIIPYEG LSGDQMGQIE KIFKVVYPVD DHHFKVILHY GTLVIDGVTP NMIDYFGRPY  60
EGIAVFDGKK ITVTGTLWNG NKIIDERLIN PDGSLLFRVT INGVTGWRLC ERILAGSSGG  120
GSSGGEPTTE NLYFQSDNGS SGGGSSGGMV FTLEDFVGDW RQTAGYNLDQ VLEQGGVSSL  180
FQNLGVSVTP IQRIVLSGEN GLKID                                       205

SEQ ID NO: 168          moltype = DNA  length = 615
```

```
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 168
atggtcatca tcccgtatga aggtctgagc ggcgatcaga tgggccagat cgaaaaaatt  60
tttaaggtgg tgtaccctgt ggatgatcat cactttaagg tgattctgca ctatggcaca  120
ctggtaatcg acggggttac gccgaacatg atcgactatt tcggacggcc gtatgaaggc  180
atcgccgtgt tcgacggcaa aaagatcact gtaaccggga ccctgtggaa cggcaacaaa  240
attatcgacg agcgcctgat caaccccgac ggctccctgc tgttccgcgt aaccatcaac  300
ggagtgaccg gctggcggct gtgcgagcgc attttggcgg gaagttctgg tggaggaagt  360
tctggtggag agcctactac tgagaacttg tacttccaga gcgataacgg aagttctggt  420
ggaggaagtt ctggtggaat ggtgtttaca ctcgaagatt tcgtagggga ctggcggcag  480
acagccggct acaacctgga ccaagtcctt gagcagggcg gtgtgtccag tttgtttcag  540
aatctcgggg tgtccgtaac tccgatccaa aggattgtcc tgagcggtga aaacggcctg  600
aagatcgaca tccat                                                  615

SEQ ID NO: 169         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 169
MVIIPYEGLS GDQMGQIEKI FKVVYPVDDH HFKVILHYGT LVIDGVTPNM IDYFGRPYEG  60
IAVFDGKKIT VTGTLWNGNK IIDERLINPD GSLLFRVTIN GVTGWRLCER ILAGSSGGGS  120
SGGEPTTENL YFQSDNGSSG GGSSGGMVFT LEDFVGDWRQ TAGYNLDQVL EQGGVSSLFQ  180
NLGVSVTPIQ RIVLSGENGL KIDIH                                       205

SEQ ID NO: 170         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 170
atgggtctga gcggcgatca gatgggccag atcgaaaaaa tttttaaggt ggtgtaccct  60
gtggatgatc atcactttaa ggtgattctg cactatggca cactggtaat cgacggggtt  120
acgccgaaca tgatcgacta tttcggacgg ccgtatgaag gcatcgccgt gttcgacggc  180
aaaaagatca ctgtaaccgg gaccctgtgg aacggcaaca aaattatcga cgagcgcctg  240
atcaaccccg acggctccct gctgttccgc gtaaccatca acggagtgac cggctggcgg  300
ctgtgcgagc gcattttggc gggaagttct ggtggaggaa gttctggtgg agagcctact  360
actgagaact tgtacttcca gagcgataac ggaagttctg gtggaggaag ttctggtgga  420
atggtgttta cactcgaaga tttcgtaggg gactggcggc agacagccgg ctacaacctg  480
gaccaagtcc ttgagcaggg cggtgtgtcc agtttgtttc agaatctcgg ggtgtccgta  540
actccgatcc aaaggattgt cctgagcggt gaaaacggcc tgaagatcga catccatgtc  600
atcatcccgt atgaa                                                  615

SEQ ID NO: 171         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 171
MGLSGDQMGQ IEKIFKVVYP VDDHHFKVIL HYGTLVIDGV TPNMIDYFGR PYEGIAVFDG  60
KKITVTGTLW NGNKIIDERL INPDGSLLFR VTINGVTGWR LCERILAGSS GGGSSGGEPT  120
TENLYFQSDN GSSGGGSSGG MVFTLEDFVG DWRQTAGYNL DQVLEQGGVS SLFQNLGVSV  180
TPIQRIVLSG ENGLKIDIHV IIPYE                                       205

SEQ ID NO: 172         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 172
atgggcgatc agatgggcca gatcgaaaaa atttttaagg tggtgtaccc tgtggatgat  60
```

-continued

```
catcacttta aggtgattct gcactatggc acactggtaa tcgacggggt tacgccgaac  120
atgatcgact atttcggacg gccgtatgaa ggcatcgccg tgttcgacgg caaaaagatc  180
actgtaaccg ggaccctgtg gaacggcaac aaaattatcg acgagcgcct gatcaacccc  240
gacggctccc tgctgttccg cgtaaccatc aacggagtga ccggctggcg gctgtgcgag  300
cgcattttgg cgggaagttc tggtggagga agttctggtg gagagcctac tactgagaac  360
ttgtacttcc agagcgataa cggaagttct ggtggaggaa gttctggtgg aatggtgttt  420
acactcgaag atttcgtagg ggactggcgg cagacagccg gctacaacct ggaccaagtc  480
cttgagcagg gcggtgtgtc cagtttgttt cagaatctcg ggtgtccgt aactccgatc  540
caaaggattg tcctgagcgg tgaaaacggc ctgaagatcg acatccatgt catcatcccg  600
tatgaaggtc tgagc                                                   615
```

```
SEQ ID NO: 173          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 173
MGDQMGQIEK IFKVVYPVDD HHFKVILHYG TLVIDGVTPN MIDYFGRPYE GIAVFDGKKI  60
TVTGTLWNGN KIIDERLINP DGSLLFRVTI NGVTGWRLCE RILAGSSGGG SSGGEPTTEN  120
LYFQSDNGSS GGGSSGGMVF TLEDFVGDWR QTAGYNLDQV LEQGGVSSLF QNLGVSVTPI  180
QRIVLSGENG LKIDIHVIIP YEGLS                                        205
```

```
SEQ ID NO: 174          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 174
atgatgggcc agatcgaaaa aatttttaag gtggtgtacc ctgtggatga tcatcacttt  60
aaggtgattc tgcactatgg cacactggta atcgacgggg ttacgccgaa catgatcgac  120
tatttcggac ggccgtatga aggcatcgcc gtgttcgacg gcaaaaagat cactgtaacc  180
gggaccctgt ggaacggcaa caaaattatc gacgagcgcc tgatcaaccc cgacggctcc  240
ctgctgttcc gcgtaaccat caacggagtg accggctggc ggctgtgcga gcgcattttg  300
gcgggaagtt ctggtggagg aagttctggt ggagagccta ctactgagaa cttgtacttc  360
cagagcgata acggaagttc tggtggagga agttctggtg gaatggtgtt tacactcgaa  420
gatttcgtag gggactggcg gcagacagcc ggctacaacc tggaccaagt ccttgagcag  480
ggcggtgtgt ccagtttgtt tcagaatctc ggggtgtccg taactccgat ccaaaggatt  540
gtcctgagcg gtgaaaacgg cctgaagatc gacatccatg tcatcatccc gtatgaaggt  600
ctgagcggcg atcag                                                   615
```

```
SEQ ID NO: 175          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 175
MMGQIEKIFK VVYPVDDHHF KVILHYGTLV IDGVTPNMID YFGRPYEGIA VFDGKKITVT  60
GTLWNGNKII DERLINPDGS LLFRVTINGV TGWRLCERIL AGSSGGGSSG GEPTTENLYF  120
QSDNGSSGGG SSGGMVFTLE DFVGDWRQTA GYNLDQVLEQ GGVSSLFQNL GVSVTPIQRI  180
VLSGENGLKI DIHVIIPYEG LSGDQ                                        205
```

```
SEQ ID NO: 176          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 176
atgatcgaaa aaatttttaa ggtggtgtac cctgtggatg atcatcactt taaggtgatt  60
ctgcactatg gcacactggt aatcgacggg gttacgccga acatgatcga ctatttcgga  120
cggccgtatg aaggcatcgc cgtgttcgac ggcaaaaaga tcactgtaac cgggaccctg  180
tggaacggca acaaaattat cgacgagcgc ctgatcaacc ccgacggctc cctgctgttc  240
cgcgtaacca tcaacggagt gaccggctgg cggctgtgcg agcgcatttt ggcgggaagt  300
tctggtggag gaagttctgg tggagagcct actactgaga acttgtactt ccagagcgat  360
aacggaagtt ctggtggagg aagttctggt ggaatggtgt ttacactcga agatttcgta  420
ggggactggc ggcagacagc cggctacaac ctggaccaag tccttgagca gggcggtgtg  480
tccagtttgt ttcagaatct cggggtgtcc gtaactccga tccaaaggat tgtcctgagc  540
ggtgaaaacg gcctgaagat cgacatccat gtcatcatcc cgtatgaagg tctgagcggc  600
```

```
gatcagatgg gccag                                                   615

SEQ ID NO: 177         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 177
MIEKIFKVVY PVDDHHFKVI LHYGTLVIDG VTPNMIDYFG RPYEGIAVFD GKKITVTGTL  60
WNGNKIIDER LINPDGSLLF RVTINGVTGW RLCERILAGS SGGGSSGGEP TTENLYFQSD  120
NGSSGGGSSG GMVFTLEDFV GDWRQTAGYN LDQVLEQGGV SSLFQNLGVS VTPIQRIVLS  180
GENGLKIDIH VIIPYEGLSG DQMGQ                                        205

SEQ ID NO: 178         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 178
atgattttta aggtggtgta ccctgtggat gatcatcact ttaaggtgat tctgcactat  60
ggcacactgg taatcgacgg ggttacgccg aacatgatcg actatttcgg acggccgtat  120
gaaggcatcg ccgtgttcga cggcaaaaag atcactgtaa ccgggaccct gtggaacggc  180
aacaaaatta tcgacgagcg cctgatcaac cccgacggct ccctgctgtt ccgcgtaacc  240
atcaacggag tgaccggctg gcggctgtgc gagcgcattt tggcgggaag ttctggtgga  300
ggaagttctg gtggagagcc tactactgag aacttgtact tccagagcga taacggaagt  360
tctggtggag gaagttctgg tggaatggtg tttacactcg aagatttcgt aggggactgg  420
cggcagacag ccggctacaa cctggaccaa gtccttgagc agggcggtgt gtccagtttg  480
tttcagaatc tcggggtgtc cgtaactccg atccaaagga ttgtcctgag cggtgaaaac  540
ggcctgaaga tcgacatcca tgtcatcatc ccgtatgaag gtctgagcgg cgatcagatg  600
ggccagatcg aaaaa                                                   615

SEQ ID NO: 179         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 179
MIFKVVYPVD DHHFKVILHY GTLVIDGVTP NMIDYFGRPY EGIAVFDGKK ITVTGTLWNG  60
NKIIDERLIN PDGSLLFRVT INGVTGWRLC ERILAGSSGG GSSGGEPTTE NLYFQSDNGS  120
SGGGSSGGMV FTLEDFVGDW RQTAGYNLDQ VLEQGGVSSL FQNLGVSVTP IQRIVLSGEN  180
GLKIDIHVII PYEGLSGDQM GQIEK                                        205

SEQ ID NO: 180         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 180
atggtggtgt accctgtgga tgatcatcac tttaaggtga ttctgcacta tggcacactg  60
gtaatcgacg gggttacgcc gaacatgatc gactatttcg gacggccgta tgaaggcatc  120
gccgtgttcg acggcaaaaa gatcactgta accgggaccc tgtggaacgg caacaaaatt  180
atcgacgagc gcctgatcaa ccccgacggc tccctgctgt tccgcgtaac catcaacgga  240
gtgaccggct ggcggctgtg cgagcgcatt ttggcgggaa gttctggtgg aggaagttct  300
ggtggagagc ctactactga gaacttgtac ttccagagcg ataacggaag ttctggtgga  360
ggaagttctg gtggaatggt gtttacactc gaagatttcg taggggactg gcggcagaca  420
gccggctaca acctggacca agtccttgag cagggcggtg tgtccagttt gtttcagaat  480
ctcggggtgt ccgtaactcc gatccaaagg attgtcctga gcggtgaaaa cggcctgaag  540
atcgacatcc atgtcatcat cccgtatgaa ggtctgagcg gcgatcagat gggccagatc  600
gaaaaaattt ttaag                                                   615

SEQ ID NO: 181         moltype = AA  length = 205
FEATURE                Location/Qualifiers
REGION                 1..205
                       note = Description of Artificial Sequence: Synthetic
                        polypeptide
source                 1..205
                       mol_type = protein
```

organism = synthetic construct
SEQUENCE: 181
MVVYPVDDHH FKVILHYGTL VIDGVTPNMI DYFGRPYEGI AVFDGKKITV TGTLWNGNKI 60
IDERLINPDG SLLFRVTING VTGWRLCERI LAGSSGGGSS GGEPTTENLY FQSDNGSSGG 120
GSSGGMVFTL EDFVGDWRQT AGYNLDQVLE QGGVSSLFQN LGVSVTPIQR IVLSGENGLK 180
IDIHVIIPYE GLSGDQMGQI EKIFK 205

SEQ ID NO: 182 moltype = DNA length = 615
FEATURE Location/Qualifiers
misc_feature 1..615
note = Description of Artificial Sequence: Synthetic
polynucleotide
source 1..615
mol_type = other DNA
organism = synthetic construct
SEQUENCE: 182
atggtgtacc ctgtggatga tcatcacttt aaggtgattc tgcactatgg cacactggta 60
atcgacgggg ttacgccgaa catgatcgac tatttcggac ggccgtatga aggcatcgcc 120
gtgttcgacg gcaaaaagat cactgtaacc gggaccctgt ggaacggcaa caaaattatc 180
gacgagcgcc tgatcaaccc cgacggctcc ctgctgttcc gcgtaaccat caacggagtg 240
accggctggc ggctgtgcga gcgcattttg gcgggaagtt ctggtggagg aagttctggt 300
ggagagccta ctactgagaa cttgtacttc cagagcgata acggaagttc tggtggagga 360
agttctggtg gaatggtgtt tacactcgaa gatttcgtag gggactggcg gcagacagcc 420
ggctacaacc tggaccaagt ccttgagcag ggcggtgtgt ccagtttgtt tcagaatctc 480
ggggtgtccg taactccgat ccaaaggatt gtcctgagcg gtgaaaacgg cctgaagatc 540
gacatccatg tcatcatccc gtatgaaggt ctgagcggcg atcagatggg ccagatcgaa 600
aaaattttta aggtg 615

SEQ ID NO: 183 moltype = AA length = 205
FEATURE Location/Qualifiers
REGION 1..205
note = Description of Artificial Sequence: Synthetic
polypeptide
source 1..205
mol_type = protein
organism = synthetic construct
SEQUENCE: 183
MVYPVDDHHF KVILHYGTLV IDGVTPNMID YFGRPYEGIA VFDGKKITVT GTLWNGNKII 60
DERLINPDGS LLFRVTINGV TGWRLCERIL AGSSGGGSSG GEPTTENLYF QSDNGSSGGG 120
SSGGMVFTLE DFVGDWRQTA GYNLDQVLEQ GGVSSLFQNL GVSVTPIQRI VLSGENGLKI 180
DIHVIIPYEG LSGDQMGQIE KIFKV 205

SEQ ID NO: 184 moltype = DNA length = 615
FEATURE Location/Qualifiers
misc_feature 1..615
note = Description of Artificial Sequence: Synthetic
polynucleotide
source 1..615
mol_type = other DNA
organism = synthetic construct
SEQUENCE: 184
atgtaccctg tggatgatca tcactttaag gtgattctgc actatggcac actggtaatc 60
gacggggtta cgccgaacat gatcgactat ttcggacggc cgtatgaagg catcgccgtg 120
ttcgacggca aaaagatcac tgtaaccggg accctgtgga acggcaacaa aattatcgac 180
gagcgcctga tcaaccccga cggctccctg ctgttccgcg taaccatcaa cggagtgacc 240
ggctggcggc tgtgcgagcg cattttggcg ggaagttctg gtggaggaag ttctggtgga 300
gagcctacta ctgagaactt gtacttccag agcgataacg gaagttctgg tggaggaagt 360
tctggtggaa tggtgtttac actcgaagat ttcgtagggg actggcggca gacagccggc 420
tacaacctgg accaagtcct tgagcagggc ggtgtgtcca gtttgtttca gaatctcggg 480
gtgtccgtaa ctccgatcca aaggattgtc ctgagcggtg aaaacggcct gaagatcgac 540
atccatgtca tcatcccgta tgaaggtctg agcggcgatc agatgggcca gatcgaaaaa 600
atttttaagg tggtg 615

SEQ ID NO: 185 moltype = AA length = 205
FEATURE Location/Qualifiers
REGION 1..205
note = Description of Artificial Sequence: Synthetic
polypeptide
source 1..205
mol_type = protein
organism = synthetic construct
SEQUENCE: 185
MYPVDDHHFK VILHYGTLVI DGVTPNMIDY FGRPYEGIAV FDGKKITVTG TLWNGNKIID 60
ERLINPDGSL LFRVTINGVT GWRLCERILA GSSGGGSSGG EPTTENLYFQ SDNGSSGGGS 120
SGGMVFTLED FVGDWRQTAG YNLDQVLEQG GVSSLFQNLG VSVTPIQRIV LSGENGLKID 180
IHVIIPYEGL SGDQMGQIEK IFKVV 205

SEQ ID NO: 186 moltype = DNA length = 615
FEATURE Location/Qualifiers

```
misc_feature          1..615
                      note = Description of Artificial Sequence: Synthetic
                       polynucleotide
source                1..615
                      mol_type = other DNA
                      organism = synthetic construct
SEQUENCE: 186
atgcctgtgg atgatcatca ctttaaggtg attctgcact atggcacact ggtaatcgac  60
ggggttacgc cgaacatgat cgactatttc ggacggccgt atgaaggcat cgccgtgttc  120
gacggcaaaa agatcactgt aaccgggacc ctgtggaacg gcaacaaaat tatcgacgag  180
cgcctgatca accccgacgg ctccctgctg ttccgcgtaa ccatcaacgg agtgaccggc  240
tggcggctgt gcgagcgcat tttggcggga agttctggtg gaggaagttc tggtggagag  300
cctactactg agaacttgta cttccagagc gataacggaa gttctggtgg aggaagttct  360
ggtggaatgg tgtttacact cgaagatttc gtaggggact ggcggcagac agccggctac  420
aacctggacc aagtccttga gcagggcggt gtgtccagtt tgtttcagaa tctcggggtg  480
tccgtaactc cgatccaaag gattgtcctg agcggtgaaa acggcctgaa gatcgacatc  540
catgtcatca tcccgtatga aggtctgagc ggcgatcaga tgggccagat cgaaaaaatt  600
tttaaggtgg tgtac                                                   615

SEQ ID NO: 187        moltype = AA  length = 205
FEATURE               Location/Qualifiers
REGION                1..205
                      note = Description of Artificial Sequence: Synthetic
                       polypeptide
source                1..205
                      mol_type = protein
                      organism = synthetic construct
SEQUENCE: 187
MPVDDHHFKV ILHYGTLVID GVTPNMIDYF GRPYEGIAVF DGKKITVTGT LWNGNKIIDE  60
RLINPDGSLL FRVTINGVTG WRLCERILAG SSGGGSSGGE PTTENLYFQS DNGSSGGGSS  120
GGMVFTLEDF VGDWRQTAGY NLDQVLEQGG VSSLFQNLGV SVTPIQRIVL SGENGLKIDI  180
HVIIPYEGLS GDQMGQIEKI FKVVY                                        205

SEQ ID NO: 188        moltype = DNA  length = 615
FEATURE               Location/Qualifiers
misc_feature          1..615
                      note = Description of Artificial Sequence: Synthetic
                       polynucleotide
source                1..615
                      mol_type = other DNA
                      organism = synthetic construct
SEQUENCE: 188
atggtggatg atcatcactt taaggtgatt ctgcactatg gcacactggt aatcgacggg  60
gttacgccga acatgatcga ctatttcgga cggccgtatg aaggcatcgc cgtgttcgac  120
ggcaaaaaga tcactgtaac cgggaccctg tggaacggca acaaaattat cgacgagcgc  180
ctgatcaacc ccgacggctc cctgctgttc cgcgtaacca tcaacggagt gaccggctgg  240
cggctgtgcg agcgcatttt ggcgggaagt tctggtggag gaagttctgg tggagagcct  300
actactgaga acttgtactt ccagagcgat aacggaagtt ctggtggagg aagttctggt  360
ggaatggtgt ttacactcga agatttcgta ggggactggc ggcagacagc cggctacaac  420
ctggaccaag tccttgagca gggcggtgtg tccagtttgt ttcagaatct cggggtgtcc  480
gtaactccga tccaaaggat tgtcctgagc ggtgaaaacg gcctgaagat cgacatccat  540
gtcatcatcc cgtatgaagg tctgagcggc gatcagatgg gccagatcga aaaaattttt  600
aaggtggtgt accct                                                   615

SEQ ID NO: 189        moltype = AA  length = 205
FEATURE               Location/Qualifiers
REGION                1..205
                      note = Description of Artificial Sequence: Synthetic
                       polypeptide
source                1..205
                      mol_type = protein
                      organism = synthetic construct
SEQUENCE: 189
MVDDHHFKVI LHYGTLVIDG VTPNMIDYFG RPYEGIAVFD GKKITVTGTL WNGNKIIDER  60
LINPDGSLLF RVTINGVTGW RLCERILAGS SGGGSSGGEP TTENLYFQSD NGSSGGGSSG  120
GMVFTLEDFV GDWRQTAGYN LDQVLEQGGV SSLFQNLGVS VTPIQRIVLS GENGLKIDIH  180
VIIPYEGLSG DQMGQIEKIF KVVYP                                        205

SEQ ID NO: 190        moltype = DNA  length = 615
FEATURE               Location/Qualifiers
misc_feature          1..615
                      note = Description of Artificial Sequence: Synthetic
                       polynucleotide
source                1..615
                      mol_type = other DNA
                      organism = synthetic construct
SEQUENCE: 190
atggatgatc atcactttaa ggtgattctg cactatggca cactggtaat cgacggggtt  60
acgccgaaca tgatcgacta tttcggacgg ccgtatgaag gcatcgccgt gttcgacggc  120
```

```
aaaaagatca ctgtaaccgg gaccctgtgg aacggcaaca aaattatcga cgagcgcctg  180
atcaaccccg acggctccct gctgttccgc gtaaccatca acggagtgac cggctggcgg  240
ctgtgcgagc gcattttggc gggaagttct ggtggaggaa gttctggtgg agagcctact  300
actgagaact tgtacttcca gagcgataac ggaagttctg gtggaggaag ttctggtgga  360
atggtgttta cactcgaaga tttcgtaggg gactggcggc agacagccgg ctacaacctg  420
gaccaagtcc ttgagcaggg cggtgtgtcc agtttgtttc agaatctcgg ggtgtccgta  480
actccgatcc aaaggattgt cctgagcggt gaaaacggcc tgaagatcga catccatgtc  540
atcatcccgt atgaaggtct gagcggcgat cagatgggcc agatcgaaaa aatttttaag  600
gtggtgtacc ctgtg                                                   615
```

```
SEQ ID NO: 191         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 191
MDDHHFKVIL HYGTLVIDGV TPNMIDYFGR PYEGIAVFDG KKITVTGTLW NGNKIIDERL  60
INPDGSLLFR VTINGVTGWR LCERILAGSS GGGSSGGEPT TENLYFQSDN GSSGGGSSGG  120
MVFTLEDFVG DWRQTAGYNL DQVLEQGGVS SLFQNLGVSV TPIQRIVLSG ENGLKIDIHV  180
IIPYEGLSGD QMGQIEKIFK VVYPV                                        205
```

```
SEQ ID NO: 192         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 192
atggatcatc actttaaggt gattctgcac tatggcacac tggtaatcga cggggttacg  60
ccgaacatga tcgactattt cggacggccg tatgaaggca tcgccgtgtt cgacggcaaa  120
aagatcactg taaccgggac cctgtggaac ggcaacaaaa ttatcgacga gcgcctgatc  180
aaccccgacg gctccctgct gttccgcgta accatcaacg gagtgaccgg ctggcggctg  240
tgcgagcgca ttttggcggg aagttctggt ggaggaagtt ctggtggaga gcctactact  300
gagaacttgt acttccagag cgataacgga agttctggtg gaggaagttc tggtggaatg  360
gtgtttacac tcgaagattt cgtaggggac tggcggcaga cagccggcta caacctggac  420
caagtccttg agcagggcgg tgtgtccagt ttgtttcaga atctcggggt gtccgtaact  480
ccgatccaaa ggattgtcct gagcggtgaa aacggcctga agatcgacat ccatgtcatc  540
atcccgtatg aaggtctgag cggcgatcag atgggccaga tcgaaaaaat ttttaaggtg  600
gtgtaccctg tggat                                                   615
```

```
SEQ ID NO: 193         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 193
MDHHFKVILH YGTLVIDGVT PNMIDYFGRP YEGIAVFDGK KITVTGTLWN GNKIIDERLI  60
NPDGSLLFRV TINGVTGWRL CERILAGSSG GGSSGGEPTT ENLYFQSDNG SSGGGSSGGM  120
VFTLEDFVGD WRQTAGYNLD QVLEQGGVSS LFQNLGVSVT PIQRIVLSGE NGLKIDIHVI  180
IPYEGLSGDQ MGQIEKIFKV VYPVD                                        205
```

```
SEQ ID NO: 194         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 194
atgcatcact ttaaggtgat tctgcactat ggcacactgg taatcgacgg ggttacgccg  60
aacatgatcg actatttcgg acggccgtat gaaggcatcg ccgtgttcga cggcaaaaag  120
atcactgtaa ccgggaccct gtggaacggc aacaaaatta tcgacgagcg cctgatcaac  180
cccgacggct ccctgctgtt ccgcgtaacc atcaacggag tgaccggctg gcggctgtgc  240
gagcgcattt tggcgggaag ttctggtgga ggaagttctg gtggagagcc tactactgag  300
aacttgtact tccagagcga taacggaagt tctggtggag gaagttctgg tggaatggtg  360
tttacactcg aagatttcgt aggggactgg cggcagacag ccggctacaa cctggaccaa  420
gtccttgagc agggcggtgt gtccagtttg tttcagaatc tcggggtgtc cgtaactccg  480
atccaaagga ttgtcctgag cggtgaaaac ggcctgaaga tcgacatcca tgtcatcatc  540
ccgtatgaag gtctgagcgg cgatcagatg ggccagatcg aaaaaatttt taaggtggtg  600
taccctgtgg atgat                                                   615
```

```
SEQ ID NO: 195          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 195
MHHFKVILHY GTLVIDGVTP NMIDYFGRPY EGIAVFDGKK ITVTGTLWNG NKIIDERLIN  60
PDGSLLFRVT INGVTGWRLC ERILAGSSGG GSSGGEPTTE NLYFQSDNGS SGGGSSGGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDD                                        205

SEQ ID NO: 196          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 196
atgcacttta aggtgattct gcactatggc acactggtaa tcgacggggt tacgccgaac  60
atgatcgact atttcggacg gccgtatgaa ggcatcgccg tgttcgacgg caaaaagatc  120
actgtaaccg ggaccctgtg gaacggcaac aaaattatcg acgagcgcct gatcaacccc  180
gacggctccc tgctgttccg cgtaaccatc aacggagtga ccggctggcg gctgtgcgag  240
cgcattttgg cgggaagttc tggtggagga agttctggtg gagagcctac tactgagaac  300
ttgtacttcc agagcgataa cggaagttct ggtggaggaa gttctggtgg aatggtgttt  360
acactcgaag atttcgtagg ggactggcgg cagacagccg gctacaacct ggaccaagtc  420
cttgagcagg gcggtgtgtc cagtttgttt cagaatctcg ggtgtccgt aactccgatc  480
caaaggattg tcctgagcgg tgaaaacggc ctgaagatcg acatccatgt catcatcccg  540
tatgaaggtc tgagcggcga tcagatgggc cagatcgaaa aaatttttaa ggtggtgtac  600
cctgtggatg atcat                                                   615

SEQ ID NO: 197          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 197
MHFKVILHYG TLVIDGVTPN MIDYFGRPYE GIAVFDGKKI TVTGTLWNGN KIIDERLINP  60
DGSLLFRVTI NGVTGWRLCE RILAGSSGGG SSGGEPTTEN LYFQSDNGSS GGGSSGGMVF  120
TLEDFVGDWR QTAGYNLDQV LEQGGVSSLF QNLGVSVTPI QRIVLSGENG LKIDIHVIIP  180
YEGLSGDQMG QIEKIFKVVY PVDDH                                        205

SEQ ID NO: 198          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 198
atgtttaagg tgattctgca ctatggcaca ctggtaatcg acggggttac gccgaacatg  60
atcgactatt tcggacggcc gtatgaaggc atcgccgtgt tcgacggcaa aaagatcact  120
gtaaccggga ccctgtggaa cggcaacaaa attatcgacg agcgcctgat caaccccgac  180
ggctccctgc tgttccgcgt aaccatcaac ggagtgaccg gctggcggct gtgcgagcgc  240
attttggcgg gaagttctgg tggaggaagt tctggtggag agcctactac tgagaacttg  300
tacttccaga gcgataacgg aagttctggt ggaggaagtt ctggtggaat ggtgtttaca  360
ctcgaagatt tcgtagggga ctggcggcag acagccggct acaacctgga ccaagtcctt  420
gagcagggcg gtgtgtccag tttgtttcag aatctcgggg tgtccgtaac tccgatccaa  480
aggattgtcc tgagcggtga aaacggcctg aagatcgaca tccatgtcat catcccgtat  540
gaaggtctga gcggcgatca gatgggccag atcgaaaaaa tttttaaggt ggtgtaccct  600
gtggatgatc atcac                                                   615

SEQ ID NO: 199          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
```

```
SEQUENCE: 199
MFKVILHYGT LVIDGVTPNM IDYFGRPYEG IAVFDGKKIT VTGTLWNGNK IIDERLINPD  60
GSLLFRVTIN GVTGWRLCER ILAGSSGGGS SGGEPTTENL YFQSDNGSSG GGSSGGMVFT  120
LEDFVGDWRQ TAGYNLDQVL EQGGVSSLFQ NLGVSVTPIQ RIVLSGENGL KIDIHVIIPY  180
EGLSGDQMGQ IEKIFKVVYP VDDHH                                        205

SEQ ID NO: 200         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 200
atgattctgc actatggcac actggtaatc gacggggtta cgccgaacat gatcgactat  60
ttcggacggc cgtatgaagg catcgccgtg ttcgacggca aaaagatcac tgtaaccggg  120
accctgtgga acggcaacaa aattatcgac gagcgcctga tcaaccccga cggctccctg  180
ctgttccgcg taaccatcaa cggagtgacc ggctggcggc tgtgcgagcg cattttggcg  240
ggaagttctg gtggaggaag ttctggtgga gagcctacta ctgagaactt gtacttccag  300
agcgataacg gaagttctgg tggaggaagt tctggtggaa tggtgtttac actcgaagat  360
ttcgtagggg actggcggca gacagccggc tacaacctgg accaagtcct tgagcagggc  420
ggtgtgtcca gtttgtttca gaatctcggg gtgtccgtaa ctccgatcca aaggattgtc  480
ctgagcggtg aaaacggcct gaagatcgac atccatgtca tcatcccgta tgaaggtctg  540
agcggcgatc agatgggcca gatcgaaaaa atttttaagg tggtgtaccc tgtggatgat  600
catcacttta aggtg                                                   615

SEQ ID NO: 201         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 201
MILHYGTLVI DGVTPNMIDY FGRPYEGIAV FDGKKITVTG TLWNGNKIID ERLINPDGSL  60
LFRVTINGVT GWRLCERILA GSSGGGSSGG EPTTENLYFQ SDNGSSGGGS SGGMVFTLED  120
FVGDWRQTAG YNLDQVLEQG GVSSLFQNLG VSVTPIQRIV LSGENGLKID IHVIIPYEGL  180
SGDQMGQIEK IFKVVYPVDD HHFKV                                        205

SEQ ID NO: 202         moltype = DNA  length = 616
FEATURE                Location/Qualifiers
misc_feature           1..616
                       note = Description of Artificial Sequence: Synthetic
                        polynucleotide
source                 1..616
                       mol_type = other DNA
                       organism = synthetic construct
SEQUENCE: 202
atgtatggca cactggtaat cgacggggtt acgccgaaca tgatcgacta tttcggacgg  60
ccgtatgaag gcatcgccgt gttcgacggc aaaaagatca ctgtaaccgg gaccctgtgg  120
aacggcaaca aaattatcga cgagcgcctg atcaaccccg acggctccct gctgttccgc  180
gtaaccatca acggagtgac cggctggcgg ctgtgcgagc gcattttggc gggaagttct  240
ggtggaggaa gttctggtgg agagcctact actgagaact tgtacttcca gagcgataac  300
ggaagttctg gtggaggaag ttctggtgga atggtgttta cactcgaaga tttcgtaggg  360
gactggcggc agacagccgg ctacaacctg gaccaagtcc ttgagcaggg cggtgtgtcc  420
agtttgtttc agaatctcgg ggtgtccgta actccgatcc aaaggattgt cctgagcggt  480
gaaaacggcc tgaagatcga catccatgtc atcatcccgt atgaaggtct gagcggcgat  540
cagatgggcc agatcgaaaa aatttttaag gtggtgtacc ctgtggatga tcatcacttt  600
aaggtgattc tgcacg                                                  616

SEQ ID NO: 203         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 203
MYGTLVIDGV TPNMIDYFGR PYEGIAVFDG KKITVTGTLW NGNKIIDERL INPDGSLLFR  60
VTINGVTGWR LCERILAGSS GGGSSGGEPT TENLYFQSDN GSSGGGSSGG MVFTLEDFVG  120
DWRQTAGYNL DQVLEQGGVS SLFQNLGVSV TPIQRIVLSG ENGLKIDIHV IIPYEGLSGD  180
QMGQIEKIFK VVYPVDDHHF KVILH                                        205

SEQ ID NO: 204         moltype = DNA  length = 615
FEATURE                Location/Qualifiers
misc_feature           1..615
```

```
                        note = Description of Artificial Sequence: Synthetic
                         polynucleotide
source                  1..615
                        mol_type = other DNA
                        organism = synthetic construct
SEQUENCE: 204
atgggcacac tggtaatcga cggggttacg ccgaacatga tcgactattt cggacggccg  60
tatgaaggca tcgccgtgtt cgacggcaaa aagatcactg taaccgggac cctgtggaac  120
ggcaacaaaa ttatcgacga gcgcctgatc aaccccgacg gctccctgct gttccgcgta  180
accatcaacg gagtgaccgg ctggcggctg tgcgagcgca ttttggcggg aagttctggt  240
ggaggaagtt ctggtggaga gcctactact gagaacttgt acttccagag cgataacgga  300
agttctggtg gaggaagttc tggtggaatg gtgtttacac tcgaagattt cgtaggggac  360
tggcggcaga cagccggcta caacctggac caagtccttg agcagggcgg tgtgtccagt  420
ttgtttcaga atctcggggt gtccgtaact ccgatccaaa ggattgtcct gagcggtgaa  480
aacggcctga agatcgacat ccatgtcatc atcccgtatg aaggtctgag cggcgatcag  540
atgggccaga tcgaaaaaat ttttaaggtg gtgtaccctg tggatgatca tcactttaag  600
gtgattctgc actat                                                    615

SEQ ID NO: 205          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 205
MGTLVIDGVT PNMIDYFGRP YEGIAVFDGK KITVTGTLWN GNKIIDERLI NPDGSLLFRV  60
TINGVTGWRL CERILAGSSG GGSSGGEPTT ENLYFQSDNG SSGGGSSGGM VFTLEDFVGD  120
WRQTAGYNLD QVLEQGGVSS LFQNLGVSVT PIQRIVLSGE NGLKIDIHVI IPYEGLSGDQ  180
MGQIEKIFKV VYPVDDHHFK VILHY                                         205

SEQ ID NO: 206          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 206
atgctggtaa tcgacggggt tacgccgaac atgatcgact atttcggacg gccgtatgaa  60
ggcatcgccg tgttcgacgg caaaaagatc actgtaaccg ggaccctgtg gaacggcaac  120
aaaattatcg acgagcgcct gatcaacccc gacggctccc tgctgttccg cgtaaccatc  180
aacggagtga ccggctggcg gctgtgcgag cgcattttgg cgggaagttc tggtggagga  240
agttctggtg gagagcctac tactgagaac ttgtacttcc agagcgataa cggaagttct  300
ggtggaggaa gttctggtgg aatggtgttt acactcgaag atttcgtagg ggactggcgg  360
cagacagccg gctacaacct ggaccaagtc cttgagcagg gcggtgtgtc cagtttgttt  420
cagaatctcg gggtgtccgt aactccgatc caaaggattg tcctgagcgg tgaaaacggc  480
ctgaagatcg acatccatgt catcatcccg tatgaaggtc tgagcggcga tcagatgggc  540
cagatcgaaa aaatttttaa ggtggtgtac cctgtggatg atcatcactt taaggtgatt  600
ctgcactatg gcaca                                                    615

SEQ ID NO: 207          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 207
MLVIDGVTPN MIDYFGRPYE GIAVFDGKKI TVTGTLWNGN KIIDERLINP DGSLLFRVTI  60
NGVTGWRLCE RILAGSSGGG SSGGEPTTEN LYFQSDNGSS GGGSSGGMVF TLEDFVGDWR  120
QTAGYNLDQV LEQGGVSSLF QNLGVSVTPI QRIVLSGENG LKIDIHVIIP YEGLSGDQMG  180
QIEKIFKVVY PVDDHHFKVI LHYGT                                         205

SEQ ID NO: 208          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 208
atggacgggg ttacgccgaa catgatcgac tatttcggac ggccgtatga aggcatcgcc  60
gtgttcgacg gcaaaaagat cactgtaacc gggaccctgt ggaacggcaa caaaattatc  120
gacgagcgcc tgatcaaccc cgacggctcc ctgctgttcc gcgtaaccat caacggagtg  180
```

```
accggctggc ggctgtgcga gcgcattttg gcgggaagtt ctggtggagg aagttctggt  240
ggagagccta ctactgagaa cttgtacttc cagagcgata acggaagttc tggtggagga  300
agttctggtg gaatggtgtt tacactcgaa gatttcgtag ggactggcg gcagacagcc  360
ggctacaacc tggaccaagt ccttgagcag ggcggtgtgt ccagtttgtt tcagaatctc  420
ggggtgtccg taactccgat ccaaaggatt gtcctgagcg gtgaaaacgg cctgaagatc  480
gacatccatg tcatcatccc gtatgaaggt ctgagcggcg atcagatggg ccagatcgaa  540
aaaattttta aggtggtgta ccctgtggat gatcatcact ttaaggtgat tctgcactat  600
ggcacactgg taatc                                                    615

SEQ ID NO: 209         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 209
MDGVTPNMID YFGRPYEGIA VFDGKKITVT GTLWNGNKII DERLINPDGS LLFRVTINGV  60
TGWRLCERIL AGSSGGGSSG GEPTTENLYF QSDNGSSGGG SSGGMVFTLE DFVGDWRQTA  120
GYNLDQVLEQ GGVSSLFQNL GVSVTPIQRI VLSGENGLKI DIHVIIPYEG LSGDQMGQIE  180
KIFKVVYPVD DHHFKVILHY GTLVI                                         205

SEQ ID NO: 210         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 210
atgggggtta cgccgaacat gatcgactat ttcggacggc cgtatgaagg catcgccgtg  60
ttcgacggca aaaagatcac tgtaaccggg accctgtgga acggcaacaa aattatcgac  120
gagcgcctga tcaaccccga cggctccctg ctgttccgcg taaccatcaa cggagtgacc  180
ggctggcggc tgtgcgagcg cattttggcg ggaagttctg gtggaggaag ttctggtgga  240
gagcctacta ctgagaactt gtacttccag agcgataacg gaagttctgg tggaggaagt  300
tctggtggaa tggtgtttac actcgaagat ttcgtagggg actggcggca gacagccggc  360
tacaacctgg accaagtcct tgagcagggc ggtgtgtcca gtttgtttca gaatctcggg  420
gtgtccgtaa ctccgatcca aaggattgtc ctgagcggtg aaaacggcct gaagatcgac  480
atccatgtca tcatcccgta tgaaggtctg agcggcgatc agatgggcca gatcgaaaaa  540
atttttaagg tggtgtaccc tgtggatgat catcacttta aggtgattct gcactatggc  600
acactggtaa tcgac                                                    615

SEQ ID NO: 211         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 211
MGVTPNMIDY FGRPYEGIAV FDGKKITVTG TLWNGNKIID ERLINPDGSL LFRVTINGVT  60
GWRLCERILA GSSGGGSSGG EPTTENLYFQ SDNGSSGGGS SGGMVFTLED FVGDWRQTAG  120
YNLDQVLEQG GVSSLFQNLG VSVTPIQRIV LSGENGLKID IHVIIPYEGL SGDQMGQIEK  180
IFKVVYPVDD HHFKVILHYG TLVID                                         205

SEQ ID NO: 212         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 212
atggttacgc cgaacatgat cgactatttc ggacggccgt atgaaggcat cgccgtgttc  60
gacggcaaaa agatcactgt aaccgggacc ctgtggaacg gcaacaaaat tatcgacgag  120
cgcctgatca accccgacgg ctccctgctg ttccgcgtaa ccatcaacgg agtgaccggc  180
tggcggctgt gcgagcgcat tttggcggga agttctggtg gaggaagttc tggtggagag  240
cctactactg agaacttgta cttccagagc gataacggaa gttctggtgg aggaagttct  300
ggtggaatgg tgtttacact cgaagatttc gtaggggact ggcggcagac agccggctac  360
aacctggacc aagtccttga gcagggcggt gtgtccagtt tgtttcagaa tctcggggtg  420
tccgtaactc cgatccaaag gattgtcctg agcggtgaaa acggcctgaa gatcgacatc  480
catgtcatca tcccgtatga aggtctgagc ggcgatcaga tgggccagat cgaaaaaatt  540
tttaaggtgg tgtaccctgt ggatgatcat cactttaagg tgattctgca ctatggcaca  600
ctggtaatcg acggg                                                    615
```

```
SEQ ID NO: 213          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 213
MVTPNMIDYF GRPYEGIAVF DGKKITVTGT LWNGNKIIDE RLINPDGSLL FRVTINGVTG  60
WRLCERILAG SSGGGSSGGE PTTENLYFQS DNGSSGGGSS GGMVFTLEDF VGDWRQTAGY  120
NLDQVLEQGG VSSLFQNLGV SVTPIQRIVL SGENGLKIDI HVIIPYEGLS GDQMGQIEKI  180
FKVVYPVDDH HFKVILHYGT LVIDG                                       205

SEQ ID NO: 214          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 214
atgacgccga acatgatcga ctatttcgga cggccgtatg aaggcatcgc cgtgttcgac  60
ggcaaaaaga tcactgtaac cgggaccctg tggaacggca acaaaattat cgacgagcgc  120
ctgatcaacc ccgacggctc cctgctgttc cgcgtaacca tcaacggagt gaccggctgg  180
cggctgtgcg agcgcatttt ggcgggaagt tctggtggag gaagttctgg tggagagcct  240
actactgaga acttgtactt ccagagcgat aacggaagtt ctggtggagg aagttctggt  300
ggaatggtgt ttacactcga agatttcgta ggggactggc ggcagacagc cggctacaac  360
ctggaccaag tccttgagca gggcggtgtg tccagtttgt ttcagaatct cggggtgtcc  420
gtaactccga tccaaaggat tgtcctgagc ggtgaaaacg gcctgaagat cgacatccat  480
gtcatcatcc cgtatgaagg tctgagcggc gatcagatgg gccagatcga aaaaattttt  540
aaggtggtgt accctgtgga tgatcatcac tttaaggtga ttctgcacta tggcacactg  600
gtaatcgacg gggtt                                                  615

SEQ ID NO: 215          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 215
MTPNMIDYFG RPYEGIAVFD GKKITVTGTL WNGNKIIDER LINPDGSLLF RVTINGVTGW  60
RLCERILAGS SGGGSSGGEP TTENLYFQSD NGSSGGGSSG GMVFTLEDFV GDWRQTAGYN  120
LDQVLEQGGV SSLFQNLGVS VTPIQRIVLS GENGLKIDIH VIIPYEGLSG DQMGQIEKIF  180
KVVYPVDDHH FKVILHYGTL VIDGV                                       205

SEQ ID NO: 216          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 216
atgccgaaca tgatcgacta tttcggacgg ccgtatgaag gcatcgccgt gttcgacggc  60
aaaaagatca ctgtaaccgg gaccctgtgg aacggcaaca aaattatcga cgagcgcctg  120
atcaaccccg acggctccct gctgttccgc gtaaccatca acggagtgac cggctggcgg  180
ctgtgcgagc gcattttggc gggaagttct ggtggaggaa gttctggtgg agagcctact  240
actgagaact tgtacttcca gagcgataac ggaagttctg gtggaggaag ttctggtgga  300
atggtgttta cactcgaaga tttcgtaggg gactggcggc agacagccgg ctacaacctg  360
gaccaagtcc ttgagcaggg cggtgtgtcc agtttgtttc agaatctcgg ggtgtccgta  420
actccgatcc aaaggattgt cctgagcggt gaaaacggcc tgaagatcga catccatgtc  480
atcatcccgt atgaaggtct gagcggcgat cagatgggcc agatcgaaaa aatttttaag  540
gtggtgtacc ctgtggatga tcatcacttt aaggtgattc tgcactatgg cacactggta  600
atcgacgggg ttacg                                                  615

SEQ ID NO: 217          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 217
```

-continued

```
MPNMIDYFGR PYEGIAVFDG KKITVTGTLW NGNKIIDERL INPDGSLLFR VTINGVTGWR  60
LCERILAGSS GGGSSGGEPT TENLYFQSDN GSSGGGSSGG MVFTLEDFVG DWRQTAGYNL  120
DQVLEQGGVS SLFQNLGVSV TPIQRIVLSG ENGLKIDIHV IIPYEGLSGD QMGQIEKIFK  180
VVYPVDDHHF KVILHYGTLV IDGVT                                        205

SEQ ID NO: 218         moltype = DNA  length = 612
FEATURE                Location/Qualifiers
misc_feature           1..612
                       note = Description of Artificial Sequence: Synthetic
                        polynucleotide
source                 1..612
                       mol_type = other DNA
                       organism = synthetic construct
SEQUENCE: 218
atgaacatga tcgactattt cggacggccg tatgaaggca tcgccgtgtt cgacggcaaa  60
aagatcactg taaccgggac cctgtggaac ggcaacaaaa ttatcgacga gcgcctgatc  120
aaccccgacg gctccctgct gttccgcgta accatcaacg gagtgaccgg ctggcggctg  180
tgcgagcgca ttttggcggg aagttctggt ggaggaagtt ctggtggaga gcctactact  240
gagaacttgt acttccagag cgataacgga agttctggtg gaggaagttc tggtggaatg  300
gtgtttacac tcgaagattt cgtaggggac tggcggcaga cagccggcta caacctggac  360
caagtccttg agcagggcgg tgtgtccagt ttgtttcaga atctcggggt gtccgtaact  420
ccgatccaaa ggattgtcct gagcggtgaa aacggcctga agatcgacat ccatgtcatc  480
atcccgtatg aaggtctgag cggcgatcag atgggccaga tcgaaaaaat ttttaaggtg  540
gtgtaccctg tggatgatca tcactttaag gtgattctgc actatggcac actggtaatc  600
gacggggtta cg                                                      612

SEQ ID NO: 219         moltype = AA  length = 204
FEATURE                Location/Qualifiers
REGION                 1..204
                       note = Description of Artificial Sequence: Synthetic
                        polypeptide
source                 1..204
                       mol_type = protein
                       organism = synthetic construct
SEQUENCE: 219
MNMIDYFGRP YEGIAVFDGK KITVTGTLWN GNKIIDERLI NPDGSLLFRV TINGVTGWRL  60
CERILAGSSG GGSSGGEPTT ENLYFQSDNG SSGGGSSGGM VFTLEDFVGD WRQTAGYNLD  120
QVLEQGGVSS LFQNLGVSVT PIQRIVLSGE NGLKIDIHVI IPYEGLSGDQ MGQIEKIFKV  180
VYPVDDHHFK VILHYGTLVI DGVT                                         204

SEQ ID NO: 220         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 220
atgatgatcg actatttcgg acggccgtat gaaggcatcg ccgtgttcga cggcaaaaag  60
atcactgtaa ccgggaccct gtggaacggc aacaaaatta tcgacgagcg cctgatcaac  120
cccgacggct ccctgctgtt ccgcgtaacc atcaacggag tgaccggctg gcggctgtgc  180
gagcgcattt tggcgggaag ttctggtgga ggaagttctg gtggagagcc tactactgag  240
aacttgtact tccagagcga taacggaagt tctggtggag gaagttctgg tggaatggtg  300
tttacactcg aagatttcgt aggggactgg cggcagacag ccggctacaa cctggaccaa  360
gtccttgagc agggcggtgt gtccagtttg tttcagaatc tcggggtgtc cgtaactccg  420
atccaaagga ttgtcctgag cggtgaaaac ggcctgaaga tcgacatcca tgtcatcatc  480
ccgtatgaag gtctgagcgg cgatcagatg ggccagatcg aaaaaatttt taaggtggtg  540
taccctgtgg atgatcatca ctttaaggtg attctgcact atggcacact ggtaatcgac  600
ggggttacgc cgaac                                                   615

SEQ ID NO: 221         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 221
MMIDYFGRPY EGIAVFDGKK ITVTGTLWNG NKIIDERLIN PDGSLLFRVT INGVTGWRLC  60
ERILAGSSGG GSSGGEPTTE NLYFQSDNGS SGGGSSGGMV FTLEDFVGDW RQTAGYNLDQ  120
VLEQGGVSSL FQNLGVSVTP IQRIVLSGEN GLKIDIHVII PYEGLSGDQM GQIEKIFKVV  180
YPVDDHHFKV ILHYGTLVID GVTPN                                        205

SEQ ID NO: 222         moltype = DNA  length = 615
FEATURE                Location/Qualifiers
misc_feature           1..615
                       note = Description of Artificial Sequence: Synthetic
```

```
                         polynucleotide
source                  1..615
                        mol_type = other DNA
                        organism = synthetic construct
SEQUENCE: 222
atgtatttcg gacggccgta tgaaggcatc gccgtgttcg acggcaaaaa gatcactgta  60
accgggaccc tgtggaacgg caacaaaatt atcgacgagc gcctgatcaa ccccgacggc  120
tccctgctgt tccgcgtaac catcaacgga gtgaccggct ggcggctgtg cgagcgcatt  180
ttggcgggaa gttctggtgg aggaagttct ggtggagagc ctactactga gaacttgtac  240
ttccagagcg ataacggaag ttctggtgga ggaagttctg gtggaatggt gtttacactc  300
gaagatttcg taggggactg gcggcagaca gccggctaca acctggacca agtccttgag  360
cagggcggtg tgtccagttt gtttcagaat ctcggggtgt ccgtaactcc gatccaaagg  420
attgtcctga gcggtgaaaa cggcctgaag atcgacatcc atgtcatcat cccgtatgaa  480
ggtctgagcg gcgatcagat gggccagatc gaaaaaattt ttaaggtggt gtaccctgtg  540
gatgatcatc actttaaggt gattctgcac tatggcacac tggtaatcga cggggttacg  600
ccgaacatga tcgac                                                  615

SEQ ID NO: 223          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 223
MYFGRPYEGI AVFDGKKITV TGTLWNGNKI IDERLINPDG SLLFRVTING VTGWRLCERI  60
LAGSSGGGSS GGEPTTENLY FQSDNGSSGG GSSGGMVFTL EDFVGDWRQT AGYNLDQVLE  120
QGGVSSLFQN LGVSVTPIQR IVLSGENGLK IDIHVIIPYE GLSGDQMGQI EKIFKVVYPV  180
DDHHFKVILH YGTLVIDGVT PNMID                                       205

SEQ ID NO: 224          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 224
atgcggccgt atgaaggcat cgccgtgttc gacggcaaaa agatcactgt aaccgggacc  60
ctgtggaacg gcaacaaaat tatcgacgag cgcctgatca accccgacgg ctccctgctg  120
ttccgcgtaa ccatcaacgg agtgaccggc tggcggctgt gcgagcgcat tttggcggga  180
agttctggtg gaggaagttc tggtggagag cctactactg agaacttgta cttccagagc  240
gataacggaa gttctggtgg aggaagttct ggtggaatgg tgtttacact cgaagatttc  300
gtaggggact ggcggcagac agccggctac aacctggacc aagtccttga gcagggcggt  360
gtgtccagtt tgtttcagaa tctcggggtg tccgtaactc cgatccaaag gattgtcctg  420
agcggtgaaa acggcctgaa gatcgacatc catgtcatca tcccgtatga aggtctgagc  480
ggcgatcaga tgggccagat cgaaaaaatt tttaaggtgg tgtaccctgt ggatgatcat  540
cactttaagg tgattctgca ctatggcaca ctggtaatcg acggggttac gccgaacatg  600
atcgactatt tcgga                                                  615

SEQ ID NO: 225          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 225
MRPYEGIAVF DGKKITVTGT LWNGNKIIDE RLINPDGSLL FRVTINGVTG WRLCERILAG  60
SSGGGSSGGE PTTENLYFQS DNGSSGGGSS GGMVFTLEDF VGDWRQTAGY NLDQVLEQGG  120
VSSLFQNLGV SVTPIQRIVL SGENGLKIDI HVIIPYEGLS GDQMGQIEKI FKVVYPVDDH  180
HFKVILHYGT LVIDGVTPNM IDYFG                                       205

SEQ ID NO: 226          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 226
atggaaggca tcgccgtgtt cgacggcaaa aagatcactg taaccgggac cctgtggaac  60
ggcaacaaaa ttatcgacga gcgcctgatc aaccccgacg gctccctgct gttccgcgta  120
accatcaacg gagtgaccgg ctggcggctg tgcgagcgca ttttggcggg aagttctggt  180
ggaggaagtt ctggtggaga gcctactact gagaacttgt acttccagag cgataacgga  240
```

```
agttctggtg gaggaagttc tggtggaatg gtgtttacac tcgaagattt cgtaggggac  300
tggcggcaga cagccggcta caacctggac caagtccttg agcagggcgg tgtgtccagt  360
ttgtttcaga atctcggggt gtccgtaact ccgatccaaa ggattgtcct gagcggtgaa  420
aacggcctga agatcgacat ccatgtcatc atcccgtatg aaggtctgag cggcgatcag  480
atgggccaga tcgaaaaaat ttttaaggtg gtgtaccctg tggatgatca tcactttaag  540
gtgattctgc actatggcac actggtaatc gacggggtta cgccgaacat gatcgactat  600
ttcggacggc cgtat                                                   615

SEQ ID NO: 227         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 227
MEGIAVFDGK KITVTGTLWN GNKIIDERLI NPDGSLLFRV TINGVTGWRL CERILAGSSG  60
GGSSGGEPTT ENLYFQSDNG SSGGGSSGGM VFTLEDFVGD WRQTAGYNLD QVLEQGGVSS  120
LFQNLGVSVT PIQRIVLSGE NGLKIDIHVI IPYEGLSGDQ MGQIEKIFKV VYPVDDHHFK  180
VILHYGTLVI DGVTPNMIDY FGRPY                                        205

SEQ ID NO: 228         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 228
atgttcgacg gcaaaaagat cactgtaacc gggaccctgt ggaacggcaa caaaattatc  60
gacgagcgcc tgatcaaccc cgacggctcc ctgctgttcc gcgtaaccat caacggagtg  120
accggctggc ggctgtgcga gcgcattttg gcgggaagtt ctggtggagg aagttctggt  180
ggagagccta ctactgagaa cttgtacttc cagagcgata acggaagttc tggtggagga  240
agttctggtg gaatggtgtt tacactcgaa gatttcgtag gggactggcg gcagacagcc  300
ggctacaacc tggaccaagt ccttgagcag ggcggtgtgt ccagtttgtt tcagaatctc  360
ggggtgtccg taactccgat ccaaaggatt gtcctgagcg gtgaaaacgg cctgaagatc  420
gacatccatg tcatcatccc gtatgaaggt ctgagcggcg atcagatggg ccagatcgaa  480
aaaattttta aggtggtgta ccctgtggat gatcatcact ttaaggtgat tctgcactat  540
ggcacactgg taatcgacgg ggttacgccg aacatgatcg actatttcgg acggccgtat  600
gaaggcatcg tggcc                                                   615

SEQ ID NO: 229         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 229
MFDGKKITVT GTLWNGNKII DERLINPDGS LLFRVTINGV TGWRLCERIL AGSSGGGSSG  60
GEPTTENLYF QSDNGSSGGG SSGGMVFTLE DFVGDWRQTA GYNLDQVLEQ GGVSSLFQNL  120
GVSVTPIQRI VLSGENGLKI DIHVIIPYEG LSGDQMGQIE KIFKVVYPVD DHHFKVILHY  180
GTLVIDGVTP NMIDYFGRPY EGIVA                                        205

SEQ ID NO: 230         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 230
atggacggca aaaagatcac tgtaaccggg accctgtgga acggcaacaa aattatcgac  60
gagcgcctga tcaaccccga cggctccctg ctgttccgcg taaccatcaa cggagtgacc  120
ggctggcggc tgtgcgagcg cattttggcg ggaagttctg gtggaggaag ttctggtgga  180
gagcctacta ctgagaactt gtacttccag agcgataacg gaagttctgg tggaggaagt  240
tctggtggaa tggtgtttac actcgaagat ttcgtagggg actggcggca gacagccggc  300
tacaacctgg accaagtcct tgagcagggc ggtgtgtcca gtttgtttca gaatctcggg  360
gtgtccgtaa ctccgatcca aaggattgtc ctgagcggtg aaaacggcct gaagatcgac  420
atccatgtca tcatcccgta tgaaggtctg agcggcgatc agatgggcca gatcgaaaaa  480
atttttaagg tggtgtaccc tgtggatgat catcacttta aggtgattct gcactatggc  540
acactggtaa tcgacggggt tacgccgaac atgatcgact atttcggacg gccgtatgaa  600
ggcatcgccg tgttc                                                   615

SEQ ID NO: 231         moltype = AA  length = 205
```

-continued

```
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 231
MDGKKITVTG TLWNGNKIID ERLINPDGSL LFRVTINGVT GWRLCERILA GSSGGGSSGG  60
EPTTENLYFQ SDNGSSGGGS SGGMVFTLED FVGDWRQTAG YNLDQVLEQG GVSSLFQNLG  120
VSVTPIQRIV LSGENGLKID IHVIIPYEGL SGDQMGQIEK IFKVVYPVDD HHFKVILHYG  180
TLVIDGVTPN MIDYFGRPYE GIAVF                                       205

SEQ ID NO: 232         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 232
atgaaaaaga tcactgtaac cgggaccctg tggaacggca acaaaattat cgacgagcgc  60
ctgatcaacc ccgacggctc cctgctgttc cgcgtaacca tcaacggagt gaccggctgg  120
cggctgtgcg agcgcatttt ggcgggaagt tctggtggag gaagttctgg tggagagcct  180
actactgaga acttgtactt ccagagcgat aacggaagtt ctggtggagg aagttctggt  240
ggaatggtgt ttacactcga agatttcgta ggggactggc ggcagacagc cggctacaac  300
ctggaccaag tccttgagca gggcggtgtg tccagtttgt ttcagaatct cggggtgtcc  360
gtaactccga tccaaaggat tgtcctgagc ggtgaaaacg gcctgaagat cgacatccat  420
gtcatcatcc cgtatgaagg tctgagcggc gatcagatgg gccagatcga aaaaattttt  480
aaggtggtgt accctgtgga tgatcatcac tttaaggtga ttctgcacta tggcacactg  540
gtaatcgacg ggttacgcc gaacatgatc gactatttcg gacggccgta tgaaggcatc  600
gccgtgttcg acggc                                                  615

SEQ ID NO: 233         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 233
MKKITVTGTL WNGNKIIDER LINPDGSLLF RVTINGVTGW RLCERILAGS SGGGSSGGEP  60
TTENLYFQSD NGSSGGGSSG GMVFTLEDFV GDWRQTAGYN LDQVLEQGGV SSLFQNLGVS  120
VTPIQRIVLS GENGLKIDIH VIIPYEGLSG DQMGQIEKIF KVVYPVDDHH FKVILHYGTL  180
VIDGVTPNMI DYFGRPYEGI AVFDG                                       205

SEQ ID NO: 234         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 234
atgaagatca ctgtaaccgg gaccctgtgg aacggcaaca aaattatcga cgagcgcctg  60
atcaaccccg acggctccct gctgttccgc gtaaccatca acggagtgac cggctggcgg  120
ctgtgcgagc gcattttggc gggaagttct ggtggaggaa gttctggtgg agagcctact  180
actgagaact tgtacttcca gagcgataac ggaagttctg gtggaggaag ttctggtgga  240
atggtgttta cactcgaaga tttcgtaggg gactggcggc agacagccgg ctacaacctg  300
gaccaagtcc ttgagcaggg cggtgtgtcc agtttgtttc agaatctcgg ggtgtccgta  360
actccgatcc aaaggattgt cctgagcggt gaaaacggcc tgaagatcga catccatgtc  420
atcatcccgt atgaaggtct gagcggcgat cagatgggcc agatcgaaaa aatttttaag  480
gtggtgtacc ctgtggatga tcatcacttt aaggtgattc tgcactatgg cacactggta  540
atcgacgggg ttacgccgaa catgatcgac tatttcggac ggccgtatga aggcatcgcc  600
gtgttcgacg gcaaa                                                  615

SEQ ID NO: 235         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 235
MKITVTGTLW NGNKIIDERL INPDGSLLFR VTINGVTGWR LCERILAGSS GGGSSGGEPT  60
```

```
TENLYFQSDN GSSGGGSSGG MVFTLEDFVG DWRQTAGYNL DQVLEQGGVS SLFQNLGVSV  120
TPIQRIVLSG ENGLKIDIHV IIPYEGLSGD QMGQIEKIFK VVYPVDDHHF KVILHYGTLV  180
IDGVTPNMID YFGRPYEGIA VFDGK                                        205

SEQ ID NO: 236          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 236
atgatcactg taaccgggac cctgtggaac ggcaacaaaa ttatcgacga gcgcctgatc  60
aaccccgacg gctccctgct gttccgcgta accatcaacg gagtgaccgg ctggcggctg  120
tgcgagcgca ttttggcggg aagttctggt ggaggaagtt ctggtggaga gcctactact  180
gagaacttgt acttccagag cgataacgga agttctggtg gaggaagttc tggtggaatg  240
gtgtttacac tcgaagattt cgtaggggac tggcggcaga cagccggcta caacctggac  300
caagtccttg agcagggcgg tgtgtccagt ttgtttcaga atctcggggt gtccgtaact  360
ccgatccaaa ggattgtcct gagcggtgaa aacggcctga agatcgacat ccatgtcatc  420
atcccgtatg aaggtctgag cggcgatcag atgggccaga tcgaaaaaat ttttaaggtg  480
gtgtaccctg tggatgatca tcactttaag gtgattctgc actatggcac actggtaatc  540
gacggggtta cgccgaacat gatcgactat ttcggacggc cgtatgaagg catcgccgtg  600
ttcgacggca aaaag                                                   615

SEQ ID NO: 237          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 237
MITVTGTLWN GNKIIDERLI NPDGSLLFRV TINGVTGWRL CERILAGSSG GGSSGGEPTT  60
ENLYFQSDNG SSGGGSSGGM VFTLEDFVGD WRQTAGYNLD QVLEQGGVSS LFQNLGVSVT  120
PIQRIVLSGE NGLKIDIHVI IPYEGLSGDQ MGQIEKIFKV VYPVDDHHFK VILHYGTLVI  180
DGVTPNMIDY FGRPYEGIAV FDGKK                                        205

SEQ ID NO: 238          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 238
atggggaccc tgtggaacgg caacaaaatt atcgacgagc gcctgatcaa ccccgacggc  60
tccctgctgt tccgcgtaac catcaacgga gtgaccggct ggcggctgtg cgagcgcatt  120
ttggcgggaa gttctggtgg aggaagttct ggtggagagc ctactactga gaacttgtac  180
ttccagagcg ataacggaag ttctggtgga ggaagttctg gtggaatggt gtttacactc  240
gaagatttcg taggggactg gcggcagaca gccggctaca acctggacca agtccttgag  300
cagggcggtg tgtccagttt gtttcagaat ctcggggtgt ccgtaactcc gatccaaagg  360
attgtcctga gcggtgaaaa cggcctgaag atcgacatcc atgtcatcat cccgtatgaa  420
ggtctgagcg gcgatcagat gggccagatc gaaaaaattt ttaaggtggt gtaccctgtg  480
gatgatcatc actttaaggt gattctgcac tatggcacac tggtaatcga cggggttacg  540
ccgaacatga tcgactattt cggacggccg tatgaaggca tcgccgtgtt cgacggcaaa  600
aagatcactg taacc                                                   615

SEQ ID NO: 239          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 239
MGTLWNGNKI IDERLINPDG SLLFRVTING VTGWRLCERI LAGSSGGGSS GGEPTTENLY  60
FQSDNGSSGG GSSGGMVFTL EDFVGDWRQT AGYNLDQVLE QGGVSSLFQN LGVSVTPIQR  120
IVLSGENGLK IDIHVIIPYE GLSGDQMGQI EKIFKVVYPV DDHHFKVILH YGTLVIDGVT  180
PNMIDYFGRP YEGIAVFDGK KITVT                                        205

SEQ ID NO: 240          moltype = DNA  length = 615
FEATURE                 Location/Qualifiers
misc_feature            1..615
                        note = Description of Artificial Sequence: Synthetic
                         polynucleotide
```

```
source                  1..615
                        mol_type = other DNA
                        organism = synthetic construct
SEQUENCE: 240
atgaccctgt ggaacggcaa caaaattatc gacgagcgcc tgatcaaccc cgacggctcc  60
ctgctgttcc gcgtaaccat caacggagtg accggctggc ggctgtgcga gcgcattttg  120
gcgggaagtt ctggtggagg aagttctggt ggagagccta ctactgagaa cttgtacttc  180
cagagcgata acggaagttc tggtggagga agttctggtg gaatggtgtt tacactcgaa  240
gatttcgtag gggactggcg gcagacagcc ggctacaacc tggaccaagt ccttgagcag  300
ggcggtgtgt ccagtttgtt tcagaatctc ggggtgtccg taactccgat ccaaaggatt  360
gtcctgagcg gtgaaaacgg cctgaagatc gacatccatg tcatcatccc gtatgaaggt  420
ctgagcggcg atcagatggg ccagatcgaa aaaattttta aggtggtgta ccctgtggat  480
gatcatcact ttaaggtgat tctgcactat ggcacactgg taatcgacgg ggttacgccg  540
aacatgatcg actatttcgg acggccgtat gaaggcatcg ccgtgttcga cggcaaaaag  600
atcactgtaa ccggg                                                  615

SEQ ID NO: 241          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 241
MTLWNGNKII DERLINPDGS LLFRVTINGV TGWRLCERIL AGSSGGGSSG GEPTTENLYF  60
QSDNGSSGGG SSGGMVFTLE DFVGDWRQTA GYNLDQVLEQ GGVSSLFQNL GVSVTPIQRI  120
VLSGENGLKI DIHVIIPYEG LSGDQMGQIE KIFKVVYPVD DHHFKVILHY GTLVIDGVTP  180
NMIDYFGRPY EGIAVFDGKK ITVTG                                       205

SEQ ID NO: 242          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 242
atgctgtgga acggcaacaa aattatcgac gagcgcctga tcaaccccga cggctccctg  60
ctgttccgcg taaccatcaa cggagtgacc ggctggcggc tgtgcgagcg cattttggcg  120
ggaagttctg gtggaggaag ttctggtgga gagcctacta ctgagaactt gtacttccag  180
agcgataacg gaagttctgg tggaggaagt tctggtggaa tggtgtttac actcgaagat  240
ttcgtagggg actggcggca gacagccggc tacaacctgg accaagtcct tgagcagggc  300
ggtgtgtcca gtttgtttca gaatctcggg gtgtccgtaa ctccgatcca aaggattgtc  360
ctgagcggtg aaaacggcct gaagatcgac atccatgtca tcatcccgta tgaaggtctg  420
agcggcgatc agatgggcca gatcgaaaaa atttttaagg tggtgtaccc tgtggatgat  480
catcacttta aggtgattct gcactatggc acactggtaa tcgacggggt tacgccgaac  540
atgatcgact atttcggacg gccgtatgaa ggcatcgccg tgttcgacgg caaaaagatc  600
actgtaaccg ggacc                                                  615

SEQ ID NO: 243          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 243
MLWNGNKIID ERLINPDGSL LFRVTINGVT GWRLCERILA GSSGGGSSGG EPTTENLYFQ  60
SDNGSSGGGS SGGMVFTLED FVGDWRQTAG YNLDQVLEQG GVSSLFQNLG VSVTPIQRIV  120
LSGENGLKID IHVIIPYEGL SGDQMGQIEK IFKVVYPVDD HHFKVILHYG TLVIDGVTPN  180
MIDYFGRPYE GIAVFDGKKI TVTGT                                       205

SEQ ID NO: 244          moltype = DNA  length = 616
FEATURE                 Location/Qualifiers
misc_feature            1..616
                        note = Description of Artificial Sequence: Synthetic
                         polynucleotide
source                  1..616
                        mol_type = other DNA
                        organism = synthetic construct
SEQUENCE: 244
atgaacggca acaaaattat cgacgagcgc ctgatcaacc ccgacggctc cctgctgttc  60
cgcgtaacca tcaacggagt gaccggctgg cggctgtgcg agcgcatttt ggcgggaagt  120
tctggtggag gaagttctgg tggagagcct actactgaga acttgtactt ccagagcgat  180
aacggaagtt ctggtggagg aagttctggt ggaatggtgt ttacactcga agatttcgta  240
ggggactggc ggcagacagc cggctacaac ctggaccaag tccttgagca gggcggtgtg  300
```

```
tccagtttgt ttcagaatct cggggtgtcc gtaactccga tccaaaggat tgtcctgagc  360
ggtgaaaacg gcctgaagat cgacatccat gtcatcatcc cgtatgaagg tctgagcggc  420
gatcagatgg gccagatcga aaaaattttt aaggtggtgt accctgtgga tgatcatcac  480
tttaaggtga ttctgcacta tggcacactg gtaatcgacg gggttacgcc gaacatgatc  540
gactatttcg gacggccgta tgaaggcatc gccgtgttcg acggcaaaaa gatcactgta  600
accgggaccc tgtggg                                                   616

SEQ ID NO: 245         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 245
MNGNKIIDER LINPDGSLLF RVTINGVTGW RLCERILAGS SGGGSSGGEP TTENLYFQSD  60
NGSSGGGSSG GMVFTLEDFV GDWRQTAGYN LDQVLEQGGV SSLFQNLGVS VTPIQRIVLS  120
GENGLKIDIH VIIPYEGLSG DQMGQIEKIF KVVYPVDDHH FKVILHYGTL VIDGVTPNMI  180
DYFGRPYEGI AVFDGKKITV TGTLW                                         205

SEQ ID NO: 246         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 246
atgaaaatta tcgacgagcg cctgatcaac cccgacggct ccctgctgtt ccgcgtaacc  60
atcaacggag tgaccggctg gcggctgtgc gagcgcattt tggcgggaag ttctggtgga  120
ggaagttctg gtggagagcc tactactgag aacttgtact tccagagcga taacggaagt  180
tctggtggag gaagttctgg tggaatggtg tttacactcg aagatttcgt aggggactgg  240
cggcagacag ccggctacaa cctggaccaa gtccttgagc agggcggtgt gtccagtttg  300
tttcagaatc tcggggtgtc cgtaactccg atccaaagga ttgtcctgag cggtgaaaac  360
ggcctgaaga tcgacatcca tgtcatcatc ccgtatgaag gtctgagcgg cgatcagatg  420
ggccagatcg aaaaaatttt taaggtggtg taccctgtgg atgatcatca ctttaaggtg  480
attctgcact atggcacact ggtaatcgac ggggttacgc cgaacatgat cgactatttc  540
ggacggccgt atgaaggcat cgccgtgttc gacggcaaaa agatcactgt aaccgggacc  600
ctgtggaacg gcaac                                                    615

SEQ ID NO: 247         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 247
MKIIDERLIN PDGSLLFRVT INGVTGWRLC ERILAGSSGG GSSGGEPTTE NLYFQSDNGS  60
SGGGSSGGMV FTLEDFVGDW RQTAGYNLDQ VLEQGGVSSL FQNLGVSVTP IQRIVLSGEN  120
GLKIDIHVII PYEGLSGDQM GQIEKIFKVV YPVDDHHFKV ILHYGTLVID GVTPNMIDYF  180
GRPYEGIAVF DGKKITVTGT LWNGN                                         205

SEQ ID NO: 248         moltype = DNA  length = 624
FEATURE                Location/Qualifiers
misc_feature           1..624
                       note = Description of Artificial Sequence: Synthetic
                        polynucleotide
source                 1..624
                       mol_type = other DNA
                       organism = synthetic construct
SEQUENCE: 248
atggacgagc gcctgatcaa ccccgacggc tccctgctgt tccgcgtaac catcaacgga  60
gtgaccggct ggcggctgtg cgagcgcatt ttggcgggaa gttctggtgg aggaagttct  120
ggtggagagc ctactactga gaacttgtac ttccagagcg ataacggaag ttctggtgga  180
ggaagttctg gtggaatggt gtttacactc gaagatttcg taggggactg gcggcagaca  240
gccggctaca acctggacca agtccttgag cagggcggtg tgtccagttt gtttcagaat  300
ctcggggtgt ccgtaactcc gatccaaagg attgtcctga gcggtgaaaa cggcctgaag  360
atcgacatcc atgtcatcat cccgtatgaa ggtctgagcg gcgatcagat gggccagatc  420
gaaaaaattt ttaaggtggt gtaccctgtg gatgatcatc actttaaggt gattctgcac  480
tatggcacac tggtaatcga cggggttacg ccgaacatga tcgactattt cggacggccg  540
tatgaaggca tcgccgtgtt cgacggcaaa aagatcactg taaccgggac cctgtggaac  600
ggcaacaaaa ttatcgacga gcgc                                          624

SEQ ID NO: 249         moltype = AA  length = 208
FEATURE                Location/Qualifiers
```

```
REGION                  1..208
                        note = Description of Artificial Sequence: Synthetic
                         polypeptide
source                  1..208
                        mol_type = protein
                        organism = synthetic construct
SEQUENCE: 249
MDERLINPDG SLLFRVTING VTGWRLCERI LAGSSGGGSS GGEPTTENLY FQSDNGSSGG  60
GSSGGMVFTL EDFVGDWRQT AGYNLDQVLE QGGVSSLFQN LGVSVTPIQR IVLSGENGLK  120
IDIHVIIPYE GLSGDQMGQI EKIFKVVYPV DDHHFKVILH YGTLVIDGVT PNMIDYFGRP  180
YEGIAVFDGK KITVTGTLWN GNKIIDER                                    208

SEQ ID NO: 250          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 250
atggagcgcc tgatcaaccc cgacggctcc ctgctgttcc gcgtaaccat caacggagtg  60
accggctggc ggctgtgcga gcgcattttg gcgggaagtt ctggtggagg aagttctggt  120
ggagagccta ctactgagaa cttgtacttc cagagcgata acggaagttc tggtggagga  180
agttctggtg gaatggtgtt tacactcgaa gatttcgtag gggactggcg gcagacagcc  240
ggctacaacc tggaccaagt ccttgagcag ggcggtgtgt ccagtttgtt tcagaatctc  300
ggggtgtccg taactccgat ccaaaggatt gtcctgagcg gtgaaaacgg cctgaagatc  360
gacatccatg tcatcatccc gtatgaaggt ctgagcggcg atcagatggg ccagatcgaa  420
aaaattttta aggtggtgta ccctgtggat gatcatcact ttaaggtgat tctgcactat  480
ggcacactgg taatcgacgg ggttacgccg aacatgatcg actatttcgg acggccgtat  540
gaaggcatcg ccgtgttcga cggcaaaaag atcactgtaa ccgggaccct gtggaacggc  600
aacaaaatta tcgac                                                  615

SEQ ID NO: 251          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 251
MERLINPDGS LLFRVTINGV TGWRLCERIL AGSSGGGSSG GEPTTENLYF QSDNGSSGGG  60
SSGGMVFTLE DFVGDWRQTA GYNLDQVLEQ GGVSSLFQNL GVSVTPIQRI VLSGENGLKI  120
DIHVIIPYEG LSGDQMGQIE KIFKVVYPVD DHHFKVILHY GTLVIDGVTP NMIDYFGRPY  180
EGIAVFDGKK ITVTGTLWNG NKIID                                       205

SEQ ID NO: 252          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 252
atgcgcctga tcaaccccga cggctccctg ctgttccgcg taaccatcaa cggagtgacc  60
ggctggcggc tgtgcgagcg cattttggcg ggaagttctg gtggaggaag ttctggtgga  120
gagcctacta ctgagaactt gtacttccag agcgataacg gaagttctgg tggaggaagt  180
tctggtggaa tggtgtttac actcgaagat ttcgtagggg actggcggca gacagccggc  240
tacaacctgg accaagtcct tgagcagggc ggtgtgtcca gtttgtttca gaatctcggg  300
gtgtccgtaa ctccgatcca aaggattgtc ctgagcggtg aaaacggcct gaagatcgac  360
atccatgtca tcatcccgta tgaaggtctg agcggcgatc agatgggcca gatcgaaaaa  420
atttttaagg tggtgtaccc tgtggatgat catcacttta aggtgattct gcactatggc  480
acactggtaa tcgacggggt tacgccgaac atgatcgact atttcggacg gccgtatgaa  540
ggcatcgccg tgttcgacgg caaaaagatc actgtaaccg ggaccctgtg gaacggcaac  600
aaaattatcg acgag                                                  615

SEQ ID NO: 253          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 253
MRLINPDGSL LFRVTINGVT GWRLCERILA GSSGGGSSGG EPTTENLYFQ SDNGSSGGGS  60
SGGMVFTLED FVGDWRQTAG YNLDQVLEQG GVSSLFQNLG VSVTPIQRIV LSGENGLKID  120
```

```
IHVIIPYEGL SGDQMGQIEK IFKVVYPVDD HHFKVILHYG TLVIDGVTPN MIDYFGRPYE  180
GIAVFDGKKI TVTGTLWNGN KIIDE                                        205

SEQ ID NO: 254         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 254
atgctgatca accccgacgg ctccctgctg ttccgcgtaa ccatcaacgg agtgaccggc  60
tggcggctgt gcgagcgcat tttggcggga agttctggtg gaggaagttc tggtggagag  120
cctactactg agaacttgta cttccagagc gataacggaa gttctggtgg aggaagttct  180
ggtggaatgg tgtttacact cgaagatttc gtaggggact ggcggcagac agccggctac  240
aacctggacc aagtccttga gcagggcggt gtgtccagtt tgtttcagaa tctcggggtg  300
tccgtaactc cgatccaaag gattgtcctg agcggtgaaa acggcctgaa gatcgacatc  360
catgtcatca tcccgtatga aggtctgagc ggcgatcaga tgggccagat cgaaaaaatt  420
tttaaggtgg tgtaccctgt ggatgatcat cactttaagg tgattctgca ctatggcaca  480
ctggtaatcg acggggttac gccgaacatg atcgactatt tcggacggcc gtatgaaggc  540
atcgccgtgt tcgacggcaa aaagatcact gtaaccggga ccctgtggaa cggcaacaaa  600
attatcgacg agcgc                                                   615

SEQ ID NO: 255         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 255
MLINPDGSLL FRVTINGVTG WRLCERILAG SSGGGSSGGE PTTENLYFQS DNGSSGGGSS  60
GGMVFTLEDF VGDWRQTAGY NLDQVLEQGG VSSLFQNLGV SVTPIQRIVL SGENGLKIDI  120
HVIIPYEGLS GDQMGQIEKI FKVVYPVDDH HFKVILHYGT LVIDGVTPNM IDYFGRPYEG  180
IAVFDGKKIT VTGTLWNGNK IIDER                                        205

SEQ ID NO: 256         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 256
atgatcaacc ccgacggctc cctgctgttc cgcgtaacca tcaacggagt gaccggctgg  60
cggctgtgcg agcgcatttt ggcgggaagt tctggtggag gaagttctgg tggagagcct  120
actactgaga acttgtactt ccagagcgat aacggaagtt ctggtggagg aagttctggt  180
ggaatggtgt ttacactcga agatttcgta ggggactggc ggcagacagc cggctacaac  240
ctggaccaag tccttgagca gggcggtgtg tccagtttgt ttcagaatct cggggtgtcc  300
gtaactccga tccaaaggat tgtcctgagc ggtgaaaacg gcctgaagat cgacatccat  360
gtcatcatcc cgtatgaagg tctgagcggc gatcagatgg gccagatcga aaaaattttt  420
aaggtggtgt accctgtgga tgatcatcac tttaaggtga ttctgcacta tggcacactg  480
gtaatcgacg gggttacgcc gaacatgatc gactatttcg gacggccgta tgaaggcatc  540
gccgtgttcg acggcaaaaa gatcactgta accgggaccc tgtggaacgg caacaaaatt  600
atcgacgagc gcctg                                                   615

SEQ ID NO: 257         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 257
MINPDGSLLF RVTINGVTGW RLCERILAGS SGGGSSGGEP TTENLYFQSD NGSSGGGSSG  60
GMVFTLEDFV GDWRQTAGYN LDQVLEQGGV SSLFQNLGVS VTPIQRIVLS GENGLKIDIH  120
VIIPYEGLSG DQMGQIEKIF KVVYPVDDHH FKVILHYGTL VIDGVTPNMI DYFGRPYEGI  180
AVFDGKKITV TGTLWNGNKI IDERL                                        205

SEQ ID NO: 258         moltype = DNA  length = 615
FEATURE                Location/Qualifiers
misc_feature           1..615
                       note = Description of Artificial Sequence: Synthetic
                        polynucleotide
source                 1..615
```

```
                        mol_type = other DNA
                        organism = synthetic construct
SEQUENCE: 258
atgaaccccg acggctccct gctgttccgc gtaaccatca acggagtgac cggctggcgg  60
ctgtgcgagc gcattttggc gggaagttct ggtggaggaa gttctggtgg agagcctact  120
actgagaact tgtacttcca gagcgataac ggaagttctg gtggaggaag ttctggtgga  180
atggtgttta cactcgaaga tttcgtaggg gactggcggc agacagccgg ctacaacctg  240
gaccaagtcc ttgagcaggg cggtgtgtcc agtttgtttc agaatctcgg ggtgtccgta  300
actccgatcc aaaggattgt cctgagcggt gaaaacggcc tgaagatcga catccatgtc  360
atcatcccgt atgaaggtct gagcggcgat cagatgggcc agatcgaaaa aatttttaag  420
gtggtgtacc ctgtggatga tcatcacttt aaggtgattc tgcactatgg cacactggta  480
atcgacgggg ttacgccgaa catgatcgac tatttcggac ggccgtatga aggcatcgcc  540
gtgttcgacg gcaaaaagat cactgtaacc gggaccctgt ggaacggcaa caaaattatc  600
gacgagcgcc tgatc                                                  615

SEQ ID NO: 259          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 259
MNPDGSLLFR VTINGVTGWR LCERILAGSS GGGSSGGEPT TENLYFQSDN GSSGGGSSGG  60
MVFTLEDFVG DWRQTAGYNL DQVLEQGGVS SLFQNLGVSV TPIQRIVLSG ENGLKIDIHV  120
IIPYEGLSGD QMGQIEKIFK VVYPVDDHHF KVILHYGTLV IDGVTPNMID YFGRPYEGIA  180
VFDGKKITVT GTLWNGNKII DERLI                                       205

SEQ ID NO: 260          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 260
atgcccgacg gctccctgct gttccgcgta accatcaacg gagtgaccgg ctggcggctg  60
tgcgagcgca ttttggcggg aagttctggt ggaggaagtt ctggtggaga gcctactact  120
gagaacttgt acttccagag cgataacgga agttctggtg gaggaagttc tggtggaatg  180
gtgtttacac tcgaagattt cgtaggggac tggcggcaga cagccggcta caacctggac  240
caagtccttg agcagggcgg tgtgtccagt ttgtttcaga atctcggggt gtccgtaact  300
ccgatccaaa ggattgtcct gagcggtgaa aacggcctga agatcgacat ccatgtcatc  360
atcccgtatg aaggtctgag cggcgatcag atgggccaga tcgaaaaaat ttttaaggtg  420
gtgtaccctg tggatgatca tcactttaag gtgattctgc actatggcac actggtaatc  480
gacggggtta cgccgaacat gatcgactat ttcggacggc cgtatgaagg catcgccgtg  540
ttcgacggca aaaagatcac tgtaaccggg accctgtgga acggcaacaa aattatcgac  600
gagcgcctga tcaac                                                  615

SEQ ID NO: 261          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 261
MPDGSLLFRV TINGVTGWRL CERILAGSSG GGSSGGEPTT ENLYFQSDNG SSGGGSSGGM  60
VFTLEDFVGD WRQTAGYNLD QVLEQGGVSS LFQNLGVSVT PIQRIVLSGE NGLKIDIHVI  120
IPYEGLSGDQ MGQIEKIFKV VYPVDDHHFK VILHYGTLVI DGVTPNMIDY FGRPYEGIAV  180
FDGKKITVTG TLWNGNKIID ERLIN                                       205

SEQ ID NO: 262          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 262
atggacggct ccctgctgtt ccgcgtaacc atcaacggag tgaccggctg gcggctgtgc  60
gagcgcattt tggcgggaag ttctggtgga ggaagttctg gtggagagcc tactactgag  120
aacttgtact tccagagcga taacggaagt tctggtggag gaagttctgg tggaatggtg  180
tttacactcg aagatttcgt aggggactgg cggcagacag ccggctacaa cctggaccaa  240
gtccttgagc agggcggtgt gtccagtttg tttcagaatc tcggggtgtc cgtaactccg  300
atccaaagga ttgtcctgag cggtgaaaac ggcctgaaga tcgacatcca tgtcatcatc  360
```

```
ccgtatgaag gtctgagcgg cgatcagatg ggccagatcg aaaaaatttt taaggtggtg  420
taccctgtgg atgatcatca ctttaaggtg attctgcact atggcacact ggtaatcgac  480
ggggttacgc cgaacatgat cgactatttc ggacggccgt atgaaggcat cgccgtgttc  540
gacggcaaaa agatcactgt aaccgggacc ctgtggaacg gcaacaaaat tatcgacgag  600
cgcctgatca acccc                                                   615

SEQ ID NO: 263          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 263
MDGSLLFRVT INGVTGWRLC ERILAGSSGG GSSGGEPTTE NLYFQSDNGS SGGGSSGGMV  60
FTLEDFVGDW RQTAGYNLDQ VLEQGGVSSL FQNLGVSVTP IQRIVLSGEN GLKIDIHVII  120
PYEGLSGDQM GQIEKIFKVV YPVDDHHFKV ILHYGTLVID GVTPNMIDYF GRPYEGIAVF  180
DGKKITVTGT LWNGNKIIDE RLINP                                        205

SEQ ID NO: 264          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 264
atgggctccc tgctgttccg cgtaaccatc aacggagtga ccggctggcg gctgtgcgag  60
cgcattttgg cgggaagttc tggtggagga agttctggtg gagagcctac tactgagaac  120
ttgtacttcc agagcgataa cggaagttct ggtggaggaa gttctggtgg aatggtgttt  180
acactcgaag atttcgtagg ggactggcgg cagacagccg gctacaacct ggaccaagtc  240
cttgagcagg gcggtgtgtc cagtttgttt cagaatctcg ggtgtccgt aactccgatc  300
caaaggattg tcctgagcgg tgaaaacggc ctgaagatcg acatccatgt catcatcccg  360
tatgaaggtc tgagcggcga tcagatgggc cagatcgaaa aaatttttaa ggtggtgtac  420
cctgtggatg atcatcactt taaggtgatt ctgcactatg gcacactggt aatcgacggg  480
gttacgccga acatgatcga ctatttcgga cggccgtatg aaggcatcgc cgtgttcgac  540
ggcaaaaaga tcactgtaac cgggaccctg tggaacggca acaaaattat cgacgagcgc  600
ctgatcaacc ccgac                                                   615

SEQ ID NO: 265          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 265
MGSLLFRVTI NGVTGWRLCE RILAGSSGGG SSGGEPTTEN LYFQSDNGSS GGGSSGGMVF  60
TLEDFVGDWR QTAGYNLDQV LEQGGVSSLF QNLGVSVTPI QRIVLSGENG LKIDIHVIIP  120
YEGLSGDQMG QIEKIFKVVY PVDDHHFKVI LHYGTLVIDG VTPNMIDYFG RPYEGIAVFD  180
GKKITVTGTL WNGNKIIDER LINPD                                        205

SEQ ID NO: 266          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 266
atgtccctgc tgttccgcgt aaccatcaac ggagtgaccg gctggcggct gtgcgagcgc  60
attttggcgg gaagttctgg tggaggaagt tctggtggag agcctactac tgagaacttg  120
tacttccaga gcgataacgg aagttctggt ggaggaagtt ctggtggaat ggtgtttaca  180
ctcgaagatt tcgtagggga ctggcggcag acagccggct acaacctgga ccaagtcctt  240
gagcagggcg gtgtgtccag tttgtttcag aatctcgggg tgtccgtaac tccgatccaa  300
aggattgtcc tgagcggtga aaacggcctg aagatcgaca tccatgtcat catcccgtat  360
gaaggtctga gcggcgatca gatgggccag atcgaaaaaa tttttaaggt ggtgtaccct  420
gtggatgatc atcactttaa ggtgattctg cactatggca cactggtaat cgacggggtt  480
acgccgaaca tgatcgacta tttcggacgg ccgtatgaag gcatcgccgt gttcgacggc  540
aaaaagatca ctgtaaccgg gaccctgtgg aacggcaaca aaattatcga cgagcgcctg  600
atcaaccccg acggc                                                   615

SEQ ID NO: 267          moltype = AA  length = 205
FEATURE                 Location/Qualifiers
REGION                  1..205
```

```
                         note = Description of Artificial Sequence: Synthetic
                          polypeptide
source                   1..205
                         mol_type = protein
                         organism = synthetic construct
SEQUENCE: 267
MSLLFRVTIN GVTGWRLCER ILAGSSGGGS SGGEPTTENL YFQSDNGSSG GGSSGGMVFT  60
LEDFVGDWRQ TAGYNLDQVL EQGGVSSLFQ NLGVSVTPIQ RIVLSGENGL KIDIHVIIPY  120
EGLSGDQMGQ IEKIFKVVYP VDDHHFKVIL HYGTLVIDGV TPNMIDYFGR PYEGIAVFDG  180
KKITVTGTLW NGNKIIDERL INPDG                                       205

SEQ ID NO: 268           moltype = DNA  length = 615
FEATURE                  Location/Qualifiers
misc_feature             1..615
                         note = Description of Artificial Sequence: Synthetic
                          polynucleotide
source                   1..615
                         mol_type = other DNA
                         organism = synthetic construct
SEQUENCE: 268
atgctgctgt tccgcgtaac catcaacgga gtgaccggct ggcggctgtg cgagcgcatt  60
ttggcgggaa gttctggtgg aggaagttct ggtggagagc ctactactga gaacttgtac  120
ttccagagcg ataacggaag ttctggtgga ggaagttctg gtggaatggt gtttacactc  180
gaagatttcg taggggactg gcggcagaca gccggctaca acctggacca agtccttgag  240
cagggcggtg tgtccagttt gtttcagaat ctcggggtgt ccgtaactcc gatccaaagg  300
attgtcctga gcggtgaaaa cggcctgaag atcgacatcc atgtcatcat cccgtatgaa  360
ggtctgagcg gcgatcagat gggccagatc gaaaaaattt ttaaggtggt gtaccctgtg  420
gatgatcatc actttaaggt gattctgcac tatggcacac tggtaatcga cggggttacg  480
ccgaacatga tcgactattt cggacggccg tatgaaggca tcgccgtgtt cgacggcaaa  540
aagatcactg taaccgggac cctgtggaac ggcaacaaaa ttatcgacga gcgcctgatc  600
aaccccgacg gctcc                                                  615

SEQ ID NO: 269           moltype = AA  length = 205
FEATURE                  Location/Qualifiers
REGION                   1..205
                         note = Description of Artificial Sequence: Synthetic
                          polypeptide
source                   1..205
                         mol_type = protein
                         organism = synthetic construct
SEQUENCE: 269
MLLFRVTING VTGWRLCERI LAGSSGGGSS GGEPTTENLY FQSDNGSSGG GSSGGMVFTL  60
EDFVGDWRQT AGYNLDQVLE QGGVSSLFQN LGVSVTPIQR IVLSGENGLK IDIHVIIPYE  120
GLSGDQMGQI EKIFKVVYPV DDHHFKVILH YGTLVIDGVT PNMIDYFGRP YEGIAVFDGK  180
KITVTGTLWN GNKIIDERLI NPDGS                                       205

SEQ ID NO: 270           moltype = DNA  length = 615
FEATURE                  Location/Qualifiers
misc_feature             1..615
                         note = Description of Artificial Sequence: Synthetic
                          polynucleotide
source                   1..615
                         mol_type = other DNA
                         organism = synthetic construct
SEQUENCE: 270
atgctgttcc gcgtaaccat caacggagtg accggctggc ggctgtgcga gcgcattttg  60
gcgggaagtt ctggtggagg aagttctggt ggagagccta ctactgagaa cttgtacttc  120
cagagcgata acggaagttc tggtggagga agttctggtg gaatggtgtt tacactcgaa  180
gatttcgtag gggactggcg gcagacagcc ggctacaacc tggaccaagt ccttgagcag  240
ggcggtgtgt ccagtttgtt tcagaatctc ggggtgtccg taactccgat ccaaaggatt  300
gtcctgagcg gtgaaaacgg cctgaagatc gacatccatg tcatcatccc gtatgaaggt  360
ctgagcggcg atcagatggg ccagatcgaa aaaattttta aggtggtgta ccctgtggat  420
gatcatcact ttaaggtgat tctgcactat ggcacactgg taatcgacgg ggttacgccg  480
aacatgatcg actatttcgg acggccgtat gaaggcatcg ccgtgttcga cggcaaaaag  540
atcactgtaa ccgggaccct gtggaacggc aacaaaatta tcgacgagcg cctgatcaac  600
cccgacggct ccctg                                                  615

SEQ ID NO: 271           moltype = AA  length = 205
FEATURE                  Location/Qualifiers
REGION                   1..205
                         note = Description of Artificial Sequence: Synthetic
                          polypeptide
source                   1..205
                         mol_type = protein
                         organism = synthetic construct
SEQUENCE: 271
MLFRVTINGV TGWRLCERIL AGSSGGGSSG GEPTTENLYF QSDNGSSGGG SSGGMVFTLE  60
DFVGDWRQTA GYNLDQVLEQ GGVSSLFQNL GVSVTPIQRI VLSGENGLKI DIHVIIPYEG  120
LSGDQMGQIE KIFKVVYPVD DHHFKVILHY GTLVIDGVTP NMIDYFGRPY EGIAVFDGKK  180
```

```
ITVTGTLWNG NKIIDERLIN PDGSL                                    205

SEQ ID NO: 272         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 272
atgttccgcg taaccatcaa cggagtgacc ggctggcggc tgtgcgagcg cattttggcg  60
ggaagttctg gtggaggaag ttctggtgga gagcctacta ctgagaactt gtacttccag  120
agcgataacg gaagttctgg tggaggaagt tctggtggaa tggtgtttac actcgaagat  180
ttcgtagggg actggcggca gacagccggc tacaacctgg accaagtcct tgagcagggc  240
ggtgtgtcca gtttgtttca gaatctcggg gtgtccgtaa ctccgatcca aaggattgtc  300
ctgagcggtg aaaacggcct gaagatcgac atccatgtca tcatcccgta tgaaggtctg  360
agcggcgatc agatgggcca gatcgaaaaa atttttaagg tggtgtaccc tgtggatgat  420
catcacttta aggtgattct gcactatggc acactggtaa tcgacggggt tacgccgaac  480
atgatcgact atttcggacg gccgtatgaa ggcatcgccg tgttcgacgg caaaaagatc  540
actgtaaccg ggaccctgtg gaacggcaac aaaattatcg acgagcgcct gatcaacccc  600
gacggctccc tgctg                                               615

SEQ ID NO: 273         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 273
MFRVTINGVT GWRLCERILA GSSGGGSSGG EPTTENLYFQ SDNGSSGGGS SGGMVFTLED  60
FVGDWRQTAG YNLDQVLEQG GVSSLFQNLG VSVTPIQRIV LSGENGLKID IHVIIPYEGL  120
SGDQMGQIEK IFKVVYPVDD HHFKVILHYG TLVIDGVTPN MIDYFGRPYE GIAVFDGKKI  180
TVTGTLWNGN KIIDERLINP DGSLL                                    205

SEQ ID NO: 274         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 274
atgaccatca acggagtgac cggctggcgg ctgtgcgagc gcattttggc gggaagttct  60
ggtggaggaa gttctggtgg agagcctact actgagaact tgtacttcca gagcgataac  120
ggaagttctg gtggaggaag ttctggtgga atggtgttta cactcgaaga tttcgtaggg  180
gactggcggc agacagccgg ctacaacctg gaccaagtcc ttgagcaggg cggtgtgtcc  240
agtttgtttc agaatctcgg ggtgtccgta actccgatcc aaaggattgt cctgagcggt  300
gaaaacggcc tgaagatcga catccatgtc atcatcccgt atgaaggtct gagcggcgat  360
cagatgggcc agatcgaaaa aatttttaag gtggtgtacc ctgtggatga tcatcacttt  420
aaggtgattc tgcactatgg cacactggta atcgacgggg ttacgccgaa catgatcgac  480
tatttcggac ggccgtatga aggcatcgcc gtgttcgacg gcaaaaagat cactgtaacc  540
gggaccctgt ggaacggcaa caaaattatc gacgagcgcc tgatcaaccc cgacggctcc  600
ctgctgttcc gcgta                                               615

SEQ ID NO: 275         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 275
MTINGVTGWR LCERILAGSS GGGSSGGEPT TENLYFQSDN GSSGGGSSGG MVFTLEDFVG  60
DWRQTAGYNL DQVLEQGGVS SLFQNLGVSV TPIQRIVLSG ENGLKIDIHV IIPYEGLSGD  120
QMGQIEKIFK VVYPVDDHHF KVILHYGTLV IDGVTPNMID YFGRPYEGIA VFDGKKITVT  180
GTLWNGNKII DERLINPDGS LLFRV                                    205

SEQ ID NO: 276         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
```

```
                         organism = synthetic construct
SEQUENCE: 276
atgaacggag tgaccggctg gcggctgtgc gagcgcattt tggcgggaag ttctggtgga  60
ggaagttctg gtggagagcc tactactgag aacttgtact tccagagcga taacggaagt  120
tctggtggag gaagttctgg tggaatggtg tttacactcg aagatttcgt aggggactgg  180
cggcagacag ccggctacaa cctggaccaa gtccttgagc agggcggtgt gtccagtttg  240
tttcagaatc tcggggtgtc cgtaactccg atccaaagga ttgtcctgag cggtgaaaac  300
ggcctgaaga tcgacatcca tgtcatcatc ccgtatgaag gtctgagcgg cgatcagatg  360
ggccagatcg aaaaaatttt taaggtggtg taccctgtgg atgatcatca ctttaaggtg  420
attctgcact atggcacact ggtaatcgac ggggttacgc cgaacatgat cgactatttc  480
ggacggccgt atgaaggcat cgccgtgttc gacggcaaaa agatcactgt aaccgggacc  540
ctgtggaacg gcaacaaaat tatcgacgag cgcctgatca accccgacgg ctccctgctg  600
ttccgcgtaa ccatc                                                   615

SEQ ID NO: 277           moltype = AA  length = 205
FEATURE                  Location/Qualifiers
REGION                   1..205
                         note = Description of Artificial Sequence: Synthetic
                          polypeptide
source                   1..205
                         mol_type = protein
                         organism = synthetic construct
SEQUENCE: 277
MNGVTGWRLC ERILAGSSGG GSSGGEPTTE NLYFQSDNGS SGGGSSGGMV FTLEDFVGDW  60
RQTAGYNLDQ VLEQGGVSSL FQNLGVSVTP IQRIVLSGEN GLKIDIHVII PYEGLSGDQM  120
GQIEKIFKVV YPVDDHHFKV ILHYGTLVID GVTPNMIDYF GRPYEGIAVF DGKKITVTGT  180
LWNGNKIIDE RLINPDGSLL FRVTI                                        205

SEQ ID NO: 278           moltype = DNA  length = 615
FEATURE                  Location/Qualifiers
misc_feature             1..615
                         note = Description of Artificial Sequence: Synthetic
                          polynucleotide
source                   1..615
                         mol_type = other DNA
                         organism = synthetic construct
SEQUENCE: 278
atgggagtga ccggctggcg gctgtgcgag cgcattttgg cgggaagttc tggtggagga  60
agttctggtg gagagcctac tactgagaac ttgtacttcc agagcgataa cggaagttct  120
ggtggaggaa gttctggtgg aatggtgttt acactcgaag atttcgtagg ggactggcgg  180
cagacagccg gctacaacct ggaccaagtc cttgagcagg gcggtgtgtc cagtttgttt  240
cagaatctcg gggtgtccgt aactccgatc caaaggattg tcctgagcgg tgaaaacggc  300
ctgaagatcg acatccatgt catcatcccg tatgaaggtc tgagcggcga tcagatgggc  360
cagatcgaaa aaatttttaa ggtggtgtac cctgtggatg atcatcactt taaggtgatt  420
ctgcactatg gcacactggt aatcgacggg gttacgccga acatgatcga ctatttcgga  480
cggccgtatg aaggcatcgc cgtgttcgac ggcaaaaaga tcactgtaac cgggaccctg  540
tggaacggca acaaaattat cgacgagcgc ctgatcaacc ccgacggctc cctgctgttc  600
cgcgtaacca tcaac                                                   615

SEQ ID NO: 279           moltype = AA  length = 205
FEATURE                  Location/Qualifiers
REGION                   1..205
                         note = Description of Artificial Sequence: Synthetic
                          polypeptide
source                   1..205
                         mol_type = protein
                         organism = synthetic construct
SEQUENCE: 279
MGVTGWRLCE RILAGSSGGG SSGGEPTTEN LYFQSDNGSS GGGSSGGMVF TLEDFVGDWR  60
QTAGYNLDQV LEQGGVSSLF QNLGVSVTPI QRIVLSGENG LKIDIHVIIP YEGLSGDQMG  120
QIEKIFKVVY PVDDHHFKVI LHYGTLVIDG VTPNMIDYFG RPYEGIAVFD GKKITVTGTL  180
WNGNKIIDER LINPDGSLLF RVTIN                                        205

SEQ ID NO: 280           moltype = DNA  length = 615
FEATURE                  Location/Qualifiers
misc_feature             1..615
                         note = Description of Artificial Sequence: Synthetic
                          polynucleotide
source                   1..615
                         mol_type = other DNA
                         organism = synthetic construct
SEQUENCE: 280
atggtgaccg gctggcggct gtgcgagcgc attttggcgg gaagttctgg tggaggaagt  60
tctggtggag agcctactac tgagaacttg tacttccaga gcgataacgg aagttctggt  120
ggaggaagtt ctggtggaat ggtgtttaca ctcgaagatt tcgtagggga ctggcggcag  180
acagccggct acaacctgga ccaagtcctt gagcagggcg gtgtgtccag tttgtttcag  240
aatctcgggg tgtccgtaac tccgatccaa aggattgtcc tgagcggtga aaacggcctg  300
aagatcgaca tccatgtcat catcccgtat gaaggtctga gcggcgatca gatgggccag  360
atcgaaaaaa tttttaaggt ggtgtaccct gtggatgatc atcactttaa ggtgattctg  420
```

```
cactatggca cactggtaat cgacggggtt acgccgaaca tgatcgacta tttcggacgg  480
ccgtatgaag gcatcgccgt gttcgacggc aaaaagatca ctgtaaccgg gaccctgtgg  540
aacggcaaca aaattatcga cgagcgcctg atcaaccccg acggctccct gctgttccgc  600
gtaaccatca acgga                                                   615

SEQ ID NO: 281         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 281
MVTGWRLCER ILAGSSGGGS SGGEPTTENL YFQSDNGSSG GGSSGGMVFT LEDFVGDWRQ  60
TAGYNLDQVL EQGGVSSLFQ NLGVSVTPIQ RIVLSGENGL KIDIHVIIPY EGLSGDQMGQ  120
IEKIFKVVYP VDDHHFKVIL HYGTLVIDGV TPNMIDYFGR PYEGIAVFDG KKITVTGTLW  180
NGNKIIDERL INPDGSLLFR VTING                                        205

SEQ ID NO: 282         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 282
atgggctggc ggctgtgcga gcgcattttg gcgggaagtt ctggtggagg aagttctggt  60
ggagagccta ctactgagaa cttgtacttc cagagcgata acggaagttc tggtggagga  120
agttctggtg gaatggtgtt tacactcgaa gatttcgtag gggactggcg gcagacagcc  180
ggctacaacc tggaccaagt ccttgagcag ggcggtgtgt ccagtttgtt tcagaatctc  240
ggggtgtccg taactccgat ccaaaggatt gtcctgagcg gtgaaaacgg cctgaagatc  300
gacatccatg tcatcatccc gtatgaaggt ctgagcggcg atcagatggg ccagatcgaa  360
aaaatttta aggtggtgta ccctgtggat gatcatcact ttaaggtgat tctgcactat  420
ggcacactgg taatcgacgg ggttacgccg aacatgatcg actatttcgg acggccgtat  480
gaaggcatcg ccgtgttcga cggcaaaaag atcactgtaa ccgggaccct gtggaacggc  540
aacaaaatta tcgacgagcg cctgatcaac cccgacggct ccctgctgtt ccgcgtaacc  600
atcaacggag tgacc                                                   615

SEQ ID NO: 283         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 283
MGWRLCERIL AGSSGGGSSG GEPTTENLYF QSDNGSSGGG SSGGMVFTLE DFVGDWRQTA  60
GYNLDQVLEQ GGVSSLFQNL GVSVTPIQRI VLSGENGLKI DIHVIIPYEG LSGDQMGQIE  120
KIFKVVYPVD DHHFKVILHY GTLVIDGVTP NMIDYFGRPY EGIAVFDGKK ITVTGTLWNG  180
NKIIDERLIN PDGSLLFRVT INGVT                                        205

SEQ ID NO: 284         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 284
atgctgtgcg agcgcatttt ggcgggaagt tctggtggag gaagttctgg tggagagcct  60
actactgaga acttgtactt ccagagcgat aacggaagtt ctggtggagg aagttctggt  120
ggaatggtgt ttacactcga agatttcgta ggggactggc ggcagacagc cggctacaac  180
ctggaccaag tccttgagca gggcggtgtg tccagtttgt ttcagaatct cggggtgtcc  240
gtaactccga tccaaaggat tgtcctgagc ggtgaaaacg gcctgaagat cgacatccat  300
gtcatcatcc cgtatgaagg tctgagcggc gatcagatgg gccagatcga aaaaattttt  360
aaggtggtgt accctgtgga tgatcatcac tttaaggtga ttctgcacta tggcacactg  420
gtaatcgacg gggttacgcc gaacatgatc gactatttcg gacggccgta tgaaggcatc  480
gccgtgttcg acggcaaaaa gatcactgta accgggaccc tgtggaacgg caacaaaatt  540
atcgacgagc gcctgatcaa ccccgacggc tccctgctgt tccgcgtaac catcaacgga  600
gtgaccggct ggcgg                                                   615

SEQ ID NO: 285         moltype = AA  length = 205
FEATURE                Location/Qualifiers
REGION                 1..205
                       note = Description of Artificial Sequence: Synthetic
```

```
                         polypeptide
source                  1..205
                        mol_type = protein
                        organism = synthetic construct
SEQUENCE: 285
MLCERILAGS SGGGSSGGEP TTENLYFQSD NGSSGGGSSG GMVFTLEDFV GDWRQTAGYN  60
LDQVLEQGGV SSLFQNLGVS VTPIQRIVLS GENGLKIDIH VIIPYEGLSG DQMGQIEKIF  120
KVVYPVDDHH FKVILHYGTL VIDGVTPNMI DYFGRPYEGI AVFDGKKITV TGTLWNGNKI  180
IDERLINPDG SLLFRVTING VTGWR                                        205

SEQ ID NO: 286          moltype = DNA  length = 615
FEATURE                 Location/Qualifiers
misc_feature            1..615
                        note = Description of Artificial Sequence: Synthetic
                         polynucleotide
source                  1..615
                        mol_type = other DNA
                        organism = synthetic construct
SEQUENCE: 286
atgcgcattt tggcgggaag ttctggtgga ggaagttctg gtggagagcc tactactgag  60
aacttgtact tccagagcga taacggaagt tctggtggag gaagttctgg tggaatggtg  120
tttacactcg aagatttcgt aggggactgg cggcagacag ccggctacaa cctggaccaa  180
gtccttgagc agggcggtgt gtccagtttg tttcagaatc tcggggtgtc cgtaactccg  240
atccaaagga ttgtcctgag cggtgaaaac ggcctgaaga tcgacatcca tgtcatcatc  300
ccgtatgaag gtctgagcgg cgatcagatg ggccagatcg aaaaaatttt taaggtggtg  360
taccctgtgg atgatcatca ctttaaggtg attctgcact atggcacact ggtaatcgac  420
ggggttacgc cgaacatgat cgactatttc ggacggccgt atgaaggcat cgccgtgttc  480
gacggcaaaa agatcactgt aaccgggacc ctgtggaacg gcaacaaaat tatcgacgag  540
cgcctgatca accccgacgg ctccctgctg ttccgcgtaa ccatcaacgg agtgaccggc  600
tggcggctgt gcgag                                                   615

SEQ ID NO: 287          moltype = AA  length = 205
FEATURE                 Location/Qualifiers
REGION                  1..205
                        note = Description of Artificial Sequence: Synthetic
                         polypeptide
source                  1..205
                        mol_type = protein
                        organism = synthetic construct
SEQUENCE: 287
MRILAGSSGG GSSGGEPTTE NLYFQSDNGS SGGGSSGGMV FTLEDFVGDW RQTAGYNLDQ  60
VLEQGGVSSL FQNLGVSVTP IQRIVLSGEN GLKIDIHVII PYEGLSGDQM GQIEKIFKVV  120
YPVDDHHFKV ILHYGTLVID GVTPNMIDYF GRPYEGIAVF DGKKITVTGT LWNGNKIIDE  180
RLINPDGSLL FRVTINGVTG WRLCE                                        205

SEQ ID NO: 288          moltype = DNA  length = 389
FEATURE                 Location/Qualifiers
misc_feature            1..389
                        note = Description of Artificial Sequence: Synthetic
                         polynucleotide
source                  1..389
                        mol_type = other DNA
                        organism = synthetic construct
SEQUENCE: 288
gagtgcaggt ggaaaccatc tccccaggag acgggcgcac cttccccaag cgcggccaga  60
cctgcgtggt gcactacacc gggatgcttg aagatggaaa gaaatttgat tcctcccggg  120
acagaaacaa gccctttaag tttatgctag gcaagcagga ggtgatccga ggctgggaag  180
aaggggttgc ccagatgagt gtgggtcaga gagccaaact gactatatct ccagattatg  240
cctatggtgc cactgggcac ccaggcatca tcccaccaca tgccactctc gtcttcgatg  300
tggagcttct aaaactggaa ggaggaggga gctccggtgg aggcagcggt ggagtgaccg  360
gctggcggct gtgcgaacgc attctggcg                                    389

SEQ ID NO: 289          moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 289
GVQVETISPG DGRTFPKRGQ TCVVHYTGML EDGKKFDSSR DRNKPFKFML GKQEVIRGWE  60
EGVAQMSVGQ RAKLTISPDY AYGATGHPGI IPPHATLVFD VELLKLEGGG SSGGGSGGVT  120
GWRLCERILA                                                         130

SEQ ID NO: 290          moltype = DNA  length = 795
FEATURE                 Location/Qualifiers
misc_feature            1..795
                        note = Description of Artificial Sequence: Synthetic
```

```
                         polynucleotide
source                  1..795
                        mol_type = other DNA
                        organism = synthetic construct
SEQUENCE: 290
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggagtg  480
accggaggag gtggctcagg tggagggagc tccgtggcca tcctctggca tgagatgtgg  540
catgaaggcc tggaagaggc atctcgtttg tactttgggg aaaggaacgt gaaaggcatg  600
tttgaggtgc tggagccctt gcatgctatg atggaacggg gcccccagac tctgaaggaa  660
acatccttta atcaggccta tggtcgagat ttaatggagg cccaagagtg gtgcaggaag  720
tacatgaaat cagggaatgt caaggacctc acccaagcct gggacctcta ttatcatgtg  780
ttccgacgaa tctca                                                  795

SEQ ID NO: 291          moltype = AA  length = 265
FEATURE                 Location/Qualifiers
REGION                  1..265
                        note = Description of Artificial Sequence: Synthetic
                         polypeptide
source                  1..265
                        mol_type = protein
                        organism = synthetic construct
SEQUENCE: 291
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGGGGSGGGS SVAILWHEMW  180
HEGLEEASRL YFGERNVKGM FEVLEPLHAM MERGPQTLKE TSFNQAYGRD LMEAQEWCRK  240
YMKSGNVKDL TQAWDLYYHV FRRIS                                       265

SEQ ID NO: 292          moltype = DNA  length = 825
FEATURE                 Location/Qualifiers
misc_feature            1..825
                        note = Description of Artificial Sequence: Synthetic
                         polynucleotide
source                  1..825
                        mol_type = other DNA
                        organism = synthetic construct
SEQUENCE: 292
ggagtgcagg tggaaaccat ctccccagga gacgggcgca ccttccccaa gcgcggccag  60
acctgcgtgg tgcactacac cgggatgctt gaagatggaa agaaatttga ttcctcccgg  120
gacagaaaca agccctttaa gtttatgcta ggcaagcagg aggtgatccg aggctgggaa  180
gaaggggttg cccagatgag tgtgggtcag agagccaaac tgactatatc tccagattat  240
gcctatggtg ccactgggca cccaggcatc atcccaccac atgccactct cgtcttcgat  300
gtggagcttc taaaactgga aggaggaggg agctccggtg gaggcagcgg tatggtcttc  360
acactcgaag atttcgttgg ggactggcga cagacagccg gctacaacct ggaccaagtc  420
cttgaacagg gaggtgtgtc cagtttgttt cagaatctcg gggtgtccgt aactccgatc  480
caaaggattg tcctgagcgg tgaaaatggg ctgaagatcg acatccatgt catcatcccg  540
tatgaaggtc tgagcggcga ccaaatgggc cagatcgaaa aaatttttaa ggtggtgtac  600
cctgtggatg atcatcactt taaggtgatc ctgcactatg gcacactggt aatcgacggg  660
gttacgccga acatgatcga ctatttcgga cggccgtatg aaggcatcgc cgtgttcgac  720
ggcaaaaaga tcactgtaac agggaccctg tggaacggca acaaaattat cgacgagcgc  780
ctgatcaacc ccgacggctc cctgctgttc cgagtaacca tcaac                 825

SEQ ID NO: 293          moltype = AA  length = 275
FEATURE                 Location/Qualifiers
REGION                  1..275
                        note = Description of Artificial Sequence: Synthetic
                         polypeptide
source                  1..275
                        mol_type = protein
                        organism = synthetic construct
SEQUENCE: 293
GVQVETISPG DGRTFPKRGQ TCVVHYTGML EDGKKFDSSR DRNKPFKFML GKQEVIRGWE  60
EGVAQMSVGQ RAKLTISPDY AYGATGHPGI IPPHATLVFD VELLKLEGGG SSGGGSGMVF  120
TLEDFVGDWR QTAGYNLDQV LEQGGVSSLF QNLGVSVTPI QRIVLSGENG LKIDIHVIIP  180
YEGLSGDQMG QIEKIFKVVY PVDDHHFKVI LHYGTLVIDG VTPNMIDYFG RPYEGIAVFD  240
GKKITVTGTL WNGNKIIDER LINPDGSLLF RVTIN                            275

SEQ ID NO: 294          moltype = DNA  length = 354
FEATURE                 Location/Qualifiers
misc_feature            1..354
                        note = Description of Artificial Sequence: Synthetic
                         polynucleotide
```

```
source                  1..354
                        mol_type = other DNA
                        organism = synthetic construct
SEQUENCE: 294
atgggagtga ccggctggcg gctgtgcgaa cgcattctgg cgggaggagg tggctcaggt  60
ggagggagct ccgtggccat cctctggcat gagatgtggc atgaaggcct ggaagaggca  120
tctcgtttgt actttgggga aaggaacgtg aaaggcatgt ttgaggtgct ggagcccttg  180
catgctatga tggaacgggg cccccagact ctgaaggaaa catcctttaa tcaggcctat  240
ggtcgagatt taatggaggc ccaagagtgg tgcaggaagt acatgaaatc agggaatgtc  300
aaggacctca cccaagcctg ggacctctat tatcatgtgt tccgacgaat ctca        354

SEQ ID NO: 295          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 295
MGVTGWRLCE RILAGGGGSG GGSSVAILWH EMWHEGLEEA SRLYFGERNV KGMFEVLEPL  60
HAMMERGPQT LKETSFNQAY GRDLMEAQEW CRKYMKSGNV KDLTQAWDLY YHVFRRIS    118

SEQ ID NO: 296          moltype = DNA  length = 554
FEATURE                 Location/Qualifiers
misc_feature            1..554
                        note = Description of Artificial Sequence: Synthetic
                         polynucleotide
source                  1..554
                        mol_type = other DNA
                        organism = synthetic construct
SEQUENCE: 296
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtacgccg  360
aacatgatcg actatttcgg acggccgtat gaaggcatcg ccgtgttcga cggcaaaaag  420
atcactgtaa cagggaccct gtggaacggc aacaaaatta tcgacgagcg cctgatcaac  480
cccgacggct ccctgctgtt ccgagtaacc atcaacggag tgaccggctg gcggctgtgc  540
gaacgcattc tggc                                                    554

SEQ ID NO: 297          moltype = AA  length = 184
FEATURE                 Location/Qualifiers
REGION                  1..184
                        note = Description of Artificial Sequence: Synthetic
                         polypeptide
source                  1..184
                        mol_type = protein
                        organism = synthetic construct
SEQUENCE: 297
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGTP  120
NMIDYFGRPY EGIAVFDGKK ITVTGTLWNG NKIIDERLIN PDGSLLFRVT INGVTGWRLC  180
ERIL                                                               184

SEQ ID NO: 298          moltype = DNA  length = 624
FEATURE                 Location/Qualifiers
misc_feature            1..624
                        note = Description of Artificial Sequence: Synthetic
                         polynucleotide
source                  1..624
                        mol_type = other DNA
                        organism = synthetic construct
SEQUENCE: 298
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttggaggagg tggctcaggt ggagggagct ccgtggccat cctctggcat  360
gagatgtggc atgaaggcct ggaagaggca tctcgtttgt actttgggga aaggaacgtg  420
aaaggcatgt ttgaggtgct ggagcccttg catgctatga tggaacgggg cccccagact  480
ctgaaggaaa catcctttaa tcaggcctat ggtcgagatt taatggaggc ccaagagtgg  540
tgcaggaagt acatgaaatc agggaatgtc aaggacctca cccaagcctg ggacctctat  600
tatcatgtgt tccgacgaat ctca                                         624

SEQ ID NO: 299          moltype = AA  length = 184
```

-continued

```
FEATURE                Location/Qualifiers
REGION                 1..184
                       note = Description of Artificial Sequence: Synthetic
                        polypeptide
source                 1..184
                       mol_type = protein
                       organism = synthetic construct
SEQUENCE: 299
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGTP  120
NMIDYFGRPY EGIAVFDGKK ITVTGTLWNG NKIIDERLIN PDGSLLFRVT INGVTGWRLC  180
ERIL                                                              184

SEQ ID NO: 300         moltype = DNA  length = 516
FEATURE                Location/Qualifiers
misc_feature           1..516
                       note = Description of Artificial Sequence: Synthetic
                        polynucleotide
source                 1..516
                       mol_type = other DNA
                       organism = synthetic construct
SEQUENCE: 300
atgacgccga acatgatcga ctatttcgga cggccgtatg aaggcatcgc cgtgttcgac  60
ggcaaaaaga tcactgtaac agggaccctg tggaacggca acaaaattat cgacgagcgc  120
ctgatcaacc ccgacggctc cctgctgttc cgagtaacca tcaacggagt gaccggctgg  180
cggctgtgcg aacgcattct ggcgggagga ggtggctcag gtggagggag ctccgtggcc  240
atcctctggc atgagatgtg gcatgaaggc ctggaagagg catctcgttt gtactttggg  300
gaaaggaacg tgaaaggcat gtttgaggtg ctggagccct tgcatgctat gatggaacgg  360
ggcccccaga ctctgaagga aacatccttt aatcaggcct atggtcgaga tttaatggag  420
gcccaagagt ggtgcaggaa gtacatgaaa tcagggaatg tcaaggacct cacccaagcc  480
tgggacctct attatcatgt gttccgacga atctca                            516

SEQ ID NO: 301         moltype = AA  length = 172
FEATURE                Location/Qualifiers
REGION                 1..172
                       note = Description of Artificial Sequence: Synthetic
                        polypeptide
source                 1..172
                       mol_type = protein
                       organism = synthetic construct
SEQUENCE: 301
MTPNMIDYFG RPYEGIAVFD GKKITVTGTL WNGNKIIDER LINPDGSLLF RVTINGVTGW  60
RLCERILAGG GGSGGGSSVA ILWHEMWHEG LEEASRLYFG ERNVKGMFEV LEPLHAMMER  120
GPQTLKETSF NQAYGRDLME AQEWCRKYMK SGNVKDLTQA WDLYYHVFRR IS          172

SEQ ID NO: 302         moltype = DNA  length = 666
FEATURE                Location/Qualifiers
misc_feature           1..666
                       note = Description of Artificial Sequence: Synthetic
                        polynucleotide
source                 1..666
                       mol_type = other DNA
                       organism = synthetic construct
SEQUENCE: 302
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggtt                                                            666

SEQ ID NO: 303         moltype = AA  length = 222
FEATURE                Location/Qualifiers
REGION                 1..222
                       note = Description of Artificial Sequence: Synthetic
                        polypeptide
source                 1..222
                       mol_type = protein
                       organism = synthetic construct
SEQUENCE: 303
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
```

-continued

```
PYEGLSGDQM GQIEKIFKVV YPVDDHHFKV ILHYGTLVID GV                    222

SEQ ID NO: 304         moltype = DNA  length = 612
FEATURE                Location/Qualifiers
misc_feature           1..612
                       note = Description of Artificial Sequence: Synthetic
                        polynucleotide
source                 1..612
                       mol_type = other DNA
                       organism = synthetic construct
SEQUENCE: 304
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtgatgat  360
catcacttta aggtgatcct gcactatggc acactggtaa tcgacggggt tacgccgaac  420
atgatcgact atttcggacg gccgtatgaa ggcatcgccg tgttcgacgg caaaaagatc  480
actgtaacag ggaccctgtg gaacggcaac aaaattatcg acgagcgcct gatcaacccc  540
gacggctccc tgctgttccg agtaaccatc aacggagtga ccggctggcg gctgtgcgaa  600
cgcattctgg cg                                                     612

SEQ ID NO: 305         moltype = AA  length = 204
FEATURE                Location/Qualifiers
REGION                 1..204
                       note = Description of Artificial Sequence: Synthetic
                        polypeptide
source                 1..204
                       mol_type = protein
                       organism = synthetic construct
SEQUENCE: 305
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGDD  120
HHFKVILHYG TLVIDGVTPN MIDYFGRPYE GIAVFDGKKI TVTGTLWNGN KIIDERLINP  180
DGSLLFRVTI NGVTGWRLCE RILA                                        204

SEQ ID NO: 306         moltype = DNA  length = 567
FEATURE                Location/Qualifiers
misc_feature           1..567
                       note = Description of Artificial Sequence: Synthetic
                        polynucleotide
source                 1..567
                       mol_type = other DNA
                       organism = synthetic construct
SEQUENCE: 306
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtgggagg aggtggctca ggtggaggga gctccgtggc catcctctgg  300
catgagatgt ggcatgaagg cctggaagag gcatctcgtt tgtactttgg ggaaaggaac  360
gtgaaaggca tgtttgaggt gctggagccc ttgcatgcta tgatggaacg gggcccccag  420
actctgaagg aaacatcctt taatcaggcc tatggtcgag atttaatgga ggcccaagag  480
tggtgcagga agtacatgaa atcagggaat gtcaaggacc tcacccaagc ctgggacctc  540
tattatcatg tgttccgacg aatctca                                     567

SEQ ID NO: 307         moltype = AA  length = 189
FEATURE                Location/Qualifiers
REGION                 1..189
                       note = Description of Artificial Sequence: Synthetic
                        polypeptide
source                 1..189
                       mol_type = protein
                       organism = synthetic construct
SEQUENCE: 307
MVFTLEDFVG DWRQTAGYNL DQVLEQGGVS SLFQNLGVSV TPIQRIVLSG ENGLKIDIHV  60
IIPYEGLSGD QMGQIEKIFK VVYPVGGGGS GGGSSVAILW HEMWHEGLEE ASRLYFGERN  120
VKGMFEVLEP LHAMMERGPQ TLKETSFNQA YGRDLMEAQE WCRKYMKSGN VKDLTQAWDL  180
YYHVFRRIS                                                         189

SEQ ID NO: 308         moltype = DNA  length = 255
FEATURE                Location/Qualifiers
misc_feature           1..255
                       note = Description of Artificial Sequence: Synthetic
                        polynucleotide
source                 1..255
                       mol_type = other DNA
                       organism = synthetic construct
```

```
SEQUENCE: 308
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtg                                                  255

SEQ ID NO: 309         moltype = AA  length = 85
FEATURE                Location/Qualifiers
REGION                 1..85
                       note = Description of Artificial Sequence: Synthetic
                        polypeptide
source                 1..85
                       mol_type = protein
                       organism = synthetic construct
SEQUENCE: 309
MVFTLEDFVG DWRQTAGYNL DQVLEQGGVS SLFQNLGVSV TPIQRIVLSG ENGLKIDIHV  60
IIPYEGLSGD QMGQIEKIFK VVYPV                                       85

SEQ ID NO: 310         moltype = DNA  length = 261
FEATURE                Location/Qualifiers
misc_feature           1..261
                       note = Description of Artificial Sequence: Synthetic
                        polynucleotide
source                 1..261
                       mol_type = other DNA
                       organism = synthetic construct
SEQUENCE: 310
atggatgatc atcactttaa ggtgatcctg cactatggca cactggtaat cgacggggtt  60
acgccgaaca tgatcgacta tttcggacgg ccgtatgaag gcatcgccgt gttcgacggc  120
aaaaagatca ctgtaacagg gaccctgtgg aacggcaaca aaattatcga cgagcgcctg  180
atcaaccccg acggctccct gctgttccga gtaaccatca acggagtgac cggctggcgg  240
ctgtgcgaac gcattctggc g                                           261

SEQ ID NO: 311         moltype = AA  length = 87
FEATURE                Location/Qualifiers
REGION                 1..87
                       note = Description of Artificial Sequence: Synthetic
                        polypeptide
source                 1..87
                       mol_type = protein
                       organism = synthetic construct
SEQUENCE: 311
MDDHHFKVIL HYGTLVIDGV TPNMIDYFGR PYEGIAVFDG KKITVTGTLW NGNKIIDERL  60
INPDGSLLFR VTINGVTGWR LCERILA                                     87

SEQ ID NO: 312         moltype = DNA  length = 609
FEATURE                Location/Qualifiers
misc_feature           1..609
                       note = Description of Artificial Sequence: Synthetic
                        polynucleotide
source                 1..609
                       mol_type = other DNA
                       organism = synthetic construct
SEQUENCE: 312
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtg                                                         609

SEQ ID NO: 313         moltype = AA  length = 203
FEATURE                Location/Qualifiers
REGION                 1..203
                       note = Description of Artificial Sequence: Synthetic
                        polypeptide
source                 1..203
                       mol_type = protein
                       organism = synthetic construct
SEQUENCE: 313
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
```

-continued

```
PYEGLSGDQM GQIEKIFKVV YPV                                   203

SEQ ID NO: 314         moltype = DNA  length = 573
FEATURE                Location/Qualifiers
misc_feature           1..573
                       note = Description of Artificial Sequence: Synthetic
                        polynucleotide
source                 1..573
                       mol_type = other DNA
                       organism = synthetic construct
SEQUENCE: 314
atggatgatc atcactttaa ggtgatcctg cactatggca cactggtaat cgacggggtt  60
acgccgaaca tgatcgacta tttcggacgg ccgtatgaag gcatcgccgt gttcgacggc  120
aaaaagatca ctgtaacagg gaccctgtgg aacggcaaca aaattatcga cgagcgcctg  180
atcaaccccg acggctccct gctgttccga gtaaccatca acggagtgac cggctggcgg  240
ctgtgcgaac gcattctggc gggaggaggt ggctcaggtg gagggagctc cgtggccatc  300
ctctggcatg agatgtggca tgaaggcctg gaagaggcat ctcgtttgta ctttggggaa  360
aggaacgtga aaggcatgtt tgaggtgctg gagcccttgc atgctatgat ggaacggggc  420
ccccagactc tgaaggaaac atcctttaat caggcctatg gtcgagattt aatggaggcc  480
caagagtggt gcaggaagta catgaaatca gggaatgtca aggacctcac ccaagcctgg  540
gacctctatt atcatgtgtt ccgacgaatc tca                         573

SEQ ID NO: 315         moltype = AA  length = 191
FEATURE                Location/Qualifiers
REGION                 1..191
                       note = Description of Artificial Sequence: Synthetic
                        polypeptide
source                 1..191
                       mol_type = protein
                       organism = synthetic construct
SEQUENCE: 315
MDDHHFKVIL HYGTLVIDGV TPNMIDYFGR PYEGIAVFDG KKITVTGTLW NGNKIIDERL  60
INPDGSLLFR VTINGVTGWR LCERILAGGG GSGGGSSVAI LWHEMWHEGL EEASRLYFGE  120
RNVKGMFEVL EPLHAMMERG PQTLKETSFN QAYGRDLMEA QEWCRKYMKS GNVKDLTQAW  180
DLYYHVFRRI S                                                191

SEQ ID NO: 316         moltype = DNA  length = 2838
FEATURE                Location/Qualifiers
misc_feature           1..2838
                       note = Description of Artificial Sequence: Synthetic
                        polynucleotide
source                 1..2838
                       mol_type = other DNA
                       organism = synthetic construct
SEQUENCE: 316
atggcagaaa tcggtactgg ctttccattc gacccccatt atgtggaagt cctgggcgag  60
cgcatgcact acgtcgatgt tggtccgcgc gatggcaccc ctgtgctgtt cctgcacggt  120
aacccgacct cctcctacgt gtggcgcaac atcatcccgc atgttgcacc gacccatcgc  180
tgcattgctc cagacctgat cggtatgggc aaatccgaca aaccagacct gggttatttc  240
ttcgacgacc acgtccgctt catggatgcc ttcatcgaag ccctgggtct ggaagaggtc  300
gtcctggtca ttcacgactg gggctccgct ctgggtttcc actgggccaa gcgcaatcca  360
gagcgcgtca aaggtattgc atttatggag ttcatccgcc ctatcccgac ctgggacgaa  420
tggccagaat ttgcccgcga gaccttccag gccttccgca ccaccgacgt cggccgcaag  480
ctgatcatcg atcagaacgt ttttatcgag ggtacgctgc cgatgggtgt cgtccgcccg  540
ctgactgaag tcgagatgga ccattaccgc gagccgttcc tgaatcctgt tgaccgcgag  600
ccactgtggc gcttcccaaa cgagctgcca atcgccggtg agccagcgaa catcgtcgcg  660
ctggtcgaag aatacatgga ctggctgcac cagtcccctg tcccgaagct gctgttctgg  720
ggcaccccag gcgttctgat cccaccggcc gaagccgctc gcctggccaa aagcctgcct  780
aactgcaagg ctgtggacat cggcccgggt ctgaatctgc tgcaagaaga caacccggac  840
ctgatcggca gcgagatcgc gcgctggctg tcgacgctcg agatttccgg cgagccaacc  900
actgaggatc tgtactttca gagcgataac gcgatcgctt tcgaaggaga tagaaccatg  960
cagccagatc ccaggcctag cggggctggg gcctgctgcc gattcctgcc cctgcagtca  1020
cagtgccctg agggggcagg ggacgcggtg atgtacgcct ccactgagtg caaggcggag  1080
gtgacgccct cccagcatgg caaccgcacc ttcagctaca ccctggagga tcataccaag  1140
caggcctttg gcatcatgaa cgagctgcgg ctcagccagc agctgtgtga cgtcacactg  1200
caggtcaagt accaggatgc accggccgcc cagttcatgg cccacaaggt ggtgctggcc  1260
tcatccagcc ctgttttcaa ggccatgttc accaacgggc tgcgggagca gggcatggag  1320
gtggtgtcca ttgagggtat ccaccccaag gtcatggagc gcctcattga attcgcctac  1380
acggcctcca tctccatggg cgagaagtgt gtcctccacg tcatgaacgg cgctgtcatg  1440
taccagatcg acagcgttgt ccgtgcctgc agtgacttcc tggtgcagca gctggacccc  1500
agcaatgcca tcggcatcgc caacttcgct gagcagattg gctgtgtgga gttgcaccag  1560
cgtgcccggg agtacatcta catgcatttt ggggaggtgg ccaagcaaga ggagttcttc  1620
aacctgtccc actgccaact ggtgaccctc atcagccggg acgacctgaa cgtgcgctgc  1680
gagtccgagg tcttccacgc ctgcatcaac tgggtcaagt acgactgcga acagcgacgg  1740
ttctacgtcc aggcgctgct gcgggccgtg cgctgccact cgttgacgcc gaacttcctg  1800
cagatgcagc tgcagaagtg cgagatcctg cagtccgact cccgctgcaa ggactacctg  1860
gtcaagatct tcgaggagct caccctgcac aagcccacgc aggtgatgcc ctgccgggcg  1920
cccaaggtgg gccgcctgat ctacaccgcg ggcggctact tccgacagtc gctcagctac  1980
ctggaggctt acaaccccag taacggcacc tggctccggt tggcggacct gcaggtgccg  2040
```

```
cggagcggcc tggccggctg cgtggtgggc gggctgttgt acgccgtggg cggcaggaac  2100
aactcgcccg acggcaacac cgactccagc gccctggact gttacaaccc catgaccaat  2160
cagtggtcgc cctgcgcccc catgagcgtg ccccgtaacc gcatcggggt gggggtcatc  2220
gatggccaca tctatgccgt cggcggctcc cacggctgca tccaccacaa cagtgtggag  2280
aggtatgagc cagagcggga tgagtggcac ttggtggccc caatgctgac acgaaggatc  2340
ggggtgggcg tggctgtcct caatcgtctg ctttatgccg tgggggggctt tgacgggaca  2400
aaccgcctta attcagctga gtgttactac ccagagagga acgagtggcg aatgatcaca  2460
gcaatgaaca ccatccgaag cggggcaggc gtctgcgtcc tgcacaactg tatctatgct  2520
gctgggggct atgatggtca ggaccagctg aacagcgtgg agcgctacga tgtggaaaca  2580
gagacgtgga ctttcgtagc ccccatgaag caccggcgaa gtgccctggg gatcactgtc  2640
caccagggga gaatctacgt ccttggaggc tatgatggtc acacgttcct ggacagtgtg  2700
gagtgttacg acccagatac agacacctgg agcgaggtga cccgaatgac atcgggccgg  2760
agtggggtgg gcgtggctgt caccatggag ccctgccgga agcagattga ccagcagaac  2820
tgtacctgtt acgtagtt                                                2838
```

```
SEQ ID NO: 317         moltype = DNA  length = 5064
FEATURE                Location/Qualifiers
misc_feature           1..5064
                       note = Description of Artificial Sequence: Synthetic
                        polynucleotide
source                 1..5064
                       mol_type = other DNA
                       organism = synthetic construct
SEQUENCE: 317
tcaatattgg ccattagcca tattattcat tggttatata gcataaatca atattggcta  60
ttggccattg catacgttgt atctatatca taatatgtac atttatattg gctcatgtcc  120
aatatgaccg ccatgttggc attgattatt gactagttat taatagtaat caattacggg  180
gtcattagtt catagcccat atatggagtt ccgcgttaca taacttacgg taaatggccc  240
gcctggctga ccgcccaacg acccccgccc attgacgtca ataatgacgt atgttcccat  300
agtaacgcca atagggactt tccattgacg tcaatgggtg gagtatttac ggtaaactgc  360
ccacttggca gtacatcaag tgtatcatat gccaagtccg ccccctattg acgtcaatga  420
cggtaaatgg cccgcctggc attatgccca gtacatgacc ttacgggact ttcctacttg  480
gcagtacatc tacgtattag tcatcgctat taccatggtg atgcggtttt ggcagtacac  540
caatgggcgt ggatagcggt ttgactcacg gggatttcca agtctccacc ccattgacgt  600
caatgggagt ttgttttggc accaaaatca acgggacttt ccaaaatgtc gtaataaccc  660
cgccccgttg acgcaaatgg gcggtaggcg tgtacggtgg gaggtctata taagcagagc  720
tggtttagtg aaccgtcaga tcactagaag ctttattgcg gtagtttatc acagttaaat  780
tgctaacgca gtcagtgctt ctgacacaac agtctcgaac ttaagctgca gaagttggtc  840
gtgaggcact gggcaggtaa gtatcaaggt tacaagacag gtttaaggag accaatagaa  900
actgggcttg tcgagacaga gaagactctt gcgtttctga taggcaccta ttggtcttac  960
tgacatccac tttgcctttc tctccacagg tgtccactcc cagttcaatt acagctctta  1020
aggctagagt attaatacga ctcactatag ggctagcgat cgccatgatg gacttggagc  1080
tgccgccgcc gggactcccg tcccagcagg acatggattt gattgacata ctttggaggc  1140
aagatataga tcttggagta agtcgagaag tatttgactt cagtcagcga cggaaagagt  1200
atgagctgga aaaacagaaa aaacttgaaa aggaaagaca agaacaactc caaaaggagc  1260
aagagaaagc ctttttcgct cagttacaac tagatgaaga gacaggtgaa tttctcccaa  1320
ttcagccagc ccagcacatc cagtcagaaa ccagttctct cggtggttca ggtggtggcg  1380
ggagcggtgg agggagcagc ggtggagtgt ttacactcga agatttcgta ggggactggc  1440
ggcagacagc cggctacaac ctggaccaag tccttgagca gggcggtgtg tccagtttgt  1500
ttcagaatct cggggtgtcc gtaactccga tccaaaggat tgtcctgagc ggtgaaaacg  1560
gcctgaagat cgacatccat gtcatcatcc cgtatgaagg tctgagcggc gatcagatgg  1620
gccagatcga aaaaattttt aaggtggtgt accctgtgga tgatcatcac tttaaggtga  1680
ttctgcacta tggcacactg gtaatcgacg gggttacgcc gaacatgatc gactatttcg  1740
gacggccgta tgaaggcatc gccgtgttcg acggcaaaaa gatcactgta accgggaccc  1800
tgtggaacgg caacaaaatt atcgacgagc gcctgatcaa ccccgacggc tccctgctgt  1860
tccgcgtaac catcaacgga gtgaccggct ggcggctgtg cgagcgcatt ttggcgtaag  1920
gccgcgactc tagagtcgac ctgcaggcat gcaagctgat ccggctgcta acaaagcccg  1980
aaaggaagct gagttggctg ctgccaccgc tgagcaataa ctagcataac cccttggggc  2040
ggccgcttcg agcagacatg ataagataca ttgatgagtt tggacaaacc acaactagaa  2100
tgcagtgaaa aaaatgcttt atttgtgaaa tttgtgatgc tattgcttta tttgtaacca  2160
ttataagctg caataaacaa gttaacaaca acaattgcat tcattttatg tttcaggttc  2220
agggggagat gtgggaggtt ttttaagca agtaaaacct ctacaaatgt ggtaaaatcg  2280
aattttaaca aaatattaac gcttacaatt tcctgatgcg gtattttctc cttacgcatc  2340
tgtgcggtat ttcacaccgc atacgcggat ctgcgcagca ccatggcctg aaataacctc  2400
tgaaagagga acttggttag gtaccttctg aggcggaaag aaccagctgt ggaatgtgtg  2460
tcagttaggg tgtggaaagt ccccaggctc cccagcaggc agaagtatgc aaagcatgca  2520
tctcaattag tcagcaacca ggtgtggaaa gtccccaggc tccccagcag gcagaagtat  2580
gcaaagcatg catctcaatt agtcagcaac catagtcccg cccctaactc cgcccatccc  2640
gcccctaact ccgcccagtt ccgcccattc tccgccccat ggctgactaa tttttttat  2700
ttatgcagag gccgaggccg cctcggcctc tgagctattc cagaagtagt gaggaggctt  2760
ttttggaggc ctaggctttt gcaaaaagct taattaactg ttgacaatta atcatcggca  2820
tagtatatcg gcatagtata atacgacaag gtgaggaact aaacccagga ggcagatcat  2880
gattgaacaa gatggattgc acgcaggttc tccggccgct tgggtggaga ggctattcgg  2940
ctatgactgg gcacaacaga caatcggctg ctctgatgcc gccgtgttcc ggctgtcagc  3000
gcaggggcgc ccggttcttt ttgtcaagac cgacctgtcc ggtgccctga atgaactgca  3060
ggacgaggca gcgcggctat cgtggctggc cacgacgggc gttccttgcg cagctgtgct  3120
cgacgttgtc actgaagcgg gaagggactg gctgctattg ggcgaagtgc cggggcagga  3180
tctcctgtca tctcaccttg ctcctgccga gaaagtatcc atcatggctg atgcaatgcg  3240
gcggctgcat acgcttgatc cggctacctg cccattcgac caccaagcga aacatcgcat  3300
```

```
cgagcgagca cgtactcgga tggaagccgg tcttgtcgat caggatgatc tggacgaaga  3360
gcatcagggg ctcgcgccag ccgaactgtt cgccaggctc aaggcgcgca tgcccgacgg  3420
cgaggatctc gtcgtgaccc atggcgatgc ctgcttgccg aatatcatgg tggaaaatgg  3480
ccgcttttct ggattcatcg actgtggccg gctgggtgtg gcggaccgct atcaggacat  3540
agcgttggct acccgtgata ttgctgaaga gcttggcggc gaatgggctg accgcttcct  3600
cgtgctttac ggtatcgccg ctcccgattc gcagcgcatc gccttctatc gccttcttga  3660
cgagttcttc tgagcgggac tctggggttc gaaatgaccg accaagcgac gcccaacctg  3720
ccatcacgat ggccgcaata aaatatcttt attttcatta catctgtgtg ttggtttttt  3780
gtgtgaatcg atagcgataa ggatcctctt tgcgcttgcg ttttcccttg tccagatagc  3840
ccagtagctg acattcatcc ggggtcagca ccgtttctgc ggactggctt tctacccggt  3900
atcagctcac tcaaaggcgg taatacggtt atccacagaa tcaggggata acgcaggaaa  3960
gaacatgtga gcaaaaggcc agcaaaaggc caggaaccgt aaaaaggccg cgttgctggc  4020
gtttttccat aggctccgcc cccctgacga gcatcacaaa aatcgacgct caagtcagag  4080
gtggcgaaac ccgacaggac tataaagata ccaggcgttt ccccctggaa gctccctcgt  4140
gcgctctcct gttccgaccc tgccgcttac cggatacctg tccgcctttc tcccttcggg  4200
aagcgtggcg ctttctcata gctcacgctg taggtatctc agttcggtgt aggtcgttcg  4260
ctccaagctg ggctgtgtgc acgaaccccc cgttcagccc gaccgctgcg ccttatccgg  4320
taactatcgt cttgagtcca acccggtaag acacgactta tcgccactgg cagcagccac  4380
tggtaacagg attagcagag cgaggtatgt aggcggtgct acagagttct tgaagtggtg  4440
gcctaactac ggctacacta gaaggacagt atttggtatc tgcgctctgc tgaagccagt  4500
taccttcgga aaaagagttg gtagctcttg atccggcaaa caaaccaccg ctggtagcgg  4560
tggttttttt gtttgcaagc agcagattac gcgcagaaaa aaaggatttc aagaagatcc  4620
tttgatcttt tctacggggt ctgacgctca gtggaacgaa aactcacgtt aagggatttt  4680
ggtcatgaga ttatcaaaaa ggatcttcac ctagatcctt ttatagtccg gaaatacagg  4740
aacgcacgct ggatggccct tcgctgggat ggtgaaacca tgaaaaatgg cagcttcagt  4800
ggattaagtg gggtaatgt ggcctgtacc ctctggttgc ataggtattc atacggttaa  4860
aatttatcag gcgcgattgc ggcagttttt cgggtggttt gttgccattt ttacctgtct  4920
gctgccgtga tcgcgctgaa cgcgttttag cggtgcgtac aattaaggga ttatggtaaa  4980
tccacttact gtctgccctc gtagccatcg agataaaccg cagtactccg gccacgatgc  5040
gtccggcgta gaggatcgag atct                                         5064
```

```
SEQ ID NO: 318         moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 318
atggtcttca cactcgaaga tttcgtaggt gactggcgac agacagccgg ctacaacctg  60
gaccaagtcc ttgaacaggg tggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaact gggaccctgt ggaacggcaa caaaattatc  420
gacgagcgcc tgatcaaccc cgacggctcc ctgctgttcc gagtaaccat caacggagtg  480
accggctggc ggctgtgcga acgcattctg gcg                              513
```

```
SEQ ID NO: 319         moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 319
atggtgttta cactcgaaga tttcgtaggg gactggcggc agacagccgg ctacaacctg  60
gaccaagtcc ttgaacaggg cggtgtgtcc agtttgtttc agaatctcgg ggtgtccgta  120
actccgatcc aaaggattgt cctgagcggt gaaaacggcc tgaagatcga catccatgtc  180
atcatcccgt atgaaggtct gagcggcgat caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                              513
```

```
SEQ ID NO: 320         moltype = DNA  length = 636
FEATURE                Location/Qualifiers
misc_feature           1..636
                       note = Description of Artificial Sequence: Synthetic
                        polynucleotide
source                 1..636
                       mol_type = other DNA
                       organism = synthetic construct
SEQUENCE: 320
atggtgttta cactcgaaga tttcgtaggg gactggcggc agacagccgg ctacaacctg  60
```

```
gaccaagtcc ttgaacaggg cggtgtgtcc agtttgtttc agaatctcgg ggtgtccgta  120
actccgatcc aaaggattgt cctgagcggt gaaaacggcc tgaagatcga catccatgtc  180
atcatcccgt atgaaggtct gagcggcgat caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcgaattcac acggctttcc gcccgaggtt  540
gaagagcaag ccgccggtac attgcctatg tcctgcgcac aagaaagcgg tatggaccgg  600
cacccagccg cttgtgcttc agctcgcatc aacgtc                            636

SEQ ID NO: 321          moltype = DNA  length = 597
FEATURE                 Location/Qualifiers
misc_feature            1..597
                        note = Description of Artificial Sequence: Synthetic
                         polynucleotide
source                  1..597
                        mol_type = other DNA
                        organism = synthetic construct
SEQUENCE: 321
atgaactcct tctccacaag cgccttcggt ccagttgcct tctccctggg cctgctcctg  60
gtgttgcctg ctgccttccc tgccccagtg tttacactcg aagatttcgt aggggactgg  120
cggcagacag ccggctacaa cctggaccaa gtccttgaac agggcggtgt gtccagtttg  180
tttcagaatc tcggggtgtc cgtaactccg atccaaagga ttgtcctgag cggtgaaaac  240
ggcctgaaga tcgacatcca tgtcatcatc ccgtatgaag gtctgagcgg cgatcaaatg  300
ggccagatcg aaaaaatttt taaggtggtg taccctgtgg atgatcatca ctttaaggtg  360
atcctgcact atggcacact ggtaatcgac ggggttacgc cgaacatgat cgactatttc  420
ggacggccgt atgaaggcat cgccgtgttc gacggcaaaa agatcactgt aaccgggacc  480
ctgtggaacg gcaacaaaat tatcgacgag cgcctgatca accccgacgg ctccctgctg  540
ttccgcgtaa ccatcaacgg agtgaccggc tggcggctgt gcgagcgcat tttggcg     597

SEQ ID NO: 322          moltype = DNA  length = 513
FEATURE                 Location/Qualifiers
misc_feature            1..513
                        note = Description of Artificial Sequence: Synthetic
                         polynucleotide
source                  1..513
                        mol_type = other DNA
                        organism = synthetic construct
SEQUENCE: 322
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggagtg  480
accggctggc ggctgtgcga acgcattctg gcg                               513

SEQ ID NO: 323          moltype = DNA  length = 636
FEATURE                 Location/Qualifiers
misc_feature            1..636
                        note = Description of Artificial Sequence: Synthetic
                         polynucleotide
source                  1..636
                        mol_type = other DNA
                        organism = synthetic construct
SEQUENCE: 323
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggagtg  480
accggctggc ggctgtgcga acgcattctg gcgaattctc acggctttcc gcctgaggtt  540
gaagagcaag ccgccggtac attgcctatg tcctgcgcac aagaaagcgg tatggaccgg  600
cacccagccg cttgtgcttc agctcgcatc aacgtc                            636

SEQ ID NO: 324          moltype = DNA  length = 597
FEATURE                 Location/Qualifiers
misc_feature            1..597
                        note = Description of Artificial Sequence: Synthetic
                         polynucleotide
source                  1..597
                        mol_type = other DNA
                        organism = synthetic construct
```

```
SEQUENCE: 324
atgaactcct tctccacaag cgccttcggt ccagttgcct tctccctggg cctgctcctg  60
gtgttgcctg ctgccttccc tgccccagtc ttcacactcg aagatttcgt tggggactgg  120
cgacagacag ccggctacaa cctggaccaa gtccttgaac agggaggtgt gtccagtttg  180
tttcagaatc tcggggtgtc cgtaactccg atccaaagga ttgtcctgag cggtgaaaat  240
gggctgaaga tcgacatcca tgtcatcatc ccgtatgaag gtctgagcgg cgaccaaatg  300
ggccagatcg aaaaaatttt taaggtggtg taccctgtgg atgatcatca ctttaaggtg  360
atcctgcact atggcacact ggtaatcgac ggggttacgc cgaacatgat cgactatttc  420
ggacggccgt atgaaggcat cgccgtgttc gacggcaaaa agatcactgt aacagggacc  480
ctgtggaacg gcaacaaaat tatcgacgag cgcctgatca accccgacgg ctccctgctg  540
ttccgagtaa ccatcaacgg agtgaccggc tggcggctgt gcgaacgcat tctggcg     597

SEQ ID NO: 325         moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 325
atggtcttca cactcgaaga tttcgtaggt gactggcgac agacagccgg ctacaacctg  60
gaccaagttc ttgaacaggg tggtgtgtcc agtttgtttc agaatctcgg ggtgtccgta  120
actccaatcc agaggatagt cctgagtggt gaaaatgggc tgaagatcga catccatgtc  180
atcatccctt atgaaggtct gagcggcgat cagatggggc agatcgaaaa aatttttaag  240
gtggtgtacc ctgtggatga tcatcacttt aaggtgatcc tgcactatgg cacactggta  300
atcgacggtg ttacgccgaa catgatcgac tatttcggac ggccgtatga aggcatcgcc  360
gtgttcgacg gcaaaaagat tactgtcact ggaaccctgt ggaatgggaa caaaattatc  420
gacgagcgcc tgatcaaccc cgacggctca ctgctgttcc gagtaaccat caatggtgtt  480
accggctggc ggctctgcga acgcattcta gca                                513

SEQ ID NO: 326         moltype = DNA  length = 636
FEATURE                Location/Qualifiers
misc_feature           1..636
                       note = Description of Artificial Sequence: Synthetic
                        polynucleotide
source                 1..636
                       mol_type = other DNA
                       organism = synthetic construct
SEQUENCE: 326
atggtcttca cactcgaaga tttcgtaggt gactggcgac agacagccgg ctacaacctg  60
gaccaagttc ttgaacaggg tggtgtgtcc agtttgtttc agaatctcgg ggtgtccgta  120
actccaatcc agaggatagt cctgagtggt gaaaatgggc tgaagatcga catccatgtc  180
atcatccctt atgaaggtct gagcggcgat cagatggggc agatcgaaaa aatttttaag  240
gtggtgtacc ctgtggatga tcatcacttt aaggtgatcc tgcactatgg cacactggta  300
atcgacggtg ttacgccgaa catgatcgac tatttcggac ggccgtatga aggcatcgcc  360
gtgttcgacg gcaaaaagat tactgtcact ggaaccctgt ggaatgggaa caaaattatc  420
gacgagcgcc tgatcaaccc cgacggctca ctgctgttcc gagtaaccat caatggtgtt  480
accggctggc ggctctgcga acgcattcta gcaaatagtc acggctttcc gcctgaggtt  540
gaagagcaag ccgccggtac attgcctatg tcctgcgcac aagaaagcgg tatggaccgg  600
cacccagccg cttgtgcttc agctcgcatc aacgtc                             636

SEQ ID NO: 327         moltype = DNA  length = 573
FEATURE                Location/Qualifiers
misc_feature           1..573
                       note = Description of Artificial Sequence: Synthetic
                        polynucleotide
source                 1..573
                       mol_type = other DNA
                       organism = synthetic construct
SEQUENCE: 327
atgaactcct tctccacaag cgccttcggt ccagtcgcct tctccctggg cctgctcctg  60
gtgttgcccg ctgcctttcc tgccccagtc ttcacactcg aagatttcgt aggtgactgg  120
cgacagacag ccggctacaa cctggaccaa gttcttgaac agggtggtgt gtccagtttg  180
tttcagaatc tcggggtgtc cgtaactcca atccagagga tagtcctgag tggtgaaaat  240
gggctgaaga tcgacatcca tgtcatcatc ccttatgaag gtctgagcgg cgatcagatg  300
gggcagatcg aaaaaatttt taaggtggtg taccctgtgg atgatcatca ctttaaggtg  360
atcctgcact atggcacact ggtaatcgac ggtgttacgc cgaacatgat cgactatttc  420
ggacggccgt atgaaggcat cgccgtgttc gacggcaaaa agattactgt cactggaacc  480
ctgtggaatg ggaacaaaat tatcgacgag cgcctgatca accccgacgg ctcactgctg  540
ttccgagtaa ccatcaatgg tgttaccggc tgg                                573

SEQ ID NO: 328         moltype = AA  length = 33
FEATURE                Location/Qualifiers
REGION                 1..33
                       note = Description of Artificial Sequence: Synthetic
                        polypeptide
source                 1..33
                       mol_type = protein
```

```
                         organism = synthetic construct
SEQUENCE: 328
GSSGGGSSGG EPTTENLYFQ SDNGSSGGGS SGG                                 33

SEQ ID NO: 329           moltype =   length =
SEQUENCE: 329
000

SEQ ID NO: 330           moltype =   length =
SEQUENCE: 330
000

SEQ ID NO: 331           moltype = DNA  length = 672
FEATURE                  Location/Qualifiers
misc_feature             1..672
                         note = Description of Artificial Sequence: Synthetic
                          polynucleotide
source                   1..672
                         mol_type = other DNA
                         organism = synthetic construct
SEQUENCE: 331
atgggcctga agatcgacat ccatgtcatc atcccgtatg aaggtctgag cggctatcag  60
atgggccaga tcgaaaaaat ttttaaggtg gtgtaccctg tggatgatca tcactttaag  120
gtgattctgc actatggcac actggtaatc gacggggtta cgccgaacat gatcgactat  180
ttcggacggc cgtatgaagg catcgccgtg ttcgacggca aaaagatcac tgtaaccggg  240
accctgtgga acggcaacaa aattatcgac gagcgcctga tcaaccccga cggctccctg  300
ctgttccgcg taaccatcaa cggagtgacc ggctggcggc tgtgcgagcg cattttggcg  360
ggaggaggtg gctcaggtgg agggagctcc gtggccatcc tctggcatga gatgtggcat  420
gaaggcctgg aagaggcatc tcgtttgtac tttggggaaa ggaacgtgaa aggcatgttt  480
gaggtgctgg agcccttgca tgctatgatg gaacggggcc cccagactct gaaggaaaca  540
tcctttaatc aggcctatgg tcgagattta atggaggccc aagagtggtg caggaagtac  600
atgaaatcag ggaatgtcaa ggacctcacc caagcctggg acctctatta tcatgtgttc  660
cgacgaatct ca                                                        672

SEQ ID NO: 332           moltype = AA  length = 224
FEATURE                  Location/Qualifiers
REGION                   1..224
                         note = Description of Artificial Sequence: Synthetic
                          polypeptide
source                   1..224
                         mol_type = protein
                         organism = synthetic construct
SEQUENCE: 332
MGLKIDIHVI IPYEGLSGYQ MGQIEKIFKV VYPVDDHHFK VILHYGTLVI DGVTPNMIDY  60
FGRPYEGIAV FDGKKITVTG TLWNGNKIID ERLINPDGSL LFRVTINGVT GWRLCERILA  120
GGGGSGGGSS VAILWHEMWH EGLEEASRLY FGERNVKGMF EVLEPLHAMM ERGPQTLKET  180
SFNQAYGRDL MEAQEWCRKY MKSGNVKDLT QAWDLYYHVF RRIS                     224

SEQ ID NO: 333           moltype = DNA  length = 468
FEATURE                  Location/Qualifiers
misc_feature             1..468
                         note = Description of Artificial Sequence: Synthetic
                          polynucleotide
source                   1..468
                         mol_type = other DNA
                         organism = synthetic construct
SEQUENCE: 333
atggtgttta cactcgaaga tttcgtaggg gactggcggc agacagccgg ctacaacctg  60
gaccaagtcc ttgagcaggg cggtctgtcc agtttgtttc agaaactcgg ggtgtccgta  120
acaccgatcc aaaagattgt cctgagcggt gaaaacggag gaggtggctc aggtggaggg  180
agctccgtgg ccatcctctg gcatgagatg tggcatgaag gcctggaaga ggcatctcgt  240
ttgtactttg gggaaaggaa cgtgaaaggc atgtttgagg tgctggagcc cttgcatgct  300
atgatggaac ggggccccca gactctgaag gaaacatcct ttaatcaggc ctatggtcga  360
gatttaatgg aggcccaaga gtggtgcagg aagtacatga aatcagggaa tgtcaaggac  420
ctcacccaag cctgggacct ctattatcat gtgttccgac gaatctca                468

SEQ ID NO: 334           moltype = AA  length = 156
FEATURE                  Location/Qualifiers
REGION                   1..156
                         note = Description of Artificial Sequence: Synthetic
                          polypeptide
source                   1..156
                         mol_type = protein
                         organism = synthetic construct
SEQUENCE: 334
MVFTLEDFVG DWRQTAGYNL DQVLEQGGLS SLFQKLGVSV TPIQKIVLSG ENGGGGSGGG  60
SSVAILWHEM WHEGLEEASR LYFGERNVKG MFEVLEPLHA MMERGPQTLK ETSFNQAYGR  120
DLMEAQEWCR KYMKSGNVKD LTQAWDLYYH VFRRIS                              156
```

```
SEQ ID NO: 335         moltype = DNA  length = 711
FEATURE                Location/Qualifiers
misc_feature           1..711
                       note = Description of Artificial Sequence: Synthetic
                        polynucleotide
source                 1..711
                       mol_type = other DNA
                       organism = synthetic construct
SEQUENCE: 335
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtggcctg  360
aagatcgaca tccatgtcat catcccgtat gaaggtctga gcggctatca gatgggccag  420
atcgaaaaaa tttttaaggt ggtgtaccct gtggatgatc atcactttaa ggtgattctg  480
cactatggca cactggtaat cgacggggtt acgccgaaca tgatcgacta tttcggacgg  540
ccgtatgaag gcatcgccgt gttcgacggc aaaaagatca ctgtaaccgg gaccctgtgg  600
aacggcaaca aaattatcga cgagcgcctg atcaaccccg acggctccct gctgttccgc  660
gtaaccatca acggagtgac cggctggcgg ctgtgcgagc gcattttggc g           711

SEQ ID NO: 336         moltype = AA  length = 237
FEATURE                Location/Qualifiers
REGION                 1..237
                       note = Description of Artificial Sequence: Synthetic
                        polypeptide
source                 1..237
                       mol_type = protein
                       organism = synthetic construct
SEQUENCE: 336
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGGL  120
KIDIHVIIPY EGLSGYQMGQ IEKIFKVVYP VDDHHFKVIL HYGTLVIDGV TPNMIDYFGR  180
PYEGIAVFDG KKITVTGTLW NGNKIIDERL INPDGSLLFR VTINGVTGWR LCERILA     237

SEQ ID NO: 337         moltype = DNA  length = 510
FEATURE                Location/Qualifiers
misc_feature           1..510
                       note = Description of Artificial Sequence: Synthetic
                        polynucleotide
source                 1..510
                       mol_type = other DNA
                       organism = synthetic construct
SEQUENCE: 337
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtg  360
tttacactcg aagatttcgt aggggactgg cggcagacag ccggctacaa cctggaccaa  420
gtccttgagc agggcggtct gtccagtttg tttcagaaac tcggggtgtc cgtaacaccg  480
atccaaaaga ttgtcctgag cggtgaaaac                                   510

SEQ ID NO: 338         moltype = AA  length = 170
FEATURE                Location/Qualifiers
REGION                 1..170
                       note = Description of Artificial Sequence: Synthetic
                        polypeptide
source                 1..170
                       mol_type = protein
                       organism = synthetic construct
SEQUENCE: 338
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGLSSL FQKLGVSVTP IQKIVLSGEN             170

SEQ ID NO: 339         moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 339
atggtgttta cactcgaaga tttcgtaggg gactggcggc agacagccgg ctacaacctg  60
gaccaagtcc ttgagcaggg cggtgtgtcc agtttgtttc agaatctcgg ggtgtccgta  120
```

```
acaccgatcc aaaggattgt cctgagcggt gaaaacggcc tgaagatcga catccatgtc  180
atcatcccgt atgaaggtct gagcggcgat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                              513

SEQ ID NO: 340         moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 340
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 341         moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 341
atggtgttta cactcgaaga tttcgtaggg gactggcggc agacagccgg ctacaacctg  60
gaccaagtcc ttgagcaggg cggtgtgtcc agtttgtttc agaatctcgg ggtgtccgta  120
actccgatcc aaaggattgt cctgagcggt gaaaacggcc tgaagatcga catccatgtc  180
atcatcccgt atgaaggtct gaacggctat cagatgggcc agatcgaaaa aatttttaag  240
gtggtgtacc ctgtggatga tcatcacttt aaggtgattc tgcactatgg cacactggta  300
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gcgcattttg gcg                              513

SEQ ID NO: 342         moltype = AA  length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 342
MVFTLEDFVG DWRQTAGYNL DQVLEQGGVS SLFQNLGVSV TPIQRIVLSG ENGLKIDIHV  60
IIPYEGLNGY QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 343         moltype = DNA  length = 690
FEATURE                Location/Qualifiers
misc_feature           1..690
                       note = Description of Artificial Sequence: Synthetic
                        polynucleotide
source                 1..690
                       mol_type = other DNA
                       organism = synthetic construct
SEQUENCE: 343
atggtcctga gcggtgaaaa tgggctgaag atcgacatcc atgtcatcat cccgtatgaa  60
ggtctgagcg gcgaccaaat gggccagatc gaaaaaattt ttaaggtggt gtaccctgtg  120
gatgatcatc actttaaggt gatcctgcac tatggcacac tggtaatcga cggggttacg  180
ccgaacatga tcgactattt cggacggccg tatgaaggca tcgccgtgtt cgacggcaaa  240
aagatcactg taacagggac cctgtggaac ggcaacaaaa ttatcgacga gcgcctgatc  300
aaccccgacg gctccctgct gttccgagta accatcaacg gagtgaccgg ctggcggctg  360
tgcgaacgca ttctggcggg aggaggtggc tcaggtggag ggagctccgt ggccatcctc  420
tggcatgaga tgtggcatga aggcctggaa gaggcatctc gtttgtactt tggggaaagg  480
aacgtgaaag gcatgtttga ggtgctggag cccttgcatg ctatgatgga acggggcccc  540
cagactctga aggaaacatc ctttaatcag gcctatggtc gagatttaat ggaggcccaa  600
gagtggtgca ggaagtacat gaaatcaggg aatgtcaagg acctcaccca agcctgggac  660
ctctattatc atgtgttccg acgaatctca                                  690

SEQ ID NO: 344         moltype = AA  length = 230
FEATURE                Location/Qualifiers
REGION                 1..230
                       note = Description of Artificial Sequence: Synthetic
```

```
                          polypeptide
source                   1..230
                         mol_type = protein
                         organism = synthetic construct
SEQUENCE: 344
MVLSGENGLK IDIHVIIPYE GLSGDQMGQI EKIFKVVYPV DDHHFKVILH YGTLVIDGVT  60
PNMIDYFGRP YEGIAVFDGK KITVTGTLWN GNKIIDERLI NPDGSLLFRV TINGVTGWRL  120
CERILAGGGG SGGGSSVAIL WHEMWHEGLE EASRLYFGER NVKGMFEVLE PLHAMMERGP  180
QTLKETSFNQ AYGRDLMEAQ EWCRKYMKSG NVKDLTQAWD LYYHVFRRIS             230

SEQ ID NO: 345           moltype = DNA  length = 492
FEATURE                  Location/Qualifiers
misc_feature             1..492
                         note = Description of Artificial Sequence: Synthetic
                          polynucleotide
source                   1..492
                         mol_type = other DNA
                         organism = synthetic construct
SEQUENCE: 345
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga tt                                                      492

SEQ ID NO: 346           moltype = AA  length = 164
FEATURE                  Location/Qualifiers
REGION                   1..164
                         note = Description of Artificial Sequence: Synthetic
                          polypeptide
source                   1..164
                         mol_type = protein
                         organism = synthetic construct
SEQUENCE: 346
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRI                   164

SEQ ID NO: 347           moltype = DNA  length = 687
FEATURE                  Location/Qualifiers
misc_feature             1..687
                         note = Description of Artificial Sequence: Synthetic
                          polynucleotide
source                   1..687
                         mol_type = other DNA
                         organism = synthetic construct
SEQUENCE: 347
atgctgagcg gtgaaaatgg gctgaagatc gacatccatg tcatcatccc gtatgaaggt  60
ctgagcggcg accaaatggg ccagatcgaa aaaatttttta aggtggtgta ccctgtggat  120
gatcatcact ttaaggtgat cctgcactat ggcacactgg taatcgacgg ggttacgccg  180
aacatgatcg actatttcgg acggccgtat gaaggcatcg ccgtgttcga cggcaaaaag  240
atcactgtaa cagggaccct gtggaacggc aacaaaatta tcgacgagcg cctgatcaac  300
cccgacggct ccctgctgtt ccgagtaacc atcaacggag tgaccggctg gcggctgtgc  360
gaacgcattc tggcgggagg aggtggctca ggtggaggga gctccgtggc catcctctgg  420
catgagatgt ggcatgaagg cctggaagag gcatctcgtt tgtactttgg ggaaaggaac  480
gtgaaaggca tgtttgaggt gctggagccc ttgcatgcta tgatggaacg gggcccccag  540
actctgaagg aaacatcctt taatcaggcc tatggtcgag atttaatgga ggcccaagag  600
tggtgcagga agtacatgaa atcagggaat gtcaaggacc tcacccaagc ctgggacctc  660
tattatcatg tgttccgacg aatctca                                      687

SEQ ID NO: 348           moltype = AA  length = 229
FEATURE                  Location/Qualifiers
REGION                   1..229
                         note = Description of Artificial Sequence: Synthetic
                          polypeptide
source                   1..229
                         mol_type = protein
                         organism = synthetic construct
SEQUENCE: 348
MLSGENGLKI DIHVIIPYEG LSGDQMGQIE KIFKVVYPVD DHHFKVILHY GTLVIDGVTP  60
NMIDYFGRPY EGIAVFDGKK ITVTGTLWNG NKIIDERLIN PDGSLLFRVT INGVTGWRLC  120
ERILAGGGGS GGGSSVAILW HEMWHEGLEE ASRLYFGERN VKGMFEVLEP LHAMMERGPQ  180
TLKETSFNQA YGRDLMEAQE WCRKYMKSGN VKDLTQAWDL YYHVFRRIS              229

SEQ ID NO: 349           moltype = DNA  length = 495
```

-continued

```
FEATURE                Location/Qualifiers
misc_feature           1..495
                       note = Description of Artificial Sequence: Synthetic
                        polynucleotide
source                 1..495
                       mol_type = other DNA
                       organism = synthetic construct
SEQUENCE: 349
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtc                                                   495

SEQ ID NO: 350         moltype = AA  length = 165
FEATURE                Location/Qualifiers
REGION                 1..165
                       note = Description of Artificial Sequence: Synthetic
                        polypeptide
source                 1..165
                       mol_type = protein
                       organism = synthetic construct
SEQUENCE: 350
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIV                  165

SEQ ID NO: 351         moltype = DNA  length = 525
FEATURE                Location/Qualifiers
misc_feature           1..525
                       note = Description of Artificial Sequence: Synthetic
                        polynucleotide
source                 1..525
                       mol_type = other DNA
                       organism = synthetic construct
SEQUENCE: 351
atggacgggg ttacgccgaa catgatcgac tatttcggac ggccgtatga aggcatcgcc  60
gtgttcgacg gcaaaaagat cactgtaaca gggaccctgt ggaacggcaa caaaattatc  120
gacgagcgcc tgatcaaccc cgacggctcc ctgctgttcc gagtaaccat caacggagtg  180
accggctggc ggctgtgcga acgcattctg gcgggaggag gtggctcagg tggagggagc  240
tccgtggcca tcctctggca tgagatgtgg catgaaggcc tggaagaggc atctcgtttg  300
tactttgggg aaaggaacgt gaaaggcatg tttgaggtgc tggagccctt gcatgctatg  360
atggaacggg gcccccagac tctgaaggaa acatccttta atcaggccta tggtcgagat  420
ttaatggagg cccaagagtg gtgcaggaag tacatgaaat cagggaatgt caaggacctc  480
acccaagcct gggacctcta ttatcatgtg ttccgacgaa tctca                  525

SEQ ID NO: 352         moltype = AA  length = 175
FEATURE                Location/Qualifiers
REGION                 1..175
                       note = Description of Artificial Sequence: Synthetic
                        polypeptide
source                 1..175
                       mol_type = protein
                       organism = synthetic construct
SEQUENCE: 352
MDGVTPNMID YFGRPYEGIA VFDGKKITVT GTLWNGNKII DERLINPDGS LLFRVTINGV  60
TGWRLCERIL AGGGGSGGGS SVAILWHEMW HEGLEEASRL YFGERNVKGM FEVLEPLHAM  120
MERGPQTLKE TSFNQAYGRD LMEAQEWCRK YMKSGNVKDL TQAWDLYYHV FRRIS        175

SEQ ID NO: 353         moltype = DNA  length = 657
FEATURE                Location/Qualifiers
misc_feature           1..657
                       note = Description of Artificial Sequence: Synthetic
                        polynucleotide
source                 1..657
                       mol_type = other DNA
                       organism = synthetic construct
SEQUENCE: 353
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
```

```
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatc     657

SEQ ID NO: 354         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 354
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVI                         219

SEQ ID NO: 355         moltype = DNA  length = 522
FEATURE                Location/Qualifiers
misc_feature           1..522
                       note = Description of Artificial Sequence: Synthetic
                        polynucleotide
source                 1..522
                       mol_type = other DNA
                       organism = synthetic construct
SEQUENCE: 355
atgggggtta cgccgaacat gatcgactat ttcggacggc cgtatgaagg catcgccgtg  60
ttcgacggca aaaagatcac tgtaacaggg accctgtgga acggcaacaa aattatcgac  120
gagcgcctga tcaaccccga cggctccctg ctgttccgag taaccatcaa cggagtgacc  180
ggctggcggc tgtgcgaacg cattctggcg ggaggaggtg gctcaggtgg agggagctcc  240
gtggccatcc tctggcatga gatgtggcat gaaggcctgg aagaggcatc tcgtttgtac  300
tttggggaaa ggaacgtgaa aggcatgttt gaggtgctgg agcccttgca tgctatgatg  360
gaacggggcc cccagactct gaaggaaaca tcctttaatc aggcctatgg tcgagattta  420
atggaggccc aagagtggtg caggaagtac atgaaatcag ggaatgtcaa ggacctcacc  480
caagcctggg acctctatta tcatgtgttc cgacgaatct ca                    522

SEQ ID NO: 356         moltype = AA  length = 174
FEATURE                Location/Qualifiers
REGION                 1..174
                       note = Description of Artificial Sequence: Synthetic
                        polypeptide
source                 1..174
                       mol_type = protein
                       organism = synthetic construct
SEQUENCE: 356
MGVTPNMIDY FGRPYEGIAV FDGKKITVTG TLWNGNKIID ERLINPDGSL LFRVTINGVT  60
GWRLCERILA GGGGSGGGSS VAILWHEMWH EGLEEASRLY FGERNVKGMF EVLEPLHAMM  120
ERGPQTLKET SFNQAYGRDL MEAQEWCRKY MKSGNVKDLT QAWDLYYHVF RRIS        174

SEQ ID NO: 357         moltype = DNA  length = 660
FEATURE                Location/Qualifiers
misc_feature           1..660
                       note = Description of Artificial Sequence: Synthetic
                        polynucleotide
source                 1..660
                       mol_type = other DNA
                       organism = synthetic construct
SEQUENCE: 357
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660

SEQ ID NO: 358         moltype = AA  length = 220
FEATURE                Location/Qualifiers
REGION                 1..220
                       note = Description of Artificial Sequence: Synthetic
                        polypeptide
source                 1..220
                       mol_type = protein
```

```
                        organism = synthetic construct
SEQUENCE: 358
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID                        220

SEQ ID NO: 359          moltype = DNA  length = 519
FEATURE                 Location/Qualifiers
misc_feature            1..519
                        note = Description of Artificial Sequence: Synthetic
                         polynucleotide
source                  1..519
                        mol_type = other DNA
                        organism = synthetic construct
SEQUENCE: 359
atggttacgc cgaacatgat cgactatttc ggacggccgt atgaaggcat cgccgtgttc  60
gacggcaaaa agatcactgt aacagggacc ctgtggaacg gcaacaaaat tatcgacgag  120
cgcctgatca accccgacgg ctccctgctg ttccgagtaa ccatcaacgg agtgaccggc  180
tggcggctgt gcgaacgcat tctggcggga ggaggtggct caggtggagg gagctccgtg  240
gccatcctct ggcatgagat gtggcatgaa ggcctggaag aggcatctcg tttgtacttt  300
ggggaaagga acgtgaaagg catgtttgag gtgctggagc ccttgcatgc tatgatggaa  360
cggggccccc agactctgaa ggaaacatcc tttaatcagg cctatggtcg agatttaatg  420
gaggcccaag agtggtgcag gaagtacatg aaatcaggga atgtcaagga cctcacccaa  480
gcctgggacc tctattatca tgtgttccga cgaatctca                         519

SEQ ID NO: 360          moltype = AA  length = 173
FEATURE                 Location/Qualifiers
REGION                  1..173
                        note = Description of Artificial Sequence: Synthetic
                         polypeptide
source                  1..173
                        mol_type = protein
                        organism = synthetic construct
SEQUENCE: 360
MVTPNMIDYF GRPYEGIAVF DGKKITVTGT LWNGNKIIDE RLINPDGSLL FRVTINGVTG  60
WRLCERILAG GGGSGGGSSV AILWHEMWHE GLEEASRLYF GERNVKGMFE VLEPLHAMME  120
RGPQTLKETS FNQAYGRDLM EAQEWCRKYM KSGNVKDLTQ AWDLYYHVFR RIS          173

SEQ ID NO: 361          moltype = DNA  length = 663
FEATURE                 Location/Qualifiers
misc_feature            1..663
                        note = Description of Artificial Sequence: Synthetic
                         polynucleotide
source                  1..663
                        mol_type = other DNA
                        organism = synthetic construct
SEQUENCE: 361
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggg                                                                 663

SEQ ID NO: 362          moltype = AA  length = 221
FEATURE                 Location/Qualifiers
REGION                  1..221
                        note = Description of Artificial Sequence: Synthetic
                         polypeptide
source                  1..221
                        mol_type = protein
                        organism = synthetic construct
SEQUENCE: 362
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID G                      221

SEQ ID NO: 363          moltype = DNA  length = 396
FEATURE                 Location/Qualifiers
misc_feature            1..396
                        note = Description of Artificial Sequence: Synthetic
```

```
                         polynucleotide
source                  1..396
                        mol_type = other DNA
                        organism = synthetic construct
SEQUENCE: 363
atgatcaacc ccgacggctc cctgctgttc cgagtaacca tcaacggagt gaccggctgg  60
cggctgtgcg aacgcattct ggcgggagga ggtggctcag gtggagggag ctccgtggcc  120
atcctctggc atgagatgtg gcatgaaggc ctggaagagg catctcgttt gtactttggg  180
gaaaggaacg tgaaaggcat gtttgaggtg ctggagccct tgcatgctat gatggaacgg  240
ggcccccaga ctctgaagga aacatccttt aatcaggcct atggtcgaga tttaatggag  300
gcccaagagt ggtgcaggaa gtacatgaaa tcagggaatg tcaaggacct cacccaagcc  360
tgggacctct attatcatgt gttccgacga atctca                             396

SEQ ID NO: 364          moltype = AA  length = 132
FEATURE                 Location/Qualifiers
REGION                  1..132
                        note = Description of Artificial Sequence: Synthetic
                         polypeptide
source                  1..132
                        mol_type = protein
                        organism = synthetic construct
SEQUENCE: 364
MINPDGSLLF RVTINGVTGW RLCERILAGG GGSGGGSSVA ILWHEMWHEG LEEASRLYFG  60
ERNVKGMFEV LEPLHAMMER GPQTLKETSF NQAYGRDLME AQEWCRKYMK SGNVKDLTQA  120
WDLYYHVFRR IS                                                      132

SEQ ID NO: 365          moltype = DNA  length = 786
FEATURE                 Location/Qualifiers
misc_feature            1..786
                        note = Description of Artificial Sequence: Synthetic
                         polynucleotide
source                  1..786
                        mol_type = other DNA
                        organism = synthetic construct
SEQUENCE: 365
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctg                                                             786

SEQ ID NO: 366          moltype = AA  length = 262
FEATURE                 Location/Qualifiers
REGION                  1..262
                        note = Description of Artificial Sequence: Synthetic
                         polypeptide
source                  1..262
                        mol_type = protein
                        organism = synthetic construct
SEQUENCE: 366
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RL                                           262

SEQ ID NO: 367          moltype = DNA  length = 390
FEATURE                 Location/Qualifiers
misc_feature            1..390
                        note = Description of Artificial Sequence: Synthetic
                         polynucleotide
source                  1..390
                        mol_type = other DNA
                        organism = synthetic construct
SEQUENCE: 367
atgcccgacg gctccctgct gttccgagta accatcaacg gagtgaccgg ctggcggctg  60
tgcgaacgca ttctggcggg aggaggtggc tcaggtggag ggagctccgt ggccatcctc  120
tggcatgaga tgtggcatga aggcctggaa gaggcatctc gtttgtactt tggggaaagg  180
aacgtgaaag gcatgtttga ggtgctggag cccttgcatg ctatgatgga acggggcccc  240
cagactctga aggaaacatc ctttaatcag gcctatggtc gagatttaat ggaggcccaa  300
```

```
gagtggtgca ggaagtacat gaaatcaggg aatgtcaagg acctcaccca agcctgggac  360
ctctattatc atgtgttccg acgaatctca                                   390

SEQ ID NO: 368         moltype = AA  length = 130
FEATURE                Location/Qualifiers
REGION                 1..130
                       note = Description of Artificial Sequence: Synthetic
                        polypeptide
source                 1..130
                       mol_type = protein
                       organism = synthetic construct
SEQUENCE: 368
MPDGSLLFRV TINGVTGWRL CERILAGGGG SGGGSSVAIL WHEMWHEGLE EASRLYFGER  60
NVKGMFEVLE PLHAMMERGP QTLKETSFNQ AYGRDLMEAQ EWCRKYMKSG NVKDLTQAWD  120
LYYHVFRRIS                                                         130

SEQ ID NO: 369         moltype = DNA  length = 792
FEATURE                Location/Qualifiers
misc_feature           1..792
                       note = Description of Artificial Sequence: Synthetic
                        polynucleotide
source                 1..792
                       mol_type = other DNA
                       organism = synthetic construct
SEQUENCE: 369
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca ac                                                      792

SEQ ID NO: 370         moltype = AA  length = 264
FEATURE                Location/Qualifiers
REGION                 1..264
                       note = Description of Artificial Sequence: Synthetic
                        polypeptide
source                 1..264
                       mol_type = protein
                       organism = synthetic construct
SEQUENCE: 370
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLIN                                         264

SEQ ID NO: 371         moltype = DNA  length = 384
FEATURE                Location/Qualifiers
misc_feature           1..384
                       note = Description of Artificial Sequence: Synthetic
                        polynucleotide
source                 1..384
                       mol_type = other DNA
                       organism = synthetic construct
SEQUENCE: 371
atgggctccc tgctgttccg agtaaccatc aacggagtga ccggctggcg gctgtgcgaa  60
cgcattctgg cgggaggagg tggctcaggt ggagggagct ccgtggccat cctctggcat  120
gagatgtggc atgaaggcct ggaagaggca tctcgtttgt actttgggga aaggaacgtg  180
aaaggcatgt ttgaggtgct ggagcccttg catgctatga tggaacgggg cccccagact  240
ctgaaggaaa catcctttaa tcaggcctat ggtcgagatt taatggaggc ccaagagtgg  300
tgcaggaagt acatgaaatc agggaatgtc aaggacctca cccaagcctg ggacctctat  360
tatcatgtgt tccgacgaat ctca                                         384

SEQ ID NO: 372         moltype = AA  length = 128
FEATURE                Location/Qualifiers
REGION                 1..128
                       note = Description of Artificial Sequence: Synthetic
                        polypeptide
source                 1..128
                       mol_type = protein
```

```
                         organism = synthetic construct
SEQUENCE: 372
MGSLLFRVTI NGVTGWRLCE RILAGGGGSG GGSSVAILWH EMWHEGLEEA SRLYFGERNV  60
KGMFEVLEPL HAMMERGPQT LKETSFNQAY GRDLMEAQEW CRKYMKSGNV KDLTQAWDLY  120
YHVFRRIS                                                          128

SEQ ID NO: 373           moltype = DNA  length = 798
FEATURE                  Location/Qualifiers
misc_feature             1..798
                         note = Description of Artificial Sequence: Synthetic
                          polynucleotide
source                   1..798
                         mol_type = other DNA
                         organism = synthetic construct
SEQUENCE: 373
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagcactt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgac                                               798

SEQ ID NO: 374           moltype = AA  length = 266
FEATURE                  Location/Qualifiers
REGION                   1..266
                         note = Description of Artificial Sequence: Synthetic
                          polypeptide
source                   1..266
                         mol_type = protein
                         organism = synthetic construct
SEQUENCE: 374
MGVQVETISP GDGRTFPKRG QTCVVHYTGM LEDGKKFDSS RDRNKHFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPD                                      266

SEQ ID NO: 375           moltype = DNA  length = 381
FEATURE                  Location/Qualifiers
misc_feature             1..381
                         note = Description of Artificial Sequence: Synthetic
                          polynucleotide
source                   1..381
                         mol_type = other DNA
                         organism = synthetic construct
SEQUENCE: 375
atgtccctgc tgttccgagt aaccatcaac ggagtgaccg gctggcggct gtgcgaacgc  60
attctggcgg gaggaggtgg ctcaggtgga gggagctccg tggccatcct ctggcatgag  120
atgtggcatg aaggcctgga agaggcatct cgtttgtact ttggggaaag gaacgtgaaa  180
ggcatgtttg aggtgctgga gcccttgcat gctatgatgg aacggggccc ccagactctg  240
aaggaaacat cctttaatca ggcctatggt cgagatttaa tggaggccca agagtggtgc  300
aggaagtaca tgaaatcagg gaatgtcaag gacctcaccc aagcctggga cctctattat  360
catgtgttcc gacgaatctc a                                           381

SEQ ID NO: 376           moltype = AA  length = 127
FEATURE                  Location/Qualifiers
REGION                   1..127
                         note = Description of Artificial Sequence: Synthetic
                          polypeptide
source                   1..127
                         mol_type = protein
                         organism = synthetic construct
SEQUENCE: 376
MSLLFRVTIN GVTGWRLCER ILAGGGGSGG GSSVAILWHE MWHEGLEEAS RLYFGERNVK  60
GMFEVLEPLH AMMERGPQTL KETSFNQAYG RDLMEAQEWC RKYMKSGNVK DLTQAWDLYY  120
HVFRRIS                                                           127

SEQ ID NO: 377           moltype = DNA  length = 801
FEATURE                  Location/Qualifiers
misc_feature             1..801
                         note = Description of Artificial Sequence: Synthetic
```

```
                          polynucleotide
source                   1..801
                         mol_type = other DNA
                         organism = synthetic construct
SEQUENCE: 377
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg c                                           801

SEQ ID NO: 378           moltype = AA  length = 267
FEATURE                  Location/Qualifiers
REGION                   1..267
                         note = Description of Artificial Sequence: Synthetic
                          polypeptide
source                   1..267
                         mol_type = protein
                         organism = synthetic construct
SEQUENCE: 378
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDG                                     267

SEQ ID NO: 379           moltype = DNA  length = 357
FEATURE                  Location/Qualifiers
misc_feature             1..357
                         note = Description of Artificial Sequence: Synthetic
                          polynucleotide
source                   1..357
                         mol_type = other DNA
                         organism = synthetic construct
SEQUENCE: 379
atgaacggag tgaccggctg gcggctgtgc gaacgcattc tggcgggagg aggtggctca  60
ggtggaggga gctccgtggc catcctctgg catgagatgt ggcatgaagg cctggaagag  120
gcatctcgtt tgtactttgg ggaaaggaac gtgaaaggca tgtttgaggt gctggagccc  180
ttgcatgcta tgatggaacg gggcccccag actctgaagg aaacatcctt taatcaggcc  240
tatggtcgag atttaatgga ggcccaagag tggtgcagga agtacatgaa atcagggaat  300
gtcaaggacc tcacccaagc ctgggacctc tattatcatg tgttccgacg aatctca    357

SEQ ID NO: 380           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 380
MNGVTGWRLC ERILAGGGGS GGGSSVAILW HEMWHEGLEE ASRLYFGERN VKGMFEVLEP  60
LHAMMERGPQ TLKETSFNQA YGRDLMEAQE WCRKYMKSGN VKDLTQAWDL YYHVFRRIS   119

SEQ ID NO: 381           moltype = DNA  length = 825
FEATURE                  Location/Qualifiers
misc_feature             1..825
                         note = Description of Artificial Sequence: Synthetic
                          polynucleotide
source                   1..825
                         mol_type = other DNA
                         organism = synthetic construct
SEQUENCE: 381
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
```

```
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatc                  825

SEQ ID NO: 382         moltype = AA  length = 275
FEATURE                Location/Qualifiers
REGION                 1..275
                       note = Description of Artificial Sequence: Synthetic
                        polypeptide
source                 1..275
                       mol_type = protein
                       organism = synthetic construct
SEQUENCE: 382
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTI                             275

SEQ ID NO: 383         moltype = DNA  length = 351
FEATURE                Location/Qualifiers
misc_feature           1..351
                       note = Description of Artificial Sequence: Synthetic
                        polynucleotide
source                 1..351
                       mol_type = other DNA
                       organism = synthetic construct
SEQUENCE: 383
atggtgaccg gctggcggct gtgcgaacgc attctggcgg gaggaggtgg ctcaggtgga  60
gggagctccg tggccatcct ctggcatgag atgtggcatg aaggcctgga agaggcatct  120
cgtttgtact ttggggaaag gaacgtgaaa ggcatgtttg aggtgctgga gcccttgcat  180
gctatgatgg aacggggccc ccagactctg aaggaaacat cctttaatca ggcctatggt  240
cgagatttaa tggaggccca agagtggtgc aggaagtaca tgaaatcagg gaatgtcaag  300
gacctcaccc aagcctggga cctctattat catgtgttcc gacgaatctc a           351

SEQ ID NO: 384         moltype = AA  length = 117
FEATURE                Location/Qualifiers
REGION                 1..117
                       note = Description of Artificial Sequence: Synthetic
                        polypeptide
source                 1..117
                       mol_type = protein
                       organism = synthetic construct
SEQUENCE: 384
MVTGWRLCER ILAGGGGSGG GSSVAILWHE MWHEGLEEAS RLYFGERNVK GMFEVLEPLH  60
AMMERGPQTL KETSFNQAYG RDLMEAQEWC RKYMKSGNVK DLTQAWDLYY HVFRRIS     117

SEQ ID NO: 385         moltype = DNA  length = 831
FEATURE                Location/Qualifiers
misc_feature           1..831
                       note = Description of Artificial Sequence: Synthetic
                        polynucleotide
source                 1..831
                       mol_type = other DNA
                       organism = synthetic construct
SEQUENCE: 385
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg a           831

SEQ ID NO: 386         moltype = AA  length = 277
FEATURE                Location/Qualifiers
REGION                 1..277
                       note = Description of Artificial Sequence: Synthetic
```

```
                         polypeptide
source                  1..277
                        mol_type = protein
                        organism = synthetic construct
SEQUENCE: 386
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTING                           277

SEQ ID NO: 387          moltype = DNA  length = 327
FEATURE                 Location/Qualifiers
misc_feature            1..327
                        note = Description of Artificial Sequence: Synthetic
                         polynucleotide
source                  1..327
                        mol_type = other DNA
                        organism = synthetic construct
SEQUENCE: 387
atgcgcattc tggcgggagg aggtggctca ggtggaggga gctccgtggc catcctctgg  60
catgagatgt ggcatgaagg cctggaagag gcatctcgtt tgtactttgg ggaaaggaac  120
gtgaaaggca tgtttgaggt gctggagccc ttgcatgcta tgatggaacg gggcccccag  180
actctgaagg aaacatcctt taatcaggcc tatggtcgag atttaatgga ggcccaagag  240
tggtgcagga agtacatgaa atcagggaat gtcaaggacc tcacccaagc ctgggacctc  300
tattatcatg tgttccgacg aatctca                                      327

SEQ ID NO: 388          moltype = AA  length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 388
MRILAGGGGS GGGSSVAILW HEMWHEGLEE ASRLYFGERN VKGMFEVLEP LHAMMERGPQ  60
TLKETSFNQA YGRDLMEAQE WCRKYMKSGN VKDLTQAWDL YYHVFRRIS              109

SEQ ID NO: 389          moltype = DNA  length = 855
FEATURE                 Location/Qualifiers
misc_feature            1..855
                        note = Description of Artificial Sequence: Synthetic
                         polynucleotide
source                  1..855
                        mol_type = other DNA
                        organism = synthetic construct
SEQUENCE: 389
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840
tggcggctgt gcgaa                                                   855

SEQ ID NO: 390          moltype = AA  length = 285
FEATURE                 Location/Qualifiers
REGION                  1..285
                        note = Description of Artificial Sequence: Synthetic
                         polypeptide
source                  1..285
                        mol_type = protein
                        organism = synthetic construct
SEQUENCE: 390
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGVTG WRLCE                  285
```

-continued

```
SEQ ID NO: 391         moltype = DNA  length = 501
FEATURE                Location/Qualifiers
misc_feature           1..501
                       note = Description of Artificial Sequence: Synthetic
                        polynucleotide
source                 1..501
                       mol_type = other DNA
                       organism = synthetic construct
SEQUENCE: 391
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag c                                            501

SEQ ID NO: 392         moltype = AA  length = 167
FEATURE                Location/Qualifiers
REGION                 1..167
                       note = Description of Artificial Sequence: Synthetic
                        polypeptide
source                 1..167
                       mol_type = protein
                       organism = synthetic construct
SEQUENCE: 392
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLS                167

SEQ ID NO: 393         moltype = DNA  length = 681
FEATURE                Location/Qualifiers
misc_feature           1..681
                       note = Description of Artificial Sequence: Synthetic
                        polynucleotide
source                 1..681
                       mol_type = other DNA
                       organism = synthetic construct
SEQUENCE: 393
atgggtgaaa atgggctgaa gatcgacatc catgtcatca tcccgtatga aggtctgagc  60
ggcgaccaaa tgggccagat cgaaaaaatt tttaaggtgg tgtaccctgt ggatgatcat  120
cactttaagg tgatcctgca ctatggcaca ctggtaatcg acggggttac gccgaacatg  180
atcgactatt tcggacggcc gtatgaaggc atcgccgtgt tcgacggcaa aaagatcact  240
gtaacaggga ccctgtggaa cggcaacaaa attatcgacg agcgcctgat caacccccgac  300
ggctccctgc tgttccgagt aaccatcaac ggagtgaccg gctggcggct gtgcgaacgc  360
attctggcgg gaggaggtgg ctcaggtgga gggagctccg tggccatcct ctggcatgag  420
atgtggcatg aaggcctgga agaggcatct cgtttgtact ttggggaaag gaacgtgaaa  480
ggcatgtttg aggtgctgga gcccttgcat gctatgatgg aacggggccc ccagactctg  540
aaggaaacat cctttaatca ggcctatggt cgagatttaa tggaggccca agagtggtgc  600
aggaagtaca tgaaatcagg gaatgtcaag gacctcaccc aagcctggga cctctattat  660
catgtgttcc gacgaatctc a                                            681

SEQ ID NO: 394         moltype = AA  length = 227
FEATURE                Location/Qualifiers
REGION                 1..227
                       note = Description of Artificial Sequence: Synthetic
                        polypeptide
source                 1..227
                       mol_type = protein
                       organism = synthetic construct
SEQUENCE: 394
MGENGLKIDI HVIIPYEGLS GDQMGQIEKI FKVVYPVDDH HFKVILHYGT LVIDGVTPNM  60
IDYFGRPYEG IAVFDGKKIT VTGTLWNGNK IIDERLINPD GSLLFRVTIN GVTGWRLCER  120
ILAGGGGSGG GSSVAILWHE MWHEGLEEAS RLYFGERNVK GMFEVLEPLH AMMERGPQTL  180
KETSFNQAYG RDLMEAQEWC RKYMKSGNVK DLTQAWDLYY HVFRRIS                227

SEQ ID NO: 395         moltype = DNA  length = 507
FEATURE                Location/Qualifiers
misc_feature           1..507
                       note = Description of Artificial Sequence: Synthetic
                        polynucleotide
source                 1..507
                       mol_type = other DNA
                       organism = synthetic construct
SEQUENCE: 395
atgggagtgc aggtggaaac catctcccca ggagacgggc gcaccttccc caagcgcggc  60
cagacctgcg tggtgcacta caccgggatg cttgaagatg gaaagaaatt tgattcctcc  120
```

```
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaa                                      507

SEQ ID NO: 396         moltype = AA  length = 169
FEATURE                Location/Qualifiers
REGION                 1..169
                       note = Description of Artificial Sequence: Synthetic
                        polypeptide
source                 1..169
                       mol_type = protein
                       organism = synthetic construct
SEQUENCE: 396
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGE              169

SEQ ID NO: 397         moltype = DNA  length = 675
FEATURE                Location/Qualifiers
misc_feature           1..675
                       note = Description of Artificial Sequence: Synthetic
                        polynucleotide
source                 1..675
                       mol_type = other DNA
                       organism = synthetic construct
SEQUENCE: 397
atgaatgggc tgaagatcga catccatgtc atcatcccgt atgaaggtct gagcggcgac  60
caaatgggcc agatcgaaaa aatttttaag gtggtgtacc ctgtggatga tcatcacttt  120
aaggtgatcc tgcactatgg cacactggta atcgacgggg ttacgccgaa catgatcgac  180
tatttcggac ggccgtatga aggcatcgcc gtgttcgacg gcaaaaagat cactgtaaca  240
gggaccctgt ggaacggcaa caaaattatc gacgagcgcc tgatcaaccc cgacggctcc  300
ctgctgttcc gagtaaccat caacggagtg accggctggc ggctgtgcga acgcattctg  360
gcgggaggag gtggctcagg tggagggagc tccgtggcca tcctctggca tgagatgtgg  420
catgaaggcc tggaagaggc atctcgtttg tactttgggg aaaggaacgt gaaaggcatg  480
tttgaggtgc tggagccctt gcatgctatg atggaacggg gcccccagac tctgaaggaa  540
acatccttta atcaggccta tggtcgagat ttaatggagg cccaagagtg gtgcaggaag  600
tacatgaaat cagggaatgt caaggacctc acccaagcct gggacctcta ttatcatgtg  660
ttccgacgaa tctca                                                   675

SEQ ID NO: 398         moltype = AA  length = 225
FEATURE                Location/Qualifiers
REGION                 1..225
                       note = Description of Artificial Sequence: Synthetic
                        polypeptide
source                 1..225
                       mol_type = protein
                       organism = synthetic construct
SEQUENCE: 398
MNGLKIDIHV IIPYEGLSGD QMGQIEKIFK VVYPVDDHHF KVILHYGTLV IDGVTPNMID  60
YFGRPYEGIA VFDGKKITVT GTLWNGNKII DERLINPDGS LLFRVTINGV TGWRLCERIL  120
AGGGGSGGGS SVAILWHEMW HEGLEEASRL YFGERNVKGM FEVLEPLHAM MERGPQTLKE  180
TSFNQAYGRD LMEAQEWCRK YMKSGNVKDL TQAWDLYYHV FRRIS                  225

SEQ ID NO: 399         moltype = DNA  length = 606
FEATURE                Location/Qualifiers
misc_feature           1..606
                       note = Description of Artificial Sequence: Synthetic
                        polynucleotide
source                 1..606
                       mol_type = other DNA
                       organism = synthetic construct
SEQUENCE: 399
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccct                                                             606

SEQ ID NO: 400         moltype = AA  length = 202
```

```
FEATURE                Location/Qualifiers
REGION                 1..202
                       note = Description of Artificial Sequence: Synthetic
                        polypeptide
source                 1..202
                       mol_type = protein
                       organism = synthetic construct
SEQUENCE: 400
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YP                                          202

SEQ ID NO: 401         moltype = DNA  length = 576
FEATURE                Location/Qualifiers
misc_feature           1..576
                       note = Description of Artificial Sequence: Synthetic
                        polynucleotide
source                 1..576
                       mol_type = other DNA
                       organism = synthetic construct
SEQUENCE: 401
atggtggatg atcatcactt taaggtgatc ctgcactatg gcacactggt aatcgacggg  60
gttacgccga acatgatcga ctatttcgga cggccgtatg aaggcatcgc cgtgttcgac  120
ggcaaaaaga tcactgtaac agggaccctg tggaacggca acaaaattat cgacgagcgc  180
ctgatcaacc ccgacggctc cctgctgttc cgagtaacca tcaacggagt gaccggctgg  240
cggctgtgcg aacgcattct ggcgggagga ggtggctcag gtggagggag ctccgtggcc  300
atcctctggc atgagatgtg gcatgaaggc ctggaagagg catctcgttt gtactttggg  360
gaaaggaacg tgaaaggcat gtttgaggtg ctggagccct tgcatgctat gatggaacgg  420
ggcccccaga ctctgaagga aacatccttt aatcaggcct atggtcgaga tttaatggag  480
gcccaagagt ggtgcaggaa gtacatgaaa tcagggaatg tcaaggacct cacccaagcc  540
tgggacctct attatcatgt gttccgacga atctca                           576

SEQ ID NO: 402         moltype = AA  length = 192
FEATURE                Location/Qualifiers
REGION                 1..192
                       note = Description of Artificial Sequence: Synthetic
                        polypeptide
source                 1..192
                       mol_type = protein
                       organism = synthetic construct
SEQUENCE: 402
MVDDHHFKVI LHYGTLVIDG VTPNMIDYFG RPYEGIAVFD GKKITVTGTL WNGNKIIDER  60
LINPDGSLLF RVTINGVTGW RLCERILAGG GGSGGGSSVA ILWHEMWHEG LEEASRLYFG  120
ERNVKGMFEV LEPLHAMMER GPQTLKETSF NQAYGRDLME AQEWCRKYMK SGNVKDLTQA  180
WDLYYHVFRR IS                                                      192

SEQ ID NO: 403         moltype = DNA  length = 612
FEATURE                Location/Qualifiers
misc_feature           1..612
                       note = Description of Artificial Sequence: Synthetic
                        polynucleotide
source                 1..612
                       mol_type = other DNA
                       organism = synthetic construct
SEQUENCE: 403
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg at                                                      612

SEQ ID NO: 404         moltype = AA  length = 204
FEATURE                Location/Qualifiers
REGION                 1..204
                       note = Description of Artificial Sequence: Synthetic
                        polypeptide
source                 1..204
                       mol_type = protein
                       organism = synthetic construct
SEQUENCE: 404
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
```

-continued

```
FTLEDFVGDW RQTAGYNLDQ VLEQGGVSSL FQNLGVSVTP IQRIVLSGEN GLKIDIHVII  180
PYEGLSGDQM GQIEKIFKVV YPVD                                         204

SEQ ID NO: 405         moltype = DNA  length = 570
FEATURE                Location/Qualifiers
misc_feature           1..570
                       note = Description of Artificial Sequence: Synthetic
                        polynucleotide
source                 1..570
                       mol_type = other DNA
                       organism = synthetic construct
SEQUENCE: 405
atggatcatc actttaaggt gatcctgcac tatggcacac tggtaatcga cggggttacg  60
ccgaacatga tcgactattt cggacggccg tatgaaggca tcgccgtgtt cgacggcaaa  120
aagatcactg taacagggac cctgtggaac ggcaacaaaa ttatcgacga gcgcctgatc  180
aaccccgacg gctccctgct gttccgagta accatcaacg gagtgaccgg ctggcggctg  240
tgcgaacgca ttctggcggg aggaggtggc tcaggtggag ggagctccgt ggccatcctc  300
tggcatgaga tgtggcatga aggcctggaa gaggcatctc gtttgtactt tggggaaagg  360
aacgtgaaag gcatgtttga ggtgctggag cccttgcatg ctatgatgga acggggcccc  420
cagactctga aggaaacatc ctttaatcag gcctatggtc gagatttaat ggaggcccaa  480
gagtggtgca ggaagtacat gaaatcaggg aatgtcaagg acctcaccca agcctgggac  540
ctctattatc atgtgttccg acgaatctca                                   570

SEQ ID NO: 406         moltype = AA  length = 190
FEATURE                Location/Qualifiers
REGION                 1..190
                       note = Description of Artificial Sequence: Synthetic
                        polypeptide
source                 1..190
                       mol_type = protein
                       organism = synthetic construct
SEQUENCE: 406
MDHHFKVILH YGTLVIDGVT PNMIDYFGRP YEGIAVFDGK KITVTGTLWN GNKIIDERLI  60
NPDGSLLFRV TINGVTGWRL CERILAGGGG SGGGSSVAIL WHEMWHEGLE EASRLYFGER  120
NVKGMFEVLE PLHAMMERGP QTLKETSFNQ AYGRDLMEAQ EWCRKYMKSG NVKDLTQAWD  180
LYYHVFRRIS                                                         190

SEQ ID NO: 407         moltype = DNA  length = 726
FEATURE                Location/Qualifiers
misc_feature           1..726
                       note = Description of Artificial Sequence: Synthetic
                        polynucleotide
source                 1..726
                       mol_type = other DNA
                       organism = synthetic construct
SEQUENCE: 407
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggc                                                             726

SEQ ID NO: 408         moltype = AA  length = 242
FEATURE                Location/Qualifiers
REGION                 1..242
                       note = Description of Artificial Sequence: Synthetic
                        polypeptide
source                 1..242
                       mol_type = protein
                       organism = synthetic construct
SEQUENCE: 408
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DG                                                                 242

SEQ ID NO: 409         moltype = DNA  length = 456
FEATURE                Location/Qualifiers
misc_feature           1..456
                       note = Description of Artificial Sequence: Synthetic
```

```
                         polynucleotide
source                  1..456
                        mol_type = other DNA
                        organism = synthetic construct
SEQUENCE: 409
atgaaaaaga tcactgtaac agggaccctg tggaacggca acaaaattat cgacgagcgc  60
ctgatcaacc ccgacggctc cctgctgttc cgagtaacca tcaacggagt gaccggctgg  120
cggctgtgcg aacgcattct ggcgggagga ggtggctcag gtggagggag ctccgtggcc  180
atcctctggc atgagatgtg gcatgaaggc ctggaagagg catctcgttt gtactttggg  240
gaaaggaacg tgaaaggcat gtttgaggtg ctggagccct tgcatgctat gatggaacgg  300
ggcccccaga ctctgaagga aacatccttt aatcaggcct atggtcgaga tttaatggag  360
gcccaagagt ggtgcaggaa gtacatgaaa tcagggaatg tcaaggacct cacccaagcc  420
tgggacctct attatcatgt gttccgacga atctca                           456

SEQ ID NO: 410          moltype = AA  length = 152
FEATURE                 Location/Qualifiers
REGION                  1..152
                        note = Description of Artificial Sequence: Synthetic
                         polypeptide
source                  1..152
                        mol_type = protein
                        organism = synthetic construct
SEQUENCE: 410
MKKITVTGTL WNGNKIIDER LINPDGSLLF RVTINGVTGW RLCERILAGG GGSGGGSSVA  60
ILWHEMWHEG LEEASRLYFG ERNVKGMFEV LEPLHAMMER GPQTLKETSF NQAYGRDLME  120
AQEWCRKYMK SGNVKDLTQA WDLYYHVFRR IS                               152

SEQ ID NO: 411          moltype = DNA  length = 729
FEATURE                 Location/Qualifiers
misc_feature            1..729
                        note = Description of Artificial Sequence: Synthetic
                         polynucleotide
source                  1..729
                        mol_type = other DNA
                        organism = synthetic construct
SEQUENCE: 411
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaa                                                         729

SEQ ID NO: 412          moltype = AA  length = 243
FEATURE                 Location/Qualifiers
REGION                  1..243
                        note = Description of Artificial Sequence: Synthetic
                         polypeptide
source                  1..243
                        mol_type = protein
                        organism = synthetic construct
SEQUENCE: 412
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGK                                                               243

SEQ ID NO: 413          moltype = DNA  length = 453
FEATURE                 Location/Qualifiers
misc_feature            1..453
                        note = Description of Artificial Sequence: Synthetic
                         polynucleotide
source                  1..453
                        mol_type = other DNA
                        organism = synthetic construct
SEQUENCE: 413
atgaagatca ctgtaacagg gaccctgtgg aacggcaaca aaattatcga cgagcgcctg  60
atcaaccccg acggctccct gctgttccga gtaaccatca acggagtgac cggctggcgg  120
ctgtgcgaac gcattctggc gggaggaggt ggctcaggtg gagggagctc cgtggccatc  180
ctctggcatg agatgtggca tgaaggcctg gaagaggcat ctcgtttgta ctttggggaa  240
aggaacgtga aaggcatgtt tgaggtgctg gagcccttgc atgctatgat ggaacggggc  300
```

```
ccccagactc tgaaggaaac atcctttaat caggcctatg gtcgagattt aatggaggcc  360
caagagtggt gcaggaagta catgaaatca gggaatgtca aggacctcac ccaagcctgg  420
gacctctatt atcatgtgtt ccgacgaatc tca                                453

SEQ ID NO: 414         moltype = AA  length = 151
FEATURE                Location/Qualifiers
REGION                 1..151
                       note = Description of Artificial Sequence: Synthetic
                        polypeptide
source                 1..151
                       mol_type = protein
                       organism = synthetic construct
SEQUENCE: 414
MKITVTGTLW NGNKIIDERL INPDGSLLFR VTINGVTGWR LCERILAGGG GSGGGSSVAI  60
LWHEMWHEGL EEASRLYFGE RNVKGMFEVL EPLHAMMERG PQTLKETSFN QAYGRDLMEA  120
QEWCRKYMKS GNVKDLTQAW DLYYHVFRRI S                                 151

SEQ ID NO: 415         moltype = DNA  length = 864
FEATURE                Location/Qualifiers
misc_feature           1..864
                       note = Description of Artificial Sequence: Synthetic
                        polynucleotide
source                 1..864
                       mol_type = other DNA
                       organism = synthetic construct
SEQUENCE: 415
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840
tggcggctgt gcgaacgcat tctg                                          864

SEQ ID NO: 416         moltype = DNA  length = 864
FEATURE                Location/Qualifiers
misc_feature           1..864
                       note = Description of Artificial Sequence: Synthetic
                        polynucleotide
source                 1..864
                       mol_type = other DNA
                       organism = synthetic construct
SEQUENCE: 416
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840
tggcggctgt gcgaacgcat tctg                                          864

SEQ ID NO: 417         moltype = AA  length = 288
FEATURE                Location/Qualifiers
REGION                 1..288
                       note = Description of Artificial Sequence: Synthetic
                        polypeptide
source                 1..288
                       mol_type = protein
                       organism = synthetic construct
SEQUENCE: 417
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
```

```
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGVTG WRLCERIL              288

SEQ ID NO: 418         moltype = DNA  length = 318
FEATURE                Location/Qualifiers
misc_feature           1..318
                       note = Description of Artificial Sequence: Synthetic
                        polynucleotide
source                 1..318
                       mol_type = other DNA
                       organism = synthetic construct
SEQUENCE: 418
atggcgggag gaggtggctc aggtggaggg agctccgtgg ccatcctctg gcatgagatg  60
tggcatgaag gcctggaaga ggcatctcgt ttgtactttg gggaaaggaa cgtgaaaggc  120
atgtttgagg tgctggagcc cttgcatgct atgatggaac ggggccccca gactctgaag  180
gaaacatcct ttaatcaggc ctatggtcga gatttaatgg aggcccaaga gtggtgcagg  240
aagtacatga aatcagggaa tgtcaaggac ctcacccaag cctgggacct ctattatcat  300
gtgttccgac gaatctca                                                 318

SEQ ID NO: 419         moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 419
MAGGGGSGGG SSVAILWHEM WHEGLEEASR LYFGERNVKG MFEVLEPLHA MMERGPQTLK  60
ETSFNQAYGR DLMEAQEWCR KYMKSGNVKD LTQAWDLYYH VFRRIS                  106

SEQ ID NO: 420         moltype = DNA  length = 858
FEATURE                Location/Qualifiers
misc_feature           1..858
                       note = Description of Artificial Sequence: Synthetic
                        polynucleotide
source                 1..858
                       mol_type = other DNA
                       organism = synthetic construct
SEQUENCE: 420
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840
tggcggctgt gcgaacgc                                                 858

SEQ ID NO: 421         moltype = AA  length = 286
FEATURE                Location/Qualifiers
REGION                 1..286
                       note = Description of Artificial Sequence: Synthetic
                        polypeptide
source                 1..286
                       mol_type = protein
                       organism = synthetic construct
SEQUENCE: 421
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGVTG WRLCER                  286

SEQ ID NO: 422         moltype = DNA  length = 324
FEATURE                Location/Qualifiers
misc_feature           1..324
                       note = Description of Artificial Sequence: Synthetic
                        polynucleotide
source                 1..324
                       mol_type = other DNA
                       organism = synthetic construct
```

```
SEQUENCE: 422
atgattctgg cgggaggagg tggctcaggt ggagggagct ccgtggccat cctctggcat  60
gagatgtggc atgaaggcct ggaagaggca tctcgtttgt actttgggga aaggaacgtg  120
aaaggcatgt ttgaggtgct ggagcccttg catgctatga tggaacgggg cccccagact  180
ctgaaggaaa catcctttaa tcaggcctat ggtcgagatt taatggaggc ccaagagtgg  240
tgcaggaagt acatgaaatc agggaatgtc aaggacctca cccaagcctg ggacctctat  300
tatcatgtgt tccgacgaat ctca                                         324

SEQ ID NO: 423          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 423
MILAGGGGSG GGSSVAILWH EMWHEGLEEA SRLYFGERNV KGMFEVLEPL HAMMERGPQT  60
LKETSFNQAY GRDLMEAQEW CRKYMKSGNV KDLTQAWDLY YHVFRRIS               108

SEQ ID NO: 424          moltype = DNA  length = 852
FEATURE                 Location/Qualifiers
misc_feature            1..852
                        note = Description of Artificial Sequence: Synthetic
                         polynucleotide
source                  1..852
                        mol_type = other DNA
                        organism = synthetic construct
SEQUENCE: 424
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840
tggcggctgt gc                                                      852

SEQ ID NO: 425          moltype = AA  length = 284
FEATURE                 Location/Qualifiers
REGION                  1..284
                        note = Description of Artificial Sequence: Synthetic
                         polypeptide
source                  1..284
                        mol_type = protein
                        organism = synthetic construct
SEQUENCE: 425
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGVTG WRLC                   284

SEQ ID NO: 426          moltype = DNA  length = 330
FEATURE                 Location/Qualifiers
misc_feature            1..330
                        note = Description of Artificial Sequence: Synthetic
                         polynucleotide
source                  1..330
                        mol_type = other DNA
                        organism = synthetic construct
SEQUENCE: 426
atggaacgca ttctggcggg aggaggtggc tcaggtggag ggagctccgt ggccatcctc  60
tggcatgaga tgtggcatga aggcctggaa gaggcatctc gtttgtactt tggggaaagg  120
aacgtgaaag gcatgtttga ggtgctggag cccttgcatg ctatgatgga acggggcccc  180
cagactctga aggaaacatc ctttaatcag gcctatggtc gagatttaat ggaggcccaa  240
gagtggtgca ggaagtacat gaaatcaggg aatgtcaagg acctcaccca agcctgggac  300
ctctattatc atgtgttccg acgaatctca                                   330

SEQ ID NO: 427          moltype = AA  length = 18
FEATURE                 Location/Qualifiers
REGION                  1..18
```

-continued

```
                        note = Description of Artificial Sequence: Dinoflagellate
                         luciferase consensus sequence
MOD_RES                 6
                        note = Val or Ile
MOD_RES                 11
                        note = Ala, Val, Thr, or Lys
MOD_RES                 12
                        note = Ala or Glu
MOD_RES                 16
                        note = Glu, Lys, Thr, or Gln
MOD_RES                 17
                        note = Ala or Val
MOD_RES                 18
                        note = Val or Ile
source                  1..18
                        mol_type = protein
                        organism = synthetic construct
SEQUENCE: 427
GRWITXSGGQ XXFIKXXX                                                   18

SEQ ID NO: 428          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 428
MERILAGGGG SGGGSSVAIL WHEMWHEGLE EASRLYFGER NVKGMFEVLE PLHAMMERGP  60
QTLKETSFNQ AYGRDLMEAQ EWCRKYMKSG NVKDLTQAWD LYYHVFRRIS             110

SEQ ID NO: 429          moltype = DNA  length = 846
FEATURE                 Location/Qualifiers
misc_feature            1..846
                        note = Description of Artificial Sequence: Synthetic
                         polynucleotide
source                  1..846
                        mol_type = other DNA
                        organism = synthetic construct
SEQUENCE: 429
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840
tggcgg                                                              846

SEQ ID NO: 430          moltype = AA  length = 282
FEATURE                 Location/Qualifiers
REGION                  1..282
                        note = Description of Artificial Sequence: Synthetic
                         polypeptide
source                  1..282
                        mol_type = protein
                        organism = synthetic construct
SEQUENCE: 430
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGVTG WR                      282

SEQ ID NO: 431          moltype = DNA  length = 336
FEATURE                 Location/Qualifiers
misc_feature            1..336
                        note = Description of Artificial Sequence: Synthetic
                         polynucleotide
source                  1..336
                        mol_type = other DNA
```

```
                         organism = synthetic construct
SEQUENCE: 431
atgctgtgcg aacgcattct ggcgggagga ggtggctcag gtggagggag ctccgtggcc  60
atcctctggc atgagatgtg gcatgaaggc ctggaagagg catctcgttt gtactttggg  120
gaaaggaacg tgaaaggcat gtttgaggtg ctggagccct tgcatgctat gatggaacgg  180
ggcccccaga ctctgaagga aacatccttt aatcaggcct atggtcgaga tttaatggag  240
gcccaagagt ggtgcaggaa gtacatgaaa tcagggaatg tcaaggacct cacccaagcc  300
tgggacctct attatcatgt gttccgacga atctca                            336

SEQ ID NO: 432           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 432
MLCERILAGG GGSGGGSSVA ILWHEMWHEG LEEASRLYFG ERNVKGMFEV LEPLHAMMER  60
GPQTLKETSF NQAYGRDLME AQEWCRKYMK SGNVKDLTQA WDLYYHVFRR IS          112

SEQ ID NO: 433           moltype = DNA  length = 840
FEATURE                  Location/Qualifiers
misc_feature             1..840
                         note = Description of Artificial Sequence: Synthetic
                          polynucleotide
source                   1..840
                         mol_type = other DNA
                         organism = synthetic construct
SEQUENCE: 433
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtgaccggc  840

SEQ ID NO: 434           moltype = AA  length = 280
FEATURE                  Location/Qualifiers
REGION                   1..280
                         note = Description of Artificial Sequence: Synthetic
                          polypeptide
source                   1..280
                         mol_type = protein
                         organism = synthetic construct
SEQUENCE: 434
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGVTG                        280

SEQ ID NO: 435           moltype = DNA  length = 342
FEATURE                  Location/Qualifiers
misc_feature             1..342
                         note = Description of Artificial Sequence: Synthetic
                          polynucleotide
source                   1..342
                         mol_type = other DNA
                         organism = synthetic construct
SEQUENCE: 435
atgtggcggc tgtgcgaacg cattctggcg ggaggaggtg gctcaggtgg agggagctcc  60
gtggccatcc tctggcatga gatgtggcat gaaggcctgg aagaggcatc tcgtttgtac  120
tttggggaaa ggaacgtgaa aggcatgttt gaggtgctgg agcccttgca tgctatgatg  180
gaacggggcc cccagactct gaaggaaaca tcctttaatc aggcctatgg tcgagattta  240
atggaggccc aagagtggtg caggaagtac atgaaatcag ggaatgtcaa ggacctcacc  300
caagcctggg acctctatta tcatgtgttc cgacgaatct ca                     342

SEQ ID NO: 436           moltype = AA  length = 114
FEATURE                  Location/Qualifiers
REGION                   1..114
```

```
                        note = Description of Artificial Sequence: Synthetic
                         polypeptide
source                  1..114
                        mol_type = protein
                        organism = synthetic construct
SEQUENCE: 436
MWRLCERILA GGGGSGGGSS VAILWHEMWH EGLEEASRLY FGERNVKGMF EVLEPLHAMM  60
ERGPQTLKET SFNQAYGRDL MEAQEWCRKY MKSGNVKDLT QAWDLYYHVF RRIS        114

SEQ ID NO: 437          moltype = DNA  length = 834
FEATURE                 Location/Qualifiers
misc_feature            1..834
                        note = Description of Artificial Sequence: Synthetic
                         polynucleotide
source                  1..834
                        mol_type = other DNA
                        organism = synthetic construct
SEQUENCE: 437
atgggagtgc aggtggaaac catctcccca ggagacgggc gcaccttccc caagcgcggc  60
cagacctgcg tggtgcacta caccgggatg cttgaagatg gaaagaaatt tgattcctcc  120
cgggacagaa acaagccctt taagtttatg ctaggcaagc aggaggtgat ccgaggctgg  180
gaagaagggg ttgcccagat gagtgtgggt cagagagcca aactgactat atctccagat  240
tatgcctatg gtgccactgg gcacccaggc atcatcccac cacatgccac tctcgtcttc  300
gatgtggagc ttctaaaact ggaaggagga gggagctccg gtggaggcag cggtatggtc  360
ttcacactcg aagatttcgt tggggactgg cgacagacag ccggctacaa cctggaccaa  420
gtccttgaac agggaggtgt gtccagtttg tttcagaatc tcggggtgtc cgtaactccg  480
atccaaagga ttgtcctgag cggtgaaaat gggctgaaga tcgacatcca tgtcatcatc  540
ccgtatgaag gtctgagcgg cgaccaaatg ggccagatcg aaaaaatttt taaggtggtg  600
taccctgtgg atgatcatca ctttaaggtg atcctgcact atggcacact ggtaatcgac  660
ggggttacgc cgaacatgat cgactatttc ggacggccgt atgaaggcat cgccgtgttc  720
gacggcaaaa agatcactgt aacagggacc ctgtggaacg gcaacaaaat tatcgacgag  780
cgcctgatca accccgacgg ctccctgctg ttccgagtaa ccatcaacgg agtg        834

SEQ ID NO: 438          moltype = AA  length = 278
FEATURE                 Location/Qualifiers
REGION                  1..278
                        note = Description of Artificial Sequence: Synthetic
                         polypeptide
source                  1..278
                        mol_type = protein
                        organism = synthetic construct
SEQUENCE: 438
MGVQVETISP GDGRTFPKRG QTCVVHYTGM LEDGKKFDSS RDRNKPFKFM LGKQEVIRGW  60
EEGVAQMSVG QRAKLTISPD YAYGATGHPG IIPPHATLVF DVELLKLEGG GSSGGGSGMV  120
FTLEDFVGDW RQTAGYNLDQ VLEQGGVSSL FQNLGVSVTP IQRIVLSGEN GLKIDIHVII  180
PYEGLSGDQM GQIEKIFKVV YPVDDHHFKV ILHYGTLVID GVTPNMIDYF GRPYEGIAVF  240
DGKKITVTGT LWNGNKIIDE RLINPDGSLL FRVTINGV                          278

SEQ ID NO: 439          moltype = DNA  length = 348
FEATURE                 Location/Qualifiers
misc_feature            1..348
                        note = Description of Artificial Sequence: Synthetic
                         polynucleotide
source                  1..348
                        mol_type = other DNA
                        organism = synthetic construct
SEQUENCE: 439
atgaccggct ggcggctgtg cgaacgcatt ctggcgggag gaggtggctc aggtggaggg  60
agctccgtgg ccatcctctg gcatgagatg tggcatgaag gcctggaaga ggcatctcgt  120
ttgtactttg gggaaaggaa cgtgaaaggc atgtttgagg tgctggagcc cttgcatgct  180
atgatggaac ggggccccca gactctgaag gaaacatcct ttaatcaggc ctatggtcga  240
gatttaatgg aggcccaaga gtggtgcagg aagtacatga aatcagggaa tgtcaaggac  300
ctcacccaag cctgggacct ctattatcat gtgttccgac gaatctca              348

SEQ ID NO: 440          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 440
MTGWRLCERI LAGGGGSGGG SSVAILWHEM WHEGLEEASR LYFGERNVKG MFEVLEPLHA  60
MMERGPQTLK ETSFNQAYGR DLMEAQEWCR KYMKSGNVKD LTQAWDLYYH VFRRIS      116

SEQ ID NO: 441          moltype = DNA  length = 447
FEATURE                 Location/Qualifiers
misc_feature            1..447
```

```
                          note = Description of Artificial Sequence: Synthetic
                           polynucleotide
source                    1..447
                          mol_type = other DNA
                          organism = synthetic construct
SEQUENCE: 441
atgtatgaaa gctttattga gtcactgcca ttccttaaat ctttggagtt ttctgcacgc  60
ctgaaagtag tagatgtgat aggcaccaaa gtatacaacg atggagaaca aatcattgct  120
cagggagatt cggctgattc ttttttcatt attgaatctg gagaagtgaa aattactatg  180
aaaagaaagg gtaaatcaga agtggaagag aatggtgcag tagaaatcgc tcgatgctcg  240
cggggacagt actttggaga gcttgccctg gtaactaaca aacctcgagc agcttctgcc  300
cacgccattg ggactgtcaa atgtttagca atggatgtgc aagcatttga aaggcttctg  360
ggaccttgca tggaaattat gaaaaggaac atcgctacct atgaagaaca gttagttgcc  420
ctgtatggaa cgaacatgga tattgta                                      447

SEQ ID NO: 442            moltype = AA  length = 149
FEATURE                   Location/Qualifiers
REGION                    1..149
                          note = Description of Artificial Sequence: Synthetic
                           polypeptide
source                    1..149
                          mol_type = protein
                          organism = synthetic construct
SEQUENCE: 442
MYESFIESLP FLKSLEFSAR LKVVDVIGTK VYNDGEQIIA QGDSADSFFI IESGEVKITM  60
KRKGKSEVEE NGAVEIARCS RGQYFGELAL VTNKPRAASA HAIGTVKCLA MDVQAFERLL  120
GPCMEIMKRN IATYEEQLVA LYGTNMDIV                                    149

SEQ ID NO: 443            moltype = DNA  length = 615
FEATURE                   Location/Qualifiers
misc_feature              1..615
                          note = Description of Artificial Sequence: Synthetic
                           polynucleotide
source                    1..615
                          mol_type = other DNA
                          organism = synthetic construct
SEQUENCE: 443
atgacagccg gctacaacct ggaccaagtc cttgagcagg gcggtgtgtc cagtttgttt  60
cagaatctcg ggtgtgtccgt aactccgatc caaaggattg tcctgagcgg tgaaaacggc  120
ctgaagatcg acatccatgt catcatcccg tatgaaggtc tgagcggcga tcagatgggc  180
cagatcgaaa aaatttttaa ggtggtgtac cctgtggatg atcatcactt taaggtgatt  240
ctgcactatg gcacactggt aatcgacggg gttacgccga acatgatcga ctatttcgga  300
cggccgtatg aaggcatcgc cgtgttcgac ggcaaaaaga tcactgtaac cgggaccctg  360
tggaacggca acaaaattat cgacgagcgc ctgatcaacc ccgacggctc cctgctgttc  420
cgcgtaacca tcaacggagt gaccggctgg cggctgtgcg agcgcatttt ggcgggaagt  480
tctggtggag gaagttctgg tggagagcct actactgaga acttgtactt ccagagcgat  540
aacggaagtt ctggtggagg aagttctggt ggaatggtgt ttacactcga agatttcgta  600
ggggactggc ggcag                                                   615

SEQ ID NO: 444            moltype = AA  length = 205
FEATURE                   Location/Qualifiers
REGION                    1..205
                          note = Description of Artificial Sequence: Synthetic
                           polypeptide
source                    1..205
                          mol_type = protein
                          organism = synthetic construct
SEQUENCE: 444
MTAGYNLDQV LEQGGVSSLF QNLGVSVTPI QRIVLSGENG LKIDIHVIIP YEGLSGDQMG  60
QIEKIFKVVY PVDDHHFKVI LHYGTLVIDG VTPNMIDYFG RPYEGIAVFD GKKITVTGTL  120
WNGNKIIDER LINPDGSLLF RVTINGVTGW RLCERILAGS SGGGSSGGEP TTENLYFQSD  180
NGSSGGGSSG GMVFTLEDFV GDWRQ                                        205

SEQ ID NO: 445            moltype = DNA  length = 615
FEATURE                   Location/Qualifiers
misc_feature              1..615
                          note = Description of Artificial Sequence: Synthetic
                           polynucleotide
source                    1..615
                          mol_type = other DNA
                          organism = synthetic construct
SEQUENCE: 445
atgcatgtca tcatcccgta tgaaggtctg agcggcgatc agatgggcca gatcgaaaaa  60
atttttaagg tggtgtaccc tgtggatgat catcacttta aggtgattct gcactatggc  120
acactggtaa tcgacggggt tacgccgaac atgatcgact atttcggacg gccgtatgaa  180
ggcatcgccg tgttcgacgg caaaaagatc actgtaaccg ggaccctgtg gaacggcaac  240
aaaattatcg acgagcgcct gatcaacccc gacggctccc tgctgttccg cgtaaccatc  300
aacggagtga ccggctggcg gctgtgcgag cgcattttgg cgggaagttc tggtggagga  360
agttctggtg gagagcctac tactgagaac ttgtacttcc agagcgataa cggaagttct  420
```

```
ggtggaggaa gttctggtgg aatggtgttt acactcgaag atttcgtagg ggactggcgg  480
cagacagccg gctacaacct ggaccaagtc cttgagcagg gcggtgtgtc cagtttgttt  540
cagaatctcg ggtgtccgt aactccgatc caaaggattg tcctgagcgg tgaaaacggc  600
ctgaagatcg acatc                                                    615

SEQ ID NO: 446         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 446
MHVIIPYEGL SGDQMGQIEK IFKVVYPVDD HHFKVILHYG TLVIDGVTPN MIDYFGRPYE  60
GIAVFDGKKI TVTGTLWNGN KIIDERLINP DGSLLFRVTI NGVTGWRLCE RILAGSSGGG  120
SSGGEPTTEN LYFQSDNGSS GGGSSGGMVF TLEDFVGDWR QTAGYNLDQV LEQGGVSSLF  180
QNLGVSVTPI QRIVLSGENG LKIDI                                         205

SEQ ID NO: 447         moltype = DNA  length = 615
FEATURE                Location/Qualifiers
misc_feature           1..615
                       note = Description of Artificial Sequence: Synthetic
                        polynucleotide
source                 1..615
                       mol_type = other DNA
                       organism = synthetic construct
SEQUENCE: 447
atggtaatcg acggggttac gccgaacatg atcgactatt tcggacggcc gtatgaaggc  60
atcgccgtgt tcgacggcaa aaagatcact gtaaccggga ccctgtggaa cggcaacaaa  120
attatcgacg agcgcctgat caaccccgac ggctccctgc tgttccgcgt aaccatcaac  180
ggagtgaccg gctggcggct gtgcgagcgc attttggcgg gaagttctgg tggaggaagt  240
tctggtggag agcctactac tgagaacttg tacttccaga gcgataacgg aagttctggt  300
ggaggaagtt ctggtggaat ggtgtttaca ctcgaagatt tcgtagggga ctggcggcag  360
acagccggct acaacctgga ccaagtcctt gagcagggcg gtgtgtccag tttgtttcag  420
aatctcgggg tgtccgtaac tccgatccaa aggattgtcc tgagcggtga aaacggcctg  480
aagatcgaca tccatgtcat catcccgtat gaaggtctga gcggcgatca gatgggccag  540
atcgaaaaaa tttttaaggt ggtgtaccct gtggatgatc atcactttaa ggtgattctg  600
cactatggca cactg                                                    615

SEQ ID NO: 448         moltype = AA  length = 205
FEATURE                Location/Qualifiers
REGION                 1..205
                       note = Description of Artificial Sequence: Synthetic
                        polypeptide
source                 1..205
                       mol_type = protein
                       organism = synthetic construct
SEQUENCE: 448
MVIDGVTPNM IDYFGRPYEG IAVFDGKKIT VTGTLWNGNK IIDERLINPD GSLLFRVTIN  60
GVTGWRLCER ILAGSSGGGS SGGEPTTENL YFQSDNGSSG GGSSGGMVFT LEDFVGDWRQ  120
TAGYNLDQVL EQGGVSSLFQ NLGVSVTPIQ RIVLSGENGL KIDIHVIIPY EGLSGDQMGQ  180
IEKIFKVVYP VDDHHFKVIL HYGTL                                         205

SEQ ID NO: 449         moltype = DNA  length = 2019
FEATURE                Location/Qualifiers
source                 1..2019
                       mol_type = genomic DNA
                       organism = Homo sapiens
SEQUENCE: 449
atggctgacg ttttcccggg caacgactcc acggcgtctc aggacgtggc caaccgcttc  60
gcccgcaaag gggcgctgag gcagaagaac gtgcacgagg tgaaggacca caaattcatc  120
gcgcgcttct tcaagcagcc caccttctgc agccactgca ccgacttcat ctgggggttt  180
gggaaacaag gcttccagtg ccaagtttgc tgttttgtgg tccacaagag gtgccatgaa  240
tttgttactt tttcttgtcc gggtgcggat aagggacccg acactgatga ccccaggagc  300
aagcacaagt tcaaaatcca cacttacgga agccccacct tctgcgatca ctgtgggtca  360
ctgctctatg gacttatcca tcaagggatg aaatgtgaca cctgcgatat gaacgttcac  420
aagcaatgcg tcatcaatgt ccccagcctc tgcggaatgg atcacactga gaagaggggg  480
cggatttacc taaaggctga ggttgctgat gaaaagctcc atgtcacagt acgagatgca  540
aaaaatctaa tccctatgga tccaaacggg ctttcagatc cttatgtgaa gctgaaactt  600
attcctgatc ccaagaatga aagcaagcaa aaaaccaaaa ccatccgctc cacactaaat  660
ccgcagtgga atgagtcctt tacattcaaa ttgaaacctt cagacaaaga ccgacgactg  720
tctgtagaaa tctgggactg ggatcgaaca acaaggaatg acttcatggg atccctttcc  780
tttggagttt cggagctgat gaagatgccg gccagtggat ggtacaagtt gcttaaccaa  840
gaagaaggtg agtactacaa cgtacccatt ccggaagggg acgaggaagg aaacatggaa  900
ctcaggcaga aattcgagaa agccaaactt ggccctgctg gcaacaaagt catcagtccc  960
tctgaagaca ggaaacaacc ttccaacaac cttgaccgag tgaaactcac ggacttcaat  1020
ttcctcatgg tgttgggaaa ggggagtttt ggaaaggtga tgcttgccga caggaagggc  1080
acagaagaac tgtatgcaat caaaatcctg aagaaggatg tggtgattca ggatgatgac  1140
```

```
gtggagtgca ccatggtaga aaagcgagtc ttggccctgc ttgacaaacc cccgttcttg  1200
acgcagctgc actcctgctt ccagacagtg gatcggctgt acttcgtcat ggaatatgtc  1260
aacggtgggg acctcatgta ccacattcag caagtaggaa aatttaagga accacaagca  1320
gtattctatg cggcagagat ttccatcgga ttgttctttc ttcataaaag aggaatcatt  1380
tatagggatc tgaagttaga taacgtcatg ttggattcag aaggacatat caaaattgct  1440
gactttggga tgtgcaagga acacatgatg gatggagtca cgaccaggac cttctgtggg  1500
actccagatt atatcgcccc agagataatc gcttatcagc cgtatggaaa atctgtggac  1560
tggtgggcct atggcgtcct gttgtatgaa atgcttgccg ggcagcctcc atttgatggt  1620
gaagatgaag acgagctatt tcagtctatc atggagcaca acgtttccta tccaaaatcc  1680
ttgtccaagg aggctgtttc tatctgcaaa ggactgatga ccaaacaccc agccaagcgg  1740
ctgggctgtg ggcctgaggg ggagagggac gtgagagagc atgccttctt ccggaggatc  1800
gactgggaaa aactggagaa cagggagatc cagccaccat tcaagcccaa agtgtgtggc  1860
aaaggagcag agaactttga caagttcttc acacgaggac agcccgtctt aacaccacct  1920
gatcagctgg ttattgctaa catagaccag tctgattttg aagggttctc gtatgtcaac  1980
ccccagtttg tgcaccccat cttacagagt gcagtagtt                         2019
```

```
SEQ ID NO: 450         moltype = AA  length = 673
FEATURE                Location/Qualifiers
source                 1..673
                       mol_type = protein
                       organism = Homo sapiens
SEQUENCE: 450
MADVFPGNDS TASQDVANRF ARKGALRQKN VHEVKDHKFI ARFFKQPTFC SHCTDFIWGF  60
GKQGFQCQVC CFVVHKRCHE FVTFSCPGAD KGPDTDDPRS KHKFKIHTYG SPTFCDHCGS  120
LLYGLIHQGM KCDTCDMNVH KQCVINVPSL CGMDHTEKRG RIYLKAEVAD EKLHVTVRDA  180
KNLIPMDPNG LSDPYVKLKL IPDPKNESKQ KTKTIRSTLN PQWNESFTFK LKPSDKDRRL  240
SVEIWDWDRT TRNDFMGSLS FGVSELMKMP ASGWYKLLNQ EEGEYYNVPI PEGDEEGNME  300
LRQKFEKAKL GPAGNKVISP SEDRKQPSNN LDRVKLTDFN FLMVLGKGSF GKVMLADRKG  360
TEELYAIKIL KKDVVIQDDD VECTMVEKRV LALLDKPPFL TQLHSCFQTV DRLYFVMEYV  420
NGGDLMYHIQ QVGKFKEPQA VFYAAEISIG LFFLHKRGII YRDLKLDNVM LDSEGHIKIA  480
DFGMCKEHMM DGVTTRTFCG TPDYIAPEII AYQPYGKSVD WWAYGVLLYE MLAGQPPFDG  540
EDEDELFQSI MEHNVSYPKS LSKEAVSICK GLMTKHPAKR LGCGPEGERD VREHAFFRRI  600
DWEKLENREI QPPFKPKVCG KGAENFDKFF TRGQPVLTPP DQLVIANIDQ SDFEGFSYVN  660
PQFVHPILQS AVV                                                     673
```

```
SEQ ID NO: 451         moltype = DNA  length = 2334
FEATURE                Location/Qualifiers
source                 1..2334
                       mol_type = genomic DNA
                       organism = Homo sapiens
SEQUENCE: 451
atggactcca aagaatcatt aactcctggt agagaagaaa accccagcag tgtgcttgct  60
caggagaggg gagatgtgat ggacttctat aaaaccctaa gaggaggagc tactgtgaag  120
gtttctgcgt cttcaccctc actggctgtc gcttctcaat cagactccaa gcagcgaaga  180
cttttggttg attttccaaa aggctcagta agcaatgcgc agcagccaga tctgtccaaa  240
gcagtttcac tctcaatggg actgtatatg ggagagacag aaacaaaagt gatgggaaat  300
gacctgggat tcccacagca gggccaaatc agcctttcct cgggggaaac agacttaaag  360
cttttggaag aaagcattgc aaacctcaat aggtcgacca gtgttccaga gaaccccaag  420
agttcagcat ccactgctgt gtctgctgcc cccacagaga aggagtttcc aaaaactcac  480
tctgatgtat cttcagaaca gcaacatttg aagggccaga ctggcaccaa cggtggcaat  540
gtgaaattgt ataccacaga ccaaagcacc tttgacattt tgcaggattt ggagttttct  600
tctgggtccc caggtaaaga gacgaatgag agtccttgga gatcagacct gttgatagat  660
gaaaactgtt tgctttctcc tctggcggga gaagacgatt cattcctttt ggaaggaaac  720
tcgaatgagg actgcaagcc tctcatttta ccggacacta aacccaaaat taaggataat  780
ggagatctgg ttttgtcaag ccccagtaat gtaacactgc cccaagtgaa aacagaaaaa  840
gaagatttca tcgaactctg caccccctggg gtaattaagc aagagaaact gggcacagtt  900
tactgtcagg caagctttcc tggagcaaat ataattggta ataaaatgtc tgccatttct  960
gttcatggtg tgagtacctc tggaggacag atgtaccact atgacatgaa tacagcatcc  1020
ctttctcaac agcaggatca gaagcctatt tttaatgtca ttccaccaat tcccgttggt  1080
tccgaaaatt ggaataggtg ccaaggatct ggagatgaca acttgacttc tctggggact  1140
ctgaacttcc ctggtcgaac agttttttct aatggctatt caagccccag catgagacca  1200
gatgtaagct ctcctccatc cagctcctca acagcaacaa caggaccacc tcccaaactc  1260
tgcctggtgt gctctgatga agcttcagga tgtcattatg gagtcttaac ttgtggaagc  1320
tgtaaagttt tcttcaaaag agcagtggaa ggacagcaca attacctatg tgctggaagg  1380
aatgattgca tcatcgataa aattcgaaga aaaaactgcc cagcatgccg ctatcgaaaa  1440
tgtcttcagg ctggaatgaa cctggaagct cgaaaaacaa agaaaaaaat aaaaggaatt  1500
cagcaggcca ctacaggagt ctcacaagaa acctctgaaa atcctggtaa caaaacaata  1560
gttcctgcaa cgttaccaca actcacccct accctggtgt cactgttgga ggttattgaa  1620
cctgaagtgt tatatgcagg atatgatagc tctgttccag actcaacttg gaggatcatg  1680
actacgctca acatgttagg agggcggcaa gtgattgcag cagtgaaatg ggcaaaggca  1740
ataccaggtt tcaggaactt acacctggat gaccaaatga ccctactgca gtactcctgg  1800
atgtttctta tggcatttgc tctggggtgg agatcatata gacaatcaag tgcaaacctg  1860
ctgtgttttg ctcctgatct gattattaat gagcagagaa tgactctacc ctgcatgtac  1920
gaccaatgta aacacatgct gtatgtttcc tctgagttac acaggcttca ggtatcttat  1980
gaagagtatc tctgtatgaa aaccttactg cttctctctt cagttcctaa ggacggtctg  2040
aagagccaag agctatttga tgaaattaga atgacctaca tcaaagagct aggaaaagcc  2100
attgtcaaga gggaaggaaa ctccagccag aactggcagc ggttttatca actgacaaaa  2160
ctcttggatt ctatgcatga agtggttgaa aatctcctta actattgctt ccaaacattt  2220
ttggataaga ccatgagtat tgaattcccc gagatgttag ctgaaatcat caccaatcag  2280
```

```
ataccaaaat attcaaatgg aaatatcaaa aaacttctgt ttcatcaaaa ggtt        2334

SEQ ID NO: 452         moltype = AA  length = 778
FEATURE                Location/Qualifiers
source                 1..778
                       mol_type = protein
                       organism = Homo sapiens
SEQUENCE: 452
MDSKESLTPG REENPSSVLA QERGDVMDFY KTLRGGATVK VSASSPSLAV ASQSDSKQRR  60
LLVDFPKGSV SNAQQPDLSK AVSLSMGLYM GETETKVMGN DLGFPQQGQI SLSSGETDLK  120
LLEESIANLN RSTSVPENPK SSASTAVSAA PTEKEFPKTH SDVSSEQQHL KGQTGTNGGN  180
VKLYTTDQST FDILQDLEFS SGSPGKETNE SPWRSDLLID ENCLLSPLAG EDDSFLLEGN  240
SNEDCKPLIL PDTKPKIKDN GDLVLSSPSN VTLPQVKTEK EDFIELCTPG VIKQEKLGTV  300
YCQASFPGAN IIGNKMSAIS VHGVSTSGGQ MYHYDMNTAS LSQQQDQKPI FNVIPPIPVG  360
SENWNRCQGS GDDNLTSLGT LNFPGRTVFS NGYSSPSMRP DVSSPPSSSS TATTGPPPKL  420
CLVCSDEASG CHYGVLTCGS CKVFFKRAVE GQHNYLCAGR NDCIIDKIRR KNCPACRYRK  480
CLQAGMNLEA RKTKKKIKGI QQATTGVSQE TSENPGNKTI VPATLPQLTP TLVSLLEVIE  540
PEVLYAGYDS SVPDSTWRIM TTLNMLGGRQ VIAAVKWAKA IPGFRNLHLD DQMTLLQYSW  600
MFLMAFALGW RSYRQSSANL LCFAPDLIIN EQRMTLPCMY DQCKHMLYVS SELHRLQVSY  660
EEYLCMKTLL LLSSVPKDGL KSQELFDEIR MTYIKELGKA IVKREGNSSQ NWQRFYQLTK  720
LLDSMHEVVE NLLNYCFQTF LDKTMSIEFP EMLAEIITNQ IPKYSNGNIK KLLFHQKV    778

SEQ ID NO: 453         moltype = DNA  length = 54
FEATURE                Location/Qualifiers
misc_feature           1..54
                       note = Description of Artificial Sequence: Synthetic
                        oligonucleotide
source                 1..54
                       mol_type = other DNA
                       organism = synthetic construct
SEQUENCE: 453
ggtggttcag gtggtggcgg gagcggtgga gggagcagcg gtggagcgat cgcc        54

SEQ ID NO: 454         moltype = AA  length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 454
GGSGGGGSGG GSSGGAIA                                                18

SEQ ID NO: 455         moltype = DNA  length = 51
FEATURE                Location/Qualifiers
misc_feature           1..51
                       note = Description of Artificial Sequence: Synthetic
                        oligonucleotide
source                 1..51
                       mol_type = other DNA
                       organism = synthetic construct
SEQUENCE: 455
tctctcggtg gttcaggtgg tggcgggagc ggtggaggga gcagcggtgg a           51

SEQ ID NO: 456         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 456
SLGGSGGGGS GGGSSGG                                                 17

SEQ ID NO: 457         moltype = DNA  length = 11
FEATURE                Location/Qualifiers
misc_feature           1..11
                       note = Description of Artificial Sequence: Synthetic
                        oligonucleotide
source                 1..11
                       mol_type = other DNA
                       organism = synthetic construct
SEQUENCE: 457
gctcgagcgg a                                                       11

SEQ ID NO: 458         moltype = AA  length = 4
FEATURE                Location/Qualifiers
REGION                 1..4
                       note = Description of Artificial Sequence: Synthetic peptide
```

```
source                  1..4
                        mol_type = protein
                        organism = synthetic construct
SEQUENCE: 458
GSSG                                                                4

SEQ ID NO: 459          moltype = DNA  length = 1080
FEATURE                 Location/Qualifiers
source                  1..1080
                        mol_type = genomic DNA
                        organism = Homo sapiens
SEQUENCE: 459
atgattctca actcttctac tgaagatggt attaaaagaa tccaagatga ttgtcccaaa  60
gctggaaggc ataattacat atttgtcatg attcctactt tatacagtat catctttgtg  120
gtgggaatat ttggaaacag cttggtggtg atagtcattt acttttatat gaagctgaag  180
actgtggcca gtgtttttct tttgaattta gcactggctg acttatgctt tttactgact  240
ttgccactat gggctgtcta cacagctatg gaataccgct ggccctttgg caattaccta  300
tgtaagattg cttcagccag cgtcagtttc aacctgtacg ctagtgtgtt tctactcacg  360
tgtctcagca ttgatcgata cctggctatt gttcacccaa tgaagtcccg ccttcgacgc  420
acaatgcttg tagccaaagt cacctgcatc atcatttggc tgctggcagg cttggccagt  480
ttgccagcta taatccatcg aaatgtattt ttcattgaga acaccaatat tacagtttgt  540
gctttccatt atgagtccca aaattcaacc cttccgatag ggctgggcct gaccaaaaat  600
atactgggtt tcctgtttcc ttttctgatc attcttacaa gttatactct tatttggaag  660
gccctaaaga aggcttatga aattcagaag aacaaaccaa gaaatgatga tatttttaag  720
ataattatgg caattgtgct tttctttttc ttttcctgga ttccccacca aatattcact  780
tttctggatg tattgattca actaggcatc atacgtgact gtagaattgc agatattgtg  840
gacacggcca tgcctatcac catttgtata gcttatttta acaattgcct gaatcctctt  900
ttttatggct ttctggggaa aaaatttaaa agatattttc tccagcttct aaaatatatt  960
cccccaaaag ccaaatccca ctcaaacctt tcaacaaaaa tgagcacgct ttcctaccgc  1020
ccctcagata atgtaagctc atccaccaag aagcctgcac catgttttga ggttgagtga  1080

SEQ ID NO: 460          moltype = AA  length = 359
FEATURE                 Location/Qualifiers
source                  1..359
                        mol_type = protein
                        organism = Homo sapiens
SEQUENCE: 460
MILNSSTEDG IKRIQDDCPK AGRHNYIFVM IPTLYSIIFV VGIFGNSLVV IVIYFYMKLK  60
TVASVFLLNL ALADLCFLLT LPLWAVYTAM EYRWPFGNYL CKIASASVSF NLYASVFLLT  120
CLSIDRYLAI VHPMKSRLRR TMLVAKVTCI IIWLLAGLAS LPAIIHRNVF FIENTNITVC  180
AFHYESQNST LPIGLGLTKN ILGFLFPFLI ILTSYTLIWK ALKKAYEIQK NKPRNDDIFK  240
IIMAIVLFFF FSWIPHQIFT FLDVLIQLGI IRDCRIADIV DTAMPITICI AYFNNCLNPL  300
FYGFLGKKFK RYFLQLLKYI PPKAKSHSNL STKMSTLSYR PSDNVSSSTK KPAPCFEVE   359

SEQ ID NO: 461          moltype = DNA  length = 87
FEATURE                 Location/Qualifiers
source                  1..87
                        mol_type = genomic DNA
                        organism = Homo sapiens
SEQUENCE: 461
atgaactcct tctccacaag cgccttcggt ccagttgcct tctccctggg gctgctcctg  60
gtgttgcctg ctgccttccc tgcccca                                       87

SEQ ID NO: 462          moltype = AA  length = 29
FEATURE                 Location/Qualifiers
source                  1..29
                        mol_type = protein
                        organism = Homo sapiens
SEQUENCE: 462
MNSFSTSAFG PVAFSLGLLL VLPAAFPAP                                     29

SEQ ID NO: 463          moltype = DNA  length = 597
FEATURE                 Location/Qualifiers
misc_feature            1..597
                        note = Description of Artificial Sequence: Synthetic
                         polynucleotide
source                  1..597
                        mol_type = other DNA
                        organism = synthetic construct
SEQUENCE: 463
atgaactcct tctccacaag cgccttcggt ccagttgcct tctccctggg gctgctcctg  60
gtgttgcctg ctgccttccc tgccccagtg tttacactcg aagatttcgt aggggactgg  120
cggcagacag ccggctacaa cctggaccaa gtccttgagc agggcggtgt gtccagtttg  180
tttcagaatc tcggggtgtc cgtaactccg atccaaagga ttgtcctgag cggtgaaaac  240
ggcctgaaga tcgacatcca tgtcatcatc ccgtatgaag gtctgagcgg cgatcagatg  300
ggccagatcg aaaaaatttt taaggtggtg taccctgtgg atgatcatca ctttaaggtg  360
attctgcact atggcacact ggtaatcgac ggggttacgc cgaacatgat cgactatttc  420
ggacggccgt atgaaggcat cgccgtgttc gacggcaaaa agatcactgt aaccgggacc  480
ctgtggaacg gcaacaaaat tatcgacgag cgcctgatca accccgacgg ctccctgctg  540
```

ttccgcgtaa ccatcaacgg agtgaccggc tggcggctgt gcgagcgcat tttggcg 597

SEQ ID NO: 464 moltype = AA length = 199
FEATURE Location/Qualifiers
REGION 1..199
note = Description of Artificial Sequence: Synthetic polypeptide
source 1..199
mol_type = protein
organism = synthetic construct
SEQUENCE: 464
MNSFSTSAFG PVAFSLGLLL VLPAAFPAPV FTLEDFVGDW RQTAGYNLDQ VLEQGGVSSL 60
FQNLGVSVTP IQRIVLSGEN GLKIDIHVII PYEGLSGDQM GQIEKIFKVV YPVDDHHFKV 120
ILHYGTLVID GVTPNMIDYF GRPYEGIAVF DGKKITVTGT LWNGNKIIDE RLINPDGSLL 180
FRVTINGVTG WRLCERILA 199

SEQ ID NO: 465 moltype = DNA length = 591
FEATURE Location/Qualifiers
misc_feature 1..591
note = Description of Artificial Sequence: Synthetic polynucleotide
source 1..591
mol_type = other DNA
organism = synthetic construct
SEQUENCE: 465
atggcttact ccacactgtt catcattgct ctcacagccg tcgtaacaca agcctcctcc 60
acacagaaaa gcaacctgac agtgtttaca ctcgaagatt tcgtagggga ctggcggcag 120
acagccggct acaacctgga ccaagtcctt gagcagggcg gtgtgtccag tttgtttcag 180
aatctcgggg tgtccgtaac tccgatccaa aggattgtcc tgagcggtga aaacggcctg 240
aagatcgaca tccatgtcat catcccgtat gaaggtctga gcggcgatca gatgggccag 300
atcgaaaaaa tttttaaggt ggtgtaccct gtggatgatc atcactttaa ggtgattctg 360
cactatggca cactggtaat cgacggggtt acgccgaaca tgatcgacta tttcggacgg 420
ccgtatgaag gcatcgccgt gttcgacggc aaaaagatca ctgtaaccgg gaccctgtgg 480
aacggcaaca aaattatcga cgagcgcctg atcaaccccg acggctccct gctgttccgc 540
gtaaccatca acggagtgac cggctggcgg ctgtgcgagc gcattttggc g 591

SEQ ID NO: 466 moltype = AA length = 197
FEATURE Location/Qualifiers
REGION 1..197
note = Description of Artificial Sequence: Synthetic polypeptide
source 1..197
mol_type = protein
organism = synthetic construct
SEQUENCE: 466
MAYSTLFIIA LTAVVTQASS TQKSNLTVFT LEDFVGDWRQ TAGYNLDQVL EQGGVSSLFQ 60
NLGVSVTPIQ RIVLSGENGL KIDIHVIIPY EGLSGDQMGQ IEKIFKVVYP VDDHHFKVIL 120
HYGTLVIDGV TPNMIDYFGR PYEGIAVFDG KKITVTGTLW NGNKIIDERL INPDGSLLFR 180
VTINGVTGWR LCERILA 197

SEQ ID NO: 467 moltype = DNA length = 1023
FEATURE Location/Qualifiers
misc_feature 1..1023
note = Description of Artificial Sequence: Synthetic polynucleotide
source 1..1023
mol_type = other DNA
organism = synthetic construct
SEQUENCE: 467
atgttcgttg gggactggcg acagacagcc ggctacaacc tggaccaagt ccttgaacag 60
ggaggtgtgt ccagtttgtt tcagaatctc ggggtgtccg taactccgat ccaaaggatt 120
gtcctgagcg gtgaaaatgg gctgaagatc gacatccatg tcatcatccc gtatgaaggt 180
ctgagcggcg accaaatggg ccagatcgaa aaaattttta aggtggtgta ccctgtggat 240
gatcatcact ttaaggtgat cctgcactat ggcacactgg taatcgacgg ggttacgccg 300
aacatgatcg actatttcgg acggccgtat gaaggcatcg ccgtgttcga cggcaaaaag 360
atcactgtaa cagggaccct gtggaacggc aacaaaatta tcgacgagcg cctgatcaac 420
cccgacggct ccctgctgtt ccgagtaacc atcaacggag tgaccggctg gcggctgtgc 480
gaacgcattc tggctagctc aagcggaggt tcaggcggtt ccggaatgta tgaaagcttt 540
attgagtcac tgccattcct taaatctttg gagttttctg cacgcctgaa agtagtagat 600
gtgataggca ccaaagtata caacgatgga gaacaaatca ttgctcaggg agattcggct 660
gattcttttt tcattattga atctggagaa gtgaaaatta ctatgaaaag aaagggtaaa 720
tcagaagtgg aagagaatgg tgcagtagaa atcgctcgat gctcgcgggg acagtacttt 780
ggagagcttg ccctggtaac taacaaacct cgagcagctt ctgcccacgc cattgggact 840
gtcaaatgtt tagcaatgga tgtgcaagca tttgaaaggc ttctgggacc ttgcatggaa 900
attatgaaaa ggaacatcgc tacctatgaa gaacagttag ttgccctgta tggaacgaac 960
atggatattg tagggtcagg tggatctgga ggtagctctt ctatggtctt cacactcgaa 1020
gat 1023

SEQ ID NO: 468 moltype = AA length = 341

```
FEATURE               Location/Qualifiers
REGION                1..341
                      note = Description of Artificial Sequence: Synthetic
                       polypeptide
source                1..341
                      mol_type = protein
                      organism = synthetic construct
SEQUENCE: 468
MFVGDWRQTA GYNLDQVLEQ GGVSSLFQNL GVSVTPIQRI VLSGENGLKI DIHVIIPYEG  60
LSGDQMGQIE KIFKVVYPVD DHHFKVILHY GTLVIDGVTP NMIDYFGRPY EGIAVFDGKK  120
ITVTGTLWNG NKIIDERLIN PDGSLLFRVT INGVTGWRLC ERILASSSGG SGGSGMYESF  180
IESLPFLKSL EFSARLKVVD VIGTKVYNDG EQIIAQGDSA DSFFIIESGE VKITMKRKGK  240
SEVEENGAVE IARCSRGQYF GELALVTNKP RAASAHAIGT VKCLAMDVQA FERLLGPCME  300
IMKRNIATYE EQLVALYGTN MDIVGSGGSG GSSSMVFTLE D                     341

SEQ ID NO: 469        moltype = DNA  length = 1023
FEATURE               Location/Qualifiers
misc_feature          1..1023
                      note = Description of Artificial Sequence: Synthetic
                       polynucleotide
source                1..1023
                      mol_type = other DNA
                      organism = synthetic construct
SEQUENCE: 469
atgcagacag ccggctacaa cctggaccaa gtccttgaac agggaggtgt gtccagtttg  60
tttcagaatc tcggggtgtc cgtaactccg atccaaagga ttgtcctgag cggtgaaaat  120
gggctgaaga tcgacatcca tgtcatcatc ccgtatgaag gtctgagcgg cgaccaaatg  180
ggccagatcg aaaaaatttt taaggtggtg taccctgtgg atgatcatca ctttaaggtg  240
atcctgcact atggcacact ggtaatcgac ggggttacgc cgaacatgat cgactatttc  300
ggacggccgt atgaaggcat cgccgtgttc gacggcaaaa agatcactgt aacagggacc  360
ctgtggaacg gcaacaaaat tatcgacgag cgcctgatca accccgacgg ctccctgctg  420
ttccgagtaa ccatcaacgg agtgaccggc tggcggctgt gcgaacgcat tctggctagc  480
tcaagcggag gttcaggcgg ttccggaatg tatgaaagct ttattgagtc actgccattc  540
cttaaatctt tggagttttc tgcacgcctg aaagtagtag atgtgatagg caccaaagta  600
tacaacgatg gagaacaaat cattgctcag ggagattcgg ctgattcttt tttcattatt  660
gaatctggag aagtgaaaat tactatgaaa agaaagggta aatcagaagt ggaagagaat  720
ggtgcagtag aaatcgctcg atgctcgcgg ggacagtact ttggagagct tgccctggta  780
actaacaaac ctcgagcagc ttctgcccac gccattggga ctgtcaaatg tttagcaatg  840
gatgtgcaag catttgaaag gcttctggga ccttgcatgg aaattatgaa aaggaacatc  900
gctacctatg aagaacagtt agttgccctg tatggaacga acatggatat tgtagggtca  960
ggtggatctg gaggtagctc ttctatggtc ttcacactcg aagatttcgt tggggactgg  1020
cga                                                               1023

SEQ ID NO: 470        moltype = AA  length = 341
FEATURE               Location/Qualifiers
REGION                1..341
                      note = Description of Artificial Sequence: Synthetic
                       polypeptide
source                1..341
                      mol_type = protein
                      organism = synthetic construct
SEQUENCE: 470
MQTAGYNLDQ VLEQGGVSSL FQNLGVSVTP IQRIVLSGEN GLKIDIHVII PYEGLSGDQM  60
GQIEKIFKVV YPVDDHHFKV ILHYGTLVID GVTPNMIDYF GRPYEGIAVF DGKKITVTGT  120
LWNGNKIIDE RLINPDGSLL FRVTINGVTG WRLCERILAS SSGGSGGSGM YESFIESLPF  180
LKSLEFSARL KVVDVIGTKV YNDGEQIIAQ GDSADSFFII ESGEVKITMK RKGKSEVEEN  240
GAVEIARCSR GQYFGELALV TNKPRAASAH AIGTVKCLAM DVQAFERLLG PCMEIMKRNI  300
ATYEEQLVAL YGTNMDIVGS GGSGGSSSMV FTLEDFVGDW R                     341

SEQ ID NO: 471        moltype = DNA  length = 1023
FEATURE               Location/Qualifiers
misc_feature          1..1023
                      note = Description of Artificial Sequence: Synthetic
                       polynucleotide
source                1..1023
                      mol_type = other DNA
                      organism = synthetic construct
SEQUENCE: 471
atgggtgaaa atgggctgaa gatcgacatc catgtcatca tcccgtatga aggtctgagc  60
ggcgaccaaa tgggccagat cgaaaaaatt tttaaggtgg tgtaccctgt ggatgatcat  120
cactttaagg tgatcctgca ctatggcaca ctggtaatcg acggggttac gccgaacatg  180
atcgactatt tcggacggcc gtatgaaggc atcgccgtgt tcgacggcaa aaagatcact  240
gtaacaggga ccctgtggaa cggcaacaaa attatcgacg agcgcctgat caaccccgac  300
ggctccctgc tgttccgagt aaccatcaac ggagtgaccg gctggcggct gtgcgaacgc  360
attctggcta gctcaagcgg aggttcaggc ggttccggaa tgtatgaaag ctttattgag  420
tcactgccat tccttaaatc tttggagttt tctgcacgcc tgaaagtagt agatgtgata  480
ggcaccaaag tatacaacga tggagaacaa atcattgctc agggagattc ggctgattct  540
tttttcatta ttgaatctgg agaagtgaaa attactatga aaagaaaggg taaatcagaa  600
gtggaagaga atggtgcagt agaaatcgct cgatgctcgc ggggacagta ctttggagag  660
```

-continued

```
cttgccctgg taactaacaa acctcgagca gcttctgccc acgccattgg gactgtcaaa  720
tgtttagcaa tggatgtgca agcatttgaa aggcttctgg gaccttgcat ggaaattatg  780
aaaaggaaca tcgctaccta tgaagaacag ttagttgccc tgtatggaac gaacatggat  840
attgtagggt caggtggatc tggaggtagc tcttctatgg tcttcacact cgaagatttc  900
gttggggact ggcgacagac agccggctac aacctggacc aagtccttga acagggaggt  960
gtgtccagtt tgtttcagaa tctcggggtg tccgtaactc cgatccaaag gattgtcctg  1020
agc                                                                1023

SEQ ID NO: 472         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 472
MGENGLKIDI HVIIPYEGLS GDQMGQIEKI FKVVYPVDDH HFKVILHYGT LVIDGVTPNM  60
IDYFGRPYEG IAVFDGKKIT VTGTLWNGNK IIDERLINPD GSLLFRVTIN GVTGWRLCER  120
ILASSSGGSG GSGMYESFIE SLPFLKSLEF SARLKVVDVI GTKVYNDGEQ IIAQGDSADS  180
FFIIESGEVK ITMKRKGKSE VEENGAVEIA RCSRGQYFGE LALVTNKPRA ASAHAIGTVK  240
CLAMDVQAFE RLLGPCMEIM KRNIATYEEQ LVALYGTNMD IVGSGGSGGS SSMVFTLEDF  300
VGDWRQTAGY NLDQVLEQGG VSSLFQNLGV SVTPIQRIVL S                      341

SEQ ID NO: 473         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 473
atgctgaaga tcgacatcca tgtcatcatc ccgtatgaag gtctgagcgg cgaccaaatg  60
ggccagatcg aaaaaatttt taaggtggtg taccctgtgg atgatcatca ctttaaggtg  120
atcctgcact atggcacact ggtaatcgac ggggttacgc cgaacatgat cgactatttc  180
ggacggccgt atgaaggcat cgccgtgttc gacggcaaaa agatcactgt aacagggacc  240
ctgtggaacg gcaacaaaat tatcgacgag cgcctgatca accccgacgg ctccctgctg  300
ttccgagtaa ccatcaacgg agtgaccggc tggcggctgt gcgaacgcat tctggctagc  360
tcaagcggag gttcaggcgg ttccggaatg tatgaaagct ttattgagtc actgccattc  420
cttaaatctt tggagttttc tgcacgcctg aaagtagtag atgtgatagg caccaaagta  480
tacaacgatg gagaacaaat cattgctcag ggagattcgg ctgattcttt tttcattatt  540
gaatctggag aagtgaaaat tactatgaaa agaaagggta aatcagaagt ggaagagaat  600
ggtgcagtag aaatcgctcg atgctcgcgg ggacagtact ttggagagct tgccctggta  660
actaacaaac ctcgagcagc ttctgcccac gccattggga ctgtcaaatg tttagcaatg  720
gatgtgcaag catttgaaag gcttctggga ccttgcatgg aaattatgaa aaggaacatc  780
gctacctatg aagaacagtt agttgccctg tatggaacga acatggatat tgtagggtca  840
ggtggatctg gaggtagctc ttctatggtc ttcacactcg aagatttcgt tggggactgg  900
cgacagacag ccggctacaa cctggaccaa gtccttgaac agggaggtgt gtccagtttg  960
tttcagaatc tcggggtgtc cgtaactccg atccaaagga ttgtcctgag cggtgaaaat  1020
ggg                                                                1023

SEQ ID NO: 474         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 474
MLKIDIHVII PYEGLSGDQM GQIEKIFKVV YPVDDHHFKV ILHYGTLVID GVTPNMIDYF  60
GRPYEGIAVF DGKKITVTGT LWNGNKIIDE RLINPDGSLL FRVTINGVTG WRLCERILAS  120
SSGGSGGSGM YESFIESLPF LKSLEFSARL KVVDVIGTKV YNDGEQIIAQ GDSADSFFII  180
ESGEVKITMK RKGKSEVEEN GAVEIARCSR GQYFGELALV TNKPRAASAH AIGTVKCLAM  240
DVQAFERLLG PCMEIMKRNI ATYEEQLVAL YGTNMDIVGS GGSGGSSSMV FTLEDFVGDW  300
RQTAGYNLDQ VLEQGGVSSL FQNLGVSVTP IQRIVLSGEN G                      341

SEQ ID NO: 475         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 475
atggacatcc atgtcatcat cccgtatgaa ggtctgagcg gcgaccaaat gggccagatc  60
gaaaaaattt ttaaggtggt gtaccctgtg gatgatcatc actttaaggt gatcctgcac  120
```

-continued

```
tatggcacac tggtaatcga cggggttacg ccgaacatga tcgactattt cggacggccg  180
tatgaaggca tcgccgtgtt cgacggcaaa aagatcactg taacagggac cctgtggaac  240
ggcaacaaaa ttatcgacga gcgcctgatc aaccccgacg gctccctgct gttccgagta  300
accatcaacg gagtgaccgg ctggcggctg tgcgaacgca ttctggctag ctcaagcgga  360
ggttcaggcg gttccggaat gtatgaaagc tttattgagt cactgccatt ccttaaatct  420
ttggagtttt ctgcacgcct gaaagtagta gatgtgatag gcaccaaagt atacaacgat  480
ggagaacaaa tcattgctca gggagattcg gctgattctt ttttcattat tgaatctgga  540
gaagtgaaaa ttactatgaa aagaaagggt aaatcagaag tggaagagaa tggtgcagta  600
gaaatcgctc gatgctcgcg gggacagtac tttggagagc ttgccctggt aactaacaaa  660
cctcgagcag cttctgccca cgccattggg actgtcaaat gtttagcaat ggatgtgcaa  720
gcatttgaaa ggcttctggg accttgcatg gaaattatga aaaggaacat cgctacctat  780
gaagaacagt tagttgccct gtatggaacg aacatggata ttgtagggtc aggtggatct  840
ggaggtagct cttctatggt cttcacactc gaagatttcg ttggggactg gcgacagaca  900
gccggctaca acctggacca agtccttgaa cagggaggtg tgtccagttt gtttcagaat  960
ctcggggtgt ccgtaactcc gatccaaagg attgtcctga gcggtgaaaa tgggctgaag  1020
atc                                                                1023
```

```
SEQ ID NO: 476         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 476
MDIHVIIPYE GLSGDQMGQI EKIFKVVYPV DDHHFKVILH YGTLVIDGVT PNMIDYFGRP  60
YEGIAVFDGK KITVTGTLWN GNKIIDERLI NPDGSLLFRV TINGVTGWRL CERILASSSG  120
GSGGSGMYES FIESLPFLKS LEFSARLKVV DVIGTKVYND GEQIIAQGDS ADSFFIIESG  180
EVKITMKRKG KSEVEENGAV EIARCSRGQY FGELALVTNK PRAASAHAIG TVKCLAMDVQ  240
AFERLLGPCM EIMKRNIATY EEQLVALYGT NMDIVGSGGS GGSSSMVFTL EDFVGDWRQT  300
AGYNLDQVLE QGGVSSLFQN LGVSVTPIQR IVLSGENGLK I                     341
```

```
SEQ ID NO: 477         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 477
atggtggatg atcatcactt taaggtgatc ctgcactatg gcacactggt aatcgacggg  60
gttacgccga acatgatcga ctatttcgga cggccgtatg aaggcatcgc cgtgttcgac  120
ggcaaaaaga tcactgtaac agggaccctg tggaacggca acaaaattat cgacgagcgc  180
ctgatcaacc ccgacggctc cctgctgttc cgagtaacca tcaacggagt gaccggctgg  240
cggctgtgcg aacgcattct ggctagctca agcggaggtt caggcggttc cggaatgtat  300
gaaagcttta ttgagtcact gccattcctt aaatctttgg agttttctgc acgcctgaaa  360
gtagtagatg tgataggcac caaagtatac aacgatggag aacaaatcat tgctcaggga  420
gattcggctg attctttttt cattattgaa tctggagaag tgaaaattac tatgaaaaga  480
aagggtaaat cagaagtgga agagaatggt gcagtagaaa tcgctcgatg ctcgcgggga  540
cagtactttg gagagcttgc cctggtaact aacaaacctc gagcagcttc tgcccacgcc  600
attgggactg tcaaatgttt agcaatggat gtgcaagcat ttgaaaggct tctgggacct  660
tgcatggaaa ttatgaaaag gaacatcgct acctatgaag aacagttagt tgccctgtat  720
ggaacgaaca tggatattgt agggtcaggt ggatctggag gtagctcttc tatggtcttc  780
acactcgaag atttcgttgg ggactggcga cagacagccg gctacaacct ggaccaagtc  840
cttgaacagg gaggtgtgtc cagtttgttt cagaatctcg ggtgtccgt aactccgatc  900
caaaggattg tcctgagcgg tgaaaatggg ctgaagatcg acatccatgt catcatcccg  960
tatgaaggtc tgagcggcga ccaaatgggc cagatcgaaa aaatttttaa ggtggtgtac  1020
cct                                                                1023
```

```
SEQ ID NO: 478         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 478
MVDDHHFKVI LHYGTLVIDG VTPNMIDYFG RPYEGIAVFD GKKITVTGTL WNGNKIIDER  60
LINPDGSLLF RVTINGVTGW RLCERILASS SGGSGGSGMY ESFIESLPFL KSLEFSARLK  120
VVDVIGTKVY NDGEQIIAQG DSADSFFIIE SGEVKITMKR KGKSEVEENG AVEIARCSRG  180
QYFGELALVT NKPRAASAHA IGTVKCLAMD VQAFERLLGP CMEIMKRNIA TYEEQLVALY  240
GTNMDIVGSG GSGGSSSMVF TLEDFVGDWR QTAGYNLDQV LEQGGVSSLF QNLGVSVTPI  300
QRIVLSGENG LKIDIHVIIP YEGLSGDQMG QIEKIFKVVY P                     341
```

```
SEQ ID NO: 479         moltype = DNA  length = 1023
FEATURE                Location/Qualifiers
```

```
misc_feature          1..1023
                      note = Description of Artificial Sequence: Synthetic
                       polynucleotide
source                1..1023
                      mol_type = other DNA
                      organism = synthetic construct
SEQUENCE: 479
atggatgatc atcactttaa ggtgatcctg cactatggca cactggtaat cgacggggtt  60
acgccgaaca tgatcgacta tttcggacgg ccgtatgaag gcatcgccgt gttcgacggc  120
aaaaagatca ctgtaacagg gaccctgtgg aacggcaaca aaattatcga cgagcgcctg  180
atcaaccccg acggctccct gctgttccga gtaaccatca acggagtgac cggctggcgg  240
ctgtgcgaac gcattctggc tagctcaagc ggaggttcag gcggttccgg aatgtatgaa  300
agctttattg agtcactgcc attccttaaa tctttggagt tttctgcacg cctgaaagta  360
gtagatgtga taggcaccaa agtatacaac gatggagaac aaatcattgc tcagggagat  420
tcggctgatt ctttttttcat tattgaatct ggagaagtga aaattactat gaaaagaaag  480
ggtaaatcag aagtggaaga gaatggtgca gtagaaatcg ctcgatgctc gcggggacag  540
tactttggag agcttgccct ggtaactaac aaacctcgag cagcttctgc ccacgccatt  600
gggactgtca aatgtttagc aatggatgtg caagcatttg aaaggcttct gggaccttgc  660
atggaaatta tgaaaaggaa catcgctacc tatgaagaac agttagttgc cctgtatgga  720
acgaacatgg atattgtagg gtcaggtgga tctggaggta gctcttctat ggtcttcaca  780
ctcgaagatt tcgttgggga ctggcgacag acagccggct acaacctgga ccaagtcctt  840
gaacagggag gtgtgtccag tttgtttcag aatctcgggg tgtccgtaac tccgatccaa  900
aggattgtcc tgagcggtga aaatgggctg aagatcgaca tccatgtcat catcccgtat  960
gaaggtctga gcggcgacca aatgggccag atcgaaaaaa tttttaaggt ggtgtaccct  1020
gtg                                                                1023

SEQ ID NO: 480        moltype = AA  length = 341
FEATURE               Location/Qualifiers
REGION                1..341
                      note = Description of Artificial Sequence: Synthetic
                       polypeptide
source                1..341
                      mol_type = protein
                      organism = synthetic construct
SEQUENCE: 480
MDDHHFKVIL HYGTLVIDGV TPNMIDYFGR PYEGIAVFDG KKITVTGTLW NGNKIIDERL  60
INPDGSLLFR VTINGVTGWR LCERILASSS GGSGGSGMYE SFIESLPFLK SLEFSARLKV  120
VDVIGTKVYN DGEQIIAQGD SADSFFIIES GEVKITMKRK GKSEVEENGA VEIARCSRGQ  180
YFGELALVTN KPRAASAHAI GTVKCLAMDV QAFERLLGPC MEIMKRNIAT YEEQLVALYG  240
TNMDIVGSGG SGGSSSMVFT LEDFVGDWRQ TAGYNLDQVL EQGGVSSLFQ NLGVSVTPIQ  300
RIVLSGENGL KIDIHVIIPY EGLSGDQMGQ IEKIFKVVYP V                      341

SEQ ID NO: 481        moltype = DNA  length = 1023
FEATURE               Location/Qualifiers
misc_feature          1..1023
                      note = Description of Artificial Sequence: Synthetic
                       polynucleotide
source                1..1023
                      mol_type = other DNA
                      organism = synthetic construct
SEQUENCE: 481
atgacgccga acatgatcga ctatttcgga cggccgtatg aaggcatcgc cgtgttcgac  60
ggcaaaaaga tcactgtaac agggaccctg tggaacggca acaaaattat cgacgagcgc  120
ctgatcaacc ccgacggctc cctgctgttc cgagtaacca tcaacggagt gaccggctgg  180
cggctgtgcg aacgcattct ggctagctca agcggaggtt caggcggttc cggaatgtat  240
gaaagcttta ttgagtcact gccattcctt aaatctttgg agttttctgc acgcctgaaa  300
gtagtagatg tgataggcac caaagtatac aacgatggag aacaaatcat tgctcaggga  360
gattcggctg attctttttt cattattgaa tctggagaag tgaaaattac tatgaaaaga  420
aagggtaaat cagaagtgga agagaatggt gcagtagaaa tcgctcgatg ctcgcgggga  480
cagtactttg gagagcttgc cctggtaact aacaaacctc gagcagcttc tgcccacgcc  540
attgggactg tcaaatgttt agcaatggat gtgcaagcat ttgaaaggct tctgggacct  600
tgcatggaaa ttatgaaaag gaacatcgct acctatgaag aacagttagt tgccctgtat  660
ggaacgaaca tggatattgt agggtcaggt ggatctggag gtagctcttc tatggtcttc  720
acactcgaag atttcgttgg ggactggcga cagacagccg gctacaacct ggaccaagtc  780
cttgaacagg gaggtgtgtc cagtttgttt cagaatctcg ggtgtccgt aactccgatc  840
caaaggattg tcctgagcgg tgaaaatggg ctgaagatcg acatccatgt catcatcccg  900
tatgaaggtc tgagcggcga ccaaatgggc cagatcgaaa aaatttttaa ggtggtgtac  960
cctgtggatg atcatcactt taaggtgatc ctgcactatg gcacactggt aatcgacggg  1020
gtt                                                                1023

SEQ ID NO: 482        moltype = AA  length = 341
FEATURE               Location/Qualifiers
REGION                1..341
                      note = Description of Artificial Sequence: Synthetic
                       polypeptide
source                1..341
                      mol_type = protein
                      organism = synthetic construct
SEQUENCE: 482
```

-continued

```
MTPNMIDYFG RPYEGIAVFD GKKITVTGTL WNGNKIIDER LINPDGSLLF RVTINGVTGW  60
RLCERILASS SGGSGGSGMY ESFIESLPFL KSLEFSARLK VVDVIGTKVY NDGEQIIAQG  120
DSADSFFIIE SGEVKITMKR KGKSEVEENG AVEIARCSRG QYFGELALVT NKPRAASAHA  180
IGTVKCLAMD VQAFERLLGP CMEIMKRNIA TYEEQLVALY GTNMDIVGSG GSGGSSSMVF  240
TLEDFVGDWR QTAGYNLDQV LEQGGVSSLF QNLGVSVTPI QRIVLSGENG LKIDIHVIIP  300
YEGLSGDQMG QIEKIFKVVY PVDDHHFKVI LHYGTLVIDG V                    341

SEQ ID NO: 483         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 483
atgttcgacg gcaaaaagat cactgtaaca gggaccctgt ggaacggcaa caaaattatc  60
gacgagcgcc tgatcaaccc cgacggctcc ctgctgttcc gagtaaccat caacggagtg  120
accggctggc ggctgtgcga acgcattctg gctagctcaa gcggaggttc aggcggttcc  180
ggaatgtatg aaagctttat tgagtcactg ccattcctta aatctttgga gttttctgca  240
cgcctgaaag tagtagatgt gataggcacc aaagtataca acgatggaga acaaatcatt  300
gctcagggag attcggctga ttctttttc attattgaat ctggagaagt gaaaattact  360
atgaaaagaa agggtaaatc agaagtggaa gagaatggtg cagtagaaat cgctcgatgc  420
tcgcggggac agtactttgg agagcttgcc ctggtaacta acaaacctcg agcagcttct  480
gcccacgcca ttgggactgt caaatgttta gcaatggatg tgcaagcatt tgaaaggctt  540
ctgggacctt gcatggaaat tatgaaaagg aacatcgcta cctatgaaga acagttagtt  600
gccctgtatg gaacgaacat ggatattgta gggtcaggtg gatctggagg tagctcttct  660
atggtcttca cactcgaaga tttcgttggg gactggcgac agacagccgg ctacaacctg  720
gaccaagtcc ttgaacaggg aggtgtgtcc agtttgtttc agaatctcgg ggtgtccgta  780
actccgatcc aaaggattgt cctgagcggt gaaaatgggc tgaagatcga catccatgtc  840
atcatcccgt atgaaggtct gagcggcgac caaatgggcc agatcgaaaa aatttttaag  900
gtggtgtacc ctgtggatga tcatcacttt aaggtgatcc tgcactatgg cacactggta  960
atcgacgggg ttacgccgaa catgatcgac tatttcggac ggccgtatga aggcatcgcc  1020
gtg                                                              1023

SEQ ID NO: 484         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 484
MFDGKKITVT GTLWNGNKII DERLINPDGS LLFRVTINGV TGWRLCERIL ASSSGGSGGS  60
GMYESFIESL PFLKSLEFSA RLKVVDVIGT KVYNDGEQII AQGDSADSFF IIESGEVKIT  120
MKRKGKSEVE ENGAVEIARC SRGQYFGELA LVTNKPRAAS AHAIGTVKCL AMDVQAFERL  180
LGPCMEIMKR NIATYEEQLV ALYGTNMDIV GSGGSGGSSS MVFTLEDFVG DWRQTAGYNL  240
DQVLEQGGVS SLFQNLGVSV TPIQRIVLSG ENGLKIDIHV IIPYEGLSGD QMGQIEKIFK  300
VVYPVDDHHF KVILHYGTLV IDGVTPNMID YFGRPYEGIA V                    341

SEQ ID NO: 485         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 485
atgaaaaaga tcactgtaac agggaccctg tggaacggca acaaaattat cgacgagcgc  60
ctgatcaacc ccgacggctc cctgctgttc cgagtaacca tcaacggagt gaccggctgg  120
cggctgtgcg aacgcattct ggctagctca agcggaggtt caggcggttc cggaatgtat  180
gaaagcttta ttgagtcact gccattcctt aaatctttgg agttttctgc acgcctgaaa  240
gtagtagatg tgataggcac caaagtatac aacgatggag aacaaatcat tgctcaggga  300
gattcggctg attctttttt cattattgaa tctggagaag tgaaaattac tatgaaaaga  360
aagggtaaat cagaagtgga agagaatggt gcagtagaaa tcgctcgatg ctcgcgggga  420
cagtactttg gagagcttgc cctggtaact aacaaacctc gagcagcttc tgcccacgcc  480
attgggactg tcaaatgttt agcaatggat gtgcaagcat ttgaaaggct tctgggacct  540
tgcatggaaa ttatgaaaag gaacatcgct acctatgaag aacagttagt tgccctgtat  600
ggaacgaaca tggatattgt agggtcaggt ggatctggag gtagctcttc tatggtcttc  660
acactcgaag atttcgttgg ggactggcga cagacagccg gctacaacct ggaccaagtc  720
cttgaacagg gaggtgtgtc cagtttgttt cagaatctcg ggtgtccgt aactccgatc  780
caaaggattg tcctgagcgg tgaaaatggg ctgaagatcg acatccatgt catcatcccg  840
tatgaaggtc tgagcggcga ccaaatgggc cagatcgaaa aaatttttaa ggtggtgtac  900
cctgtggatg atcatcactt taaggtgatc ctgcactatg gcacactggt aatcgacggg  960
gttacgccga acatgatcga ctatttcgga cggccgtatg aaggcatcgc cgtgttcgac  1020
ggc                                                              1023
```

```
SEQ ID NO: 486          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 486
MKKITVTGTL WNGNKIIDER LINPDGSLLF RVTINGVTGW RLCERILASS SGGSGGSGMY  60
ESFIESLPFL KSLEFSARLK VVDVIGTKVY NDGEQIIAQG DSADSFFIIE SGEVKITMKR  120
KGKSEVEENG AVEIARCSRG QYFGELALVT NKPRAASAHA IGTVKCLAMD VQAFERLLGP  180
CMEIMKRNIA TYEEQLVALY GTNMDIVGSG GSGGSSSMVF TLEDFVGDWR QTAGYNLDQV  240
LEQGGVSSLF QNLGVSVTPI QRIVLSGENG LKIDIHVIIP YEGLSGDQMG QIEKIFKVVY  300
PVDDHHFKVI LHYGTLVIDG VTPNMIDYFG RPYEGIAVFD G                    341

SEQ ID NO: 487          moltype = DNA  length = 1023
FEATURE                 Location/Qualifiers
misc_feature            1..1023
                        note = Description of Artificial Sequence: Synthetic
                         polynucleotide
source                  1..1023
                        mol_type = other DNA
                        organism = synthetic construct
SEQUENCE: 487
atgaagatca ctgtaacagg gaccctgtgg aacggcaaca aaattatcga cgagcgcctg  60
atcaaccccg acggctccct gctgttccga gtaaccatca acggagtgac cggctggcgg  120
ctgtgcgaac gcattctggc tagctcaagc ggaggttcag gcggttccgg aatgtatgaa  180
agctttattg agtcactgcc attccttaaa tctttggagt ttctgcacg cctgaaagta  240
gtagatgtga taggcaccaa agtatacaac gatggagaac aaatcattgc tcagggagat  300
tcggctgatt ctttttcat tattgaatct ggagaagtga aaattactat gaaaagaaag  360
ggtaaatcag aagtggaaga gaatggtgca gtagaaatcg ctcgatgctc gcggggacag  420
tactttggag agcttgccct ggtaactaac aaacctcgag cagcttctgc ccacgccatt  480
gggactgtca aatgtttagc aatggatgtg caagcatttg aaaggcttct gggaccttgc  540
atggaaatta tgaaaaggaa catcgctacc tatgaagaac agttagttgc cctgtatgga  600
acgaacatgg atattgtagg gtcaggtgga tctggaggta gctcttctat ggtcttcaca  660
ctcgaagatt tcgttgggga ctggcgacag acagccggct acaacctgga ccaagtcctt  720
gaacagggag gtgtgtccag tttgtttcag aatctcgggg tgtccgtaac tccgatccaa  780
aggattgtcc tgagcggtga aaatgggctg aagatcgaca tccatgtcat catcccgtat  840
gaaggtctga gcggcgacca aatgggccag atcgaaaaaa tttttaaggt ggtgtaccct  900
gtggatgatc atcactttaa ggtgatcctg cactatggca cactggtaat cgacggggtt  960
acgccgaaca tgatcgacta tttcggacgg ccgtatgaag gcatcgccgt gttcgacggc  1020
aaa                                                              1023

SEQ ID NO: 488          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 488
MKITVTGTLW NGNKIIDERL INPDGSLLFR VTINGVTGWR LCERILASSS GGSGGSGMYE  60
SFIESLPFLK SLEFSARLKV VDVIGTKVYN DGEQIIAQGD SADSFFIIES GEVKITMKRK  120
GKSEVEENGA VEIARCSRGQ YFGELALVTN KPRAASAHAI GTVKCLAMDV QAFERLLGPC  180
MEIMKRNIAT YEEQLVALYG TNMDIVGSGG SGGSSSMVFT LEDFVGDWRQ TAGYNLDQVL  240
EQGGVSSLFQ NLGVSVTPIQ RIVLSGENGL KIDIHVIIPY EGLSGDQMGQ IEKIFKVVYP  300
VDDHHFKVIL HYGTLVIDGV TPNMIDYFGR PYEGIAVFDG K                    341

SEQ ID NO: 489          moltype = DNA  length = 1023
FEATURE                 Location/Qualifiers
misc_feature            1..1023
                        note = Description of Artificial Sequence: Synthetic
                         polynucleotide
source                  1..1023
                        mol_type = other DNA
                        organism = synthetic construct
SEQUENCE: 489
atgatcactg taacagggac cctgtggaac ggcaacaaaa ttatcgacga gcgcctgatc  60
aaccccgacg gctccctgct gttccgagta accatcaacg gagtgaccgg ctggcggctg  120
tgcgaacgca ttctggctag ctcaagcgga ggttcaggcg gttccggaat gtatgaaagc  180
tttattgagt cactgccatt ccttaaatct ttggagtttt ctgcacgcct gaaagtagta  240
gatgtgatag gcaccaaagt atacaacgat ggagaacaaa tcattgctca gggagattcg  300
gctgattctt ttttcattat tgaatctgga gaagtgaaaa ttactatgaa aagaaagggt  360
aaatcagaag tggaagagaa tggtgcagta gaaatcgctc gatgctcgcg gggacagtac  420
tttggagagc ttgccctggt aactaacaaa cctcgagcag cttctgccca cgccattggg  480
actgtcaaat gtttagcaat ggatgtgcaa gcatttgaaa ggcttctggg accttgcatg  540
gaaattatga aaaggaacat cgctacctat gaagaacagt tagttgccct gtatggaacg  600
```

```
aacatggata ttgtagggtc aggtggatct ggaggtagct cttctatggt cttcacactc  660
gaagatttcg ttggggactg gcgacagaca gccggctaca acctggacca agtccttgaa  720
cagggaggtg tgtccagttt gtttcagaat ctcggggtgt ccgtaactcc gatccaaagg  780
attgtcctga gcggtgaaaa tgggctgaag atcgacatcc atgtcatcat cccgtatgaa  840
ggtctgagcg gcgaccaaat gggccagatc gaaaaaattt ttaaggtggt gtaccctgtg  900
gatgatcatc actttaaggt gatcctgcac tatggcacac tggtaatcga cggggttacg  960
ccgaacatga tcgactattt cggacggccg tatgaaggca tcgccgtgtt cgacggcaaa  1020
aag                                                                1023

SEQ ID NO: 490         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 490
MITVTGTLWN GNKIIDERLI NPDGSLLFRV TINGVTGWRL CERILASSSG GSGGSGMYES  60
FIESLPFLKS LEFSARLKVV DVIGTKVYND GEQIIAQGDS ADSFFIIESG EVKITMKRKG  120
KSEVEENGAV EIARCSRGQY FGELALVTNK PRAASAHAIG TVKCLAMDVQ AFERLLGPCM  180
EIMKRNIATY EEQLVALYGT NMDIVGSGGS GGSSSMVFTL EDFVGDWRQT AGYNLDQVLE  240
QGGVSSLFQN LGVSVTPIQR IVLSGENGLK IDIHVIIPYE GLSGDQMGQI EKIFKVVYPV  300
DDHHFKVILH YGTLVIDGVT PNMIDYFGRP YEGIAVFDGK K                      341

SEQ ID NO: 491         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 491
atgaccctgt ggaacggcaa caaaattatc gacgagcgcc tgatcaaccc cgacggctcc  60
ctgctgttcc gagtaaccat caacggagtg accggctggc ggctgtgcga acgcattctg  120
gctagctcaa gcggaggttc aggcggttcc ggaatgtatg aaagctttat tgagtcactg  180
ccattcctta aatctttgga gttttctgca cgcctgaaag tagtagatgt gataggcacc  240
aaagtataca acgatggaga acaaatcatt gctcagggag attcggctga ttcttttttc  300
attattgaat ctggagaagt gaaaattact atgaaaagaa agggtaaatc agaagtggaa  360
gagaatggtg cagtagaaat cgctcgatgc tcgcggggac agtactttgg agagcttgcc  420
ctggtaacta acaaacctcg agcagcttct gcccacgcca ttgggactgt caaatgttta  480
gcaatggatg tgcaagcatt tgaaaggctt ctgggacctt gcatggaaat tatgaaaagg  540
aacatcgcta cctatgaaga acagttagtt gccctgtatg gaacgaacat ggatattgta  600
gggtcaggtg gatctggagg tagctcttct atggtcttca cactcgaaga tttcgttggg  660
gactggcgac agacagccgg ctacaacctg gaccaagtcc ttgaacaggg aggtgtgtcc  720
agtttgtttc agaatctcgg ggtgtccgta actccgatcc aaaggattgt cctgagcggt  780
gaaaatgggc tgaagatcga catccatgtc atcatcccgt atgaaggtct gagcggcgac  840
caaatgggcc agatcgaaaa aatttttaag gtggtgtacc ctgtggatga tcatcacttt  900
aaggtgatcc tgcactatgg cacactggta atcgacgggg ttacgccgaa catgatcgac  960
tatttcggac ggccgtatga aggcatcgcc gtgttcgacg gcaaaaagat cactgtaaca  1020
ggg                                                                1023

SEQ ID NO: 492         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 492
MTLWNGNKII DERLINPDGS LLFRVTINGV TGWRLCERIL ASSSGGSGGS GMYESFIESL  60
PFLKSLEFSA RLKVVDVIGT KVYNDGEQII AQGDSADSFF IIESGEVKIT MKRKGKSEVE  120
ENGAVEIARC SRGQYFGELA LVTNKPRAAS AHAIGTVKCL AMDVQAFERL LGPCMEIMKR  180
NIATYEEQLV ALYGTNMDIV GSGGSGGSSS MVFTLEDFVG DWRQTAGYNL DQVLEQGGVS  240
SLFQNLGVSV TPIQRIVLSG ENGLKIDIHV IIPYEGLSGD QMGQIEKIFK VVYPVDDHHF  300
KVILHYGTLV IDGVTPNMID YFGRPYEGIA VFDGKKITVT G                      341

SEQ ID NO: 493         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 493
atgcccgacg gctccctgct gttccgagta accatcaacg gagtgaccgg ctggcggctg  60
```

-continued

```
tgcgaacgca ttctggctag ctcaagcgga ggttcaggcg gttccggaat gtatgaaagc  120
tttattgagt cactgccatt ccttaaatct ttggagtttt ctgcacgcct gaaagtagta  180
gatgtgatag gcaccaaagt atacaacgat ggagaacaaa tcattgctca gggagattcg  240
gctgattctt ttttcattat tgaatctgga gaagtgaaaa ttactatgaa aagaaagggt  300
aaatcagaag tggaagagaa tggtgcagta gaaatcgctc gatgctcgcg gggacagtac  360
tttggagagc ttgccctggt aactaacaaa cctcgagcag cttctgccca cgccattggg  420
actgtcaaat gtttagcaat ggatgtgcaa gcatttgaaa ggcttctggg accttgcatg  480
gaaattatga aaaggaacat cgctacctat gaagaacagt tagttgccct gtatggaacg  540
aacatggata ttgtagggtc aggtggatct ggaggtagct cttctatggt cttcacactc  600
gaagatttcg ttggggactg gcgacagaca gccggctaca acctggacca agtccttgaa  660
cagggaggtg tgtccagttt gtttcagaat ctcggggtgt ccgtaactcc gatccaaagg  720
attgtcctga gcggtgaaaa tgggctgaag atcgacatcc atgtcatcat cccgtatgaa  780
ggtctgagcg gcgaccaaat gggccagatc gaaaaaattt ttaaggtggt gtaccctgtg  840
gatgatcatc actttaaggt gatcctgcac tatggcacac tggtaatcga cggggttacg  900
ccgaacatga tcgactattt cggacggccg tatgaaggca tcgccgtgtt cgacggcaaa  960
aagatcactg taacagggac cctgtggaac ggcaacaaaa ttatcgacga gcgcctgatc  1020
aac                                                               1023

SEQ ID NO: 494          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 494
MPDGSLLFRV TINGVTGWRL CERILASSSG GSGGSGMYES FIESLPFLKS LEFSARLKVV  60
DVIGTKVYND GEQIIAQGDS ADSFFIIESG EVKITMKRKG KSEVEENGAV EIARCSRGQY  120
FGELALVTNK PRAASAHAIG TVKCLAMDVQ AFERLLGPCM EIMKRNIATY EEQLVALYGT  180
NMDIVGSGGS GGSSSMVFTL EDFVGDWRQT AGYNLDQVLE QGGVSSLFQN LGVSVTPIQR  240
IVLSGENGLK IDIHVIIPYE GLSGDQMGQI EKIFKVVYPV DDHHFKVILH YGTLVIDGVT  300
PNMIDYFGRP YEGIAVFDGK KITVTGTLWN GNKIIDERLI N                     341

SEQ ID NO: 495          moltype = DNA  length = 1023
FEATURE                 Location/Qualifiers
misc_feature            1..1023
                        note = Description of Artificial Sequence: Synthetic
                         polynucleotide
source                  1..1023
                        mol_type = other DNA
                        organism = synthetic construct
SEQUENCE: 495
atgtccctgc tgttccgagt aaccatcaac ggagtgaccg gctggcggct gtgcgaacgc  60
attctggcta gctcaagcgg aggttcaggc ggttccggaa tgtatgaaag ctttattgag  120
tcactgccat tccttaaatc tttggagttt tctgcacgcc tgaaagtagt agatgtgata  180
ggcaccaaag tatacaacga tggagaacaa atcattgctc agggagattc ggctgattct  240
tttttcatta ttgaatctgg agaagtgaaa attactatga aaagaaaggg taaatcagaa  300
gtggaagaga atggtgcagt agaaatcgct cgatgctcgc ggggacagta ctttggagag  360
cttgccctgg taactaacaa acctcgagca gcttctgccc acgccattgg gactgtcaaa  420
tgtttagcaa tggatgtgca agcatttgaa aggcttctgg gaccttgcat ggaaattatg  480
aaaaggaaca tcgctaccta tgaagaacag ttagttgccc tgtatggaac gaacatggat  540
attgtagggt caggtggatc tggaggtagc tcttctatgg tcttcacact cgaagatttc  600
gttggggact ggcgacagac agccggctac aacctggacc aagtccttga acagggaggt  660
gtgtccagtt tgtttcagaa tctcggggtg tccgtaactc cgatccaaag gattgtcctg  720
agcggtgaaa atgggctgaa gatcgacatc catgtcatca tcccgtatga aggtctgagc  780
ggcgaccaaa tgggccagat cgaaaaaatt tttaaggtgg tgtaccctgt ggatgatcat  840
cactttaagg tgatcctgca ctatggcaca ctggtaatcg acggggttac gccgaacatg  900
atcgactatt tcggacggcc gtatgaaggc atcgccgtgt tcgacggcaa aaagatcact  960
gtaacaggga ccctgtggaa cggcaacaaa attatcgacg agcgcctgat caaccccgac  1020
ggc                                                               1023

SEQ ID NO: 496          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 496
MSLLFRVTIN GVTGWRLCER ILASSSGGSG GSGMYESFIE SLPFLKSLEF SARLKVVDVI  60
GTKVYNDGEQ IIAQGDSADS FFIIESGEVK ITMKRKGKSE VEENGAVEIA RCSRGQYFGE  120
LALVTNKPRA ASAHAIGTVK CLAMDVQAFE RLLGPCMEIM KRNIATYEEQ LVALYGTNMD  180
IVGSGGSGGS SSMVFTLEDF VGDWRQTAGY NLDQVLEQGG VSSLFQNLGV SVTPIQRIVL  240
SGENGLKIDI HVIIPYEGLS GDQMGQIEKI FKVVYPVDDH HFKVILHYGT LVIDGVTPNM  300
IDYFGRPYEG IAVFDGKKIT VTGTLWNGNK IIDERLINPD G                     341

SEQ ID NO: 497          moltype = DNA  length = 1023
```

```
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 497
atgggagtga ccggctggcg gctgtgcgaa cgcattctgg ctagctcaag cggaggttca  60
ggcggttccg gaatgtatga aagctttatt gagtcactgc cattccttaa atctttggag  120
ttttctgcac gcctgaaagt agtagatgtg ataggcacca aagtatacaa cgatggagaa  180
caaatcattg ctcagggaga ttcggctgat tcttttttca ttattgaatc tggagaagtg  240
aaaattacta tgaaaagaaa gggtaaatca gaagtggaag agaatggtgc agtagaaatc  300
gctcgatgct cgcggggaca gtactttgga gagcttgccc tggtaactaa caaacctcga  360
gcagcttctg cccacgccat tgggactgtc aaatgtttag caatggatgt gcaagcattt  420
gaaaggcttc tgggaccttg catggaaatt atgaaaagga acatcgctac ctatgaagaa  480
cagttagttg ccctgtatgg aacgaacatg gatattgtag ggtcaggtgg atctggaggt  540
agctcttcta tggtcttcac actcgaagat ttcgttgggg actggcgaca gacagccggc  600
tacaacctgg accaagtcct tgaacaggga ggtgtgtcca gtttgtttca gaatctcggg  660
gtgtccgtaa ctccgatcca aaggattgtc ctgagcggtg aaaatgggct gaagatcgac  720
atccatgtca tcatcccgta tgaaggtctg agcggcgacc aaatgggcca gatcgaaaaa  780
atttttaagg tggtgtaccc tgtggatgat catcacttta aggtgatcct gcactatggc  840
acactggtaa tcgacggggt tacgccgaac atgatcgact atttcggacg gccgtatgaa  900
ggcatcgccg tgttcgacgg caaaaagatc actgtaacag ggaccctgtg gaacggcaac  960
aaaattatcg acgagcgcct gatcaacccc gacggctccc tgctgttccg agtaaccatc  1020
aac                                                                1023

SEQ ID NO: 498         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 498
MGVTGWRLCE RILASSSGGS GGSGMYESFI ESLPFLKSLE FSARLKVVDV IGTKVYNDGE  60
QIIAQGDSAD SFFIIESGEV KITMKRKGKS EVEENGAVEI ARCSRGQYFG ELALVTNKPR  120
AASAHAIGTV KCLAMDVQAF ERLLGPCMEI MKRNIATYEE QLVALYGTNM DIVGSGGSGG  180
SSSMVFTLED FVGDWRQTAG YNLDQVLEQG GVSSLFQNLG VSVTPIQRIV LSGENGLKID  240
IHVIIPYEGL SGDQMGQIEK IFKVVYPVDD HHFKVILHYG TLVIDGVTPN MIDYFGRPYE  300
GIAVFDGKKI TVTGTLWNGN KIIDERLINP DGSLLFRVTI N                     341

SEQ ID NO: 499         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 499
atggtcttca cactcgaaga tagcgctagc ggaggttcag gcggttccgg aatgtatgaa  60
agctttattg agtcactgcc attccttaaa tctttggagt tttctgcacg cctgaaagta  120
gtagatgtga taggcaccaa agtatacaac gatggagaac aaatcattgc tcagggagat  180
tcggctgatt cttttttcat tattgaatct ggagaagtga aaattactat gaaaagaaag  240
ggtaaatcag aagtggaaga gaatggtgca gtagaaatcg ctcgatgctc gcggggacag  300
tactttggag agcttgccct ggtaactaac aaacctcgag cagcttctgc ccacgccatt  360
gggactgtca aatgtttagc aatggatgtg caagcatttg aaaggcttct gggaccttgc  420
atggaaatta tgaaaaggaa catcgctacc tatgaagaac agttagttgc cctgtatgga  480
acgaacatgg atattgtagg gtcaggtgga tctggaggta gctcttcttt cgttggggac  540
tggcgacaga cagccggcta caacctggac caagtccttg aacagggagg tgtgtccagt  600
ttgtttcaga atctcggggt gtccgtaact ccgatccaaa ggattgtcct gagcggtgaa  660
aatgggctga agatcgacat ccatgtcatc atcccgtatg aaggtctgag cggcgaccaa  720
atgggccaga tcgaaaaaat ttttaaggtg gtgtaccctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 500         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 500
```

```
MVFTLEDSAS GGSGGSGMYE SFIESLPFLK SLEFSARLKV VDVIGTKVYN DGEQIIAQGD  60
SADSFFIIES GEVKITMKRK GKSEVEENGA VEIARCSRGQ YFGELALVTN KPRAASAHAI  120
GTVKCLAMDV QAFERLLGPC MEIMKRNIAT YEEQLVALYG TNMDIVGSGG SGGSSSFVGD  180
WRQTAGYNLD QVLEQGGVSS LFQNLGVSVT PIQRIVLSGE NGLKIDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                       340

SEQ ID NO: 501         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 501
atggtcttca cactcgaaga tttcgttggg gactggcgaa gcgctagcgg aggttcaggc  60
ggttccggaa tgtatgaaag ctttattgag tcactgccat tccttaaatc tttggagttt  120
tctgcacgcc tgaaagtagt agatgtgata ggcaccaaag tatacaacga tggagaacaa  180
atcattgctc agggagattc ggctgattct tttttcatta ttgaatctgg agaagtgaaa  240
attactatga aaagaaaggg taaatcagaa gtggaagaga atggtgcagt agaaatcgct  300
cgatgctcgc ggggacagta ctttggagag cttgccctgg taactaacaa acctcgagca  360
gcttctgccc acgccattgg gactgtcaaa tgtttagcaa tggatgtgca agcatttgaa  420
aggcttctgg gaccttgcat ggaaattatg aaaaggaaca tcgctaccta tgaagaacag  480
ttagttgccc tgtatggaac gaacatggat attgtagggt caggtggatc tggaggtagc  540
tcttctcaga cagccggcta caacctggac caagtccttg aacagggagg tgtgtccagt  600
ttgtttcaga atctcggggt gtccgtaact ccgatccaaa ggattgtcct gagcggtgaa  660
aatgggctga agatcgacat ccatgtcatc atcccgtatg aaggtctgag cggcgaccaa  720
atgggccaga tcgaaaaaat ttttaaggtg gtgtaccctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 502         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 502
MVFTLEDFVG DWRSASGGSG GSGMYESFIE SLPFLKSLEF SARLKVVDVI GTKVYNDGEQ  60
IIAQGDSADS FFIIESGEVK ITMKRKGKSE VEENGAVEIA RCSRGQYFGE LALVTNKPRA  120
ASAHAIGTVK CLAMDVQAFE RLLGPCMEIM KRNIATYEEQ LVALYGTNMD IVGSGGSGGS  180
SSQTAGYNLD QVLEQGGVSS LFQNLGVSVT PIQRIVLSGE NGLKIDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                       340

SEQ ID NO: 503         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 503
atggtcttca cactcgaaga tttcgttggg gactggcgac agacagccgg ctacaacctg  60
gaccaagtcc ttgaacaggg aagcgctagc ggaggttcag gcggttccgg aatgtatgaa  120
agctttattg agtcactgcc attccttaaa tctttggagt tttctgcacg cctgaaagta  180
gtagatgtga taggcaccaa agtatacaac gatggagaac aaatcattgc tcagggagat  240
tcggctgatt ctttttcat tattgaatct ggagaagtga aaattactat gaaaagaaag  300
ggtaaatcag aagtggaaga gaatggtgca gtagaaatcg ctcgatgctc gcggggacag  360
tactttggag agcttgccct ggtaactaac aaacctcgag cagcttctgc ccacgccatt  420
gggactgtca aatgtttagc aatggatgtg caagcatttg aaaggcttct gggaccttgc  480
atggaaatta tgaaaaggaa catcgctacc tatgaagaac agttagttgc cctgtatgga  540
acgaacatgg atattgtagg gtcaggtgga tctggaggta gctcttctgg tgtgtccagt  600
ttgtttcaga atctcggggt gtccgtaact ccgatccaaa ggattgtcct gagcggtgaa  660
aatgggctga agatcgacat ccatgtcatc atcccgtatg aaggtctgag cggcgaccaa  720
atgggccaga tcgaaaaaat ttttaaggtg gtgtaccctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 504         moltype = AA  length = 340
FEATURE                Location/Qualifiers
```

```
REGION                  1..340
                        note = Description of Artificial Sequence: Synthetic
                         polypeptide
source                  1..340
                        mol_type = protein
                        organism = synthetic construct
SEQUENCE: 504
MVFTLEDFVG DWRQTAGYNL DQVLEQGSAS GGSGGSGMYE SFIESLPFLK SLEFSARLKV  60
VDVIGTKVYN DGEQIIAQGD SADSFFIIES GEVKITMKRK GKSEVEENGA VEIARCSRGQ  120
YFGELALVTN KPRAASAHAI GTVKCLAMDV QAFERLLGPC MEIMKRNIAT YEEQLVALYG  180
TNMDIVGSGG SGGSSSGVSS LFQNLGVSVT PIQRIVLSGE NGLKIDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                        340

SEQ ID NO: 505          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 505
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattag cgctagcgga ggttcaggcg gttccggaat gtatgaaagc  180
tttattgagt cactgccatt ccttaaatct ttggagtttt ctgcacgcct gaaagtagta  240
gatgtgatag gcaccaaagt atacaacgat ggagaacaaa tcattgctca gggagattcg  300
gctgattctt ttttcattat tgaatctgga gaagtgaaaa ttactatgaa aagaaagggt  360
aaatcagaag tggaagagaa tggtgcagta gaaatcgctc gatgctcgcg gggacagtac  420
tttggagagc ttgccctggt aactaacaaa cctcgagcag cttctgccca cgccattggg  480
actgtcaaat gtttagcaat ggatgtgcaa gcatttgaaa ggcttctggg accttgcatg  540
gaaattatga aaaggaacat cgctacctat gaagaacagt tagttgccct gtatggaacg  600
aacatggata ttgtagggtc aggtggatct ggaggtagct cttctgtcct gagcggtgaa  660
aatgggctga agatcgacat ccatgtcatc atcccgtatg aaggtctgag cggcgaccaa  720
atgggccaga tcgaaaaaat ttttaaggtg gtgtaccctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 506          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 506
MVFTLEDFVG DWRQTAGYNL DQVLEQGGVS SLFQNLGVSV TPIQRISASG GSGGSGMYES  60
FIESLPFLKS LEFSARLKVV DVIGTKVYND GEQIIAQGDS ADSFFIIESG EVKITMKRKG  120
KSEVEENGAV EIARCSRGQY FGELALVTNK PRAASAHAIG TVKCLAMDVQ AFERLLGPCM  180
EIMKRNIATY EEQLVALYGT NMDIVGSGGS GGSSSVLSGE NGLKIDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                        340

SEQ ID NO: 507          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 507
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcagc gctagcggag gttcaggcgg ttccggaatg  180
tatgaaagct ttattgagtc actgccattc cttaaatctt tggagttttc tgcacgcctg  240
aaagtagtag atgtgatagg caccaaagta tacaacgatg gagaacaaat cattgctcag  300
ggagattcgg ctgattcttt tttcattatt gaatctggag aagtgaaaat tactatgaaa  360
agaaagggta aatcagaagt ggaagagaat ggtgcagtag aaatcgctcg atgctcgcgg  420
ggacagtact ttggagagct tgccctggta actaacaaac ctcgagcagc ttctgcccac  480
gccattggga ctgtcaaatg tttagcaatg gatgtgcaag catttgaaag gcttctggga  540
ccttgcatgg aaattatgaa aaggaacatc gctacctatg aagaacagtt agttgccctg  600
tatggaacga acatggatat tgtagggtca ggtggatctg gaggtagctc ttctggtgaa  660
aatgggctga agatcgacat ccatgtcatc atcccgtatg aaggtctgag cggcgaccaa  720
atgggccaga tcgaaaaaat ttttaaggtg gtgtaccctg tggatgatca tcactttaag  780
```

```
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 508          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 508
MVFTLEDFVG DWRQTAGYNL DQVLEQGGVS SLFQNLGVSV TPIQRIVLSS ASGGSGGSGM  60
YESFIESLPF LKSLEFSARL KVVDVIGTKV YNDGEQIIAQ GDSADSFFII ESGEVKITMK  120
RKGKSEVEEN GAVEIARCSR GQYFGELALV TNKPRAASAH AIGTVKCLAM DVQAFERLLG  180
PCMEIMKRNI ATYEEQLVAL YGTNMDIVGS GGSGGSSSGE NGLKIDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                       340

SEQ ID NO: 509          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 509
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatggga gcgctagcgg aggttcaggc  180
ggttccggaa tgtatgaaag ctttattgag tcactgccat tccttaaatc tttggagttt  240
tctgcacgcc tgaaagtagt agatgtgata ggcaccaaag tatacaacga tggagaacaa  300
atcattgctc agggagattc ggctgattct tttttcatta ttgaatctgg agaagtgaaa  360
attactatga aaagaaaggg taaatcagaa gtggaagaga atggtgcagt agaaatcgct  420
cgatgctcgc ggggacagta ctttggagag cttgccctgg taactaacaa acctcgagca  480
gcttctgccc acgccattgg gactgtcaaa tgtttagcaa tggatgtgca agcatttgaa  540
aggcttctgg gaccttgcat ggaaattatg aaaaggaaca tcgctaccta tgaagaacag  600
ttagttgccc tgtatggaac gaacatggat attgtagggt caggtggatc tggaggtagc  660
tcttctctga agatcgacat ccatgtcatc atcccgtatg aaggtctgag cggcgaccaa  720
atgggccaga tcgaaaaaat ttttaaggtg gtgtaccctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 510          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 510
MVFTLEDFVG DWRQTAGYNL DQVLEQGGVS SLFQNLGVSV TPIQRIVLSG ENGSASGGSG  60
GSGMYESFIE SLPFLKSLEF SARLKVVDVI GTKVYNDGEQ IIAQGDSADS FFIIESGEVK  120
ITMKRKGKSE VEENGAVEIA RCSRGQYFGE LALVTNKPRA ASAHAIGTVK CLAMDVQAFE  180
RLLGPCMEIM KRNIATYEEQ LVALYGTNMD IVGSGGSGGS SSLKIDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                       340

SEQ ID NO: 511          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 511
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcag cgctagcgga  180
ggttcaggcg gttccggaat gtatgaaagc tttattgagt cactgccatt ccttaaatct  240
ttggagtttt ctgcacgcct gaaagtagta gatgtgatag gcaccaaagt atacaacgat  300
ggagaacaaa tcattgctca gggagattcg gctgattctt ttttcattat tgaatctgga  360
```

```
gaagtgaaaa ttactatgaa aagaaagggt aaatcagaag tggaagagaa tggtgcagta  420
gaaatcgctc gatgctcgcg gggacagtac tttggagagc ttgccctggt aactaacaaa  480
cctcgagcag cttctgccca cgccattggg actgtcaaat gtttagcaat ggatgtgcaa  540
gcatttgaaa ggcttctggg accttgcatg gaaattatga aaaggaacat cgctacctat  600
gaagaacagt tagttgccct gtatggaacg aacatggata ttgtagggtc aggtggatct  660
ggaggtagct cttctgacat ccatgtcatc atcccgtatg aaggtctgag cggcgaccaa  720
atgggccaga tcgaaaaaat ttttaaggtg gtgtaccctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 512         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 512
MVFTLEDFVG DWRQTAGYNL DQVLEQGGVS SLFQNLGVSV TPIQRIVLSG ENGLKISASG  60
GSGGSGMYES FIESLPFLKS LEFSARLKVV DVIGTKVYND GEQIIAQGDS ADSFFIIESG  120
EVKITMKRKG KSEVEENGAV EIARCSRGQY FGELALVTNK PRAASAHAIG TVKCLAMDVQ  180
AFERLLGPCM EIMKRNIATY EEQLVALYGT NMDIVGSGGS GGSSSDIHVI IPYEGLSGDQ  240
MGQIEKIFKV VYPVDDHHFK VILHYGTLVI DGVTPNMIDY FGRPYEGIAV FDGKKITVTG  300
TLWNGNKIID ERLINPDGSL LFRVTINGVT GWRLCERILA                      340

SEQ ID NO: 513         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 513
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctagcgctag cggaggttca ggcggttccg gaatgtatga aagctttatt  300
gagtcactgc cattccttaa atctttggag ttttctgcac gcctgaaagt agtagatgtg  360
ataggcacca aagtatacaa cgatggagaa caaatcattg ctcagggaga ttcggctgat  420
tctttttttca ttattgaatc tggagaagtg aaaattacta tgaaaagaaa gggtaaatca  480
gaagtggaag agaatggtgc agtagaaatc gctcgatgct cgcggggaca gtactttgga  540
gagcttgccc tggtaactaa caaacctcga gcagcttctg cccacgccat tgggactgtc  600
aaatgtttag caatggatgt gcaagcattt gaaaggcttc tgggaccttg catggaaatt  660
atgaaaagga acatcgctac ctatgaagaa cagttagttg ccctgtatgg aacgaacatg  720
gatattgtag ggtcaggtgg atctggaggt agctcttctg tggatgatca tcactttaag  780
gtgatcctgc actatggcac actggtaatc gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 514         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 514
MVFTLEDFVG DWRQTAGYNL DQVLEQGGVS SLFQNLGVSV TPIQRIVLSG ENGLKIDIHV  60
IIPYEGLSGD QMGQIEKIFK VVYPSASGGS GGSGMYESFI ESLPFLKSLE FSARLKVVDV  120
IGTKVYNDGE QIIAQGDSAD SFFIIESGEV KITMKRKGKS EVEENGAVEI ARCSRGQYFG  180
ELALVTNKPR AASAHAIGTV KCLAMDVQAF ERLLGPCMEI MKRNIATYEE QLVALYGTNM  240
DIVGSGGSGG SSSVDDHHFK VILHYGTLVI DGVTPNMIDY FGRPYEGIAV FDGKKITVTG  300
TLWNGNKIID ERLINPDGSL LFRVTINGVT GWRLCERILA                      340

SEQ ID NO: 515         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
```

SEQUENCE: 515
atggtcttca cactcgaaga tttcgttggg gactggcgac agacagccgg ctacaacctg 60
gaccaagtcc ttgaacaggg aggtgtgtcc agtttgtttc agaatctcgg ggtgtccgta 120
actccgatcc aaaggattgt cctgagcggt gaaaatgggc tgaagatcga catccatgtc 180
atcatcccgt atgaaggtct gagcggcgac caaatgggcc agatcgaaaa aatttttaag 240
gtggtgtacc ctgtgagcgc tagcggaggt tcaggcggtt ccggaatgta tgaaagcttt 300
attgagtcac tgccattcct taaatctttg gagttttctg cacgcctgaa agtagtagat 360
gtgataggca ccaaagtata caacgatgga gaacaaatca ttgctcaggg agattcggct 420
gattcttttt tcattattga atctggagaa gtgaaaatta ctatgaaaag aaagggtaaa 480
tcagaagtgg aagagaatgg tgcagtagaa atcgctcgat gctcgcgggg acagtacttt 540
ggagagcttg ccctggtaac taacaaacct cgagcagctt ctgcccacgc cattgggact 600
gtcaaatgtt tagcaatgga tgtgcaagca tttgaaaggc ttctgggacc ttgcatggaa 660
attatgaaaa ggaacatcgc tacctatgaa gaacagttag ttgccctgta tggaacgaac 720
atggatattg tagggtcagg tggatctgga ggtagctctt ctgatgatca tcactttaag 780
gtgatcctgc actatggcac actggtaatc gacggggtta cgccgaacat gatcgactat 840
ttcggacggc cgtatgaagg catcgccgtg ttcgacggca aaaagatcac tgtaacaggg 900
accctgtgga acggcaacaa aattatcgac gagcgcctga tcaaccccga cggctccctg 960
ctgttccgag taaccatcaa cggagtgacc ggctggcggc tgtgcgaacg cattctggct 1020

SEQ ID NO: 516 moltype = AA length = 340
FEATURE Location/Qualifiers
REGION 1..340
note = Description of Artificial Sequence: Synthetic
polypeptide
source 1..340
mol_type = protein
organism = synthetic construct
SEQUENCE: 516
MVFTLEDFVG DWRQTAGYNL DQVLEQGGVS SLFQNLGVSV TPIQRIVLSG ENGLKIDIHV 60
IIPYEGLSGD QMGQIEKIFK VVYPVSASGG SGGSGMYESF IESLPFLKSL EFSARLKVVD 120
VIGTKVYNDG EQIIAQGDSA DSFFIIESGE VKITMKRKGK SEVEENGAVE IARCSRGQYF 180
GELALVTNKP RAASAHAIGT VKCLAMDVQA FERLLGPCME IMKRNIATYE EQLVALYGTN 240
MDIVGSGGSG GSSSDDHHFK VILHYGTLVI DGVTPNMIDY FGRPYEGIAV FDGKKITVTG 300
TLWNGNKIID ERLINPDGSL LFRVTINGVT GWRLCERILA 340

SEQ ID NO: 517 moltype = DNA length = 1020
FEATURE Location/Qualifiers
misc_feature 1..1020
note = Description of Artificial Sequence: Synthetic
polynucleotide
source 1..1020
mol_type = other DNA
organism = synthetic construct
SEQUENCE: 517
atggtcttca cactcgaaga tttcgttggg gactggcgac agacagccgg ctacaacctg 60
gaccaagtcc ttgaacaggg aggtgtgtcc agtttgtttc agaatctcgg ggtgtccgta 120
actccgatcc aaaggattgt cctgagcggt gaaaatgggc tgaagatcga catccatgtc 180
atcatcccgt atgaaggtct gagcggcgac caaatgggcc agatcgaaaa aatttttaag 240
gtggtgtacc ctgtggatag cgctagcgga ggttcaggcg gttccggaat gtatgaaagc 300
tttattgagt cactgccatt ccttaaatct ttggagtttt ctgcacgcct gaaagtagta 360
gatgtgatag gcaccaaagt atacaacgat ggagaacaaa tcattgctca gggagattcg 420
gctgattctt ttttcattat tgaatctgga gaagtgaaaa ttactatgaa aagaaagggt 480
aaatcagaag tggaagagaa tggtgcagta gaaatcgctc gatgctcgcg gggacagtac 540
tttggagagc ttgccctggt aactaacaaa cctcgagcag cttctgccca cgccattggg 600
actgtcaaat gtttagcaat ggatgtgcaa gcatttgaaa ggcttctggg accttgcatg 660
gaaattatga aaaggaacat cgctacctat gaagaacagt tagttgccct gtatggaacg 720
aacatggata ttgtagggtc aggtggatct ggaggtagct cttctgatca tcactttaag 780
gtgatcctgc actatggcac actggtaatc gacggggtta cgccgaacat gatcgactat 840
ttcggacggc cgtatgaagg catcgccgtg ttcgacggca aaaagatcac tgtaacaggg 900
accctgtgga acggcaacaa aattatcgac gagcgcctga tcaaccccga cggctccctg 960
ctgttccgag taaccatcaa cggagtgacc ggctggcggc tgtgcgaacg cattctggct 1020

SEQ ID NO: 518 moltype = AA length = 340
FEATURE Location/Qualifiers
REGION 1..340
note = Description of Artificial Sequence: Synthetic
polypeptide
source 1..340
mol_type = protein
organism = synthetic construct
SEQUENCE: 518
MVFTLEDFVG DWRQTAGYNL DQVLEQGGVS SLFQNLGVSV TPIQRIVLSG ENGLKIDIHV 60
IIPYEGLSGD QMGQIEKIFK VVYPVDSASG GSGGSGMYES FIESLPFLKS LEFSARLKVV 120
DVIGTKVYND GEQIIAQGDS ADSFFIIESG EVKITMKRKG KSEVEENGAV EIARCSRGQY 180
FGELALVTNK PRAASAHAIG TVKCLAMDVQ AFERLLGPCM EIMKRNIATY EEQLVALYGT 240
NMDIVGSGGS GGSSSDHHFK VILHYGTLVI DGVTPNMIDY FGRPYEGIAV FDGKKITVTG 300
TLWNGNKIID ERLINPDGSL LFRVTINGVT GWRLCERILA 340

SEQ ID NO: 519 moltype = DNA length = 1020

```
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 519
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcagcgcta gcggaggttc aggcggttcc ggaatgtatg aaagctttat tgagtcactg  360
ccattcctta aatctttgga gttttctgca cgcctgaaag tagtagatgt gataggcacc  420
aaagtataca acgatggaga acaaatcatt gctcagggag attcggctga ttcttttttc  480
attattgaat ctggagaagt gaaaattact atgaaaagaa agggtaaatc agaagtggaa  540
gagaatggtg cagtagaaat cgctcgatgc tcgcggggac agtactttgg agagcttgcc  600
ctggtaacta acaaacctcg agcagcttct gcccacgcca ttgggactgt caaatgttta  660
gcaatggatg tgcaagcatt tgaaaggctt ctgggacctt gcatggaaat tatgaaaagg  720
aacatcgcta cctatgaaga acagttagtt gccctgtatg gaacgaacat ggatattgta  780
gggtcaggtg gatctggagg tagctcttct gacggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 520         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 520
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV ISASGGSGGS GMYESFIESL  120
PFLKSLEFSA RLKVVDVIGT KVYNDGEQII AQGDSADSFF IIESGEVKIT MKRKGKSEVE  180
ENGAVEIARC SRGQYFGELA LVTNKPRAAS AHAIGTVKCL AMDVQAFERL LGPCMEIMKR  240
NIATYEEQLV ALYGTNMDIV GSGGSGGSSS DGVTPNMIDY FGRPYEGIAV FDGKKITVTG  300
TLWNGNKIID ERLINPDGSL LFRVTINGVT GWRLCERILA                       340

SEQ ID NO: 521         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 521
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacagcg ctagcggagg ttcaggcggt tccggaatgt atgaaagctt tattgagtca  360
ctgccattcc ttaaatcttt ggagttttct gcacgcctga aagtagtaga tgtgataggc  420
accaaagtat acaacgatgg agaacaaatc attgctcagg gagattcggc tgattctttt  480
ttcattattg aatctggaga agtgaaaatt actatgaaaa gaaagggtaa atcagaagtg  540
gaagagaatg gtgcagtaga aatcgctcga tgctcgcggg gacagtactt tggagagctt  600
gccctggtaa ctaacaaacc tcgagcagct tctgcccacg ccattgggac tgtcaaatgt  660
ttagcaatgg atgtgcaagc atttgaaagg cttctgggac cttgcatgga aattatgaaa  720
aggaacatcg ctacctatga agaacagtta gttgccctgt atggaacgaa catggatatt  780
gtagggtcag gtggatctgg aggtagctct tctggggtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 522         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 522
MVFTLEDFVG DWRQTAGYNL DQVLEQGGVS SLFQNLGVSV TPIQRIVLSG ENGLKIDIHV  60
```

-continued

```
IIPYEGLSGD QMGQIEKIFK VVYPVDDHHF KVILHYGTLV IDSASGGSGG SGMYESFIES  120
LPFLKSLEFS ARLKVVDVIG TKVYNDGEQI IAQGDSADSF FIIESGEVKI TMKRKGKSEV  180
EENGAVEIAR CSRGQYFGEL ALVTNKPRAA SAHAIGTVKC LAMDVQAFER LLGPCMEIMK  240
RNIATYEEQL VALYGTNMDI VGSGGSGGSS SGVTPNMIDY FGRPYEGIAV FDGKKITVTG  300
TLWNGNKIID ERLINPDGSL LFRVTINGVT GWRLCERILA                       340

SEQ ID NO: 523          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 523
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacggga gcgctagcgg aggttcaggc ggttccggaa tgtatgaaag ctttattgag  360
tcactgccat tccttaaatc tttggagttt tctgcacgcc tgaaagtagt agatgtgata  420
ggcaccaaag tatacaacga tggagaacaa atcattgctc agggagattc ggctgattct  480
tttttcatta ttgaatctgg agaagtgaaa attactatga aaagaaaggg taaatcagaa  540
gtggaagaga atggtgcagt agaaatcgct cgatgctcgc ggggacagta ctttggagag  600
cttgccctgg taactaacaa acctcgagca gcttctgccc acgccattgg gactgtcaaa  660
tgtttagcaa tggatgtgca agcatttgaa aggcttctgg gaccttgcat ggaaattatg  720
aaaaggaaca tcgctaccta tgaagaacag ttagttgccc tgtatggaac gaacatggat  780
attgtagggt caggtggatc tggaggtagc tcttctgtta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 524          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 524
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGSASGGSG GSGMYESFIE  120
SLPFLKSLEF SARLKVVDVI GTKVYNDGEQ IIAQGDSADS FFIIESGEVK ITMKRKGKSE  180
VEENGAVEIA RCSRGQYFGE LALVTNKPRA ASAHAIGTVK CLAMDVQAFE RLLGPCMEIM  240
KRNIATYEEQ LVALYGTNMD IVGSGGSGGS SSVTPNMIDY FGRPYEGIAV FDGKKITVTG  300
TLWNGNKIID ERLINPDGSL LFRVTINGVT GWRLCERILA                       340

SEQ ID NO: 525          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 525
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttagcgctag cggaggttca ggcggttccg gaatgtatga aagctttatt  360
gagtcactgc cattccttaa atctttggag ttttctgcac gcctgaaagt agtagatgtg  420
ataggcacca aagtatacaa cgatggagaa caaatcattg ctcagggaga ttcggctgat  480
tctttttttca ttattgaatc tggagaagtg aaaattacta tgaaaagaaa gggtaaatca  540
gaagtggaag agaatggtgc agtagaaatc gctcgatgct cgcggggaca gtactttgga  600
gagcttgccc tggtaactaa caaacctcga gcagcttctg cccacgccat tgggactgtc  660
aaatgtttag caatggatgt gcaagcattt gaaaggcttc tgggaccttg catggaaatt  720
atgaaaagga acatcgctac ctatgaagaa cagttagttg ccctgtatgg aacgaacatg  780
gatattgtag ggtcaggtgg atctggaggt agctcttcta cgccgaacat gatcgactat  840
ttcggacggc cgtatgaagg catcgccgtg ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 526          moltype = AA  length = 340
FEATURE                 Location/Qualifiers
REGION                  1..340
```

```
                        note = Description of Artificial Sequence: Synthetic
                         polypeptide
source                  1..340
                        mol_type = protein
                        organism = synthetic construct
SEQUENCE: 526
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVSASGGS GGSGMYESFI  120
ESLPFLKSLE FSARLKVVDV IGTKVYNDGE QIIAQGDSAD SFFIIESGEV KITMKRKGKS  180
EVEENGAVEI ARCSRGQYFG ELALVTNKPR AASAHAIGTV KCLAMDVQAF ERLLGPCMEI  240
MKRNIATYEE QLVALYGTNM DIVGSGGSGG SSSTPNMIDY FGRPYEGIAV FDGKKITVTG  300
TLWNGNKIID ERLINPDGSL LFRVTINGVT GWRLCERILA                        340

SEQ ID NO: 527          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 527
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgagcgcta gcggaggttc aggcggttcc ggaatgtatg aaagctttat tgagtcactg  420
ccattcctta aatctttgga gttttctgca cgcctgaaag tagtagatgt gataggcacc  480
aaagtataca acgatggaga acaaatcatt gctcagggag attcggctga ttcttttttc  540
attattgaat ctggagaagt gaaaattact atgaaaagaa agggtaaatc agaagtggaa  600
gagaatggtg cagtagaaat cgctcgatgc tcgcggggac agtactttgg agagcttgcc  660
ctggtaacta acaaacctcg agcagcttct gcccacgcca ttgggactgt caaatgttta  720
gcaatggatg tgcaagcatt tgaaaggctt ctgggacctt gcatggaaat tatgaaaagg  780
aacatcgcta cctatgaaga acagttagtt gccctgtatg gaacgaacat ggatattgta  840
gggtcaggtg gatctggagg tagctcttct ttcgacggca aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 528          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 528
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VSASGGSGGS GMYESFIESL PFLKSLEFSA RLKVVDVIGT KVYNDGEQII AQGDSADSFF  180
IIESGEVKIT MKRKGKSEVE ENGAVEIARC SRGQYFGELA LVTNKPRAAS AHAIGTVKCL  240
AMDVQAFERL LGPCMEIMKR NIATYEEQLV ALYGTNMDIV GSGGSGGSSS FDGKKITVTG  300
TLWNGNKIID ERLINPDGSL LFRVTINGVT GWRLCERILA                        340

SEQ ID NO: 529          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 529
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcagcgctag cggaggttca ggcggttccg gaatgtatga aagctttatt  420
gagtcactgc cattccttaa atctttggag ttttctgcac gcctgaaagt agtagatgtg  480
ataggcacca aagtatacaa cgatggagaa caaatcattg ctcagggaga ttcggctgat  540
tctttttttca ttattgaatc tggagaagtg aaaattacta tgaaaagaaa gggtaaatca  600
gaagtggaag agaatggtgc agtagaaatc gctcgatgct cgcggggaca gtactttgga  660
gagcttgccc tggtaactaa caaacctcga gcagcttctg cccacgccat tgggactgtc  720
aaatgtttag caatggatgt gcaagcattt gaaaggcttc tgggaccttg catggaaatt  780
atgaaaagga acatcgctac ctatgaagaa cagttagttg ccctgtatgg aacgaacatg  840
```

```
gatattgtag ggtcaggtgg atctggaggt agctcttcta aaaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 530         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 530
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGSASGGS GGSGMYESFI ESLPFLKSLE FSARLKVVDV IGTKVYNDGE QIIAQGDSAD  180
SFFIIESGEV KITMKRKGKS EVEENGAVEI ARCSRGQYFG ELALVTNKPR AASAHAIGTV  240
KCLAMDVQAF ERLLGPCMEI MKRNIATYEE QLVALYGTNM DIVGSGGSGG SSSKKITVTG  300
TLWNGNKIID ERLINPDGSL LFRVTINGVT GWRLCERILA                      340

SEQ ID NO: 531         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 531
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaagcgc tagcggaggt tcaggcggtt ccggaatgta tgaaagcttt  420
attgagtcac tgccattcct taaatctttg gagttttctg cacgcctgaa agtagtagat  480
gtgataggca ccaaagtata caacgatgga gaacaaatca ttgctcaggg agattcggct  540
gattcttttt tcattattga atctggagaa gtgaaaatta ctatgaaaag aaagggtaaa  600
tcagaagtgg aagagaatgg tgcagtagaa atcgctcgat gctcgcgggg acagtacttt  660
ggagagcttg ccctggtaac taacaaacct cgagcagctt ctgcccacgc cattgggact  720
gtcaaatgtt tagcaatgga tgtgcaagca tttgaaaggc ttctgggacc ttgcatggaa  780
attatgaaaa ggaacatcgc tacctatgaa gaacagttag ttgccctgta tggaacgaac  840
atggatattg tagggtcagg tggatctgga ggtagctctt ctaagatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 532         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 532
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKSASGG SGGSGMYESF IESLPFLKSL EFSARLKVVD VIGTKVYNDG EQIIAQGDSA  180
DSFFIIESGE VKITMKRKGK SEVEENGAVE IARCSRGQYF GELALVTNKP RAASAHAIGT  240
VKCLAMDVQA FERLLGPCME IMKRNIATYE EQLVALYGTN MDIVGSGGSG GSSSKITVTG  300
TLWNGNKIID ERLINPDGSL LFRVTINGVT GWRLCERILA                      340

SEQ ID NO: 533         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 533
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagag cgctagcgga ggttcaggcg gttccggaat gtatgaaagc  420
```

```
tttattgagt cactgccatt ccttaaatct ttggagtttt ctgcacgcct gaaagtagta  480
gatgtgatag gcaccaaagt atacaacgat ggagaacaaa tcattgctca gggagattcg  540
gctgattctt ttttcattat tgaatctgga gaagtgaaaa ttactatgaa aagaaagggt  600
aaatcagaag tggaagagaa tggtgcagta gaaatcgctc gatgctcgcg gggacagtac  660
tttggagagc ttgccctggt aactaacaaa cctcgagcag cttctgccca cgccattggg  720
actgtcaaat gtttagcaat ggatgtgcaa gcatttgaaa ggcttctggg accttgcatg  780
gaaattatga aaaggaacat cgctacctat gaagaacagt tagttgccct gtatggaacg  840
aacatggata ttgtagggtc aggtggatct ggaggtagct cttctatcac tgtaacaggg  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 534          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 534
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKSASG GSGGSGMYES FIESLPFLKS LEFSARLKVV DVIGTKVYND GEQIIAQGDS  180
ADSFFIIESG EVKITMKRKG KSEVEENGAV EIARCSRGQY FGELALVTNK PRAASAHAIG  240
TVKCLAMDVQ AFERLLGPCM EIMKRNIATY EEQLVALYGT NMDIVGSGGS GGSSSITVTG  300
TLWNGNKIID ERLINPDGSL LFRVTINGVT GWRLCERILA                      340

SEQ ID NO: 535          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 535
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggagcgcta gcggaggttc aggcggttcc  420
ggaatgtatg aaagctttat tgagtcactg ccattcctta aatctttgga gttttctgca  480
cgcctgaaag tagtagatgt gataggcacc aaagtataca acgatggaga acaaatcatt  540
gctcagggag attcggctga ttcttttttc attattgaat ctggagaagt gaaaattact  600
atgaaaagaa agggtaaatc agaagtggaa gagaatggtg cagtagaaat cgctcgatgc  660
tcgcggggac agtactttgg agagcttgcc ctggtaacta acaaacctcg agcagcttct  720
gcccacgcca ttgggactgt caaatgttta gcaatggatg tgcaagcatt tgaaaggctt  780
ctgggacctt gcatggaaat tatgaaaagg aacatcgcta cctatgaaga acagttagtt  840
gccctgtatg gaacgaacat ggatattgta gggtcaggtg gatctggagg tagctcttct  900
accctgtgga acggcaacaa aattatcgac gagcgcctga tcaaccccga cggctccctg  960
ctgttccgag taaccatcaa cggagtgacc ggctggcggc tgtgcgaacg cattctggct  1020

SEQ ID NO: 536          moltype = AA  length = 340
FEATURE                 Location/Qualifiers
REGION                  1..340
                        note = Description of Artificial Sequence: Synthetic
                         polypeptide
source                  1..340
                        mol_type = protein
                        organism = synthetic construct
SEQUENCE: 536
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GSASGGSGGS GMYESFIESL PFLKSLEFSA RLKVVDVIGT KVYNDGEQII  180
AQGDSADSFF IIESGEVKIT MKRKGKSEVE ENGAVEIARC SRGQYFGELA LVTNKPRAAS  240
AHAIGTVKCL AMDVQAFERL LGPCMEIMKR NIATYEEQLV ALYGTNMDIV GSGGSGGSSS  300
TLWNGNKIID ERLINPDGSL LFRVTINGVT GWRLCERILA                      340

SEQ ID NO: 537          moltype = DNA  length = 1020
FEATURE                 Location/Qualifiers
misc_feature            1..1020
                        note = Description of Artificial Sequence: Synthetic
                         polynucleotide
source                  1..1020
                        mol_type = other DNA
                        organism = synthetic construct
SEQUENCE: 537
```

```
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa cagcgctagc  420
ggaggttcag gcggttccgg aatgtatgaa agctttattg agtcactgcc attccttaaa  480
tctttggagt tttctgcacg cctgaaagta gtagatgtga taggcaccaa agtatacaac  540
gatggagaac aaatcattgc tcagggagat tcggctgatt cttttttcat tattgaatct  600
ggagaagtga aaattactat gaaaagaaag ggtaaatcag aagtggaaga gaatggtgca  660
gtagaaatcg ctcgatgctc gcggggacag tactttggag agcttgccct ggtaactaac  720
aaacctcgag cagcttctgc ccacgccatt gggactgtca aatgtttagc aatggatgtg  780
caagcatttg aaaggcttct gggaccttgc atggaaatta tgaaaaggaa catcgctacc  840
tatgaagaac agttagttgc cctgtatgga acgaacatgg atattgtagg gtcaggtgga  900
tctggaggta gctcttctaa aattatcgac gagcgcctga tcaaccccga cggctccctg  960
ctgttccgag taaccatcaa cggagtgacc ggctggcggc tgtgcgaacg cattctggct  1020
```

```
SEQ ID NO: 538         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 538
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNSAS GGSGGSGMYE SFIESLPFLK SLEFSARLKV VDVIGTKVYN  180
DGEQIIAQGD SADSFFIIES GEVKITMKRK GKSEVEENGA VEIARCSRGQ YFGELALVTN  240
KPRAASAHAI GTVKCLAMDV QAFERLLGPC MEIMKRNIAT YEEQLVALYG TNMDIVGSGG  300
SGGSSSKIID ERLINPDGSL LFRVTINGVT GWRLCERILA                       340
```

```
SEQ ID NO: 539         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 539
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgagcgctag cggaggttca ggcggttccg gaatgtatga aagctttatt  480
gagtcactgc cattccttaa atctttggag ttttctgcac gcctgaaagt agtagatgtg  540
ataggcacca aagtatacaa cgatggagaa caaatcattg ctcagggaga ttcggctgat  600
tcttttttca ttattgaatc tggagaagtg aaaattacta tgaaaagaaa gggtaaatca  660
gaagtggaag agaatggtgc agtagaaatc gctcgatgct cgcggggaca gtactttgga  720
gagcttgccc tggtaactaa caaacctcga gcagcttctg cccacgccat tgggactgtc  780
aaatgtttag caatggatgt gcaagcattt gaaaggcttc tgggaccttg catggaaatt  840
atgaaaagga acatcgctac ctatgaagaa cagttagttg ccctgtatgg aacgaacatg  900
gatattgtag ggtcaggtgg atctggaggt agctcttcta tcaaccccga cggctccctg  960
ctgttccgag taaccatcaa cggagtgacc ggctggcggc tgtgcgaacg cattctggct  1020
```

```
SEQ ID NO: 540         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 540
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLSASGGS GGSGMYESFI ESLPFLKSLE FSARLKVVDV  180
IGTKVYNDGE QIIAQGDSAD SFFIIESGEV KITMKRKGKS EVEENGAVEI ARCSRGQYFG  240
ELALVTNKPR AASAHAIGTV KCLAMDVQAF ERLLGPCMEI MKRNIATYEE QLVALYGTNM  300
DIVGSGGSGG SSSINPDGSL LFRVTINGVT GWRLCERILA                       340
```

```
SEQ ID NO: 541         moltype = DNA  length = 1020
FEATURE                Location/Qualifiers
```

```
misc_feature          1..1020
                      note = Description of Artificial Sequence: Synthetic
                       polynucleotide
source                1..1020
                      mol_type = other DNA
                      organism = synthetic construct
SEQUENCE: 541
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaacag cgctagcgga ggttcaggcg gttccggaat gtatgaaagc  480
tttattgagt cactgccatt ccttaaatct ttggagtttt ctgcacgcct gaaagtagta  540
gatgtgatag gcaccaaagt atacaacgat ggagaacaaa tcattgctca gggagattcg  600
gctgattctt ttttcattat tgaatctgga gaagtgaaaa ttactatgaa aagaaagggt  660
aaatcagaag tggaagagaa tggtgcagta gaaatcgctc gatgctcgcg gggacagtac  720
tttggagagc ttgccctggt aactaacaaa cctcgagcag cttctgccca cgccattggg  780
actgtcaaat gtttagcaat ggatgtgcaa gcatttgaaa ggcttctggg accttgcatg  840
gaaattatga aaaggaacat cgctacctat gaagaacagt tagttgccct gtatggaacg  900
aacatggata ttgtagggtc aggtggatct ggaggtagct cttctcccga cggctccctg  960
ctgttccgag taaccatcaa cggagtgacc ggctggcggc tgtgcgaacg cattctggct  1020

SEQ ID NO: 542        moltype = AA  length = 340
FEATURE               Location/Qualifiers
REGION                1..340
                      note = Description of Artificial Sequence: Synthetic
                       polypeptide
source                1..340
                      mol_type = protein
                      organism = synthetic construct
SEQUENCE: 542
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINSASG GSGGSGMYES FIESLPFLKS LEFSARLKVV  180
DVIGTKVYND GEQIIAQGDS ADSFFIIESG EVKITMKRKG KSEVEENGAV EIARCSRGQY  240
FGELALVTNK PRAASAHAIG TVKCLAMDVQ AFERLLGPCM EIMKRNIATY EEQLVALYGT  300
NMDIVGSGGS GGSSSPDGSL LFRVTINGVT GWRLCERILA                       340

SEQ ID NO: 543        moltype = DNA  length = 1020
FEATURE               Location/Qualifiers
misc_feature          1..1020
                      note = Description of Artificial Sequence: Synthetic
                       polynucleotide
source                1..1020
                      mol_type = other DNA
                      organism = synthetic construct
SEQUENCE: 543
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacagcgct agcggaggtt caggcggttc cggaatgtat  480
gaaagcttta ttgagtcact gccattcctt aaatctttgg agttttctgc acgcctgaaa  540
gtagtagatg tgataggcac caaagtatac aacgatggag aacaaatcat tgctcaggga  600
gattcggctg attctttttt cattattgaa tctggagaag tgaaaattac tatgaaaaga  660
aagggtaaat cagaagtgga agagaatggt gcagtagaaa tcgctcgatg ctcgcgggga  720
cagtactttg gagagcttgc cctggtaact aacaaacctc gagcagcttc tgcccacgcc  780
attgggactg tcaaatgttt agcaatggat gtgcaagcat ttgaaaggct tctgggacct  840
tgcatggaaa ttatgaaaag gaacatcgct acctatgaag aacagttagt tgccctgtat  900
ggaacgaaca tggatattgt agggtcaggt ggatctggag gtagctcttc tggctccctg  960
ctgttccgag taaccatcaa cggagtgacc ggctggcggc tgtgcgaacg cattctggct  1020

SEQ ID NO: 544        moltype = AA  length = 340
FEATURE               Location/Qualifiers
REGION                1..340
                      note = Description of Artificial Sequence: Synthetic
                       polypeptide
source                1..340
                      mol_type = protein
                      organism = synthetic construct
SEQUENCE: 544
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
```

-continued

```
VFDGKKITVT GTLWNGNKII DERLINPDSA SGGSGGSGMY ESFIESLPFL KSLEFSARLK  180
VVDVIGTKVY NDGEQIIAQG DSADSFFIIE SGEVKITMKR KGKSEVEENG AVEIARCSRG  240
QYFGELALVT NKPRAASAHA IGTVKCLAMD VQAFERLLGP CMEIMKRNIA TYEEQLVALY  300
GTNMDIVGSG GSGGSSSGSL LFRVTINGVT GWRLCERILA                        340

SEQ ID NO: 545         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 545
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggcagc gctagcggag gttcaggcgg ttccggaatg  480
tatgaaagct ttattgagtc actgccattc cttaaatctt tggagttttc tgcacgcctg  540
aaagtagtag atgtgatagg caccaaagta tacaacgatg gagaacaaat cattgctcag  600
ggagattcgg ctgattcttt tttcattatt gaatctggag aagtgaaaat tactatgaaa  660
agaaagggta aatcagaagt ggaagagaat ggtgcagtag aaatcgctcg atgctcgcgg  720
ggacagtact ttggagagct tgccctggta actaacaaac ctcgagcagc ttctgcccac  780
gccattggga ctgtcaaatg tttagcaatg gatgtgcaag catttgaaag gcttctggga  840
ccttgcatgg aaattatgaa aaggaacatc gctacctatg aagaacagtt agttgccctg  900
tatggaacga acatggatat tgtagggtca ggtggatctg gaggtagctc ttcttccctg  960
ctgttccgag taaccatcaa cggagtgacc ggctggcggc tgtgcgaacg cattctggct  1020

SEQ ID NO: 546         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 546
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS ASGGSGGSGM YESFIESLPF LKSLEFSARL  180
KVVDVIGTKV YNDGEQIIAQ GDSADSFFII ESGEVKITMK RKGKSEVEEN GAVEIARCSR  240
GQYFGELALV TNKPRAASAH AIGTVKCLAM DVQAFERLLG PCMEIMKRNI ATYEEQLVAL  300
YGTNMDIVGS GGSGGSSSSL LFRVTINGVT GWRLCERILA                        340

SEQ ID NO: 547         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 547
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat cagcgctagc  480
ggaggttcag gcggttccgg aatgtatgaa agctttattg agtcactgcc attccttaaa  540
tctttggagt tttctgcacg cctgaaagta gtagatgtga taggcaccaa agtatacaac  600
gatggagaac aaatcattgc tcagggagat tcggctgatt ctttttttcat tattgaatct  660
ggagaagtga aaattactat gaaaagaaag ggtaaatcag aagtggaaga gaatggtgca  720
gtagaaatcg ctcgatgctc gcggggacag tactttggag agcttgccct ggtaactaac  780
aaacctcgag cagcttctgc ccacgccatt gggactgtca aatgtttagc aatggatgtg  840
caagcatttg aaaggcttct gggaccttgc atggaaatta tgaaaaggaa catcgctacc  900
tatgaagaac agttagttgc cctgtatgga acgaacatgg atattgtagg gtcaggtgga  960
tctggaggta gctcttctaa cggagtgacc ggctggcggc tgtgcgaacg cattctggct  1020

SEQ ID NO: 548         moltype = AA  length = 340
FEATURE                Location/Qualifiers
REGION                 1..340
                       note = Description of Artificial Sequence: Synthetic
```

```
                          polypeptide
source                   1..340
                         mol_type = protein
                         organism = synthetic construct
SEQUENCE: 548
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTISAS GGSGGSGMYE SFIESLPFLK  180
SLEFSARLKV VDVIGTKVYN DGEQIIAQGD SADSFFIIES GEVKITMKRK GKSEVEENGA  240
VEIARCSRGQ YFGELALVTN KPRAASAHAI GTVKCLAMDV QAFERLLGPC MEIMKRNIAT  300
YEEQLVALYG TNMDIVGSGG SGGSSSNGVT GWRLCERILA                        340

SEQ ID NO: 549           moltype = DNA  length = 1020
FEATURE                  Location/Qualifiers
misc_feature             1..1020
                         note = Description of Artificial Sequence: Synthetic
                          polynucleotide
source                   1..1020
                         mol_type = other DNA
                         organism = synthetic construct
SEQUENCE: 549
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacagcgct  480
agcggaggtt caggcggttc cggaatgtat gaaagcttta ttgagtcact gccattcctt  540
aaatctttgg agttttctgc acgcctgaaa gtagtagatg tgataggcac caaagtatac  600
aacgatggag aacaaatcat tgctcaggga gattcggctg attctttttt cattattgaa  660
tctggagaag tgaaaattac tatgaaaaga aagggtaaat cagaagtgga agagaatggt  720
gcagtagaaa tcgctcgatg ctcgcgggga cagtactttg gagagcttgc cctggtaact  780
aacaaacctc gagcagcttc tgcccacgcc attgggactg tcaaatgttt agcaatggat  840
gtgcaagcat ttgaaaggct tctgggacct tgcatggaaa ttatgaaaag gaacatcgct  900
acctatgaag aacagttagt tgccctgtat ggaacgaaca tggatattgt agggtcaggt  960
ggatctggag gtagctcttc tggagtgacc ggctggcggc tgtgcgaacg cattctggct  1020

SEQ ID NO: 550           moltype = AA  length = 340
FEATURE                  Location/Qualifiers
REGION                   1..340
                         note = Description of Artificial Sequence: Synthetic
                          polypeptide
source                   1..340
                         mol_type = protein
                         organism = synthetic construct
SEQUENCE: 550
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINSA SGGSGGSGMY ESFIESLPFL  180
KSLEFSARLK VVDVIGTKVY NDGEQIIAQG DSADSFFIIE SGEVKITMKR KGKSEVEENG  240
AVEIARCSRG QYFGELALVT NKPRAASAHA IGTVKCLAMD VQAFERLLGP CMEIMKRNIA  300
TYEEQLVALY GTNMDIVGSG GSGGSSSGVT GWRLCERILA                        340

SEQ ID NO: 551           moltype = DNA  length = 1020
FEATURE                  Location/Qualifiers
misc_feature             1..1020
                         note = Description of Artificial Sequence: Synthetic
                          polynucleotide
source                   1..1020
                         mol_type = other DNA
                         organism = synthetic construct
SEQUENCE: 551
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggaagc  480
gctagcggag gttcaggcgg ttccggaatg tatgaaagct ttattgagtc actgccattc  540
cttaaatctt tggagttttc tgcacgcctg aaagtagtag atgtgatagg caccaaagta  600
tacaacgatg gagaacaaat cattgctcag ggagattcgg ctgattcttt tttcattatt  660
gaatctggag aagtgaaaat tactatgaaa agaaagggta aatcagaagt ggaagagaat  720
ggtgcagtag aaatcgctcg atgctcgcgg ggacagtact ttggagagct tgccctggta  780
actaacaaac ctcgagcagc ttctgcccac gccattggga ctgtcaaatg tttagcaatg  840
gatgtgcaag catttgaaag gcttctggga ccttgcatgg aaattatgaa aaggaacatc  900
```

```
gctacctatg aagaacagtt agttgccctg tatggaacga acatggatat tgtagggtca  960
ggtggatctg gaggtagctc ttctgtgacc ggctggcggc tgtgcgaacg cattctggct  1020

SEQ ID NO: 552         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 552
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGS ASGGSGGSGM YESFIESLPF  180
LKSLEFSARL KVVDVIGTKV YNDGEQIIAQ GDSADSFFII ESGEVKITMK RKGKSEVEEN  240
GAVEIARCSR GQYFGELALV TNKPRAASAH AIGTVKCLAM DVQAFERLLG PCMEIMKRNI  300
ATYEEQLVAL YGTNMDIVGS GGSGGSSSVT GWRLCERILA                       340

SEQ ID NO: 553         moltype = DNA  length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 553
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggagtg  480
accggctggc ggctgtgcga aagcgctagc ggaggttcag gcggttccgg aatgtatgaa  540
agctttattg agtcactgcc attccttaaa tctttggagt ttctgcacg cctgaaagta  600
gtagatgtga taggcaccaa agtatacaac gatggagaac aaatcattgc tcagggagat  660
tcggctgatt ctttttcat tattgaatct ggagaagtga aaattactat gaaaagaaag  720
ggtaaatcag aagtggaaga gaatggtgca gtagaaatcg ctcgatgctc gcggggacag  780
tactttggag agcttgccct ggtaactaac aaacctcgag cagcttctgc ccacgccatt  840
gggactgtca aatgtttagc aatggatgtg caagcatttg aaaggcttct gggaccttgc  900
atggaaatta tgaaaaggaa catcgctacc tatgaagaac agttagttgc cctgtatgga  960
acgaacatgg atattgtagg gtcaggtgga tctggaggta gctcttctcg cattctggct  1020

SEQ ID NO: 554         moltype = AA  length = 340
FEATURE                Location/Qualifiers
REGION                 1..340
                       note = Description of Artificial Sequence: Synthetic
                        polypeptide
source                 1..340
                       mol_type = protein
                       organism = synthetic construct
SEQUENCE: 554
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCESAS GGSGGSGMYE  180
SFIESLPFLK SLEFSARLKV VDVIGTKVYN DGEQIIAQGD SADSFFIIES GEVKITMKRK  240
GKSEVEENGA VEIARCSRGQ YFGELALVTN KPRAASAHAI GTVKCLAMDV QAFERLLGPC  300
MEIMKRNIAT YEEQLVALYG TNMDIVGSGG SGGSSSRILA                       340

SEQ ID NO: 555         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 555
atgggtgtgt ccagtttgtt tcagaatctc ggggtgtccg taactccgat ccaaaggatt  60
gtcctgagcg gtgaaaatgg gctgaagatc gacatccatg tcatcatccc gtatgaaggt  120
ctgagcggcg accaaatggg ccagatcgaa aaaattttta aggtggtgta ccctgtggat  180
gatcatcact ttaaggtgat cctgcactat ggcacactgg taatcgacgg ggttacgccg  240
aacatgatcg actatttcgg acggccgtat gaaggcatcg ccgtgttcga cggcaaaaag  300
atcactgtaa cagggaccct gtggaacggc aacaaaatta tcgacgagcg cctgatcaac  360
cccgacggct ccctgctgtt ccgagtaacc atcaacggag tgaccggctg gcggctgtgc  420
gaacgcattc tggctagctc aagcggaggt tcaggcggtt ccggaatgta tgaaagcttt  480
```

-continued

```
attgagtcac tgccattcct taaatctttg gagttttctg cacgcctgaa agtagtagat  540
gtgataggca ccaaagtata caacgatgga gaacaaatca ttgctcaggg agattcggct  600
gattcttttt tcattattga atctggagaa gtgaaaatta ctatgaaaag aaagggtaaa  660
tcagaagtgg aagagaatgg tgcagtagaa atcgctcgat gctcgcgggg acagtacttt  720
ggagagcttg ccctggtaac taacaaacct cgagcagctt ctgcccacgc cattgggact  780
gtcaaatgtt tagcaatgga tgtgcaagca tttgaaaggc ttctgggacc ttgcatggaa  840
attatgaaaa ggaacatcgc tacctatgaa gaacagttag ttgccctgta tggaacgaac  900
atggatattg tagggtcagg tggatctgga ggtagctctt ctatggtctt cacactcgaa  960
gatttcgttg gggactggcg acagacagcc ggctacaacc tggaccaagt ccttgaacag  1020
gga                                                                1023

SEQ ID NO: 556         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 556
MGVSSLFQNL GVSVTPIQRI VLSGENGLKI DIHVIIPYEG LSGDQMGQIE KIFKVVYPVD  60
DHHFKVILHY GTLVIDGVTP NMIDYFGRPY EGIAVFDGKK ITVTGTLWNG NKIIDERLIN  120
PDGSLLFRVT INGVTGWRLC ERILASSSGG SGGSGMYESF IESLPFLKSL EFSARLKVVD  180
VIGTKVYNDG EQIIAQGDSA DSFFIIESGE VKITMKRKGK SEVEENGAVE IARCSRGQYF  240
GELALVTNKP RAASAHAIGT VKCLAMDVQA FERLLGPCME IMKRNIATYE EQLVALYGTN  300
MDIVGSGGSG GSSSMVFTLE DFVGDWRQTA GYNLDQVLEQ G                      341

SEQ ID NO: 557         moltype = DNA  length = 1023
FEATURE                Location/Qualifiers
misc_feature           1..1023
                       note = Description of Artificial Sequence: Synthetic
                        polynucleotide
source                 1..1023
                       mol_type = other DNA
                       organism = synthetic construct
SEQUENCE: 557
atggtcctga gcggtgaaaa tggcctgaag atcgacatcc atgtcatcat cccgtatgaa  60
ggtctgagcg gcgaccaaat gggccagatc gaaaaaattt ttaaggtggt gtaccctgtg  120
gatgatcatc actttaaggt gatcctgcac tatggcacac tggtaatcga cggggttacg  180
ccgaacatga tcgactattt cggacggccg tatgaaggca tcgccgtgtt cgacggcaaa  240
aagatcactg taacagggac cctgtggaac ggcaacaaaa ttatcgacga gcgcctgatc  300
aaccccgacg gctccctgct gttccgagta accatcaacg gagtgaccgg ctggcggctg  360
tgcgaacgca ttctggctag ctcaagcgga ggttcaggcg gttccggaat gtatgaaagc  420
tttattgagt cactgccatt ccttaaatct ttggagtttt ctgcacgcct gaaagtagta  480
gatgtgatag gcaccaaagt atacaacgat ggagaacaaa tcattgctca gggagattcg  540
gctgattctt ttttcattat tgaatctgga gaagtgaaaa ttactatgaa aagaaagggt  600
aaatcagaag tggaagagaa tggtgcagta gaaatcgctc gatgctcgcg gggacagtac  660
tttggagagc ttgccctggt aactaacaaa cctcgagcag cttctgccca cgccattggg  720
actgtcaaat gtttagcaat ggatgtgcaa gcatttgaaa ggcttctggg accttgcatg  780
gaaattatga aaaggaacat cgctacctat gaagaacagt tagttgccct gtatggaacg  840
aacatggata ttgtagggtc aggtggatct ggaggtagct cttctatggt cttcacactc  900
gaagatttcg ttggggactg gcgacagaca gccggctaca acctggacca agtccttgaa  960
cagggaggtg tgtccagttt gtttcagaat ctcggggtgt ccgtaactcc gatccaaagg  1020
att                                                                1023

SEQ ID NO: 558         moltype = AA  length = 341
FEATURE                Location/Qualifiers
REGION                 1..341
                       note = Description of Artificial Sequence: Synthetic
                        polypeptide
source                 1..341
                       mol_type = protein
                       organism = synthetic construct
SEQUENCE: 558
MVLSGENGLK IDIHVIIPYE GLSGDQMGQI EKIFKVVYPV DDHHFKVILH YGTLVIDGVT  60
PNMIDYFGRP YEGIAVFDGK KITVTGTLWN GNKIIDERLI NPDGSLLFRV TINGVTGWRL  120
CERILASSSG GSGGSGMYES FIESLPFLKS LEFSARLKVV DVIGTKVYND GEQIIAQGDS  180
ADSFFIIESG EVKITMKRKG KSEVEENGAV EIARCSRGQY FGELALVTNK PRAASAHAIG  240
TVKCLAMDVQ AFERLLGPCM EIMKRNIATY EEQLVALYGT NMDIVGSGGS GGSSSMVFTL  300
EDFVGDWRQT AGYNLDQVLE QGGVSSLFQN LGVSVTPIQR I                      341

SEQ ID NO: 559         moltype = DNA  length = 1026
FEATURE                Location/Qualifiers
misc_feature           1..1026
                       note = Description of Artificial Sequence: Synthetic
                        polynucleotide
source                 1..1026
                       mol_type = other DNA
                       organism = synthetic construct
```

```
SEQUENCE: 559
atggacgggg ttacgccgaa catgatcgac tatttcggac ggccgtatga aggcatcgcc  60
gtgttcgacg gcaaaaagat cactgtaaca gggaccctgt ggaacggcaa caaaattatc  120
gacgagcgcc tgatcaaccc cgacggctcc ctgctgttcc gagtaaccat caacggagtg  180
accggctggc ggctgtgcga acgcattctg gctagctcaa gcggaggttc aggcggttcc  240
ggaatgtatg aaagctttat tgagtcactg ccattcctta aatctttgga gttttctgca  300
cgcctgaaag tagtagatgt gataggcacc aaagtataca acgatggaga acaaatcatt  360
gctcagggag attcggctga ttctttttc attattgaat ctggagaagt gaaaattact  420
atgaaaagaa agggtaaatc agaagtggaa gagaatggtg cagtagaaat cgctcgatgc  480
tcgcggggac agtactttgg agagcttgcc ctggtaacta acaaacctcg agcagcttct  540
gcccacgcca ttgggactgt caaatgttta gcaatggatg tgcaagcatt tgaaaggctt  600
ctgggacctt gcatggaaat tatgaaaagg aacatcgcta cctatgaaga acagttagtt  660
gccctgtatg gaacgaacat ggatattgta gggtcaggtg gatctggagg tagctcttct  720
atggtcttca cactcgaaga tttcgttggg gactggcgac agacagccgg ctacaacctg  780
gaccaagtcc ttgaacaggg aggtgtgtcc agtttgtttc agaatctcgg ggtgtccgta  840
actccgatcc aaaggattgt cctgagcggt gaaaatgggc tgaagatcga catccatgtc  900
atcatcccgt atgaaggtct gagcggcgac caaatgggcc agatcgaaaa aatttttaag  960
gtggtgtacc ctgtggatga tcatcacttt aaggtgatcc tgcactatgg cacactggta  1020
atcgac                                                              1026

SEQ ID NO: 560         moltype = AA  length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 560
MDGVTPNMID YFGRPYEGIA VFDGKKITVT GTLWNGNKII DERLINPDGS LLFRVTINGV  60
TGWRLCERIL ASSSGGSGGS GMYESFIESL PFLKSLEFSA RLKVVDVIGT KVYNDGEQII  120
AQGDSADSFF IIESGEVKIT MKRKGKSEVE ENGAVEIARC SRGQYFGELA LVTNKPRAAS  180
AHAIGTVKCL AMDVQAFERL LGPCMEIMKR NIATYEEQLV ALYGTNMDIV GSGGSGGSSS  240
MVFTLEDFVG DWRQTAGYNL DQVLEQGGVS SLFQNLGVSV TPIQRIVLSG ENGLKIDIHV  300
IIPYEGLSGD QMGQIEKIFK VVYPVDDHHF KVILHYGTLV ID                     342

SEQ ID NO: 561         moltype = DNA  length = 1026
FEATURE                Location/Qualifiers
misc_feature           1..1026
                       note = Description of Artificial Sequence: Synthetic
                        polynucleotide
source                 1..1026
                       mol_type = other DNA
                       organism = synthetic construct
SEQUENCE: 561
atgggggtta cgccgaacat gatcgactat ttcggacggc cgtatgaagg catcgccgtg  60
ttcgacggca aaaagatcac tgtaacaggg accctgtgga acggcaacaa aattatcgac  120
gagcgcctga tcaaccccga cggctccctg ctgttccgag taaccatcaa cggagtgacc  180
ggctggcggc tgtgcgaacg cattctggct agctcaagcg gaggttcagg cggttccgga  240
atgtatgaaa gctttattga gtcactgcca ttccttaaat ctttggagtt ttctgcacgc  300
ctgaaagtag tagatgtgat aggcaccaaa gtatacaacg atggagaaca aatcattgct  360
cagggagatt cggctgattc tttttcatt attgaatctg gagaagtgaa aattactatg  420
aaaagaaagg gtaaatcaga agtggaagag aatggtgcag tagaaatcgc tcgatgctcg  480
cggggacagt actttggaga gcttgccctg gtaactaaca aacctcgagc agcttctgcc  540
cacgccattg ggactgtcaa atgtttagca atggatgtgc aagcatttga aaggcttctg  600
ggaccttgca tggaaattat gaaaaggaac atcgctacct atgaagaaca gttagttgcc  660
ctgtatggaa cgaacatgga tattgtaggg tcaggtggat ctggaggtag ctcttctatg  720
gtcttcacac tcgaagattt cgttggggac tggcgacaga cagccggcta caacctggac  780
caagtccttg aacagggagg tgtgtccagt ttgtttcaga atctcggggt gtccgtaact  840
ccgatccaaa ggattgtcct gagcggtgaa aatgggctga agatcgacat ccatgtcatc  900
atcccgtatg aaggtctgag cggcgaccaa atgggccaga tcgaaaaaat ttttaaggtg  960
gtgtaccctg tggatgatca tcactttaag gtgatcctgc actatggcac actggtaatc  1020
gacggg                                                              1026

SEQ ID NO: 562         moltype = AA  length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 562
MGVTPNMIDY FGRPYEGIAV FDGKKITVTG TLWNGNKIID ERLINPDGSL LFRVTINGVT  60
GWRLCERILA SSSGGSGGSG MYESFIESLP FLKSLEFSAR LKVVDVIGTK VYNDGEQIIA  120
QGDSADSFFI IESGEVKITM KRKGKSEVEE NGAVEIARCS RGQYFGELAL VTNKPRAASA  180
HAIGTVKCLA MDVQAFERLL GPCMEIMKRN IATYEEQLVA LYGTNMDIVG SGGSGGSSSM  240
VFTLEDFVGD WRQTAGYNLD QVLEQGGVSS LFQNLGVSVT PIQRIVLSGE NGLKIDIHVI  300
IPYEGLSGDQ MGQIEKIFKV VYPVDDHHFK VILHYGTLVI DG                     342
```

```
SEQ ID NO: 563          moltype = DNA  length = 1026
FEATURE                 Location/Qualifiers
misc_feature            1..1026
                        note = Description of Artificial Sequence: Synthetic
                         polynucleotide
source                  1..1026
                        mol_type = other DNA
                        organism = synthetic construct
SEQUENCE: 563
atggttacgc cgaacatgat cgactatttc ggacggccgt atgaaggcat cgccgtgttc  60
gacggcaaaa agatcactgt aacagggacc ctgtggaacg gcaacaaaat tatcgacgag  120
cgcctgatca accccgacgg ctccctgctg ttccgagtaa ccatcaacgg agtgaccggc  180
tggcggctgt gcgaacgcat tctggctagc tcaagcggag gttcaggcgg ttccggaatg  240
tatgaaagct ttattgagtc actgccattc cttaaatctt tggagttttc tgcacgcctg  300
aaagtagtag atgtgatagg caccaaagta tacaacgatg gagaacaaat cattgctcag  360
ggagattcgg ctgattcttt tttcattatt gaatctggag aagtgaaaat tactatgaaa  420
agaaagggta aatcagaagt ggaagagaat ggtgcagtag aaatcgctcg atgctcgcgg  480
ggacagtact ttggagagct tgccctggta actaacaaac ctcgagcagc ttctgcccac  540
gccattggga ctgtcaaatg tttagcaatg gatgtgcaag catttgaaag gcttctggga  600
ccttgcatgg aaattatgaa aaggaacatc gctacctatg aagaacagtt agttgccctg  660
tatggaacga acatggatat tgtagggtca ggtggatctg gaggtagctc ttctatggtc  720
ttcacactcg aagatttcgt tggggactgg cgacagacag ccggctacaa cctggaccaa  780
gtccttgaac agggaggtgt gtccagtttg tttcagaatc tcggggtgtc cgtaactccg  840
atccaaagga ttgtcctgag cggtgaaaat gggctgaaga tcgacatcca tgtcatcatc  900
ccgtatgaag gtctgagcgg cgaccaaatg ggccagatcg aaaaaatttt taaggtggtg  960
taccctgtgg atgatcatca ctttaaggtg atcctgcact atggcacact ggtaatcgac  1020
ggggtt                                                              1026

SEQ ID NO: 564          moltype = AA  length = 342
FEATURE                 Location/Qualifiers
REGION                  1..342
                        note = Description of Artificial Sequence: Synthetic
                         polypeptide
source                  1..342
                        mol_type = protein
                        organism = synthetic construct
SEQUENCE: 564
MVTPNMIDYF GRPYEGIAVF DGKKITVTGT LWNGNKIIDE RLINPDGSLL FRVTINGVTG  60
WRLCERILAS SSGGSGGSGM YESFIESLPF LKSLEFSARL KVVDVIGTKV YNDGEQIIAQ  120
GDSADSFFII ESGEVKITMK RKGKSEVEEN GAVEIARCSR GQYFGELALV TNKPRAASAH  180
AIGTVKCLAM DVQAFERLLG PCMEIMKRNI ATYEEQLVAL YGTNMDIVGS GGSGGSSSMV  240
FTLEDFVGDW RQTAGYNLDQ VLEQGGVSSL FQNLGVSVTP IQRIVLSGEN GLKIDIHVII  300
PYEGLSGDQM GQIEKIFKVV YPVDDHHFKV ILHYGTLVID GV                      342

SEQ ID NO: 565          moltype = DNA  length = 1026
FEATURE                 Location/Qualifiers
misc_feature            1..1026
                        note = Description of Artificial Sequence: Synthetic
                         polynucleotide
source                  1..1026
                        mol_type = other DNA
                        organism = synthetic construct
SEQUENCE: 565
atgatcaacc ccgacggctc cctgctgttc cgagtaacca tcaacggagt gaccggctgg  60
cggctgtgcg aacgcattct ggctagctca agcggaggtt caggcggttc cggaatgtat  120
gaaagcttta ttgagtcact gccattcctt aaatctttgg agttttctgc acgcctgaaa  180
gtagtagatg tgataggcac caaagtatac aacgatggag aacaaatcat tgctcaggga  240
gattcggctg attctttttt cattattgaa tctggagaag tgaaaattac tatgaaaaga  300
aagggtaaat cagaagtgga agagaatggt gcagtagaaa tcgctcgatg ctcgcgggga  360
cagtactttg gagagcttgc cctggtaact aacaaacctc gagcagcttc tgcccacgcc  420
attgggactg tcaaatgttt agcaatggat gtgcaagcat ttgaaaggct tctgggacct  480
tgcatggaaa ttatgaaaag gaacatcgct acctatgaag aacagttagt tgccctgtat  540
ggaacgaaca tggatattgt agggtcaggt ggatctggag gtagctcttc tatggtcttc  600
acactcgaag atttcgttgg ggactggcga cagacagccg gctacaacct ggaccaagtc  660
cttgaacagg gaggtgtgtc cagtttgttt cagaatctcg gggtgtccgt aactccgatc  720
caaaggattg tcctgagcgg tgaaaatggg ctgaagatcg acatccatgt catcatcccg  780
tatgaaggtc tgagcggcga ccaaatgggc cagatcgaaa aaatttttaa ggtggtgtac  840
cctgtggatg atcatcactt taaggtgatc ctgcactatg gcacactggt aatcgacggg  900
gttacgccga acatgatcga ctatttcgga cggccgtatg aaggcatcgc cgtgttcgac  960
ggcaaaaaga tcactgtaac agggaccctg tggaacggca acaaaattat cgacgagcgc  1020
ctgatc                                                              1026

SEQ ID NO: 566          moltype = AA  length = 342
FEATURE                 Location/Qualifiers
REGION                  1..342
                        note = Description of Artificial Sequence: Synthetic
                         polypeptide
source                  1..342
```

```
                         mol_type = protein
                         organism = synthetic construct
SEQUENCE: 566
MINPDGSLLF RVTINGVTGW RLCERILASS SGGSGGSGMY ESFIESLPFL KSLEFSARLK  60
VVDVIGTKVY NDGEQIIAQG DSADSFFIIE SGEVKITMKR KGKSEVEENG AVEIARCSRG  120
QYFGELALVT NKPRAASAHA IGTVKCLAMD VQAFERLLGP CMEIMKRNIA TYEEQLVALY  180
GTNMDIVGSG GSGGSSMVF TLEDFVGDWR QTAGYNLDQV LEQGGVSSLF QNLGVSVTPI  240
QRIVLSGENG LKIDIHVIIP YEGLSGDQMG QIEKIFKVVY PVDDHHFKVI LHYGTLVIDG  300
VTPNMIDYFG RPYEGIAVFD GKKITVTGTL WNGNKIIDER LI                    342

SEQ ID NO: 567           moltype = DNA  length = 1026
FEATURE                  Location/Qualifiers
misc_feature             1..1026
                         note = Description of Artificial Sequence: Synthetic
                          polynucleotide
source                   1..1026
                         mol_type = other DNA
                         organism = synthetic construct
SEQUENCE: 567
atgggctccc tgctgttccg agtaaccatc aacggagtga ccggctggcg gctgtgcgaa  60
cgcattctgg ctagctcaag cggaggttca ggcggttccg gaatgtatga aagctttatt  120
gagtcactgc cattccttaa atctttggag ttttctgcac gcctgaaagt agtagatgtg  180
ataggcacca aagtatacaa cgatggagaa caaatcattg ctcagggaga ttcggctgat  240
tctttttca ttattgaatc tggagaagtg aaaattacta tgaaaagaaa gggtaaatca  300
gaagtggaag agaatggtgc agtagaaatc gctcgatgct cgcggggaca gtactttgga  360
gagcttgccc tggtaactaa caaacctcga gcagcttctg cccacgccat tgggactgtc  420
aaatgtttag caatggatgt gcaagcattt gaaaggcttc tgggaccttg catggaaatt  480
atgaaaagga acatcgctac ctatgaagaa cagttagttg ccctgtatgg aacgaacatg  540
gatattgtag ggtcaggtgg atctggaggt agctcttcta tggtcttcac actcgaagat  600
ttcgttgggg actggcgaca gacagccggc tacaacctgg accaagtcct tgaacaggga  660
ggtgtgtcca gtttgtttca gaatctcggg gtgtccgtaa ctccgatcca aaggattgtc  720
ctgagcggtg aaaatgggct gaagatcgac atccatgtca tcatcccgta tgaaggtctg  780
agcggcgacc aaatgggcca gatcgaaaaa atttttaagg tggtgtaccc tgtggatgat  840
catcacttta aggtgatcct gcactatggc acactggtaa tcgacggggt tacgccgaac  900
atgatcgact atttcggacg gccgtatgaa ggcatcgccg tgttcgacgg caaaaagatc  960
actgtaacag ggaccctgtg gaacggcaac aaaattatcg acgagcgcct gatcaacccc  1020
gacggc                                                            1026

SEQ ID NO: 568           moltype = AA  length = 342
FEATURE                  Location/Qualifiers
REGION                   1..342
                         note = Description of Artificial Sequence: Synthetic
                          polypeptide
source                   1..342
                         mol_type = protein
                         organism = synthetic construct
SEQUENCE: 568
MGSLLFRVTI NGVTGWRLCE RILASSSGGS GGSGMYESFI ESLPFLKSLE FSARLKVVDV  60
IGTKVYNDGE QIIAQGDSAD SFFIIESGEV KITMKRKGKS EVEENGAVEI ARCSRGQYFG  120
ELALVTNKPR AASAHAIGTV KCLAMDVQAF ERLLGPCMEI MKRNIATYEE QLVALYGTNM  180
DIVGSGGSGG SSSMVFTLED FVGDWRQTAG YNLDQVLEQG GVSSLFQNLG VSVTPIQRIV  240
LSGENGLKID IHVIIPYEGL SGDQMGQIEK IFKVVYPVDD HHFKVILHYG TLVIDGVTPN  300
MIDYFGRPYE GIAVFDGKKI TVTGTLWNGN KIIDERLINP DG                    342

SEQ ID NO: 569           moltype = DNA  length = 1026
FEATURE                  Location/Qualifiers
misc_feature             1..1026
                         note = Description of Artificial Sequence: Synthetic
                          polynucleotide
source                   1..1026
                         mol_type = other DNA
                         organism = synthetic construct
SEQUENCE: 569
atgaacggag tgaccggctg gcggctgtgc gaacgcattc tggctagctc aagcggaggt  60
tcaggcggtt ccggaatgta tgaaagcttt attgagtcac tgccattcct taaatctttg  120
gagttttctg cacgcctgaa agtagtagat gtgataggca ccaaagtata caacgatgga  180
gaacaaatca ttgctcaggg agattcggct gattcttttt tcattattga atctggagaa  240
gtgaaaatta ctatgaaaag aaagggtaaa tcagaagtgg aagagaatgg tgcagtagaa  300
atcgctcgat gctcgcgggg acagtacttt ggagagcttg ccctggtaac taacaaacct  360
cgagcagctt ctgcccacgc cattgggact gtcaaatgtt tagcaatgga tgtgcaagca  420
tttgaaaggc ttctgggacc ttgcatggaa attatgaaaa ggaacatcgc tacctatgaa  480
gaacagttag ttgccctgta tggaacgaac atggatattg tagggtcagg tggatctgga  540
ggtagctctt ctatggtctt cacactcgaa gatttcgttg gggactggcg acagacagcc  600
ggctacaacc tggaccaagt ccttgaacag ggaggtgtgt ccagtttgtt tcagaatctc  660
ggggtgtccg taactccgat ccaaaggatt gtcctgagcg gtgaaaatgg gctgaagatc  720
gacatccatg tcatcatccc gtatgaaggt ctgagcggcg accaaatggg ccagatcgaa  780
aaaattttta aggtggtgta ccctgtggat gatcatcact ttaaggtgat cctgcactat  840
ggcacactgg taatcgacgg ggttacgccg aacatgatcg actatttcgg acggccgtat  900
gaaggcatcg ccgtgttcga cggcaaaaag atcactgtaa cagggaccct gtggaacggc  960
```

-continued

```
aacaaaatta tcgacgagcg cctgatcaac cccgacggct ccctgctgtt ccgagtaacc  1020
atcaac                                                             1026

SEQ ID NO: 570         moltype = AA  length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 570
MNGVTGWRLC ERILASSSGG SGGSGMYESF IESLPFLKSL EFSARLKVVD VIGTKVYNDG  60
EQIIAQGDSA DSFFIIESGE VKITMKRKGK SEVEENGAVE IARCSRGQYF GELALVTNKP  120
RAASAHAIGT VKCLAMDVQA FERLLGPCME IMKRNIATYE EQLVALYGTN MDIVGSGGSG  180
GSSSMVFTLE DFVGDWRQTA GYNLDQVLEQ GGVSSLFQNL GVSVTPIQRI VLSGENGLKI  240
DIHVIIPYEG LSGDQMGQIE KIFKVVYPVD DHHFKVILHY GTLVIDGVTP NMIDYFGRPY  300
EGIAVFDGKK ITVTGTLWNG NKIIDERLIN PDGSLLFRVT IN                     342

SEQ ID NO: 571         moltype = DNA  length = 1026
FEATURE                Location/Qualifiers
misc_feature           1..1026
                       note = Description of Artificial Sequence: Synthetic
                        polynucleotide
source                 1..1026
                       mol_type = other DNA
                       organism = synthetic construct
SEQUENCE: 571
atggtgaccg gctggcggct gtgcgaacgc attctggcta gctcaagcgg aggttcaggc  60
ggttccggaa tgtatgaaag ctttattgag tcactgccat tccttaaatc tttggagttt  120
tctgcacgcc tgaaagtagt agatgtgata ggcaccaaag tatacaacga tggagaacaa  180
atcattgctc agggagattc ggctgattct tttttcatta ttgaatctgg agaagtgaaa  240
attactatga aaagaaaggg taaatcagaa gtggaagaga atggtgcagt agaaatcgct  300
cgatgctcgc ggggacagta ctttggagag cttgccctgg taactaacaa acctcgagca  360
gcttctgccc acgccattgg gactgtcaaa tgtttagcaa tggatgtgca agcatttgaa  420
aggcttctgg gaccttgcat ggaaattatg aaaaggaaca tcgctaccta tgaagaacag  480
ttagttgccc tgtatggaac gaacatggat attgtagggt caggtggatc tggaggtagc  540
tcttctatgg tcttcacact cgaagatttc gttggggact ggcgacagac agccggctac  600
aacctggacc aagtccttga acagggaggt gtgtccagtt tgtttcagaa tctcggggtg  660
tccgtaactc cgatccaaag gattgtcctg agcggtgaaa atgggctgaa gatcgacatc  720
catgtcatca tcccgtatga aggtctgagc ggcgaccaaa tgggccagat cgaaaaaatt  780
tttaaggtgg tgtaccctgt ggatgatcat cactttaagg tgatcctgca ctatggcaca  840
ctggtaatcg acggggttac gccgaacatg atcgactatt tcggacggcc gtatgaaggc  900
atcgccgtgt tcgacggcaa aaagatcact gtaacaggga ccctgtggaa cggcaacaaa  960
attatcgacg agcgcctgat caaccccgac ggctccctgc tgttccgagt aaccatcaac  1020
ggagtg                                                             1026

SEQ ID NO: 572         moltype = AA  length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 572
MVTGWRLCER ILASSSGGSG GSGMYESFIE SLPFLKSLEF SARLKVVDVI GTKVYNDGEQ  60
IIAQGDSADS FFIIESGEVK ITMKRKGKSE VEENGAVEIA RCSRGQYFGE LALVTNKPRA  120
ASAHAIGTVK CLAMDVQAFE RLLGPCMEIM KRNIATYEEQ LVALYGTNMD IVGSGGSGGS  180
SSMVFTLEDF VGDWRQTAGY NLDQVLEQGG VSSLFQNLGV SVTPIQRIVL SGENGLKIDI  240
HVIIPYEGLS GDQMGQIEKI FKVVYPVDDH HFKVILHYGT LVIDGVTPNM IDYFGRPYEG  300
IAVFDGKKIT VTGTLWNGNK IIDERLINPD GSLLFRVTIN GV                     342

SEQ ID NO: 573         moltype = DNA  length = 1026
FEATURE                Location/Qualifiers
misc_feature           1..1026
                       note = Description of Artificial Sequence: Synthetic
                        polynucleotide
source                 1..1026
                       mol_type = other DNA
                       organism = synthetic construct
SEQUENCE: 573
atgcgcattc tggctagctc aagcggaggt tcaggcggtt ccggaatgta tgaaagcttt  60
attgagtcac tgccattcct taaatctttg gagttttctg cacgcctgaa agtagtagat  120
gtgataggca ccaaagtata caacgatgga gaacaaatca ttgctcaggg agattcggct  180
gattcttttt tcattattga atctggagaa gtgaaaatta ctatgaaaag aaagggtaaa  240
tcagaagtgg aagagaatgg tgcagtagaa atcgctcgat gctcgcgggg acagtacttt  300
ggagagcttg ccctggtaac taacaaacct cgagcagctt ctgcccacgc cattgggact  360
gtcaaatgtt tagcaatgga tgtgcaagca tttgaaaggc ttctgggacc ttgcatggaa  420
```

-continued

```
attatgaaaa ggaacatcgc tacctatgaa gaacagttag ttgccctgta tggaacgaac  480
atggatattg tagggtcagg tggatctgga ggtagctctt ctatggtctt cacactcgaa  540
gatttcgttg gggactggcg acagacagcc ggctacaacc tggaccaagt ccttgaacag  600
ggaggtgtgt ccagtttgtt tcagaatctc ggggtgtccg taactccgat ccaaaggatt  660
gtcctgagcg gtgaaaatgg gctgaagatc gacatccatg tcatcatccc gtatgaaggt  720
ctgagcggcg accaaatggg ccagatcgaa aaaattttta aggtggtgta ccctgtggat  780
gatcatcact ttaaggtgat cctgcactat ggcacactgg taatcgacgg ggttacgccg  840
aacatgatcg actatttcgg acggccgtat gaaggcatcg ccgtgttcga cggcaaaaag  900
atcactgtaa cagggaccct gtggaacggc aacaaaatta tcgacgagcg cctgatcaac  960
cccgacggct ccctgctgtt ccgagtaacc atcaacggag tgaccggctg gcggctgtgc  1020
gaacgc                                                            1026

SEQ ID NO: 574         moltype = AA  length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 574
MRILASSSGG SGGSGMYESF IESLPFLKSL EFSARLKVVD VIGTKVYNDG EQIIAQGDSA  60
DSFFIIESGE VKITMKRKGK SEVEENGAVE IARCSRGQYF GELALVTNKP RAASAHAIGT  120
VKCLAMDVQA FERLLGPCME IMKRNIATYE EQLVALYGTN MDIVGSGGSG GSSSMVFTLE  180
DFVGDWRQTA GYNLDQVLEQ GGVSSLFQNL GVSVTPIQRI VLSGENGLKI DIHVIIPYEG  240
LSGDQMGQIE KIFKVVYPVD DHHFKVILHY GTLVIDGVTP NMIDYFGRPY EGIAVFDGKK  300
ITVTGTLWNG NKIIDERLIN PDGSLLFRVT INGVTGWRLC ER                    342

SEQ ID NO: 575         moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 575
gggtcaggtg gatctggagg tagctcttct                                  30

SEQ ID NO: 576         moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 576
agctcaagcg gaggttcagg cggttccgga                                  30

SEQ ID NO: 577         moltype = DNA  length = 377
FEATURE                Location/Qualifiers
source                 1..377
                       mol_type = genomic DNA
                       organism = Homo sapiens
SEQUENCE: 577
atgccgtccg agaagacctt caaacagcgc cggagcttcg aacaaagagt ggaagatgtc  60
cggctcatcc gggagcagca ccccaccaag atcccagtga ttatagagcg atacaagggt  120
gagaagcagc tgcccgtcct ggacaagacc agttccttgt acctgatcac gtgaatatga  180
gcgaactcat caagataatt agaaggcgcc tgcagctcaa tgctaaccaa gccttcttcc  240
tcctggtgaa tgggcacagc atggtgagtg tgtccacacc catctctgaa gtgtacgaga  300
gcgagagaga tgaagacggc ttcctgtaca tggtctatgc ctcccaggag acgttcggga  360
cagcactggc tgtgtaa                                                377

SEQ ID NO: 578         moltype = AA  length = 125
FEATURE                Location/Qualifiers
source                 1..125
                       mol_type = protein
                       organism = Homo sapiens
SEQUENCE: 578
MPSEKTFKQR RSFEQRVEDV RLIREQHPTK IPVIIERYKG EKQLPVLDKT KFLVPDHVNM  60
SELIKIIRRR LQLNANQAFF LLVNGHSMVS VSTPISEVYE SERDEDGFLY MVYASQETFG  120
TALAV                                                             125

SEQ ID NO: 579         moltype = AA  length = 6
FEATURE                Location/Qualifiers
REGION                 1..6
                       note = Description of Artificial Sequence: Synthetic peptide
source                 1..6
```

```
                         mol_type = protein
                         organism = synthetic construct
SEQUENCE: 579
GSAIVK                                                                     6

SEQ ID NO: 580           moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 580
NHGK                                                                       4

SEQ ID NO: 581           moltype = AA  length = 4
FEATURE                  Location/Qualifiers
REGION                   1..4
                         note = Description of Unknown: Caspase-3 cleavage sequence
source                   1..4
                         mol_type = protein
                         organism = unidentified
SEQUENCE: 581
SILM                                                                       4

SEQ ID NO: 582           moltype =   length =
SEQUENCE: 582
000

SEQ ID NO: 583           moltype =   length =
SEQUENCE: 583
000

SEQ ID NO: 584           moltype =   length =
SEQUENCE: 584
000

SEQ ID NO: 585           moltype =   length =
SEQUENCE: 585
000

SEQ ID NO: 586           moltype =   length =
SEQUENCE: 586
000

SEQ ID NO: 587           moltype =   length =
SEQUENCE: 587
000

SEQ ID NO: 588           moltype =   length =
SEQUENCE: 588
000

SEQ ID NO: 589           moltype =   length =
SEQUENCE: 589
000

SEQ ID NO: 590           moltype =   length =
SEQUENCE: 590
000

SEQ ID NO: 591           moltype =   length =
SEQUENCE: 591
000

SEQ ID NO: 592           moltype = DNA  length = 936
FEATURE                  Location/Qualifiers
misc_feature             1..936
                         note = Description of Artificial Sequence: Synthetic
                          polynucleotide
source                   1..936
                         mol_type = other DNA
                         organism = synthetic construct
SEQUENCE: 592
atggtgttta cactcgaaga tttcgtaggg gactggcggc agacagccgg ctacaacctg  60
gaccaagtcc ttgagcaggg cggtgtgtcc agtttgtttc agaatctcgg ggtgtccgta  120
actccgatcc aaaggattgt cctgagcggt gaaaacggcc tgaagatcga catccatgtc  180
atcatcccgt atgaaggtct gagcggcgat cagatgggcc agatcgaaaa aatttttaag  240
gtggtgtacc ctgtggatga tcatcacttt aaggtgattc tgcactatgg cacactggta  300
```

-continued

```
atcgacgggg ttacgccgaa catgatcgac tatttcggac ggccgtatga aggcatcgcc  360
gtgttcgacg gcaaaaagat cactgtaacc gggaccctgt ggaacggcaa caaaattatc  420
gacgagcgcc tgatcaaccc cgacggctcc ctgctgttcc gcgtaaccat caacggagtg  480
accggctggc ggctgtgcga gagaattttg gcgggctcga gcggaggtgg aggttcaggt  540
ggtggcggga gcggtggaat gccgtccgag aagaccttca aacagcgccg gagcttcgaa  600
caaagagtgg aagatgtccg gctcatccgg gagcagcacc ccaccaagat cccagtgatt  660
atagagcgat acaagggtga gaagcagctg cccgtcctgg acaagaccaa gttccttgta  720
cctgatcacg tgaatatgag cgaactcatc aagataatta gaaggcgcct gcagctcaat  780
gctaaccaag ccttcttcct cctggtgaat gggcacagca tggtgagtgt gtccacaccc  840
atctctgaag tgtacgagag cgagagagat gaagacggct tcctgtacat ggtctatgcc  900
tcccaggaga cgttcgggac agcactggct gtgtaa                              936

SEQ ID NO: 593         moltype = AA  length = 311
FEATURE                Location/Qualifiers
REGION                 1..311
                       note = Description of Artificial Sequence: Synthetic
                        polypeptide
source                 1..311
                       mol_type = protein
                       organism = synthetic construct
SEQUENCE: 593
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL AGSSGGGGSG  180
GGGSGGMPSE KTFKQRRSFE QRVEDVRLIR EQHPTKIPVI IERYKGEKQL PVLDKTKFLV  240
PDHVNMSELI KIIRRRLQLN ANQAFFLLVN GHSMVSVSTP ISEVYESERD EDGFLYMVYA  300
SQETFGTALA V                                                         311
```

*OPLOPHORUS*-DERIVED LUCIFERASES, NOVEL COELENTERAZINE SUBSTRATES, AND METHODS OF USE

CROSS REFERENCE TO RELATED APPLICATIONS

This application is a continuation of U.S. patent application Ser. No. 17/332,459, filed May 27, 2021, now U.S. Pat. No. 12,215,375, which is a continuation of U.S. patent application Ser. No. 17/011,597, filed Sep. 3, 2020, now U.S. Pat. No. 11,661,623, which is a continuation of U.S. patent application Ser. No. 15/948,070, filed Apr. 9, 2018, now U.S. Pat. No. 10,774,364, which is a continuation of U.S. patent application Ser. No. 14/160,282, filed Jan. 21, 2014, now U.S. Pat. No. 9,951,373, which is a divisional of U.S. patent application Ser. No. 13/287,986, filed Nov. 2, 2011, now U.S. Pat. No. 8,669,103, which claims priority to U.S. Provisional Application No. 61/409,422, filed Nov. 2, 2010, each of which is incorporated herein by reference in its entirety.

SEQUENCE LISTING

The instant application contains a Sequence Listing which has been submitted electronically in xml. format and is hereby incorporated by reference in its entirety. Said xml. copy was created on Jan. 11, 2024, named PRMG_33071_308_Sequence Listing.xml, and has 1,045, 154 bytes. No new matter has been added.

BACKGROUND

The luciferase secreted from the deep-sea shrimp *Oplophorus gracilirostris* has been shown to possess many interesting characteristics, such as high activity, high quantum yield, and broad substrate specificity (including, e.g., coelenterazine as well as various coelenterazine analogs). The bioluminescent reaction of *Oplophorus* takes place when the oxidation of coelenterazine (substrate) with molecular oxygen is catalyzed by *Oplophorus* luciferase, resulting in light of maximum intensity at 462 nm and the products $CO_2$ and coelenteramide (Shimomura et al., *Biochemistry,* 17:994 (1978)). Optimum luminescence occurs at pH 9 in the presence of 0.05-0.1 M NaCl at 40° C., and, due to the unusual resistance of this enzyme to heat, visible luminescence occurs at temperatures above 50° C. when the highly purified enzyme is used or at over 70° C. when partially purified enzyme is used. At pH 8.7, the native luciferase was reported by Shimomura et al. (1978) to have a molecular weight of approximately 130 kDa, apparently comprising four monomers of 31 kDa each; at lower pH, the native luciferase tends to polymerize.

Later work has shown that the *Oplophorus gracilirostris* luciferase is a complex of native 35 kDa and 19 kDa proteins, i.e., a heterotetramer consisting of two 19 kDa components and two 35 kDa components. Inouye et al. (2000) reported the molecular cloning of the cDNAs encoding the 35 kDa and 19 kDa proteins of *Oplophorus* luciferase, and the identification of the protein component that catalyzes the luminescence reaction. The cDNAs encoding the proteins were expressed in bacterial and mammalian cells, and the 19 kDa protein was identified as the component capable of catalyzing the luminescent oxidation of coelenterazine (Inouye et al., 2000).

The 19 kDa protein of *Oplophorus* luciferase (GenBank accession BAB13776, 196 amino acids) appears to be the smallest catalytic component having luciferase function, and its primary structure has no significant similarity with any reported luciferase including imidazopyrazinone luciferases (Lorenz et al., *PNAS USA,* 88:4438 (1991); Thompson et al., *PNAS USA,* 86:6567 (1989)). Expression of the 19 kDa protein in *E. coli* resulted in the formation of inclusion bodies (Inouye and Sasaki, *Protein Expression and Purification,* 56:261-268 (2007)). The formation of inclusion bodies is likely due to the instability of the protein.

The substrate specificity of *Oplophorus* luciferase is unexpectedly broad (Inouye and Shimomura. *BBRC,* 223: 349 (1997)). For instance, bisdeoxycoelenterazine (i.e., coelenterazine-hh), an analog of coelenterazine, is an excellent substrate for *Oplophorus* luciferase comparable to coelenterazine (Nakamura et al., *Tetrahedron Lett.,* 38:6405 (1997)). Moreover, *Oplophorus* luciferase is a secreted enzyme, like the luciferase of the marine ostracod *Cypridina* (*Vargula*) *hilgendorfii* (Johnson and Shimomura, *Meth. Enzyme,* 57:331 (1978)), which also uses an imidazopyrazinone-type luciferin to emit light.

SUMMARY

In an aspect, the disclosure relates to a compound of formula (Ia) or (Ib):

(Ia)

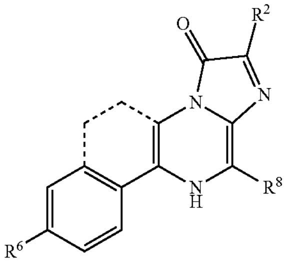

or (Ib)

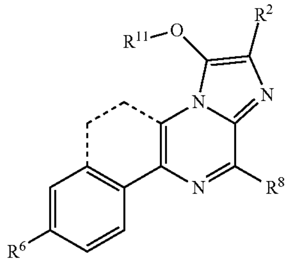

wherein $R^2$ is selected from the group consisting of

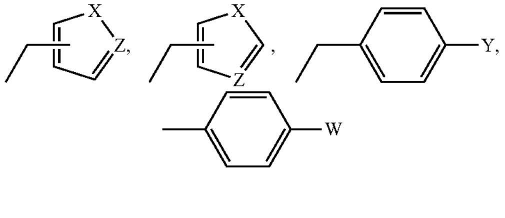

or $C_{2-5}$ straight chain alkyl;

$R^6$ is selected from the group consisting of —H, —OH, —$NH_2$, —OC(O)R or —$OCH_2OC(O)R$;

$R^8$ is selected from the group consisting of

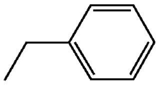, 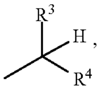,

H or lower cycloalkyl;

wherein $R^3$ and $R^4$ are both H or both $C_{1-2}$ alkyl;

W is —$NH_2$, halo, —OH, —NHC(O)R, —$CO_2R$;

X is —S—, —O— or —$NR^{22}$—;

Y is —H, —OH, or —$OR^{11}$;

Z is —CH— or —N—;

each $R^{11}$ is independently —C(O)R" or —$CH_2OC(O)R$";

$R^{22}$ is H, $CH_3$ or $CH_2CH_3$;

each R is independently $C_{1-7}$ straight-chain alkyl or $C_{1-7}$ branched alkyl;

R" is $C_{1-7}$ straight-chain alkyl or $C_{1-7}$ branched alkyl;

the dashed bonds indicate the presence of an optional ring, which may be saturated or unsaturated;

with the proviso that when $R^2$ is

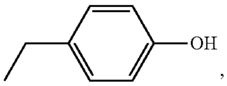, 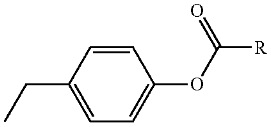, or

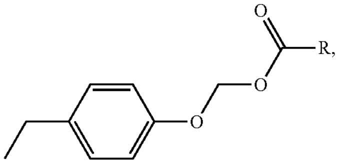

$R^8$ is not

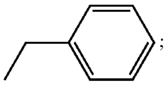;

with the proviso that when $R^2$ is

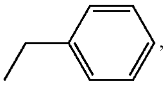, $R^8$ is

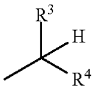

or lower cycloalkyl;

with the proviso that when $R^6$ is $NH_2$, $R^2$ is,

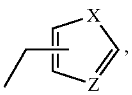, or $C_{2-5}$ alkyl;

or $R^8$ is not

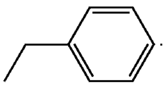.

In another aspect, the disclosure relates to a compound selected from

3882

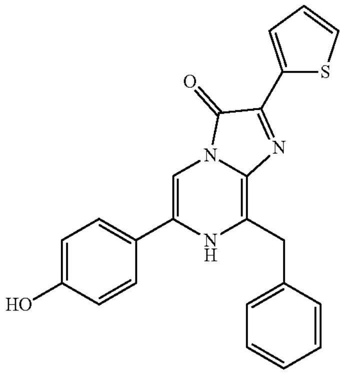

3881

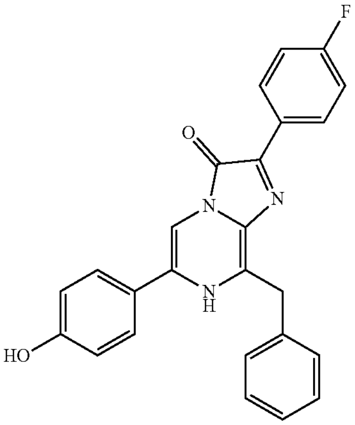

3899

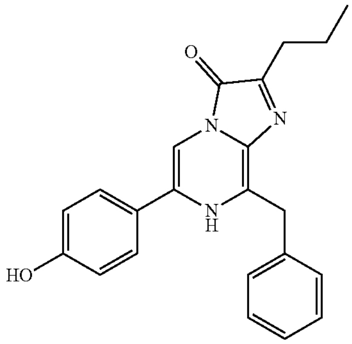

-continued
3900
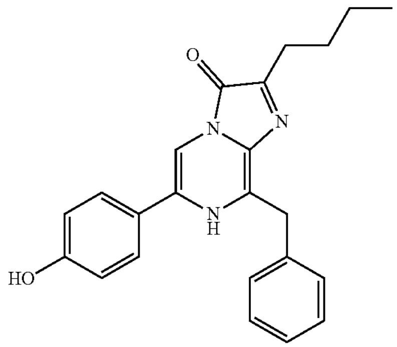
3945
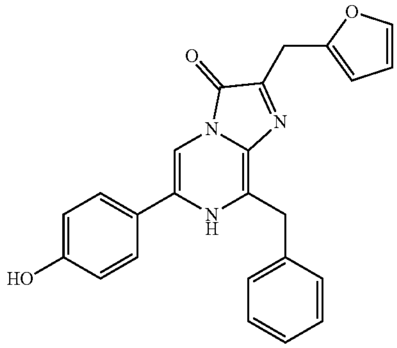
4002
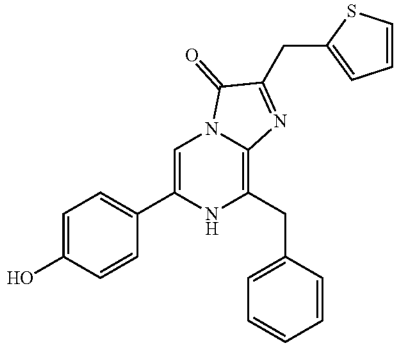
3840
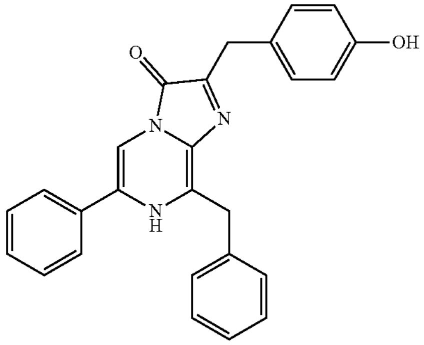
-continued
3886
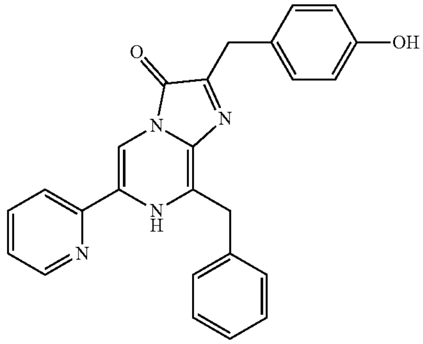
3857
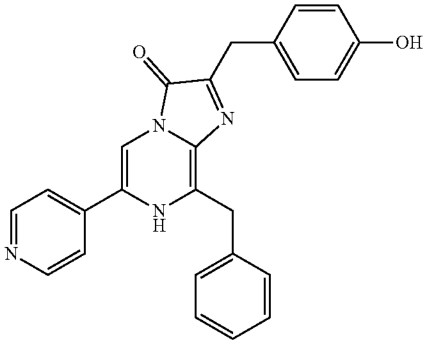
3887
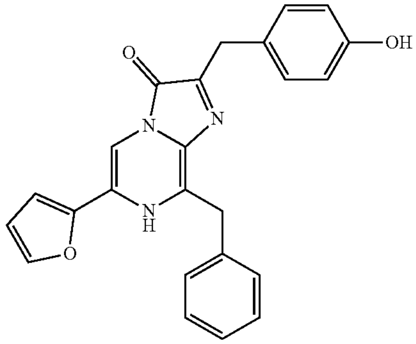
3913
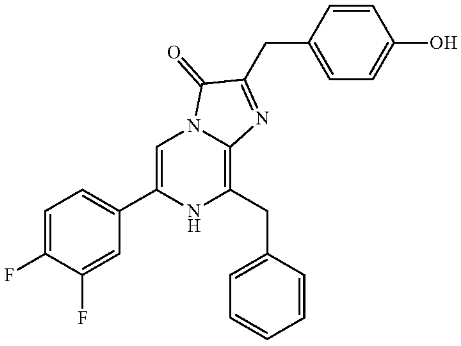

-continued
3932
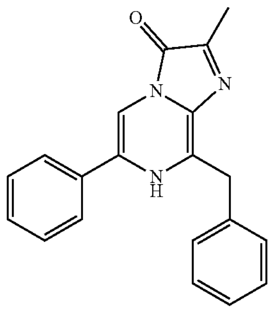
3925
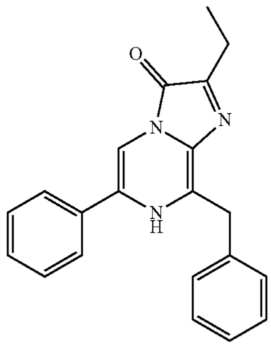
3933
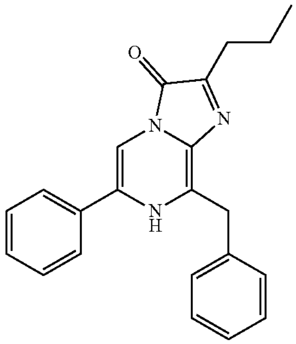
3946
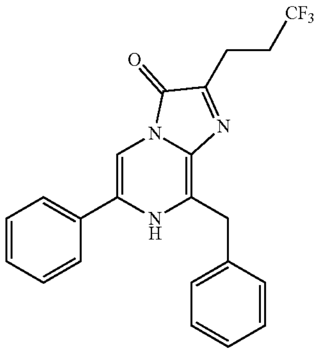
-continued
3889
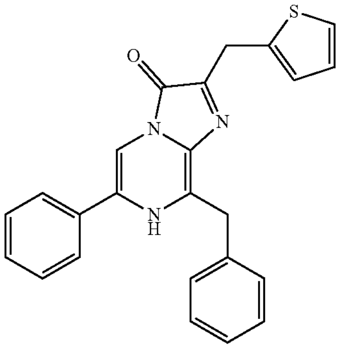
3939
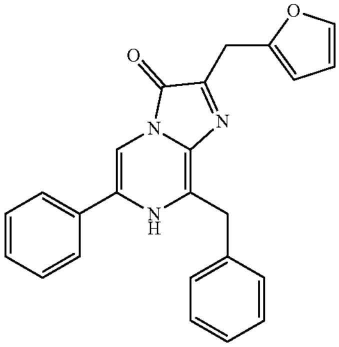
3894
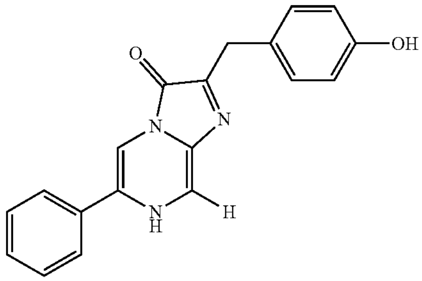
3896
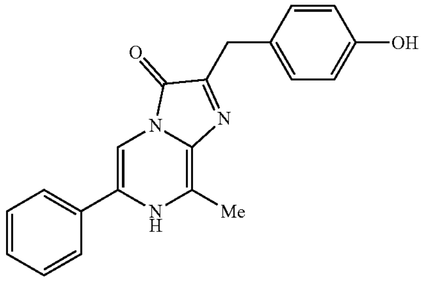
3897
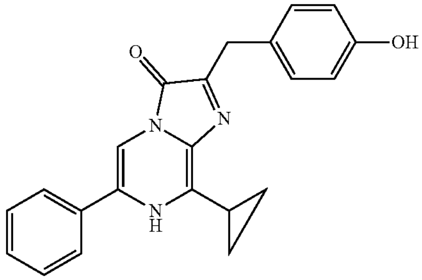

-continued

3841

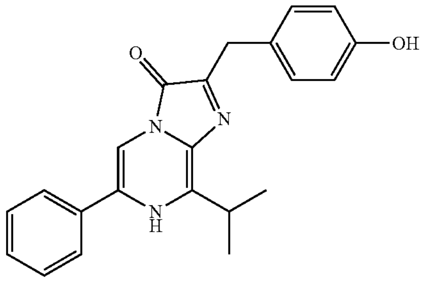

3842

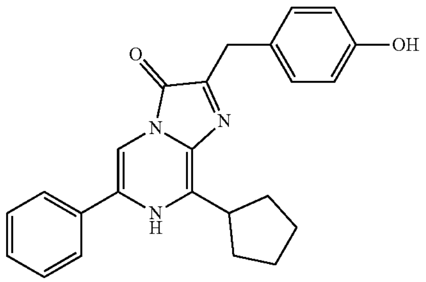

4525

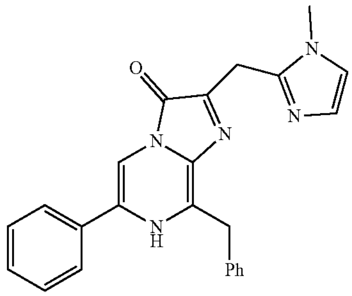

4540

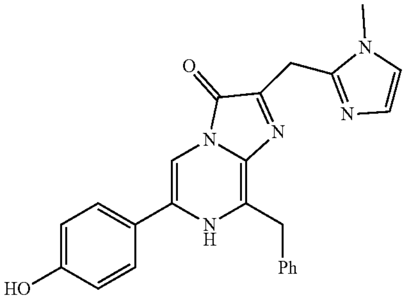

4541

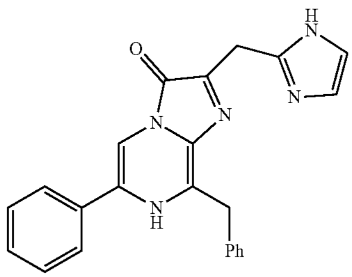

-continued

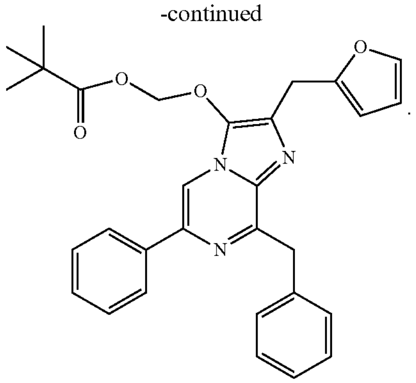

In an aspect, the disclosure relates to a compound of formula

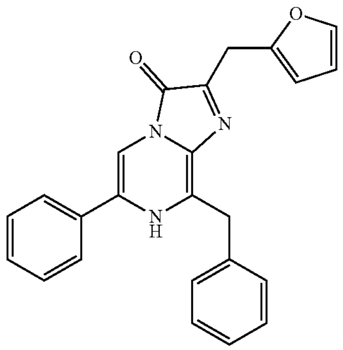

or

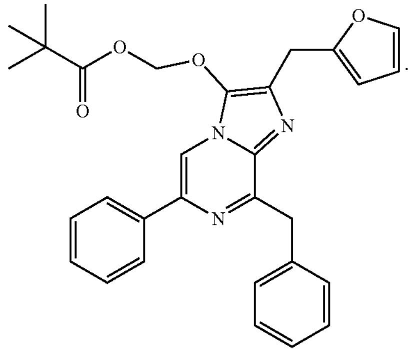

In an aspect, the disclosure relates to an isolated polynucleotide encoding an OgLuc variant polypeptide having at least 60% amino acid sequence identity to SEQ ID NO: 1 comprising at least one amino acid substitution at a position corresponding to an amino acid in SEQ ID NO: 1 wherein the OgLuc variant polypeptide has enhanced luminescence.

In an aspect, the disclosure relates to an isolated polynucleotide encoding an OgLuc variant polypeptide having at least 60% amino acid sequence identity to SEQ ID NO: 1 comprising at least one amino acid substitution at a position corresponding to an amino acid in SEQ ID NO: 1 wherein the OgLuc variant polypeptide has enhanced luminescence relative to an OgLuc polypeptide of SEQ ID NO: 3 with the proviso that the polypeptide encoded by the polynucleotide is not one of those listed in Table 47.

In an aspect, the disclosure relates to an isolated polynucleotide encoding an OgLuc variant polypeptide having at least 60% amino acid sequence identity to SEQ ID NO: 1 comprising at least one amino acid substitution at a position corresponding to an amino acid in SEQ ID NO: 1 wherein the OgLuc variant polypeptide has enhanced luminescence relative to a polypeptide of SEQ ID NO: 31 with the proviso that the polypeptide encoded by the polynucleotide is not SEQ ID NO: 3 or 15.

In an aspect, the disclosure relates to an isolated polynucleotide encoding an OgLuc variant polypeptide having at least 60% amino acid sequence identity to SEQ ID NO: 1 comprising at least one amino acid substitution at a position corresponding to an amino acid in SEQ ID NO: 1 wherein the OgLuc variant polypeptide has enhanced luminescence relative to a polypeptide of SEQ ID NO: 29 with the proviso that the polypeptide encoded by the polynucleotide is not SEQ ID NO: 3 or 15.

In an aspect, the disclosure relates to an isolated polynucleotide encoding an OgLuc variant polypeptide having at least 80% amino acid sequence identity to an OgLuc polypeptide of SEQ ID NO: 1 comprising amino acid substitutions A4E, Q11R, A33K, V44I, P115E, Q124K, Y138I, N166R, I90V, F54I, Q18L, F68Y, L72Q, and M75K corresponding to SEQ ID NO: 1 and the OgLuc variant polypeptide having luciferase activity.

In an aspect, the disclosure relates to an isolated polynucleotide encoding an OgLuc variant polypeptide having at least 80% amino acid sequence identity to an OgLuc polypeptide of SEQ ID NO: 1, wherein the amino acid at position 4 is glutamate, at position 11 is arginine, at position 18 is leucine, at position 33 is lysine, at position 44 is isoleucine, at position 54 is isoleucine, at position 68 is tyrosine, at position 72 is glutamine, at position 75 is lysine, at position 90 is valine, at position 115 is glutamate, at position 124 is lysine, at position 138 is isoleucine, and at position 166 is arginine corresponding to SEQ ID NO: 1 and the OgLuc variant polypeptide having luciferase activity.

In an aspect, the disclosure relates to an isolated polynucleotide encoding an OgLuc variant polypeptide having at least 80% amino acid sequence identity to an OgLuc polypeptide of SEQ ID NO: 1 comprising amino acid substitutions A4E, Q11R, A33K, V44I, P115E, Q124K, Y138I, N166R, Q18L, F54I, L92H, and Y109F corresponding to SEQ ID NO: 1 and the OgLuc variant polypeptide having luciferase activity.

In an aspect, the disclosure relates to an isolated polynucleotide encoding an OgLuc variant polypeptide having at least 80% amino acid sequence identity to an OgLuc polypeptide of SEQ ID NO: 1 comprising amino acid substitutions A4E, Q11R, A33K, V44I, A54I, F77Y, I90V, P115E, Q124K, Y138I and N166R corresponding to SEQ ID NO: 1 and the OgLuc variant polypeptide having luciferase activity.

In an aspect, the disclosure relates to an isolated polynucleotide encoding an OgLuc variant polypeptide having at least 80% amino acid sequence identity to an OgLuc polypeptide of SEQ ID NO: 1, wherein the amino acid at position 4 is glutamate, at position 11 is arginine, at position 18 is leucine, at position 33 is lysine, at position 44 is isoleucine, at position 54 is isoleucine, at position 92 is histidine, at position 109 is phenylalanine, at position 115 is glutamate, at position 124 is lysine, at position 138 is isoleucine, and at position 166 is arginine corresponding to SEQ ID NO: 1 and the OgLuc variant polypeptide having luciferase activity.

In an aspect, the disclosure relates to an isolated polynucleotide encoding an OgLuc variant polypeptide having at least 80% amino acid sequence identity to an OgLuc polypeptide of SEQ ID NO: 1, wherein the amino acid at position 4 is glutamate, at position 11 is arginine, at position 33 is lysine, at position 44 is isoleucine, at position 54 is isoleucine, at position 77 is tyrosine, at position 90 is valine, at position 115 is glutamate, at position 124 is lysine, at position 138 is isoleucine, and at position 166 is arginine corresponding to SEQ ID NO: 1 and the OgLuc variant polypeptide having luciferase activity.

In an aspect, the disclosure relates to an isolated polynucleotide comprising the polynucleotide encoding the polypeptide of SEQ ID NO: 19.

In an aspect, the disclosure relates to an isolated polynucleotide comprising the polynucleotide of SEQ ID NO: 18, SEQ ID NO: 24, SEQ ID NO: 25, SEQ ID NO: 42, SEQ ID NO: 88, or SEQ ID NO: 92.

In an aspect, the disclosure relates to an isolated polynucleotide encoding a decapod luciferase polypeptide having at least 30% amino acid sequence identity to SEQ ID NO: 1, the polypeptide comprising a sequence pattern corresponding to the sequence pattern of Formula (VII) and including no more than 5 differences, wherein differences include differences from pattern positions 1, 2, 3, 5, 8, 10, 12, 14, 15, 17, or 18 relative to Formula (VII) according to the OgLuc pattern listed in Table 4 as well as gaps or insertions between any of the pattern positions of Formula (VII) according to the OgLuc pattern listed in Table 4, wherein the decapod luciferase produces luminescence in the presence of a coelenterazine.

In an aspect, the disclosure relates to a synthetic nucleotide sequence encoding an OgLuc variant polypeptide comprising a fragment of at least 100 nucleotides having 80% or less nucleic acid sequence identity to a parent nucleic acid sequence having SEQ ID NO: 2 and having 90% or more nucleic acid sequence identity to SEQ ID NO: 22, SEQ ID NO: 23, SEQ ID NO: 24, or SEQ ID NO: 25 or the complement thereof, wherein the decreased sequence identity is a result of different codons in the synthetic nucleotide sequence relative to the codons in the parent nucleic acid sequence, wherein the synthetic nucleotide sequence encodes a OgLuc variant which has at least 85% amino acid sequence identity to the corresponding luciferase encoded by the parent nucleic acid sequence, and wherein the synthetic nucleotide sequence has a reduced number of regulatory sequences relative to the parent nucleic acid sequence.

In an aspect, the disclosure relates to a synthetic nucleotide sequence encoding an OgLuc variant polypeptide comprising a fragment of at least 300 nucleotides having 80% or less nucleic acid sequence identity to a parent nucleic acid sequence having SEQ ID NO: 14 and having 90% or more nucleic acid sequence identity to SEQ ID NO: 22 or SEQ ID NO: 23 or the complement thereof, wherein the decreased sequence identity is a result of different codons in the synthetic nucleotide sequence relative to the codons in the parent nucleic acid sequence, wherein the synthetic nucleotide sequence encodes a firefly luciferase which has at least 85% amino acid sequence identity to the corresponding luciferase encoded by the parent nucleic acid sequence, and wherein the synthetic nucleotide sequence has a reduced number of regulatory sequences relative to the parent nucleic acid sequence.

In an aspect, the disclosure relates to a synthetic nucleotide sequence encoding an OgLuc variant polypeptide comprising a fragment of at least 100 nucleotides having 80% or less nucleic acid sequence identity to a parent nucleic acid sequence having SEQ ID NO: 18 and having 90% or more nucleic acid sequence identity to SEQ ID NO: 24 or SEQ ID NO: 25 or the complement thereof, wherein the decreased sequence identity is a result of different codons in the synthetic nucleotide sequence relative to the codons in the parent nucleic acid sequence, wherein the synthetic nucleotide sequence encodes a OgLuc variant which has at least 85% amino acid sequence identity to the corresponding luciferase encoded by the parent nucleic acid sequence, and wherein the synthetic nucleotide sequence has a reduced number of regulatory sequences relative to the parent nucleic acid sequence.

In an aspect, the disclosure relates to a fusion peptide comprising a signal peptide from *Oplophorus gracilirostris* fused to a heterologous protein, wherein said signal peptide is SEQ ID NO: 54, wherein the fusion peptide is expressed in a cell and secreted from the cell.

In an aspect, the disclosure relates to a method of generating a polynucleotide encoding a OgLuc variant polypeptide comprising: (a) using a parental fusion protein construct comprising a parental OgLuc polypeptide and at least one heterologous polypeptide to generate a library of variant fusion proteins; and (b) screening the library for at least one of enhanced luminescence, enhanced enzyme stability or enhanced biocompatibility relative to the parental fusion protein construct.

In an aspect, the disclosure relates to a method of generating codon-optimized polynucleotides encoding a luciferase for use in an organism, comprising: for each amino acid in the luciferase, randomly selecting a codon from the two most commonly used codons used in the organism to encode for the amino acid to produce a first codon-optimized polynucleotide.

Other aspects of the invention will become apparent by consideration of the detailed description and accompanying drawings.

BRIEF DESCRIPTION OF THE DRAWINGS

FIG. 2 shows the chemical structure of novel coelenterazines PBI-3939, PBI-3889, PBI-3945, PBI-4002, PBI-3841, PBI-3897, PBI-3896, PBI-3925, PBI-3894, PBI-3932, and PBI-3840.

FIG. 4 shows the chemical structure of various novel coelenterazines of the present invention.

FIGS. 5A, 5C-5G show independent experiments measuring the luminescence in RLUs generated by C1+A4E with known and novel coelenterazines using native coelenterazine as a comparison. FIG. 5B shows the fold-decrease in luminescence generated by C1+4AE using the substrates shown in FIG. 5A compared to native coelenterazine.

FIGS. 6A-D show the luminescence generated from lysed bacterial cells expressing various OgLuc variants using native coelenterazine ("Coelente"), known coelenterazine-h ("h"), known coelenterazine-hh ("h,h"), known 2-methyl coelenterazine ("2-me"), known coelenterazine-v ("v"), and novel coelenterazines PBI-3840, PBI-3897, PBI-3889, PBI-3899, PBI-3900, PBI-3912, PBI-3913, PBI-3925, PBI-3897, PBI-3899, PBI-3889, PBI-3939, PBI-3933, PBI-3932, PBI-3946, PBI-3897, PBI-3841, PBI-3896, PBI-3925, and PBI-3945 as substrates.

FIG. 7 shows the amino acid substitutions in various OgLuc variants.

FIGS. 8A-B show the luminescence generated from lysed bacterial cells expressing OgLuc variants listed in FIG. 7 using native coelenterazine ("Coelenterazine"), known coelenterazine-h ("H"), known coelenterazine-hh ("h,h"), and novel coelenterazines PBI-3840, PBI-3925, PBI-3912, PBI-3889, PBI-3939, PBI-3933, PBI-3932, PBI-3946, PBI-3941, and PBI-3896 as substrates.

FIG. 9 shows the luminescence generated from lysed bacterial cells expressing various OgLuc variants using native coelenterazine ("Coelenterazine"), known coelenterazine-hh ("h,h"), and novel coelenterazines PBI-3939, PBI-3945, PBI-3840, PBI-3932, PBI-3925, PBI-9894, and PBI-3896 as substrates.

FIG. 10 shows the amino acid substitutions in various OgLuc variants.

FIG. 11 shows the luminescence generated from lysed bacterial cells expressing OgLuc variants listed in FIG. 10 using native coelenterazine ("Coelenterazine"), known coelenterazine-hh ("h,h"), and novel coelenterazines PBI-3939, PBI-3945, PBI-3840, PBI-3932, PBI-3925, PBI-3894, and PBI-3896, as substrates.

FIG. 12 shows the luminescence generated from lysed bacterial cells expressing OgLuc variants using native coelenterazine ("Coelenterazine"), known coelenterazine-hh ("h,h"), and novel coelenterazines PBI-3939, PBI-3945, PBI-3889, PBI-3840, PBI-3932, PBI-3925, PBI-3894, PBI-3896, and PBI-3897 as substrates.

FIG. 13 shows the luminescence generated from lysed bacterial cells expressing OgLuc variants using native coelenterazine ("Coelenterazine"), known coelenterazine-hh ("H,H"), and novel coelenterazines PBI-3897, PBI-3896, and PBI-3894 as substrates.

FIG. 14 shows the amino acid substitutions in various OgLuc variants.

FIG. 15 shows the luminescence generated from lysed bacterial cells expressing OgLuc variants listed in FIG. 14 using native coelenterazine ("Coelenterazine"), known coelenterazine-hh ("h,h"), and novel coelenterazines PBI-3897, PBI-3841, PBI-3896, and PBI-3894 as substrates.

FIG. 16 shows the luminescence generated from lysed bacterial cells expressing OgLuc variants using native coelenterazine ("Coelenterazine"), known coelenterazine-h ("H"), known coelenterazine-hh ("HH"), and novel coelenterazines PBI-3841 and PBI-3897 as substrates.

FIG. 18 shows the luminescence generated from lysed bacterial cells expressing various OgLuc variants using native coelenterazine ("Coelenterazine"), known coelenterazine-hh ("h,h"), and novel coelenterazines PBI-3939, PBI-3945, PBI-3889, and PBI-4002 as substrates.

FIG. 19 shows the luminescence generated from lysed bacterial cells expressing various OgLuc variants using native coelenterazine ("Coelenterazine"), known coelenterazine-h ("H"), known coelenterazine-hh ("h,h"), and novel coelenterazines PBI-3939, PBI-3945, PBI-3889, and PBI-4002 as substrates.

FIG. 20 shows the amino acid substitutions in various OgLuc variants.

FIG. 21 shows the luminescence generated from lysed bacterial cells expressing OgLuc variants listed in FIG. 20 using native coelenterazine ("Coelenterazine"), known coelenterazine-h ("H"), known coelenterazine-hh ("h,h"), and novel coelenterazines PBI-3939, PBI-3945, PBI-4002, PBI-3932, and PBI-3840 as substrates.

FIG. 22 shows the amino acid substitutions in various OgLuc variants.

FIG. 23 shows the luminescence generated from lysed bacterial cells expressing OgLuc variants listed in FIG. 22 using native coelenterazine ("Coelenterazine"), known coelenterazine-h ("H"), known coelenterazine-hh ("h,h"), and novel coelenterazines PBI-3939, PBI-3945, PBI-3889, PBI-4002, PBI-3932, and PBI-3840 as substrates.

FIG. 26 shows the amino acid substitutions in various OgLuc variants.

FIG. 27 shows the luminescence generated from lysed bacterial cells expressing OgLuc variants listed in FIG. 26 using native coelenterazine ("Coelenterazine"), known coelenterazine-h ("H"), known coelenterazine-hh ("h,h"), and novel coelenterazines PBI-3939, PBI-3945, PBI-3889, and PBI-4002 as substrates.

FIGS. 30A-D show mutational analysis at position 166 using native coelenterazine (FIG. 30A), coelenterazine-h (FIG. 30B), and PBI-399 (FIG. 30C).

(FIG. 39A) and 37° C. (FIG. 39B) compared to *Renilla* (hRL) and firefly luciferase (Luc2).

FIGS. 52A-E show the inhibition analysis of the OgLuc variants 9B8 and L27V by Suramin and Tyr ag 835 (FIGS. 52A-C) and the chemical structures of Suramin (FIG. 52D) and Tyr ag 835 (FIG. 52E).

FIGS. 59A-C show the luminescence of the OgLuc variant L27V reporter constructs in various cell lines and with various response elements.

FIGS. 73A-H show the luminescence of the various CP-TEV protease L27V constructs expressed in wheat germ extract (FIGS. 73A-D), *E. coli* (FIG. 73F-G) and HEK 293 cells (FIG. 73H). FIGS. 73A-D show the basal luminescence of the various CP-TEV protease L27V constructs prior to TEV addition. FIG. 73E shows the response of the CP-TEV protease L27V constructs of FIGS. 73A-D.

DETAILED DESCRIPTION

Figure 1:
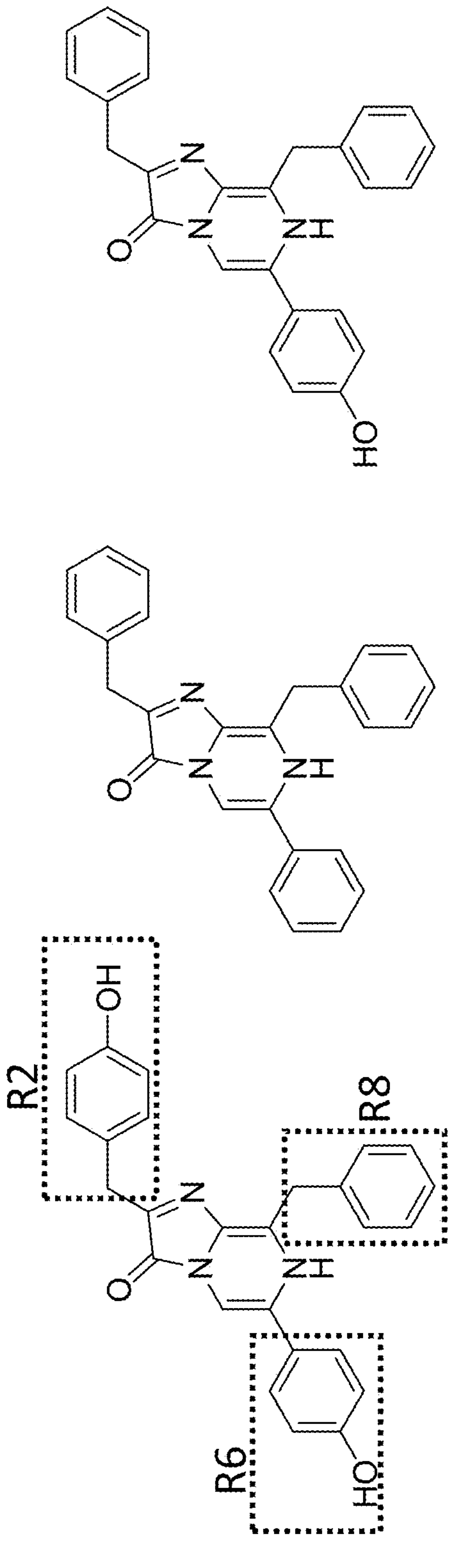
FIG. 1 shows the chemical structure of native coelenterazine, known bis-coelenterazine (coelenterazine-hh), and known coelenterazine-h, where R2, R6 and R8 represent the regions of the molecule where modifications were made.

Before any embodiments of the invention are explained in detail, it is to be understood that the invention is not limited in its application to the details of structure, synthesis, and arrangement of components set forth in the following description or illustrated in the following drawings. The invention is described with respect to specific embodiments and techniques, however, the invention is capable of other embodiments and of being practiced or of being carried out in various ways.

In the following description of the methods of the invention, process steps are carried out at room temperature (about 22° C.) and atmospheric pressure unless otherwise specified. It also is specifically understood that any numerical range recited herein includes all values from the lower value to the upper value. For example, if a concentration range or beneficial effect range is stated as 1% to 50%, it is intended that values such as 2% to 40%, 10% to 30%, or 1% to 3%, etc. are expressly enumerated in this specification. Similarly, if a sequence identity range is given as between, e.g., 60% to <100%, it is intended that intermediate values such as 65%, 75%, 85%, 90%, 95%, etc. are expressly enumerated in this specification. These are only examples of what is specifically intended, and all possible numerical values from the lowest value to the highest value are considered expressly stated in the application.

Unless expressly specified otherwise, the term "comprising" is used in the context of the present application to indicate that further members may optionally be present in addition to the members of the list introduced by "comprising". It is, however, contemplated as a specific embodiment of the present invention that the term "comprising" encompasses the possibility of no further members being present, i.e., for the purpose of this embodiment "comprising" is to be understood as having the meaning of "consisting of".

The following detailed description discloses specific and/or preferred variants of the individual features of the invention. The present invention also contemplates, as particularly preferred embodiments, those embodiments which are generated by combining two or more of the specific and/or preferred variants described for two or more of the features of the present invention.

Unless expressly specified otherwise, all indications of relative amounts in the present application are made on a weight/weight basis. Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount. More preferably, no other variants or members covered by the generic term are present at all.

Overview

In various aspects, the invention is drawn to novel compounds, novel luciferases, and combinations thereof. The invention encompasses methods, compositions, and kits including the novel compounds, novel luciferases, and/or combinations thereof.

The novel compounds are novel coelenterazines, which can be used as substrates by proteins that utilize coelenterazines to produce luminescence, including, but not limited to, luciferases and photoproteins found in various marine organisms such as cnidarians (e.g., *Renilla* luciferase), jellyfish (e.g., aequorin from the *Aequorea* jellyfish) and decapods luciferases (e.g., luciferase complex of *Oplophorus gracilirostris*). In various embodiments, the novel coelenterazines of the present invention have at least one of enhanced physical stability (e.g., enhanced coelenterazine stability), reduced autoluminescence, and increased biocompatibility with cells (e.g., less toxic to cells, including heterologous cell types) relative to native coelenterazine.

The novel luciferases disclosed herein include variants of the active subunit of a decapod luciferase. The novel luciferases can utilize various coelenterazines as substrates, including, but not limited to, native and known coelenterazines as well as the novel coelenterazines of the present invention. The novel luciferases display at least one of: enhanced luminescence (including increased brightness, enhanced signal stability and/or signal duration); enhanced enzyme stability (i.e., enhanced enzymatic activity including enhanced resistance to elevated temperature, changes in pH, inhibitors, denaturants, and/or detergents); altered substrate specificity (i.e., change in relative substrate specificity); and enhanced biocompatibility (including at least one of improved expression in cells, reduced toxicity, and/or cell stress). In various embodiments, the present invention encompasses novel luciferases that are present in solution as soluble, active monomers, chemically linked to other molecules (e.g., fusion proteins), or attached onto a solid surface (e.g., particles, capillaries, or assay tubes or plates).

Certain combinations of the novel coelenterazines and the novel luciferases provide significant technical advantages for bioluminescent assays including enhanced luminescence, wherein enhanced luminescence may be due to one or more factors including enhanced signal stability and enhanced coelenterazine stability. Additionally, many of the novel coelenterazines were designed to be smaller than commercially-available and/or known coelenterazines. In some cases, the novel luciferases of the present invention preferentially utilize the novel, smaller coelenterazines over the commercially-available and/or known larger coelenterazines.

The invention encompasses combinations of: the novel luciferase variants with the novel coelenterazines; the novel luciferase variants with known or native coelenterazines; and the novel coelenterazines with any known or native protein (e.g., luciferases or photoproteins) that uses coelenterazine as a substrate.

The term "coelenterazine" refers to naturally-occurring ("native") coelenterazine as well as analogs thereof, including coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100 and U.S. application Ser. No. 12/056,073 (paragraph [0086]), the disclosures of which are incorporated by reference herein. The term "coelenterazine" also refers to the novel coelenterazines disclosed herein (see below). The term "known coelenterazine" refers to a coelenterazine analog known prior to the present invention.

The term "OgLuc" refers to a decapod luciferase protein, or a variant of such a protein, which generates light in the presence of a coelenterazine. The OgLuc protein may, in its naturally-occurring form, be a monomer or may be a subunit of a protein complex. The OgLuc used in the exemplary embodiments disclosed herein is the 19 kDa subunit from the luciferase complex of *Oplophorus gracilirostris*, although comparable polypeptides from other decapod species (including other *Oplophorus* species) could also be employed and are encompassed within the invention (see R. D. Dennell, Observations on the luminescence of bathypelagic Crustacea decapoda of the Bermuda area, *Zool. J. Linn. Soc., Lond.* 42 (1955), pp. 393-406; see also Poupin et al. September 1999. Inventaire documenté des espècies et bilan des formes les plus communes de la mer d'Iroise. *Rapport Scientifique du Laboratoire d'Océanographie de l'École Navale* (*LOEN*), Brest (83 pgs), each of which is incorporated by reference herein); examples include, without limitation, luciferases of the Aristeidae family, including *Plesiopenaeus coruscans*; the Pandalidea family, including *Heterocarpus* and *Parapandalus richardi*, the Solenoceridae family, including *Hymenopenaeus debilis* and *Mesopenaeus tropicalis*; the Luciferidae family, including *Lucifer typus*; the Sergestidae family, including *Sergestes atlanticus, Sergestes arcticus, Sergestes armatus, Sergestes pediformis, Sergestes cornutus, Sergestes edwardsi, Sergestes henseni, Sergestes pectinatus, Sergestes sargassi, Sergestes similis, Sergestes vigilax, Sergia challengeri, Sergia grandis, Sergia lucens, Sergia prehensilis, Sergia potens, Sergia robusta, Sergia scintillans, and Sergia splendens*; the Pasiphaeidae family, including *Glyphus marsupialis, Leptochela bermudensis, Parapasiphae sulcatifrons*, and *Pasiphea tarda*; the Oplophoridae family, including *Acanthephyra acanthitelsonis, Acanthephyra acutifrons, Acanthephyra brevirostris, Acanthephyra cucullata, Acanthephyra curtirostris, Acanthephyra eximia, Acanthephyra gracilipes, Acanthephyra kingsleyi, Acanthephyra media, Acanthephyra microphthalma, Acanthephyra pelagica, Acanthephyra prionota, Acanthephyra purpurea, Acanthephyra sanguinea, Acanthephyra sibogae, Acanthephyra stylorostratis, Ephyrina bifida, Ephyrinafigueirai, Ephyrina koskynii, Ephyrina ombango, Hymenodora glacialis, Hymenodora gracilis, Meningodora miccyla, Meningodora mollis, Meningodora vesca, Notostomus gibbosus, Notostomus auriculatus, Oplophorus gracilirostris, Oplophorus grimaldii, Oplophorus novaezealandiae, Oplophorus spinicauda, Oplophorus foliaceus, Oplophorus spinosus, Oplophorus typus, Systellaspis braueri, Systellaspis cristata, Systellaspis debilis, and Systellaspis pellucida*; and the Thalassocaridae family, including *Chlorotocoides spinicauda, Thalassocaris crinita*, and *Thalassocaris lucida.*

The polypeptide sequence of the mature (i.e., with no signal sequence) 19 kDa subunit of the naturally-occurring form of the *Oplophorus gracilirostris* luciferase (i.e., 169 amino acids, residues 28 to 196 of BAB 13776) is given in SEQ ID NO: 1. In various embodiments, a methionine residue and a valine residue are inserted at the beginning of the synthetic OgLuc sequence (e.g., as indicated in the C1+A4E polypeptide sequence, SEQ ID NO: 3) to facilitate cloning and expression in heterologous systems. Nevertheless, for consistency, the position numbers of the various amino acid substitutions referred to herein are specified "relative to" SEQ ID NO: 1, i.e., the polypeptide sequence of the mature (with no signal sequence), native 19 kDa subunit of the *Oplophorus gracilirostris* luciferase protein complex.

Specifically, a protein is a decapod luciferase if, upon alignment of its amino acid sequence with SEQ ID NO: 1, the sequence identity is >30%, preferably >40%, and most preferably >50%, and the protein can utilize coelenterazine as a substrate to catalyze the emission of luminescence, and the amino acid sequence beginning at the position corresponding to position 8 of SEQ ID NO: 1 is:

```
                                      (SEQ ID NO. 330)
[GSAIVK]-{FE}-[FYW]-x-[LIVMFSYQ]-x-x-{K}-x-[NHGK]-

x-[DE]-x-[LIVMFY]-[LIVMWF]-x-{G}-[LIVMAKRG] (VII),
```

with no more than 5 differences, or more preferably no more than 4, 3, 2, or 1 difference, or most preferably no differences, wherein the differences occur in positions corresponding to pattern position 1, 2, 3, 5, 8, 10, 12, 14, 15, 17, or 18 of Formula (VII) according to Table 4. Differences may also include gaps or insertions between the pattern positions of Table 4.

The term "variant" refers to a modified version of a starting polypeptide or polynucleotide sequence. The term "parental" is a relative term that refers to a starting sequence which is then modified. The parental sequence is generally used as a reference for the protein encoded by the resulting modified sequence, e.g., to compare the activity levels or other properties of the proteins encoded by the parental and the modified sequences. The starting sequence can be a naturally-occurring (i.e., native or wild-type) sequence. The starting sequence can also be a variant sequence which is then further modified. A polypeptide sequence is "modified" when one or more amino acids (which may be naturally-occurring or synthetic) are substituted, deleted, and/or added at the beginning, middle, and/or end of the sequence. A polynucleotide sequence is "modified" when one or more nucleotides are substituted, deleted, and/or added at the beginning, middle, and/or end of the sequence, but which may or may not alter the amino acid encoded by the sequence. In some embodiments, the modifications produce a variant that is a functional fragment of a particular OgLuc or OgLuc variant. A functional fragment is a fragment which is less than a full-length parental sequence which has the same functional activity as the full-length parental sequence. Functional activity is the ability to exhibit luminescence. In some embodiments, the modifications produce a variant that is a permuted sequence of the parental sequence, such as a circularly permuted sequence and permuted sequences comprising deletions and/or insertions.

Several of the OgLuc variants disclosed herein have been assigned shorthand names to facilitate discussion. The term "C1+A4E" (also referred to as "C1A4E") refers to a particular OgLuc variant with the amino acid substitutions A4E, Q11R, A33K, V44I, A54F, P115E, Q124K, Y138I, and N166R relative to SEQ ID NO: 1 (SEQ ID NOs: 2 and 3) (where the format "x#y" indicates a parent amino acid 'x' at a position '#' that is changed to variant amino acid 'y'). Variants of the C1+A4E OgLuc variant which are presented herein contain at least the amino acid substitutions found in C1+A4E, unless otherwise indicated. The term "IVY" refers to a variant of the C1+A4E OgLuc variant having additional amino acid substitutions F54I, 190V, and F77Y relative to SEQ ID NO: 1 (SEQ ID NOs: 8 and 9). The term "IV" refers to another variant of the C1+A4E OgLuc variant having additional amino acid substitutions F54I and I90V relative to SEQ ID NO: 1 (SEQ ID NOs: 14 and 15). The term "QC27" refers to yet another variant of the C1+A4E OgLuc variant having additional amino acid substitutions Q18L, F54I, L92H, and Y109F relative to SEQ ID NO: 1 (SEQ ID NOs: 4 and 5). The term "QC27-9a" refers to a variant of the QC27 OgLuc variant with additional amino acid substitutions V21L, F68Y, L72Q, M75K, H92R, and V158F relative to SEQ ID NO: 1 (SEQ ID NOs: 6 and 7). The term "9B8" refers to a variant of the IV OgLuc variant with additional amino acid substitutions Q18L, F68Y, L72Q, and M75K relative to SEQ ID NO: 1 (SEQ ID NOs: 18 and 19). The term "9B8 opt" refers to the codon optimized version of the 9B8 variant (SEQ ID NO: 24). The term "9B8 opt+K33N" refers to a variant of the 9B8 opt variant with additional amino acid substitution K33N relative to SEQ ID NO: 1 (SEQ ID NOs: 42 and 43). The term "9B8 opt+K33N+170G" refers to a variant of the "9B8 opt+K33N" variant with an additional glycine appended to the C-terminus of the variant, i.e., 170G relative to SEQ ID NO: 1 (SEQ ID NO: 68 and 69). The terms "L27V+T39T+K43R+Y68D" and "L27V" refers to a variant of the 9B8 opt+K33N" variant with additional amino acid substitutions L27V, T39T, K43R, and Y68D relative to SEQ ID NO: 1 (SEQ ID NOs: 88 and 89). The terms "T39T+K43R+Y68D" and "V2" refers to a variant of the "9B8 opt+K33N" variant with additional amino acid substitutions T39T, K43R, and Y68D relative to SEQ ID NO: 1 (SEQ ID NOs: 92 and 93).

In general, "enhanced" means that the particular property (e.g., luminescence, signal stability, biocompatibility, protein stability (e.g., enzyme stability), or protein expression) is increased relative to that of the reference luciferase plus coelenterazine combination or luciferase under consideration, where the increase is at least 1%, at least 5%, at least 10%, at least 20%, at least 25%, at least 50%, at least 75%, at least 90%, at least 100%, at least 200%, at least 500%, or at least 1000% greater than the reference luciferase plus coelenterazine combination or luciferase under consideration.

The term "luminescence" refers to the light output of the OgLuc variant under appropriate conditions, e.g., in the presence of a suitable substrate such as a coelenterazine. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine, buffer, etc., into a reaction chamber (e.g., a well of a multiwell plate such as a 96-well plate) containing the luminescent protein. In still other embodiments, the OgLuc variant and/or novel coelenterazine are introduced into a host and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

The "enhanced luminescence" of an OgLuc variant may be due to one or more of the following characteristics: enhanced light output (i.e., brightness), enhanced substrate specificity, enhanced signal stability, and/or enhanced signal duration. Enhanced signal stability includes an increase in how long the signal from a luciferase continues to luminesce, for example, as measured by the half-life of decay of the signal in a time-course. Enhanced luminescence may be determined relative to the comparable property of a luciferase such as wild-type OgLuc, an OgLuc variant protein, *Renilla* luciferase (e.g., hRluc), or firefly luciferase (e.g., Luc2 luciferase from *Photinus pyralis*) combined with a native, known, or novel substrate, as shown in the Examples below. For example, the luminescence of a given OgLuc variant in combination with a particular coelenterazine (including native, known, or novel coelenterazines) may be compared to the properties of one of OgLuc variants C1+A4E, IV, or IVY combined with any of a native, known, or novel coelenterazine disclosed herein, using one or more of the assays disclosed in the Examples below. In particular, enhanced luminescence may be determined by measuring the luminescence signal (RLU) resulting from the incubation of bacterial lysates containing OgLuc variants in question with the substrate, PBI-3939. Measurements are taken in a reagent which may contain TERGITOL™ to provide Glo-like kinetics, e.g., in which enzyme inactivation is slowed and the luminescence signal is stabilized, which is described elsewhere in the application. In some embodiments, some luciferase variants, e.g., L27V, with certain compounds, e.g., PBI-3939, provide extended duration of the luminescent emission, or glow-like kinetics, in the absence of TERGI- TOL™. The luminescence signal may be compared to that of a reference point such as the C1+A4E variant with coelenterazine or coelenterazine-h or *Renilla* luciferase with native coelenterazine.

"Enzyme stability" refers to the stability of enzyme activity (i.e., tolerance of enzymatic activity to reaction conditions). Enhanced enzyme stability refers to enhanced stability of enzyme activity (i.e., enhanced tolerance to reaction conditions). Enhanced enzyme stability includes enhanced thermal stability (e.g., stability at elevated temperatures) and chemical stability (e.g., stability in the presence of inhibitors or denaturants such as detergents, including, e.g., TRITON™ X-100). Enzyme stability can be used as a measure of protein stability, particularly under conditions known to be disruptive of protein structure, such as high temperatures or the presence of chemical denaturants. In particular, enhanced protein stability may be determined using thermal analysis as described elsewhere in the application (e.g., in Example 28). The luminescence signal may be compared to the reference point of C1+A4E variant with coelenterazine or coelenterazine-h or *Renilla* luciferase with native coelenterazine.

"Biocompatibility" refers to the tolerance of a cell (e.g., prokaryotic or eukaryotic) to a luciferase and/or coelenterazine compound. Biocompatibility of a luciferase and/or coelenterazine compound is related to the stress it causes on the host cell. For example, a luciferase that is not tolerated by the cell (i.e., one that stresses a cell) may not be expressed efficiently within the cell, for example, the luciferase may be expressed within the cell, but exhibit reduced activity due to the formation of inclusion bodies by the expressed protein. Biocompatibility of a luciferase is related to the ability of the cells to tolerate the insertion of the foreign gene, i.e., a transgene containing the gene encoding the luciferase or fragment thereof, whereby the cells with the transgene do not exhibit manifestations of stress, including induction of stress response pathways, reduced rate of growth, and/or reduced viability (e.g., reduced number of living cells, reduced membrane integrity, or increased rates of apoptosis). Other indications of cell stress may include changes in gene expression, signaling pathways, and/or regulatory pathways. Enhanced biocompatibility of an OgLuc variant may be due to factors such as enhanced protein expression and/or reduced cell stress. Enhanced expression of luminescence for a particular polynucleotide encoding an OgLuc variant may be determined relative to luminescence expression levels for a polynucleotide encoding wild-type OgLuc or an OgLuc variant protein, including codon-optimized polynucleotides, where luminescence activity can be used as a means to monitor protein expression levels.

In particular, enhanced biocompatibility of the OgLuc variant, novel coelenterazine compound and/or a combination thereof, may be determined by measuring cell viability and/or growth rate of cells. For example, enhanced biocompatibility of the OgLuc variants may be determined by measuring cell viability and/or growth rate of cells containing the OgLuc variants compared to cells containing firefly or *Renilla* luciferase or no luciferase, in the absence of any coelenterazine compound to determine how compatible and/or toxic the luciferase is to the cells. Enhanced biocompatibility of the novel coelenterazine compounds may be determined by measuring cell viability in the absence of luciferase expression of cells exposed to the novel coelenterazine compound compared to native or known coelenterazines to determine how compatible and/or toxic the coelenterazine compound is to the cells. Enhanced biocompatibility of a combination of an OgLuc variant with a novel coelenterazine compound may be determined by measuring cell viability and/or growth rate of cells containing the OgLuc variant and exposed to the novel coelenterazine and compared to cells containing firefly or *Renilla* luciferase or no luciferase and exposed to native or known coelenterazines.

In particular, enhanced biocompatibility may be determined using cell viability analysis as described elsewhere in the application (e.g., using a CELLTITER-GLO® assay as described in Example 18 or an apoptosis assay such as one using CASPASE-GLO® technology according to the manufacturer's instructions) or one known in the art. The effect of an OgLuc variant on cell viability or apoptosis may be compared to the effect of a reference luciferase, such as the C1+A4E variant, a firefly luciferase or *Renilla* luciferase. The effect of the novel coelenterazine compound on cell viability or apoptosis may be compared to the effect of native or known coelenterazine compounds on cell viability or apoptosis.

Enhanced biocompatibility may also be determined by measuring the effect of the OgLuc variant and/or novel coelenterazine compound on cell growth or gene expression. For examples, enhanced biocompatibility of the OgLuc variant may be determined by measuring the cell number after a period of time or by determining the expression of stress response genes in a sample of cells that contain the OgLuc variant compared to cells that contain another luciferase or no luciferase. Enhanced biocompatibility of the novel coelenterazine compound may be determined by measuring the cell number after a period of time or by determining the expression of stress response genes in a sample of cells that are exposed to the novel coelenterazine compound compared to cells exposed to native or known coelenterazines or no coelenterazines. The effect of the OgLuc variant on cell growth or gene expression may be compared to a reference luciferase, such as C1+A4E variant, a firefly luciferase or *Renilla* luciferase. The effect of the novel coelenterazine on cell growth or gene expression may be compared to native or known coelenterazines.

The identification of robust, stable cell lines expressing an OgLuc variant of the present invention, either in the cytoplasm or as a secreted form, can be facilitated by the bright signal of the luciferase and the small size of the OgLuc gene. The relatively small gene sequence is expected to reduce the likelihood of genetic instability resulting from the integration of the foreign DNA into a cell's genome. As a result of the increased brightness of the OgLuc variants and/or the novel coelenterazines of the present invention, less protein expression, and thereby less DNA needed for transfection, may produce a given level of brightness compared to other known luciferases such as native OgLuc, firefly, or *Renilla* luciferase, which contributes to an enhanced biocompatibility for the OgLuc variants and/or novel coelenterazines. Enhanced biocompatibility of the OgLuc variants may be measured by the amount of DNA or reagents, e.g., transfection chemicals, needed in transient transfections to generate cells with the same level of luminescence as cells transfected with other luciferases, e.g., native OgLuc, firefly or *Renilla* luciferase. In some embodiments, the amount of OgLuc variant DNA or reagents needed for transfection is less than the amount needed for another luciferase, e.g., native OgLuc, firefly, or *Renilla* luciferase, to generate transfected cells with the same level of luminescence obtained with the other luciferase. Enhanced biocompatibility of the OgLuc variants may be measured by the recovery time of the cells after transfection. In some embodiments, the amount of time needed for recovery after transfection with the OgLuc variant is less than the time needed for another luciferase, e.g., native OgLuc, firefly or *Renilla* luciferase.

"Relative substrate specificity" is determined by dividing the luminescence of a luciferase in the presence of a test coelenterazine substrate by the luminescence of the luciferase in the presence of a reference coelenterazine substrate. For example, relative specificity may be determined by dividing the luminescence of a luciferase with a novel coelenterazine of the present invention by the luminescence of the luciferase with a different coelenterazine (e.g., native or known coelenterazine, see FIG. 1 for examples, or a different novel coelenterazine of the present invention). The test coelenterazine substrate and the reference coelenterazine substrate that are compared are considered a comparison substrate pair for determining relative substrate specificity.

A "change in relative substrate specificity" is determined by dividing the relative substrate specificity of a test luciferase using a comparison substrate pair by the relative substrate specificity of a reference luciferase using the same comparison substrate pair. For example, a change in relative specificity may be determined by dividing the relative substrate specificity of a test luciferase with a novel coelenterazine of the present invention compared to a different coelenterazine (e.g., native or known coelenterazine or a different novel coelenterazine of the present invention), by the relative substrate specificity of a reference luciferase with the same novel coelenterazine of the present invention compared to the same different coelenterazine used for the test luciferase.

In some embodiments, the luminescence with one novel coelenterazine is compared to the luminescence with a different novel coelenterazine. In some embodiments, the luminescence with one native or known coelenterazine is compared to the luminescence with another native or known coelenterazine. In still other embodiments, the luminescence with one native or known coelenterazine is compared to the luminescence with a novel coelenterazine.

The novel coelenterazines of the present invention include properties such as enhanced physical stability (e.g., enhanced coelenterazine stability) or reduced autoluminescence. The physical stability of the coelenterazine refers to how stable the coelenterazine is in certain conditions such that it maintains the ability to luminesce when used as a substrate by a luciferase. Luminescence that is not dependent on the activity of a luciferase or photoprotein is termed autoluminescence. Autoluminescence is the luminescence of a substance produced by energy released in the form of light during decay or decomposition. For example, autoluminescence can be caused by spontaneous oxidation of the luminogenic substrate coelenterazine.

As used herein, "pure" or "purified" means an object species is the predominant species present (i.e., on a molar and/or mass basis, it is more abundant than any other individual species, apart from water, solvents, buffers, or other common components of an aequeous system in the composition), and, in some embodiments, a purified fraction is a composition wherein the object species comprises at least about 50% (on a molar basis) of all macromolecular species present. Generally, a "substantially pure" composition will comprise more than about 80% of all macromolecular species present in the composition, in some embodiments more than about 85%, more than about 90%, more than about 95%, or more than about 99%. In some embodiments, the object species is purified to essential homogeneity (contaminant species cannot be detected in the composition by conventional detection methods) wherein the composition consists essentially of a single macromolecular species.

Coelenterazine Derivatives

In some embodiments, the present invention provides novel coelenterazine derivatives of formula (Ia) or (Ib):

(Ia)

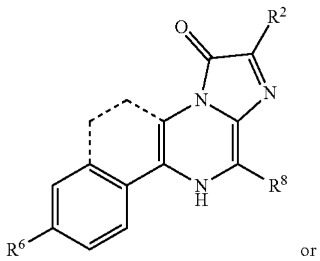

or (Ib)

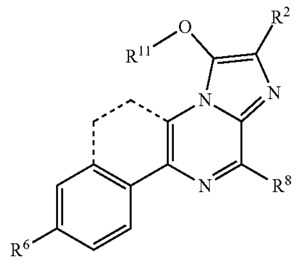

wherein $R^2$ is selected from the group consisting of

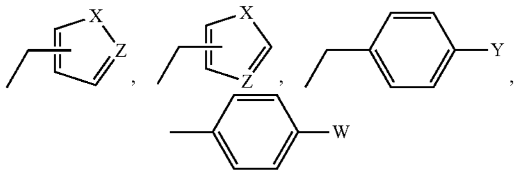

or $C_{2-5}$ straight chain alkyl;

$R^6$ is selected from the group consisting of —H, —OH, —$NH_2$, —OC(O)R or —$OCH_2OC(O)R$;

$R^8$ is selected from the group consisting of

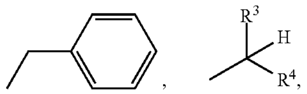

H or lower cycloalkyl;

wherein $R^3$ and $R^4$ are both H or both $C_{1-2}$ alkyl;

W is —$NH_2$, halo, —OH, —NHC(O)R, —$CO_2R$;

X is —S—, —O— or —$NR^{22}$—;

Y is —H, —OH, or —$OR^{11}$;

Z is —CH— or —N—;

each $R^{11}$ is independently —C(O)R" or —$CH_2OC(O)R$";

$R^{22}$ is H, $CH_3$, or $CH_2CH_3$ each R is independently $C_{1-7}$ straight-chain alkyl or $C_{1-7}$ branched alkyl;

R" is $C_{1-7}$ straight-chain alkyl or $C_{1-7}$ branched alkyl;

the dashed bonds indicate the presence of an optional ring, which may be saturated or unsaturated;

with the proviso that when $R^2$ is

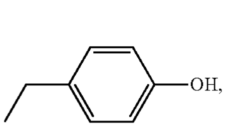

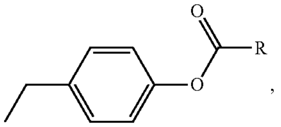

, or

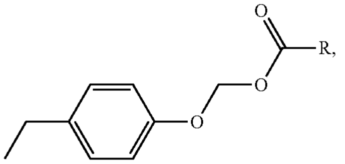

$R^8$ is not

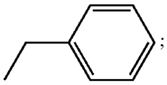

;

with the proviso that when $R^2$ is

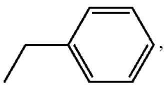

, $R^8$ is

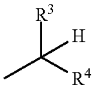

or lower cycloalkyl; and with the proviso that when $R^6$ is $NH_2$, $R^2$ is

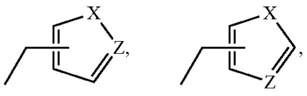

or $C_{2-5}$ alkyl;

or $R^8$ is not

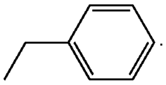

.

The term "alkyl", as used herein, pertains to a monovalent moiety obtained by removing a hydrogen atom from a hydrocarbon compound, and which may be saturated, partially unsaturated, or fully unsaturated. The alkyl group may be a straight-chain or branched. An alkyl group may be optionally substituted with, for example, halo. Examples of straight-chain alkyl groups include, but are not limited to, ethyl, n-propyl, n-butyl, and n-propyl, n-hexyl and n-heptyl. Examples of unsaturated alkyl groups which have one or more carbon-carbon double bonds include, but are not limited to, ethenyl (vinyl, $—CH{=}CH_2$), 2-propenyl (allyl, $—CH—CH{=}CH_2$), and butenyl. Examples of unsaturated alkyl which have one or more carbon-carbon triple bonds include, but are not limited to, ethynyl and 2-propynyl (propargyl). Examples of branched alkyl groups included isopropyl, iso-butyl, sec-butyl, t-butyl and iso-pentyl.

The term "lower cycloalkyl", as used herein, pertains to a monovalent moiety obtained by removing a hydrogen atom from a hydrocarbon compound having from 3 to 5 carbon atoms. Examples of saturated lower cycloalkyl groups include, but are not limited to, groups such as cyclopropyl, cyclobutyl and cyclopentyl. Examples of unsaturated lower cycloalkyl groups which have one or more carbon-carbon double bonds include, but are not limited to, groups such as cyclopropenyl, cyclobutenyl and cyclopentenyl.

The term "halo", as used herein, pertains to a halogen, such as Cl, F, Br or I.

In some embodiments, $R^2$ is

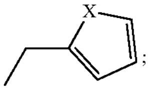

;

and X is O or S. In other embodiments, $R^2$ is $C_{2-5}$ straight chain alkyl. In certain embodiments, $R^8$ is

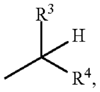

, lower cycloalkyl or H. In other embodiments, $R^8$ is benzyl. In some embodiments, R" is $—C(CH_3)_3$, $—CH(CH_3)_2$, $—CH_2C(CH_3)_3$, or $—CH_2CH(CH_3)_2$.

In some embodiments, the present invention provides compounds according to Formula (IIa) or (IIb):

(IIa)

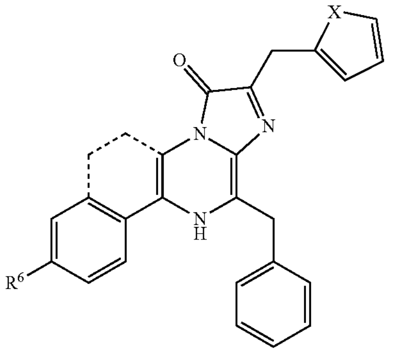

or (IIb)

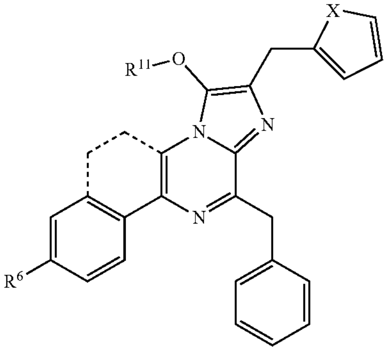

wherein X is O or S, $R^6$ is H or OH, $R^{11}$ is as defined above, and the dashed bonds indicate the presence of an optional ring.

In some embodiments, the invention provides compounds according to Formula (IIIa) or (IIIb):

(IIIa)

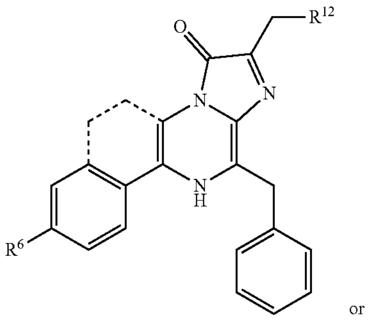

or (IIIb)

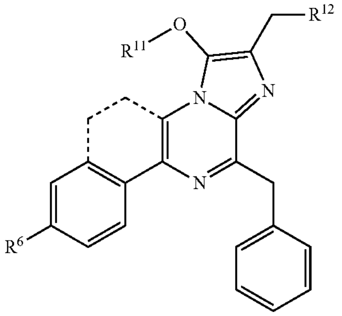

wherein $R^{12}$ is $C_{2-5}$ straight-chain alkyl, furyl or thienyl, $R^6$ is H or OH, $R^{11}$ is as defined above, and the dashed bonds indicate the presence of an optional ring.

In some embodiments, the invention provides compounds according to Formula (IVa) or (IVb):

(IVa)

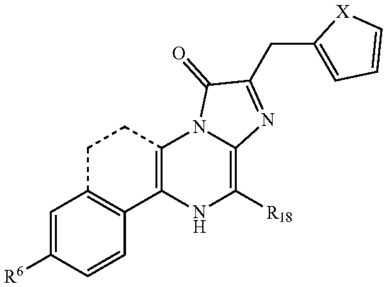

or (IVb)

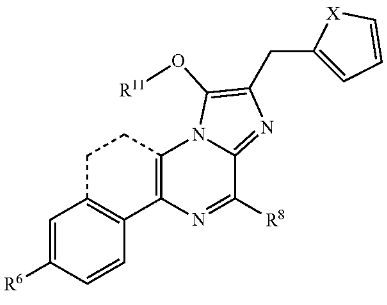

wherein X is O or S, $R^6$ is H or OH, $R^{18}$ is H,

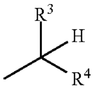

or lower cycloalkyl, $R^3$, $R^4$ and $R^{11}$ are as defined above, and the dashed bonds indicate the presence of an optional ring.

In some embodiments, the invention provides a compound according to Formula (Va) or (Vb):

(Va)

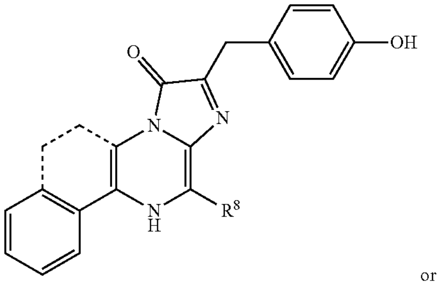

or (Vb)

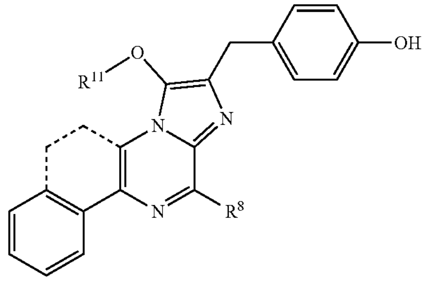

wherein $R^8$ is benzyl, $R^{11}$ is as defined above, and the dashed bonds indicate the presence of an optional ring.

In some embodiments, the present invention provides novel coelenterazine derivatives of formula (VIa) or (VIb):

(VIa)

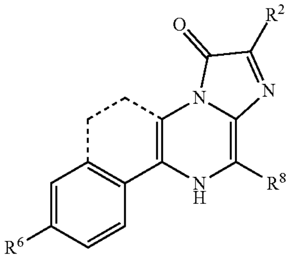

or (VIb)

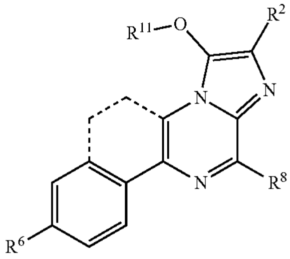

wherein $R^2$ is selected from the group consisting of

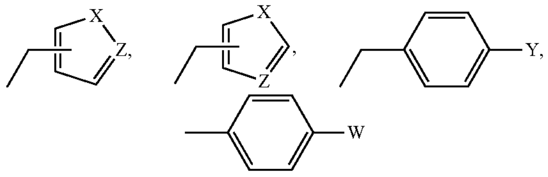

or $C_{2-5}$ straight chain alkyl;

$R^6$ is selected from the group consisting of —H, —OH, —$NH_2$, —OC(O)R or —$OCH_2OC(O)R$;

$R^8$ is selected from the group consisting of

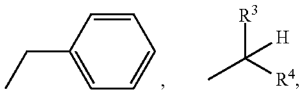

H or lower cycloalkyl;

wherein $R^3$ and $R^4$ are both H or both $C_{1-2}$ alkyl;

W is —$NH_2$, halo, —OH, —NHC(O)R, —$CO_2R$;

X is —S—, —O— or —NH—;

Y is —H, —OH, or —$OR^{11}$;

Z is —CH— or —N—;

each $R^{11}$ is independently —C(O)R" or —$CH_2OC(O)R$";

each R is independently $C_{1-7}$ straight-chain alkyl or $C_{1-7}$ branched alkyl;

R" is $C_{1-7}$ straight-chain alkyl or $C_{1-7}$ branched alkyl;

the dashed bonds indicate the presence of an optional ring, which may be saturated or unsaturated;

with the proviso that when $R^2$ is

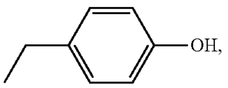

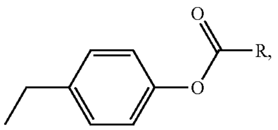 or

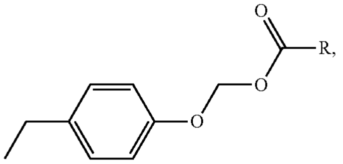

$R^8$is not

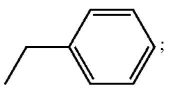

with the proviso that when $R^2$ is

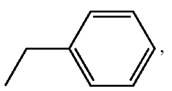

$R^8$ is

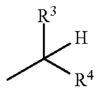

or lower cycloalkyl; and with the proviso that when $R^6$ is $NH_2$, $R^2$ is

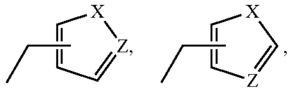

or $C_{2-5}$ alkyl;

or $R^8$ is not

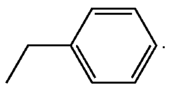

Suitable compounds according to the present invention include

3882

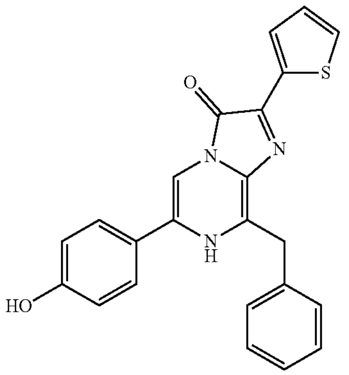

3881

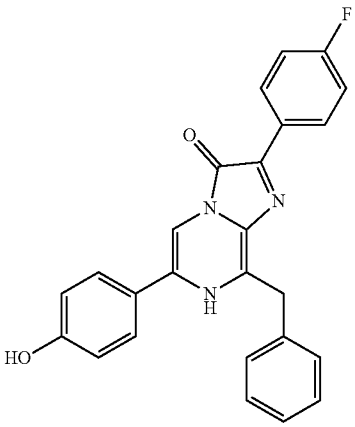

3899
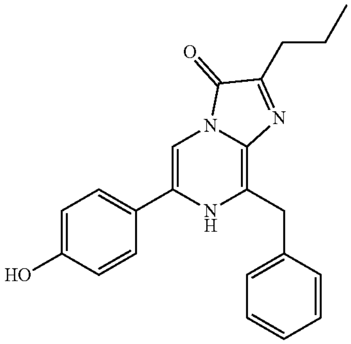
3900
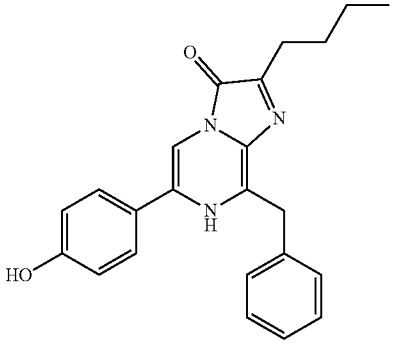
3945
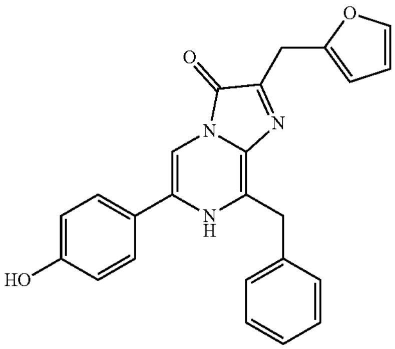
4002
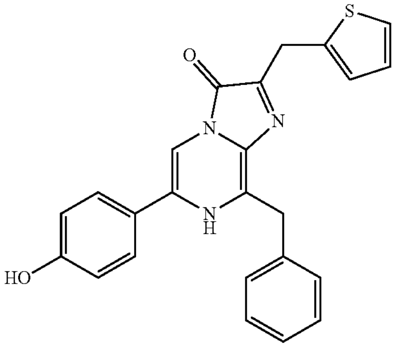
3840
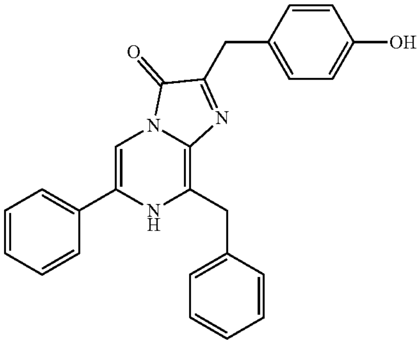
3886
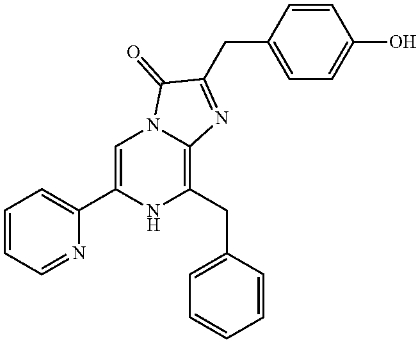
3857
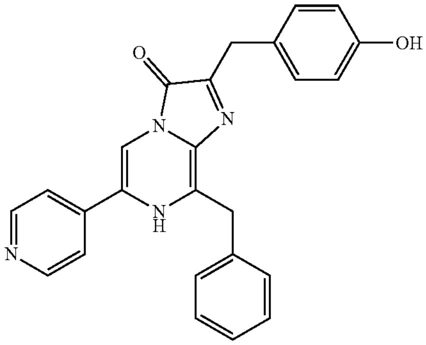
3887
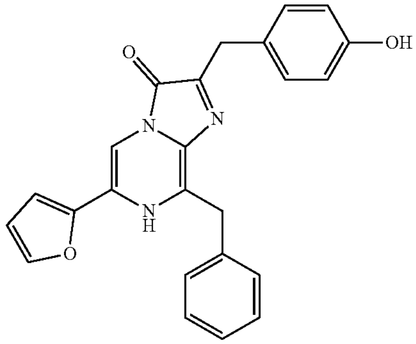

-continued
3913
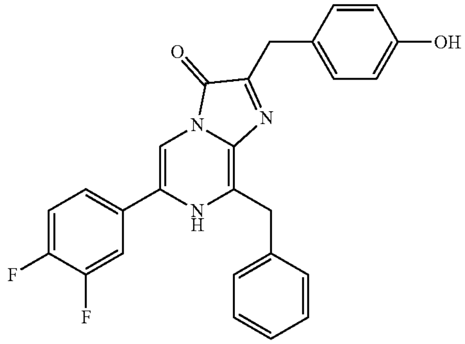
3932
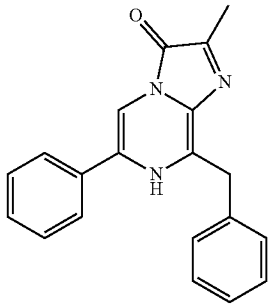
3925
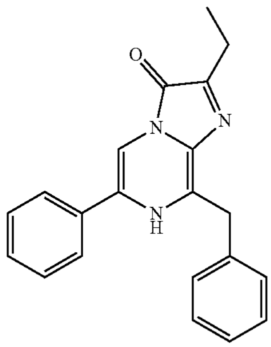
3933
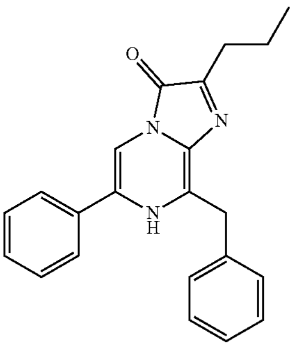
-continued
3946
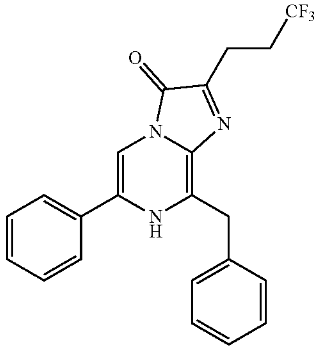
3889
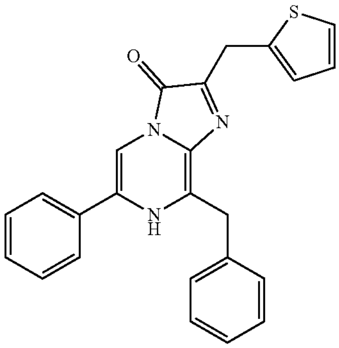
3939
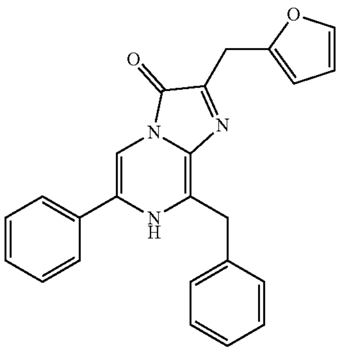
3894
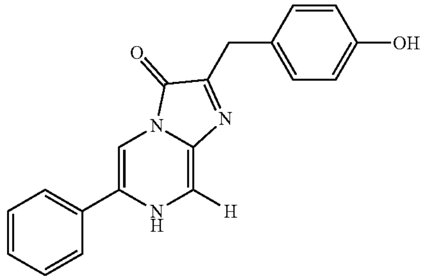
3896
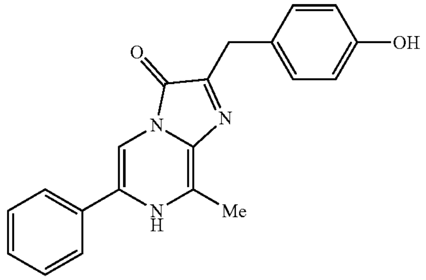

-continued

3897

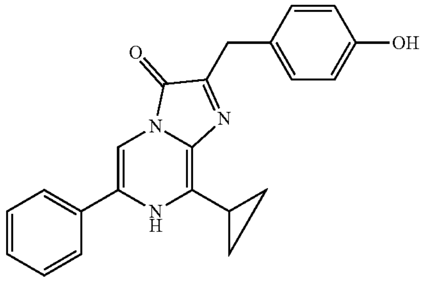

3841

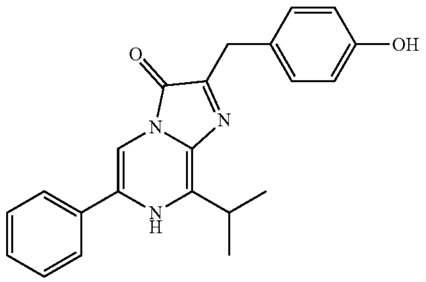

3842

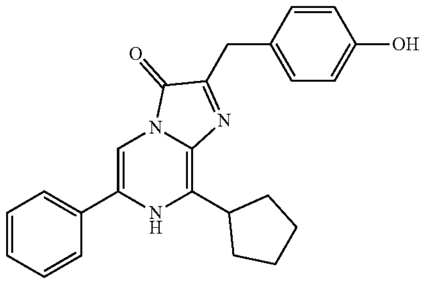

4525

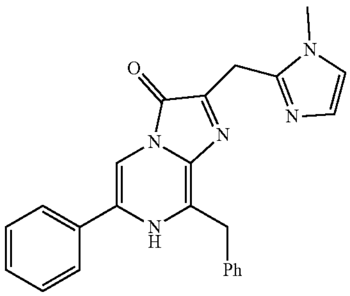

4540

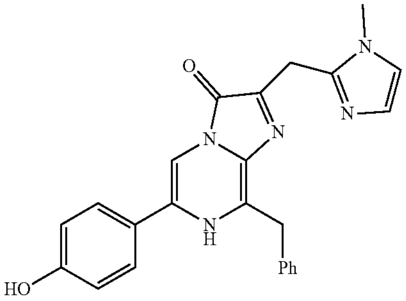

-continued

4541

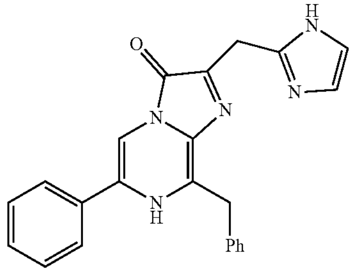

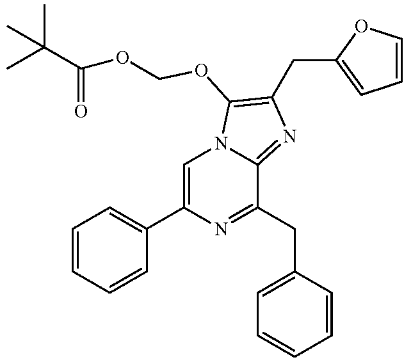

Isomers, Salts and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo and exo-forms; R-, S-, and meso-forms; D- and L-forms; d- and 1-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half-chair forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e., isomers which differ in the connections between atoms rather than merely by the position of atoms in space). For example, a reference to a methoxy group, $—OCH_3$, is not to be construed as a reference to its structural isomer, a hydroxymethyl group, $—CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and paramethoxyphenyl).

Note that specifically included in the term "isomer" are compounds with one or more isotopic substitutions. For example, H may be in any isotopic form, including $^{1}H$, $^{2}H$ (D), and $^{3}H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below. It may be convenient or desirable to prepare, purify, and/or handle a corresponding salt of the active compound, for example, a pharmaceutically-acceptable salt. Examples of pharmaceutically acceptable salts are discussed in Berge et al., *J. Pharm. Sci.,* 66:1-19 (1977).

For example, if the compound is anionic, or has a functional group which may be anionic (e.g., —COOH may be —COO—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH^{4+}$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester ($—OC(═O)CH_3$, —OAc). For example, an aldehyde or ketone group may be protected as an acetal or ketal, respectively, in which the carbonyl group (>C═O) is converted to a diether ($>C(OR)_2$), by reaction with, for example, a primary alcohol. The aldehyde or ketone group is readily regenerated by hydrolysis using a large excess of water in the presence of acid. For example, an amine group may be protected, for example, as an amide or a urethane, for example, as: a methyl amide ($—NHCO—CH_3$); a benzyloxy amide ($—NHCO—OCH_2C_6H_5$, —NHCbz); as a t-butoxy amide ($—NHCO—OC(CH_3)_3$, —NH-Boc); a 2-biphenyl-2-propoxy amide ($—NHCO—OC(CH_3)_2C_6H_4C_6H_5$, —NH-Bpoc), as a 9-fluorenylmethoxy amide (—NH—Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide.

For example, a carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkylester); a tri$C_{1-7}$ alkylsilyl-$C_{1-7}$ alkyl ester; or a $C_{5-20}$ aryl-$C_{1-7}$ alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether ($—S—CH_2NHC(═O)CH_3$).

Synthesis of Coelenterazine Derivatives

Coelenterazine derivatives according to the present invention may be synthesized according those methods detailed in Examples 1-16.

Mutant *Oplophorus* Luciferases

In embodiments of the present invention, various techniques as described herein were used to identify sites for amino acid substitution to produce an improved synthetic OgLuc polypeptide. Additional techniques were used to optimize codons of the polynucleotides encoding the various polypeptides in order to enhance expression of the polypeptides. It was found that making one or more amino acid substitutions, either alone or in various combinations, produced synthetic OgLuc-type polypeptides having enhanced luminescence (e.g., enhanced brightness, enhanced signal stability, enhanced enzyme stability, and/or change in relative substrate specificity). Furthermore, including one or more codon-optimizing substitutions in the polynucleotides which encode for the various synthetic OgLuc variant polypeptides produced enhanced expression of the polypeptides in various eukaryotic and prokaryotic expression systems. One embodiment of the present invention is a polynucleotide that encodes a synthetic OgLuc variant polypeptide which is soluble and active in the monomeric form when expressed in prokaryotic and/or eukaryotic cells.

The OgLuc variants of the present invention may be coupled to any protein of interest or molecule of interest. In some embodiments, the variants are fusion proteins, for example some variants are coupled to a HaloTag® polypeptide attached at either the N-terminus or the C-terminus. Unless otherwise noted, the variants that are HaloTag® fusions include 'HT7' as part of the name, e.g., 'IVY-HT7'.

In some embodiments, a signal sequence (e.g., the naturally-occurring *Oplophorus gracilirostris* signal sequence) is attached to the N-terminus of the fusion protein to facilitate the secretion of the fusion protein from the cell. Signal sequences, other than the naturally-occuring signal sequence of OgLuc luciferase, are known in the art to facilitate protein secretion in mammalian cells or other cell types. Signal sequences, in combination with membrane anchoring sequences, may be used to position or display OgLuc variants on the outer surface of the cellular membrane. Other methods, known in the art may also be used to position OgLuc variants to the membrane or other locations within the cell.

In some embodiments, the invention provides a modified decapod luciferase which has enhanced luminescence relative to a corresponding parental variant decapod luciferase. For example, the parental, variant OgLuc is C1+A4E, IVY, IV, QC27, QC27-9a, 9B8, 9B8 opt+K33N, 9B8 opt+K33N+170G, V2 or "L27V". In another embodiment, the invention provides a modified decapod luciferase which utilizes a novel coelenterazine. In one embodiment, the modified decapod luciferase has a change in relative specificity for native, known or novel coelenterazines. In one embodiment, the modified decapod luciferase has a change in relative specificity relative to a corresponding parental, variant decapod luciferase.

In some embodiments, the corresponding parental, variant decapod luciferase is a decapod species, including various species from families within the decapod order including, without limitation, luciferases of the Aristeidae family, including *Plesiopenaeus coruscans*; the Pandalidea family, including *Heterocarpus* and *Parapandalus richardi*, the Solenoceridae family, including *Hymenopenaeus debilis* and *Mesopenaeus tropicalis*; the Luciferidae family, including *Lucifer typus*; the Sergestidae family, including *Sergestes atlanticus, Sergestes arcticus, Sergestes armatus, Sergestes pediformis, Sergestes cornutus, Sergestes edwardsi, Sergestes henseni, Sergestes pectinatus, Sergestes sargassi, Sergestes similis, Sergestes vigilax, Sergia challengeri, Sergia grandis, Sergia lucens, Sergia prehensilis, Sergia potens, Sergia robusta, Sergia scintillans*, and *Sergia splendens*; the Pasiphaeidae family, including *Glyphus marsupialis, Leptochela bermudensis, Parapasiphae sulcatifrons*, and *Pasiphea tarda*; the Oplophoridae family, including *Acanthephyra acanthitelsonis, Acanthephyra acutifrons, Acanthephyra brevirostris, Acanthephyra cucullata, Acanthephyra curtirostris, Acanthephyra eximia, Acanthephyra gracilipes, Acanthephyra kingsleyi, Acanthephyra media, Acanthephyra microphthalma, Acanthephyra pelagica, Acanthephyra prionota, Acanthephyra purpurea, Acanthephyra sanguinea, Acanthephyra sibogae, Acanthephyra stylorostratis, Ephyrina bifida, Ephyrinafigueirai, Ephyrina koskynii, Ephyrina ombango, Hymenodora glacialis, Hymenodora gracilis, Meningodora miccyla, Meningodora mollis, Meningodora vesca, Notostomus gibbosus, Notostomus auriculatus, Oplophorus gracilirostris, Oplophorus grimaldii, Oplophorus novaezealandiae, Oplophorus spinicauda, Oplophorus foliaceus, Oplophorus spinosus, Oplophorus typus, Systellaspis braueri, Systellaspis cristata, Systellaspis debilis*, and *Systellaspis pellucida*; and the Thalassocaridae family, including *Chlorotocoides spinicauda, Thalassocaris crinita*, and *Thalassocaris lucida*. In certain embodiments, the modified luciferase has increased luminescence emission, e.g., at least 1.3-fold, at least 2-fold, or at least 4-fold, in a prokaryotic cell and/or a eukaryotic cell relative to the corresponding wild-type luciferase. In some embodiments, one or more properties of the modified decapod luciferase is compared to comparable properties of a luciferase from another species, e.g., a firefly luciferase or a *Renilla* luciferase.

In some embodiments, the OgLuc variant has at least 60%, e.g., at least 65%, 70%, 75%, 80%, 85%, 90%, 95%, 96%, 97%, 98%, or 99%, or 100%, amino acid sequence identity to SEQ ID NOs: 3, 5, 7, 9, 11, 13, 15, 17, 19, 21, 27, 35, 37, 39, 41, 43, 45, 47, 49, 51, 53, 56, 58, 60, 62, 64, 69, 71, 73, 75, 77, 79, 81, 83, 85, 87, 89, 91, 93, or 95. In some embodiments, the OgLuc variant, or a functional fragment thereof, has no more than 5 differences, or more preferably, no more than 4, 3, 2, or 1 difference, or most preferably no differences, wherein the differences occur in positions corresponding to pattern position 1, 2, 3, 5, 8, 10, 12, 14, 15, 17, or 18 of Formula (VII) according to Table 4. Differences may also include gaps or insertions between the pattern positions of Table 4.

In some embodiments, the OgLuc variant of the invention has one or more heterologous amino acid sequences at the N-terminus, C-terminus, or both (a fusion polypeptide such as one with an epitope or fusion tag), which optionally directly or indirectly interact with a molecule of interest. In some embodiments, the presence of the heterologous sequence(s) does not substantially alter the luminescence of the OgLuc variant either before or after the interaction with the molecule of interest. In some embodiments, the heterologous amino acid sequence is an epitope tag. In some embodiments, the heterologous amino acid sequence is one which, during or after interaction with a molecule of interest, undergoes a conformational change, which in turn alters the activity of the OgLuc variant e.g., an OgLuc variant with such an amino acid sequence is useful to detect allosteric interactions. The OgLuc variant or a fusion with the OgLuc variant or a fragment thereof may be employed as a reporter.

In some embodiments, a fragment of an OgLuc variant of the invention is fused to a heterologous amino acid sequence, the fusion thereby forming a beta-barrel, which fusion protein is capable of generating luminescence from a naturally-occurring coelenterazine or an analog thereof including the various known coelenterazines discussed herein, or a novel coelenterazine of the present invention.

Also provided is a polynucleotide encoding an OgLuc variant of the invention or a fusion thereof, an isolated host cell having the polynucleotide or the OgLuc variant or a fusion thereof, and methods of using the polynucleotide, OgLuc variant or a fusion thereof or host cell of the invention.

The term "identity," in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. Methods of alignment of sequence for comparison are well-known in the art. Optimal alignment of sequences for comparison can be conducted by the algorithm of Smith et al., (*J. Mol. Biol.* 147:195-197 (1981)), by the homology alignment algorithm of Needleman and Wunsch, (*J. Mol. Biol.*, 48:443-453 (1970)), by the search for similarity method of Pearson and Lipman, (*Proc. Natl. Acad. Sci. USA*, 85:2444-2448 (1988)), by computerized implementations of algorithms e.g., FASTA, SSEARCH, GGSEARCH (available at the University of Virginia FASTA server by William R. Pearson http://fasta.bioch.virginia.edu/fasta_www2/fasta_intro.shtml), the Clustal series of programs (Chenna et al., *Nucl. Acids Res.* 31(13):3497-3500 (2003); or other sequence analysis software. It is known in the art that generating alignments with maximum correspondence between polypeptide sequences with significant sequence alterations (e.g., altered domain order, missing/added domains, repeated domains, shuffled domains, circular permutation) may involve the use of specialized methods, such as the ABA method (Raphael et al., *Genome Res.* 14(11): 2336-2346 (2004)), other suitable methods, or performing the alignment with two concatenated identical copies of the polypeptide sequences.

The term "nucleic acid molecule," "polynucleotide" or "nucleic acid sequence" as used herein, refers to nucleic acid, including DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A polynucleotide encoding a protein or polypeptide means a nucleic acid sequence comprising the coding region of a gene, or in other words, the nucleic acid sequence encoding a gene product. The coding region may be present in a cDNA, genomic DNA or RNA form. When present in a DNA form, the oligonucleotide may be single stranded (e.g., the sense strand) or double stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Other control or regulatory elements include, but are not limited to, transcription factor binding sites, splicing signals, polyadenylation signals, termination signals and enhancer elements.

By "peptide," "protein" and "polypeptide" is meant amino acid chains of varying lengths, regardless of post-translational modification (e.g., glycosylation or phosphorylation). The nucleic acid molecules of the invention encode a variant of a man made (i.e., synthetic) variant protein or polypeptide fragment thereof, which has an amino acid sequence that is at least 60%, e.g., at least 65%, 70%, 75%, 80%, 85%, 90%, 95%, 96%, 97%, 98%, 99%, or 100%, amino acid sequence identity to the amino acid sequence of the parental protein from which it is derived, where the parental protein can be a naturally-occurring (native or wild-type) sequence or a variant sequence which is subsequently modified further. The term "fusion polypeptide" or "fusion protein" refers to a chimeric protein containing a reference protein (e.g., OgLuc variant) joined at the N- and/or C-terminus to one or more heterologous sequences (e.g., a non-OgLuc polypeptide). The heterologous sequence can include, but is not limited to, reporter proteins such as the HALOTAG® fusion protein (Promega Corp.), FlAsH (fluorescein arsenical helix binder), and ReAsH (red arsenical helix binder) (e.g., LUMIO™ tag recognition sequence (Invitrogen)), chloramphenicol acetyltransferase (CAT), β-galactosidase (β-Gal), lactamase (P-gal), neomycin resistance (Neo), GUS, galactopyranoside, green fluorescent protein (GFP), luciferase (e.g., a *Renilla reniformis* luciferase, a firefly luciferase (e.g., *Photinus pyralis* or *Photuris pennsylvanica*), or a click beetle luciferase (e.g., *Pyrophorus plagiophthalamus* or *Pyrearinus termitilluminans*) or a glowworm luciferase (e.g., *Phrixothrix hirtus*), xylosidase, thymidine kinase, arabinosidase and SNAP-tag, CLIP-tag, ACP-tag and MCP-tag (New England Biolabs). In one embodiment, a chimeric protein contains an OgLuc variant joined at the N-terminus to a HALOTAG® fusion protein (Promega Corp.). In another embodiment, a chimeric protein contains an OgLuc variant joined at the C-terminus to a HALOTAG® fusion protein.

Nucleic acids are known to contain different types of "mutations", which refers to an alteration in the sequence of a nucleotide at a particular base position relative to the wild-type sequence. Mutations may also refer to insertion or deletion of one or more bases so that the nucleic acid sequence differs from a reference, e.g., a wild-type sequence, or replacement with a stop codon. A "substitution" refers to a change in an amino acid at a particular position in a sequence, e.g., a change from A to E at position 4.

The term "vector" refers to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The term "wild-type" or "native" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics when compared to the wild-type gene or gene product.

Exemplary Polynucleotides and Proteins

The invention includes an OgLuc variant or protein fragments thereof, e.g., those with deletions, for instance a deletion of 1 to about 5 residues, and chimeras (fusions) thereof (see U.S. Patent Publication No. 2009/0253131 and WIPO Publication No. WO 2007/120522, the disclosures of which are incorporated by reference herein) having at least one amino acid substitution relative to a wild-type OgLuc, which substitution results in the OgLuc variant having enhanced stability, enhanced luminescence, e.g., increased luminescence emission, greater stability of the luminescence kinetics, and/or altered luminescence color. The sequences of an OgLuc variant are substantially the same as the amino acid sequence of a corresponding wild-type OgLuc. A polypeptide or peptide having substantially the same sequence means that an amino acid sequence is largely, but is not entirely, the same and retains the functional activity of the sequence to which it is related. In general, two amino acid sequences are substantially the same if they are at least 60%, e.g., at least 65%, 70%, 75%, 80%, 85%, 90%, 95%, 96%, 97%, 98%, or 99%, but less than 100%, amino acid sequence identity. In some embodiments, the OgLuc variant is encoded by a recombinant polynucleotide. In some embodiments, the OgLuc variant, or a functional fragment thereof, has no more than 5 differences, or more preferably no more than 4, 3, 2, or 1 difference, or most preferably no differences, wherein the differences occur in positions corresponding to pattern position 1, 2, 3, 5, 8, 10, 12, 14, 15, 17, or 18 of Formula (VII) according to Table 4. Differences may also include gaps, insertions, or permutations between the pattern positions of Table 4.

The OgLuc variant proteins or fusion proteins of the invention may be prepared by recombinant methods or by solid phase chemical peptide synthesis methods. Such methods are known in the art.

Methods of Use and Kits

The compounds and proteins of the invention may be used in any way that luciferases and luciferase substrates, e.g., coelenterazines, have been used. For example, they may be used in a bioluminogenic method which employs an analog of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels). In some embodiments the OgLuc variant can be used in luminescence-based assays to detect an enzyme of interest, e.g., CYP450 enzyme, MAO A or B enzyme, a caspase, etc. The novel coelenterazines could be used with photoproteins such as aequorin, obelin, or iPhotina. In some embodiment, the OgLuc variant can be used as an energy donor to another molecule (e.g., to a fluorophore, a chromophore, or a nanoparticle).

The invention also provides a polynucleotide encoding a transcriptional reporter. In some embodiments, the OgLuc variant or fragment thereof could be operably linked to transcription regulatory sequences, e.g., one or more enhancer, a promoter, a transcription termination sequence or a combination thereof, to form an expression cassette. For example, the OgLuc variant could be operably linked to a minimal promoter and a cAMP-response element (CRE).

The proteins of the invention may be used as biosensors, e.g., an OgLuc variant, which, in the presence of another molecule (e.g, one or more molecules of interest), or under certain conditions, has one or more altered activities. Upon interacting with a molecule of interest or being subject to certain conditions, the biosensor undergoes a conformational change or is chemically altered which causes an alteration of the enzyme activity or luminescence, e.g., specific activity, spectral distribution, or emission kinetics. For example, the OgLuc variant of the present invention, for example a circularly permuted variant, can comprise an interaction domain for a molecule of interest. Alternatively, for example, the OgLuc variant may be coupled to an energy acceptor, for example a fluorescent protein, and comprise an interaction domain that alters the efficiency of energy transfer from the enzyme to the energy acceptor. For example, the biosensor could be generated to detect proteases, kinases, a ligand, a binding protein such as an antibody, cyclic nucleotides such as cAMP or cGMP, or a metal such as calcium, by insertion of a suitable sensor region into the OgLuc variant sequence. One or more sensor region can be inserted at the C-terminus, the N-terminus, and/or at one or more suitable location in the polypeptide sequence, where the sensor region comprises one or more amino acids. In the case of a circularly-permuted OgLuc variant, the sensor region may be inserted between the N- and C-termini of the parent OgLuc variant. In addition, one or all of the inserted sensor regions may include linker amino acids to couple the sensor to the remainder of the OgLuc variant polypeptide. Examples of luciferase biosensors are disclosed in U.S. Pat. Appl. Publ. Nos. 2005/0153310 and 2009/0305280 and PCT Publ. No. WO 2007/120522 A2, each of which is incorporated by reference herein.

In various embodiments, the OgLuc variants disclosed herein may be used to transfer energy to an energy acceptor, for example in Bioluminescence Resonance Energy Transfer (BRET) analysis. For example, the OgLuc variants used in BRET analysis can be used to determine if two molecules are capable of binding each other or co-localize in a cell. For example, an OgLuc variant can be used as a bioluminescence donor molecule which is combined with a molecule or protein of interest to create a first fusion protein. In various embodiments, the first fusion protein contains an OgLuc variant and a protein of interest. In various embodiments, the first fusion proteins containing the OgLuc variant can be used in BRET analysis to detect protein/protein interaction in systems including but not limited to cell lysates, intact cells, and living animals. In various embodiments, HALOTAG® can be used as a fluorescent acceptor molecule. In some embodiments, HALOTAG® can be fused to a second protein of interest or to an OgLuc variant. For example, an OgLuc variant can be fused to HALOTAG®, expressed in cells or animals, and labeled with a fluorescent HALOTAG® ligand such as HALOTAG® TMR ligand. The fusion can subsequently be excited to fluoresce in the presence of a cell-permeant OgLuc substrate. In some embodiments, BRET may be performed using OgLuc variants in combination with fluorescent proteins, including but not limited to Green Fluorescent Protein (GFP) or Red Fluorescent Protein (RFP) or fluorescent labels including fluorescein, rhodamine green, Oregon green, or Alexa 488, to name a few non-limiting examples.

In various embodiments, the OgLuc variants and/or the novel coelenterazines of the present invention may be used in protein complementation assays (PCA) to detect the interaction of two biomolecules, e.g., polypeptides. For example, an OgLuc variant of the present invention can be separated into two fragments at a site(s) tolerant to separation and each fragment of the separated OgLuc variant can be fused to one of a pair of polypeptides of interest believed to interact, e.g., FKBP and FRB. If the two polypeptides of interest do in fact interact, the OgLuc fragments then come into close proximity with each other to reconstitute the functional, active OgLuc variant. In some embodiments, the activity of the reconstituted OgLuc variant can then be detected and measured using a native or known coelenterazine or a novel coelenterazine of the present invention. In some embodiments, the split OgLuc variant can be used in a more general complementation system similar to lac-Z (Langley et al., *PNAS* 72:1254-1257 (1975)) or ribonuclease S (Levit and Berger, *J. Biol. Chem.* 251:1333-1339 (1976)). In some embodiments, an OgLuc variant fragment (designated "A") known to complement with another OgLuc variant fragment ("B") can be fused to a target protein, and the resulting fusion can be monitored via luminescence in a cell or cell lysate containing fragment B. In some embodiments, the source of fragment B could be the same cell (e.g., if the gene for fragment B is integrated into the genome of the cell or is contained on another plasmid within the cell) or it could be a lysate or purified protein derived from another cell. In some embodiments, this same fusion protein (fragment A) could be captured or immobilized using a fusion between fragment B and a polypeptide such as HALOTAG® capable of attachment to a solid support. In some embodiments, luminescence can be used to demonstrate successful capture or to quantify the amount of material captured.

In various embodiments, the OgLuc variants and/or the novel coelenterazines of the present invention may be used to quantify coelenterazine. In some embodiments, a coelenterazine (e.g., a native or known coelenterazine, or a novel coelenterazine of the present invention) can be used as a probe of a specific biochemical activity, e.g., apoptosis and drug metabolism. In some embodiments, the coelenterazine concentration is coupled to a specific enzyme activity by a "pro-coelenterazine" or "pro-substrate" that can be acted on by the specific enzyme of interest. In some embodiments, the pro-coelenterazine is a molecule that cannot support luminescence directly when combined with luciferase, but can be converted into coelenterazine through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. For example, coelenterazine (e.g., a native or known coelenterazine, or a novel coelenterazine of the present invention) can be modified to contain a cleavable group, such as 6'-O-methyl. In some embodiments, when incubated with a specific cytochrome P450 enzyme, the 6'O-methyl is cleaved, and the pro-coelenterazine converted to coelenterazine which can be detected with an OgLuc variant of the present invention. In some embodiments, the pro-coelenterazine can be combined with other components necessary to support luminescence, e.g., luminescent protein such as an OgLuc variant of the present invention, to provide a single reagent and a homogeneous assay. For example, when the reagent is added to a sample, luminescence is generated as pro-coelenterazine is converted to coelenterazine. In various embodiments, similar assays can be developed for other enzymes, small molecules, or other cellular processes that can be linked to the generation of coelenterazines from pro-coelenterazines.

In various embodiments, the OgLuc variants and/or the novel coelenterazines of the present invention may be used as genetic transcriptional reporter systems. In some embodiments, the OgLuc variants can be multiplexed with a luciferase that emits light at a different wavelength, e.g., red click beetle luciferase (CHROMA-LUC™; Promega Corp.). For example, if an OgLuc variant of the present invention is used as a functional reporter, then the red CHROMA-LUC™ luciferase could be used to control for non-specific effects on genetic regulation or to normalize for transfection efficiency. In some embodiments, luminescence generated from the OgLuc variant (approximately 460 nm) and red CHROMA-LUC™ (approximately 610 nm) can be easily resolved using a luminometer with wavelength-discriminating filters, enabling the measurement of both signals from the same sample. In another example, an OgLuc variant of the present invention could be used as a transcriptional reporter and paired with a luciferase that emits light at a different wavelength contained in an assay reagent. For example, an OgLuc variant of the present invention could be used as transcriptional reporter and paired with either aequorin or a cAMP circularly-permuted firefly luciferase biosensor, or both simultaneously, to detect multiple pathways in a single sample. In such a system, for example, aequorin could be used for the detection and/or measurement of calcium, the biosensor for the detection and/or measurement of cAMP, and an OgLuc variant for monitoring of downstream gene expression. In another example, an OgLuc variant may be used with one or more additional luciferases, where the luminescence of each luciferase may be separately measured through the use of selective enzyme inhibitors. For example, the luminescence of a first luciferase may be measured upon addition of appropriate substrates and buffers, followed by measurement of a second luciferase upon a subsequent addition of appropriate substrates and buffers and one or more inhibitors selective for the first luciferase. In another example, the luciferase contained in an assay reagent may be used for measuring a specific aspect of cellular physiology, for example ATP to estimate cell viability, or caspase activity to estimate cellular apoptosis.

In various embodiments, the OgLuc variants of the present invention may be used as reporters in difficult to transfect cell lines or perhaps even in non-dividing primary cells, e.g., stem cells or HepG2 cells. Due to their high signal intensity, the OgLuc variants of the present invention will enable detectable luminescence when transfection efficiency is low. In some embodiments, the OgLuc variants can be used as reporters in cells that are especially sensitive to conditions associated with transfection, e.g., which are sensitive to elevated DNA concentrations or the addition of transfection reagent. Thus, in various embodiments, due to the enhanced luminescence of the OgLuc variants of the present invention, an adequate level of luminescence can be achieved using lower DNA concentrations, less transfection reagent, and/or shorter post-transfection times prior to beginning an assay so that there is a reduced toxicity burden on sensitive cells. In various embodiments, the enhanced luminescence of the OgLuc variants will also allow for a signal to be detected at much later time points. In still other embodiments, the OgLuc variants could be used as reporters for single-copy native promoters.

In various embodiments, the OgLuc variants of the present invention may be used as fusion tags for a target protein of interest as a way to monitor intracellular levels of the target protein. In some embodiments, the OgLuc variants can be used to monitor specific proteins involved in stress response pathways (e.g., DNA damage, oxidative stress, inflammation) in cells as a way to probe the role various types of stimuli may play in these pathways. In some embodiments, the OgLuc variants can also be used as a means to monitor cellular trafficking of a target protein. For example, the OgLuc variants can also be fused to viral genomes (e.g., HIV, HCV) so that titer levels, i.e., infectivity, can be monitored in cells following treatment with potential antiviral agents. In some embodiments, the variants can also be fused to green fluorescent protein (GFP) or HALOTAG® (in addition to a target protein) for fluorescence activated cell sorting (FACS) to identify high expression clones.

In various embodiments, identification of robust, stable cell lines expressing an OgLuc variant of the present invention, either in the cytoplasm or as a secreted form, can be facilitated by the enhanced signal of the OgLuc variant and the small size of the OgLuc gene. The relatively small gene sequence should reduce the likelihood of genetic instability resulting from the integration of the foreign DNA into a cell's genome.

In various embodiments, the OgLuc variants of the present invention can be integrated into a variety of different immunoassay concepts. For example, an OgLuc variant can be fused to a primary or secondary antibody to provide a method of detection for a particular analyte. As another example, an OgLuc variant can be fused to protein A or protein G, and the fusion could then be used to detect a specific antibody bound to a particular analyte. As another example, an OgLuc variant can be fused to streptavidin and used to detect a specific biotinylated antibody bound to a particular analyte. As yet another example, complementary fragments of an OgLuc variant can be fused to primary and secondary antibodies, where the primary antibody recognizes a particular analyte, and the secondary antibody recognizes the primary antibody. In some embodiments, the OgLuc variant activity would be reconstituted in the presence of analyte. As still another example, an OgLuc variant can be conjugated to an analyte (e.g., prostaglandins) and used in a competitive sandwich ELISA format. The OgLuc variant conjugated to an analyte may also be used to detect antibodies capable of binding the analyte, where the binding activity allows the OgLuc variant to be selectively linked to the antibody. An example using *Renilla* luciferase for quantitatively measuring patient antibody titers to an antigenic target is the Luciferase Immunoprecipitation System (Burbelo et al., Expert Review of Vaccines 9(6):567-578 (2010))

In various embodiments, the OgLuc variants and novel substrates of the present invention can be used for detecting luminescence in live cells. In some embodiments, an OgLuc variant can be expressed in cells (as a reporter or otherwise), and the cells treated with a coelenterazine, e.g., a novel coelenterazine such as PBI-3939, which will permeate cells in culture, react with the OgLuc variant and generate luminescence. In addition to being cell permeant, PBI-3939 shows comparable biocompatibility to native coelenterazine in terms of cell viability. In some embodiments, a version of PBI-3939 containing chemical modifications known to increase the stability of native coelenterazine in media can be synthesized and used for more robust, live cell OgLuc variant-based reporter assays. In still other embodiments, a sample (including cells, tissues, animals, etc.) containing an OgLuc variant and/or a novel coelenterazine of the present invention may be assayed using various microscopy and imaging techniques. In still other embodiments, a secretable OgLuc variant is expressed in cells as part of a live-cell reporter system.

In various embodiments, the OgLuc variants and/or novel coelenterazines disclosed herein may be provided as part of a kit. The kit may include one or more OgLuc variants as disclosed herein (in the form of a polypeptide, a polynucleotide, or both) and/or a coelenterazine, along with suitable reagents and instructions to enable a user to perform assays such as those disclosed herein. The coelenterazine may be any of the native, known, or novel coelenterazines disclosed herein. The kit may also include one or more buffers, such as those disclosed herein.

Vectors and Host Cells Encoding the Modified Luciferase or Fusions Thereof

Once a desirable nucleic acid molecule encoding an OgLuc variant or a fragment thereof, such as one with luminescence activity or which may be complemented by another molecule to result in luminescence activity, or a fusion thereof with luminescence activity, is prepared, an expression cassette encoding the OgLuc variant or a fragment thereof, e.g., one for complementation, or a fusion thereof with luminescence activity, may be prepared. For example, a nucleic acid molecule comprising a nucleic acid sequence encoding an OgLuc variant is optionally operably linked to transcription regulatory sequences, e.g., one or more enhancers, a promoter, a transcription termination sequence or a combination thereof, to form an expression cassette. The nucleic acid molecule or expression cassette may be introduced to a vector, e.g., a plasmid or viral vector, which optionally includes a selectable marker gene, and the vector introduced to a cell of interest, for example, a prokaryotic cell such as *E. coli*, *Streptomyces* spp., *Bacillus* spp., *Staphylococcus* spp. and the like, as well as eukaryotic cells including a plant (dicot or monocot), fungus (including yeast, e.g., *Pichia*, *Saccharomyces* or *Schizosaccharomyces*), or a mammalian cell, lysates thereof, or to an in vitro transcription/translation mixture. Mammalian cells include but are not limited to bovine, caprine, ovine, canine, feline, non-human primate, e.g., simian, and human cells. Mammalian cell lines include, but are not limited to, CHO, COS, HEK293, HeLa, CV-1, SH-SY5Y, and NIH 3T3 cells, although numerous other cell lines can also be used as well.

The expression of an encoded OgLuc variant may be controlled by any promoter capable of expression in prokaryotic cells or eukaryotic cells including synthetic promoters. Prokaryotic promoters include, but are not limited to, SP6, T7, T5, tac, bla, trp, gal, lac or maltose promoters, including any fragment that has promoter activity. Eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE, including any fragment that has promoter activity. The expression of an encoded OgLuc variant may also be controlled by post-transcriptional processes, such as by regulation of RNA processing or regulation of translation, for example by RNAi, miRNA, shRNA, siRNA, or by RNA or protein degradation. The nucleic acid molecule, expression cassette and/or vector of the invention may be introduced to a cell by any method including, but not limited to, calcium-mediated transformation, electroporation, microinjection, lipofection, and the like.

Optimized Sequences, and Vectors and Host Cells Encoding the OgLuc Variants

Also provided is an isolated nucleic acid molecule (polynucleotide) comprising a nucleic acid sequence encoding an OgLuc variant of the invention, a functional fragment thereof or a fusion protein thereof. In some embodiments, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. Such optimized sequences can provide enhanced expression, e.g., increased levels of protein expression, when introduced into a host cell. Examples of optimized sequences are disclosed in U.S. Pat. No. 7,728,118 and U.S. Pat. Appl. Publ. Nos. 2008/0070299, 2008/0090291, and 2006/0068395, each of which is incorporated by reference herein.

In some embodiments, the polynucleotide includes a nucleic acid sequence encoding an OgLuc variant of the invention, which nucleic acid sequence is optimized for expression in a mammalian host cell. In some embodiments, an optimized polynucleotide no longer hybridizes to the corresponding non-optimized sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often used when it is desired that nucleic acids that are not completely complementary to one another be hybridized or annealed together. The art knows well that numerous equivalent conditions can be employed to comprise medium or low stringency conditions.

In some embodiments, the polynucleotide has less than 90%, e.g., less than 80%, nucleic acid sequence identity to the corresponding non-optimized sequence and optionally encodes a polypeptide having at least 60%, e.g., at least 65%, 70%, 75%, 80%, 85%, 90%, 95%, 96%, 97%, 98%, 99%, or 100%, amino acid sequence identity with the polypeptide encoded by the non-optimized sequence. Constructs, e.g., expression cassettes, and vectors comprising the isolated nucleic acid molecule, e.g., with optimized nucleic acid sequence, as well as kits comprising the isolated nucleic acid molecule, construct or vector are also provided.

A nucleic acid molecule comprising a nucleic acid sequence encoding an OgLuc variant of the invention, a fragment thereof or a fusion thereof is optionally optimized for expression in a particular host cell and also optionally operably linked to transcription regulatory sequences, e.g., one or more enhancers, a promoter, a transcription termination sequence or a combination thereof, to form an expression cassette.

In some embodiments, a nucleic acid sequence encoding an OgLuc variant of the invention, a fragment thereof or a fusion thereof is optimized by replacing codons, e.g., at least 25% of the codons in a parental OgLuc sequence with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Examples of undesirable structural attributes include, but not limited to, restriction enzyme sites, eukaryotic sequence elements, vertebrate promoter modules and transcription factor binding sites, response elements, *E. coli* sequence elements, mRNA secondary structure. Thus, the optimized nucleic acid product may have an improved level of expression due to improved codon usage frequency, and a reduced risk of inappropriate transcriptional behavior due to a reduced number of undesirable transcription regulatory sequences.

An isolated and optimized nucleic acid molecule may have a codon composition that differs from that of the corresponding wild-type nucleic acid sequence at more than 30%, 35%, 40% or more than 45%, e.g., 50%, 55%, 60% or more of the codons. Exemplary codons for use in the invention are those which are employed more frequently than at least one other codon for the same amino acid in a particular organism and, in some embodiments, are also not low-usage codons in that organism and are not low-usage codons in the organism used to clone or screen for the expression of the nucleic acid molecule. Moreover, codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In some embodiments of the invention, the codons that are different are those employed more frequently in a mammal, while in still other embodiments, the codons that are different are those employed more frequently in a plant. Preferred codons for different organisms are known to the art. A particular type of mammal, e.g., a human, may have a different set of preferred codons than another type of mammal. Likewise, a particular type of plant may have a different set of preferred codons than another type of plant. In one embodiment of the invention, the majority of the codons that differ are ones that are preferred codons in a desired host cell. Preferred codons for organisms including mammals (e.g., humans) and plants are known to the art (e.g., Wada et al., *Nucl. Acids Res.,* 18:2367 (1990); Murray et al., *Nucl. Acids Res.,* 17:477 (1989)).

EXAMPLES

Reference Example 1—Synthesis of α-Aminonitrile (Compound 1)

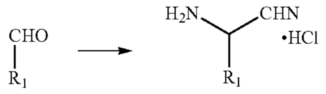

1

A flask was charged with sodium bisulfite (71.4 mmol) and 17 mL of water. To this, a solution of aldehyde (69.3 mmol) in 14 mL of tetrahydrofuran (THF) was added dropwise at a rate that kept the internal temperature below 60° C. The resulting suspension was stirred at ambient temperature for 40 min, and ammonium hydroxide solution (4.85 mL) added over 2 min. The resulting solution was magnetically stirred while being heated in an oil bath at 60° C. for 1 hr and then left at ambient temperature overnight. The solution was cooled in an ice/saltwater bath until the internal temperature measured below 5° C. To this, a solution of sodium cyanide (71.4 mmol) in 14 mL of water was added dropwise over 30 min. The resulting mixture was stirred at approximately 10° C. for 20 min, 30° C. for 2 hrs, and at ambient temperature for 18 hrs. The reaction mixture was extracted into three 200 mL portions of diethyl ether, and the combined extracts dried over anhydrous sodium sulfate. The mixture was filtered, and the solution cooled in an ice bath for 20 min. To the stirred solution, hydrogen chloride gas was added until precipitation ceased, and the suspension stirred for 1 hr. The solid was isolated by filtration and rinsed with three 50 mL portions of diethyl ether. The material was dried under vacuum, and 6.4 g (47.5 mmol) of a white solid was obtained (69%). Procedure was adapted from: Freifelder and Hasbrouck, "Synthesis of Primary 1,2-Diamines by Hydrogenation of alpha-Aminonitriles," *Journal of the American Chemical Society,* 82(3): 696-698 (1960).

Reference Example 2—Synthesis of 2-oxo-2-phenylacetaldehyde oxime (Compound 2)

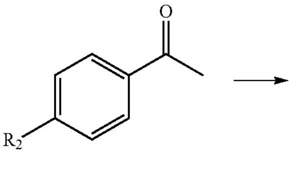

-continued

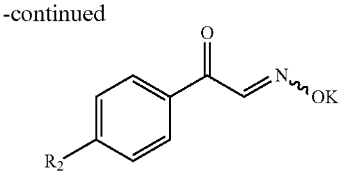

2

A flask was charged with potassium tert-butoxide (58 mmol) and 63 mL of tert-butyl alcohol. The mixture was stirred until a solution was formed, and a solution of the appropriate benzophenone (50 mmol) in 35 mL of tert-butyl alcohol added dropwise over 15 min. The reaction mixture was stirred for 1 hr, and the neat isoamyl nitrite (75 mmol) added over five min. The reaction mixture was monitored for completion and then diluted with 100 mL of heptanes. The resulting solid (38 mmol) was collected via suction filtration and dried to a constant weight under vacuum. Procedure was adapted from: Hagedorn et al., *Chem. Ber.,* 98:193 (1965).

Reference Example 3—Synthesis of Pyrazine Derivatives (Compound 3)

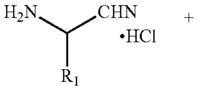

1

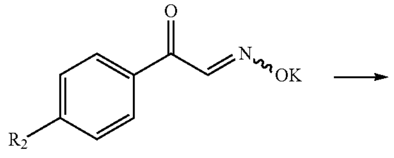

2

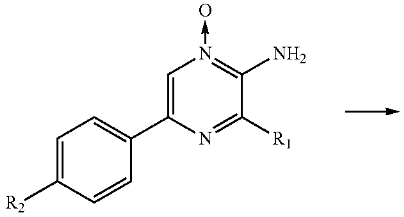

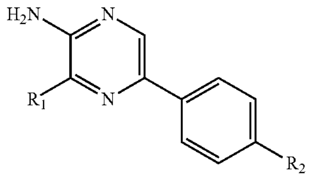

3

A 3-neck flask was fitted with a thermometer, septum, and argon line. To this, aminonitrile (47.5 mmol), dry pyridine (190 mL), and oxime (61.75 mmol) was added. The mixture was well stirred for 15 min, and tetra-chloro(bis-pyridyl) titanium complex (94.9 mmol) added in five portions over 35 min making sure the internal temperature remained below 40° C. After the addition was complete, the reaction mixture was stirred overnight at ambient temperature. The reaction mixture was slowly added to a solution of sodium bicarbonate (21.75 g in 174 mL water) in small portions. The resulting mixture was well stirred for 15 min and 80 g of celite was added. The suspension was stirred for 30 min and filtered through a Buchner funnel. The filtrate was removed to a separatory funnel, and the filter cake was suspended in 400 mL of methanol. The mixture was stirred for 30 min and filtered again. This process was repeated a total of four times. The methanolic filtrates were combined and concentrated, and the residue dissolved in 200 mL of ethyl acetate (EtOAc). The solution was added to the separatory funnel containing the original filtrate, and the mixture further extracted with three 100 mL portions of EtOAc. The combined extracts were washed with two 100 mL portions of saturated sodium carbonate and two 100 mL portions of brine solution. The organic solvent was evaporated, and the crude pyazine-oxide obtained as a brown oil. The material was dissolved in 3 mL of methanol, and 89 mL of dichloromethane (DCM) was added. To this solution, zinc dust (80.7 mmol) was added, and the mixture cooled in an ice bath until an internal temperature of 15° C. was reached. The mixture was treated with glacial acetic acid (3 mL) and warmed to an internal temperature of 30° C. in an oil bath for 40 min. The reaction mixture was cooled to room temperature and filtered through a pad of celite. The filter cake was rinsed with DCM, and the combined filtrates washed with an aqueous solution of saturated sodium bicarbonate. The crude product was purified by chromatography over silica gel using a heptane/EtOAc gradient. This gave 2.9 g (29%) of the pyrazine as a brown solid. Procedure was adapted from: Kishi et al., "The structure confirmation of the light-emitting moiety of bioluminescent jellyfish." *Tetrahedron Lett.,* 13(27):2747 (1972).

Reference Example 4—Synthesis of Coelenterazines

Method A: (the following compounds can be synthesized by Method A: compounds PBI-3840, PBI-3886, PBI-3857, PBI-3887, PBI-3913, PBI-3894, PBI-3896, PBI-3897, PBI-3841 and PBI-3842)

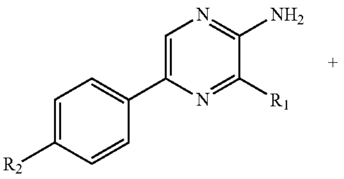

3

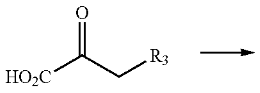

4

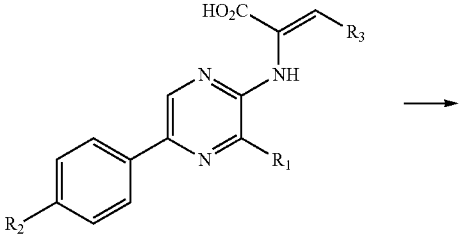

5

-continued

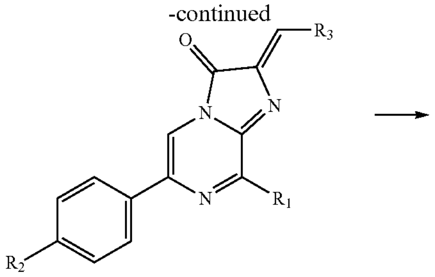

6

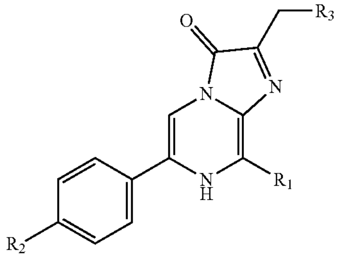

7

A flask was charged with pyrazine (8.25 mmol), pyruvic acid (14.0 mmol), camphor sulfonic acid (0.8 mmol), and anhydrous 2-methyl THE (150 mL). The flask was equipped with a condenser and soxhlet extractor charged with 4-angstrom molecular sieves, and the reaction mixture heated in an oil bath at 110° C. for 18 hrs. The sieves were replaced with fresh ones, and reflux continued for 24 hrs. The reaction mixture was filtered and concentrated, and the residue dissolved in EtOAc (200 mL). This solution was washed with three 25 mL portions of saturated sodium bicarbonate solution, 100 mL of 0.1 M sodium acetate buffer, pH 5, and 100 mL of brine solution. The solution was dried over magnesium sulfate, filtered, and concentrated to give 2.3 g (6.2 mmol, 75%) of the crude enamine/acid. This material was dissolved in anhydrous THF (30 mL), and the solution cooled in an ice/water bath for 10 min. To this, the carbodiimide (9.0 mmol) and neat diisopropylethyl amine (14.9 mmol) was added. The cold bath was removed after 10 min, and the reaction mixture stirred at ambient temperature for 3 hrs. To the reaction mixture, 50 mL of 0.1 M sodium acetate buffer, pH 5 was added, and the mixture well stirred for 10 min. The biphasic mixture was extracted with three 100 mL portions of EtOAc, and the combined extracts washed with brine solution. The organic solution was concentrated, and the residue purified by chromatography over silica gel using a DCM/methanol gradient. This gave 336 mg (0.94 mmol, 16%) of the dehydrocoelenterazine as a red solid. This material was suspended in 10 mL of methanol, and the mixture cooled in an ice bath. To this, sodium borohydride (100 mg, 2.6 mmol) was added in three portions over 1 hr. The reaction mixture was stirred for an additional 30 min, and neat glacial acetic acid added drop wise until a pH of 5 was reached. The solution was concentrated, and the residue triturated with 15 mL of water. The solid was isolated via suction filtration and dried under vacuum for several hours to give 318 mg (94%) of the crude coelenterazine as a yellow solid. Procedure was adapted from: Kakoi and Inoue, *Chem. Lett.* 11(3):299-300 (1980).

Method B: (the following compounds can be synthesized by method B: compounds PBI-3882, PBI-3932, PBI-3881)

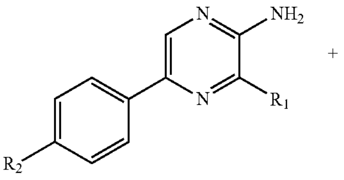

3

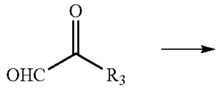

8

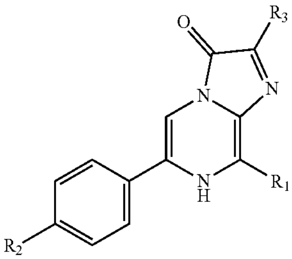

9

A flask was charged with the glyoxal (2.2 mmol), aminopyrazine (1.1 mmol), ethanol (20 mL), 12N HCl (0.6 mL), and water (1 mL). The reaction mixture was heated at reflux for 24 hrs and concentrated. The residue was purified by column chromatography over silica gel using a DCM/methanol gradient. This gave 100 mg (0.25 mmol, 23%) of the coelenterazine product as a dark solid. Procedure was adapted from: Inoue et al. "Squid bioluminescence. II. Isolation from *Watasenia scintillans* and synthesis of 2-(p-hydroxybenzyl)-6-(p-hydroxyphenyl)-3,7-dihydroimidazo [1,2-a]pyrazin-3-one." *Chem. Lett.,* 4(2):141-4 (1975).

Method C: Synthesis of Novel Coelenterazines (the Following Compounds can be Synthesized by Method C: PBI-3939, PBI-3945, PBI-3889, PBI-4002)

The compound 4-(5-amino-6-benzylpyrazin-2-yl)phenol can be prepared according to previously described methods (Kishi et al., *Tetrahedron Lett.,* 13:2747 (1972); Mosrin et al., *Organic Letters,* 11:3406 (2009); Kakoi, *Chem. Pharm. Bull.,* 50:301 (2002)).

Synthesis of 2-amino-3-benzyl-5-phenylpyrazine. A round bottomed flask was charged with 5 g (33.5 mmol) of 2-isonitrosoacetophenone, 6.7 g (36.8 mmol) of 2-amino-3-phenylpropanenitrile hydrochloride and 100 mL of dry pyridine. The mixture was cooled to −20° C. and 4.6 mL (40.0 mmol) of $TiCl_4$ was added dropwise. The reaction was kept at −20° C. for 30 min and heated to 80° C. for 2.5 hrs. The solvent was evaporated, and the residue taken up in 1 L of DCM. This solution was washed with saturated $NaHCO_3$ and brine. All volatiles were evaporated, and the residue redissolved in ethanol (400 mL). Raney Ni (2.0 g, aqueous suspension) was added, and the reaction allowed to stir for 5 days under 1 atm of hydrogen. The mixture was passed through celite, and volatiles removed. The residue was chromatographed on silica gel (heptanes/DCM) to give 2.5 g (29%) of 2-amino-3-benzyl-5-phenylpyrazine.

Synthesis of 2-amino-3-phenylpropanenitrile hydrochloride. A round bottomed flask was charged with 65 g (0.624 mol) of sodium hydrogensulfite and 150 mL of water. A solution of 75 g (0.624 mol) of phenylacetaldehyde in 150 mL of THE was added dropwise. After stirring for 20 min, 37 mL of 14 M ammonium hydroxide was added in one portion, and the mixture heated to 60° C. for 60 min. After cooling to 0° C., the mix was diluted with 150 mL of water, and a solution of sodium cyanide (27.5 g, 0.560 mol) in 100 mL of water added dropwise keeping internal temperature below 10° C. Upon addition, the mixture was heated to 30° C. for 2 hrs and extracted with ether. After drying with sodium sulfate, all volatiles were evaporated, and the residue dissolved in 3.5 L of ether and treated with 400 mL of 3.3 M ethanolic HCl. The resulting precipitate was filtered and dried in vacuum to give 55 g (60%) of product.

Synthesis of 3-(furan-2-yl)-2-oxopropanoic acid. To a 100 mL flask, 3-(furan-2-yl)-2-oxopropanoate (940 mg) along with 23 mL cold 6N NaOH was added. The insoluble mixture was stirred in a 90° C. bath for 5 min until dissolved. Cold 1N HCl was added until solution was acidic (approx 120 mL). Solution was extracted 2×50 mL EtOAc. Combined organic layers were washed with 40 mL brine and dried with $Na_2SO_4$. Solution was evaporated to yield 540 mg brown solid. Solid was further purified by reversed-phase high-performance liquid chromatography (HPLC) ramping from 97% aqueous trifluoroacetic acid (TFA) to acetonitrile (ACN).

Synthesis of ethyl 3-(furan-2-yl)-2-oxopropanoate. To a 500 mL flask containing the mixture of isomers (E/Z)-ethyl 2-formamido-3-(furan-2-yl)acrylate (5.0 g), a chilled solution of 220 mL 1.4M (5%) HCl in 50/50 ethanol/water was added. After 5 hrs, the reaction was partitioned between 200 mL of EtOAc and 30 mL brine. The aqueous layer was extracted 2×50 mL EtOAc. Combined organic layers were washed with 1×50 mL water, and 1×50 mL brine and dried over $Na_2SO_4$. Organic layers were co-evaporated with 26 g celite and eluted over 80 g silica gold ramping from heptane to EtOAc. The appropriate combined fractions were evaporated to yield 2.1 g.

Synthesis of (E/Z)-ethyl 2-formamido-3-(furan-2-yl)acrylate. To a 500 mL flask, 50 mL diethyl ether, $Cu_2O$ (320 mg), and furyl aldehyde (5.2 mL) was added. The flasked was cooled in an ice bath, and ethyl 2-isocyanoacetate (5.3 mL) added. After 1.5 hrs, potassium tert-butoxide (5 g) was added to the reaction. After 4 hrs, the heterogeneous reaction was filtered. 60 mL 30% citric acid and 20 mL EtOAc was added and stirred for 10 min. Aqueous layer was extracted with 50 mL EtOAc. Combined organic layers were dried over anhydrous sodium sulfate. EtOAc layers were co-evaporated with 24 g celite and eluted over 80 g silica gold ramping from heptane to EtOAc. Yellow syrup was used without further purification.

Synthesis of 2-oxo-3-(thiophen-2-yl)propanoic acid. To a 250 mL flask, (E/Z)-5-(thiophen-2-ylmethylene)imidazolidine-2,4-dione (5.0 g) and 100 mL of cold 6N NaOH were added. The mixture was heated to 100° C. for 1 hr. Concentrated HCl was added to the cooled solution until acidic (pH=1). The mixture was extracted 8×50 mL diethylether. The combined ether layers were washed with 50 mL brine, dried over $Na_2SO_4$ and evaporated to yield 3.36 g solid. Sample was further purified by recrystalization with α,α,α-trifluorotoluene to yield 1.63 g.

Synthesis of (E/Z)-5-(thiophen-2-ylmethylene)imidazolidine-2,4-dione. To a 250 mL flask, hydantoin (9.8 g) and thiophene-2-carbaldehyde (10 g) were added. To the mixture was dripped piperidine (9.6 mL). The mixture was heated to 100° C. for 1 hr and then poured into 300 mL of 1N HCl. The solid was filtered, washed with water and dried in vacuo to yield 4.9 g solid.

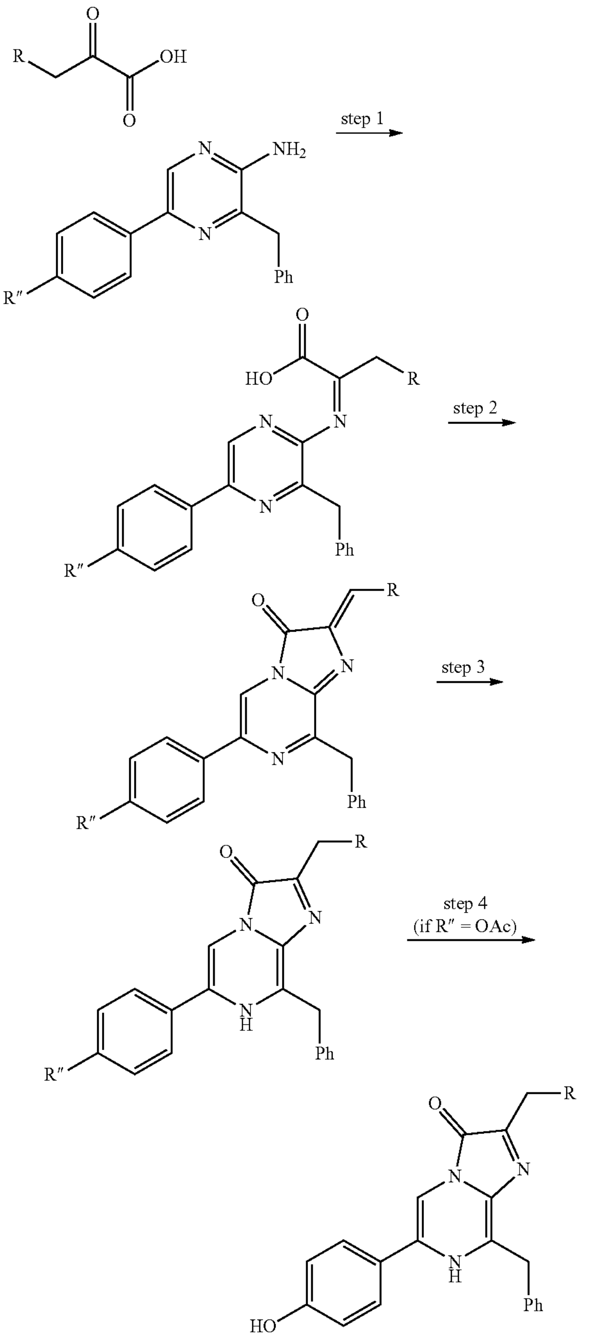

Steps 1—To a microwave vial (10 mL), the appropriate phenylpyrazin-2-amine (100 mg), the appropriate pyruvic acid (2 Equivalents), DCM (1 mL), and 1,1,1-trifluoroethanol (1 mL) were heated with stirring for 30 min at 80° C. Reaction was co-adsorbed on 2 grams of celite, and solvents removed in vacuo. The celite was loaded on 24 g of spherical silica gel and eluted with a ramp of heptanes to ethylacetate. Appropriate fractions were combined and evaporated.

Step 2—The material isolated in step 1 dissolved in THE (0.5 mL) was chilled in an ice bath. Acetic anhydride (25 μL), dimethylaminopyridine (8.5 mg), and triethylamine (25 μL) were added. After 2 hrs, the majority of THE was removed in vacuo. The product was precipitated with an aqueous solution of 30% citric acid (2 mL). The solid was washed with water (2 mL) and then dissolved in 3 mL DCM. The DCM was washed 1×2 mL water followed by 1×2 mL brine. The DCM layer was co-adsorbed on 2 grams of celite, and solvent removed in vacuo. The celite was loaded on 12 g of spherical silica gel and eluted with a ramp of heptanes to DCM. Appropriate fractions were combined and evaporated.

Step 3—The material from step 2 dissolved in DCM (1 mL) was chilled in an ice bath. To the solution, methanol (0.5 mL) and sodium borohydride solution in diglyme (325 μL of 0.5 M) were added. After 2 hrs, acetic acid (10 μL) was added, and the solution quickly partitioned between an aqueous solution of 30% citric acid (1 mL) and DCM (2 mL). The DCM layer was co-adsorbed on 1 gram of celite, and solvent removed in vacuo. The celite was loaded on 4 g of spherical silica gel and eluted with a ramp of DCM to EtOAc. Appropriate fractions were combined and evaporated.

Step 4 (only if R"=OAc)—The material in step 3 was dissolved in THF (200 μL) and chilled in an ice bath. 1 equivalent of 1.35 M potassium methoxide in THF was added to the solution. After 30 min, the reaction was partitioned between DCM (1 mL) and 30% citric acid (1 mL). The DCM layer was co-adsorbed on 0.5 g celite, and solvent removed in vacuo. The celite was loaded on 4 g of spherical silica gel and eluted with a ramp of DCM to EtOAc. Appropriate fractions were combined and evaporated.

Method D: (the following compounds can be synthesized by method D: compounds PBI-3899, PBI-3900, PBI-3925, PBI-3933, PBI-3946)—In general, an aminopyrazine was condensed with 2 equivalents of a 2-oxoacid under an atmosphere of hydrogen in the presence of palladium catalyst. The alpha-amino acid produced was purified and subsequently activated for intramolecular condensation giving rise to the corresponding imidazopyrazinone.

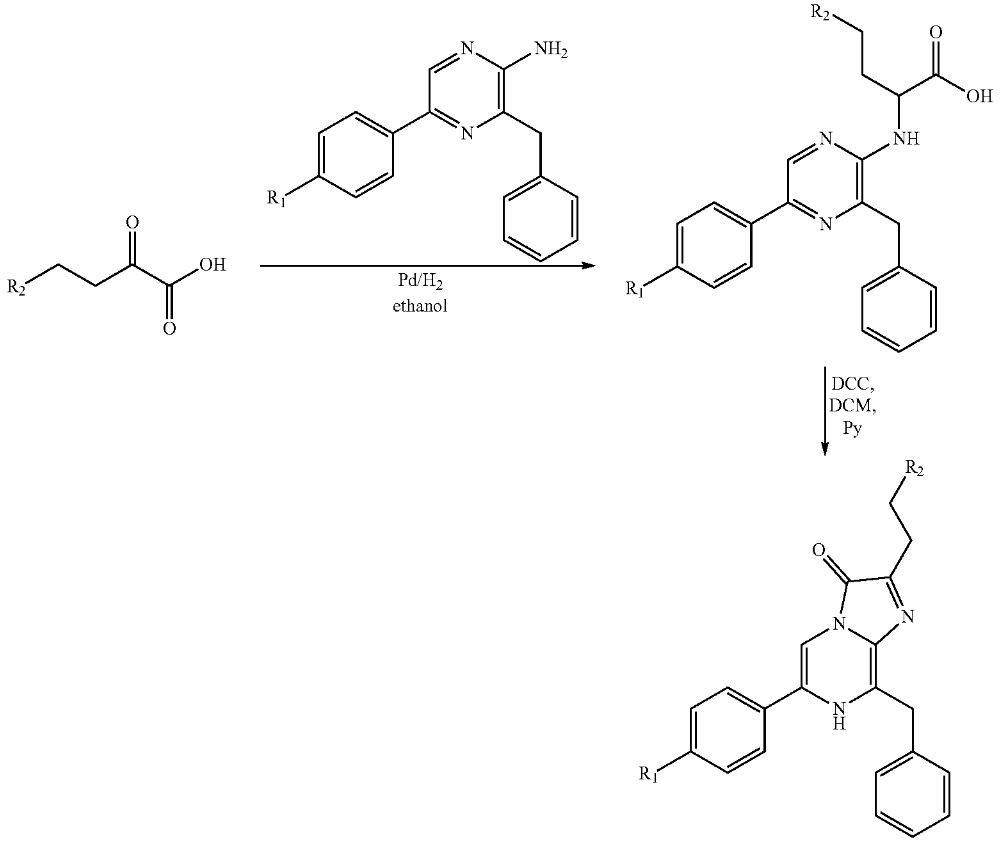

Example 5—Synthesis of 8-benzyl-6-(4-hydroxyphenyl)-2-propylimidazo[1,2-a]pyrazin-3(7H)-one 2-((3-benzyl-5-(4-hydroxyphenyl)pyrazin-2-yl)amino) pentanoic acid. 4-(5-amino-6-benzylpyrazin-2-yl)phenol (100 mg, 0.36 mmol) was mixed with 2-Oxovaleric acid (84 mg, 0.72 mmol) in ethanol (20 mL). Pd/C (10% Palladium in active carbon, 40 mg) was added, and the reaction mixture heated to 65° C. Air was bubbled out by $N_2$ gas, and a hydrogen balloon applied to the reaction flask. The reaction was continuously stirred for 4 hrs. After cooling down, it was filtered, and the resulting solution purified by flash chromatography (eluting solvent: 50% EtOAc in heptanes) to give the product as a yellow powder (70 mg, 52%). $^1H$ NMR (300 MHz, $CD_2Cl_2$, δ): 8.31 (s, 1H), 7.82 (d, 2H, J=9.0 Hz), 7.31 (m, 5H), 6.92 (d, 2H, J=9.0 Hz), 5.34 (s, 2H), 4.20 (m, 1H), 1.10 (m, 2H), 0.98 (m, 2H), 0.87 (t, 3H); MS (ESI) m/z 378.3 (M+1).

8-benzyl-6-(4-hydroxyphenyl)-2-propylimidazo[1,2-a] pyrazin-3(7H)-one. 2-((3-benzyl-5-(4-hydroxyphenyl) pyrazin-2-yl)amino)pentanoic acid (49 mg, 0.13 mmol) was dissolved in DCM (10 mL). Pyridine (0.5 mL) was added followed by N,N'-Dicyclohexylcarbodiimide (54 mg, 0.26 mmol). The reaction mixture was slowly stirred at room temperature for 1 hr. The solvent was evaporated, and the residue purified by flash chromatography (eluting solvent: EtOAc to DCM to 10% methanol in DCM) to give the product as a yellow powder (40 mg, 86%). $^1$H NMR (300 MHz, $CD_3OD$, δ): 7.35 (m, 8H), 6.88 (d, J=9.0 Hz, 2H), 4.40 (s, 2H), 2.81 (t, J=7.5 Hz, 2H), 1.81 (m, 2H), 1.02 (t, J=7.5 Hz, 3H); MS (ESI) m/z 359.0.

Example 6—Synthesis of 8-benzyl-2-butyl-6-(4-hydroxyphenyl)imidazo[1,2-a]pyrazin-3(7H)-one 2-((3-benzyl-5-(4-hydroxyphenyl)pyrazin-2-yl)amino)hexanoic acid. 4-(5-amino-6-benzylpyrazin-2-yl)phenol (200 mg, 0.72 mmol) was mixed with 2-Ketohexanoic acid sodium salt (220 mg, 1.44 mmol) in ethanol (20 mL). Pd/C (10% Palladium in active carbon, 100 mg) was added with a few drops of acetic acid, and the reaction mixture heated to 65° C. Air was bubbled out by $N_2$ gas, and a hydrogen balloon applied to the reaction flask. The reaction was continuously stirred for 4 hrs. After cooling down, it was filtered and the resulting solution was purified by flash chromatography (eluting solvent: 50% EtOAc in heptanes) to give the product as a yellow powder (130 mg, 46%). MS (ESI): m/z 392.2 (M+1).

8-benzyl-2-butyl-6-(4-hydroxyphenyl)imidazo[1,2-a]pyrazin-3(7H)-one. 2-((3-benzyl-5-(4-hydroxyphenyl)pyrazin-2-yl)amino)hexanoic acid (130 mg, 0.33 mmol) was dissolved in DCM (10 mL). Pyridine (0.5 mL) was added followed by N,N'-Dicyclohexylcarbodiimide (137 mg, 0.67 mmol). The reaction mixture was slowly stirred at room temperature for 1 hr. The solvent was evaporated, and the residue purified by flash chromatography (eluting solvent: EtOAc to DCM to 10% methanol in DCM) to give the product as a yellow powder (110 mg, 89%). $^1$H NMR (300 MHz, $CD_3OD$, δ): 7.30 (m, 8H), 6.88 (d, 2H), 4.40 (s, 2H), 2.84 (t, 2H), 1.77 (m, 2H), 1.51 (m, 2H), 0.89 (m, 3H); MS (ESI) m/z 374.3 (M+1).

Example 7—Synthesis of 8-benzyl-2-ethyl-6-phenylimidazo[1,2-a]pyrazin-3(7H)-one (PBI-3925)

2-((3-benzyl-5-phenylpyrazin-2-yl)amino)butanoic acid. 3-benzyl-5-phenylpyrazin-2-amine (200 mg, 0.77 mmol) was mixed with 2-Oxobutyric acid (157 mg, 1.54 mmol) in ethanol (20 mL). Pd/C (10% Palladium in active carbon, 100 mg) was added, and the reaction mixture heated to 65° C. Air was bubbled out by N2 gas, and a hydrogen balloon applied to the reaction flask. The reaction was continuously stirred for 4 hrs. After cooling down, it was filtered, and the resulting solution purified by flash chromatography (eluting solvent: 50% EtOAc in heptanes) to give the product as a yellow powder (90 mg, 34%). $^1$H NMR (300 MHz, $CD_2Cl_2$, δ): 7.72 (s, 1H), 7.32-7.48 (m, 10H), 4.46 (s, 2H), 4.20 (m, 2H), 2.25 (q, 2H), 0.99 (t, 3H); MS (ESI): m/z 348.3 (M+1).

2-((3-benzyl-5-phenylpyrazin-2-yl)amino)butanoic acid was dissolved in DCM (10 mL). Pyridine (0.5 mL) was added followed by N,N'-Dicyclohexylcarbodiimide (137 mg, 0.67 mmol). The reaction mixture was slowly stirred at room temperature for 1 hr. The solvent was evaporated, and the residue purified by flash chromatography (eluting solvent: EtOAc to DCM to 10% methanol in DCM) to give the product as a yellow powder (110 mg, 89%). $^1$H NMR (300 MHz, $CD_3OD$, δ): 7.26 (m, 3H), 6.84-7.07 (m, 8H), 4.03 (s, 2H), 2.47 (q, J=9.0 Hz, 2H), 0.96 (t, J=9.0 Hz, 3H); MS (ESI): m/z 330.2 (M+1).

Example 8—Synthesis of 8-benzyl-6-phenyl-2-(3,3,3-trifluoropropyl)imidazo[1,2-a]pyrazin-3(7H)-one

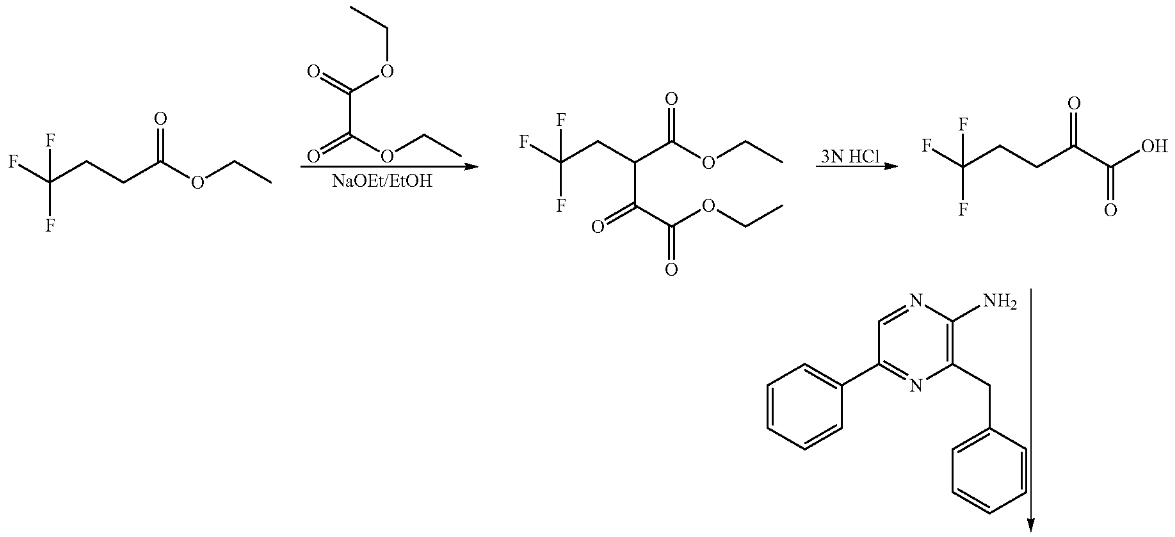

-continued

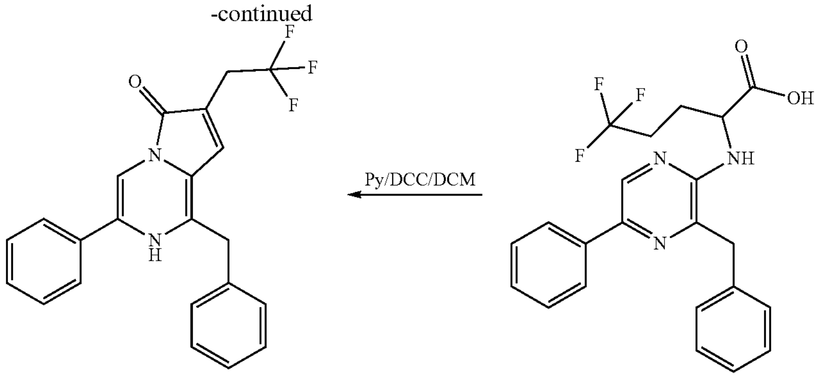

5,5,5-trifluoro-2-oxopentanoic acid. Ethyl 4,4,4-trifluorobutyrate (1 g, 5.88 mmol) and diethyl oxalate (3.87 g, 26.5 mmol) was dissolved in ethanol. Sodium ethoxide (21% in ethanol, 2.09 g) was added to the solution, and the reaction mixture stirred for 0.5 hrs. Solvent was distilled, and the residue extracted with EtOAc/water. The organic layers were collected and dried over sodium sulfate. After filtration, solvent was removed to give a clear liquid. MS (ESI): m/z 269.1 (M−1). The liquid was then dissolved in 3N HCl (20 mL), and the reaction mixture refluxed for 4 hrs. After cooling down, the reaction mixture was extracted with EtOAc. The organic layers were collected and dried over sodium sulfate. After filtration, solvent was removed, and the residue used directly in the next step. MS (ESI): m/z 169.7 (M−1).

5,5,5-trifluoro-2-((3-benzyl-5-phenylpyrazin-2-yl)amino) butanoic acid. 3-benzyl-5-phenylpyrazin-2-amine (240 mg, 0.92 mmol) was mixed with 5,5,5-trifluoro-2-oxopentanoic acid (150 mg, 0.88 mmol) in ethanol (20 mL). Pd/C (10% Palladium in active carbon, 100 mg) was added, and the reaction mixture heated to 65° C. Air was bubbled out by $N_2$ gas, and a hydrogen balloon applied to the reaction flask. The reaction was continuously stirred for 4 hrs. After cooling down, it was filtered, and the resulting solution purified by flash chromatography (eluting solvent: 50% EtOAc in heptanes) to give the product as a yellow powder (200 mg, 54%). $^1H$ NMR (300 MHz, $CD_2Cl_2$, δ): 11.45 (s, 1H), 10.20 (s, 1H), 7.94 (s, 1H), 7.34 (m, 10H), 5.34 (s, 2H), 3.96-4.23 (m, 2H), 3.02-3.28 (m, 2H); FNMR: −76.3; MS (ESI): m/z 416.1 (M+1).

Coelenterazine ($R_1$=H, $R_2$=—$CH_2CH_2CF_3$). 5,5,5-trifluoro-2-((3-benzyl-5-phenylpyrazin-2-yl)amino)butanoic acid (100 mg, 0.24 mmol) was dissolved in DCM (10 mL). Pyridine (0.5 mL) was added followed by N,N'-Dicyclohexylcarbodiimide (100 mg, 0.48 mmol). The reaction mixture was slowly stirred at room temperature for 1 hr. The solvent was evaporated, and the residue purified by flash chromatography (eluting solvent: EtOAc to DCM to 10% methanol in DCM) to give the product as a yellow powder (80 mg, 87%). $^1H$ NMR (300 MHz, $CD_2Cl_2$, δ): 7.36 (m, 11H), 3.43 (s, 2H), 1.60-1.92 (m, 4H); FNMR: 67.4 (t, J=18 Hz); MS (ESI): m/z 398.2 (M+1).

Example 9—Synthesis of 8-benzyl-2-(furan-2-ylmethyl)-6-phenylimidazo[1,2-a]pyrazin-3(7H)-one (PBI-3939)

PBI-3939

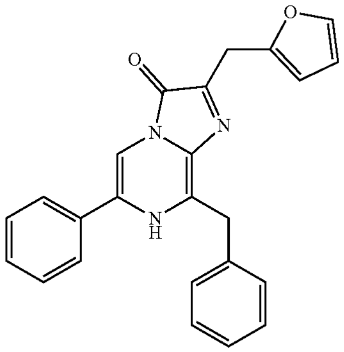

8-benzyl-2-(furan-2-ylmethyl)-6-phenylimidazo[1,2-a] pyrazin-3(7H)-one: Synthesized from method C using 3-(furan-2-yl)-2-oxopropanoic acid and 3-benzyl-5-phenylpyrazin-2-amine as starting materials. $^1H$ NMR (300 MHz, dmso) δ 8.88 (s, 1H), 8.02 (d, J=7.9, 2H), 7.61-7.38 (m, 6H), 7.37-7.14 (m, 3H), 6.38 (s, 1H), 6.26 (d, J=3.2, 1H), 4.64 (s, 3H), 4.40 (s, 3H); exact mass calculated for $C_{24}H_{20}N_3O_2^+$ m/z+382.16, found m/z+382.

Example 10—Synthesis of 8-benzyl-6-phenyl-2-(thiophen-2-ylmethyl)imidazo[1,2-a]pyrazin-3(7H)-one (PBI-3889)

PBI-3889

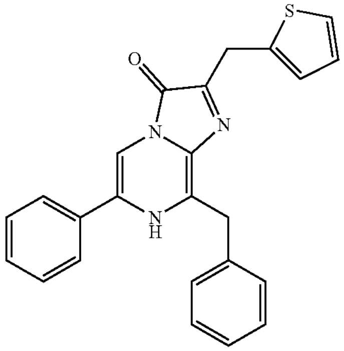

8-benzyl-6-phenyl-2-(thiophen-2-ylmethyl)imidazo[1,2-α]pyrazin-3(7H)-one: Synthesized from method C using 2-oxo-3-(thiophen-2-yl)propanoic acid and 3-benzyl-5-phenylpyrazin-2-amine as starting materials. $^1H$ NMR (300 MHz, dmso) δ 8.85 (s, 1H), 7.99 (d, J=6.8, 2H), 7.63-7.02 (m, 10H), 6.94 (dd, J=3.5, 5.1, 1H), 4.62 (s, 2H), 4.58 (s, 2H), 2.69 (contaminate); exact mass calculated for $C_{24}H_{20}N_3OS^+$ m/z+398.13, found m/z+398.

Example 11—Synthesis of 8-cyclopropyl-2-(4-hydroxybenzyl)-6-phenylimidazo[1,2-a]pyrazin-3(7H)-one (PBI-3897)

PBI-3897

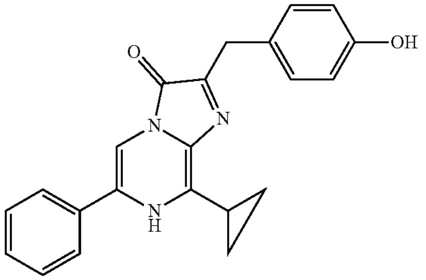

8-cyclopropyl-2-(4-hydroxybenzyl)-6-phenylimidazo[1,2-a]pyrazin-3(7H)-one: Synthesized using method A with 3-cyclopropyl-5-phenylpyrazin-2-amine and 3-(4-hydroxyphenyl)-2-oxopropanoic acid as starting materials. Exact mass calculated for $C_{22}H_{18}N_3O_2^-$ m/z−356.14, found m/z−356.

Example 12—Synthesis of 8-benzyl-2-methyl-6-phenylimidazo[1,2-a]pyrazin-3(7H)-one (PBI-3932)

PBI-3932

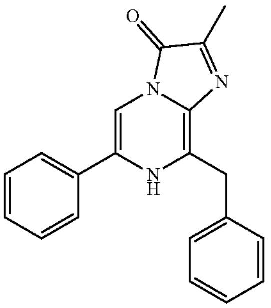

8-benzyl-2-methyl-6-phenylimidazo[1,2-a]pyrazin-3(7H)-one: Synthesized using method B with 1,1-dimethoxypropan-2-one and 3-benzyl-5-phenylpyrazin-2-amine as starting materials. Exact mass calculated for $C_{20}H_{18}N_3O^+$ m/z+316.14, found m/z+316.

Example 13—Synthesis of 2-(4-hydroxybenzyl)-8-methyl-6-phenylimidazo[1,2-a]pyrazin-3(7H)-one (PBI-3896)

PBI-3896

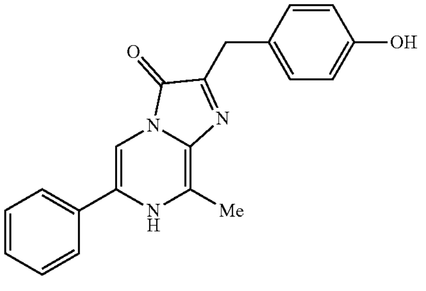

2-(4-hydroxybenzyl)-8-methyl-6-phenylimidazo[1,2-a]pyrazin-3(7H)-one: Synthesized using method A with 3-methyl-5-phenylpyrazin-2-amine and 3-(4-hydroxyphenyl)-2-oxopropanoic acid as starting materials. $^1H$ NMR (300 MHz, dmso) δ 8.84 (s, 1H), 8.00 (d, J=7.6, 2H), 7.47 (dd, J=8.6, 16.2, 3H), 7.17 (d, J=7.3, 2H), 6.69 (d, J=8.4, 2H), 6.26 (s, 4H), 4.17 (s, 2H), 2.86 (s, 3H), 2.48 (s, 1H).

Example 14—Synthesis of 8-benzyl-2-(4-hydroxybenzyl)-6-phenylimidazo[1,2-a]pyrazin-3(7H)-one (PBI-3840)

PBI-3840

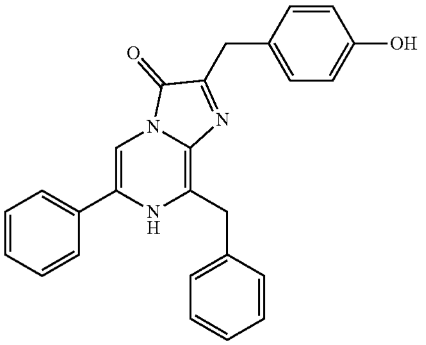

8-benzyl-2-(4-hydroxybenzyl)-6-phenylimidazo[1,2-a]pyrazin-3 (7H)-one: Synthesized using method A with 3-(4-hydroxyphenyl)-2-oxopropanoic acid and 3-benzyl-5-phenylpyrazin-2-amine as starting materials. Exact mass calculated for $C_{26}H_{22}N_3O_2^+$ m/z+408.17, found m/z+408.

Example 15—Synthesis of Protected Coelenterazine (Stabilized) (PBI-4377)

To a mixture of PBI-3939, potassium carbonate (1.1 equiv) and potassium iodide (1.1 equiv) in dimethylformamide (DMF), under an argon atmosphere, was added one equivalent of chloromethyl pivalate at room temperature. Reaction progress was monitored by thin layer chromatography, and upon completion, the reaction mixture was cooled in an ice bath for several minutes before addition of a volume of water equal to the reaction volume. The resulting mixture was extracted with a suitable organic solvent (e.g., EtOAc), and the extract was concentrated to give the crude product. The material was further purified by chromatography over silica gel.

Example 16—Synthesis of 8-benzyl-2-((1-methyl-1H-imidazol-2-yl)methyl)-6-phenylimidazo[1,2-a] pyrazin-3 (7H)-one (PBI-4525), 8-benzyl-6-(4-hydroxyphenyl)-2-((1-methyl-1H-imidazol-2-yl) methyl)-6-phenylimidazo[1,2-a]pyrazin-3 (7H)-one (PBI-4540) and 2-((1H-imidazol-2-yl)methyl)-8-benzyl-6-phenylimidazo[1,2-a]pyrazin-3 (7H)-one (PBI-4541)

PBI-4525 PBI-4540

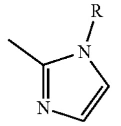

1 R = Me
2 R = Ph3C

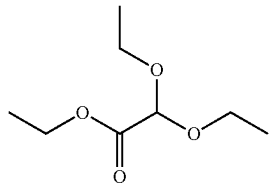

3

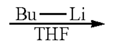

PBI-4541

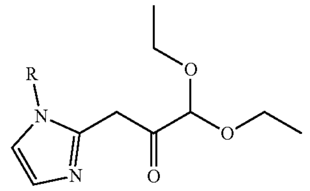

4 R = Me
5 R = Ph3C

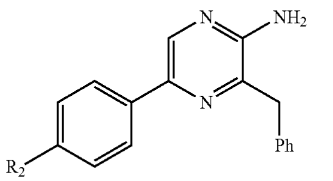

6 R2 = H
7 R2 = OH

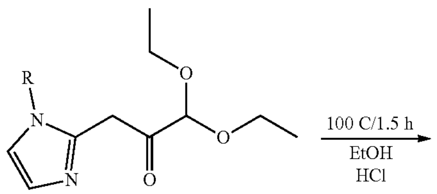

8 R = Me
9 R = Ph3C

-continued

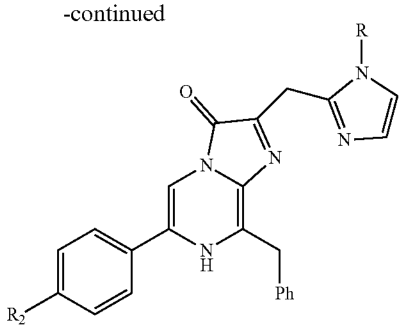

10 R = Me, R2 = H
11 R = Me, R2 = OH
12 R = H, R2 = H

To a flask containing 10 mmol of 2-methyl imidazole derivative 1 or 2 under an argon atmosphere, 20 mL of dry THE was added, and the solution was cooled in a dry ice/acetone bath to approximately −78° C. To the cold mixture, 9.3 mmol of a solution of n-butyllithium (2.46 M in Hexanes) was added dropwise over several minutes. The resulting solution was stirred at approximately −78° C. for 30 min, and 6.7 mmol of compound 3 was added via syringe. The reaction mixture was stirred for 3 hrs and quenched with the addition of 20 mL saturated ammonium chloride solution and 20 mL of saturated sodium bicarbonate solution. The cold bath was removed, and after warming to room temperature, the mixture was extracted with 3×100 mL of EtOAc. The combined extracts were dried ($MgSO_4$), concentrated in vacuo, and the crude compounds 4 or 5 were purified by column chromatography using silica gel (EtOAc/Heptane).

A microwave vial was charged with 100 mg (1 eq) of compound 6 or 7 and 2 equivalents of compound 8 or 9. To the mixture, 4.5 mL of ethanol and 0.25 mL of concentrated HCl was added. The reaction mixture was heated in a microwave at 100° C. for 1.5 hr. The resulting mixture was added to 50 mL of EtOAc and washed sequentially with 20 mL of saturated sodium bicarbonate solution and 20 mL of brine. The organic phase was concentrated in vacuo, and the residue purified by column chromatography using silica gel (methanol/dichloromethane) to give compounds 10-12.

Example 17—Stability and Auto-Luminescence Characterization of Novel Coelenterazines The stability and auto-luminescence characterization of the novel coelenterazines PBI-3939, PBI-3889, PBI-3945, PBI-4002, or PBI-3896 were determined. Higher stability and less auto-luminescence is an attractive technical feature in a substrate/reagent.

To determine stability, 20 μM of novel coelenterazines PBI-3939, PBI-3889, PBI-3945, PBI-4002, or PBI-3896, 30 μM native coelenterazine, or 22 μM of known coelenterazine-h or known coelenterazine-hh, were placed in a reporter reagent buffer containing 50 mM CDTA, 150 mM KCl, 50 mM DTT, 35 mM thiourea, 1% TERGITOL® NP-9 (v/v), and 0.1% MAZU® DF 204. Replicate samples were incubated at room temperature (i.e., 22-24° C.) for various lengths of time and then transferred to −70° C. After all the samples were collected and frozen, they were thawed and mixed with 10 μL of bacterial cell lysate containing the OgLuc variant IV in 40 μL of DMEM without phenol red+0.1% PRIONEX®. The luminescence of the sample was read at 5 min after IV addition.

"$T_{90}$" indicates the amount of time for the luminescent signal to decay by 10% (i.e., loss in activity by 10%) at ambient temperature, i.e., 22° C. The rate of decay of the luminescent signal ("$T_{90}$") was determined from the slope of the linear fit of the data plotted as ln RLU vs. time, which was calculated from the following equation: t=ln $(A/A_0)\div(-k)$, where A=intensity at time t, $A_0$=intensity at time 0, and k=the rate of decay. As shown in Table 1, the $T_{90}$ values for known coelenterazines-h and -hh, novel coelenterazines PBI-3939, PBI-3889, PBI-3945, PBI-4002, and PBI-3896 were higher than for native coelenterazine, indicating that these coelenterazines were more stable compounds than native coelenterazine.

To determine the auto-luminescence characterization, HEK293 cells were grown overnight at 15,000 cells per well in DMEM+10% FBS+pyruvate. Media was removed and replaced with 20 μM each of the novel coelenterazines shown in FIG. 2, i.e., PBI-3939, PBI-3889, PBI-3945, PBI-4002, PBI-3841, PBI-3897, PBI-3896, PBI-3925, PBI-3894, PBI-3932, and PBI-3840, native coelenterazine and known coelenterazines, coelenterazine-h and coelenterazine-hh, diluted into $CO_2$ independent media plus 10% FBS. Luminescence was measured shortly after substrate addition on the GLOMAX® Luminometer (1 sec/well). Background luminescence was 154±15 RLU. Table 1 shows the auto-luminescence characterization normalized to native coelenterazine ("Autolum (norm to coel)"). While coelenterazine-h had more auto-luminescence than native coelenterazine, all of the other coelenterazines tested had less auto-luminescence.

TABLE 1

Stability Experiments and Autoluminescence Characterization of IV with Various Coelenterazines.

| Substrate ID | Stability (pH 8) ($T_{90}$ in hrs) | Autolum (norm to coel) |
|---|---|---|
| Coel | 1.7 | 1 |
| Coel h | 2.1 | 1.2 |
| Coel hh | 2.0 | 0.3 |
| 3939 | 4.1 | 0.2 |
| 3889 | 2.9 | 0.2 |
| 3945 | 3.3 | 0.5 |
| 4002 | 3.5 | 0.6 |
| 3841 | | 0.1 |
| 3897 | | 0.1 |
| 3896 | 2.8 | 0.1 |
| 3894 | | 0.2 |
| 3932 | | 0.1 |
| 3840 | | 0.2 |
| 3925 | | 0.2 |

Example 18—Toxicity of Novel Coelenterazines

The toxicity of the novel coelenterazines were investigated in HEK293 cells. HEK293 cells were grown overnight at 15,000/well in DMEM+10% FBS+pyruvate. The media was removed and replaced with the novel coelenterazine compounds (or DMSO control) diluted into $CO_2$ independent media plus 10% FBS. Cell viability was measured 24 hrs after compound addition using CELLTITER-GLO® assay reagent (Promega Corp.) according to the manufacturer's instructions, and luminescence was measured on the GLOMAX® Luminometer (1 sec/well). Table 2 shows the toxicity of the native coelenterazine, known coelenterazine-h and coelenterazine-hh, and the novel coelenterazines PBI-3939, PBI-3889, PBI-3841, PBI-3897, PBI-3945, PBI-4002, and PBI-3840 in HEK293 cells. With the exception of PBI-3840, the novel coelenterazines had at least the same toxicity as coelenterazine-hh. Some of the novel coelenterazines had the same toxicity as native coelenterazine and coelenterazine-h.

TABLE 2

Toxicity of Various Coelenterazines in HEK293 Cells Based on CELLTITER-GLO ®

| Substrate | Viability (normalized to vehicle (DMSO) control) (%) |
|---|---|
| Native coelenterazine | 100 |
| Coelenterazine h | 100 |
| Coelenterazine hh | 87 |
| PBI-3939 | 89 |
| PBI-3889 | 90 |
| PBI-3841 | 100 |
| PBI-3897 | 100 |
| PBI-3945 | 100 |
| PBI-4002 | 100 |
| PBI-3840 | 60 |

Example 19—Km of PBI-3939

Figure 3:
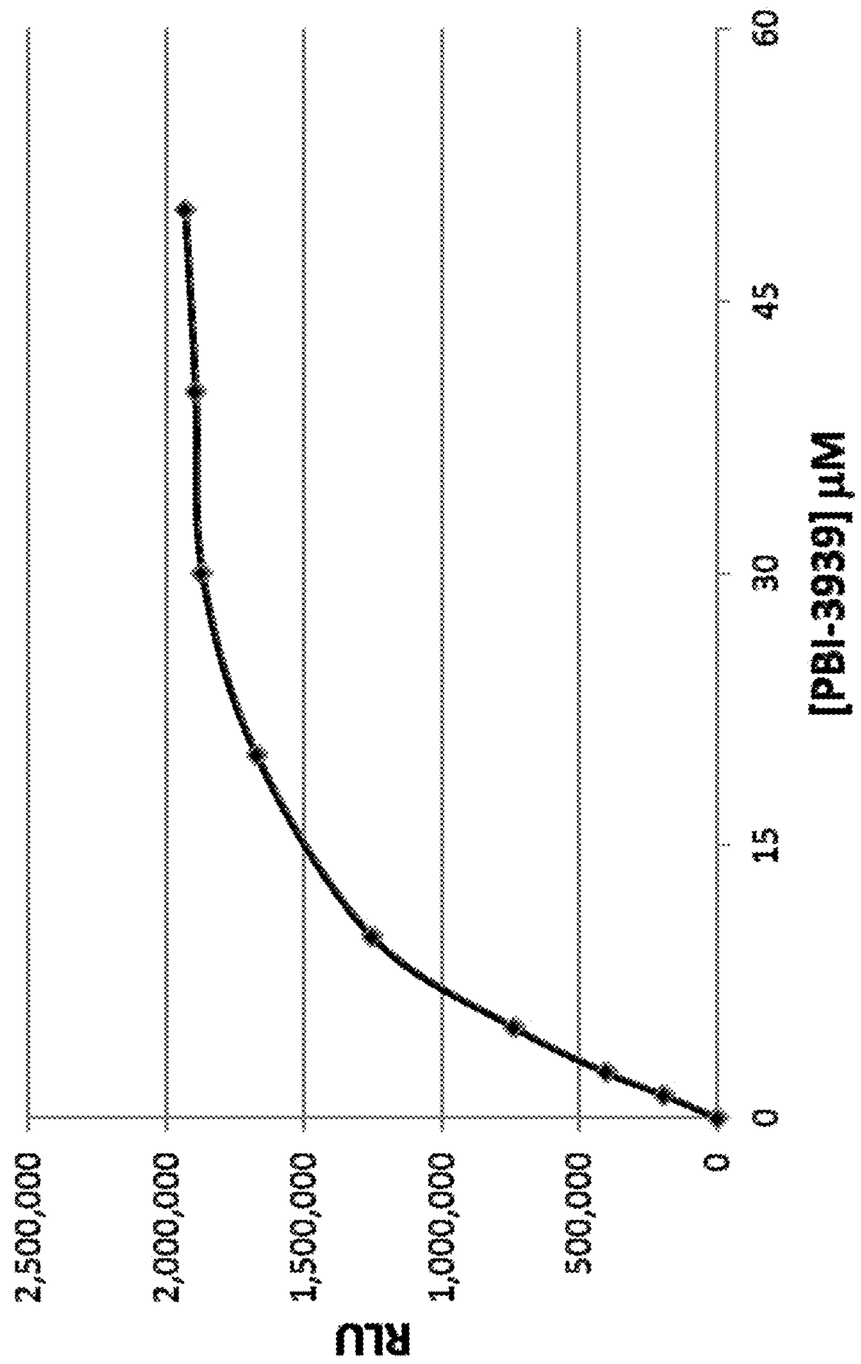
FIG. 3 shows the Km determination of PBI-3939.

To determine the Km of PBI-3939, the OgLuc variant L27V (described in Example 26) was purified via HALOTAG® fusion using the HALOTAG® Protein Purification System according to the manufacturer's instructions and diluted in DMEM without Phenol Red and 0.1% PRIONEX®. 50 μL assay buffer (100 mM MES pH 6, 35 mM Thiourea, 0.5% TERGITOL® NP-9 (v/v), 1 mM CDTA, 2 mM DTT and 150 mM KCl) with varying amounts of PBI-3939 was added to 50 μL diluted enzyme (approximately 20 μM final enzyme concentration), and luminescence measured at 3 min at 22° C. As the data in FIG. 3 demonstrates, the Km of PBI-3939 is approximately 10 μM.

Example 20—Characterization of Compounds PBI-4525, PBI-4540 and PBI-4541

Compounds PBI-4525, PBI-4540 and PBI-4541 were screened for their ability to detect luminescence. For analysis, 20 μM of each compound was added to assay buffer (100 mM MES pH 6, 35 mM Thiourea, 0.5% TERGITOL® NP-9 (v/v), 1 mM CDTA, 2 mM DTT and 150 mM KCl) which was adjusted to pH 7 with 100 mM HEPES pH 7 to create an assay reagent. The assay reagent was then mixed with 36 pM purified L27V02 enzyme (described in Example 25B), in DMEM without Phenol Red and 0.1% PRIONEX®. As a control, assay buffer with 20 μM PBI-3939 or PBI-4528 was used. Luminescence was measured as previously described 3 min after the assay reagent was added to the enzyme mixture. Table 3 demonstrates that compounds PBI-4525, PBI-4540 and PBI-4541 can be used to detect luminescence from a coelenterazine-utilizing luciferase.

TABLE 3

| cmpd | RLU | +/− |
|---|---|---|
| 4525 | 20,655 | 1,006 |
| 4528 | 202,080 | 5,688 |
| 3939 | 9,808,880 | 307,565 |
| 4540 | 909 | 7 |
| 4541 | 5,676 | 80 |

Example 21—OgLuc Pattern Sequence

Enzyme families, including different classes of luciferases, can be recognized by having common three-dimensional structures and defined catalytic activity. Because enzyme families share evolutionary histories with other enzyme families, they will also exhibit similarities in their three-dimensional structures. Through various means of structural and functional analysis, the inventors have determined that OgLuc, as a representative of decapod luciferases, has a strikingly similar three-dimensional structure to Fatty Acid Binding Proteins (FABPs), indicating commonality of evolutionary history. Thus, decapod luciferase may be defined as having a characteristic three-dimensional structure similar to FABPs and utilizing coelenterazine as a substrate to catalyze the emission of luminescence. Other luciferases, e.g., firefly luciferase, *Renilla* luciferase, bacterial luciferase, and so forth, have clearly distinct three-dimensional structures, indicating that they belong to different enzyme families and do not share evolutionary histories. Dinoflagellate luciferase has a three-dimensional structure exhibiting some similarities to FABPs, suggesting a shared evolutionary history, but does not utilize coelenterazine as a substrate, and thus does not belong to the same enzyme family as decapod luciferases.

Because amino acid sequences are not as well conserved as three-dimensional structures, defining enzyme families based only on sequence comparisons can be difficult. For example, even though FABPs all have a characteristic barrel-shaped three-dimensional shape, comparisons of their amino acid sequences often reveal very low levels of sequence identity. Nonetheless, sequence identity can be used to demonstrate commonality of three-dimensional structures. Two proteins will have analogous three-dimensional structures if their amino acid sequences can be aligned to reveal >30% sequence identity, preferably >40% sequence identity, and most preferably >50% sequence identity (Chothia and Lesk, *EMBO J.* 5(4):823-826 (1986); Tramontano, *Genomics,* 4:402-405 (2003)). Thus, a protein is a decapod luciferase if, upon alignment of its amino acid sequence with the sequence of OgLuc, the sequence identity is >30%, preferably >40%, and most preferably >50%, and the protein can utilize coelenterazine as a substrate to catalyze the emission of luminescence.

Because of structural constraints necessary to sustain the characteristic three-dimensional structure of an enzyme family, some portions of the amino acid sequences in an enzyme family exhibit greater amounts of conservation (i.e., a greater level of sequence identity). Thus, these conserved regions can serve as further evidence of a common three-dimensional structure shared between two proteins. A conserved sequence pattern, also called a signature, motif, or fingerprint, can be generated by manual or computational methods that are known in the art. Patterns can be found in public databases such as PROSITE (http://expasy.org/prosite; Sigrist et al., *Nucleic Acids Res.* 38(suppl 1):D161-D166 (2010)).

For example, a pattern of conserved amino acids can be found upon examination of a large number of known FABPs. PROSITE (Release 20.67, of 5 Oct. 2010) contains an FABP pattern (accession number PS00214, created April-1990, data updated April-2006). This FABP pattern spans 18 amino acid positions and is defined as:

```
                                      (SEQ ID NO: 329)
[GSAIVK]-{FE}-[FYW]-x-[LIVMF]-x-x-{K}-x-[NHG]-
[FY]-[DE]-x-[LIVMFY]-[LIVM]-{N}-{G}-[LIVMAKR]
(VI),
```

where:

the standard IUPAC one-letter codes for the amino acids are used.

the symbol 'x' is used for a position where any amino acid is accepted.

alternative amino acids at a site are indicated by listing the amino acids between square parentheses '[ ]' (for example: [ALT] represents the possibility of an Ala, Leu, or Thr at the position).

the absence of particular amino acids at a site is indicated by curly brackets '{ }' (for example: {AM} represents any amino acid at a position except Ala and Met).

each sequence position (or element in the pattern) is separated from its neighbor by '-'.

each sequence position is referred to as a "pattern position", for example the [GSAIVK] would be considered pattern position 1 of Formula (VI), {FE} is considered pattern position 2 of Formula (VI), etc.

Although a conserved sequence pattern results from a common underlying three-dimensional structure, some changes to the sequence pattern may be allowed without disruption to the three-dimensional structure. For example, for some members of the FABP family, differences are found at four sites in the PROSITE pattern. These additional members of the FABP family include five proteins listed in PROSITE as false negative hits, i.e., FABP protein family members not picked up by the FABP pattern (UniProt database accession numbers FBP12_HUMAN, FABP1_FASGI, FABP2_FASHE, FABPL_SCHBI, RET5_BOVIN) and one protein known to have an FABP fold (Protein Data Bank accession number 2A02). Although OgLuc shares a closely similar three-dimensional structure with FABPs, the sequence patterns of the native and variant amino acid sequences also differ slightly, having differences at 5 positions from the PROSITE pattern. In various embodiments, the pattern in OgLuc begins at a position corresponding to position 8 of SEQ ID NO: 1. An amino acid substitution, deletion, or insertion the sequence pattern is counted as a difference.

Combining the sequence information from these additional FABPs and the OgLuc variants, an improved sequence pattern can be derived:

```
                                      (SEQ ID NO: 330)
[GSAIVK]-{FE}-[FYW]-x-[LIVMFSYQ]-x-x-{K}-x-[NHGK]-
x-[DE]-x-[LIVMFY]-[LIVMWF]-x-{G}-[LIVMAKRG] (VII).
```

The sequence information used to derive this pattern is shown in Table 4. Column 1 identifies the pattern position (listed N- to C-terminus; pattern length is 18 amino acids), and column 6 identifies the corresponding sequence position in OgLuc (numbering according to SEQ ID NO: 1). Column 2 shows the PROSITE FABP pattern (Formula (VI)) element for each pattern position. Column 3 lists amino acids present in six FABP family members that are not represented by the PROSITE FABP pattern. Column 4 lists amino acids present in OgLuc (SEQ ID NO: 1) or OgLuc variants that are not represented by the PROSITE pattern. Column 5 lists the improved pattern ("OgLuc pattern") (Formula (VII)) created by merging pattern information from columns 2, 3, and 4.

Column 7 lists the amino acids in OgLuc (SEQ ID NO: 1) corresponding to the PROSITE FABP pattern positions. Column 8 lists the amino acids found in dinoflagellate luciferase sequences (8 different species) at positions corresponding to the improved pattern (GenBank accession numbers 2021262A, AAA68491, AAC36472, AAV35379, AAV35380, AAL40676, AAL40677, AAV35378, AAV35377, AAV35381, and Protein Data Bank accession number 1VPR).

The improved pattern (Formula (VII)) serves as an indication (i.e., a fingerprint) of the three-dimensional protein structure shared between FABPs and OgLuc. However, strict agreement with this pattern is not needed to indicate commonality of the three-dimensional structure. From the examples given here, a common three-dimensional structure may exist even with as many as 5 changes in the pattern. Also, for example, although the dinoflagellate luciferase has a similar three-dimensional structure to FABPs and OgLuc, it has 4 differences from the improved pattern.

Thus, although a protein may be recognized as being a decapod luciferase based on sequence similarity and utilization of coelenterazine for luminescence, it can be further recognized by also having the improved sequence pattern. Specifically, a protein is a decapod luciferase if, upon alignment of its amino acid sequence with SEQ ID NO: 1 or variants thereof, the sequence identity is >30%, preferably >40%, and most preferably >50%, and the protein can utilize coelenterazine as a substrate to catalyze the emission of luminescence, and the amino acid sequence beginning at the position corresponding to position 8 of SEQ ID NO: 1 is:

(SEQ ID NO: 330)

[GSAIVK]-{FE}-[FYW]-x-[LIVMFSYQ]-x-x-{K}-x-[NHGK]-x-[DE]-x-[LIVMFY]-[LIVMWF]-x-{G}-[LIVMAKRG] (VII), with no more than 5 differences, or more preferably no more than 4, 3, 2, or 1 difference, or most preferably no differences, wherein the differences occur in positions corresponding to pattern position 1, 2, 3, 5, 8, 10, 12, 14, 15, 17, or 18 of Formula (VII) according to Table 4. Differences may also include gaps or insertions between the pattern positions of Table 4.

TABLE 4

| Protein sequence patterns | | | | | | | | |
|---|---|---|---|---|---|---|---|---|
| Pattern position | PRO SITE FABP pattern PS00214 | Other FABPs | OgLuc wt & variants | OgLuc pattern | OgLuc position | OgLuc wt sequence | Dinofl. Luc |
| 1 | [GSAIVK] (SEQ ID NO: 427) | | | [GSAIVK] (SEQ ID NO: 579) | 8 | G | G |
| 2 | {FE} | | | {FE} | 9 | D | R |
| 3 | [FYW] | | | [FYW] | 10 | W | W |
| 4 | x | | | x | 11 | Q | I |
| 5 | [LIVMF] (SEQ ID NO: 590) | SY | Q | [LIVMFSYQ] (SEQ ID NO: 591) | 12 | Q | *T* |
| 6 | x | | | x | 13 | T | [VI] |
| 7 | x | | | x | 14 | A | S |
| 8 | {K} | | | {K} | 15 | G | G |
| 9 | x | | | x | 16 | Y | G |
| 10 | [NHG] | K | | [NHGK] (SEQ ID NO: 580) | 17 | N | *Q* |
| 11 | [FY] | SILM (SEQ ID NO: 581) | {FY} | x | 18 | Q | [AVTK] (SEQ ID NO: 582) |
| 12 | [DE] | | | [DE] | 19 | D | [AE] |
| 13 | x | | | x | 20 | Q | F |
| 14 | [LIVMFY] (SEQ ID NO: 583) | | | [LIVMFY] (SEQ ID NO: 584) | 21 | V | I |
| 15 | [LIVM] (SEQ ID NO: 585) | W | F | [LIVMWF] (SEQ ID NO: 586) | 22 | L | *K* |
| 16 | {K} | | K | x | 23 | E | [EKTQ] (SEQ ID NO: 587) |
| 17 | {G} | | | {G} | 24 | Q | [AV] |
| 18 | [LIVMAKR] (SEQ ID NO: 588) | | G | [LIVMAKRG] (SEQ ID NO: 589) | 25 | G | [VI] |

Example 22—Generation of OgLuc Variants

Experimental Details

Unless otherwise stated, further variants of a starting OgLuc variant sequence with random substitutions were generated using the error-prone, mutagenic PCR-based system GeneMorph II Random Mutagenesis Kit (Stratagene; Daughtery, *PNAS USA,* 97(5):2029 (2000)), according to manufacturer's instructions, and NNK site saturation (Zheng et al., *Nucleic Acids Research,* 32:e115 (2004)).

Further variants of a starting OgLuc variant having specific mutations were generated using the oligo-based site-directed mutagenesis kit QuikChange Site-Directed Mutagenesis Kit (Stratagene; Kunkel, *PNAS USA,* 82(2):488 (1985)), according to the manufacturer's instructions.

The resulting variants were constructed in the context of pF1K FLEXI® vector for T7 promoter-based expression (Promega Corp.). Alternatively, the resulting variants were constructed in the context of pF4Ag vector (a version of the commercially-available pF4A (Promega Corp.), which contained T7 and CMV promoters modified to contain an *E. coli* ribosome-binding site with or without a C-terminal HALOTAG® (Promega Corp.; referred herein as "HT7") (Ohana et al., *Protein Expression and Purification,* 68:110-120 (2009)) to generate a fusion protein. For example, to obtain C1+A4E variants, NNK saturation mutagenesis experiments were performed in a pF1K vector background. The C1+A4E library was generated in a pF4Ag vector background with no HT7. The QC27, QC27-9a, and IVY libraries were generated in a pF4Ag vector background with a C-terminal HT7. The IV-based variants were generated in a pF4Ag vector background without HT7. The resulting vectors were used to transform KRX *E. coli* using techniques known in the art.

Generated OgLuc variants are named for the amino acid substitutions identified in the variant and/or for the *E. coli* clone that contained the variant, e.g., FIG. 6A shows, among other results, that *E. coli* clone $16C_5$ has the substitution Q20R.

Screening Details

Resulting libraries were expressed in *E. coli* and primarily screened with a robotic system for OgLuc variants having increased light output (i.e., increased luminescence, increased brightness, or increased light emission) or a change in relative specificity compared to the corresponding starting OgLuc variant. The robotic primary screen was conducted as follows: individual colonies from the generated library were used to inoculate minimal media in 96-well plates and grown at 37° C. for 17 to 20 hrs ("M1 culture"). The M1 culture was diluted 1:20 with fresh minimal media and grown at 37° C. for 17-20 hrs ("M2 culture"). The M2 culture was diluted 1:20 into induction media and grown 17-20 hrs at 25° C. with walk-away induction, i.e., autoinduction (Schagat et al., "KRX Autoinduction Protocol: A Convenient Method for Protein Expression." *Promega Notes,* 98:16-18 (2008)). The induction media contained rhamnose and glucose when novel coelenterazines PBI-3841, PBI-3842, PBI-3857, PBI-3880, PBI-3881, PBI-3886, PBI-3887, PBI-3897, PBI-3896, or PBI-3894 were used as substrates in the primary screen. The induction media did not contain rhamnose or glucose when native coelenterazine, known coelenterazine-h, or novel coelenterazines PBI-3840, PBI-3889, PBI-3899, or PBI-3900 were used as substrates in the primary screen. The use of the different induction media was determined based on the luminescence generated between C1+A4E and the novel coelenterazines, i.e., the induction media containing rhamnose and glucose were used with novel coelenterazines that generated less luminescence with C1+A4E compared to the other novel coelenterazines with C1+A4E.

Ten μL of induced cells were lysed using 60 μL lysis buffer containing 300 mM HEPES pH 8.0, 300 mM thiourea, 0.3× Passive Lysis Buffer ("PLB"; Promega Corp. Cat. No. E194A), 0.3 mg/mL lysozyme, and 0.003 U/μL RQ1 DNase and measured for luminescence with 50 μL assay buffer containing 150 mM KCl, 1 mM CDTA, 10 mM DTT, 0.5% TERGITOL® NP-9 (v/v), and 20 μM of a native, known, or novel coelenterazine as a substrate. Luminescence measurements for each variant were taken 3 min after reagent addition and relative luminescence unit (RLU) values were normalized to an average of 8 control wells of the corresponding starting OgLuc variant for each plate. Assay was completed on a TECAN® robotic system.

OgLuc variants of interest were sequenced using standard sequencing techniques known in the art to identify any additional amino acid substitutions in each such variant. A secondary screen using a non-robotic (manual) system was performed on the variant clones of interest. The manual screen was conducted as follows: Variant clones were grown, in triplicate, in 96-well plates and expressed and assayed as described for the automated assay except the assay buffer was added manually with a multichannel pipette. For each variant, luminescence was measured, averaged, and normalized to the corresponding starting OgLuc variant. Luminescence measurements were made using a TECAN® INFINITE® F500 luminometer.

Determining Change in Relative Specificity

Relative substrate specificity was determined by dividing the luminescence of a luciferase in the presence of a test coelenterazine substrate by the luminescence of the luciferase in the presence of a reference coelenterazine substrate. For example, relative specificity was determined by dividing the luminescence of a luciferase with a novel coelenterazine of the present invention by the luminescence of the luciferase with a different coelenterazine (e.g., native or known coelenterazine, or a different novel coelenterazine of the present invention). The test coelenterazine substrate and the reference coelenterazine substrate that were compared were considered a comparison substrate pair for determining relative substrate specificity.

A change in relative substrate specificity was determined by dividing the relative substrate specificity of a test luciferase using a comparison substrate pair by the relative substrate specificity of a reference luciferase using the same comparison substrate pair. For example, a change in relative specificity was determined by dividing the relative substrate specificity of a test luciferase with a novel coelenterazine of the present invention compared to a different coelenterazine (e.g., native or known coelenterazine or a different novel coelenterazine of the present invention), by the relative substrate specificity of a reference luciferase with the same novel coelenterazine of the present invention compared to the same different coelenterazine used for the test luciferase.

The luminescence with one novel coelenterazine was compared to the luminescence with a different novel coelenterazine. The luminescence with one native or known coelenterazine was compared to the luminescence with another native or known coelenterazine. The luminescence with one native or known coelenterazine was compared to the luminescence with a novel coelenterazine.

An increase in luminescence (RLUs) for the OgLuc variant compared to the corresponding starting OgLuc template for novel coelenterazine and a decrease or no change in luminescence for a reference coelenterazine was indicative of a change in relative specificity. A decrease in luminescence of an OgLuc variant for both the novel and reference coelenterazines compared to the corresponding starting OgLuc, but the luminescence of the OgLuc variant with the novel coelenterazine decreasing more, was also indicative of a change in relative specificity. An increase in luminescence of the OgLuc variant compared to the corresponding starting OgLuc for the novel and reference coelenterazines indicated an improvement in activity/stability/expression. If the luminescence of the OgLuc variant with both the novel and the reference coelenterazines increased, but the increase in luminescence with the novel coelenterazine was greater, it indicated an increase in relative specificity and an improvement in activity/stability/expression of the OgLuc variant.

A. C1+A4E Variants

Figure 5B:
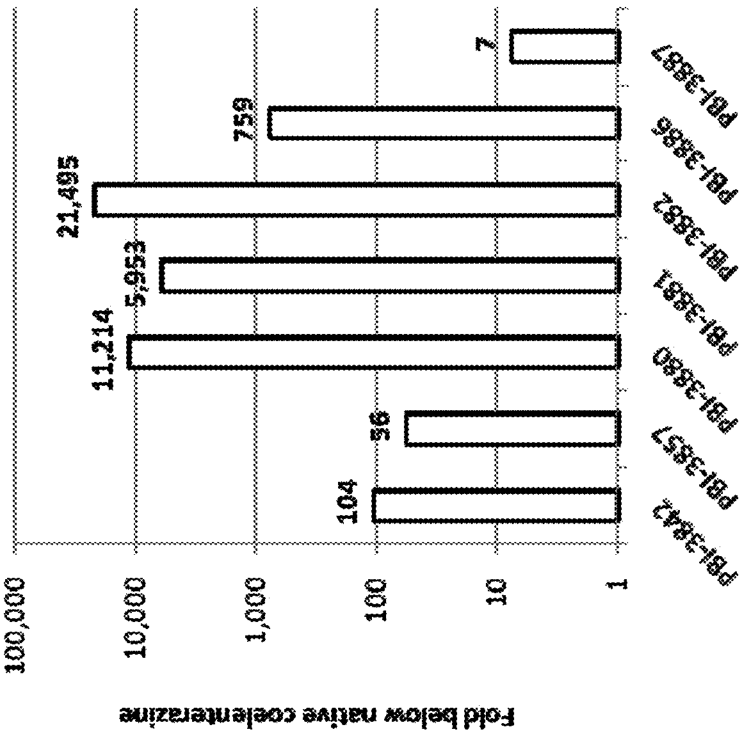
FIGS. 5A-G show the luminescence (RLUs) generated from lysed bacterial cells expressing C1+A4E using native, known, and novel coelenterazine as substrates.
Figure 5A:
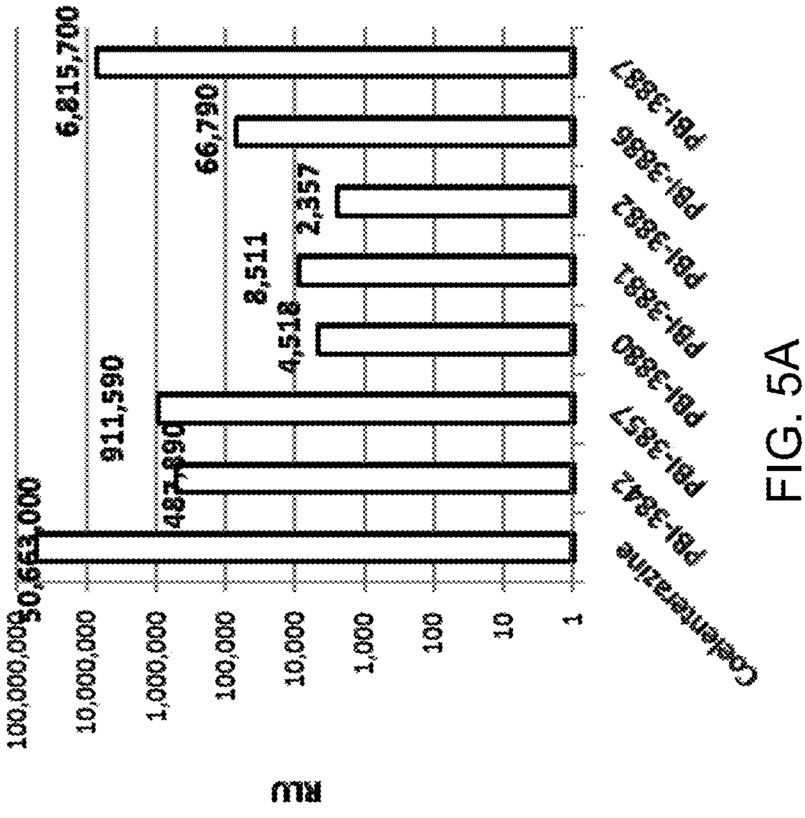
Figure 5C:
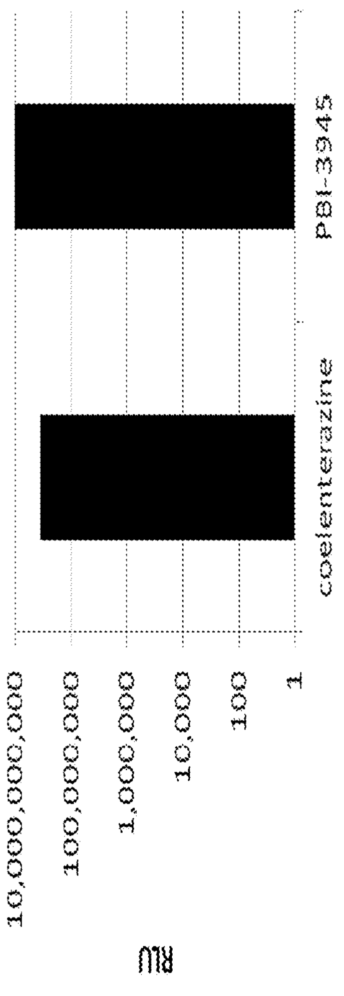
Figure 5D:
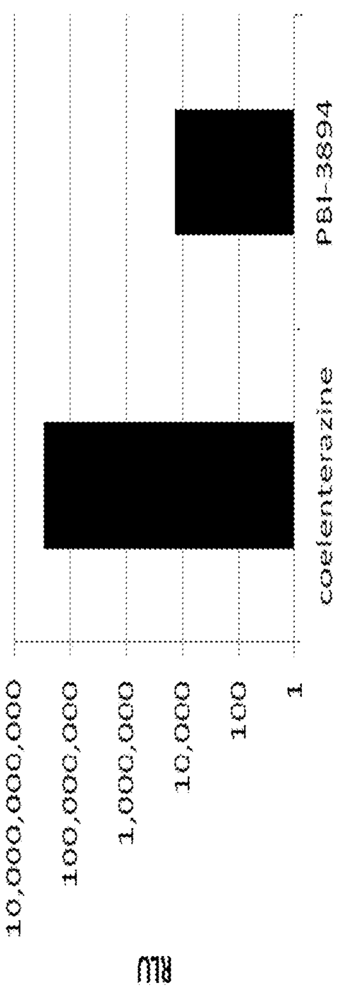
Figure 5E:
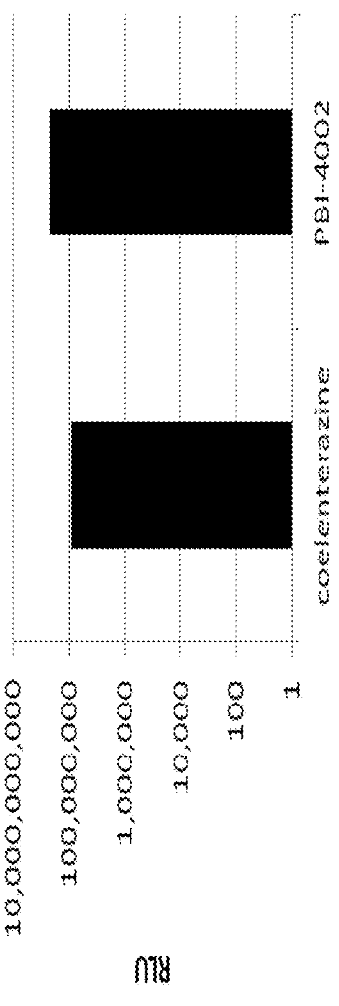
Figure 5F:
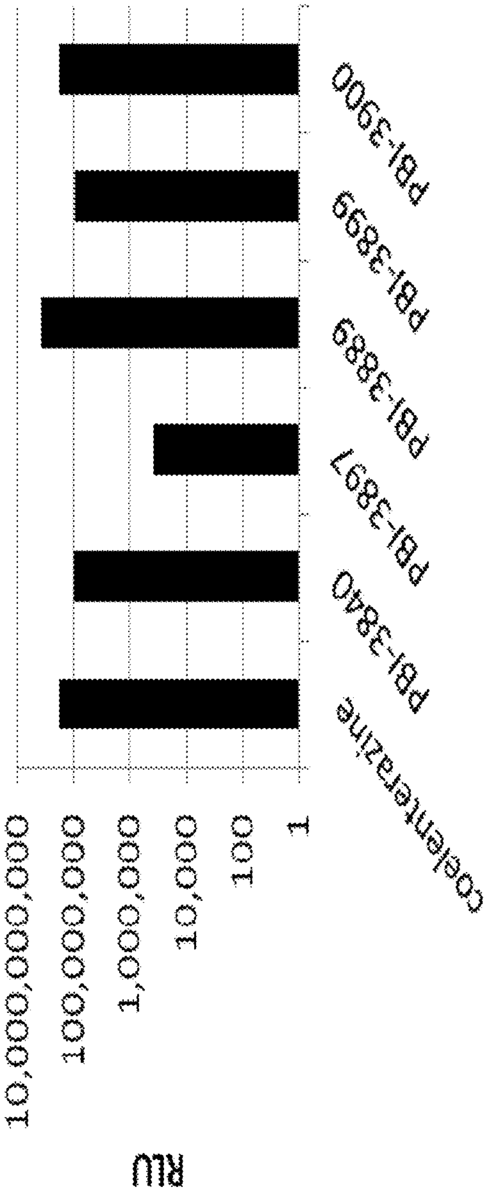
Figure 5G:
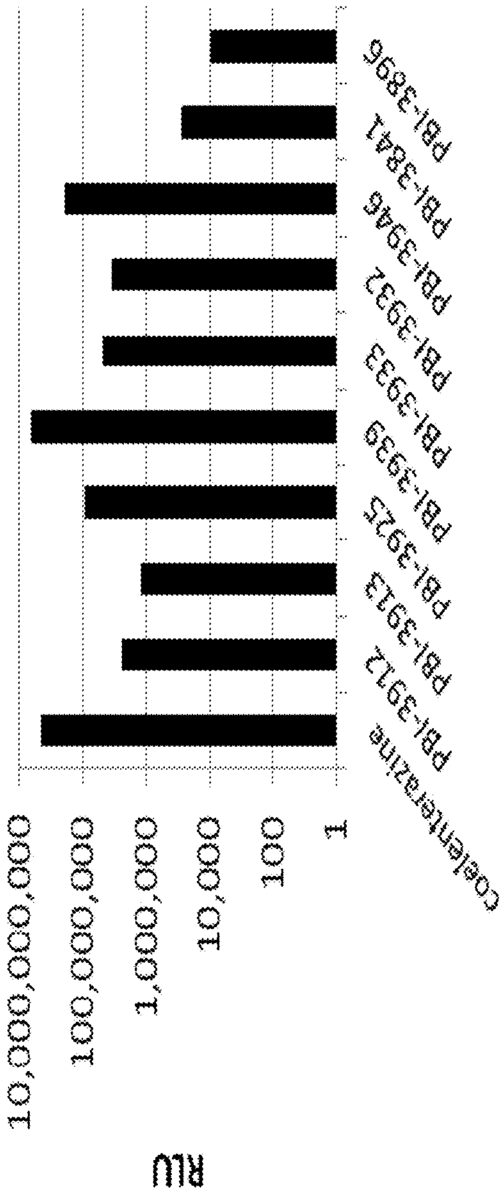

C1+A4E (SEQ ID NOs: 2 and 3), previously described in U.S. Serial application Ser. No. 12/773,002 (U.S. Published Application No. 2010/0281552), was used as a primary starting sequence (i.e., the parental sequence) for generating additional, synthetic OgLuc variants. C1+A4E has the following amino acid substitutions: A4E, Q11R, A33K, V44I, A54F, P115E, Q124K, Y138I, and N166R, relative to SEQ ID NO: 1. Luminescence of C1+A4E containing bacterial lysates, using the novel coelenterazines described in Examples 1-14 (see FIG. 4 for examples) as substrates, was measured as described previously and compared to the luminescence using native and known coelenterazines as substrates (FIGS. 5A-G). FIG. 5A shows the luminescence of C1+A4E using native coelenterazine ("coelenterazine"), known PBI-3880, and novel coelenterazines PBI-3842, PBI-3857, PBI-3881, PBI-3882, PBI-3886, and PBI-3887 as substrates. The luminescence measurements using known and novel coelenterazines were normalized to the luminescence of C1+A4E using native coelenterazine and the fold-decrease compared to native coelenterazine (FIG. 5B). FIGS. 5C-E show the luminescence of C1+A4E using native coelenterazine and novel coelenterazines PBI-3945, PBI-3894, and PBI-4002, respectively. FIG. 5F shows the luminescence of C1+A4E using native coelenterazine and novel coelenterazines PBI-3840, PBI-3897, PBI-3889, PBI-3899, and PBI-3900. FIG. 5G shows the luminescence of C1+A4E using native coelenterazine, known coelenterazine PBI-3912 and novel coelenterazines PBI-3913, PBI-3925, PBI-3939, PBI-3933, PBI-3932, PBI-3946, PBI-3841, and PBI-3896. The data indicates the C1+A4E variant can use each of the novel coelenterazines as substrates.

C1+A4E variants were generated that had at least the amino acid substitutions identified in C1+A4E, unless otherwise indicated. A library (Library 1) of 4400 variant clones of C1+A4E was generated by random mutagenesis as described previously and screened as described previously for improvement in relative specificity change and/or activity change, e.g., brightness. The variants were primarily screened with native coelenterazine, known coelenterazine-h, known PBI-3880, and novel coelenterazines PBI-3840, PBI-3841, PBI-3842, PBI-3857, PBI-3881, PBI-3886, PBI-3887, PBI-3889, PBI-3897, and PBI-3900 as substrates. In addition, half of the variants were screened with novel coelenterazines PBI-3896 and PBI-3894 as substrates. Plates containing variants having known mutations of interest identified from screening previous novel compounds were selected. Variants that showed improvement (either relative specificity change or activity change) for one or more of the novel coelenterazines tested in the primary screen were isolated, sequenced, and screened in a secondary screen.

In the secondary manual screen, the variants were tested with known coelenterazines PBI-3912, coelenterazine-h, coelenterazine-hh, 2-methyl coelenterazine, and coelenterazine v; and novel coelenterazines PBI-3840, PBI-3897, PBI-3889, PBI-3899, PBI-3900, PBI-3925, PBI-3944, PBI-3932, PBI-3945, PBI-3913, and PBI-3896 as substrates. FIGS. 6A-D summarize the average luminescence normalized to C1+A4E for the variants ("Clone"). FIGS. 6A-D summarize the substitutions in these variants ("AA sequence"), which had at least one of the following additional amino acid substitutions: A14V, G15R, Q18L, Q20R, L22I, E23K, L27V, L27M, K33N, T39I, E49K, F54S, F54I, D55G, I56V, V58I, V58L, I59T, S66T, G67S, F68S, L72Q, M75K, I76N, F77T, F77C, K89E, I90V, I90T, L92H, H93R, M106K, Y109F, P113T, I117F, T126R, V127A, L136M, D139G, P145L, S148T, C164S, or A169V.

Amino acid substitutions at position 54, 92, and 109 were of interest as substitutions at these positions provided greater light output or improved relative specificity, i.e., specificity away from native coelenterazine and towards at least one novel coelenterazine, as shown in FIGS. 6A-C. The amino acid substitution F54I in clone 29H7 provided greater light output with native coelenterazine and several of the novel coelenterazines. The amino acid substitution Q18L in clone 40H11, the amino acid substitution L92H in clone 04A12, and the amino acid substitution Y109F in clone 43F9 provided improved relative specificity.

Table 5 lists C1+A4E variants with an additional amino acid substitution at position 77, 92, or 109 ("AA change"), generated as described previously. These variants were analyzed for increased light output as described previously, i.e., screened for variants that were at least 1.3× brighter than C1+A4E, using native coelenterazine, known coelenterazine-hh, and novel coelenterazines PBI-3939, PBI-3894, PBI-3896, PBI-3897, PBI-3932, or PBI-3925 as a substrate. The following additional substitutions yielded a variant that was at least 1.3× brighter than C1+A4E: L92G, L92Q, L92S, L92A, L92M, L92H, L92Y, F77W, F77Y, F77S, F77T, F77V, F77A, F77G, F77C, F77D, F77M, and Y109F. As shown in Table 5, L92H, F77W and F77A substitutions had the most dramatic improvements with PBI-3897, PBI-3896, and PBI-3932.

TABLE 5

Site Saturation of Positions 77, 92 and 109

| AA Change | native | hh | PBI-3939 | PBI-3894 | PBI-3896 | PBI-3897 | PBI-3932 | PBI-3925 |
|---|---|---|---|---|---|---|---|---|
| L92G | 2.2 | | | | | | | |
| L92Q | 2 | 1.8 | 1.6 | 1.3 | 1.4 | 2.8 | 1.4 | 3.4 |
| L92S | 2.9 | | | | 1.5 | 2.9 | 2.7 | 6 |
| L92A | 2.5 | 1.3 | | | | | | |
| L92M | | 1.3 | | | | | | |
| L92H | | | | 2.2 | 21 | 9.1 | 3.4 | 5.9 |
| L92Y | | | | | | | | 2.5 |
| F77W | 1.4 | | 1.4 | 1.4 | 8.3 | 3.2 | 1.7 | 2.3 |
| F77Y | | | | | 1.6 | 1.3 | 4.9 | 6.5 |
| F77S | | | | | | | 2.6 | |
| F77T | | | | | | | 2.3 | |
| F77V | | | | | | | 2.3 | |
| F77A | | | | | | | 7.9 | 2.5 |
| F77G | | | | | | | 3.1 | |
| F77C | | | | | | | 2.3 | |
| F77D | | | | | | | 1.5 | |
| F77M | | | | | | | 1.5 | 1.6 |
| Y109F | | | | | 1.34 | 14 | | |

Additional C1+A4E variants (Group A) were generated by site-directed mutagenesis as described previously to have an additional substitution in at least one of the following amino acid positions relative to SEQ ID NO: 1: 18, 20, 54, 59, 72, 77, 89, 92, 109, 113, 127, 136, or 164. These amino acid positions were chosen because, based on the primary and secondary screens of Library 1, substitutions at these positions had increased total light output compared to C1+A4E using at least one of the following as a substrate: novel coelenterazines PBI-3841, PBI-3896, PBI-3897, PBI-3894, PBI-3925, or PBI-3932, or known coelenterazines 2-methyl coelenterazine or PBI-3912. FIG. 7 lists the variants ("Clone") and the additional amino acid substitutions contained in each variant. Variant clones were assayed in triplicate as described for the secondary manual screen as described previously and normalized to C1+A4E. FIGS. 8A-B and 9 show the normalized average luminescence of the variants listed in FIG. 7 with various coelenterazines as substrates. FIGS. 8A-B and 9 show variants with either large increases in luminescence for the listed novel compounds compared to C1+A4E or no change or a decrease in luminescence for the known coelenterazine compared to C1+A4E. Clone QC27, which has additional amino acid substitutions Q18L, F54I, L92H, and Y109F, had a 561.32-fold-increase in luminescence with PBI-3896, a 392.98-fold-increase with PBI-3894, and a 283.85-fold-increase with PBI-3896 compared to C1+A4E. This data shows that Q18L, L92H, and Y109F can be combined with each other and with additional substitutions to result in variants with improved relative specificity.

Other substitutions of interest identified from Library 1 were combined to generate additional variants (Group B) (FIG. 10). Additional amino acid substitutions were made in at least one of the following amino acid positions relative to SEQ ID NO: 1: 18, 20, 54, 71, 77, 90, 92, 109, or 127. These substitutions showed improvement with at least one of the following novel coelenterazines as a substrate: PBI-3841, PBI-3896, PBI-3897, PBI-3894, PBI-3925, or PBI-3932. These variants were assayed as described for Group A variants using native coelenterazine, known coelenterazine-hh, and novel coelenterazines PBI-3939, PBI-3945, PBI-3840, PBI-3932, PBI-3925, PBI-3894, and PBI-3896. Variant clones were assayed in triplicate as described for the secondary manual screen as described previously and normalized to C1+A4E. FIG. 11 shows the normalized average luminescence of the variants listed in FIG. 10 with the various coelenterazines as substrates. FIG. 11 shows variants with either large increases in luminescence for the listed novel coelenterazines compared to C1+A4E or no change or a decrease in luminescence for the native and known coelenterazine compared to C1+A4E.

Additional variants were generated with the additional amino acid substitution I90V and/or Y109F (Group C) and compared to variants generated from Group A or B (see FIG. 12). Clones containing variants with an I90V substitution ("I90V"), a Y109F substitution ("Y109F"), or both substitutions ("LE2") were compared to clones QC #27, QC #2 E7, QC #2 F4, and QC #1 All using assays as described for Group A recombinants with native coelenterazine, known coelenterazine-hh, and novel coelenterazines PBI-3939, PBI-3945, PBI-3889, PBI-3840, PBI-3925, PBI-3932, PBI-3894, PBI-3896, and PBI-3897 as substrates (FIG. 12). Variant clones were assayed in triplicate as described for the secondary manual screen as previously described and normalized to C1+A4E (FIG. 12). FIG. 12 shows variants with either large increases in luminescence for the listed novel coelenterazines compared to C1+A4E and no change or a decrease in luminescence for the native or known coelenterazine compared to C1+A4E. FIG. 12 shows that I90V provided greater light output for native coelenterazine and several of the novel substrates.

B. QC27 Variants

The variant QC27 (SEQ ID NOs: 4 and 5) from A, which has additional amino acid substitutions Q18L, F54I, L92H, and Y109F, was cloned into a pF4A modified vector as described previously to create a C-terminal HT7 (Promega Corp.) fusion protein ("QC27-HT7") (SEQ ID NOs: 44 and 45). 4400 variants of QC27-HT7 (Library 2) were generated by random mutagenesis as described previously, and primarily screened for increased relative specificity change as described previously using native coelenterazine and novel coelenterazines PBI-3896 and PBI-3897 as substrates. Variant clones were selected, sequenced, and assayed in a secondary manual screen as described previously using native coelenterazine, known coelenterazine-hh, and novel coelenterazines PBI-3897, PBI-3896, and PBI-3894 as substrates.

FIG. 13 lists the additional amino acid substitutions ("Sequence") identified in these variants ("Sample"), and the luminescence of the variants using native coelenterazine, known coelenterazine-hh, and novel coelenterazines PBI-3897, PBI-3896, and PBI-3894 as substrates in the secondary screen normalized to the corresponding starting QC27-HT7. The variants in FIG. 14, had at least one of the following additional amino acid substitutions: F1I, R11Q, L18I, L18Q, V21L, V21M, L22F, F31I, Q32H, V45E, L46Q, S47P, G48R, E49D, G51E, D55E, G67S, F68Y, F68L, Q69H, L72Q, E74K, E74I, M75K, I76F, I76V, H86R, I90T, H92Q, H92R, T96A, V98F, I99V, I99T, V102M, M106I, F109Y, L142V, V158I, T159S, L168F, or G170R (the G170R is located in the linker region between HT7 and the OgLuc variant).

The amino acid substitutions F68Y in variant 24B12, L72Q in variant 29C4, and M75K in variant 3H11 each provided greater light output for native coelenterazine and several of the novel substrates. The amino acid substitutions V21L in variant 25A11 and H92R in variant 1B6 provided improved relative specificity. Both of these substitutions were cases where luminescence signals were down using the novel coelenterazines as substrates, but were down more using native and known coelenterazines as substrates.

Additional QC27-HT7 variants were generated to have specific amino acid substitutions (FIG. 14) using site-directed mutagenesis as described previously. Additional substitutions were made in at least one of the following amino acid positions relative to SEQ ID NO: 1: 21, 68, 72, 75, 76, 90, 92, and 158, as these positions showed improvement in relative specificity change as shown in FIG. 14. FIG. 15 shows the luminescence of the QC27-HT7 variants using native coelenterazine, known coelenterazine-hh, and novel coelenterazines PBI-3897, PBI-3841, PBI-3896, and PBI-3894 as substrates normalized to the corresponding starting QC27-HT7. As seen in FIG. 15, combining the three amino acid substitutions F68Y, L72Q, and M75K with V158I, as for example in variant QC27 #1, provided greater light output for each coelenterazine tested.

C. QC27-9a Variants

The variant QC27-9a (SEQ ID NOs: 6 and 7) from B, a QC27-HT7 fusion protein with additional amino acid substitutions V21L, H29R, F68Y, L72Q, M75K, and V158I, was used as a starting sequence to generate a library. 4400 variants of QC27-9a (Library 3) were generated by random mutagenesis as described previously and screened for increased relative specificity change using native coelenterazine and novel coelenterazines PBI-3841 and PBI-3897. Variant clones were selected, sequenced, and assayed in a secondary manual screen as described previously using native coelenterazine, known coelenterazine-hh, known coelenterazine-h, and novel coelenterazines PBI-3841 and PBI-3897 as substrates. FIG. 16 lists the additional substitutions ("AA change") identified in the variants ("Sample"), and the average luminescence of the variants using native coelenterazine, known coelenterazine-hh, known coelenterazine-h, and novel coelenterazines PBI-3841 and PBI-3897 as substrates in the secondary screen normalized to the corresponding starting QC27-9a. The increase in relative specificity represents cases where there was a decrease in luminescence for the variant with the novel, native, and known coelenterazines compared to the starting template, but luminescence with the native and known coelenterazines decreased more. For example, the variant 30D12 with the amino acid substitution L22F had an approximately three-fold loss in activity with the novel coelenterazines PBI-3841 and PBI-3897. However, with native coelenterazine, known coelenterazine-h, and known coelenterazine-hh, the luminescence of the variant 30D12 was down by ten-fold or more.

Figure 17:
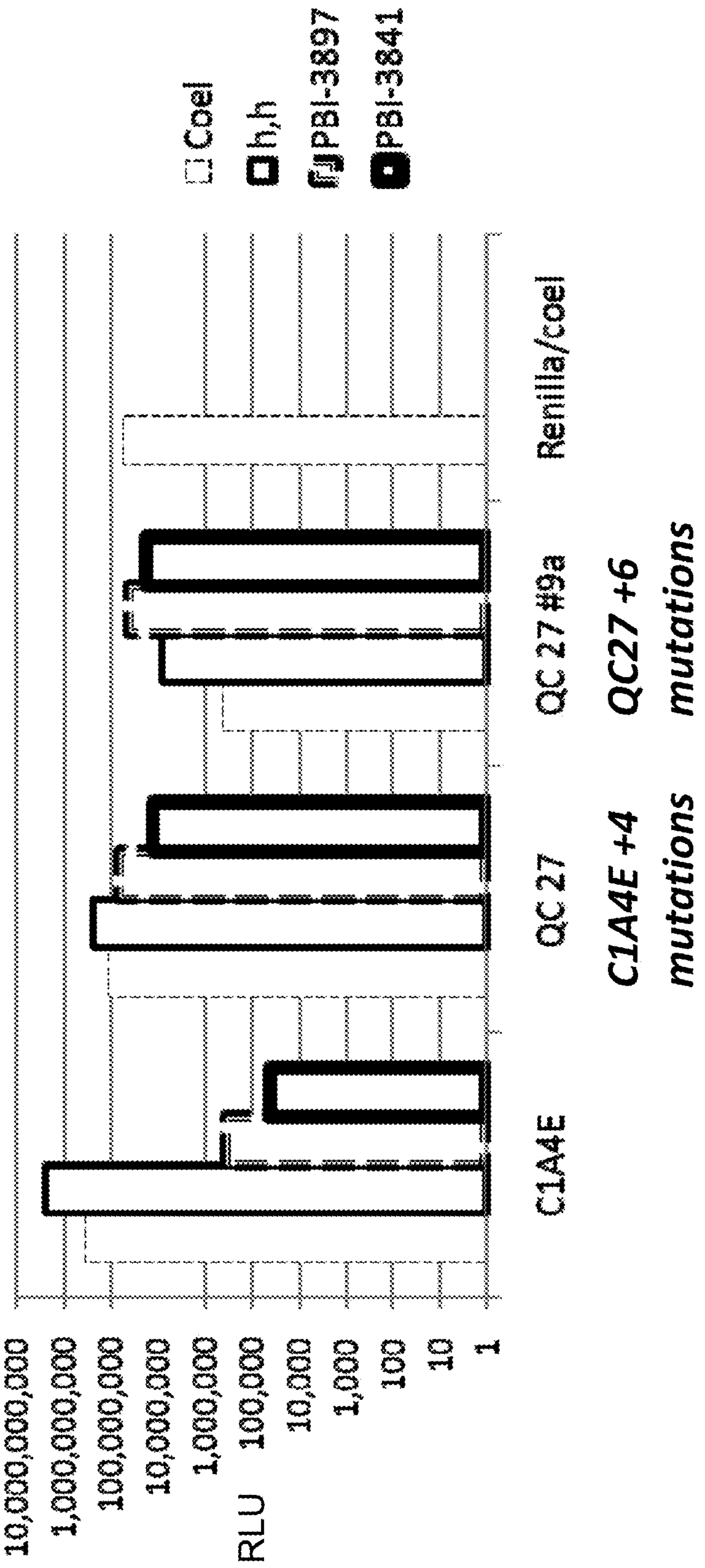
FIG. 17 shows the luminescence generated from lysed bacterial cells expressing various OgLuc variants and humanized *Renilla* luciferase (hRL) using native coelenterazine ("Coel"), known coelenterazine-hh ("h,h"), and novel coelenterazines PBI-3897 and PBI-3841 as substrates.

FIG. 17 shows a comparison of the luminescence of $C_1$+A4E, QC27-HT7 and QC27-9a compared to humanized *Renilla* luciferase (referred herein as "hRL") (SEQ ID NOs: 30 and 31) using native coelenterazine, known coelenterazine-hh, and novel coelenterazines PBI-3841 and PBI-3897 as substrates. Although the reaction of QC27-9a with PBI-3897 was brighter than QC27-9a with PBI-3841 (see FIG. 17), the evolution trend, i.e., magnitude of improvement in luminescence, was greatest for PBI-3841 (Table 6). Combining the improvement in luminescence (440-fold) with the decrease in luminescence for native coelenterazine (800-fold) indicated a change in relative specificity (350,000-fold) of QC27-9a using PBI-3841 compared to native coelenterazine.

TABLE 6

The Change in Relative Specificity of the OgLuc Variants for PBI-3897 and PBI-3841 Compared to Native Coelenterazine and coelenterazine-hh.

| Compound | Evolution trend: C1A4E to QC27 #9a | Change in relative specificity (novel coelenterazine/native coelenterazine) |
|---|---|---|
| coelenterazine | DOWN 800X | |
| coelenterazine-hh | DOWN 300X | |
| PBI-3897 | UP 100X | 80,000X |
| PBI-3841 | UP 440X | 350,000X |

D. IVY Variants

IVY (SEQ ID NOs: 8 and 9), a C1+A4E variant with additional amino acid substitutions F54I, I90V, and F77Y, was cloned into a pF4A modified vector as described previously to create a C-terminal HT7 fusion protein ("IVY-HT7"). 4400 variants of IVY-HT7 (Library 4) were generated by random mutagenesis and screened for increased light output (i.e., increased brightness) and increased relative specificity using native coelenterazine, known coelenterazine-hh, and novel coelenterazines PBI-3840, PBI-3889, PBI-3925, PBI-3932, and PBI-3945 as substrates. Variant clones were selected, sequenced, and assayed in triplicate in a secondary screen as described previously using native coelenterazine, known coelenterazine-hh, and novel coelenterazines PBI-3889, PBI-3939, PBI-3945, and PBI-4002 as substrates. FIGS. 18 and 19 lists the additional substitutions ("AA change") identified in the variants ("Sample") and the average luminescence of the variants normalized to IVY-HT7 using native coelenterazine, known coelenterazine-hh, and novel coelenterazines PBI-3889, PBI-3939, PBI-3945, and PBI-4002 as substrates in the secondary screen. FIG. 18 lists those variants chosen based on performance with PBI-3945 (Group A), which had at least one of the following amino acid substitutions: Q18H, D19N, Q20P, Q32P, K33N, V38I, V38F, K43N, I44F, E49G, I60V, Q69H, I76N, Y77N, Y94F, G95S, G95D, F110I, V119M, K124M, L149I, or R152S. FIG. 19 lists those variants chosen based on performance with PBI-3889 (Group B), which had at least one of the following amino acid substitutions: F6Y, Q18L, L27V, S28Y, Q32L, K33N, V36E, P40T, Q42H, N50K, G51R, H86L, N135D, or I155T.

Additional IVY-HT7 variants were generated to have additional specific amino acid substitutions using site-directed mutagenesis as described previously. FIG. 20 lists variants with at least one of the following additional amino acid positions relative to SEQ ID NO: 1: 19, 20, 27, 32, 38, 43, 49, 58, 77, 95, 110, and 149, as these substitutions were identified in the variants of FIG. 18, which showed specificity towards PBI-3945 and PBI-4002. FIG. 21 shows the luminescence of the variants listed in FIG. 20 normalized to IVY-HT7 using native coelenterazine, known coelenterazine-h, known coelenterazine-hh, and novel coelenterazines PBI-3939, PBI-3945, PBI-4002, PBI-3932 and PBI-3840 as substrates. None of the variants showed an improvement over IVY-HT7, but there were instances, such as variant C5.19 (SEQ ID NOs: 12 and 13) where luminescence with native or a known coelenterazine decreased about 3-4 logs, but luminescence with PBI-3945 and PBI-4002 decreased only two-fold. Variant C5.19 has additional amino acid substitutions L27V, V38I, and L149I.

FIG. 22 lists variants with at least one of the following additional amino acid positions relative to SEQ ID NO: 1: 6, 18, 27, 28, 33, 34, 36, 40, 50, 51, 135, and 155, as these substitutions were identified in the variants of FIG. 19, which showed specificity towards PBI-3889 and PBI-3939. FIG. 23 shows the luminescence of the variants listed in FIG. 21 using native coelenterazine, known coelenterazine-h, known coelenterazine-hh, and novel coelenterazines PBI-3939, PBI-3945, PBI-3889, PBI-4002, PBI-3932, and PBI-3840 as substrates normalized to IVY-HT7. Luminescence decreased for each of the variants compared to IVY-HT7. Variant C1.3 (SEQ ID NOs: 10 and 11) had about 2000-fold more luminescence with PBI-3939 than with native or known coelenterazine. Variant C1.3 has additional amino acid substitutions F6Y, K33N, N135D, and I155T.

Figure 24:
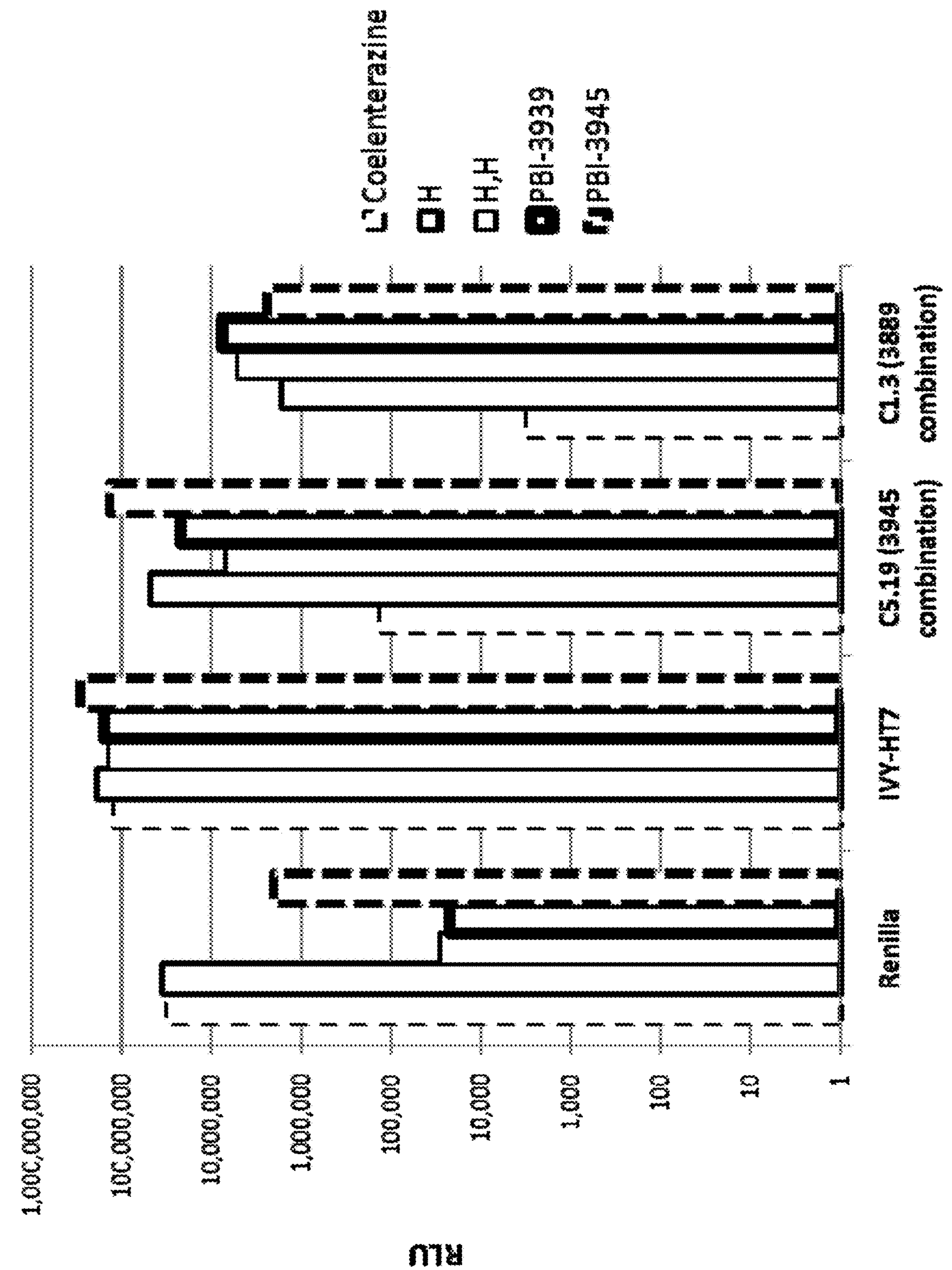
FIG. 24 shows the luminescence generated from lysed bacterial cells expressing various OgLuc variants and hRL ("*Renilla*") using native coelenterazine ("Coelenterazine"), known coelenterazine-h ("H"), known coelenterazine-hh ("H,H"), and novel coelenterazines PBI-3939 and PBI-3945 as substrates.

The best IVY-HT7 variants for relative specificity change compared to hRL and IVY-HT7 were C5.19, which had the best luminescence with PBI-3945, and C1.3, which had the best luminescence with PBI-3889. FIG. 24 shows the luminescence of hRL, IVY-HT7, C5.19 (a C-terminal HT7 fusion), and C1.3 (a C-terminal HT7 fusion) with native coelenterazine, known coelenterazine-h, known coelenterazine-hh, and novel coelenterazines PBI-3939 and PBI-3945.

E. IV Variants

Figure 25:
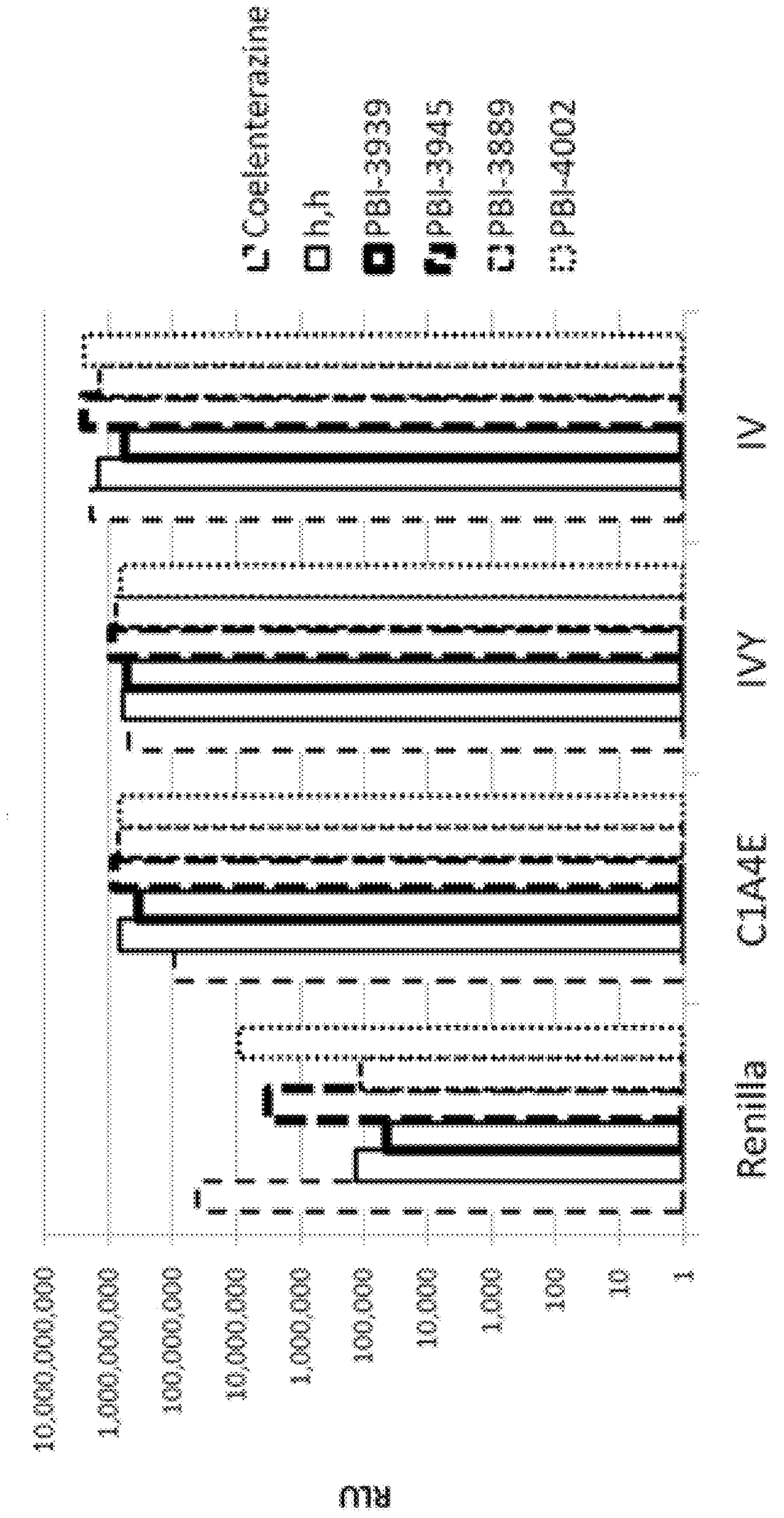
FIG. 25 shows the luminescence generated from lysed bacterial cells expressing various OgLuc variants and hRL ("*Renilla*") using native coelenterazine ("Coelenterazine"), known coelenterazine-hh ("h,h"), and novel coelenterazines PBI-3939, PBI-3945, PBI-3889, and PBI-4002 as substrates.

IV (SEQ ID NOs: 14 and 15), a C1+A4E variant with additional amino acid substitutions F54I and I90V, was generated as previously described. To determine the brightest variant for use as a transcriptional reporter, luminescence was measured as described previously provided for C1+A4E (SEQ ID NOs: 2 and 3), IVY (SEQ ID NOs: 8 and 9), and IV (SEQ ID NOs: 14 and 15) using native coelenterazine, known coelenterazine-hh, and novel coelenterazines PBI-3939, PBI-3945, PBI-3889, and PBI-4002 as substrates. hRL was used as a control. As seen in FIG. 25, IV was brighter than both C1+A4E and IVY. The amino acid substitution F54I in IV provided greater light output for native coelenterazine and several of the novel substrates. All three variants were brighter than hRL with the tested coelenterazines.

The data from A, B and D (i.e., screenings of the libraries generated from C1+A4E, IVY, and QC27 as the starting sequences) were reviewed to determine those additional amino acid substitutions with increased light output (i.e., increased brightness) with a variety of coelenterazines. IV variants were generated as described previously to have additional substitutions which had reduced specificity for native coelenterazine by two- to ten-fold. As listed in FIG. 26, the IV variants ("clone") had an additional amino acid substitution ("Sequence") of at least one of the following amino acid substitutions: F1I, E4K, Q18L, L27V, K33N, V38I, F68Y, M70V, L72Q, M75K, or V102E.

Sixteen plates of variant clones for all combinations of amino acid substitutions were primarily screened and assayed using the automated robot method described previously with native coelenterazine, known coelenterazine-h, known coelenterazine-hh, and novel coelenterazines PBI-3889 and PBI-3945 as substrates. Variants with improved luminescence were selected, sequenced, and assayed in triplicate using the manual screen as described previously. Luminescence was measured using native coelenterazine, known coelenterazine-h, known coelenterazine-hh, and novel coelenterazines PBI-3889, PBI-3939, PBI-3945, and PBI-4002 as substrates. Corresponding starting sequences IV and hRL were used as controls.

FIG. 26 lists the variants, and the additional amino acid substitutions identified in the variants. FIG. 27 shows the average luminescence of the variants in the secondary screen normalized to IV. Variant 8A3 (SEQ ID NOs: 26 and 27), which has additional amino acid substitutions F1I, L27V, and V38I, had improved relative specificity with novel coelenterazines, but was not brighter than IV. Variant 8F2 (SEQ ID NOs: 46 and 47), which has additional amino acid substitution L27V, offered improved relative specificity and brightness with 3 of the 4 novel coelenterazines used. Variant 9B8 (SEQ ID NOs: 18 and 19), which has additional amino acid substitutions Q18L, F68Y, L72Q, and M75K, was brighter for all substrates and offered some relative specificity advantage over native coelenterazine as well. Variant 9F6 (SEQ ID NOs: 20 and 21), which has additional amino acid substitutions Q18L, L27V, V38I, F68Y, L72Q, and M75K, showed similar improvements as was seen with 8F2. Variant 15C1 (SEQ ID NOs: 16 and 17), which has additional amino acid substitutions E4K, K33N, F68Y, L72Q, and M75K, was brighter for all novel coelenterazines, but did not have any improved relative specificity benefit. The amino acid substitution Q18L in variant 1D6 provided improved relative specificity, i.e., away from native coelenterazine and towards novel substrates, in the context of IV. In general, the amino acid substitution L27V provided improved relative specificity in the context of IV.

Figure 28:
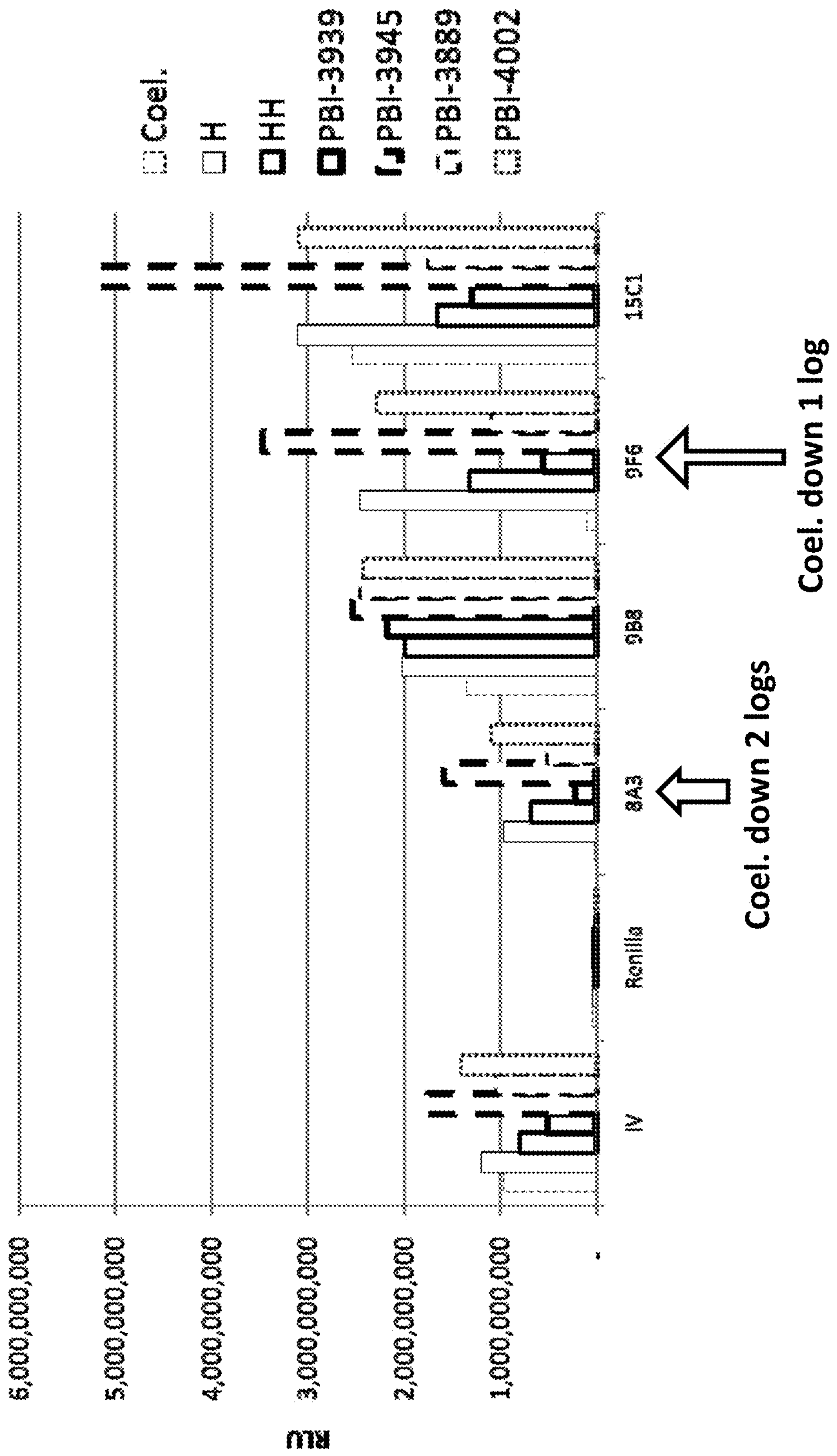
FIG. 28 shows the luminescence generated from lysed bacterial cells expressing various OgLuc variants and hRL ("*Renilla*") using native coelenterazine ("Coel."), known coelenterazine-h ("H"), known coelenterazine-hh ("H,H"), and novel coelenterazines PBI-3939, PBI-3945, PBI-3889, and PBI-4002 as substrates.

FIG. 28 shows the luminescence of the 8A3, 9B8, 9F6, and 15C1 variants in the secondary screen using native coelenterazine, known coelenterazine-hh, known coelenterazine-h, and novel coelenterazines PBI-3939, PBI-3945, PBI-3889, and PBI-4002 as substrates compared to IV and hRL. Variant 8A3 had 2 logs decrease in brightness with native coelenterazine compared to IV. Variant 9F6 had 1 log decrease in brightness with native coelenterazine compared to IV. Variant 15C1 with PBI-3945 was the brightest, but the signal half-life was short (see Example 27).

F. 9B8 Variants

The 9B8 variant from E was further modified to generate additional variants with increased light emission and/or improved relative specificity for PBI-3939. Amino acid substitution L72Q appeared to be a beneficial amino acid substitution for increased light emission (i.e., brightness) as this substitution was identified in the variants 9B8, 9F6, and 15C1, all of which showed improved light emission. To determine if other amino acid substitutions at position 72 would provide similar increases in brightness, additional variants of 9B8 were generated as described previously by saturating position 72 with alternative residues. Four replicates of *E. coli* lysates were prepared and analyzed for brightness as described previously using PBI-3939 as a substrate except the assay buffer contained 10 mM CDTA, 150 mM KCl, 10 mM DTT, 100 mM HEPES, pH 7.0, 35 mM thiourea, and 0.5% TERGITOL® NP-9 (v/v). Table 7 lists 9B8 variants ("Variant") with similar or improved luminescence compared to 9B8 as indicated by luminescence normalized to 9B8 ("RLU (normalized to 9B8)"), i.e., fold improvement. The amino acid substitutions of A, G, N, R, and M at position 72 provided at least the same brightness benefit as amino acid Q, i.e., 1-fold.

TABLE 7

Variants with Similar Luminescence Compared to Variant 9B8.

| Variant | RLU (normalized to 9B8) |
|---|---|
| 9B8 + Q72A | 1.1 |
| 9B8 + Q72G | 1 |
| 9B8 + Q72N | 1 |
| 9B8 + Q72R | 1 |
| 9B8 + Q72M | 1 |

Additional variants with improved relative specificity to novel PBI-3939 were generated as described previously by saturating amino acid positions 18, 68, 72, 75, and 90 in variant 9B8. *E. coli* lysates were prepared and analyzed for brightness as described previously using native coelenterazine and novel PBI-3939 as substrates. Relative specificity was determined from the ratio of the luminescence of the variant with PBI-3939 to the luminescence of the variant with native coelenterazine, normalized to the ratio of corresponding luminescence of 9B8. Table 8 lists 9B8 variants ("Variant") with at least 1.1× fold-increase in relative specificity for PBI-3939. The results demonstrate that at least one additional change at each of the sites provided improved relative specificity for PBI-3939 versus native coelenterazine. 9B8 variants with amino acid substitutions K, D, F, G, Y, W, and H at position 18 had the highest fold improvement in relative specificity.

TABLE 8

Variants with Improved Relative Specificity for PBI-3939

| Variant | Relative specificity (PBI-3939 RLU/ native coelenterazine RLU; normalized to 9B8) |
|---|---|
| 9B8 + L18K | 40.7 |
| 9B8 + L18D | 25.8 |
| 9B8 + L18F | 25.6 |
| 9B8 + L18G | 18.2 |
| 9B8 + L18Y | 17.8 |
| 9B8 + L18W | 11.2 |
| 9B8 + L18H | 9.1 |
| 9B8 + L18R | 3.5 |
| 9B8 + L18M | 3.4 |
| 9B8 + L18N | 2.9 |
| 9B8 + L18P | 2.6 |

TABLE 8-continued

Variants with Improved Relative Specificity for PBI-3939

| Variant | Relative specificity (PBI-3939 RLU/ native coelenterazine RLU; normalized to 9B8) |
|---|---|
| 9B8 + L18S | 2.3 |
| 9B8 + Y68W | 1.1 |
| 9B8 + Q72W | 6.1 |
| 9B8 + Q72Y | 2.5 |
| 9B8 + Q72F | 2.2 |
| 9B8 + Q72V | 2.2 |
| 9B8 + Q72I | 2.1 |
| 9B8 + Q72T | 1.9 |
| 9B8 + Q72N | 1.8 |
| 9B8 + Q72R | 1.7 |
| 9B8 + Q72P | 1.6 |
| 9B8 + Q72G | 1.5 |
| 9B8 + Q72A | 1.4 |
| 9B8 + Q72M | 1.3 |
| 9B8 + Q72C | 1.3 |
| 9B8 + Q72H | 1.2 |
| 9B8 + Q72S | 1.2 |
| 9B8 + M75F | 1.2 |
| 9B8 + V90R | 2.4 |
| 9B8 + V90Y | 1.6 |
| 9B8 + V90D | 1.4 |
| 9B8 + V90P | 1.4 |
| 9B8 + V90K | 1.3 |
| 9B8 + V90Q | 1.2 |

G. 9B8+K33N Variants

An additional variant, 9B38 opt+K33N (SEQ ID NOs: 42 and 43) was generated to investigate the benefits of amino acid substitution K33N for brightness, relative specificity, and thermal stability. 9B38 opt+K33N was examined and compared to 9B38 opt (described in Example 25A) in various applications.

Figure 29:
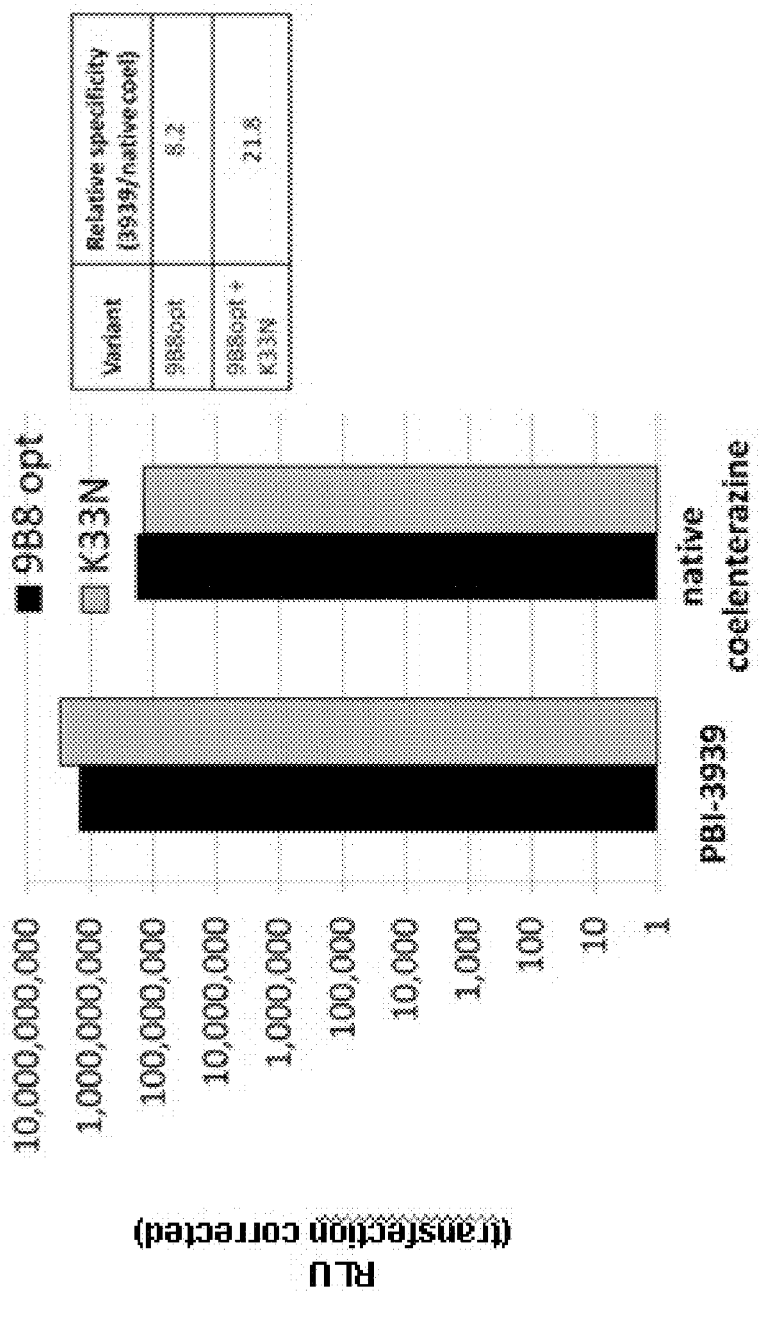
FIG. 29 shows the luminescence of 9B8 opt and 9B8 opt+K33N in bacterial lysates using native coelenterazine and PBI-3939 as substrates and the relative specificity of these variants for PBI-3939 compared to native coelenterazine.

*E. coli* lysates containing the variant 9B38 opt or 9B38 opt+K33N were prepared and analyzed as described previously except the assay buffer contained 0.1% TERGITOL® NP-9 (v/v). Luminescence generated from the lysates was measured using the novel PBI-3939 and native coelenterazine as substrates. The relative specificity of the variants for PBI-3939 and native coelenterazine was calculated as described previously. 9B38 opt+K33N ("K33N") had greater light output (RLU) and a higher relative specificity for PBI-3939 than native coelenterazine compared to 9B38 opt (FIG. 29), indicating that the K33N substitution provided greater light output and improved relative specificity.

A new OgLuc library was created using 9B8opt+K33N as a starting template. The random library was created using DIVERSIFY® PCR Random Mutagenesis Kit (ClonTech; Catalog #630703). Condition 5 (as listed in the user manual) was used to generate additional variants, and the average mutation rate was calculated to be 2.6 mutations per gene by compiling sequence data from 83 randomly selected clones. This PCR library was cloned into the pF4Ag-based, non-fusion vector background described previously and the sandwich background, i.e., Id-OgLuc-HT7 (described in Example 45). Variants in the pF4Ag-base non-fusion vector background are designated with (NF). Variants in the sandwich vector background are designated with (F). In order to clone the PCR product into both vectors, an amino acid, i.e., a glycine, was appended to the variant sequence in pF4Ag, generating a new position 170 in the OgLuc variant ("170G"). The 170G is present in the sandwich construct, but in this case is considered part of the linker between OgLuc and HT7. For each library, 4,400 *E. coli* clones were assayed as described previously with the following exceptions. The lysis buffer contained 300 mM MES pH 6.0 instead of HEPES, and 0.5% TERGITOL® NP-9 (v/v), but did not contain thiourea. The assay buffer contained 100 mM MES pH 6.0 instead of HEPES, and 35 mM thiourea. The assay volumes were as follows: 10 µL cells, 40 µL lysis buffer, and 50 µL assay buffer.

The PCR library in the pF4Ag-based non-fusion background was screened for additional variants with increased luminescence compared to 9B8 opt+K33N+170G (SEQ ID NOs: 68 and 69). Selected variants were then assayed in HEK293 and NIH3T3 cells. For each cell type, 15,000 cells were plated and grown overnight at 37° C. The next day, the cells were transfected as described in Example 25 with 10 ng pGL4.13 (Promega Corp.) as a transfection control and 100 ng of the OgLuc test DNA. The media was removed, and the cells were lysed with 100 µL of lysis buffer as described in Example 25 except the lysis buffer contained 100 mM MES pH 6.0 instead of HEPES, and luminescence measured using a GLOMAX® Luminometer. For each sample, 10 µL of lysate was assayed with 50 µL of lysis buffer containing 20 µM PBI-3939. For the transfection control, 10 µL of lysate was assayed with 50 µL of BRIGHT-GLO™ Assay Reagent.

Table 9 shows the fold-increase in luminescence of variants in *E. coli*, HEK293, and NIH3T3 cells and the amino acid substitutions found in the variants. The variants 27A5 (NF) (SEQ ID NOs: 70 and 71), 23D4 (NF) (SEQ ID NOs: 72 and 73) and 24C2 (NF) (SEQ ID NOs: 74 and 75) had at least 1.3 fold-increase in luminescence in *E. coli* and HEK293 cells.

TABLE 9

Increase in Luminescence Generated by OgLuc Variants Compared to 9B8 opt + K33N + 170G in *E. coli*, HEK293 and NIH3T3 Cells

| Sample | Sequence | Fold over 9B8 opt + K33N + 170G | | |
|---|---|---|---|---|
| | | *E. coli* | HEK293 | NIH3T3 |
| 27A5 (NF) | T39T, 170G | 1.3 | 1.5 | 1.3 |
| 23D4 (NF) | G26G, M106L, R112R, 170G | 1.5 | 1.6 | 1.2 |
| 24C2 (NF) | R11Q, T39T, 170G | 1.5 | 1.5 | 1.1 |

Based on the above data, further combination variants were designed and generated (see Table 10) in the context of the pF4Ag-based non-fusion vector background without the 170G. The variants were analyzed in *E. coli*, HEK293 and NIH3T3 cells as described above and compared to 9B8 opt+K33N. The variants were also examined for luminescence with native coelenterazine. Table 10 shows the fold-increase in luminescence of the variants in *E. coli*, HEK293, and NIH3T3 cells, and the amino acid substitutions found in the variants ("Sample"). The variants were named by adding the additional amino acid substitutions in the variant to the prefix "9B8 opt+K33N." Table 11 shows the relative specificity of the different variants for PBI-3939 compared to native coelenterazine in *E. coli*, NIH3T3, and HEK293 cells. As shown in Table 10, the variant 9B8 opt+K33N+T39T+K43R+Y68D ("V2"; SEQ ID NOs: 92 and 93) had improved luminescence in *E. coli* and a slight improvement in luminescence in NIH3T3 cells. The variant 9B8 opt+K33N+L27V+K43R+Y68D ("L27V, K43R, Y68D") had a neutral improvement in luminescence (Table 10) and 5× fold-increase in relative specificity over 9B8 opt+K33N (Table 11) in the three cell types examined.

TABLE 10

Increase in Luminescence Generated by OgLuc Combination Variants Compared to 9B8 opt + K33N in *E. coli*, NIH3T3 and HEK293 Cells

| | Fold over 9B8 opt + K33N | | |
|---|---|---|---|
| Sample | *E. coli* | NIH3T3 | HEK293 |
| T39T | 1.8 | 1.1 | 1.1 |
| K43R | 1.2 | 1.1 | 1.1 |
| T39T, K43R | 1.3 | 0.9 | 1.1 |
| Y68D | 1.0 | 1.0 | 1.2 |
| K43R, Y68D | 1.2 | 1.2 | 1.2 |
| T39T, K43R, Y68D ("V2") | 1.8 | 1.1 | 1.3 |
| L27V | 0.9 | 0.7 | 0.8 |
| L27V, K43R | 0.7 | 0.6 | 0.6 |
| L27V, K43R, Y68D | 1.2 | 0.8 | 0.9 |
| L27V, Y68D | 1.2 | 0.8 | 0.7 |
| S66N, K43R | 0.9 | 1.1 | 1.1 |
| L27V, K43R, S66N | 1.0 | 0.6 | 0.7 |
| 9B8 opt + K33N | 1.0 | 1.0 | 1.0 |

TABLE 11

Change in Relative Specificity of OgLuc Combination Variants for PBI-3939 Compared to Native Coelenterazine in *E. coli*, NIH3T3 and HEK293 Cells

| | Fold over Native Coelenterazine | | |
|---|---|---|---|
| Sample | *E. coli* | NIH3T3 | HEK293 |
| T39T | 18.2 | 18 | 20 |
| K43R | 29.5 | 31 | 32 |
| T39T, K43R | 29.4 | 30 | 32 |
| Y68D | 11.4 | 10 | 12 |
| K43R, Y68D | 18.6 | 19 | 21 |
| T39T, K43R, Y68D ("V2") | 18.5 | 18 | 21 |
| L27V | 85.2 | 85 | 97 |
| L27V, K43R | 120.1 | 131 | 147 |
| L27V, K43R, Y68D | 98.3 | 98 | 101 |
| L27V, Y68D | 59.9 | 61 | 64 |
| S66N, K43R | 22.9 | 23 | 25 |
| L27V, K43R, S66N | 100.4 | 97 | 106 |
| 9B8 opt + K33N | 19.0 | 19 | 19 |

Additional OgLuc variants were generated from 9B8 opt+K33N to contain at least one of the following additional amino acid substitutions relative to SEQ ID NO: 1: L27V, T39T, K43R, Y68D, or S66N (see "Sample" in Table 12 for the amino acid substitutions in the variants). The variants were named by adding the additional amino acid substitutions in the variant after the prefix "9B8 opt+K33N." These additional variants and the variants 9B8 opt+K33N+L27V+Y68D ("L27V, Y68D)"), 9B8 opt+K33N+L27V+K43R+Y68D ("L27V, K43R, Y68D)"), 9B8 opt+K33N+L27V+K43R+S66N ("L27V, K43R, S66N"), and 9B8 opt+K33N+T39T+K43R+Y68D ("T39T, K43R, Y68D)"; also known as "V2") from above, were examined for brightness, relative specificity, signal stability and thermal stability. The variants were compared to the variants 9B8 opt ("9B8") and 9B8 opt+K33N ("K33N").

*E. coli* lysates containing the variants were prepared and analyzed as described previously. Luminescence generated from the lysates was measured using the novel PBI-3939 and native coelenterazine as substrates. The luminescence of the variants was normalized to the luminescence generated by 9B8 opt (Table 12). The relative specificity of the variants for PBI-3939 and native coelenterazine was calculated by dividing the luminescence of the variants using PBI-3939 as a substrate with the luminescence of the variants using native coelenterazine as a substrate (Table 12). This data indicates that the amino acid substitution L27V lowers specificity for native coelenterazine.

TABLE 12

Increase in Luminescence Generated by OgLuc Variants Compared to 9B8 and Change in Specificity of OgLuc Variants for PBI-3939 Compared to Native Coelenterazine in Bacterial Lysates

| Sample | Fold over 9B8 | Fold over coelenterazine |
|---|---|---|
| 9B8 | 1.0 | 7 |
| K33N | 1.1 | 21 |
| T39T, Y68D | 0.9 | 12 |
| T39T, L27V, K43R | 1.2 | 149 |
| L27V, T39T, K43R, Y68D | 1.8 | 110 |
| T39T, K43R, Y68D | 1.6 | 21 |
| L27V, T39T, K43R, S66N | 1.3 | 114 |
| L27V, K43R, Y68D | 1.3 | 110 |
| L27V, Y68D | 1.0 | 63 |
| L27V, K43R, S66N | 1.1 | 114 |

H. V2 Variants

A set of additional variants were designed using V2 (9B8opt with the additional amino acid substitutions K33N+T39T+K43R+Y68D) as a template. The substitutions shown in Table 13 were designed based on either 1) the known diversity according to the structure-based alignment of 28 fatty acid binding proteins (1VYF, 1FDQ, 2A0A, 1O8V, 1BWY, 2ANS, 1VIV, 1PMP, 1FTP, 2HNX, 1JJJ, 1CBR, 2CBS, 1LPJ, 1KQW, 2RCQ, 1EII, 1CRB, 1IFC, 2PYI, 2JU3, 1MVG, 2QO4, 1P6P, 2FT9, 1MDC, 1O1U, 1EIO; See U.S. Published Application No. 2010/0281552), or 2) the probing of alternative residues at positions previously identified to play a role in substrate specificity. Changes listed under "Consensus" in Table 13 relate to residues identified in at least 50% of the aligned, above-mentioned fatty acid binding proteins. Changes listed under "Predominant Minority" relate to residues identified in many of the fatty acid binding proteins mentioned above, but found in fewer than 50% of the aligned sequences. Changes listed under "Other" relate to residues were identified less frequently than the predominant minority residue at a given position in the aligned sequences. Finally, changes listed under "Specificity" relate to positions suspected to be involved in determining a variant's specificity for coelenterazine or a coelenterazine analog. For example, the designed specificity changes at position 27 (leucine residue in the parental sequence, i.e., V2) were changed to other hydrophobic residues or amino acids representing alternative chemistries (e.g., other hydrophobic residues containing rings, residues containing uncharged polar side chains, or residues containing charged side chains); and the designed specificity changes at position 40 (proline in the parental sequence), were to a sampling of different chemistries (chemistries (e.g., other hydrophobic residues containing rings, residues containing uncharged polar side chains, or residues containing charged side chains); note that glycine, glutamine, isoleucine, and leucine are identified at this position the aligned fatty acid binding proteins).

TABLE 13

| Consensus | Predominant minority | Other | Specificity |
|---|---|---|---|
| 9 T | 9 K | 9 R | 27 A, T, M, G, D |
| 14 S | 10 Y | 40 G | 40 T, S, F, D, Y |
| 16 E | 23 R | | |

TABLE 13-continued

| Consensus | Predominant minority | Other | Specificity |
|---|---|---|---|
| 22 M | 32 I | | |
| 23 K | 63 T | | |
| 24 A | 87 T | | |
| 25 L | 100 I | | |
| 32 R | 111 N, D | | |
| 35 A | 118 I | | |
| 39 K | 134 K | | |
| 46 Q | 142 K, W | | |
| 57 F | 147 N | | |
| 63 S | 149 M | | |
| 87 N | 152 E | | |
| 97 E | 162 Q | | |
| 98 F | | | |
| 100 E | | | |
| 102 T | | | |
| 110 D | | | |
| 113 K | | | |
| 118 V | | | |
| 125 L | | | |
| 126 V | | | |
| 129 Q | | | |
| 130 K | | | |
| 142 E | | | |
| 146 G | | | |
| 147 D | | | |
| 150 V | | | |
| 152 T | | | |
| 165 K | | | |

The variants were constructed using standard site-directed mutagenesis protocols (see previous examples), and the resulting plasmids transformed into *E. coli* for analysis. Cultures were grown per standard walk away induction in minimal media as described previously. To 10 μL of the cultured, transformed *E. coli* cells, 40 μL of lysis buffer (100 mM MES pH 6.0, 0.3×PLB, 0.3 mg/mL Lysozyme, 0.003 U/μL RQ1 DNaseI and 0.25% TERGITOL® NP-9 (v/v)) was added followed by the additional of an equal volume (50 μL) of assay reagent (1 mM CDTA, 150 mM KCl, 2 mM DTT, 20 μM PBI-3939 or native coelenterazine, 100 mM MES pH 6.0, 35 mM thiourea, and 0.5% TERGITOL® NP-9 (v/v)). Luminescence was measured on a GLOMAX® 96 Microplate Luminometer (Promega Corp.).

Table 14 summarizes the different amino acid substitutions identified in the analysis. The data is presented as normalized to the parental clone (V2) with regards to the luminescence measured for both PBI-3939 and native coelenterazine. The relative change in specificity to PBI-3939 with respect to native coelenterazine is also shown.

TABLE 14

| Substitution | PBI-3939 NORMALIZED | COELENTERAZINE NORMALIZED | RELATIVE CHANGE IN SPECIFICITY FOR PBI-3939 |
|---|---|---|---|
| 10 Y | 0.7 | 0.2 | 3.5 |
| 14 S | 1.3 | 1.2 | 1.1 |
| 16 E | 0.5 | 0.2 | 2.5 |
| 23 K | 1.3 | 4 | 0.3 |
| 24 A | 0.4 | 0.2 | 2.0 |
| 25 L | 0.0001 | 0.000023 | 4.3 |
| 27 A | 0.8 | 0.1 | 8.0 |
| 27 D | 0.006 | 0.001 | 6.0 |
| 27 G | 0.088 | 0.005 | 17.6 |
| 27 I | 0.2 | 0.024 | 8.3 |
| 27 M | 2.2 | 0.9 | 2.4 |
| 40 I | 0.0017 | 0.0002 | 8.5 |
| 40 L | 0.0007 | 0.0001 | 7.0 |
| 40 Q | 0.0001 | 0.000026 | 3.8 |
| 87 N | 1.2 | 1.5 | 0.8 |
| 87 T | 1.3 | 1.6 | 0.8 |
| 97 E | 0.014 | 0.01 | 1.4 |
| 100 I | 0.002 | 0.002 | 1.0 |
| 102 T | 1.1 | 1.1 | 1.0 |
| 111 N | 0.6 | 0.6 | 1.0 |
| 113 K | 1.2 | 0.6 | 2.0 |
| 125 L | 0.6 | 0.4 | 1.5 |
| 129 Q | 0.0003 | 0.0001 | 3.0 |
| 130 K | 1.1 | 0.9 | 1.2 |
| 142 E | 0.9 | 0.3 | 3.0 |
| 142 K | 0.9 | 0.3 | 3.0 |
| 142 W | 0.8 | 0.4 | 2.0 |
| 146 G | 0.9 | 0.8 | 1.1 |
| 147 N | 0.4 | 0.4 | 1.0 |
| 149 M | 0.7 | 0.4 | 1.8 |
| 150 V | 0.9 | 0.4 | 2.3 |
| 152 E | 0.9 | 0.5 | 1.8 |
| 152 T | 0.9 | 0.3 | 3.0 |

I. L27V Variants

Using the OgLuc variant L27V as a starting template, i.e., starting sequence or parental sequence, additional variants were made in which some of the amino acids (Table 15) in the L27V variant were reverted to the amino acids found in the native OgLuc luciferase of SEQ ID NO: 1. The variants were constructed by site-directed mutagenesis as previously described. The variants were then screened as previously described for relative activity with either native coelenterazine or PBI-3939. Luminescence was measured on a TECAN® INFINITE® F500 5 min after substrate/assay reagent (as described in H) was added and normalized to the L27V variant starting template. SDS-PAGE analysis of the lysates indicates comparable expression levels (data not shown).

Table 15 shows the relative activities of the L27V variants with native coelenterazine or PBI-3939. Relative activities <1 indicate the reversion is detrimental compared to the residue at that site in the L27V variant. Relative activities >1 indicate the reversion is favorable for activity compared to the residue at that site in the L27V variant. Some additional data on these mutants indicated the following: 166K, 54F, 54A and L27V were tested for thermal stability. The $T_{1/2}$ 60° C. for 166K, 54F, and 54A were 87, 74, and 33%, respectively, indicating these substitutions cause a reduction in thermal stability. The Km values for these same 4 variants were the following: for native coelenterazine, L27V was 16 μM, 54A was 23 μM, 54F was 40 μM, and 166K was 21 μM; for PBI-3939, L27V was 18 μM, 54A was 62 μM, 54F was 163 μM, and 166K was 23 μM. This indicates higher substrate affinity for L27V, particularly for the position 54 substitutions.

TABLE 15

| Native coelenterazine (50 mM) | | PBI-3939 (50 mM) | |
|---|---|---|---|
| AA substitution | Relative activity (5 min) | AA substitution | Relative activity (5 min) |
| 72L | 0.2 | 72L | 0.6 |
| 4A | 1.0 | 4A | 1.0 |
| 124Q | 1.6 | 124Q | 1.0 |
| 43K | 1.9 | 43K | 1.1 |

TABLE 15-continued

| Native coelenterazine (50 mM) | | PBI-3939 (50 mM) | |
|---|---|---|---|
| AA substitution | Relative activity (5 min) | AA substitution | Relative activity (5 min) |
| 115P | 0.6 | 115P | 0.9 |
| 166N | 2 | 166N | 2.0 |
| 75M | 1.1 | 75M | 1.2 |
| 54F | 0.1 | 54F | 0.4 |
| 68F | 0.5 | 68F | 0.9 |
| 33A | 1.7 | 33A | 1.0 |
| 138Y | 1.0 | 138Y | 1.0 |
| 54A | 0.6 | 54A | 1.6 |
| 90I | 0.8 | 90I | 0.6 |
| 33K | 4.2 | 33K | 0.8 |
| 44V | 0.7 | 44V | 1 |
| 166K | 2.1 | 166K | 2 |
| 11Q | 1.6 | 11Q | 1.3 |
| 166F | 0.3 | 166F | 0.4 |
| 18Q | 4.1 | 18Q | 0.6 |

Example 23—Mutational Analysis of Position 166

A. To assess the effect of different amino acids at position 166 on the luciferase activity, the arginine (R) residue at position 166 was substituted to each of the other 19 amino acids using site-directed mutagenesis as previously described in the context of a pF4Ag vector (i.e., in the context of the wild-type OgLuc sequence SEQ ID NO: 1). These position 166 variants were then expressed in *E. coli* as previously described.

To create lysates, 50 μL 0.5× FASTBREAK™ Cell Lysis Reagent (Promega Corp.) was added to 950 μl of induced cultures, and the mixtures incubated for 30 min at 22° C. For the analysis, 50 μL of lysate was assayed in 50 μL of assay reagent (as previously described in Example 22H) with either 100 μM PBI-3939, 30 μM native coelenterazine, or 22 μM coelenterazine-h). Luminescence was measured as previously described (FIGS. 30A-C). FIGS. 30A-C show the relative activity of the N166 mutants. Western analysis confirmed comparable expression of all variants (data not shown).

B. The specific single amino acid substitutions, L27V, A33N, K43R, M75K, T39T, L72Q and F68D were assessed in the wild-type OgLuc or N166R background. The single amino acid substitutions were generated via site-directed mutagenesis as previously described, expressed in *E. coli* as previously described, and luminescence measured using the assay reagent (previously described in Example 22H) with 22 μM native coelenterazine (FIG. 30D). Western analysis confirmed comparable expression of all variants (data not shown).

Example 24—Deletion Variants

Deletions to the L27V variant were made as follows:

TABLE 16

| Deletion # | Deletion Made |
|---|---|
| 27 | Residues 1-27 and Val -1 |
| 52 | Residues 1-52 and Val -1 |
| 64 | Residues 1-64 and Val -1 |
| 84 | Residues 1-84 and Val -1 |
| 19 | Residues 65-83 |
| 23 | Residues 65-87 |
| 23A1 | Residues 65-87 + G64D |

Figure 31:
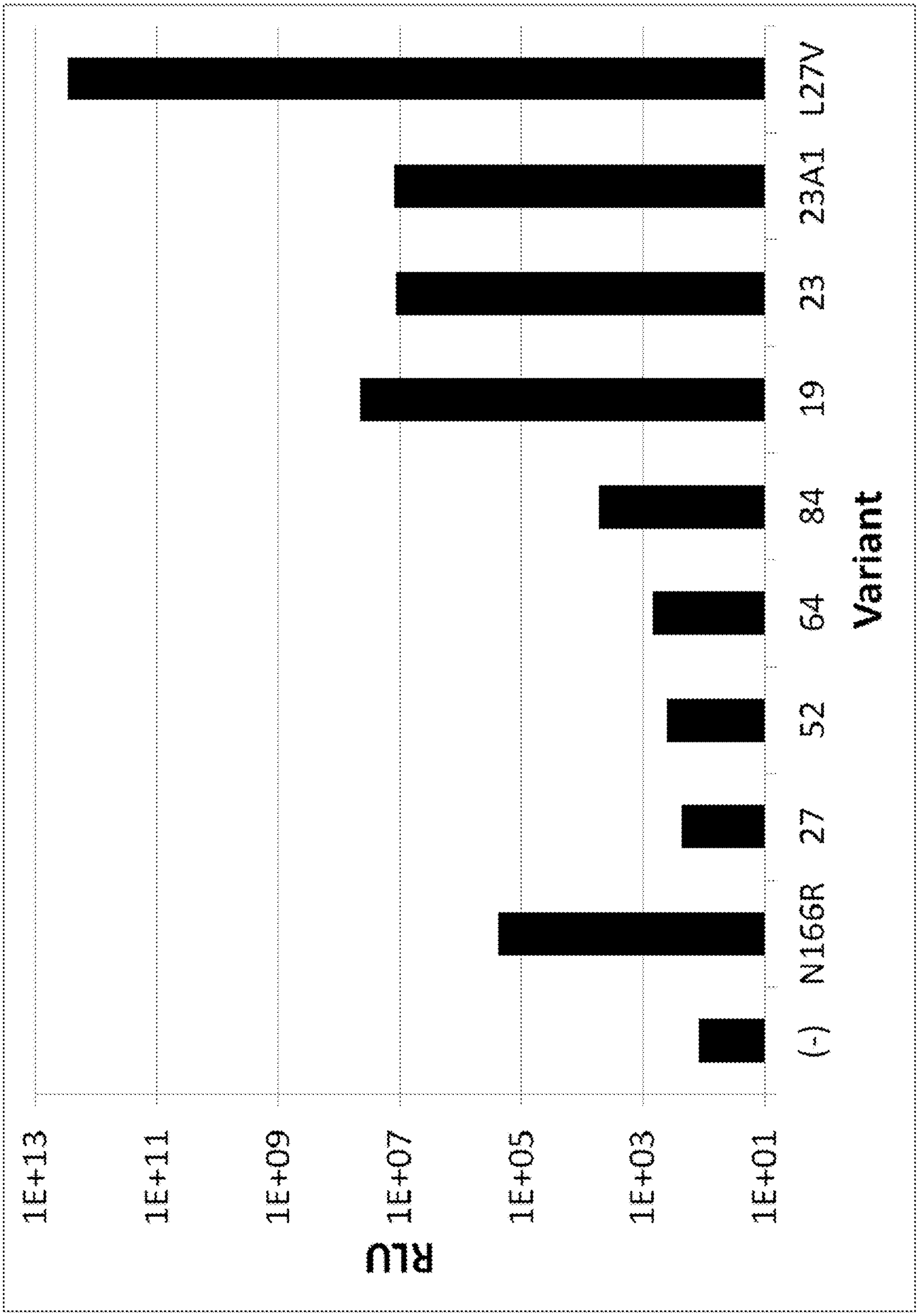
FIG. 31 shows the luminescence of various deletions in the OgLuc variant L27V where (−) is the machine background.

The N-terminus of the OgLuc variant L27V is methionine, valine and phenylalanine, i.e., MVF. For numbering purposes, the phenylalanine was considered the first amino acid. "Val-1" indicates that the Valine in "MVF" was deleted. The methionine of "MVF" was included in these deletions. The L27 deletion variants were cloned in the pF4Ag vector and expressed in *E. coli* KRX cells as previously described. Inductions and lysate preparations were performed as described Lysates were analyzed using the assay reagent (previously described; 100 μM PBI-3939), and luminescence measured as previously described (FIG. 31). The data demonstrates that smaller fragments of the OgLuc variants can also generate luminescence.

Example 25—Codon Optimization of OgLuc Variants

A. IV and 9B8

The IV and 9B8 OgLuc variants were used as templates for codon optimization. The goals, as understood by those skilled in the art, were two-fold: 1) to remove known transcription factor binding sites, or other regulatory sequences, e.g., promoter modules, splice donor/acceptor sites, splice silencers, Kozak sequences, and poly-A signals, that could potentially interfere with the regulation or expression of the OgLuc variants, and 2) to alter the DNA sequence (via silent mutations that do not alter protein sequence) to eliminate rarely used codons, and favor the most commonly used codons in cells of *E. coli*, human, other mammalian, or other eukaryotic organisms (Wada et al., *Nucleic Acids Res.*, 18:2367 (1990)).

Two different optimized sequences for IV and 9B8, referred to as opt (aka optA) and optB, were designed for each variant. The first optimized sequence, i.e., opt/optA for each variant, was designed by identifying the two best, i.e., most common, human codons for each site (see Table 17) and then randomly picking one of the two for incorporation at each site. For the optB versions, the previous, codon-usage, optimized version, i.e., opt/optA, was used as a starting template, and each codon replaced with the other of the two best human codons identified for this codon-optimization strategy. As an example, the leucine at position 3 in either the IV or 9B8 sequence is encoded by the codon TTG. TTG is not one of the two most common codons for leucine in a human cell, and therefore the codon was changed to the alternative, more common codons for leucine, CTC (opt/optA) or CTG (optB). This same process was repeated for all leucines in the sequence, and due to the random nature of the approach, a CTC codon could end up in optB and the CTG could end up in optA. Because of this two codon-usage approach to optimization, sequences opt/optA and opt B were maximally codon-distinct.

TABLE 17

| Codons used in Codon Optimization | | |
|---|---|---|
| Amino acid | Choice#1 | Choice#2 |
| Gly | GGC | GGG |
| Glu | GAG | GAA |
| Asp | GAC | GAT |
| Val | GTG | GTC |
| Ala | GCC | GCT |
| Ser | AGC | TTC |
| Lys | AAG | AAA |
| Asn | AAC | AAT |
| Met | ATG | |
| Ile | ATC | ATT |

TABLE 17-continued

| Codons used in Codon Optimization | | |
|---|---|---|
| Amino acid | Choice#1 | Choice#2 |
| Thr | ACC | ACA |
| Trp | TGG | |
| Cys | TGC | TGT |
| Tyr | TAC | TAT |
| Phe | TTC | TTT |
| Arg | CGG | CGC |
| Gln | CAG | CAA |
| His | CAC | CAT |
| Leu | CTG | CTC |
| Pro | CCC | CCT |

Each of the 4 sequences (IV opt, IV optB; 9B8 opt, 9B8 optB) were then analyzed (Genomatix Software, Germany) for the presence of transcription factor binding sites or other regulatory sequences as described above, and these undesirable sequences were disrupted via silent nucleotide changes. In some cases, where there were other non-rare codons for both human and *E. coli*, the transcription factor binding sites or other regulatory elements was removed by changing to one of these codons, even though they are not choice #1 or choice #2 (see Table 18). In cases, where removing a transcription factor binding site or other regulatory element would have involved introducing a rare codon, the transcription binding site (or other regulatory element) was usually not changed.

TABLE 18

| Additional Codons used to Remove Transcription Factor Binding Sites and Other Regulatory Elements | | |
|---|---|---|
| Amino Acid | Choice #3 | Choice #4 |
| Gly | GGA | GGT |
| Val | GTA | GTT |
| Ala | GCG | GCA |
| Ser | AGT | TCA |
| Thr | ACG | ACT |
| Leu | TTG | CTT |
| Pro | CCG | CCA |

Codon optimized versions of IV ("IV opt" (SEQ ID NO: 22) and "IV optB" (SEQ ID NO: 23)) and 9B8 ("9B8 opt" (SEQ ID NO: 24) and "9B8 optB" (SEQ ID NO: 25)) were generated and cloned into pF4Ag by methods known in the art. HEK293 cells were plated in 96-well plates at 15,000 cells/well and grown overnight at 37° C. The following day, the cells were transiently transfected in 6 well replicates using TRANSIT®-LT1 Transfection Reagent (Mirus Bio) with 100 ng of plasmid DNA encoding the codon optimized versions in pF4Ag and grown overnight at 37° C. HEK293 cells were also transfected with either pGL4.13 (Luc2/SV40) (Paguio et al., "pGL4 Vectors: A New Generation of Luciferase Reporter Vectors" *Promega Notes,* 89:7-10 (2005)) or pGL4.73 (hRL/SV40) (Id.) to normalize for differences in transfection efficiency. Ten ng/transfection or 10% of the total DNA transfected was used. Media was removed, and cells were lysed with 100 μL lysis buffer which contained 10 mM CDTA, 150 mM KCl, 10 mM DTT, 100 mM HEPES, pH 7.0, 35 mM thiourea, and 0.5% TERGITOL® NP-9 (v/v) to create a lysate sample. Luminescence of the lysate sample was measured on a TECAN® INFINITE® F500 luminometer as follows: for hRL and the OgLuc variants, 10 μL of the lysate sample was assayed for luminescence with 50 μL of lysis buffer containing 20 μM of substrate (native coelenterazine for hRL and PBI-3939 for the OgLuc variants). For Luc2 (SEQ ID NOs: 28 and 29), a firefly luciferase, 10 μL of lysate sample was assayed for luminescence with 50 μL of BRIGHT-GLO™ Luciferase Assay Reagent (Promega Corp.).

Figure 32:
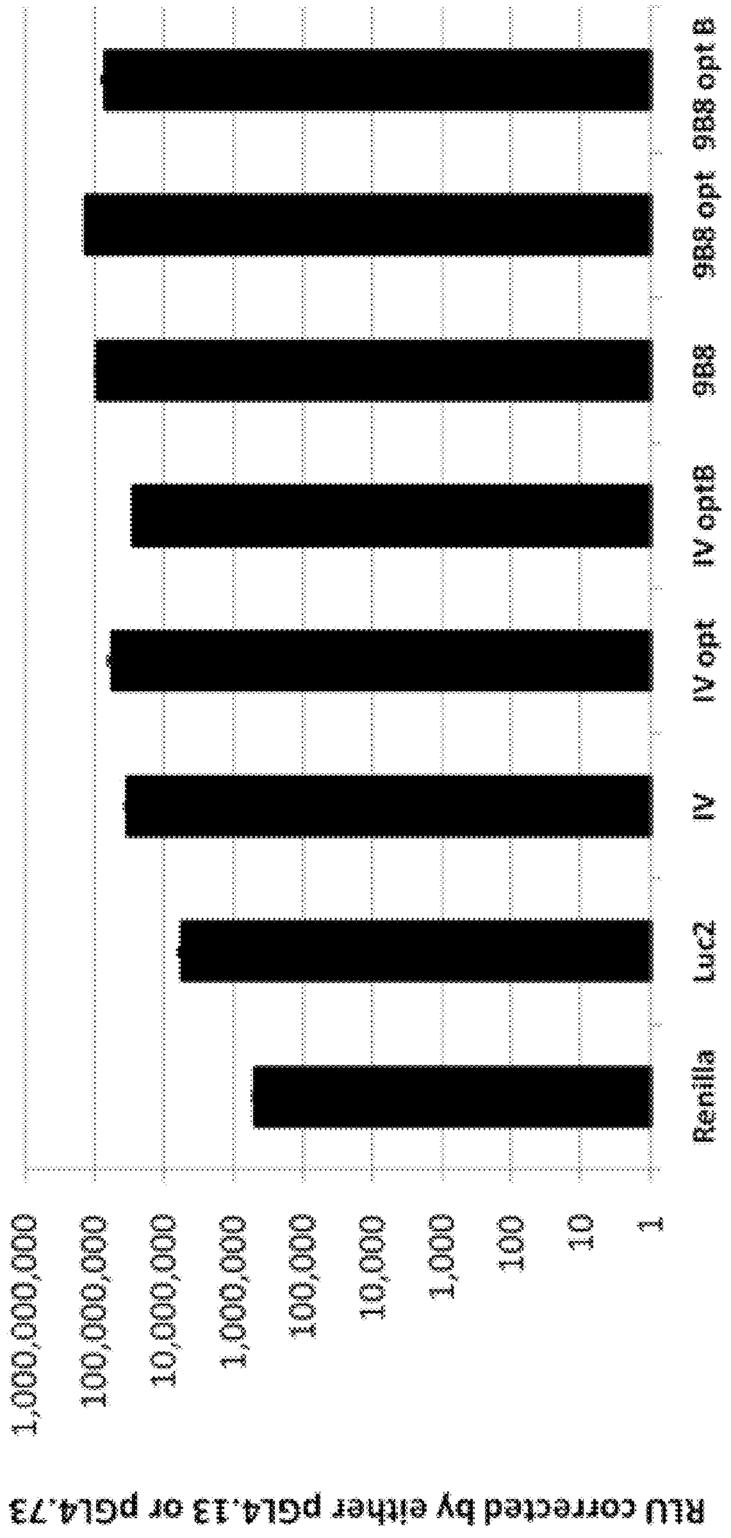
FIG. 32 shows the normalized luminescence generated from lysed HEK293 cells expressing hRL ("*Renilla*") using native coelenterazine as a substrate, firefly luciferase (Luc2) using luciferin (BRIGHT-GLO™ Assay Reagent) as a substrate, and various OgLuc variants using novel PBI-3939 as a substrate.

FIG. 32 shows a comparison of the luminescence measured for the lysates containing the codon optimized versions of the OgLuc variants compared to hRL and Luc2. hRL and the OgLuc variants were normalized to pGL4.13 and Luc2 was normalized to pGL4.73 using methods known in the art. As shown in FIG. 32, Luc2 had approximately 14 fold higher luminescence than hRL. The OgLuc variants had higher luminescence compared to Luc2 and hRL. The codon optimized versions of IV ("IV opt" and "IV optB") and 9B8 ("9B8 opt") showed increased luminescence compared to the non-optimized versions.

As a result of this optimization, the "opt/optA" versions expressed better in human HEK293 cells than their parental sequence, while the "optB" versions did not express as well in HEK293 cells compared to the parental sequence.

B. L27V

The L27V variant (SEQ ID NO: 88) was optimized to minimize the occurrence of common vertebrate response elements (any transcription factor binding site (TFBS) in the Genomatix database). Three different optimized versions of the L27V variant were created:

1. L27V01—version 1 (SEQ ID NO: 319)—Promoter modules and all other undesired sequence elements (additional details below) were removed by nucleotide substitutions except for individual TFBSs.
2. L27V02—version 2—L27V01 was used as the starting, i.e., parental, sequence, and as many TFBSs were removed as possible using high stringency match criteria (A higher stringency involves a better match to the binding site and will thus find fewer matches than a lower stringency). There were two versions, A (SEQ ID NO: 322) & B ((SEQ ID NO: 318)), created for L27V02. These two versions were created by selecting different codons for each version to remove undesired sequence elements. Both versions were analyzed by searching for TFBSs with lower stringency.
3. L27V03—version 3 (SEQ ID NO: 325)—L27V02B (SEQ ID NO: 318) was used as the starting sequence. Lower stringency TFBS matches were removed where possible. L27V03 was created to be very codon distinct from L27V02A.

The following criteria were used to create the L27V optimized variants:

1. Codon usage: Preferably, the best two human codons were used for each amino acid (as was done for the IV variant), and the use of rare human codons (HS; coding for <10% of amino acids) was avoided (Table 19). The use of rare *E. coli* codons (EC) was used, if necessary, to remove undesired sequence elements.

TABLE 19

| Amino acid | Best Codons | Avoid Codons |
|---|---|---|
| A | GCT | |
| A | GCC | |
| C | TGT | |
| C | TGC | |
| D | GAT | |
| D | GAC | |
| E | GAG | |
| E | GAA | |
| F | TTT | |

TABLE 19-continued

| Amino acid | Best Codons | Avoid Codons |
|---|---|---|
| F | TTC | |
| G | GGG | |
| G | GGC | |
| H | CAT | |
| H | CAC | |
| I | ATT | |
| I | ATC | |
| K | AAG | |
| K | AAA | |
| L | CTG | TTA |
| | CTC | [HS] |
| | | CTA |
| L | | [HS, EC] |
| M | ATG | |
| N | AAT | |
| N | AAC | |
| P | CCT | |
| P | CCC | |
| Q | CAG | |
| Q | CAA | |
| R | CGG | |
| R | CGC | CGT |
| | | [HS] |
| S | AGC | TCG |
| | | [HS] |
| S | TCC | |
| T | ACA | |
| T | ACC | |
| V | GTG | |
| V | GTC | |
| W | TGG | |
| Y | TAT | |
| Y | TAC | |

2. Undesired sequence elements that were removed where possible

A. Restriction Enzyme (RE) Sites: RE sites were removed that would be useful for cloning and should otherwise not be present in open reading frame (ORF).

B. Eukaryotic Sequence Elements: Splice donor and acceptor sites, splice silencers, Kozak sequence and PolyA sequences in the (+) mRNA strand were removed.

C. Vertebrate Promoter Modules (PM) (in Genomatix category: Vertebrate) were removed.

D. Vertebrate TFBS (in Genomatix categories: Vertebrate, general Core Promoter Elements, and miscellaneous other sequences) were removed where possible. This applied only to L27V optimized versions 2 and 3, but not to version 1.

E. *E. coli* Sequence Elements: *E. coli* promoters were removed.

F. mRNA Secondary Structure: Strong secondary structures (high mRNA folding energy) near the 5'end (Zuker, *Nucleic Acid Res.* 31(13): 3406-3415 (2003)) and other strong hairpin structures were removed.

A sequence comparison, percent pair-wise sequence identity is provided in Table 20 ("0" indicate number of nucleotide differences).

TABLE 20

| | L27V01 | L27V02A | L27V02B | L27V03 |
|---|---|---|---|---|
| L27V00 | 99% (3) | 97% | 97% | 94% |
| L27V01 | | 98% (12) | 98% | 94% (32) |
| L27V02A | | | 99% (4) | 95% (26) |
| L27V02B | | | | 96% |

Example 26—Signal Stability of OgLuc Variants

A. 15C1, 9B and IV

The signal stability of $15C_1$ with PBI-3945 and 9B8 with PBI-3889 was measured and compared to IV. *E. coli* containing plasmid DNA encoding 15C1, 9B8, or IV were grown and induced as described previously in 8-well replicates. Cells were lysed using a lysis buffer containing of 300 mM HEPES pH 8.0, 0.3× Passive Lysis Buffer ("PLB"; Promega Corp. Cat. No. E194A), 0.3 mg/mL lysozyme, and 0.003 U/μL RQ1 DNase. Lysates were diluted 1:1000 in lysis buffer and measured for luminescence using a TECAN® INFINITE® F500 luminometer. Measurements were taken immediately after the addition to 10 μL of diluted lysate sample of 50 μL of "Glo" 0.5% TERGITOL assay buffer ("0.5% TERGITOL"), which contained 150 mM KCl, 1 mM CDTA, 10 mM DTT, 100 mM thiourea, 0.5% TERGITOL® NP-9 (v/v), and 20 μM of either novel coelenterazines PBI-3945 or PBI 3889.

Figure 33:
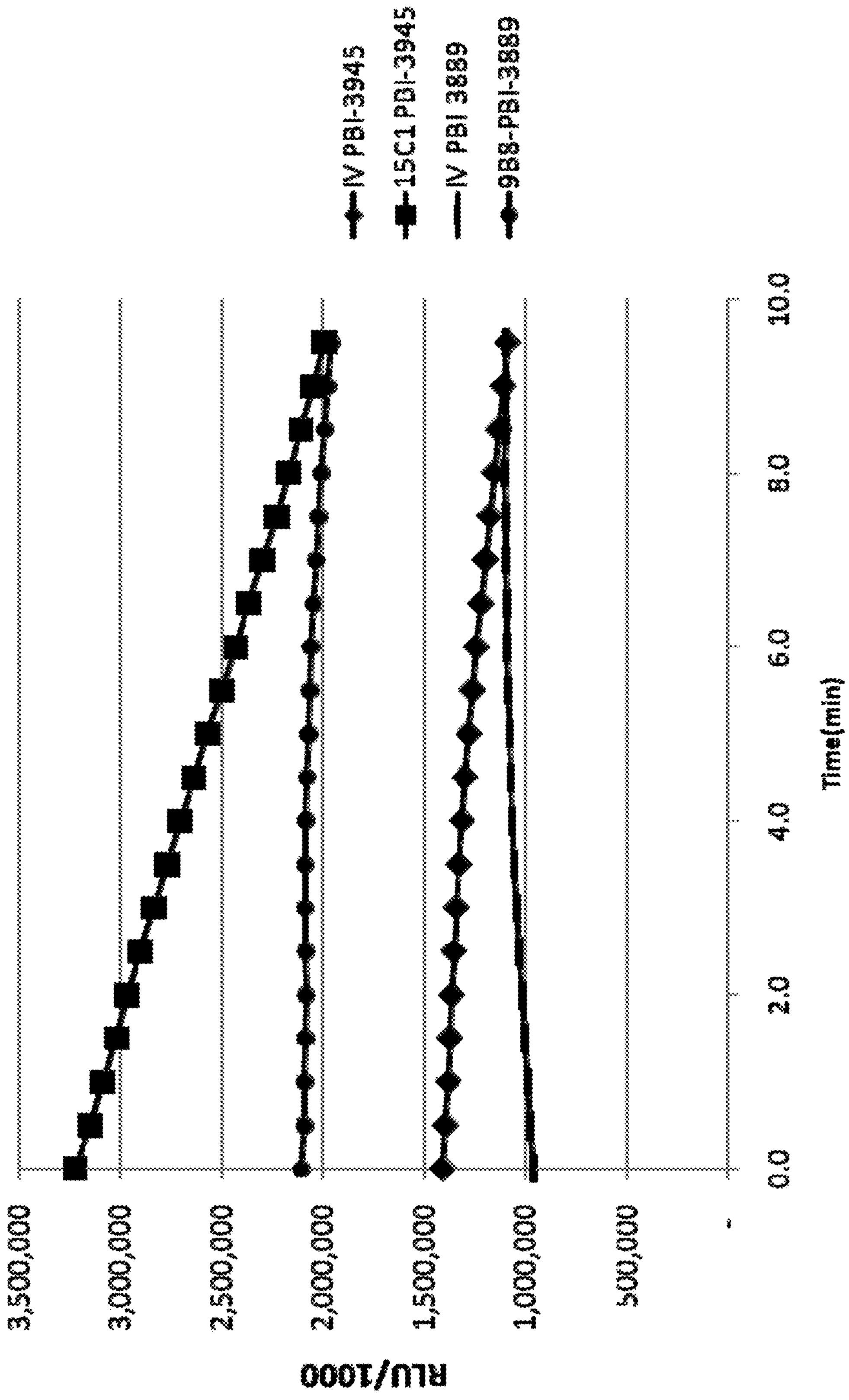
FIG. 33 shows the signal stability of IV and 15C1 in bacterial lysates using the novel coelenterazine PBI-3945 as a substrate and IV and 9B8 in bacterial lysates using the novel coelenterazine PBI-3889 as a substrate.

The signal stability of the variants was determined by re-reading the plate every 30 seconds for a length of time after the addition of the assay buffer to the sample. The signal half-life was determined from these measurements using methods known in the art. The average signal half-life was compared between the variants and IV. Both 15C1 and 9B8 had a signal half-life of at least 30 min (FIG. 33). Although 15C1, assayed with PBI-3945 had a higher luminescence at t=0, the signal decayed more rapidly than variant 9B8 assayed with PBI-3889. At t=10 min, luminescence for 15C1 with PBI-3945 and 9B8 with PBI-3889 were equivalent.

B. 9B8 opt+K33N

The signal stability of the 9B8 opt+K33N variants was examined. *E. coli* lysates containing the variants were prepared and analyzed as described previously except the assay buffer contained 0.25% TERGITOL® NP-9 (v/v), 100 mM MES pH 6.0, 1 mM CDTA, 150 mM KCl, 35 mM thiourea, 2 mM DTT, and 20 μM PBI-3939. Table 22 shows the signal half-life in min of the variants and indicates that the amino acid substitution L27V improves signal stability.

TABLE 22

Signal stability of OgLuc variants in bacterial lysates

| sample | signal half life (min) |
|---|---|
| 9B8 | 74 |
| K33N | 55 |
| T39T, Y68D | 87 |
| T39T, L27V, K43R | 139 |
| L27V, T39T, K43R, Y68D | 114 |
| T39T, K43R, Y68D | 61 |
| L27V, T39T, K43R, S66N | 124 |
| L27V, K43R, Y68D | 122 |
| L27V, Y68D | 139 |
| L27V, K43R, S66N | 124 |

Figure 34A:
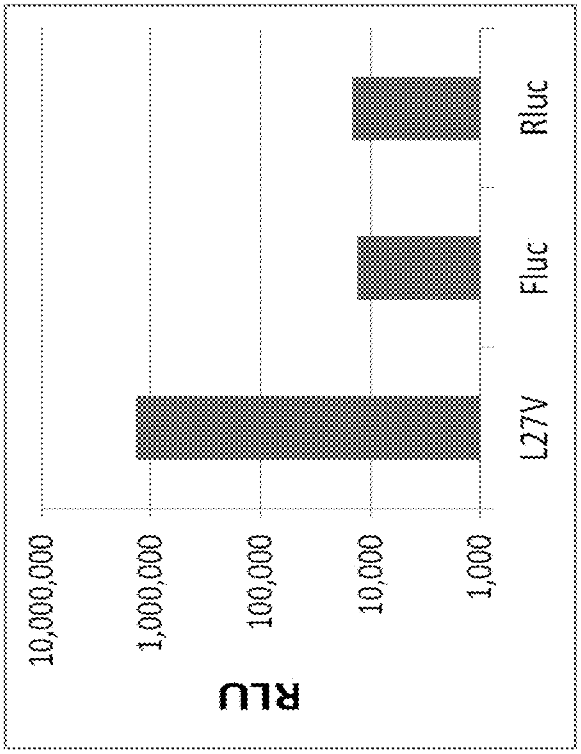
FIGS. 34A-B show the higher activity (FIG. 34A) and signal stability (FIG. 34B) of the OgLuc variant L27V compared to Firefly (Fluc) and *Renilla* (Rluc) luciferases.
Figure 34B:
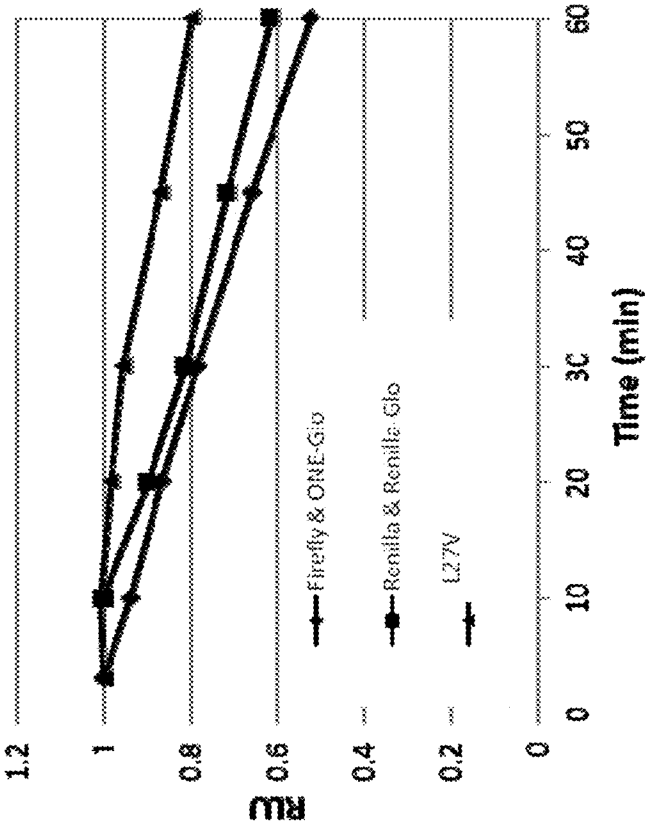

The signal activity and stability of the L27V variant (9B8+K33N+L27V+T39T+K43R+Y68D; SEQ ID NO: 88 and 89) was measured and compared to that of firefly (Luc2) and *Renilla* luciferases. The L27V variant, Luc2 and *Renilla* luciferases were fused to HALOTAG® and expressed in *E. coli*. The luciferases were purified using HALOTAG® as a purification tag according to the manufacturer's protocol (pFN18A; HALOTAG® Protein Purification System). 10 μM of each purified luciferase (diluted in DMEM without phenol red containing 0.01% PRIONEX®) was then mixed with an equal volume of an assay reagent (100 mM MES pH 6, 35 mM thiourea, 0.5% TERGITOL® NP-9 (v/v), 1 mM CDTA, 2 mM DTT, 150 mM KCl, and 100 μM PBI-3939 for the L27V variant; ONE-GLO™ Luciferase Assay System (Promega Corp.) for firefly luciferase; and *RENILLA*-GLO™ Luciferase Assay System (Promega Corp.) for *Renilla* luciferase), and luminescence was monitored over time (3, 10, 20, 30, 45 and 60 min). FIGS. 34A-B demonstrates the high specific activity (FIG. 34A) and signal stability (FIG. 34B) of the L27V variant when compared to firefly and *Renilla* luciferase.

Example 27—Enzyme Kinetics of OgLuc Variants

A. IV, 15C1, 9B8, 9F6 and 9A3

Figure 35:
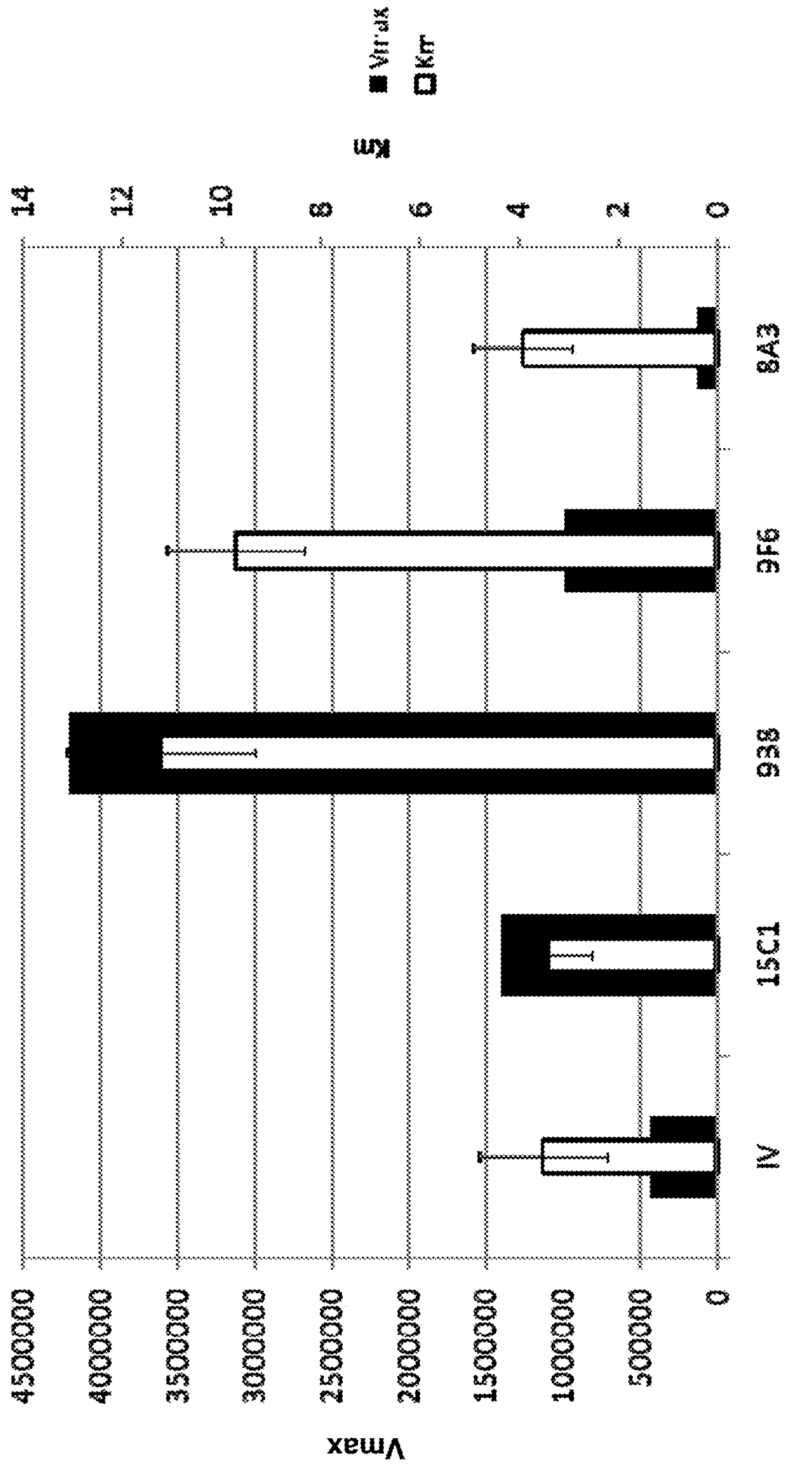
FIG. 35 shows the Vmax (RLU/sec) and Km (μM) values for various OgLuc variants in bacterial lysates using the novel coelenterazine PBI-3939 as a substrate.

Using methods known in the art, enzyme kinetic assays measuring luminescence were performed with the lysates of *E. coli* containing IV and the IV variants 15C1, 9B8, 9F6, and 9A3. Cells were induced, lysed, and diluted as described in Example 26 except the lysis buffer had a pH of 7.5. Two fold serial dilutions of PBI-3939 in the assay buffer described previously in Example 26 were assayed with the diluted lysates. FIG. 35 shows the Km and Vmax values calculated using a hyperbolic fit for IV and the variants 15C1, 9B8, 9F6, and 9A3. Variants 9B8 and 9F6 had higher Km values compared to IV while Km values for the other variants were unchanged. Variants 15C1, 9B8, and 9F6 all had higher Vmax values, while 8A3 had a lower Vmax value compared to IV.

Figure 36:
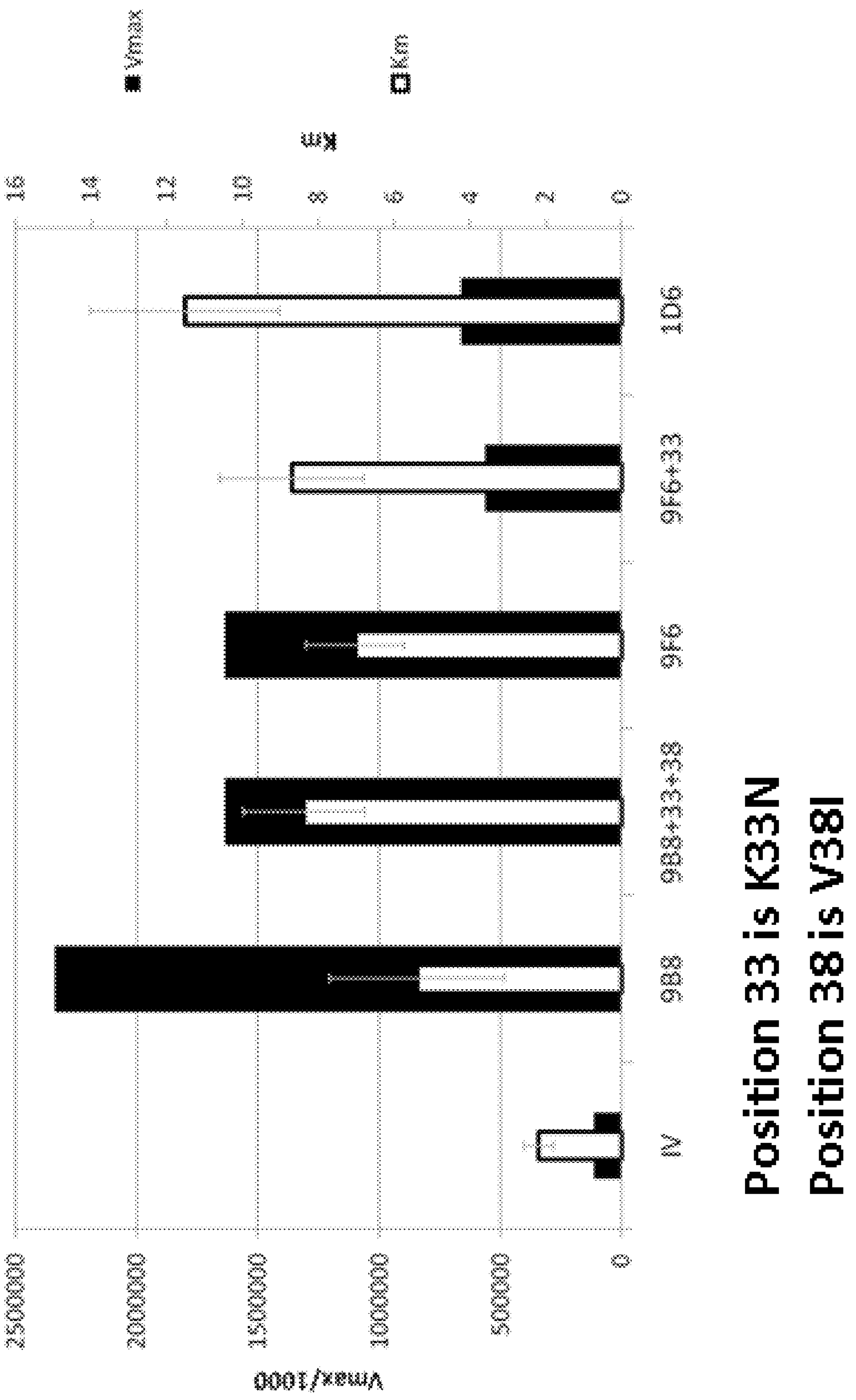
FIG. 36 shows the Vmax (RLU/sec) and Km (μM) values for various OgLuc variants in bacterial lysates using the novel coelenterazine PBI-3939 as a substrate.

15C1, which had the highest luminescence with PBI-3945 contained the amino acid substitution K33N, indicating that K33N provided increased luminescence. A 9B8 variant was generated to have this additional substitution to provide improvement in luminescence for this variant. Additional variants of 9B8 and 9F6 were generated to have at least one of amino acid substitutions K33N or V38I ("9B8+K33N+V38I" and "9F6+K33N"). Variant 1D6 was used to highlight the importance of amino acid substitutions at positions 68, 72, and 75 for increasing light output and stability. FIG. 36 shows the Km and Vmax values calculated using a hyperbolic fit for IV and the variants 9B8, 9B8+K33N+V38I, 9F6, 9F6+K33N, and 1D6. While the actual Km values were different between FIGS. 35 and 36 for 9B8 and 9F6, the general trend between the variants was consistent.

Figure 37:
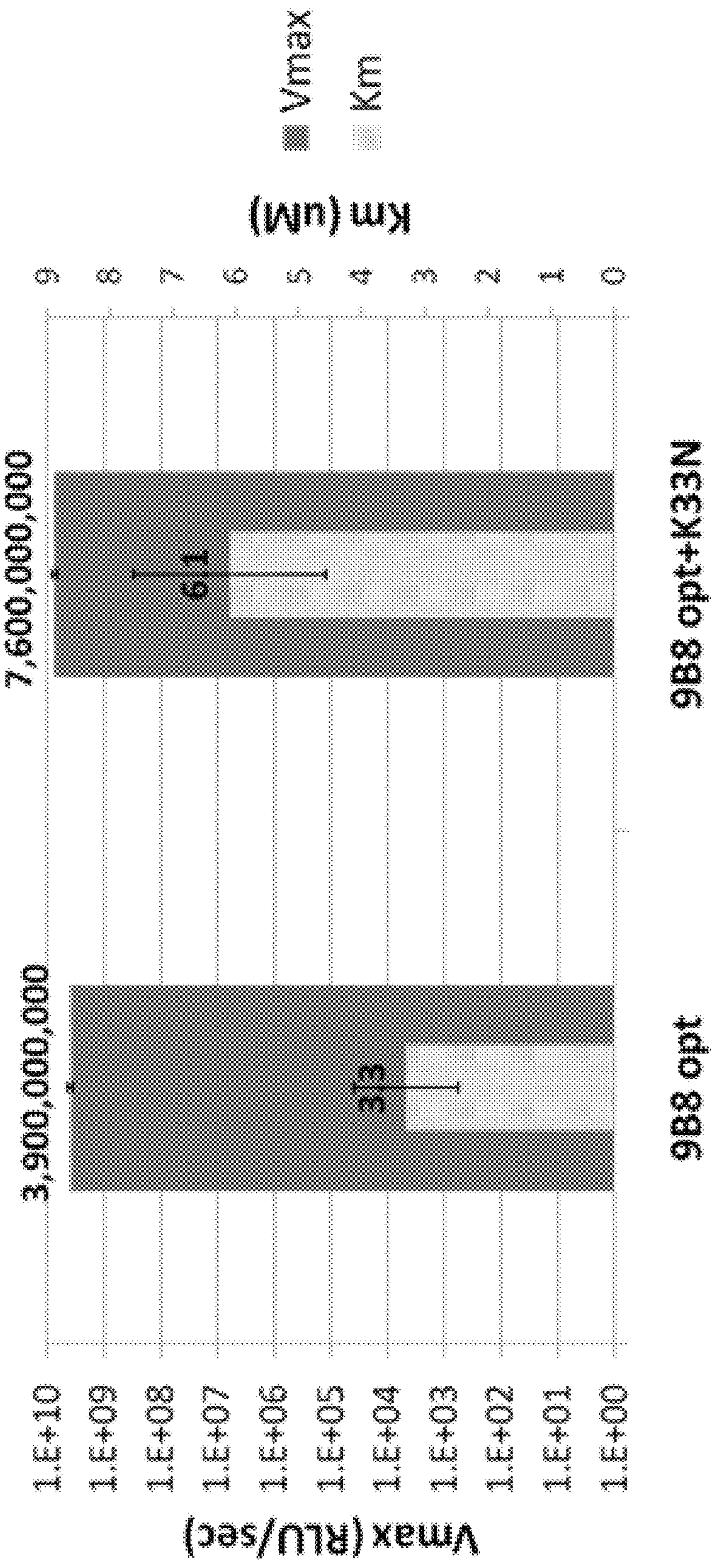
FIG. 37 shows the Vmax (RLU/sec) and Km (μM) values for 9B8 opt and 9B8 opt+K33N both in bacterial lysates using the novel coelenterazine PBI-3939 as a substrate.

The enzyme kinetics, i.e., Vmax and Km values, were determined and compared for the variants 9B8 opt and 9B8 opt+K33N as described above except the *E. coli* lysates were assayed with a buffer containing 1 mM CTDA, 150 mM KCl, 2 mM DTT, 100 mM MES pH 6.0, 35 mM thiourea, 0.25% TERGITOL® NP-9 (v/v), 10 mg/mL 2-hydroxypropyl-β-cyclodextrin, and 20 μM PBI-3939. Luminescence was measured on a TECAN® INFINITE® F500 luminometer. As shown in FIG. 37, the Vmax and Km values for 9B8 opt+K33N were higher than 9B8 opt, indicating that this clone is brighter and has a lower affinity for substrate.

B. 9B8 OPT+K33N VARIANTS

The enzyme kinetics values were determined for the OgLuc variants as described previously, except luminescence was measured using a GLOMAX® luminometer. Three replicates were used for each variant. Table 23 shows the average Km and Vmax values with the standard deviation ("Km(+/−)" and "Vmax(+/−)" respectively) calculated using HYPER.EXE, Version 1.0.

TABLE 23

Vmax (RLU/0.5 sec) and Km (μM) values for OgLuc Variants

| sample | Km | Km (+/−) | Vmax | Vmax (+/−) |
|---|---|---|---|---|
| 9B8 | 7.7 | 2.0 | 86,000,000 | 14,000,000 |
| K33N | 12.5 | 3.0 | 110,000,000 | 17,000,000 |
| T39T, Y68D | 7.9 | 1.8 | 74,000,000 | 10,000,000 |
| T39T, L27V, K43R | 21.4 | 5.4 | 150,000,000 | 28,000,000 |
| L27V, T39T, K43R, Y68D | 13.9 | 2.9 | 190,000,000 | 28,000,000 |
| T39T, K43R, Y68D | 10.5 | 2.8 | 140,000,000 | 25,000,000 |
| L27V, T39T, K43R, S66N | 16.3 | 4.8 | 130,000,000 | 28,000,000 |
| L27V, K43R, Y68D | 13.7 | 4.3 | 130,000,000 | 28,000,000 |
| L27V, Y68D | 10.2 | 3.0 | 97,000,000 | 19,000,000 |
| L27V K43R, S66N | 20.0 | 6.2 | 130,000,000 | 30,000,000 |

Example 28—Protein Stability of OgLuc Variants

As stability of the luciferase protein is another factor affecting luminescence, protein stability, i.e., thermal stability, of the variants was determined.

A. 15C1, 9B8, 9F6, 8A3 and IV

Lysates of *E. coli* containing 15C1, 9B8, 9F6, 8A3 or IV and *E. coli* expressing hRL (SEQ ID NO: 30 and 31) were prepared from induced cultures as described previously. Lysate samples were diluted 1:1000 with a buffer containing 10 mM HEPES pH 7.5 with 0.1% gelatin. Diluted lysate (100 μL) samples, in replicate 96-well plates, were incubated at 50° C. At different time points, plates were placed at −70° C. (minus seventy degrees Celsius). Prior to measuring the luminescence as described previously, each plate was thawed at room temperature, i.e., 22° C., for 10 min. Samples (10 μL of each thawed sample) were assayed using native coelenterazine as a substrate. Luminescence was measured immediately after addition of assay buffer for each time point plate. The half-life of the protein, which indicated protein stability, was calculated from the luminescence data for each time point using methods known in the art.

Table 24 shows the protein stability of variants 15C1, 9B8, 9F6, and 8A3 having half-lives in min (hrs) of 630.1 (10.5), 346.6 (5.8), 770.2 (12.8) and 65.4 (1.1), respectively. In comparison, hRL had a half-life of 9.6 min, while IV had a half-life of 27.2 min. Table 24 also shows that at 4 hrs, 79%, 61%, and 80% of 15C1, 9B8, and 9F6, respectively, remained active.

TABLE 24

Protein Stability of OgLuc Variants at 50° C.

| Sample | ½ life (min) | ½ life (hrs) | % remaining at t = 4 hrs |
|---|---|---|---|
| *Renilla* | 9.6 | | |
| IV | 27.2 | | |
| 15C1 | 630.1 | 10.5 | 79% |
| 9B8 | 346.6 | 5.8 | 61% |
| 9F6 | 770.2 | 12.8 | 80% |
| 8A3 | 65.4 | 1.1 | |

B. 1D6, 9B8, 9B8+K33N+V38I, 9F6, 9F6+K33N, and IV

Figure 38:
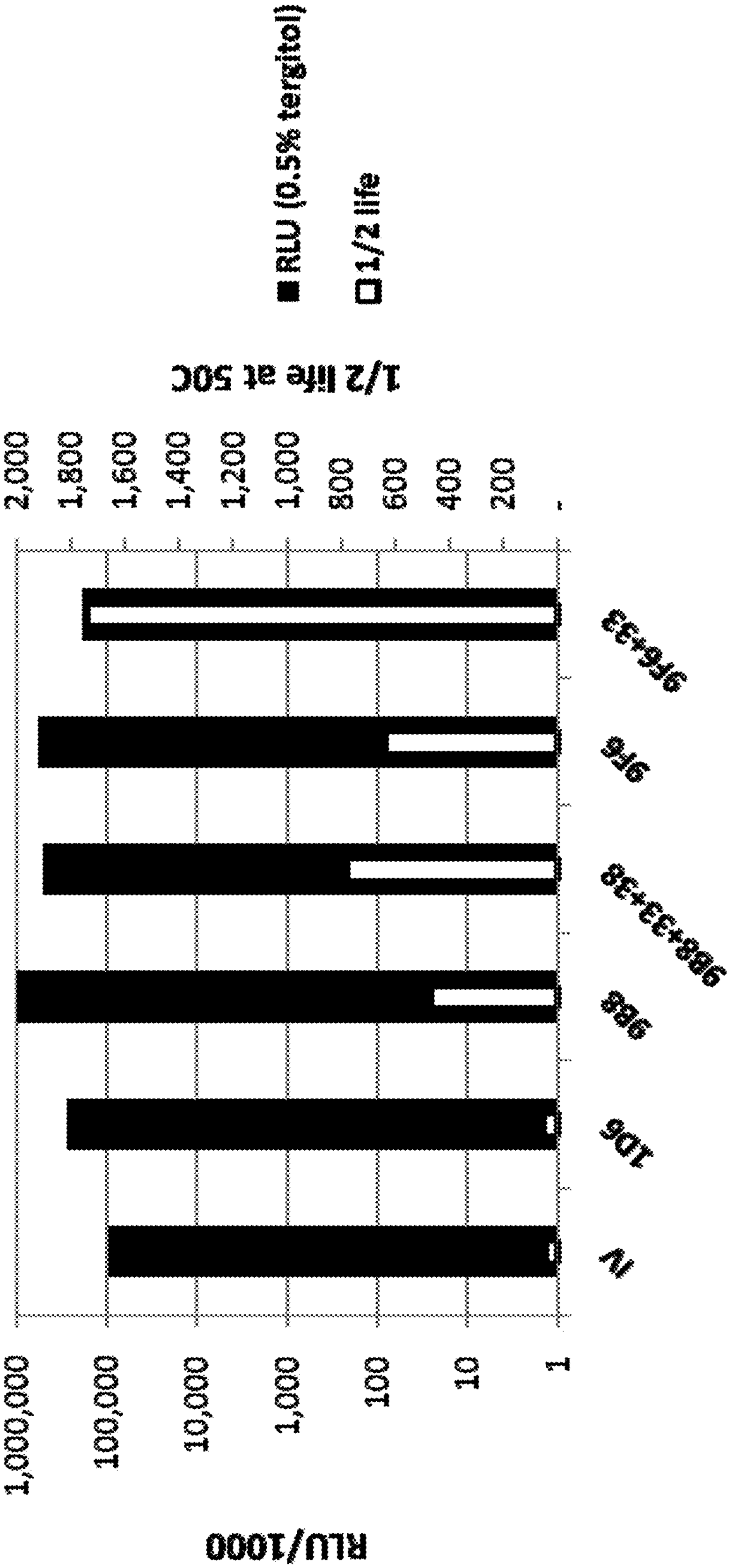
FIG. 38 shows the protein stability at 50° C. of various OgLuc variants in bacterial lysates using native coelenterazine as a substrate as the luminescence at t=0 and half-life in min

Lysates of *E. coli* containing 1D6, 9B8, 9B8+K33N+V38I, 9F6, 9F6+K33N, or IV were prepared from induced cultures and assayed for luminescence as described previously. Protein stability, i.e., thermal stability of the lysates, was assayed as described above in this Example. FIG. 38 shows the half-life in minutes (min) of the variants at 50° C., and the luminescence of the sample measured at the start of the incubation period, i.e., t=0, using native coelenterazine as a substrate. The difference between variant 9B8+33+38 and 9F6 was one amino acid substitution, L27V, indicating that this amino acid substitution increased stability. The addition of "activity/expression" substitutions in positions 68, 72, and 75 increased stability. FIG. 38 shows K33N provided greater thermal stability to variant 9F6 and that variant 9B8 had greater light output and stability than variant 1D6. The difference between these two variants, i.e., 9B8 contains additional amino acid substitutions F68Y, L72Q, and M75K, indicated the importance of these three substitutions.

Figure 39A:
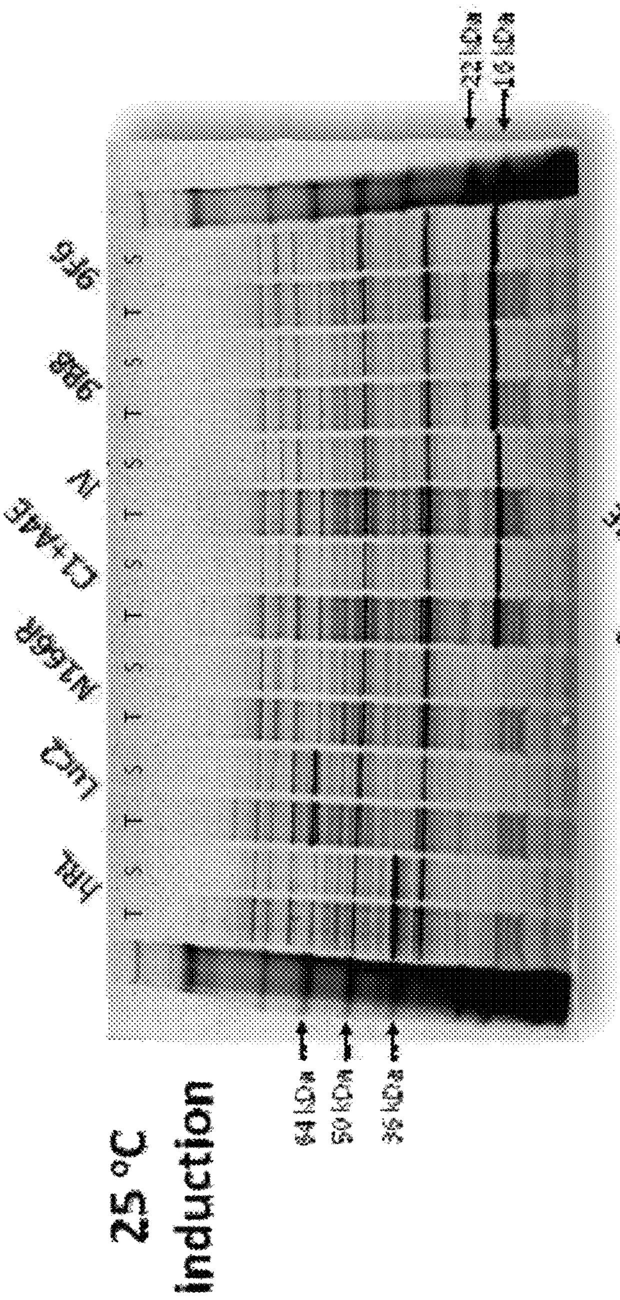
FIGS. 39A-B show the structural integrity (determined by expression, stability, and solubility as shown by SDS-PAGE analysis) in bacterial lysates of various OgLuc variants at 25° C.
Figure 39B:
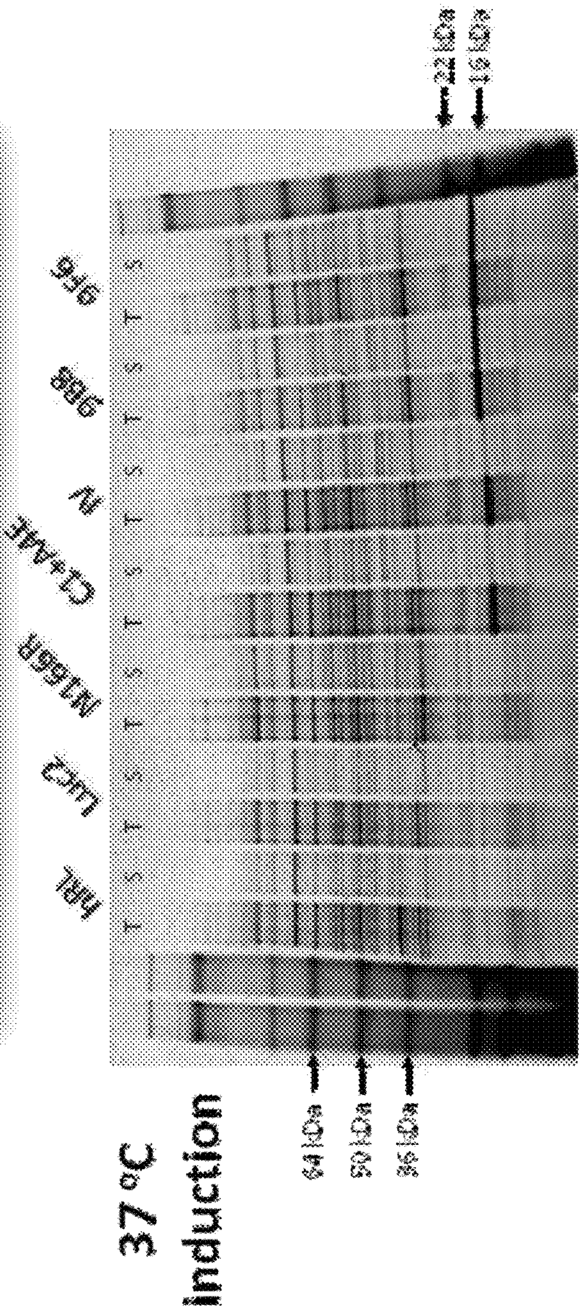

In addition to thermal stability, structural integrity determined by expression, stability, and solubility can also affect luminescence. As a way to further test the structural integrity of the improved variants, KRX *E. coli* harboring pF4Ag-based (i.e., no HT7) OgLuc variants N166R (previously described in U.S. Serial application Ser. No. 12/773,002 (U.S. Published Application No. 2010/0281552)), C1+A4E, IV, 9B8, and 9F6 were grown at 37° C. in Luria broth (LB) to an $OD_{600}$=0.6 and then induced for overexpression by the addition of rhamnose (0.2% final concentration). Duplicate induced cultures were then grown at either 25 or 37° C. for 17 hrs at which time total (T) and soluble (S) fractions were prepared and analyzed by SDS-PAGE using SIMPLYBLUE™ SafeStain (Invitrogen) to stain the gels (FIGS. 39A-B). hRL and Luc2 were used as controls.

The OgLuc variants, hRL and Luc2 expressed well and were soluble when the induction occurred at 25° C. (FIG. 39A; note the approximately 19 kDa dark band in the "soluble" fraction for the OgLuc variants, excluding the N166R variant, and the approximately 36 and 64 kDa bands in the "soluble" fraction for hRL and Luc2, respectively). In contrast, although C1+A4E, IV, 9B8, and 9F6 expressed well at 37° C. (significantly better than hRL or Luc2, as shown in the "total" fraction), only the 9B8 and 9F6 variants were soluble when the elevated induction temperature was employed (see FIG. 39B; note the approximately 19 kDa dark band in the "soluble" fraction for 9B8 and 9F6). These results tracked with the thermal stability data shown in Table 24 and FIG. 38.

C. 9B8 OPT AND 9B8 OPT+K33N

Figures 40A, 40B:
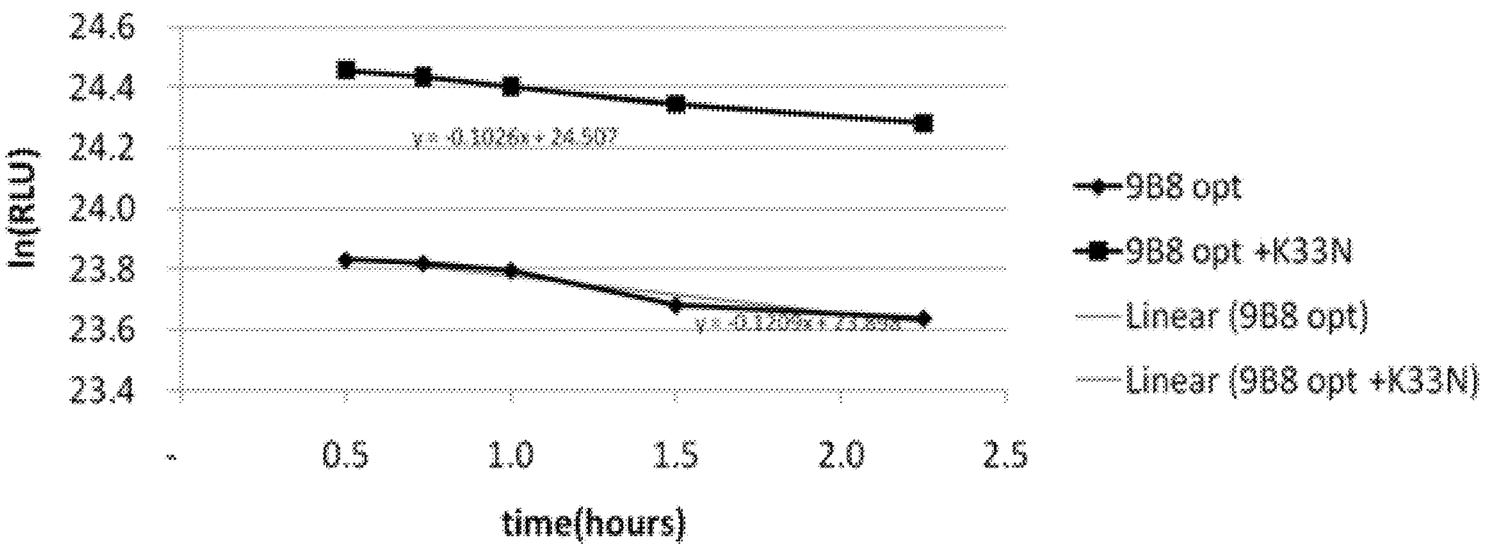
FIGS. 40A-B show the protein stability at 60° C. in bacterial lysates of 9B8 opt and 9B8 opt+K33N using the novel coelenterazine PBI-3939 as a substrate as the natural log (ln) of the luminescence (in RLU) over time (FIG. 40A) and as the half-life in hrs (FIG. 40B).

The thermal stability of the variants 9B8 opt and 9B8 opt+K33N was compared. *E. coli* lysates containing the variant 9B8 opt or 9B8 opt+K33N were prepared and analyzed as described previously with the following exceptions: Lysates were diluted 1:100 in the lysis buffer described previously and replicate diluted lysates were incubated at 60° C. in a thermocycler. Aliquots were removed at different time-points and placed on dry ice to freeze the samples. Frozen lysates were thawed at 22° C. and assayed with a buffer containing 20 mM CDTA, 150 mM KCl, 10 mM DTT, 20 μM PBI-3939, 100 mM HEPES pH 7.0, 35 mM thiourea, and 0.1% TERGITOL® NP-9 (v/v). Luminescence was measured on a GLOMAX® luminometer (Promega Corp.). FIG. 40A shows the light output time course of the natural logarithm (ln) value of luminescence measured in RLU overtime in min. As shown in FIG. 40B, 9B8 opt+K33N had a half-life at 60° C. of 6.8 hrs, which was longer than the 5.7 hrs half-life of 9B8 opt.

Table 25 shows the thermal stability at 60° C. ("$T_{1/2}$ (60° C.)") of 9B8 opt and 9B8 opt+K33N, and the luminescence ("RLU") data at the start of the incubation period (i.e., t=0). 9B8 opt+K33N was more stable and approximately 1.8-fold brighter than 9B8 opt, indicating that the amino acid substitution K33N provided both greater light output and higher thermal stability.

TABLE 25

Thermal Stability and Luminescence Data for 9B8 opt and 9B8 opt + K33N

| Variant | $T_{1/2}$ (60° C.) | RLU |
|---|---|---|
| 9B8 opt | 5.7 hrs | 23,283,252,000 |
| 9B8 opt + K33N | 6.8 hrs | 42,278,732,000 |

D. 9B8+K33N Variants

Figure 41:
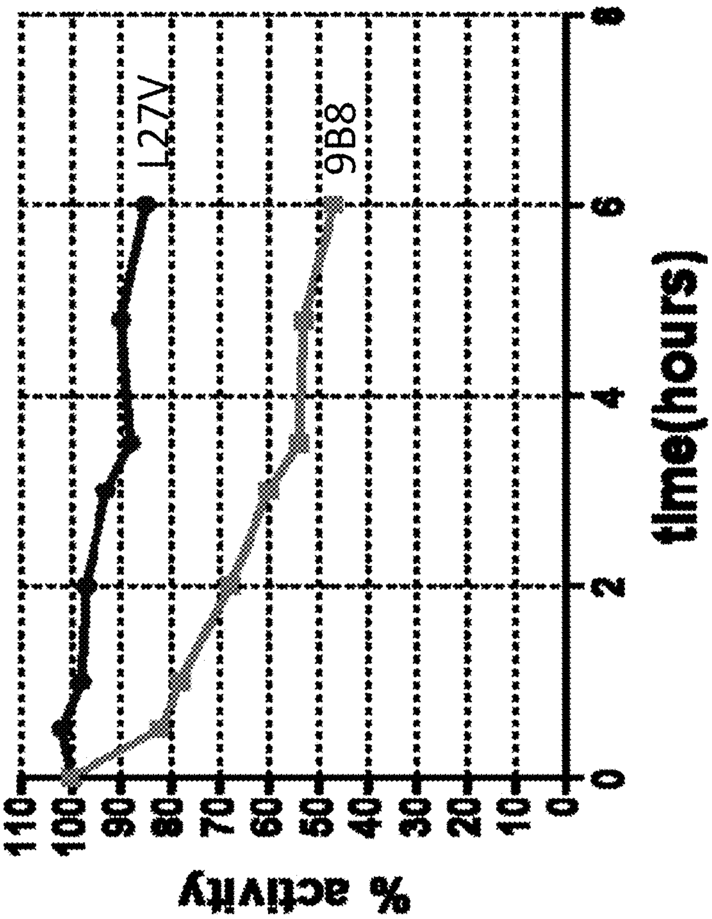
FIG. 41 shows the percent activity of the OgLuc variants 9B8 and L27V at 60° C.

The thermal stability of the variants at 60° C. was examined as described above, except the assay buffer contained 100 mM MES pH 6.0 instead of HEPES. Table 26 and FIG. 41 shows the half-life in hrs of the variants at 60° C. The data indicates that the amino acid substitution L27V improves thermal stability.

TABLE 26

Thermal stability of OgLuc variants at 60° C.

| Sample | ½ life hours |
|---|---|
| 9B8 | 5.1 |
| K33N | 6.7 |
| T39T, Y68D | 16.3 |
| T39T, L27V, K43R | 11.8 |
| L27V, T39T, K43R, Y68D | 21.7 |
| T39T, K43R, Y68D | 15.2 |
| L27V, T39T, K43R, S66N | 11.8 |
| L27V, K43R, Y68D | 23.2 |
| L27V, Y68D | 28.5 |
| L27V, K43R, S66N | 10.7 |

The variants 9B8 and V2 (9B8+K33N+T39T+K43R+Y68D) were also screened in HEK293 cells to determine their stability. The variants were cloned into pF4Ag and transfected into HEK293 cells (15,000 cells/well) as previously described. After transfection, the cells were lysed in assay reagent (as previously described; no PBI-3939), and luminescence measured using the assay reagent with 20 μM PBI-3939. 9B8 had a half-life of 5.2 hrs while V2 had a half-life of 16.8 hrs. This is consistent with the half-life seen for these variants in *E. coli* (Table 26).

E. L27V variant

Figure 42A:
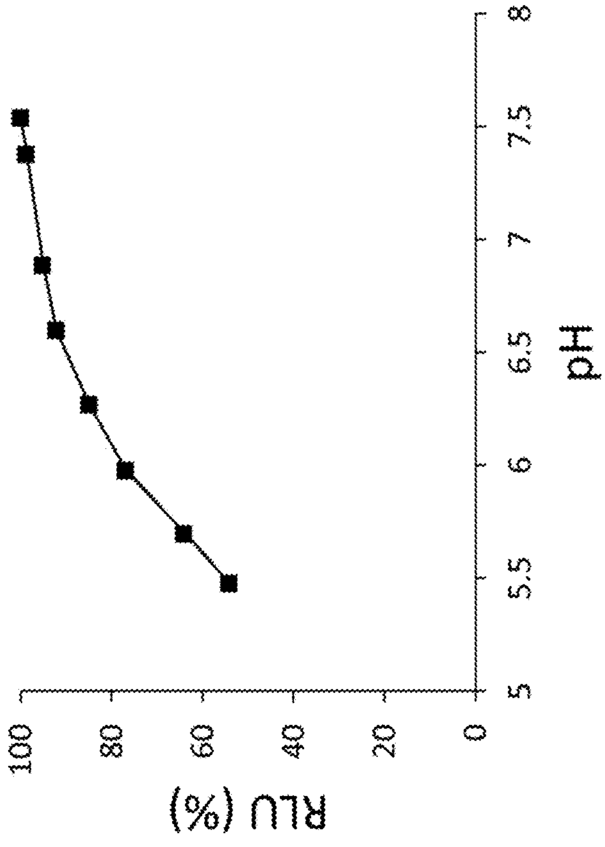
FIGS. 42A-B show the protein stability of the OgLuc variant L27V at various pH (FIG. 42A) and salt concentrations (FIG. 42B).
Figure 42B:
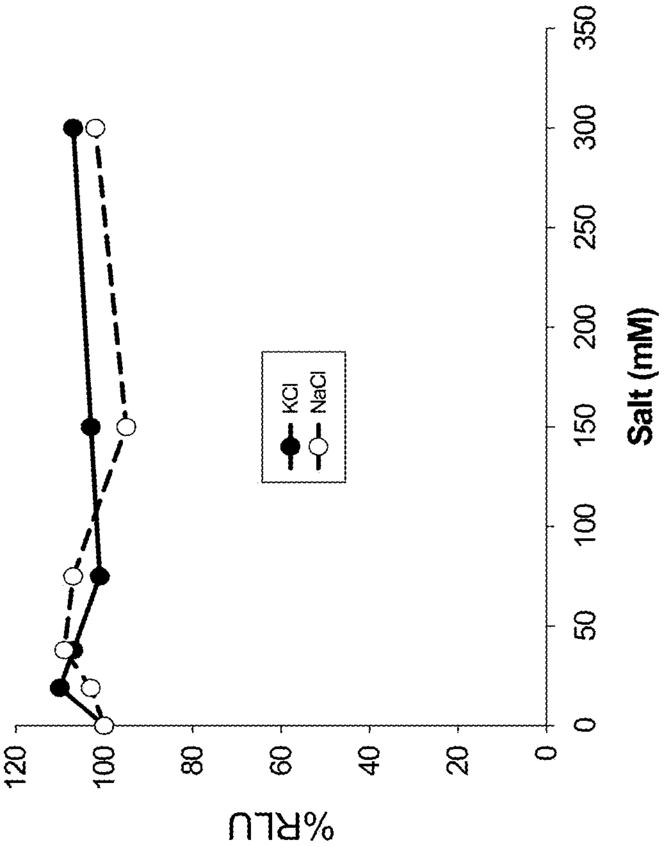

The activity of the L27V variant (9B8+K33N+L27V+T39T+K43R+Y68D) was assessed at various pHs and different salt conditions. 9B8 and 9B8+K33N were previously shown to have similar stability at pH 6 and pH 7 (data not shown). For assessing activity at various salt conditions, 50 μL of assay buffer with 20 μM PBI-3939 and varying amounts of KCl or NaCl was mixed with 50 μL of HEK293 cells transiently transfected with L27V (pF4Ag). Luminescence was measured, and the percent activity (the ratio of luminescence to no salt) determined (FIG. 42B). For assessing activity in various pHs, a reagent was made containing 100 mM citrate, 100 mM MES, 100 mM PIPES, 100 mM HEPES, 100 mM TAPS, 0.5% TERGITOL® NP-9 (v/v), 0.05% MAZU® DF 204, 1 mM CDTA, and 1 mM DTT titrated to various pH values. 362 μM L27V in assay reagent was mixed with substrate 100 μM PBI-3939 and luminescence was measured. (FIG. 42A).

Example 29—Gel Filtration Chromatographic Analysis of OgLuc Variants

A. C1+A4E and 9B8

Figure 43A:
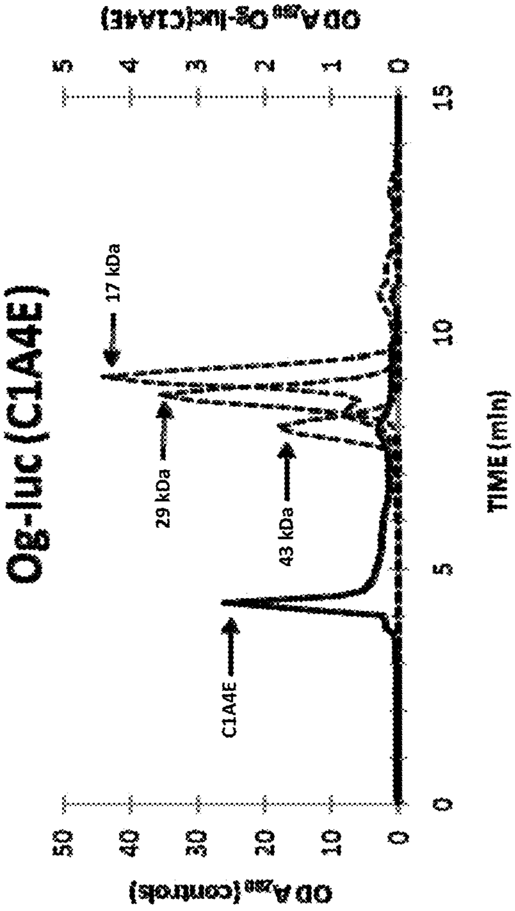
FIGS. 43A-B shows the gel filtration chromatographic analysis of purified C1+A4E (FIG. 43A) and 9B8 (FIG. 43B).
Figure 43B:
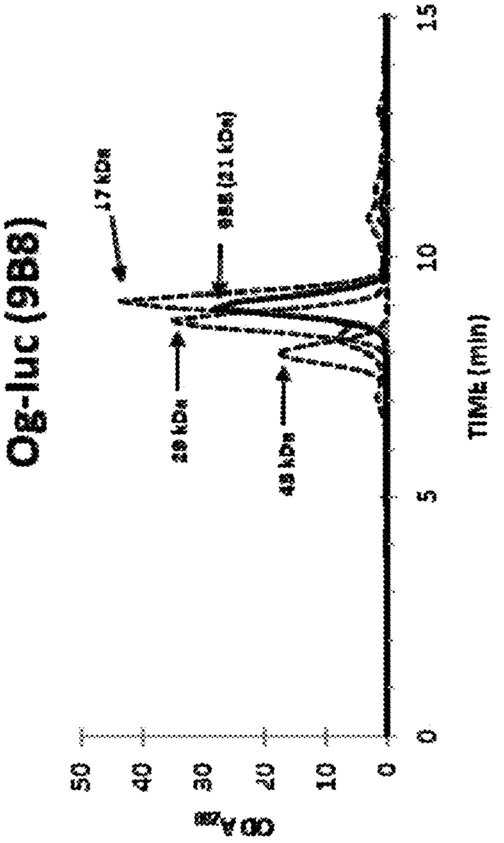

Gel filtration analysis was used to verify the expected molecular weight of the purified OgLuc proteins based on the theoretical values and consequently to determine their oligomeric state. A comparison between the relative hydrodynamic volume of the OgLuc variants C1+A4E and 9B8 was made by gel filtration chromatography. For this analysis, the nucleotide sequence for the OgLuc variants, C1+A4E and 9B8, were cloned into a HQ-Tagged FLEXI® Vector (Promega Corp.) to create a HQHQHQ N-terminally tagged protein that was overexpressed in *E. coli* KRX cells. The overexpressed proteins were purified using the HIS-LINK™ Protein Purification System (Promega Corp.) according to manufacturer's instructions. Samples of each individual standard and sample protein were analyzed by gel filtration chromatography, which was performed at 24° C. on an Agilent 1200 HPLC, using a Superdex 200 5/150 GL column (GE Healthcare) with a flow rate of 0.25 mL/min (FIGS. 43A-B). The mobile phase (i.e., running buffer) consisted of 50 mM Tris and 150 mM NaCl, pH 7.5. Protein elution was monitored at 214 and 280 nm. A standard calibration curve was generated using: 1) Ovalbumin, 43 kDa (GE Healthcare), 2) Carbonic Anhydrase, 29 kDa (Sigma) and 3) Myoglobin, 17 kDa (Horse Heart, Sigma). The molecular weights of the purified proteins were calculated directly from the calibration curve.

The relative elution of the proteins observed with this column was Ovalbumin at 7.98 min, Carbonic Anhydrase at 8.65 min, 9B8 at 8.97 min, and Myoglobin at 9.06 min (FIGS. 43A-B). As shown in FIG. 43B, 9B8 eluted as a 21 kDa protein (predicted MW is approximately 19 kDa) indicating that the 9B8 variant existed as a monomer, whereas C1+A4E eluted at approximately 4.3 min (FIG. 43A), indicating that C1+A4E was expressed and exists as multimer, e.g., possibly as a tetrameric complex or something larger.

B. L27V Variant

Figure 44:
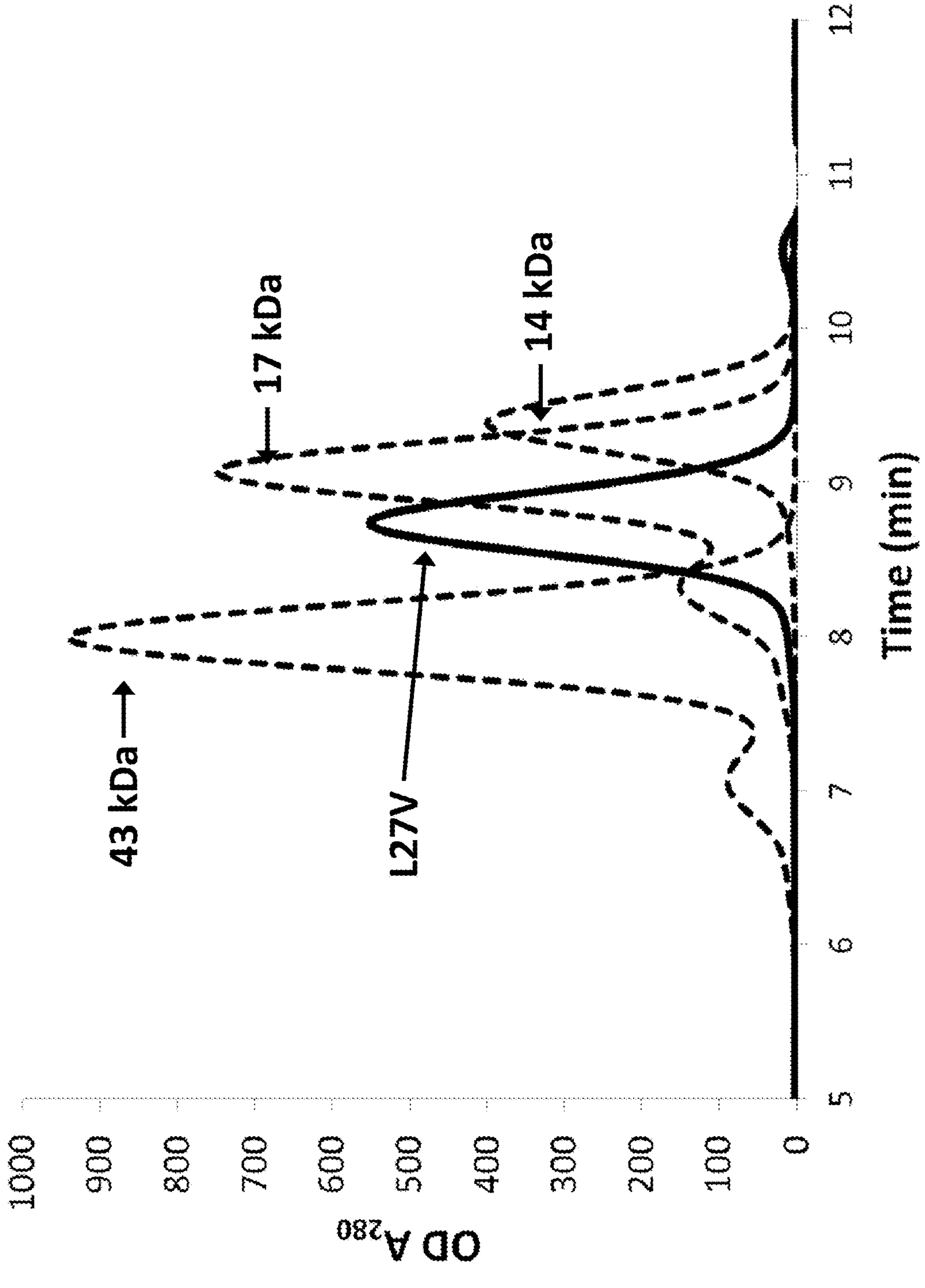
FIG. 44 shows the gel filtration chromatographic analysis demonstrating that the OgLuc variant L27V exists in a monomeric form.
Figure 56:
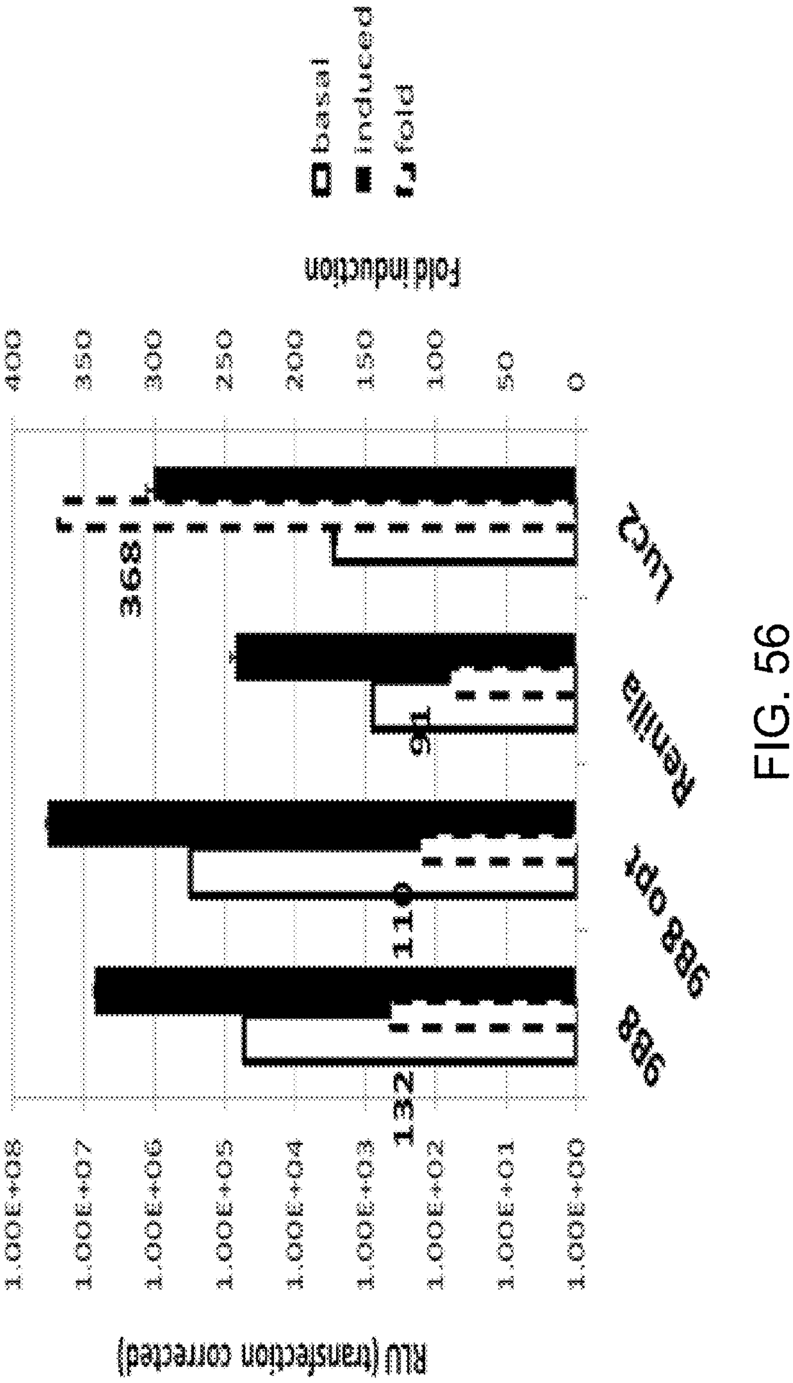
FIG. 56 shows the normalized luminescence generated from lysed HEK293 cells expressing the 9B8, 9B8 opt, hRL ("*Renilla*") or firefly luciferase ("Luc2") cAMP transcriptional reporter using PBI-3939 (for 9B8 and 9B8 opt), native coelenterazine (for hRL) or luciferin (BRIGHT-GLO™ Assay Reagent; for Luc2) as a substrate with ("+FSK") or without ("−FSK") forskolin treatment and the fold induction (response) due to forskolin treatment ("FOLD").

To demonstrate that the OgLuc variant L27V exists in a monomeric state, gel filtration analysis was used to verify the expected molecular weight of the purified L27V protein based on the theoretical value, and consequently to determine its oligomeric state. The relative hydrodynamic volume of the L27V variant was made by gel filtration chromatography. For this analysis, the nucleotide sequence for the L27V variant was cloned into a HaloTag® vector pFN18A (Promega Corp.) to create a HaloTag®-terminally tagged protein that was overexpressed in *E. coli* KRX cells (Promega Corp.). The overexpressed protein was purified using the HaloTag® Protein Purification System (Promega Corp.) according to manufacturer's instructions. Samples of each individual standard and sample protein were analyzed by gel filtration chromatography performed at 24° C. on an Agilent 1200 HPLC using a Superdex 200 5/150 GL column (GE Healthcare) with a flow rate of 0.25 mL/min (FIG. 56). The mobile phase (i.e., running buffer) consisted of 50 mM Tris and 150 mM NaCl, pH 7.5. Protein elution was monitored at 214 and 280 nm. A standard calibration curve was generated using: 1) Ovalbumin, 43 kDa (GE Healthcare), 2) Myoglobin, 17 kDa (Horse Heart, Sigma), and 3) Ribonuclease, 14 kDa (Bovine pancreas, GE Healthcare). As shown in FIG. 44, the L27V variant eluted as a 24 kDa protein (predicted MW is approximately 19 kDa) indicating that it existed as a monomer.

Example 30—Protein Expression Levels of OgLuc Variants

A. IV, 8A3, 8F2, 9B8, 9F6 and 15C

Figure 45B:
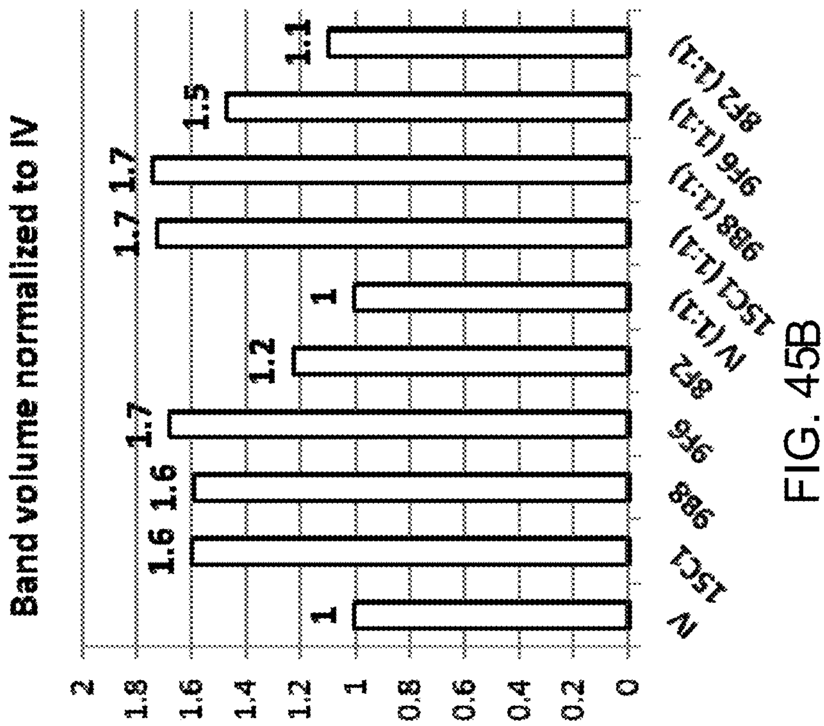
FIGS. 45A-B show the protein expression levels of various OgLuc variant-HALOTAG® (HT7) fusion proteins in undiluted and 1:1 diluted bacterial lysate samples analyzed by SDS-PAGE (FIG. 45A) and the normalized protein expression levels (FIG. 45B).
Figure 45A:
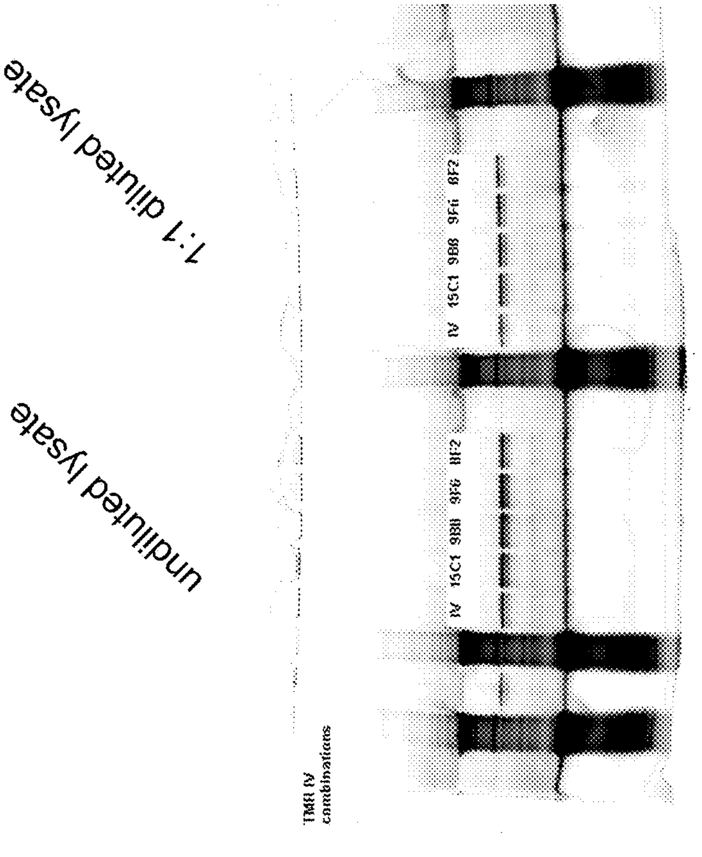

Normalizing for protein expression provides information about potential differences in specific activity. To provide a means for quantifying protein expression, OgLuc variants were cloned into a pF4Ag vector containing a C-terminal HT7 to generate OgLuc variant-HT7 fusion proteins as described previously. The following fusion proteins were generated: IV-HT7 (SEQ ID NOs: 48 and 49), 8A3-HT7 (SEQ ID NOs: 34 and 35), 8F2-HT7 (SEQ ID NOs: 50 and 51), 9B8-HT7 (SEQ ID NOs: 36 and 37), 9F6-HT7 (SEQ ID NOs: 38 and 39), and 15C1-HT7 (SEQ ID NOs: 52 and 53). *E. coli* containing the OgLuc variant-HT7 fusions were grown and induced as described previously. 900 μL of cell culture was lysed with 100 μL of 10× FASTBREAK™ Cell Lysis Reagent (Promega Corp.). HALOTAG® TMR-ligand (Promega Corp.) was added to each bacterial lysate sample to obtain a final concentration of 0.5 μM. Bacterial lysates were incubated with the HALOTAG® TMR-ligand for 30 min at room temperature according to manufacture's instructions. 10 μL of each sample was diluted 1:1 with 1× FASTBREAK™, i.e., 10 μL sample to 10 μL 1× FASTBREAK™. 15 μL of the lysate and 15 μL of the 1:1 dilution for each sample were analyzed by SDS PAGE. The labeled fusion proteins were resolved by SDS-PAGE, stained with SIMPLYBLUE™ SafeStain (FIG. 45A) and fluorimaged (GE Healthcare Typhoon). Bands were quantitated using Imagequant software (GE Healthcare). FIG. 45B shows the band volume measured from FIG. 45A for IV-HT7 ("IV"), 15C1-HT7 ("15C1"), 9B8-HT7 ("9B8"), 9F6-HT7 ("9F6"), and 8F2-HT7 ("8F2"), normalized to IV-HT7. The data shows that the IV variants expressed well compared to IV.

B. 9B8 opt, V2 and L27V

Figure 46A:
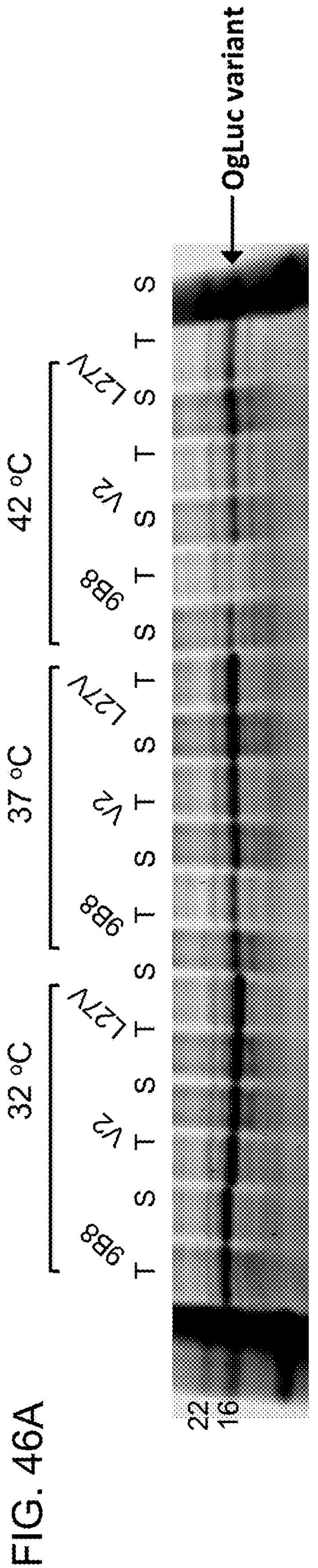
FIGS. 46A-B show the protein expression (FIG. 46A) and solubility of the OgLuc variants 9B8 opt, V2 and L27V (FIG. 46B).
Figure 46B:
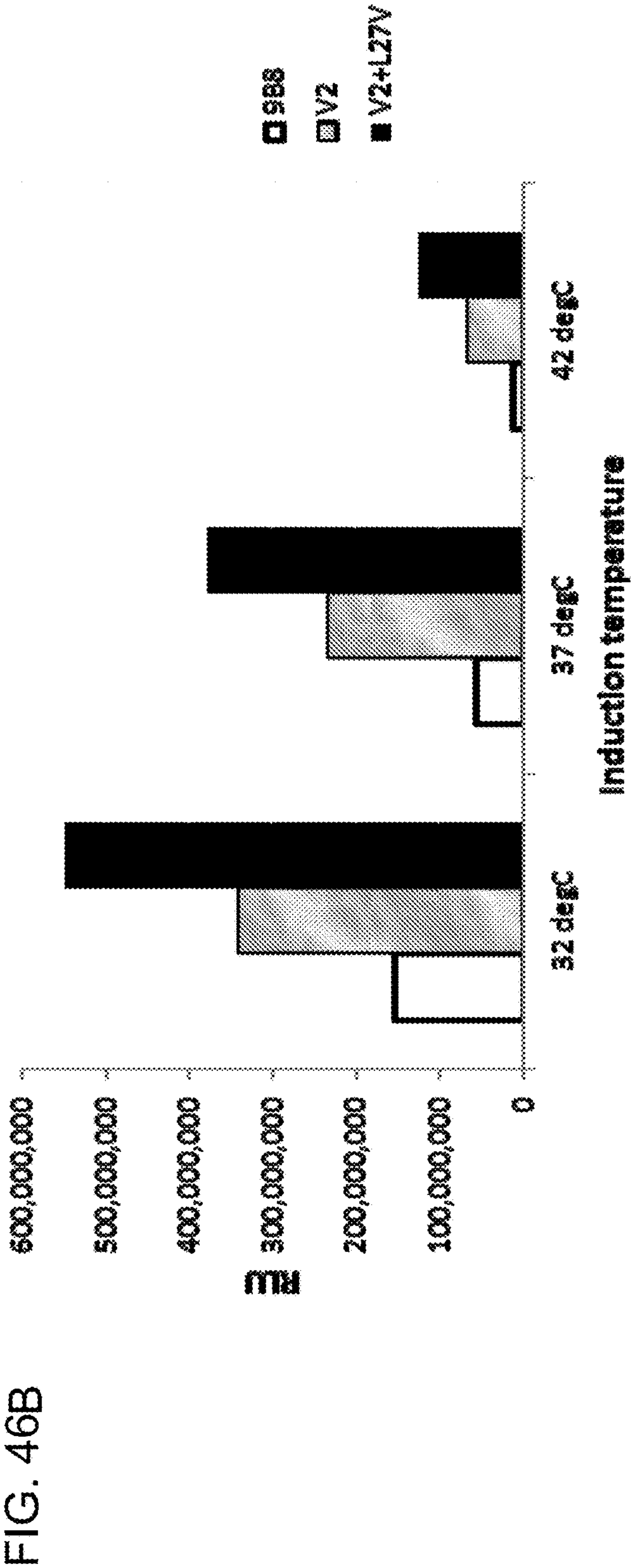

The expression levels and solubility of 9B8 opt, V2 and L27V were compared. These three variants, in the context of a pF4Ag background, were used to transform *E. coli* KRX cells. The resulting clones were used for an expression experiment where single colonies were grown overnight at 30° C., diluted 1:100 in LB, grown to an $OD_{600}$ approximately 0.5, and then induced with 0.2% rhamnose for 18 hrs at 25° C. Cells were then incubated for 30 min at room temperature in the presence of 0.5× FASTBREAK™ Lysis Reagent (Promega Corp.), and the resulting lysates stored at −20° C. Following a slow-thaw on ice, soluble fractions were prepared by high-speed centrifugation for 10 min at 4° C. Crude total (T) and soluble (S) fractions were then analyzed for expression levels using SDS-PAGE+Simply blue staining (FIG. 46A) as well as by measuring luminescence (FIG. 46B). For luminescence measurement, 50 μL of soluble lysates in 96-well microtiter plates were mixed with 50 μL assay reagent (previously described; 40 μM PBI-3939), and luminescence measured using a TECAN® INFINITE® F500 multi-detection plate reader. These results indicate that the ranking for these three variants, in terms of their expression levels and solubility, is L27V >V2 >9B8opt.

Example 31—Brightness of OgLuc Variants Expressed in Mammalian Cells

A. IV and 9B8

Figure 47:
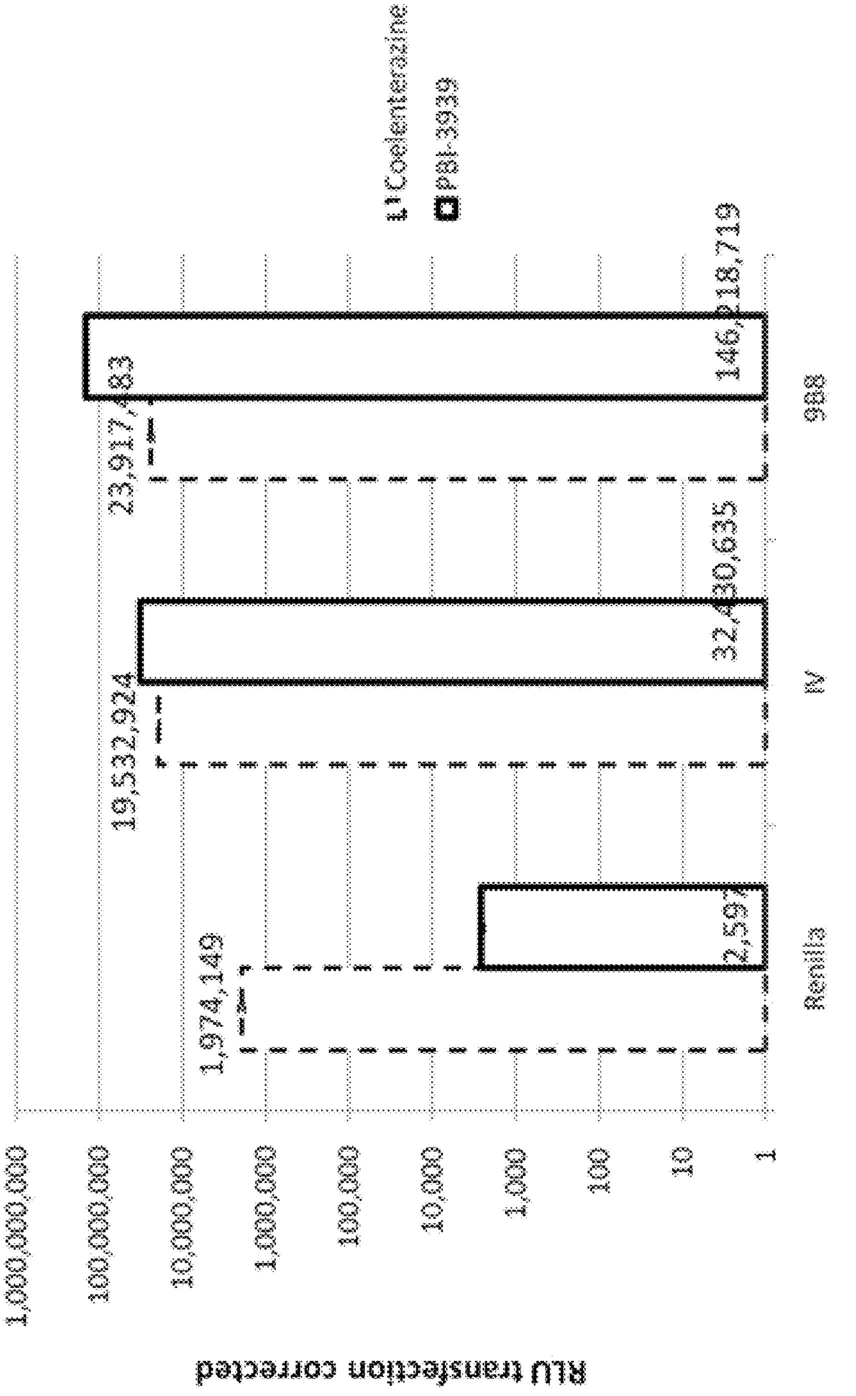
FIG. 47 shows the normalized luminescence in RLUs generated from lysed HEK293 cells expressing IV, 9B8, and hRL ("*Renilla*") using native coelenterazine and the novel coelenterazine PBI-3939 as substrates.

The IV and 9B8 variant in pF4Ag vector (i.e., no HT7) were evaluated for brightness in HEK293 cells. hRL was used as a control. Briefly, HEK293 cells, plated at 15,000 cells/well in a 96-well plate, were transiently transfected using TRANSIT®-LT1 with plasmid DNAs encoding the various variants and/or control sequences. Cells were grown, lysed, and treated as described in Example 25. Cells were co-transfected with pGL4.13 (Promega Corp.) as a transfection control (10 ng/transfection or 10% of the total DNA transfected was used). Luminescence was measured as described previously using native coelenterazine as a substrate for hRL or PBI-3939 as a substrate for the OgLuc variants. The OgLuc variant data was corrected for transfection efficiency using Luc2 luminescence (i.e., measuring luminescence after the addition of luciferin substrate). The OgLuc variants IV and 9B8 had greater luminescence compared to hRL ("*Renilla*") (FIG. 47).

For comparison of brightness on a per mole basis in mammalian cells, the C-terminal HT7 fusion protein of variant 9B8 ("pF4Ag-OgLuc-9B8-HT7") described in Example 30 was analyzed and compared with C-terminal HT7-hRL fusion protein ("pF4Ag-*Renilla*-HT7") and C-terminal HT7-Luc2 fusion protein ("pF4Ag-Luc2-HT7"). HEK293 cells (15,000) were plated and grown overnight at 37° C. These cells were transfected with 100 ng of DNA from pF4Ag-*Renilla*-HT7, pF4Ag-Luc2-HT7, or pF4Ag-OgLuc-9B8-HT7 and grown overnight at 37° C. Media was removed and cells were lysed as described previously. 10 μL of each sample was assayed for luminescence (RLU) with 50 μL BRIGHT-GLO™ for Luc2, 50 μL of 20 μM native coelenterazine for hRL, and 50 μL of 20 μM PBI-3939 for variant 9B8.

Figure 48:
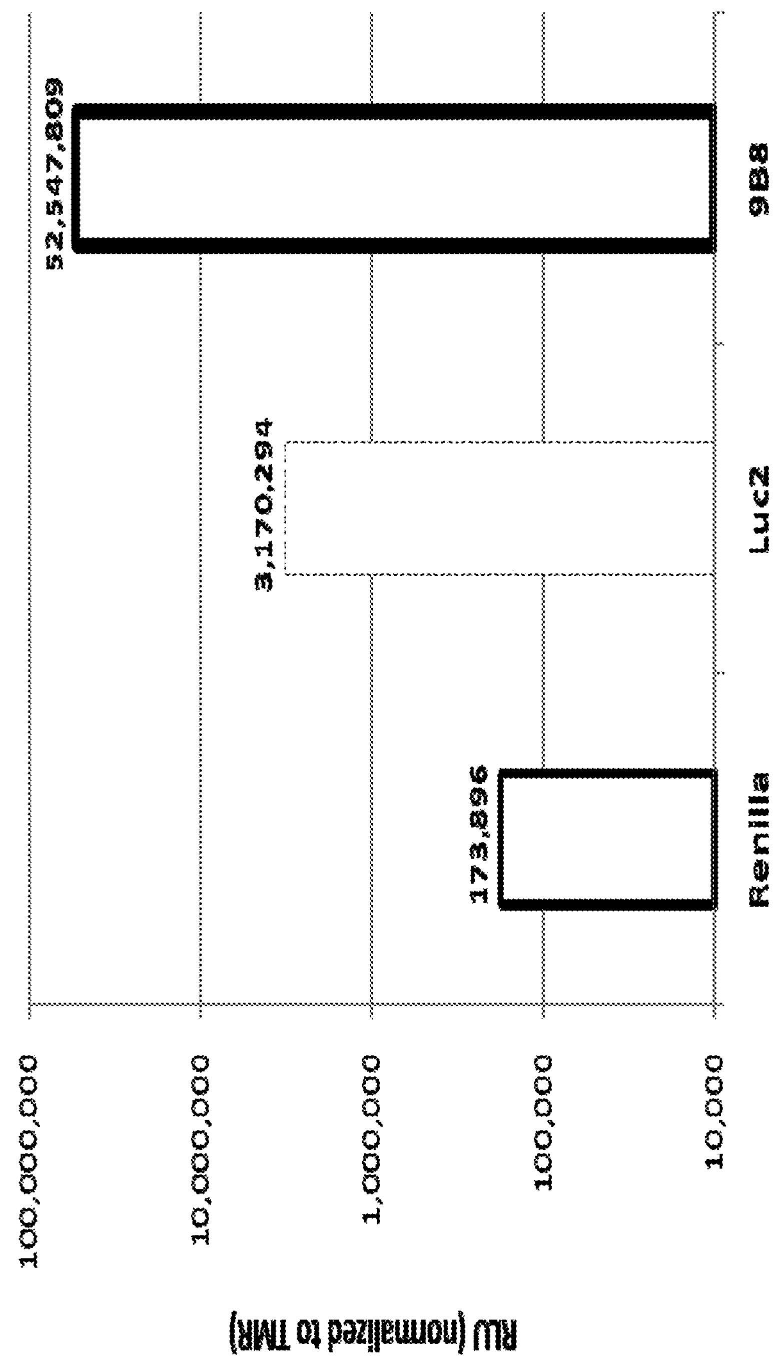
FIG. 48 shows the normalized luminescence in RLUs generated from lysed HEK293 cells expressing pF4Ag-Ogluc-9B8-HT7, pF4Ag-Luc2-HT7 and pF4Ag-*Renilla*-HT7 using PBI-3939, Luciferin (BRIGHT-GLO™ Assay Reagent), and native coelenterazine, respectively, as a substrate.

The lysates from 6 wells were pooled and labeled with HALOTAG® TMR-ligand as described in Example 30. The labeled fusion proteins were resolved by SDS-PAGE and fluorimaged (GE Healthcare Typhoon). The band densities were determined to quantitate the relative number of moles present for each luciferase enzyme and the RLU value for each sample was normalized by the calculated band density to normalize expression levels of each protein, i.e., RLUs normalized using TMR label quantitation (FIG. 48). On a mole-to-mole basis, the 9B8 variant was approximately 15-fold brighter than Luc2 and >100-fold brighter than hRL. This data represented differences in specific activity.

B. 9B8 opt and 9B8 opt+K33N

Figure 49:
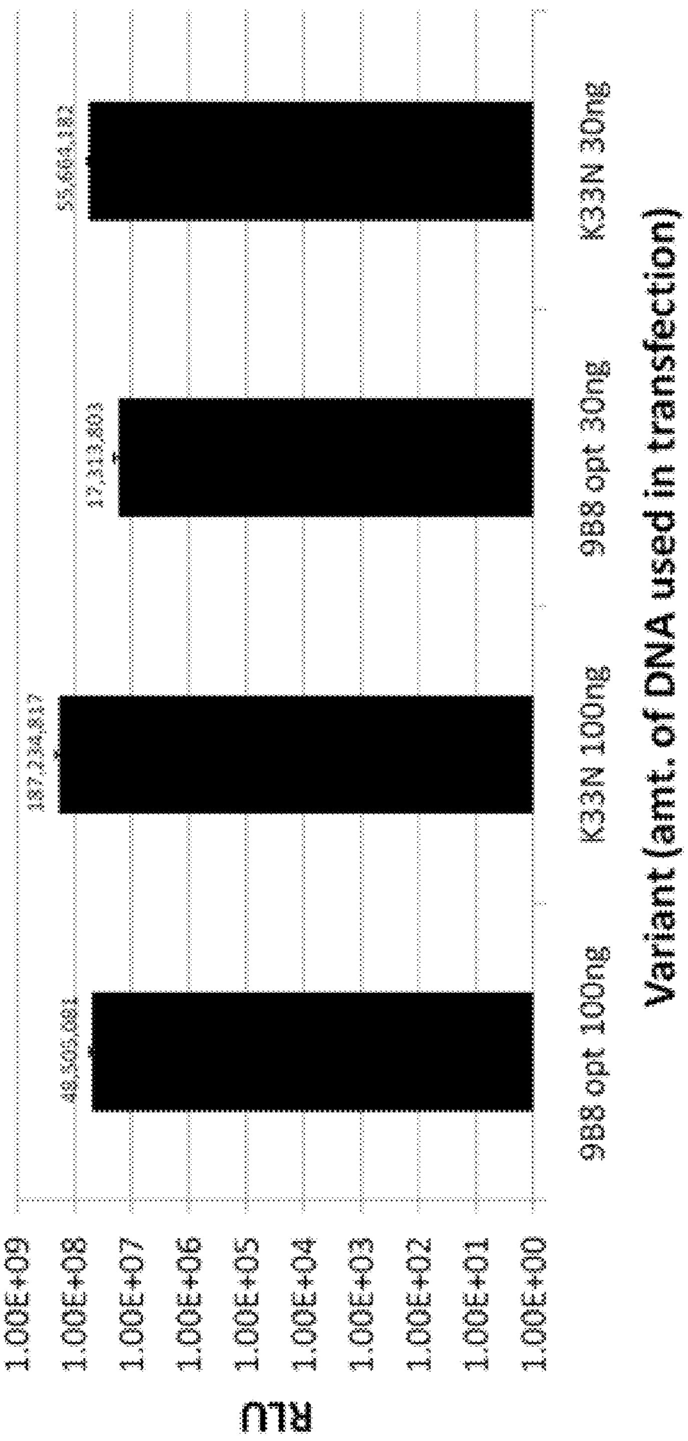
FIG. 49 shows the luminescence generated from lysed HEK293 cells expressing 30 or 100 ng of plasmid DNA encoding either 9B8 opt or 9B8 opt+K33N ("K33N") using the novel coelenterazine PBI-3939 as a substrate.

The brightness of the variants 9B8 opt and 9B8 opt+K33N expressed in HEK293 cells was measured and compared as described for the variants without the HT7 in Example 31. 30 and 100 ng of plasmid DNA containing the variant DNA was used to transfect HEK293 cells. Cells were grown and induced as described in Example 31 except the cells were lysed with a lysis buffer containing 1 mM CTDA, 150 mM KCl, 2 mM DTT, 100 mM MES pH 6.0, 35 mM thiourea, 0.25% TERGITOL® NP-9 (v/v), and 10 mg/mL 2-hydroxypropyl-β-cyclodextrin. The lysates were assayed with lysis buffer containing 20 μM PBI-3939 and luminescence was measured on a TECAN® GENIOS™ Pro luminometer. As shown in FIG. 49, 9B8 opt+K33N had greater luminescence compared to 9B8 opt in HEK293 cells, which tracks with the bacterial expression data in Table 25 and FIG. 29.

C. 9B8+K33N Variants

The brightness of the variants expressed in HEK293 and NIH3T3 cells was measured as described previously. The luminescence of the variants was normalized to the luminescence generated by 9B8 opt (Table 27).

TABLE 27

Increase in Luminescence generated by OgLuc combination variants in NIH3T3 and HEK293 cells

| Sample | HEK293 | NIH3T3 |
|---|---|---|
| 9B8 | 1.0 | 1.0 |
| K33N | 1.8 | 1.5 |
| T39T, Y68D | 1.9 | 1.5 |
| T39T, L27V, K43R | 1.3 | 0.9 |
| L27V, T39T, K43R, Y68D | 1.6 | 1.6 |
| T39T, K43R, Y68D | 1.9 | 1.9 |

TABLE 27-continued

Increase in Luminescence generated by OgLuc combination variants in NIH3T3 and HEK293 cells

| Sample | HEK293 | NIH3T3 |
|---|---|---|
| L27V, T39T, K43R, S66N | 1.3 | 1.2 |
| L27V, K43R, Y68D | 1.6 | 1.5 |
| L27V, Y68D | 1.7 | 1.4 |
| L27V, K43R, S66N | 1.2 | 1.0 |

D. L27V

A comparison of the luminescence of the L27V variant to firefly luciferase alone and as a fusion was performed. HEK293 and HeLa cells were plated at 15,000 and 10,000 cells/well, respectively, into wells of 12-well plates and incubated overnight at 37° C., 5% $CO_2$. The cells were then transfected with serial dilutions of pF4Ag containing L27V or Luc2. 20 ng of pGL4.13 (Promega Corp.) was co-transfected with L27V, and 20 ng of pGL4.73 (Promega Corp.) was co-transfected with Luc2 to act as carrier DNA for lower dilutions of the L27V or Luc2 plasmid DNA. The plasmid DNA was then transfected into the cells (6 replicates for each dilution for each cell type) using TRANSIT®-LTI transfection reagent according to the manufacturer's instructions. The cells were then incubated for 24 hrs at 37° C., 5% $CO_2$.

Figures 50A, 50B:
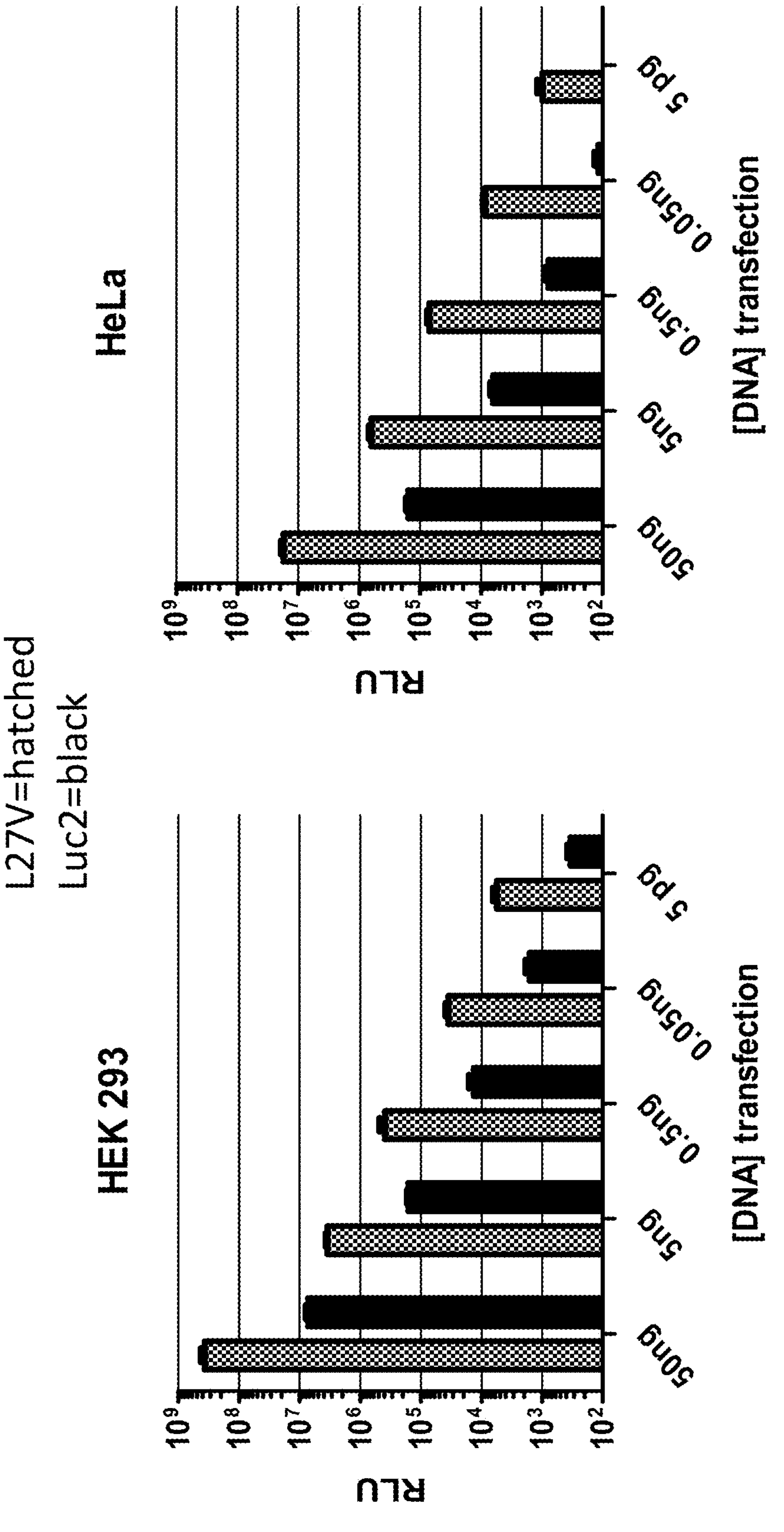
FIGS. 50A-E show the luminescence of the OgLuc variant L27V compared to firefly luciferase (Luc2) in HEK 293 (FIG. 50A) and HeLa cells (non-fusion) (FIG. 50B), the luminescence of HaloTag® fusion compared to the OgLuc variant L27V (FIG. 50C) and firefly luciferase (Luc2) (FIG. 50D), and the protein expression of HaloTag®-OgLuc L27V compared to HaloTag®-Firefly luciferase (Luc2) in HEK 293 ("HEK") and HeLa cells ("HeLa").

After transfection, the media was removed from the cells, and 100 μL PBS with 0.5% TERGITOL® NP-9 (v/v) added and shaken for 10 min at room temperature. 10 μL of each cell lysate was assayed using ONE-GLO™ Luciferase Assay System (Promega Corp.; Luc2) or assay reagent (Example 22H with 20 μM PBI-3939; OgLuc). Luminescence was measured as previously described for the HEK293 (FIG. 50A) and HeLa cells (FIG. 50B).

Figure 50D:
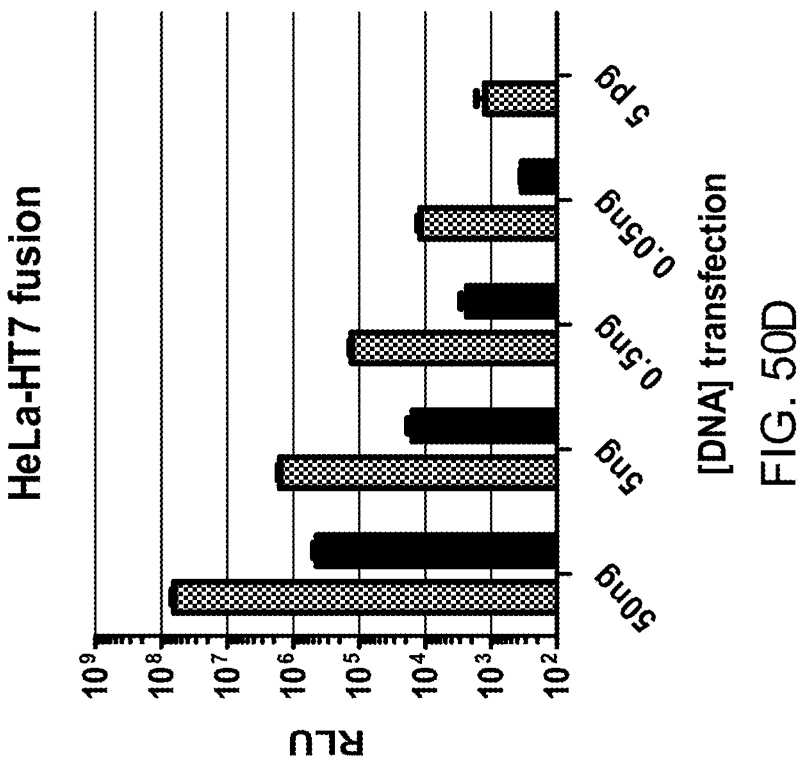
Figure 50C:
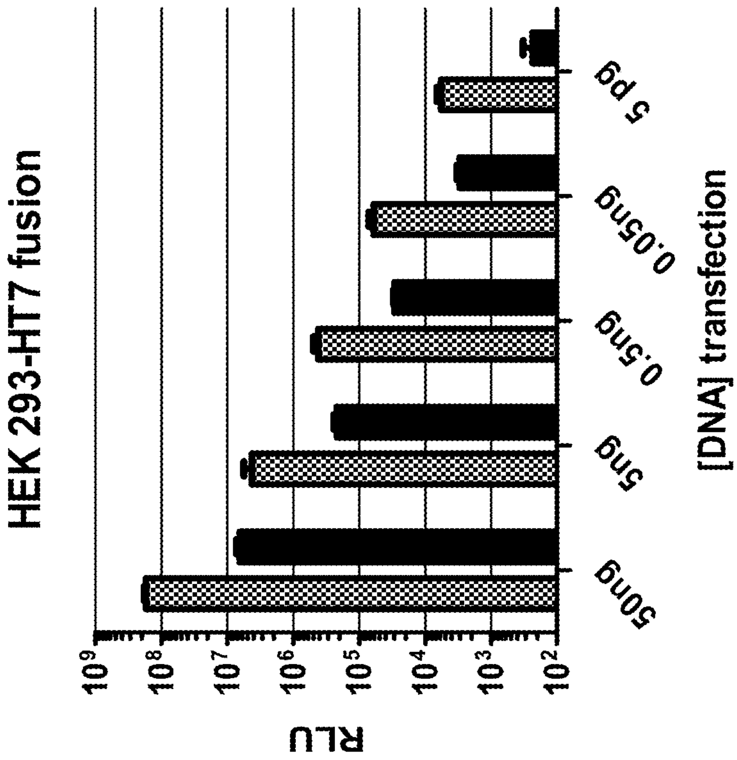

Comparison of L27V and Luc2 as fusion partners was performed as described above. L27V and Luc2 were fused to HALOTAG® protein in pF4Ag. FIGS. 50C-D show the luminescence measured with the different fusions in HEK293 (FIG. 50C) and HeLa cells (FIG. 50D).

Figure 50E:
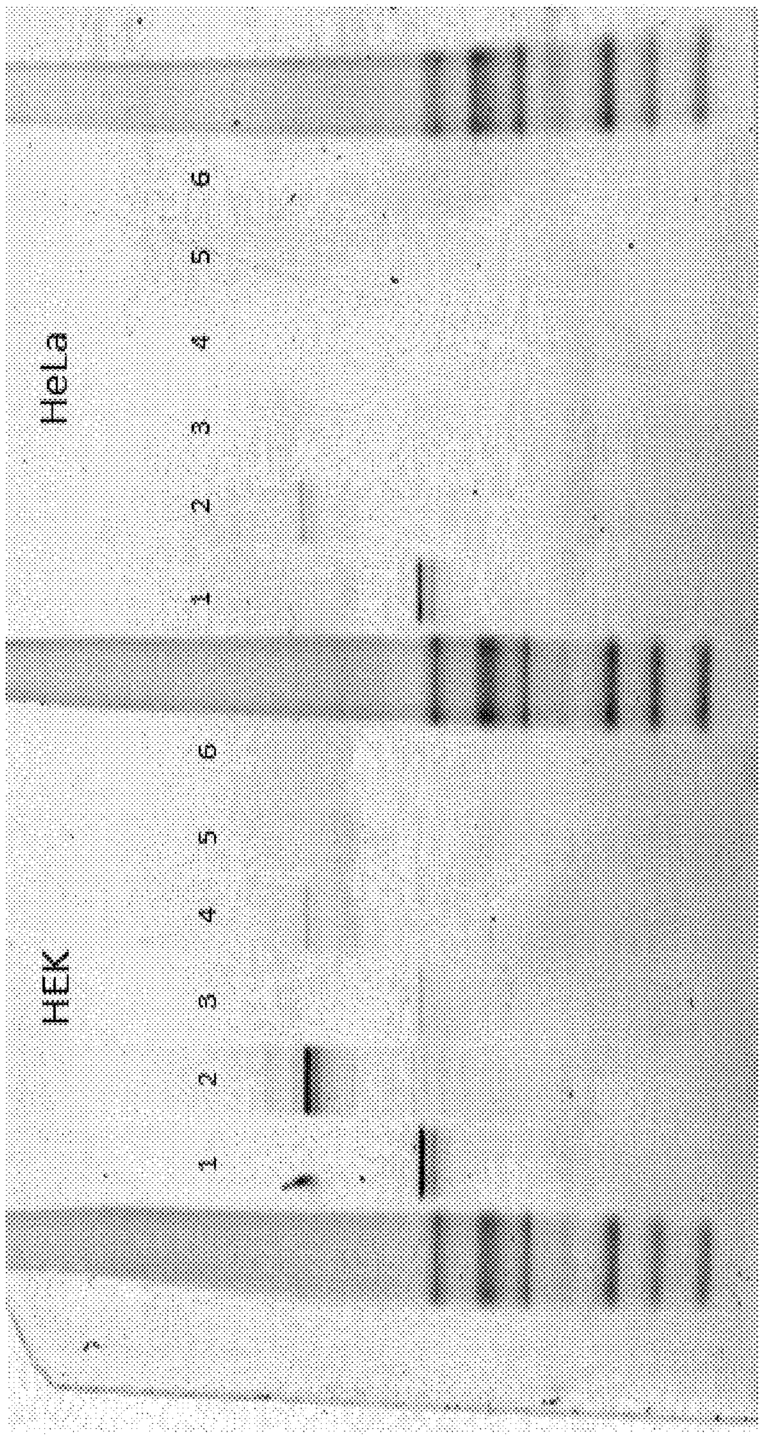

In addition to measuring luminescence, protein expression was also analyzed. The transfection was performed as described above. After transfection, the media was removed from the cells, and the cells washed in 1×PBS. 100 μL 0.1×Mammalian Lysis Buffer (Promega Corp.) containing 1 μM HALOTAG® TMR ligand (Promega Corp.) and 20 U DNase I was added, and the cells incubated with slow shaking for 45 min at room temperature. The cell samples were then frozen at −20° C. For protein analysis, 32.5 μL 4×SDS loading dye was added to each sample, and the samples heated at 95° C. for 2 min. 10 μL of sample was then loaded onto an SDS-PAGE gel and imaged on a Typhoon Scanner as previously described (FIG. 50E).

Example 32—Brightness of Purified OgLuc Variant Compared to Firefly Luciferase The 9B8 OgLuc variant was overexpressed and purified as described in Example 33. Reactions between diluted enzyme and substrate were performed using the following 2×buffer/assay reagent: 100 mM MES pH 6.0, 1 mM CDTA, 150 mM KCl, 35 mM thiourea, 2 mM DTT, 0.25% TERGITOL® NP-9 (v/v), 0.025% MAZU® DF 204, 10 mg/mL 2-hydroxy-β-cyclodextrin, and 20 μM PBI-3939. The final assay concentrations of purified enzyme and substrate were 0.5 μM and 10 μM, respectively. In parallel, reactions between diluted purified firefly luciferase (i.e., QUANTI- LUM® Recombinant Luciferase (Promega Corp.)) and luciferin were analyzed. The assay buffer/reagent for the firefly luciferase reaction was BRIGHT-GLO™ and the final assay concentrations were 0.5 μM enzyme and 500 μM luciferin. As the buffers/reagents for each reaction were known to provide "glow" kinetics, a 15 min time point was used to collect luminescence data. The results from this experiment showed that 9B8 opt using PBI-3939 (19,200 RLU) was approximately 8-fold brighter than QUANTI-LUM® Recombinant Luciferase with BRIGHT-GLO™ (2,300 RLU).

Example 33—Inhibition Analysis

To determine the susceptibility of the OgLuc variants to off-target interactions, the activity of the 9B8 and L27V variants was screened against a LOPAC (library of pharmacologically active compounds) library. A LOPAC 1280 library (Sigma) was prepared by diluting the compounds to 1 mM in DMSO. On the day of the assay, the compounds were diluted to 20 μM in 1×PBS, and 10 μL transferred to a 96-well, white plate. To each well, 10 μL of purified 9B8, L27V or firefly luciferase (Luc2) enzyme diluted $10^{-4}$ in Glo Lysis Buffer (Promega Corp.) was added and incubated at room temperature for 2 min. To the samples, 20 μL assay reagent (1 mM CDTA, 150 mM KCl, 2 mM DTT, 100 mM MES pH 6.0, 35 mM Thiourea, 0.5% TERGITOL® NP-9 (v/v) and 60 μM PBI-3939) was added, incubated for 3 min, and luminescence measured on a TECAN® GENIOS™ Pro Luminometer. For assaying firefly luciferase, the BRIGHT-GLO™ Assay reagent (Promega Corp.) was used according to the manufacturer's protocol. As a negative control, 8 wells of each plate contained 1×PBS+2% glycerol. As a positive control, 8 wells of each plate contained 2 mM Suramin in 2% DMSO or 2 mM luciferase inhibitor 1 in 2% DMSO (Calbiochem). Suramin was identified in the preliminary screen of the LOPAC library (i.e., the LOPAC library was screened using the 9B8 variant with a lower substrate concentration of 20 μM) to be an inhibitor of OgLuc.

Figure 51:
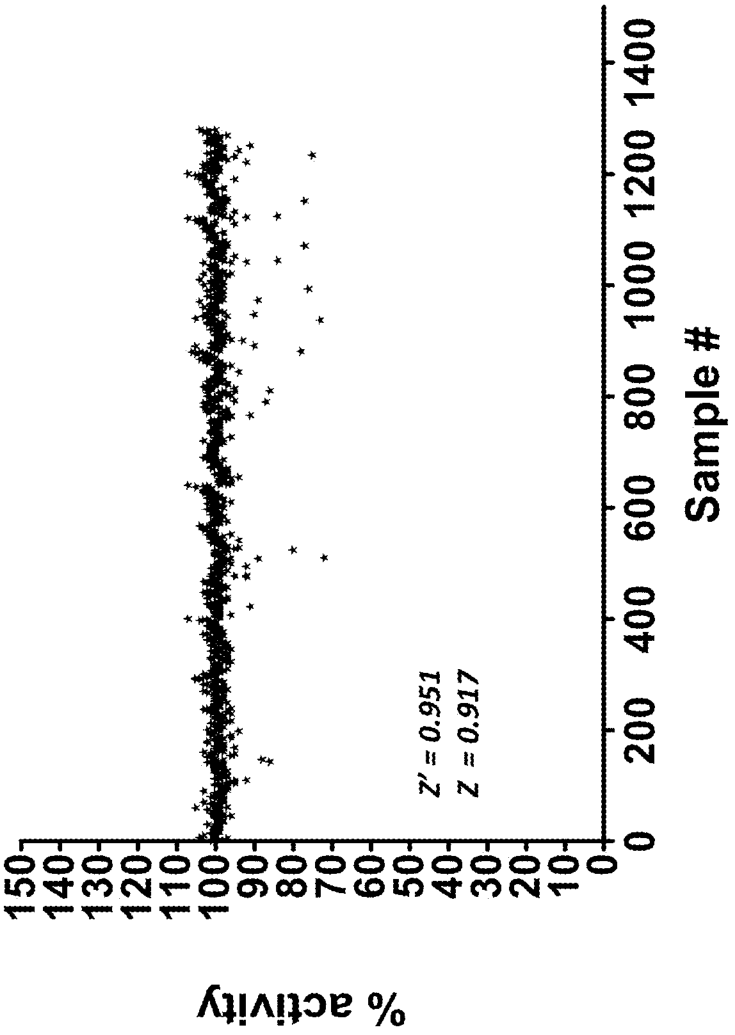
FIG. 51 shows inhibition analysis of the OgLuc variants 9B8 and L27V against a LOPAC library to determine their susceptibility to off-target interactions.

The results in FIG. 51 indicate a general low frequency of off-target interactions between the compounds in the LOPAC library and L27V. This suggests a potential use for L27V as a screening tool for large libraries of diverse chemicals and therapeutic candidates, including live cell-based formats (e.g., high-throughput screening).

To further examine inhibition resistance, purified 9B8 and L27V were screened against various concentrations of Suramin (Sigma S-2671) and Tyrphostin AG 835 ("Tyr ag 835") (Sigma T-5568) (FIGS. 52A-C). FIGS. 52E-D show the chemical structures for Suramin and Tyr ag 835, respectively. Purified 9B8 and L27V were prepared as described above. Serial dilutions (0, 2 μM, 6 μM, 20 μM, 60 μM, 200 μM and 2 mM) of the inhibitors were prepared in 1×PBS with 2% DMSO. To wells of a 96-well, white assay plate, 10 μL of diluted enzyme and 10 μL of diluted inhibitor were added and incubated at room temperature for 2 min. 20 μL assay reagent (described above) was added, and luminescence measured on a GLOMAX®-96 luminometer (FIGS. 52A-C). FIGS. 52A-B show the dose response curves of 9B8 and L27V to Suramin (FIG. 52A) and Tyr ag 835 (FIG. 52B). FIG. 52C shows the half maximal inhibitory concentration ($IC_{50}$) of Suramin and Tyr ag 835 for 9B8 and L27V. The data indicates that L27V is a robust reporter that could be used as a screening tool for large libraries of diverse chemicals and/or therapeutic candidates.

Example 34—Resistance to Non-specific Protein Interactions

1. Purified 9B8 and L27V enzyme were serial diluted in 1:10 in buffer (1×PBS, 1 mM DTT, and 0.005% IGEPAL® CA-630) with or without 0.5 mg/mL BSA (4 sets of each dilution) to 200 μL into PCR strip tubes. The samples were incubated at 60° C. wherein at 0, 2, 4, and 6 hrs one set of dilutions for each variant was transferred to −70° C.

Figure 53:
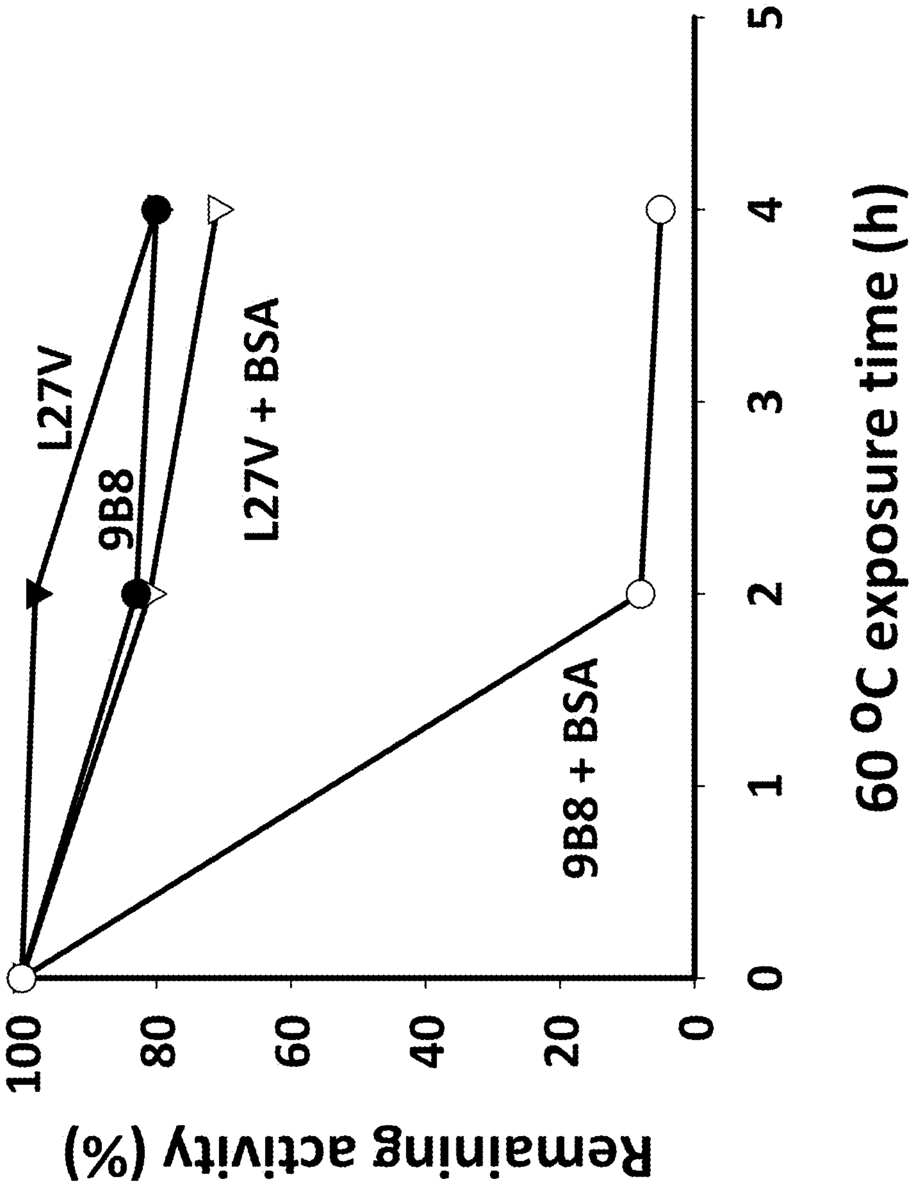
FIG. 53 shows the activity of the OgLuc variants 9B8 and L27V was analyzed in the presence of BSA to determine resistance to non-specific protein interactions.

To analyze activity, the samples were thawed to room temperature in a water bath. 50 μL assay reagent (as previously described with 100 μM PBI-3939) was added, and luminescence measured for each minute for 30 min on a TECAN® INFINITE® F500 plate reader. Activity was calculated using the average luminescence of the $1\times10^6$ and $1\times10^7$ dilutions (FIG. 53).

2. To demonstrate the reactivity of the OgLuc variants to plastic, purified 9B8 and L27V were exposed to polystyrene plates, and their activity measured.

Figure 54:
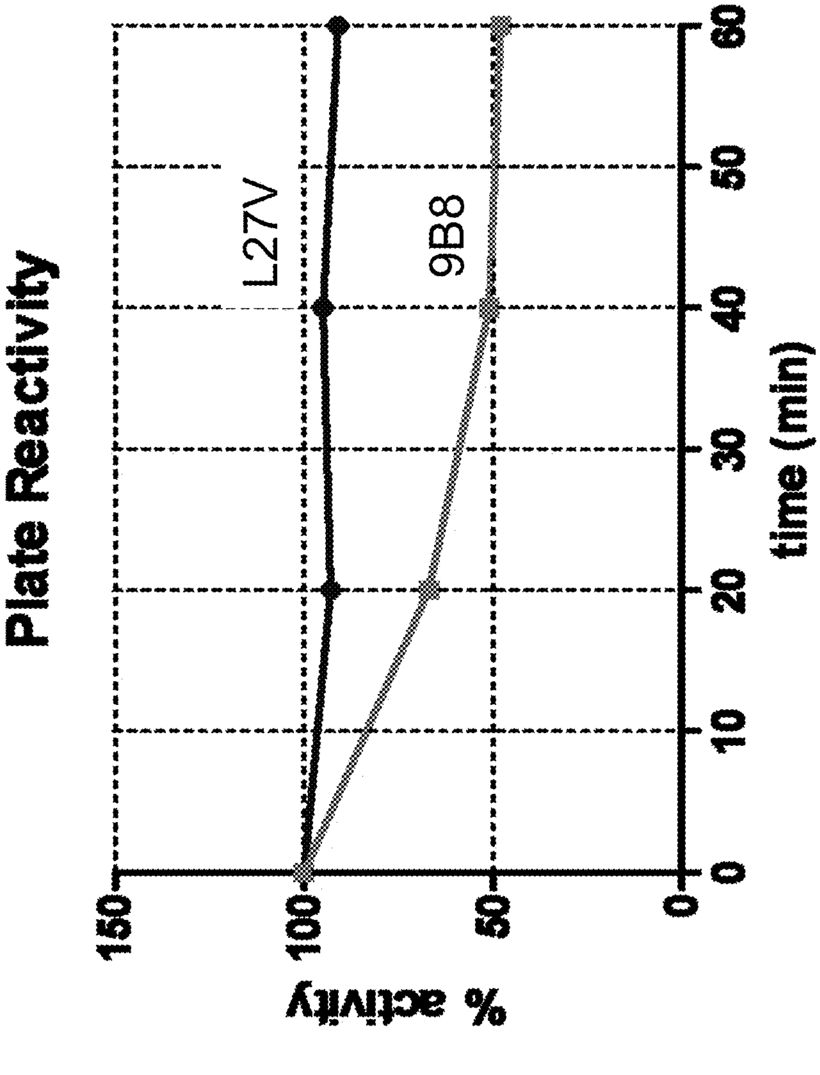
FIG. 54 shows the percent activity of the OgLuc variants 9B8 and L27V to determine reactivity to plastic.

50 μL purified 9B8 (45.3 μM) and L27V (85.9 μM) in DMEM without phenol red with 0.1% PRIONEX® was placed into wells of a 96-well, polystyrene microtiter plate at 60, 40, 20 and 0 min. To the samples, 50 μL assay reagent (described above) containing 20 μM PBI-3939 was added and incubated for 5 min at room temperature. Luminescence was measured as previously described, and percent activity determined (FIG. 54; ratio of luminescence to time 0).

Example 35—Post Translational Modification

To determine if the OgLuc variants undergo any post translation modifications when expressed in mammalian cells, the 9B8 and L27V variants were expressed in both mammalian cells and *E. coli* and analyzed via mass spectrometry (MS).

9B8 and L27V variants were expressed as N-terminal HALOTAG® fusions (pFN18K for *E. coli*; pFN21K for HEK293 cells) in HEK293 and *E. coli* KRX (Promega Corp.) cells and purified using the HALOTAG® Protein Purification System (Promega Corp.) according to the manufacture's instructions. Approximately 5 pmols of purified enzyme was analyzed via LC/MS using a C4 column (Waters Xbridge BEH300, 3.5 μm) interfaced to an LTQ Orbitrap Velos mass spectrometer (Thermo Scientific). Data was acquired from 600-2000 m/z using the LTQ for detection and processed using the MagTran v1.03 software (Zhang et al., *J. Am. Soc. Mass Spectrom.,* 9:225-233 (1998)). Both purified enzymes had an experimentally determined mass of 19,666 Da, compared to a calculated mass of an un-modified OgLuc variant, i.e., absent of any post translational modifications, of 19,665 Da.

Example 36—Evaluation of OgLuc Variants as a Transcriptional Reporter

A. IV

The use of the OgLuc variants as a transcriptional reporter was examined. To generate a transcriptional reporter of cAMP, hRL and IV were sub-cloned using methods known in the art into a modified pGL4 vector (Promega Corp.) containing a barnase sequence, which was replaced by the DNA fragment of interest. The leader sequence of the modified pGL4 contained a minimal promoter and a cAMP-response element (CRE; SEQ ID NO: 96), so that upon stimulation with a cAMP agonist such as forskolin (FSK), cells accumulating cAMP activated the reporter and generated luminescence. In this experiment, 2 ng DNA of either the hRL or IV transcriptional reporter construct was used to transfect HEK293 cells as described in Example 25. At 24 hrs post transfection, the cells were treated with 100 μM FSK. Cells that were not treated with FSK were used as a control. After 6 hrs, a reporter reagent was added to treated and control cells. For hRL, the reporter reagent was *Renilla*-Glo™ reagent (Promega Corp.). For IV, the reporter reagent contained 1 mM CDTA pH 5.5, 150 mM KCl, 10 mM DTT, 0.5% TERGITOL® NP-9 (v/v), 20 μM coelenterazine-h, and 150 mM thiourea. After 10 min, luminescence was read on a Varioskan® Flash (Thermo Scientific).

Figure 55:
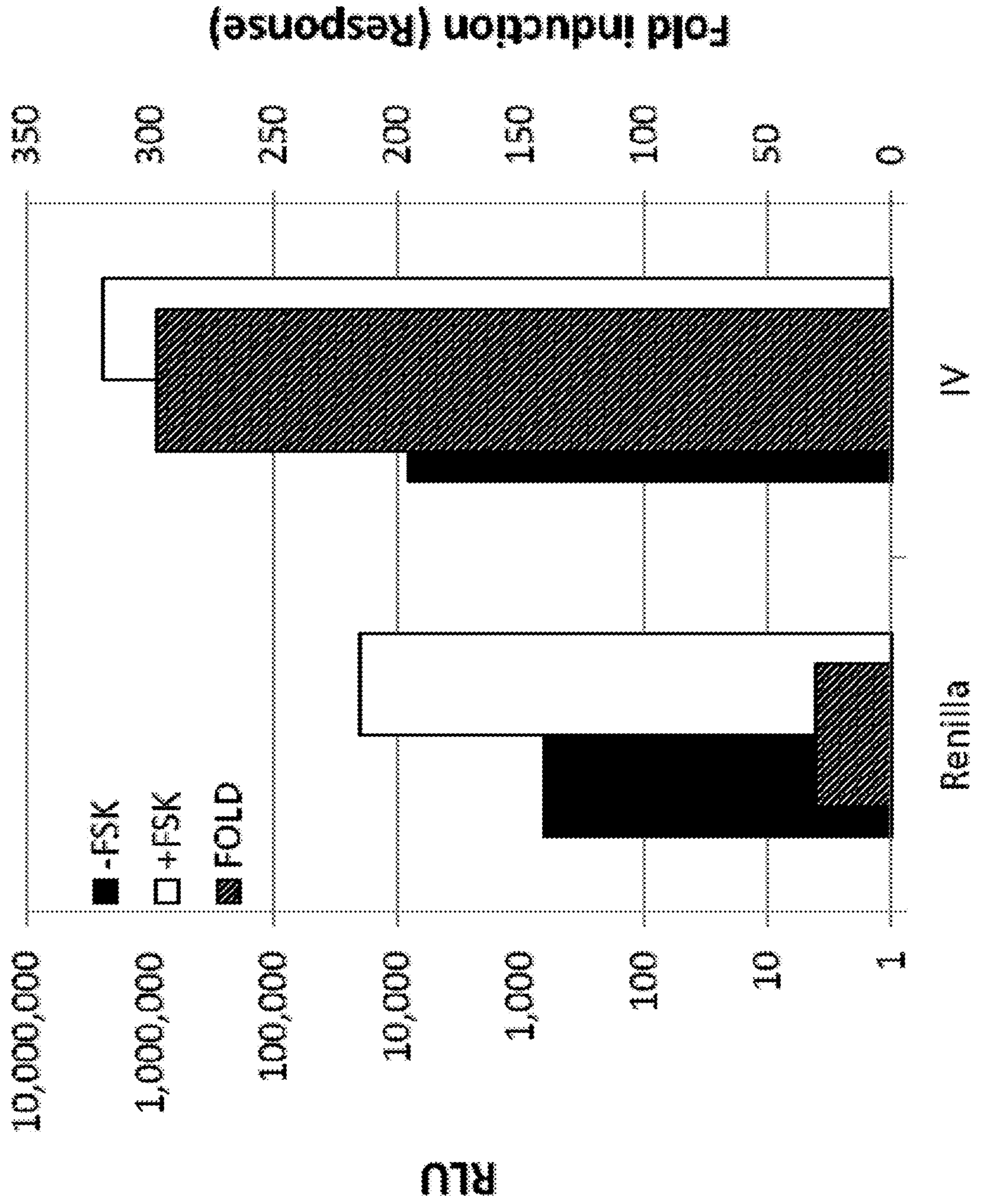
FIG. 55 shows the luminescence generated from lysed HEK293 cells expressing the IV cAMP transcriptional reporter compared to hRL ("*Renilla*") using known coelenterazine-h as a substrate with ("induced") or without ("basal") forskolin treatment and the fold induction (response) due to forskolin treatment ("fold").

FIG. 55 shows the normalized luminescence of HEK293 cells containing the hRL ("*Renilla*") or IV transcriptional reporter treated ("+FSK") or not treated ("−FSK") with FSK. The response, i.e., fold-induction or fold-increase ("FOLD") in luminescence was determined by dividing the luminescence from the treated cells (+FSK) with the luminescence from the control cells (−FSK). As shown in FIG. 55, the response for hRL was <50, while for IV it was >300, demonstrating the use of IV as a transcriptional reporter.

B. 9B8 and 9B8 opt

The use of variants 9B8 and 9B8 opt as a transcriptional reporter was also examined and compared to hRL and Luc2 transcriptional reporters as previously described for the IV transcriptional reporter with the following modifications. Transcriptional reporters of cAMP containing either variants 9B8 or 9B8 opt were generated as described above. After 6 hrs of FSK induction, the media was removed from the cells and replaced with 100 μL of the lysis buffer described in Example 25 creating a lysate. The lysate of transfected cells treated with or without FSK were assayed for luminescence as described in Example 25. 10 μL of the Luc2 lysate was assayed with 50 μL of BRIGHT-GLO™ Luciferase Assay Reagent. 10 μL of the hRL lysate was assayed with 50 μL of lysis buffer containing 20 μM native coelenterazine. 10 μL of the variants 9B8 and 9B8 opt lysates were assayed with 50 μL of lysis buffer containing 20 μM PBI-3939.

FIG. 56 shows the normalized luminescence of HEK293 cells containing the 9B8, 9B8 opt, hRL, or Luc2 transcriptional reporter treated ("induced") or not treated ("basal") with FSK. The response, i.e., fold-induction or fold-increase ("fold") in luminescence, was determined by dividing the induced luminescence by the basal luminescence (FIG. 56). Although the fold induction values are similar for each of the reporters except Luc2, the luminescence generated by the induced 9B8 opt transcriptional reporter was approximately 2.5 logs higher than the induced *Renilla* transcriptional reporter and approximately 1.5 logs higher than the Luc2 transcriptional reporter. FIG. 56 demonstrated the use of 9B8 and 9B8 opt as transcriptional reporters.

C. 9B8 opt and 9B8 opt+K33N

Figure 57:
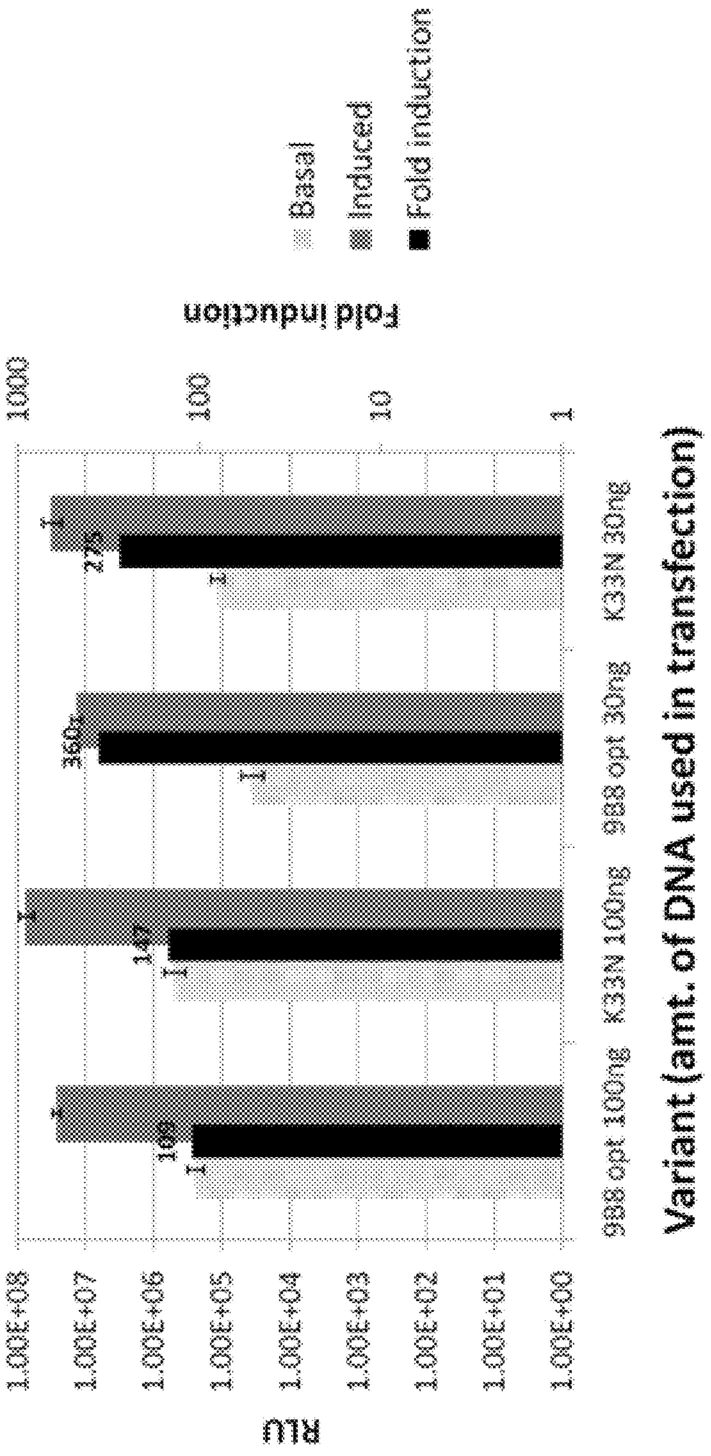
FIG. 57 shows the luminescence generated from lysed HEK293 cells expressing 9B8 opt and 9B8 opt+K33N ("K33N") cAMP transcriptional reporters using the novel coelenterazine PBI-3939 as a substrate with ("Induced") or without ("Basal") forskolin treatment and the fold induction due to forskolin treatment ("Fold Induction").

The variants 9B8 opt and 9B8 opt+K33N were compared in a lytic transcriptional reporter assay. The variant 9B8 opt+K33N was cloned using methods known in the art into a pGL4.29 vector (Promega Corp.), which contains a cyclic AMP response element (CRE). The 9B8 opt+K33N transcriptional reporter was tested and compared to the 9B8 opt transcriptional reporter as described above in HEK293 cells. 30 and 100 ng of plasmid DNA containing the transcriptional reporter versions of the variants were used to transfect HEK293 cells. The cells were induced with FSK for 5 hrs prior to measurement for luminescence. Cells were lysed with a lysis buffer containing 1 mM CTDA, 150 mM KCl, 2 mM DTT, 100 mM MES pH 6.0, 35 mM thiourea, 0.25% TERGITOL® NP-9 (v/v), and 10 mg/mL 2-hydroxypropyl-β-cyclodextrin. Luminescence was measured on a TECAN® GENIOS™ Pro luminometer. The lysate was assayed with the lysis buffer containing 20 μM PBI-3939. FIG. 57 shows the normalized luminescence (transfection corrected) of HEK293 cells expressing the 9B8 opt or 9B8 opt+K33N transcriptional reporter construct treated ("Induced") or not treated ("Basal") with FSK. As shown in FIG. 57, the fold-induction for 9B8 opt was 360 when 30 ng of DNA was used for transfection and 109 when 100 ng was used for transfection, while the fold-induction for 9B8 opt+K33N was 275 and 147, respectively. When higher amounts of DNA were used for transfection, K33N provided a greater response.

D. L27V

Figure 58A:
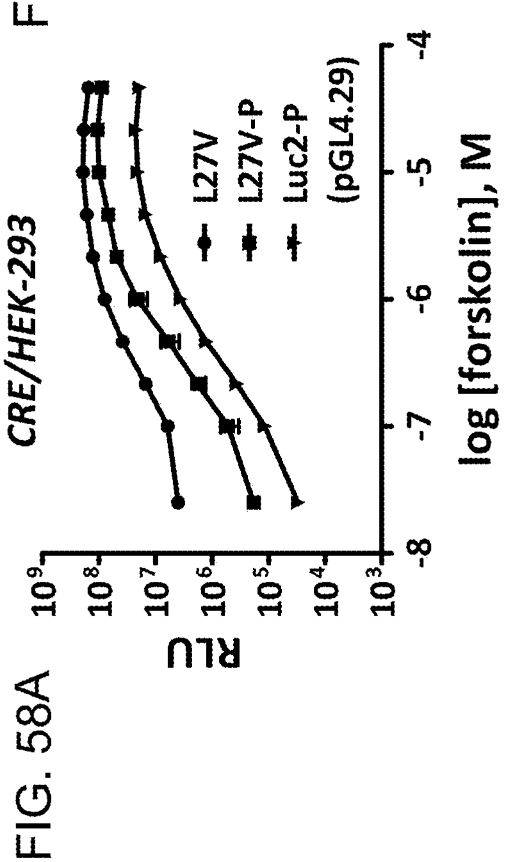
FIGS. 58A-C show the luminescence of the OgLuc variants 9B8 and L27V lytic reporter constructs for multiple pathways in multiple cell types.
Figure 58B:
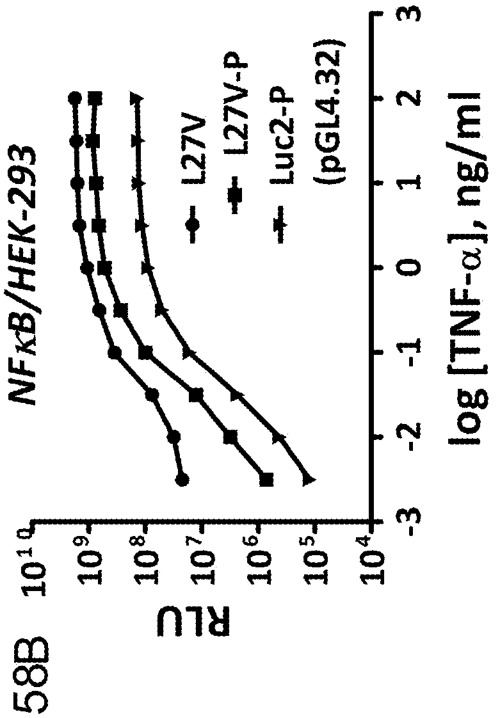
Figure 58C:
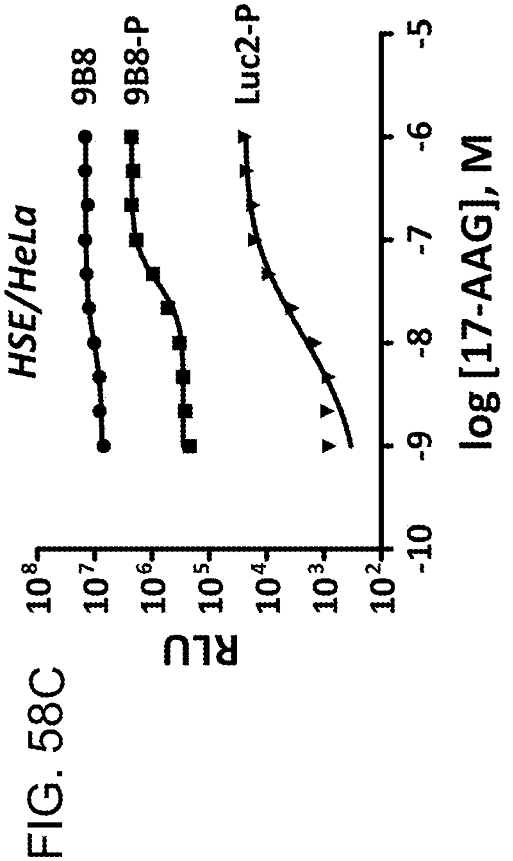

1. L27V was cloned into a reporter vector as described in C of this Example containing a CRE, NFkB or HSE (Heat shock element) response element. Reporter constructs were then transfected into HEK293 cells or HeLa cells as previously described. The cells were then induced using FSK for CRE, TNFα for NFkB or 17-AAG for HSE. Luminescence was measured as previously described using the assay reagent with 20 μM PBI-3939 (FIGS. 58A-C). The reporter constructs were all validated in HEK293, HeLa, NIH3T3, U2OS and Jurkat cell lines (data not shown).

Figures 59A, 59B:
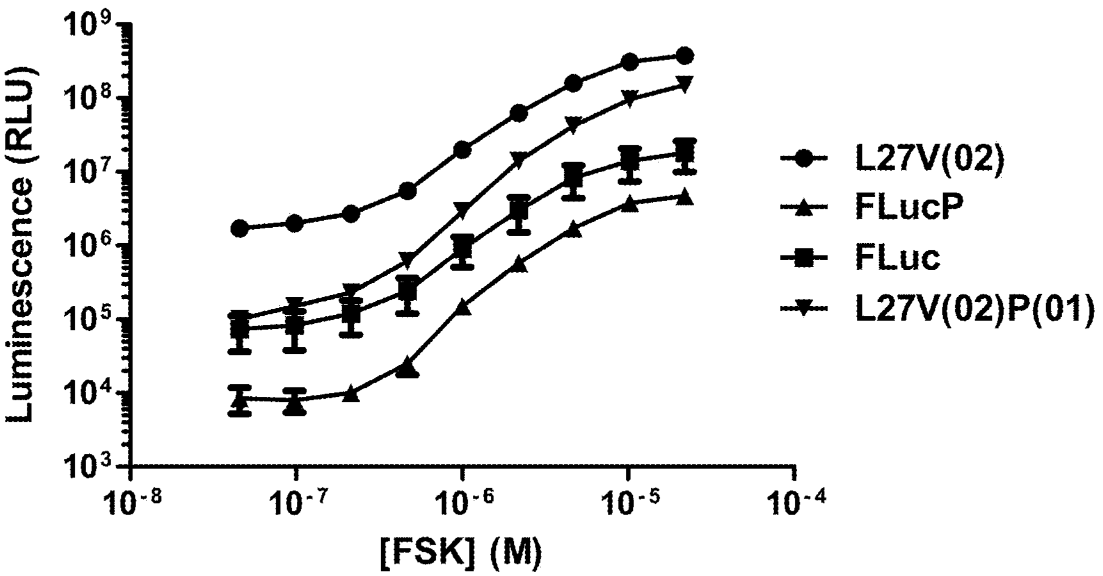

2. L27V02 and L27V02P (containing a PEST sequence; SEQ ID NO: 323) were cloned into a reporter vector (pGL4.32 based) as described in C of this Example. Other OgLuc variants containing a PEST sequence include L27V01-PEST00 and L27V03-PEST02 (SEQ ID NOs: 320 and 326, respectively). The reporter construct was then transfected into HEK293 cells as previously described. The cells were then induced using FSK, and luminescence was measured as previously described using the assay reagent with 20 μM PBI-3939 (FIGS. 59A-B). Various other reporter constructs were also created and tested in various cell lines (FIG. 59C). FIG. 59A shows the full dose response for the CRE system in HEK293 cells. FIG. 59B summarizes FIG. 59B. FIG. 59C summarizes the data in FIGS. 59A-B and shows the same type of data for the NFkB response element. Both CRE and NFkB report constructs were examined in HEK293, HeLa, HepG2, Jurkat, ME180, HCT116, and U2OS cell lines.

3. HEK293 cells ($0.9\times10^6$ cells in a T25 flask) were transfected with pNFkB-L27V secretion construct (SEQ ID NOS: 463 & 464; wherein the IL-6 secretion sequence (SEQ ID NOs: 461 and 462) replaced the native OgLuc secretion sequence SEQ ID NO: 54), *Metridia longa* (Clontech), pNFkB-L27V (native secretion sequence; SEQ ID NOs: 465 and 466) or firefly luciferase (Luc2; pGL4.32-based) plasmid DNA using FUGENE® HD (Promega Corp.) according to the manufacturer's instructions. Cells were incubated at 37° C., 5% $CO_2$ for 8 hrs, then trypsinized in 0.5 mL TrypLE (Invitrogen). The lysates were then resuspended in 8 mL DMEM with 10% FBS, 1×NEAA and 1×sodium pyruvate. 100 μL of the resuspended sample was then added to wells of a 96-well plate and incubated for 16 hrs at 37° C., 5% $CO_2$.

Figure 60A:
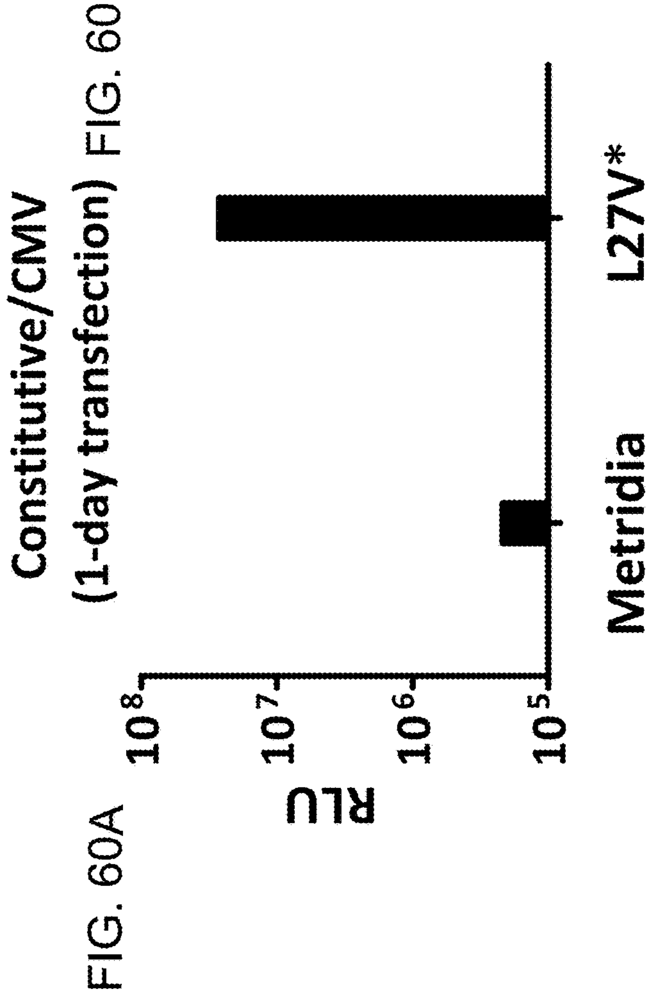
FIGS. 60A-B show the luminescence of the OgLuc variant L27V secretable reporter compared to *Metridia longa* luciferase with a CMV promoter (FIG. 60A) or a NFkB response element (FIG. 60B).
Figure 60B:
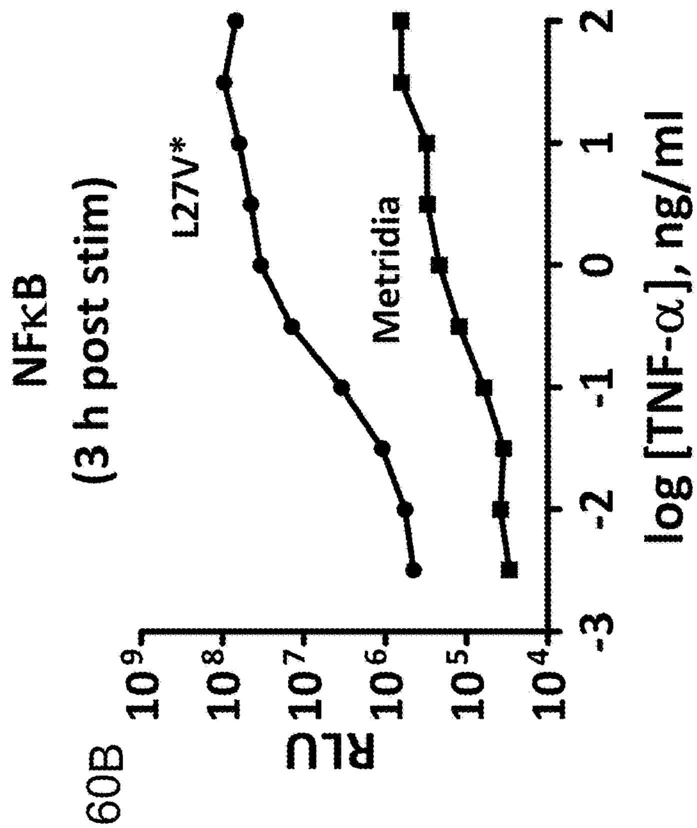

Following incubation, the media was removed from the cells and replaced with 100 μL fresh media with our without TNFα (serially diluted). To assay for secretion, at 3 and 6 hrs, 5 μL of media (in triplicate) was removed from the cells, brought to 50 μL with PBS and mixed with 50 μL assay reagent (as previously described with 100 μM PBI-3939). Luminescence was measured at 0 and 10 min as previously described (FIG. 60).

For measuring *Metridia longa* luciferase activity, the Ready-To-Glow™ Secreted Luciferase System (Clontech) was used according to the manufacturer's protocol. Briefly, 5 μL Ready-to-Glow™ reagent was added to 5 μL of sample and 45 μL of PBS. Luminescence was measured immediately after reagent addition (FIG. 60).

E. L27V Optimized Variants.

Plasmid DNAs (pGL4.32-L27V00, pGL4.32-L27V01, pGL4.32-L27V02, pGL4.32-L27V03, and pGL4.13) were prepared for transfection using FUGENE® HD according to the manufacturer's protocol. The pGL4.32 vector (Promega Corp.) contains the NF-κB response element. The L27V codon optimized sequences replaced the Luc2P sequence in the vector. pGL4.13 vector (Promega Corp.) contains the Luc2 gene driven by the SV40 promoter.

Figure 61B:
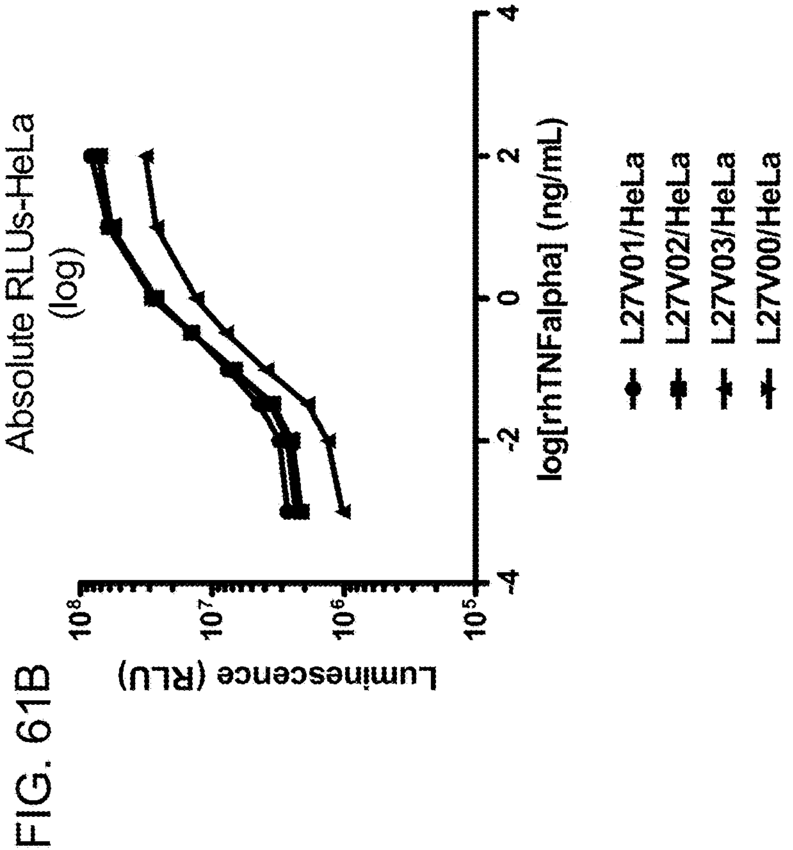
FIGS. 61A-F show the absolute luminescence (FIGS. 61A and 61B), the normalized luminescence (FIGS. 61C and 61D) and the fold response (FIGS. 61E and 61F) of optimized versions of L27V (L27V01, L27V02 and L27V03) compared to L27V (L27V00) expressed in HeLa cells.
Figure 61A:
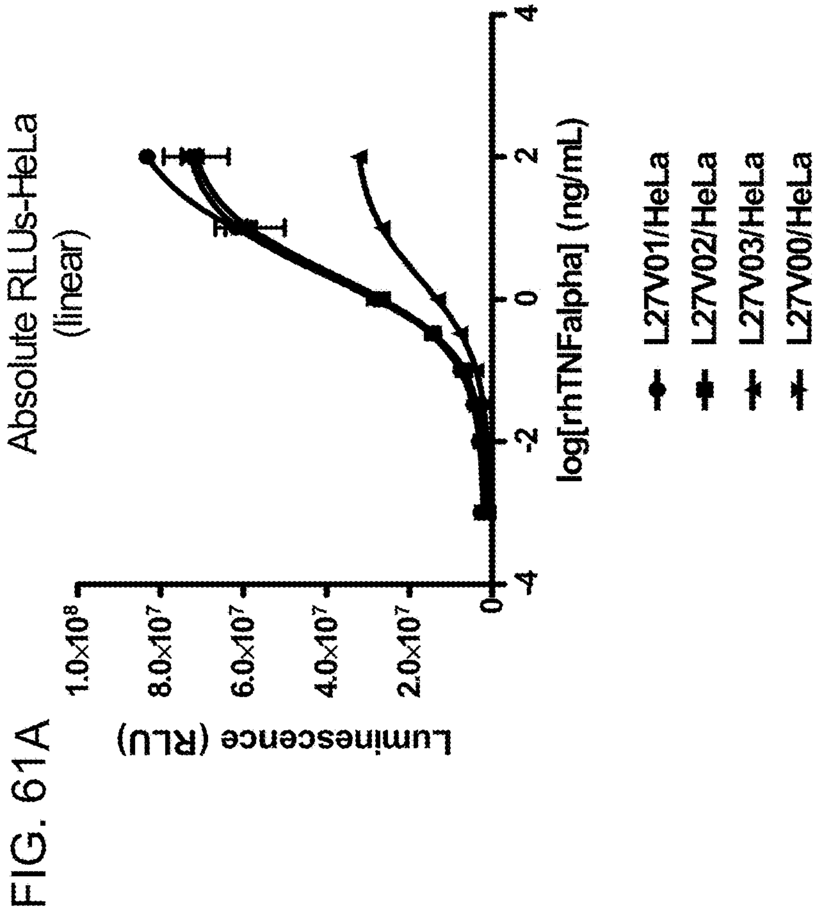
Figure 61D:
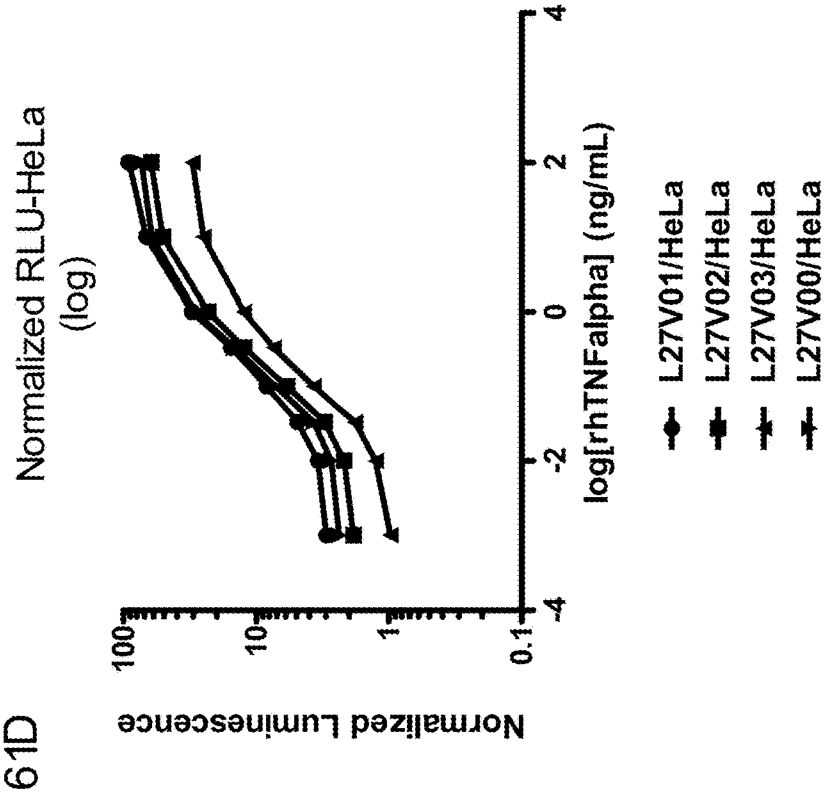
Figure 61C:
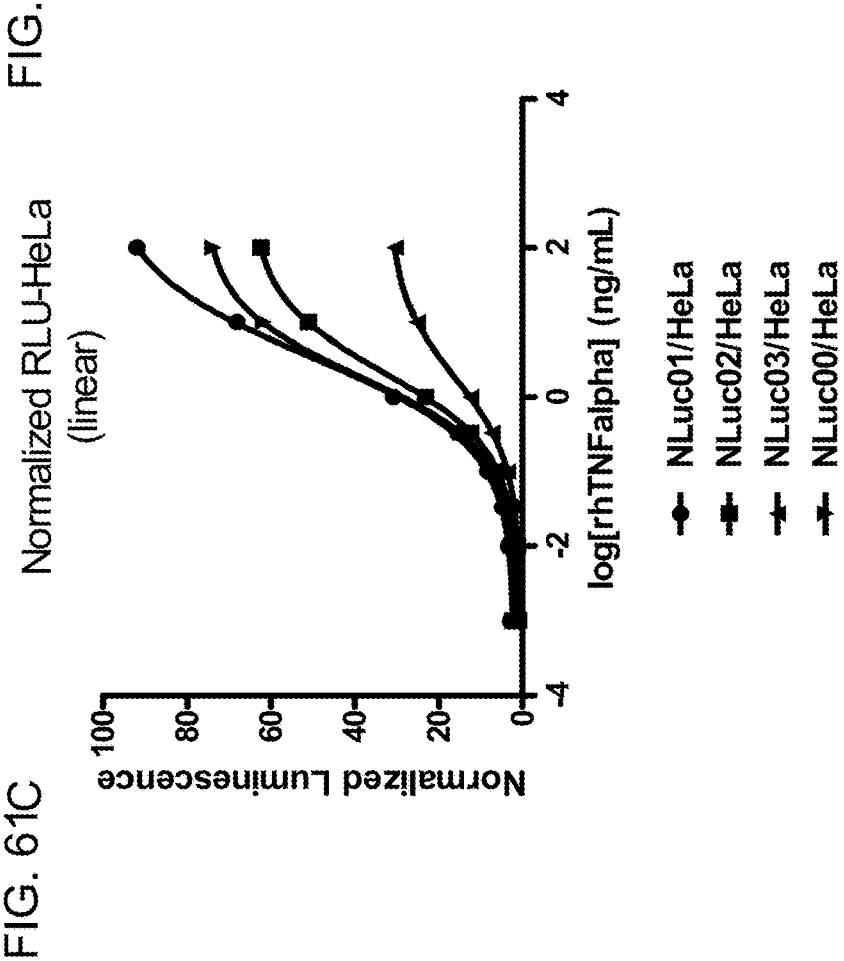
Figure 61E:
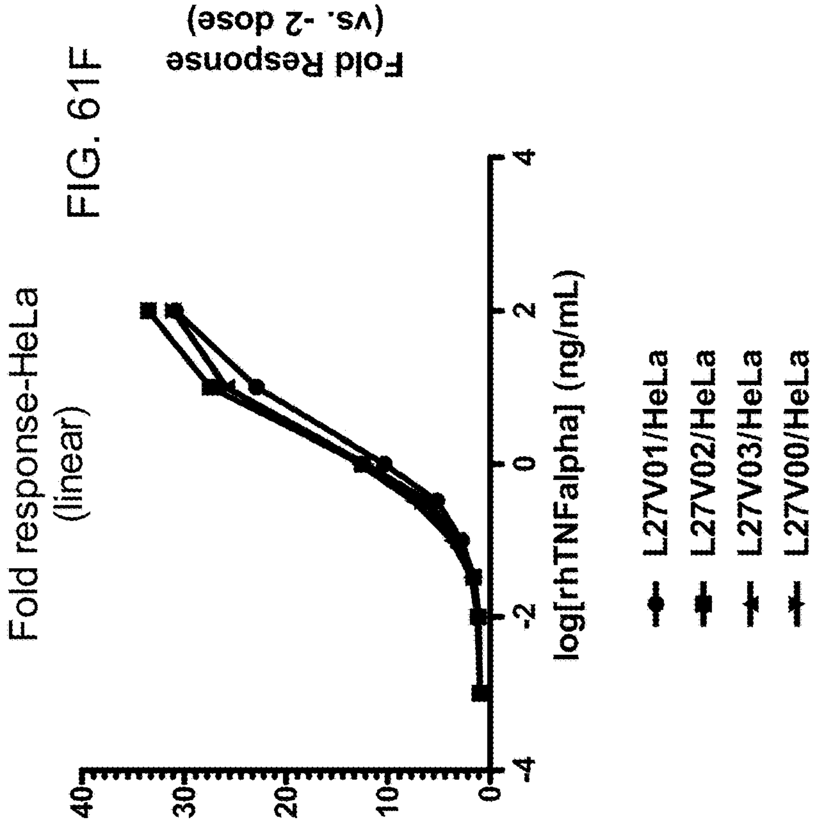
Figure 61F:
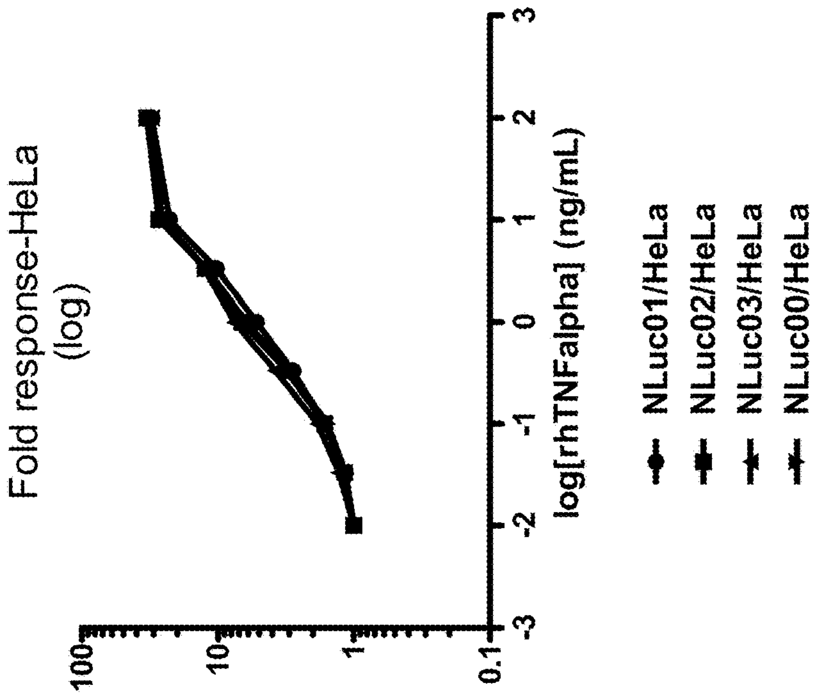

300 μL of DNA transfection mixture was then mixed with 6 mL of HeLa cell suspension ($2\times10^5$ cells/mL), homogenized, and 100 μL plated into wells of a 96-well plate. The cells were then incubated overnight at 37° C., 5% $CO_2$. Following incubation, 10 μL of 10×rhTNFu in DPBS with BSA was added to the wells and incubated for 4.5 hrs at 37° C., 5% $CO_2$. Six wells were given vehicle only. The cells were then allowed to equilibrate at room temperature for 20 min, and then 100 μL assay reagent (as previously described with 100 μM PBI-3939) was added. To cells expressing Luc2 or receiving vehicle only treatment, 100 μL of the ONE-GLO™ Luciferase Assay Reagent was added. Luminescence was measured 12 min post-assay reagent addition as previously described. FIGS. 61A-B shows the absolute luminescence, FIGS. 61C-D shows normalized luminescence and FIGS. 61E-F shows fold response.

Example 37—OgLuc Variants in a Transcription Reporter Assay

To demonstrate the ability of the OgLuc variants of the present invention to be used as transcription reporters, the transfected with either 10 ng or 100 ng plasmid DNA/well of pGL4.29 9B8 opt, pGL4.29 9B8 opt-P, or pGL4.29. Plasmid DNA was mixed with 850 μL of OPTI-MEM® (Invitrogen) and 32.4 μL of FUGENE® HD transfection reagent (Promega Corp.) and incubated at room temperature for 10 min. Eight μL of the transfection/reporter DNA mixture was added to the appropriate wells (2 constructs/plate). Cells were incubated for 4 hrs at 37° C. The medium was replaced with OPTI-MEM®+0.5% dialyzed FBS+1× NEAA+1×sodium pyruvate+1×Penn-Strep and incubated overnight at 37° C.

Following incubation, 10 nM or 10 μM FSK (from a 10×stock) in OPTI-MEM® was added to the cells and incubated for 3 hrs at 37° C. A lytic reagent containing 100 mM MES pH 6.1, 1 mM CDTA, 150 mM KCl, 35 mM thiourea, 2 mM DTT, 0.25% TERGITOL® NP-9 (v/v), 0.025% MAZU® DF 204, and 20 μM PBI-3939 was added to the cells containing pGL4.29 9B8 opt or pGL4.29 9B8 opt-P and allowed to incubated for 10 min at room temperature (100 μL lytic reagent added to 100 μL cells). ONE-GLO™ assay reagent (Promega Corp.) was added to cells containing pGL4.29 and used according to the manufacturer's protocol (100 μL reagent added to 100 μL cells). Luminescence was measured on a GLOMAX® Luminometer. Table 26 shows the luminescence of the HEK293 cells expressing the transcriptional reporters containing CRE treated with 10 nM ("baseline") or 10 mM FSK, and the response to FSK (i.e., the luminescence generated by the 10 mM FSK treated cells divided by the luminescence generated of the 10 nM FSK treated cells.)

The results shown in Table 28 indicate that 9B8 opt and 9B8 opt-P were brighter than luc2P, and that all the luciferase reporters responded to FSK when 100 ng of DNA was used for the transfection. However, when only 10 ng of DNA was used for the transfection, the luminescence for the luc2P reporter was below the detection level for the luminometer.

TABLE 28

Transcriptional Reporters Containing CRE in HEK293 Cells (3 h timepoint)

| Reporter construct | 100 ng DNA for transfection baseline | RLU (10 mM FSK) | Response | 10 ng DNA for transfection baseline | RLU (10 mM FSK) | Response |
|---|---|---|---|---|---|---|
| 9B8 opt | 3,078,418 | 104,687,723 | 34 | 192810 | 12,926,465 | 67 |
| 9B8 opt-P | 122,071 | 20,544,753 | 168 | 11179 | 1,353,459 | 121 |
| luc2P | 356 | 5,293 | 15 | 0 | 0 | — |

OgLuc variant 9B8 opt was used as a transcriptional reporter in a forward, reverse, and bulk transfection. These methods of transfection were chosen because they are representative of the approaches commonly used for the transient expression of genetic transcriptional reporters.

Forward Transfection

Transcriptional reporters containing the cAMP response element (CRE) and 9B8 opt or 9B8 opt further comprising the PEST protein degradation sequence (9B8 opt-P) were prepared in the pGL4.29 (Promega Corp.) backbone, i.e., the luc2P gene of the pGL4.29 vector was replaced with 9B9 opt (SEQ ID NO: 24) or 9B8 opt-P (SEQ ID NO: 65). pGL4.29 was used as a control/benchmark.

HEK293 cells were plated at 15,000 cells/well in six 96-well tissue culture plates. Cells were grown in 100 μL of DMEM+10% FBS+1× non-essential amino acids (NEAA) and incubated overnight at 37° C. The cells were transiently Reverse Transfection Transcriptional reporters containing the antioxidant response element (ARE) and 9B8 opt or 9B8 opt-P were prepared in the pGL4.29 (Promega Corp.) backbone, i.e., the luc2P gene of the pGL4.29 vector was replaced with 9B9 opt or 9B8 opt-P, and CRE was replaced with 2×ARE (SEQ ID NO: 66) using methods known in the arts.

HEK293 cells were trypsinized (T75 flask, 3 mL trypsin) and resuspended in $1\times10^5$ cells/mL (approximately $8.9\times10^6$ total cells) in medium containing DMEM+10% FBS+1× NEAA. Each transcriptional reporter was prepared for transfection by mixing 1.2 mL OPTI-MEM®, 12□ μL transcription reporter DNA (100 ng) and 36 μL FUGENE® HD transfection reagent together and incubated at room temperature for 35 min. Following incubation, 624 μL of the transfection/reporter DNA mixture was added to 12 mL of cell suspension and mixed by inversion. After mixing, 100

μL of the cell/DNA mixture was added to wells of a 96-well plate (2 constructs/plate). The cells were incubated at 37° C. for 22 hrs. Tert-butylhydroquinone (a Nrf2 stabilizer; tBHQ; 1 μM ("baseline") or 20 μM) or sulphoraphane, (an organo-sulfer antioxidant known to activate Nrf2; 1 μM ("baseline") or 20 μM) in OPTI-MEM® was added to each well and incubated at 37° C. for 24 hrs. Cells were lysed with 100 μL lytic reagent as described above for the forward transfection. Luminescence was measured on a GLOMAX® Luminometer.

Table 29 shows the luminescence of the HEK293 cells expressing the transcriptional reporters containing ARE treated with 1 μM ("baseline") or 20 μM sulphoraphane and the response to sulphoraphane (i.e., the luminescence generated by the 1 μM sulphoraphane treated cells divided by the luminescence generated of the 20 μM sulphoraphane treated cells). Table 30 shows the luminescence of the HEK293 cells expressing the transcriptional reporters containing ARE treated with 1 μM ("baseline") or 20 μM tBHQ, and the response to tBHQ (i.e., the luminescence generated by the 1 μM tBHQ treated cells divided by the luminescence generated of the 20 μM tBHQ treated cells). Tables 29 and 30 show that 9B8 opt and 9B8 opt-P could report the presences of two different known stimuli for ARE.

TABLE 29

Transcriptional Reporters Containing ARE in HEK293 Cells (24 h time point)

| | 100 ng DNA for transfection | | |
|---|---|---|---|
| Reporter construct | baseline | RLU (20 mM sulphoraphane) | Response |
| 9B8 opt | 15,600,000 | 89,600,000 | 5.8 |
| 9B8 opt-P | 258,406 | 3,940,000 | 15 |

TABLE 30

Transcriptional Reporters Containing ARE in HEK293 Cells (24 h time point)

| | 100 ng DNA for transfection | | |
|---|---|---|---|
| Reporter construct | baseline | RLU (20 mM tBHQ) | Response |
| 9B8 opt | 15,100,000 | 120,000,000 | 8 |
| 9B8 opt-P | 317,238 | 8,460,000 | 27 |

Bulk Transfection

The transcriptional reporters containing CRE and 9B8 opt or 9B8 opt-P described in the forward transfection were used in the bulk transfection of HEK293 and NIH3T3 cells. Transcriptional reporters containing the heat shock response element (HRE; SEQ ID NO: 67) and 9B8 opt or 9B8 opt-P were prepared in the pGL4.29 (Promega Corp.) backbone, i.e., the luc2P gene of the pGL4.29 vector was replaced with 9B9 opt or 9B8 opt-P, and the CRE was replaced with HRE. The transcriptional reporter containing HRE and 9B8 opt-P was used in the bulk transfection of HeLa cells HEK293, NIH3T3, or HeLa cells were plated to a single well of a 6-well tissue culture plate the day before transfection at a density of $4.5\times10^5$ cells/well in 3 mL complete medium (DMEM+10% FBS+1×NEAA+1×sodium pyruvate) for HEK293 cells, $3\times10^5$ cells/well in 3 mL complete medium (DMEM+10% fetal calf serum (FCS)+1×NEAA+1×sodium pyruvate) for NIH3T3 cells, or $9.9\times10^5$ cells/well in 3 mL complete medium (DMEM+10% FBS+1×NEAA) for HeLa cells. Cells were grown overnight at 37° C.

3,300 ng of reporter plasmid DNA in 155 μL OPTI-MEM® was mixed with 9.9 μL FUGENE® HD transfection reagent, vortexed briefly, and incubated at room temperature for 10 min. The CRE transcriptional reporters were used to transfect HEK293 and NIH3T3 cells. The HRE transcriptional reporters were used to transfect HeLa cells. The reporter mixture was added to cells and mixed by gentle rocking followed by incubation at 37° C. for 6 hrs (HEK293 and NIH3T3) or 3 hrs (HeLa). Cells were then trypsinized and resuspended in medium (DMEM+10% FBS+1×NEAA+1×sodium pyruvate for HEK293 cells, DMEM+10% FCS+1×NEAA+1×sodium pyruvate for NIH3T3 cells, or DMEM+10% FBS+1×NEAA for HeLa cells), followed by plating to the individual wells of a 96-well plate (20,000 cells/100 μL for HEK293, 10,000 cells/100 μL for NIH3T3, or 13,000 cells/μL for HeLa) and incubated at 37° C. overnight.

FSK (CRE stimulator) or 17-AAG (HRE stimulator; 17-Allylamino-demethoxy geldanamycin) in OPTI-MEM® was added to the cells (10 nM or 10 μM final concentration for FSK; 1 nM or 1 μM final concentration for 17-AAG) and incubated at 37° C. for 4 hrs (FSK) or 6 hrs (17-AAG). Plates were removed from the incubator and allowed to equilibrate to room temperature for 25 min. Cells were lysed with 100 μL lytic reagent as described above for the forward transfection. Luminescence was measured on a GLOMAX® Luminometer.

Table 31 shows the luminescence of the HEK293 cells expressing the transcriptional reporters containing CRE treated with 10 nM ("baseline") or 10 mM FSK and the response to FSK. Table 32 shows the luminescence of the NIH3T3 cells expressing the transcriptional reporters containing CRE treated with 10 nM ("baseline") or 10 mM FSK and the response to FSK. Table 33 shows the luminescence of the HeLa cells expressing the transcriptional reporters containing HRE treated with 10 nM ("baseline") or 10 mM 17-AAG and the response to 17-AAG.

Tables 29-31 show that 1) both versions of the 9B8opt OgLuc variant can report the presence and stimulatory effects of FSK on CRE in the context of two different cell lines, HEK293 and NIH3T3, and 2) 9B8 optP can report the presence and stimulatory effects of 17-AAG on HRE in the context of HeLa cells.

TABLE 31

Transcriptional Reporters Containing CRE in HEK293 Cells (4 h time point)

| | 100 ng DNA for transfection | | |
|---|---|---|---|
| Reporter construct | baseline | RLU (10 mM FSK) | Response |
| 9B8 opt | 39,700,000 | 654,000,000 | 16 |
| 9B8 opt-P | 3,960,000 | 460,000,000 | 116 |

TABLE 32

| Transcriptional Reporters Containing CRE in NIH3T3 Cells (4 h time point) | | | |
|---|---|---|---|
| | 100 ng DNA for transfection | | |
| Reporter construct | baseline | RLU (10 mM FSK) | Response |
| 9B8 opt | 9,187,000 | 23,600,000 | 2.6 |
| 9B8 opt-P | 410,461 | 3,720,000 | 9 |

TABLE 33

| Transcriptional Reporters Containing HRE in HeLa Cells (6 h time point) | | | |
|---|---|---|---|
| | 100 ng DNA for transfection | | |
| Reporter construct | baseline | RLU (1 mM 17-AAG) | Response |
| 9B8 opt-P | 278,118 | 3,204,000 | 12 |

Example 38—Lytic and Secretable Reporter in Difficult to Express Cells

HepG2 cells, $1\times10^5$ cells/mL in a cell suspension, were reverse transfected with plasmid DNA (pGL4.32 backbone; Promega Corp.) containing L27V02, luc2P (Promega Corp.), luc2 (Promega Corp.) or L27V02-IL6 (L27V02 with the native secretion sequence replaced with the IL-6 secretion sequence; ("IL601-L27V02A"; SEQ ID NO: 324) using FUGENE® HD according to the manufacturer's instructions (1:20 DNA-transfection mixture to cells). 100 μL cell suspension was then plated into wells of a 96-well plate and incubated for 22 hrs at 37° C., 5% $CO_2$. Other OgLuc constructs which have the native secretion sequence replaced by the IL-6 secretion sequence include IL601-L27V01 and IL602-L27V03 (SEQ ID NOs: 321 and 327, respectively).

Figure 62A:
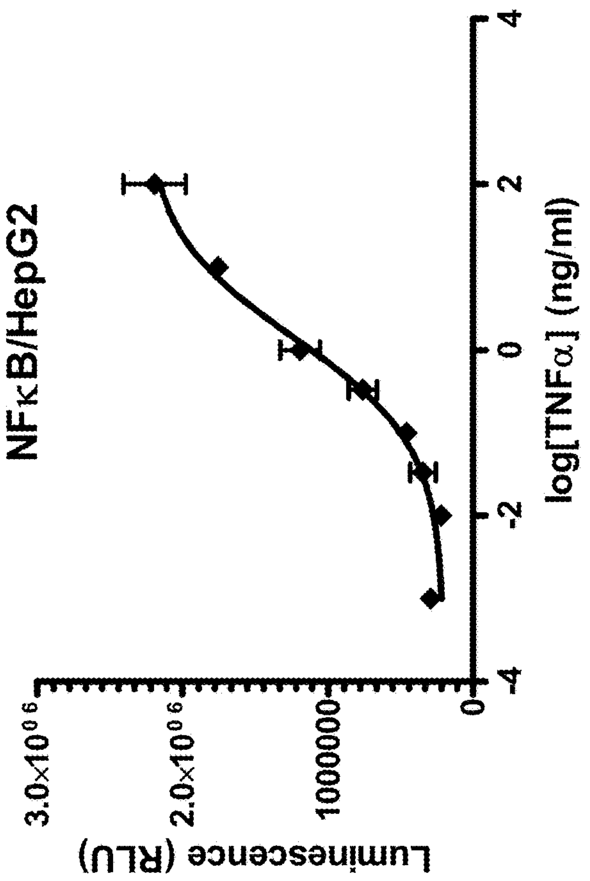
FIGS. 62A-B show the luminescence of secreted OgLuc variant L27V02 (containing the IL-6 secretion signal) reporter (FIG. 62A) and L27V02 ("L27V(02)"), L27V02P ("L27V(02)P(O1)") and luc2 ("Fluc") reporters (FIG. 62A) expressed in HepG2 cells treated with various doses of rhTNFα ("TNFα").

For secretion analysis, the media was removed from the cells, and the cells washed in 100 μL DPBS. 100 μL complete media (DMEM+10% FBS+1×NEAA) was added along with varying doses (1 pg/mL-100 ng/mL) of rhTNFα ("TNFα") for 4.5 h. 10 μL of the media was then removed, added to 90 μL complete media, and 100 μL assay reagent (as previously described; 100 μM PBI-3939) added. Luminescence was measured as previously described (FIG. 62A).

Figure 62B:
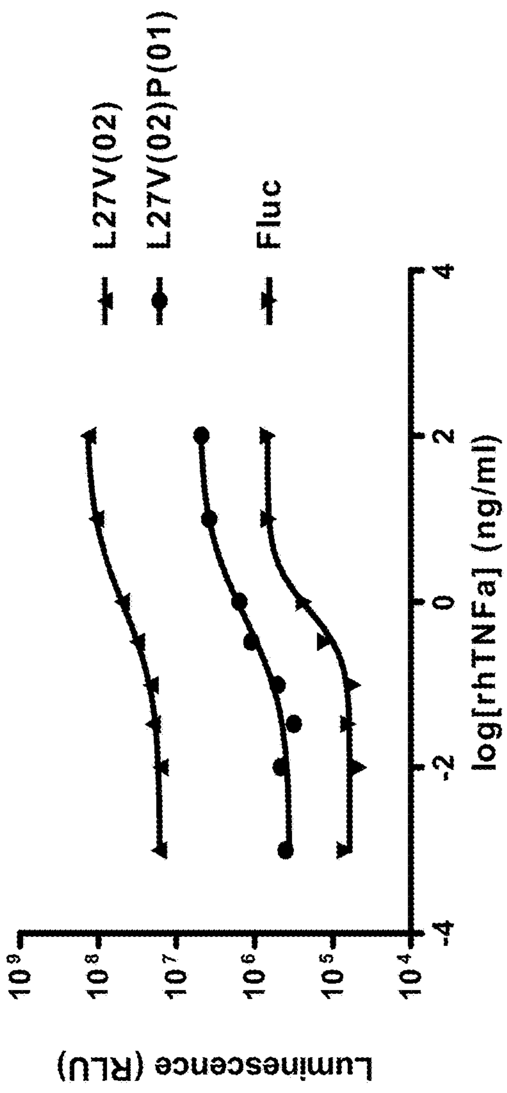

For lytic analysis, following plating, the cells were incubated for 4.5 hrs at 37° C., 5% $CO_2$. The cells were then allowed to equilibrate to room temperature for 20 min. Assay reagent (as previously described; 100 μM PBI-3939) was added to the cells, and luminescence measured as previously described (FIG. 62B).

Example 39—Additional Lytic Reporter Features

The OgLuc variants of the present invention in the context of a cell-based, lytic transcriptional reporter should offer a luminescent signal of a magnitude such that the signal appears sooner than it might with other luciferases. The bright luminescence should also allow for weak promoters to be examined.

Example 40—Mammalian Cell Transfections

The OgLuc variants of the present invention were used as reporters in difficult to transfect cell lines, e.g., Jurkat, HepG2, primary cells, non-dividing primary cells, or stem cells. (See e.g., FIG. 59C) Due to their high signal intensity, the OgLuc variants enable detectable luminescence when transfection efficiency is low. The OgLuc variants can also be used as reporters in cells that are especially sensitive to conditions associated with transfection, i.e., DNA concentration, transfection reagent addition. Due to the brightness of the OgLuc variants, an adequate level of luminescence can be achieved using lower DNA concentrations, less transfection reagent, and perhaps shorter post-transfection times prior to beginning an assay. This will place less of a toxicity burden on what would otherwise be sensitive cells. The bright luminescence of the OgLuc variants should also allow for a signal to be detected at very long time points in the event such an output is desirable. As another example, the OgLuc variants could be used as reporters for single copy native promoters, e.g., HSB thymidylate kinase (TK) promoter, HOX genes, or LIN28.

Example 41—Stable Cell Lines

The identification of robust, stable cell lines expressing an OgLuc variant of the present invention, either in the cytoplasm or as a secreted form, can be facilitated by the bright signal of the luciferase and the small size of the OgLuc gene. The relatively small gene sequence should reduce the likelihood of genetic instability resulting from the integration of the foreign DNA.

To generate stable cell lines using an OgLuc variant of the present invention, plasmid DNA comprising a nucleotide sequence for an OgLuc variant and a selectable marker gene, e.g., neomycin, hygromycin, or puromycin, is used to transfect a cell line of interest, e.g., HEK293 cells. Cells of an early passage number, e.g., less than 10 passages, are plated into T25 ($1\times10^6$) or T75 ($3\times10^6$) tissue culture flasks and allowed to grow overnight to approximately 75% confluency. Cells are then transfected using the above plasmid DNA and an appropriate transfection reagent, e.g., TRANSIT®-LT1 or FUGENE® HD. Forty-eight hrs post-transfection, the media is replaced on the cells with selection media containing the selection drug, e.g., G418, hygromycin or puromycin, at a concentration previously determined to kill untransfected cells. Selection of cells containing the plasmid DNA occurs over 2-4 weeks. During this time, the cells are re-plated in selection media at various concentrations into either T25 or T75 tissue culture flasks. The media on the re-plated cells is replaced every 3-4 days for 2-3 weeks with fresh selection media. The flasks are monitored for the formation of live cell colonies. Eventually, the flasks will contain many large colonies and few dead cells.

From the pool of stable colonies in the flasks, single colonies are isolated and expanded into a single 24-well tissue culture plate. Briefly, cells are harvested using the trypsin/EDTA method, i.e., cells are harvested by removing media, rinsing with $Ca^{2+}$ and $Mg^{2+}$ free PBS and detached by treatment with Trypsin/EDTA. The cells are counted using a hemocytometer and diluted $1\times10^5$ in complete media. The cells are then diluted to 100 cells/mL, 33 cells/mL, 10 cells/mL, and 3.3 cells/mL in complete media. 100 μL of each dilution is plated into all wells of 96-well tissue culture plate (1 plate for each dilution) and allowed to grow 4-5 days after which 50 μL of selection media is added to the cells. Approximately a week after plating, cells are visually screened for colony growth and another 50 μL of selection media is added. The cells continue to be monitored until a single colony covers 40-60% of the well area. When a colony is ready for expansion and screening, colonies are harvested using the trypsin/EDTA method. Each colony is transferred to selection media as follows: 1) Dilute 1:10 into 6 wells of a 96-well assay plate for functional assay, e.g., luminescence detection; 2) Dilute 1:10 into 3 wells of a clear bottom 96-well assay plate for cell viability assay, e.g., CELLTITER-GLO® Luminescent Cell Viability Assay (Promega Corp.); and 3) Dilute 1:10 into a 24-well tissue culture plate for expansion. Cells in the plates for the functional and cell viability assay are then grown 2-3 days and the functional and cell viability assays performed. Positive clones in the 24-well plate are further tested with the functional and cell viability assays as well as for stability of expression and response for at least 20 passages, normal growth rate morphology, and frozen for future use at the earliest possible passage.

Example 42—OgLuc Secretion Signal Analysis a. IV Opt

Figure 63:
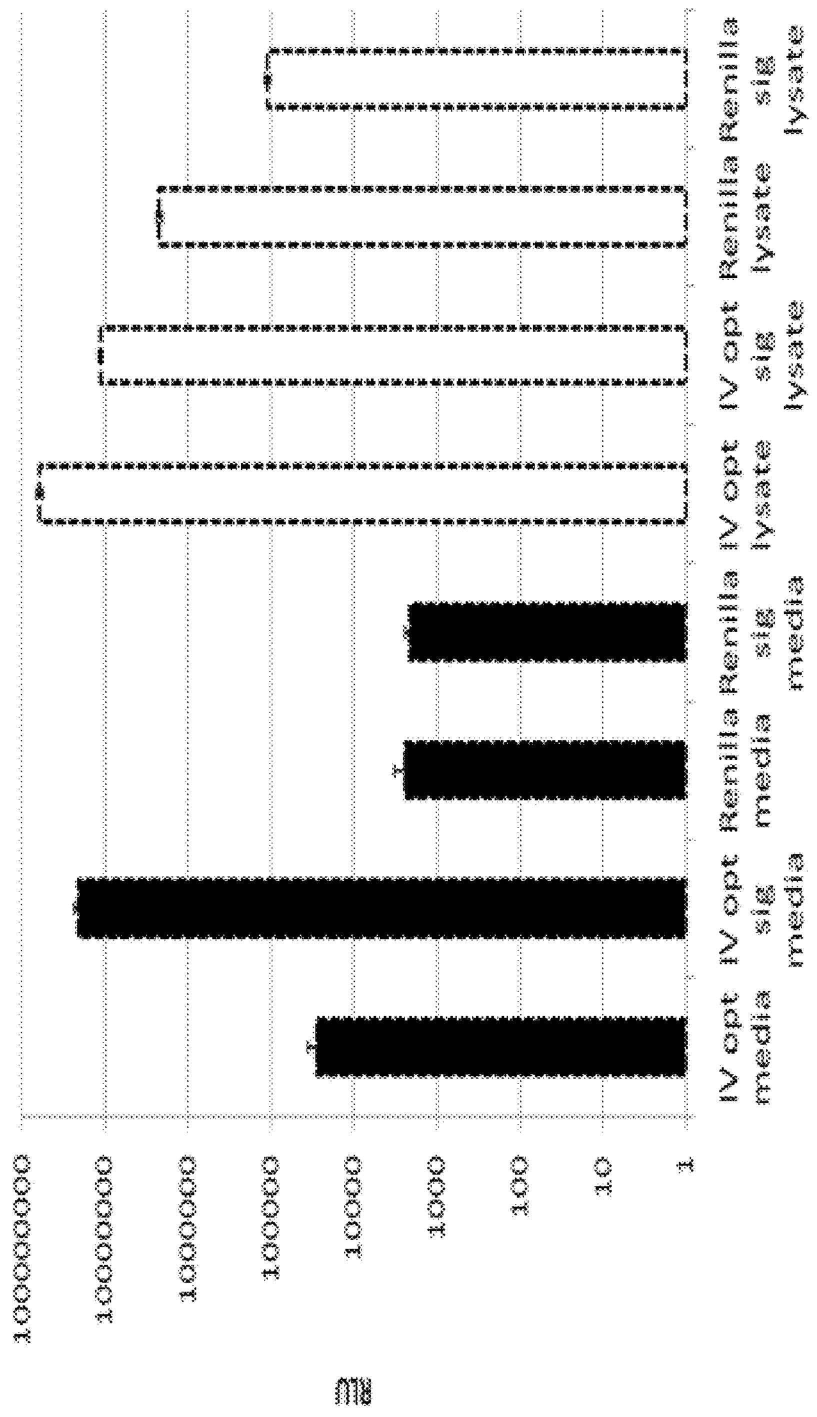
FIG. 63 shows the luminescence generated from media and lysate samples of HEK293 cells expressing the codon optimized variant IV opt with or without the secretion signal sequence using the novel PBI-3939 as a substrate compared to hRL ("*Renilla*") with or without the secretion signal sequence using native coelenterazine as a substrate.
Figures 64A, 64B:
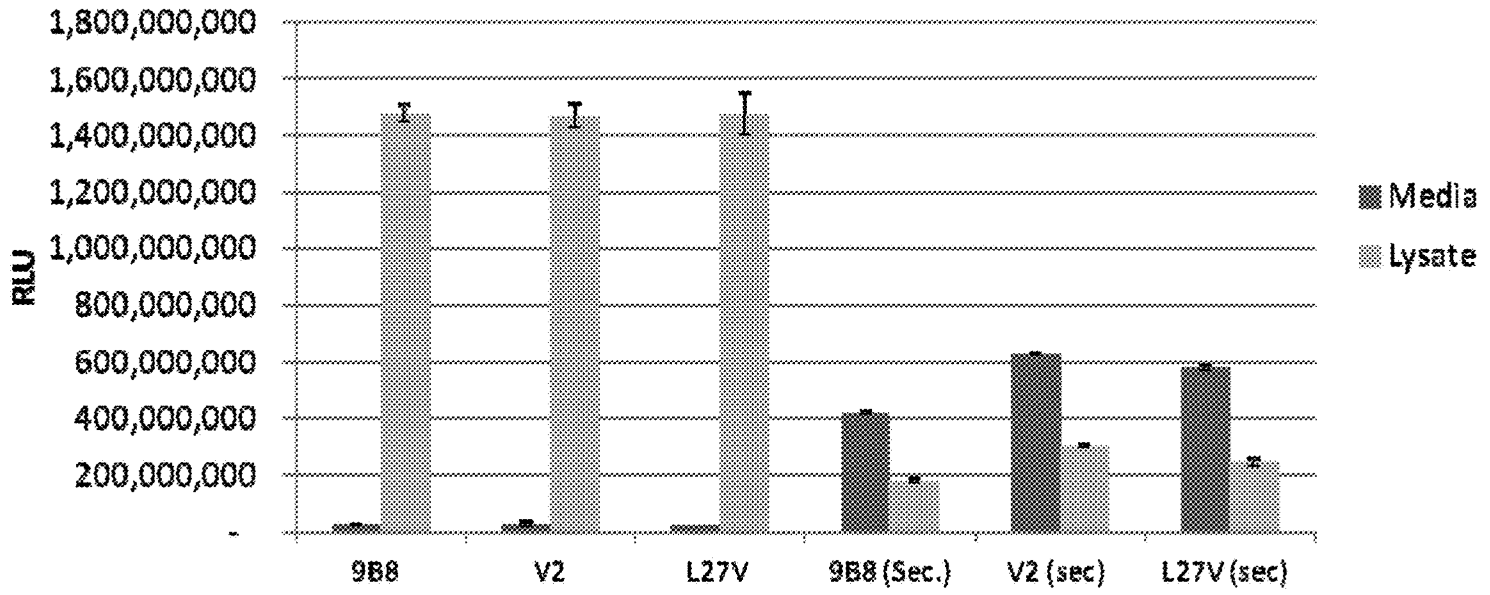
FIGS. 64A-D show the luminescence of the secreted OgLuc variants 9B8, V2 and L27V reporters expressed in CHO cells (FIGS. 64A and 64B) and HeLa (FIGS. 64C and 64D).
Figures 64C, 64D:
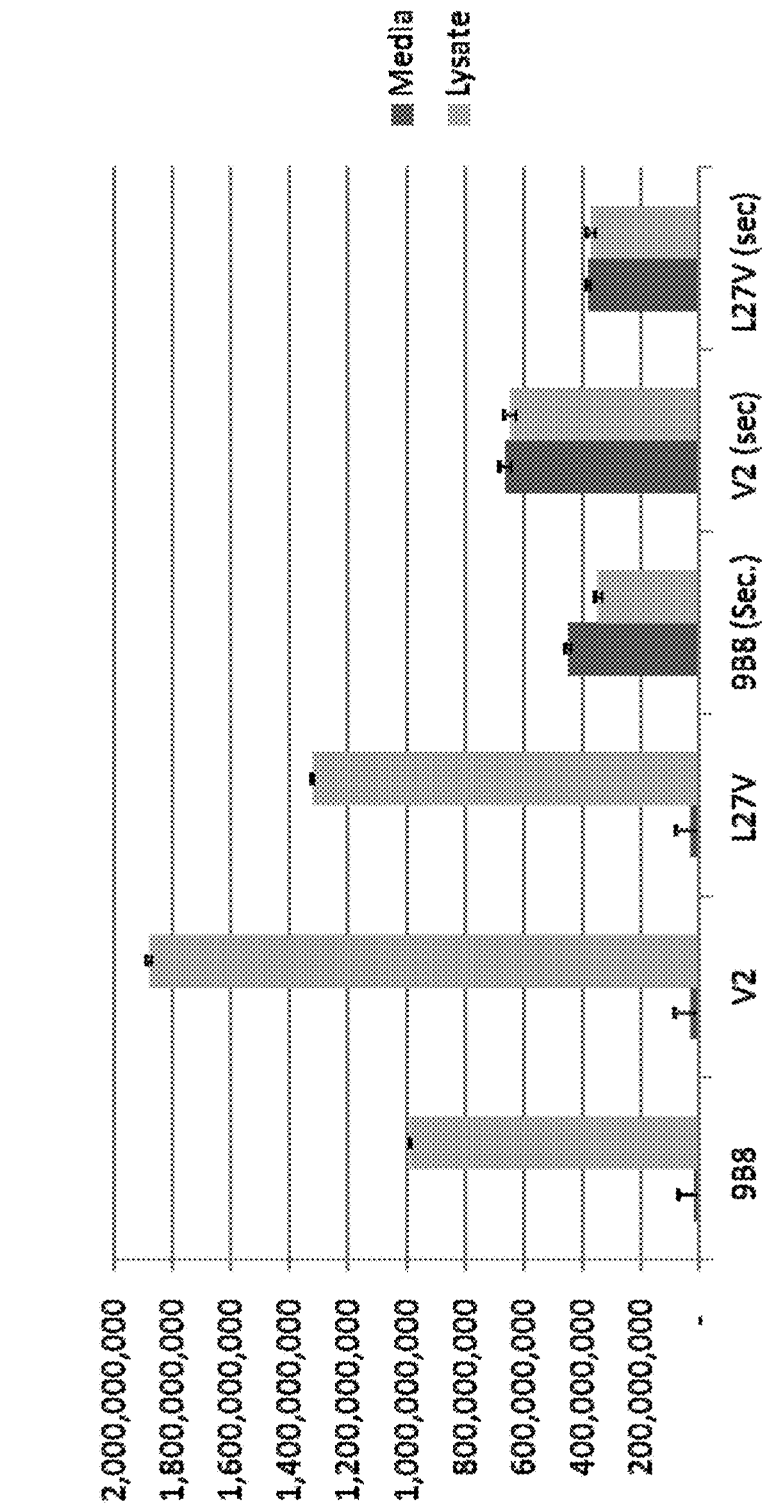

The wild-type OgLuc is processed after synthesis into a mature protein with the secretion signal sequence cleaved off. To determine if the secretion signal sequence would facilitate secretion of the OgLuc variant, the IV opt variant of Example 25 and hRL were cloned into pF4Ag containing an N-terminal OgLuc secretion signal (SEQ ID NO: 54). HEK293 cells (15,000) in 100 μL Dulbecco's Modified Eagle's medium ("DMEM") with 10% fetal bovine serum (FBS) were transfected as described in Example 25 with 100 ng of plasmid DNA, i.e., hRL or IV opt with or without the secretion signal and grown overnight at 37° C. 50 μL of media was removed to a new plate and saved for a later assay generating a "media" sample. The rest of the media was removed, and the cells were lysed with 100 μL of lysis buffer described in Example 25 to generate a "lysate" sample. 10 μL of media sample and 10 μL of lysate sample were assayed for luminescence (FIG. 63). Samples for hRL with ("*Renilla* sig") or without ("*Renilla*") the OgLuc secretion signal sequence were measured using 50 μL of lysis buffer containing 20 μM native coelenterazine. Samples for IV opt with ("IV opt sig") or without ("IV opt") the OgLuc secretion signal sequence were measured using 50 μL of lysis buffer containing 20 μM PBI-3939.

In FIG. 63, the filled bars represent the amount of light that was detected from the media in the absence of any lytic reagent. The open bars represent the total light (secreted+non-secreted) that was detected upon addition of a lytic reagent. FIG. 63 shows that IV opt was secreted from HEK293 cells into the growth media and that the secretion signal sequence was functional in mammalian cells. "IV opt sig" represents the only situation where a significant amount of luciferase was detected in the media. The results also indicate that this particular signal peptide did not facilitate secretion of hRL.

B. 9B8, V2 and L27V

To determine if the secretion signal sequence of OgLuc facilitates its secretion, the OgLuc variants 9B8, V2 and L27V were cloned into pF4Ag containing an N-terminal OgLuc secretion signal sequence. The variants were also cloned into vectors without the secretion signal sequence. CHO or HeLa cells were then plates at 100,000 cells/well in 1 mL F12 media with 10% FBS and 1×sodium pyruvate (CHO cells) or DMEM with 10% FBS and 1×sodium pyruvate (HeLa cells) into 12-well plates and incubated overnight at 37° C., 5% $CO_2$.

After the overnight incubation, the cells were transfected with 1 μg plasmid DNA containing 9B8, V2, or L27V with or without the secretion signal sequence using the TRANSIT®-LT1 transfection reagent (Mirus Bio) and OPTI-MEM® media (Invitrogen). The cells were again incubated overnight at 37° C., 5% $CO_2$.

After the second overnight incubation, the media was removed and saved for analysis. To the cells, 1 mL of assay buffer (1 mM CDTA, 150 mM KCl, 2 mM DTT, 100 mM MES pH 6.0, 35 mM Thiourea and 0.5% TERGITOL® NP-9 (v/v)) was added to create a cell lysate. To 10 μL of cell lysate or saved media from each sample, 50 μL assay buffer with 40 μM PBI-3939 was added, and luminescence measured as described above. FIGS. 64A-D demonstrates that 9B8, V2 and L27V variants can be used in a secretable system.

To determine the stability of the secreted variants, 150 μL aliquots of the saved media from each sample was placed at 37° C. or 50° C. The aliquots were then removed at different time points (0, 1, 2, 3, 5, 6, and 7 min), frozen on dry ice, and kept at −20° C. until assayed. To assay for stability, the media aliquots were thawed to room temperature, and 10 μL of each aliquot was mixed with assay buffer with PBI-3939 (pH 6.0) as described above. Luminescence was measured as above, and the half-life ($t_{50}$) determined (Table 34).

TABLE 34

| sample | |
|---|---|
| | ½ life 37 C. (days) |
| 9B8 | 8 |
| V2 | 10 |
| L27V | 17 |
| | ½ life 50 C. (hours) |
| 9B8 | 3 |
| V2 | 7 |
| L27V | 11 |

C. 9B8 and V2 Comparison to Secreted Luciferase of *Metridia longa*

Figures 65A, 65B:
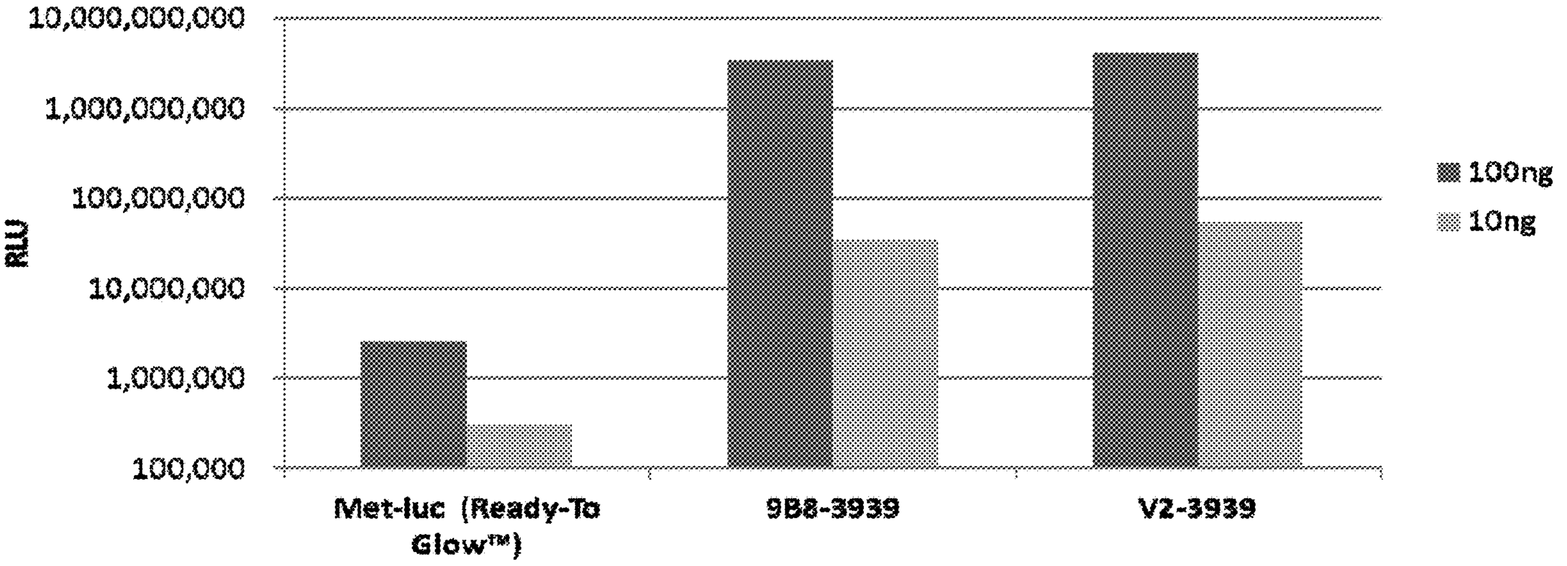
FIGS. 65A-B show a comparison of the luminescence from the secreted OgLuc variants 9B8 and V2 using PBI-3939 as a substrate to that of the secreted luciferase of *Metridia longa* using Ready-to-Glow™ as a substrate numerically (FIG. 65A) and graphically (FIG. 65B).

The secretion of the OgLuc variants 9B8 and V2 was compared to that of the secreted luciferase from *Metridia longa*. CHO cells were plated at 300,000 cells/well in 3 mL F12 media with 10% FBS into wells of 6-well plates and incubated overnight at 37° C., 5% $CO_2$. The cells were then transfected with either 10 or 100 ng of each variant or *Metridia* luciferase (Clontech) plasmid DNA using TRANSIT®-LTI according to the manufacturer's instructions and incubated for 20 hrs at 37° C., 5% $CO_2$. After transfection, the media was removed from the cells and assayed. For the OgLuc variants, 50 μL of media was assayed with 50 μL of assay reagent (previously described; 40 μM PBI-3939). For *Metridia* luciferase, the media was assayed using the Ready-to-Glo™ Secreted Luciferase Reporter System (Clontech) according to the manufacture's protocol. Briefly, 5 μL of the 1×substrate/reaction buffer was added to 50 μL of media sample. Luminescence was then measured as previously described (FIGS. 65A-B).

Figure 66B:
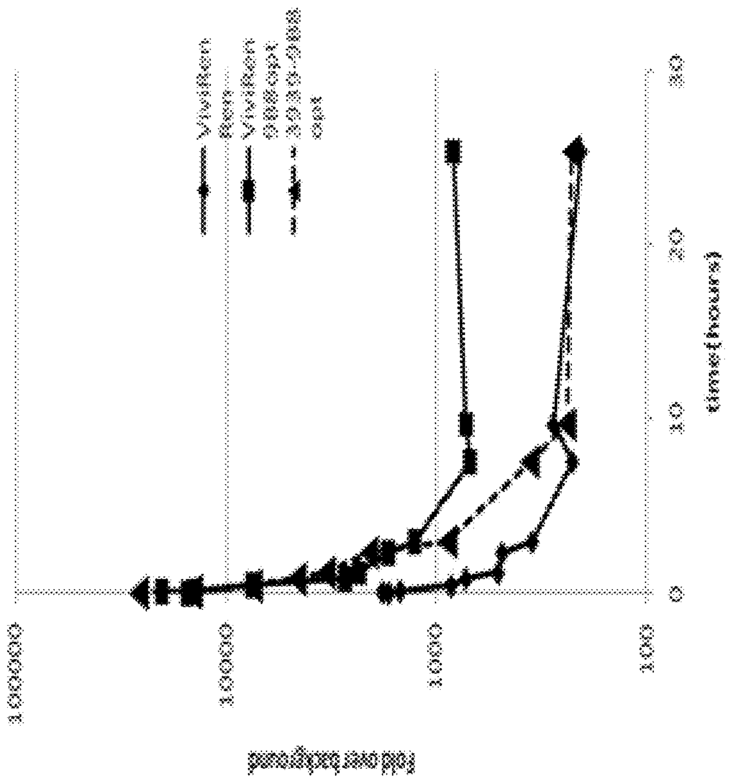
FIGS. 66A-B show the fold-increase in luminescence over background generated from HEK293 cells expressing hRL ("Ren") and 9B8 opt using the coelenterazine derivatives ENDUREN™ (FIG. 66A) and VIVIREN™ (FIG. 66B) and the novel coelenterazine PBI-3939 (FIG. 66B) as substrates.
Figure 66A:
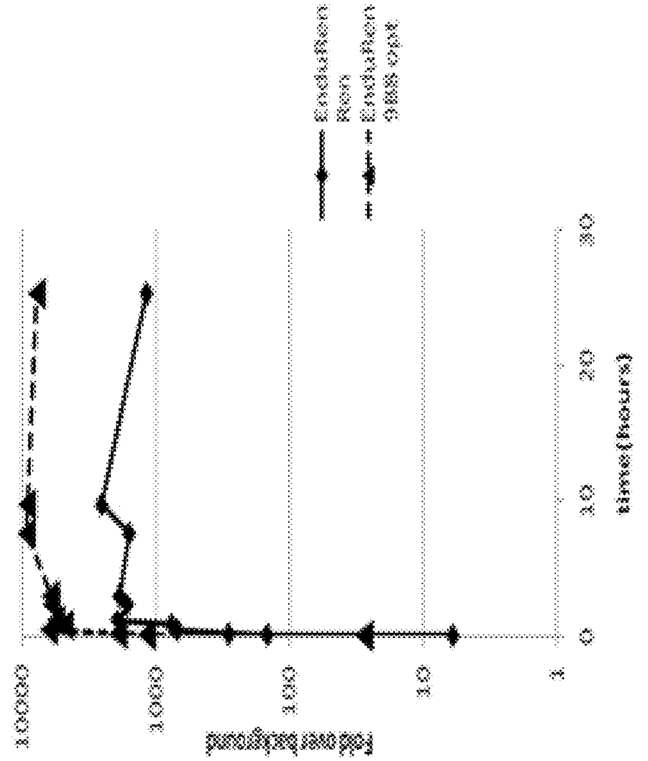

Example 43—Evaluation of OgLuc Variants and Novel Coelenterazine in Live Cells A. The use of OgLuc variants and PBI-3939 in live cells was examined. HEK293 cells were plated in 96-well plates at 15,000 cells/well and grown overnight at 37° C. The following day, the cells were transiently transfected using TRANSIT®-LT1 in 3 replicates with 100 ng of hRL or 9B8 opt in pF4Ag and grown overnight at 37° C. The following day the growth media was removed and replaced with media containing 60 μM VIVIREN™ Live Cell Substrate (Promega Corp.), 60 μM ENDUREN™ Live Cell Substrate (Promega Corp.), or 60 μM PBI-3939 for both hRL and 9B8 opt transfected cells. Non-transfected cells were used as background control. The plate was incubated at 37° C. during the course of one day and periodically measured on a TECAN® GENIOS™ Pro luminometer, i.e., 11 times over the course of 24 hrs. FIGS. 66A-B shows the luminescence of the transfected cells divided by the luminescence of the non-transfected cells for each of the substrates, i.e., the signal to background ratio. The data shows that 9B8 opt generated luminescence in a live cell setting (i.e., no lysis) by incubating cells with VIVIREN™ ENDUREN™, or PBI-3939. The data also demonstrated that PBI-3939 can permeate cells in culture, react with the OgLuc variant, and generate luminescence, thus making it compatible with use in a live cell assay.

B. To demonstrate live cell analysis using the OgLuc variants, L27V was fused to HALOTAG® and expressed and monitored in live cells. U2OS cells were plated at 40,000 cells/mL into imaging chamber wells and incubated overnight at 37° C., 5% $CO_2$. Cells were than transfected using FUGENE® HD according to the manufacturer's protocol with the plasmids pFC14K, pFN21K or pF4Ag (all Promega Corp.) containing L27V or pF4Ag containing L27V with the native or IL-6 secretion sequence. Cells were then incubated for 24 hrs at 37° C., 5% $CO_2$.

Figure 67A:
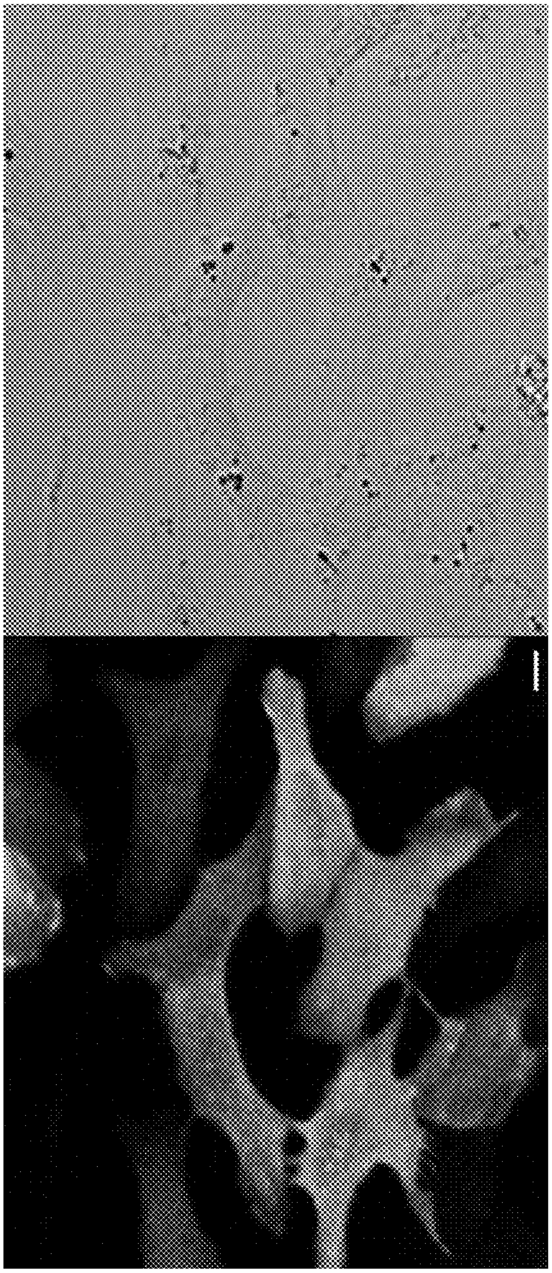
FIGS. 67A-D show confocal images of U2OS cells transiently expressing L27V-HaloTag® fusion (FIG. 67A) or IL6-L27V fusion (FIGS. 67B-D). Scale bars=20 μm.
Figure 67B:
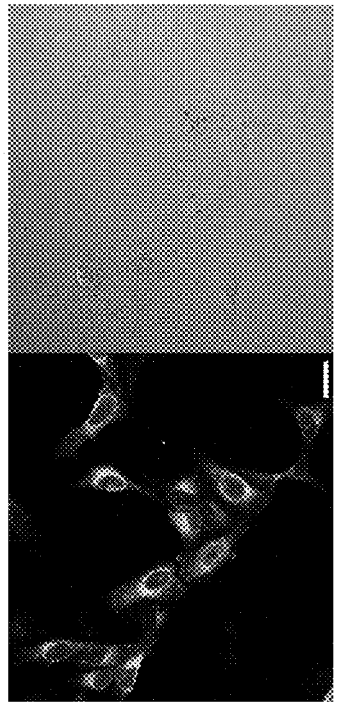

Following incubation, the cells were exposed to HALOTAG® TMR ligand (Promega Corp.), imaged, and fixed. Immunocytochemistry (ICC) was then performed according to the ICC protocol in the HALOTAG® Technology: Focus on Imaging technical manual (Promega Corp.; TM260). The primary antibody used was a polyclonal rabbit, anti-OgLuc 9B8 antibody (1:1000). The secondary antibody used was an Alexa 488 conjugated secondary antibody (green) (FIG. 67A). FIG. 67A shows green fluorescent channel and FIG. 67B shows the differential interference contrast (DIC). Images were acquired using an Olympus Fluoview FV500 confocal microscope (Olympus, USA) outfitted with a 37° C.+CO2 environmental chamber (Solent Scientific Ltd., UK).

Figure 67C:
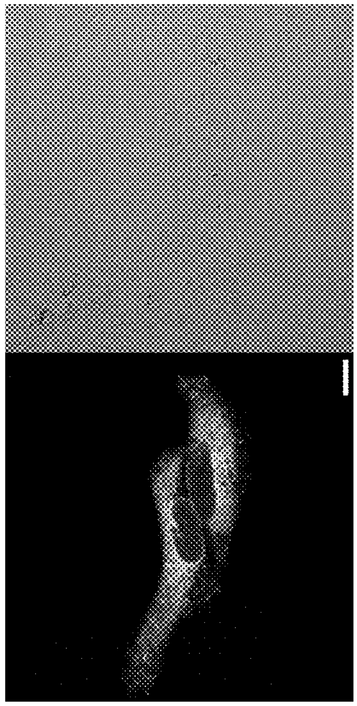
Figure 67D:
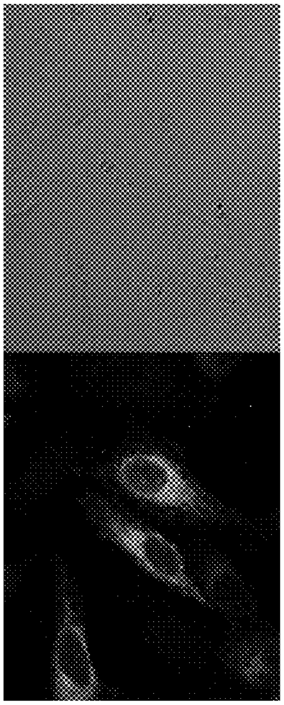

FIGS. 67B-D shows the ICC images with native or IL-6 secretion sequence. Both signal sequences dramatically decrease the amount of enzyme in the nucleus. The punctuate nature of the labeling in the cytoplasm is indicative of vesicle formation expected to occur during the secretion process. The data demonstrates that the presence of a signal peptide reduces the amount of luciferase in the nucleus.

C. As shown above, the OgLuc variants and novel substrates of the present invention are biocompatible. A reporter system is envisioned where the OgLuc variant is cloned into an expression vector with a promoter of interest and expressed in cells as a reporter protein. The cells are then treated with PBI-3939 which will permeate cells in culture, react with the OgLuc variant, and generate luminescence.

In addition to being cell permeant, PBI-3939 shows comparable biocompatibility to native coelenterazine in terms of cell viability. A version of compound 3939 containing chemical modifications known to increase the stability of native coelenterazine in media can be synthesized and used for more robust, live cell OgLuc variant-based reporter assays. Another example of live cell reporting includes the use of a secretable OgLuc variant as a reporter. The native secretion signal peptide (or other known secretion signal peptides) can be fused to the N-terminus of an OgLuc variant so that when the fusion is expressed in mammalian cells, a portion of it will be secreted through the cell membrane into the culture media. Upon addition of substrate luminescence is generated.

Example 44—Protein Fusion Reporters

The OgLuc variants of the present invention can be used as fusion tags for a target protein of interest as a way to monitor intracellular levels of that target protein. Specific proteins involved in stress response pathways, e.g., DNA damage, oxidative stress, inflammation, can be monitored in cells as a way to probe the role various types of stimuli may play in these pathways. The variants can also be used as a means to monitor cellular trafficking of a target protein. The variants can also be fused to viral genomes (e.g., HIV, HCV) so that titer levels, i.e., infectivity, can be monitored in cells following treatment with potential antiviral agents. The variants can also be fused to green fluorescent protein (GFP) or HALOTAG® (in addition to a target protein) so that FACS could be used to identify high expression clones and to provide localization information.

Example 45—Evaluation of OgLuc Variant in 3-Component Fusion Protein ("Sandwich")

3-component fusion proteins, or "sandwich" fusions, can be used to place bioluminescent and fluorescent proteins close to one another for optimization of a biosensor based on BRET.

A. C1+4AE, IV, 9B8 and 9F6

The OgLuc variants C1+4AE (SEQ ID NOs: 55 and 56), IV (SEQ ID NOs: 57 and 58), 9B8 (SEQ ID NOs: 61 and 62), and 9F6 (SEQ ID NOs: 63 and 64), and hRL (SEQ ID NOs: 32 and 33) were cloned into a pF4Ag fusion vector with an N-terminal Id (Benezra et al., *Cell,* 61(1):49-59 (1990)), known to be a poor fusion partner, and a C-terminal HT7, which was used for normalization. The gene of interest was "sandwiched" between Id and HT7, i.e., Id-Luciferase-HT7. *E. coli* lysates, containing the variant constructs in pF4Ag or pF4Ag sandwich background, were prepared as described in Example 26 and then assayed with 20 μM native coelenterazine in the buffer described in Example 25.

Figure 68:
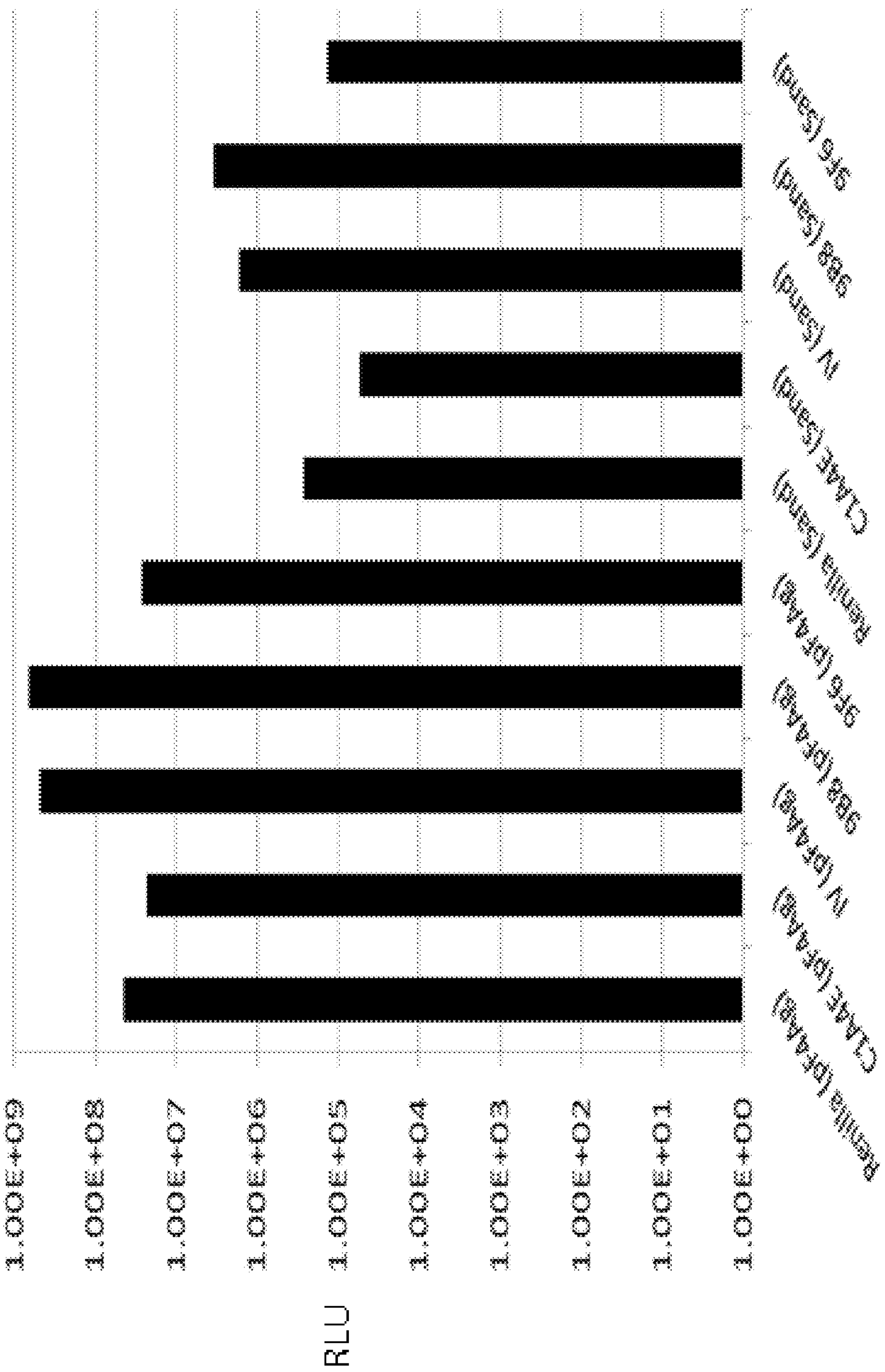
FIG. 68 shows the luminescence generated from lysed bacterial cells expressing various OgLuc variants and hRL ("*Renilla*") in the presence ("Sand") or absence of sandwich background ("pF4Ag") using native coelenterazine as a substrate.
Figure 69:
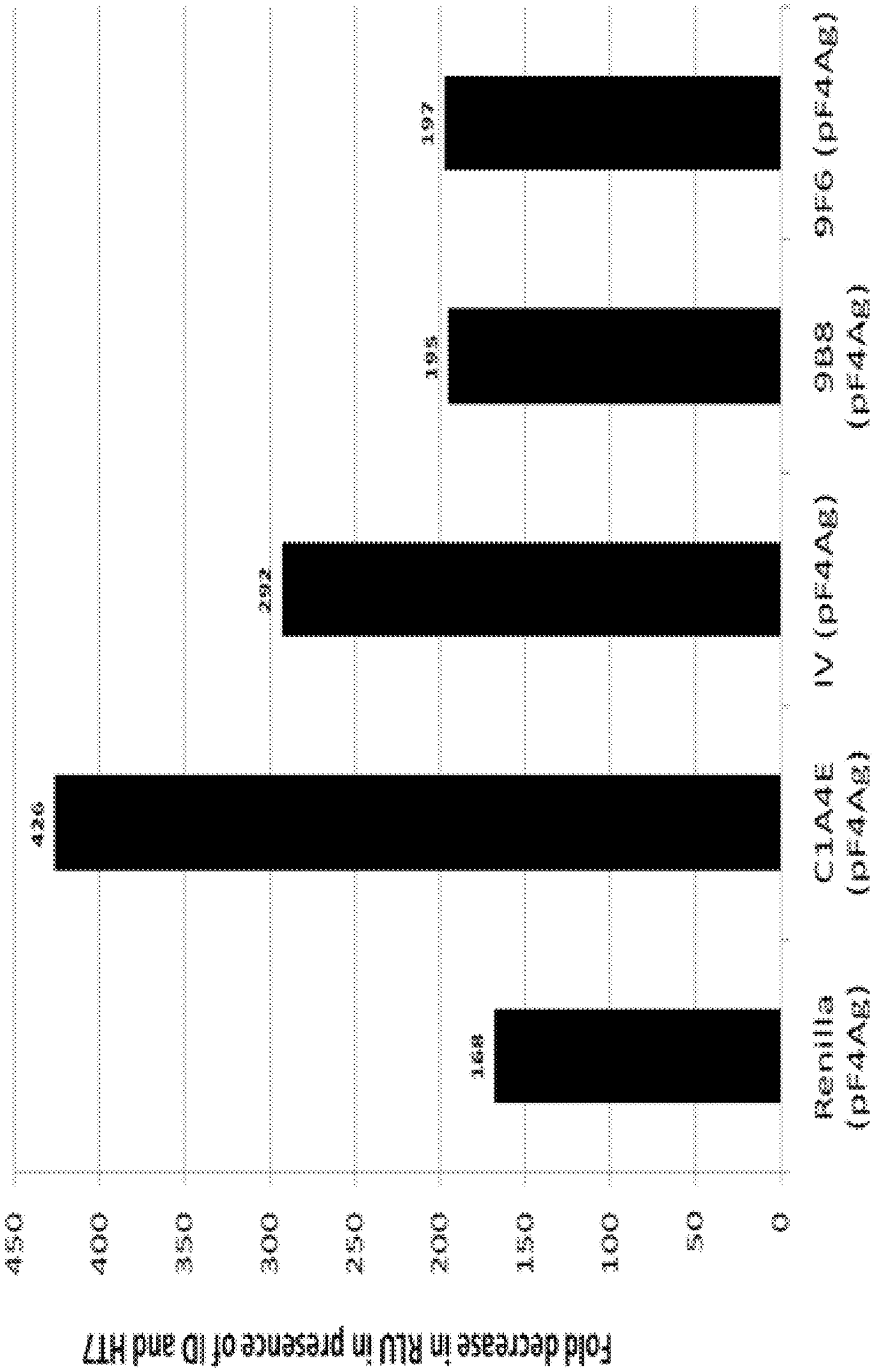
FIG. 69 shows the fold-decrease in activity of various OgLuc variants and hRL ("*Renilla*") due to the presence of the sandwich background using native coelenterazine as a substrate.

FIG. 68 shows the luminescence for each variant in either pF4Ag or pF4Ag sandwich background ("Sand"). FIG. 69 shows the fold-decrease in luminescence due to the presence of Id and HT7 and determined by dividing the luminescence of the variant in pF4Ag by the luminescence of the variant in the pF4Ag-sandwich. Samples with the largest values showed the most sensitivity to the poor fusion partner Id. The variant 9B8 was the brightest in the sandwich context.

B. 9B8 OPT AND 9B8 OPT+K33N

Figure 70:
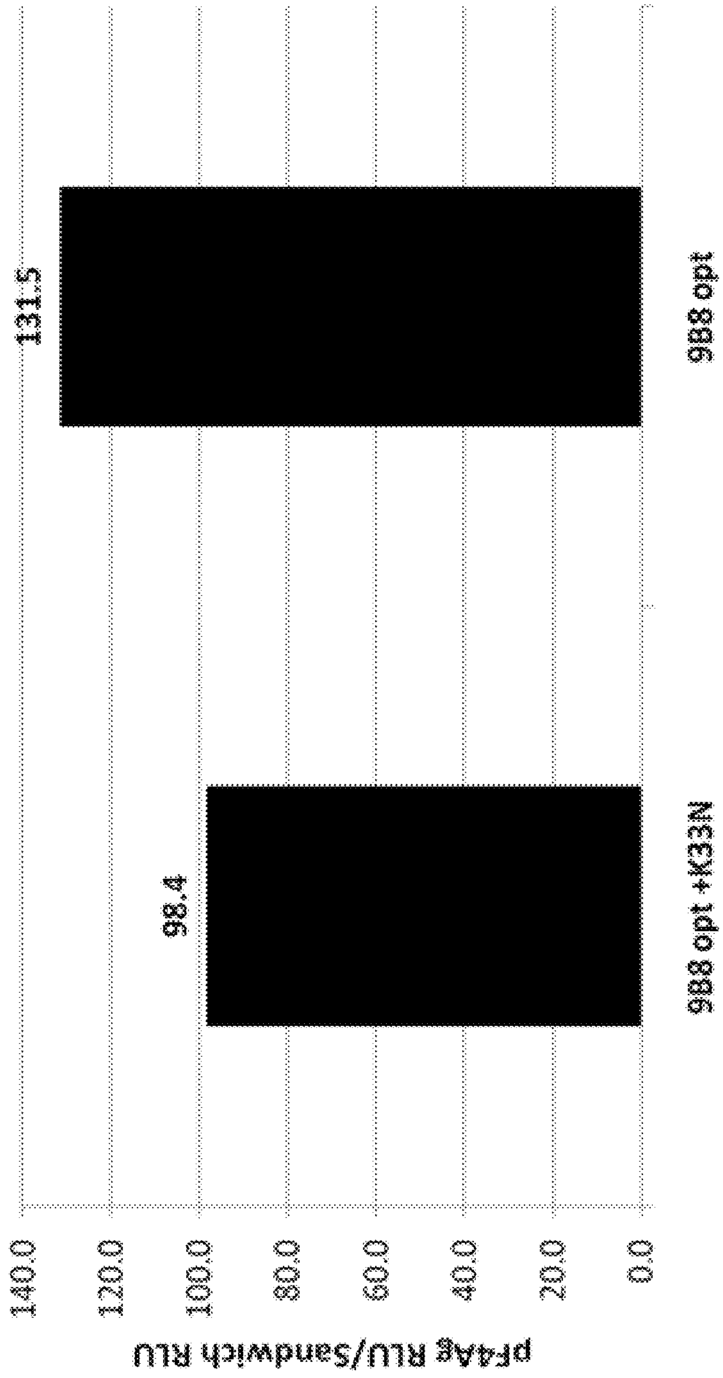
FIG. 70 shows the fold-decrease in activity of 9B8 opt and 9B8 opt+K33N in bacterial lysates due to the presence of the sandwich background using the novel coelenterazine PBI-3939 as a substrate.

The variants 9B8 opt and 9B8 opt+K33N were analyzed in a sandwich background as described above. Sandwich constructs for 9B8 opt (SEQ ID NOs: 40 and 41) and 9B8 opt+K33N (SEQ ID NOs: 59 and 60) were generated as described above. *E. coli* lysates were assayed and measured using the same assay buffer and luminometer as used for generating FIG. 40. FIG. 70 shows the fold-decrease in the presence of a sandwich background indicating that 9B8 opt+K33N is less sensitive to the poor fusion partner Id than 9B8 opt.

C. 23D2 and 24C2

Variants 23D4 (NF) and 24C2 (NF) were subcloned into the Id-OgLuc-HT7 sandwich background and assayed in *E. coli*. The sandwich variants, 23D4 (F) (SEQ ID NOs: 76 and 77) and 24C2 (F) (SEQ ID NOs: 78 and 79) were compared to 9B8 opt+K33N in the sandwich background (SEQ ID NO: 59 and 60). Table 35 shows the variants had at least the same luminescence as 9B8 opt+K33N in the sandwich background context.

TABLE 35

Increase in Luminescence Generated by OgLuc Variants Compared to 9B8 opt + K33N + 170G in Sandwich Background

| Sample | Sequence | Fold over 9B8 opt + K33N sandwich (*E. coli*) |
|---|---|---|
| 23D4 (F) | G26G, M106L, R112R, 170G | 1.0 |
| 24C2 (F) | R11Q, T39T, 170G | 1.0 |

D. 1F7 and 15H1

The PCR library in the Id-OgLuc-HT7 sandwich background was screened for additional variants with increased luminescence compared to 9B8 opt+K33N in sandwich background. Selected variants were then assayed in HEK293 and NIH3T3 cells. Table 36 shows the fold-increase in luminescence of the sandwich variants in *E. coli*, HEK293 and NIH3T3 cells, and the amino acid substitutions found in the variants. 1F7 (F) (SEQ ID NOs: 84 and 85) and 15H1 (F) (SEQ ID NOs: 86 and 87) had at least 1.3 fold-increase in luminescence in *E. coli.* 1F7 (F) was brighter than 9B8 opt+K33N in the sandwich background in HEK293 and NIH3T3 cells.

TABLE 36

Increase in Luminescence Generated by OgLuc Variants Compared to 9B8 opt + K33N in Sandwich Background

| | | Fold over 9B8 opt + K33N sandwich | | |
|---|---|---|---|---|
| Sample | Sequence | *E. coli* | HEK293 | NIH3T3 |
| 1F7 (F) | K43R, Y68D | 1.9 | 2.4 | 1.4 |
| 15H1 (F) | D19D, S66N | 1.5 | 0.9 | 1.2 |

The sandwich variants were subcloned into the pF4Ag-based non-fusion background vector to generate 1F7 (NF) (SEQ ID NOs: 80 and 81) and 15H1 (NF) (SEQ ID NOs: 82 and 83) and were analyzed as described above and compared to 9B8 opt+K33N. Table 37 shows the fold-increase in luminescence of the variants in *E. coli*, HEK293 and NIH3T3 cells. 1F7 (NF) and 15H1 (F) had at least 1.3 fold-increase in luminescence in *E. coli* and HEK293 cells.

TABLE 37

Increase in Luminescence Generated by OgLuc Variants Compared to 9B8 opt + K33N + 170G

| | | Fold over 9B8 opt + K33N + 170G | | |
|---|---|---|---|---|
| Sample | Sequence | *E. coli* | HEK293 | NIH3T3 |
| 1F7 (NF) | K43R, Y68D | 1.5 | 1.5 | 1.1 |
| 15H1 (NF) | D19D, S66N | 1.7 | 1.7 | 1.2 |

E. V2, 9B8 opt+K33N+L27V+K43R+Y68D, 9B8 opt+K33N+L27V+T39T+K43R+S66N and L27V

The variants 9B8 opt+K33N+T39T+K43R+Y68D ("V2"; SEQ ID NOs: 92 and 93), 9B8 opt+K33N+L27V+K43R+Y68D (SEQ ID NOs: 339 and 340), 9B8 opt+K33N+L27V+T39T+K43R+S66N (SEQ ID NOs: 341 and 342), and 9B8 opt+K33N+L27V+T39T+K43R+Y68D ("L27V"; SEQ ID NOs: 88 and 89) were subcloned into the Id-OgLuc-HT7 sandwich background as described above and assayed in HEK293 and NIH3T3 cells as described above. The luminescence generated by the sandwiched variants were compared to the luminescence generated by the 9B9 opt+K33N sandwich (SEQ ID NOs: 59 and 60) (Table 38). The L27V sandwich (SEQ ID NOs: 90 and 91) and V2 sandwich (SEQ ID NOs: 94 and 95) had at least 1.3× fold-increase in luminescence in HEK293 and NIH3T3 cells.

TABLE 38

Increase in Luminescence Generated by OgLuc variants in sandwich background compared to 9B8 opt + K33N in sandwich background

| Sample | NIH 3T3 cells | HEK 293 |
|---|---|---|
| K33N Sand | 1.0 | 1.0 |
| T39T, K43R, Y68D Sand | 1.6 | 2.3 |
| L27V, K43R, Y68D Sand | 1.4 | 1.7 |
| L27V, T39T, K43R, S66N Sand | 0.7 | 0.7 |
| L27V, T39T, K43R, Y68D Sand | 1.4 | 1.7 |

The sandwich and non-sandwich versions of the variants V2, 9B8 opt+K33N+L27V+K43R+Y68D, 9B8 opt+K33N+L27V+T39T+K43R+S66N, and L27V were assayed in HEK293 and NIH3T3 cells as described in Example 37. The luminescence generated by the non-sandwiched variants was compared to the luminescence generated by the sandwiched variants (Table 39). The data shown in Table 39 indicates that the fold-decrease in luminescence for the 9B8 opt+K33N sandwich was less in mammalian cells than in *E. coli* cells as shown in FIG. 70.

TABLE 39

Fold-Decrease in Luminescence of the OgLuc Variants in the Presence of Sandwich Background

| Sample | NIH 3T3 cells | HEK 293 |
|---|---|---|
| K33N | 29 | 15 |
| T39T, K43R, Y68D | 20 | 6 |
| L27V, K43R, Y68D | 22 | 8 |
| L27V, T39T, K43R, S66N | 25 | 12 |
| L27V, T39T, K43R, Y68D | 18 | 6 |

Example 46—Multiplexing

A. Lysates of *E. coli* expressing the variant 9B8 opt were prepared as previously described in Example 27 and diluted 1000-fold in DMEM without phenol red+0.1% PRIONEX®. Luminescence from a sample containing 6.3 pg/mL of purified red click beetle luciferase and *E. coli* lysate expressing the variant 9B8 opt was detected using a modified DUAL-GLO® Luciferase Assay System (Promega Corp.). DUAL-GLO® STOP&GLO® Reagent containing 20 μM coelenterazine-h and DUAL-GLO® STOP&GLO® Reagent containing 20 μM PBI 3939 were used, according to the manufacturer's protocol, to detect the red click beetle luciferase and OgLuc variant 9B8 luciferase from a single sample. Three replicates were performed.

Luminescence was detected on a Turner MODULUS™ luminometer. Table 40 shows the average luminescence generated by the red click beetle luciferase ("click beetle"), and the luminescence generated by 9B8 opt ("Ogluc") with coelenterazine-h ("coel h") or PBI-3939 ("3939"). The standard deviation ("+/−") and coefficient of variance ("CV") are also shown. A "no coelenterazine" control was performed to illustrate the amount of quenching of the red click beetle signal by the DUAL-GLO® STOP&GLO® Reagent of the DUAL-GLO® Luciferase Assay System in the absence of coelenterazine. The "no coelenterazine" control yielded a 349-fold quench. Table 40 shows that large luminescent signals from both the red click beetle and OgLuc variant 9B8 was detected in a single sample. This demonstrates that each signal can be read sequentially in a two-step assay, and the signal from the first enzyme can be quenched enough to not contribute significantly to the signal from the second enzyme.

TABLE 40

Average Luminescence Generated by the Red Click Beetle and 9B8 opt Luciferases Using a Modified DUAL-LUCIFERASE ™ Reporter Assay

| | click beetle | +/− | CV | Ogluc | +/− | CV | fold-quench | +/− coel |
|---|---|---|---|---|---|---|---|---|
| no coel | 5,061,163 | 147,145 | 2.9% | 14,504 | 214 | 1.5% | 349 | |
| coel h | 5,082,100 | 152,254 | 3.0% | 921,440 | 47,623 | 5.2% | | 64 |
| 3939 | 5,078,547 | 41,753 | 0.8% | 2,996,940 | 187,300 | 6.2% | | 207 |

B. To demonstrate that the multiplex reporter assay described above could be done in reverse, i.e., OgLuc luminescence detected first, quenched and a second luminescence detected, e.g., red click beetle or firefly luciferase, various *Renilla* luciferase inhibitors (see U.S. Published Application No. 2008/0248511) were screened for their ability to also inhibit OgLuc. Two different, previously identified, *Renilla* inhibitors, PBI-3077 and 1424, were added at various concentrations (see Table 41) to *E. coli* lysate samples expressing the variant 9B8 (diluted as above) and a buffer containing 100 mM MES pH 6.0, 1 mM CDTA, 150 mM KCl, 35 mM Thiourea, 2 mM DTT, 0.25% TERGITOL® NP-9 (v/v), 0.025% MAZU® DF 204, and 20 μM PBI-3939. Luminescence was measured as described previously except luminescence was measured using the GLOMAX®-Multi Microplate luminometer (Promega Corp.; also known as Turner MODULUS™). As shown in Table 41, both compounds were able to inhibit OgLuc luminescence. This demonstrates that an OgLuc variant can be multiplexed in a reporter assay with another luciferase wherein luminescence from an OgLuc variant is detected first in the reporter assay.

TABLE 41

The effect of PBI-3077 and PBI-1424 on Luminescence Generated by Bacterial Lysates Expressing 9B8 opt Using PBI-3939 as a Substrate

| | (mM or %) | RLU | +/− | % |
|---|---|---|---|---|
| | control | 27,794,600 | 626,862 | 100% |
| AI (3077) | 3 | 15,473,100 | 209,567 | 56% |
| mM | 0.3 | 22,210,433 | 102,888 | 80% |
| | 0.03 | 22,484,933 | 927,459 | 81% |
| AC (1424) | 0.4 | 176,868 | 9,579 | 0.64% |
| % | 0.04 | 24,267,533 | 363,861 | 87% |
| | 0.004 | 25,126,900 | 1,569,453 | 90% |

Figure 71:
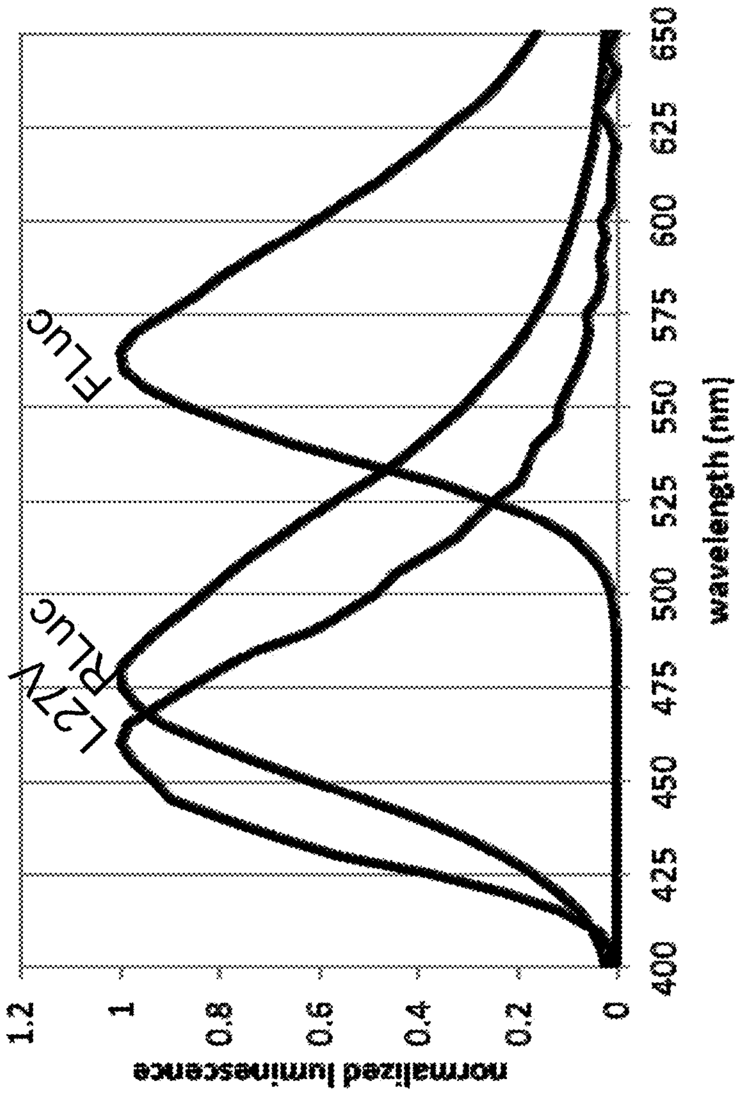
FIG. 71 shows the spectral profile of the OgLuc variant L27V.

C. The spectral resolution between OgLuc Variant L27V and firefly luciferase (Fluc) was analyzed. Purified L27V (previously described; 9.54 μM) in DMEM without phenol red+0.1% PRIONEX® was mixed with assay reagent (previously described) containing 20 μM PBI-3939. Purified firefly luciferase enzyme (QUANTILUM® Recombinant Luciferase; Promega Corp.; 271 ng/mL) in the same media was mixed with a test reagent (100 mM HEPES, pH 7.4, 1 mM CDTA, 16 mM MgSO4, 1% TERGITOL® NP-9 (v/v), 0.1% MAZU® DF 204, 5 mM ATP, 50 mM DTT, 333 μM luciferin). Purified *Renilla* luciferase (5 ng/mL GST-*Renilla*) in 1×*Renilla* Luciferase Assay Lysis Buffer (Promega Corp.) was mixed with 10.5 μM native coelenterazine in *Renilla* Luciferase Assay Buffer. Luminescence was measured after 3 min for L27V and Fluc and after 10 min for *Renilla* luciferase (FIG. 71)

D. As another example, an OgLuc variant of the present invention could be used as transcriptional reporter and paired with either aequorin or a cAMP circularly permuted firefly luciferase biosensor (or both simultaneously) to detect multiple pathways in a single sample, e.g., aequorin for the detection and/or measurement of calcium, the biosensor for the detection and/or measurement of cAMP, and an OgLuc variant for monitoring of downstream gene expression.

E. Other examples for multiplexing with the OgLuc variants of the present invention include:

i) Transfecting cells with constructs containing an OgLuc variant of the present invention and Firefly luciferase. After transfection, a first reagent could be added to lyse the cells as well as provide the substrate to generate luminescence for the first luciferase. Luminescence from the first luciferase would then be measured. A second reagent would then be added to quench luminescence from the first luciferase as well as provide the substrate to generate luminescence from the second luciferase. Luminescence from the second luciferase would then be measured. The choice of which luciferase to measure first would only depend on the ability to quench the luminescence from the first luciferase with the second reagent. For this example, luminescence from the OgLuc variant could be measured first as high concentrations of luciferin (substrate for firefly luciferase) has been shown to inhibit OgLuc variant activity.

ii) Transfecting cells with constructs containing an OgLuc variant of the present invention and Firefly luciferase. After transfection, a first reagent could be added which contained a live cell substrate to generate luminescence for the first luciferase. Luminescence from the first luciferase would then be measured. A second reagent would then be added to lyse the cells, quench luminescence from the first luciferase and provide the substrate to generate luminescence from the second luciferase. Luminescence from the second luciferase would then be measured. This is similar to i) except cell lysis will further limit usage of the live cell substrate and contribute to the quenching of luminescence from the first luciferase.

iii) Transfecting cells with constructs containing an OgLuc variant of the present invention and Firefly luciferase. After transfection, one reagent could be added which contained substrates to generate luminescence from both luciferases, but the luminescence from each luciferase is spectrally different. The emission max of the OgLuc variants is approximately 460 nm, and certain substrates for Firefly luciferase, for example 5'-chloroluciferin and 5'-methylluciferin, can yield an emission max of approximately 610 nm. Therefore, although there may be some overlap from the blue emission into the red emission, there would be no overlap of the red emission into the blue emission suggesting that little to no mathematical correction would be involved.

iv) Transfecting cells with constructs containing an OgLuc variant of the present invention and Firefly luciferase. After transfection, one reagent could be added which contained live cell substrates to generate luminescence from both luciferases. The unique feature of this example is that firefly luminescence tends to shift to red at live cell assay temperatures, e.g., 37° C., therefore, a number of different luciferin derivatives could be chosen as a live cell substrate for firefly luciferase to generate luminescence which is spectrally different from that of the OgLuc variant.

v) Transfecting cells with constructs containing an OgLuc variant of the present invention and *Renilla* luciferase. After transfection, a first reagent could be added to lyse the cells as well as provide the substrate to generate luminescence for the first luciferase. Luminescence from the first luciferase would then be measured. A second reagent would then be added to quench luminescence from the first luciferase as well as provide the substrate to generate luminescence from the second luciferase. Luminescence from the second luciferase would then be measured. The choice of which luciferase to measure first would only depend on the ability to quench the luminescence from the first luciferase with the second reagent. For this example, inhibitors to quench either the OgLuc variant or *Renilla* luciferase luminescence would need to be used.

vi) Transfecting cells with constructs containing an OgLuc variant of the present invention and click beetle luciferase. After transfection, one reagent could be added which contained substrates to generate luminescence from both luciferases, but the luminescence from each luciferase is spectrally different as click beetle luciferase generates red-shifted luminescence with native luciferin.

Example 47—Circular Permutation

Two circularly permuted (CP) versions of the L27V variant were made: CP84 and CP95. The number designation refers to the N-terminal residue (e.g., "84" indicates the new N-terminus of the CP version).

Figure 72:
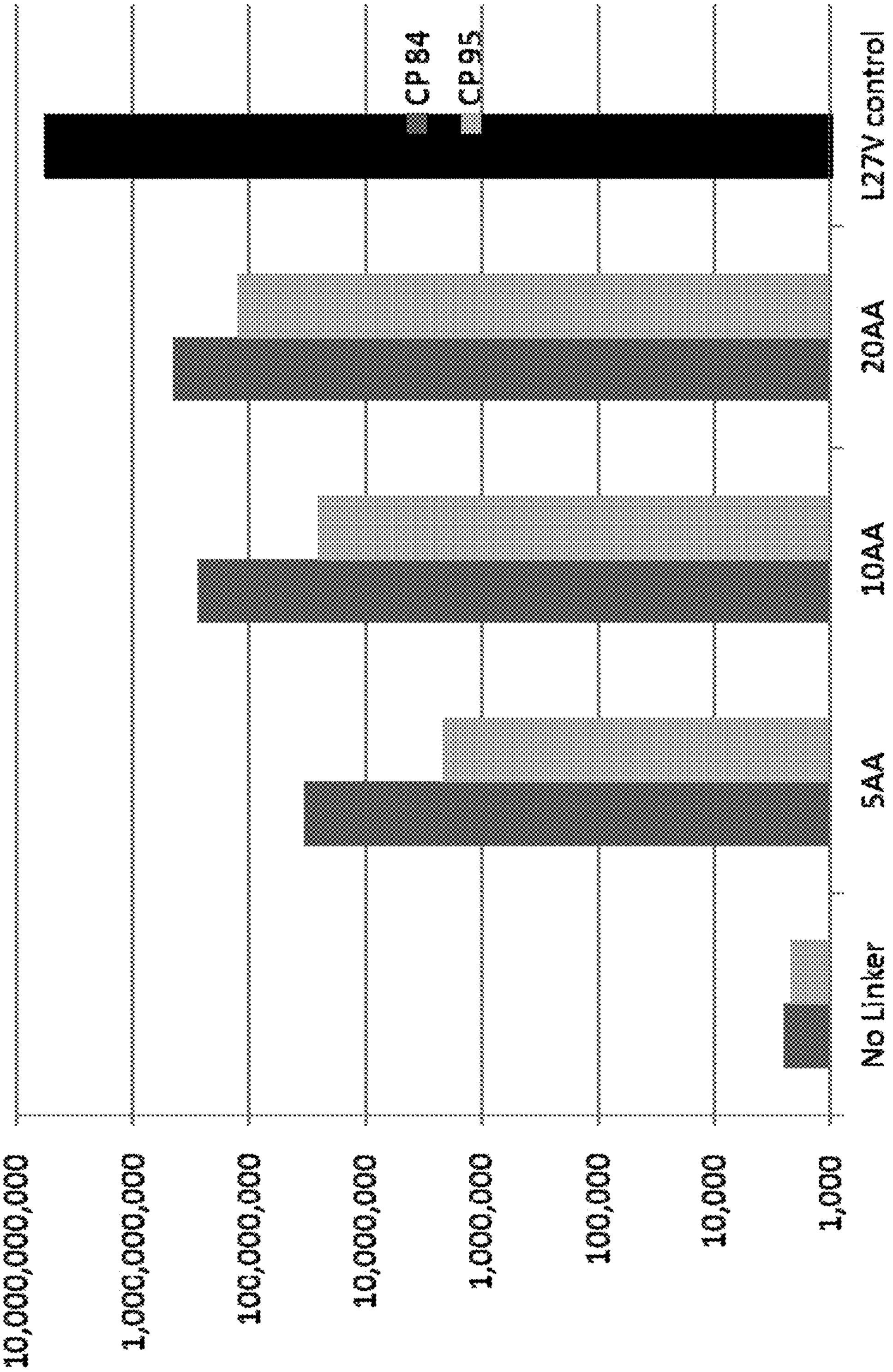
FIG. 72 shows the luminescence of two circulated permuted (CP) versions of the OgLuc variant L27V, CP84 and CP95, either with no linker or with a 5, 10, or 20 amino acid linker.

To create the circular permutations, the prior N- and C-termini are fused together with no linker ("CP84 no linker" (SEQ ID NOs: 97 and 98) and "CP95 no linker" (SEQ ID NOs: 105 and 106)) or a 5 ("CP84 5AA linker" (SEQ ID NOs: 99 and 100) and "CP95 5AA linker" (SEQ ID NOs: 107 and 108), 10 ("CP84 10AA linker" (SEQ ID NOs: 101 and 102) and "CP95 10AA linker" (SEQ ID NOs: 109 and 110), or 20 ("CP84 20AA linker" (SEQ ID NOs: 103 and 104) and "CP95 20AA linker" (SEQ ID NOs: 111 and 112) amino acid linker, (GSSGG)n (SEQ ID NO: 113) in between the N- and C-termini ends. (Note: L27V starts with the phenylalanine at the N-terminus, i.e., MVF. The "MV" is present in the "no linker" construct, but not in the "linker" constructs). Once circularly permuted, the CP L27V variants were cloned into the pF1K vector. *E. coli* cells were transformed with the CP vectors and grown in minimal media using the standard walk away induction protocol previously described. For each CP construct, cells were grown in 8 wells of a 96-well plate. After induction, the 8 wells from each sample were pooled, and 10 μL lysed in 40 μL lysis buffer (100 mM MES pH 6.0, 0.3×PLB, 0.3 mg/mL lysozyme, 0.003 U/μL DNase I, and 0.25% TERGITOL® NP-9 (v/v)). The lysates were then diluted 1:100 (CP versions with linker) or 1:1000 (non-CP versions) in lysis buffer. The CP version without linker was not diluted. The lysates or lysate dilutions were assayed in triplicate in 50 μL assay reagent (previously described). Luminescence was measured as previously described (FIG. 72).

Example 48—Identifying Additional Sites for Circular Permutation

Figure 73A:
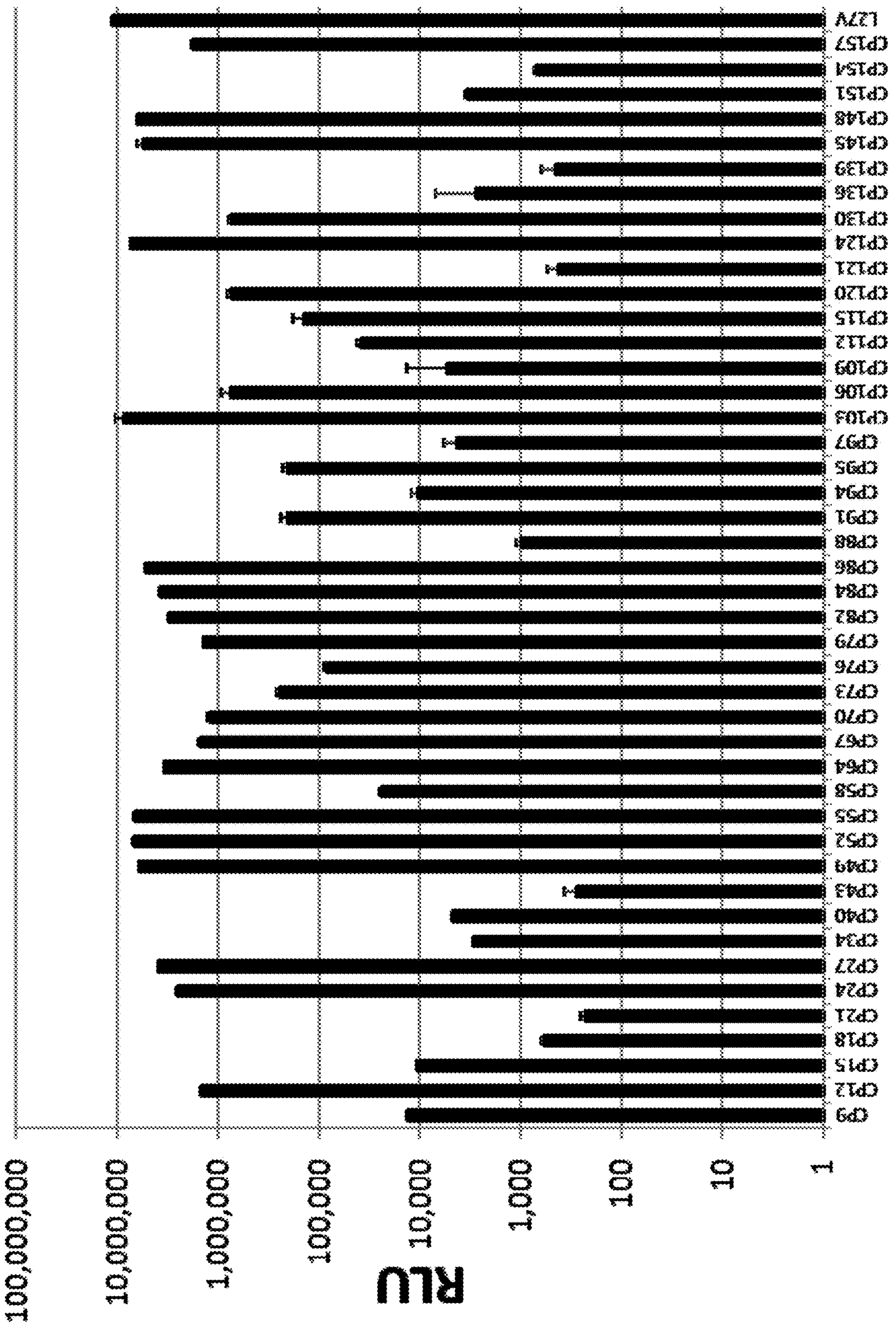
Figure 73B:
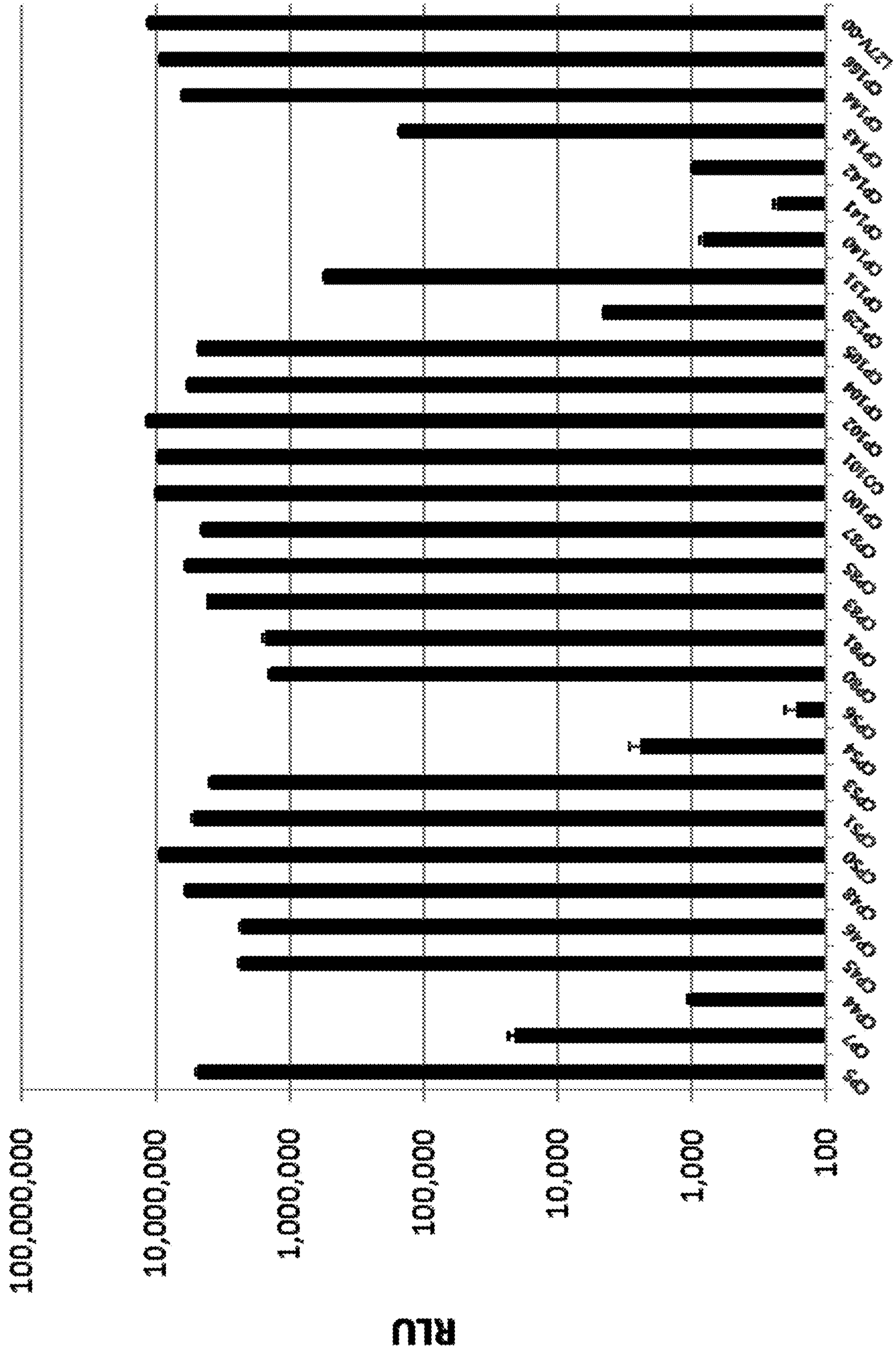
Figure 73C:
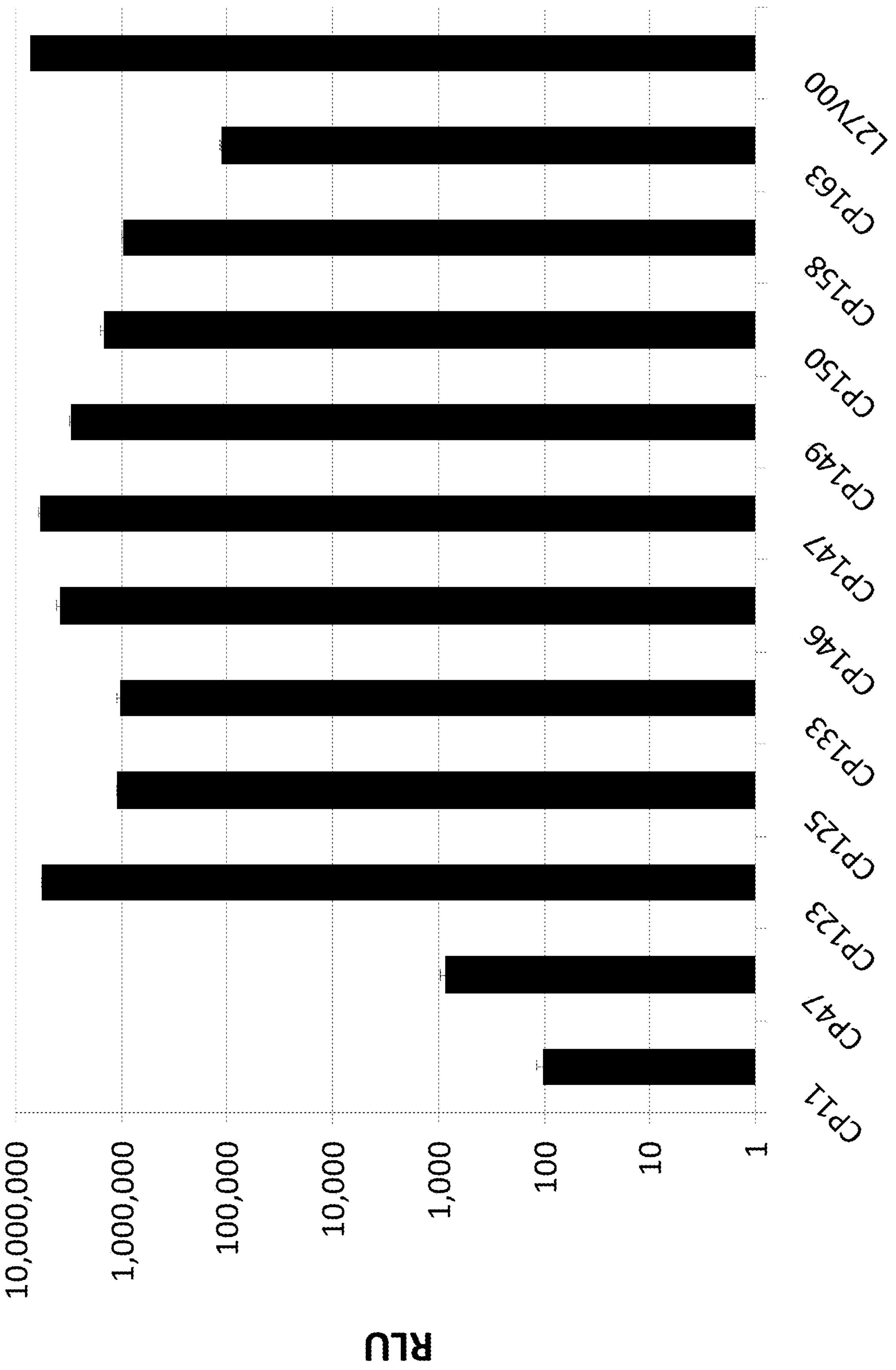
Figure 73D:
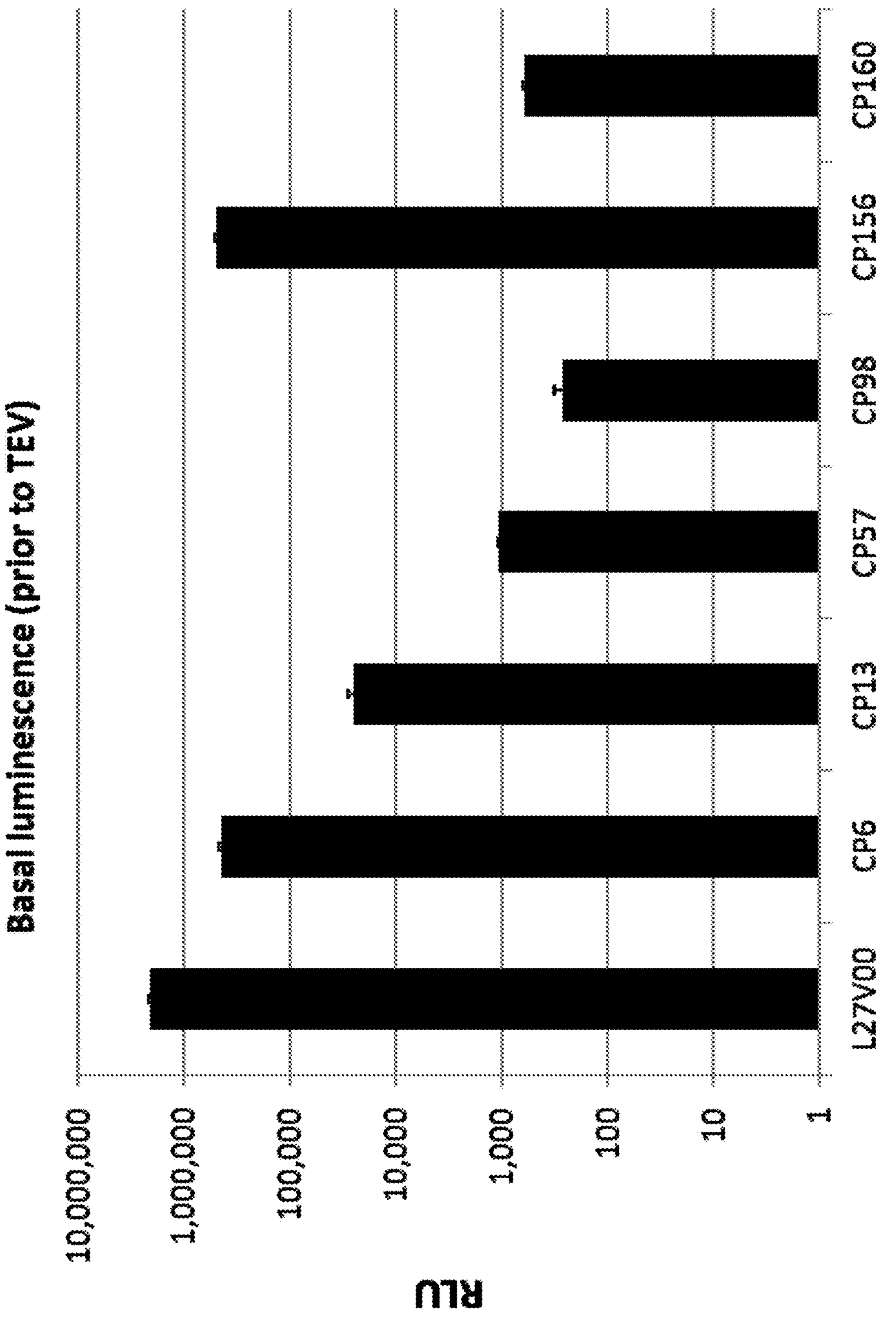

To identify additional CP sites, determine the impact of the CP sites on luciferase activity and investigate the use of a "tether" between fragments, CP constructs were made with a circular permutation made at approximately every $3^{rd}$ site (i.e., amino acid) of the L27V variant (See FIG. 73E). One skilled in the art would understand that other sites, e.g., the $1^{st}$ and $2^{nd}$ site, could also be tested and used in circular permuted OgLuc variants described herein using the methods described here. For example, the L27V variant has been found to be particularly tolerant to circular permutation, particularly situations in which a relatively large binding domain is placed in between the permuted fragments (e.g. cAMP/RIIbB-based sensors). At each site, the linker GSSGG-GSSGG-EPTT-ENLYFQS-DN-GSSGG-GSSGG (SEQ ID NO: 328) was added. The underscored sequence refers to a TEV protease recognition site. The purpose of the linker is to provide a long enough tether between the two variant fragments so they can associate in a way that produces a functional luciferase enzyme. The TEV protease recognition site was used to provide a means to disrupt the tether (in the presence of TEV protease) so that its importance to maintaining activity could be investigated. The use of the TEV protease recognition site created a mode to predict which CP sites would be useful for protein complementation assays (PCA) or for biosensor applications (e.g., insertion of a response element between the CP sites).

The activity that is seen prior to TEV cleavage represents how the two halves of the variant enzyme behaves in a tethered state. TEV binding to the recognition site causes cleavage, thereby separating the two halves of the variant enzyme. Samples that have been cleaved with TEV would represent the un-induced state and provide an indication of how much background could be expected. Lower activity after TEV cleavage indicates that the two halves cannot come together without induction. Samples that show a large loss in activity after TEV cleavage indicate sites that would function in PCA and biosensor applications. In the case of PCA, the two halves of the variant enzyme would be fused to binding partners that are able to come together (tether) after an induced binding event. In the case of a biosensor, the two halves would "tether" after a binding-induced conformational change occurs. One example for PCA would be to fuse one half of L27V to FRB and the other half to FKBP. The two halves would be brought into proximity with exposure to rapamycin (Banaszynski et al., *J. Am. Chem. Soc,* 127(13):4715-4721(2005)). One example of a biosensor application would be to insert a Cyclic AMP binding domain (e.g., RIIbB) between the CP sites and induce a conformational change by binding of Cyclic AMP to the binding domain.

Once each CP L27V construct was made, the CP enzyme was expressed in wheat germ, *E. coli* and mammalian cells and digested with TEV protease to investigate luciferase activity.

1. For analysis in wheat germ, the CP constructs were expressed using the TnT® T7 Coupled Wheat Germ Extract System (Promega Corp.) according to the manufacture's instructions. The TnT® reactions were then diluted 1:100 in 1×PBS+0.1% gelatin, and 20 μL added to 25 μL of TEV reaction reagent (5 μL 20× ProTEV buffer (Promega Corp.), 1 μL 100 mM DTT, and 2 μL 10 U ProTEV Plus (Promega Corp.)). The volume of the digestion reactions was the brought to 100 μL with water and incubated at 30° C. for 60 min. Control samples without TEV protease were also prepared. 10 μL of the digested samples were then added to 40 μl DMEM to a final volume of 50 μL and assayed in 50 μL assay reagent (as previously described; 100 μM PBI-3939). Luminescence was measured as previously described (FIGS. 73A-D).

Figures 73F, 73G:
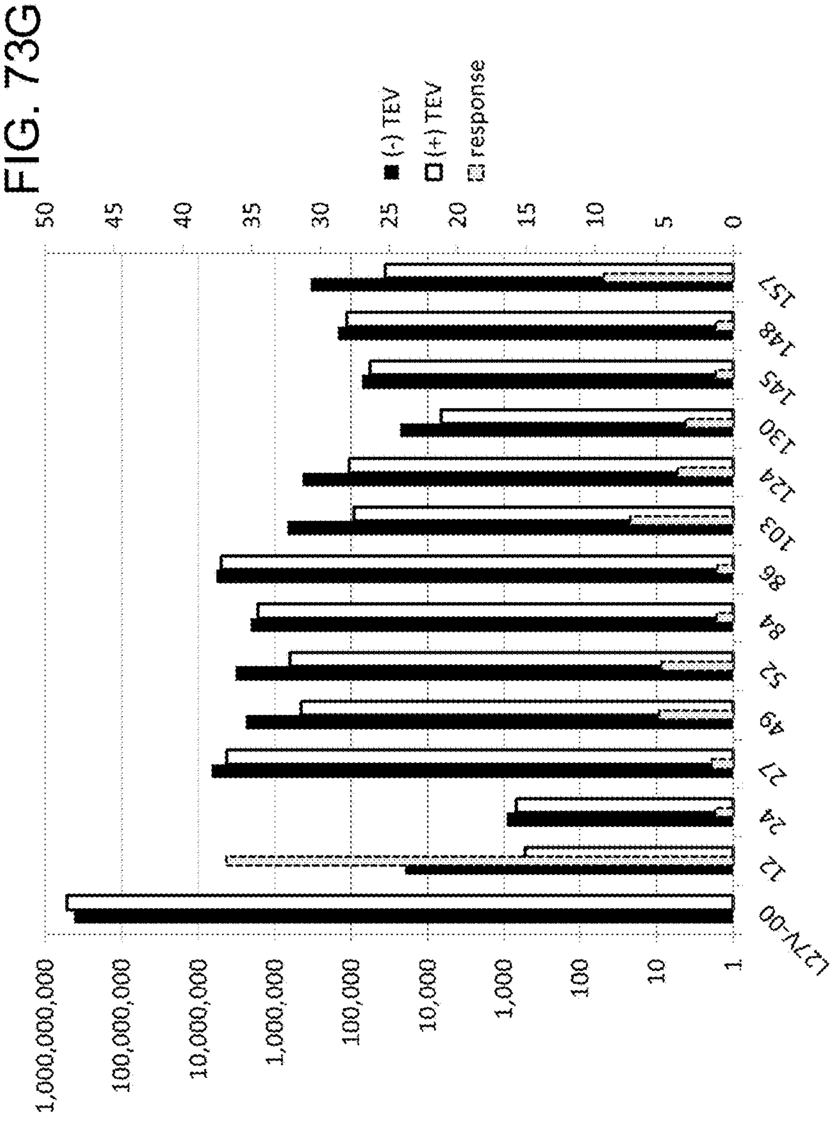
Figure 73H:
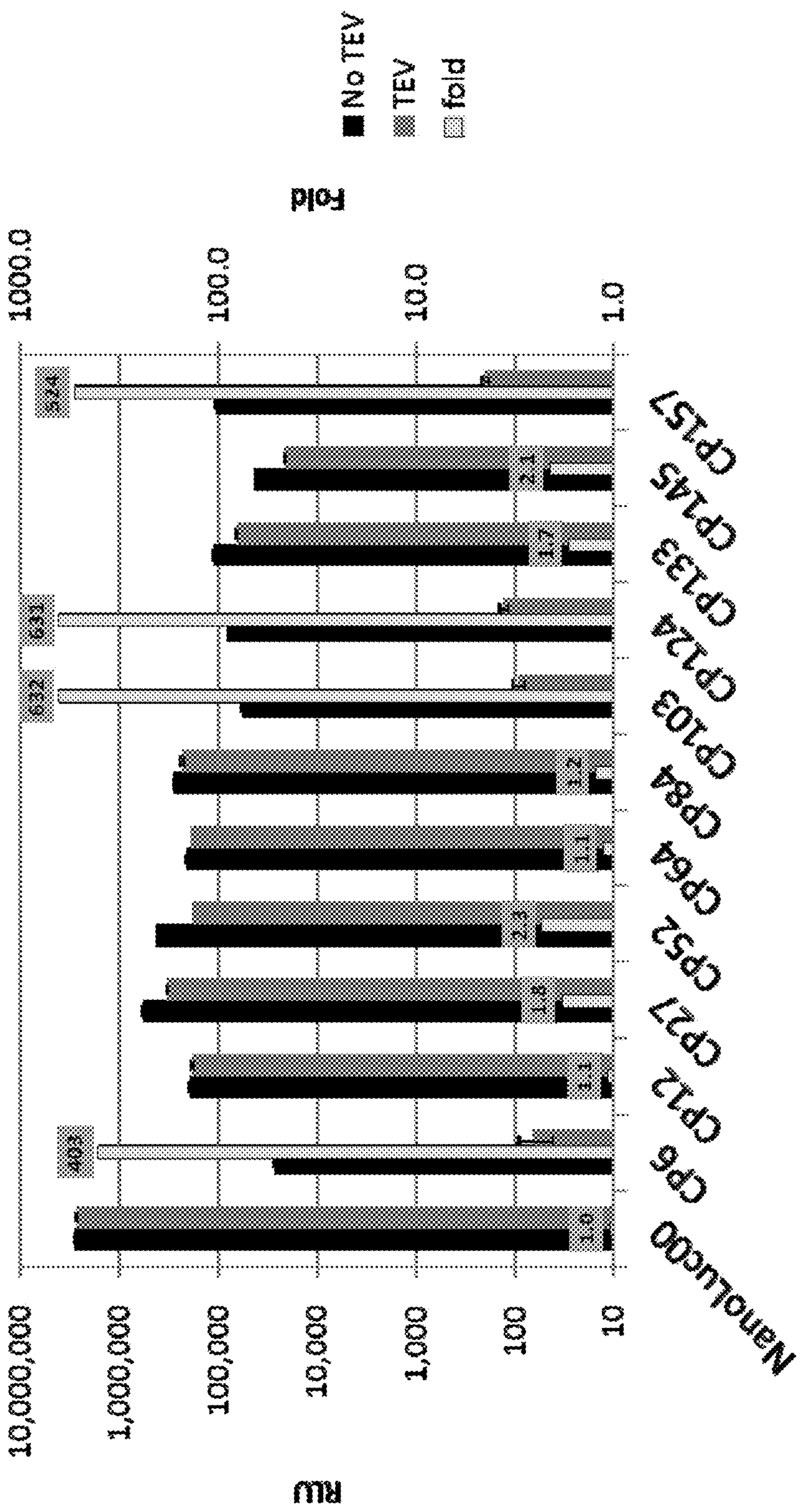

2. For analysis in mammalian cells, HEK293 cells were transfected with the CP L27V variants using a reverse transfection protocol. Briefly, 1 ng CP L27V plasmid DNA was mixed with 1 pg carrier DNA and added to cells in a well of a 12-well plate. Cells were then incubated for 16 hrs at 37° C., 5% $CO_2$. Cell lysates were then prepared by removing the media from the cells, washing them in 1×PBS, and adding 1 mL 1×PLB. Lysates were then diluted 1:10 in 1×PBS with 0.1% gelatin. 40 μL of the diluted lysate was then used in a TEV protease digestion as described above. 10 μL of the digestion was mixed with 40 μL DMEM without phenol red, and 50 μL assay reagent (previously described; 100 μM PBI-3939) added. Luminescence was measured as previously described (FIG. 73H).

3. For analysis in *E. coli, E. coli* cultures expressing the CP L27V variants were grown overnight at 30° C. These cultures were used (1:100 diluted in LB+antibiotic) to make new starter cultures for eventual induction. The starter cultures were incubated at 37° C. with shaking for 2.5 hrs ($OD_{600}$ is approximately 0.5). Rhamnose (final concentration of 0.2%) was added, the cultures moved to 25° C., and incubated with shaking for 18 hrs.

To create lysates, 50 μL 0.5×FASTBREAK™ Cell Lysis Reagent (Promega Corp.) was added to 950 μL of induced cultures, and the mixtures incubated for 30 min at 22° C. 50 μL of the lysed culture was then digested with TEV protease as described above and incubated at room temperature for 2 hrs.

For analysis, lysates were diluted 1:10,000 in HaloTag® Mammalian Purification Buffer (Promega Corp.), and 50 μL assayed in 50 μL of assay reagent (as previously described; 100 μM PBI-3939). Basal and TEV induced luminescence was measured at 5 min time points (FIG. 73F) and the response (FIG. 73G) was determined as previously described.

FIGS. 73A-D show the basal luminescence of various CP-TEV protease L27V constructs expressed in wheat germ extract. FIG. 73E summarizes the derived CP variants that responded to TEV protease (response is fold decreased), indicating that the CP variants can be used as TEV sensors, i.e., they are indicative of "tether dependence." Variants showing at least a 1.2-fold change were further validated as signification using Student's Test (unpaired p values; confidence level of 0.03). These results indicate that each CP variant is capable of generating luminescence.

Various CP-TEV protease L27V constructs were expressed in HEK293 cells. The reverse transfection protocol, previously described was used to transfect 1 ng DNA/well with 1 μg of carrier DNA. Each cell sample was grown in 1 mL of media in a 12 well plate. Cell lysates were prepared by removing media and adding 1 mL of 1×PLB. Samples were diluted 1:10 in 1×PBS+0.1% gelatin. 40 μL of the dilution sample was set up for TEV digestion. 10 μL of the digestion reaction was added to 40 μL of DMEM without phenol red and 50 μL of PBI-3939 as previously described. FIG. 73H shows the luminescence of the various CP-TEV protease L27V constructs expressed in HEK293 cells.

The data in FIGS. 73A-H demonstrates that the L27V variant can be circularly permuted at various sites, and different sites have different dependencies regarding tether length. The mammalian cell data and Wheat Germ data show similar fold reduction with TEV cleavage. The CP L27V variants that are more dependent on the tether, i.e., are more sensitive to TEV protease cleavage, are potential candidates for PCA. CP L27V variants that are less dependent on the tether may be potential candidates for self-complementation/dimerization assays.

Example 49—Protein Complementation Assays

Protein complementation assays (PCA) provide a means to detect the interaction of two biomolecules, e.g., polypeptides. PCA utilizes two fragments of the same protein, e.g., enzyme, that when brought into close proximity with each other can reconstitute into a functional, active protein. An OgLuc variant of the present invention can be separated into two fragments at a site(s) tolerant to separation. Then, each fragment of the separated OgLuc variant can be fused to one of a pair of polypeptides of interest believed to interact, e.g., FKBP and FRB. If the two polypeptides of interest do in fact interact, the OgLuc fragments then come into close proximity with each other to reconstitute the functional, active OgLuc variant. The activity of the reconstituted OgLuc variant can then be detected and measured using a native or known coelenterazine or a novel coelenterazine of the present invention. In another example, the split OgLuc variant can be used in a more general complementation system similar to lac-Z (Langley et al., *PNAS,* 72:1254-1257 (1975)) or ribonuclease S (Levit and Berger, *J. Biol. Chem.,* 251:1333-1339 (1976)). Specifically, an OgLuc variant fragment (designated "A") known to complement with another OgLuc variant fragment ("B") can be fused to a target protein, and the resulting fusion can be monitored via luminescence in a cell or a cell lysate containing fragment B. The source of fragment B could be the same cell (either in the chromosome or on another plasmid), or it could be a lysate or purified protein derived from another cell. This same fusion protein (fragment A) could be captured or immobilized using a fusion between fragment B and a polypeptide such as HALOTAG® capable of attachment to a solid support. Luminescence can then be used to demonstrate successful capture or to quantitate the amount of material captured. Methods for protein complementation can be carried out according to U.S. Published Application No. 2005/0153310, incorporated herein by reference.

1. 9B8 opt PCA constructs were made as follows:

p9B8PCA 1/4=pF5A/Met-[9B8 opt (51-169)]-GGGGSGGGSS-FRB (SEQ ID NOs: 331 and 332) & pF5A/FKBP-GGGSSGGGSG-[9B8 opt (1-50)](SEQ ID NOs: 337 and 338)

p9B8PCA 1/2=pF5A/Met-[9B8 opt (51-169)]-GGGGSGGGSS-FRB (SEQ ID NOs: 331 and 332) & pF5A/[9B8 opt (1-50)]-GGGGSGGGSS-FRB (SEQ ID NOs: 333 and 334)

p9B8PCA 2/3=pF5A/[9B8 opt (1-50)]-GGGGSGGGSS-FRB (SEQ ID NOs: 333 and 334) & pF5A/FKBP-GGGSSGGGSG-[9B8 opt (51-169)](SEQ ID NOs: 335 and 336)

p9B8PCA 3/4=pF5A/FKBP-GGGSSGGGSG-[9B8 opt (51-169)](SEQ ID NOs: 335 and 336) & pF5A/FKBP-GGGSSGGGSG-[9B8 opt (1-50)](SEQ ID NOs: 337 and 338)

The PCA constructs were transfected into HEK293 cells (15,000 cells/well) into a 96-well plate using FUGENE®

Figure 74:
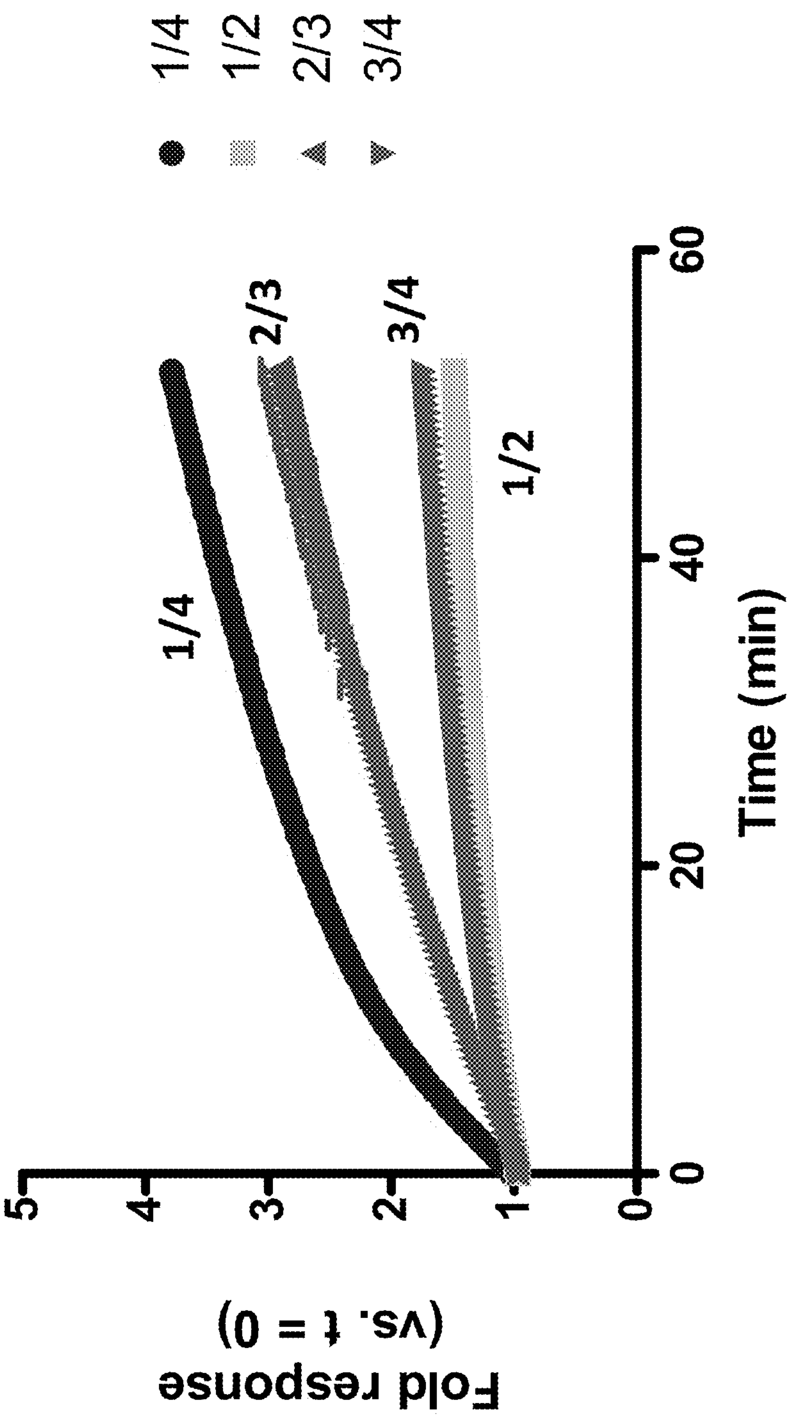
FIG. 74 shows the fold response of various protein complementation L27V pairs.
Figure 75A:
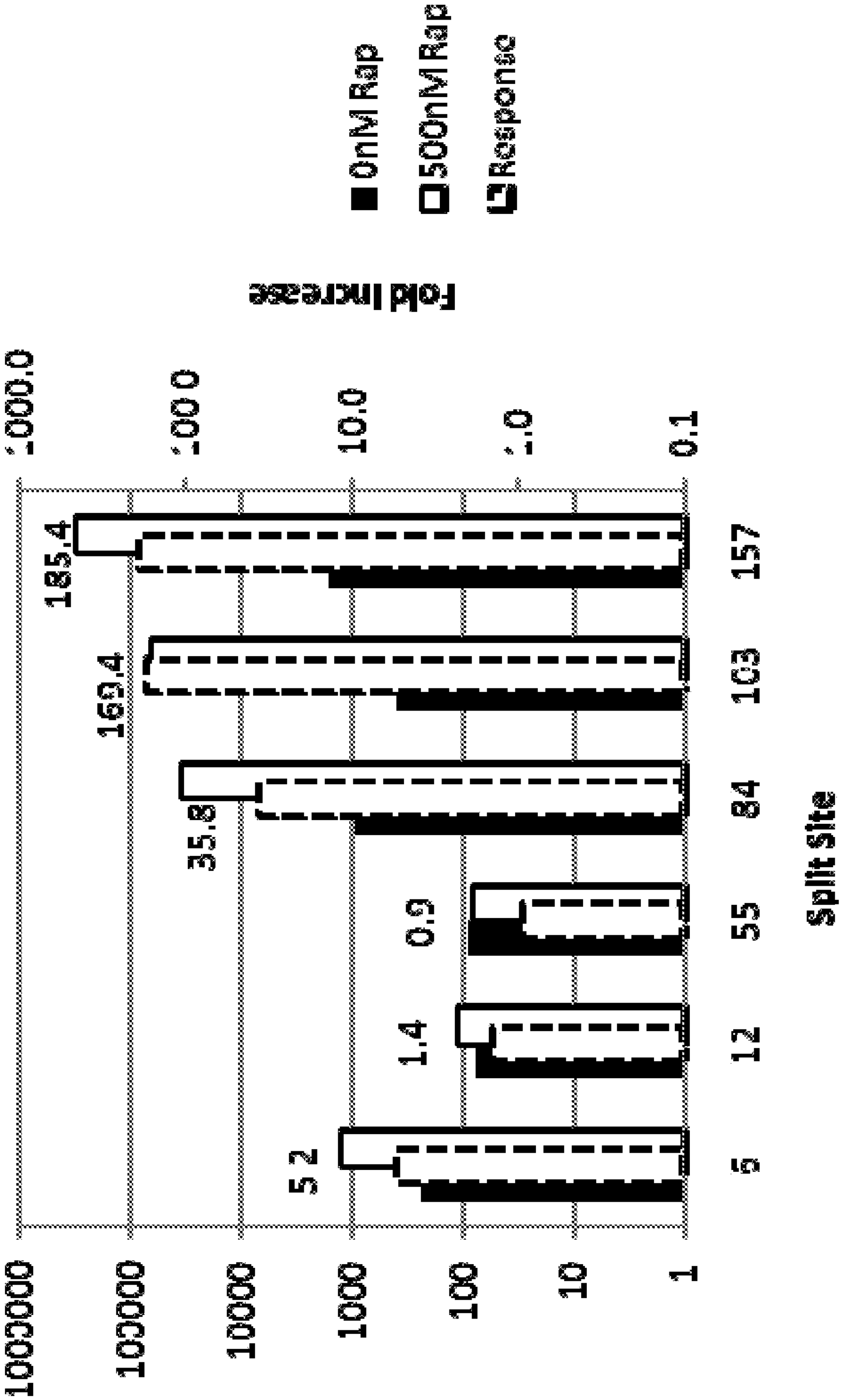
FIGS. 75A-C show the luminescence of various protein complementation (PCA) L27V pairs: one L27V fragment of each pair was fused to either FKBP or FRB using a 1/4 configuration (FIG. 75A) or a 2/3 configuration (FIG. 75B), and the interaction of FKBP and FRB monitored in HEK 293 cells. The luminescence of various protein complementation (PCA) negative controls was also monitored (FIG. 75C).
Figure 75B:
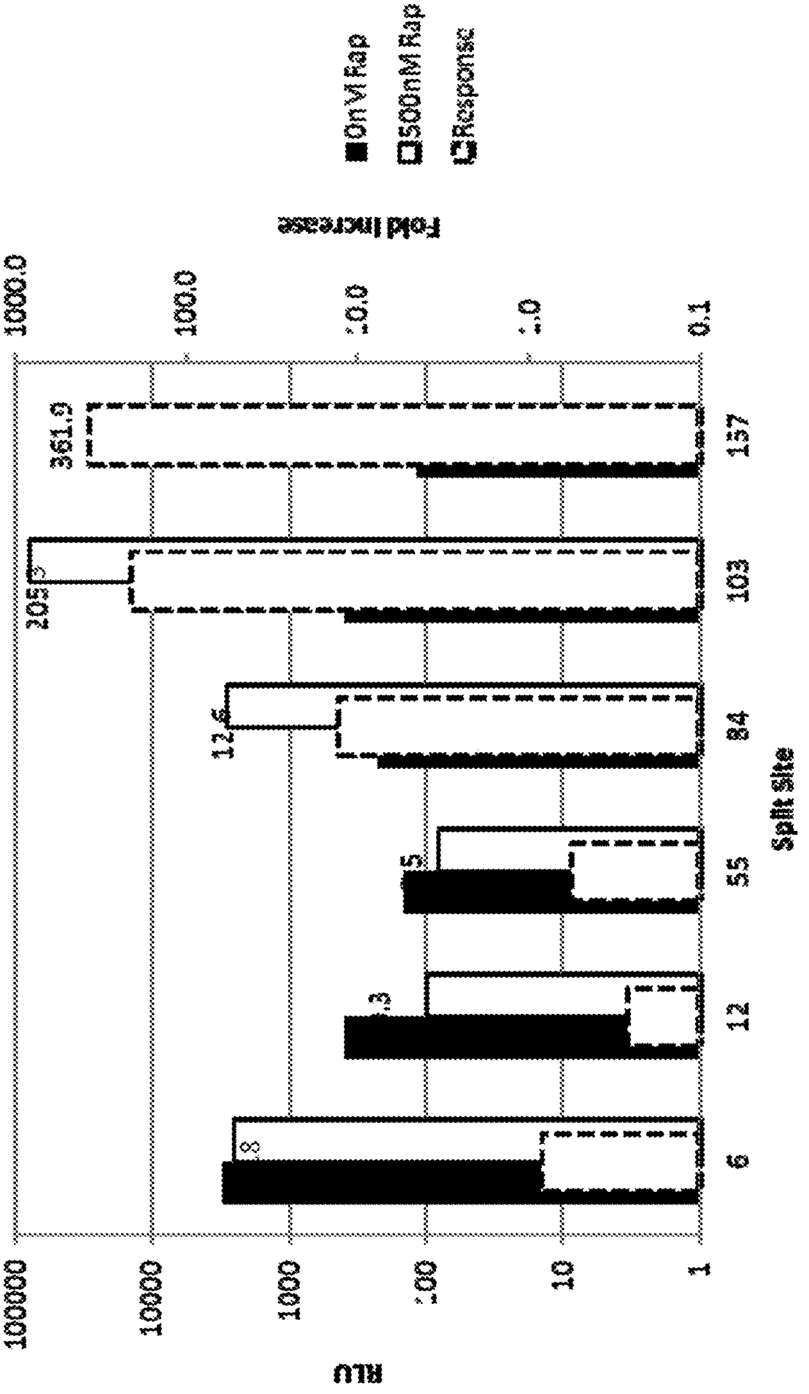
Figure 75C:
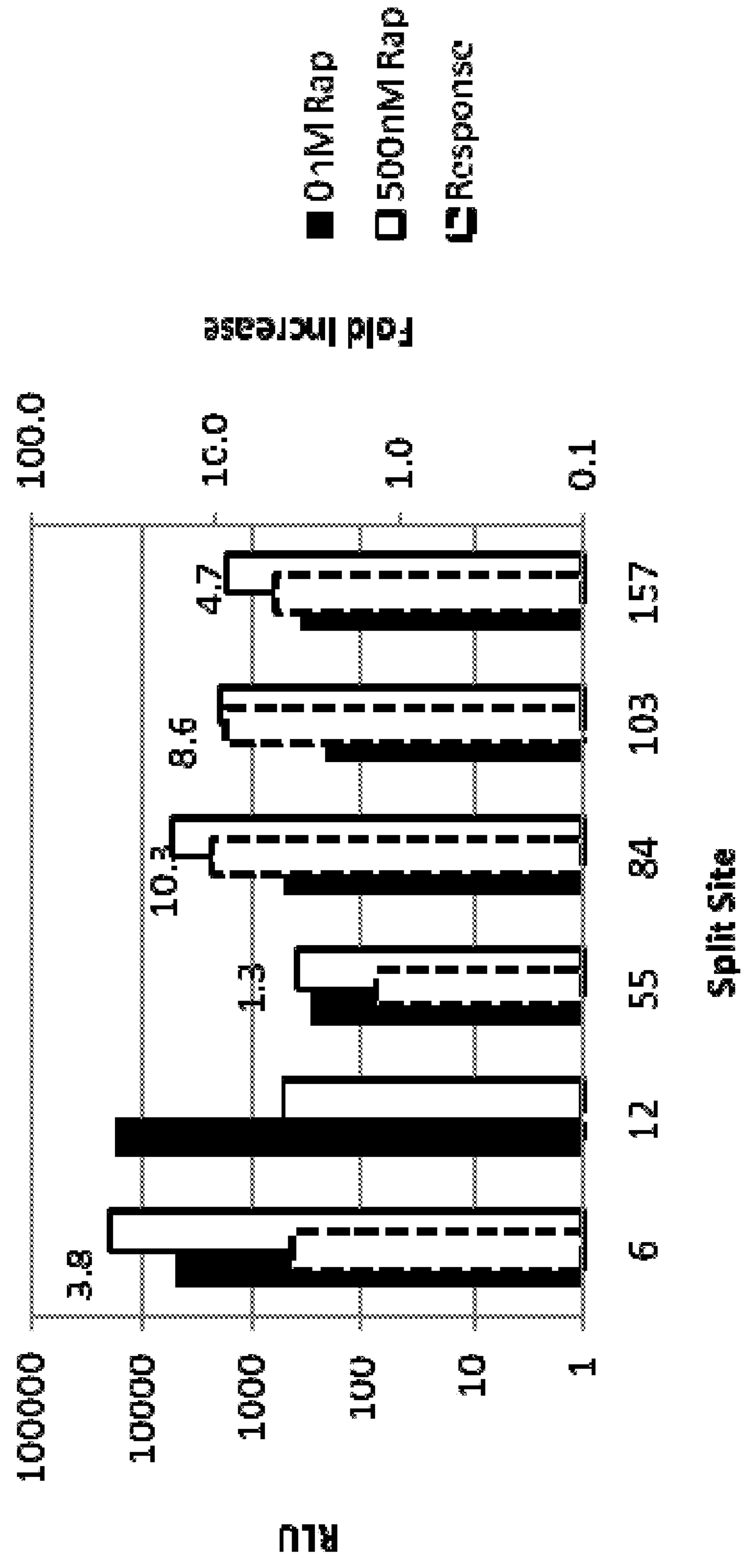

HD according to the manufacturer's instructions. The cells were then incubated overnight at 37° C., 5% $CO_2$. After transfection, the media on the cells was replaced with $CO_2$-independent media with 10% FBS. Assay reagent with 20 μM PBI-3939 was then added, and luminescence measured on a Varioskan Flash at 28° C. 100 μM rapamycin was then added to the wells, and luminescence continuously measured for 1 hr. Fold response was calculated by dividing all luminescence of a given well by the pre-rapamycin treatment luminescence for the same well (FIG. 74).

2. To demonstrate the use of the OgLuc variants in PCA, the L27V02A variant fragments were complementated with FKBP or FRB, and the interaction between FKBP and FRB measured.

Table 42 lists the various protein complementation (PCA) constructs made and tested. "2/3" designates the variant complementation pairs where 1) the "old" C-terminus of L27V02A ("old"=original C-terminus of L27V02A) is the C-terminal partner of FKBP; and 2) the "old" N-terminus of L27V02A is the N-terminal partner of FRB. "1/4" designates the variant pairs where 1) the "old" N-terminus of L27V02A is the C-terminal partner of FKBP; and 2) the "old" C-terminus of L27V02A is the N-terminal partner of FRB. For all constructs, FKBP was located at the N-terminus of the L27V02A fragment, and FRB was located at the C-terminus of the L27V02A fragment. For example, PCA constructs were made with split sites at position 157 (see Table 42, "2/3" and "1/4" #s 11 and 12 (SEQ ID NOs: 288-295)), 103 (see Table 42, "2/3" and "1/4" #s 9 and 10 (SEQ ID NOs: 296-303)), and 84 (see Table 42, "2/3" and "1/4" #s 7 and 8 (SEQ ID NOs: 304-315)). Other PCA constructs were made (SEQ ID NOs: 343-426 and 428-440) (See Table 21)

TABLE 42

| "⅔" | | "¼" | |
|---|---|---|---|
| 1. | FKBP-L27V 6-169 | 1. | FKBP-L27V 1-5 |
| 2. | L27V 1-5-FRB | 2 | L27V 6-169-FRB |
| 3. | FKBP-L27V 12-169 | 3. | FKBP-L27V 1-11 |
| 4. | L27V 1-11-FRB | 4. | L27V 12-169-FRB |
| 5. | FKBP-L27V 55-169 | 5. | FKBP-L27V 1-54 |
| 6. | L27V 1-54-FRB | 6. | L27V 55-169-FRB |
| 7. | FKBP-L27V 84-169 | 7. | FKBP-L27V 1-83 |
| 8. | L27V 1-83-FRB | 8. | L27V 84-169-FRB |
| 9. | FKBP-L27V 103-169 | 9. | FKBP-L27V 1-102 |
| 10. | L27V 1-102-FRB | 10. | L27V 103-169-FRB |
| 11. | FKBP-L27V 157-169 | 11. | FKBP-L27V 1-156 |
| 12. | L27V 1-156-FRB | 12. | L27V 157-169-FRB |
| 1. | FKBP-L27V 6-169 | 1. | FKBP-L27V 1-5 |
| 2. | L27V 1-5-FRB | 2. | L27V 6-169-FRB |
| 3. | FKBP-L27V 12-169 | 3. | FKBP-L27V 1-11 |
| 4. | L27V 1-11-FRB | 4. | L27V 12-169-FRB |
| 5. | FKBP-L27V 55-169 | 5. | FKBP-L27V 1-54 |
| 6. | L27V 1-54-FRB | 6. | L27V 55-169-FRB |
| 7. | FKBP-L27V 84-169 | 7. | FKBP-L27V 1-83 |
| 8. | L27V 1-83-FRB | 8. | L27V 84-169-FRB |
| 9. | FKBP-L27V 103-169 | 9. | FKBP-L27V 1-102 |
| 10. | L27V 1-102-FRB | 10. | L27V 103-169-FRB |
| 11. | FKBP-L27V 157-169 | 11. | FKBP-L27V 1-156 |
| 12. | L27V 1-156-FRB | 12. | L27V 157-169-FRB |

TABLE 21

| pCA constructs |
|---|
| SEQ ID NO: 343 (pCA 31 pCA L27V02A 45-169 FRB) |
| SEQ ID NO: 344 (pCA 31 pCA L27V02A 45-169 FRB) |
| SEQ ID NO: 345 (pCA 32 FKBP L27V02A 1-44) |
| SEQ ID NO: 346 (pCA 32 FKBP L27V02A 1-44) |

TABLE 21-continued

| pCA constructs |
|---|
| SEQ ID NO: 347 (pCA 33 pCA L27V02A 46-169 FRB) |
| SEQ ID NO: 348 (pCA 33 pCA L27V02A 46-169 FRB) |
| SEQ ID NO: 349 (pCA 34 pCA FKBP 1-45 L27V02A) |
| SEQ ID NO: 350 (pCA 34 pCA FKBP 1-45 L27V02A) |
| SEQ ID NO: 351 (pCA 35 pCA L27V02A 100-169 FRB) |
| SEQ ID NO: 352 (pCA 35 pCA L27V02A 100-169 FRB) |
| SEQ ID NO: 353 (pCA 36 FKBP L27V02A 1-99) |
| SEQ ID NO: 354 (pCA 36 FKBP L27V02A 1-99) |
| SEQ ID NO: 355 (pCA 37 L27V02A 101-169 FRB) |
| SEQ ID NO: 356 (pCA 37 L27V02A 101-169 FRB) |
| SEQ ID NO: 357 (pCA 38 FKBP 1-100 L27V02A) |
| SEQ ID NO: 358 (pCA 38 FKBP 1-100 L27V02A) |
| SEQ ID NO: 359 (pCA 39 L27V02A 102-169 FRB) |
| SEQ ID NO: 360 (pCA 39 L27V02A 102-169 FRB) |
| SEQ ID NO: 361 (pCA 40 FKBP L27V02A 1-101) |
| SEQ ID NO: 362 (pCA 40 FKBP L27V02A 1-101) |
| SEQ ID NO: 363 (pCA 41 L27V02A 143-169 FRB) |
| SEQ ID NO: 364 (pCA 41 L27V02A 143-169 FRB) |
| SEQ ID NO: 365 (pCA 42 FKBP 1-142 L27V02A) |
| SEQ ID NO: 366 (pCA 42 FKBP 1-142 L27V02A) |
| SEQ ID NO: 367 (pCA 43 L27V02A 145-169 FRB) |
| SEQ ID NO: 368 (pCA 43 L27V02A 145-169 FRB) |
| SEQ ID NO: 369 (pCA 44 FKBP 1-144 L27V02A) |
| SEQ ID NO: 370 (pCA 44 FKBP 1-144 L27V02A) |
| SEQ ID NO: 371 (pCA 45 L27V02A 147-169 FRB) |
| SEQ ID NO: 372 (pCA 45 L27V02A 147-169 FRB) |
| SEQ ID NO: 373 (pCA 46 FKBP- L27V02A 1-146) |
| SEQ ID NO: 374 (pCA 46 L27V02A-FKBP 1-146) |
| SEQ ID NO: 375 (pCA 47 L27V02A 148-169 FRB) |
| SEQ ID NO: 376 (pCA 47 L27V02A 148-169 FRB) |
| SEQ ID NO: 377 (pCA 48 FKBP- L27V02A 1-147) |
| SEQ ID NO: 378 (pCA 48 FKBP- L27V02A 1-147) |
| SEQ ID NO: 379 (pCA 49 L27V02A 156-169 FRB) |
| SEQ ID NO: 380 (pCA 49 L27V02A 156-169 FRB) |
| SEQ ID NO: 381 (pCA 50 FKBP-L27V02A 1-155) |
| SEQ ID NO: 382 (pCA 50 FKBP-L27V02A 1-155) |
| SEQ ID NO: 383 (pCA 51 L27V02A 158-169 FRB) |
| SEQ ID NO: 384 (pCA 51 L27V02A 158-169 FRB) |
| SEQ ID NO: 385 (pCA 52 FKBP 1-157 L27V02A) |
| SEQ ID NO: 386 (pCA 52 FKBP 1-157 L27V02A) |
| SEQ ID NO: 387 (pCA 53 L27V02A 166-169 FRB) |
| SEQ ID NO: 388 (pCA 53 L27V02A 166-169 FRB) |
| SEQ ID NO: 389 (pCA 54 FKBP L27V02A 1-165) |
| SEQ ID NO: 390 (pCA 54 FKBP L27V02A 1-165) |
| SEQ ID NO: 391 (pCA 55 FKBP L27V02A 1-47) |
| SEQ ID NO: 392 (pCA 55 FKBP L27V02A 1-47) |
| SEQ ID NO: 393 (pCA 56 L27V02A 48-169-FRB) |
| SEQ ID NO: 394 (pCA 56 L27V02A 48-169-FRB) |
| SEQ ID NO: 395 (pCA 57 FKBP L27V02A 1-49) |
| SEQ ID NO: 396 (pCA 57 FKBP L27V02A 1-49) |
| SEQ ID NO: 397 (pCA 58 pCA L27V02A 50-169 FRB) |
| SEQ ID NO: 398 (pCA 58 pCA L27V02A 50-169 FRB) |
| SEQ ID NO: 399 (pCA 59 FKBP L27V02A 1-82) |
| SEQ ID NO: 400 (pCA 59 FKBP L27V02A 1-82) |
| SEQ ID NO: 401 (pCA 60 L27V02A 83-169-FRB) |
| SEQ ID NO: 402 (pCA 60 L27V02A 83-16-FRB) |
| SEQ ID NO: 403 (pCA 61 FKBP L27V02A 1-84) |
| SEQ ID NO: 404 (pCA 61 FKBP L27V02A 1-84) |
| SEQ ID NO: 405 (pCA 62 L27V02A 85-169-FRB) |
| SEQ ID NO: 406 (pCA 62 L27V02A 85-169-FRB) |
| SEQ ID NO: 407 (pCA 63 FKBP L27V02A 1-122) |
| SEQ ID NO: 408 (pCA 63 FKBP L27V02A 1-122) |
| SEQ ID NO: 409 (pCA 64 L27V02A 123-169-FRB) |
| SEQ ID NO: 410 (pCA 64 L27V02A 123-169-FRB) |
| SEQ ID NO: 411 (pCA 65 FKBP L27V02A 1-123) |
| SEQ ID NO: 412 (pCA 65 FKBP L27V02A 1-123) |
| SEQ ID NO: 413 (pCA 66 L27V02A 124-169 FRB) |
| SEQ ID NO: 414 (pCA 66 L27V02A 124-169 FRB) |
| SEQ ID NO: 415 (pCA 67 L27V02A 1-168) |
| SEQ ID NO: 416 (pCA 67 L27V02A 1-168) |
| SEQ ID NO: 417 (pCA 67 L27V02A 1-168) |
| SEQ ID NO: 418 (*pCA 68 L27V02A 169 FRB) |
| SEQ ID NO: 419 (*pCA 68 L27V02A 169 FRB) |
| SEQ ID NO: 420 (pCA 69 FKBP L27V02A 1-166) |
| SEQ ID NO: 421 (pCA 69 FKBP L27V02A 1-166) |
| SEQ ID NO: 422 (*pCA 70 L27V02A 167-169 FRB) |
| SEQ ID NO: 423 (*pCA 70 L27V02A 167-169 FRB) |
| SEQ ID NO: 424 (pCA 71 FKBP L27V02A 1-164) |

TABLE 21-continued

| pCA constructs |
| --- |
| SEQ ID NO: 425 (pCA 71 FKBP L27V02A 1-164) |
| SEQ ID NO: 426 (pCA 72 L27V02A 165-169 FRB) |
| SEQ ID NO: 428 (pCA 72 L27V02A 165-169 FRB) |
| SEQ ID NO: 429 (pCA 73 FKBP L27V02A 1-162) |
| SEQ ID NO: 430 (pCA 73 FKBP L27V02A 1-162) |
| SEQ ID NO: 431 (pCA 74 L27V02A 163-169 FRB) |
| SEQ ID NO: 432 (pCA 74 L27V02A 163-169 FRB) |
| SEQ ID NO: 433 (pCA 75 FKBP L27V02A 1-160) |
| SEQ ID NO: 434 (pCA 75 FKBP L27V02A 1-160) |
| SEQ ID NO: 435 (pCA 76 L27V02A 161-169 FRB) |
| SEQ ID NO: 436 (pCA 76 L27V02A 161-169 FRB) |
| SEQ ID NO: 437 (pCA 77 FKBP L27V02A 1-158) |
| SEQ ID NO: 438 (pCA 77 FKBP L27V02A 1-158) |
| SEQ ID NO: 439 (pCA 78 L27V02A 159-169 FRB) |
| SEQ ID NO: 440 (pCA 78 L27V02A 159-169 FRB) |

The complementation pairs described in Table 42 were cloned into the pF4Ag vector as previously described. The PCA constructs (900 μL) were then expressed in rabbit reticulocyte lysate (RRL; Promega Corp.) or wheat germ extract (Promega Corp.) following the manufacture's instructions. 1.25 μL of the expression reactions for each PCA pair were mixed with 10 μL of 2× Binding Buffer (100 mM HEPES, 200 mM NaCl, 0.2% CHAPS, 2 mM EDTA, 20% glycerol, 20 mM DTT, pH 7.5) and 7.5 μL water, and 18 μL transferred to wells of a 96-well plate. 2 μL of 5 μM Rapamycin (final concentration 0.5 μM) was added and incubated for 10 min at room temperature.

Figure 76A:
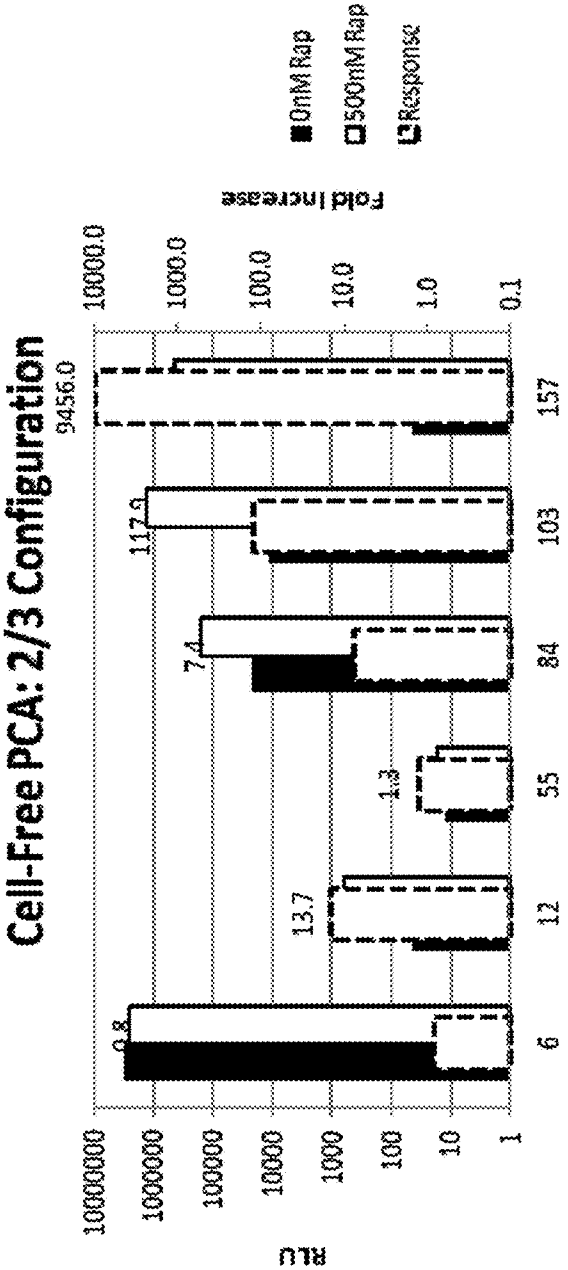
FIGS. 76A-H show the luminescence of various protein complementation (PCA) L27V pairs: one L27V fragment of each pair was fused to either FKBP or FRB using a 2/3 configuration (FIGS. 76A and 76C) or a 1/4 configuration (FIGS. 76B and 76D), and the interaction of FKBP and FRB monitored in wheat germ extract (FIGS. 76A and 76B) and rabbit reticulocyte lysate (RRL) (FIGS. 76C and 76D). The luminescence of various protein complementation (PCA) negative controls was also measured (FIG. 76E) in cell free system. The 1/4 configuration was used in a cell free system (FIG. 76F), HEK293 cells (FIG. 76G) and in a lytic system (FIG. 76H).
Figure 76B:
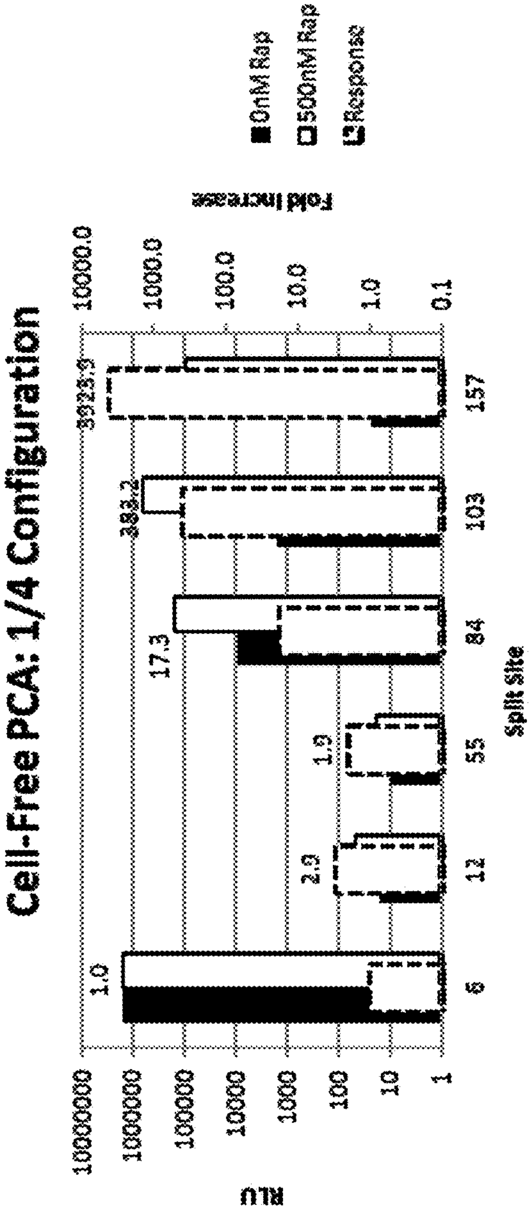
Figure 76C:
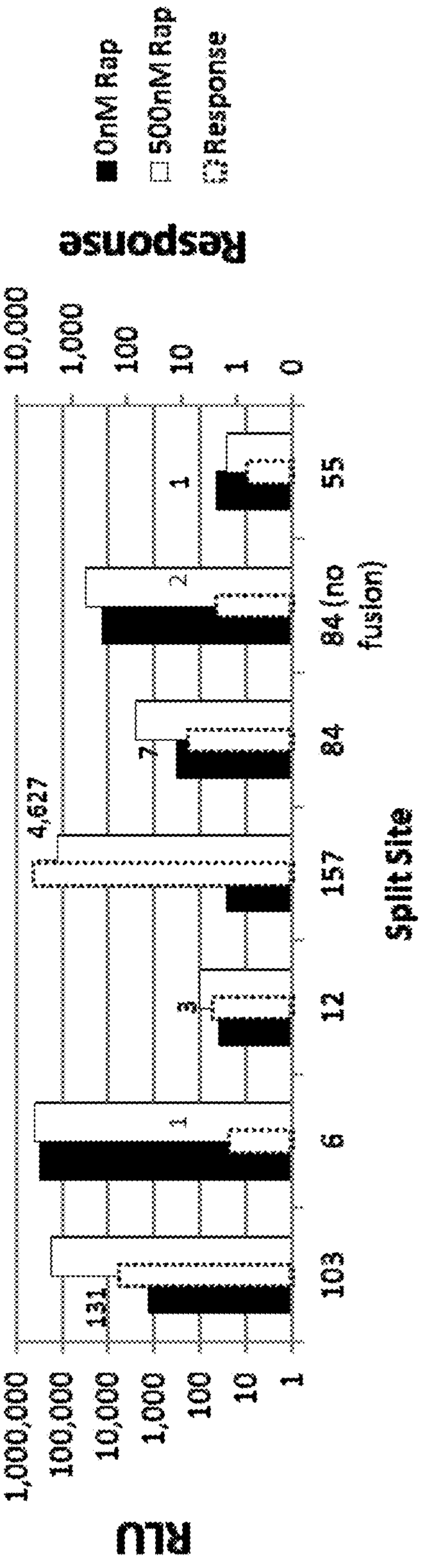
Figure 76D:
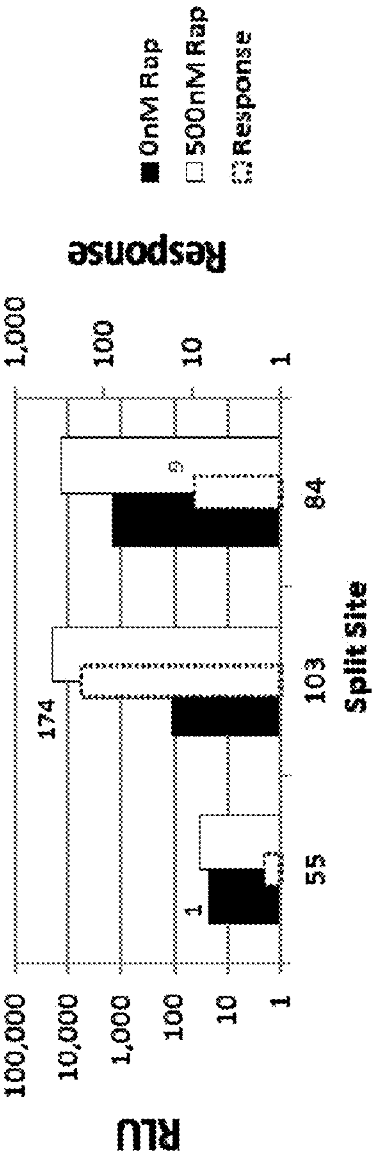
Figure 76E:
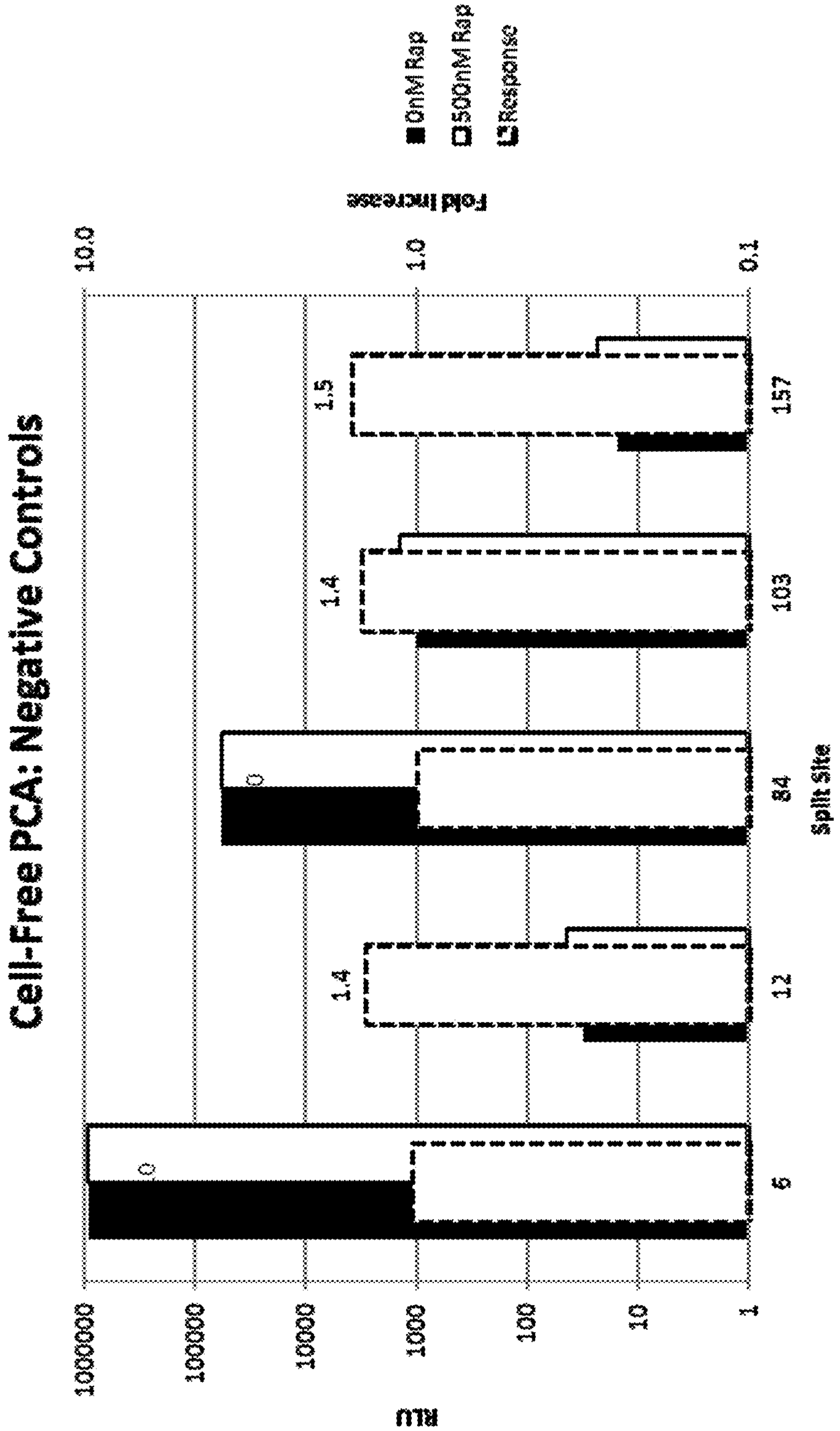
Figure 76F:
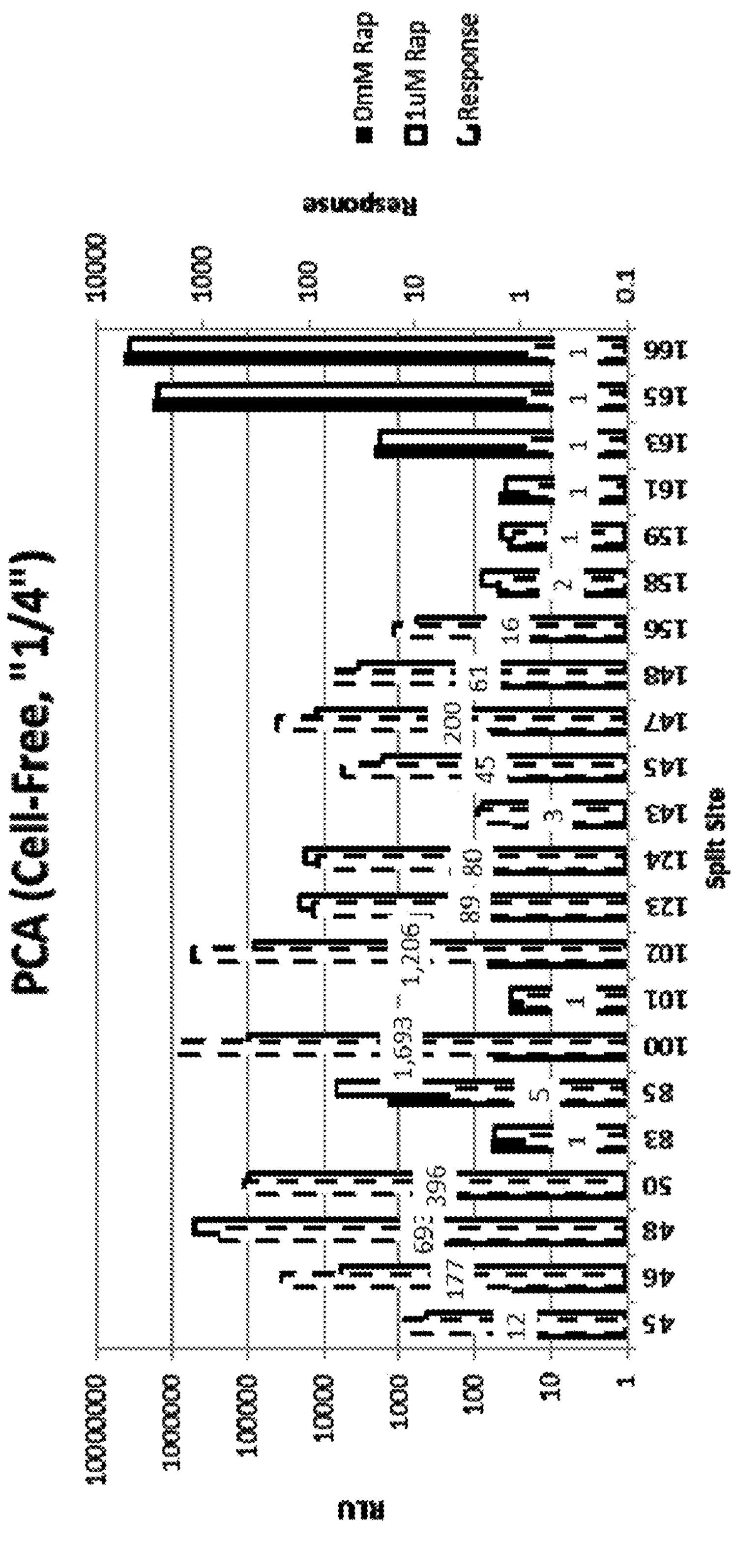
Figure 76G:

Following incubation, 100 μL of PBI-3939 (50× stock diluted to 1× in assay buffer) and incubate for 3 min at room temperature. Luminescence was measured as previously described (FIG. 76A-B: wheat germ; FIG. 76C-D: rabbit reticulocyte; FIG. 76E-F: cell free system [which system? WG or RRL?]; FIG. 76G: HEK293 cells).

FIG. 76A-G show the luminescence of various protein complementation (PCA) L27V pairs: one L27V fragment of each pair was fused to either FKBP or FRB using a 2/3 configuration (FIGS. 76A and 76C) or a 1/4 configuration (FIGS. 76B and 76D) as described, and the interaction of FKBP and FRB monitored in wheat germ extract (FIGS. 76A and 76B) and rabbit reticulocyte lysate (RRL) (FIGS. 76C and 76D); and the luminescence of various protein complementation (PCA) negative controls (FIG. 76E). The luminescence of various protein complementation L27V using a 1/4 configuration in a cell free system (RRL) (FIG. 76F) and HEK293 cells (FIG. 76G) was measured. The data in FIGS. 76A-G demonstrates that a variety of different deletions, i.e., small fragments of the L27V variant, are functional.

3. To demonstrate the use of the PCA constructs for cell-based PCA, the constructs were transfected into HEK293 cells and assayed with PBI-4377. Plasmid DNA (5 ng) from each PCA pair (6, 12, 55, 84, and 103) were mixed with 40 ng carrier DNA (pGEM-3fz) and 5 μL OPTI-MEM® and incubated at room temperature for 5 min. FUGENE® HD (0.15 μL) was then added and again incubated at room temperature for 15 min. The DNA transfection mixtures were added to 100 μL HEK293 cells ($1.5\times10^5$ cells/mL) in DMEM with 10% FBS (no antibiotics), transferred to wells of a 96-well plate, and incubated overnight at 37° C., 5% $CO_2$.

After transfection, the media was removed and replaced with $CO_2$-independent media with 20 μM or 50×PBI-4377 and incubated at 37° C. without $CO_2$ regulation for 2 hrs. Luminescence was measured, 10 μL rapamycin added, and luminescence measured again every 2 min for 2 hrs (FIGS. 76A-C).

4. To demonstrate the use of the PCA constructs to identify inhibitors of protein-protein interactions, the constructs described in #2 of this example were used.

Figure 77A:
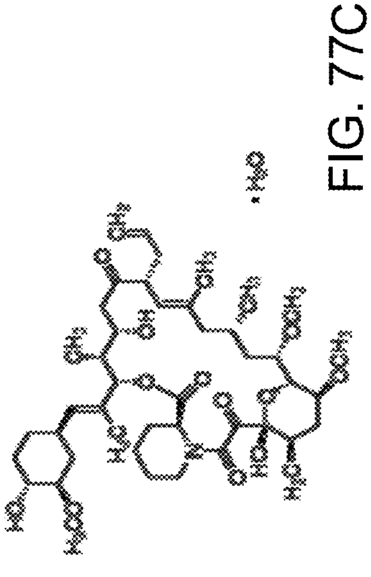
FIGS. 77A-C show the luminescence of various protein complementation L27V pairs treated with FK506 and rapamycin (FIG. 77A) and the chemical structure of FK506 (FIG. 77A) and rapamycin (FIG. 77B).
Figure 77B:
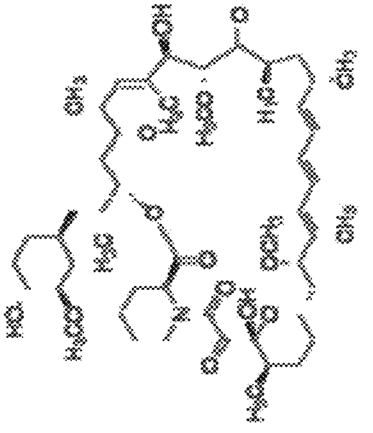
Figure 77C:
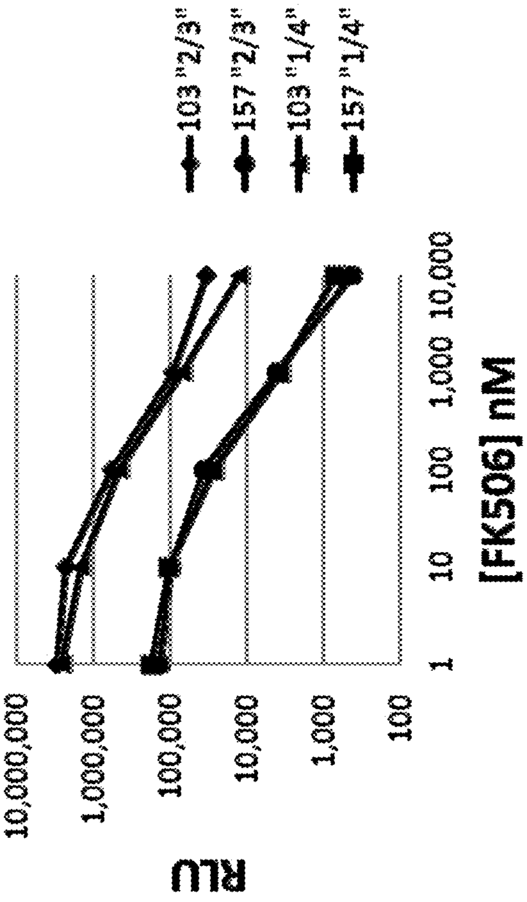

The complementation pairs, 103 "2/3", 157 "2/3", 103 "1/4" and 157 "1/4" described in Table 42 were cloned into the pF4Ag vector as previously described. The PCA constructs (25 μL) were then expressed in rabbit reticulocyte lysate (RRL; Promega Corp.) following the manufacture's instructions. 1.25 μL of the expression reactions for each PCA pair were mixed with 10 μL of 2×Binding Buffer (100 mM HEPES, 200 mM NaCl, 0.2% CHAPS, 2 mM EDTA, 20% glycerol, 20 mM DTT, pH 7.5) and 7.5 μL water, and 16.2 μL transferred to wells of a 96-well plate. Rapamycin was examined with various amounts of FK506. To the reactions, the FRB-FKBP binding inhibitor, FK506 (10×) was added, and the reactions incubated at room temperature for 10 min. 15 nM rapamycin (10× stock solution) was added to get a final concentration of 1.5 nM rapamycin and incubated for 2 hrs at room temperature. Following incubation, 100 μL of PBI-3939 (50×stock diluted to 1× in assay buffer) and incubated for 3 min at room temperature. Luminescence was measured on a GLOMAX® luminometer. FIG. 77 demonstrates that the PCA constructs disclosed herein can be used to identify inhibitors of protein-protein interactions.

5. To demonstrate the use of the PCA constructs in a lytic format, the complementation pairs, 103 "2/3", 157 "2/3", and 103 "1/4" were transfected into HEK293 cells and assayed with PBI-3939. 0.5 ng plasmid from each PCA pair was mixed with 5 μL OPTI-MEM® and 49 ng pGEM-3zf (Promega Corp.). The sample mixture was incubated at room temperature for 5 min. 0.15 μL FUGENE® HD was then added to the sample mixture and incubated at room temperature for 15 min. 100 μL of HEK293 cells in DMEM with 10% FBS (no antibiotics) at a concentration of $1.5\times10^5$ cells/mL was added to each sample mixture. The cell sample was then transferred to a well of a 96-well plate and incubated at 37° C., 5% $CO_2$ overnight.

Figure 76H:
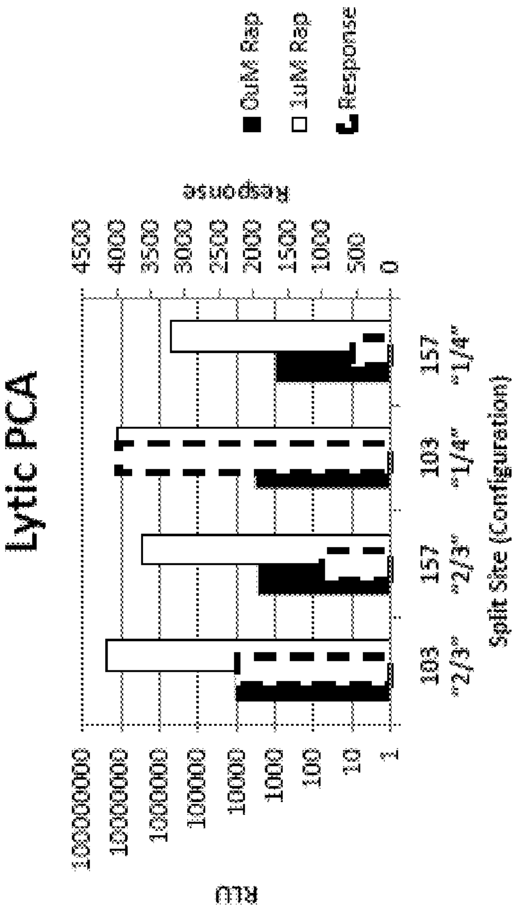

The next day, 11.1 μL of 10 μM Rapamycin (Final concentration 1 μM) was added to half of the wells and 11.1 μL water was added to other half of the wells. The 96-well plates were incubated at 37° C. for 1 hr. 100 μL of assay reagent+PBI-3939 (2 μL 50×PBI-3939 mixed with 98 μL assay reagent, previously described) was added to each well and the plates were incubated at 37° C. for 4 min. Luminescence was measured on a GLOMAX® luminometer at 37° C. with 0.5 s integration time and 1 read. (FIG. 76H).

Example 50—OgLuc cAMP Biosensor

The OgLuc variants of the present invention can be linked to light output not only through concentration, but also through modulation of enzymatic activity. For example, a cAMP biosensor can be developed by incorporating a cAMP-binding domain from Protein Kinase A into a circularly permuted OgLuc variant. An OgLuc variant of the present invention can be circularly permuted at a site(s) tolerable to such permutation by methods known in the art (e.g., U.S. Published Application No. 2005/0153310). The resulting circularly permuted OgLuc variant chimeric protein can function as an intracellular biosensor for cAMP when expressed in mammalian cells. Upon binding of cAMP to the biosensor, the biosensor undergoes a conformational change that creates an active luciferase enzyme.

Treating the cells with forskolin, an activator for adenylate cyclase, should result in an increase in luminescence with increasing concentrations of forskolin. Similar biosensors for targets including but not limited to calcium (Ca+2), cGMP, and proteases such as caspases and tobacco etch virus (TEV) can be developed by incorporating the appropriate binding domain or cleavage site for each into a circularly permuted OgLuc variant.

The utility of OgLuc as a biosensor was demonstrated by analysis of variant 9B8 opt in the context of a cAMP sensor. Circularly permuted constructs containing the RIIβB subunit of Protein Kinase-A flanked by OgLuc variant sequences were made and expressed in a cell free system as described in described in PCT application PCT/US2007/008176, except the sites for circular permutation were chosen as described below. The nascent protein was assayed in the presence and absence of cAMP. Response to cAMP is defined as the ratio of activity (+) cAMP/(−) cAMP.

A structural model for OgLuc has been created, based on similarities to certain fatty acid binding proteins of known structure, previously described in PCT/US2010/33449. The model predicts an ordered sequence of the standard protein structural motifs; α-helix and β-sheet. The regions that transition between these structural elements as circular permutation sites were chosen (see Table 43).

1. The template for expression of the biosensor constructs consisted of: C-terminal OgLuc sequence-RIIβB sequence-N-terminal OgLuc sequence in plasmid pF5 (Promega Corp.). The TNT® T7 Coupled Wheat Germ Extract System (Promega Part #L4140) was used to translate the construct. The TNT® Wheat Germ Extract Reaction included 25 μL TNT® Wheat Germ Extract (L411A), 2 μL TNT® Reaction Buffer (L462A), 1 μL Amino Acid Mixture, Complete (L446A), 1 μL RNasin® (40 U/μL) (N2615), 1 μL TNT® T7 RNA Polymerase (L516A), 1.0 μg DNA template and Nuclease-Free Water to bring the total volume to 50 μL. The reaction mixture was incubated at 30° C. for 120 min.

An OgLuc activity assay was performed by adding to the 50 μL OgLuc translation mixture, 50 μL OgLuc Glo Reagent (100 mM MES (pH 6.0), 1 mM CDTA, 150 mM KCl, 35 mM thiourea, 2 mM DTT, 0.25% TERGITOL® NP-9 (v/v), 0.025% MAZU® DF 204, and 20 μM PBI-3939) with or without 100 μM cAMP, and performing a kinetic read for 30 min (TECAN® INFINITE® F500 Plate Reader). Response is determined by dividing the luminescence generated by the biosensor with cAMP by the luminescence generated by the biosensor without cAMP (Table 43).

TABLE 43

Response of Circularly-Permuted OgLuc Biosensors to cAMP

| CP-SITE | RESPONSE |
|---|---|
| 27 | 2.6X |
| 51 | 2.2X |
| 84 | 1.5X |
| 122 | 4.3X |
| 147 | 1.9X |
| 157 | 5.6X |

Figure 78:
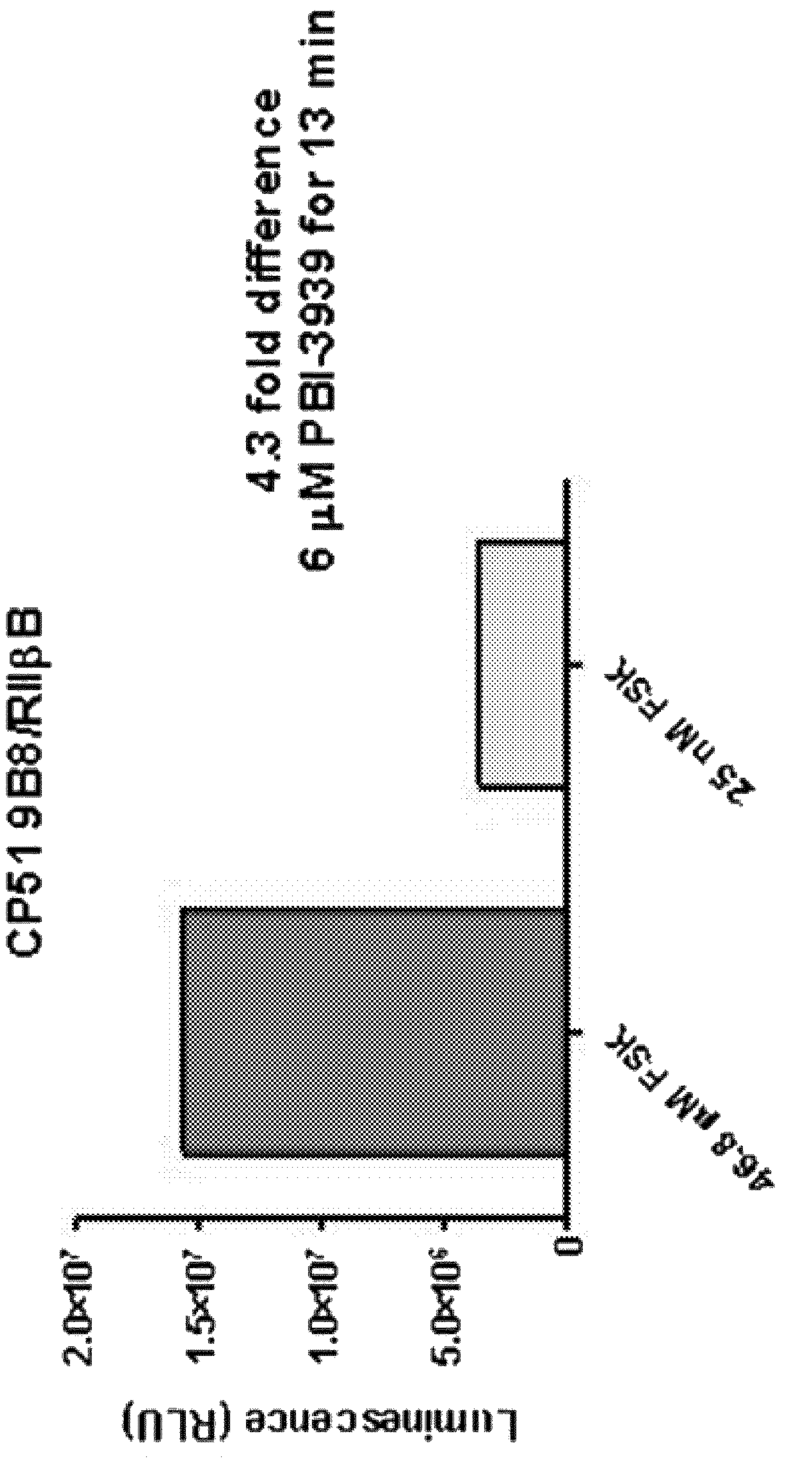
FIG. 78 shows the activity of the OgLuc variant 9B8 cAMP biosensor with forskolin treatment.

2. A cAMP biosensor of 9B8opt circularly permuted at the CP-site 51 was created as described in 1. The biosensor was then transfected into HEK293 cells (15,000 cells/well) using FUGENE® HD according to the manufacturer's instructions into a 96-well plate, and incubated overnight at 37° C., 5% $CO_2$. After transfection, the media was removed and replaced with $CO_2$-independent media with 10% FBS. The cells were then incubated for 2 hrs at 37° C., 5% $CO_2$ after which varying amounts of FSK were added. The cells were then again incubated for 3 hrs at 37° C., 5% $CO_2$. 6 μM PBI-3939 was then added, and luminescence measured after 13 min (FIG. 78).

Figure 79A:
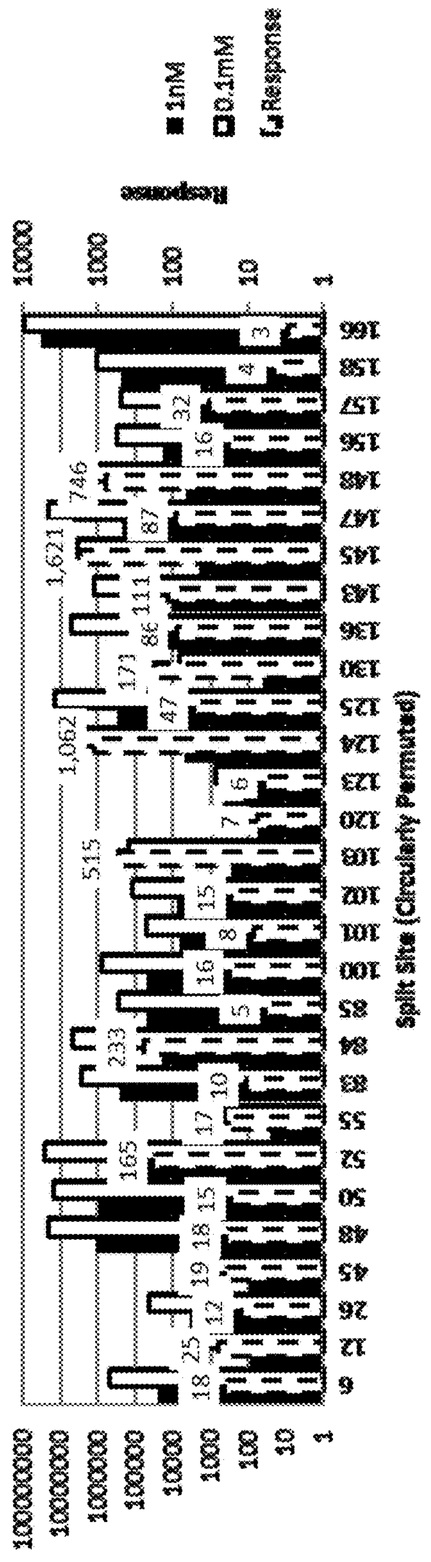
FIGS. 79A-D show the luminescence of circularly permuted (FIGS. 79A and 79C) and straight split (FIGS. 79B and 79D) L27V variants in rabbit reticulocyte lysate (FIGS. 79A-B) and HEK293 cells (FIGS. 79C-D).
Figure 79B:
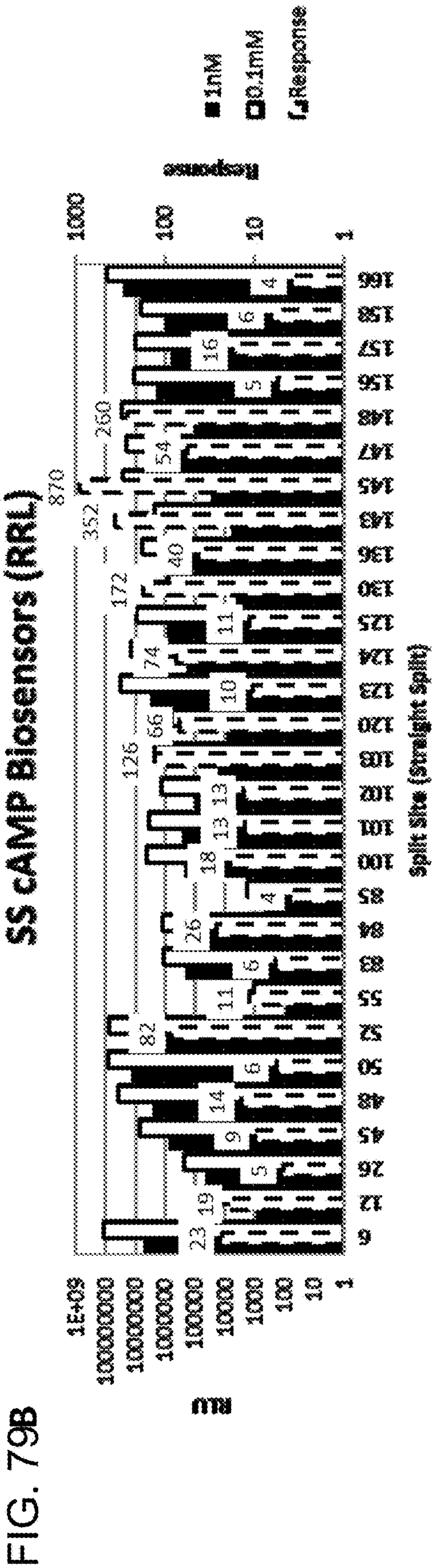
Figure 79C:
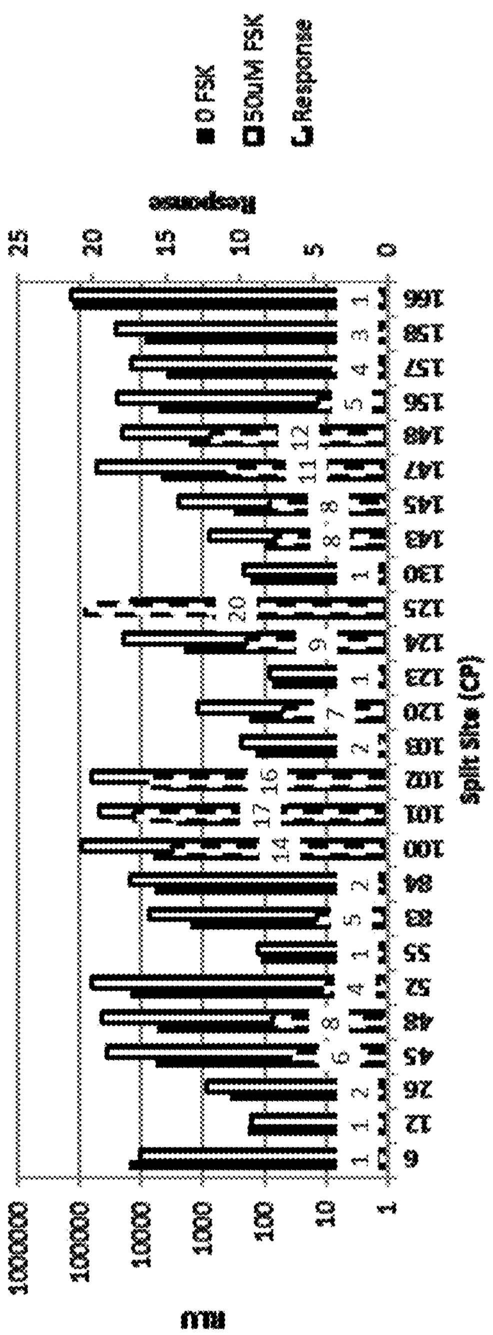
Figure 79D:
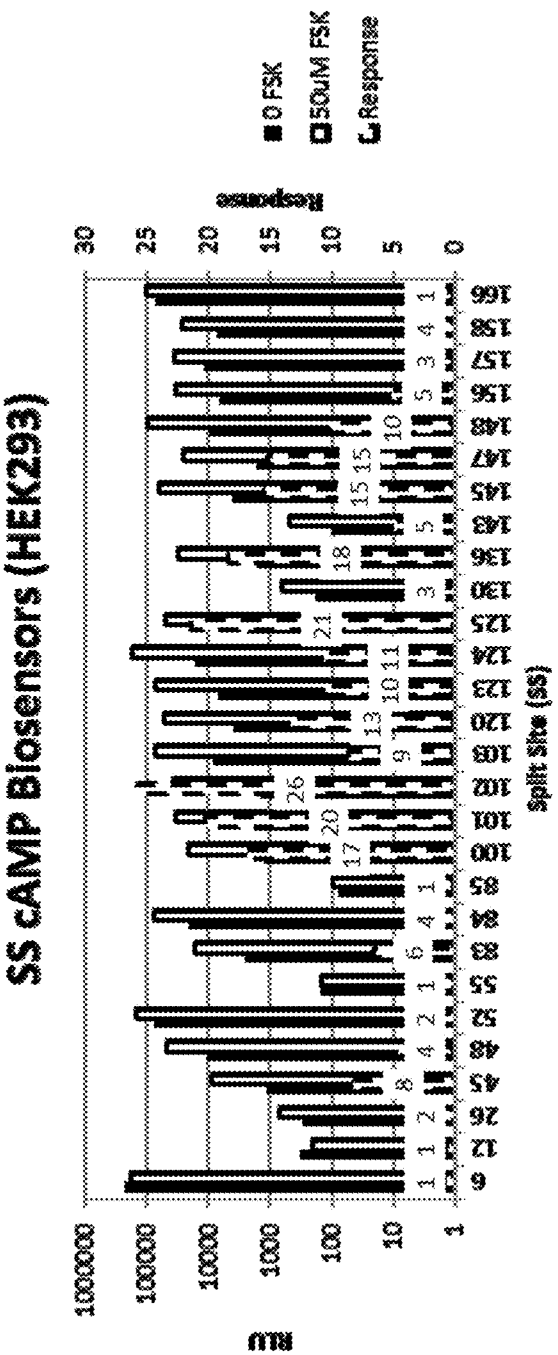

3. Circularly permuted ("CP"; e.g., CP6 refers to the old residue 6 being new residue 1 after Met) and Straight Split ("SS"; e.g., SS6 refers to a sensor orientated as follows: OgLuc (1-6)-RIIβb binding site (SEQ ID NOs: 441 and 442)-OgLuc (7-169)) versions of L27V were used as cAMP biosensors (SEQ ID NOs: 467-574). CP (SEQ ID NOs: 467-498 and 555-574) and SS (SEQ ID NOs: 499-554) versions of the L27V variant were derived as previously described and expressed in expressed in rabbit reticulocyte lysate (RRL; Promega Corp.) following the manufacture's instructions. The linker sequence between the C-terminus of the RIIβb binding site and OgLuc luciferase sequence was GGGTCAGGTGGATCTGGAGGTAGCTCTTCT (SEQ ID NO: 575). The linker sequence between the N-terminus of the RIIβb binding site and OgLuc luciferase sequence was AGCTCAAGCGGAGGTTCAGGCGGTTCCGGA (SEQ ID NO: 576) 3.75 μL of the expression reactions were mixed with 1.25 μL 4×cAMP (final concentration 1 nM-0.1 mM), and incubated at room temperature for 15 min. Following incubation, 100 μL of PBI-3939 (50×stock diluted to 1× in assay buffer) and incubated for 3 min at room temperature. Luminescence was measured on a GLOMAX® luminometer (FIGS. 79A-B). Luminescence was also measured for CP and SS versions of the L27V variant expressed in HEK293 cells and treated with forskolin as previously described (FIGS. 79C-D). FIGS. 79A-D demonstrates that circularly permuted and straight split versions of the OgLuc variants disclosed herein can be used as biosensors.

Example 51—Subcellular Distribution and Localization

Figures 80A, 80B:
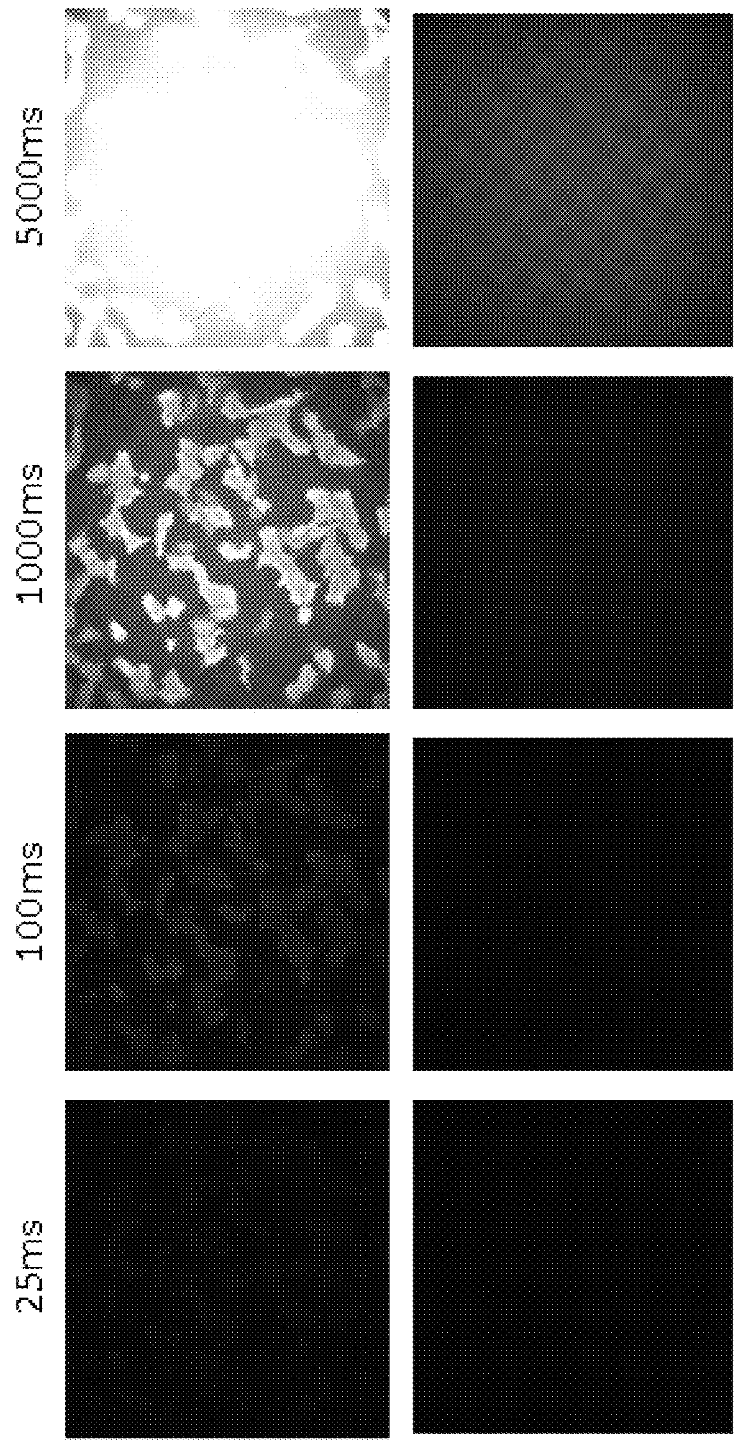
FIGS. 80A-B show the subcellular distribution of the OgLuc variant L27V (FIG. 80A) and control vector pGEM3ZF (FIG. 80B) in U2OS cells for various exposure times.

To analysis subcellular distribution, U2OS cells were plated at $2\times10^4$ cells/$cm^2$ into glass-bottom culture dishes in McCoy's 5A media (Invitrogen) containing 10% FBS. The cells were then incubated for 24 hrs at 37° C., 5% $CO_2$. Cells were then transfected with 1/20 volume transfection mixture (FUGENE® HD and pF5A-CMV-L27V (the L27V variant (SEQ ID NO: 88) cloned into the pF5A vector with CMV promoter (Promega Corp.)) or pGEM3ZF (Promega Corp.; negative control)) and incubated for 24 hrs at 37° C., 5% $CO_2$. Following incubation, the cell media was replaced with $CO_2$-independent media with 0.5% FBS and 100 μM PBI-4378. After a 30 min incubation at 37° C., unfiltered images were captured on an Olympus LV200 bioluminescence microscope using a 60× objective (FIGS. 80A-B) for 25, 100, 1000, and 5000 ms.

Figure 81A:
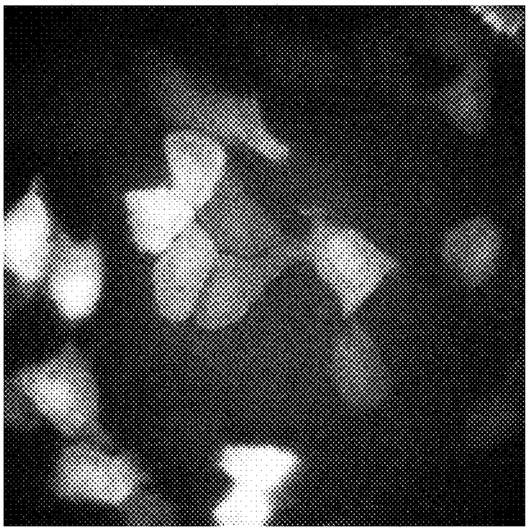
FIGS. 81A-C show the subcellular location of the OgLuc variant L27V fused to either the transcription factor Nrf2 (FIG. 81B) or GPCR (FIG. 81C) compared to an unfused L27V control (FIG. 81A).
Figure 81B:
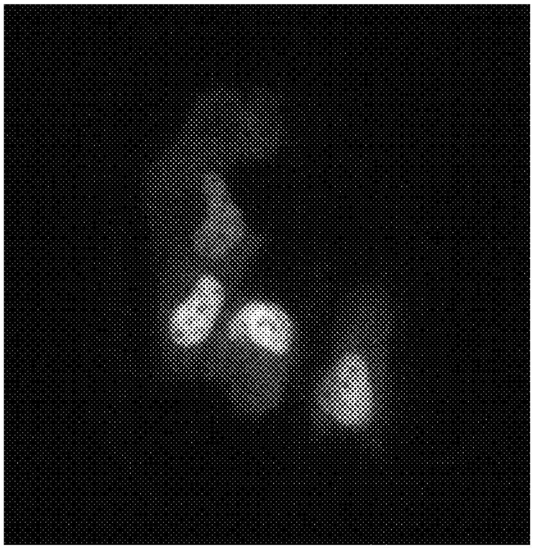
Figure 81C:
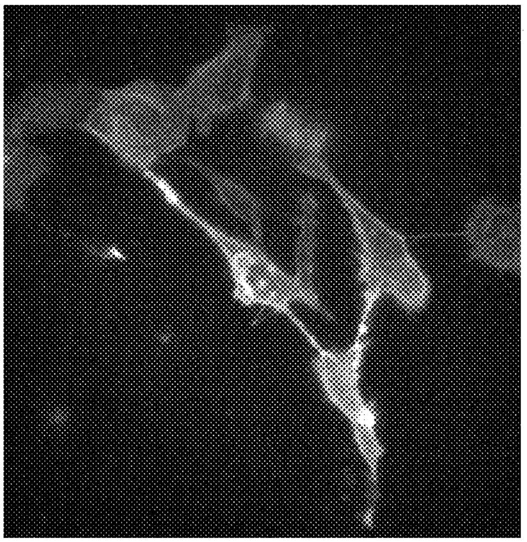

To analyze subcellular localization, N-terminal L27V fusions with the GPCR AT1R (Angiotensin type 1 receptor (SEQ ID NOs: 459 and 460)) with IL-6 secretion sequence (SEQ ID NOs: 461 and 462) or the transcription factor, Nrf2 (SEQ ID NO: 317), were made using a GSSG linker (SEQ ID NOs: 457 and 458) and transfected into U2OS cells as described above (FIGS. 81A-C). FIG. 81C ("GPRC") shows expression of a construct where the IL6 signal sequence is upstream of the L27V variant sequence and the AT1R is downstream of the L27V variant sequence. The L27V variant alone was also transfected ("Unfused"). After a 24 hr incubation at 37° C., 5% $CO_2$, cell media was replaced with $CO_2$-independent media with 0.5% FBS and equilibrated for 1 hr at 37° C. in a non-$CO_2$-regulated atmosphere. An equal volume of media+200 μM PBI-3939 was then added, and unfiltered images were captured immediately on an Olympus LV200 bioluminescence microscope using a 60× or 150× objective (FIGS. 81A-C). For cells expressing L27V alone, PBI-3939 was washed off the cells immediately before image capture.

Example 52—Monitoring Intracellular Signal Pathways

This example provides two examples of the novel luciferase being used to monitor intracellular signal pathways at the protein level (as opposed to the response element examples which represent transcriptional activation). The variant 9B8opt (SEQ ID NO: 24) was fused to either IkB (Gross et al., *Nature Methods* 2(8):607-614 (2005)) (at the C-terminus, i.e., N-IkB-(9B8opt)-C)) or ODD(oxygen-dependent degradation domain of Hif-1-α (Moroz et al., *PLoS One* 4(4):e5077 (2009)) (at the N-terminus, i.e., N-(9B8opt)-ODD-C)). IKB is known to be degraded in cells upon stimulation with TNFα; therefore, the IKB-(9B8opt) construct could be used as a live cell TNFα sensor. ODD (Hif-1-α) is known to accumulate inside cells upon stimulation with compounds that induce hypoxia; therefore, the ODD-(9B8opt) construct could be used as a live cell hypoxia sensor.

Figure 82A:
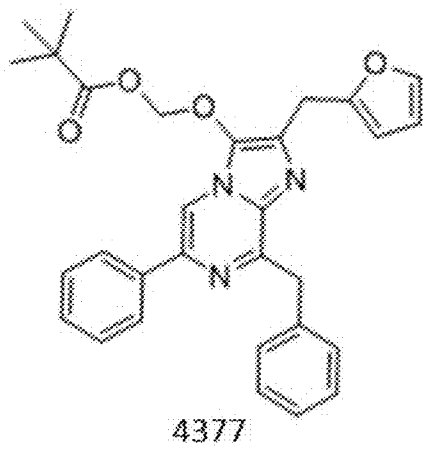
FIGS. 82A-C show the use of the OgLuc variant 9B8 opt to monitor intracellular signaling pathways using PBI-4377 (FIG. 82A). The 9B8 opt luciferase was fused to either IkB (FIG. 82B) or ODD (oxygen-dependent degradation domain of Hif-1α) (FIG. 82C), and fold response to a stimulus (TNFα for IkB and phenanthroline for ODD) was monitored via luminescence.
Figure 82B:
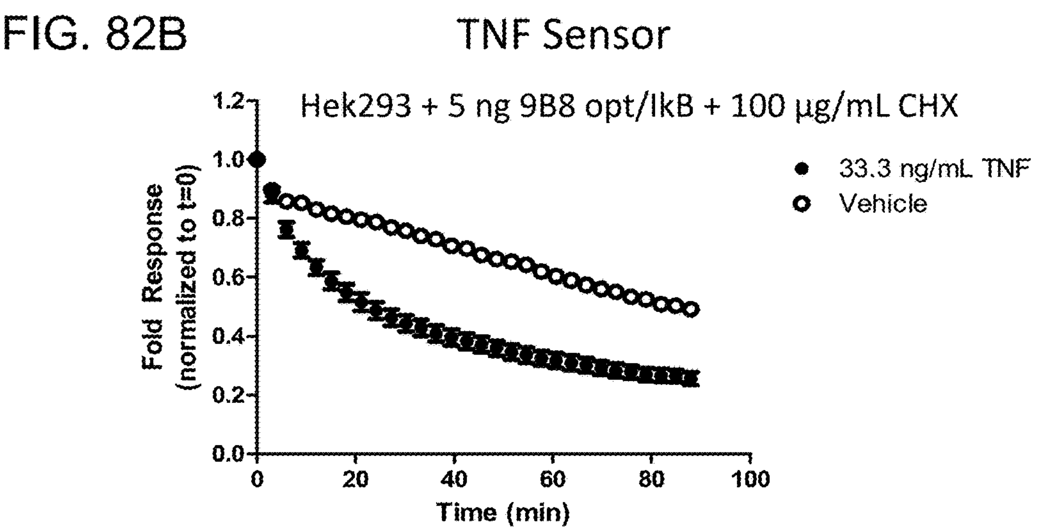
Figure 82C:
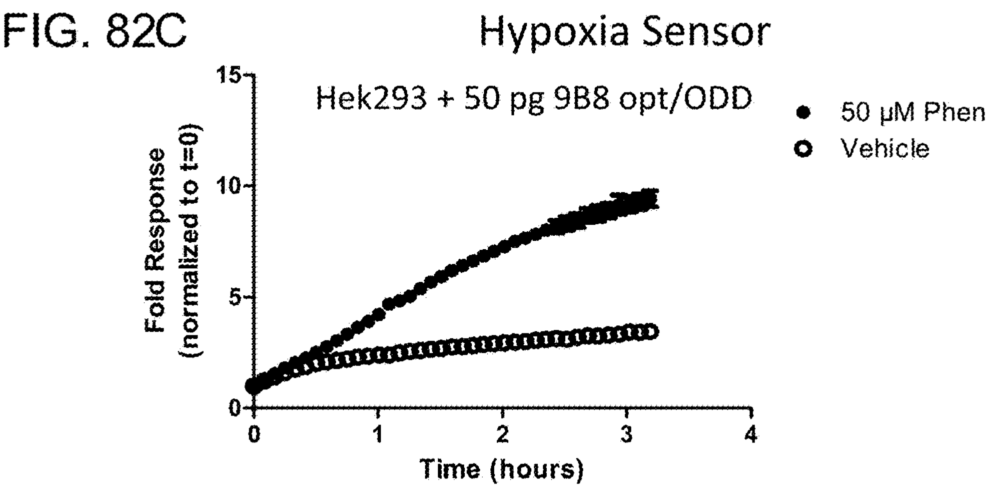

Constructs containing fusions with IkB or ODD with 9B8opt (pF5A) were expressed in HEK293 cells via reverse transfection (5 ng (IkB) or 0.05 ng (ODD) DNA (mixed with carrier DNA to give a total of 50 ng)) as previously described and incubated for 24 hrs at 37° C., 5% $CO_2$. After transfection, the media was replaced with fresh $CO_2$-independent media containing 0.5% FBS and 20 μM PBI-4377 and allowed to equilibrate for 4 hrs at 37° C., atmospheric $CO_2$. Cells were then exposed to a stimulus: TNFα for IkB fusion expressing cells and phenanthroline for ODD fusion expressing cells. DMSO (vehicle) was added to control cells. For the TNFα/IKB samples, 100 μg/mL cycloheximide was added approximately 15 min prior to adding the stimulus to prevent synthesis of new protein. At the indicated time points following treatment, cells were assayed for luminescence. For data normalization, the RLU of each sample at a given time point were divided by the RLU from the same sample immediately after stimulation. Fold response for each sensor was then determined (FIGS. 82A-C).

B. L27V was used to monitor the oxidative stress signal pathways at the protein level. L27V or *Renilla* luciferase (Rluc) was fused to Nrf2/NFE2L2 in a pF5K expression vector (at the C-terminus; i.e., N-Nrf2-(L27V)-C or N-Nrf2-(Rluc)-C). Keap1 is a negative regulator of Nrf2 (SEQ ID NO: 217). In order to faithfully represent regulation of Nrf2-L27V02 protein levels, Keap1, was co-expressed to keep Nrf2 levels low (via ubiquitination).

Figure 83A:
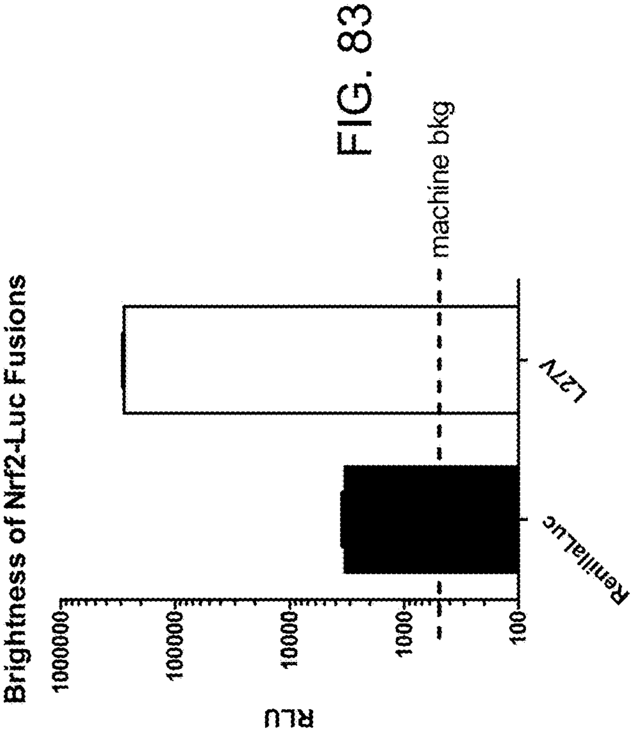
FIGS. 83A-C show the monitoring of oxidative stress signal pathways using the OgLuc variant (FIG. 83A), L27V02 (FIG. 83B), or *Renilla* luciferase (Rluc) (FIG. 83C).
Figure 83B:
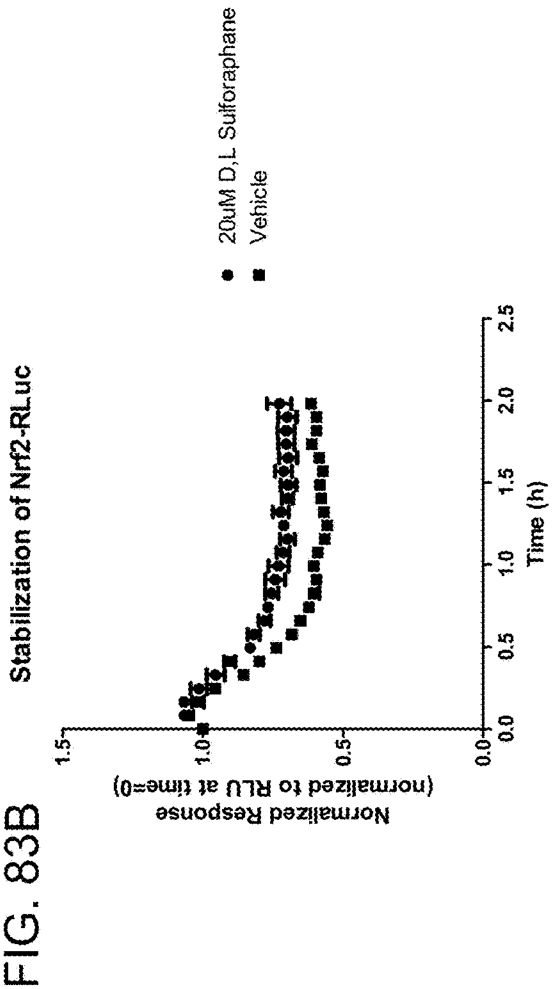
Figure 83C:
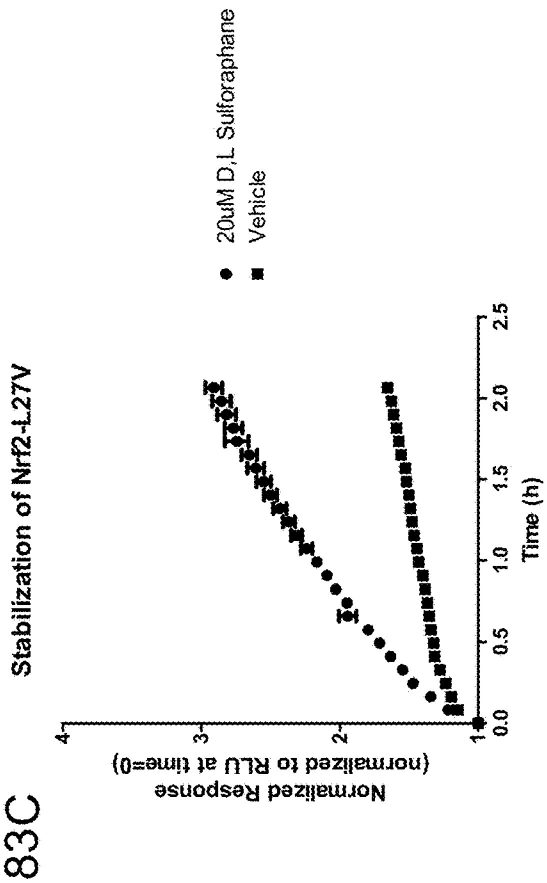

Nrf2-L27V or Nrf2-Rluc (5 ng, pF5K) and a HALOTAG®-Keap1 fusion protein (pFN21-HT7-Keap1 (SEQ ID NO: 316); 50 ng) were expressed in HEK293 cells by transfection of the cells at the time of seeding into the 96-well plates as previously described and incubated for 24 hrs at 37° C., 5% $CO_2$. After transfection, the media was replaced with fresh $CO_2$-independent media with 0.5% FBS and 20 μM PBI-4377 for L27V or 20 μM ENDUREN™ (Promega Corp.) for *Renilla* luciferase, and the cells equilibrated for 4 hrs at 37° C. under atmospheric $CO_2$. For kinetic analysis, 20 μM D,L sulforaphane or vehicle (DMSO) were used. In FIG. 83A, luminescence was measured as previously described at the indicated time points following treatment. For data normalization, the luminescence of each sample at a given time point was divided by the luminescence from the same sample immediately after stimulation (FIGS. 83B-C).

Figure 84A:
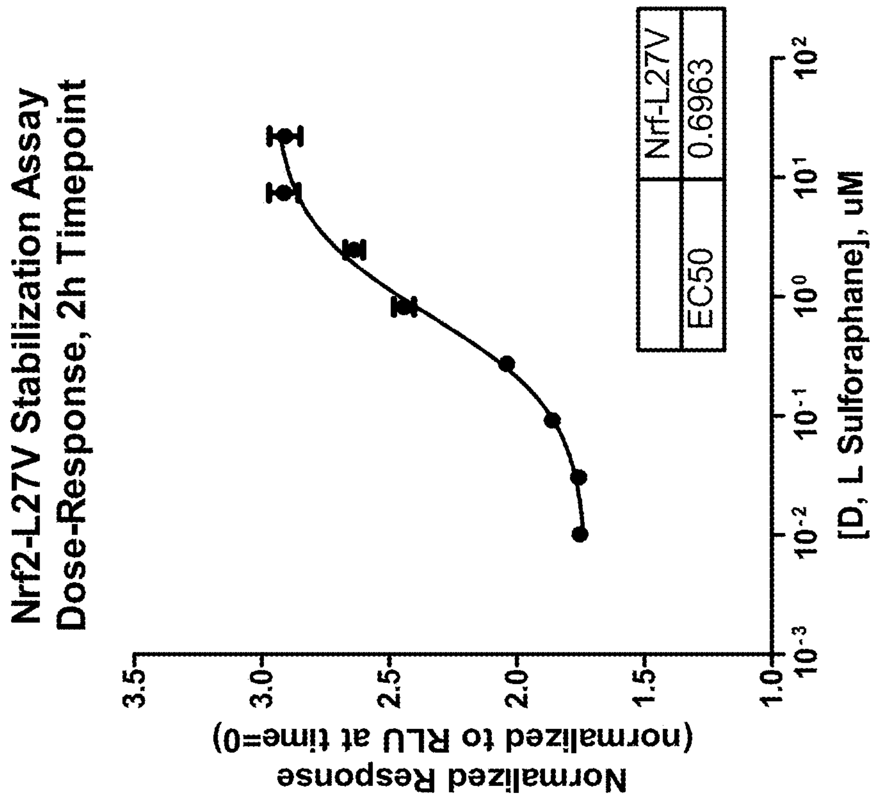
FIGS. 84A-B show the comparison of the Nrf2-L27V02 sensor (FIG. 84A) and Nrf2(ARE)-Luc2P reporter (FIG. 84B).
Figure 84B:
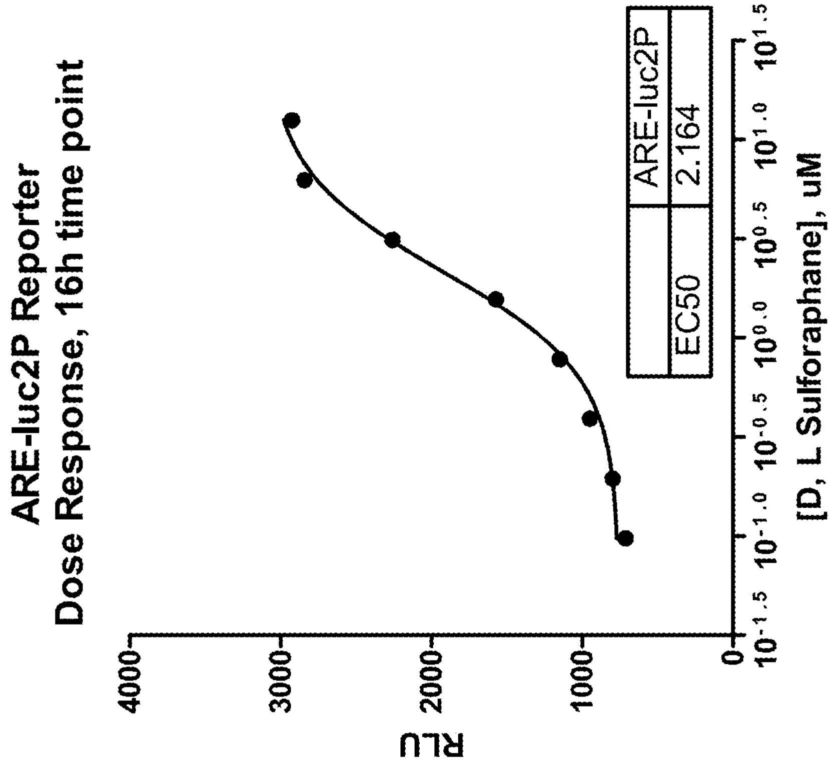
Figure 85A:
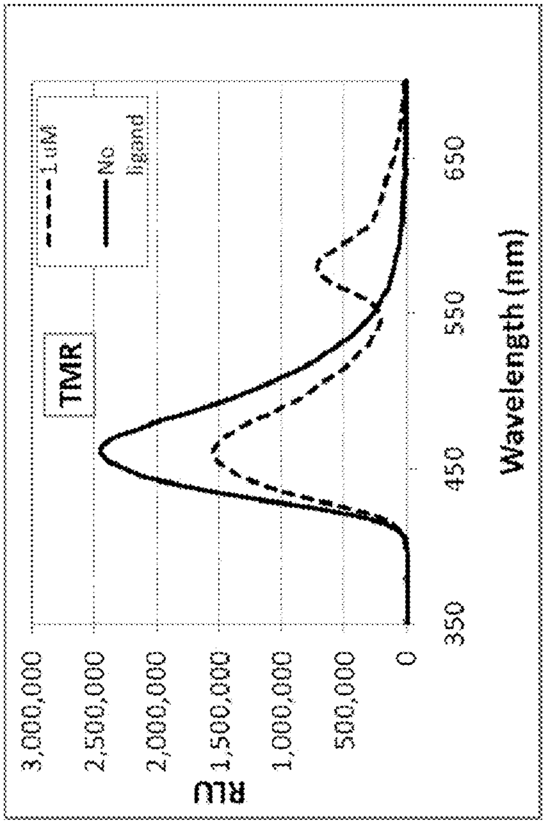
FIGS. 85A-B show the emission spectra of IV-HT7 with and without ligand, using 1 μM TMR (FIG. 85A) or 10 μM Rhodamine 110 (FIG. 85B) as a ligand for HT7 and coelenterazine-h as a substrate for IV.
Figure 85B:
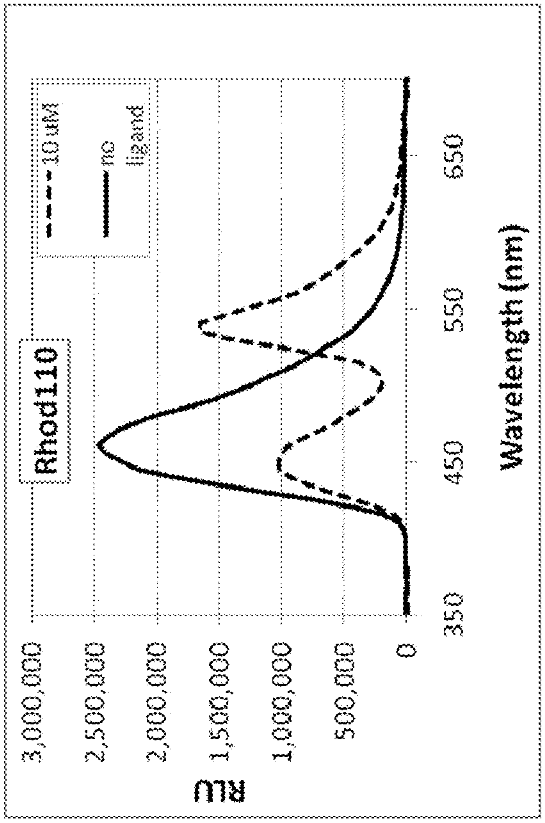

C. A comparison of the response of the Nrf2 sensor described in B and Nrf2(ARE)-Luc2P reporter (Promega Corp.) was performed. Both the Nrf2 sensor and reporter were screened as described in section B above. For the firefly (Luc2P) reporter gene assay, the ONE-GLO™ assay reagent was used. FIGS. 84A-B provides the normalized response of Nrf2-L27V at 2 hrs and Nrf2(ARE)-Luc2P at 16 hrs Example 53—Evaluation of OgLuc Variant as Bioluminescent Reporter with BRET Bioluminescence resonance energy transfer (BRET) allows monitoring of protein-protein interactions. The intramolecular energy transfer was examined between IV and a HT7 fusion partner where HT7 was previously labeled with a fluorophore, i.e., TMR (excitation/emission (ex/em) wavelength=555/585 nm) or Rhodamine 110 (excitation/emission wavelength=502/527 nm). 50 μL of a bacterial cell lysate containing the IV-HT7 fusion protein of Example 34 was incubated with or without 0.001-10 μM fluorophore ligand for 1 hr at room temperature. After the incubation, 50 μL of RENILLA-GLO™, which contains 22 μM coelenterazine-h, was added to 50 μL of the enzyme-ligand mixture, and the emission spectrum was recorded at 5 min. Example spectra of IV-HT7 with TMR (FIG. 83A) or Rhodamine 110 ("Rhod110") (FIG. 85B) are shown indicating BRET was greater when the ex/em of the ligand was closer to the 460 nm luminescent peak of OgLuc, i.e., greater with Rhodamine 110. This data shows that intramolecular energy transfer can occur between OgLuc variants and a fluorophore on a fusion protein. Three different controls were used for comparison (data not shown): 1) a non-HT fusion, 2) a HT-fusion that was not labeled with a HT ligand, and 3) a labeled HT-fusion that was proteolytically cleaved at a TEV site between OgLuc and HT (which indicated the involvement of proximity/distance). BRET was not observed in the three different controls suggesting that HT was involved to achieve BRET. BRET was greater for $C_1$+A4E and IV with a C-terminal HT7 compared to N-terminal HT7.

Example 54—Protein Proximity Assays for Live Cells or Lytic Formats

In one example, circularly permuted (CP) or straight split (SS) OgLuc fusion proteins is applied to measurements of protein proximity. OgLuc is permuted or split via insertion of a protease substrate amino acid sequence (e.g., TEV) to generate low bioluminescence. The inactive luciferase is tethered (e.g., via genetic fusion) to a monitor protein. A potential interacting protein is tethered (e.g., via genetic fusion) to a protease (e.g., TEV). When the two monitor proteins interact or are in sufficient proximity (e.g., via a constitutive interaction, a drug stimulus or a pathway response), the luciferase is cleaved to generate increased bioluminescence activity. The example may be applied to measurements of protein proximity in cells or in biochemical assays. Furthermore, the high thermal stability of an OgLuc variant luciferase could enable measurements of antibody-antigen interactions in lysed cells or biochemical assays.

Example 55—Bioluminescent Assays

Figure 86:
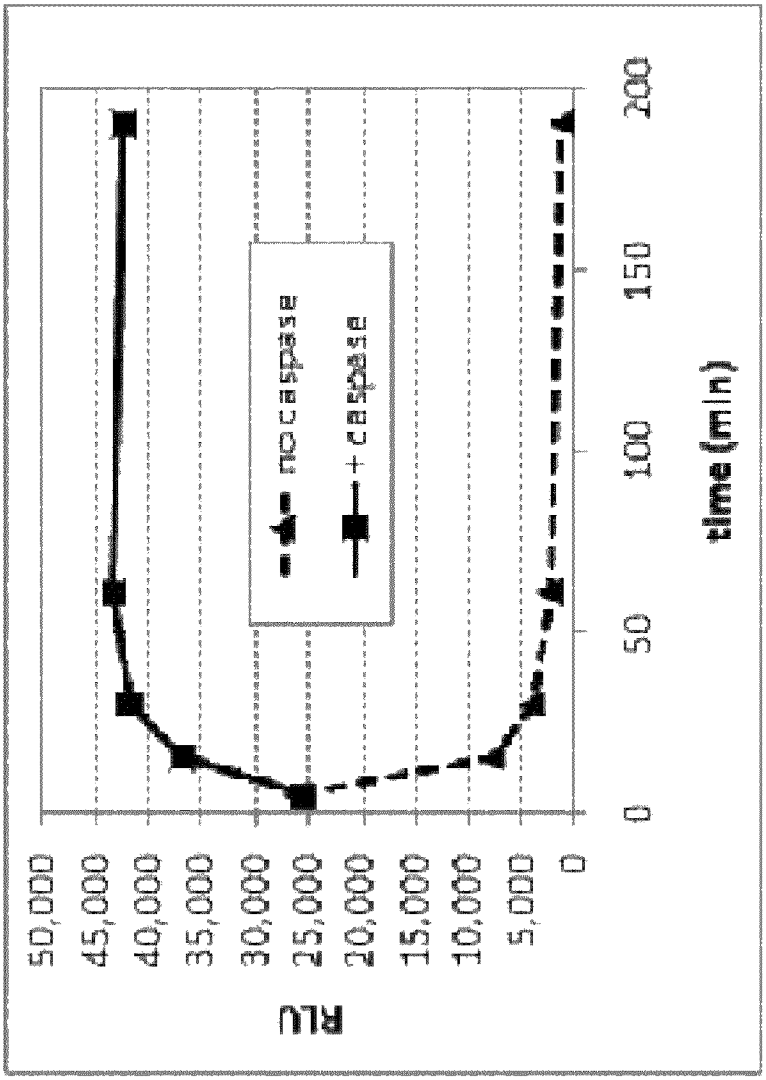
FIG. 86 shows the luminescence generated from lysed bacterial cells expressing 9B8 opt mixed with ("+ caspase") or without ("no caspase") caspase-3 using a pro-coelenterazine substrate.

1. To demonstrate the use of an OgLuc variant in a bioluminescent assay to detect caspase-3 enzyme, the 9B8 opt variant was used in a bioluminescent assay using a pro-coelenterazine substrate comprising the DEVD caspase-3 cleavage sequence. Purified caspase-3 enzyme was mixed with an *E. coli* lysate sample expressing the variant 9B8 opt, which was prepared as described in Example 27, and diluted 10-fold in a buffer containing 100 mM MES pH 6.0, 1 mM CDTA, 150 mM KCl, 35 mM thiourea, 2 mM DTT, 0.25% TERGITOL® NP-9 (v/v), 0.025% MAZU® DF 204, with or without 23.5 μM z-DEVD-coelenterazine-h in 100 mM HEPES pH 7.5. The caspase-3 enzyme was incubated with the lysate sample for 3 hrs at room temperature, and luminescence detected on a Turner MODULUS™ luminometer at various time points. A sample containing only bacterial lysate and a sample containing only caspase-3 were used as controls. Three replicates were used. FIG. 86 and Table 44 demonstrate that 9B8 opt, and thus other OgLuc variants of the present invention, can be used in a bioluminescent assay with a pro-coelenterazine substrate to detect an enzyme of interest.

TABLE 44

Average luminescence in RLU generated from bacterial lysates expressing the 9B8 opt variant incubated with or without purified caspase-3 using z-DEVD-coelenterazine-h as a substrate.

| time (min) | no caspase (RLU) | +caspase (RLU) |
|---|---|---|
| 5 | 26,023 | 25,411 |
| 15.3 | 7,707 | 36,906 |
| 29.9 | 4,013 | 41,854 |
| 60.9 | 2,305 | 43,370 |
| 190.3 | 1,155 | 42,448 |

2. The L27V variant was used in a bioluminescent assay using a pro-coelenterazine substrate comprising the DEVD caspase-3 cleavage sequence. Purified caspase-3 enzyme (1 mg/mL) in 100 mM MES pH 6 (50 μL) was mixed with 227 nM L27V02 variant and 47 μM PBI-3741 (z-DEVD-coelenterazine-h) in assay buffer (50 μL). Reactions were incubated for 3 hrs at room temperature, and luminescence detected as previously described. The assay with the L27V variant was compared to a firefly luciferase version of the assay, CASPASE-GLO® 3/7-Assay system (Caspase-Glo; Promega Corp.). Table 45 demonstrate that L27V variant, and thus other OgLuc variants of the present invention, can be used in a bioluminescent assay with a pro-coelenterazine substrate to detect an enzyme of interest.

TABLE 45

| | (+) caspase | +/− | (−) caspase | +/− |
|---|---|---|---|---|
| L27V | 11,532 | 93 | 803 | 25 |
| Caspase-Glo | 15,156,567 | 793,981 | 302 | 5 |

Example 56—Immunoassays

The OgLuc variants of the present invention are integrated into a variety of different immunoassay concepts. For example, an OgLuc variant is genetically-fused or chemically conjugated to a primary or secondary antibody to provide a method of detection for a particular analyte. As another example, an OgLuc variant is genetically-fused or chemically conjugated to protein A, protein G, protein L, or any other peptide or protein known to bind to Ig fragments, and this could then be used to detect a specific antibody bound to a particular analyte. As another example, an OgLuc variant is genetically-fused or chemically conjugated to streptavidin and used to detect a specific biotinylated antibody bound to a particular analyte. As another example, complementary fragments of an OgLuc variant are genetically-fused or chemically conjugated to primary and secondary antibodies, where the primary antibody recognizes a particular immobilized analyte, and the secondary antibody recognizes the primary antibody, all in an ELISA-like format. The OgLuc variant activity, i.e., luminescence, is reconstituted in the presence of immobilized analyte and used as a means to quantify the analyte.

As another example, complementary fragments of an OgLuc variant can be fused to two antibodies, where one antibody recognizes a particular analyte at one epitope, and the second antibody recognizes the analyte at a separate epitope. The OgLuc variant activity would be reconstituted in the presence of analyte. The method would be amenable to measurements of analyte quantification in a complex milieu such as a cell lysate or cell medium. As another example, complementary fragments of an OgLuc variant can be fused to two antibodies, where one antibody recognizes a particular analyte regardless of modification, and the second antibody recognizes only the modified analyte (for example, following post-translational modification). The OgLuc variant activity would be reconstituted in the presence of analyte only when it is modified. The method would be amenable to measurements of modified analyte in a complex milieu such as a cell lysate. As another example, an OgLuc variant can be conjugated to an analyte (e.g., prostaglandins) and used in a competitive sandwich ELISA format.

Example 57—Dimerization Assay

This example demonstrates that full-length circularly permuted OgLuc variants can be fused to respective binding partners, e.g., FRB and FKBP, and used in a protein complementation-type assay. The key difference between the method disclosed herein and traditional protein complementation is that there was no complementation, but rather there was dimerization of two full length enzymes, e.g., circularly permuted OgLuc variants.

Figure 87A:
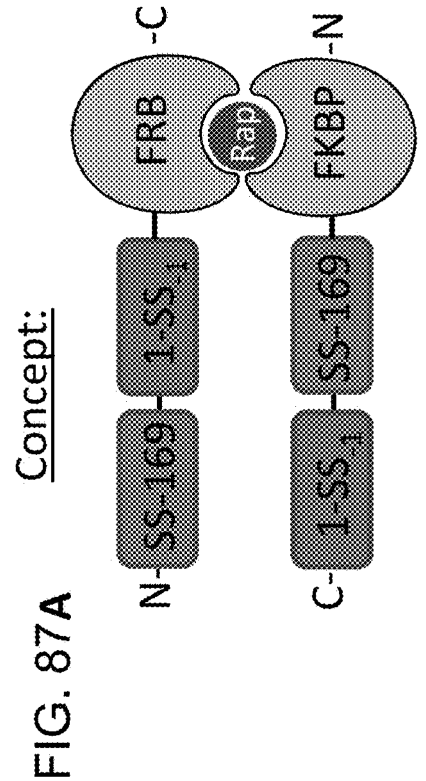
FIGS. 87A-C show the luminescence generated from circularly permuted, straight split L27V variants CP84 and CP103 using PBI-3939 as a substrate with (FIG. 87B) or without (not shown) rapamycin treatment and the response (FIG. 87C) due to rapamycin treatment. The concept of the circularly permuted straight split variants is shown in FIG. 87A.

Briefly, the circularly permuted reporter proteins similarly configured for low activity were fused to both of the fusion protein partners (See FIG. 87A). For example, each fusion partner may be linked to identically structured, permuted reporters. Interaction of the fusion partners brought the permuted reporters into close proximity, thereby allowing reconstitution of a hybrid reporter having higher activity. The new hybrid reporter included portions of each of the circularly permuted reporters in a manner to reduce the structural constraint.

Figure 87B:
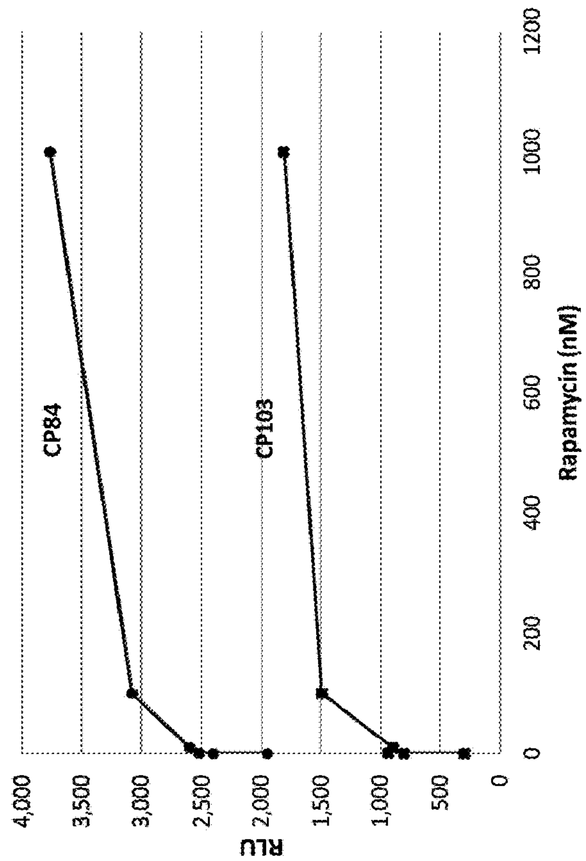
Figure 87C:
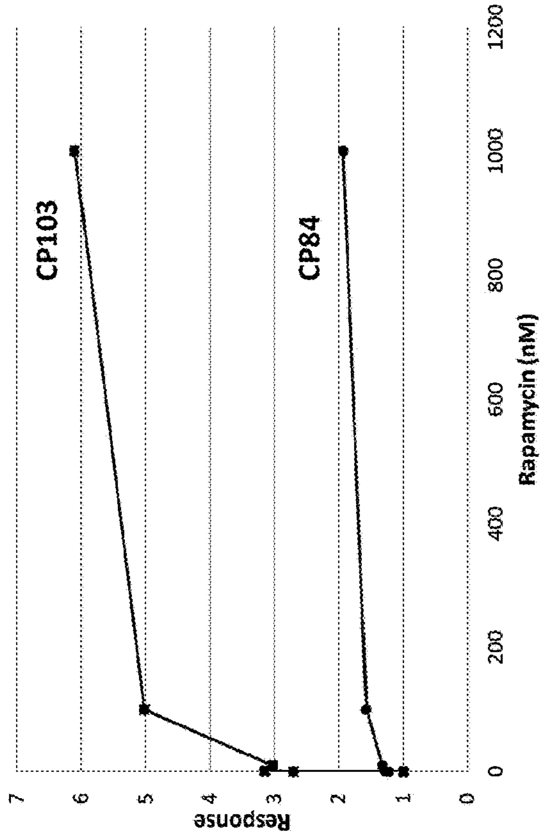

Circularly permuted, straight split L27V variants CP84 and CP103 (N-(SS-169)-(1-$SS_1$)-FRB-C and C-(1-$SS_1$)-(SS-169)-FKBP) were cloned as previously described and expressed (25 μL) in rabbit reticulocyte lysate (RRL; Promega Corp.) following the manufacture's instructions. 1.25 μL of the expression reactions for each dimerization pair were mixed with 10 μL of 2×Binding Buffer (100 mM HEPES, 200 mM NaCl, 0.2% CHAPS, 2 mM EDTA, 20% glycerol, 20 mM DTT, pH 7.5) and 7.5 μL water, and 18 μL transferred to wells of a 96-well plate. To the reactions, 2 μL rapamycin (final concentration 0 and 0.1-1000 nM) was added, and the reactions incubated at room temperature for 10 min. Following incubation, 100 μL of PBI-3939 (50× stock diluted to 1× in assay buffer) and incubated for 3 min at room temperature. Luminescence was measured on a GLOMAX® luminometer (FIG. 87B) and the response was determined (FIG. 87C). FIGS. 87B-C demonstrates that the OgLuc variants of the present invention can be used to detect protein-protein interactions via a PCA-type dimerization assay.

Example 58—Intercellular Half-Life

The intracellular half-life of the OgLuc variants 9B8, 9B8+K33N, V2, L27V, and V2+L27M were determined. CHO cells (500,000) in 15-100 mm plates in F12 media with 10% FBS and 1×sodium pyruvate were transfected with 30 μL 100 ng/μL plasmid DNA containing 9B8, 9B8+K33N, V2, L27V ("V2+L27V") or V2+L27M (all in pF4A vector background) using TRANSIT®-LT1 (Mirus) according to the manufacture's instructions. The cells were then incubated for 6 hrs.

After incubation, the media was removed and 1 mL Trypsin added to dissociate the cells from the plate. 3 mL of F12 media was then added, and the cells counted. Cells were then plated at 10,000 cells/well into 6 wells of a 96-well plate (6 wells/variant) and incubated overnight at 37° C. Samples were distributed over 3 plates. Each plate had 6 replicates for different time point measurements.

After overnight incubation, the media was removed from the cells for t=0 samples, and 100 μL assay buffer (previously described; no substrate) was added. The sample was frozen on dry ice and stored at −20° C. Cycloheximide (100 mg/mL) was diluted 1:100 to a final concentration of 1 mg/mL in OPTI-MEM®. DMSO (100%) was also diluted 1:100 (final concentration 1%) in OPTI-MEM®. The diluted cycloheximide (1 mg/mL) was added (11 μL) to 3 replicates of each transfected variant sample and 11 μL of the diluted DMSO (1%) was added to the other 3 replicates. The cells were then incubated at 37° C., 5% $CO_2$ and removed at various timepoints (i.e., 0, 0.5, 0.9, 2.5, 4.3, and 6.2 hrs) and processed as the t=0 samples.

For analysis, the samples were thawed to room temperature, and 10 μL assayed in 50 μL assay reagent. Luminescence was measured on a GLOMAX® luminometer. At each time-point, luminescence was measured for untreated and cycloheximide-treated samples. The RLU for the cells treated with cycloheximide was normalized by the RLU for the untreated cells.

The intracellular half-life of each variant was calculated by measuring the ratio of the luminescence from the cycloheximide (CHX)-treated to the untreated at each time-point. The ratio was then plotted ln (% treated to untreated) over time, and the half-life calculated (Table 46). The OgLuc variants had intracellular half-lives of approximately 6-9 hrs with a full strength CMV promoter, but the half lives were reduced with a CMV deletion variant (d2). The presence of a PEST degradation signal combined with the full strength CMV promoter reduces half-life significantly.

TABLE 46

| Sample | CMV no deg. | CMV d2 no deg. | CMV Pest |
|---|---|---|---|
| 9B8 | 6.32 | 3.87 | 1.43 |
| K33N | 9.24 | 3.70 | 1.18 |
| V2 | 9.63 | 4.28 | 1.61 |
| V2 + L27V | 6.66 | 4.78 | 1.63 |
| V2 + L27M | 8.89 | 6.98 | 1.63 |

Another experiment was completed using the reverse transfection protocol described in Example 52 with HEK293 cells (data not shown). The results from this experiment indicate that the intracellular half-life for the L27V variant with PEST is 10 min. The L27V variant with no degradation signal used in this experiment did not show a decay over the course of this experiment. In this case the decay was normalized to untreated cells at t=0.

Example 59—Exposure of OgLuc Variants to Urea

Figure 88:
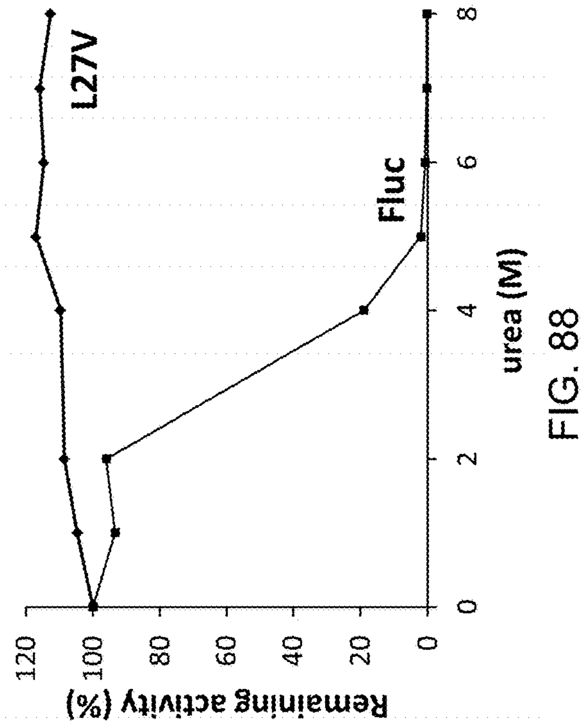
FIG. 88 shows percent remaining activity of the L27V variant after exposure to various amounts of urea.

Since Firefly luciferase is known to be relatively unstable, it is much more sensitive to urea exposure. To determine whether this was also the case with the OgLuc variants, the sensitivity of the OgLuc to urea was determined. 5 μl of 45.3 μM L27V enzyme was mixed with 100 μL of a urea solution (100 mM MOPS, pH 7.2, 100 mM NaCl, 1 mM CDTA, 5% glycerol and various concentrations of urea) and incubated for 30 min at room temperature. 5 μL of the urea+L27V enzyme solution was diluted 10,000-fold into DMEM without phenol red+0.1% PRIONEX®, 50 μL was mixed with 50 μL of assay reagent containing 100 μM PBI-3939 (previously described) and the luminescence was read at 10 min. (FIG. 88). FIG. 88 indicates that L27V is either resistant to urea or refolds to a functional enzyme very quickly upon removal of urea. This suggests that L27V could be used as a reporter enzyme when chemical denaturing conditions are involved, e.g., multiplexing in conditions where a denaturant is used to stop an enzymatic reaction prior to the OgLuc variant-based reaction.

Figure 89:
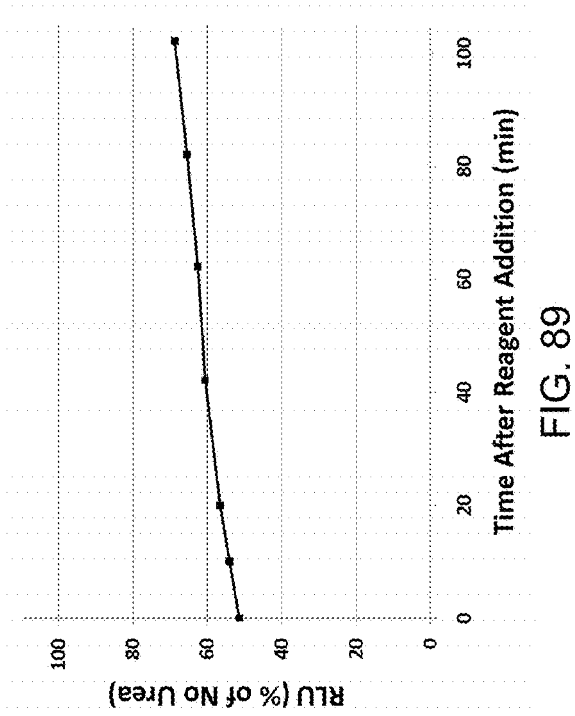
FIG. 89 shows the effect of 3M urea on the activity of the L27V variant.

A 0.31 mg/mL stock of purified L27V variant was diluted 100,000-fold into buffer (PBS+1 mM DTT+0.005% IGEPAL) and incubated with 3 M urea for 30 min at 25° C. and then mixed 1:1 (50 μL+50 μL) with an assay reagent containing 100 μM PBI-3939 (previously described). The reactions were read on a TECAN® INFINITE® F500 luminometer as described previously (for 100 min; 1 min read intervals) (FIG. 89). The results indicate that 3M urea reduces the activity of L27V variant by approximately 50%, but, upon diluting out the urea by 2-fold (to a 1.5 M final concentration) the activity increases, presumably due to refolding.

Example 60—Imaging of OgLuc Fusion Proteins

This example demonstrates the use of OgLuc and OgLuc variants to monitor protein translocation in living cells without the need for fluorescence excitation. OgLuc variants were fused to human glucocorticoid receptor (GR; SEQ ID NOs: 451 and 452), human protein kinase C alpha (PKCa; SEQ ID NOs: 449 and 450) or LC3 (SEQ ID NOs: 577 and 578)._To analyze subcellular protein translocation using bioluminescence imaging, HeLa cells were plated at $2\times10^4$ cells/$cm^2$ into glass-bottom culture dishes (MatTek) in DMEM medium (Invitrogen) containing 10% FBS. The cells were then incubated for 24 hrs at 37° C., 5% C02. Cells were then transfected with 1/20 volume transfection mixture (FUGENE® HD and DNA encoding L27V02-GR (SEQ ID NOs: 453 and 454) or L27V02-PKC alpha (SEQ ID NOs: 455 and 456) cloned into the pF5A vector (Promega Corp.)). The plasmid DNA for L27V02-GR was diluted 1:20 into pGEM-3ZF (Promega Corp.) to achieve appropriate expression levels of L27V02-GR. The plasmid DNA for L27V02-LC3 and L27V02-PKC alpha was used undiluted. Cells were then incubated for 24 hrs at 37° C., 5% $CO_2$. Cells transfected with GR fusion proteins were starved of GR agonist for 20 hrs using MEM medium supplemented with 1% charcoal/dextran-treated FBS (Invitrogen). Twenty-four hrs post-transfection (for PKC alpha measurements) or 48 hrs post-transfection (for GR measurements), the cell media was replaced with $CO_2$-independent media containing 100 μM PBI-3939 immediately before imaging. Unfiltered images were immediately captured on an Olympus LV200 bioluminescence microscope using a 150× objective.

Cytosol-to-nucleus translocation of L27V02-GR fusion protein was achieved via stimulation with 0.5 mM dexamethasone for 15 min. Cytosol-to-plasma membrane translocation of L27V02-PKC alpha fusion protein was achieved via stimulation with 100 nM PMA for 20 min. L27V02-LC3 fusion protein transfected cells were left untreated or treated with 50 mM Chloroquine in DMEM medium (Invitrogen) containing 10% FBS.

L27V02-Glucocorticoid Receptor

Figure 90B:
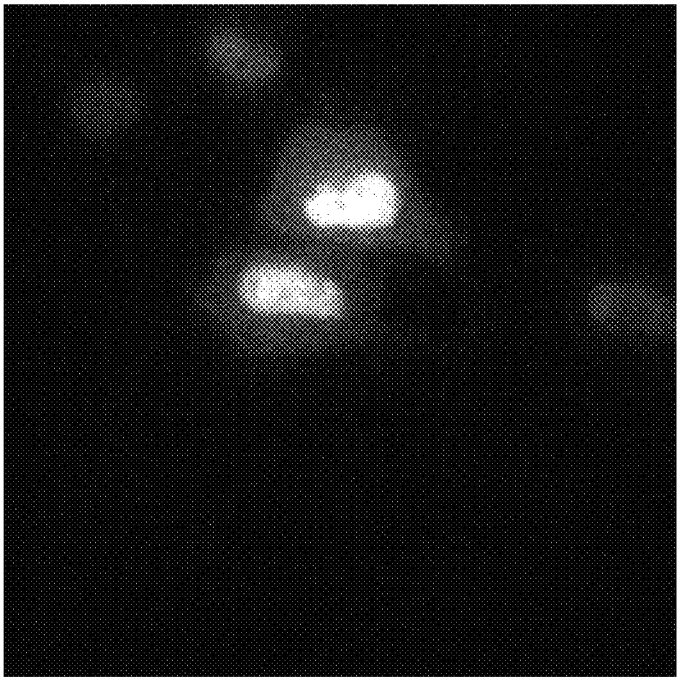
FIGS. 90A-B show the bioluminescence imaging of hormone-induced nuclear receptor (NR) translocation of OgLuc fusions using PBI-3939 substrate.
Figure 90A:
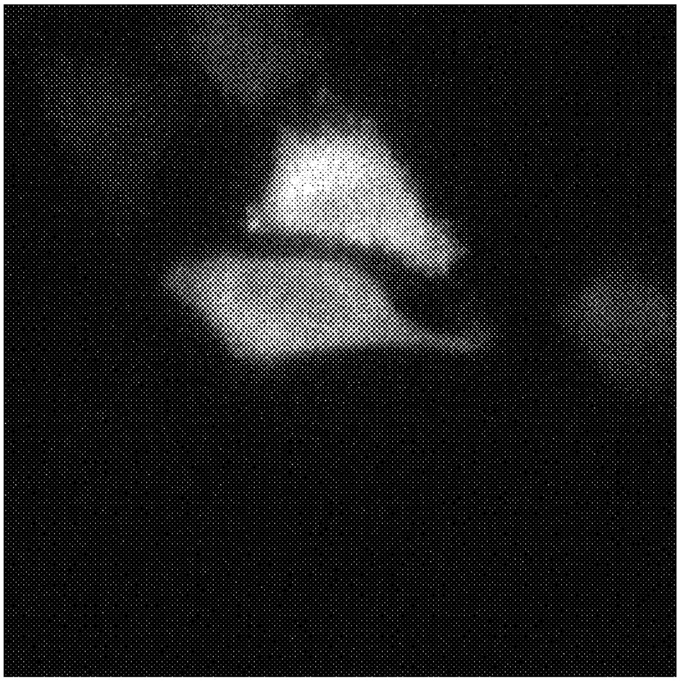

In the absence of glucocorticoids, glucocorticoid receptor (GR) is complexed to Hsp90 proteins and resides in the cytosol. Upon interaction of GR with glucocorticoids, such as dexamethasone, GR proteins dissociate from these protein complexes and translocate to the nucleus to regulate gene transcription. FIGS. 90A-B show the bioluminescence imaging of dexamethasone-induced cytosol to nuclear receptor (NR) translocation of L27V02-glucocorticoid receptor (GR) fusion proteins using PBI-3939 substrate in HeLa cells.

L27V02-PKCa

Figure 91A:
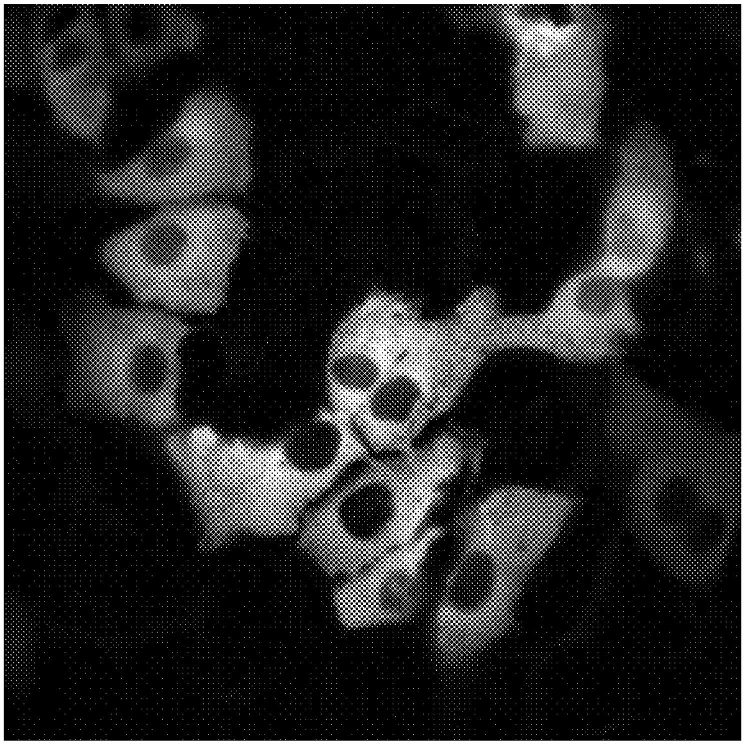
FIGS. 91A-B show the bioluminescence imaging of phorbol ester-induced Protein Kinase C alpha (PKC alpha) translocation of OgLuc fusions using PBI-3939 substrate.
Figure 91B:
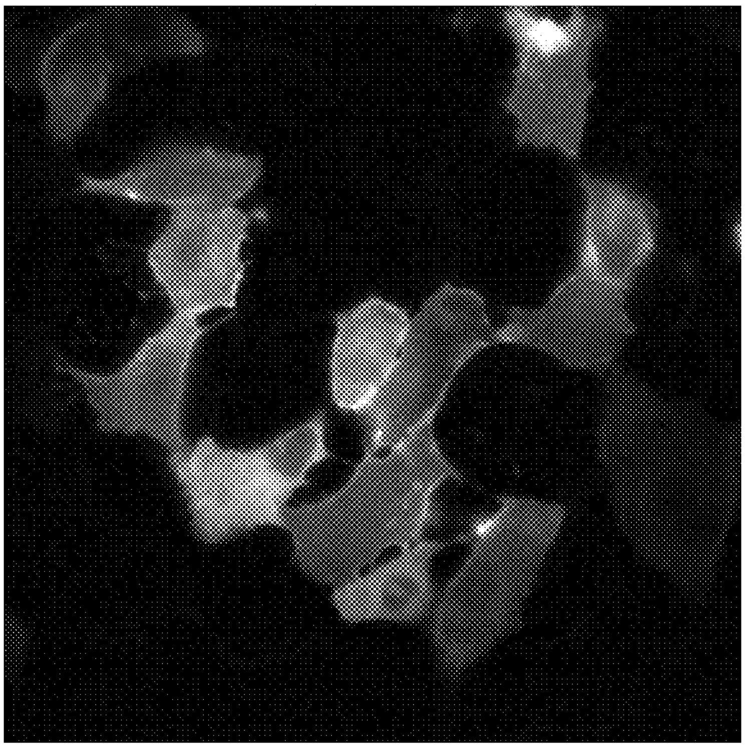

Upon treatment with phorbol esters, PKC alpha proteins are recruited to the plasma membrane and regulate cellular responses including membrane dynamics and signal transduction. FIGS. 91A-B show the bioluminescence imaging of phorbol ester-induced Protein Kinase C alpha (PKC alpha) cytosol to plasma membrane translocation of OgLuc L27V02-PKC alpha fusions using PBI3939 substrate in U-2 OS cells.

L27V-LC3

Figure 92B:
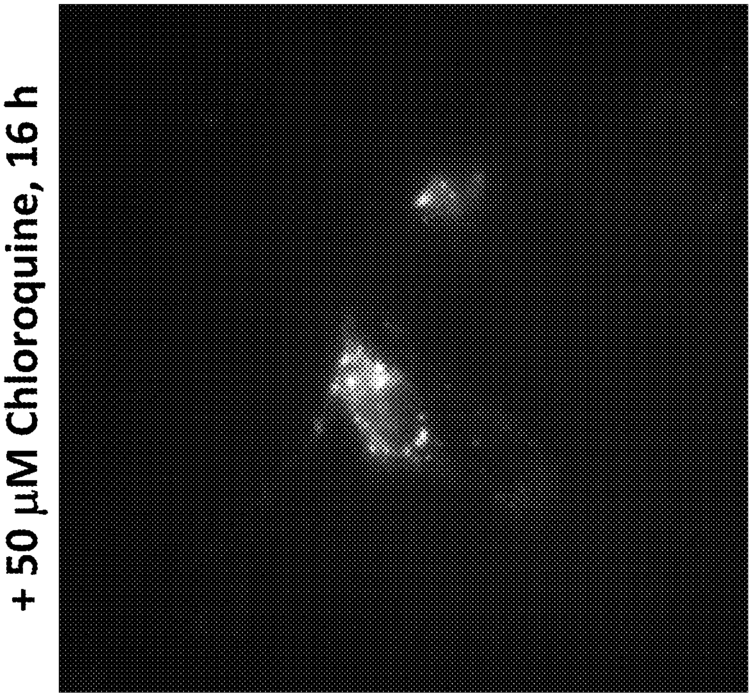
FIGS. 92A-B show the bioluminescence imaging of autophagosomal protein translocation of OgLuc fusions using PBI-3939 substrate.
Figure 92A:
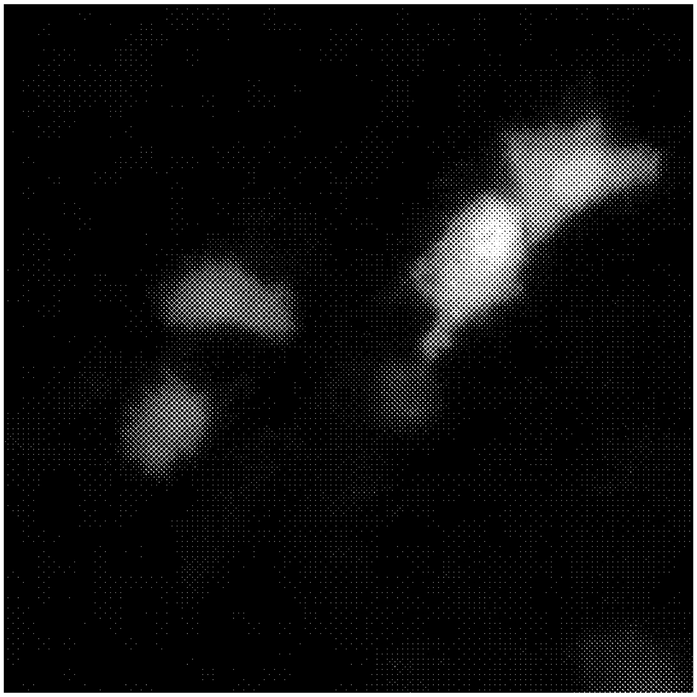

Association of processed LC-3 proteins with autophagosomes represents a hallmark step in autophagy. Chloroquine treatment arrests autophagic flux at this stage, resulting in accumulation of LC-3 proteins on autophagosomes (producing a punctate subcellular distribution). FIGS. 92A-B show the bioluminescence imaging of chloroquine-induced autophagosomal protein translocation of OgLuc L27V-LC3 fusions proteins (SEQ ID NOs: 592 and 593) using PBI-3939 substrate in two representative HeLa cell samples.

TABLE 47

| Proviso List | | | | | | |
|---|---|---|---|---|---|---|
| C1 + A4E | Additional Substitutions | | | | | |
| C1 + A4E | L92G | | | | | |
| C1 + A4E | L92Q | | | | | |
| C1 + A4E | L92S | | | | | |
| C1 + A4E | L92A | | | | | |
| C1 + A4E | L72Q | | | | | |
| C1 + A4E | I90T | | | | | |
| C1 + A4E | Q20R | | | | | |
| C1 + A4E | C164S | | | | | |
| C1 + A4E | M75K | | | | | |
| C1 + A4E | V79I | | | | | |
| C1 + A4E | F54I | | | | | |
| C1 + A4E | K89E | | | | | |
| C1 + A4E | I90V | | | | | |
| C1 + A4E | F77W | F68S | I90V | | | |
| C1 + A4E | F54I | M75K | | | | |
| C1 + A4E | F54I | M75K | I90V | | | |
| C1 + A4E | F54I | F68S | M75K | | | |
| C1 + A4E | F54I | I90V | | | | |
| C1 + A4E | F54I | | | | | |
| C1 + A4E | F54T | N135K | I167V | P104L | D139E | |
| C1 + A4E | V45E | L34M | G51V | I99V | I143L | |
| C1 + A4E | S28P | L34M | G51V | I99V | I143L | F54T |
| C1 + A4E | S28P | L34M | G51V | I99V | I143L | F54T |
| C1 + A4E | S28P | | | | | |

SEQUENCE LISTING

SEQ ID NO: 1 (Native mature OgLuc protein) *Oplophorus gracilirostris*
FTLADFVGDWQQTAGYNQDQVLEQGGLSSLFQALGVSVTPIQKVVLSGENGLKADIHVIIPYEGLSGFQMGLIEMIFK
VVYPVDDHHFKIILHYGTLVIDGVTPNMIDYFGRPYPGIAVFDGKQITVTGTLWNGNKIYDERLINPDGSLLFRVTIN
GVTGWRLCENILA SEQ ID NO: 2 (C1A4E nucleotide)
ATGGTGTTTACATTGGAGGATTTCGTTGGAGACTGGCGGCAGACAGCTGGATACAACCAAGATCAAGTGTTAGAACAA
GGAGGATTGTCTAGTCTGTTCCAAAAGCTGGGAGTGTCAGTCACCCCAATCCAGAAAATTGTGCTGTCTGGGGAGAAT
GGGTTAAAATTTGATATTCATGTCATCATCCCTTACGAGGGACTCAGTGGTTTTCAAATGGGTCTGATTGAAATGATC
TTCAAAGTTGTTTACCCAGTGGATGATCATCATTTCAAGATTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC SEQ ID NO: 3 (C1A4E protein)
MVFTLEDFVGDWRQTAGYNQDQVLEQGGLSSLFQKLGVSVTPIQKIVLSGENGLKFDIHVIIPYEGLSGFQMGLIEMI
FKVVYPVDDHHFKIILHYGTLVIDGVTPNMIDYFGRPYEGIAVFDGKKITVTGTLWNGNKIIDERLINPDGSLLFRVT
INGVTGWRLCERILA SEQ ID NO: 4 (QC27 nucleotide)
ATGGTGTTTACATTGGAGGATTTCGTTGGAGACTGGCGGCAGACAGCTGGATACAACCTAGATCAAGTGTTAGAACAA
GGAGGATTGTCTAGTCTGTTCCAAAAGCTGGGAGTGTCAGTCACCCCAATCCAGAAAATTGTGCTGTCTGGGGAGAAT
GGGTTAAAAATTGATATTCATGTCATCATCCCTTACGAGGGACTCAGTGGTTTTCAAATGGGTCTGATTGAAATGATC
TTCAAAGTTGTTTACCCAGTGGATGATCATCATTTCAAGATTATTCACCATTATGGTACACTCGTTATTGACGGTGTG
ACACCAAACATGATTGACTTCTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC SEQ ID NO: 5 (QC27 protein)
MVFTLEDFVGDWRQTAGYNLDQVLEQGGLSSLFQKLGVSVTPIQKIVLSGENGLKIDIHVIIPYEGLSGFQMGLIEMI
FKVVYPVDDHHFKIIHHYGTLVIDGVTPNMIDFFGRPYEGIAVFDGKKITVTGTLWNGNKIIDERLINPDGSLLFRVT
INGVTGWRLCERILA -continued

SEQUENCE LISTING

SEQ ID NO: 6 (QC27 9a nucleotide)
ATGGTGTTTACATTGGAGGATTTCGTTGGAGACTGGCGGCAGACAGCTGGATACAACCTAGATCAACTGTTAGAACAA
GGAGGATTGTCTAGTCTGTTCCAAAAGCTGGGAGTGTCAGTCACCCCAATCCAGAAAATTGTGCTGTCTGGGGAGAAT
GGGTTAAAAATTGATATTCATGTCATCATCCCTTACGAGGGACTCAGTGGTTATCAAATGGGTCAGATTGAAAAGATC
TTCAAAGTTGTTTACCCAGTGGATGATCATCATTTCAAGATTATTCGCCATTATGGTACACTCGTTATTGACGGTGTG
ACACCAAACATGATTGACTTCTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAATCACCGGATGGCGCCTTTGCGAGCGTATTCTTGCC SEQ ID NO: 7 (QC27 9a protein)
MVFTLEDFVGDWRQTAGYNLDQLLEQGGLSSLFQKLGVSVTPIQKIVLSGENGLKIDIHVIIPYEGLSGYQMGQIEKI
FKVVYPVDDHHFKIIRHYGTLVIDGVTPNMIDFFGRPYEGIAVFDGKKITVTGTLWNGNKIIDERLINPDGSLLFRVT
INGITGWRLCERILA SEQ ID NO: 8 (IVY nucleotide)
ATGGTGTTTACATTGGAGGATTTCGTTGGAGACTGGCGGCAGACAGCTGGATACAACCAAGATCAAGTGTTAGAACAA
GGAGGATTGTCTAGTCTGTTCCAAAAGCTGGGAGTGTCAGTCACCCCAATCCAGAAAATTGTGCTGTCTGGGGAGAAT
GGGTTAAAAATTGATATTCATGTCATCATCCCTTACGAGGGACTCAGTGGTTTTCAAATGGGTCTGATTGAAATGATC
TACAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC SEQ ID NO: 9 (IVY protein)
MVFTLEDFVGDWRQTAGYNQDQVLEQGGLSSLFQKLGVSVTPIQKIVLSGENGLKIDIHVIIPYEGLSGFQMGLIEMI
YKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 10 (IVY + C1.3 nucleotide)
ATGGTGTTTACATTGGAGGATTACGTTGGAGACTGGCGGCAGACAGCTGGATACAACCAAGATCAAGTGTTAGAACAA
GGAGGATTGTCTAGTCTGTTCCAAAATCTGGGAGTGTCTGTCACCCCAATCCAGAAAATTGTGCTGTCTGGGGAGAAT
GGGTTAAAAATTGATATTCATGTCATCATCCCTTACGAGGGACTCAGTGGTTTTCAAATGGGTCTGATTGAAATGATC
TACAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCGACAAGATCATTGATGAGCGCCTGATCAACCCAGATGGTTCACTCCTCTTCCGCGTTACT
ACCAATGGAGTCACCGGATGGCGCCTTTGCGAGCGTATTCTTGCC SEQ ID NO: 11 (IVY + C1.3 protein)
MVFTLEDYVGDWRQTAGYNQDQVLEQGGLSSLFQNLGVSVTPIQKIVLSGENGLKIDIHVIIPYEGLSGFQMGLIEMI
YKVVYPVDDHHFKVILHYGTLVIDGVTPNMIDYFGRPYEGIAVFDGKKITVTGTLWNGDKIIDERLINPDGSLLFRVT
TNGVTGWRLCERILA SEQ ID NO: 12 (IVY C5.19 nucleotide)
ATGGTGTTTACATTGGAGGATTTCGTTGGAGACTGGCGGCAGACAGCTGGATACAACCAAGATCAAGTGTTAGAACAA
GGAGGAGTGTCTAGTCTGTTCCAAAAGCTGGGAGTGTCAATCACCCCAATCCAGAAAATTGTGCTGTCTGGGGAGAAT
GGGTTAAAAATTGATATTCATGTCATCATCCCTTACGAGGGACTCAGTGGTTTTCAAATGGGTCTGATTGAAATGATC
TACAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCAATCCTCTTCCGCGTTACT
ATCAATGGAGTCACCGGATGGCGCCTTTGCGAGCGTATTCTTGCC SEQ ID NO: 13 (IVY C5.19 protein)
MVFTLEDFVGDWRQTAGYNQDQVLEQGGVSSLFQKLGVSITPIQKIVLSGENGLKIDIHVIIPYEGLSGFQMGLIEMI
YKVVYPVDDHHFKVILHYGTLVIDGVTPNMIDYFGRPYEGIAVFDGKKITVTGTLWNGNKIIDERLINPDGSILFRVT
INGVTGWRLCERILA SEQ ID NO: 14 (IV nucleotide)
ATGGTGTTTACATTGGAGGATTTCGTTGGAGACTGGCGGCAGACAGCTGGATACAACCAAGATCAAGTGTTAGAACAA
GGAGGATTGTCTAGTCTGTTCCAAAAGCTGGGAGTGTCAGTCACCCCAATCCAGAAAATTGTGCTGTCTGGGGAGAAT
GGGTTAAAAATTGATATTCATGTCATCATCCCTTACGAGGGACTCAGTGGTTTTCAAATGGGTCTGATTGAAATGATC
TTCAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC SEQ ID NO: 15 (IV protein)
MVFTLEDFVGDWRQTAGYNQDQVLEQGGLSSLFQKLGVSVTPIQKIVLSGENGLKIDIHVIIPYEGLSGFQMGLIEMI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 16 (15C1 nucleotide)
ATGGTGTTTACATTGAAGGATTTCGTTGGAGACTGGCGGCAGACAGCTGGATACAACCAAGATCAAGTGTTAGAACAA
GGAGGATTGTCTAGTCTGTTCCAAAATCTGGGAGTGTCAGTCACCCCAATCCAGAAAATTGTGCTGTCTGGGGAGAAT
GGGTTAAAAATTGATATTCATGTCATCATCCCTTACGAGGGACTCAGTGGTTATCAAATGGGTCAGATTGAAAAGATC
TTCAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT -continued

SEQUENCE LISTING

GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC

SEQ ID NO: 17 (15C1 protein)
MVFTLKDFVGDWRQTAGYNQDQVLEQGGLSSLFQNLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 18 (9B8 nucleotide)
ATGGTGTTTACATTGGAGGATTTCGTTGGAGACTGGCGGCAGACAGCTGGATACAACCTAGATCAAGTGTTAGAACAA
GGAGGATTGTCTAGTCTGTTCCAAAAGCTGGGAGTGTCAGTCACCCCAATCCAGAAAATTGTGCTGTCTGGGGAGAAT
GGGTTAAAAATTGATATTCATGTCATCATCCCTTACGAGGGACTCAGTGGTTATCAAATGGGTCAGATTGAAAAGATC
TTCAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC SEQ ID NO: 19 (9B8 protein)
MVFTLEDFVGDWRQTAGYNLDQVLEQGGLSSLFQKLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 20 (9F6 nucleotide)
ATGGTGTTTACATTGGAGGATTTCGTTGGAGACTGGCGGCAGACAGCTGGATACAACCTAGATCAAGTGTTAGAACAA
GGAGGAGTGTCTAGTCTGTTCCAAAAGCTGGGAGTGTCAATCACCCCAATCCAGAAAATTGTGCTGTCTGGGGAGAAT
GGGTTAAAAATTGATATTCATGTCATCATCCCTTACGAGGGACTCAGTGGTTATCAAATGGGTCAGATTGAAAAGATC
TTCAAAGTTGTTTACCCAGTGGATGATCATCATTTCAAGGTTATTCTCCATTATGGTACACTCGTTATTGACGGTGTG
ACACCAAACATGATTGACTACTTTGGACGCCCTTACGAGGGAATTGCTGTGTTTGACGGCAAGAAGATCACAGTTACT
GGAACTCTGTGGAACGGCAACAAGATCATTGATGAGCGCCTGATCAACCCAGATGGTTCACTCCTCTTCCGCGTTACT
ATCAATGGAGTCACCGGATGGCGCCTTTGCGAGCGTATTCTTGCC SEQ ID NO: 21 (9F6 protein)
MVFTLEDFVGDWRQTAGYNLDQVLEQGGVSSLFQKLGVSITPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 22 (IV opt nucleotide)
atggtgtttacactcgaagatttcgtaggggactggcggcagacagccggctacaaccaagaccaagtccttgagcag
ggcggtctgtccagtttgtttcagaaactcggggtgtccgtaacaccgatccaaaagattgtcctgagcggtgaaaac
ggcctgaagatcgacatccatgtcatcatcccgtatgaaggtctgagcggcttccagatgggcctcattgagatgatc
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 23 (IV optB nucleotide)
atggtattcacactggaggattttgtcggtgattggcggcaaaccgctgggtacaaccaggaccaggttctcgaacaa
gggggcctcagctccctgtttcaaaaactgggtgttagcgttacacctattcaaaaaatcgtgctctccggggaaaac
gggctcaaaatcgatattcatgtgattatcccttacgaagggctctccgggtttcagatggggctgatcgaaatgatc
tttaaggtcgtctatcccgtagatgatcaccacttcaaggtgatcctccactacgggaccctcgtaattgatggcgtg
acccccaacatgatcgactattttgggcgcccttacgaggggattgctgtcttcgatggcaaaaaaattacagtgaca
ggcacactctggaacgggaataagatcattgatgagcgcctgattaatcccgatgggagcctgctctttcgggtgaca
attaacggcgtaacaggctggcgcctctgtgaacggattctggcg SEQ ID NO: 24 (9B8 opt nucleotide)
atggtgtttacactcgaagatttcgtaggggactggcggcagacagccggctacaacctggaccaagtccttgagcag
ggcggtctgtccagtttgtttcagaaactcggggtgtccgtaacaccgatccaaaagattgtcctgagcggtgaaaac
ggcctgaagatcgacatccatgtcatcatcccgtatgaaggtctgagcggctatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 25 (9B8 optB nucleotide)
atggtattcacactggaggattttgtcggtgattggcggcaaaccgctgggtacaacctcgaccaggttctcgaacaa
gggggcctcagctccctgtttcaaaaactgggtgttagcgttacacctattcaaaaaatcgtgctctccggggaaaac
gggctcaaaatcgatattcatgtgattatcccttacgaagggctctccgggtatcagatggggcagatcgaaaaaatc
tttaaggtcgtctatcccgtagatgatcaccacttcaaggtgatcctccactacgggaccctcgtaattgatggcgtg
acccccaacatgatcgactattttgggcgcccttacgaggggattgctgtcttcgatggcaaaaaaattacagtgaca
ggcacactctggaacgggaataagatcattgatgagcgcctgattaatcccgatgggagcctgctctttcgggtgaca
attaacggcgtaacaggctggcgcctctgtgaacggattctggcg SEQ ID NO: 26 (8A3 nucleotide)
Atggtgattacattggaggatttcgttggagactggcggcagacagctggatacaaccaagatcaagtgttagaacaa
ggaggagtgtctagtctgttccaaaagctgggagtgtcaatcaccccaatccagaaaattgtgctgtctggggagaat
gggttaaaaattgatattcatgtcatcatcccttacgagggactcagtggttttcaaatgggtctgattgaaatgatc
ttcaaagttgtttacccagtggatgatcatcatttcaaggttattctccattatggtacactcgttattgacggtgtg -continued

SEQUENCE LISTING acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgcc SEQ ID NO: 27 (8A3 protein)
MVITLEDFVGDWRQTAGYNQDQVLEQGGVSSLFQKLGVSITPIQKIVLSGENGLKIDIHVIIPYEGLSGFQMGLIEMI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 28 (Luc2 nucleotide)
atggaagatgccaaaaacattaagaagggcccagcgccattctacccactcgaagacgggaccgccggcgagcagctg
cacaaagccatgaagcgctacgccctggtgcccggcaccatcgcctttaccgacgcacatatcgaggtggacattacc
tacgccgagtacttcgagatgagcgttcggctggcagaagctatgaagcgctatgggctgaatacaaaccatcggatc
gtggtgtgcagcgagaatagcttgcagttcttcatgcccgtgttgggtgccctgttcatcggtgtggctgtggcccca
gctaacgacatctacaacgagcgcgagctgctgaacagcatgggcatcagccagcccaccgtcgtattcgtgagcaag
aaagggctgcaaaagatcctcaacgtgcaaaagaagctaccgatcatacaaaagatcatcatcatggatagcaagacc
gactaccagggcttccaaagcatgtacaccttcgtgacttcccatttgccacccggcttcaacgagtacgacttcgtg
cccgagagcttcgaccgggacaaaaccatcgccctgatcatgaacagtagtggcagtaccggattgcccaagggcgta
gccctaccgcaccgcaccgcttgtgtccgattcagtcatgcccgcgaccccatcttcggcaaccagatcatccccgac
accgctatcctcagcgtggtgccatttcaccacggcttcggcatgttcaccacgctgggctacttgatctgcggcttt
cgggtcgtgctcatgtaccgcttcgaggaggagctattcttgcgcagcttgcaagactataagattcaatctgccctg
ctggtgcccacactatttagcttcttcgctaagagcactctcatcgacaagtacgacctaagcaacttgcacgagatc
gccagcggcggggcgccgctcagcaaggaggtaggtgaggccgtggccaaacgcttccacctaccaggcatccgccag
ggctacggcctgacagaaacaaccagcgccattctgatcacccccgaaggggacgacaagcctggcgcagtaggcaag
gtggtgcccttcttcgaggctaaggtggtggacttggacaccggtaagacactgggtgtgaaccagcgcggcgagctg
tgcgtccgtggccccatgatcatgagcggctacgttaacaaccccgaggctacaaacgctctcatcgacaaggacggc
tggctgcacagcggcgacatcgcctactgggacgaggacgagcacttcttcatcgtggaccggctgaagagcctgatc
aaatacaagggctaccaggtagccccagccgaactggagagcatcctgctgcaacaccccaacatcttcgacgccggg
gtcgccggcctgcccgacgacgatgccggcgagctgcccgccgcagtcgtcgtgctggaacacggtaaaaccatgacc
gagaaggagatcgtggactatgtggccagccaggttacaaccgccaagaagctgcgcggtggtgttgtgttcgtggac
gaggtgcctaaaggactgaccggcaagttggacgcccgcaagatccgcgagattctcattaaggccaagaagggcggc
aagatcgccgtt SEQ ID NO: 29 (Luc2 protein)
medaknikkgpapfypledgtageqlhkamkryalvpgtiaftdahievdityaeyfemsvrlaeamkryglntnhri
vvcsenslqffmpvlgalfigvavapandiynerellnsmgisqptvvfvskkglqkilnvqkklpiiqkiiimdskt
dyqgfqsmytfvtshlppgfneydfvpesfdrdktialimnssgstglpkgvalphrtacvrfshardpifgnqiipd
tailsvvpfhhgfgmfttlgylicgfrvvlmyrfeeelflrslqdykiqsallvptlfsffakstlidkydlsnlhei
asggaplskevgeavakrfhlpgirqgygltettsailitpegddkpgavgkvvpffeakvvdldtgktlgvnqrgel
cvrgpmimsgyvnnpeatnalidkdgwlhsgdiaywdedehffivdrlkslikykgyqvapaelesillqhpnifdag
vaglpdddagelpaavvvlehgktmtekeivdyvasqvttakklrggvvfvdevpkgltgkldarkireilikakkgg
kiav SEQ ID NO: 30 (HRL (Humanized Renilla) nucleotide)
Atggcttccaaggtgtacgaccccgagcaacgcaaacgcatgatcactgggcctcagtggtgggctcgctgcaagcaa
atgaacgtgctggactccttcatcaactactatgattccgagaagcacgccgagaacgccgtgatttttctgcatggt
aacgctgcctccagctacctgtggaggcacgtcgtgcctcacatcgagcccgtggctagatgcatcatccctgatctg
atcggaatgggtaagtccggcaagagcgggaatggctcatatcgcctcctggatcactacaagtacctcaccgcttgg
ttcgagctgctgaaccttccaaagaaaatcatctttgtgggccacgactgggggggcttgtctggcctttcactactcc
tacgagcaccaagacaagatcaaggccatcgtccatgctgagagtgtcgtggacgtgatcgagtcctgggacgagtgg
cctgacatcgaggaggatatcgccctgatcaagagcgaagagggcgagaaaatggtgcttgagaataacttcttcgtc
gagaccatgctcccaagcaagatcatgcggaaactggagcctgaggagttcgctgcctacctggagccattcaaggag
aagggcgaggttagacggcctaccctctcctggcctcgcgagatccctctcgttaagggaggcaagcccgacgtcgtc
cagattgtccgcaactacaacgcctaccttcgggccagcgacgatctgcctaagatgttcatcgagtccgaccctggg
ttcttttccaacgctattgtcgagggagctaagaagttccctaacaccgagttcgtgaaggtgaagggcctccacttc
agccaggaggacgctccagatgaaatgggtaagtacatcaagagcttcgtggagcgcgtgctgaagaacgagcag SEQ ID NO: 31 (HRL (Humanized Renilla) protein)
MASKVYDPEQRKRMITGPQWWARCKQMNVLDSFINYYDSEKHAENAVIFLHGNAASSYLWRHVVPHIEPVARCIIPDL
IGMGKSGKSGNGSYRLLDHYKYLTAWFELLNLPKKIIFVGHDWGACLAFHYSYEHQDKIKAIVHAESVVDVIESWDEW
PDIEEDIALIKSEEGEKMVLENNFFVETMLPSKIMRKLEPEEFAAYLEPFKEKGEVRRPTLSWPREIPLVKGGKPDVV
QIVRNYNAYLRASDDLPKMFIESDPGFFSNAIVEGAKKFPNTEFVKVKGLHFSQEDAPDEMGKYIKSFVERVLKNEQ SEQ ID NO: 32 (Id-HRL-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggcttccaaggtgtacgaccccgagcaacgcaaacgcatgatcact
gggcctcagtggtgggctcgctgcaagcaaatgaacgtgctggactccttcatcaactactatgattccgagaagcac
gccgagaacgccgtgatttttctgcatggtaacgctgcctccagctacctgtggaggcacgtcgtgcctcacatcgag
cccgtggctagatgcatcatccctgatctgatcggaatgggtaagtccggcaagagcgggaatggctcatatcgcctc
ctggatcactacaagtacctcaccgcttggttcgagctgctgaaccttccaaagaaaatcatctttgtgggccacgac
tgggggggcttgtctggcctttcactactcctacgagcaccaagacaagatcaaggccatcgtccatgctgagagtgtc
gtggacgtgatcgagtcctgggacgagtggcctgacatcgaggaggatatcgccctgatcaagagcgaagagggcgag
aaaatggtgcttgagaataacttcttcgtcgagaccatgctcccaagcaagatcatgcggaaactggagcctgaggag -continued

SEQUENCE LISTING ttcgctgcctacctggagccattcaaggagaagggcgaggttagacggcctaccctctcctggcctcgcgagatccct
ctcgttaagggaggcaagcccgacgtcgtccagattgtccgcaactacaacgcctaccttcgggccagcgacgatctg
cctaagatgttcatcgagtccgaccctgggttcttttccaacgctattgtcgagggagctaagaagttccctaacacc
gagttcgtgaaggtgaagggcctccacttcagccaggaggacgctccagatgaaatgggtaagtacatcaagagcttc
gtggagcgcgtgctgaagaacgagcaggtttctctcgagccaaccactgaggatctgtactttcagagcgataacgat
ggatccgaaatcggtactggctttccattcgaccccattatgtggaagtcctgggcgagcgcatgcactacgtcgat
gttggtccgcgcgatggcacccctgtgctgttcctgcacggtaacccgacctcctcctacgtgtggcgcaacatcatc
ccgcatgttgcaccgacccatcgctgcattgctccagacctgatcggtatgggcaaatccgacaaaccagacctgggt
tatttcttcgacgaccacgtccgcttcatggatgccttcatcgaagccctgggtctggaagaggtcgtcctggtcatt
cacgactggggctccgctctgggtttccactgggccaagcgcaatccagagcgcgtcaaaggtattgcatttatggag
ttcatccgccctatcccgacctgggacgaatggccagaatttgcccgcgagaccttccaggccttccgcaccaccgac
gtcggccgcaagctgatcatcgatcagaacgtttttatcgagggtacgctgccgatgggtgtcgtccgcccgctgact
gaagtcgagatggaccattaccgcgagccgttcctgaatcctgttgaccgcgagccactgtggcgcttcccaaacgag
ctgccaatcgccggtgagccagcgaacatcgtcgcgctggtcgaagaatacatggactggctgcaccagtcccctgtc
ccgaagctgctgttctggggcaccccaggcgttctgatcccaccggccgaagccgctcgcctggccaaaagcctgcct
aactgcaaggctgtggacatcggcccgggtctgaatctgctgcaagaagacaacccggacctgatcggcagcgagatc
gcgcgctggctgtctactctggagatttccggt SEQ ID NO: 33 (Id-HRL-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMASKVYDPEQRKRMIT
GPQWWARCKQMNVLDSFINYYDSEKHAENAVIFLHGNAASSYLWRHVVPHIEPVARCIIPDLIGMGKSGKSGNGSYRL
LDHYKYLTAWFELLNLPKKIIFVGHDWGACLAFHYSYEHQDKIKAIVHAESVVDVIESWDEWPDIEEDIALIKSEEGE
KMVLENNFFVETMLPSKIMRKLEPEEFAAYLEPFKEKGEVRRPTLSWPREIPLVKGGKPDVVQIVRNYNAYLRASDDL
PKMFIESDPGFFSNAIVEGAKKFPNTEFVKVKGLHFSQEDAPDEMGKYIKSFVERVLKNEQVSLEPTTEDLYFQSDND
GSEIGTGFPFDPHYVEVLGERMHYVDVGPRDGTPVLFLHGNPTSSYVWRNIIPHVAPTHRCIAPDLIGMGKSDKPDLG
YFFDDHVRFMDAFIEALGLEEVVLVIHDWGSALGFHWAKRNPERVKGIAFMEFIRPIPTWDEWPEFARETFQAFRTTD
VGRKLIIDQNVFIEGTLPMGVVRPLTEVEMDHYREPFLNPVDREPLWRFPNELPIAGEPANIVALVEEYMDWLHQSPV
PKLLFWGTPGVLIPPAEAARLAKSLPNCKAVDIGPGLNLLQEDNPDLIGSEIARWLSTLEISG SEQ ID NO: 34 (8A3-HT7 fusion nucleotide)
atggtgattacattggaggatttcgttggagactggcggcagacagctggatacaaccaagatcaagtgttagaacaa
ggaggagtgtctagtctgttccaaaagctgggagtgtcaatcaccccaatccagaaaattgtgctgtctggggagaat
gggttaaaaattgatattcatgtcatcatcccttacgagggactcagtggttttcaaatgggtctgattgaaatgatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgacccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt
gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg
ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 35 (8A3-HT7 fusion protein)
MVITLEDFVGDWRQTAGYNQDQVLEQGGVSSLFQKLGVSITPIQKIVLSGENGLKIDIHVIIPYEGLSGFQMGLIEMI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG SEQ ID NO: 36 (9B8-HT7 fusion nucleotide)
atggtgtttacattggaggatttcgttggagactggcggcagacagctggatacaacctagatcaagtgttagaacaa
ggaggattgtctagtctgttccaaaagctgggagtgtcagtcaccccaatccagaaaattgtgctgtctggggagaat
gggttaaaaattgatattcatgtcatcatcccttacgagggactcagtggttatcaaatgggtcagattgaaaagatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgacccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt
gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg -continued

SEQUENCE LISTING ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 37 (9B8-HT7 fusion protein)
MVFTLEDFVGDWRQTAGYNLDQVLEQGGLSSLFQKLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG SEQ ID NO: 38 (9F6-HT7 fusion nucleotide)
atggtgtttacattggaggatttcgttggagactggcggcagacagctggatacaacctagatcaagtgttagaacaa
ggaggagtgtctagtctgttccaaaagctgggagtgtcaatcaccccaatccagaaaattgtgctgtctggggagaat
gggttaaaaattgatattcatgtcatcatcccttacgagggactcagtggttatcaaatgggtcagattgaaaagatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgacccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt
gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg
ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 39 (9F6-HT7 fusion protein)
MVFTLEDFVGDWRQTAGYNLDQVLEQGGVSSLFQKLGVSITPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG SEQ ID NO: 40 (Id-9B8 opt-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggaccaagtccttgagcagggcggtctgtccagtttgtttcagaaactcggggtgtccgtaacaccg
atccaaaagattgtcctgagcggtgaaaacggcctgaagatcgacatccatgtcatcatcccgtatgaaggtctgagc
ggctatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccggaccctgtggaacggcaacaaaattatcgacgagcgcctgatcaac
cccgacggctccctgctgttccgcgtaaccatcaacggagtgaccggctggcggctgtgcgagcgtattcttgccgga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggtt SEQ ID NO: 41 (Id-9B8 opt-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQKLGVSVTPIQKIVLSGENGLKIDIHVIIPYEGLSGYQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE -continued

SEQUENCE LISTING

WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G

SEQ ID NO: 42 (9B8 opt + K33N nucleotide)
Atggtgtttacactcgaagatttcgtaggggactggcggcagacagccggctacaacctggaccaagtccttgagcag
ggcggtctgtccagtttgtttcagaatctcggggtgtccgtaacaccgatccaaaagattgtcctgagcggtgaaaac
ggcctgaagatcgacatccatgtcatcatcccgtatgaaggtctgagcggctatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 43 (9B8 opt + K33N protein)
MVFTLEDFVGDWRQTAGYNLDQVLEQGGLSSLFQNLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 44 (QC27-HT7 nucleotide)
atggtgtttacattggaggatttcgttggagactggcggcagacagctggatacaacctagatcaagtgttagaacaa
ggaggattgtctagtctgttccaaaagctgggagtgtcagtcaccccaatccagaaaattgtgctgtctggggagaat
gggttaaaaattgatattcatgtcatcatcccttacgagggactcagtggttttcaaatgggtctgattgaaatgatc
ttcaaagttgtttacccagtggatgatcatcatttcaagattattcaccattatggtacactcgttattgacggtgtg
acaccaaacatgattgacttctttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgaccccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt
gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg
ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 45 (QC27-HT7 protein)
MVFTLEDFVGDWRQTAGYNLDQVLEQGGLSSLFQKLGVSVTPIQKIVLSGENGLKIDIHVIIPYEGLSGFQMGLIEMI
FKVVYPVDDHHFKIIHHYGTLVIDGVTPNMIDFFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG SEQ ID NO: 46 (8F2)
atggtgtttacattggaggatttcgttggagactggcggcagacagctggatacaaccaagatcaagtgttagaacaa
ggaggagtgtctagtctgttccaaaagctgggagtgtcagtcaccccaatccagaaaattgtgctgtctggggagaat
gggttaaaaattgatattcatgtcatcatcccttacgagggactcagtggttttcaaatgggtctgattgaaatgatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgcc SEQ ID NO: 47 (8F2 protein)
MVFTLEDFVGDWRQTAGYNQDQVLEQGGVSSLFQKLGVSVTPIQKIVLSGENGLKIDIHVIIPYEGLSGFQMGLIEMI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 48 (IV-HT7 nucleotide)
atggtgtttacattggaggatttcgttggagactggcggcagacagctggatacaaccaagatcaagtgttagaacaa
ggaggattgtctagtctgttccaaaagctgggagtgtcagtcaccccaatccagaaaattgtgctgtctggggagaat
gggttaaaaattgatattcatgtcatcatcccttacgagggactcagtggttttcaaatgggtctgattgaaatgatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgaccccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt -continued

SEQUENCE LISTING gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg
ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 49 (IV-HT7 protein)
MVFTLEDFVGDWRQTAGYNQDQVLEQGGLSSLFQKLGVSVTPIQKIVLSGENGLKIDIHVIIPYEGLSGFQMGLIEMI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG SEQ ID NO: 50 (8F2-HT7 nucleotide)
atggtgtttacattggaggatttcgttggagactggcggcagacagctggatacaaccaagatcaagtgttagaacaa
ggaggagtgtctagtctgttccaaaagctgggagtgtcagtcaccccaatccagaaaattgtgctgtctggggagaat
gggttaaaaattgatattcatgtcatcatcccttacgagggactcagtggttttcaaatgggtctgattgaaatgatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgaccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt
gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg
ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 51 (8F2-HT7 protein)
MVFTLEDFVGDWRQTAGYNQDQVLEQGGVSSLFQKLGVSVTPIQKIVLSGENGLKIDIHVIIPYEGLSGFQMGLIEMI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG SEQ ID NO: 52 (15C1-HT7 nucleotide)
atggtgtttacattgaaggatttcgttggagactggcggcagacagctggatacaaccaagatcaagtgttagaacaa
ggaggattgtctagtctgttccaaaatctgggagtgtcagtcaccccaatccagaaaattgtgctgtctggggagaat
gggttaaaaattgatattcatgtcatcatcccttacgagggactcagtggttatcaaatgggtcagattgaaaagatc
ttcaaagttgtttacccagtggatgatcatcatttcaaggttattctccattatggtacactcgttattgacggtgtg
acaccaaacatgattgactactttggacgcccttacgagggaattgctgtgtttgacggcaagaagatcacagttact
ggaactctgtggaacggcaacaagatcattgatgagcgcctgatcaacccagatggttcactcctcttccgcgttact
atcaatggagtcaccggatggcgcctttgcgagcgtattcttgccggatatctcgagccaaccactgaggatctgtac
tttcagagcgataacgatggatccgaaatcggtactggctttccattcgaccccattatgtggaagtcctgggcgag
cgcatgcactacgtcgatgttggtccgcgcgatggcacccctgtgctgttcctgcacggtaacccgacctcctcctac
gtgtggcgcaacatcatcccgcatgttgcaccgacccatcgctgcattgctccagacctgatcggtatgggcaaatcc
gacaaaccagacctgggttatttcttcgacgaccacgtccgcttcatggatgccttcatcgaagccctgggtctggaa
gaggtcgtcctggtcattcacgactggggctccgctctgggtttccactgggccaagcgcaatccagagcgcgtcaaa
ggtattgcatttatggagttcatccgccctatcccgacctgggacgaatggccagaatttgcccgcgagaccttccag
gccttccgcaccaccgacgtcggccgcaagctgatcatcgatcagaacgtttttatcgagggtacgctgccgatgggt
gtcgtccgcccgctgactgaagtcgagatggaccattaccgcgagccgttcctgaatcctgttgaccgcgagccactg
tggcgcttcccaaacgagctgccaatcgccggtgagccagcgaacatcgtcgcgctggtcgaagaatacatggactgg
ctgcaccagtcccctgtcccgaagctgctgttctggggcaccccaggcgttctgatcccaccggccgaagccgctcgc
ctggccaaaagcctgcctaactgcaaggctgtggacatcggcccgggtctgaatctgctgcaagaagacaacccggac
ctgatcggcagcgagatcgcgcgctggctgtctactctggagatttccggt SEQ ID NO: 53 (15C1-HT7 protein)
MVFTLKDFVGDWRQTAGYNQDQVLEQGGLSSLFQNLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGYLEPTTEDLYFQSDNDGSEIGTGFPFDPHYVEVLGERMHYVDVGPRDGTPVLFLHGNPTSSY
VWRNIIPHVAPTHRCIAPDLIGMGKSDKPDLGYFFDDHVRFMDAFIEALGLEEVVLVIHDWGSALGFHWAKRNPERVK
GIAFMEFIRPIPTWDEWPEFARETFQAFRTTDVGRKLIIDQNVFIEGTLPMGVVRPLTEVEMDHYREPFLNPVDREPL
WRFPNELPIAGEPANIVALVEEYMDWLHQSPVPKLLFWGTPGVLIPPAEAARLAKSLPNCKAVDIGPGLNLLQEDNPD
LIGSEIARWLSTLEISG -continued

SEQUENCE LISTING

SEQ ID NO: 54 (OgLuc Secretion Signal Peptide) *Oplophorus gracilirostris*
atggcttactccacactgttcatcattgctctcacagccgtcgtaacacaagcctcctccacacagaaaagcaacctg
aca SEQ ID NO: 55 (Id-C1A4E-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacattggaggatttcgttggagactggcggcagacagct
ggatacaaccaagatcaagtgttagaacaaggaggattgtctagtctgttccaaaagctgggagtgtcagtcacccca
atccagaaaattgtgctgtctggggagaatgggttaaaatttgatattcatgtcatcatcccttacgagggactcagt
ggttttcaaatgggtctgattgaaatgatcttcaaagttgtttacccagtggatgatcatcatttcaagattattctc
cattatggtacactcgttattgacggtgtgacaccaaacatgattgactactttggacgcccttacgagggaattgct
gtgtttgacggcaagaagatcacagttactggaactctgtggaacggcaacaagatcattgatgagcgcctgatcaac
ccagatggttcactcctcttccgcgttactatcaatggagtcaccggatggcgcctttgcgagcgtattcttgccgga
tctctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 56 (Id-C1A4E-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNQDQVLEQGGLSSLFQKLGVSVTPIQKIVLSGENGLKFDIHVIIPYEGLSGFQMGLIEMIFKVVYPVDDHHFKIIL
HYGTLVIDGVTPNMIDYFGRPYEGIAVFDGKKITVTGTLWNGNKIIDERLINPDGSLLFRVTINGVTGWRLCERILAG
SLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 57 (Id-IV-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacattggaggatttcgttggagactggcggcagacagct
ggatacaaccaagatcaagtgttagaacaaggaggattgtctagtctgttccaaaagctgggagtgtcagtcacccca
atccagaaaattgtgctgtctggggagaatgggttaaaaattgatattcatgtcatcatcccttacgagggactcagt
ggttttcaaatgggtctgattgaaatgatcttcaaagttgtttacccagtggatgatcatcatttcaaggttattctc
cattatggtacactcgttattgacggtgtgacaccaaacatgattgactactttggacgcccttacgagggaattgct
gtgtttgacggcaagaagatcacagttactggaactctgtggaacggcaacaagatcattgatgagcgcctgatcaac
ccagatggttcactcctcttccgcgttactatcaatggagtcaccggatggcgcctttgcgagcgtattcttgccgtt
tctctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 58 (Id-IV-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNQDQVLEQGGLSSLFQKLGVSVTPIQKIVLSGENGLKIDIHVIIPYEGLSGFQMGLIEMIFKVVYPVDDHHFKVIL
HYGTLVIDGVTPNMIDYFGRPYEGIAVFDGKKITVTGTLWNGNKIIDERLINPDGSLLFRVTINGVTGWRLCERILAV
SLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE -continued

SEQUENCE LISTING

WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G

SEQ ID NO: 59 (Id-9B8 opt + K33N-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggaccaagtccttgagcagggcggtctgtccagtttgtttcagaatctcggggtgtccgtaacaccg
atccaaaagattgtcctgagcggtgaaaacggcctgaagatcgacatccatgtcatcatcccgtatgaaggtctgagc
ggctatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 60 (Id-9B8 opt + K33N-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQNLGVSVTPIQKIVLSGENGLKIDIHVIIPYEGLSGYQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 61 (Id-9B8-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacattggaggatttcgttggagactggcggcagacagct
ggatacaacctagatcaagtgttagaacaaggaggattgtctagtctgttccaaaagctgggagtgtcagtcacccca
atccagaaaattgtgctgtctggggagaatgggttaaaaattgatattcatgtcatcatcccttacgagggactcagt
ggttatcaaatgggtcagattgaaaagatcttcaaagttgtttacccagtggatgatcatcatttcaaggttattctc
cattatggtacactcgttattgacggtgtgacaccaaacatgattgactactttggacgcccttacgagggaattgct
gtgtttgacggcaagaagatcacagttactggaactctgtggaacggcaacaagatcattgatgagcgcctgatcaac
ccagatggttcactcctcttccgcgttactatcaatggagtcaccggatggcgcctttgcgagcgtattcttgccgtt
tctctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 62 (Id-9B8-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQKLGVSVTPIQKIVLSGENGLKIDIHVIIPYEGLSGYQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAV
SLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI -continued

SEQUENCE LISTING

VALVEEYMDWLHQSPVPKLLFWGTPGVLIPPAEAARLAKSLPNCKAVDIGPGLNLLQEDNPDLIGSEIARWLSTLEIS
G

SEQ ID NO: 63 (Id-9F6-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacattggaggatttcgttggagactggcggcagacagct
ggatacaacctagatcaagtgttagaacaaggaggagtgtctagtctgttccaaaagctgggagtgtcaatcacccca
atccagaaaattgtgctgtctggggagaatgggttaaaaattgatattcatgtcatcatcccttacgagggactcagt
ggttatcaaatgggtcagattgaaaagatcttcaaagttgtttacccagtggatgatcatcatttcaaggttattctc
cattatggtacactcgttattgacggtgtgacaccaaacatgattgactactttggacgcccttacgagggaattgct
gtgtttgacggcaagaagatcacagttactggaactctgtggaacggcaacaagatcattgatgagcgcctgatcaac
ccagatggttcactcctcttccgcgttactatcaatggagtcaccggatggcgcctttgcgagcgtattcttgccgtt
tctctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 64 (Id-9F6-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGVSSLFQKLGVSITPIQKIVLSGENGLKIDIHVIIPYEGLSGYQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAV
SLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 65 (9B8 opt-P nucleotide)
atggtgtttacactcgaagatttcgtaggggactggcggcagacagccggctacaacctggaccaagtccttgagcag
ggcggtctgtccagtttgtttcagaaactcggggtgtccgtaacaccgatccaaaagattgtcctgagcggtgaaaac
ggcctgaagatcgacatccatgtcatcatcccgtatgaaggtctgagcggctatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcgaattctcacggcttccctcccgaggtggaggag
caggccgccggcaccctgcccatgagctgcgcccaggagagcggcatggatagacaccctgctgcttgcgccagcgcc
aggatcaacgtc SEQ ID NO: 66 (2X ARE)
TAGCTTGGAAATGACATTGCTAATGGTGACAAAGCAACTTTTAGCTTGGAAATGACATTGCTAATGGTGACAAAGCAA
CTTT

SEQ ID NO: 67 (HRE)
CTGGAATTTTCTAGACTGGAATTTTCTAGACTGGAATTTTCTAGA

SEQ ID NO: 68 (K33N + 170G nucleotide)
atggtgtttacactcgaagatttcgtaggggactggcggcagacagccggctacaacctggaccaagtccttgagcag
ggcggtctgtccagtttgtttcagaatctcggggtgtccgtaacaccgatccaaaagattgtcctgagcggtgaaaac
ggcctgaagatcgacatccatgtcatcatcccgtatgaaggtctgagcggctatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcggga SEQ ID NO: 69 (K33N + 170G protein)
MVFTLEDFVGDWRQTAGYNLDQVLEQGGLSSLFQNLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAG SEQ ID NO: 70 (27A5 (NF) nucleotide)
ATGGTGTTTACACTCGAAGATTTCGTAGGGGACTGGCGGCAGACAGCCGGCTACAACCTGGACCAAGTCCTTGAGCAG
GGCGGTCTGTCCAGTTTGTTTCAGAATCTCGGGGTGTCCGTAACTCCGATCCAAAAGATTGTCCTGAGCGGTGAAAAC
GGCCTGAAGATCGACATCCATGTCATCATCCCGTATGAAGGTCTGAGCGGCTATCAGATGGGCCAGATCGAAAAAATT -continued

SEQUENCE LISTING

TTTAAGGTGGTGTACCCTGTGGATGATCATCACTTTAAGGTGATTCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCGGGA

SEQ ID NO: 71 (27A5 (NF) protein)
MVFTLEDFVGDWRQTAGYNLDQVLEQGGLSSLFQNLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAG SEQ ID NO: 72 (23D4 (NF) nucleotide)
ATGGTGTTTACACTCGAAGATTTCGTAGGGGACTGGCGGCAGACAGCCGGCTACAACCTGGACCAAGTCCTTGAGCAG
GGCGGCCTGTCCAGTTTGTTTCAGAATCTCGGGGTGTCCGTAACACCGATCCAAAAGATTGTCCTGAGCGGTGAAAAC
GGCCTGAAGATCGACATCCATGTCATCATCCCGTATGAAGGTCTGAGCGGCTATCAGATGGGCCAGATCGAAAAAATT
TTTAAGGTGGTGTACCCTGTGGATGATCATCACTTTAAGGTGATTCTGCACTATGGCACACTGGTAATCGACGGGGTT
ACGCCGAACTTGATCGACTATTTCGGACGTCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCGGGA SEQ ID NO: 73 (23D4 (NF) protein)
MVFTLEDFVGDWRQTAGYNLDQVLEQGGLSSLFQNLGVSVTPIQKIVLSGENGLKIDIHVIIPYEGLSGYQMGQIEKI
FKVVYPVDDHHFKVILHYGTLVIDGVTPNLIDYFGRPYEGIAVFDGKKITVTGTLWNGNKIIDERLINPDGSLLFRVT
INGVTGWRLCERILAG SEQ ID NO: 74 (24C2 (NF) nucleotide)
ATGGTGTTTACACTCGAAGATTTCGTAGGGGACTGGCAGCAGACAGCCGGCTACAACCTGGACCAAGTCCTTGAGCAG
GGCGGTCTGTCCAGTTTGTTTCAGAATCTCGGGGTGTCCGTAACTCCGATCCAAAAGATTGTCCTGAGCGGTGAAAAC
GGCCTGAAGATCGACATCCATGTCATCATCCCGTATGAAGGTCTGAGCGGCTATCAGATGGGCCAGATCGAAAAAATT
TTTAAGGTGGTGTACCCTGTGGATGATCATCACTTTAAGGTGATTCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCGGGA SEQ ID NO: 75 (24C2 (NF) protein)
MVFTLEDFVGDWQQTAGYNLDQVLEQGGLSSLFQNLGVSVTPIQKIVLSGENGLKIDIHVIIPYEGLSGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAG SEQ ID NO: 76 (Id-23D4-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggaccaagtccttgagcagggcggcctgtccagtttgtttcagaatctcggggtgtccgtaacaccg
atccaaaagattgtcctgagcggtgaaaacggcctgaagatcgacatccatgtcatcatcccgtatgaaggtctgagc
ggctatcagatgggccagatcgaaaaaatttttaaggtggtgtaccctgtggatgatcatcactttaaggtgattctg
cactatggcacactggtaatcgacggggttacgccgaacttgatcgactatttcggacgtccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctg SEQ ID NO: 77 (Id-23D4-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQNLGVSVTPIQKIVLSGENGLKIDIHVIIPYEGLSGYQMGQIEKIFKVVYPVDDHHFKVIL
HYGTLVIDGVTPNLIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGL SEQ ID NO: 78 (Id-24C2-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac -continued

SEQUENCE LISTING cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcagcagacagcc
ggctacaacctggaccaagtccttgagcagggcggtctgtccagtttgtttcagaatctcggggtgtccgtaactccg
atccaaaagattgtcctgagcggtgaaaacggcctgaagatcgacatccatgtcatcatcccgtatgaaggtctgagc
ggctatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 79 (Id-24C2-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWQQTA
GYNLDQVLEQGGLSSLFQNLGVSVTPIQKIVLSGENGLKIDIHVIIPYEGLSGYQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 80 (1F7 (NF) nucleotide)
ATGGTGTTTACACTCGAAGATTTCGTAGGGGACTGGCGGCAGACAGCCGGCTACAACCTGGACCAAGTCCTTGAGCAG
GGCGGTCTGTCCAGTTTGTTTCAGAATCTCGGGGTGTCCGTAACACCGATCCAAAGGATTGTCCTGAGCGGTGAAAAC
GGCCTGAAGATCGACATCCATGTCATCATCCCGTATGAAGGTCTGAGCGGCGATCAGATGGGCCAGATCGAAAAAATT
TTTAAGGTGGTGTACCCTGTGGATGATCATCACTTTAAGGTGATTCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCGGGA SEQ ID NO: 81 (1F7 (NF) protein)
MVFTLEDFVGDWRQTAGYNLDQVLEQGGLSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAG SEQ ID NO: 82 (15H1 (NF) nucleotide)
ATGGTGTTTACACTCGAAGATTTCGTAGGGGACTGGCGGCAGACAGCCGGCTACAACCTGGATCAAGTCCTTGAGCAG
GGCGGTCTGTCCAGTTTGTTTCAGAATCTCGGGGTGTCCGTAACACCGATCCAAAAGATTGTCCTGAGCGGTGAAAAC
GGCCTGAAGATCGACATCCATGTCATCATCCCGTATGAAGGTCTGAACGGCTATCAGATGGGCCAGATCGAAAAAATT
TTTAAGGTGGTGTACCCTGTGGATGATCATCACTTTAAGGTGATTCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCGGGA SEQ ID NO: 83 (15H1 (NF) protein)
MVFTLEDFVGDWRQTAGYNLDQVLEQGGLSSLFQNLGVSVTPIQKIVLSGENGLKIDIHVIIPYEGLNGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAG SEQ ID NO: 84 (Id-1F7-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggaccaagtccttgagcagggcggtctgtccagtttgtttcagaatctcggggtgtccgtaacaccg
atccaaaggattgtcctgagcggtgaaaacggcctgaagatcgacatccatgtcatcatcccgtatgaaggtctgagc
ggcgatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc -continued

SEQUENCE LISTING gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggag SEQ ID NO: 85 (Id-1F7-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQNLGVSVTPIQRIVLSGENGLKIDIHVIIPYEGLSGDQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 86 (Id-15H1-HT7 sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggatcaagtccttgagcagggcggtctgtccagtttgtttcagaatctcggggtgtccgtaacaccg
atccaaaagattgtcctgagcggtgaaaacggcctgaagatcgacatccatgtcatcatcccgtatgaaggtctgaac
ggctatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 87 (Id-15H1-HT7 sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQNLGVSVTPIQKIVLSGENGLKIDIHVIIPYEGLNGYQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 88 (9B8 opt + K33N + L27V + T39T + K43R + Y68D nucleotide)
Atggtgtttacactcgaagatttcgtaggggactggcggcagacagccggctacaacctggaccaagtccttgagcag
ggcggtgtgtccagtttgtttcagaatctcggggtgtccgtaactccgatccaaaggattgtcctgagcggtgaaaac
ggcctgaagatcgacatccatgtcatcatcccgtatgaaggtctgagcggcgatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 89 (9B8 opt + K33N + L27V + T39T + K43R + Y68D protein)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA -continued

SEQUENCE LISTING

SEQ ID NO: 90 (9B8 opt + K33N + L27V + T39T + K43R + Y68D sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggaccaagtccttgagcagggcggtgtgtccagtttgtttcagaatctcggggtgtccgtaactccg
atccaaaggattgtcctgagcggtgaaaacggcctgaagatcgacatccatgtcatcatcccgtatgaaggtctgagc
ggcgatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt
ctgaatctgctgcaagaagacaacccggacctgatcggcagcgagatcgcgcgctggctgtctactctggagatttcc
ggt SEQ ID NO: 91 (9B8 opt + K33N + L27V + T39T + K43R + Y68D sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGVSSLFQNLGVSVTPIQRIVLSGENGLKIDIHVIIPYEGLSGDQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 92 (9B8 opt + K33N + T39T + K43R + Y68D nucleotide)
Atggtgtttacactcgaagatttcgtaggggactggcggcagacagccggctacaacctggaccaagtccttgagcag
ggcggtctgtccagtttgtttcagaatctcggggtgtccgtaactccgatccaaaggattgtcctgagcggtgaaaac
ggcctgaagatcgacatccatgtcatcatcccgtatgaaggtctgagcggcgatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 93 (9B8 opt + K33N + T39T + K43R + Y68D protein)
MVFTLEDFVGDWRQTAGYNLDQVLEQGGLSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 94 (9B8 opt + K33N + T39T + K43R + Y68D sandwich fusion nucleotide)
atgcttggtctgtcggagcaaagcgtgtccatctcgcgctgcgctgggacgcgcctgcccgccttgctggacgagcag
caggtgaacgtcctgctctacgacatgaacggctgctactcacgcctcaaggagctggtgcccaccctgccccagaac
cgcaaagtgagcaaggtggagatcctgcagcatgtaatcgactacatcagggacctgcagctggagctgaactcggag
tctgaagtcgggaccaccggaggccggggactgcctgtccgcgccccgctcagcaccctgaacggcgagatcagtgcc
ttggcggccgaggcggcatgtgttccagccgacgatcgcatcttgtgtcgcgtttctcttgagaatctttattttcag
gcgtctggaggtggtggcggagcgatcgccatggtgtttacactcgaagatttcgtaggggactggcggcagacagcc
ggctacaacctggaccaagtccttgagcagggcggtctgtccagtttgtttcagaatctcggggtgtccgtaactccg
atccaaaggattgtcctgagcggtgaaaacggcctgaagatcgacatccatgtcatcatcccgtatgaaggtctgagc
ggcgatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
tatctcgagccaaccactgaggatctgtactttcagagcgataacgatggatccgaaatcggtactggctttccattc
gacccccattatgtggaagtcctgggcgagcgcatgcactacgtcgatgttggtccgcgcgatggcacccctgtgctg
ttcctgcacggtaacccgacctcctcctacgtgtggcgcaacatcatcccgcatgttgcaccgacccatcgctgcatt
gctccagacctgatcggtatgggcaaatccgacaaaccagacctgggttatttcttcgacgaccacgtccgcttcatg
gatgccttcatcgaagccctgggtctggaagaggtcgtcctggtcattcacgactggggctccgctctgggtttccac
tgggccaagcgcaatccagagcgcgtcaaaggtattgcatttatggagttcatccgccctatcccgacctgggacgaa
tggccagaatttgcccgcgagaccttccaggccttccgcaccaccgacgtcggccgcaagctgatcatcgatcagaac
gtttttatcgagggtacgctgccgatgggtgtcgtccgcccgctgactgaagtcgagatggaccattaccgcgagccg
ttcctgaatcctgttgaccgcgagccactgtggcgcttcccaaacgagctgccaatcgccggtgagccagcgaacatc
gtcgcgctggtcgaagaatacatggactggctgcaccagtcccctgtcccgaagctgctgttctggggcaccccaggc
gttctgatcccaccggccgaagccgctcgcctggccaaaagcctgcctaactgcaaggctgtggacatcggcccgggt -continued

SEQUENCE LISTING ctgaatctgctgcaagaagacaacccggacctgatcggcagcgagatcgcgcgctggctgtctactctggagatttcc
ggt SEQ ID NO: 95 (9B8 opt + K33N + T39T + K43R + Y68D sandwich fusion protein)
MLGLSEQSVSISRCAGTRLPALLDEQQVNVLLYDMNGCYSRLKELVPTLPQNRKVSKVEILQHVIDYIRDLQLELNSE
SEVGTTGGRGLPVRAPLSTLNGEISALAAEAACVPADDRILCRVSLENLYFQASGGGGGAIAMVFTLEDFVGDWRQTA
GYNLDQVLEQGGLSSLFQNLGVSVTPIQRIVLSGENGLKIDIHVIIPYEGLSGDQMGQIEKIFKVVYPVDDHHFKVIL
HYGTLVIDGVTPNMIDYFGRPYEGIAVFDGKKITVTGTLWNGNKIIDERLINPDGSLLFRVTINGVTGWRLCERILAG
YLEPTTEDLYFQSDNDGSEIGTGFPFDPHYVEVLGERMHYVDVGPRDGTPVLFLHGNPTSSYVWRNIIPHVAPTHRCI
APDLIGMGKSDKPDLGYFFDDHVRFMDAFIEALGLEEVVLVIHDWGSALGFHWAKRNPERVKGIAFMEFIRPIPTWDE
WPEFARETFQAFRTTDVGRKLIIDQNVFIEGTLPMGVVRPLTEVEMDHYREPFLNPVDREPLWRFPNELPIAGEPANI
VALVEEYMDWLHQSPVPKLLFWGTPGVLIPPAEAARLAKSLPNCKAVDIGPGLNLLQEDNPDLIGSEIARWLSTLEIS
G SEQ ID NO: 96 (CRE)
GCACCAGACAGTGACGTCAGCTGCCAGATCCCATGGCCGTCATACTGTGACGTCTTTCAGACACCCCTTGACGTCAAT
GGGAGAACA SEQ ID NO: 97 (Nucleotide CP 84 no linker)
Atggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcgatggtgtttacactcgaagatttcgtaggggactggcggcagacagccggc
tacaacctggaccaagtccttgagcagggcggtgtgtccagtttgtttcagaatctcggggtgtccgtaactccgatc
caaaggattgtcctgagcggtgaaaacggcctgaagatcgacatccatgtcatcatcccgtatgaaggtctgagcggc
gatcagatgggccagatcgaaaaaatttttaaggtggtgtaccctgtg SEQ ID NO: 98 (Protein CP 84 no linker)
MDDHHFKVILHYGTLVIDGVTPNMIDYFGRPYEGIAVFDGKKITVTGTLWNGNKIIDERLINPDGSLLFRVTINGVTG
WRLCERILAMVFTLEDFVGDWRQTAGYNLDQVLEQGGVSSLFQNLGVSVTPIQRIVLSGENGLKIDIHVIIPYEGLSG
DQMGQIEKIFKVVYPV SEQ ID NO: 99 (Nucleotide CP 84 5AA linker)
Atggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcggggagctccggtggaatggtgtttacactcgaagatttcgtaggggactgg
cggcagacagccggctacaacctggaccaagtccttgagcagggcggtgtgtccagtttgtttcagaatctcggggtg
tccgtaactccgatccaaaggattgtcctgagcggtgaaaacggcctgaagatcgacatccatgtcatcatcccgtat
gaaggtctgagcggcgatcagatgggccagatcgaaaaaatttttaaggtggtgtaccctgtg SEQ ID NO: 100 (Protein CP 84 5AA linker)
MDDHHFKVILHYGTLVIDGVTPNMIDYFGRPYEGIAVFDGKKITVTGTLWNGNKIIDERLINPDGSLLFRVTINGVTG
WRLCERILAGSSGGMVFTLEDFVGDWRQTAGYNLDQVLEQGGVSSLFQNLGVSVTPIQRIVLSGENGLKIDIHVIIPY
EGLSGDQMGQIEKIFKVVYPV SEQ ID NO: 101 (Nucleotide CP 84 10AA linker)
Atggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcgggaagttctggtggagggagctccggtggaatggtgtttacactcgaagat
ttcgtaggggactggcggcagacagccggctacaacctggaccaagtccttgagcagggcggtgtgtccagtttgttt
cagaatctcggggtgtccgtaactccgatccaaaggattgtcctgagcggtgaaaacggcctgaagatcgacatccat
gtcatcatcccgtatgaaggtctgagcggcgatcagatgggccagatcgaaaaaatttttaaggtggtgtaccctgtg SEQ ID NO: 102 (Protein CP 84 10AA linker)
MDDHHFKVILHYGTLVIDGVTPNMIDYFGRPYEGIAVFDGKKITVTGTLWNGNKIIDERLINPDGSLLFRVTINGVTG
WRLCERILAGSSGGGSSGGMVFTLEDFVGDWRQTAGYNLDQVLEQGGVSSLFQNLGVSVTPIQRIVLSGENGLKIDIH
VIIPYEGLSGDQMGQIEKIFKVVYPV SEQ ID NO: 103 (Nucleotide CP 84 20AA linker)
Atggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcgggaagttctggtggagggagctccggtggaggaagttctggtggagggagc
tccggtggaatggtgtttacactcgaagatttcgtaggggactggcggcagacagccggctacaacctggaccaagtc
cttgagcagggcggtgtgtccagtttgtttcagaatctcggggtgtccgtaactccgatccaaaggattgtcctgagc
ggtgaaaacggcctgaagatcgacatccatgtcatcatcccgtatgaaggtctgagcggcgatcagatgggccagatc
gaaaaaatttttaaggtggtgtaccctgtg SEQ ID NO: 104 (Protein CP 84 20AA linker)
MDDHHFKVILHYGTLVIDGVTPNMIDYFGRPYEGIAVFDGKKITVTGTLWNGNKIIDERLINPDGSLLFRVTINGVTG
WRLCERILAGSSGGGSSGGGSSGGGSSGGMVFTLEDFVGDWRQTAGYNLDQVLEQGGVSSLFQNLGVSVTPIQRIVLS
GENGLKIDIHVIIPYEGLSGDQMGQIEKIFKVVYPV -continued

SEQUENCE LISTING

SEQ ID NO: 105 (Nucleotide CP 95 no linker)
Atgggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcgatggtg
tttacactcgaagatttcgtaggggactggcggcagacagccggctacaacctggaccaagtccttgagcagggcggt
gtgtccagtttgtttcagaatctcggggtgtccgtaactccgatccaaaggattgtcctgagcggtgaaaacggcctg
aagatcgacatccatgtcatcatcccgtatgaaggtctgagcggcgatcagatgggccagatcgaaaaaatttttaag
gtggtgtaccctgtggatgatcatcactttaaggtgattctgcactat SEQ ID NO: 106 (Protein CP 95 no linker)
MGTLVIDGVTPNMIDYFGRPYEGIAVFDGKKITVTGTLWNGNKIIDERLINPDGSLLFRVTINGVTGWRLCERILAMV
FTLEDFVGDWRQTAGYNLDQVLEQGGVSSLFQNLGVSVTPIQRIVLSGENGLKIDIHVIIPYEGLSGDQMGQIEKIFK
VVYPVDDHHFKVILHY SEQ ID NO: 107 (Nucleotide CP 95 5AA linker)
Atgggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcggggagc
tccggtggaatggtgtttacactcgaagatttcgtaggggactggcggcagacagccggctacaacctggaccaagtc
cttgagcagggcggtgtgtccagtttgtttcagaatctcggggtgtccgtaactccgatccaaaggattgtcctgagc
ggtgaaaacggcctgaagatcgacatccatgtcatcatcccgtatgaaggtctgagcggcgatcagatgggccagatc
gaaaaaatttttaaggtggtgtaccctgtggatgatcatcactttaaggtgattctgcactat SEQ ID NO: 108 (Protein CP 95 5AA linker)
MGTLVIDGVTPNMIDYFGRPYEGIAVFDGKKITVTGTLWNGNKIIDERLINPDGSLLFRVTINGVTGWRLCERILAGS
SGGMVFTLEDFVGDWRQTAGYNLDQVLEQGGVSSLFQNLGVSVTPIQRIVLSGENGLKIDIHVIIPYEGLSGDQMGQI
EKIFKVVYPVDDHHFKVILHY SEQ ID NO: 109 (Nucleotide CP 95 10AA linker)
Atgggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcgggaagt
tctggtggagggagctccggtggaatggtgtttacactcgaagatttcgtaggggactggcggcagacagccggctac
aacctggaccaagtccttgagcagggcggtgtgtccagtttgtttcagaatctcggggtgtccgtaactccgatccaa
aggattgtcctgagcggtgaaaacggcctgaagatcgacatccatgtcatcatcccgtatgaaggtctgagcggcgat
cagatgggccagatcgaaaaaatttttaaggtggtgtaccctgtggatgatcatcactttaaggtgattctgcactat SEQ ID NO: 110 (Protein CP 95 10AA linker)
MGTLVIDGVTPNMIDYFGRPYEGIAVFDGKKITVTGTLWNGNKIIDERLINPDGSLLFRVTINGVTGWRLCERILAGS
SGGGSSGGMVFTLEDFVGDWRQTAGYNLDQVLEQGGVSSLFQNLGVSVTPIQRIVLSGENGLKIDIHVIIPYEGLSGD
QMGQIEKIFKVVYPVDDHHFKVILHY SEQ ID NO: 111 (Nucleotide CP 95 20AA linker)
Atgggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcgggaagt
tctggtggagggagctccggtggaggaagttctggtggagggagctccggtggaatggtgtttacactcgaagatttc
gtaggggactggcggcagacagccggctacaacctggaccaagtccttgagcagggcggtgtgtccagtttgtttcag
aatctcggggtgtccgtaactccgatccaaaggattgtcctgagcggtgaaaacggcctgaagatcgacatccatgtc
atcatcccgtatgaaggtctgagcggcgatcagatgggccagatcgaaaaaatttttaaggtggtgtaccctgtggat
gatcatcactttaaggtgattctgcactat SEQ ID NO: 112 (Protein CP 95 20AA linker)
MGTLVIDGVTPNMIDYFGRPYEGIAVFDGKKITVTGTLWNGNKIIDERLINPDGSLLFRVTINGVTGWRLCERILAGS
SGGGSSGGGSSGGGSSGGMVFTLEDFVGDWRQTAGYNLDQVLEQGGVSSLFQNLGVSVTPIQRIVLSGENGLKIDIHV
IIPYEGLSGDQMGQIEKIFKVVYPVDDHHFKVILHY SEQ ID NO: 113 (Linker)
$(GSGG)_N$ SEQ ID NO: 114 (L27V CP 5 TEV)
Atggatttcgtaggggactggcggcagacagccggctacaacctggaccaagtccttgagcagggcggtgtgtccagt
ttgtttcagaatctcggggtgtccgtaactccgatccaaaggattgtcctgagcggtgaaaacggcctgaagatcgac
atccatgtcatcatcccgtatgaaggtctgagcggcgatcagatgggccagatcgaaaaaatttttaaggtggtgtac
cctgtggatgatcatcactttaaggtgattctgcactatggcacactggtaatcgacggggttacgccgaacatgatc
gactatttcggacggccgtatgaaggcatcgccgtgttcgacggcaaaaagatcactgtaaccgggaccctgtggaac
ggcaacaaaattatcgacgagcgcctgatcaaccccgacggctccctgctgttccgcgtaaccatcaacggagtgacc
ggctggcggctgtgcgagcgcattttggcgggaagttctggtggaggaagttctggtggagagcctactactgagaac
ttgtacttccagagcgataacggaagttctggtggaggaagttctggtggaatggtgtttacactcgaa SEQ ID NO: 115 (L27V CP 5 TEV)
MDFVGDWRQTAGYNLDQVLEQGGVSSLFQNLGVSVTPIQRIVLSGENGLKIDIHVIIPYEGLSGDQMGQIEKIFKVVY
PVDDHHFKVILHYGTLVIDGVTPNMIDYFGRPYEGIAVFDGKKITVTGTLWNGNKIIDERLINPDGSLLFRVTINGVT
GWRLCERILAGSSGGGSSGGEPTTENLYFQSDNGSSGGGSSGGMVFTLE -continued

SEQUENCE LISTING

SEQ ID NO: 116 (L27V CP 6 TEV)
atgttcgtaggggactggcggcagacagccggctacaacctggaccaagtccttgagcagggcggtgtgtccagtttg
tttcagaatctcggggtgtccgtaactccgatccaaaggattgtcctgagcggtgaaaacggcctgaagatcgacatc
catgtcatcatcccgtatgaaggtctgagcggcgatcagatgggccagatcgaaaaaatttttaaggtggtgtaccct
gtggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcgggaagttctggtggaggaagttctggtggagagcctactactgagaacttg
tacttccagagcgataacggaagttctggtggaggaagttctggtggaatggtgtttacactcgaagat SEQ ID NO: 117 (L27V CP 6 TEV)
MFVGDWRQTAGYNLDQVLEQGGVSSLFQNLGVSVTPIQRIVLSGENGLKIDIHVIIPYEGLSGDQMGQIEKIFKVVYP
VDDHHFKVILHYGTLVIDGVTPNMIDYFGRPYEGIAVFDGKKITVTGTLWNGNKIIDERLINPDGSLLFRVTINGVTG
WRLCERILAGSSGGGSSGGEPTTENLYFQSDNGSSGGGSSGGMVFTLED SEQ ID NO: 118 (L27V CP 7 TEV)
atggtaggggactggcggcagacagccggctacaacctggaccaagtccttgagcagggcggtgtgtccagtttgttt
cagaatctcggggtgtccgtaactccgatccaaaggattgtcctgagcggtgaaaacggcctgaagatcgacatccat
gtcatcatcccgtatgaaggtctgagcggcgatcagatgggccagatcgaaaaaatttttaaggtggtgtaccctgtg
gatgatcatcactttaaggtgattctgcactatggcacactggtaatcgacggggttacgccgaacatgatcgactat
ttcggacggccgtatgaaggcatcgccgtgttcgacggcaaaaagatcactgtaaccgggaccctgtggaacggcaac
aaaattatcgacgagcgcctgatcaaccccgacggctccctgctgttccgcgtaaccatcaacggagtgaccggctgg
cggctgtgcgagcgcattttggcgggaagttctggtggaggaagttctggtggagagcctactactgagaacttgtac
ttccagagcgataacggaagttctggtggaggaagttctggtggaatggtgtttacactcgaagatttc SEQ ID NO: 119 (L27V CP 7 TEV)
MVGDWRQTAGYNLDQVLEQGGVSSLFQNLGVSVTPIQRIVLSGENGLKIDIHVIIPYEGLSGDQMGQIEKIFKVVYPV
DDHHFKVILHYGTLVIDGVTPNMIDYFGRPYEGIAVFDGKKITVTGTLWNGNKIIDERLINPDGSLLFRVTINGVTGW
RLCERILAGSSGGGSSGGEPTTENLYFQSDNGSSGGGSSGGMVFTLEDF SEQ ID NO: 120 (L27V CP 9 TEV)
atggactggcggcagacagccggctacaacctggaccaagtccttgagcagggcggtgtgtccagtttgtttcagaat
ctcggggtgtccgtaactccgatccaaaggattgtcctgagcggtgaaaacggcctgaagatcgacatccatgtcatc
atcccgtatgaaggtctgagcggcgatcagatgggccagatcgaaaaaatttttaaggtggtgtaccctgtggatgat
catcactttaaggtgattctgcactatggcacactggtaatcgacggggttacgccgaacatgatcgactatttcgga
cggccgtatgaaggcatcgccgtgttcgacggcaaaaagatcactgtaaccgggaccctgtggaacggcaacaaaatt
atcgacgagcgcctgatcaaccccgacggctccctgctgttccgcgtaaccatcaacggagtgaccggctggcggctg
tgcgagcgcattttggcgggaagttctggtggaggaagttctggtggagagcctactactgagaacttgtacttccag
agcgataacggaagttctggtggaggaagttctggtggaatggtgtttacactcgaagatttcgtaggg SEQ ID NO: 121 (L27V CP 9 TEV)
MDWRQTAGYNLDQVLEQGGVSSLFQNLGVSVTPIQRIVLSGENGLKIDIHVIIPYEGLSGDQMGQIEKIFKVVYPVDD
HHFKVILHYGTLVIDGVTPNMIDYFGRPYEGIAVFDGKKITVTGTLWNGNKIIDERLINPDGSLLFRVTINGVTGWRL
CERILAGSSGGGSSGGEPTTENLYFQSDNGSSGGGSSGGMVFTLEDFVG SEQ ID NO: 122 (L27V CP 11 TEV)
Atgcggcagacagccggctacaacctggaccaagtccttgagcagggcggtgtgtccagtttgtttcagaatctcggg
gtgtccgtaactccgatccaaaggattgtcctgagcggtgaaaacggcctgaagatcgacatccatgtcatcatcccg
tatgaaggtctgagcggcgatcagatgggccagatcgaaaaaatttttaaggtggtgtaccctgtggatgatcatcac
tttaaggtgattctgcactatggcacactggtaatcgacggggttacgccgaacatgatcgactatttcggacggccg
tatgaaggcatcgccgtgttcgacggcaaaaagatcactgtaaccgggaccctgtggaacggcaacaaaattatcgac
gagcgcctgatcaaccccgacggctccctgctgttccgcgtaaccatcaacggagtgaccggctggcggctgtgcgag
cgcattttggcgggaagttctggtggaggaagttctggtggagagcctactactgagaacttgtacttccagagcgat
aacggaagttctggtggaggaagttctggtggaatggtgtttacactcgaagatttcgtaggggactgg SEQ ID NO: 123 (L27V CP 11 TEV)
MRQTAGYNLDQVLEQGGVSSLFQNLGVSVTPIQRIVLSGENGLKIDIHVIIPYEGLSGDQMGQIEKIFKVVYPVDDHH
FKVILHYGTLVIDGVTPNMIDYFGRPYEGIAVFDGKKITVTGTLWNGNKIIDERLINPDGSLLFRVTINGVTGWRLCE
RILAGSSGGGSSGGEPTTENLYFQSDNGSSGGGSSGGMVFTLEDFVGDW SEQ ID NO: 124 (L27V CP 12 TEV)
Cagacagccggctacaacctggaccaagtccttgagcagggcggtgtgtccagtttgtttcagaatctcggggtgtcc
gtaactccgatccaaaggattgtcctgagcggtgaaaacggcctgaagatcgacatccatgtcatcatcccgtatgaa
ggtctgagcggcgatcagatgggccagatcgaaaaaatttttaaggtggtgtaccctgtggatgatcatcactttaag
gtgattctgcactatggcacactggtaatcgacggggttacgccgaacatgatcgactatttcggacggccgtatgaa
ggcatcgccgtgttcgacggcaaaaagatcactgtaaccgggaccctgtggaacggcaacaaaattatcgacgagcgc
ctgatcaaccccgacggctccctgctgttccgcgtaaccatcaacggagtgaccggctggcggctgtgcgagcgcatt
ttggcgggaagttctggtggaggaagttctggtggagagcctactactgagaacttgtacttccagagcgataacgga
agttctggtggaggaagttctggtggaatggtgtttacactcgaagatttcgtaggg SEQ ID NO: 125 (L27V CP 12 TEV)
QTAGYNLDQVLEQGGVSSLFQNLGVSVTPIQRIVLSGENGLKIDIHVIIPYEGLSGDQMGQIEKIFKVVYPVDDHHFK
VILHYGTLVIDGVTPNMIDYFGRPYEGIAVFDGKKITVTGTLWNGNKIIDERLINPDGSLLFRVTINGVTGWRLCERI
LAGSSGGGSSGGEPTTENLYFQSDNGSSGGGSSGGMVFTLEDFVG

SEQUENCE LISTING

SEQ ID NO: 126 (L27V CP 15 TEV)
atgggctacaacctggaccaagtccttgagcagggcggtgtgtccagtttgtttcagaatctcggggtgtccgtaact
ccgatccaaaggattgtcctgagcggtgaaaacggcctgaagatcgacatccatgtcatcatcccgtatgaaggtctg
agcggcgatcagatgggccagatcgaaaaaatttttaaggtggtgtaccctgtggatgatcatcactttaaggtgatt
ctgcactatggcacactggtaatcgacggggttacgccgaacatgatcgactatttcggacggccgtatgaaggcatc
gccgtgttcgacggcaaaaagatcactgtaaccgggaccctgtggaacggcaacaaaattatcgacgagcgcctgatc
aaccccgacggctccctgctgttccgcgtaaccatcaacggagtgaccggctggcggctgtgcgagcgcattttggcg
ggaagttctggtggaggaagttctggtggagagcctactactgagaacttgtacttccagagcgataacggaagttct
ggtggaggaagttctggtggaatggtgtttacactcgaagatttcgtaggggactggcggcagacagcc SEQ ID NO: 127 (L27V CP 15 TEV)
MGYNLDQVLEQGGVSSLFQNLGVSVTPIQRIVLSGENGLKIDIHVIIPYEGLSGDQMGQIEKIFKVVYPVDDHHFKVI
LHYGTLVIDGVTPNMIDYFGRPYEGIAVFDGKKITVTGTLWNGNKIIDERLINPDGSLLFRVTINGVTGWRLCERILA
GSSGGGSSGGEPTTENLYFQSDNGSSGGGSSGGMVFTLEDFVGDWRQTA SEQ ID NO: 128 (L27V CP 18 TEV)
ctggaccaagtccttgagcagggcggtgtgtccagtttgtttcagaatctcggggtgtccgtaactccgatccaaagg
attgtcctgagcggtgaaaacggcctgaagatcgacatccatgtcatcatcccgtatgaaggtctgagcggcgatcag
atgggccagatcgaaaaaatttttaaggtggtgtaccctgtggatgatcatcactttaaggtgattctgcactatggc
acactggtaatcgacggggttacgccgaacatgatcgactatttcggacggccgtatgaaggcatcgccgtgttcgac
ggcaaaaagatcactgtaaccgggaccctgtggaacggcaacaaaattatcgacgagcgcctgatcaaccccgacggc
tccctgctgttccgcgtaaccatcaacggagtgaccggctggcggctgtgcgagcgcattttggcgggaagttctggt
ggaggaagttctggtggagagcctactactgagaacttgtacttccagagcgataacggaagttctggtggaggaagt
tctggtggaatggtgtttacactcgaagatttcgtaggggactggcggcagacagccggctacaac SEQ ID NO: 129 (L27V CP 18 TEV)
LDQVLEQGGVSSLFQNLGVSVTPIQRIVLSGENGLKIDIHVIIPYEGLSGDQMGQIEKIFKVVYPVDDHHFKVILHYG
TLVIDGVTPNMIDYFGRPYEGIAVFDGKKITVTGTLWNGNKIIDERLINPDGSLLFRVTINGVTGWRLCERILAGSSG
GGSSGGEPTTENLYFQSDNGSSGGGSSGGMVFTLEDFVGDWRQTAGYN SEQ ID NO: 130 (L27V CP 21 TEV)
gtccttgagcagggcggtgtgtccagtttgtttcagaatctcggggtgtccgtaactccgatccaaaggattgtcctg
agcggtgaaaacggcctgaagatcgacatccatgtcatcatcccgtatgaaggtctgagcggcgatcagatgggccag
atcgaaaaaatttttaaggtggtgtaccctgtggatgatcatcactttaaggtgattctgcactatggcacactggta
atcgacggggttacgccgaacatgatcgactatttcggacggccgtatgaaggcatcgccgtgttcgacggcaaaaag
atcactgtaaccgggaccctgtggaacggcaacaaaattatcgacgagcgcctgatcaaccccgacggctccctgctg
ttccgcgtaaccatcaacggagtgaccggctggcggctgtgcgagcgcattttggcgggaagttctggtggaggaagt
tctggtggagagcctactactgagaacttgtacttccagagcgataacggaagttctggtggaggaagttctggtgga
atggtgtttacactcgaagatttcgtaggggactggcggcagacagccggctacaacctggaccaa SEQ ID NO: 131 (L27V CP 21 TEV)
VLEQGGVSSLFQNLGVSVTPIQRIVLSGENGLKIDIHVIIPYEGLSGDQMGQIEKIFKVVYPVDDHHFKVILHYGTLV
IDGVTPNMIDYFGRPYEGIAVFDGKKITVTGTLWNGNKIIDERLINPDGSLLFRVTINGVTGWRLCERILAGSSGGGS
SGGEPTTENLYFQSDNGSSGGGSSGGMVFTLEDFVGDWRQTAGYNLDQ SEQ ID NO: 132 (L27V CP 24 TEV)
cagggcggtgtgtccagtttgtttcagaatctcggggtgtccgtaactccgatccaaaggattgtcctgagcggtgaa
aacggcctgaagatcgacatccatgtcatcatcccgtatgaaggtctgagcggcgatcagatgggccagatcgaaaaa
atttttaaggtggtgtaccctgtggatgatcatcactttaaggtgattctgcactatggcacactggtaatcgacggg
gttacgccgaacatgatcgactatttcggacggccgtatgaaggcatcgccgtgttcgacggcaaaaagatcactgta
accgggaccctgtggaacggcaacaaaattatcgacgagcgcctgatcaaccccgacggctccctgctgttccgcgta
accatcaacggagtgaccggctggcggctgtgcgagcgcattttggcgggaagttctggtggaggaagttctggtgga
gagcctactactgagaacttgtacttccagagcgataacggaagttctggtggaggaagttctggtggaatggtgttt
acactcgaagatttcgtaggggactggcggcagacagccggctacaacctggaccaagtccttgag SEQ ID NO: 133 (L27V CP 24 TEV)
QGGVSSLFQNLGVSVTPIQRIVLSGENGLKIDIHVIIPYEGLSGDQMGQIEKIFKVVYPVDDHHFKVILHYGTLVIDG
VTPNMIDYFGRPYEGIAVFDGKKITVTGTLWNGNKIIDERLINPDGSLLFRVTINGVTGWRLCERILAGSSGGGSSGG
EPTTENLYFQSDNGSSGGGSSGGMVFTLEDFVGDWRQTAGYNLDQVLE SEQ ID NO: 134 (L27V CP 27 TEV)
gtgtccagtttgtttcagaatctcggggtgtccgtaactccgatccaaaggattgtcctgagcggtgaaaacggcctg
aagatcgacatccatgtcatcatcccgtatgaaggtctgagcggcgatcagatgggccagatcgaaaaaatttttaag
gtggtgtaccctgtggatgatcatcactttaaggtgattctgcactatggcacactggtaatcgacggggttacgccg
aacatgatcgactatttcggacggccgtatgaaggcatcgccgtgttcgacggcaaaaagatcactgtaaccgggacc
ctgtggaacggcaacaaaattatcgacgagcgcctgatcaaccccgacggctccctgctgttccgcgtaaccatcaac
ggagtgaccggctggcggctgtgcgagcgcattttggcgggaagttctggtggaggaagttctggtggagagcctact
actgagaacttgtacttccagagcgataacggaagttctggtggaggaagttctggtggaatggtgtttacactcgaa
gatttcgtaggggactggcggcagacagccggctacaacctggaccaagtccttgagcagggcggt SEQ ID NO: 135 (L27V CP 27 TEV)
VSSLFQNLGVSVTPIQRIVLSGENGLKIDIHVIIPYEGLSGDQMGQIEKIFKVVYPVDDHHFKVILHYGTLVIDGVTP
NMIDYFGRPYEGIAVFDGKKITVTGTLWNGNKIIDERLINPDGSLLFRVTINGVTGWRLCERILAGSSGGGSSGGEPT
TENLYFQSDNGSSGGGSSGGMVFTLEDFVGDWRQTAGYNLDQVLEQGG -continued

SEQUENCE LISTING

SEQ ID NO: 136 (L27V CP 34 TEV)
atgctcggggtgtccgtaactccgatccaaaggattgtcctgagcggtgaaaacggcctgaagatcgacatccatgtc
atcatcccgtatgaaggtctgagcggcgatcagatgggccagatcgaaaaaatttttaaggtggtgtaccctgtggat
gatcatcactttaaggtgattctgcactatggcacactggtaatcgacggggttacgccgaacatgatcgactatttc
ggacggccgtatgaaggcatcgccgtgttcgacggcaaaaagatcactgtaaccgggaccctgtggaacggcaacaaa
attatcgacgagcgcctgatcaaccccgacggctccctgctgttccgcgtaaccatcaacggagtgaccggctggcgg
ctgtgcgagcgcattttggcgggaagttctggtggaggaagttctggtggagagcctactactgagaacttgtacttc
cagagcgataacggaagttctggtggaggaagttctggtggaatggtgtttacactcgaagatttcgtaggggactgg
cggcagacagccggctacaacctggaccaagtccttgagcagggcggtgtgtccagtttgtttcagaat SEQ ID NO: 137 (L27V CP 34 TEV)
MLGVSVTPIQRIVLSGENGLKIDIHVIIPYEGLSGDQMGQIEKIFKVVYPVDDHHFKVILHYGTLVIDGVTPNMIDYF
GRPYEGIAVFDGKKITVTGTLWNGNKIIDERLINPDGSLLFRVTINGVTGWRLCERILAGSSGGGSSGGEPTTENLYF
QSDNGSSGGGSSGGMVFTLEDFVGDWRQTAGYNLDQVLEQGGVSSLFQN SEQ ID NO: 138 (L27V CP 40 TEV)
Atgccgatccaaaggattgtcctgagcggtgaaaacggcctgaagatcgacatccatgtcatcatcccgtatgaaggt
ctgagcggcgatcagatgggccagatcgaaaaaatttttaaggtggtgtaccctgtggatgatcatcactttaaggtg
attctgcactatggcacactggtaatcgacggggttacgccgaacatgatcgactatttcggacggccgtatgaaggc
atcgccgtgttcgacggcaaaaagatcactgtaaccgggaccctgtggaacggcaacaaaattatcgacgagcgcctg
atcaaccccgacggctccctgctgttccgcgtaaccatcaacggagtgaccggctggcggctgtgcgagcgcattttg
gcgggaagttctggtggaggaagttctggtggagagcctactactgagaacttgtacttccagagcgataacggaagt
tctggtggaggaagttctggtggaatggtgtttacactcgaagatttcgtaggggactggcggcagacagccggctac
aacctggaccaagtccttgagcagggcggtgtgtccagtttgtttcagaatctcggggtgtccgtaact SEQ ID NO: 139 (L27V CP 40 TEV)
MPIQRIVLSGENGLKIDIHVIIPYEGLSGDQMGQIEKIFKVVYPVDDHHFKVILHYGTLVIDGVTPNMIDYFGRPYEG
IAVFDGKKITVTGTLWNGNKIIDERLINPDGSLLFRVTINGVTGWRLCERILAGSSGGGSSGGEPTTENLYFQSDNGS
SGGGSSGGMVFTLEDFVGDWRQTAGYNLDQVLEQGGVSSLFQNLGVSVT SEQ ID NO: 140 (L27V CP 43 TEV)
Atgaggattgtcctgagcggtgaaaacggcctgaagatcgacatccatgtcatcatcccgtatgaaggtctgagcggc
gatcagatgggccagatcgaaaaaatttttaaggtggtgtaccctgtggatgatcatcactttaaggtgattctgcac
tatggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcgggaagt
tctggtggaggaagttctggtggagagcctactactgagaacttgtacttccagagcgataacggaagttctggtgga
ggaagttctggtggaatggtgtttacactcgaagatttcgtaggggactggcggcagacagccggctacaacctggac
caagtccttgagcagggcggtgtgtccagtttgtttcagaatctcggggtgtccgtaactccgatccaa SEQ ID NO: 141 (L27V CP 43 TEV)
MRIVLSGENGLKIDIHVIIPYEGLSGDQMGQIEKIFKVVYPVDDHHFKVILHYGTLVIDGVTPNMIDYFGRPYEGIAV
FDGKKITVTGTLWNGNKIIDERLINPDGSLLFRVTINGVTGWRLCERILAGSSGGGSSGGEPTTENLYFQSDNGSSGG
GSSGGMVFTLEDFVGDWRQTAGYNLDQVLEQGGVSSLFQNLGVSVTPIQ SEQ ID NO: 142 (L27V CP 44 TEV)
Atgattgtcctgagcggtgaaaacggcctgaagatcgacatccatgtcatcatcccgtatgaaggtctgagcggcgat
cagatgggccagatcgaaaaaatttttaaggtggtgtaccctgtggatgatcatcactttaaggtgattctgcactat
ggcacactggtaatcgacggggttacgccgaacatgatcgactatttcggacggccgtatgaaggcatcgccgtgttc
gacggcaaaaagatcactgtaaccgggaccctgtggaacggcaacaaaattatcgacgagcgcctgatcaaccccgac
ggctccctgctgttccgcgtaaccatcaacggagtgaccggctggcggctgtgcgagcgcattttggcgggaagttct
ggtggaggaagttctggtggagagcctactactgagaacttgtacttccagagcgataacggaagttctggtggagga
agttctggtggaatggtgtttacactcgaagatttcgtaggggactggcggcagacagccggctacaacctggaccaa
gtccttgagcagggcggtgtgtccagtttgtttcagaatctcggggtgtccgtaactccgatccaaagg SEQ ID NO: 143 (L27V CP 44 TEV)
MIVLSGENGLKIDIHVIIPYEGLSGDQMGQIEKIFKVVYPVDDHHFKVILHYGTLVIDGVTPNMIDYFGRPYEGIAVF
DGKKITVTGTLWNGNKIIDERLINPDGSLLFRVTINGVTGWRLCERILAGSSGGGSSGGEPTTENLYFQSDNGSSGGG
SSGGMVFTLEDFVGDWRQTAGYNLDQVLEQGGVSSLFQNLGVSVTPIQR SEQ ID NO: 144 (L27V CP 45 TEV)
Atggtcctgagcggtgaaaacggcctgaagatcgacatccatgtcatcatcccgtatgaaggtctgagcggcgatcag
atgggccagatcgaaaaaatttttaaggtggtgtaccctgtggatgatcatcactttaaggtgattctgcactatggc
acactggtaatcgacggggttacgccgaacatgatcgactatttcggacggccgtatgaaggcatcgccgtgttcgac
ggcaaaaagatcactgtaaccgggaccctgtggaacggcaacaaaattatcgacgagcgcctgatcaaccccgacggc
tccctgctgttccgcgtaaccatcaacggagtgaccggctggcggctgtgcgagcgcattttggcgggaagttctggt
ggaggaagttctggtggagagcctactactgagaacttgtacttccagagcgataacggaagttctggtggaggaagt
tctggtggaatggtgtttacactcgaagatttcgtaggggactggcggcagacagccggctacaacctggaccaagtc
cttgagcagggcggtgtgtccagtttgtttcagaatctcggggtgtccgtaactccgatccaaaggatt SEQ ID NO: 145 (L27V CP 45 TEV)
MVLSGENGLKIDIHVIIPYEGLSGDQMGQIEKIFKVVYPVDDHHFKVILHYGTLVIDGVTPNMIDYFGRPYEGIAVFD
GKKITVTGTLWNGNKIIDERLINPDGSLLFRVTINGVTGWRLCERILAGSSGGGSSGGEPTTENLYFQSDNGSSGGGS
SGGMVFTLEDFVGDWRQTAGYNLDQVLEQGGVSSLFQNLGVSVTPIQRI

SEQUENCE LISTING

SEQ ID NO: 146 (L27V CP 46 TEV)
Atgctgagcggtgaaaacggcctgaagatcgacatccatgtcatcatcccgtatgaaggtctgagcggcgatcagatg
ggccagatcgaaaaaatttttaaggtggtgtaccctgtggatgatcatcactttaaggtgattctgcactatggcaca
ctggtaatcgacggggttacgccgaacatgatcgactatttcggacggccgtatgaaggcatcgccgtgttcgacggc
aaaaagatcactgtaaccgggaccctgtggaacggcaacaaaattatcgacgagcgcctgatcaaccccgacggctcc
ctgctgttccgcgtaaccatcaacggagtgaccggctggcggctgtgcgagcgcattttggcgggaagttctggtgga
ggaagttctggtggagagcctactactgagaacttgtacttccagagcgataacggaagttctggtggaggaagttct
ggtggaatggtgtttacactcgaagatttcgtaggggactggcggcagacagccggctacaacctggaccaagtcctt
gagcagggcggtgtgtccagtttgtttcagaatctcggggtgtccgtaactccgatccaaaggatt SEQ ID NO: 147 (L27V CP 46 TEV)
MLSGENGLKIDIHVIIPYEGLSGDQMGQIEKIFKVVYPVDDHHFKVILHYGTLVIDGVTPNMIDYFGRPYEGIAVFDG
KKITVTGTLWNGNKIIDERLINPDGSLLFRVTINGVTGWRLCERILAGSSGGGSSGGEPTTENLYFQSDNGSSGGGSS
GGMVFTLEDFVGDWRQTAGYNLDQVLEQGGVSSLFQNLGVSVTPIQRI SEQ ID NO: 148 (L27V CP 47 TEV)
atgagcggtgaaaacggcctgaagatcgacatccatgtcatcatcccgtatgaaggtctgagcggcgatcagatgggc
cagatcgaaaaaattttttaaggtggtgtaccctgtggatgatcatcactttaaggtgattctgcactatggcacactg
gtaatcgacggggttacgccgaacatgatcgactatttcggacggccgtatgaaggcatcgccgtgttcgacggcaaa
aagatcactgtaaccgggaccctgtggaacggcaacaaaattatcgacgagcgcctgatcaaccccgacggctccctg
ctgttccgcgtaaccatcaacggagtgaccggctggcggctgtgcgagcgcattttggcgggaagttctggtggagga
agttctggtggagagcctactactgagaacttgtacttccagagcgataacggaagttctggtggaggaagttctggt
ggaatggtgtttacactcgaagatttcgtaggggactggcggcagacagccggctacaacctggaccaagtccttgag
cagggcggtgtgtccagtttgtttcagaatctcggggtgtccgtaactccgatccaaaggattgtcctg SEQ ID NO: 149 (L27V CP 47 TEV)
MSGENGLKIDIHVIIPYEGLSGDQMGQIEKIFKVVYPVDDHHFKVILHYGTLVIDGVTPNMIDYFGRPYEGIAVFDGK
KITVTGTLWNGNKIIDERLINPDGSLLFRVTINGVTGWRLCERILAGSSGGGSSGGEPTTENLYFQSDNGSSGGGSSG
GMVFTLEDFVGDWRQTAGYNLDQVLEQGGVSSLFQNLGVSVTPIQRIVL SEQ ID NO: 150 (L27V CP 48 TEV)
atgggtgaaaacggcctgaagatcgacatccatgtcatcatcccgtatgaaggtctgagcggcgatcagatgggccag
atcgaaaaaattttttaaggtggtgtaccctgtggatgatcatcactttaaggtgattctgcactatggcacactggta
atcgacggggttacgccgaacatgatcgactatttcggacggccgtatgaaggcatcgccgtgttcgacggcaaaaag
atcactgtaaccgggaccctgtggaacggcaacaaaattatcgacgagcgcctgatcaaccccgacggctccctgctg
ttccgcgtaaccatcaacggagtgaccggctggcggctgtgcgagcgcattttggcgggaagttctggtggaggaagt
tctggtggagagcctactactgagaacttgtacttccagagcgataacggaagttctggtggaggaagttctggtgga
atggtgtttacactcgaagatttcgtaggggactggcggcagacagccggctacaacctggaccaagtccttgagcag
ggcggtgtgtccagtttgtttcagaatctcggggtgtccgtaactccgatccaaaggattgtcctgagcg SEQ ID NO: 151 (L27V CP 48 TEV)
MGENGLKIDIHVIIPYEGLSGDQMGQIEKIFKVVYPVDDHHFKVILHYGTLVIDGVTPNMIDYFGRPYEGIAVFDGKK
ITVTGTLWNGNKIIDERLINPDGSLLFRVTINGVTGWRLCERILAGSSGGGSSGGEPTTENLYFQSDNGSSGGGSSGG
MVFTLEDFVGDWRQTAGYNLDQVLEQGGVSSLFQNLGVSVTPIQRIVLS SEQ ID NO: 152 (L27V CP 49 TEV)
atggaaaacggcctgaagatcgacatccatgtcatcatcccgtatgaaggtctgagcggcgatcagatgggccagatc
gaaaaaattttttaaggtggtgtaccctgtggatgatcatcactttaaggtgattctgcactatggcacactggtaatc
gacggggttacgccgaacatgatcgactatttcggacggccgtatgaaggcatcgccgtgttcgacggcaaaaagatc
actgtaaccgggaccctgtggaacggcaacaaaattatcgacgagcgcctgatcaaccccgacggctccctgctgttc
cgcgtaaccatcaacggagtgaccggctggcggctgtgcgagcgcattttggcgggaagttctggtggaggaagttct
ggtggagagcctactactgagaacttgtacttccagagcgataacggaagttctggtggaggaagttctggtggaatg
gtgtttacactcgaagatttcgtaggggactggcggcagacagccggctacaacctggaccaagtccttgagcagggc
ggtgtgtccagtttgtttcagaatctcggggtgtccgtaactccgatccaaaggattgtcctgagcggt SEQ ID NO: 153 (L27V CP 49 TEV)
MENGLKIDIHVIIPYEGLSGDQMGQIEKIFKVVYPVDDHHFKVILHYGTLVIDGVTPNMIDYFGRPYEGIAVFDGKKI
TVTGTLWNGNKIIDERLINPDGSLLFRVTINGVTGWRLCERILAGSSGGGSSGGEPTTENLYFQSDNGSSGGGSSGGM
VFTLEDFVGDWRQTAGYNLDQVLEQGGVSSLFQNLGVSVTPIQRIVLSG SEQ ID NO: 154 (L27V CP 50 TEV)
atgaacggcctgaagatcgacatccatgtcatcatcccgtatgaaggtctgagcggcgatcagatgggccagatcgaa
aaaatttttaaggtggtgtaccctgtggatgatcatcactttaaggtgattctgcactatggcacactggtaatcgac
ggggttacgccgaacatgatcgactatttcggacggccgtatgaaggcatcgccgtgttcgacggcaaaaagatcact
gtaaccgggaccctgtggaacggcaacaaaattatcgacgagcgcctgatcaaccccgacggctccctgctgttccgc
gtaaccatcaacggagtgaccggctggcggctgtgcgagcgcattttggcgggaagttctggtggaggaagttctggt
ggagagcctactactgagaacttgtacttccagagcgataacggaagttctggtggaggaagttctggtggaatggtg
tttacactcgaagatttcgtaggggactggcggcagacagccggctacaacctggaccaagtccttgagcagggcggt
gtgtccagtttgtttcagaatctcggggtgtccgtaactccgatccaaaggattgtcctgagcggtgaa SEQ ID NO: 155 (L27V CP 50 TEV)
MNGLKIDIHVIIPYEGLSGDQMGQIEKIFKVVYPVDDHHFKVILHYGTLVIDGVTPNMIDYFGRPYEGIAVFDGKKIT
VTGTLWNGNKIIDERLINPDGSLLFRVTINGVTGWRLCERILAGSSGGGSSGGEPTTENLYFQSDNGSSGGGSSGGMV
FTLEDFVGDWRQTAGYNLDQVLEQGGVSSLFQNLGVSVTPIQRIVLSGE -continued

SEQUENCE LISTING

SEQ ID NO: 156 (L27V CP 51 TEV)
atgggcctgaagatcgacatccatgtcatcatcccgtatgaaggtctgagcggcgatcagatgggccagatcgaaaaa
atttttaaggtggtgtaccctgtggatgatcatcactttaaggtgattctgcactatggcacactggtaatcgacggg
gttacgccgaacatgatcgactatttcggacggccgtatgaaggcatcgccgtgttcgacggcaaaaagatcactgta
accgggaccctgtggaacggcaacaaaattatcgacgagcgcctgatcaaccccgacggctccctgctgttccgcgta
accatcaacggagtgaccggctggcggctgtgcgagcgcattttggcgggaagttctggtggaggaagttctggtgga
gagcctactactgagaacttgtacttccagagcgataacggaagttctggtggaggaagttctggtggaatggtgttt
acactcgaagatttcgtaggggactggcggcagacagccggctacaacctggaccaagtccttgagcagggcggtgtg
tccagtttgtttcagaatctcggggtgtccgtaactccgatccaaaggattgtcctgagcggtgaaaac SEQ ID NO: 157 (L27V CP 51 TEV)
MGLKIDIHVIIPYEGLSGDQMGQIEKIFKVVYPVDDHHFKVILHYGTLVIDGVTPNMIDYFGRPYEGIAVFDGKKITV
TGTLWNGNKIIDERLINPDGSLLFRVTINGVTGWRLCERILAGSSGGGSSGGEPTTENLYFQSDNGSSGGGSSGGMVF
TLEDFVGDWRQTAGYNLDQVLEQGGVSSLFQNLGVSVTPIQRIVLSGEN SEQ ID NO: 158 (L27V CP 52 TEV)
atgctgaagatcgacatccatgtcatcatcccgtatgaaggtctgagcggcgatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcgggaagttctggtggaggaagttctggtggagag
cctactactgagaacttgtacttccagagcgataacggaagttctggtggaggaagttctggtggaatggtgtttaca
ctcgaagatttcgtaggggactggcggcagacagccggctacaacctggaccaagtccttgagcagggcggtgtgtcc
agtttgtttcagaatctcggggtgtccgtaactccgatccaaaggattgtcctgagcggtgaaaacggc SEQ ID NO: 159 (L27V CP 52 TEV)
MLKIDIHVIIPYEGLSGDQMGQIEKIFKVVYPVDDHHFKVILHYGTLVIDGVTPNMIDYFGRPYEGIAVFDGKKITVT
GTLWNGNKIIDERLINPDGSLLFRVTINGVTGWRLCERILAGSSGGGSSGGEPTTENLYFQSDNGSSGGGSSGGMVFT
LEDFVGDWRQTAGYNLDQVLEQGGVSSLFQNLGVSVTPIQRIVLSGENG SEQ ID NO: 160 (L27V CP 53 TEV)
atgaagatcgacatccatgtcatcatcccgtatgaaggtctgagcggcgatcagatgggccagatcgaaaaaattttt
aaggtggtgtaccctgtggatgatcatcactttaaggtgattctgcactatggcacactggtaatcgacggggttacg
ccgaacatgatcgactatttcggacggccgtatgaaggcatcgccgtgttcgacggcaaaaagatcactgtaaccggg
accctgtggaacggcaacaaaattatcgacgagcgcctgatcaaccccgacggctccctgctgttccgcgtaaccatc
aacggagtgaccggctggcggctgtgcgagcgcattttggcgggaagttctggtggaggaagttctggtggagagcct
actactgagaacttgtacttccagagcgataacggaagttctggtggaggaagttctggtggaatggtgtttacactc
gaagatttcgtaggggactggcggcagacagccggctacaacctggaccaagtccttgagcagggcggtgtgtccagt
ttgtttcagaatctcggggtgtccgtaactccgatccaaaggattgtcctgagcggtgaaaacggcctg SEQ ID NO: 161 (L27V CP 53 TEV)
MKIDIHVIIPYEGLSGDQMGQIEKIFKVVYPVDDHHFKVILHYGTLVIDGVTPNMIDYFGRPYEGIAVFDGKKITVTG
TLWNGNKIIDERLINPDGSLLFRVTINGVTGWRLCERILAGSSGGGSSGGEPTTENLYFQSDNGSSGGGSSGGMVFTL
EDFVGDWRQTAGYNLDQVLEQGGVSSLFQNLGVSVTPIQRIVLSGENGL SEQ ID NO: 162 (L27V CP 54 TEV)
atgatcgacatccatgtcatcatcccgtatgaaggtctgagcggcgatcagatgggccagatcgaaaaaatttttaag
gtggtgtaccctgtggatgatcatcactttaaggtgattctgcactatggcacactggtaatcgacggggttacgccg
aacatgatcgactatttcggacggccgtatgaaggcatcgccgtgttcgacggcaaaaagatcactgtaaccgggacc
ctgtggaacggcaacaaaattatcgacgagcgcctgatcaaccccgacggctccctgctgttccgcgtaaccatcaac
ggagtgaccggctggcggctgtgcgagcgcattttggcgggaagttctggtggaggaagttctggtggagagcctact
actgagaacttgtacttccagagcgataacggaagttctggtggaggaagttctggtggaatggtgtttacactcgaa
gatttcgtaggggactggcggcagacagccggctacaacctggaccaagtccttgagcagggcggtgtgtccagtttg
tttcagaatctcggggtgtccgtaactccgatccaaaggattgtcctgagcggtgaaaacggcctgaag SEQ ID NO: 163 (L27V CP 54 TEV)
MIDIHVIIPYEGLSGDQMGQIEKIFKVVYPVDDHHFKVILHYGTLVIDGVTPNMIDYFGRPYEGIAVFDGKKITVTGT
LWNGNKIIDERLINPDGSLLFRVTINGVTGWRLCERILAGSSGGGSSGGEPTTENLYFQSDNGSSGGGSSGGMVFTLE
DFVGDWRQTAGYNLDQVLEQGGVSSLFQNLGVSVTPIQRIVLSGENGLK SEQ ID NO: 164 (L27V CP 55 TEV)
atggacatccatgtcatcatcccgtatgaaggtctgagcggcgatcagatgggccagatcgaaaaaatttttaaggtg
gtgtaccctgtggatgatcatcactttaaggtgattctgcactatggcacactggtaatcgacggggttacgccgaac
atgatcgactatttcggacggccgtatgaaggcatcgccgtgttcgacggcaaaaagatcactgtaaccgggaccctg
tggaacggcaacaaaattatcgacgagcgcctgatcaaccccgacggctccctgctgttccgcgtaaccatcaacgga
gtgaccggctggcggctgtgcgagcgcattttggcgggaagttctggtggaggaagttctggtggagagcctactact
gagaacttgtacttccagagcgataacggaagttctggtggaggaagttctggtggaatggtgtttacactcgaagat
ttcgtaggggactggcggcagacagccggctacaacctggaccaagtccttgagcagggcggtgtgtccagtttgttt
cagaatctcggggtgtccgtaactccgatccaaaggattgtcctgagcggtgaaaacggcctgaagatc SEQ ID NO: 165 (L27V CP 55 TEV)
MDIHVIIPYEGLSGDQMGQIEKIFKVVYPVDDHHFKVILHYGTLVIDGVTPNMIDYFGRPYEGIAVFDGKKITVTGTL
WNGNKIIDERLINPDGSLLFRVTINGVTGWRLCERILAGSSGGGSSGGEPTTENLYFQSDNGSSGGGSSGGMVFTLED
FVGDWRQTAGYNLDQVLEQGGVSSLFQNLGVSVTPIQRIVLSGENGLKI -continued

SEQUENCE LISTING

SEQ ID NO: 166 (L27V CP 56 TEV)
Atgatccatgtcatcatcccgtatgaaggtctgagcggcgatcagatgggccagatcgaaaaaatttttaaggtggtg
taccctgtggatgatcatcactttaaggtgattctgcactatggcacactggtaatcgacggggttacgccgaacatg
atcgactatttcggacggccgtatgaaggcatcgccgtgttcgacggcaaaaagatcactgtaaccgggaccctgtgg
aacggcaacaaaattatcgacgagcgcctgatcaaccccgacggctccctgctgttccgcgtaaccatcaacggagtg
accggctggcggctgtgcgagcgcattttggcgggaagttctggtggaggaagttctggtggagagcctactactgag
aacttgtacttccagagcgataacggaagttctggtggaggaagttctggtggaatggtgtttacactcgaagatttc
gtaggggactggcggcagacagccggctacaacctggaccaagtccttgagcagggcggtgtgtccagtttgtttcag
aatctcggggtgtccgtaactccgatccaaaggattgtcctgagcggtgaaaacggcctgaagatcga SEQ ID NO: 167 (L27V CP 56 TEV)
MIHVIIPYEGLSGDQMGQIEKIFKVVYPVDDHHFKVILHYGTLVIDGVTPNMIDYFGRPYEGIAVFDGKKITVTGTLW
NGNKIIDERLINPDGSLLFRVTINGVTGWRLCERILAGSSGGGSSGGEPTTENLYFQSDNGSSGGGSSGGMVFTLEDF
VGDWRQTAGYNLDQVLEQGGVSSLFQNLGVSVTPIQRIVLSGENGLKID SEQ ID NO: 168 (L27V CP 58 TEV)
atggtcatcatcccgtatgaaggtctgagcggcgatcagatgggccagatcgaaaaaatttttaaggtggtgtaccct
gtggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcgggaagttctggtggaggaagttctggtggagagcctactactgagaacttg
tacttccagagcgataacggaagttctggtggaggaagttctggtggaatggtgtttacactcgaagatttcgtaggg
gactggcggcagacagccggctacaacctggaccaagtccttgagcagggcggtgtgtccagtttgtttcagaatctc
ggggtgtccgtaactccgatccaaaggattgtcctgagcggtgaaaacggcctgaagatcgacatccat SEQ ID NO: 169 (L27V CP 58 TEV)
MVIIPYEGLSGDQMGQIEKIFKVVYPVDDHHFKVILHYGTLVIDGVTPNMIDYFGRPYEGIAVFDGKKITVTGTLWNG
NKIIDERLINPDGSLLFRVTINGVTGWRLCERILAGSSGGGSSGGEPTTENLYFQSDNGSSGGGSSGGMVFTLEDFVG
DWRQTAGYNLDQVLEQGGVSSLFQNLGVSVTPIQRIVLSGENGLKIDIH SEQ ID NO: 170 (L27V CP 64 TEV)
atgggtctgagcggcgatcagatgggccagatcgaaaaaatttttaaggtggtgtaccctgtggatgatcatcacttt
aaggtgattctgcactatggcacactggtaatcgacggggttacgccgaacatgatcgactatttcggacggccgtat
gaaggcatcgccgtgttcgacggcaaaaagatcactgtaaccgggaccctgtggaacggcaacaaaattatcgacgag
cgcctgatcaaccccgacggctccctgctgttccgcgtaaccatcaacggagtgaccggctggcggctgtgcgagcgc
attttggcgggaagttctggtggaggaagttctggtggagagcctactactgagaacttgtacttccagagcgataac
ggaagttctggtggaggaagttctggtggaatggtgtttacactcgaagatttcgtaggggactggcggcagacagcc
ggctacaacctggaccaagtccttgagcagggcggtgtgtccagtttgtttcagaatctcggggtgtccgtaactccg
atccaaaggattgtcctgagcggtgaaaacggcctgaagatcgacatccatgtcatcatcccgtatgaa SEQ ID NO: 171 (L27V CP 64 TEV)
MGLSGDQMGQIEKIFKVVYPVDDHHFKVILHYGTLVIDGVTPNMIDYFGRPYEGIAVFDGKKITVTGTLWNGNKIIDE
RLINPDGSLLFRVTINGVTGWRLCERILAGSSGGGSSGGEPTTENLYFQSDNGSSGGGSSGGMVFTLEDFVGDWRQTA
GYNLDQVLEQGGVSSLFQNLGVSVTPIQRIVLSGENGLKIDIHVIIPYE SEQ ID NO: 172 (L27V CP 67 TEV)
atgggcgatcagatgggccagatcgaaaaaatttttaaggtggtgtaccctgtggatgatcatcactttaaggtgatt
ctgcactatggcacactggtaatcgacggggttacgccgaacatgatcgactatttcggacggccgtatgaaggcatc
gccgtgttcgacggcaaaaagatcactgtaaccgggaccctgtggaacggcaacaaaattatcgacgagcgcctgatc
aaccccgacggctccctgctgttccgcgtaaccatcaacggagtgaccggctggcggctgtgcgagcgcattttggcg
ggaagttctggtggaggaagttctggtggagagcctactactgagaacttgtacttccagagcgataacggaagttct
ggtggaggaagttctggtggaatggtgtttacactcgaagatttcgtaggggactggcggcagacagccggctacaac
ctggaccaagtccttgagcagggcggtgtgtccagtttgtttcagaatctcggggtgtccgtaactccgatccaaagg
attgtcctgagcggtgaaaacggcctgaagatcgacatccatgtcatcatcccgtatgaaggtctgagc SEQ ID NO: 173 (L27V CP 67 TEV)
MGDQMGQIEKIFKVVYPVDDHHFKVILHYGTLVIDGVTPNMIDYFGRPYEGIAVFDGKKITVTGTLWNGNKIIDERLI
NPDGSLLFRVTINGVTGWRLCERILAGSSGGGSSGGEPTTENLYFQSDNGSSGGGSSGGMVFTLEDFVGDWRQTAGYN
LDQVLEQGGVSSLFQNLGVSVTPIQRIVLSGENGLKIDIHVIIPYEGLS SEQ ID NO: 174 (L27V CP 70 TEV)
atgatgggccagatcgaaaaaatttttaaggtggtgtaccctgtggatgatcatcactttaaggtgattctgcactat
ggcacactggtaatcgacggggttacgccgaacatgatcgactatttcggacggccgtatgaaggcatcgccgtgttc
gacggcaaaaagatcactgtaaccgggaccctgtggaacggcaacaaaattatcgacgagcgcctgatcaaccccgac
ggctccctgctgttccgcgtaaccatcaacggagtgaccggctggcggctgtgcgagcgcattttggcgggaagttct
ggtggaggaagttctggtggagagcctactactgagaacttgtacttccagagcgataacggaagttctggtggagga
agttctggtggaatggtgtttacactcgaagatttcgtaggggactggcggcagacagccggctacaacctggaccaa
gtccttgagcagggcggtgtgtccagtttgtttcagaatctcggggtgtccgtaactccgatccaaaggattgtcctg
agcggtgaaaacggcctgaagatcgacatccatgtcatcatcccgtatgaaggtctgagcggcgatcag SEQ ID NO: 175 (L27V CP 70 TEV)
MMGQIEKIFKVVYPVDDHHFKVILHYGTLVIDGVTPNMIDYFGRPYEGIAVFDGKKITVTGTLWNGNKIIDERLINPD
GSLLFRVTINGVTGWRLCERILAGSSGGGSSGGEPTTENLYFQSDNGSSGGGSSGGMVFTLEDFVGDWRQTAGYNLDQ
VLEQGGVSSLFQNLGVSVTPIQRIVLSGENGLKIDIHVIIPYEGLSGDQ -continued

SEQUENCE LISTING

SEQ ID NO: 176 (L27V CP 73 TEV)
atgatcgaaaaaattttttaaggtggtgtaccctgtggatgatcatcactttaaggtgattctgcactatggcacactg
gtaatcgacggggttacgccgaacatgatcgactatttcggacggccgtatgaaggcatcgccgtgttcgacggcaaa
aagatcactgtaaccgggaccctgtggaacggcaacaaaattatcgacgagcgcctgatcaaccccgacggctccctg
ctgttccgcgtaaccatcaacggagtgaccggctggcggctgtgcgagcgcattttggcgggaagttctggtggagga
agttctggtggagagcctactactgagaacttgtacttccagagcgataacggaagttctggtggaggaagttctggt
ggaatggtgtttacactcgaagatttcgtaggggactggcggcagacagccggctacaacctggaccaagtccttgag
cagggcggtgtgtccagtttgtttcagaatctcggggtgtccgtaactccgatccaaaggattgtcctgagcggtgaa
aacggcctgaagatcgacatccatgtcatcatcccgtatgaaggtctgagcggcgatcagatgggccag SEQ ID NO: 177 (L27V CP 73 TEV)
MIEKIFKVVYPVDDHHFKVILHYGTLVIDGVTPNMIDYFGRPYEGIAVFDGKKITVTGTLWNGNKIIDERLINPDGSL
LFRVTINGVTGWRLCERILAGSSGGGSSGGEPTTENLYFQSDNGSSGGGSSGGMVFTLEDFVGDWRQTAGYNLDQVLE
QGGVSSLFQNLGVSVTPIQRIVLSGENGLKIDIHVIIPYEGLSGDQMGQ SEQ ID NO: 178 (L27V CP 76 TEV)
atgattttttaaggtggtgtaccctgtggatgatcatcactttaaggtgattctgcactatggcacactggtaatcgac
ggggttacgccgaacatgatcgactatttcggacggccgtatgaaggcatcgccgtgttcgacggcaaaaagatcact
gtaaccgggaccctgtggaacggcaacaaaattatcgacgagcgcctgatcaaccccgacggctccctgctgttccgc
gtaaccatcaacggagtgaccggctggcggctgtgcgagcgcattttggcgggaagttctggtggaggaagttctggt
ggagagcctactactgagaacttgtacttccagagcgataacggaagttctggtggaggaagttctggtggaatggtg
tttacactcgaagatttcgtaggggactggcggcagacagccggctacaacctggaccaagtccttgagcagggcggt
gtgtccagtttgtttcagaatctcggggtgtccgtaactccgatccaaaggattgtcctgagcggtgaaaacggcctg
aagatcgacatccatgtcatcatcccgtatgaaggtctgagcggcgatcagatgggccagatcgaaaaa SEQ ID NO: 179 (L27V CP 76 TEV)
MIFKVVYPVDDHHFKVILHYGTLVIDGVTPNMIDYFGRPYEGIAVFDGKKITVTGTLWNGNKIIDERLINPDGSLLFR
VTINGVTGWRLCERILAGSSGGGSSGGEPTTENLYFQSDNGSSGGGSSGGMVFTLEDFVGDWRQTAGYNLDQVLEQGG
VSSLFQNLGVSVTPIQRIVLSGENGLKIDIHVIIPYEGLSGDQMGQIEK SEQ ID NO: 180 (L27V CP 79 TEV)
Atggtggtgtaccctgtggatgatcatcactttaaggtgattctgcactatggcacactggtaatcgacggggttacg
ccgaacatgatcgactatttcggacggccgtatgaaggcatcgccgtgttcgacggcaaaaagatcactgtaaccggg
accctgtggaacggcaacaaaattatcgacgagcgcctgatcaaccccgacggctccctgctgttccgcgtaaccatc
aacggagtgaccggctggcggctgtgcgagcgcattttggcgggaagttctggtggaggaagttctggtggagagcct
actactgagaacttgtacttccagagcgataacggaagttctggtggaggaagttctggtggaatggtgtttacactc
gaagatttcgtaggggactggcggcagacagccggctacaacctggaccaagtccttgagcagggcggtgtgtccagt
ttgtttcagaatctcggggtgtccgtaactccgatccaaaggattgtcctgagcggtgaaaacggcctgaagatcgac
atccatgtcatcatcccgtatgaaggtctgagcggcgatcagatgggccagatcgaaaaaattttttaag SEQ ID NO: 181 (L27V CP 79 TEV)
MVVYPVDDHHFKVILHYGTLVIDGVTPNMIDYFGRPYEGIAVFDGKKITVTGTLWNGNKIIDERLINPDGSLLFRVTI
NGVTGWRLCERILAGSSGGGSSGGEPTTENLYFQSDNGSSGGGSSGGMVFTLEDFVGDWRQTAGYNLDQVLEQGGVSS
LFQNLGVSVTPIQRIVLSGENGLKIDIHVIIPYEGLSGDQMGQIEKIFK SEQ ID NO: 182 (L27V CP 80 TEV)
atggtgtaccctgtggatgatcatcactttaaggtgattctgcactatggcacactggtaatcgacggggttacgccg
aacatgatcgactatttcggacggccgtatgaaggcatcgccgtgttcgacggcaaaaagatcactgtaaccgggacc
ctgtggaacggcaacaaaattatcgacgagcgcctgatcaaccccgacggctccctgctgttccgcgtaaccatcaac
ggagtgaccggctggcggctgtgcgagcgcattttggcgggaagttctggtggaggaagttctggtggagagcctact
actgagaacttgtacttccagagcgataacggaagttctggtggaggaagttctggtggaatggtgtttacactcgaa
gatttcgtaggggactggcggcagacagccggctacaacctggaccaagtccttgagcagggcggtgtgtccagtttg
tttcagaatctcggggtgtccgtaactccgatccaaaggattgtcctgagcggtgaaaacggcctgaagatcgacatc
catgtcatcatcccgtatgaaggtctgagcggcgatcagatgggccagatcgaaaaaatttttaaggtg SEQ ID NO: 183 (L27V CP 80 TEV)
MVYPVDDHHFKVILHYGTLVIDGVTPNMIDYFGRPYEGIAVFDGKKITVTGTLWNGNKIIDERLINPDGSLLFRVTIN
GVTGWRLCERILAGSSGGGSSGGEPTTENLYFQSDNGSSGGGSSGGMVFTLEDFVGDWRQTAGYNLDQVLEQGGVSSL
FQNLGVSVTPIQRIVLSGENGLKIDIHVIIPYEGLSGDQMGQIEKIFKV SEQ ID NO: 184 (L27V CP 81 TEV)
atgtaccctgtggatgatcatcactttaaggtgattctgcactatggcacactggtaatcgacggggttacgccgaac
atgatcgactatttcggacggccgtatgaaggcatcgccgtgttcgacggcaaaaagatcactgtaaccgggaccctg
tggaacggcaacaaaattatcgacgagcgcctgatcaaccccgacggctccctgctgttccgcgtaaccatcaacgga
gtgaccggctggcggctgtgcgagcgcattttggcgggaagttctggtggaggaagttctggtggagagcctactact
gagaacttgtacttccagagcgataacggaagttctggtggaggaagttctggtggaatggtgtttacactcgaagat
ttcgtaggggactggcggcagacagccggctacaacctggaccaagtccttgagcagggcggtgtgtccagtttgttt
cagaatctcggggtgtccgtaactccgatccaaaggattgtcctgagcggtgaaaacggcctgaagatcgacatccat
gtcatcatcccgtatgaaggtctgagcggcgatcagatgggccagatcgaaaaaattttttaaggtggtg SEQ ID NO: 185 (L27V CP 81 TEV)
MYPVDDHHFKVILHYGTLVIDGVTPNMIDYFGRPYEGIAVFDGKKITVTGTLWNGNKIIDERLINPDGSLLFRVTING
VTGWRLCERILAGSSGGGSSGGEPTTENLYFQSDNGSSGGGSSGGMVFTLEDFVGDWRQTAGYNLDQVLEQGGVSSLF
QNLGVSVTPIQRIVLSGENGLKIDIHVIIPYEGLSGDQMGQIEKIFKVV -continued

SEQUENCE LISTING

SEQ ID NO: 186 (L27V CP 82 TEV)
atgcctgtggatgatcatcactttaaggtgattctgcactatggcacactggtaatcgacggggttacgccgaacatg
atcgactatttcggacggccgtatgaaggcatcgccgtgttcgacggcaaaaagatcactgtaaccgggaccctgtgg
aacggcaacaaaattatcgacgagcgcctgatcaaccccgacggctccctgctgttccgcgtaaccatcaacggagtg
accggctggcggctgtgcgagcgcattttggcgggaagttctggtggaggaagttctggtggagagcctactactgag
aacttgtacttccagagcgataacggaagttctggtggaggaagttctggtggaatggtgtttacactcgaagatttc
gtaggggactggcggcagacagccggctacaacctggaccaagtccttgagcagggcggtgtgtccagtttgtttcag
aatctcggggtgtccgtaactccgatccaaaggattgtcctgagcggtgaaaacggcctgaagatcgacatccatgtc
atcatcccgtatgaaggtctgagcggcgatcagatgggccagatcgaaaaaatttttaaggtggtgtac SEQ ID NO: 187 (L27V CP 82 TEV)
MPVDDHHFKVILHYGTLVIDGVTPNMIDYFGRPYEGIAVFDGKKITVTGTLWNGNKIIDERLINPDGSLLFRVTINGV
TGWRLCERILAGSSGGGSSGGEPTTENLYFQSDNGSSGGGSSGGMVFTLEDFVGDWRQTAGYNLDQVLEQGGVSSLFQ
NLGVSVTPIQRIVLSGENGLKIDIHVIIPYEGLSGDQMGQIEKIFKVVY SEQ ID NO: 188 (L27V CP 83 TEV)
atggtggatgatcatcactttaaggtgattctgcactatggcacactggtaatcgacggggttacgccgaacatgatc
gactatttcggacggccgtatgaaggcatcgccgtgttcgacggcaaaaagatcactgtaaccgggaccctgtggaac
ggcaacaaaattatcgacgagcgcctgatcaaccccgacggctccctgctgttccgcgtaaccatcaacggagtgacc
ggctggcggctgtgcgagcgcattttggcgggaagttctggtggaggaagttctggtggagagcctactactgagaac
ttgtacttccagagcgataacggaagttctggtggaggaagttctggtggaatggtgtttacactcgaagatttcgta
ggggactggcggcagacagccggctacaacctggaccaagtccttgagcagggcggtgtgtccagtttgtttcagaat
ctcggggtgtccgtaactccgatccaaaggattgtcctgagcggtgaaaacggcctgaagatcgacatccatgtcatc
atcccgtatgaaggtctgagcggcgatcagatgggccagatcgaaaaaatttttaaggtggtgtaccct SEQ ID NO: 189 (L27V CP 83 TEV)
MVDDHHFKVILHYGTLVIDGVTPNMIDYFGRPYEGIAVFDGKKITVTGTLWNGNKIIDERLINPDGSLLFRVTINGVT
GWRLCERILAGSSGGGSSGGEPTTENLYFQSDNGSSGGGSSGGMVFTLEDFVGDWRQTAGYNLDQVLEQGGVSSLFQN
LGVSVTPIQRIVLSGENGLKIDIHVIIPYEGLSGDQMGQIEKIFKVVYP SEQ ID NO: 190 (L27V CP 84 TEV)
atggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacggagtgaccggc
tggcggctgtgcgagcgcattttggcgggaagttctggtggaggaagttctggtggagagcctactactgagaacttg
tacttccagagcgataacggaagttctggtggaggaagttctggtggaatggtgtttacactcgaagatttcgtaggg
gactggcggcagacagccggctacaacctggaccaagtccttgagcagggcggtgtgtccagtttgtttcagaatctc
ggggtgtccgtaactccgatccaaaggattgtcctgagcggtgaaaacggcctgaagatcgacatccatgtcatcatc
ccgtatgaaggtctgagcggcgatcagatgggccagatcgaaaaaatttttaaggtggtgtaccctgtg SEQ ID NO: 191 (L27V CP 84 TEV)
MDDHHFKVILHYGTLVIDGVTPNMIDYFGRPYEGIAVFDGKKITVTGTLWNGNKIIDERLINPDGSLLFRVTINGVTG
WRLCERILAGSSGGGSSGGEPTTENLYFQSDNGSSGGGSSGGMVFTLEDFVGDWRQTAGYNLDQVLEQGGVSSLFQNL
GVSVTPIQRIVLSGENGLKIDIHVIIPYEGLSGDQMGQIEKIFKVVYPV SEQ ID NO: 192 (L27V CP 85 TEV)
atggatcatcactttaaggtgattctgcactatggcacactggtaatcgacggggttacgccgaacatgatcgactat
ttcggacggccgtatgaaggcatcgccgtgttcgacggcaaaaagatcactgtaaccgggaccctgtggaacggcaac
aaaattatcgacgagcgcctgatcaaccccgacggctccctgctgttccgcgtaaccatcaacggagtgaccggctgg
cggctgtgcgagcgcattttggcgggaagttctggtggaggaagttctggtggagagcctactactgagaacttgtac
ttccagagcgataacggaagttctggtggaggaagttctggtggaatggtgtttacactcgaagatttcgtaggggac
tggcggcagacagccggctacaacctggaccaagtccttgagcagggcggtgtgtccagtttgtttcagaatctcggg
gtgtccgtaactccgatccaaaggattgtcctgagcggtgaaaacggcctgaagatcgacatccatgtcatcatcccg
tatgaaggtctgagcggcgatcagatgggccagatcgaaaaaatttttaaggtggtgtaccctgtggat SEQ ID NO: 193 (L27V CP 85 TEV)
MDHHFKVILHYGTLVIDGVTPNMIDYFGRPYEGIAVFDGKKITVTGTLWNGNKIIDERLINPDGSLLFRVTINGVTGW
RLCERILAGSSGGGSSGGEPTTENLYFQSDNGSSGGGSSGGMVFTLEDFVGDWRQTAGYNLDQVLEQGGVSSLFQNLG
VSVTPIQRIVLSGENGLKIDIHVIIPYEGLSGDQMGQIEKIFKVVYPVD SEQ ID NO: 194 (L27V CP 86 TEV)
atgcatcactttaaggtgattctgcactatggcacactggtaatcgacggggttacgccgaacatgatcgactatttc
ggacggccgtatgaaggcatcgccgtgttcgacggcaaaaagatcactgtaaccgggaccctgtggaacggcaacaaa
attatcgacgagcgcctgatcaaccccgacggctccctgctgttccgcgtaaccatcaacggagtgaccggctggcgg
ctgtgcgagcgcattttggcgggaagttctggtggaggaagttctggtggagagcctactactgagaacttgtacttc
cagagcgataacggaagttctggtggaggaagttctggtggaatggtgtttacactcgaagatttcgtaggggactgg
cggcagacagccggctacaacctggaccaagtccttgagcagggcggtgtgtccagtttgtttcagaatctcggggtg
tccgtaactccgatccaaaggattgtcctgagcggtgaaaacggcctgaagatcgacatccatgtcatcatcccgtat
gaaggtctgagcggcgatcagatgggccagatcgaaaaaatttttaaggtggtgtaccctgtggatgat SEQ ID NO: 195 (L27V CP 86 TEV)
MHHFKVILHYGTLVIDGVTPNMIDYFGRPYEGIAVFDGKKITVTGTLWNGNKIIDERLINPDGSLLFRVTINGVTGWR
LCERILAGSSGGGSSGGEPTTENLYFQSDNGSSGGGSSGGMVFTLEDFVGDWRQTAGYNLDQVLEQGGVSSLFQNLGV
SVTPIQRIVLSGENGLKIDIHVIIPYEGLSGDQMGQIEKIFKVVYPVDD -continued

SEQUENCE LISTING

SEQ ID NO: 196 (L27V CP 87 TEV)
atgcactttaaggtgattctgcactatggcacactggtaatcgacggggttacgccgaacatgatcgactatttcgga
cggccgtatgaaggcatcgccgtgttcgacggcaaaaagatcactgtaaccgggaccctgtggaacggcaacaaaatt
atcgacgagcgcctgatcaaccccgacggctccctgctgttccgcgtaaccatcaacggagtgaccggctggcggctg
tgcgagcgcattttggcgggaagttctggtggaggaagttctggtggagagcctactactgagaacttgtacttccag
agcgataacggaagttctggtggaggaagttctggtggaatggtgtttacactcgaagatttcgtaggggactggcgg
cagacagccggctacaacctggaccaagtccttgagcagggcggtgtgtccagtttgtttcagaatctcggggtgtcc
gtaactccgatccaaaggattgtcctgagcggtgaaaacggcctgaagatcgacatccatgtcatcatcccgtatgaa
ggtctgagcggcgatcagatgggccagatcgaaaaaatttttaaggtggtgtaccctgtggatgatcat SEQ ID NO: 197 (L27V CP 87 TEV)
MHFKVILHYGTLVIDGVTPNMIDYFGRPYEGIAVFDGKKITVTGTLWNGNKIIDERLINPDGSLLFRVTINGVTGWRL
CERILAGSSGGGSSGGEPTTENLYFQSDNGSSGGGSSGGMVFTLEDFVGDWRQTAGYNLDQVLEQGGVSSLFQNLGVS
VTPIQRIVLSGENGLKIDIHVIIPYEGLSGDQMGQIEKIFKVVYPVDDH SEQ ID NO: 198 (L27V CP 88 TEV)
atgtttaaggtgattctgcactatggcacactggtaatcgacggggttacgccgaacatgatcgactatttcggacgg
ccgtatgaaggcatcgccgtgttcgacggcaaaaagatcactgtaaccgggaccctgtggaacggcaacaaaattatc
gacgagcgcctgatcaaccccgacggctccctgctgttccgcgtaaccatcaacggagtgaccggctggcggctgtgc
gagcgcattttggcgggaagttctggtggaggaagttctggtggagagcctactactgagaacttgtacttccagagc
gataacggaagttctggtggaggaagttctggtggaatggtgtttacactcgaagatttcgtaggggactggcggcag
acagccggctacaacctggaccaagtccttgagcagggcggtgtgtccagtttgtttcagaatctcggggtgtccgta
actccgatccaaaggattgtcctgagcggtgaaaacggcctgaagatcgacatccatgtcatcatcccgtatgaaggt
ctgagcggcgatcagatgggccagatcgaaaaaatttttaaggtggtgtaccctgtggatgatcatcac SEQ ID NO: 199 (L27V CP 88 TEV)
MFKVILHYGTLVIDGVTPNMIDYFGRPYEGIAVFDGKKITVTGTLWNGNKIIDERLINPDGSLLFRVTINGVTGWRLC
ERILAGSSGGGSSGGEPTTENLYFQSDNGSSGGGSSGGMVFTLEDFVGDWRQTAGYNLDQVLEQGGVSSLFQNLGVSV
TPIQRIVLSGENGLKIDIHVIIPYEGLSGDQMGQIEKIFKVVYPVDDHH SEQ ID NO: 200 (L27V CP 91 TEV)
atgattctgcactatggcacactggtaatcgacggggttacgccgaacatgatcgactatttcggacggccgtatgaa
ggcatcgccgtgttcgacggcaaaaagatcactgtaaccgggaccctgtggaacggcaacaaaattatcgacgagcgc
ctgatcaaccccgacggctccctgctgttccgcgtaaccatcaacggagtgaccggctggcggctgtgcgagcgcatt
ttggcgggaagttctggtggaggaagttctggtggagagcctactactgagaacttgtacttccagagcgataacgga
agttctggtggaggaagttctggtggaatggtgtttacactcgaagatttcgtaggggactggcggcagacagccggc
tacaacctggaccaagtccttgagcagggcggtgtgtccagtttgtttcagaatctcggggtgtccgtaactccgatc
caaaggattgtcctgagcggtgaaaacggcctgaagatcgacatccatgtcatcatcccgtatgaaggtctgagcggc
gatcagatgggccagatcgaaaaaatttttaaggtggtgtaccctgtggatgatcatcactttaaggtg SEQ ID NO: 201 (L27V CP 91 TEV)
MILHYGTLVIDGVTPNMIDYFGRPYEGIAVFDGKKITVTGTLWNGNKIIDERLINPDGSLLFRVTINGVTGWRLCERI
LAGSSGGGSSGGEPTTENLYFQSDNGSSGGGSSGGMVFTLEDFVGDWRQTAGYNLDQVLEQGGVSSLFQNLGVSVTPI
QRIVLSGENGLKIDIHVIIPYEGLSGDQMGQIEKIFKVVYPVDDHHFKV SEQ ID NO: 202 (L27V CP 94 TEV)
atgtatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
agttctggtggaggaagttctggtggagagcctactactgagaacttgtacttccagagcgataacggaagttctggt
ggaggaagttctggtggaatggtgtttacactcgaagatttcgtaggggactggcggcagacagccggctacaacctg
gaccaagtccttgagcagggcggtgtgtccagtttgtttcagaatctcggggtgtccgtaactccgatccaaaggatt
gtcctgagcggtgaaaacggcctgaagatcgacatccatgtcatcatcccgtatgaaggtctgagcggcgatcagatg
ggccagatcgaaaaaatttttaaggtggtgtaccctgtggatgatcatcactttaaggtgattctgcacg SEQ ID NO: 203 (L27V CP 94 TEV)
MYGTLVIDGVTPNMIDYFGRPYEGIAVFDGKKITVTGTLWNGNKIIDERLINPDGSLLFRVTINGVTGWRLCERILAG
SSGGGSSGGEPTTENLYFQSDNGSSGGGSSGGMVFTLEDFVGDWRQTAGYNLDQVLEQGGVSSLFQNLGVSVTPIQRI
VLSGENGLKIDIHVIIPYEGLSGDQMGQIEKIFKVVYPVDDHHFKVILH SEQ ID NO: 204 (L27V CP 95 TEV)
atgggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcgggaagt
tctggtggaggaagttctggtggagagcctactactgagaacttgtacttccagagcgataacggaagttctggtgga
ggaagttctggtggaatggtgtttacactcgaagatttcgtaggggactggcggcagacagccggctacaacctggac
caagtccttgagcagggcggtgtgtccagtttgtttcagaatctcggggtgtccgtaactccgatccaaaggattgtc
ctgagcggtgaaaacggcctgaagatcgacatccatgtcatcatcccgtatgaaggtctgagcggcgatcagatgggc
cagatcgaaaaaatttttaaggtggtgtaccctgtggatgatcatcactttaaggtgattctgcactat SEQ ID NO: 205 (L27V CP 95 TEV)
MGTLVIDGVTPNMIDYFGRPYEGIAVFDGKKITVTGTLWNGNKIIDERLINPDGSLLFRVTINGVTGWRLCERILAGS
SGGGSSGGEPTTENLYFQSDNGSSGGGSSGGMVFTLEDFVGDWRQTAGYNLDQVLEQGGVSSLFQNLGVSVTPIQRIV
LSGENGLKIDIHVIIPYEGLSGDQMGQIEKIFKVVYPVDDHHFKVILHY -continued

SEQUENCE LISTING

SEQ ID NO: 206 (L27V CP 97 TEV)
atgctggtaatcgacggggttacgccgaacatgatcgactatttcggacggccgtatgaaggcatcgccgtgttcgac
ggcaaaaagatcactgtaaccgggaccctgtggaacggcaacaaaattatcgacgagcgcctgatcaaccccgacggc
tccctgctgttccgcgtaaccatcaacggagtgaccggctggcggctgtgcgagcgcattttggcgggaagttctggt
ggaggaagttctggtggagagcctactactgagaacttgtacttccagagcgataacggaagttctggtggaggaagt
tctggtggaatggtgtttacactcgaagatttcgtaggggactggcggcagacagccggctacaacctggaccaagtc
cttgagcagggcggtgtgtccagtttgtttcagaatctcggggtgtccgtaactccgatccaaaggattgtcctgagc
ggtgaaaacggcctgaagatcgacatccatgtcatcatcccgtatgaaggtctgagcggcgatcagatgggccagatc
gaaaaaatttttaaggtggtgtaccctgtggatgatcatcactttaaggtgattctgcactatggcaca SEQ ID NO: 207 (L27V CP 97 TEV)
MLVIDGVTPNMIDYFGRPYEGIAVFDGKKITVTGTLWNGNKIIDERLINPDGSLLFRVTINGVTGWRLCERILAGSSG
GGSSGGEPTTENLYFQSDNGSSGGGSSGGMVFTLEDFVGDWRQTAGYNLDQVLEQGGVSSLFQNLGVSVTPIQRIVLS
GENGLKIDIHVIIPYEGLSGDQMGQIEKIFKVVYPVDDHHFKVILHYGT SEQ ID NO: 208 (L27V CP 100 TEV)
Atggacggggttacgccgaacatgatcgactatttcggacggccgtatgaaggcatcgccgtgttcgacggcaaaaag
atcactgtaaccgggaccctgtggaacggcaacaaaattatcgacgagcgcctgatcaaccccgacggctccctgctg
ttccgcgtaaccatcaacggagtgaccggctggcggctgtgcgagcgcattttggcgggaagttctggtggaggaagt
tctggtggagagcctactactgagaacttgtacttccagagcgataacggaagttctggtggaggaagttctggtgga
atggtgtttacactcgaagatttcgtaggggactggcggcagacagccggctacaacctggaccaagtccttgagcag
ggcggtgtgtccagtttgtttcagaatctcggggtgtccgtaactccgatccaaaggattgtcctgagcggtgaaaac
ggcctgaagatcgacatccatgtcatcatcccgtatgaaggtctgagcggcgatcagatgggccagatcgaaaaaatt
tttaaggtggtgtaccctgtggatgatcatcactttaaggtgattctgcactatggcacactggtaatc SEQ ID NO: 209 (L27V CP 100 TEV)
MDGVTPNMIDYFGRPYEGIAVFDGKKITVTGTLWNGNKIIDERLINPDGSLLFRVTINGVTGWRLCERILAGSSGGGS
SGGEPTTENLYFQSDNGSSGGGSSGGMVFTLEDFVGDWRQTAGYNLDQVLEQGGVSSLFQNLGVSVTPIQRIVLSGEN
GLKIDIHVIIPYEGLSGDQMGQIEKIFKVVYPVDDHHFKVILHYGTLVI SEQ ID NO: 210 (L27V CP 101 TEV)
atgggggttacgccgaacatgatcgactatttcggacggccgtatgaaggcatcgccgtgttcgacggcaaaaagatc
actgtaaccgggaccctgtggaacggcaacaaaattatcgacgagcgcctgatcaaccccgacggctccctgctgttc
cgcgtaaccatcaacggagtgaccggctggcggctgtgcgagcgcattttggcgggaagttctggtggaggaagttct
ggtggagagcctactactgagaacttgtacttccagagcgataacggaagttctggtggaggaagttctggtggaatg
gtgtttacactcgaagatttcgtaggggactggcggcagacagccggctacaacctggaccaagtccttgagcagggc
ggtgtgtccagtttgtttcagaatctcggggtgtccgtaactccgatccaaaggattgtcctgagcggtgaaaacggc
ctgaagatcgacatccatgtcatcatcccgtatgaaggtctgagcggcgatcagatgggccagatcgaaaaaattttt
aaggtggtgtaccctgtggatgatcatcactttaaggtgattctgcactatggcacactggtaatcgac SEQ ID NO: 211 (L27V CP 101 TEV)
MGVTPNMIDYFGRPYEGIAVFDGKKITVTGTLWNGNKIIDERLINPDGSLLFRVTINGVTGWRLCERILAGSSGGGSS
GGEPTTENLYFQSDNGSSGGGSSGGMVFTLEDFVGDWRQTAGYNLDQVLEQGGVSSLFQNLGVSVTPIQRIVLSGENG
LKIDIHVIIPYEGLSGDQMGQIEKIFKVVYPVDDHHFKVILHYGTLVID SEQ ID NO: 212 (L27V CP 102 TEV)
atggttacgccgaacatgatcgactatttcggacggccgtatgaaggcatcgccgtgttcgacggcaaaaagatcact
gtaaccgggaccctgtggaacggcaacaaaattatcgacgagcgcctgatcaaccccgacggctccctgctgttccgc
gtaaccatcaacggagtgaccggctggcggctgtgcgagcgcattttggcgggaagttctggtggaggaagttctggt
ggagagcctactactgagaacttgtacttccagagcgataacggaagttctggtggaggaagttctggtggaatggtg
tttacactcgaagatttcgtaggggactggcggcagacagccggctacaacctggaccaagtccttgagcagggcggt
gtgtccagtttgtttcagaatctcggggtgtccgtaactccgatccaaaggattgtcctgagcggtgaaaacggcctg
aagatcgacatccatgtcatcatcccgtatgaaggtctgagcggcgatcagatgggccagatcgaaaaaatttttaag
gtggtgtaccctgtggatgatcatcactttaaggtgattctgcactatggcacactggtaatcgacggg SEQ ID NO: 213 (L27V CP 102 TEV)
MVTPNMIDYFGRPYEGIAVFDGKKITVTGTLWNGNKIIDERLINPDGSLLFRVTINGVTGWRLCERILAGSSGGGSSG
GEPTTENLYFQSDNGSSGGGSSGGMVFTLEDFVGDWRQTAGYNLDQVLEQGGVSSLFQNLGVSVTPIQRIVLSGENGL
KIDIHVIIPYEGLSGDQMGQIEKIFKVVYPVDDHHFKVILHYGTLVIDG SEQ ID NO: 214 (L27V CP 103 TEV)
atgacgccgaacatgatcgactatttcggacggccgtatgaaggcatcgccgtgttcgacggcaaaaagatcactgta
accgggaccctgtggaacggcaacaaaattatcgacgagcgcctgatcaaccccgacggctccctgctgttccgcgta
accatcaacggagtgaccggctggcggctgtgcgagcgcattttggcgggaagttctggtggaggaagttctggtgga
gagcctactactgagaacttgtacttccagagcgataacggaagttctggtggaggaagttctggtggaatggtgttt
acactcgaagatttcgtaggggactggcggcagacagccggctacaacctggaccaagtccttgagcagggcggtgtg
tccagtttgtttcagaatctcggggtgtccgtaactccgatccaaaggattgtcctgagcggtgaaaacggcctgaag
atcgacatccatgtcatcatcccgtatgaaggtctgagcggcgatcagatgggccagatcgaaaaaatttttaaggtg
gtgtaccctgtggatgatcatcactttaaggtgattctgcactatggcacactggtaatcgacggggtt SEQ ID NO: 215 (L27V CP 103 TEV)
MTPNMIDYFGRPYEGIAVFDGKKITVTGTLWNGNKIIDERLINPDGSLLFRVTINGVTGWRLCERILAGSSGGGSSGG
EPTTENLYFQSDNGSSGGGSSGGMVFTLEDFVGDWRQTAGYNLDQVLEQGGVSSLFQNLGVSVTPIQRIVLSGENGLK
IDIHVIIPYEGLSGDQMGQIEKIFKVVYPVDDHHFKVILHYGTLVIDGV -continued

SEQUENCE LISTING

SEQ ID NO: 216 (L27V CP 104 TEV)
atgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcgggaagttctggtggaggaagttctggtggagag
cctactactgagaacttgtacttccagagcgataacggaagttctggtggaggaagttctggtggaatggtgtttaca
ctcgaagatttcgtaggggactggcggcagacagccggctacaacctggaccaagtccttgagcagggcggtgtgtcc
agtttgtttcagaatctcggggtgtccgtaactccgatccaaaggattgtcctgagcggtgaaaacggcctgaagatc
gacatccatgtcatcatcccgtatgaaggtctgagcggcgatcagatgggccagatcgaaaaaatttttaaggtggtg
taccctgtggatgatcatcactttaaggtgattctgcactatggcacactggtaatcgacggggttacg SEQ ID NO: 217 (L27V CP 104 TEV)
MPNMIDYFGRPYEGIAVFDGKKITVTGTLWNGNKIIDERLINPDGSLLFRVTINGVTGWRLCERILAGSSGGGSSGGE
PTTENLYFQSDNGSSGGGSSGGMVFTLEDFVGDWRQTAGYNLDQVLEQGGVSSLFQNLGVSVTPIQRIVLSGENGLKI
DIHVIIPYEGLSGDQMGQIEKIFKVVYPVDDHHFKVILHYGTLVIDGVT SEQ ID NO: 218 (L27V CP 105 TEV)
atgaacatgatcgactatttcggacggccgtatgaaggcatcgccgtgttcgacggcaaaaagatcactgtaaccggg
accctgtggaacggcaacaaaattatcgacgagcgcctgatcaaccccgacggctccctgctgttccgcgtaaccatc
aacggagtgaccggctggcggctgtgcgagcgcattttggcgggaagttctggtggaggaagttctggtggagagcct
actactgagaacttgtacttccagagcgataacggaagttctggtggaggaagttctggtggaatggtgtttacactc
gaagatttcgtaggggactggcggcagacagccggctacaacctggaccaagtccttgagcagggcggtgtgtccagt
ttgtttcagaatctcggggtgtccgtaactccgatccaaaggattgtcctgagcggtgaaaacggcctgaagatcgac
atccatgtcatcatcccgtatgaaggtctgagcggcgatcagatgggccagatcgaaaaaatttttaaggtggtgtac
cctgtggatgatcatcactttaaggtgattctgcactatggcacactggtaatcgacggggttacg SEQ ID NO: 219 (L27V CP 105 TEV)
MNMIDYFGRPYEGIAVFDGKKITVTGTLWNGNKIIDERLINPDGSLLFRVTINGVTGWRLCERILAGSSGGGSSGGEP
TTENLYFQSDNGSSGGGSSGGMVFTLEDFVGDWRQTAGYNLDQVLEQGGVSSLFQNLGVSVTPIQRIVLSGENGLKID
IHVIIPYEGLSGDQMGQIEKIFKVVYPVDDHHFKVILHYGTLVIDGVT SEQ ID NO: 220 (L27V CP 106 TEV)
atgatgatcgactatttcggacggccgtatgaaggcatcgccgtgttcgacggcaaaaagatcactgtaaccgggacc
ctgtggaacggcaacaaaattatcgacgagcgcctgatcaaccccgacggctccctgctgttccgcgtaaccatcaac
ggagtgaccggctggcggctgtgcgagcgcattttggcgggaagttctggtggaggaagttctggtggagagcctact
actgagaacttgtacttccagagcgataacggaagttctggtggaggaagttctggtggaatggtgtttacactcgaa
gatttcgtaggggactggcggcagacagccggctacaacctggaccaagtccttgagcagggcggtgtgtccagtttg
tttcagaatctcggggtgtccgtaactccgatccaaaggattgtcctgagcggtgaaaacggcctgaagatcgacatc
catgtcatcatcccgtatgaaggtctgagcggcgatcagatgggccagatcgaaaaaatttttaaggtggtgtaccct
gtggatgatcatcactttaaggtgattctgcactatggcacactggtaatcgacggggttacgccgaac SEQ ID NO: 221 (L27V CP 106 TEV)
MMIDYFGRPYEGIAVFDGKKITVTGTLWNGNKIIDERLINPDGSLLFRVTINGVTGWRLCERILAGSSGGGSSGGEPT
TENLYFQSDNGSSGGGSSGGMVFTLEDFVGDWRQTAGYNLDQVLEQGGVSSLFQNLGVSVTPIQRIVLSGENGLKIDI
HVIIPYEGLSGDQMGQIEKIFKVVYPVDDHHFKVILHYGTLVIDGVTPN SEQ ID NO: 222 (L27V CP 109 TEV)
atgtatttcggacggccgtatgaaggcatcgccgtgttcgacggcaaaaagatcactgtaaccgggaccctgtggaac
ggcaacaaaattatcgacgagcgcctgatcaaccccgacggctccctgctgttccgcgtaaccatcaacggagtgacc
ggctggcggctgtgcgagcgcattttggcgggaagttctggtggaggaagttctggtggagagcctactactgagaac
ttgtacttccagagcgataacggaagttctggtggaggaagttctggtggaatggtgtttacactcgaagatttcgta
ggggactggcggcagacagccggctacaacctggaccaagtccttgagcagggcggtgtgtccagtttgtttcagaat
ctcggggtgtccgtaactccgatccaaaggattgtcctgagcggtgaaaacggcctgaagatcgacatccatgtcatc
atcccgtatgaaggtctgagcggcgatcagatgggccagatcgaaaaaatttttaaggtggtgtaccctgtggatgat
catcactttaaggtgattctgcactatggcacactggtaatcgacggggttacgccgaacatgatcgac SEQ ID NO: 223 (L27V CP 109 TEV)
MYFGRPYEGIAVFDGKKITVTGTLWNGNKIIDERLINPDGSLLFRVTINGVTGWRLCERILAGSSGGGSSGGEPTTEN
LYFQSDNGSSGGGSSGGMVFTLEDFVGDWRQTAGYNLDQVLEQGGVSSLFQNLGVSVTPIQRIVLSGENGLKIDIHVI
IPYEGLSGDQMGQIEKIFKVVYPVDDHHFKVILHYGTLVIDGVTPNMID SEQ ID NO: 224 (L27V CP 112 TEV)
atgcggccgtatgaaggcatcgccgtgttcgacggcaaaaagatcactgtaaccgggaccctgtggaacggcaacaaa
attatcgacgagcgcctgatcaaccccgacggctccctgctgttccgcgtaaccatcaacggagtgaccggctggcgg
ctgtgcgagcgcattttggcgggaagttctggtggaggaagttctggtggagagcctactactgagaacttgtacttc
cagagcgataacggaagttctggtggaggaagttctggtggaatggtgtttacactcgaagatttcgtaggggactgg
cggcagacagccggctacaacctggaccaagtccttgagcagggcggtgtgtccagtttgtttcagaatctcggggtg
tccgtaactccgatccaaaggattgtcctgagcggtgaaaacggcctgaagatcgacatccatgtcatcatcccgtat
gaaggtctgagcggcgatcagatgggccagatcgaaaaaatttttaaggtggtgtaccctgtggatgatcatcacttt
aaggtgattctgcactatggcacactggtaatcgacggggttacgccgaacatgatcgactatttcgga SEQ ID NO: 225 (L27V CP 112 TEV)
MRPYEGIAVFDGKKITVTGTLWNGNKIIDERLINPDGSLLFRVTINGVTGWRLCERILAGSSGGGSSGGEPTTENLYF
QSDNGSSGGGSSGGMVFTLEDFVGDWRQTAGYNLDQVLEQGGVSSLFQNLGVSVTPIQRIVLSGENGLKIDIHVIIPY
EGLSGDQMGQIEKIFKVVYPVDDHHFKVILHYGTLVIDGVTPNMIDYFG -continued

SEQUENCE LISTING

SEQ ID NO: 226 (L27V CP 115 TEV)
atggaaggcatcgccgtgttcgacggcaaaaagatcactgtaaccgggaccctgtggaacggcaacaaaattatcgac
gagcgcctgatcaaccccgacggctccctgctgttccgcgtaaccatcaacggagtgaccggctggcggctgtgcgag
cgcattttggcgggaagttctggtggaggaagttctggtggagagcctactactgagaacttgtacttccagagcgat
aacggaagttctggtggaggaagttctggtggaatggtgtttacactcgaagatttcgtaggggactggcggcagaca
gccggctacaacctggaccaagtccttgagcagggcggtgtgtccagtttgtttcagaatctcggggtgtccgtaact
ccgatccaaaggattgtcctgagcggtgaaaacggcctgaagatcgacatccatgtcatcatcccgtatgaaggtctg
agcggcgatcagatgggccagatcgaaaaaatttttaaggtggtgtaccctgtggatgatcatcactttaaggtgatt
ctgcactatggcacactggtaatcgacggggttacgccgaacatgatcgactatttcggacggccgtat SEQ ID NO: 227 (L27V CP 115 TEV)
MEGIAVFDGKKITVTGTLWNGNKIIDERLINPDGSLLFRVTINGVTGWRLCERILAGSSGGGSSGGEPTTENLYFQSD
NGSSGGGSSGGMVFTLEDFVGDWRQTAGYNLDQVLEQGGVSSLFQNLGVSVTPIQRIVLSGENGLKIDIHVIIPYEGL
SGDQMGQIEKIFKVVYPVDDHHFKVILHYGTLVIDGVTPNMIDYFGRPY SEQ ID NO: 228 (L27V CP 120 TEV)
atgttcgacggcaaaaagatcactgtaaccgggaccctgtggaacggcaacaaaattatcgacgagcgcctgatcaac
cccgacggctccctgctgttccgcgtaaccatcaacggagtgaccggctggcggctgtgcgagcgcattttggcggga
agttctggtggaggaagttctggtggagagcctactactgagaacttgtacttccagagcgataacggaagttctggt
ggaggaagttctggtggaatggtgtttacactcgaagatttcgtaggggactggcggcagacagccggctacaacctg
gaccaagtccttgagcagggcggtgtgtccagtttgtttcagaatctcggggtgtccgtaactccgatccaaaggatt
gtcctgagcggtgaaaacggcctgaagatcgacatccatgtcatcatcccgtatgaaggtctgagcggcgatcagatg
ggccagatcgaaaaaatttttaaggtggtgtaccctgtggatgatcatcactttaaggtgattctgcactatggcaca
ctggtaatcgacggggttacgccgaacatgatcgactatttcggacggccgtatgaaggcatcgtggcc SEQ ID NO: 229 (L27V CP 120 TEV)
MFDGKKITVTGTLWNGNKIIDERLINPDGSLLFRVTINGVTGWRLCERILAGSSGGGSSGGEPTTENLYFQSDNGSSG
GGSSGGMVFTLEDFVGDWRQTAGYNLDQVLEQGGVSSLFQNLGVSVTPIQRIVLSGENGLKIDIHVIIPYEGLSGDQM
GQIEKIFKVVYPVDDHHFKVILHYGTLVIDGVTPNMIDYFGRPYEGIVA SEQ ID NO: 230 (L27V CP 121 TEV)
atggacggcaaaaagatcactgtaaccgggaccctgtggaacggcaacaaaattatcgacgagcgcctgatcaacccc
gacggctccctgctgttccgcgtaaccatcaacggagtgaccggctggcggctgtgcgagcgcattttggcgggaagt
tctggtggaggaagttctggtggagagcctactactgagaacttgtacttccagagcgataacggaagttctggtgga
ggaagttctggtggaatggtgtttacactcgaagatttcgtaggggactggcggcagacagccggctacaacctggac
caagtccttgagcagggcggtgtgtccagtttgtttcagaatctcggggtgtccgtaactccgatccaaaggattgtc
ctgagcggtgaaaacggcctgaagatcgacatccatgtcatcatcccgtatgaaggtctgagcggcgatcagatgggc
cagatcgaaaaaatttttaaggtggtgtaccctgtggatgatcatcactttaaggtgattctgcactatggcacactg
gtaatcgacggggttacgccgaacatgatcgactatttcggacggccgtatgaaggcatcgccgtgttc SEQ ID NO: 231 (L27V CP 121 TEV)
MDGKKITVTGTLWNGNKIIDERLINPDGSLLFRVTINGVTGWRLCERILAGSSGGGSSGGEPTTENLYFQSDNGSSGG
GSSGGMVFTLEDFVGDWRQTAGYNLDQVLEQGGVSSLFQNLGVSVTPIQRIVLSGENGLKIDIHVIIPYEGLSGDQMG
QIEKIFKVVYPVDDHHFKVILHYGTLVIDGVTPNMIDYFGRPYEGIAVF SEQ ID NO: 232 (L27V CP 123 TEV)
atgaaaaagatcactgtaaccgggaccctgtggaacggcaacaaaattatcgacgagcgcctgatcaaccccgacggc
tccctgctgttccgcgtaaccatcaacggagtgaccggctggcggctgtgcgagcgcattttggcgggaagttctggt
ggaggaagttctggtggagagcctactactgagaacttgtacttccagagcgataacggaagttctggtggaggaagt
tctggtggaatggtgtttacactcgaagatttcgtaggggactggcggcagacagccggctacaacctggaccaagtc
cttgagcagggcggtgtgtccagtttgtttcagaatctcggggtgtccgtaactccgatccaaaggattgtcctgagc
ggtgaaaacggcctgaagatcgacatccatgtcatcatcccgtatgaaggtctgagcggcgatcagatgggccagatc
gaaaaaatttttaaggtggtgtaccctgtggatgatcatcactttaaggtgattctgcactatggcacactggtaatc
gacggggttacgccgaacatgatcgactatttcggacggccgtatgaaggcatcgccgtgttcgacggc SEQ ID NO: 233 (L27V CP 123 TEV)
MKKITVTGTLWNGNKIIDERLINPDGSLLFRVTINGVTGWRLCERILAGSSGGGSSGGEPTTENLYFQSDNGSSGGGS
SGGMVFTLEDFVGDWRQTAGYNLDQVLEQGGVSSLFQNLGVSVTPIQRIVLSGENGLKIDIHVIIPYEGLSGDQMGQI
EKIFKVVYPVDDHHFKVILHYGTLVIDGVTPNMIDYFGRPYEGIAVFDG SEQ ID NO: 234 (L27V CP 124 TEV)
Atgaagatcactgtaaccgggaccctgtggaacggcaacaaaattatcgacgagcgcctgatcaaccccgacggctcc
ctgctgttccgcgtaaccatcaacggagtgaccggctggcggctgtgcgagcgcattttggcgggaagttctggtgga
ggaagttctggtggagagcctactactgagaacttgtacttccagagcgataacggaagttctggtggaggaagttct
ggtggaatggtgtttacactcgaagatttcgtaggggactggcggcagacagccggctacaacctggaccaagtcctt
gagcagggcggtgtgtccagtttgtttcagaatctcggggtgtccgtaactccgatccaaaggattgtcctgagcggt
gaaaacggcctgaagatcgacatccatgtcatcatcccgtatgaaggtctgagcggcgatcagatgggccagatcgaa
aaaatttttaaggtggtgtaccctgtggatgatcatcactttaaggtgattctgcactatggcacactggtaatcgac
ggggttacgccgaacatgatcgactatttcggacggccgtatgaaggcatcgccgtgttcgacggcaaa SEQ ID NO: 235 (L27V CP 124 TEV)
MKITVTGTLWNGNKIIDERLINPDGSLLFRVTINGVTGWRLCERILAGSSGGGSSGGEPTTENLYFQSDNGSSGGGSS
GGMVFTLEDFVGDWRQTAGYNLDQVLEQGGVSSLFQNLGVSVTPIQRIVLSGENGLKIDIHVIIPYEGLSGDQMGQIE
KIFKVVYPVDDHHFKVILHYGTLVIDGVTPNMIDYFGRPYEGIAVFDGK -continued

SEQUENCE LISTING

SEQ ID NO: 236 (L27V CP 125 TEV)
atgatcactgtaaccgggaccctgtggaacggcaacaaaattatcgacgagcgcctgatcaaccccgacggctccctg
ctgttccgcgtaaccatcaacggagtgaccggctggcggctgtgcgagcgcattttggcgggaagttctggtggagga
agttctggtggagagcctactactgagaacttgtacttccagagcgataacggaagttctggtggaggaagttctggt
ggaatggtgtttacactcgaagatttcgtaggggactggcggcagacagccggctacaacctggaccaagtccttgag
cagggcggtgtgtccagtttgtttcagaatctcggggtgtccgtaactccgatccaaaggattgtcctgagcggtgaa
aacggcctgaagatcgacatccatgtcatcatcccgtatgaaggtctgagcggcgatcagatgggccagatcgaaaaa
atttttaaggtggtgtaccctgtggatgatcatcactttaaggtgattctgcactatggcacactggtaatcgacggg
gttacgccgaacatgatcgactatttcggacggccgtatgaaggcatcgccgtgttcgacggcaaaaag SEQ ID NO: 237 (L27V CP 125 TEV)
MITVTGTLWNGNKIIDERLINPDGSLLFRVTINGVTGWRLCERILAGSSGGGSSGGEPTTENLYFQSDNGSSGGGSSG
GMVFTLEDFVGDWRQTAGYNLDQVLEQGGVSSLFQNLGVSVTPIQRIVLSGENGLKIDIHVIIPYEGLSGDQMGQIEK
IFKVVYPVDDHHFKVILHYGTLVIDGVTPNMIDYFGRPYEGIAVFDGKK SEQ ID NO: 238 (L27V CP 129 TEV)
atggggaccctgtggaacggcaacaaaattatcgacgagcgcctgatcaaccccgacggctccctgctgttccgcgta
accatcaacggagtgaccggctggcggctgtgcgagcgcattttggcgggaagttctggtggaggaagttctggtgga
gagcctactactgagaacttgtacttccagagcgataacggaagttctggtggaggaagttctggtggaatggtgttt
acactcgaagatttcgtaggggactggcggcagacagccggctacaacctggaccaagtccttgagcagggcggtgtg
tccagtttgtttcagaatctcggggtgtccgtaactccgatccaaaggattgtcctgagcggtgaaaacggcctgaag
atcgacatccatgtcatcatcccgtatgaaggtctgagcggcgatcagatgggccagatcgaaaaaatttttaaggtg
gtgtaccctgtggatgatcatcactttaaggtgattctgcactatggcacactggtaatcgacggggttacgccgaac
atgatcgactatttcggacggccgtatgaaggcatcgccgtgttcgacggcaaaaagatcactgtaacc SEQ ID NO: 239 (L27V CP 129 TEV)
MGTLWNGNKIIDERLINPDGSLLFRVTINGVTGWRLCERILAGSSGGGSSGGEPTTENLYFQSDNGSSGGGSSGGMVF
TLEDFVGDWRQTAGYNLDQVLEQGGVSSLFQNLGVSVTPIQRIVLSGENGLKIDIHVIIPYEGLSGDQMGQIEKIFKV
VYPVDDHHFKVILHYGTLVIDGVTPNMIDYFGRPYEGIAVFDGKKITVT SEQ ID NO: 240 (L27V CP 130 TEV)
atgaccctgtggaacggcaacaaaattatcgacgagcgcctgatcaaccccgacggctccctgctgttccgcgtaacc
atcaacggagtgaccggctggcggctgtgcgagcgcattttggcgggaagttctggtggaggaagttctggtggagag
cctactactgagaacttgtacttccagagcgataacggaagttctggtggaggaagttctggtggaatggtgtttaca
ctcgaagatttcgtaggggactggcggcagacagccggctacaacctggaccaagtccttgagcagggcggtgtgtcc
agtttgtttcagaatctcggggtgtccgtaactccgatccaaaggattgtcctgagcggtgaaaacggcctgaagatc
gacatccatgtcatcatcccgtatgaaggtctgagcggcgatcagatgggccagatcgaaaaaatttttaaggtggtg
taccctgtggatgatcatcactttaaggtgattctgcactatggcacactggtaatcgacggggttacgccgaacatg
atcgactatttcggacggccgtatgaaggcatcgccgtgttcgacggcaaaaagatcactgtaaccggg SEQ ID NO: 241 (L27V CP 130 TEV)
MTLWNGNKIIDERLINPDGSLLFRVTINGVTGWRLCERILAGSSGGGSSGGEPTTENLYFQSDNGSSGGGSSGGMVFT
LEDFVGDWRQTAGYNLDQVLEQGGVSSLFQNLGVSVTPIQRIVLSGENGLKIDIHVIIPYEGLSGDQMGQIEKIFKVV
YPVDDHHFKVILHYGTLVIDGVTPNMIDYFGRPYEGIAVFDGKKITVTG SEQ ID NO: 242 (L27V CP 131 TEV)
atgctgtggaacggcaacaaaattatcgacgagcgcctgatcaaccccgacggctccctgctgttccgcgtaaccatc
aacggagtgaccggctggcggctgtgcgagcgcattttggcgggaagttctggtggaggaagttctggtggagagcct
actactgagaacttgtacttccagagcgataacggaagttctggtggaggaagttctggtggaatggtgtttacactc
gaagatttcgtaggggactggcggcagacagccggctacaacctggaccaagtccttgagcagggcggtgtgtccagt
ttgtttcagaatctcggggtgtccgtaactccgatccaaaggattgtcctgagcggtgaaaacggcctgaagatcgac
atccatgtcatcatcccgtatgaaggtctgagcggcgatcagatgggccagatcgaaaaaatttttaaggtggtgtac
cctgtggatgatcatcactttaaggtgattctgcactatggcacactggtaatcgacggggttacgccgaacatgatc
gactatttcggacggccgtatgaaggcatcgccgtgttcgacggcaaaaagatcactgtaaccgggacc SEQ ID NO: 243 (L27V CP 131 TEV)
MLWNGNKIIDERLINPDGSLLFRVTINGVTGWRLCERILAGSSGGGSSGGEPTTENLYFQSDNGSSGGGSSGGMVFTL
EDFVGDWRQTAGYNLDQVLEQGGVSSLFQNLGVSVTPIQRIVLSGENGLKIDIHVIIPYEGLSGDQMGQIEKIFKVVY
PVDDHHFKVILHYGTLVIDGVTPNMIDYFGRPYEGIAVFDGKKITVTGT SEQ ID NO: 244 (L27V CP 133 TEV)
atgaacggcaacaaaattatcgacgagcgcctgatcaaccccgacggctccctgctgttccgcgtaaccatcaacgga
gtgaccggctggcggctgtgcgagcgcattttggcgggaagttctggtggaggaagttctggtggagagcctactact
gagaacttgtacttccagagcgataacggaagttctggtggaggaagttctggtggaatggtgtttacactcgaagat
ttcgtaggggactggcggcagacagccggctacaacctggaccaagtccttgagcagggcggtgtgtccagtttgttt
cagaatctcggggtgtccgtaactccgatccaaaggattgtcctgagcggtgaaaacggcctgaagatcgacatccat
gtcatcatcccgtatgaaggtctgagcggcgatcagatgggccagatcgaaaaaatttttaaggtggtgtaccctgtg
gatgatcatcactttaaggtgattctgcactatggcacactggtaatcgacggggttacgccgaacatgatcgactat
ttcggacggccgtatgaaggcatcgccgtgttcgacggcaaaaagatcactgtaaccgggaccctgtggg SEQ ID NO: 245 (L27V CP 133 TEV)
MNGNKIIDERLINPDGSLLFRVTINGVTGWRLCERILAGSSGGGSSGGEPTTENLYFQSDNGSSGGGSSGGMVFTLED
FVGDWRQTAGYNLDQVLEQGGVSSLFQNLGVSVTPIQRIVLSGENGLKIDIHVIIPYEGLSGDQMGQIEKIFKVVYPV
DDHHFKVILHYGTLVIDGVTPNMIDYFGRPYEGIAVFDGKKITVTGTLW -continued

SEQUENCE LISTING

SEQ ID NO: 246 (L27V CP 136 TEV)
atgaaaattatcgacgagcgcctgatcaaccccgacggctccctgctgttccgcgtaaccatcaacggagtgaccggc
tggcggctgtgcgagcgcattttggcgggaagttctggtggaggaagttctggtggagagcctactactgagaacttg
tacttccagagcgataacggaagttctggtggaggaagttctggtggaatggtgtttacactcgaagatttcgtaggg
gactggcggcagacagccggctacaacctggaccaagtccttgagcagggcggtgtgtccagtttgtttcagaatctc
ggggtgtccgtaactccgatccaaaggattgtcctgagcggtgaaaacggcctgaagatcgacatccatgtcatcatc
ccgtatgaaggtctgagcggcgatcagatgggccagatcgaaaaaatttttaaggtggtgtaccctgtggatgatcat
cactttaaggtgattctgcactatggcacactggtaatcgacggggttacgccgaacatgatcgactatttcggacgg
ccgtatgaaggcatcgccgtgttcgacggcaaaaagatcactgtaaccgggaccctgtggaacggcaac SEQ ID NO: 247 (L27V CP 136 TEV)
MKIIDERLINPDGSLLFRVTINGVTGWRLCERILAGSSGGGSSGGEPTTENLYFQSDNGSSGGGSSGGMVFTLEDFVG
DWRQTAGYNLDQVLEQGGVSSLFQNLGVSVTPIQRIVLSGENGLKIDIHVIIPYEGLSGDQMGQIEKIFKVVYPVDDH
HFKVILHYGTLVIDGVTPNMIDYFGRPYEGIAVFDGKKITVTGTLWNGN SEQ ID NO: 248 (L27V CP 139 TEV)
atggacgagcgcctgatcaaccccgacggctccctgctgttccgcgtaaccatcaacggagtgaccggctggcggctg
tgcgagcgcattttggcgggaagttctggtggaggaagttctggtggagagcctactactgagaacttgtacttccag
agcgataacggaagttctggtggaggaagttctggtggaatggtgtttacactcgaagatttcgtaggggactggcgg
cagacagccggctacaacctggaccaagtccttgagcagggcggtgtgtccagtttgtttcagaatctcggggtgtcc
gtaactccgatccaaaggattgtcctgagcggtgaaaacggcctgaagatcgacatccatgtcatcatcccgtatgaa
ggtctgagcggcgatcagatgggccagatcgaaaaaatttttaaggtggtgtaccctgtggatgatcatcactttaag
gtgattctgcactatggcacactggtaatcgacggggttacgccgaacatgatcgactatttcggacggccgtatgaa
ggcatcgccgtgttcgacggcaaaaagatcactgtaaccgggaccctgtggaacggcaacaaaattatcgacgagcgc SEQ ID NO: 249 (L27V CP 139 TEV)
MDERLINPDGSLLFRVTINGVTGWRLCERILAGSSGGGSSGGEPTTENLYFQSDNGSSGGGSSGGMVFTLEDFVGDWR
QTAGYNLDQVLEQGGVSSLFQNLGVSVTPIQRIVLSGENGLKIDIHVIIPYEGLSGDQMGQIEKIFKVVYPVDDHHFK
VILHYGTLVIDGVTPNMIDYFGRPYEGIAVFDGKKITVTGTLWNGNKIIDER SEQ ID NO: 250 (L27V CP 140 TEV)
atggagcgcctgatcaaccccgacggctccctgctgttccgcgtaaccatcaacggagtgaccggctggcggctgtgc
gagcgcattttggcgggaagttctggtggaggaagttctggtggagagcctactactgagaacttgtacttccagagc
gataacggaagttctggtggaggaagttctggtggaatggtgtttacactcgaagatttcgtaggggactggcggcag
acagccggctacaacctggaccaagtccttgagcagggcggtgtgtccagtttgtttcagaatctcggggtgtccgta
actccgatccaaaggattgtcctgagcggtgaaaacggcctgaagatcgacatccatgtcatcatcccgtatgaaggt
ctgagcggcgatcagatgggccagatcgaaaaaatttttaaggtggtgtaccctgtggatgatcatcactttaaggtg
attctgcactatggcacactggtaatcgacggggttacgccgaacatgatcgactatttcggacggccgtatgaaggc
atcgccgtgttcgacggcaaaaagatcactgtaaccgggaccctgtggaacggcaacaaaattatcgac SEQ ID NO: 251 (L27V CP 140 TEV)
MERLINPDGSLLFRVTINGVTGWRLCERILAGSSGGGSSGGEPTTENLYFQSDNGSSGGGSSGGMVFTLEDFVGDWRQ
TAGYNLDQVLEQGGVSSLFQNLGVSVTPIQRIVLSGENGLKIDIHVIIPYEGLSGDQMGQIEKIFKVVYPVDDHHFKV
ILHYGTLVIDGVTPNMIDYFGRPYEGIAVFDGKKITVTGTLWNGNKIID SEQ ID NO: 252 (L27V CP 141 TEV)
atgcgcctgatcaaccccgacggctccctgctgttccgcgtaaccatcaacggagtgaccggctggcggctgtgcgag
cgcattttggcgggaagttctggtggaggaagttctggtggagagcctactactgagaacttgtacttccagagcgat
aacggaagttctggtggaggaagttctggtggaatggtgtttacactcgaagatttcgtaggggactggcggcagaca
gccggctacaacctggaccaagtccttgagcagggcggtgtgtccagtttgtttcagaatctcggggtgtccgtaact
ccgatccaaaggattgtcctgagcggtgaaaacggcctgaagatcgacatccatgtcatcatcccgtatgaaggtctg
agcggcgatcagatgggccagatcgaaaaaatttttaaggtggtgtaccctgtggatgatcatcactttaaggtgatt
ctgcactatggcacactggtaatcgacggggttacgccgaacatgatcgactatttcggacggccgtatgaaggcatc
gccgtgttcgacggcaaaaagatcactgtaaccgggaccctgtggaacggcaacaaaattatcgacgag SEQ ID NO: 253 (L27V CP 141 TEV)
MRLINPDGSLLFRVTINGVTGWRLCERILAGSSGGGSSGGEPTTENLYFQSDNGSSGGGSSGGMVFTLEDFVGDWRQT
AGYNLDQVLEQGGVSSLFQNLGVSVTPIQRIVLSGENGLKIDIHVIIPYEGLSGDQMGQIEKIFKVVYPVDDHHFKVI
LHYGTLVIDGVTPNMIDYFGRPYEGIAVFDGKKITVTGTLWNGNKIIDE SEQ ID NO: 254 (L27V CP 142 TEV)
atgctgatcaaccccgacggctccctgctgttccgcgtaaccatcaacggagtgaccggctggcggctgtgcgagcgc
attttggcgggaagttctggtggaggaagttctggtggagagcctactactgagaacttgtacttccagagcgataac
ggaagttctggtggaggaagttctggtggaatggtgtttacactcgaagatttcgtaggggactggcggcagacagcc
ggctacaacctggaccaagtccttgagcagggcggtgtgtccagtttgtttcagaatctcggggtgtccgtaactccg
atccaaaggattgtcctgagcggtgaaaacggcctgaagatcgacatccatgtcatcatcccgtatgaaggtctgagc
ggcgatcagatgggccagatcgaaaaaatttttaaggtggtgtaccctgtggatgatcatcactttaaggtgattctg
cactatggcacactggtaatcgacggggttacgccgaacatgatcgactatttcggacggccgtatgaaggcatcgcc
gtgttcgacggcaaaaagatcactgtaaccgggaccctgtggaacggcaacaaaattatcgacgagcgc SEQ ID NO: 255 (L27V CP 142 TEV)
MLINPDGSLLFRVTINGVTGWRLCERILAGSSGGGSSGGEPTTENLYFQSDNGSSGGGSSGGMVFTLEDFVGDWRQTA
GYNLDQVLEQGGVSSLFQNLGVSVTPIQRIVLSGENGLKIDIHVIIPYEGLSGDQMGQIEKIFKVVYPVDDHHFKVIL
HYGTLVIDGVTPNMIDYFGRPYEGIAVFDGKKITVTGTLWNGNKIIDER -continued

SEQUENCE LISTING

SEQ ID NO: 256 (L27V CP 143 TEV)
atgatcaaccccgacggctccctgctgttccgcgtaaccatcaacggagtgaccggctggcggctgtgcgagcgcatt
ttggcgggaagttctggtggaggaagttctggtggagagcctactactgagaacttgtacttccagagcgataacgga
agttctggtggaggaagttctggtggaatggtgtttacactcgaagatttcgtaggggactggcggcagacagccggc
tacaacctggaccaagtccttgagcagggcggtgtgtccagtttgtttcagaatctcggggtgtccgtaactccgatc
caaaggattgtcctgagcggtgaaaacggcctgaagatcgacatccatgtcatcatcccgtatgaaggtctgagcggc
gatcagatgggccagatcgaaaaaatttttaaggtggtgtaccctgtggatgatcatcactttaaggtgattctgcac
tatggcacactggtaatcgacggggttacgccgaacatgatcgactatttcggacggccgtatgaaggcatcgccgtg
ttcgacggcaaaaagatcactgtaaccgggaccctgtggaacggcaacaaaattatcgacgagcgcctg SEQ ID NO: 257 (L27V CP 143 TEV)
MINPDGSLLFRVTINGVTGWRLCERILAGSSGGGSSGGEPTTENLYFQSDNGSSGGGSSGGMVFTLEDFVGDWRQTAG
YNLDQVLEQGGVSSLFQNLGVSVTPIQRIVLSGENGLKIDIHVIIPYEGLSGDQMGQIEKIFKVVYPVDDHHFKVILH
YGTLVIDGVTPNMIDYFGRPYEGIAVFDGKKITVTGTLWNGNKIIDERL SEQ ID NO: 258 (L27V CP 144 TEV)
atgaaccccgacggctccctgctgttccgcgtaaccatcaacggagtgaccggctggcggctgtgcgagcgcattttg
gcgggaagttctggtggaggaagttctggtggagagcctactactgagaacttgtacttccagagcgataacggaagt
tctggtggaggaagttctggtggaatggtgtttacactcgaagatttcgtaggggactggcggcagacagccggctac
aacctggaccaagtccttgagcagggcggtgtgtccagtttgtttcagaatctcggggtgtccgtaactccgatccaa
aggattgtcctgagcggtgaaaacggcctgaagatcgacatccatgtcatcatcccgtatgaaggtctgagcggcgat
cagatgggccagatcgaaaaaatttttaaggtggtgtaccctgtggatgatcatcactttaaggtgattctgcactat
ggcacactggtaatcgacggggttacgccgaacatgatcgactatttcggacggccgtatgaaggcatcgccgtgttc
gacggcaaaaagatcactgtaaccgggaccctgtggaacggcaacaaaattatcgacgagcgcctgatc SEQ ID NO: 259 (L27V CP 144 TEV)
MNPDGSLLFRVTINGVTGWRLCERILAGSSGGGSSGGEPTTENLYFQSDNGSSGGGSSGGMVFTLEDFVGDWRQTAGY
NLDQVLEQGGVSSLFQNLGVSVTPIQRIVLSGENGLKIDIHVIIPYEGLSGDQMGQIEKIFKVVYPVDDHHFKVILHY
GTLVIDGVTPNMIDYFGRPYEGIAVFDGKKITVTGTLWNGNKIIDERLI SEQ ID NO: 260 (L27V CP 145 TEV)
atgcccgacggctccctgctgttccgcgtaaccatcaacggagtgaccggctggcggctgtgcgagcgcattttggcg
ggaagttctggtggaggaagttctggtggagagcctactactgagaacttgtacttccagagcgataacggaagttct
ggtggaggaagttctggtggaatggtgtttacactcgaagatttcgtaggggactggcggcagacagccggctacaac
ctggaccaagtccttgagcagggcggtgtgtccagtttgtttcagaatctcggggtgtccgtaactccgatccaaagg
attgtcctgagcggtgaaaacggcctgaagatcgacatccatgtcatcatcccgtatgaaggtctgagcggcgatcag
atgggccagatcgaaaaaatttttaaggtggtgtaccctgtggatgatcatcactttaaggtgattctgcactatggc
acactggtaatcgacggggttacgccgaacatgatcgactatttcggacggccgtatgaaggcatcgccgtgttcgac
ggcaaaaagatcactgtaaccgggaccctgtggaacggcaacaaaattatcgacgagcgcctgatcaac SEQ ID NO: 261 (L27V CP 145 TEV)
MPDGSLLFRVTINGVTGWRLCERILAGSSGGGSSGGEPTTENLYFQSDNGSSGGGSSGGMVFTLEDFVGDWRQTAGYN
LDQVLEQGGVSSLFQNLGVSVTPIQRIVLSGENGLKIDIHVIIPYEGLSGDQMGQIEKIFKVVYPVDDHHFKVILHYG
TLVIDGVTPNMIDYFGRPYEGIAVFDGKKITVTGTLWNGNKIIDERLIN SEQ ID NO: 262 (L27V CP 146 TEV)
atggacggctccctgctgttccgcgtaaccatcaacggagtgaccggctggcggctgtgcgagcgcattttggcggga
agttctggtggaggaagttctggtggagagcctactactgagaacttgtacttccagagcgataacggaagttctggt
ggaggaagttctggtggaatggtgtttacactcgaagatttcgtaggggactggcggcagacagccggctacaacctg
gaccaagtccttgagcagggcggtgtgtccagtttgtttcagaatctcggggtgtccgtaactccgatccaaaggatt
gtcctgagcggtgaaaacggcctgaagatcgacatccatgtcatcatcccgtatgaaggtctgagcggcgatcagatg
ggccagatcgaaaaaatttttaaggtggtgtaccctgtggatgatcatcactttaaggtgattctgcactatggcaca
ctggtaatcgacggggttacgccgaacatgatcgactatttcggacggccgtatgaaggcatcgccgtgttcgacggc
aaaaagatcactgtaaccgggaccctgtggaacggcaacaaaattatcgacgagcgcctgatcaacccc SEQ ID NO: 263 (L27V CP 146 TEV)
MDGSLLFRVTINGVTGWRLCERILAGSSGGGSSGGEPTTENLYFQSDNGSSGGGSSGGMVFTLEDFVGDWRQTAGYNL
DQVLEQGGVSSLFQNLGVSVTPIQRIVLSGENGLKIDIHVIIPYEGLSGDQMGQIEKIFKVVYPVDDHHFKVILHYGT
LVIDGVTPNMIDYFGRPYEGIAVFDGKKITVTGTLWNGNKIIDERLINP SEQ ID NO: 264 (L27V CP 147 TEV)
atgggctccctgctgttccgcgtaaccatcaacggagtgaccggctggcggctgtgcgagcgcattttggcgggaagt
tctggtggaggaagttctggtggagagcctactactgagaacttgtacttccagagcgataacggaagttctggtgga
ggaagttctggtggaatggtgtttacactcgaagatttcgtaggggactggcggcagacagccggctacaacctggac
caagtccttgagcagggcggtgtgtccagtttgtttcagaatctcggggtgtccgtaactccgatccaaaggattgtc
ctgagcggtgaaaacggcctgaagatcgacatccatgtcatcatcccgtatgaaggtctgagcggcgatcagatgggc
cagatcgaaaaaatttttaaggtggtgtaccctgtggatgatcatcactttaaggtgattctgcactatggcacactg
gtaatcgacggggttacgccgaacatgatcgactatttcggacggccgtatgaaggcatcgccgtgttcgacggcaaa
aagatcactgtaaccgggaccctgtggaacggcaacaaaattatcgacgagcgcctgatcaaccccgac SEQ ID NO: 265 (L27V CP 147 TEV)
MGSLLFRVTINGVTGWRLCERILAGSSGGGSSGGEPTTENLYFQSDNGSSGGGSSGGMVFTLEDFVGDWRQTAGYNLD
QVLEQGGVSSLFQNLGVSVTPIQRIVLSGENGLKIDIHVIIPYEGLSGDQMGQIEKIFKVVYPVDDHHFKVILHYGTL
VIDGVTPNMIDYFGRPYEGIAVFDGKKITVTGTLWNGNKIIDERLINPD

SEQUENCE LISTING

SEQ ID NO: 266 (L27V CP 148 TEV)
atgtccctgctgttccgcgtaaccatcaacggagtgaccggctggcggctgtgcgagcgcattttggcgggaagttct
ggtggaggaagttctggtggagagcctactactgagaacttgtacttccagagcgataacggaagttctggtggagga
agttctggtggaatggtgtttacactcgaagatttcgtaggggactggcggcagacagccggctacaacctggaccaa
gtccttgagcagggcggtgtgtccagtttgtttcagaatctcggggtgtccgtaactccgatccaaaggattgtcctg
agcggtgaaaacggcctgaagatcgacatccatgtcatcatcccgtatgaaggtctgagcggcgatcagatgggccag
atcgaaaaaatttttaaggtggtgtaccctgtggatgatcatcactttaaggtgattctgcactatggcacactggta
atcgacggggttacgccgaacatgatcgactatttcggacggccgtatgaaggcatcgccgtgttcgacggcaaaaag
atcactgtaaccgggaccctgtggaacggcaacaaaattatcgacgagcgcctgatcaaccccgacggc SEQ ID NO: 267 (L27V CP 148 TEV)
MSLLFRVTINGVTGWRLCERILAGSSGGGSSGGEPTTENLYFQSDNGSSGGGSSGGMVFTLEDFVGDWRQTAGYNLDQ
VLEQGGVSSLFQNLGVSVTPIQRIVLSGENGLKIDIHVIIPYEGLSGDQMGQIEKIFKVVYPVDDHHFKVILHYGTLV
IDGVTPNMIDYFGRPYEGIAVFDGKKITVTGTLWNGNKIIDERLINPDG SEQ ID NO: 268 (L27V CP 149 TEV)
atgctgctgttccgcgtaaccatcaacggagtgaccggctggcggctgtgcgagcgcattttggcgggaagttctggt
ggaggaagttctggtggagagcctactactgagaacttgtacttccagagcgataacggaagttctggtggaggaagt
tctggtggaatggtgtttacactcgaagatttcgtaggggactggcggcagacagccggctacaacctggaccaagtc
cttgagcagggcggtgtgtccagtttgtttcagaatctcggggtgtccgtaactccgatccaaaggattgtcctgagc
ggtgaaaacggcctgaagatcgacatccatgtcatcatcccgtatgaaggtctgagcggcgatcagatgggccagatc
gaaaaaatttttaaggtggtgtaccctgtggatgatcatcactttaaggtgattctgcactatggcacactggtaatc
gacggggttacgccgaacatgatcgactatttcggacggccgtatgaaggcatcgccgtgttcgacggcaaaaagatc
actgtaaccgggaccctgtggaacggcaacaaaattatcgacgagcgcctgatcaaccccgacggctcc SEQ ID NO: 269 (L27V CP 149 TEV)
MLLFRVTINGVTGWRLCERILAGSSGGGSSGGEPTTENLYFQSDNGSSGGGSSGGMVFTLEDFVGDWRQTAGYNLDQV
LEQGGVSSLFQNLGVSVTPIQRIVLSGENGLKIDIHVIIPYEGLSGDQMGQIEKIFKVVYPVDDHHFKVILHYGTLVI
DGVTPNMIDYFGRPYEGIAVFDGKKITVTGTLWNGNKIIDERLINPDGS SEQ ID NO: 270 (L27V CP 150 TEV)
atgctgttccgcgtaaccatcaacggagtgaccggctggcggctgtgcgagcgcattttggcgggaagttctggtgga
ggaagttctggtggagagcctactactgagaacttgtacttccagagcgataacggaagttctggtggaggaagttct
ggtggaatggtgtttacactcgaagatttcgtaggggactggcggcagacagccggctacaacctggaccaagtcctt
gagcagggcggtgtgtccagtttgtttcagaatctcggggtgtccgtaactccgatccaaaggattgtcctgagcggt
gaaaacggcctgaagatcgacatccatgtcatcatcccgtatgaaggtctgagcggcgatcagatgggccagatcgaa
aaaatttttaaggtggtgtaccctgtggatgatcatcactttaaggtgattctgcactatggcacactggtaatcgac
ggggttacgccgaacatgatcgactatttcggacggccgtatgaaggcatcgccgtgttcgacggcaaaaagatcact
gtaaccgggaccctgtggaacggcaacaaaattatcgacgagcgcctgatcaaccccgacggctccctg SEQ ID NO: 271 (L27V CP 150 TEV)
MLFRVTINGVTGWRLCERILAGSSGGGSSGGEPTTENLYFQSDNGSSGGGSSGGMVFTLEDFVGDWRQTAGYNLDQVL
EQGGVSSLFQNLGVSVTPIQRIVLSGENGLKIDIHVIIPYEGLSGDQMGQIEKIFKVVYPVDDHHFKVILHYGTLVID
GVTPNMIDYFGRPYEGIAVFDGKKITVTGTLWNGNKIIDERLINPDGSL SEQ ID NO: 272 (L27V CP 151 TEV)
atgttccgcgtaaccatcaacggagtgaccggctggcggctgtgcgagcgcattttggcgggaagttctggtggagga
agttctggtggagagcctactactgagaacttgtacttccagagcgataacggaagttctggtggaggaagttctggt
ggaatggtgtttacactcgaagatttcgtaggggactggcggcagacagccggctacaacctggaccaagtccttgag
cagggcggtgtgtccagtttgtttcagaatctcggggtgtccgtaactccgatccaaaggattgtcctgagcggtgaa
aacggcctgaagatcgacatccatgtcatcatcccgtatgaaggtctgagcggcgatcagatgggccagatcgaaaaa
atttttaaggtggtgtaccctgtggatgatcatcactttaaggtgattctgcactatggcacactggtaatcgacggg
gttacgccgaacatgatcgactatttcggacggccgtatgaaggcatcgccgtgttcgacggcaaaaagatcactgta
accgggaccctgtggaacggcaacaaaattatcgacgagcgcctgatcaaccccgacggctccctgctg SEQ ID NO: 273 (L27V CP 151 TEV)
MFRVTINGVTGWRLCERILAGSSGGGSSGGEPTTENLYFQSDNGSSGGGSSGGMVFTLEDFVGDWRQTAGYNLDQVLE
QGGVSSLFQNLGVSVTPIQRIVLSGENGLKIDIHVIIPYEGLSGDQMGQIEKIFKVVYPVDDHHFKVILHYGTLVIDG
VTPNMIDYFGRPYEGIAVFDGKKITVTGTLWNGNKIIDERLINPDGSLL SEQ ID NO: 274 (L27V CP 154 TEV)
atgaccatcaacggagtgaccggctggcggctgtgcgagcgcattttggcgggaagttctggtggaggaagttctggt
ggagagcctactactgagaacttgtacttccagagcgataacggaagttctggtggaggaagttctggtggaatggtg
tttacactcgaagatttcgtaggggactggcggcagacagccggctacaacctggaccaagtccttgagcagggcggt
gtgtccagtttgtttcagaatctcggggtgtccgtaactccgatccaaaggattgtcctgagcggtgaaaacggcctg
aagatcgacatccatgtcatcatcccgtatgaaggtctgagcggcgatcagatgggccagatcgaaaaaatttttaag
gtggtgtaccctgtggatgatcatcactttaaggtgattctgcactatggcacactggtaatcgacggggttacgccg
aacatgatcgactatttcggacggccgtatgaaggcatcgccgtgttcgacggcaaaaagatcactgtaaccgggacc
ctgtggaacggcaacaaaattatcgacgagcgcctgatcaaccccgacggctccctgctgttccgcgta -continued

SEQUENCE LISTING

SEQ ID NO: 275 (L27V CP 154 TEV)
MTINGVTGWRLCERILAGSSGGGSSGGEPTTENLYFQSDNGSSGGGSSGGMVFTLEDFVGDWRQTAGYNLDQVLEQGG
VSSLFQNLGVSVTPIQRIVLSGENGLKIDIHVIIPYEGLSGDQMGQIEKIFKVVYPVDDHHFKVILHYGTLVIDGVTP
NMIDYFGRPYEGIAVFDGKKITVTGTLWNGNKIIDERLINPDGSLLFRV

SEQ ID NO: 276 (L27V CP 156 TEV)
atgaacggagtgaccggctggcggctgtgcgagcgcattttggcgggaagttctggtggaggaagttctggtggagag
cctactactgagaacttgtacttccagagcgataacggaagttctggtggaggaagttctggtggaatggtgtttaca
ctcgaagatttcgtaggggactggcggcagacagccggctacaacctggaccaagtccttgagcagggcggtgtgtcc
agtttgtttcagaatctcggggtgtccgtaactccgatccaaaggattgtcctgagcggtgaaaacggcctgaagatc
gacatccatgtcatcatcccgtatgaaggtctgagcggcgatcagatgggccagatcgaaaaaatttttaaggtggtg
taccctgtggatgatcatcactttaaggtgattctgcactatggcacactggtaatcgacggggttacgccgaacatg
atcgactatttcggacggccgtatgaaggcatcgccgtgttcgacggcaaaaagatcactgtaaccgggaccctgtgg
aacggcaacaaaattatcgacgagcgcctgatcaaccccgacggctccctgctgttccgcgtaaccatc SEQ ID NO: 277 (L27V CP 156 TEV)
MNGVTGWRLCERILAGSSGGGSSGGEPTTENLYFQSDNGSSGGGSSGGMVFTLEDFVGDWRQTAGYNLDQVLEQGGVS
SLFQNLGVSVTPIQRIVLSGENGLKIDIHVIIPYEGLSGDQMGQIEKIFKVVYPVDDHHFKVILHYGTLVIDGVTPNM
IDYFGRPYEGIAVFDGKKITVTGTLWNGNKIIDERLINPDGSLLFRVTI SEQ ID NO: 278 (L27V CP 157 TEV)
atgggagtgaccggctggcggctgtgcgagcgcattttggcgggaagttctggtggaggaagttctggtggagagcct
actactgagaacttgtacttccagagcgataacggaagttctggtggaggaagttctggtggaatggtgtttacactc
gaagatttcgtaggggactggcggcagacagccggctacaacctggaccaagtccttgagcagggcggtgtgtccagt
ttgtttcagaatctcggggtgtccgtaactccgatccaaaggattgtcctgagcggtgaaaacggcctgaagatcgac
atccatgtcatcatcccgtatgaaggtctgagcggcgatcagatgggccagatcgaaaaaatttttaaggtggtgtac
cctgtggatgatcatcactttaaggtgattctgcactatggcacactggtaatcgacggggttacgccgaacatgatc
gactatttcggacggccgtatgaaggcatcgccgtgttcgacggcaaaaagatcactgtaaccgggaccctgtggaac
ggcaacaaaattatcgacgagcgcctgatcaaccccgacggctccctgctgttccgcgtaaccatcaac SEQ ID NO: 279 (L27V CP 157 TEV)
MGVTGWRLCERILAGSSGGGSSGGEPTTENLYFQSDNGSSGGGSSGGMVFTLEDFVGDWRQTAGYNLDQVLEQGGVSS
LFQNLGVSVTPIQRIVLSGENGLKIDIHVIIPYEGLSGDQMGQIEKIFKVVYPVDDHHFKVILHYGTLVIDGVTPNMI
DYFGRPYEGIAVFDGKKITVTGTLWNGNKIIDERLINPDGSLLFRVTIN SEQ ID NO: 280 (L27V CP 158 TEV)
atggtgaccggctggcggctgtgcgagcgcattttggcgggaagttctggtggaggaagttctggtggagagcctact
actgagaacttgtacttccagagcgataacggaagttctggtggaggaagttctggtggaatggtgtttacactcgaa
gatttcgtaggggactggcggcagacagccggctacaacctggaccaagtccttgagcagggcggtgtgtccagtttg
tttcagaatctcggggtgtccgtaactccgatccaaaggattgtcctgagcggtgaaaacggcctgaagatcgacatc
catgtcatcatcccgtatgaaggtctgagcggcgatcagatgggccagatcgaaaaaatttttaaggtggtgtaccct
gtggatgatcatcactttaaggtgattctgcactatggcacactggtaatcgacggggttacgccgaacatgatcgac
tatttcggacggccgtatgaaggcatcgccgtgttcgacggcaaaaagatcactgtaaccgggaccctgtggaacggc
aacaaaattatcgacgagcgcctgatcaaccccgacggctccctgctgttccgcgtaaccatcaacgga SEQ ID NO: 281 (L27V CP 158 TEV)
MVTGWRLCERILAGSSGGGSSGGEPTTENLYFQSDNGSSGGGSSGGMVFTLEDFVGDWRQTAGYNLDQVLEQGGVSSL
FQNLGVSVTPIQRIVLSGENGLKIDIHVIIPYEGLSGDQMGQIEKIFKVVYPVDDHHFKVILHYGTLVIDGVTPNMID
YFGRPYEGIAVFDGKKITVTGTLWNGNKIIDERLINPDGSLLFRVTING SEQ ID NO: 282 (L27V CP 160 TEV)
atgggctggcggctgtgcgagcgcattttggcgggaagttctggtggaggaagttctggtggagagcctactactgag
aacttgtacttccagagcgataacggaagttctggtggaggaagttctggtggaatggtgtttacactcgaagatttc
gtaggggactggcggcagacagccggctacaacctggaccaagtccttgagcagggcggtgtgtccagtttgtttcag
aatctcggggtgtccgtaactccgatccaaaggattgtcctgagcggtgaaaacggcctgaagatcgacatccatgtc
atcatcccgtatgaaggtctgagcggcgatcagatgggccagatcgaaaaaatttttaaggtggtgtaccctgtggat
gatcatcactttaaggtgattctgcactatggcacactggtaatcgacggggttacgccgaacatgatcgactatttc
ggacggccgtatgaaggcatcgccgtgttcgacggcaaaaagatcactgtaaccgggaccctgtggaacggcaacaaa
attatcgacgagcgcctgatcaaccccgacggctccctgctgttccgcgtaaccatcaacggagtgacc SEQ ID NO: 283 (L27V CP 160 TEV)
MGWRLCERILAGSSGGGSSGGEPTTENLYFQSDNGSSGGGSSGGMVFTLEDFVGDWRQTAGYNLDQVLEQGGVSSLFQ
NLGVSVTPIQRIVLSGENGLKIDIHVIIPYEGLSGDQMGQIEKIFKVVYPVDDHHFKVILHYGTLVIDGVTPNMIDYF
GRPYEGIAVFDGKKITVTGTLWNGNKIIDERLINPDGSLLFRVTINGVT SEQ ID NO: 284 (L27V CP 163 TEV)
atgctgtgcgagcgcattttggcgggaagttctggtggaggaagttctggtggagagcctactactgagaacttgtac
ttccagagcgataacggaagttctggtggaggaagttctggtggaatggtgtttacactcgaagatttcgtaggggac
tggcggcagacagccggctacaacctggaccaagtccttgagcagggcggtgtgtccagtttgtttcagaatctcggg
gtgtccgtaactccgatccaaaggattgtcctgagcggtgaaaacggcctgaagatcgacatccatgtcatcatcccg
tatgaaggtctgagcggcgatcagatgggccagatcgaaaaaatttttaaggtggtgtaccctgtggatgatcatcac
tttaaggtgattctgcactatggcacactggtaatcgacggggttacgccgaacatgatcgactatttcggacggccg
tatgaaggcatcgccgtgttcgacggcaaaaagatcactgtaaccgggaccctgtggaacggcaacaaaattatcgac
gagcgcctgatcaaccccgacggctccctgctgttccgcgtaaccatcaacggagtgaccggctggcgg -continued

SEQUENCE LISTING

SEQ ID NO: 285 (L27V CP 163 TEV)
MLCERILAGSSGGGSSGGEPTTENLYFQSDNGSSGGGSSGGMVFTLEDFVGDWRQTAGYNLDQVLEQGGVSSLFQNLG
VSVTPIQRIVLSGENGLKIDIHVIIPYEGLSGDQMGQIEKIFKVVYPVDDHHFKVILHYGTLVIDGVTPNMIDYFGRP
YEGIAVFDGKKITVTGTLWNGNKIIDERLINPDGSLLFRVTINGVTGWR

SEQ ID NO: 286 (L27V CP 166 TEV)
Atgcgcatttggcgggaagttctggtggaggaagttctggtggagagcctactactgagaacttgtacttccagagc
gataacggaagttctggtggaggaagttctggtggaatggtgtttacactcgaagatttcgtaggggactggcggcag
acagccggctacaacctggaccaagtccttgagcagggcggtgtgtccagtttgtttcagaatctcggggtgtccgta
actccgatccaaaggattgtcctgagcggtgaaaacggcctgaagatcgacatccatgtcatcatcccgtatgaaggt
ctgagcggcgatcagatgggccagatcgaaaaaattttttaaggtggtgtaccctgtggatgatcatcactttaaggtg
attctgcactatggcacactggtaatcgacggggttacgccgaacatgatcgactatttcggacggccgtatgaaggc
atcgccgtgttcgacggcaaaaagatcactgtaaccgggaccctgtggaacggcaacaaaattatcgacgagcgcctg
atcaaccccgacggctccctgctgttccgcgtaaccatcaacggagtgaccggctggcggctgtgcgag SEQ ID NO: 287 (L27V CP 166 TEV)
MRILAGSSGGGSSGGEPTTENLYFQSDNGSSGGGSSGGMVFTLEDFVGDWRQTAGYNLDQVLEQGGVSSLFQNLGVSV
TPIQRIVLSGENGLKIDIHVIIPYEGLSGDQMGQIEKIFKVVYPVDDHHFKVILHYGTLVIDGVTPNMIDYFGRPYEG
IAVFDGKKITVTGTLWNGNKIIDERLINPDGSLLFRVTINGVTGWRLCE SEQ ID NO: 288 (pCA 9 FKBP-L27V02A 157-169)
gagtgcaggtggaaaccatctccccaggagacgggcgcaccttccccaagcgcggccagacctgcgtggtgcactaca
ccgggatgcttgaagatggaaagaaatttgattcctcccgggacagaaacaagccctttaagtttatgctaggcaagc
aggaggtgatccgaggctgggaagaaggggttgcccagatgagtgtgggtcagagagccaaactgactatatctccag
attatgcctatggtgccactgggcacccaggcatcatcccaccacatgccactctcgtcttcgatgtggagcttctaa
aactggaaggaggagggagctccggtggaggcagcggtggagtgaccggctggcggctgtgcgaacgcattctggcg SEQ ID NO: 289 (pCA 9 FKBP-L27V02A 157-169)
GVQVETISPGDGRTFPKRGQTCVVHYTGMLEDGKKFDSSRDRNKPFKFMLGKQEVIRGWEEGVAQMSVGQRAKLTISP
DYAYGATGHPGIIPPHATLVFDVELLKLEGGGSSGGGSGGVTGWRLCERILA SEQ ID NO: 290 (pCA 10 L27V02A 1-156-FRB)
atggtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaaccccgacggctccctgctgttccgagtaacc
atcaacggagtgaccggaggaggtggctcaggtggagggagctccgtggccatcctctggcatgagatgtggcatgaa
ggcctggaagaggcatctcgtttgtactttggggaaaggaacgtgaaaggcatgtttgaggtgctggagcccttgcat
gctatgatggaacggggcccccagactctgaaggaaacatcctttaatcaggcctatggtcgagatttaatggaggcc
caagagtggtgcaggaagtacatgaaatcagggaatgtcaaggacctcacccaagcctgggacctctattatcatgtg
ttccgacgaatctca SEQ ID NO: 291 (pCA 10 L27V02A 1-156-FRB)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGGGGSGGGSSVAILWHEMWHEGLEEASRLYFGERNVKGMFEVLEPLHAMMERGPQTLKETSFNQAYGRDLMEA
QEWCRKYMKSGNVKDLTQAWDLYYHVFRRIS SEQ ID NO: 292 (pCA 26 FKBP-L27V02A 1-156)
ggagtgcaggtggaaaccatctccccaggagacgggcgcaccttccccaagcgcggccagacctgcgtggtgcactac
accgggatgcttgaagatggaaagaaatttgattcctcccgggacagaaacaagccctttaagtttatgctaggcaag
caggaggtgatccgaggctgggaagaaggggttgcccagatgagtgtgggtcagagagccaaactgactatatctcca
gattatgcctatggtgccactgggcacccaggcatcatcccaccacatgccactctcgtcttcgatgtggagcttcta
aaactggaaggaggagggagctccggtggaggcagcggtatggtcttcacactcgaagatttcgttggggactggcga
cagacagccggctacaacctggaccaagtccttgaacagggaggtgtgtccagtttgtttcagaatctcggggtgtcc
gtaactccgatccaaaggattgtcctgagcggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaac SEQ ID NO: 293 (pCA 26 FKBP-L27V02A 1-156)
GVQVETISPGDGRTFPKRGQTCVVHYTGMLEDGKKFDSSRDRNKPFKFMLGKQEVIRGWEEGVAQMSVGQRAKLTISP
DYAYGATGHPGIIPPHATLVFDVELLKLEGGGSSGGGSGMVFTLEDFVGDWRQTAGYNLDQVLEQGGVSSLFQNLGVS
VTPIQRIVLSGENGLKIDIHVIIPYEGLSGDQMGQIEKIFKVVYPVDDHHFKVILHYGTLVIDGVTPNMIDYFGRPYE
GIAVFDGKKITVTGTLWNGNKIIDERLINPDGSLLFRVTIN SEQ ID NO: 294 (pCA 25 L27V02A 157-169-FRB)
atgggagtgaccggctggcggctgtgcgaacgcattctggcgggaggaggtggctcaggtggagggagctccgtggcc
atcctctggcatgagatgtggcatgaaggcctggaagaggcatctcgtttgtactttggggaaaggaacgtgaaaggc
atgtttgaggtgctggagcccttgcatgctatgatggaacggggcccccagactctgaaggaaacatcctttaatcag
gcctatggtcgagatttaatggaggcccaagagtggtgcaggaagtacatgaaatcagggaatgtcaaggacctcacc
caagcctgggacctctattatcatgtgttccgacgaatctca -continued

SEQUENCE LISTING

SEQ ID NO: 295 (pCA 25 L27V02A 157-169-FRB)
MGVTGWRLCERILAGGGGSGGGSSVAILWHEMWHEGLEEASRLYFGERNVKGMFEVLEPLHAMMERGPQTLKETSFNQ
AYGRDLMEAQEWCRKYMKSGNVKDLTQAWDLYYHVFRRIS

SEQ ID NO: 296 (pCA 3 FKBP-L27V02A 103-169)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtgcgaacgc
attctggc SEQ ID NO: 297 (pCA 3 FKBP-L27V02A 103-169)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGTPNMIDYFGRPYEGIAVFDGKKITVTGTLWNGNKIIDE
RLINPDGSLLFRVTINGVTGWRLCERIL SEQ ID NO: 298 (pCA 4 L27V02A 1-102-FRB)
atggtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
ggaggaggtggctcaggtggagggagctccgtggccatcctctggcatgagatgtggcatgaaggcctggaagaggca
tctcgtttgtactttggggaaaggaacgtgaaaggcatgtttgaggtgctggagcccttgcatgctatgatggaacgg
ggcccccagactctgaaggaaacatcctttaatcaggcctatggtcgagatttaatggaggcccaagagtggtgcagg
aagtacatgaaatcagggaatgtcaaggacctcacccaagcctgggacctctattatcatgtgttccgacgaatctca SEQ ID NO: 299 (pCA 4 L27V02A 1-102-FRB)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGTPNMIDYFGRPYEGIAVFDGKKITVTGTLWNGNKIIDE
RLINPDGSLLFRVTINGVTGWRLCERIL SEQ ID NO: 300 (pCA 19 L27V02A 103-169-FRB)
atgacgccgaacatgatcgactatttcggacggccgtatgaaggcatcgccgtgttcgacggcaaaaagatcactgta
acagggaccctgtggaacggcaacaaaattatcgacgagcgcctgatcaaccccgacggctccctgctgttccgagta
accatcaacggagtgaccggctggcggctgtgcgaacgcattctggcgggaggaggtggctcaggtggagggagctcc
gtggccatcctctggcatgagatgtggcatgaaggcctggaagaggcatctcgtttgtactttggggaaaggaacgtg
aaaggcatgtttgaggtgctggagcccttgcatgctatgatggaacggggcccccagactctgaaggaaacatccttt
aatcaggcctatggtcgagatttaatggaggcccaagagtggtgcaggaagtacatgaaatcagggaatgtcaaggac
ctcacccaagcctgggacctctattatcatgtgttccgacgaatctca SEQ ID NO: 301 (pCA 19 L27V02A 103-169-FRB)
MTPNMIDYFGRPYEGIAVFDGKKITVTGTLWNGNKIIDERLINPDGSLLFRVTINGVTGWRLCERILAGGGGSGGGSS
VAILWHEMWHEGLEEASRLYFGERNVKGMFEVLEPLHAMMERGPQTLKETSFNQAYGRDLMEAQEWCRKYMKSGNVKD
LTQAWDLYYHVFRRIS SEQ ID NO: 302 (pCA 20 FKBP-L27V02A 1-102)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggtt SEQ ID NO: 303 (pCA 20 FKBP-L27V02A 1-102)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGV SEQ ID NO: 304 (pCA 11 FKBP-L27V02A 84-169)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtgatgatcatcactttaaggtgatcctgcactatggc
acactggtaatcgacggggttacgccgaacatgatcgactatttcggacggccgtatgaaggcatcgccgtgttcgac
ggcaaaaagatcactgtaacagggaccctgtggaacggcaacaaaattatcgacgagcgcctgatcaaccccgacggc
tccctgctgttccgagtaaccatcaacggagtgaccggctggcggctgtgcgaacgcattctggcg -continued

SEQUENCE LISTING

SEQ ID NO: 305 (pCA 11 FKBP-L27V02A 84-169)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGDDHHFKVILHYGTLVIDGVTPNMIDYFGRPYEGIAVFD
GKKITVTGTLWNGNKIIDERLINPDGSLLFRVTINGVTGWRLCERILA

SEQ ID NO: 306 (pCA 12 L27V02A 1-83-FRB)
atggtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtgggaggaggtggctcaggtggagggagctccgtggccatcctctggcatgagatgtgg
catgaaggcctggaagaggcatctcgtttgtactttggggaaaggaacgtgaaaggcatgtttgaggtgctggagccc
ttgcatgctatgatggaacggggcccccagactctgaaggaaacatcctttaatcaggcctatggtcgagatttaatg
gaggcccaagagtggtgcaggaagtacatgaaatcagggaatgtcaaggacctcacccaagcctgggacctctattat
catgtgttccgacgaatctca SEQ ID NO: 307 (pCA 12 L27V02A 1-83-FRB)
MVFTLEDFVGDWRQTAGYNLDQVLEQGGVSSLFQNLGVSVTPIQRIVLSGENGLKIDIHVIIPYEGLSGDQMGQIEKI
FKVVYPVGGGGSGGGSSVAILWHEMWHEGLEEASRLYFGERNVKGMFEVLEPLHAMMERGPQTLKETSFNQAYGRDLM
EAQEWCRKYMKSGNVKDLTQAWDLYYHVFRRIS SEQ ID NO: 308 (pCA 14 L27V02A 1-83 (no fusion))
atggtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtg SEQ ID NO: 309 (pCA 14 L27V02A 1-83 (no fusion))
MVFTLEDFVGDWRQTAGYNLDQVLEQGGVSSLFQNLGVSVTPIQRIVLSGENGLKIDIHVIIPYEGLSGDQMGQIEKI
FKVVYPV SEQ ID NO: 310 (pCA 13 L27V02A 84-169 (no fusion))
atggatgatcatcactttaaggtgatcctgcactatggcacactggtaatcgacggggttacgccgaacatgatcgac
tatttcggacggccgtatgaaggcatcgccgtgttcgacggcaaaaagatcactgtaacagggaccctgtggaacggc
aacaaaattatcgacgagcgcctgatcaaccccgacggctccctgctgttccgagtaaccatcaacggagtgaccggc
tggcggctgtgcgaacgcattctggcg SEQ ID NO: 311 (pCA 13 L27V02A 84-169 (no fusion))
MDDHHFKVILHYGTLVIDGVTPNMIDYFGRPYEGIAVFDGKKITVTGTLWNGNKIIDERLINPDGSLLFRVTINGVTG
WRLCERILA SEQ ID NO: 312 (pCA 28 FKBP 1-83)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtg SEQ ID NO: 313 (pCA 28 FKBP 1-83)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPV SEQ ID NO: 314 (pCA 27 L27V02A 84-169 FRB)
atggatgatcatcactttaaggtgatcctgcactatggcacactggtaatcgacggggttacgccgaacatgatcgac
tatttcggacggccgtatgaaggcatcgccgtgttcgacggcaaaaagatcactgtaacagggaccctgtggaacggc
aacaaaattatcgacgagcgcctgatcaaccccgacggctccctgctgttccgagtaaccatcaacggagtgaccggc
tggcggctgtgcgaacgcattctggcgggaggaggtggctcaggtggagggagctccgtggccatcctctggcatgag
atgtggcatgaaggcctggaagaggcatctcgtttgtactttggggaaaggaacgtgaaaggcatgtttgaggtgctg
gagcccttgcatgctatgatggaacggggcccccagactctgaaggaaacatcctttaatcaggcctatggtcgagat
ttaatggaggcccaagagtggtgcaggaagtacatgaaatcagggaatgtcaaggacctcacccaagcctgggacctc
tattatcatgtgttccgacgaatctca SEQ ID NO: 315 (pCA 27 L27V02A 84-169 FRE)
MDDHHFKVILHYGTLVIDGVTPNMIDYFGRPYEGIAVFDGKKITVTGTLWNGNKIIDERLINPDGSLLFRVTINGVTG
WRLCERILAGGGGSGGGSSVAILWHEMWHEGLEEASRLYFGERNVKGMFEVLEPLHAMMERGPQTLKETSFNQAYGRD
LMEAQEWCRKYMKSGNVKDLTQAWDLYYHVFRRIS SEQ ID NO: 316 (HT7-Keap1)
atggcagaaatcggtactggctttccattcgacccccattatgtggaagtcctgggcgagcgcatgcactacgtcgat
gttggtccgcgcgatggcacccctgtgctgttcctgcacggtaacccgacctcctcctacgtgtggcgcaacatcatc
ccgcatgttgcaccgacccatcgctgcattgctccagacctgatcggtatgggcaaatccgacaaaccagacctgggt
tatttcttcgacgaccacgtccgcttcatggatgccttcatcgaagccctgggtctggaagaggtcgtcctggtcatt
cacgactggggctccgctctgggtttccactgggccaagcgcaatccagagcgcgtcaaaggtattgcatttatggag -continued

SEQUENCE LISTING ttcatccgccctatcccgacctgggacgaatggccagaatttgcccgcgagaccttccaggccttccgcaccaccgac
gtcggccgcaagctgatcatcgatcagaacgtttttatcgagggtacgctgccgatgggtgtcgtccgcccgctgact
gaagtcgagatggaccattaccgcgagccgttcctgaatcctgttgaccgcgagccactgtggcgcttcccaaacgag
ctgccaatcgccggtgagccagcgaacatcgtcgcgctggtcgaagaatacatggactggctgcaccagtcccctgtc
ccgaagctgctgttctggggcaccccaggcgttctgatcccaccggccgaagccgctcgcctggccaaaagcctgcct
aactgcaaggctgtggacatcggcccgggtctgaatctgctgcaagaagacaacccggacctgatcggcagcgagatc
gcgcgctggctgtcgacgctcgagatttccggcgagccaaccactgaggatctgtactttcagagcgataacgcgatc
gctttcgaaggagatagaaccatgcagccagatcccaggcctagcggggctggggcctgctgccgattcctgcccctg
cagtcacagtgccctgagggggcaggggacgcggtgatgtacgcctccactgagtgcaaggcggaggtgacgccctcc
cagcatggcaaccgcaccttcagctacaccctggaggatcataccaagcaggcctttggcatcatgaacgagctgcgg
ctcagccagcagctgtgtgacgtcacactgcaggtcaagtaccaggatgcaccggccgcccagttcatggcccacaag
gtggtgctggcctcatccagccctgttttcaaggccatgttcaccaacgggctgcgggagcagggcatggaggtggtg
tccattgagggtatccaccccaaggtcatggagcgcctcattgaattcgcctacacggcctccatctccatgggcgag
aagtgtgtcctccacgtcatgaacggcgctgtcatgtaccagatcgacagcgttgtccgtgcctgcagtgacttcctg
gtgcagcagctggaccccagcaatgccatcggcatcgccaacttcgctgagcagattggctgtgtggagttgcaccag
cgtgcccgggagtacatctacatgcattttggggaggtggccaagcaagaggagttcttcaacctgtcccactgccaa
ctggtgaccctcatcagccgggacgacctgaacgtgcgctgcgagtccgaggtcttccacgcctgcatcaactgggtc
aagtacgactgcgaacagcgacggttctacgtccaggcgctgctgcgggccgtgcgctgccactcgttgacgccgaac
ttcctgcagatgcagctgcagaagtgcgagatcctgcagtccgactcccgctgcaaggactacctggtcaagatcttc
gaggagctcaccctgcacaagcccacgcaggtgatgccctgccgggcgcccaaggtgggccgcctgatctacaccgcg
ggcggctacttccgacagtcgctcagctacctggaggcttacaaccccagtaacggcacctggctccggttggcggac
ctgcaggtgccgcggagcggcctggccggctgcgtggtgggcgggctgttgtacgccgtgggcggcaggaacaactcg
cccgacggcaacaccgactccagcgccctggactgttacaaccccatgaccaatcagtggtcgccctgcgcccccatg
agcgtgccccgtaaccgcatcggggtgggggtcatcgatggccacatctatgccgtcggcggctcccacggctgcatc
caccacaacagtgtggagaggtatgagccagagcgggatgagtggcacttggtggccccaatgctgacacgaaggatc
ggggtgggcgtggctgtcctcaatcgtctgctttatgccgtgggggctttgacgggacaaaccgccttaattcagct
gagtgttactacccagagaggaacgagtggcgaatgatcacagcaatgaacaccatccgaagcggggcaggcgtctgc
gtcctgcacaactgtatctatgctgctgggggctatgatggtcaggaccagctgaacagcgtggagcgctacgatgtg
gaaacagagacgtggactttcgtagcccccatgaagcaccggcgaagtgccctggggatcactgtccaccaggggaga
atctacgtccttggaggctatgatggtcacacgttcctggacagtgtggagtgttacgacccagatacagacacctgg
agcgaggtgacccgaatgacatcgggccggagtggggtgggcgtggctgtcaccatggagccctgccggaagcagatt
gaccagcagaactgtacctgttacgtagtt SEQ ID NO: 317 (Nrf2)
TCAATATTGGCCATTAGCCATATTATTCATTGGTTATATAGCATAAATCAATATTGGCTATTGGCCATTGCATACGTT
GTATCTATATCATAATATGTACATTTATATTGGCTCATGTCCAATATGACCGCCATGTTGGCATTGATTATTGACTAG
TTATTAATAGTAATCAATTACGGGGTCATTAGTTCATAGCCCATATATGGAGTTCCGCGTTACATAACTTACGGTAAA
TGGCCCGCCTGGCTGACCGCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGTACATCAAGTGTATCATAT
GCCAAGTCCGCCCCCTATTGACGTCAATGACGGTAAATGGCCCGCCTGGCATTATGCCCAGTACATGACCTTACGGGA
CTTTCCTACTTGGCAGTACATCTACGTATTAGTCATCGCTATTACCATGGTGATGCGGTTTTGGCAGTACACCAATGG
GCGTGGATAGCGGTTTGACTCACGGGGATTTCCAAGTCTCCACCCCATTGACGTCAATGGGAGTTTGTTTTGGCACCA
AAATCAACGGGACTTTCCAAAATGTCGTAATAACCCCGCCCCGTTGACGCAAATGGGCGGTAGGCGTGTACGGTGGGA
GGTCTATATAAGCAGAGCTGGTTTAGTGAACCGTCAGATCACTAGAAGCTTTATTGCGGTAGTTTATCACAGTTAAAT
TGCTAACGCAGTCAGTGCTTCTGACACAACAGTCTCGAACTTAAGCTGCAGAAGTTGGTCGTGAGGCACTGGGCAGGT
AAGTATCAAGGTTACAAGACAGGTTTAAGGAGACCAATAGAAACTGGGCTTGTCGAGACAGAGAAGACTCTTGCGTTT
CTGATAGGCACCTATTGGTCTTACTGACATCCACTTTGCCTTTCTCTCCACAGGTGTCCACTCCCAGTTCAATTACAG
CTCTTAAGGCTAGAGTATTAATACGACTCACTATAGGGCTAGCGATCGCCATGATGGACTTGGAGCTGCCGCCGCCGG
GACTCCCGTCCCAGCAGGACATGGATTTGATTGACATACTTTGGAGGCAAGATATAGATCTTGGAGTAAGTCGAGAAG
TATTTGACTTCAGTCAGCGACGGAAAGAGTATGAGCTGGAAAAACAGAAAAAACTTGAAAAGGAAAGACAAGAACAAC
TCCAAAAGGAGCAAGAGAAAGCCTTTTTCGCTCAGTTACAACTAGATGAAGAGACAGGTGAATTTCTCCCAATTCAGC
CAGCCCAGCACATCCAGTCAGAAACCAGTTCTCTCGGTGGTTCAGGTGGTGGCGGGAGCGGTGGAGGGAGCAGCGGTG
GAGTGTTTACACTCGAAGATTTCGTAGGGGACTGGCGGCAGACAGCCGGCTACAACCTGGACCAAGTCCTTGAGCAGG
GCGGTGTGTCCAGTTTGTTTCAGAATCTCGGGGTGTCCGTAACTCCGATCCAAAGGATTGTCCTGAGCGGTGAAAACG
GCCTGAAGATCGACATCCATGTCATCATCCCGTATGAAGGTCTGAGCGGCGATCAGATGGGCCAGATCGAAAAAATTT
TTAAGGTGGTGTACCCTGTGGATGATCATCACTTTAAGGTGATTCTGCACTATGGCACACTGGTAATCGACGGGGTTA
CGCCGAACATGATCGACTATTTCGGACGGCCGTATGAAGGCATCGCCGTGTTCGACGGCAAAAAGATCACTGTAACCG
GGACCCTGTGGAACGGCAACAAAATTATCGACGAGCGCCTGATCAACCCCGACGGCTCCCTGCTGTTCCGCGTAACCA
TCAACGGAGTGACCGGCTGGCGGCTGTGCGAGCGCATTTTGGCGTAAGGCCGCGACTCTAGAGTCGACCTGCAGGCAT
GCAAGCTGATCCGGCTGCTAACAAAGCCCGAAAGGAAGCTGAGTTGGCTGCTGCCACCGCTGAGCAATAACTAGCATA
ACCCCTTGGGGCGGCCGCTTCGAGCAGACATGATAAGATACATTGATGAGTTTGGACAAACCACAACTAGAATGCAGT
GAAAAAAATGCTTTATTTGTGAAATTTGTGATGCTATTGCTTTATTTGTAACCATTATAAGCTGCAATAAACAAGTTA
ACAACAACAATTGCATTCATTTTATGTTTCAGGTTCAGGGGGAGATGTGGGAGGTTTTTTAAAGCAAGTAAAACCTCT
ACAAATGTGGTAAAATCGAATTTTAACAAAATATTAACGCTTACAATTTCCTGATGCGGTATTTTCTCCTTACGCATC
TGTGCGGTATTTCACACCGCATACGCGGATCTGCGCAGCACCATGGCCTGAAATAACCTCTGAAAGAGGAACTTGGTT
AGGTACCTTCTGAGGCGGAAAGAACCAGCTGTGGAATGTGTGTCAGTTAGGGTGTGGAAAGTCCCCAGGCTCCCCAGC
AGGCAGAAGTATGCAAAGCATGCATCTCAATTAGTCAGCAACCAGGTGTGGAAAGTCCCCAGGCTCCCCAGCAGGCAG
AAGTATGCAAAGCATGCATCTCAATTAGTCAGCAACCATAGTCCCGCCCCTAACTCCGCCCATCCCGCCCCTAACTCC
GCCCAGTTCCGCCCATTCTCCGCCCCATGGCTGACTAATTTTTTTTATTTATGCAGAGGCCGAGGCCGCCTCGGCCTC
TGAGCTATTCCAGAAGTAGTGAGGAGGCTTTTTTGGAGGCCTAGGCTTTTGCAAAAAGCTTAATTAACTGTTGACAAT
TAATCATCGGCATAGTATATCGGCATAGTATAATACGACAAGGTGAGGAACTAAACCCAGGAGGCAGATCATGATTGA
ACAAGATGGATTGCACGCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCAAGACCGACCTGTCCGG
TGCCCTGAATGAACTGCAGGACGAGGCAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCGGGGCAGGATCTCCTGTCATCTCACCT
TGCTCCTGCCGAGAAAGTATCCATCATGGCTGATGCAATGCGGCGGCTGCATACGCTTGATCCGGCTACCTGCCCATT
CGACCACCAAGCGAAACATCGCATCGAGCGAGCACGTACTCGGATGGAAGCCGGTCTTGTCGATCAGGATGATCTGGA -continued

SEQUENCE LISTING

CGAAGAGCATCAGGGGCTCGCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTGGATTCATCGACTGTGGCCG
GCTGGGTGTGGCGGACCGCTATCAGGACATAGCGTTGGCTACCCGTGATATTGCTGAAGAGCTTGGCGGCGAATGGGC
TGACCGCTTCCTCGTGCTTTACGGTATCGCCGCTCCCGATTCGCAGCGCATCGCCTTCTATCGCCTTCTTGACGAGTT
CTTCTGAGCGGGACTCTGGGGTTCGAAATGACCGACCAAGCGACGCCCAACCTGCCATCACGATGGCCGCAATAAAAT
ATCTTTATTTTCATTACATCTGTGTGTTGGTTTTTTGTGTGAATCGATAGCGATAAGGATCCTCTTTGCGCTTGCGTT
TTCCCTTGTCCAGATAGCCCAGTAGCTGACATTCATCCGGGGTCAGCACCGTTTCTGCGGACTGGCTTTCTACCCGGT
ATCAGCTCACTCAAAGGCGGTAATACGGTTATCCACAGAATCAGGGGATAACGCAGGAAAGAACATGTGAGCAAAAGG
CCAGCAAAAGGCCAGGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCAGCAGATTACGCGCAGAAAAAA
AGGATTTCAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTATAGTCCGGAAATACAGGAACGCACGCTGGATGGCC
CTTCGCTGGGATGGTGAAACCATGAAAAATGGCAGCTTCAGTGGATTAAGTGGGGGTAATGTGGCCTGTACCCTCTGG
TTGCATAGGTATTCATACGGTTAAAATTTATCAGGCGCGATTGCGGCAGTTTTTCGGGTGGTTTGTTGCCATTTTTAC
CTGTCTGCTGCCGTGATCGCGCTGAACGCGTTTTAGCGGTGCGTACAATTAAGGGATTATGGTAAATCCACTTACTGT
CTGCCCTCGTAGCCATCGAGATAAACCGCAGTACTCCGGCCACGATGCGTCCGGCGTAGAGGATCGAGATCT

SEQ ID NO: 318 (L27V02B)
ATGGTCTTCACACTCGAAGATTTCGTAGGTGACTGGCGACAGACAGCCGGCTACAACCTGGACCAAGTCCTTGAACAG
GGTGGTGTGTCCAGTTTGTTTCAGAATCTCGGGGTGTCCGTAACTCCGATCCAAAGGATTGTCCTGAGCGGTGAAAAT
GGGCTGAAGATCGACATCCATGTCATCATCCCGTATGAAGGTCTGAGCGGCGACCAAATGGGCCAGATCGAAAAAATT
TTTAAGGTGGTGTACCCTGTGGATGATCATCACTTTAAGGTGATCCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACT
GGGACCCTGTGGAACGGCAACAAAATTATCGACGAGCGCCTGATCAACCCCGACGGCTCCCTGCTGTTCCGAGTAACC
ATCAACGGAGTGACCGGCTGGCGGCTGTGCGAACGCATTCTGGCG

SEQ ID NO: 319 (L27V01)
ATGGTGTTTACACTCGAAGATTTCGTAGGGGACTGGCGGCAGACAGCCGGCTACAACCTGGACCAAGTCCTTGAACAG
GGCGGTGTGTCCAGTTTGTTTCAGAATCTCGGGGTGTCCGTAACTCCGATCCAAAGGATTGTCCTGAGCGGTGAAAAC
GGCCTGAAGATCGACATCCATGTCATCATCCCGTATGAAGGTCTGAGCGGCGATCAAATGGGCCAGATCGAAAAAATT
TTTAAGGTGGTGTACCCTGTGGATGATCATCACTTTAAGGTGATCCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCG

SEQ ID NO: 320 (L27V01-PEST00)
ATGGTGTTTACACTCGAAGATTTCGTAGGGGACTGGCGGCAGACAGCCGGCTACAACCTGGACCAAGTCCTTGAACAG
GGCGGTGTGTCCAGTTTGTTTCAGAATCTCGGGGTGTCCGTAACTCCGATCCAAAGGATTGTCCTGAGCGGTGAAAAC
GGCCTGAAGATCGACATCCATGTCATCATCCCGTATGAAGGTCTGAGCGGCGATCAAATGGGCCAGATCGAAAAAATT
TTTAAGGTGGTGTACCCTGTGGATGATCATCACTTTAAGGTGATCCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCGAATTCACACGGCTTTCCGCCCGAGGTTGAAGAG
CAAGCCGCCGGTACATTGCCTATGTCCTGCGCACAAGAAAGCGGTATGGACCGGCACCCAGCCGCTTGTGCTTCAGCT
CGCATCAACGTC

SEQ ID NO: 321 (IL601-L27V01)
ATGAACTCCTTCTCCACAAGCGCCTTCGGTCCAGTTGCCTTCTCCCTGGGCCTGCTCCTGGTGTTGCCTGCTGCCTTC
CCTGCCCCAGTGTTTACACTCGAAGATTTCGTAGGGGACTGGCGGCAGACAGCCGGCTACAACCTGGACCAAGTCCTT
GAACAGGGCGGTGTGTCCAGTTTGTTTCAGAATCTCGGGGTGTCCGTAACTCCGATCCAAAGGATTGTCCTGAGCGGT
GAAAACGGCCTGAAGATCGACATCCATGTCATCATCCCGTATGAAGGTCTGAGCGGCGATCAAATGGGCCAGATCGAA
AAAATTTTTAAGGTGGTGTACCCTGTGGATGATCATCACTTTAAGGTGATCCTGCACTATGGCACACTGGTAATCGAC
GGGGTTACGCCGAACATGATCGACTATTTCGGACGGCCGTATGAAGGCATCGCCGTGTTCGACGGCAAAAAGATCACT
GTAACCGGGACCCTGTGGAACGGCAACAAAATTATCGACGAGCGCCTGATCAACCCCGACGGCTCCCTGCTGTTCCGC
GTAACCATCAACGGAGTGACCGGCTGGCGGCTGTGCGAGCGCATTTTGGCG

SEQ ID NO: 322 (L27V02A)
ATGGTCTTCACACTCGAAGATTTCGTTGGGGACTGGCGACAGACAGCCGGCTACAACCTGGACCAAGTCCTTGAACAG
GGAGGTGTGTCCAGTTTGTTTCAGAATCTCGGGGTGTCCGTAACTCCGATCCAAAGGATTGTCCTGAGCGGTGAAAAT
GGGCTGAAGATCGACATCCATGTCATCATCCCGTATGAAGGTCTGAGCGGCGACCAAATGGGCCAGATCGAAAAAATT
TTTAAGGTGGTGTACCCTGTGGATGATCATCACTTTAAGGTGATCCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACA
GGGACCCTGTGGAACGGCAACAAAATTATCGACGAGCGCCTGATCAACCCCGACGGCTCCCTGCTGTTCCGAGTAACC
ATCAACGGAGTGACCGGCTGGCGGCTGTGCGAACGCATTCTGGCG

SEQ ID NO: 323 (L27V02A-PEST01)
ATGGTCTTCACACTCGAAGATTTCGTTGGGGACTGGCGACAGACAGCCGGCTACAACCTGGACCAAGTCCTTGAACAG
GGAGGTGTGTCCAGTTTGTTTCAGAATCTCGGGGTGTCCGTAACTCCGATCCAAAGGATTGTCCTGAGCGGTGAAAAT
GGGCTGAAGATCGACATCCATGTCATCATCCCGTATGAAGGTCTGAGCGGCGACCAAATGGGCCAGATCGAAAAAATT
TTTAAGGTGGTGTACCCTGTGGATGATCATCACTTTAAGGTGATCCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACA

-continued

SEQUENCE LISTING

GGGACCCTGTGGAACGGCAACAAAATTATCGACGAGCGCCTGATCAACCCCGACGGCTCCCTGCTGTTCCGAGTAACC
ATCAACGGAGTGACCGGCTGGCGGCTGTGCGAACGCATTCTGGCGAATTCTCACGGCTTTCCGCCTGAGGTTGAAGAG
CAAGCCGCCGGTACATTGCCTATGTCCTGCGCACAAGAAAGCGGTATGGACCGGCACCCAGCCGCTTGTGCTTCAGCT
CGCATCAACGTC

SEQ ID NO: 324 (IL601-L27V02A)
ATGAACTCCTTCTCCACAAGCGCCTTCGGTCCAGTTGCCTTCTCCCTGGGCCTGCTCCTGGTGTTGCCTGCTGCCTTC
CCTGCCCCAGTCTTCACACTCGAAGATTTCGTTGGGGACTGGCGACAGACAGCCGGCTACAACCTGGACCAAGTCCTT
GAACAGGGAGGTGTGTCCAGTTTGTTTCAGAATCTCGGGGTGTCCGTAACTCCGATCCAAAGGATTGTCCTGAGCGGT
GAAAATGGGCTGAAGATCGACATCCATGTCATCATCCCGTATGAAGGTCTGAGCGGCGACCAAATGGGCCAGATCGAA
AAAATTTTTAAGGTGGTGTACCCTGTGGATGATCATCACTTTAAGGTGATCCTGCACTATGGCACACTGGTAATCGAC
GGGGTTACGCCGAACATGATCGACTATTTCGGACGGCCGTATGAAGGCATCGCCGTGTTCGACGGCAAAAAGATCACT
GTAACAGGGACCCTGTGGAACGGCAACAAAATTATCGACGAGCGCCTGATCAACCCCGACGGCTCCCTGCTGTTCCGA
GTAACCATCAACGGAGTGACCGGCTGGCGGCTGTGCGAACGCATTCTGGCG

SEQ ID NO: 325 (L27V03)
ATGGTCTTCACACTCGAAGATTTCGTAGGTGACTGGCGACAGACAGCCGGCTACAACCTGGACCAAGTTCTTGAACAG
GGTGGTGTGTCCAGTTTGTTTCAGAATCTCGGGGTGTCCGTAACTCCAATCCAGAGGATAGTCCTGAGTGGTGAAAAT
GGGCTGAAGATCGACATCCATGTCATCATCCCTTATGAAGGTCTGAGCGGCGATCAGATGGGGCAGATCGAAAAAATT
TTTAAGGTGGTGTACCCTGTGGATGATCATCACTTTAAGGTGATCCTGCACTATGGCACACTGGTAATCGACGGTGTT
ACGCCGAACATGATCGACTATTTCGGACGGCCGTATGAAGGCATCGCCGTGTTCGACGGCAAAAAGATTACTGTCACT
GGAACCCTGTGGAATGGGAACAAAATTATCGACGAGCGCCTGATCAACCCCGACGGCTCACTGCTGTTCCGAGTAACC
ATCAATGGTGTTACCGGCTGGCGGCTCTGCGAACGCATTCTAGCA

SEQ ID NO: 326 (L27V03-PEST02)
ATGGTCTTCACACTCGAAGATTTCGTAGGTGACTGGCGACAGACAGCCGGCTACAACCTGGACCAAGTTCTTGAACAG
GGTGGTGTGTCCAGTTTGTTTCAGAATCTCGGGGTGTCCGTAACTCCAATCCAGAGGATAGTCCTGAGTGGTGAAAAT
GGGCTGAAGATCGACATCCATGTCATCATCCCTTATGAAGGTCTGAGCGGCGATCAGATGGGGCAGATCGAAAAAATT
TTTAAGGTGGTGTACCCTGTGGATGATCATCACTTTAAGGTGATCCTGCACTATGGCACACTGGTAATCGACGGTGTT
ACGCCGAACATGATCGACTATTTCGGACGGCCGTATGAAGGCATCGCCGTGTTCGACGGCAAAAAGATTACTGTCACT
GGAACCCTGTGGAATGGGAACAAAATTATCGACGAGCGCCTGATCAACCCCGACGGCTCACTGCTGTTCCGAGTAACC
ATCAATGGTGTTACCGGCTGGCGGCTCTGCGAACGCATTCTAGCAAATAGTCACGGCTTTCCGCCTGAGGTTGAAGAG
CAAGCCGCCGGTACATTGCCTATGTCCTGCGCACAAGAAAGCGGTATGGACCGGCACCCAGCCGCTTGTGCTTCAGCT
CGCATCAACGTC

SEQ ID NO: 327 (IL602-L27V03)
ATGAACTCCTTCTCCACAAGCGCCTTCGGTCCAGTCGCCTTCTCCCTGGGCCTGCTCCTGGTGTTGCCCGCTGCCTTT
CCTGCCCCAGTCTTCACACTCGAAGATTTCGTAGGTGACTGGCGACAGACAGCCGGCTACAACCTGGACCAAGTTCTT
GAACAGGGTGGTGTGTCCAGTTTGTTTCAGAATCTCGGGGTGTCCGTAACTCCAATCCAGAGGATAGTCCTGAGTGGT
GAAAATGGGCTGAAGATCGACATCCATGTCATCATCCCTTATGAAGGTCTGAGCGGCGATCAGATGGGGCAGATCGAA
AAAATTTTTAAGGTGGTGTACCCTGTGGATGATCATCACTTTAAGGTGATCCTGCACTATGGCACACTGGTAATCGAC
GGTGTTACGCCGAACATGATCGACTATTTCGGACGGCCGTATGAAGGCATCGCCGTGTTCGACGGCAAAAAGATTACT
GTCACTGGAACCCTGTGGAATGGGAACAAAATTATCGACGAGCGCCTGATCAACCCCGACGGCTCACTGCTGTTCCGA
GTAACCATCAATGGTGTTACCGGCTGG

SEQ ID NO: 328 (Linker)
GSSGGGSSGGEPTTENLYFQSDNGSSGGGSSGG

SEQ ID NO: 329 (FABP Consensus Sequence)
[GSAIVK]-{FE}-[FYW]-x-[LIVMF]-x-x-{K}-x-[NHG]-[FY]-[DE]-x-[LIVMFY]- [LIVM]-
{N}-{G}-[LIVMAKR]

SEQ ID NO: 330 (OGLUC Consensus Sequence)
[GSAIVK]-{FE}-[FYW]-x-[LIVMFSYQ]-x-x-{K}-x-[NHGK]-x-[DE]-x-[LIVMFY]-[LIVMWF]-
x-{G}-[LIVMAKRG]

SEQ ID NO: 331 (9B8 PCA1 (pF5A/Met-[9B8 opt (51-169)]-GGGGSGGGSS-FRB)
Atgggcctgaagatcgacatccatgtcatcatcccgtatgaaggtctgagcggctatcagatgggccagatcgaaaaa
atttttaaggtggtgtaccctgtggatgatcatcactttaaggtgattctgcactatggcacactggtaatcgacggg
gttacgccgaacatgatcgactatttcggacggccgtatgaaggcatcgccgtgttcgacggcaaaaagatcactgta
accgggaccctgtggaacggcaacaaaattatcgacgagcgcctgatcaaccccgacggctccctgctgttccgcgta
accatcaacggagtgaccggctggcggctgtgcgagcgcattttggcgggaggaggtggctcaggtggagggagctcc
gtggccatcctctggcatgagatgtggcatgaaggcctggaagaggcatctcgtttgtactttggggaaaggaacgtg
aaaggcatgtttgaggtgctggagcccttgcatgctatgatggaacggggcccccagactctgaaggaaacatccttt
aatcaggcctatggtcgagatttaatggaggcccaagagtggtgcaggaagtacatgaaatcagggaatgtcaaggac
ctcacccaagcctgggacctctattatcatgtgttccgacgaatctca SEQ ID NO: 332 (9B8 PCA1 (pF5A/Met-[9B8 opt (51-169)]-GGGGSGGGSS-FRB)
MGLKIDIHVIIPYEGLSGYQMGQIEKIFKVVYPVDDHHFKVILHYGTLVIDGVTPNMIDYFGRPYEGIAVFDGKKITV
TGTLWNGNKIIDERLINPDGSLLFRVTINGVTGWRLCERILAGGGGSGGGSSVAILWHEMWHEGLEEASRLYFGERNV
KGMFEVLEPLHAMMERGPQTLKETSFNQAYGRDLMEAQEWCRKYMKSGNVKDLTQAWDLYYHVFRRIS SEQ ID NO: 333 (9B8 PCA2 (pF5A/[9B8 opt (1-50)]-GGGGSGGGSS-FRB)
Atggtgtttacactcgaagatttcgtaggggactggcggcagacagccggctacaacctggaccaagtccttgagcag
ggcggtctgtccagtttgtttcagaaactcggggtgtccgtaacaccgatccaaaagattgtcctgagcggtgaaaac
ggaggaggtggctcaggtggagggagctccgtggccatcctctggcatgagatgtggcatgaaggcctggaagaggca
tctcgtttgtactttggggaaaggaacgtgaaaggcatgtttgaggtgctggagcccttgcatgctatgatggaacgg -continued

SEQUENCE LISTING ggcccccagactctgaaggaaacatcctttaatcaggcctatggtcgagatttaatggaggcccaagagtggtgcagg
aagtacatgaaatcagggaatgtcaaggacctcacccaagcctgggacctctattatcatgtgttccgacgaatctca SEQ ID NO: 334 (9B8 PCA2 (pF5A/[9B8 opt (1-50)]-GGGGSGGGSS-FRB)
MVFTLEDFVGDWRQTAGYNLDQVLEQGGLSSLFQKLGVSVTPIQKIVLSGENGGGGSGGGSSVAILWHEMWHEGLEEA
SRLYFGERNVKGMFEVLEPLHAMMERGPQTLKETSFNQAYGRDLMEAQEWCRKYMKSGNVKDLTQAWDLYYHVFRRIS SEQ ID NO: 335 (9B8 PCA 3 (& pF5A/FKBP-GGGSSGGGSG-[9B8 opt (51-169)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtggcctgaagatcgacatccatgtcatcatcccgtat
gaaggtctgagcggctatcagatgggccagatcgaaaaaatttttaaggtggtgtaccctgtggatgatcatcacttt
aaggtgattctgcactatggcacactggtaatcgacggggttacgccgaacatgatcgactatttcggacggccgtat
gaaggcatcgccgtgttcgacggcaaaaagatcactgtaaccgggaccctgtggaacggcaacaaaattatcgacgag
cgcctgatcaaccccgacggctccctgctgttccgcgtaaccatcaacggagtgaccggctggcggctgtgcgagcgc
attttggcg SEQ ID NO: 336 (9B8 PCA 3 (& pF5A/FKBP-GGGSSGGGSG-[9B8 opt (51-169)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGGLKIDIHVIIPYEGLSGYQMGQIEKIFKVVYPVDDHHF
KVILHYGTLVIDGVTPNMIDYFGRPYEGIAVFDGKKITVTGTLWNGNKIIDERLINPDGSLLFRVTINGVTGWRLCER
ILA SEQ ID NO: 337 (9B8 PCA 4 (pF5A/FKBP-GGGSSGGGSG-[9B8 opt (1-50)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtgtttacactcgaagatttcgtaggggactgg
cggcagacagccggctacaacctggaccaagtccttgagcagggcggtctgtccagtttgtttcagaaactcggggtg
tccgtaacaccgatccaaaagattgtcctgagcggtgaaaac SEQ ID NO: 338 (9B8 PCA 4 (pF5A/FKBP-GGGSSGGGSG-[9B8 opt (1-50)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGLSSLFQKLGV
SVTPIQKIVLSGEN SEQ ID NO: 339 (K33N + L27V + K43R + Y68D)
Atggtgtttacactcgaagatttcgtaggggactggcggcagacagccggctacaacctggaccaagtccttgagcag
ggcggtgtgtccagtttgtttcagaatctcggggtgtccgtaacaccgatccaaaggattgtcctgagcggtgaaaac
ggcctgaagatcgacatccatgtcatcatcccgtatgaaggtctgagcggcgatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 340 (K33N + L27V + K43R + Y68D)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 341 (K33N + L27V + T39T + K43R + S66N)
Atggtgtttacactcgaagatttcgtaggggactggcggcagacagccggctacaacctggaccaagtccttgagcag
ggcggtgtgtccagtttgtttcagaatctcggggtgtccgtaactccgatccaaaggattgtcctgagcggtgaaaac
ggcctgaagatcgacatccatgtcatcatcccgtatgaaggtctgaacggctatcagatgggccagatcgaaaaaatt
tttaaggtggtgtaccctgtggatgatcatcactttaaggtgattctgcactatggcacactggtaatcgacggggtt
acgccgaacatgatcgactatttcggacggccgtatgaaggcatcgccgtgttcgacggcaaaaagatcactgtaacc
gggaccctgtggaacggcaacaaaattatcgacgagcgcctgatcaaccccgacggctccctgctgttccgcgtaacc
atcaacggagtgaccggctggcggctgtgcgagcgcattttggcg SEQ ID NO: 342 (K33N + L27V + T39T + K43R + S66N)
MVFTLEDFVGDWRQTAGYNLDQVLEQGGVSSLFQNLGVSVTPIQRIVLSGENGLKIDIHVIIPYEGLNGYQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILA SEQ ID NO: 343 (pCA 31 pCA L27V02A 45-169 FRB)
atggtcctgagcggtgaaaatgggctgaagatcgacatccatgtcatcatcccgtatgaaggtctgagcggcgaccaa
atgggccagaccgaaaaaatttttaaggtggtgcaccctgtggatgatcatcactttaaggtgatcctgcactatggc
acactggtaatcgacggggttacgccgaacatgatcgactatttcggacggccgtatgaaggcatcgccgtgttcgac
ggcaaaaagatcactgtaacagggaccctgtggaacggcaacaaaattatcgacgagcgcctgatcaaccccgacggc
tccctgctgttccgagtaaccatcaacggagtgaccggctggcggctgtgcgaacgcattctggcgggaggaggtggc
tcaggcggagggagctccgtggccatcctctggcatgagacgcggcatgaaggcctggaagaggcatctcgcttgtac
tctggggaaaggaacgtgaaaggcatgtttgaggtgctggagcccttgcatgccatgatggaacggggcccccagact
ccgaaggaaacatcctttaatcaggccrarggccgagattraacggaggcccaagagtggtgcaggaagcacatgaaa
tcagggaatgtcaaggacctcacccaagcctgggacctctattatcatgtgttccgacgaatctca -continued

SEQUENCE LISTING

SEQ ID NO: 344 (pCA 31 pCA L27V02A 45-169 FRB)
MVLSGENGLKIDIHVIIPYEGLSGDQMGQIEKIFKWYPVDDHHFKVILHYGTLVIDGVTPNMIDYFGRPYEGIAVFD
GKKITVTGTLWNGNKIIDERLINPDGSLLFRVTINGVTGWLCERILAGGGGSGGGSSVAILWHEMWHEGLEEASRLY
FGERNVKGMFEVLEPLHAMMERGPQTLKETSFNQAYGRDLMEAQEWCRKYMKSGNVKDLTQAWDLYYHVFRRIS

SEQ ID NO: 345 (pCA 32 FKBP L27V02A 1-44)
atgggagtgcaggtggaaaccatctccccaggagacgggcgcaccttccccaagcgcggccagacctgcgtggtgcac
tacaccgggatgctcgaagatggaaagaaatttgattcctcccgggacagaaacaagccccttaagtctatgccaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ccaaaaccggaaggaggagggagctccggtggaggcagcggcacggtctccacacccgaagatctcgccggggaccgg
cgacagacagccggctacaacctggaccaagtccccgaacagggaggtgcgtccagcttgcttcagaatctcggggcg
tccgtaactccgatccaaaggatt SEQ ID NO: 346 (pCA 32 FKBP L27V02A 1-44)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRI SEQ ID NO: 347 (pCA 33 pCA L27V02A 46-169 FRB)
acgctgagcggtgaaaatgggctgaagatcgacacccatgccatcatcccgtatgaaggtctgagcggcgaccaaatg
ggccagatcgaaaaaatttttaaggtggtgcaccccgtggatgatcatcactttaaggcgatcctgcactatggcaca
ctggtaatcgacggggttacgccgaacatgatcgactatttcggacggcccgtatgaaggcatcgccgtgttcgacggc
aaaaagatcactgtaacagggaccctgtggaacggcaacaaaattatcgacgagcgcctgatcaaccccgacggctcc
ccgctgttccgagtaaccatcaacggagtgaccggctggcggctgtgcgaacgcattctggcgggaggaggtggctca
ggtggagggagctccgcggccatcctctggcatgagatgcggcatgaaggcctggaagaggcacctcgtttgcactct
ggggaaaggaacgtgaaaggcatgttcgaggtgccggagcccttgcatgccatgatggaacggggcccccagactctg
aaggaaacatcctttaatcaggcctatggtcgagatttaatggaggcccaagagtggtgcaggaagtacatgaaatca
gggaatgtcaaggacctcacccaagccttgggacctctattatcatgtgttccgacgaatctca SEQ ID NO: 348 (pCA 33 pCA L27V02A 46-169 FRB)
MLSGENGLKIDIHVIIPYEGLSGDQMGQIEKIFKVVYPVDDHHFKVILHYGTLVIDGVTPNMIDYFGRPYEGIAVFDG
KKITVTGTLWNGNKIIDERLINPDGSLLFRVTINGVTGWRLCERILAGGGGSGGGSSVAILWHEMWHEGLEEASRLYF
GERNVKGMFEVLEPLHAMMERGPQTLKETSFNQAYGRDLMEAQEWCRKYMKSGNVKDLTQAWDLYYHVFRRIS SEQ ID NO: 349 (pCA 34 pCA FKBP 1-45 L27V02A)
atgggagtgcaggcggaaaccatctccccaggagacgggcgcaccttccccaagcgcggccagacctgcgtggtgcac
tacaccgggatgcttgaagacggaaagaaatttgattcctcccgggacagaaacaagccctttaagcttatgccaggc
aagcaggaggtgatccgaggctgggaagaaggggttgcccagatgagtgtgggtcagagagccaaactgactatatct
ccagatcatgcctatggcgccaccgggcacccaggcatcatcccaccacatgccaccctcgtcctcgacgtggagcct
ctaaaactggaaggaggagggagctccggtggaggcagcggtacggtcttcacactcgaagatctcgctggggactgg
cgacagacagccggctacaacctggaccaagtccttgaacagggaggtgtgtccagtttgtttcagaatctcggggtg
tccgtaactccgatccaaaggatcgtc SEQ ID NO: 350 (pCA 34 pCA FKBP 1-45 L27V02A)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIV SEQ ID NO: 351 (pCA 35 pCA L27V02A 100-169 FRB)
atggacggggttacgccgaacatgatcgaccatttcggacggcccgtatgaaggcatcgccgtgctcgacggcaaaaag
atcaccgtaacagggaccctgtggaacggcaacaaaattaccgacgagcgcctgatcaaccccgacggctccctgctg
ttccgagtaaccatcaacggagtgaccggctggcggctgtgcgaacgcattctggcgggaggaggtggctcaggtgga
gggagctccgtggccatcctctggcatgagatgtggcatgaaggcctggaagaggcatctcgtttgtactttggggaa
aggaacgtgaaaggcatgtttgaggtgctggagcccttgcatgctatgatggaacggggccccccagactctgaaggaa
acatcctttaatcaggcctatggtcgagatttaatggaggcccaagagtggtgcaggaagtacatgaaatcagggaat
gtcaaggacctcacccaagcctgggacctctattatcatgtgttccgacgaatctca SEQ ID NO: 352 (pCA 35 pCA L27V02A 100-169 FRB)
MDGVTPNMIDYFGRPYEGIAVFDGKKITVTGTLWNGNKIIDERLINPDGSLLFRVTINGVTGWRLCERILAGGGGSGG
GSSVAILWHEMWHEGLEEASRLYFGERNVKGMFEVLEPLHAMMERGPQTLKETSFNQAYGRDLMEAQEWCRKYMKSGN
VKDLTQAWDLYYHVFRRIS SEQ ID NO: 353 (pCA 36 FKBP L27V02A 1-99)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatc -continued

SEQUENCE LISTING

SEQ ID NO: 354 (pCA 36 FKBP L27V02A 1-99)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVI

SEQ ID NO: 355 (pCA 37 L27V02A 101-169 FRB)
atgggggttacgccgaacatgatcgactatttcggacggccgtatgaaggcatcgccgtgttcgacggcaaaaagatc
actgtaacagggaccctgtggaacggcaacaaaattatcgacgagcgcctgatcaaccccgacggctccctgctgttc
cgagtaaccatcaacggagtgaccggctggcggctgtgcgaacgcattctggcgggaggaggtggctcaggtggaggg
agctccgtggccatcctctggcatgagatgtggcatgaaggcctggaagaggcatctcgtttgtactttggggaaagg
aacgtgaaaggcatgtttgaggtgctggagcccttgcatgctatgatggaacggggcccccagactctgaaggaaaca
tcctttaatcaggcctatggtcgagatttaatggaggcccaagagtggtgcaggaagtacatgaaatcagggaatgtc
aaggacctcacccaagcctgggacctctattatcatgtgttccgacgaatctca SEQ ID NO: 356 (pCA 37 L27V02A 101-169 FRB)
MGVTPNMIDYFGRPYEGIAVFDGKKITVTGTLWNGNKIIDERLINPDGSLLFRVTINGVTGWRLCERILAGGGGSGGG
SSVAILWHEMWHEGLEEASRLYFGERNVKGMFEVLEPLHAMMERGPQTLKETSFNQAYGRDLMEAQEWCRKYMKSGNV
KDLTQAWDLYYHVFRRIS SEQ ID NO: 357 (pCA 38 FKBP 1-100 L27V02A)
Atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgac SEQ ID NO: 358 (pCA 38 FKBP 1-100 L27V02A)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVID SEQ ID NO: 359 (pCA 39 L27V02A 102-169 FRB)
Atggttacgccgaacatgatcgactatttcggacggccgtatgaaggcatcgccgtgttcgacggcaaaaagatcact
gtaacagggaccctgtggaacggcaacaaaattatcgacgagcgcctgatcaaccccgacggctccctgctgttccga
gtaaccatcaacggagtgaccggctggcggctgtgcgaacgcattctggcgggaggaggtggctcaggtggagggagc
tccgtggccatcctctggcatgagatgtggcatgaaggcctggaagaggcatctcgtttgtactttggggaaaggaac
gtgaaaggcatgtttgaggtgctggagcccttgcatgctatgatggaacggggcccccagactctgaaggaaacatcc
tttaatcaggcctatggtcgagatttaatggaggcccaagagtggtgcaggaagtacatgaaatcagggaatgtcaag
gacctcacccaagcctgggacctctattatcatgtgttccgacgaatctca SEQ ID NO: 360 (pCA 39 L27V02A 102-169 FRB)
MVTPNMIDYFGRPYEGIAVFDGKKITVTGTLWNGNKIIDERLINPDGSLLFRVTINGVTGWRLCERILAGGGGSGGGS
SVAILWHEMWHEGLEEASRLYFGERNVKGMFEVLEPLHAMMERGPQTLKETSFNQAYGRDLMEAQEWCRKYMKSGNVK
DLTQAWDLYYHVFRRIS SEQ ID NO: 361 (pCA 40 FKBP L27V02A 1-101)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggg SEQ ID NO: 362 (pCA 40 FKBP L27V02A 1-101)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDG SEQ ID NO: 363 (pCA 41 L27V02A 143-169 FRB)
atgatcaaccccgacggctccctgctgttccgagtaaccatcaacggagtgaccggctggcggctgtgcgaacgcatt
ctggcgggaggaggtggctcaggtggagggagctccgtggccatcctctggcatgagatgtggcatgaaggcctggaa
gaggcatctcgtttgtactttggggaaaggaacgtgaaaggcatgtttgaggtgctggagcccttgcatgctatgatg
gaacggggcccccagactctgaaggaaacatcctttaatcaggcctatggtcgagatttaatggaggcccaagagtgg
tgcaggaagtacatgaaatcagggaatgtcaaggacctcacccaagcctgggacctctattatcatgtgttccgacga
atctca SEQ ID NO: 364 (pCA 41 L27V02A 143-169 FRB)
MINPDGSLLFRVTINGVTGWRLCERILAGGGGSGGGSSVAILWHEMWHEGLEEASRLYFGERNVKGMFEVLEPLHAMM
ERGPQTLKETSFNQAYGRDLMEAQEWCRKYMKSGNVKDLTQAWDLYYHVFRRIS -continued

SEQUENCE LISTING

SEQ ID NO: 365 (pCA 42 FKBP 1-142 L27V02A)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctg SEQ ID NO: 366 (pCA 42 FKBP 1-142 L27V02A)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERL SEQ ID NO: 367 (pCA 43 L27V02A 145-169 FRB)
atgcccgacggctccctgctgttccgagtaaccatcaacggagtgaccggctggcggctgtgcgaacgcattctggcg
ggaggaggtggctcaggtggagggagctccgtggccatcctctggcatgagatgtggcatgaaggcctggaagaggca
tctcgtttgtactttggggaaaggaacgtgaaaggcatgtttgaggtgctggagcccttgcatgctatgatggaacgg
ggcccccagactctgaaggaaacatcctttaatcaggcctatggtcgagatttaatggaggcccaagagtggtgcagg
aagtacatgaaatcagggaatgtcaaggacctcacccaagcctgggacctctattatcatgtgttccgacgaatctca SEQ ID NO: 368 (pCA 43 L27V02A 145-169 FRB)
MPDGSLLFRVTINGVTGWRLCERILAGGGGSGGGSSVAILWHEMWHEGLEEASRLYFGERNVKGMFEVLEPLHAMMER
GPQTLKETSFNQAYGRDLMEAQEWCRKYMKSGNVKDLTQAWDLYYHVFRRIS SEQ ID NO: 369 (pCA 44 FKBP 1-144 L27V02A)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaac SEQ ID NO: 370 (pCA 44 FKBP 1-144 L27V02A)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLIN SEQ ID NO: 371 (pCA 45 L27V02A 147-169 FRB)
atgggctccctgctgttccgagtaaccatcaacggagtgaccggctggcggctgtgcgaacgcattctggcgggagga
ggtggctcaggtggagggagctccgtggccatcctctggcatgagatgtggcatgaaggcctggaagaggcatctcgt
ttgtactttggggaaaggaacgtgaaaggcatgtttgaggtgctggagcccttgcatgctatgatggaacggggcccc
cagactctgaaggaaacatcctttaatcaggcctatggtcgagatttaatggaggcccaagagtggtgcaggaagtac
atgaaatcagggaatgtcaaggacctcacccaagcctgggacctctattatcatgtgttccgacgaatctca SEQ ID NO: 372 (pCA 45 L27V02A 147-169 FRB)
MGSLLFRVTINGVTGWRLCERILAGGGGSGGGSSVAILWHEMWHEGLEEASRLYFGERNVKGMFEVLEPLHAMMERGP
QTLKETSFNQAYGRDLMEAQEWCRKYMKSGNVKDLTQAWDLYYHVFRRIS SEQ ID NO: 373 (pCA 46 FKBP- L27V02A 1-146)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagcactttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgac SEQ ID NO: 374 (pCA 46 L27V02A-FKBP 1-146)
MGVQVETISPGDGRTFPKRGQTCVVHYTGMLEDGKKFDSSRDRNKHFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV

SEQUENCE LISTING

SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPD

SEQ ID NO: 375 (pCA 47 L27V02A 148-169 FRB)
atgtccctgctgttccgagtaaccatcaacggagtgaccggctggcggctgtgcgaacgcattctggcgggaggaggt
ggctcaggtggagggagctccgtggccatcctctggcatgagatgtggcatgaaggcctggaagaggcatctcgtttg
tactttggggaaaggaacgtgaaaggcatgtttgaggtgctggagcccttgcatgctatgatggaacggggcccccag
actctgaaggaaacatcctttaatcaggcctatggtcgagatttaatggaggcccaagagtggtgcaggaagtacatg
aaatcagggaatgtcaaggacctcacccaagcctgggacctctattatcatgtgttccgacgaatctca SEQ ID NO: 376 (pCA 47 L27V02A 148-169 FRB)
MSLLFRVTINGVTGWRLCERILAGGGGSGGGSSVAILWHEMWHEGLEEASRLYFGERNVKGMFEVLEPLHAMMERGPQ
TLKETSFNQAYGRDLMEAQEWCRKYMKSGNVKDLTQAWDLYYHVFRRIS SEQ ID NO: 377 (pCA 48 FKBP- L27V02A 1-147)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggc SEQ ID NO: 378 (pCA 48 FKBP- L27V02A 1-147)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDG SEQ ID NO: 379 (pCA 49 L27V02A 156-169 FRB)
atgaacggagtgaccggctggcggctgtgcgaacgcattctggcgggaggaggtggctcaggtggagggagctccgtg
gccatcctctggcatgagatgtggcatgaaggcctggaagaggcatctcgtttgtactttggggaaaggaacgtgaaa
ggcatgtttgaggtgctggagcccttgcatgctatgatggaacggggcccccagactctgaaggaaacatcctttaat
caggcctatggtcgagatttaatggaggcccaagagtggtgcaggaagtacatgaaatcagggaatgtcaaggacctc
acccaagcctgggacctctattatcatgtgttccgacgaatctca SEQ ID NO: 380 (pCA 49 L27V02A 156-169 FRB)
MNGVTGWRLCERILAGGGGSGGGSSVAILWHEMWHEGLEEASRLYFGERNVKGMFEVLEPLHAMMERGPQTLKETSFN
QAYGRDLMEAQEWCRKYMKSGNVKDLTQAWDLYYHVFRRIS SEQ ID NO: 381 (pCA 50 FKBP-L27V02A 1-155)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatc SEQ ID NO: 382 (pCA 50 FKBP-L27V02A 1-155)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTI SEQ ID NO: 383 (pCA 51 L27V02A 158-169 FRB)
atggtgaccggctggcggctgtgcgaacgcattctggcgggaggaggtggctcaggtggagggagctccgtggccatc
ctctggcatgagatgtggcatgaaggcctggaagaggcatctcgtttgtactttggggaaaggaacgtgaaaggcatg
tttgaggtgctggagcccttgcatgctatgatggaacggggcccccagactctgaaggaaacatcctttaatcaggcc
tatggtcgagatttaatggaggcccaagagtggtgcaggaagtacatgaaatcagggaatgtcaaggacctcacccaa
gcctgggacctctattatcatgtgttccgacgaatctca SEQ ID NO: 384 (pCA 51 L27V02A 158-169 FRB)
MVTGWRLCERILAGGGGSGGGSSVAILWHEMWHEGLEEASRLYFGERNVKGMFEVLEPLHAMMERGPQTLKETSFNQA
YGRDLMEAQEWCRKYMKSGNVKDLTQAWDLYYHVFRRIS SEQ ID NO: 385 (pCA 52 FKBP 1-157 L27V02A)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc

SEQUENCE LISTING aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacgga SEQ ID NO: 386 (pCA 52 FKBP 1-157 L27V02A)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTING SEQ ID NO: 387 (pCA 53 L27V02A 166-169 FRB)
atgcgcattctggcgggaggaggtggctcaggtggagggagctccgtggccatcctctggcatgagatgtggcatgaa
ggcctggaagaggcatctcgtttgtactttggggaaaggaacgtgaaaggcatgtttgaggtgctggagcccttgcat
gctatgatggaacggggcccccagactctgaaggaaacatcctttaatcaggcctatggtcgagatttaatggaggcc
caagagtggtgcaggaagtacatgaaatcagggaatgtcaaggacctcacccaagcctgggacctctattatcatgtg
ttccgacgaatctca SEQ ID NO: 388 (pCA 53 L27V02A 166-169 FRB)
MRILAGGGGSGGGSSVAILWHEMWHEGLEEASRLYFGERNVKGMFEVLEPLHAMMERGPQTLKETSFNQAYGRDLMEA
QEWCRKYMKSGNVKDLTQAWDLYYHVFRRIS SEQ ID NO: 389 (pCA 54 FKBP L27V02A 1-165)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtgcgaa SEQ ID NO: 390 (pCA 54 FKBP L27V02A 1-165)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGVTGWRLCE SEQ ID NO: 391 (pCA 55 FKBP L27V02A 1-47)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagc SEQ ID NO: 392 (pCA 55 FKBP L27V02A 1-47)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLS SEQ ID NO: 393 (pCA 56 L27V02A 48-169-FRB)
Atgggtgaaaatgggctgaagatcgacatccatgtcatcatcccgtatgaaggtctgagcggcgaccaaatgggccag
atcgaaaaaatttttaaggtggtgtaccctgtggatgatcatcactttaaggtgatcctgcactatggcacactggta
atcgacggggttacgccgaacatgatcgactatttcggacggccgtatgaaggcatcgccgtgttcgacggcaaaaag
atcactgtaacagggaccctgtggaacggcaacaaaattatcgacgagcgcctgatcaaccccgacggctccctgctg
ttccgagtaaccatcaacggagtgaccggctggcggctgtgcgaacgcattctggcgggaggaggtggctcaggtgga
gggagctccgtggccatcctctggcatgagatgtggcatgaaggcctggaagaggcatctcgtttgtactttggggaa
aggaacgtgaaaggcatgtttgaggtgctggagcccttgcatgctatgatggaacggggcccccagactctgaaggaa
acatcctttaatcaggcctatggtcgagatttaatggaggcccaagagtggtgcaggaagtacatgaaatcagggaat
gtcaaggacctcacccaagcctgggacctctattatcatgtgttccgacgaatctca SEQ ID NO: 394 (pCA 56 L27V02A 48-169-FRB)
MGENGLKIDIHVIIPYEGLSGDQMGQIEKIFKVVYPVDDHHFKVILHYGTLVIDGVTPNMIDYFGRPYEGIAVFDGKK
ITVTGTLWNGNKIIDERLINPDGSLLFRVTINGVTGWRLCERILAGGGGSGGGSSVAILWHEMWHEGLEEASRLYFGE
RNVKGMFEVLEPLHAMMERGPQTLKETSFNQAYGRDLMEAQEWCRKYMKSGNVKDLTQAWDLYYHVFRRIS -continued

SEQUENCE LISTING

SEQ ID NO: 395 (pCA 57 FKBP L27V02A 1-49)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaa SEQ ID NO: 396 (pCA 57 FKBP L27V02A 1-49)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGE SEQ ID NO: 397 (pCA 58 pCA L27V02A 50-169 FRB)
atgaatgggctgaagatcgacatccatgtcatcatcccgtatgaaggtctgagcggcgaccaaatgggccagatcgaa
aaaatttttaaggtggtgtaccctgtggatgatcatcactttaaggtgatcctgcactatggcacactggtaatcgac
ggggttacgccgaacatgatcgactatttcggacggccgtatgaaggcatcgccgtgttcgacggcaaaaagatcact
gtaacagggaccctgtggaacggcaacaaaattatcgacgagcgcctgatcaaccccgacggctccctgctgttccga
gtaaccatcaacggagtgaccggctggcggctgtgcgaacgcattctggcgggaggaggtggctcaggtggagggagc
tccgtggccatcctctggcatgagatgtggcatgaaggcctggaagaggcatctcgtttgtactttggggaaaggaac
gtgaaaggcatgtttgaggtgctggagcccttgcatgctatgatggaacggggcccccagactctgaaggaaacatcc
tttaatcaggcctatggtcgagatttaatggaggcccaagagtggtgcaggaagtacatgaaatcagggaatgtcaag
gacctcacccaagcctgggacctctattatcatgtgttccgacgaatctca SEQ ID NO: 398 (pCA 58 pCA L27V02A 50-169 FRB)
MNGLKIDIHVIIPYEGLSGDQMGQIEKIFKVVYPVDDHHFKVILHYGTLVIDGVTPNMIDYFGRPYEGIAVFDGKKIT
VTGTLWNGNKIIDERLINPDGSLLFRVTINGVTGWRLCERILAGGGGSGGGSSVAILWHEMWHEGLEEASRLYFGERN
VKGMFEVLEPLHAMMERGPQTLKETSFNQAYGRDLMEAQEWCRKYMKSGNVKDLTQAWDLYYHVFRRIS SEQ ID NO: 399 (pCA 59 FKBP L27V02A 1-82)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccct SEQ ID NO: 400 (pCA 59 FKBP L27V02A 1-82)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYP SEQ ID NO: 401 (pCA 60 L27V02A 83-169-FRB)
atggtggatgatcatcactttaaggtgatcctgcactatggcacactggtaatcgacggggttacgccgaacatgatc
gactatttcggacggccgtatgaaggcatcgccgtgttcgacggcaaaaagatcactgtaacagggaccctgtggaac
ggcaacaaaattatcgacgagcgcctgatcaaccccgacggctccctgctgttccgagtaaccatcaacggagtgacc
ggctggcggctgtgcgaacgcattctggcgggaggaggtggctcaggtggagggagctccgtggccatcctctggcat
gagatgtggcatgaaggcctggaagaggcatctcgtttgtactttggggaaaggaacgtgaaaggcatgtttgaggtg
ctggagcccttgcatgctatgatggaacggggcccccagactctgaaggaaacatcctttaatcaggcctatggtcga
gatttaatggaggcccaagagtggtgcaggaagtacatgaaatcagggaatgtcaaggacctcacccaagcctgggac
ctctattatcatgtgttccgacgaatctca SEQ ID NO: 402 (pCA 60 L27V02A 83-16-FRB)
MVDDHHFKVILHYGTLVIDGVTPNMIDYFGRPYEGIAVFDGKKITVTGTLWNGNKIIDERLINPDGSLLFRVTINGVT
GWRLCERILAGGGGSGGGSSVAILWHEMWHEGLEEASRLYFGERNVKGMFEVLEPLHAMMERGPQTLKETSFNQAYGR
DLMEAQEWCRKYMKSGNVKDLTQAWDLYYHVFRRIS SEQ ID NO: 403 (pCA 61 FKBP L27V02A 1-84)
Atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggat SEQ ID NO: 404 (pCA 61 FKBP L27V02A 1-84)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVD -continued

SEQUENCE LISTING

SEQ ID NO: 405 (pCA 62 L27V02A 85-169-FRB)
atggatcatcactttaaggtgatcctgcactatggcacactggtaatcgacggggttacgccgaacatgatcgactat
ttcggacggccgtatgaaggcatcgccgtgttcgacggcaaaaagatcactgtaacagggaccctgtggaacggcaac
aaaattatcgacgagcgcctgatcaaccccgacggctccctgctgttccgagtaaccatcaacggagtgaccggctgg
cggctgtgcgaacgcattctggcgggaggaggtggctcaggtggagggagctccgtggccatcctctggcatgagatg
tggcatgaaggcctggaagaggcatctcgtttgtactttggggaaaggaacgtgaaaggcatgtttgaggtgctggag
cccttgcatgctatgatggaacggggcccccagactctgaaggaaacatcctttaatcaggcctatggtcgagattta
atggaggcccaagagtggtgcaggaagtacatgaaatcagggaatgtcaaggacctcacccaagcctgggacctctat
tatcatgtgttccgacgaatctca SEQ ID NO: 406 (pCA 62 L27V02A 85-169-FRB)
MDHHFKVILHYGTLVIDGVTPNMIDYFGRPYEGIAVFDGKKITVTGTLWNGNKIIDERLINPDGSLLFRVTINGVTGW
RLCERILAGGGGSGGGSSVAILWHEMWHEGLEEASRLYFGERNVKGMFEVLEPLHAMMERGPQTLKETSFNQAYGRDL
MEAQEWCRKYMKSGNVKDLTQAWDLYYHVFRRIS SEQ ID NO: 407 (pCA 63 FKBP L27V02A 1-122)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggc SEQ ID NO: 408 (pCA 63 FKBP L27V02A 1-122)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDG SEQ ID NO: 409 (pCA 64 L27V02A 123-169-FRB)
atgaaaaagatcactgtaacagggaccctgtggaacggcaacaaaattatcgacgagcgcctgatcaaccccgacggc
tccctgctgttccgagtaaccatcaacggagtgaccggctggcggctgtgcgaacgcattctggcgggaggaggtggc
tcaggtggagggagctccgtggccatcctctggcatgagatgtggcatgaaggcctggaagaggcatctcgtttgtac
tttggggaaaggaacgtgaaaggcatgtttgaggtgctggagcccttgcatgctatgatggaacggggcccccagact
ctgaaggaaacatcctttaatcaggcctatggtcgagatttaatggaggcccaagagtggtgcaggaagtacatgaaa
tcagggaatgtcaaggacctcacccaagcctgggacctctattatcatgtgttccgacgaatctca SEQ ID NO: 410 (pCA 64 L27V02A 123-169-FRB)
MKKITVTGTLWNGNKIIDERLINPDGSLLFRVTINGVTGWRLCERILAGGGGSGGGSSVAILWHEMWHEGLEEASRLY
FGERNVKGMFEVLEPLHAMMERGPQTLKETSFNQAYGRDLMEAQEWCRKYMKSGNVKDLTQAWDLYYHVFRRIS SEQ ID NO: 411 (pCA 65 FKBP L27V02A 1-123)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaa SEQ ID NO: 412 (pCA 65 FKBP L27V02A 1-123)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGK SEQ ID NO: 413 (pCA 66 L27V02A 124-169 FRB)
atgaagatcactgtaacagggaccctgtggaacggcaacaaaattatcgacgagcgcctgatcaaccccgacggctcc
ctgctgttccgagtaaccatcaacggagtgaccggctggcggctgtgcgaacgcattctggcgggaggaggtggctca
ggtggagggagctccgtggccatcctctggcatgagatgtggcatgaaggcctggaagaggcatctcgtttgtacttt
ggggaaaggaacgtgaaaggcatgtttgaggtgctggagcccttgcatgctatgatggaacggggcccccagactctg
aaggaaacatcctttaatcaggcctatggtcgagatttaatggaggcccaagagtggtgcaggaagtacatgaaatca
gggaatgtcaaggacctcacccaagcctgggacctctattatcatgtgttccgacgaatctca SEQ ID NO: 414 (pCA 66 L27V02A 124-169 FRB)
MKITVTGTLWNGNKIIDERLINPDGSLLFRVTINGVTGWRLCERILAGGGGSGGGSSVAILWHEMWHEGLEEASRLYF
GERNVKGMFEVLEPLHAMMERGPQTLKETSFNQAYGRDLMEAQEWCRKYMKSGNVKDLTQAWDLYYHVFRRIS

SEQUENCE LISTING

SEQ ID NO: 415 (pCA 67 L27V02A 1-168)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtgcgaacgc
attctg SEQ ID NO: 416 (pCA 67 L27V02A 1-168)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtgcgaacgc
attctg SEQ ID NO: 417 (pCA 67 L27V02A 1-168)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGVTGWRLCERIL SEQ ID NO: 418 (*pCA 68 L27V02A 169 FRB)
Atggcgggaggaggtggctcaggtggagggagctccgtggccatcctctggcatgagatgtggcatgaaggcctggaa
gaggcatctcgtttgtactttggggaaaggaacgtgaaaggcatgtttgaggtgctggagcccttgcatgctatgatg
gaacggggcccccagactctgaaggaaacatcctttaatcaggcctatggtcgagatttaatggaggcccaagagtgg
tgcaggaagtacatgaaatcagggaatgtcaaggacctcacccaagcctgggacctctattatcatgtgttccgacga
atctca SEQ ID NO: 419 (*pCA 68 L27V02A 169 FRB)
MAGGGGSGGGSSVAILWHEMWHEGLEEASRLYFGERNVKGMFEVLEPLHAMMERGPQTLKETSFNQAYGRDLMEAQEW
CRKYMKSGNVKDLTQAWDLYYHVFRRIS SEQ ID NO: 420 (pCA 69 FKBP L27V02A 1-166)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtgcgaacgc SEQ ID NO: 421 (pCA 69 FKBP L27V02A 1-166)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGVTGWRLCER SEQ ID NO: 422 (*pCA 70 L27V02A 167-169 FRB)
Atgattctggcgggaggaggtggctcaggtggagggagctccgtggccatcctctggcatgagatgtggcatgaaggc
ctggaagaggcatctcgtttgtactttggggaaaggaacgtgaaaggcatgtttgaggtgctggagcccttgcatgct
atgatggaacggggcccccagactctgaaggaaacatcctttaatcaggcctatggtcgagatttaatggaggcccaa
gagtggtgcaggaagtacatgaaatcagggaatgtcaaggacctcacccaagcctgggacctctattatcatgtgttc
cgacgaatctca SEQ ID NO: 423 (*pCA 70 L27V02A 167-169 FRB)
MILAGGGGSGGGSSVAILWHEMWHEGLEEASRLYFGERNVKGMFEVLEPLHAMMERGPQTLKETSFNQAYGRDLMEAQ
EWCRKYMKSGNVKDLTQAWDLYYHVFRRIS -continued

SEQUENCE LISTING

SEQ ID NO: 424 (pCA 71 FKBP L27V02A 1-164)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtgc SEQ ID NO: 425 (pCA 71 FKBP L27V02A 1-164)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGVTGWRLC SEQ ID NO: 426 (pCA 72 L27V02A 165-169 FRB)
atggaacgcattctggcgggaggaggtggctcaggtggagggagctccgtggccatcctctggcatgagatgtggcat
gaaggcctggaagaggcatctcgtttgtactttggggaaaggaacgtgaaaggcatgtttgaggtgctggagcccttg
catgctatgatggaacggggcccccagactctgaaggaaacatcctttaatcaggcctatggtcgagatttaatggag
gcccaagagtggtgcaggaagtacatgaaatcagggaatgtcaaggacctcacccaagcctgggacctctattatcat
gtgttccgacgaatctca SEQ ID NO: 427 (pattern sequence)
GSAIVK SEQ ID NO: 428 (pCA 72 L27V02A 165-169 FRB)
MERILAGGGGSGGGSSVAILWHEMWHEGLEEASRLYFGERNVKGMFEVLEPLHAMMERGPQTLKETSFNQAYGRDLME
AQEWCRKYMKSGNVKDLTQAWDLYYHVFRRIS SEQ ID NO: 429 (pCA 73 FKBP L27V02A 1-162)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcgg SEQ ID NO: 430 (pCA 73 FKBP L27V02A 1-162)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGVTGWR SEQ ID NO: 431 (pCA 74 L27V02A 163-169 FRB)
atgctgtgcgaacgcattctggcgggaggaggtggctcaggtggagggagctccgtggccatcctctggcatgagatg
tggcatgaaggcctggaagaggcatctcgtttgtactttggggaaaggaacgtgaaaggcatgtttgaggtgctggag
cccttgcatgctatgatggaacggggcccccagactctgaaggaaacatcctttaatcaggcctatggtcgagattta
atggaggcccaagagtggtgcaggaagtacatgaaatcagggaatgtcaaggacctcacccaagcctgggacctctat
tatcatgtgttccgacgaatctca SEQ ID NO: 432 (pCA 74 L27V02A 163-169 FRB)
MLCERILAGGGGSGGGSSVAILWHEMWHEGLEEASRLYFGERNVKGMFEVLEPLHAMMERGPQTLKETSFNQAYGRDL
MEAQEWCRKYMKSGNVKDLTQAWDLYYHVFRRIS SEQ ID NO: 433 (pCA 75 FKBP L27V02A 1-160)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggc

SEQUENCE LISTING

SEQ ID NO: 434 (pCA 75 FKBP L27V02A 1-160)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGVTG

SEQ ID NO: 435 (pCA 76 L27V02A 161-169 FRB)
atgtggcggctgtgcgaacgcattctggcgggaggaggtggctcaggtggagggagctccgtggccatcctctggcat
gagatgtggcatgaaggcctggaagaggcatctcgtttgtactttggggaaaggaacgtgaaaggcatgtttgaggtg
ctggagcccttgcatgctatgatggaacggggcccccagactctgaaggaaacatcctttaatcaggcctatggtcga
gatttaatggaggcccaagagtggtgcaggaagtacatgaaatcagggaatgtcaaggacctcacccaagcctgggac
ctctattatcatgtgttccgacgaatctca SEQ ID NO: 436 (pCA 76 L27V02A 161-169 FRB)
MWRLCERILAGGGGSGGGSSVAILWHEMWHEGLEEASRLYFGERNVKGMFEVLEPLHAMMERGPQTLKETSFNQAYGR
DLMEAQEWCRKYMKSGNVKDLTQAWDLYYHVFRRIS SEQ ID NO: 437 (pCA 77 FKBP L27V02A 1-158)
atgggagtgcaggtggaaaccatctccccaggagacgggcgcaccttccccaagcgcggccagacctgcgtggtgcac
tacaccgggatgcttgaagatggaaagaaatttgattcctcccgggacagaaacaagccctttaagtttatgctaggc
aagcaggaggtgatccgaggctgggaagaaggggttgcccagatgagtgtgggtcagagagccaaactgactatatct
ccagattatgcctatggtgccactgggcacccaggcatcatcccaccacatgccactctcgtcttcgatgtggagctt
ctaaaactggaaggaggagggagctccggtggaggcagcggtatggtcttcacactcgaagatttcgttggggactgg
cgacagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtg SEQ ID NO: 438 (pCA 77 FKBP L27V02A 1-158)
MGVQVETISPGDGRTFPKRGQTCVVHYTGMLEDGKKFDSSRDRNKPFKFMLGKQEVIRGWEEGVAQMSVGQRAKLTIS
PDYAYGATGHPGIIPPHATLVFDVELLKLEGGGSSGGGSGMVFTLEDFVGDWRQTAGYNLDQVLEQGGVSSLFQNLGV
SVTPIQRIVLSGENGLKIDIHVIIPYEGLSGDQMGQIEKIFKVVYPVDDHHFKVILHYGTLVIDGVTPNMIDYFGRPY
EGIAVFDGKKITVTGTLWNGNKIIDERLINPDGSLLFRVTINGV SEQ ID NO: 439 (pCA 78 L27V02A 159-169 FRB)
Atgaccggctggcggctgtgcgaacgcattctggcgggaggaggtggctcaggtggagggagctccgtggccatcctc
tggcatgagatgtggcatgaaggcctggaagaggcatctcgtttgtactttggggaaaggaacgtgaaaggcatgttt
gaggtgctggagcccttgcatgctatgatggaacggggcccccagactctgaaggaaacatcctttaatcaggcctat
ggtcgagatttaatggaggcccaagagtggtgcaggaagtacatgaaatcagggaatgtcaaggacctcacccaagcc
tgggacctctattatcatgtgttccgacgaatctca SEQ ID NO: 440 (pCA 78 L27V02A 159-169 FRB)
MTGWRLCERILAGGGGSGGGSSVAILWHEMWHEGLEEASRLYFGERNVKGMFEVLEPLHAMMERGPQTLKETSFNQAY
GRDLMEAQEWCRKYMKSGNVKDLTQAWDLYYHVFRRIS SEQ ID NO: 441 RIIbB (nt seq)
ATGTATGAAAGCTTTATTGAGTCACTGCCATTCCTTAAATCTTTGGAGTTTTCTGCACGCCTGAAAGTAGTAGATGTG
ATAGGCACCAAAGTATACAACGATGGAGAACAAATCATTGCTCAGGGAGATTCGGCTGATTCTTTTTTCATTATTGAA
TCTGGAGAAGTGAAAATTACTATGAAAAGAAAGGGTAAATCAGAAGTGGAAGAGAATGGTGCAGTAGAAATCGCTCGA
TGCTCGCGGGGACAGTACTTTGGAGAGCTTGCCCTGGTAACTAACAAACCTCGAGCAGCTTCTGCCCACGCCATTGGG
ACTGTCAAATGTTTAGCAATGGATGTGCAAGCATTTGAAAGGCTTCTGGGACCTTGCATGGAAATTATGAAAAGGAAC
ATCGCTACCTATGAAGAACAGTTAGTTGCCCTGTATGGAACGAACATGGATATTGTA SEQ ID NO: 442 RIIbB (aa seq)
MYESFIESLPFLKSLEFSARLKVVDVIGTKVYNDGEQIIAQGDSADSFFIIESGEVKITMKRKGKSEVEENGAVEIAR
CSRGQYFGELALVTNKPRAASAHAIGTVKCLAMDVQAFERLLGPCMEIMKRNIATYEEQLVALYGTNMDIV SEQ ID NO: 443 (L27V CP 13 TEV)
atgacagccggctacaacctggaccaagtccttgagcagggcggtgtgtccagtttgtttcagaatctcggggtgtcc
gtaactccgatccaaaggattgtcctgagcggtgaaaacggcctgaagatcgacatccatgtcatcatcccgtatgaa
ggtctgagcggcgatcagatgggccagatcgaaaaaatttttaaggtggtgtaccctgtggatgatcatcactttaag
gtgattctgcactatggcacactggtaatcgacggggttacgccgaacatgatcgactatttcggacggccgtatgaa
ggcatcgccgtgttcgacggcaaaaagatcactgtaaccgggaccctgtggaacggcaacaaaattatcgacgagcgc
ctgatcaaccccgacggctccctgctgttccgcgtaaccatcaacggagtgaccggctggcggctgtgcgagcgcatt
ttggcgggaagttctggtggaggaagttctggtggagagcctactactgagaacttgtacttccagagcgataacgga
agttctggtggaggaagttctggtggaatggtgtttacactcgaagatttcgtaggggactggcggcag SEQ ID NO: 444 (L27V CP 13 TEV)
MTAGYNLDQVLEQGGVSSLFQNLGVSVTPIQRIVLSGENGLKIDIHVIIPYEGLSGDQMGQIEKIFKVVYPVDDHHFK
VILHYGTLVIDGVTPNMIDYFGRPYEGIAVFDGKKITVTGTLWNGNKIIDERLINPDGSLLFRVTINGVTGWRLCERI
LAGSSGGGSSGGEPTTENLYFQSDNGSSGGGSSGGMVFTLEDFVGDWRQ SEQ ID NO: 445 (L27V CP 57 TEV)
Atgcatgtcatcatcccgtatgaaggtctgagcggcgatcagatgggccagatcgaaaaaatttttaaggtggtgtac
cctgtggatgatcatcactttaaggtgattctgcactatggcacactggtaatcgacggggttacgccgaacatgatc -continued

SEQUENCE LISTING gactatttcggacggccgtatgaaggcatcgccgtgttcgacggcaaaaagatcactgtaaccgggaccctgtggaac
ggcaacaaaattatcgacgagcgcctgatcaaccccgacggctccctgctgttccgcgtaaccatcaacggagtgacc
ggctggcggctgtgcgagcgcattttggcgggaagttctggtggaggaagttctggtggagagcctactactgagaac
ttgtacttccagagcgataacggaagttctggtggaggaagttctggtggaatggtgtttacactcgaagatttcgta
ggggactggcggcagacagccggctacaacctggaccaagtccttgagcagggcggtgtgtccagtttgtttcagaat
ctcggggtgtccgtaactccgatccaaaggattgtcctgagcggtgaaaacggcctgaagatcgacatc SEQ ID NO: 446 (L27V CP 57 TEV)
MHVIIPYEGLSGDQMGQIEKIFKVVYPVDDHHFKVILHYGTLVIDGVTPNMIDYFGRPYEGIAVFDGKKITVTGTLWN
GNKIIDERLINPDGSLLFRVTINGVTGWRLCERILAGSSGGGSSGGEPTTENLYFQSDNGSSGGGSSGGMVFTLEDFV
GDWRQTAGYNLDQVLEQGGVSSLFQNLGVSVTPIQRIVLSGENGLKIDI SEQ ID NO: 447 (L27V CP 98 TEV)
atggtaatcgacggggttacgccgaacatgatcgactatttcggacggccgtatgaaggcatcgccgtgttcgacggc
aaaaagatcactgtaaccgggaccctgtggaacggcaacaaaattatcgacgagcgcctgatcaaccccgacggctcc
ctgctgttccgcgtaaccatcaacggagtgaccggctggcggctgtgcgagcgcattttggcgggaagttctggtgga
ggaagttctggtggagagcctactactgagaacttgtacttccagagcgataacggaagttctggtggaggaagttct
ggtggaatggtgtttacactcgaagatttcgtaggggactggcggcagacagccggctacaacctggaccaagtcctt
gagcagggcggtgtgtccagtttgtttcagaatctcggggtgtccgtaactccgatccaaaggattgtcctgagcggt
gaaaacggcctgaagatcgacatccatgtcatcatcccgtatgaaggtctgagcggcgatcagatgggccagatcgaa
aaaatttttaaggtggtgtaccctgtggatgatcatcactttaaggtgattctgcactatggcacactg SEQ ID NO: 448 (L27V CP 98 TEV)
MVIDGVTPNMIDYFGRPYEGIAVFDGKKITVTGTLWNGNKIIDERLINPDGSLLFRVTINGVTGWRLCERILAGSSGG
GSSGGEPTTENLYFQSDNGSSGGGSSGGMVFTLEDFVGDWRQTAGYNLDQVLEQGGVSSLFQNLGVSVTPIQRIVLSG
ENGLKIDIHVIIPYEGLSGDQMGQIEKIFKVVYPVDDHHFKVILHYGTL SEQ ID NO: 449 (Human Protein Kinase C alpha (PKCa) (nt sequence)
ATGGCTGACGTTTTCCCGGGCAACGACTCCACGGCGTCTCAGGACGTGGCCAACCGCTTCGCCCGCAAAGGGGCGCTG
AGGCAGAAGAACGTGCACGAGGTGAAGGACCACAAATTCATCGCGCGCTTCTTCAAGCAGCCCACCTTCTGCAGCCAC
TGCACCGACTTCATCTGGGGGTTTGGGAAACAAGGCTTCCAGTGCCAAGTTTGCTGTTTTGTGGTCCACAAGAGGTGC
CATGAATTTGTTACTTTTTCTTGTCCGGGTGCGGATAAGGGACCCGACACTGATGACCCCAGGAGCAAGCACAAGTTC
AAAATCCACACTTACGGAAGCCCCACCTTCTGCGATCACTGTGGGTCACTGCTCTATGGACTTATCCATCAAGGGATG
AAATGTGACACCTGCGATATGAACGTTCACAAGCAATGCGTCATCAATGTCCCCAGCCTCTGCGGAATGGATCACACT
GAGAAGAGGGGGCGGATTTACCTAAAGGCTGAGGTTGCTGATGAAAAGCTCCATGTCACAGTACGAGATGCAAAAAAT
CTAATCCCTATGGATCCAAACGGGCTTTCAGATCCTTATGTGAAGCTGAAACTTATTCCTGATCCCAAGAATGAAAGC
AAGCAAAAAACCAAAACCATCCGCTCCACACTAAATCCGCAGTGGAATGAGTCCTTTACATTCAAATTGAAACCTTCA
GACAAAGACCGACGACTGTCTGTAGAAATCTGGGACTGGGATCGAACAACAAGGAATGACTTCATGGGATCCCTTTCC
TTTGGAGTTTCGGAGCTGATGAAGATGCCGGCCAGTGGATGGTACAAGTTgCTTAACCAAGAAGAAGGTGAGTACTAC
AACGTACCCATTCCGGAAGGGGACGAGGAAGGAAACATGGAACTCAGGCAGAAATTCGAGAAAGCCAAACTTGGCCCT
GCTGGCAACAAAGTCATCAGTCCCTCTGAAGACAGGAAACAACCTTCCAACAACCTTGACCGAGTGAAACTCACGGAC
TTCAATTTCCTCATGGTGTTGGGAAAGGGGAGTTTTGGAAAGGTGATGCTTGCCGACAGGAAGGGCACAGAAGAACTG
TATGCAATCAAAATCCTGAAGAAGGATGTGGTGATTCAGGATGATGACGTGGAGTGCACCATGGTAGAAAAGCGAGTC
TTGGCCCTGCTTGACAAACCCCCGTTCTTGACGCAGCTGCACTCCTGCTTCCAGACAGTGGATCGGCTGTACTTCGTC
ATGGAATATGTCAACGGTGGGGACCTCATGTACCACATTCAGCAAGTAGGAAAATTTAAGGAACCACAAGCAGTATTC
TATGCGGCAGAGATTTCCATCGGATTGTTCTTTCTTCATAAAAGAGGAATCATTTATAGGGATCTGAAGTTAGATAAC
GTCATGTTGGATTCAGAAGGACATATCAAAATTGCTGACTTTGGGATGTGCAAGGAACACATGATGGATGGAGTCACG
ACCAGGACCTTCTGTGGGACTCCAGATTATATCGCCCCAGAGATAATCGCTTATCAGCCGTATGGAAAATCTGTGGAC
TGGTGGGCCTATGGCGTCCTGTTGTATGAAATGCTTGCCGGGCAGCCTCCATTTGATGGTGAAGATGAAGACGAGCTA
TTTCAGTCTATCATGGAGCACAACGTTTCCTATCCAAAATCCTTGTCCAAGGAGGCTGTTTCTATCTGCAAAGGACTG
ATGACCAAACACCCAGCCAAGCGGCTGGGCTGTGGGCCTGAGGGGGAGAGGGACGTGAGAGAGCATGCCTTCTTCCGG
AGGATCGACTGGGAAAAACTGGAGAACAGGGAGATCCAGCCACCATTCAAGCCCAAAGTGTGTGGCAAAGGAGCAGAG
AACTTTGACAAGTTCTTCACACGAGGACAGCCCGTCTTAACACCACCTGATCAGCTGGTTATTGCTAACATAGACCAG
TCTGATTTTGAAGGGTTCTCGTATGTCAACCCCCAGTTTGTGCACCCCATCTTACAGAGTGCAGTAGTT SEQ ID NO: 450 (Human Protein Kinase C alpha (PKCa) (aa sequence)
MADVFPGNDSTASQDVANRFARKGALRQKNVHEVKDHKFIARFFKQPTFCSHCTDFIWGFGKQGFQCQVCCFVVHKRC
HEFVTFSCPGADKGPDTDDPRSKHKFKIHTYGSPTFCDHCGSLLYGLIHQGMKCDTCDMNVHKQCVINVPSLCGMDHT
EKRGRIYLKAEVADEKLHVTVRDAKNLIPMDPNGLSDPYVKLKLIPDPKNESKQKTKTIRSTLNPQWNESFTFKLKPS
DKDRRLSVEIWDWDRTTRNDFMGSLSFGVSELMKMPASGWYKLLNQEEGEYYNVPIPEGDEEGNMELRQKFEKAKLGP
AGNKVISPSEDRKQPSNNLDRVKLTDFNFLMVLGKGSFGKVMLADRKGTEELYAIKILKKDVVIQDDDVECTMVEKRV
LALLDKPPFLTQLHSCFQTVDRLYFVMEYVNGGDLMYHIQQVGKFKEPQAVFYAAEISIGLFFLHKRGIIYRDLKLDN
VMLDSEGHIKIADFGMCKEHMMDGVTTRTFCGTPDYIAPEIIAYQPYGKSVDWWAYGVLLYEMLAGQPPFDGEDEDEL
FQSIMEHNVSYPKSLSKEAVSICKGLMTKHPAKRLGCGPEGERDVREHAFFRRIDWEKLENREIQPPFKPKVCGKGAE
NFDKFFTRGQPVLTPPDQLVIANIDQSDFEGFSYVNPQFVHPILQSAVV SEQ ID NO: 451 (Human Glucocorticoid receptor (GR) (nt sequence)
ATGGACTCCAAAGAATCATTAACTCCTGGTAGAGAAGAAAACCCCAGCAGTGTGCTTGCTCAGGAGAGGGGAGATGTG
ATGGACTTCTATAAAACCCTAAGAGGAGGAGCTACTGTGAAGGTTTCTGCGTCTTCACCCTCACTGGCTGTCGCTTCT
CAATCAGACTCCAAGCAGCGAAGACTTTTGGTTGATTTTCCAAAAGGCTCAGTAAGCAATGCGCAGCAGCCAGATCTG
TCCAAAGCAGTTTCACTCTCAATGGGACTGTATATGGGAGAGACAGAAACAAAAGTGATGGGAAATGACCTGGGATTC
CCACAGCAGGGCCAAATCAGCCTTTCCTCGGGGGAAACAGACTTAAAGCTTTTGGAAGAAAGCATTGCAAACCTCAAT
AGGTCGACCAGTGTTCCAGAGAACCCCAAGAGTTCAGCATCCACTGCTGTGTCTGCTGCCCCCACAGAGAAGGAGTTT
CCAAAAACTCACTCTGATGTATCTTCAGAACAGCAACATTTGAAGGGCCAGACTGGCACCAACGGTGGCAATGTGAAA
TTGTATACCACAGACCAAAGCACCTTTGACATTTTGCAGGATTTGGAGTTTTCTTCTGGGTCCCCAGGTAAAGAGACG
AATGAGAGTCCTTGGAGATCAGACCTGTTGATAGATGAAAACTGTTTGCTTTCTCCTCTGGCGGGAGAAGACGATTCA
TTCCTTTTGGAAGGAAACTCGAATGAGGACTGCAAGCCTCTCATTTTACCGGACACTAAACCCAAAATTAAGGATAAT

SEQUENCE LISTING

GGAGATCTGGTTTTGTCAAGCCCCAGTAATGTAACACTGCCCCAAGTGAAAACAGAAAAAGAAGATTTCATCGAACTC
TGCACCCCTGGGGTAATTAAGCAAGAGAAACTGGGCACAGTTTACTGTCAGGCAAGCTTTCCTGGAGCAAATATAATT
GGTAATAAAATGTCTGCCATTTCTGTTCATGGTGTGAGTACCTCTGGAGGACAGATGTACCACTATGACATGAATACA
GCATCCCTTTCTCAACAGCAGGATCAGAAGCCTATTTTTAATGTCATTCCACCAATTCCCGTTGGTTCCGAAAATTGG
AATAGGTGCCAAGGATCTGGAGATGACAACTTGACTTCTCTGGGGACTCTGAACTTCCCTGGTCGAACAGTTTTTTCT
AATGGCTATTCAAGCCCCAGCATGAGACCAGATGTAAGCTCTCCTCCATCCAGCTCCTCAACAGCAACAACAGGACCA
CCTCCCAAACTCTGCCTGGTGTGCTCTGATGAAGCTTCAGGATGTCATTATGGAGTCTTAACTTGTGGAAGCTGTAAA
GTTTTCTTCAAAAGAGCAGTGGAAGGACAGCACAATTACCTATGTGCTGGAAGGAATGATTGCATCATCGATAAAATT
CGAAGAAAAAACTGCCCAGCATGCCGCTATCGAAAATGTCTTCAGGCTGGAATGAACCTGGAAGCTCGAAAAACAAAG
AAAAAAATAAAAGGAATTCAGCAGGCCACTACAGGAGTCTCACAAGAAACCTCTGAAAATCCTGGTAACAAAACAATA
GTTCCTGCAACGTTACCACAACTCACCCCTACCCTGGTGTCACTGTTGGAGGTTATTGAACCTGAAGTGTTATATGCA
GGATATGATAGCTCTGTTCCAGACTCAACTTGGAGGATCATGACTACGCTCAACATGTTAGGAGGGCGGCAAGTGATT
GCAGCAGTGAAATGGGCAAAGGCAATACCAGGTTTCAGGAACTTACACCTGGATGACCAAATGACCCTACTGCAGTAC
TCCTGGATGTTTCTTATGGCATTTGCTCTGGGGTGGAGATCATATAGACAATCAAGTGCAAACCTGCTGTGTTTTGCT
CCTGATCTGATTATTAATGAGCAGAGAATGACTCTACCCTGCATGTACGACCAATGTAAACACATGCTGTATGTTTCC
TCTGAGTTACACAGGCTTCAGGTATCTTATGAAGAGTATCTCTGTATGAAAACCTTACTGCTTCTCTCTTCAGTTCCT
AAGGACGGTCTGAAGAGCCAAGAGCTATTTGATGAAATTAGAATGACCTACATCAAAGAGCTAGGAAAAGCCATTGTC
AAGAGGGAAGGAAACTCCAGCCAGAACTGGCAGCGGTTTTATCAACTGACAAAACTCTTGGATTCTATGCATGAAGTG
GTTGAAAATCTCCTTAACTATTGCTTCCAAACATTTTTGGATAAGACCATGAGTATTGAATTCCCCGAGATGTTAGCT
GAAATCATCACCAATCAGATACCAAAATATTCAAATGGAAATATCAAAAAACTTCTGTTTCATCAAAAGGTT

SEQ ID NO: 452 (Human Glucocorticoid receptor (GR) (aa sequence)
MDSKESLTPGREENPSSVLAQERGDVMDFYKTLRGGATVKVSASSPSLAVASQSDSKQRRLLVDFPKGSVSNAQQPDL
SKAVSLSMGLYMGETETKVMGNDLGFPQQGQISLSSGETDLKLLEESIANLNRSTSVPENPKSSASTAVSAAPTEKEF
PKTHSDVSSEQQHLKGQTGTNGGNVKLYTTDQSTFDILQDLEFSSGSPGKETNESPWRSDLLIDENCLLSPLAGEDDS
FLLEGNSNEDCKPLILPDTKPKIKDNGDLVLSSPSNVTLPQVKTEKEDFIELCTPGVIKQEKLGTVYCQASFPGANII
GNKMSAISVHGVSTSGGQMYHYDMNTASLSQQQDQKPIFNVIPPIPVGSENWNRCQGSGDDNLTSLGTLNFPGRTVFS
NGYSSPSMRPDVSSPPSSSSTATTGPPPKLCLVCSDEASGCHYGVLTCGSCKVFFKRAVEGQHNYLCAGRNDCIIDKI
RRKNCPACRYRKCLQAGMNLEARKTKKKIKGIQQATTGVSQETSENPGNKTIVPATLPQLTPTLVSLLEVIEPEVLYA
GYDSSVPDSTWRIMTTLNMLGGRQVIAAVKWAKAIPGFRNLHLDDQMTLLQYSWMFLMAFALGWRSYRQSSANLLCFA
PDLIINEQRMTLPCMYDQCKHMLYVSSELHRLQVSYEEYLCMKTLLLLSSVPKDGLKSQELFDEIRMTYIKELGKAIV
KREGNSSQNWQRFYQLTKLLDSMHEVVENLLNYCFQTFLDKTMSIEFPEMLAEIITNQIPKYSNGNIKKLLFHQKV SEQ ID NO: 453 (L27V02-GR/L27V02-PKCa linker (nt sequence)
GGTGGTTCAGGTGGTGGCGGGAGCGGTGGAGGGAGCAGCGGTGGAGCGATCGCC SEQ ID NO: 454 (L27V02-GR/L27V02-PKCa linker (aa sequence)
GGSGGGGSGGGSSGGAIA SEQ ID NO: 455 (GR-L27V02/PKCa-L27V02 linker (nt sequence)
TCTCTCGGTGGTTCAGGTGGTGGCGGGAGCGGTGGAGGGAGCAGCGGTGGA SEQ ID NO: 456 (GR-L27V02/PKCa-L27V02 linker (aa sequence)
SLGGSGGGGSGGGSSGG SEQ ID NO: 457 (GSSG linker (nt sequence)
GCTCGAGCGGA SEQ ID NO: 458 (GSSG linker (aa sequence)
GSSG SEQ ID NO: 459 (AT1R (nt sequence)
ATGATTCTCAACTCTTCTACTGAAGATGGTATTAAAAGAATCCAAGATGATTGTCCCAAAGCTGGAAGGCATAATTAC
ATATTTGTCATGATTCCTACTTTATACAGTATCATCTTTGTGGTGGGAATATTTGGAAACAGCTTGGTGGTGATAGTC
ATTTACTTTTATATGAAGCTGAAGACTGTGGCCAGTGTTTTTCTTTTGAATTTAGCACTGGCTGACTTATGCTTTTTA
CTGACTTTGCCACTATGGGCTGTCTACACAGCTATGGAATACCGCTGGCCCTTTGGCAATTACCTATGTAAGATTGCT
TCAGCCAGCGTCAGTTTCAACCTGTACGCTAGTGTGTTTCTACTCACGTGTCTCAGCATTGATCGATACCTGGCTATT
GTTCACCCAATGAAGTCCCGCCTTCGACGCACAATGCTTGTAGCCAAAGTCACCTGCATCATCATTTGGCTGCTGGCA
GGCTTGGCCAGTTTGCCAGCTATAATCCATCGAAATGTATTTTTCATTGAGAACACCAATATTACAGTTTGTGCTTTC
CATTATGAGTCCCAAAATTCAACCCTTCCGATAGGGCTGGGCCTGACCAAAAATATACTGGGTTTCCTGTTTCCTTTT
CTGATCATTCTTACAAGTTATACTCTTATTTGGAAGGCCCTAAAGAAGGCTTATGAAATTCAGAAGAACAAACCAAGA
AATGATGATATTTTTAAGATAATTATGGCAATTGTGCTTTTCTTTTTCTTTTCCTGGATTCCCCACCAAATATTCACT
TTTCTGGATGTATTGATTCAACTAGGCATCATACGTGACTGTAGAATTGCAGATATTGTGGACACGGCCATGCCTATC
ACCATTTGTATAGCTTATTTTAACAATTGCCTGAATCCTCTTTTTTATGGCTTTCTGGGGAAAAAATTTAAAAGATAT
TTTCTCCAGCTTCTAAAATATATTCCCCCAAAAGCCAAATCCCACTCAAACCTTTCAACAAAAATGAGCACGCTTTCC
TACCGCCCCTCAGATAATGTAAGCTCATCCACCAAGAAGCCTGCACCATGTTTTGAGGTTGAGTGA SEQ ID NO: 460 (AT1R (aa sequence)
MILNSSTEDGIKRIQDDCPKAGRHNYIFVMIPTLYSIIFVVGIFGNSLVVIVIYFYMKLKTVASVFLLNLALADLCFL
LTLPLWAVYTAMEYRWPFGNYLCKIASASVSFNLYASVFLLTCLSIDRYLAIVHPMKSRLRRTMLVAKVTCIIIWLLA
GLASLPAIIHRNVFFIENTNITVCAFHYESQNSTLPIGLGLTKNILGFLFPFLIILTSYTLIWKALKKAYEIQKNKPR
NDDIFKIIMAIVLFFFFSWIPHQIFTFLDVLIQLGIIRDCRIADIVDTAMPITICIAYFNNCLNPLFYGFLGKKFKRY
FLQLLKYIPPKAKSHSNLSTKMSTLSYRPSDNVSSSTKKPAPCFEVE SEQ ID NO: 461 (IL6-00 signal peptide (nt sequence)
ATGAACTCCTTCTCCACAAGCGCCTTCGGTCCAGTTGCCTTCTCCCTGGGGCTGCTCCTGGTGTTGCCTGCTGCCTTC
CCTGCCCCA -continued

SEQUENCE LISTING

SEQ ID NO: 462 (IL6-00 signal peptide (aa sequence)
MNSFSTSAFGPVAFSLGLLLVLPAAFPAP SEQ ID NO: 463 (IL6-00 L27V-00 (nt sequence)
ATGAACTCCTTCTCCACAAGCGCCTTCGGTCCAGTTGCCTTCTCCCTGGGGCTGCTCCTGGTGTTGCCTGCTGCCTTC
CCTGCCCCAGTGTTTACACTCGAAGATTTCGTAGGGGACTGGCGGCAGACAGCCGGCTACAACCTGGACCAAGTCCTT
GAGCAGGGCGGTGTGTCCAGTTTGTTTCAGAATCTCGGGGTGTCCGTAACTCCGATCCAAAGGATTGTCCTGAGCGGT
GAAAACGGCCTGAAGATCGACATCCATGTCATCATCCCGTATGAAGGTCTGAGCGGCGATCAGATGGGCCAGATCGAA
AAAATTTTTAAGGTGGTGTACCCTGTGGATGATCATCACTTTAAGGTGATTCTGCACTATGGCACACTGGTAATCGAC
GGGGTTACGCCGAACATGATCGACTATTTCGGACGGCCGTATGAAGGCATCGCCGTGTTCGACGGCAAAAAGATCACT
GTAACCGGGACCCTGTGGAACGGCAACAAAATTATCGACGAGCGCCTGATCAACCCCGACGGCTCCCTGCTGTTCCGC
GTAACCATCAACGGAGTGACCGGCTGGCGGCTGTGCGAGCGCATTTTGGCG SEQ ID NO: 464 (IL6-00 L27V-00 (aa sequence)
MNSFSTSAFGPVAFSLGLLLVLPAAFPAPVFTLEDEVGDWRQTAGYNLDQVLEQGGVSSLFQNLGVSVTPIQRIVLSG
ENGLKIDIHVIIPYEGLSGDQMGQIEKIFKVVYPVDDHHFKVILHYGTLVIDGVTPNMIDYFGRPYEGIAVFDGKKIT
VTGTLWNGNKIIDERLINPDGSLLFRVTINGVTGWRLCERILA SEQ ID NO: 465 (Native secretion signal + L27V (nt sequence)
atggcttactccacactgttcatcattgctctcacagccgtcgtaacacaagcctcctccacacagaaaagcaacctg
acaGTGTTTACACTCGAAGATTTCGTAGGGGACTGGCGGCAGACAGCCGGCTACAACCTGGACCAAGTCCTTGAGCAG
GGCGGTGTGTCCAGTTTGTTTCAGAATCTCGGGGTGTCCGTAACTCCGATCCAAAGGATTGTCCTGAGCGGTGAAAAC
GGCCTGAAGATCGACATCCATGTCATCATCCCGTATGAAGGTCTGAGCGGCGATCAGATGGGCCAGATCGAAAAAATT
TTTAAGGTGGTGTACCCTGTGGATGATCATCACTTTAAGGTGATTCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGCGCATTTTGGCG SEQ ID NO: 466 (Native secretion signal + L27V (aa sequence)
MAYSTLFIIALTAVVTQASSTQKSNLTVFTLEDEVGDWRQTAGYNLDQVLEQGGVSSLFQNLGVSVTPIQRIVLSGEN
GLKIDIHVIIPYEGLSGDQMGQIEKIFKVVYPVDDHHFKVILHYGTLVIDGVTPNMIDYFGRPYEGIAVFDGKKITVT
GTLWNGNKIIDERLINPDGSLLFRVTINGVTGWRLCERILA SEQ ID NO: 467 (CP 6 L27V (RIIbB) (nt sequence) (nt sequence)
Atgttcgttggggactggcgacagacagccggctacaacctggaccaagtccttgaacagggaggtgtgtccagtttg
tttcagaatctcggggtgtccgtaactccgatccaaaggattgtcctgagcggtgaaaatgggctgaagatcgacatc
catgtcatcatcccgtatgaaggtctgagcggcgaccaaatgggccagatcgaaaaaatttttaaggtggtgtaccct
gtggatgatcatcactttaaggtgatcctgcactatggcacactggtaatcgacggggttacgccgaacatgatcgac
tatttcggacggccgtatgaaggcatcgccgtgttcgacggcaaaaagatcactgtaacagggaccctgtggaacggc
aacaaaattatcgacgagcgcctgatcaaccccgacggctccctgctgttccgagtaaccatcaacggagtgaccggc
tggcggctgtGCGAACGCATTCTGGCtAGCTCAAGCGGAGGTTCAGGCGGTTCCGGAATGTATGAAAGCTTTATTGAG
TCACTGCCATTCCTTAAATCTTTGGAGTTTTCTGCACGCCTGAAAGTAGTAGATGTGATAGGCACCAAAGTATACAAC
GATGGAGAACAAATCATTGCTCAGGGAGATTCGGCTGATTCTTTTTTCATTATTGAATCTGGAGAAGTGAAAATTACT
ATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATG
GATGTGCAAGCATTTGAAAGGCTTCTGGGACCTTGCATGGAAATTATGAAAAGGAACATCGCTACCTATGAAGAACAG
TTAGTTGCCCTGTATGGAACGAACATGGATATTGTAGGGTCAGGTGGATCTGGAGGTAGCTCTTCTatggtCttcaca
ctcgaagat SEQ ID NO: 468 (CP 6 L27V (RIIbB) (aa seq)
MFVGDWRQTAGYNLDQVLEQGGVSSLFQNLGVSVTPIQRIVLSGENGLKIDIHVIIPYEGLSGDQMGQIEKIFKVVYP
VDDHHFKVILHYGTLVIDGVTPNMIDYFGRPYEGIAVFDGKKITVTGTLWNGNKIIDERLINPDGSLLFRVTINGVTG
WRLCERILASSSGGSGGSGMYESFIESLPFLKSLEFSARLKVVDVIGTKVYNDGEQIIAQGDSADSFFIIESGEVKIT
MKRKGKSEVEENGAVEIARCSRGQYFGELALVTNKPRAASAHAIGTVKCLAMDVQAFERLLGPCMEIMKRNIATYEEQ
LVALYGTNMDIVGSGGSGGSSSMVFTLED SEQ ID NO: 469 (CP 12 L27V (RIIbB) (nt sequence) (nt sequence)
ATGcagacagccggctacaacctggaccaagtccttgaacagggaggtgtgtccagtttgtttcagaatctcggggtg
tccgtaactccgatccaaaggattgtcctgagcggtgaaaatgggctgaagatcgacatccatgtcatcatcccgtat
gaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgag
cgcctgatcaaccccgacggctccctgctgttccgagtaaccatcaacggagtgaccggctggcggctgtGCGAACGC
ATTCTGGCtAGCTCAAGCGGAGGTTCAGGCGGTTCCGGAATGTATGAAAGCTTTATTGAGTCACTGCCATTCCTTAAA
TCTTTGGAGTTTTCTGCACGCCTGAAAGTAGTAGATGTGATAGGCACCAAAGTATACAACGATGGAGAACAAATCATT
GCTCAGGGAGATTCGGCTGATTCTTTTTTCATTATTGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTA
ACTAACAAACCTCGAGCAGCTTCTGCCCACGCCATTGGGACTGTCAAATGTTTAGCAATGGATGTGCAAGCATTTGAA
AGGCTTCTGGGACCTTGCATGGAAATTATGAAAAGGAACATCGCTACCTATGAAGAACAGTTAGTTGCCCTGTATGGA
ACGAACATGGATATTGTAGGGTCAGGTGGATCTGGAGGTAGCTCTTCTatggtcttcacactcgaagatttcgttggg
gactggcga SEQ ID NO: 470 (CP 12 L27V (RIIbB) (aa seq)
MQTAGYNLDQVLEQGGVSSLFQNLGVSVTPIQRIVLSGENGLKIDIHVIIPYEGLSGDQMGQIEKIFKVVYPVDDHHF
KVILHYGTLVIDGVTPNMIDYFGRPYEGIAVFDGKKITVTGTLWNGNKIIDERLINPDGSLLFRVTINGVTGWRLCER
ILASSSGGSGGSGMYESFIESLPFLKSLEFSARLKVVDVIGTKVYNDGEQIIAQGDSADSFFIIESGEVKITMKRKGK

SEQUENCE LISTING

SEVEENGAVEIARCSRGQYFGELALVTNKPRAASAHAIGTVKCLAMDVQAFERLLGPCMEIMKRNIATYEEQLVALYG
TNMDIVGSGGSGGSSSMVFTLEDFVGDWR

SEQ ID NO: 471 (CP 48 L27V (RIIbB) (nt sequence)
ATGggtgaaaatgggctgaagatcgacatccatgtcatcatcccgtatgaaggtctgagcggcgaccaaatgggccag
atcgaaaaaatttttaaggtggtgtaccctgtggatgatcatcactttaaggtgatcctgcactatggcacactggta
atcgacggggttacgccgaacatgatcgactatttcggacggccgtatgaaggcatcgccgtgttcgacggcaaaaag
atcactgtaacagggaccctgtggaacggcaacaaaattatcgacgagcgcctgatcaaccccgacggctccctgctg
ttccgagtaaccatcaacggagtgaccggctggcggctgtGCGAACGCATTCTGGCtAGCTCAAGCGGAGGTTCAGGC
GGTTCCGGAATGTATGAAAGCTTTATTGAGTCACTGCCATTCCTTAAATCTTTGGAGTTTTCTGCACGCCTGAAAGTA
GTAGATGTGATAGGCACCAAAGTATACAACGATGGAGAACAAATCATTGCTCAGGGAGATTCGGCTGATTCTTTTTTC
ATTATTGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCAC
GCCATTGGGACTGTCAAATGTTTAGCAATGGATGTGCAAGCATTTGAAAGGCTTCTGGGACCTTGCATGGAAATTATG
AAAAGGAACATCGCTACCTATGAAGAACAGTTAGTTGCCCTGTATGGAACGAACATGGATATTGTAGGGTCAGGTGGA
TCTGGAGGTAGCTCTTCTatggtcttcacactcgaagatttcgttggggactggcgacagacagccggctacaacctg
gaccaagtccttgaacagggaggtgtgtccagtttgtttcagaatctcggggtgtccgtaactccgatccaaaggatt
gtcctgagc SEQ ID NO: 472 (CP 48 L27V (RIIbB) (aa seq)
MGENGLKIDIHVIIPYEGLSGDQMGQIEKIFKVVYPVDDHHFKVILHYGTLVIDGVTPNMIDYFGRPYEGIAVFDGKK
ITVTGTLWNGNKIIDERLINPDGSLLFRVTINGVTGWRLCERILASSSGGSGGSGMYESFIESLPFLKSLEFSARLKV
VDVIGTKVYNDGEQIIAQGDSADSFFIIESGEVKITMKRKGKSEVEENGAVEIARCSRGQYFGELALVTNKPRAASAH
AIGTVKCLAMDVQAFERLLGPCMEIMKRNIATYEEQLVALYGTNMDIVGSGGSGGSSSMVFTLEDFVGDWRQTAGYNL
DQVLEQGGVSSLFQNLGVSVTPIQRIVLS SEQ ID NO: 473 (CP 52 L27V (RIIbB) (nt sequence)
ATGCTGAAGATCGACATCCATGTCATCATCCCGTATGAAGGTCTGAGCGGCGACCAAATGGGCCAGATCGAAAAAATT
TTTAAGGTGGTGTACCCTGTGGATGATCATCACTTTAAGGTGATCCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACA
GGGACCCTGTGGAACGGCAACAAAATTATCGACGAGCGCCTGATCAACCCCGACGGCTCCCTGCTGTTCCGAGTAACC
ATCAACGGAGTGACCGGCTGGCGGCTGTGCGAACGCATTCTGGCTAGCTCAAGCGGAGGTTCAGGCGGTTCCGGAATG
TATGAAAGCTTTATTGAGTCACTGCCATTCCTTAAATCTTTGGAGTTTTCTGCACGCCTGAAAGTAGTAGATGTGATA
GGCACCAAAGTATACAACGATGGAGAACAAATCATTGCTCAGGGAGATTCGGCTGATTCTTTTTTCATTATTGAATCT
GGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACT
GTCAAATGTTTAGCAATGGATGTGCAAGCATTTGAAAGGCTTCTGGGACCTTGCATGGAAATTATGAAAAGGAACATC
GCTACCTATGAAGAACAGTTAGTTGCCCTGTATGGAACGAACATGGATATTGTAGGGTCAGGTGGATCTGGAGGTAGC
TCTTCTATGGTCTTCACACTCGAAGATTTCGTTGGGGACTGGCGACAGACAGCCGGCTACAACCTGGACCAAGTCCTT
GAACAGGGAGGTGTGTCCAGTTTGTTTCAGAATCTCGGGGTGTCCGTAACTCCGATCCAAAGGATTGTCCTGAGCGGT
GAAAATGGG SEQ ID NO: 474 (CP 52 L27V (RIIbB) (aa seq)
MLKIDIHVIIPYEGLSGDQMGQIEKIFKVVYPVDDHHFKVILHYGTLVIDGVTPNMIDYFGRPYEGIAVFDGKKITVT
GTLWNGNKIIDERLINPDGSLLFRVTINGVTGWRLCERILASSSGGSGGSGMYESFIESLPFLKSLEFSARLKVVDVI
GTKVYNDGEQIIAQGDSADSFFIIESGEVKITMKRKGKSEVEENGAVEIARCSRGQYFGELALVTNKPRAASAHAIGT
VKCLAMDVQAFERLLGPCMEIMKRNIATYEEQLVALYGTNMDIVGSGGSGGSSSMVFTLEDFVGDWRQTAGYNLDQVL
EQGGVSSLFQNLGVSVTPIQRIVLSGENG SEQ ID NO: 475 (CP 55 L27V (RIIbB) (nt sequence)
Atggacatccatgtcatcatcccgtatgaaggtctgagcggcgaccaaatgggccagatcgaaaaaatttttaaggtg
gtgtaccctgtggatgatcatcactttaaggtgatcctgcactatggcacactggtaatcgacggggttacgccgaac
atgatcgactatttcggacggccgtatgaaggcatcgccgtgttcgacggcaaaaagatcactgtaacagggaccctg
tggaacggcaacaaaattatcgacgagcgcctgatcaaccccgacggctccctgctgttccgagtaaccatcaacgga
gtgaccggctggcggctgtGCGAACGCATTCTGGCtAGCTCAAGCGGAGGTTCAGGCGGTTCCGGAATGTATGAAAGC
TTTATTGAGTCACTGCCATTCCTTAAATCTTTGGAGTTTTCTGCACGCCTGAAAGTAGTAGATGTGATAGGCACCAAA
GTATACAACGATGGAGAACAAATCATTGCTCAGGGAGATTCGGCTGATTCTTTTTTCATTATTGAATCTGGAGAAGTG
AAAATTACTATGAAAAGAAAGGGTAAATCAGAAGTGGAAGAGAATGGTGCAGTAGAAATCGCTCGATGCTCGCGGGGA
CAGTACTTTGGAGAGCTTGCCCTGGTAACTAACAAACCTCGAGCAGCTTCTGCCCACGCCATTGGGACTGTCAAATGT
TTAGCAATGGATGTGCAAGCATTTGAAAGGCTTCTGGGACCTTGCATGGAAATTATGAAAAGGAACATCGCTACCTAT
GAAGAACAGTTAGTTGCCCTGTATGGAACGAACATGGATATTGTAGGGTCAGGTGGATCTGGAGGTAGCTCTTCTatg
gtcttcacactcgaagatttcgttggggactggcgacagacagccggctacaacctggaccaagtccttgaacaggga
ggtgtgtccagtttgtttcagaatctcggggtgtccgtaactccgatccaaaggattgtcctgagcggtgaaaatggg
ctgaagatc SEQ ID NO: 476 (CP 55 L27V (RIIbB) (aa seq)
MDIHVIIPYEGLSGDQMGQIEKIFKVVYPVDDHHFKVILHYGTLVIDGVTPNMIDYFGRPYEGIAVFDGKKITVTGTL
WNGNKIIDERLINPDGSLLFRVTINGVTGWRLCERILASSSGGSGGSGMYESFIESLPFLKSLEFSARLKVVDVIGTK
VYNDGEQIIAQGDSADSFFIIESGEVKITMKRKGKSEVEENGAVEIARCSRGQYFGELALVTNKPRAASAHAIGTVKC
LAMDVQAFERLLGPCMEIMKRNIATYEEQLVALYGTNMDIVGSGGSGGSSSMVFTLEDFVGDWRQTAGYNLDQVLEQG
GVSSLFQNLGVSVTPIQRIVLSGENGLKI SEQ ID NO: 477 (CP 83 L27V (RIIbB) (nt sequence)
ATGgtggatgatcatcactttaaggtgatcctgcactatggcacactggtaatcgacggggttacgccgaacatgatc
gactatttcggacggccgtatgaaggcatcgccgtgttcgacggcaaaaagatcactgtaacagggaccctgtggaac
ggcaacaaaattatcgacgagcgcctgatcaaccccgacggctccctgctgttccgagtaaccatcaacggagtgacc
ggctggcggctgtGCGAACGCATTCTGGCtAGCTCAAGCGGAGGTTCAGGCGGTTCCGGAATGTATGAAAGCTTTATT

SEQUENCE LISTING

GAGTCACTGCCATTCCTTAAATCTTTGGAGTTTTCTGCACGCCTGAAAGTAGTAGATGTGATAGGCACCAAAGTATAC
AACGATGGAGAACAAATCATTGCTCAGGGAGATTCGGCTGATTCTTTTTTCATTATTGAATCTGGAGAAGTGAAAATT
ACTATGAAAAGAAAGGGTAAATCAGAAGTGGAAGAGAATGGTGCAGTAGAAATCGCTCGATGCTCGCGGGGACAGTAC
TTTGGAGAGCTTGCCCTGGTAACTAACAAACCTCGAGCAGCTTCTGCCCACGCCATTGGGACTGTCAAATGTTTAGCA
ATGGATGTGCAAGCATTTGAAAGGCTTCTGGGACCTTGCATGGAAATTATGAAAAGGAACATCGCTACCTATGAAGAA
CAGTTAGTTGCCCTGTATGGAACGAACATGGATATTGTAGGGTCAGGTGGATCTGGAGGTAGCTCTTCTatggtcttc
acactcgaagatttcgttggggactggcgacagacagccggctacaacctggaccaagtccttgaacagggaggtgtg
tccagtttgtttcagaatctcggggtgtccgtaactccgatccaaaggattgtcctgagcggtgaaaatgggctgaag
atcgacatccatgtcatcatcccgtatgaaggtctgagcggcgaccaaatgggccagatcgaaaaaatttttaaggtg
gtgtaccct SEQ ID NO: 478 (CP 83 L27V (RIIbB) (aa seq)
MVDDHHFKVILHYGTLVIDGVTPNMIDYFGRPYEGIAVFDGKKITVTGTLWNGNKIIDERLINPDGSLLFRVTINGVT
GWRLCERILASSSGGSGGSGMYESFIESLPFLKSLEFSARLKVVDVIGTKVYNDGEQIIAQGDSADSFFIIESGEVKI
TMKRKGKSEVEENGAVEIARCSRGQYFGELALVTNKPRAASAHAIGTVKCLAMDVQAFERLLGPCMEIMKRNIATYEE
QLVALYGTNMDIVGSGGSGGSSSMVFTLEDFVGDWRQTAGYNLDQVLEQGGVSSLFQNLGVSVTPIQRIVLSGENGLK
IDIHVIIPYEGLSGDQMGQIEKIFKVVYP SEQ ID NO: 479 (CP 84 L27V (RIIbB) (nt sequence)
atggatgatcatcactttaaggtgatcctgcactatggcacactggtaatcgacggggttacgccgaacatgatcgac
tatttcggacggccgtatgaaggcatcgccgtgttcgacggcaaaaagatcactgtaacagggaccctgtggaacggc
aacaaaattatcgacgagcgcctgatcaaccccgacggctccctgctgttccgagtaaccatcaacggagtgaccggc
tggcggctgtGCGAACGCATTCTGGCtAGCTCAAGCGGAGGTTCAGGCGGTTCCGGAATGTATGAAAGCTTTATTGAG
TCACTGCCATTCCTTAAATCTTTGGAGTTTTCTGCACGCCTGAAAGTAGTAGATGTGATAGGCACCAAAGTATACAAC
GATGGAGAACAAATCATTGCTCAGGGAGATTCGGCTGATTCTTTTTTCATTATTGAATCTGGAGAAGTGAAAATTACT
ATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATG
GATGTGCAAGCATTTGAAAGGCTTCTGGGACCTTGCATGGAAATTATGAAAAGGAACATCGCTACCTATGAAGAACAG
TTAGTTGCCCTGTATGGAACGAACATGGATATTGTAGGGTCAGGTGGATCTGGAGGTAGCTCTTCTatggtcttcaca
ctcgaagatttcgttggggactggcgacagacagccggctacaacctggaccaagtccttgaacagggaggtgtgtcc
agtttgtttcagaatctcggggtgtccgtaactccgatccaaaggattgtcctgagcggtgaaaatgggctgaagatc
gacatccatgtcatcatcccgtatgaaggtctgagcggcgaccaaatgggccagatcgaaaaaatttttaaggtggtg
taccctgtg SEQ ID NO: 480 (CP 84 L27V (RIIbB) (aa seq)
MDDHHFKVILHYGTLVIDGVTPNMIDYFGRPYEGIAVFDGKKITVTGTLWNGNKIIDERLINPDGSLLFRVTINGVTG
WRLCERILASSSGGSGGSGMYESFIESLPFLKSLEFSARLKVVDVIGTKVYNDGEQIIAQGDSADSFFIIESGEVKIT
MKRKGKSEVEENGAVEIARCSRGQYFGELALVTNKPRAASAHAIGTVKCLAMDVQAFERLLGPCMEIMKRNIATYEEQ
LVALYGTNMDIVGSGGSGGSSSMVFTLEDFVGDWRQTAGYNLDQVLEQGGVSSLFQNLGVSVTPIQRIVLSGENGLKI
DIHVIIPYEGLSGDQMGQIEKIFKVVYPV SEQ ID NO: 481 (CP 103 L27V (RIIbB) (nt sequence)
ATGacgccgaacatgatcgactatttcggacggccgtatgaaggcatcgccgtgttcgacggcaaaaagatcactgta
acagggaccctgtggaacggcaacaaaattatcgacgagcgcctgatcaaccccgacggctccctgctgttccgagta
accatcaacggagtgaccggctggcggctgtGCGAACGCATTCTGGCtAGCTCAAGCGGAGGTTCAGGCGGTTCCGGA
ATGTATGAAAGCTTTATTGAGTCACTGCCATTCCTTAAATCTTTGGAGTTTTCTGCACGCCTGAAAGTAGTAGATGTG
ATAGGCACCAAAGTATACAACGATGGAGAACAAATCATTGCTCAGGGAGATTCGGCTGATTCTTTTTTCATTATTGAA
TCTGGAGAAGTGAAAATTACTATGAAAAGAAAGGGTAAATCAGAAGTGGAAGAGAATGGTGCAGTAGAAATCGCTCGA
TGCTCGCGGGGACAGTACTTTGGAGAGCTTGCCCTGGTAACTAACAAACCTCGAGCAGCTTCTGCCCACGCCATTGGG
ACTGTCAAATGTTTAGCAATGGATGTGCAAGCATTTGAAAGGCTTCTGGGACCTTGCATGGAAATTATGAAAAGGAAC
ATCGCTACCTATGAAGAACAGTTAGTTGCCCTGTATGGAACGAACATGGATATTGTAGGGTCAGGTGGATCTGGAGGT
AGCTCTTCTatggtcttcacactcgaagatttcgttggggactggcgacagacagccggctacaacctggaccaagtc
cttgaacagggaggtgtgtccagtttgtttcagaatctcggggtgtccgtaactccgatccaaaggattgtcctgagc
ggtgaaaatgggctgaagatcgacatccatgtcatcatcccgtatgaaggtctgagcggcgaccaaatgggccagatc
gaaaaaatttttaaggtggtgtaccctgtggatgatcatcactttaaggtgatcctgcactatggcacactggtaatc
gacggggtt SEQ ID NO: 482 (CP 103 L27V (RIIbB) (aa seq)
MTPNMIDYFGRPYEGIAVFDGKKITVTGTLWNGNKIIDERLINPDGSLLFRVTINGVTGWRLCERILASSSGGSGGSG
MYESFIESLPFLKSLEFSARLKVVDVIGTKVYNDGEQIIAQGDSADSFFIIESGEVKITMKRKGKSEVEENGAVEIAR
CSRGQYFGELALVTNKPRAASAHAIGTVKCLAMDVQAFERLLGPCMEIMKRNIATYEEQLVALYGTNMDIVGSGGSGG
SSSMVFTLEDFVGDWRQTAGYNLDQVLEQGGVSSLFQNLGVSVTPIQRIVLSGENGLKIDIHVIIPYEGLSGDQMGQI
EKIFKVVYPVDDHHFKVILHYGTLVIDGV SEQ ID NO: 483 (CP 120 L27V (RIIbB) (nt sequence)
ATGttcgacggcaaaaagatcactgtaacagggaccctgtggaacggcaacaaaattatcgacgagcgcctgatcaac
cccgacggctccctgctgttccgagtaaccatcaacggagtgaccggctggcggctgtGCGAACGCATTCTGGCtAGC
TCAAGCGGAGGTTCAGGCGGTTCCGGAATGTATGAAAGCTTTATTGAGTCACTGCCATTCCTTAAATCTTTGGAGTTT
TCTGCACGCCTGAAAGTAGTAGATGTGATAGGCACCAAAGTATACAACGATGGAGAACAAATCATTGCTCAGGGAGAT
TCGGCTGATTCTTTTTTCATTATTGAATCTGGAGAAGTGAAAATTACTATGAAAAGAAAGGGTAAATCAGAAGTGGAA
GAGAATGGTGCAGTAGAAATCGCTCGATGCTCGCGGGGACAGTACTTTGGAGAGCTTGCCCTGGTAACTAACAAACCT
CGAGCAGCTTCTGCCCACGCCATTGGGACTGTCAAATGTTTAGCAATGGATGTGCAAGCATTTGAAAGGCTTCTGGGA
CCTTGCATGGAAATTATGAAAAGGAACATCGCTACCTATGAAGAACAGTTAGTTGCCCTGTATGGAACGAACATGGAT
ATTGTAGGGTCAGGTGGATCTGGAGGTAGCTCTTCTatggtcttcacactcgaagatttcgttggggactggcgacag
acagccggctacaacctggaccaagtccttgaacagggaggtgtgtccagtttgtttcagaatctcggggtgtccgta
actccgatccaaaggattgtcctgagcggtgaaaatgggctgaagatcgacatccatgtcatcatcccgtatgaaggt
ctgagcggcgaccaaatgggccagatcgaaaaaatttttaaggtggtgtaccctgtggatgatcatcactttaaggtg

SEQUENCE LISTING atcctgcactatggcacactggtaatcgacggggttacgccgaacatgatcgactatttcggacggccgtatgaaggc
atcgccgtg SEQ ID NO: 484 (CP 120 L27V (RIIbB) (aa seq)
MFDGKKITVTGTLWNGNKIIDERLINPDGSLLFRVTINGVTGWRLCERILASSSGGSGGSGMYESFIESLPFLKSLEF
aARLKVVDVIGTKVYNDGEQIIAQGDSADSFFIIESGEVKITMKRKGKSEVEENGAVEIARCSRGQYFGELALVTNKP
RAASAHAIGTVKCLAMDVQAFERLLGPCMEIMKRNIATYEEQLVALYGTNMDIVGSGGSGGSSSMVFTLEDFVGDWRQ
TAGYNLDQVLEQGGVSSLFQNLGVSVTPIQRIVLSGENGLKIDIHVIIPYEGLSGDQMGQIEKIFKVVYPVDDHHFKV
ILHYGTLVIDGVTPNMIDYFGRPYEGIAV SEQ ID NO: 485 (CP 123 L27V (RIIbB) (nt sequence)
ATGaaaaagatcactgtaacagggaccctgtggaacggcaacaaaattatcgacgagcgcctgatcaaccccgacggc
tccctgctgttccgagtaaccatcaacggagtgaccggctggcggctgtGCGAACGCATTCTGGCtAGCTCAAGCGGA
GGTTCAGGCGGTTCCGGAATGTATGAAAGCTTTATTGAGTCACTGCCATTCCTTAAATCTTTGGAGTTTTCTGCACGC
CTGAAAGTAGTAGATGTGATAGGCACCAAAGTATACAACGATGGAGAACAAATCATTGCTCAGGGAGATTCGGCTGAT
TCTTTTTTCATTATTGAATCTGGAGAAGTGAAAATTACTATGAAAAGAAAGGGTAAATCAGAAGTGGAAGAGAATGGT
GCAGTAGAAATCGCTCGATGCTCGCGGGGACAGTACTTTGGAGAGCTTGCCCTGGTAACTAACAAACCTCGAGCAGCT
TCTGCCCACGCCATTGGGACTGTCAAATGTTTAGCAATGGATGTGCAAGCATTTGAAAGGCTTCTGGGACCTTGCATG
GAAATTATGAAAAGGAACATCGCTACCTATGAAGAACAGTTAGTTGCCCTGTATGGAACGAACATGGATATTGTAGGG
TCAGGTGGATCTGGAGGTAGCTCTTCTatggtcttcacactcgaagatttcgttggggactggcgacagacagccggc
tacaacctggaccaagtccttgaacagggaggtgtgtccagtttgtttcagaatctcggggtgtccgtaactccgatc
caaaggattgtcctgagcggtgaaaatgggctgaagatcgacatccatgtcatcatcccgtatgaaggtctgagcggc
gaccaaatgggccagatcgaaaaaatttttaaggtggtgtaccctgtggatgatcatcactttaaggtgatcctgcac
tatggcacactggtaatcgacggggttacgccgaacatgatcgactatttcggacggccgtatgaaggcatcgccgtg
ttcgacggc SEQ ID NO: 486 (CP 123 L27V (RIIbB) (aa seq)
MKKITVTGTLWNGNKIIDERLINPDGSLLFRVTINGVTGWRLCERILASSSGGSGGSGMYESFIESLPFLKSLEFSAR
LKVVDVIGTKVYNDGEQIIAQGDSADSFFIIESGEVKITMKRKGKSEVEENGAVEIARCSRGQYFGELALVTNKPRAA
SAHAIGTVKCLAMDVQAFERLLGPCMEIMKRNIATYEEQLVALYGTNMDIVGSGGSGGSSSMVFTLEDFVGDWRQTAG
YNLDQVLEQGGVSSLFQNLGVSVTPIQRIVLSGENGLKIDIHVIIPYEGLSGDQMGQIEKIFKVVYPVDDHHFKVILH
YGTLVIDGVTPNMIDYFGRPYEGIAVFDG SEQ ID NO: 487 (CP 124 L27V (RIIbB) (nt sequence)
ATGaagatcactgtaacagggaccctgtggaacggcaacaaaattatcgacgagcgcctgatcaaccccgacggctcc
ctgctgttccgagtaaccatcaacggagtgaccggctggcggctgtGCGAACGCATTCTGGCtAGCTCAAGCGGAGGT
TCAGGCGGTTCCGGAATGTATGAAAGCTTTATTGAGTCACTGCCATTCCTTAAATCTTTGGAGTTTTCTGCACGCCTG
AAAGTAGTAGATGTGATAGGCACCAAAGTATACAACGATGGAGAACAAATCATTGCTCAGGGAGATTCGGCTGATTCT
TTTTTCATTATTGAATCTGGAGAAGTGAAAATTACTATGAAAAGAAAGGGTAAATCAGAAGTGGAAGAGAATGGTGCA
GTAGAAATCGCTCGATGCTCGCGGGGACAGTACTTTGGAGAGCTTGCCCTGGTAACTAACAAACCTCGAGCAGCTTCT
GCCCACGCCATTGGGACTGTCAAATGTTTAGCAATGGATGTGCAAGCATTTGAAAGGCTTCTGGGACCTTGCATGGAA
ATTATGAAAAGGAACATCGCTACCTATGAAGAACAGTTAGTTGCCCTGTATGGAACGAACATGGATATTGTAGGGTCA
GGTGGATCTGGAGGTAGCTCTTCTatggtcttcacactcgaagatttcgttggggactggcgacagacagccggctac
aacctggaccaagtccttgaacagggaggtgtgtccagtttgtttcagaatctcggggtgtccgtaactccgatccaa
aggattgtcctgagcggtgaaaatgggctgaagatcgacatccatgtcatcatcccgtatgaaggtctgagcggcgac
caaatgggccagatcgaaaaaatttttaaggtggtgtaccctgtggatgatcatcactttaaggtgatcctgcactat
ggcacactggtaatcgacggggttacgccgaacatgatcgactatttcggacggccgtatgaaggcatcgccgtgttc
gacggcaaa SEQ ID NO: 488 (CP 124 L27V (RIIbB) (aa seq)
MKITVTGTLWNGNKIIDERLINPDGSLLFRVTINGVTGWRLCERILASSSGGSGGSGMYESFIESLPFLKSLEFSARL
KVVDVIGTKVYNDGEQIIAQGDSADSFFIIESGEVKITMKRKGKSEVEENGAVEIARCSRGQYFGELALVTNKPRAAS
AHAIGTVKCLAMDVQAFERLLGPCMEIMKRNIATYEEQLVALYGTNMDIVGSGGSGGSSSMVFTLEDFVGDWRQTAGY
NLDQVLEQGGVSSLFQNLGVSVTPIQRIVLSGENGLKIDIHVIIPYEGLSGDQMGQIEKIFKVVYPVDDHHFKVILHY
GTLVIDGVTPNMIDYFGRPYEGIAVFDGK SEQ ID NO: 489 (CP 125 L27V (RIIbB) (nt sequence)
ATGatcactgtaacagggaccctgtggaacggcaacaaaattatcgacgagcgcctgatcaaccccgacggctccctg
ctgttccgagtaaccatcaacggagtgaccggctggcggctgtGCGAACGCATTCTGGCtAGCTCAAGCGGAGGTTCA
GGCGGTTCCGGAATGTATGAAAGCTTTATTGAGTCACTGCCATTCCTTAAATCTTTGGAGTTTTCTGCACGCCTGAAA
GTAGTAGATGTGATAGGCACCAAAGTATACAACGATGGAGAACAAATCATTGCTCAGGGAGATTCGGCTGATTCTTTT
TTCATTATTGAATCTGGAGAAGTGAAAATTACTATGAAAAGAAAGGGTAAATCAGAAGTGGAAGAGAATGGTGCAGTA
GAAATCGCTCGATGCTCGCGGGGACAGTACTTTGGAGAGCTTGCCCTGGTAACTAACAAACCTCGAGCAGCTTCTGCC
CACGCCATTGGGACTGTCAAATGTTTAGCAATGGATGTGCAAGCATTTGAAAGGCTTCTGGGACCTTGCATGGAAATT
ATGAAAAGGAACATCGCTACCTATGAAGAACAGTTAGTTGCCCTGTATGGAACGAACATGGATATTGTAGGGTCAGGT
GGATCTGGAGGTAGCTCTTCTatggtcttcacactcgaagatttcgttggggactggcgacagacagccggctacaac
ctggaccaagtccttgaacagggaggtgtgtccagtttgtttcagaatctcggggtgtccgtaactccgatccaaagg
attgtcctgagcggtgaaaatgggctgaagatcgacatccatgtcatcatcccgtatgaaggtctgagcggcgaccaa
atgggccagatcgaaaaaatttttaaggtggtgtaccctgtggatgatcatcactttaaggtgatcctgcactatggc
acactggtaatcgacggggttacgccgaacatgatcgactatttcggacggccgtatgaaggcatcgccgtgttcgac
ggcaaaaag SEQ ID NO: 490 (CP 125 L27V (RIIbB) (aa seq)
MITVTGTLWNGNKIIDERLINPDGSLLFRVTINGVTGWRLCERILASSSGGSGGSGMYESFIESLPFLKSLEFSARLK
VVDVIGTKVYNDGEQIIAQGDSADSFFIIESGEVKITMKRKGKSEVEENGAVEIARCSRGQYFGELALVTNKPRAASA
HAIGTVKCLAMDVQAFERLLGPCMEIMKRNIATYEEQLVALYGTNMDIVGSGGSGGSSSMVFTLEDFVGDWRQTAGYN

SEQUENCE LISTING

LDQVLEQGGVSSLFQNLGVSVTPIQRIVLSGENGLKIDIHVIIPYEGLSGDQMGQIEKIFKVVYPVDDHHFKVILHYG
TLVIDGVTPNMIDYFGRPYEGIAVFDGKK

SEQ ID NO: 491 (CP 130 L27V (RIIbB) (nt sequence)
ATGaccctgtggaacggcaacaaaattatcgacgagcgcctgatcaaccccgacggctccctgctgttccgagtaacc
atcaacggagtgaccggctggcggctgtGCGAACGCATTCTGGCtAGCTCAAGCGGAGGTTCAGGCGGTTCCGGAATG
TATGAAAGCTTTATTGAGTCACTGCCATTCCTTAAATCTTTGGAGTTTTCTGCACGCCTGAAAGTAGTAGATGTGATA
GGCACCAAAGTATACAACGATGGAGAACAAATCATTGCTCAGGGAGATTCGGCTGATTCTTTTTTCATTATTGAATCT
GGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACT
GTCAAATGTTTAGCAATGGATGTGCAAGCATTTGAAAGGCTTCTGGGACCTTGCATGGAAATTATGAAAAGGAACATC
GCTACCTATGAAGAACAGTTAGTTGCCCTGTATGGAACGAACATGGATATTGTAGGGTCAGGTGGATCTGGAGGTAGC
TCTTCTatggtcttcacactcgaagatttcgttggggactggcgacagacagccggctacaacctggaccaagtcctt
gaacagggaggtgtgtccagtttgtttcagaatctcggggtgtccgtaactccgatccaaaggattgtcctgagcggt
gaaaatgggctgaagatcgacatccatgtcatcatcccgtatgaaggtctgagcggcgaccaaatgggccagatcgaa
aaaatttttaaggtggtgtaccctgtggatgatcatcactttaaggtgatcctgcactatggcacactggtaatcgac
ggggttacgccgaacatgatcgactatttcggacggccgtatgaaggcatcgccgtgttcgacggcaaaaagatcact
gtaacaggg SEQ ID NO: 492 (CP 130 L27V (RIIbB) (aa seq)
MTLWNGNKIIDERLINPDGSLLFRVTINGVTGWRLCERILASSSGGSGGSGMYESFIESLPFLKSLEFSARLKVVDVI
GTKVYNDGEQIIAQGDSADSFFIIESGEVKITMKRKGKSEVEENGAVEIARCSRGQYFGELALVTNKPRAASAHAIGT
VKCLAMDVQAFERLLGPCMEIMKRNIATYEEQLVALYGTNMDIVGSGGSGGSSSMVFTLEDFVGDWRQTAGYNLDQVL
EQGGVSSLFQNLGVSVTPIQRIVLSGENGLKIDIHVIIPYEGLSGDQMGQIEKIFKVVYPVDDHHFKVILHYGTLVID
GVTPNMIDYFGRPYEGIAVFDGKKITVTG SEQ ID NO: 493 (CP 145 L27V (RIIbB) (nt sequence)
ATGcccgacggctccctgctgttccgagtaaccatcaacggagtgaccggctggcggctgtGCGAACGCATTCTGGCt
AGCTCAAGCGGAGGTTCAGGCGGTTCCGGAATGTATGAAAGCTTTATTGAGTCACTGCCATTCCTTAAATCTTTGGAG
TTTTCTGCACGCCTGAAAGTAGTAGATGTGATAGGCACCAAAGTATACAACGATGGAGAACAAATCATTGCTCAGGGA
GATTCGGCTGATTCTTTTTTCATTATTGAATCTGGAGAAGTGAAAATTACTATGAAAAGAAAGGGTAAATCAGAAGTG
GAAGAGAATGGTGCAGTAGAAATCGCTCGATGCTCGCGGGGACAGTACTTTGGAGAGCTTGCCCTGGTAACTAACAAA
CCTCGAGCAGCTTCTGCCCACGCCATTGGGACTGTCAAATGTTTAGCAATGGATGTGCAAGCATTTGAAAGGCTTCTG
GGACCTTGCATGGAAATTATGAAAAGGAACATCGCTACCTATGAAGAACAGTTAGTTGCCCTGTATGGAACGAACATG
GATATTGTAGGGTCAGGTGGATCTGGAGGTAGCTCTTCTatggtcttcacactcgaagatttcgttggggactggcga
cagacagccggctacaacctggaccaagtccttgaacagggaggtgtgtccagtttgtttcagaatctcggggtgtcc
gtaactccgatccaaaggattgtcctgagcggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaac SEQ ID NO: 494 (CP 145 L27V (RIIbB) (aa seq)
MPDGSLLFRVTINGVTGWRLCERILASSSGGSGGSGMYESFIESLPFLKSLEFSARLKVVDVIGTKVYNDGEQIIAQG
DSADSFFIIESGEVKITMKRKGKSEVEENGAVEIARCSRGQYFGELALVTNKPRAASAHAIGTVKCLAMDVQAFERLL
GPCMEIMKRNIATYEEQLVALYGTNMDIVGSGGSGGSSSMVFTLEDFVGDWRQTAGYNLDQVLEQGGVSSLFQNLGVS
VTPIQRIVLSGENGLKIDIHVIIPYEGLSGDQMGQIEKIFKVVYPVDDHHFKVILHYGTLVIDGVTPNMIDYFGRPYE
GIAVFDGKKITVTGTLWNGNKIIDERLIN SEQ ID NO: 495 (CP 148 L27V (RIIbB) (nt sequence)
ATGtccctgctgttccgagtaaccatcaacggagtgaccggctggcggctgtGCGAACGCATTCTGGCtAGCTCAAGC
GGAGGTTCAGGCGGTTCCGGAATGTATGAAAGCTTTATTGAGTCACTGCCATTCCTTAAATCTTTGGAGTTTTCTGCA
CGCCTGAAAGTAGTAGATGTGATAGGCACCAAAGTATACAACGATGGAGAACAAATCATTGCTCAGGGAGATTCGGCT
GATTCTTTTTTCATTATTGAATCTGGAGAAGTGAAAATTACTATGAAAAGAAAGGGTAAATCAGAAGTGGAAGAGAAT
GGTGCAGTAGAAATCGCTCGATGCTCGCGGGGACAGTACTTTGGAGAGCTTGCCCTGGTAACTAACAAACCTCGAGCA
GCTTCTGCCCACGCCATTGGGACTGTCAAATGTTTAGCAATGGATGTGCAAGCATTTGAAAGGCTTCTGGGACCTTGC
ATGGAAATTATGAAAAGGAACATCGCTACCTATGAAGAACAGTTAGTTGCCCTGTATGGAACGAACATGGATATTGTA
GGGTCAGGTGGATCTGGAGGTAGCTCTTCTatggtcttcacactcgaagatttcgttggggactggcgacagacagcc
ggctacaacctggaccaagtccttgaacagggaggtgtgtccagtttgtttcagaatctcggggtgtccgtaactccg
atccaaaggattgtcctgagcggtgaaaatgggctgaagatcgacatccatgtcatcatcccgtatgaaggtctgagc
ggcgaccaaatgggccagatcgaaaaaatttttaaggtggtgtaccctgtggatgatcatcactttaaggtgatcctg
cactatggcacactggtaatcgacggggttacgccgaacatgatcgactatttcggacggccgtatgaaggcatcgcc
gtgttcgacggcaaaaagatcactgtaacagggaccctgtggaacggcaacaaaattatcgacgagcgcctgatcaac
cccgacggc SEQ ID NO: 496 (CP 148 L27V (RIIbB) (aa seq)
MSLLFRVTINGVTGWRLCERILASSSGGSGGSGMYESFIESLPFLKSLEFSARLKVVDVIGTKVYNDGEQIIAQGDSA
DSFFIIESGEVKITMKRKGKSEVEENGAVEIARCSRGQYFGELALVTNKPRAASAHAIGTVKCLAMDVQAFERLLGPC
MEIMKRNIATYEEQLVALYGTNMDIVGSGGSGGSSSMVFTLEDFVGDWRQTAGYNLDQVLEQGGVSSLFQNLGVSVTP
IQRIVLSGENGLKIDIHVIIPYEGLSGDQMGQIEKIFKVVYPVDDHHFKVILHYGTLVIDGVTPNMIDYFGRPYEGIA
VFDGKKITVTGTLWNGNKIIDERLINPDG SEQ ID NO: 497 (CP 157 L27V (RIIbB) (nt sequence)
AtGGGAGTGACCGGCTGGCGGCTGTGCGAACGCATTCTGGCTAGCTCAAGCGGAGGTTCAGGCGGTTCCGGAATGTAT
GAAAGCTTTATTGAGTCACTGCCATTCCTTAAATCTTTGGAGTTTTCTGCACGCCTGAAAGTAGTAGATGTGATAGGC
ACCAAAGTATACAACGATGGAGAACAAATCATTGCTCAGGGAGATTCGGCTGATTCTTTTTTCATTATTGAATCTGGA
GAAGTGAAAATTACTATGAAAAGAAAGGGTAAATCAGAAGTGGAAGAGAATGGTGCAGTAGAAATCGCTCGATGCTCG -continued

SEQUENCE LISTING

CGGGGACAGTACTTTGGAGAGCTTGCCCTGGTAACTAACAAACCTCGAGCAGCTTCTGCCCACGCCATTGGGACTGTC
AAATGTTTAGCAATGGATGTGCAAGCATTTGAAAGGCTTCTGGGACCTTGCATGGAAATTATGAAAAGGAACATCGCT
ACCTATGAAGAACAGTTAGTTGCCCTGTATGGAACGAACATGGATATTGTAGGGTCAGGTGGATCTGGAGGTAGCTCT
TCTATGGTCTTCACACTCGAAGATTTCGTTGGGGACTGGCGACAGACAGCCGGCTACAACCTGGACCAAGTCCTTGAA
CAGGGAGGTGTGTCCAGTTTGTTTCAGAATCTCGGGGTGTCCGTAACTCCGATCCAAAGGATTGTCCTGAGCGGTGAA
AATGGGCTGAAGATCGACATCCATGTCATCATCCCGTATGAAGGTCTGAGCGGCGACCAAATGGGCCAGATCGAAAAA
ATTTTTAAGGTGGTGTACCCTGTGGATGATCATCACTTTAAGGTGATCCTGCACTATGGCACACTGGTAATCGACGGG
GTTACGCCGAACATGATCGACTATTTCGGACGGCCGTATGAAGGCATCGCCGTGTTCGACGGCAAAAAGATCACTGTA
ACAGGGACCCTGTGGAACGGCAACAAAATTATCGACGAGCGCCTGATCAACCCCGACGGCTCCCTGCTGTTCCGAGTA
ACCATCAAC

SEQ ID NO: 498 (CP 157 L27V (RIIbB) (aa seq)
MGVTGWRLCERILASSSGGSGGSGMYESFIESLPFLKSLEFSARLKVVDVIGTKVYNDGEQIIAQGDSADSFFIIESG
EVKITMKRKGKSEVEENGAVEIARCSRGQYFGELALVTNKPRAASAHAIGTVKCLAMDVQAFERLLGPCMEIMKRNIA
TYEEQLVALYGTNMDIVGSGGSGGSSSMVFTLEDFVGDWRQTAGYNLDQVLEQGGVSSLFQNLGVSVTPIQRIVLSGE
NGLKIDIHVIIPYEGLSGDQMGQIEKIFKVVYPVDDHHFKVILHYGTLVIDGVTPNMIDYFGRPYEGIAVFDGKKITV
TGTLWNGNKIIDERLINPDGSLLFRVTIN SEQ ID NO: 499 (SS 6 L27V (RIIbB) (nt sequence)
ATGgtcttcacactcgaagatAGCgctAGCGGAGGTTCAGGCGGTTCCGGAatgtatgaaagctttattgagtcactg
ccattccttaaatctttggagttttctgcacgcctgaaagtagtagatgtgataggcaccaaagtatacaacgatgga
gaacaaatcattgctcagggagattcggctgattctttttttcattattgaatctggagaagtgaaaattactatgaaa
agaaagggtaaatcagaagtggaagagaatggtgcagtagaaatcgctcgatgctcgcggggacagtactttggagag
cttgccctggtaactaacaaacctcgagcagcttctgcccacgccattgggactgtcaaatgtttagcaatggatgtg
caagcatttgaaaggcttctgggaccttgcatggaaattatgaaaaggaacatcgctacctatgaagaacagttagtt
gccctgTATggaacgaacatggatattgtaggGTCAGGTGGATCTGGAGGtAGCTCttcTttcgttggggactggcga
cagacagccggctacaacctggaccaagtccttgaacagggaggtgtgtccagtttgtttcagaatctcggggtgtcc
gtaactccgatccaaaggattgtcctgagcggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 500 (SS 6 L27V (RIIbB) (aa seq)
MVFTLEDSASGGSGGSGMYESFIESLPFLKSLEFSARLKVVDVIGTKVYNDGEQIIAQGDSADSFFIIESGEVKITMK
RKGKSEVEENGAVEIARCSRGQYFGELALVTNKPRAASAHAIGTVKCLAMDVQAFERLLGPCMEIMKRNIATYEEQLV
ALYGTNMDIVGSGGSGGSSSFVGDWRQTAGYNLDQVLEQGGVSSLFQNLGVSVTPIQRIVLSGENGLKIDIHVIIPYE
GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 501 (SS 12 L27V (RIIbB) (nt sequence)
ATGgtcttcacactcgaagatttcgttggggactggcgaAGCgctAGCGGAGGTTCAGGCGGTTCCGGAatgtatgaa
agctttattgagtcactgccattccttaaatctttggagttttctgcacgcctgaaagtagtagatgtgataggcacc
aaagtatacaacgatggagaacaaatcattgctcagggagattcggctgattctttttttcattattgaatctggagaa
gtgaaaattactatgaaaagaaagggtaaatcagaagtggaagagaatggtgcagtagaaatcgctcgatgctcgcgg
ggacagtactttggagagcttgccctggtaactaacaaacctcgagcagcttctgcccacgccattgggactgtcaaa
tgtttagcaatggatgtgcaagcatttgaaaggcttctgggaccttgcatggaaattatgaaaaggaacatcgctacc
tatgaagaacagttagttgccctgTATggaacgaacatggatattgtaggGTCAGGTGGATCTGGAGGtAGCTCttcT
cagacagccggctacaacctggaccaagtccttgaacagggaggtgtgtccagtttgtttcagaatctcggggtgtcc
gtaactccgatccaaaggattgtcctgagcggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 502 (SS 12 L27V (RIIbB) (aa seq)
MVFTLEDFVGDWRSASGGSGGSGMYESFIESLPFLKSLEFSARLKVVDVIGTKVYNDGEQIIAQGDSADSFFIIESGE
VKITMKRKGKSEVEENGAVEIARCSRGQYFGELALVTNKPRAASAHAIGTVKCLAMDVQAFERLLGPCMEIMKRNIAT
YEEQLVALYGTNMDIVGSGGSGGSSSQTAGYNLDQVLEQGGVSSLFQNLGVSVTPIQRIVLSGENGLKIDIHVIIPYE
GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 503 (SS 26 L27V (RIIbB) (nt sequence)
ATGgtcttcacactcgaagatttcgttggggactggcgacagacagccggctacaacctggaccaagtccttgaacag
ggaAGCgctAGCGGAGGTTCAGGCGGTTCCGGAatgtatgaaagctttattgagtcactgccattccttaaatctttg
gagttttctgcacgcctgaaagtagtagatgtgataggcaccaaagtatacaacgatggagaacaaatcattgctcag
ggagattcggctgattctttttttcattattgaatctggagaagtgaaaattactatgaaaagaaagggtaaatcagaa
gtggaagagaatggtgcagtagaaatcgctcgatgctcgcggggacagtactttggagagcttgccctggtaactaac
aaacctcgagcagcttctgcccacgccattgggactgtcaaatgtttagcaatggatgtgcaagcatttgaaaggctt
ctgggaccttgcatggaaattatgaaaaggaacatcgctacctatgaagaacagttagttgccctgTATggaacgaac
atggatattgtaggGTCAGGTGGATCTGGAGGtAGCTCttcTggtgtgtccagtttgtttcagaatctcggggtgtcc
gtaactccgatccaaaggattgtcctgagcggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc

SEQUENCE LISTING ctgatcaaccccgacggctccctgctgttccgagtaaccatcaacggagtgaccggctggcggctgtGCGAACGCATT
CTGGCt SEQ ID NO: 504 (SS 26 L27V (RIIbB) (aa seq)
MVFTLEDFVGDWRQTAGYNLDQVLEQGSASGGSGGSGMYESFIESLPFLKSLEFSARLKVVDVIGTKVYNDGEQIIAQ
GDSADSFFIIESGEVKITMKRKGKSEVEENGAVEIARCSRGQYFGELALVTNKPRAASAHAIGTVKCLAMDVQAFERL
LGPCMEIMKRNIATYEEQLVALYGTNMDIVGSGGSGGSSSGVSSLFQNLGVSVTPIQRIVLSGENGLKIDIHVIIPYE
GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 505 (SS 45 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattAGCgctAGCGGAGGTTCA
GGCGGTTCCGGAatgtatgaaagctttattgagtcactgccattccttaaatctttggagttttctgcacgcctgaaa
gtagtagatgtgataggcaccaaagtatacaacgatggagaacaaatcattgctcagggagattcggctgattctttt
ttcattattgaatctggagaagtgaaaattactatgaaaagaaagggtaaatcagaagtggaagagaatggtgcagta
gaaatcgctcgatgctcgcggggacagtactttggagagcttgccctggtaactaacaaacctcgagcagcttctgcc
cacgccattgggactgtcaaatgtttagcaatggatgtgcaagcatttgaaaggcttctgggaccttgcatggaaatt
atgaaaaggaacatcgctacctatgaagaacagttagttgccctgTATggaacgaacatggatattgtaggGTCAGGT
GGATCTGGAGGtAGCTCttcTgtcctgagcggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 506 (SS 45 L27V (RIIbB) (aa seq)
MVFTLEDFVGDWRQTAGYNLDQVLEQGGVSSLFQNLGVSVTPIQRISASGGSGGSGMYESFIESLPFLKSLEFSARLK
VVDVIGTKVYNDGEQIIAQGDSADSFFIIESGEVKITMKRKGKSEVEENGAVEIARCSRGQYFGELALVTNKPRAASA
HAIGTVKCLAMDVQAFERLLGPCMEIMKRNIATYEEQLVALYGTNMDIVGSGGSGGSSSVLSGENGLKIDIHVIIPYE
GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 507 (SS 48 L27V (RIIbB) (nt sequence)
atggtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcAGCgctAGC
GGAGGTTCAGGCGGTTCCGGAatgtatgaaagctttattgagtcactgccattccttaaatctttggagttttctgca
cgcctgaaagtagtagatgtgataggcaccaaagtatacaacgatggagaacaaatcattgctcagggagattcggct
gattcttttttcattattgaatctggagaagtgaaaattactatgaaaagaaagggtaaatcagaagtggaagagaat
ggtgcagtagaaatcgctcgatgctcgcggggacagtactttggagagcttgccctggtaactaacaaacctcgagca
gcttctgcccacgccattgggactgtcaaatgtttagcaatggatgtgcaagcatttgaaaggcttctgggaccttgc
atggaaattatgaaaaggaacatcgctacctatgaagaacagttagttgccctgTATggaacgaacatggatattgta
ggGTCAGGTGGATCTGGAGGtAGCTCttcTggtgaaaatgggctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 508 (SS 48 L27V (RIIbB) (aa seq)
MVFTLEDFVGDWRQTAGYNLDQVLEQGGVSSLFQNLGVSVTPIQRIVLSSASGGSGGSGMYESFIESLPFLKSLEFSA
RLKVVDVIGTKVYNDGEQIIAQGDSADSFFIIESGEVKITMKRKGKSEVEENGAVEIARCSRGQYFGELALVTNKPRA
ASAHAIGTVKCLAMDVQAFERLLGPCMEIMKRNIATYEEQLVALYGTNMDIVGSGGSGGSSSGENGLKIDIHVIIPYE
GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 509 (SS 52 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggAGCgctAGCGGAGGTTCAGGCGGTTCCGGAatgtatgaaagctttattgagtcactgccattccttaaatctttg
gagttttctgcacgcctgaaagtagtagatgtgataggcaccaaagtatacaacgatggagaacaaatcattgctcag
ggagattcggctgattcttttttcattattgaatctggagaagtgaaaattactatgaaaagaaagggtaaatcagaa
gtggaagagaatggtgcagtagaaatcgctcgatgctcgcggggacagtactttggagagcttgccctggtaactaac
aaacctcgagcagcttctgcccacgccattgggactgtcaaatgtttagcaatggatgtgcaagcatttgaaaggctt
ctgggaccttgcatggaaattatgaaaaggaacatcgctacctatgaagaacagttagttgccctgTATggaacgaac
atggatattgtaggGTCAGGTGGATCTGGAGGtAGCTCttcTctgaagatcgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 510 (SS 52 L27V (RIIbB) (aa seq)
MVFTLEDFVGDWRQTAGYNLDQVLEQGGVSSLFQNLGVSVTPIQRIVLSGENGSASGGSGGSGMYESFIESLPFLKSL
EFSARLKVVDVIGTKVYNDGEQIIAQGDSADSFFIIESGEVKITMKRKGKSEVEENGAVEIARCSRGQYFGELALVTN
KPRAASAHAIGTVKCLAMDVQAFERLLGPCMEIMKRNIATYEEQLVALYGTNMDIVGSGGSGGSSSLKIDIHVIIPYE -continued

SEQUENCE LISTING

GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA

SEQ ID NO: 511 (SS 55 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcAGCgctAGCGGAGGTTCAGGCGGTTCCGGAatgtatgaaagctttattgagtcactgccattcctt
aaatctttggagttttctgcacgcctgaaagtagtagatgtgataggcaccaaagtatacaacgatggagagaacaaatc
attgctcagggagattcggctgattctttttttcattattgaatctggagaagtgaaaattactatgaaaagaaagggt
aaatcagaagtggaagagaatggtgcagtagaaatcgctcgatgctcgcggggacagtactttggagagcttgccctg
gtaactaacaaacctcgagcagcttctgcccacgccattgggactgtcaaatgtttagcaatggatgtgcaagcattt
gaaaggcttctgggaccttgcatggaaattatgaaaaggaacatcgctacctatgaagaacagttagttgccctgTAT
ggaacgaacatggatattgtaggGTCAGGTGGATCTGGAGGtAGCTCttcTgacatccatgtcatcatcccgtatgaa
ggtctgagcggcgaccaaatgggccagatcgaaaaaatttttaaggtggtgtaccctgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 512 (SS 55 L27V (RIIbB) (aa seq)
MVFTLEDFVGDWRQTAGYNLDQVLEQGGVSSLFQNLGVSVTPIQRIVLSGENGLKISASGGSGGSGMYESFIESLPFL
KSLEFSARLKVVDVIGTKVYNDGEQIIAQGDSADSFFIIESGEVKITMKRKGKSEVEENGAVEIARCSRGQYFGELAL
VTNKPRAASAHAIGTVKCLAMDVQAFERLLGPCMEIMKRNIATYEEQLVALYGTNMDIVGSGGSGGSSSDIHVIIPYE
GLSGDQMGQIEKIFKVVYPVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 513 (SS 83 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctAGCgctAGCGGAGGTTCAGGCGGTTCCGGAatgtatgaaagctttattgagtcactgcca
ttccttaaatctttggagttttctgcacgcctgaaagtagtagatgtgataggcaccaaagtatacaacgatggagaa
caaatcattgctcagggagattcggctgattctttttttcattattgaatctggagaagtgaaaattactatgaaaaga
aagggtaaatcagaagtggaagagaatggtgcagtagaaatcgctcgatgctcgcggggacagtactttggagagctt
gccctggtaactaacaaacctcgagcagcttctgcccacgccattgggactgtcaaatgtttagcaatggatgtgcaa
gcatttgaaaggcttctgggaccttgcatggaaattatgaaaaggaacatcgctacctatgaagaacagttagttgcc
ctgTATggaacgaacatggatattgtaggGTCAGGTGGATCTGGAGGtAGCTCttcTgtggatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 514 (SS 83 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPSASGGSGGSGMYESFIESLPFLKSLEFSARLKVVDVIGTKVYNDGEQIIAQGDSADSFFIIESGEVKITMKR
KGKSEVEENGAVEIARCSRGQYFGELALVTNKPRAASAHAIGTVKCLAMDVQAFERLLGPCMEIMKRNIATYEEQLVA
LYGTNMDIVGSGGSGGSSSVDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 515 (SS 84 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtgAGCgctAGCGGAGGTTCAGGCGGTTCCGGAatgtatgaaagctttattgagtcactg
ccattccttaaatctttggagttttctgcacgcctgaaagtagtagatgtgataggcaccaaagtatacaacgatgga
gaacaaatcattgctcagggagattcggctgattctttttttcattattgaatctggagaagtgaaaattactatgaaa
agaaagggtaaatcagaagtggaagagaatggtgcagtagaaatcgctcgatgctcgcggggacagtactttggagag
cttgccctggtaactaacaaacctcgagcagcttctgcccacgccattgggactgtcaaatgtttagcaatggatgtg
caagcatttgaaaggcttctgggaccttgcatggaaattatgaaaaggaacatcgctacctatgaagaacagttagtt
gccctgTATggaacgaacatggatattgtaggGTCAGGTGGATCTGGAGGtAGCTCttcTgatgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 516 (SS 84 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVSASGGSGGSGMYESFIESLPFLKSLEFSARLKVVDVIGTKVYNDGEQIIAQGDSADSFFIIESGEVKITMK
RKGKSEVEENGAVEIARCSRGQYFGELALVTNKPRAASAHAIGTVKCLAMDVQAFERLLGPCMEIMKRNIATYEEQLV
ALYGTNMDIVGSGGSGGSSSDDHHFKVILHYGTLVIDGVTPNMIDYFGRPYEGIAVFDGKKITVTGTLWNGNKIIDER
LINPDGSLLFRVTINGVTGWRLCERILA SEQ ID NO: 517 (SS 85 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatAGCgctAGCGGAGGTTCAGGCGGTTCCGGAatgtatgaaagctttattgagtca

SEQUENCE LISTING ctgccattccttaaatctttggagttttctgcacgcctgaaagtagtagatgtgataggcaccaaagtatacaacgat
ggagaacaaatcattgctcagggagattcggctgattctttttttcattattgaatctggagaagtgaaaattactatg
aaaagaaagggtaaatcagaagtggaagagaatggtgcagtagaaatcgctcgatgctcgcggggacagtactttgga
gagcttgccctggtaactaacaaacctcgagcagcttctgcccacgccattgggactgtcaaatgtttagcaatggat
gtgcaagcatttgaaaggcttctgggaccttgcatggaaattatgaaaaggaacatcgctacctatgaagaacagtta
gttgccctgTATggaacgaacatggatattgtaggGTCAGGTGGATCTGGAGGtAGCTCttcTgatcatcactttaag
gtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 518 (SS 85 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDSASGGSGGSGMYESFIESLPFLKSLEFSARLKVVDVIGTKVYNDGEQIIAQGDSADSFFIIESGEVKITM
KRKGKSEVEENGAVEIARCSRGQYFGELALVTNKPRAASAHAIGTVKCLAMDVQAFERLLGPCMEIMKRNIATYEEQL
VALYGTNMDIVGSGGSGGSSSDHHFKVILHYGTLVIDGVTPNMIDYFGRPYEGIAVFDGKKITVTGTLWNGNKIIDER
LINPDGSLLFRVTINGVTGWRLCERILA SEQ ID NO: 519 (SS 100 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcAGCgctAGC
GGAGGTTCAGGCGGTTCCGGAatgtatgaaagctttattgagtcactgccattccttaaatctttggagttttctgca
cgcctgaaagtagtagatgtgataggcaccaaagtatacaacgatggagaacaaatcattgctcagggagattcggct
gattctttttttcattattgaatctggagaagtgaaaattactatgaaaagaaagggtaaatcagaagtggaagagaat
ggtgcagtagaaatcgctcgatgctcgcggggacagtactttggagagcttgccctggtaactaacaaacctcgagca
gcttctgcccacgccattgggactgtcaaatgtttagcaatggatgtgcaagcatttgaaaggcttctgggaccttgc
atggaaattatgaaaaggaacatcgctacctatgaagaacagttagttgccctgTATggaacgaacatggatattgta
ggGTCAGGTGGATCTGGAGGtAGCTCttcTgacggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 520 (SS 100 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVISASGGSGGSGMYESFIESLPFLKSLEFSARLKVVDVIGTKVYNDGEQIIAQGDSA
DSFFIIESGEVKITMKRKGKSEVEENGAVEIARCSRGQYFGELALVTNKPRAASAHAIGTVKCLAMDVQAFERLLGPC
MEIMKRNIATYEEQLVALYGTNMDIVGSGGSGGSSSDGVTPNMIDYFGRPYEGIAVFDGKKITVTGTLWNGNKIIDER
LINPDGSLLFRVTINGVTGWRLCERILA SEQ ID NO: 521 (SS 101 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacAGCgct
AGCGGAGGTTCAGGCGGTTCCGGAatgtatgaaagctttattgagtcactgccattccttaaatctttggagttttct
gcacgcctgaaagtagtagatgtgataggcaccaaagtatacaacgatggagaacaaatcattgctcagggagattcg
gctgattctttttttcattattgaatctggagaagtgaaaattactatgaaaagaaagggtaaatcagaagtggaagag
aatggtgcagtagaaatcgctcgatgctcgcggggacagtactttggagagcttgccctggtaactaacaaacctcga
gcagcttctgcccacgccattgggactgtcaaatgtttagcaatggatgtgcaagcatttgaaaggcttctgggacct
tgcatggaaattatgaaaaggaacatcgctacctatgaagaacagttagttgccctgTATggaacgaacatggatatt
gtaggGTCAGGTGGATCTGGAGGtAGCTCttcTggggttacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 522 (SS 101 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDSASGGSGGSGMYESFIESLPFLKSLEFSARLKVVDVIGTKVYNDGEQIIAQGDS
ADSFFIIESGEVKITMKRKGKSEVEENGAVEIARCSRGQYFGELALVTNKPRAASAHAIGTVKCLAMDVQAFERLLGP
CMEIMKRNIATYEEQLVALYGTNMDIVGSGGSGGSSSGVTPNMIDYFGRPYEGIAVFDGKKITVTGTLWNGNKIIDER
LINPDGSLLFRVTINGVTGWRLCERILA SEQ ID NO: 523 (SS 102 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacgggAGC
gctAGCGGAGGTTCAGGCGGTTCCGGAatgtatgaaagctttattgagtcactgccattccttaaatctttggagttt
tctgcacgcctgaaagtagtagatgtgataggcaccaaagtatacaacgatggagaacaaatcattgctcagggagat
tcggctgattctttttttcattattgaatctggagaagtgaaaattactatgaaaagaaagggtaaatcagaagtggaa
gagaatggtgcagtagaaatcgctcgatgctcgcggggacagtactttggagagcttgccctggtaactaacaaacct
cgagcagcttctgcccacgccattgggactgtcaaatgtttagcaatggatgtgcaagcatttgaaaggcttctggga
ccttgcatggaaattatgaaaaggaacatcgctacctatgaagaacagttagttgccctgTATggaacgaacatggat
attgtaggGTCAGGTGGATCTGGAGGtAGCTCttcTgttacgccgaacatgatcgactatttcggacggccgtatgaa
ggcatcgccgtgttcgacggcaaaaagatcactgtaacagggaccctgtggaacggcaacaaaattatcgacgagcgc

SEQUENCE LISTING ctgatcaaccccgacggctccctgctgttccgagtaaccatcaacggagtgaccggctggcggctgtGCGAACGCATT
CTGGCt SEQ ID NO: 524 (SS 102 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGSASGGSGGSGMYESFIESLPFLKSLEFSARLKVVDVIGTKVYNDGEQIIAQGD
SADSFFIIESGEVKITMKRKGKSEVEENGAVEIARCSRGQYFGELALVTNKPRAASAHAIGTVKCLAMDVQAFERLLG
PCMEIMKRNIATYEEQLVALYGTNMDIVGSGGSGGSSSVTPNMIDYFGRPYEGIAVFDGKKITVTGTLWNGNKIIDER
LINPDGSLLFRVTINGVTGWRLCERILA SEQ ID NO: 525 (SS 103 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
AGCgctAGCGGAGGTTCAGGCGGTTCCGGAatgtatgaaagctttattgagtcactgccattccttaaatctttggag
ttttctgcacgcctgaaagtagtagatgtgataggcaccaaagtatacaacgatggagaacaaatcattgctcaggga
gattcggctgattctttttttcattattgaatctggagaagtgaaaattactatgaaaagaaagggtaaatcagaagtg
gaagagaatggtgcagtagaaatcgctcgatgctcgcggggacagtactttggagagcttgccctggtaactaacaaa
cctcgagcagcttctgcccacgccattgggactgtcaaatgtttagcaatggatgtgcaagcatttgaaaggcttctg
ggaccttgcatggaaattatgaaaaggaacatcgctacctatgaagaacagttagttgccctgTATggaacgaacatg
gatattgtaggGTCAGGTGGATCTGGAGGtAGCTCttcTacgccgaacatgatcgactatttcggacggccgtatgaa
ggcatcgccgtgttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 526 (SS 103 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVSASGGSGGSGMYESFIESLPFLKSLEFSARLKVVDVIGTKVYNDGEQIIAQG
DSADSFFIIESGEVKITMKRKGKSEVEENGAVEIARCSRGQYFGELALVTNKPRAASAHAIGTVKCLAMDVQAFERLL
GPCMEIMKRNIATYEEQLVALYGTNMDIVGSGGSGGSSSTPNMIDYFGRPYEGIAVFDGKKITVTGTLWNGNKIIDER
LINPDGSLLFRVTINGVTGWRLCERILA SEQ ID NO: 527 (SS 120 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgAGCgctAGCGGAGGTTCAGGCGGTTCC
GGAatgtatgaaagctttattgagtcactgccattccttaaatctttggagttttctgcacgcctgaaagtagtagat
gtgataggcaccaaagtatacaacgatggagaacaaatcattgctcagggagattcggctgattctttttttcattatt
gaatctggagaagtgaaaattactatgaaaagaaagggtaaatcagaagtggaagagaatggtgcagtagaaatcgct
cgatgctcgcggggacagtactttggagagcttgccctggtaactaacaaacctcgagcagcttctgcccacgccatt
gggactgtcaaatgtttagcaatggatgtgcaagcatttgaaaggcttctgggaccttgcatggaaattatgaaaagg
aacatcgctacctatgaagaacagttagttgccctgTATggaacgaacatggatattgtaggGTCAGGTGGATCTGGA
GGtAGCTCttcTttcgacggcaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 528 (SS 120 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVSASGGSGGSGMYESFIESLPFLKSLEFSARLKVVD
VIGTKVYNDGEQIIAQGDSADSFFIIESGEVKITMKRKGKSEVEENGAVEIARCSRGQYFGELALVTNKPRAASAHAI
GTVKCLAMDVQAFERLLGPCMEIMKRNIATYEEQLVALYGTNMDIVGSGGSGGSSSFDGKKITVTGTLWNGNKIIDER
LINPDGSLLFRVTINGVTGWRLCERILA SEQ ID NO: 529 (SS 123 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcAGCgctAGCGGAGGTTCA
GGCGGTTCCGGAatgtatgaaagctttattgagtcactgccattccttaaatctttggagttttctgcacgcctgaaa
gtagtagatgtgataggcaccaaagtatacaacgatggagaacaaatcattgctcagggagattcggctgattctttt
ttcattattgaatctggagaagtgaaaattactatgaaaagaaagggtaaatcagaagtggaagagaatggtgcagta
gaaatcgctcgatgctcgcggggacagtactttggagagcttgccctggtaactaacaaacctcgagcagcttctgcc
cacgccattgggactgtcaaatgtttagcaatggatgtgcaagcatttgaaaggcttctgggaccttgcatggaaatt
atgaaaaggaacatcgctacctatgaagaacagttagttgccctgTATggaacgaacatggatattgtaggGTCAGGT
GGATCTGGAGGtAGCTCttcTaaaaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 530 (SS 123 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGSASGGSGGSGMYESFIESLPFLKSLEFSARLK
VVDVIGTKVYNDGEQIIAQGDSADSFFIIESGEVKITMKRKGKSEVEENGAVEIARCSRGQYFGELALVTNKPRAASA

SEQUENCE LISTING

HAIGTVKCLAMDVQAFERLLGPCMEIMKRNIATYEEQLVALYGTNMDIVGSGGSGGSSSKKITVTGTLWNGNKIIDER
LINPDGSLLFRVTINGVTGWRLCERILA

SEQ ID NO: 531 (SS 124 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaAGCgctAGCGGAGGT
TCAGGCGGTTCCGGAatgtatgaaagctttattgagtcactgccattccttaaatctttggagttttctgcacgcctg
aaagtagtagatgtgataggcaccaaagtatacaacgatggagagaacaaatcattgctcagggagattcggctgattct
tttttcattattgaatctggagaagtgaaaattactatgaaaagaaagggtaaatcagaagtggaagagaatggtgca
gtagaaatcgctcgatgctcgcggggacagtactttggagagcttgccctggtaactaacaaacctcgagcagcttct
gcccacgccattgggactgtcaaatgtttagcaatggatgtgcaagcatttgaaaggcttctgggaccttgcatggaa
attatgaaaaggaacatcgctacctatgaagaacagttagttgccctgTATggaacgaacatggatattgtagggGTCA
GGTGGATCTGGAGGtAGCTCttcTaagatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 532 (SS 124 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKSASGGSGGSGMYESFIESLPFLKSLEFSARL
KVVDVIGTKVYNDGEQIIAQGDSADSFFIIESGEVKITMKRKGKSEVEENGAVEIARCSRGQYFGELALVTNKPRAAS
AHAIGTVKCLAMDVQAFERLLGPCMEIMKRNIATYEEQLVALYGTNMDIVGSGGSGGSSSKITVTGTLWNGNKIIDER
LINPDGSLLFRVTINGVTGWRLCERILA SEQ ID NO: 533 (SS 125 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagAGCgctAGCGGA
GGTTCAGGCGGTTCCGGAatgtatgaaagctttattgagtcactgccattccttaaatctttggagttttctgcacgc
ctgaaagtagtagatgtgataggcaccaaagtatacaacgatggagagaacaaatcattgctcagggagattcggctgat
tctttttttcattattgaatctggagaagtgaaaattactatgaaaagaaagggtaaatcagaagtggaagagaatggt
gcagtagaaatcgctcgatgctcgcggggacagtactttggagagcttgccctggtaactaacaaacctcgagcagct
tctgcccacgccattgggactgtcaaatgtttagcaatggatgtgcaagcatttgaaaggcttctgggaccttgcatg
gaaattatgaaaaggaacatcgctacctatgaagaacagttagttgccctgTATggaacgaacatggatattgtaggG
TCAGGTGGATCTGGAGGtAGCTCttcTatcactgtaacagggaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 534 (SS 125 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKSASGGSGGSGMYESFIESLPFLKSLEFSAR
LKVVDVIGTKVYNDGEQIIAQGDSADSFFIIESGEVKITMKRKGKSEVEENGAVEIARCSRGQYFGELALVTNKPRAA
SAHAIGTVKCLAMDVQAFERLLGPCMEIMKRNIATYEEQLVALYGTNMDIVGSGGSGGSSSITVTGTLWNGNKIIDER
LINPDGSLLFRVTINGVTGWRLCERILA SEQ ID NO: 535 (SS 130 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggAGCgctAGCGGAGGTTCAGGCGGTTCCGGAatgtatgaaagctttattgagtcactgccattccttaaatctttg
gagttttctgcacgcctgaaagtagtagatgtgataggcaccaaagtatacaacgatggagagaacaaatcattgctcag
ggagattcggctgattctttttttcattattgaatctggagaagtgaaaattactatgaaaagaaagggtaaatcagaa
gtggaagagaatggtgcagtagaaatcgctcgatgctcgcggggacagtactttggagagcttgccctggtaactaac
aaacctcgagcagcttctgcccacgccattgggactgtcaaatgtttagcaatggatgtgcaagcatttgaaaggctt
ctgggaccttgcatggaaattatgaaaaggaacatcgctacctatgaagaacagttagttgccctgTATggaacgaac
atggatattgtaggGTCAGGTGGATCTGGAGGtAGCTCttcTaccctgtggaacggcaacaaaattatcgacgagcgc
ctgatcaaccccgacggctccctgctgttccgagtaaccatcaacggagtgaccggctggcggctgtGCGAACGCATT
CTGGCt SEQ ID NO: 536 (SS 130 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGSASGGSGGSGMYESFIESLPFLKSL
EFSARLKVVDVIGTKVYNDGEQIIAQGDSADSFFIIESGEVKITMKRKGKSEVEENGAVEIARCSRGQYFGELALVTN
KPRAASAHAIGTVKCLAMDVQAFERLLGPCMEIMKRNIATYEEQLVALYGTNMDIVGSGGSGGSSSTLWNGNKIIDER
LINPDGSLLFRVTINGVTGWRLCERILA SEQ ID NO: 537 (SS 136 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt

SEQUENCE LISTING acgccgaacatgatcgactatttcggacggccgtatgaaggcatcgccgtgttcgacggcaaaaagatcactgtaaca
gggaccctgtggaacggcaacAGCgctAGCGGAGGTTCAGGCGGTTCCGGAatgtatgaaagctttattgagtcactg
ccattccttaaatctttggagttttctgcacgcctgaaagtagtagatgtgatagcgcaccaaagtatacaacgatgga
gaacaaatcattgctcagggagattcggctgattcttttttcattattgaatctggagaagtgaaaattactatgaaa
agaaagggtaaatcagaagtggaagagaatggtgcagtagaaatcgctcgatgctcgcggggacagtactttggagag
cttgccctggtaactaacaaacctcgagcagcttctgcccacgccattgggactgtcaaatgtttagcaatggatgtg
caagcatttgaaaggcttctgggaccttgcatggaaattatgaaaaggaacatcgctacctatgaagaacagttagtt
gccctgTATggaacgaacatggatattgtaggGTCAGGTGGATCTGGAGGtAGCTCttcTaaaattatcgacgagcgc
ctgatcaaccccgacggctccctgctgttccgagtaaccatcaacggagtgaccggctggcggctgtGCGAACGCATT
CTGGCt SEQ ID NO: 538 (SS 136 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNSASGGSGGSGMYESFIESL
PFLKSLEFSARLKVVDVIGTKVYNDGEQIIAQGDSADSFFIIESGEVKITMKRKGKSEVEENGAVEIARCSRGQYFGE
LALVTNKPRAASAHAIGTVKCLAMDVQAFERLLGPCMEIMKRNIATYEEQLVALYGTNMDIVGSGGSGGSSSKIIDER
LINPDGSLLFRVTINGVTGWRLCERILA SEQ ID NO: 539 (SS 143 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgAGCgctAGCGGAGGTTCAGGCGGTTCCGGAatgtat
gaaagctttattgagtcactgccattccttaaatctttggagttttctgcacgcctgaaagtagtagatgtgataggc
accaaagtatacaacgatggagaacaaatcattgctcagggagattcggctgattcttttttcattattgaatctgga
gaagtgaaaattactatgaaaagaaagggtaaatcagaagtggaagagaatggtgcagtagaaatcgctcgatgctcg
cggggacagtactttggagagcttgccctggtaactaacaaacctcgagcagcttctgcccacgccattgggactgtc
aaatgtttagcaatggatgtgcaagcatttgaaaggcttctgggaccttgcatggaaattatgaaaaggaacatcgct
acctatgaagaacagttagttgccctgTATggaacgaacatggatattgtaggGTCAGGTGGATCTGGAGGtAGCTCt
tcTatcaaccccgacggctccctgctgttccgagtaaccatcaacggagtgaccggctggcggctgtGCGAACGCATT
CTGGCt SEQ ID NO: 540 (SS 143 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLSASGGSGGSGMY
ESFIESLPFLKSLEFSARLKVVDVIGTKVYNDGEQIIAQGDSADSFFIIESGEVKITMKRKGKSEVEENGAVEIARCS
RGQYFGELALVTNKPRAASAHAIGTVKCLAMDVQAFERLLGPCMEIMKRNIATYEEQLVALYGTNMDIVGSGGSGGSS
SINPDGSLLFRVTINGVTGWRLCERILA SEQ ID NO: 541 (SS 145 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaacAGCgctAGCGGAGGTTCAGGCGGTTCCGGA
atgtatgaaagctttattgagtcactgccattccttaaatctttggagttttctgcacgcctgaaagtagtagatgtg
ataggcaccaaagtatacaacgatggagaacaaatcattgctcagggagattcggctgattcttttttcattattgaa
tctggagaagtgaaaattactatgaaaagaaagggtaaatcagaagtggaagagaatggtgcagtagaaatcgctcga
tgctcgcggggacagtactttggagagcttgccctggtaactaacaaacctcgagcagcttctgcccacgccattggg
actgtcaaatgtttagcaatggatgtgcaagcatttgaaaggcttctgggaccttgcatggaaattatgaaaaggaac
atcgctacctatgaagaacagttagttgccctgTATggaacgaacatggatattgtaggGTCAGGTGGATCTGGAGGt
AGCTCttcTcccgacggctccctgctgttccgagtaaccatcaacggagtgaccggctggcggctgtGCGAACGCATT
CTGGCt SEQ ID NO: 542 (SS 145 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINSASGGSGGSG
MYESFIESLPFLKSLEFSARLKVVDVIGTKVYNDGEQIIAQGDSADSFFIIESGEVKITMKRKGKSEVEENGAVEIAR
CSRGQYFGELALVTNKPRAASAHAIGTVKCLAMDVQAFERLLGPCMEIMKRNIATYEEQLVALYGTNMDIVGSGGSGG
SSSPDGSLLFRVTINGVTGWRLCERILA SEQ ID NO: 543 (SS 147 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaaccccgacAGCgctAGCGGAGGTTCAGGCGGT
TCCGGAatgtatgaaagctttattgagtcactgccattccttaaatctttggagttttctgcacgcctgaaagtagta
gatgtgataggcaccaaagtatacaacgatggagaacaaatcattgctcagggagattcggctgattcttttttcatt
attgaatctggagaagtgaaaattactatgaaaagaaagggtaaatcagaagtggaagagaatggtgcagtagaaatc
gctcgatgctcgcggggacagtactttggagagcttgccctggtaactaacaaacctcgagcagcttctgcccacgcc
attgggactgtcaaatgtttagcaatggatgtgcaagcatttgaaaggcttctgggaccttgcatggaaattatgaaa
aggaacatcgctacctatgaagaacagttagttgccctgTATggaacgaacatggatattgtaggGTCAGGTGGATCT -continued

SEQUENCE LISTING

GGAGGtAGCTCttcTggctccctgctgttccgagtaaccatcaacggagtgaccggctggcggctgtGCGAACGCATT
CTGGCt SEQ ID NO: 544 (SS 147 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDSASGGSGG
SGMYESFIESLPFLKSLEFSARLKVVDVIGTKVYNDGEQIIAQGDSADSFFIIESGEVKITMKRKGKSEVEENGAVEI
ARCSRGQYFGELALVTNKPRAASAHAIGTVKCLAMDVQAFERLLGPCMEIMKRNIATYEEQLVALYGTNMDIVGSGGS
GGSSSGSLLFRVTINGVTGWRLCERILA SEQ ID NO: 545 (SS 148 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaacccgacggcAGCgctAGCGGAGGTTCAGGC
GGTTCCGGAatgtatgaaagctttattgagtcactgccattccttaaatctttggagttttctgcacgcctgaaagta
gtagatgtgataggcaccaaagtatacaacgatggagaacaaatcattgctcagggagattcggctgattctttttttc
attattgaatctggagaagtgaaaattactatgaaaagaaagggtaaatcagaagtggaagagaatggtgcagtagaa
atcgctcgatgctcgcggggacagtactttggagagcttgccctggtaactaacaaacctcgagcagcttctgcccac
gccattgggactgtcaaatgtttagcaatggatgtgcaagcatttgaaaggcttctgggaccttgcatggaaattatg
aaaaggaacatcgctacctatgaagaacagttagttgccctgTATggaacgaacatggatattgtaggGTCAGGTGGA
TCTGGAGGtAGCTCttcTtccctgctgttccgagtaaccatcaacggagtgaccggctggcggctgtGCGAACGCATT
CTGGCt SEQ ID NO: 546 (SS 148 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSASGGSG
GSGMYESFIESLPFLKSLEFSARLKVVDVIGTKVYNDGEQIIAQGDSADSFFIIESGEVKITMKRKGKSEVEENGAVE
IARCSRGQYFGELALVTNKPRAASAHAIGTVKCLAMDVQAFERLLGPCMEIMKRNIATYEEQLVALYGTNMDIVGSGG
SGGSSSSLLFRVTINGVTGWRLCERILA SEQ ID NO: 547 (SS 156 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaacccgacggctccctgctgttccgagtaacc
atcAGCgctAGCGGAGGTTCAGGCGGTTCCGGAatgtatgaaagctttattgagtcactgccattccttaaatctttg
gagttttctgcacgcctgaaagtagtagatgtgataggcaccaaagtatacaacgatggagaacaaatcattgctcag
ggagattcggctgattctttttttcattattgaatctggagaagtgaaaattactatgaaaagaaagggtaaatcagaa
gtggaagagaatggtgcagtagaaatcgctcgatgctcgcggggacagtactttggagagcttgccctggtaactaac
aaacctcgagcagcttctgcccacgccattgggactgtcaaatgtttagcaatggatgtgcaagcatttgaaaggctt
ctgggaccttgcatggaaattatgaaaaggaacatcgctacctatgaagaacagttagttgccctgTATggaacgaac
atggatattgtaggGTCAGGTGGATCTGGAGGtAGCTCttcTaacggagtgaccggctggcggctgtGCGAACGCATT
CTGGCt SEQ ID NO: 548 (SS 156 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
ISASGGSGGSGMYESFIESLPFLKSLEFSARLKVVDVIGTKVYNDGEQIIAQGDSADSFFIIESGEVKITMKRKGKSE
VEENGAVEIARCSRGQYFGELALVTNKPRAASAHAIGTVKCLAMDVQAFERLLGPCMEIMKRNIATYEEQLVALYGTN
MDIVGSGGSGGSSSNGVTGWRLCERILA SEQ ID NO: 549 (SS 157 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaacccgacggctccctgctgttccgagtaacc
atcaacAGCgctAGCGGAGGTTCAGGCGGTTCCGGAatgtatgaaagctttattgagtcactgccattccttaaatct
ttggagttttctgcacgcctgaaagtagtagatgtgataggcaccaaagtatacaacgatggagaacaaatcattgct
cagggagattcggctgattctttttttcattattgaatctggagaagtgaaaattactatgaaaagaaagggtaaatca
gaagtggaagagaatggtgcagtagaaatcgctcgatgctcgcggggacagtactttggagagcttgccctggtaact
aacaaacctcgagcagcttctgcccacgccattgggactgtcaaatgtttagcaatggatgtgcaagcatttgaaagg
cttctgggaccttgcatggaaattatgaaaaggaacatcgctacctatgaagaacagttagttgccctgTATggaacg
aacatggatattgtaggGTCAGGTGGATCTGGAGGtAGCTCttcTggagtgaccggctggcggctgtGCGAACGCATT
CTGGCt SEQ ID NO: 550 (SS 157 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INSASGGSGGSGMYESFIESLPFLKSLEFSARLKVVDVIGTKVYNDGEQIIAQGDSADSFFIIESGEVKITMKRKGKS -continued

SEQUENCE LISTING

EVEENGAVEIARCSRGQYFGELALVTNKPRAASAHAIGTVKCLAMDVQAFERLLGPCMEIMKRNIATYEEQLVALYGT
NMDIVGSGGSGGSSSGVTGWRLCERILA

SEQ ID NO: 551 (SS 158 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaaccccgacggctccctgctgttccgagtaacc
atcaacggaAGCgctAGCGGAGGTTCAGGCGGTTCCGGAatgtatgaaagctttattgagtcactgccattccttaaa
tctttggagttttctgcacgcctgaaagtagtagatgtgataggcaccaaagtatacaacgatggagaacaaatcatt
gctcagggagattcggctgattctttttttcattattgaatctggagaagtgaaaattactatgaaaagaaagggtaaa
tcagaagtggaagagaatggtgcagtagaaatcgctcgatgctcgcggggacagtactttggagagcttgccctggta
actaacaaacctcgagcagcttctgcccacgccattgggactgtcaaatgtttagcaatggatgtgcaagcatttgaa
aggcttctgggaccttgcatggaaattatgaaaaggaacatcgctacctatgaagaacagttagttgccctgTATgga
acgaacatggatattgtaggGTCAGGTGGATCTGGAGGtAGCTCttcTgtgaccggctggcggctgtGCGAACGCATT
CTGGCt SEQ ID NO: 552 (SS 158 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGSASGGSGGSGMYESFIESLPFLKSLEFSARLKVVDVIGTKVYNDGEQIIAQGDSADSFFIIESGEVKITMKRKGK
SEVEENGAVEIARCSRGQYFGELALVTNKPRAASAHAIGTVKCLAMDVQAFERLLGPCMEIMKRNIATYEEQLVALYG
TNMDIVGSGGSGGSSSVTGWRLCERILA SEQ ID NO: 553 (SS 166 L27V (RIIbB) (nt sequence)
ATGgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaaccccgacggctccctgctgttccgagtaacc
atcaacggagtgaccggctggcggctgtGCGAAAGCgctAGCGGAGGTTCAGGCGGTTCCGGAatgtatgaaagcttt
attgagtcactgccattccttaaatctttggagttttctgcacgcctgaaagtagtagatgtgataggcaccaaagta
tacaacgatggagaacaaatcattgctcagggagattcggctgattctttttttcattattgaatctggagaagtgaaa
attactatgaaaagaaagggtaaatcagaagtggaagagaatggtgcagtagaaatcgctcgatgctcgcggggacag
tactttggagagcttgccctggtaactaacaaacctcgagcagcttctgcccacgccattgggactgtcaaatgttta
gcaatggatgtgcaagcatttgaaaggcttctgggaccttgcatggaaattatgaaaaggaacatcgctacctatgaa
gaacagttagttgccctgTATggaacgaacatggatattgtaggGTCAGGTGGATCTGGAGGtAGCTCttcTCGCATT
CTGGCt SEQ ID NO: 554 (SS 166 L27V (RIIbB) (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCESASGGSGGSGMYESFIESLPFLKSLEFSARLKVVDVIGTKVYNDGEQIIAQGDSADSFFIIESGEVK
ITMKRKGKSEVEENGAVEIARCSRGQYFGELALVTNKPRAASAHAIGTVKCLAMDVQAFERLLGPCMEIMKRNIATYE
EQLVALYGTNMDIVGSGGSGGSSSRILA SEQ ID NO: 555 (CP 26 L27V (RIIbB) (nt sequence)
ATGggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaaccccgacggctccctgctgttccgagtaacc
atcaacggagtgaccggctggcggctgtGCGAACGCATTCTGGCtAGCTCAAGCGGAGGTTCAGGCGGTTCCGGAATG
TATGAAAGCTTTATTGAGTCACTGCCATTCCTTAAATCTTTGGAGTTTTCTGCACGCCTGAAAGTAGTAGATGTGATA
GGCACCAAAGTATACAACGATGGAGAACAAATCATTGCTCAGGGAGATTCGGCTGATTCTTTTTTCATTATTGAATCT
GGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACT
GTCAAATGTTTAGCAATGGATGTGCAAGCATTTGAAAGGCTTCTGGGACCTTGCATGGAAATTATGAAAAGGAACATC
GCTACCTATGAAGAACAGTTAGTTGCCCTGTATGGAACGAACATGGATATTGTAGGGTCAGGTGGATCTGGAGGTAGC
TCTTCTatggtcttcacactcgaagatttcgttggggactggcgacagacagccggctacaacctggaccaagtcctt
gaacaggga SEQ ID NO: 556 (CP 26 L27V (RIIbB) (aa seq)
MGVSSLFQNLGVSVTPIQRIVLSGENGLKIDIHVIIPYEGLSGDQMGQIEKIFKVVYPVDDHHFKVILHYGTLVIDGV
TPNMIDYFGRPYEGIAVFDGKKITVTGTLWNGNKIIDERLINPDGSLLFRVTINGVTGWRLCERILASSSGGSGGSGM
YESFIESLPFLKSLEFSARLKVVDVIGTKVYNDGEQIIAQGDSADSFFIIESGEVKITMKRKGKSEVEENGAVEIARC
SRGQYFGELALVTNKPRAASAHAIGTVKCLAMDVQAFERLLGPCMEIMKRNIATYEEQLVALYGTNMDIVGSGGSGGS
SSMVFTLEDFVGDWRQTAGYNLDQVLEQG SEQ ID NO: 557 (CP 45 L27V (RIIbB) (nt sequence)
ATGgtcctgagcggtgaaaatgggctgaagatcgacatccatgtcatcatcccgtatgaaggtctgagcggcgaccaa
atgggccagatcgaaaaaatttttaaggtggtgtaccctgtggatgatcatcactttaaggtgatcctgcactatggc
acactggtaatcgacggggttacgccgaacatgatcgactatttcggacggccgtatgaaggcatcgccgtgttcgac
ggcaaaaagatcactgtaacagggaccctgtggaacggcaacaaaattatcgacgagcgcctgatcaaccccgacggc -continued

SEQUENCE LISTING tccctgctgttccgagtaaccatcaacggagtgaccggctggcggctgtGCGAACGCATTCTGGCtAGCTCAAGCGGA
GGTTCAGGCGGTTCCGGAATGTATGAAAGCTTTATTGAGTCACTGCCATTCCTTAAATCTTTGGAGTTTTCTGCACGC
CTGAAAGTAGTAGATGTGATAGGCACCAAAGTATACAACGATGGAGAACAAATCATTGCTCAGGGAGATTCGGCTGAT
TCTTTTTTCATTATTGAATCTGGAGAAGTGAAAATTACTATGAAAAGAAAGGGTAAATCAGAAGTGGAAGAGAATGGT
GCAGTAGAAATCGCTCGATGCTCGCGGGGACAGTACTTTGGAGAGCTTGCCCTGGTAACTAACAAACCTCGAGCAGCT
TCTGCCCACGCCATTGGGACTGTCAAATGTTTAGCAATGGATGTGCAAGCATTTGAAAGGCTTCTGGGACCTTGCATG
GAAATTATGAAAAGGAACATCGCTACCTATGAAGAACAGTTAGTTGCCCTGTATGGAACGAACATGGATATTGTAGGG
TCAGGTGGATCTGGAGGTAGCTCTTCTatggtcttcacactcgaagatttcgttggggactggcgacagacagccggc
tacaacctggaccaagtccttgaacagggaggtgtgtccagtttgtttcagaatctcggggtgtccgtaactccgatc
caaaggatt SEQ ID NO: 558 (CP 45 L27V (RIIbB) (aa seq)
MVLSGENGLKIDIHVIIPYEGLSGDQMGQIEKIFKVVYPVDDHHFKVILHYGTLVIDGVTPNMIDYFGRPYEGIAVFD
GKKITVTGTLWNGNKIIDERLINPDGSLLFRVTINGVTGWRLCERILASSSGGSGGSGMYESFIESLPFLKSLEFSAR
LKVVDVIGTKVYNDGEQIIAQGDSADSFFIIESGEVKITMKRKGKSEVEENGAVEIARCSRGQYFGELALVTNKPRAA
SAHAIGTVKCLAMDVQAFERLLGPCMEIMKRNIATYEEQLVALYGTNMDIVGSGGSGGSSSMVFTLEDFVGDWRQTAG
YNLDQVLEQGGVSSLFQNLGVSVTPIQRI SEQ ID NO: 559 (CP 100(+1) L27V (RIIbB) (nt sequence)
ATGgacggggttacgccgaacatgatcgactatttcggacggccgtatgaaggcatcgccgtgttcgacggcaaaaag
atcactgtaacagggaccctgtggaacggcaacaaaattatcgacgagcgcctgatcaaccccgacggctccctgctg
ttccgagtaaccatcaacggagtgaccggctggcggctgtGCGAACGCATTCTGGCtAGCTCAAGCGGAGGTTCAGGC
GGTTCCGGAATGTATGAAAGCTTTATTGAGTCACTGCCATTCCTTAAATCTTTGGAGTTTTCTGCACGCCTGAAAGTA
GTAGATGTGATAGGCACCAAAGTATACAACGATGGAGAACAAATCATTGCTCAGGGAGATTCGGCTGATTCTTTTTTC
ATTATTGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCAC
GCCATTGGGACTGTCAAATGTTTAGCAATGGATGTGCAAGCATTTGAAAGGCTTCTGGGACCTTGCATGGAAATTATG
AAAAGGAACATCGCTACCTATGAAGAACAGTTAGTTGCCCTGTATGGAACGAACATGGATATTGTAGGGTCAGGTGGA
TCTGGAGGTAGCTCTTCTatggtcttcacactcgaagatttcgttggggactggcgacagacagccggctacaacctg
gaccaagtccttgaacagggaggtgtgtccagtttgtttcagaatctcggggtgtccgtaactccgatccaaaggatt
gtcctgagcggtgaaaatgggctgaagatcgacatccatgtcatcatcccgtatgaaggtctgagcggcgaccaaatg
ggccagatcgaaaaaatttttaaggtggtgtaccctgtggatgatcatcactttaaggtgatcctgcactatggcaca
ctggtaatcGAC SEQ ID NO: 560 (CP 100(+1) L27V (RIIbB) (aa seq)
MDGVTPNMIDYFGRPYEGIAVFDGKKITVTGTLWNGNKIIDERLINPDGSLLFRVTINGVTGWRLCERILASSSGGSG
GSGMYESFIESLPFLKSLEFSARLKVVDVIGTKVYNDGEQIIAQGDSADSFFIIESGEVKITMKRKGKSEVEENGAVE
IARCSRGQYFGELALVTNKPRAASAHAIGTVKCLAMDVQAFERLLGPCMEIMKRNIATYEEQLVALYGTNMDIVGSGG
SGGSSSMVFTLEDFVGDWRQTAGYNLDQVLEQGGVSSLFQNLGVSVTPIQRIVLSGENGLKIDIHVIIPYEGLSGDQM
GQIEKIFKVVYPVDDHHFKVILHYGTLVID SEQ ID NO: 561 (CP 101(+1) L27V (RIIbB) (nt sequence)
ATGggggttacgccgaacatgatcgactatttcggacggccgtatgaaggcatcgccgtgttcgacggcaaaaagatc
actgtaacagggaccctgtggaacggcaacaaaattatcgacgagcgcctgatcaaccccgacggctccctgctgttc
cgagtaaccatcaacggagtgaccggctggcggctgtGCGAACGCATTCTGGCtAGCTCAAGCGGAGGTTCAGGCGGT
TCCGGAATGTATGAAAGCTTTATTGAGTCACTGCCATTCCTTAAATCTTTGGAGTTTTCTGCACGCCTGAAAGTAGTA
GATGTGATAGGCACCAAAGTATACAACGATGGAGAACAAATCATTGCTCAGGGAGATTCGGCTGATTCTTTTTTCATT
ATTGAATCTGGAGAAGTGAAAATTACTATGAAAAGAAAGGGTAAATCAGAAGTGGAAGAGAATGGTGCAGTAGAAATC
GCTCGATGCTCGCGGGGACAGTACTTTGGAGAGCTTGCCCTGGTAACTAACAAACCTCGAGCAGCTTCTGCCCACGCC
ATTGGGACTGTCAAATGTTTAGCAATGGATGTGCAAGCATTTGAAAGGCTTCTGGGACCTTGCATGGAAATTATGAAA
AGGAACATCGCTACCTATGAAGAACAGTTAGTTGCCCTGTATGGAACGAACATGGATATTGTAGGGTCAGGTGGATCT
GGAGGTAGCTCTTCTatggtcttcacactcgaagatttcgttggggactggcgacagacagccggctacaacctggac
caagtccttgaacagggaggtgtgtccagtttgtttcagaatctcggggtgtccgtaactccgatccaaaggattgtc
ctgagcggtgaaaatgggctgaagatcgacatccatgtcatcatcccgtatgaaggtctgagcggcgaccaaatgggc
cagatcgaaaaaatttttaaggtggtgtaccctgtggatgatcatcactttaaggtgatcctgcactatggcacactg
gtaatcgacGGG SEQ ID NO: 562 (CP 101(+1) L27V (RIIbB) (aa seq)
MGVTPNMIDYFGRPYEGIAVFDGKKITVTGTLWNGNKIIDERLINPDGSLLFRVTINGVTGWRLCERILASSSGGSGG
SGMYESFIESLPFLKSLEFSARLKVVDVIGTKVYNDGEQIIAQGDSADSFFIIESGEVKITMKRKGKSEVEENGAVEI
ARCSRGQYFGELALVTNKPRAASAHAIGTVKCLAMDVQAFERLLGPCMEIMKRNIATYEEQLVALYGTNMDIVGSGGS
GGSSSMVFTLEDFVGDWRQTAGYNLDQVLEQGGVSSLFQNLGVSVTPIQRIVLSGENGLKIDIHVIIPYEGLSGDQMG
QIEKIFKVVYPVDDHHFKVILHYGTLVIDG SEQ ID NO: 563 (CP 102(+1) L27V (RIIbB) (nt sequence)
ATGgttacgccgaacatgatcgactatttcggacggccgtatgaaggcatcgccgtgttcgacggcaaaaagatcact
gtaacagggaccctgtggaacggcaacaaaattatcgacgagcgcctgatcaaccccgacggctccctgctgttccga
gtaaccatcaacggagtgaccggctggcggctgtGCGAACGCATTCTGGCtAGCTCAAGCGGAGGTTCAGGCGGTTCC
GGAATGTATGAAAGCTTTATTGAGTCACTGCCATTCCTTAAATCTTTGGAGTTTTCTGCACGCCTGAAAGTAGTAGAT
GTGATAGGCACCAAAGTATACAACGATGGAGAACAAATCATTGCTCAGGGAGATTCGGCTGATTCTTTTTTCATTATT
GAATCTGGAGAAGTGAAAATTACTATGAAAAGAAAGGGTAAATCAGAAGTGGAAGAGAATGGTGCAGTAGAAATCGCT
CGATGCTCGCGGGGACAGTACTTTGGAGAGCTTGCCCTGGTAACTAACAAACCTCGAGCAGCTTCTGCCCACGCCATT
GGGACTGTCAAATGTTTAGCAATGGATGTGCAAGCATTTGAAAGGCTTCTGGGACCTTGCATGGAAATTATGAAAAGG
AACATCGCTACCTATGAAGAACAGTTAGTTGCCCTGTATGGAACGAACATGGATATTGTAGGGTCAGGTGGATCTGGA
GGTAGCTCTTCTatggtcttcacactcgaagatttcgttggggactggcgacagacagccggctacaacctggaccaa
gtccttgaacagggaggtgtgtccagtttgtttcagaatctcggggtgtccgtaactccgatccaaaggattgtcctg
agcggtgaaaatgggctgaagatcgacatccatgtcatcatcccgtatgaaggtctgagcggcgaccaaatgggccag -continued

SEQUENCE LISTING atcgaaaaaatttttaaggtggtgtaccctgtggatgatcatcactttaaggtgatcctgcactatggcacactggta
atcgacgggGTT SEQ ID NO: 564 (CP 102(+1) L27V (RIIbB) (aa seq)
MVTPNMIDYFGRPYEGIAVFDGKKITVTGTLWNGNKIIDERLINPDGSLLFRVTINGVTGWRLCERILASSSGGSGGS
GMYESFIESLPFLKSLEFSARLKVVDVIGTKVYNDGEQIIAQGDSADSFFIIESGEVKITMKRKGKSEVEENGAVEIA
RCSRGQYFGELALVTNKPRAASAHAIGTVKCLAMDVQAFERLLGPCMEIMKRNIATYEEQLVALYGTNMDIVGSGGSG
GSSSMVFTLEDFVGDWRQTAGYNLDQVLEQGGVSSLFQNLGVSVTPIQRIVLSGENGLKIDIHVIIPYEGLSGDQMGQ
IEKIFKVVYPVDDHHFKVILHYGTLVIDGV SEQ ID NO: 565 (CP 143(+1) L27V (RIIbB) (nt sequence)
ATGatcaaccccgacggctccctgctgttccgagtaaccatcaacggagtgaccggctggcggctgtGCGAACGCATT
CTGGCtAGCTCAAGCGGAGGTTCAGGCGGTTCCGGAATGTATGAAAGCTTTATTGAGTCACTGCCATTCCTTAAATCT
TTGGAGTTTTCTGCACGCCTGAAAGTAGTAGATGTGATAGGCACCAAAGTATACAACGATGGAGAACAAATCATTGCT
CAGGGAGATTCGGCTGATTCTTTTTTCATTATTGAATCTGGAGAAGTGAAAATTACTATGAAAAGAAAGGGTAAATCA
GAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGG
CTTCTGGGACCTTGCATGGAAATTATGAAAAGGAACATCGCTACCTATGAAGAACAGTTAGTTGCCCTGTATGGAACG
AACATGGATATTGTAGGGTCAGGTGGATCTGGAGGTAGCTCTTCTatggtcttcacactcgaagatttcgttggggac
tggcgacagacagccggctacaacctggaccaagtccttgaacagggaggtgtgtccagtttgtttcagaatctcggg
gtgtccgtaactccgatccaaaggattgtcctgagcggtgaaaatgggctgaagatcgacatccatgtcatcatcccg
tatgaaggtctgagcggcgaccaaatgggccagatcgaaaaaatttttaaggtggtgtaccctgtggatgatcatcac
tttaaggtgatcctgcactatggcacactggtaatcgacggggttacgccgaacatgatcgactatttcggacggccg
tatgaaggcatcgccgtgttcgacggcaaaaagatcactgtaacagggaccctgtggaacggcaacaaaattatcgac
gagcgcctgATC SEQ ID NO: 566 (CP 143(+1) L27V (RIIbB) (aa seq)
MINPDGSLLFRVTINGVTGWRLCERILASSSGGSGGSGMYESFIESLPFLKSLEFSARLKVVDVIGTKVYNDGEQIIA
QGDSADSFFIIESGEVKITMKRKGKSEVEENGAVEIARCSRGQYFGELALVTNKPRAASAHAIGTVKCLAMDVQAFER
LLGPCMEIMKRNIATYEEQLVALYGTNMDIVGSGGSGGSSSMVFTLEDFVGDWRQTAGYNLDQVLEQGGVSSLFQNLG
VSVTPIQRIVLSGENGLKIDIHVIIPYEGLSGDQMGQIEKIFKVVYPVDDHHFKVILHYGTLVIDGVTPNMIDYFGRP
YEGIAVFDGKKITVTGTLWNGNKIIDERLI SEQ ID NO: 567 (CP 147(+1) L27V (RIIbB) (nt sequence)
ATGggctccctgctgttccgagtaaccatcaacggagtgaccggctggcggctgtGCGAACGCATTCTGGCtAGCTCA
AGCGGAGGTTCAGGCGGTTCCGGAATGTATGAAAGCTTTATTGAGTCACTGCCATTCCTTAAATCTTTGGAGTTTTCT
GCACGCCTGAAAGTAGTAGATGTGATAGGCACCAAAGTATACAACGATGGAGAACAAATCATTGCTCAGGGAGATTCG
GCTGATTCTTTTTTCATTATTGAATCTGGAGAAGTGAAAATTACTATGAAAAGAAAGGGTAAATCAGAAGTGGAAGAG
AATGGTGCAGTAGAAATCGCTCGATGCTCGCGGGGACAGTACTTTGGAGAGCTTGCCCTGGTAACTAACAAACCTCGA
GCAGCTTCTGCCCACGCCATTGGGACTGTCAAATGTTTAGCAATGGATGTGCAAGCATTTGAAAGGCTTCTGGGACCT
TGCATGGAAATTATGAAAAGGAACATCGCTACCTATGAAGAACAGTTAGTTGCCCTGTATGGAACGAACATGGATATT
GTAGGGTCAGGTGGATCTGGAGGTAGCTCTTCTatggtcttcacactcgaagatttcgttggggactggcgacagaca
gccggctacaacctggaccaagtccttgaacagggaggtgtgtccagtttgtttcagaatctcggggtgtccgtaact
ccgatccaaaggattgtcctgagcggtgaaaatgggctgaagatcgacatccatgtcatcatcccgtatgaaggtctg
agcggcgaccaaatgggccagatcgaaaaaatttttaaggtggtgtaccctgtggatgatcatcactttaaggtgatc
ctgcactatggcacactggtaatcgacggggttacgccgaacatgatcgactatttcggacggccgtatgaaggcatc
gccgtgttcgacggcaaaaagatcactgtaacagggaccctgtggaacggcaacaaaattatcgacgagcgcctgatc
aaccccgacGGC SEQ ID NO: 568 (CP 147(+1) L27V (RIIbB) (aa seq)
MGSLLFRVTINGVTGWRLCERILASSSGGSGGSGMYESFIESLPFLKSLEFSARLKVVDVIGTKVYNDGEQIIAQGDS
ADSFFIIESGEVKITMKRKGKSEVEENGAVEIARCSRGQYFGELALVTNKPRAASAHAIGTVKCLAMDVQAFERLLGP
CMEIMKRNIATYEEQLVALYGTNMDIVGSGGSGGSSSMVFTLEDFVGDWRQTAGYNLDQVLEQGGVSSLFQNLGVSVT
PIQRIVLSGENGLKIDIHVIIPYEGLSGDQMGQIEKIFKVVYPVDDHHFKVILHYGTLVIDGVTPNMIDYFGRPYEGI
AVFDGKKITVTGTLWNGNKIIDERLINPDG SEQ ID NO: 569 (CP 156(+1) L27V (RIIbB) (nt sequence)
ATGaacggagtgaccggctggcggctgtGCGAACGCATTCTGGCtAGCTCAAGCGGAGGTTCAGGCGGTTCCGGAATG
TATGAAAGCTTTATTGAGTCACTGCCATTCCTTAAATCTTTGGAGTTTTCTGCACGCCTGAAAGTAGTAGATGTGATA
GGCACCAAAGTATACAACGATGGAGAACAAATCATTGCTCAGGGAGATTCGGCTGATTCTTTTTTCATTATTGAATCT
GGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACT
GTCAAATGTTTAGCAATGGATGTGCAAGCATTTGAAAGGCTTCTGGGACCTTGCATGGAAATTATGAAAAGGAACATC
GCTACCTATGAAGAACAGTTAGTTGCCCTGTATGGAACGAACATGGATATTGTAGGGTCAGGTGGATCTGGAGGTAGC
TCTTCTatggtcttcacactcgaagatttcgttggggactggcgacagacagccggctacaacctggaccaagtcctt
gaacagggaggtgtgtccagtttgtttcagaatctcggggtgtccgtaactccgatccaaaggattgtcctgagcggt
gaaaatgggctgaagatcgacatccatgtcatcatcccgtatgaaggtctgagcggcgaccaaatgggccagatcgaa
aaaatttttaaggtggtgtaccctgtggatgatcatcactttaaggtgatcctgcactatggcacactggtaatcgac
ggggttacgccgaacatgatcgactatttcggacggccgtatgaaggcatcgccgtgttcgacggcaaaaagatcact
gtaacagggaccctgtggaacggcaacaaaattatcgacgagcgcctgatcaaccccgacggctccctgctgttccga
gtaaccatcAAC SEQ ID NO: 570 (CP 156(+1) L27V (RIIbB) (aa seq)
MNGVTGWRLCERILASSSGGSGGSGMYESFIESLPFLKSLEFSARLKVVDVIGTKVYNDGEQIIAQGDSADSFFIIES
GEVKITMKRKGKSEVEENGAVEIARCSRGQYFGELALVTNKPRAASAHAIGTVKCLAMDVQAFERLLGPCMEIMKRNI
ATYEEQLVALYGTNMDIVGSGGSGGSSSMVFTLEDEVGDWRQTAGYNLDQVLEQGGVSSLFQNLGVSVTPIQRIVLSG

SEQUENCE LISTING

ENGLKIDIHVIIPYEGLSGDQMGQIEKIFKVVYPVDDHHFKVILHYGTLVIDGVTPNMIDYFGRPYEGIAVFDGKKIT
VTGTLWNGNKIIDERLINPDGSLLFRVTIN

SEQ ID NO: 571 (CP 158(+1) L27V (RIIbB) (nt sequence)
ATGgtgaccggctggcggctgtGCGAACGCATTCTGGCtAGCTCAAGCGGAGGTTCAGGCGGTTCCGGAATGTATGAA
AGCTTTATTGAGTCACTGCCATTCCTTAAATCTTTGGAGTTTTCTGCACGCCTGAAAGTAGTAGATGTGATAGGCACC
AAAGTATACAACGATGGAGAACAAATCATTGCTCAGGGAGATTCGGCTGATTCTTTTTTCATTATTGAATCTGGAGAA
GTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAA
TGTTTAGCAATGGATGTGCAAGCATTTGAAAGGCTTCTGGGACCTTGCATGGAAATTATGAAAAGGAACATCGCTACC
TATGAAGAACAGTTAGTTGCCCTGTATGGAACGAACATGGATATTGTAGGGTCAGGTGGATCTGGAGGTAGCTCTTCT
atggtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatt
tttaaggtggtgtaccctgtggatgatcatcactttaaggtgatcctgcactatggcacactggtaatcgacggggtt
acgccgaacatgatcgactatttcggacggccgtatgaaggcatcgccgtgttcgacggcaaaaagatcactgtaaca
gggaccctgtggaacggcaacaaaattatcgacgagcgcctgatcaaccccgacggctccctgctgttccgagtaacc
atcaacggaGTG SEQ ID NO: 572 (CP 158(+1) L27V (RIIbB) (aa seq)
MVTGWRLCERILASSSGGSGGSGMYESFIESLPFLKSLEFSARLKVVDVIGTKVYNDGEQIIAQGDSADSFFIIESGE
VKITMKRKGKSEVEENGAVEIARCSRGQYFGELALVTNKPRAASAHAIGTVKCLAMDVQAFERLLGPCMEIMKRNIAT
YEEQLVALYGTNMDIVGSGGSGGSSSMVFTLEDEVGDWRQTAGYNLDQVLEQGGVSSLFQNLGVSVTPIQRIVLSGEN
GLKIDIHVIIPYEGLSGDQMGQIEKIFKVVYPVDDHHFKVILHYGTLVIDGVTPNMIDYFGRPYEGIAVFDGKKITVT
GTLWNGNKIIDERLINPDGSLLFRVTINGV SEQ ID NO: 573 (CP 166(+1) L27V (RIIbB) (nt sequence)
ATGCGCATTCTGGCtAGCTCAAGCGGAGGTTCAGGCGGTTCCGGAATGTATGAAAGCTTTATTGAGTCACTGCCATTC
CTTAAATCTTTGGAGTTTTCTGCACGCCTGAAAGTAGTAGATGTGATAGGCACCAAAGTATACAACGATGGAGAACAA
ATCATTGCTCAGGGAGATTCGGCTGATTCTTTTTTCATTATTGAATCTGGAGAAGTGAAAATTACTATGAAAAGAAAG
GGTAAATCAGAAGTGGAAGAGAATGGTGCAGTAGAAATCGCTCGATGCTCGCGGGGACAGTACTTTGGAGAGCTTGCC
CTGGTAACTAACAAACCTCGAGCAGCTTCTGCCCACGCCATTGGGACTGTCAAATGTTTAGCAATGGATGTGCAAGCA
TTTGAAAGGCTTCTGGGACCTTGCATGGAAATTATGAAAAGGAACATCGCTACCTATGAAGAACAGTTAGTTGCCCTG
TATGGAACGAACATGGATATTGTAGGGTCAGGTGGATCTGGAGGTAGCTCTTCTatggtcttcacactcgaagatttc
gttggggactggcgacagacagccggctacaacctggaccaagtccttgaacagggaggtgtgtccagtttgtttcag
aatctcggggtgtccgtaactccgatccaaaggattgtcctgagcggtgaaaatgggctgaagatcgacatccatgtc
atcatcccgtatgaaggtctgagcggcgaccaaatgggccagatcgaaaaaatttttaaggtggtgtaccctgtggat
gatcatcactttaaggtgatcctgcactatggcacactggtaatcgacggggttacgccgaacatgatcgactatttc
ggacggccgtatgaaggcatcgccgtgttcgacggcaaaaagatcactgtaacagggaccctgtggaacggcaacaaa
attatcgacgagcgcctgatcaaccccgacggctccctgctgttccgagtaaccatcaacggagtgaccggctggcgg
ctgtGCGAACGC SEQ ID NO: 574 (CP 166(+1) L27V (RIIbB) (aa seq)
MRILASSSGGSGGSGMYESFIESLPFLKSLEFSARLKVVDVIGTKVYNDGEQIIAQGDSADSFFIIESGEVKITMKRK
GKSEVEENGAVEIARCSRGQYFGELALVTNKPRAASAHAIGTVKCLAMDVQAFERLLGPCMEIMKRNIATYEEQLVAL
YGTNMDIVGSGGSGGSSSMVFTLEDFVGDWRQTAGYNLDQVLEQGGVSSLFQNLGVSVTPIQRIVLSGENGLKIDIHV
IIPYEGLSGDQMGQIEKIFKVVYPVDDHHFKVILHYGTLVIDGVTPNMIDYFGRPYEGIAVFDGKKITVTGTLWNGNK
IIDERLINPDGSLLFRVTINGVTGWRLCER SEQ ID NO: 575 (linker)
GGGTCAGGTGGATCTGGAGGTAGCTCTTCT SEQ ID NO: 576 (linker)
AGCTCAAGCGGAGGTTCAGGCGGTTCCGGA SEQ ID NO: 577 (LC3 (nt sequence))
ATGCCGTCCGAGAAGACCTTCAAACAGCGCCGGAGCTTCGAACAAAGAGTGGAAGATGTCCGGCTCATCCGGGAGCAG
CACCCCACCAAGATCCCAGTGATTATAGAGCGATACAAGGGTGAGAAGCAGCTGCCCGTCCTGGACAAGACCAGTTCC
TTGTACCTGATCACGTGAATATGAGCGAACTCATCAAGATAATTAGAAGGCGCCTGCAGCTCAATGCTAACCAAGCCT
TCTTCCTCCTGGTGAATGGGCACAGCATGGTGAGTGTGTCCACACCCATCTCTGAAGTGTACGAGAGCGAGAGAGATG
AAGACGGCTTCCTGTACATGGTCTATGCCTCCCAGGAGACGTTCGGGACAGCACTGGCTGTGTAA SEQ ID NO: 578 (LC3 (aa sequence))
MPSEKTFKQRRSFEQRVEDVRLIREQHPTKIPVIIERYKGEKQLPVLDKTKFLVPDHVNMSELIKIIRRRLQLNANQA
FFLLVNGHSMVSVSTPISEVYESERDEDGFLYMVYASQETFGTALAV SEQ ID NO: 579 (pattern sequence)
GSAIVK SEQ ID NO: 580 (pattern sequence)
NHGK SEQ ID NO: 581 (pattern sequence)
SILM SEQ ID NO: 582 (pattern sequence)
AVTK -continued

SEQUENCE LISTING

```
SEQ ID NO: 583 (pattern sequence)
LIVMFY

SEQ ID NO: 584 (pattern sequence)
LIVMFY

SEQ ID NO: 585 (pattern sequence)
LIVM

SEQ ID NO: 586 (pattern sequence)
LIVMWF

SEQ ID NO: 587 (pattern sequence)
EKTQ

SEQ ID NO: 588 (pattern sequence)
LIVMAKR

SEQ ID NO: 589 (pattern sequence)
LIVMAKRG

SEQ ID NO: 590 (pattern sequence)
LIVMF

SEQ ID NO: 591 (pattern sequence)
LIVMFSYQ

SEQ ID NO:  592 OgLuc L27V-LC3 fusions proteins (Nt seq)
ATGGTGTTTACACTCGAAGATTTCGTAGGGGACTGGCGGCAGACAGCCGGCTACAACCTGGACCAAGTCCTTGAGCAG
GGCGGTGTGTCCAGTTTGTTTCAGAATCTCGGGGTGTCCGTAACTCCGATCCAAAGGATTGTCCTGAGCGGTGAAAAC
GGCCTGAAGATCGACATCCATGTCATCATCCCGTATGAAGGTCTGAGCGGCGATCAGATGGGCCAGATCGAAAAAATT
TTTAAGGTGGTGTACCCTGTGGATGATCATCACTTTAAGGTGATTCTGCACTATGGCACACTGGTAATCGACGGGGTT
ACGCCGAACATGATCGACTATTTCGGACGGCCGTATGAAGGCATCGCCGTGTTCGACGGCAAAAAGATCACTGTAACC
GGGACCCTGTGGAACGGCAACAAAATTATCGACGAGCGCCTGATCAACCCCGACGGCTCCCTGCTGTTCCGCGTAACC
ATCAACGGAGTGACCGGCTGGCGGCTGTGCGAGAGAATTTTGGCGGGCTCGAGCGGAGGTGGAGGTTCAGGTGGTGGC
GGGAGCGGTGGAATGCCGTCCGAGAAGACCTTCAAACAGCGCCGGAGCTTCGAACAAAGAGTGGAAGATGTCCGGCTC
ATCCGGGAGCAGCACCCCACCAAGATCCCAGTGATTATAGAGCGATACAAGGGTGAGAAGCAGCTGCCCGTCCTGGAC
AAGACCAAGTTCCTTGTACCTGATCACGTGAATATGAGCGAACTCATCAAGATAATTAGAAGGCGCCTGCAGCTCAAT
GCTAACCAAGCCTTCTTCCTCCTGGTGAATGGGCACAGCATGGTGAGTGTGTCCACACCCATCTCTGAAGTGTACGAG
AGCGAGAGAGATGAAGACGGCTTCCTGTACATGGTCTATGCCTCCCAGGAGACGTTCGGGACAGCACTGGCTGTGTAA

SEQ ID NO:  593 OgLuc L27V-LC3 fusions proteins (aa seq)
MVFTLEDFVGDWRQTAGYNLDQVLEQGGVSSLFQNLGVSVTPIQRIVLSGENGLKIDIHVIIPYEGLSGDQMGQIEKI
FKVVYPVDDHHFKVILHYGTLVIDGVTPNMIDYFGRPYEGIAVFDGKKITVTGTLWNGNKIIDERLINPDGSLLFRVT
INGVTGWRLCERILAGSSGGGGSGGGGSGGMPSEKTFKQRRSFEQRVEDVRLIREQHPTKIPVIIERYKGEKQLPVLD
KTKFLVPDHVNMSELIKIIRRRLQLNANQAFFLLVNGHSMVSVSTPISEVYESERDEDGFLYMVYASQETFGTALAV
```

What is claimed:

1. A composition comprising a circularly permuted polypeptide having an N-terminal segment linked to a C-terminal segment, wherein the N-terminal segment of the circularly permuted polypeptide has at least 95% sequence identity to a portion of SEQ ID NO: 89 from a circular permutation site to the C-terminus of SEQ ID NO: 89, wherein the C-terminal segment of the circularly permuted polypeptide has at least 95% sequence identity to a portion of SEQ ID NO: 89 from the N-terminus to the circular permutation site of SEQ ID NO: 89, wherein the circular permutation site is within a transition between predicted protein structural motifs of a polypeptide of SEQ ID NO: 89, and wherein the circularly permuted polypeptide exhibits luciferase activity in the presence of a coelenterazine substrate.

2. The composition of claim 1, wherein the N-terminal and C-terminal segments of the circularly permuted polypeptide are fused together by a peptide linker.

3. The composition of claim 2, wherein the peptide linker comprises a protease cleavage site.

4. The composition of claim 1, wherein the N-terminal and C-terminal segments of the circularly permuted polypeptide together have 100% sequence identity to the amino acid sequence of SEQ ID NO: 89.

5. The composition of claim 1, further comprising a coelenterazine substrate.

* * * * *